(12) United States Patent
Tsuda et al.

(10) Patent No.: US 12,370,263 B2
(45) Date of Patent: Jul. 29, 2025

(54) CYCLIC DINUCLEOTIDE DERIVATIVE BASED ANTIBODY-DRUG CONJUGATES

(71) Applicant: DAIICHI SANKYO COMPANY, LIMITED, Tokyo (JP)

(72) Inventors: Toshifumi Tsuda, Tokyo (JP); Toshiki Tabuchi, Tokyo (JP); Hideaki Watanabe, Tokyo (JP); Hiroyuki Kobayashi, Tokyo (JP); Masayuki Ishizaki, Tokyo (JP); Kyoko Hara, Tokyo (JP); Teiji Wada, Tokyo (JP); Masami Arai, Tokyo (JP)

(73) Assignee: DAIICHI SANKYO COMPANY, LIMITED, Tokyo (JP)

( * ) Notice: Subject to any disclaimer, the term of this patent is extended or adjusted under 35 U.S.C. 154(b) by 1098 days.

(21) Appl. No.: 17/273,666

(22) PCT Filed: Sep. 6, 2019

(86) PCT No.: PCT/JP2019/035198
§ 371 (c)(1),
(2) Date: Mar. 4, 2021

(87) PCT Pub. No.: WO2020/050406
PCT Pub. Date: Mar. 12, 2020

(65) Prior Publication Data
US 2022/0008549 A1    Jan. 13, 2022

(30) Foreign Application Priority Data
Sep. 6, 2018    (JP) ................................. 2018-167369

(51) Int. Cl.
A61K 47/68    (2017.01)
A61K 47/54    (2017.01)
A61P 35/00    (2006.01)
C07K 16/32    (2006.01)

(52) U.S. Cl.
CPC ........ *A61K 47/6807* (2017.08); *A61K 47/545* (2017.08); *A61K 47/6855* (2017.08); *A61P 35/00* (2018.01); *C07K 16/32* (2013.01)

(58) Field of Classification Search
CPC ................................ A61P 35/00; C07K 16/32
See application file for complete search history.

(56) References Cited

U.S. PATENT DOCUMENTS

| | | |
|---|---|---|
| 5,821,337 A | 10/1998 | Carter et al. |
| 10,981,901 B1 | 4/2021 | Romano et al. |
| 11,453,697 B1 | 9/2022 | Altman et al. |
| 2005/0180969 A1 | 8/2005 | Hardy et al. |
| 2008/0025980 A1 | 1/2008 | Hardy et al. |
| 2008/0138855 A1 | 6/2008 | Wang |
| 2009/0263386 A1 | 10/2009 | Hardy et al. |
| 2011/0070607 A1 | 3/2011 | Wang |
| 2012/0226024 A1 | 9/2012 | Wang et al. |
| 2013/0131325 A1 | 5/2013 | Wang |
| 2013/0137857 A1 | 5/2013 | Wang |
| 2014/0205653 A1 | 7/2014 | Dubensky et al. |
| 2014/0341976 A1 | 11/2014 | Dubensky et al. |
| 2015/0056224 A1 | 2/2015 | Dubensky et al. |
| 2015/0087811 A1 | 3/2015 | Wang |
| 2015/0087814 A1 | 3/2015 | Wang et al. |
| 2015/0343056 A1 | 12/2015 | Chen et al. |
| 2016/0068560 A1 | 3/2016 | Patel et al. |
| 2016/0137995 A1 | 5/2016 | Wang |
| 2016/0235861 A1 | 8/2016 | Van Delft et al. |
| 2016/0250347 A1 | 9/2016 | Van Delft et al. |
| 2016/0257764 A1 | 9/2016 | Van Delft et al. |
| 2016/0280797 A1 | 9/2016 | Van Delft et al. |
| 2016/0287698 A1 | 10/2016 | Yan et al. |
| 2016/0361436 A1 | 12/2016 | Davis et al. |
| 2017/0044206 A1 | 2/2017 | Altman et al. |
| 2017/0058040 A1 | 3/2017 | Wang et al. |
| 2017/0121421 A1 | 5/2017 | Cortez et al. |
| 2017/0158724 A1 | 6/2017 | Adams et al. |
| 2017/0158772 A1 | 6/2017 | Thompson et al. |
| 2017/0210856 A1 | 7/2017 | Schildbach et al. |
| 2017/0218008 A1 | 8/2017 | Dubensky et al. |
| 2017/0233430 A1 | 8/2017 | Adams et al. |
| 2017/0283454 A1 | 10/2017 | Dubensky et al. |
| 2017/0296655 A1 | 10/2017 | Chen et al. |

(Continued)

FOREIGN PATENT DOCUMENTS

| | | |
|---|---|---|
| CN | 107849084 A | 3/2018 |
| CN | 108137641 A | 6/2018 |

(Continued)

OTHER PUBLICATIONS

Extended European Search Report issued in corresponding European Patent Application No. 19857433.7 dated May 4, 2022.

(Continued)

*Primary Examiner* — Elly-Gerald Stoica
(74) *Attorney, Agent, or Firm* — Foley & Lardner LLP

(57) ABSTRACT

Desired is development of novel CDN derivatives having STING agonist activity; and a therapeutic agents and/or therapeutic methods using the novel CDN derivatives for diseases associated with STING agonist activity. Further desired is development of a therapeutic agents and/or therapeutic methods capable of delivering the novel CDN derivatives specifically to targeted cells and organs for diseases associated with STING agonist activity. The present invention provides novel CDN derivatives having potent STING agonist activity, and antibody-CDN derivative conjugates including the novel CDN derivatives.

73 Claims, 22 Drawing Sheets

Specification includes a Sequence Listing.

(56) References Cited

U.S. PATENT DOCUMENTS

| | | |
|---|---|---|
| 2017/0298139 A1 | 10/2017 | Thompson et al. |
| 2017/0333552 A1 | 11/2017 | Dubensky et al. |
| 2017/0349861 A1 | 12/2017 | O'Connell et al. |
| 2018/0064745 A1 | 3/2018 | Katibah et al. |
| 2018/0092937 A1 | 4/2018 | Oost et al. |
| 2018/0093964 A1 | 4/2018 | Altman et al. |
| 2018/0105514 A1 | 4/2018 | Mehlmann et al. |
| 2018/0117171 A1 | 5/2018 | Mooney et al. |
| 2018/0118777 A1 | 5/2018 | Patel et al. |
| 2018/0127454 A1 | 5/2018 | Patel et al. |
| 2018/0147292 A1 | 5/2018 | Noguchi et al. |
| 2018/0186828 A1 | 7/2018 | Biggadike et al. |
| 2018/0186847 A1 | 7/2018 | Wang et al. |
| 2018/0208915 A1 | 7/2018 | Kawaguchi et al. |
| 2018/0230177 A1 | 8/2018 | Zhong et al. |
| 2018/0230178 A1 | 8/2018 | Altman et al. |
| 2018/0237469 A1 | 8/2018 | Altman et al. |
| 2018/0244712 A1 | 8/2018 | Altman et al. |
| 2018/0258132 A1 | 9/2018 | Adams et al. |
| 2019/0002476 A1 | 1/2019 | Bartels et al. |
| 2019/0015502 A1 | 1/2019 | Yan et al. |
| 2019/0016750 A1 | 1/2019 | Glick et al. |
| 2019/0031708 A1 | 1/2019 | Glick et al. |
| 2019/0062365 A1 | 2/2019 | Katibah et al. |
| 2019/0169293 A1 | 6/2019 | Iwamoto et al. |
| 2019/0185511 A1 | 6/2019 | Kanne et al. |
| 2019/0192549 A1 | 6/2019 | Yoshikawa et al. |
| 2019/0225706 A1 | 7/2019 | Van Delft et al. |
| 2019/0262372 A1 | 8/2019 | Iyer et al. |
| 2019/0263851 A1 | 8/2019 | Chen et al. |
| 2019/0270757 A1 | 9/2019 | Bartels et al. |
| 2019/0292435 A1 | 9/2019 | Goodman et al. |
| 2019/0330257 A1 | 10/2019 | Patel et al. |
| 2019/0330368 A1 | 10/2019 | Jikoh et al. |
| 2019/0336615 A1 | 11/2019 | Thompson et al. |
| 2019/0337917 A1 | 11/2019 | Altman et al. |
| 2019/0337918 A1 | 11/2019 | Altman et al. |
| 2019/0345191 A1 | 11/2019 | Glick et al. |
| 2019/0367570 A1 | 12/2019 | Wang et al. |
| 2020/0002370 A1 | 1/2020 | Adams et al. |
| 2020/0040028 A1 | 2/2020 | Genieser et al. |
| 2020/0102342 A1 | 4/2020 | Chen et al. |
| 2020/0113924 A1 | 4/2020 | Cemerski et al. |
| 2020/0140477 A1 | 5/2020 | Chen et al. |
| 2020/0165288 A1 | 5/2020 | Glick et al. |
| 2020/0179431 A1 | 6/2020 | Katibah et al. |
| 2020/0282049 A1 | 9/2020 | Dubensky et al. |
| 2020/0308216 A1 | 10/2020 | Chen et al. |
| 2020/0325126 A1 | 10/2020 | Charnley et al. |
| 2020/0347323 A1 | 11/2020 | O'Connell et al. |
| 2021/0040814 A1 | 2/2021 | Roback et al. |
| 2021/0106607 A1 | 4/2021 | Yoshikawa et al. |
| 2021/0139473 A1 | 5/2021 | Charnley et al. |
| 2021/0139604 A1 | 5/2021 | Thompson et al. |
| 2021/0147467 A1 | 5/2021 | Glick et al. |
| 2021/0346387 A1 | 11/2021 | Cortez et al. |
| 2022/0008549 A1 | 1/2022 | Tsuda et al. |

FOREIGN PATENT DOCUMENTS

| | | |
|---|---|---|
| CN | 108430503 A | 8/2018 |
| EA | 29856 B1 | 6/2018 |
| ES | 2549303 T3 | 10/2015 |
| JP | 2018-090562 | 6/2018 |
| JP | 2018-522914 | 8/2018 |
| JP | 2018-522915 A | 8/2018 |
| JP | 2019-090562 A | 6/2019 |
| TW | 201825509 A | 7/2018 |
| TW | I825170 B | 12/2023 |
| WO | WO-2007/133855 A2 | 11/2007 |
| WO | WO-2013/120066 A1 | 8/2013 |
| WO | WO-2014/093936 | 6/2014 |
| WO | WO-2014/099824 | 6/2014 |
| WO | WO-2014/179335 | 11/2014 |
| WO | WO-2014/189805 | 11/2014 |
| WO | WO-2014/189806 | 11/2014 |
| WO | WO-2015/057063 A1 | 4/2015 |
| WO | WO-2015/057064 A1 | 4/2015 |
| WO | WO-2015/057065 A1 | 4/2015 |
| WO | WO-2015/057066 A1 | 4/2015 |
| WO | WO-2015/074145 | 5/2015 |
| WO | WO-2015/185565 | 12/2015 |
| WO | WO-2016/012305 | 1/2016 |
| WO | WO-2016/096714 | 6/2016 |
| WO | WO-2016/145102 | 9/2016 |
| WO | WO-2016/161372 A1 | 10/2016 |
| WO | WO-2017/010559 | 1/2017 |
| WO | WO-2017/027645 | 2/2017 |
| WO | WO-2017/027646 | 2/2017 |
| WO | WO-2017/072662 A1 | 5/2017 |
| WO | WO-2017/075477 | 5/2017 |
| WO | WO-2017/093933 | 6/2017 |
| WO | WO-2017/100305 | 6/2017 |
| WO | WO-2017/123669 | 7/2017 |
| WO | WO-2017/161349 | 9/2017 |
| WO | WO-2017/175147 | 10/2017 |
| WO | WO-2017/175156 | 10/2017 |
| WO | WO-2018/003983 | 1/2018 |
| WO | WO-2018/009466 | 1/2018 |
| WO | WO-2018/009648 | 1/2018 |
| WO | WO-2018/045204 | 3/2018 |
| WO | WO-2018/060323 | 4/2018 |
| WO | WO-2018/065360 | 4/2018 |
| WO | WO-2018/066626 A1 | 4/2018 |
| WO | WO-2018/067423 | 4/2018 |
| WO | WO-2018/100558 | 6/2018 |
| WO | WO-2018/118665 A1 | 6/2018 |
| WO | WO-2018/140831 A2 | 8/2018 |

OTHER PUBLICATIONS

Abe et al., "Cytosolic-DNA-Mediated, STING-Dependent Proinflammatory Gene Induction Necessitates Canonical NF-kB Activation through TBK1", J. Virol., 2014, vol. 88, pp. 5328-5341.

Challa et al., "Pharmacodynamic and preclinical studies of SB 11285, a highly potent, and systematically bioavailable STING agonist as a novel immuno-therapeutic agent", AACR Tumor Immunology and Immunotherapy, 2017, Poster#A25.

Conlon et al., "Mouse, but not Human STING, Binds and Signals in Response to the Vascular Disrupting Agent 5,6-Dimethylxanthenone-4-Acetic Acid", J. Immunol., 2013, vol. 190, pp. 5216-5225.

Corrales et al., "Direct Activation of STING in the Tumor Microenvironment Leads to Potent and Systemic Tumor Regression and Immunity", Cell Rep. 2015, vol. 11, pp. 1018-1030.

Deng et al., "STING-Dependent Cytosolic DNA Sensing Promotes Radiation-Induced Type I Interferon-Dependent Antitumor Immunity in Immunogenic Tumors", Immunity, 2014, vol. 41, pp. 843-852.

Goodfellow et al., "An Endoglycosidase with Alternative Glycan Specificity Allows Broadened Glycoprotein Remodelling", J. Am. Chem. Soc., 2012, vol. 134, pp. 8030-8033.

Huang et al., "Chemoenzymatic Glycoengineering of Intact IgG Antibodies for Gain of Functions", J. Am. Chem. Soc., 2012, vol. 134, pp. 12308-12318.

International Search Report on PCT/JP2019/035198 dated Nov. 5, 2019.

Ishikawa et al., "STING is an endoplasmic reticulum adaptor that facilities innate immune signalling", Nature, 2008, vol. 455, pp. 674-678.

Kranzusch et al., "Ancient Origin of cGAS-STING Reveals Mechanism of Universal 2',3' cGAMP Signaling", Mol. Cell, 2015, vol. 59, pp. 891-903.

Lara Jr et al., "Randomized Phase III Placebo-Controlled Trial of Carboplatin and Paclitaxel With or Without the Vascular Disrupting Agent Vadimezan (ASA404) in Advanced Non-Small-Cell Lung Cancer", J. Clin. Oncol. 2011, vol. 29, pp. 2965-2971.

Li et al., "Antitumor Activity of cGAMP via Stimulation of cGAS-cGAMP-STING-IRF3 Mediated Innate Immune Response", Sci. Rep. 2016, vol. 6, pp. 1-14.

(56) References Cited

OTHER PUBLICATIONS

Liu et al., "CD47 blockade triggers T cell-mediated destruction of immunogenic tumors", Nat. Med. 2015, vol. 21, pp. 1209-1215.
Liu et al., "Phosphorylation of innate immune adaptor proteins MAVS, STING, and TRIF induces IRF3 activation", Science 2015, vol. 347, pp. aaa2630.
Parsons et al., "Optimal Synthetic Glycosylation of a Therapeutic Antibody", Angew. Chem. Int. Ed., 2016, vol. 55, pp. 2361-2367.
Perera et al., "Activation of LPS-inducible genes by the antitumor agent 5,6-dimethylxanthenone-4-acetic acid in primary murine macrophages. Dissection of signaling pathways leading to gene induction and tyrosine phosphorylation", J. Immunol., 1994, vol. 153, pp. 4684-4693.
Van Geel et a., "Chemoenzymatic Conjugation of Toxic Payloads to the Globally Conserved N-Glycan of Native mAbs Provides Homogeneous and Highly Efficacious Antibody-Drug Conjugates", Bioconjugate Chemistry, 2015, vol. 26, pp. 2233-2242.
Woo et al., "STING-Dependent Cytosolic DNA Sensing Mediates Innate Recognition of Immunogenic Tumors", Immunity, 2014, vol. 41, pp. 830-842.
Written Opinion on PCT/JP2019/035198 dated Nov. 5, 2019.
Zhang et al., "Cyclic GMP-AMP Containing Mixed Phosphodiester Linkages Is An Endogenous High-Affinity Ligand for STING", Mol. Cell, 2013, vol. 51, pp. 226-235.
Office Action issued in corresponding Russian Patent Application No. 2021105345/04, dated Jun. 20, 2022.
Office Action issued in corresponding Russian Patent Application No. 202110105345/04, dated Jun. 20, 2020.
Office Action issued in corresponding Singaporean Patent Application No. 11202101526Y, dated May 11, 2022.
Office Action, dated Jul. 17, 2023, issued in corresponding Singaporean Patent Application No. 11202101526Y (7 pages).
Office Action, dated Jul. 20, 2023, issued in corresponding Chinese Patent Application No. 201980058151.3 (23 pages).
Office Action, dated May 26, 2023, issued in corresponding Colombian Patent Application No. NC2021/0004032 (19 pages).
Office Action issued in corresponding Colombian Patent Application No. NC2021/0004032 dated Sep. 24, 2023 (18 pages).
Office Action issued in corresponding Taiwanese Patent Application No. 108132368 dated Sep. 4, 2023 (7 pages).
Office Action, dated Aug. 1, 2023, issued in corresponding Australian Patent Application No. 2019337051 (3 pages).
Office Action issued in corresponding Taiwanese Patent Application No. 112114344 dated Jul. 8, 2024.
Office Action issued in corresponding Indian Patent Application No. 202117014105 dated Jan. 10, 2025.
Office Action issued in corresponding Australian Patent Application No. 2023201159 dated Feb. 25, 2025.
Office Action issued in corresponding Philippines Patent Application No. 1/2021/550442 dated Mar. 27, 2025.
European Extended Search Report issued in corresponding European Patent Application No. 25154566.1 dated May 6, 2025.

[Figure 1]
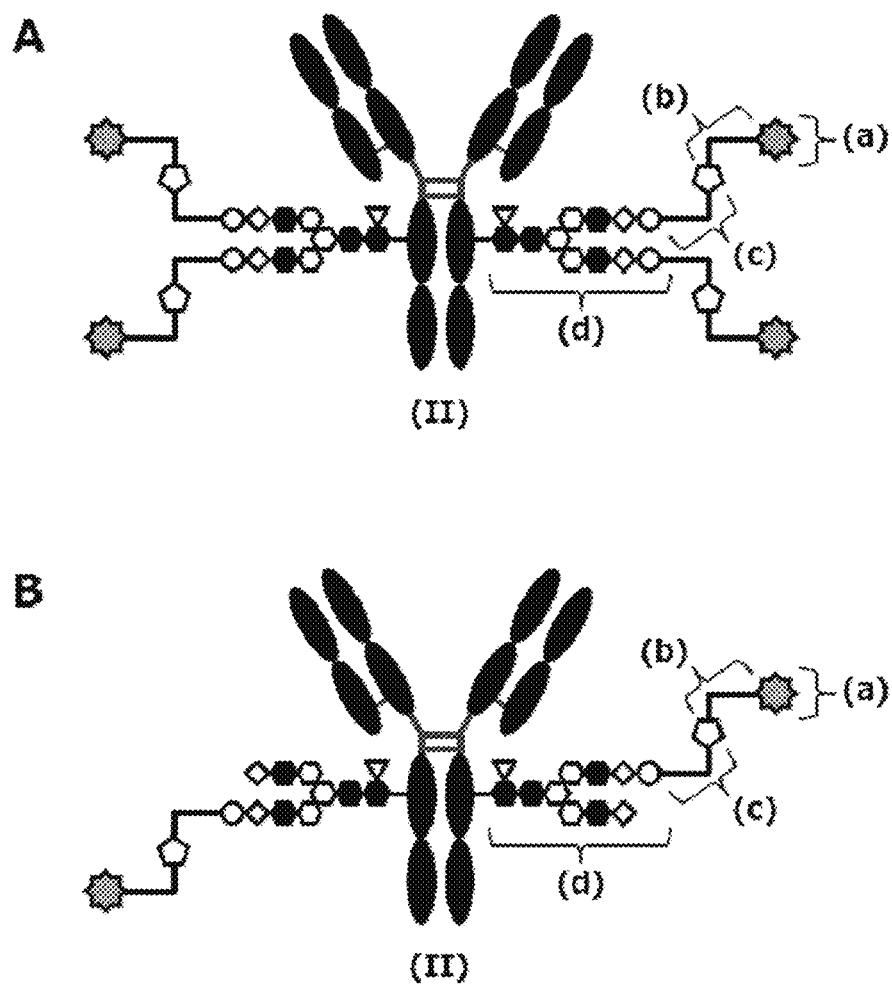

[Figure 2]
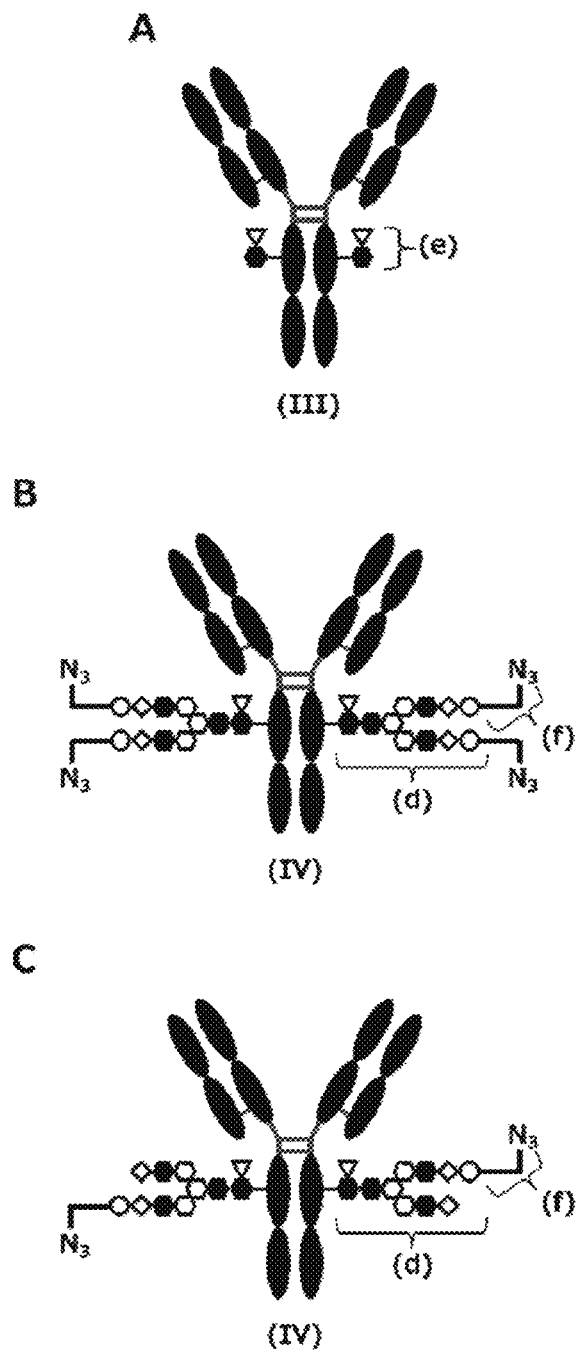

[Figure 3]
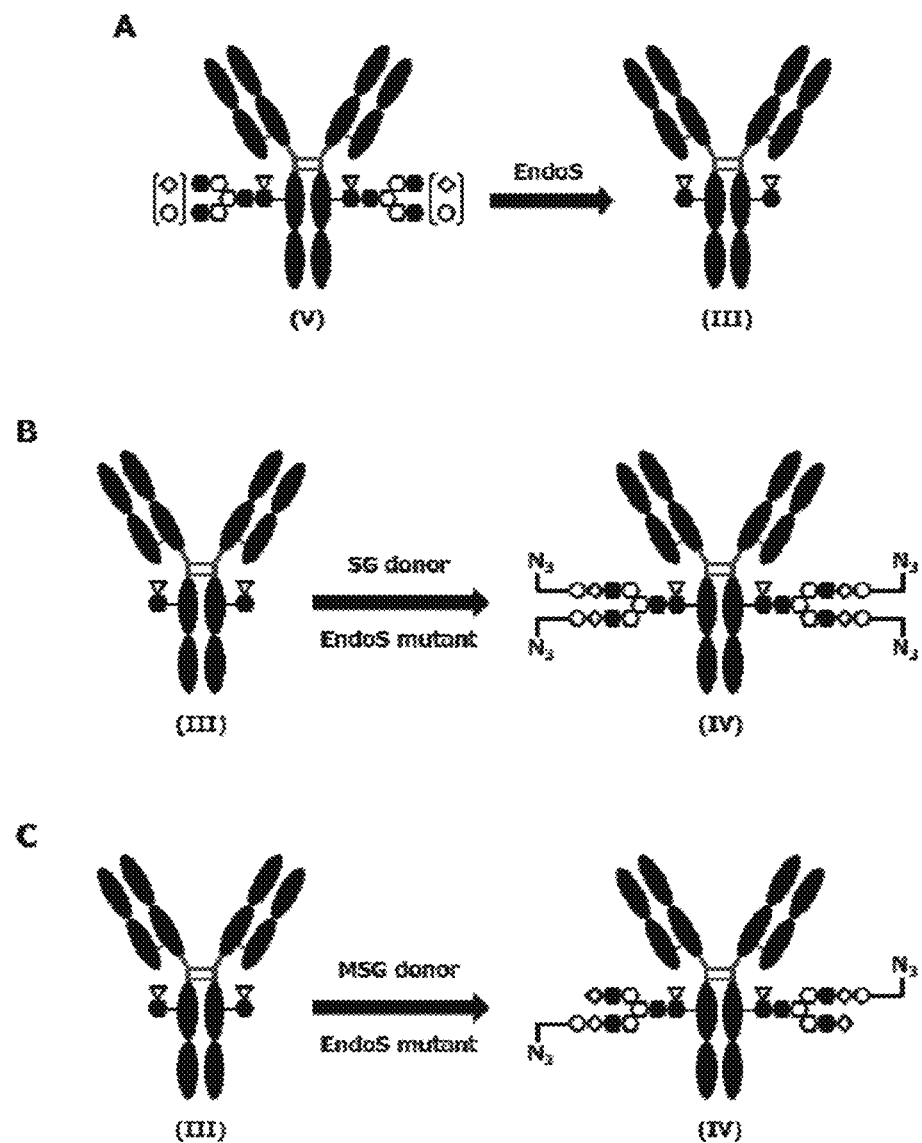

[Figure 4]

Amino acid sequence of trastuzumab light chain (SEQ ID NO: 1)

DIQMTQSPSSLSASVGDRVTITCRASQDVNTAVAWYQQKPGKAPKLLIYSASFLYSGVPS
RFSGSRSGTDFTLTISSLQPEDFATYYCQQHYTTPPTFGQGTKVEIKRTVAAPSVFIFPP
SDEQLKSGTASVVCLLNNFYPREAKVQWKVDNALQSGNSQESVTEQDSKDSTYSLSSTLT
LSKADYEKHKVYACEVTHQGLSSPVTKSFNRGEC

Amino acid sequence of trastuzumab heavy chain (SEQ ID NO: 2)
EVQLVESGGGLVQPGGSLRLSCAASGFNIKDTYIHWVRQAPGKGLEWVARIYPTNGYTRY
ADSVKGRFTISADTSKNTAYLQMNSLRAEDTAVYYCSRWGGDGFYAMDYWGQGTLVTVSS
ASTKGPSVFPLAPSSKSTSGGTAALGCLVKDYFPEPVTVSWNSGALTSGVHTFPAVLQSS
GLYSLSSVVTVPSSSLGTQTYICNVNHKPSNTKVDKKVEPKSCDKTHTCPPCPAPELLGG
PSVFLFPPKPKDTLMISRTPEVTCVVVDVSHEDPEVKFNWYVDGVEVHNAKTKPREEQYN
STYRVVSVLTVLHQDWLNGKEYKCKVSNKALPAPIEKTISKAKGQPREPQVYTLPPSREE
MTKNQVSLTCLVKGFYPSDIAVEWESNGQPENNYKTTPPVLDSDGSFFLYSKLTVDKSRW
QQGNVFSCSVMHEALHNHYTQKSLSLSPGK

[Figure 5]

Amino acid sequence of light chain of modified anti-HER2 antibody (SEQ ID NO: 1)

DIQMTQSPSSLSASVGDRVTITCRASQDVNTAVAWYQQKPGKAPKLLIYSASFLYSGVPS
RFSGSRSGTDFTLTISSLQPEDFATYYCQQHYTTPPTFGQGTKVEIKRTVAAPSVFIFPP
SDEQLKSGTASVVCLLNNFYPREAKVQWKVDNALQSGNSQESVTEQDSKDSTYSLSSTLT
LSKADYEKHKVYACEVTHQGLSSPVTKSFNRGEC

Amino acid sequence of heavy chain of modified anti-HER2 antibody (SEQ ID NO: 3)
EVQLVESGGGLVQPGGSLRLSCAASGFNIKDTYIHWVRQAPGKGLEWVARIYPTNGYTRY
ADSVKGRFTISADTSKNTAYLQMNSLRAEDTAVYYCSRWGGDGFYAMDYWGQGTLVTVSS
ASTKGPSVFPLAPSSKSTSGGTAALGCLVKDYFPEPVTVSWNSGALTSGVHTFPAVLQSS
GLYSLSSVVTVPSSSLGTQTYICNVNHKPSNTKVDKKVEPKSCDKTHTCPPCPAPE<u>AA</u>G
GPSVFLFPPKPKDTLMISRTPEVTCVVVDVSHEDPEVKFNWYVDGVEVHNAKTKPREEQY
NSTYRVVSVLTVLHQDWLNGKEYKCKVSNKALPAPIEKTISKAKGQPREPQVYTLPPSRE
EMTKNQVSLTCLVKGFYPSDIAVEWESNGQPENNYKTTPPVLDSDGSFFLYSKLTVDKSR
WQQGNVFSCSVMHEALHNHYTQKSLSLSPGK (The underline indicates a position of LALA mutation.)

[Figure 6]

(a) Amino acid sequence of wild-type human STING

MPHSSLHPSIPCPRGHGAQKAALVLLSACLVTLWGLGEPPEHTLRYLVLHLASLQLGLLL
NGVCSLAEELRHIHSRYRGSYWRTVRACLGCPLRRGALLLLSIYFYYSLPNAVGPPFTWM
LALLGLSQALNILLGLKGLAPAEISAVCEKGNFNVAHGLAWSYYIGYLRLILPELQARIR
TYNQHYNNLLRGAVSQRLYILLPLDCGVPDNLSMADPNIRFLDKLPQQTGDRAGIKDRVY
SNSIYELLENGQRAGTCVLEYATPLQTLFAMSQYSQAGFSREDRLEQAKLFCRTLEDILA
DAPESQNNCRLIAYQEPADDSSFSLSQEVLRHLRQEEKEEVTVGSLKTSAVPSTSTMSQE
PELLISGMEKPLPLRTDFS (b) Amino acid sequence of REF-mutated (R232H) human STING
MPHSSLHPSIPCPRGHGAQKAALVLLSACLVTLWGLGEPPEHTLRYLVLHLASLQLGLLL
NGVCSLAEELRHIHSRYRGSYWRTVRACLGCPLRRGALLLLSIYFYYSLPNAVGPPFTWM
LALLGLSQALNILLGLKGLAPAEISAVCEKGNFNVAHGLAWSYYIGYLRLILPELQARIR
TYNQHYNNLLRGAVSQRLYILLPLDCGVPDNLSMADPNIRFLDKLPQQTGD<u>H</u>AGIKDRVY
SNSIYELLENGQRAGTCVLEYATPLQTLFAMSQYSQAGFSREDRLEQAKLFCRTLEDILA
DAPESQNNCRLIAYQEPADDSSFSLSQEVLRHLRQEEKEEVTVGSLKTSAVPSTSTMSQE
PELLISGMEKPLPLRTDFS
(The underline indicates a position of R232H mutation.)

(c) Amino acid sequence of HAQ mutant (R71H, G230A, R293Q) of human STING
MPHSSLHPSIPCPRGHGAQKAALVLLSACLVTLWGLGEPPEHTLRYLVLHLASLQLGLLL
NGVCSLAEEL<u>H</u>HIHSRYRGSYWRTVRACLGCPLRRGALLLLSIYFYYSLPNAVGPPFTWM
LALLGLSQALNILLGLKGLAPAEISAVCEKGNFNVAHGLAWSYYIGYLRLILPELQARIR
TYNQHYNNLLRGAVSQRLYILLPLDCGVPDNLSMADPNIRFLDKLPQQT<u>A</u>DRAGIKDRVY
SNSIYELLENGQRAGTCVLEYATPLQTLFAMSQYSQAGFSREDRLEQAKLFC<u>Q</u>TLEDILA
DAPESQNNCRLIAYQEPADDSSFSLSQEVLRHLRQEEKEEVTVGSLKTSAVPSTSTMSQE
PELLISGMEKPLPLRTDFS
(The three underlines indicate positions of R71H mutation, G230A mutation, and R293Q mutation, respectively.)

[Figure 7]
(a)
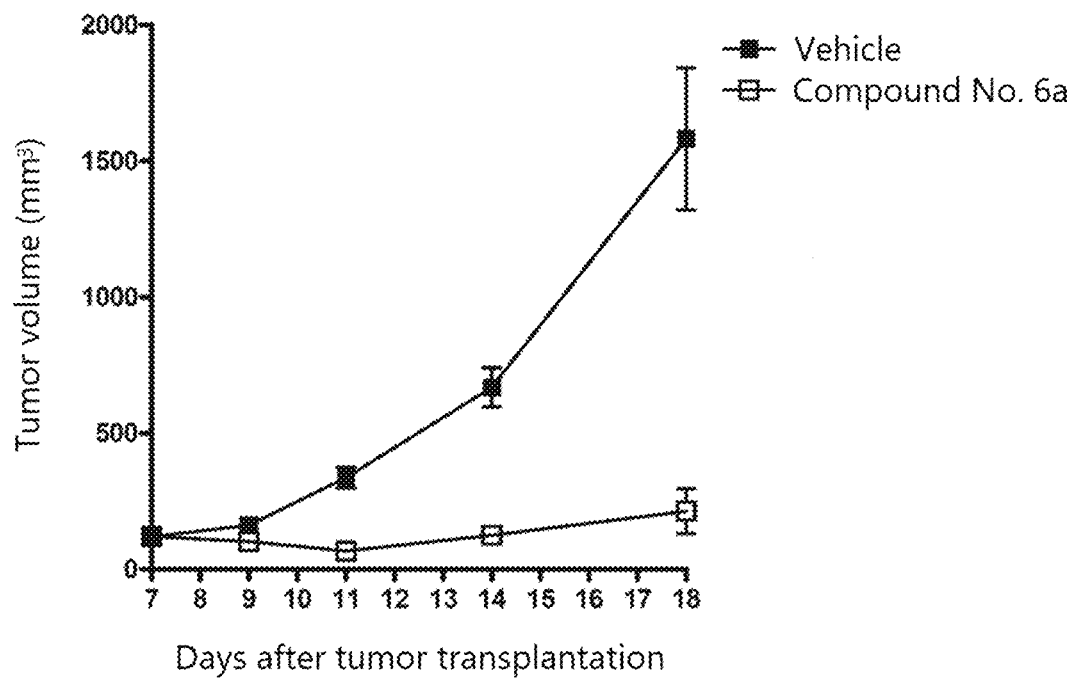
(b)
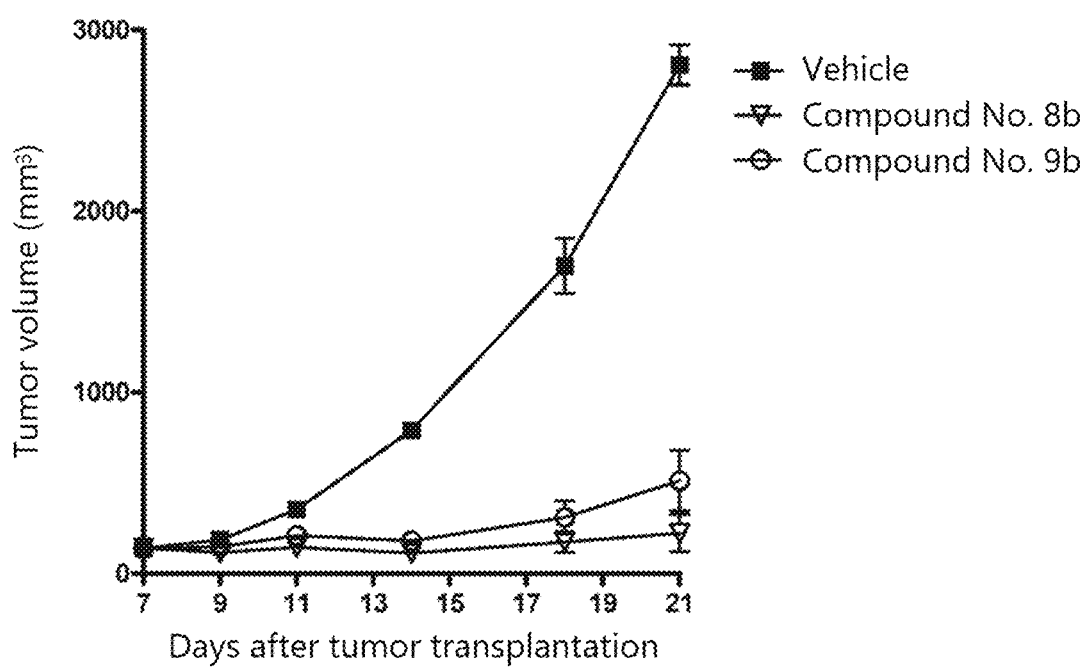

[Figure 8]
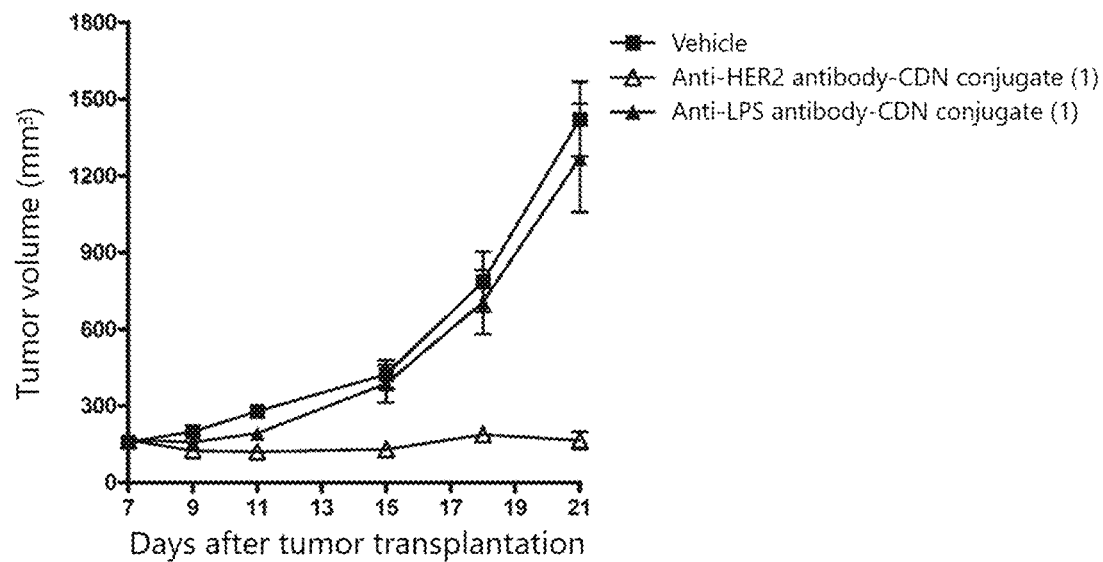
[Figure 9]
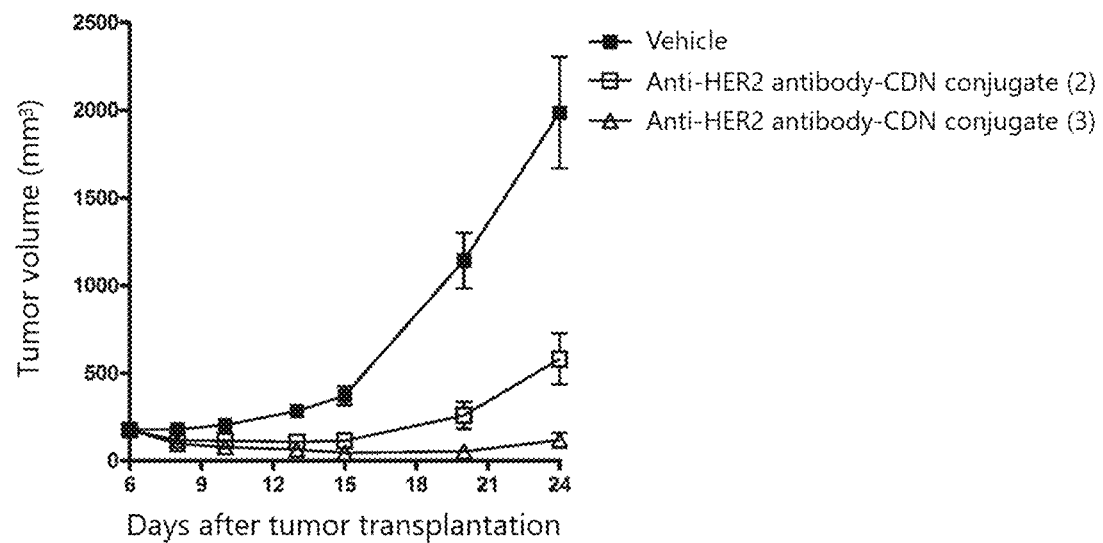

[Figure 10]
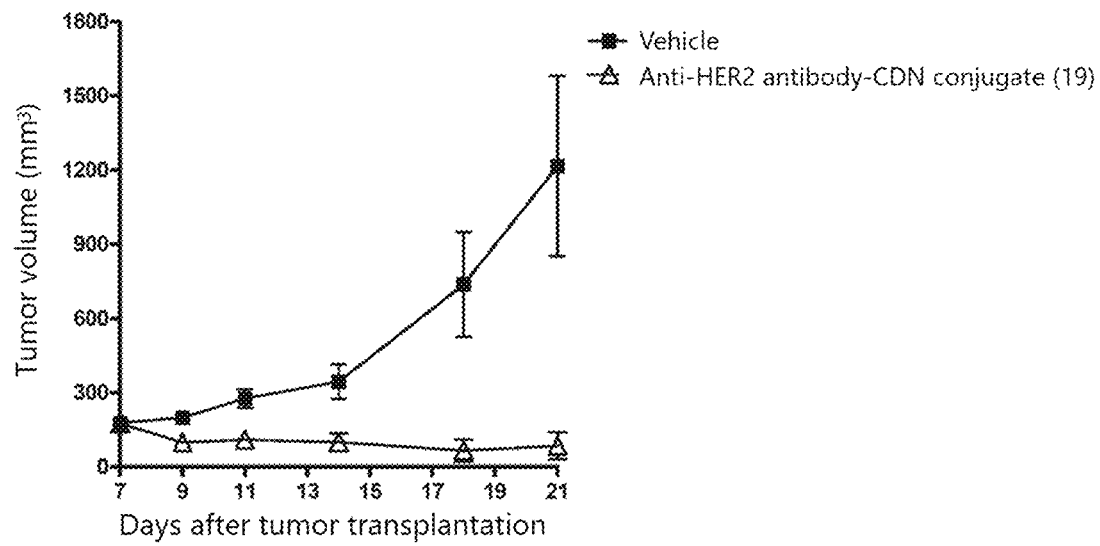
[Figure 11]
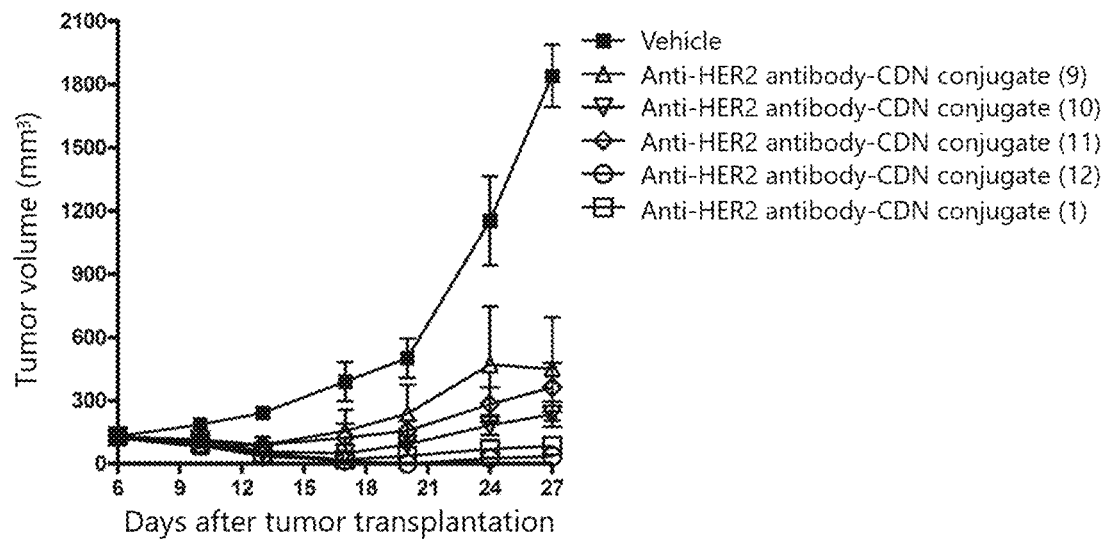

[Figure 12]
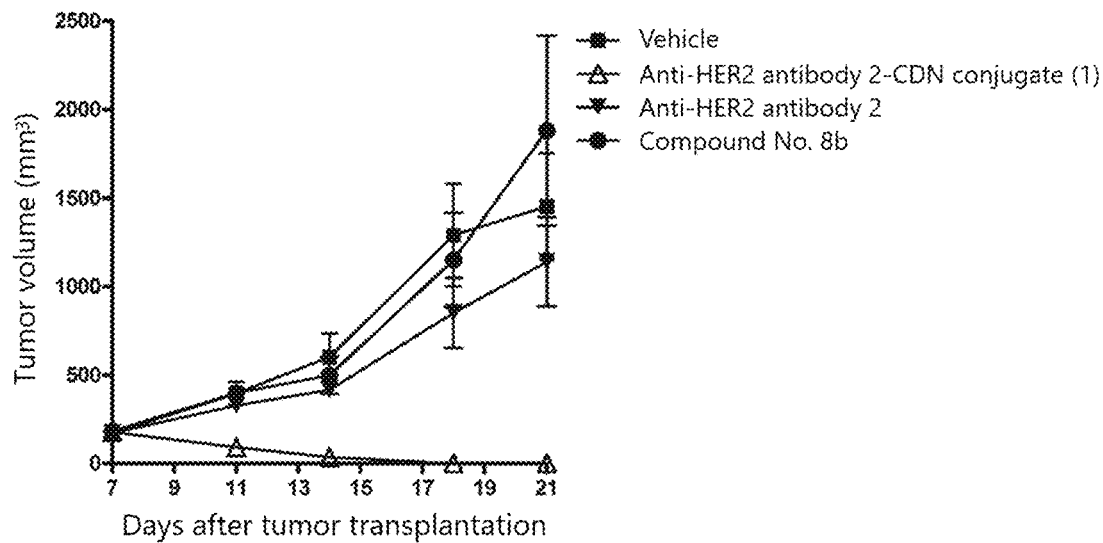
[Figure 13(a)]
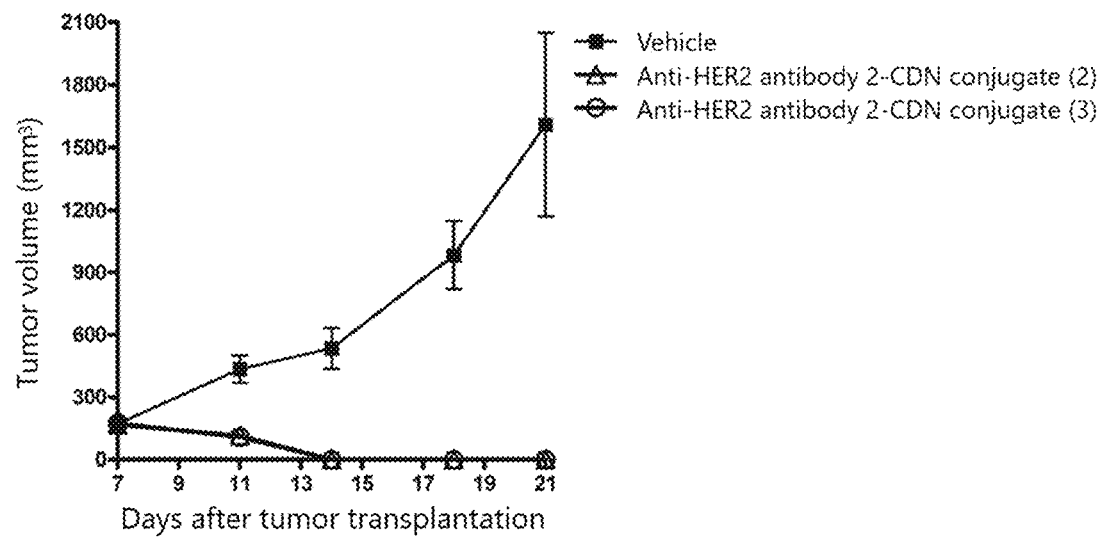

[Figure 13(b)]
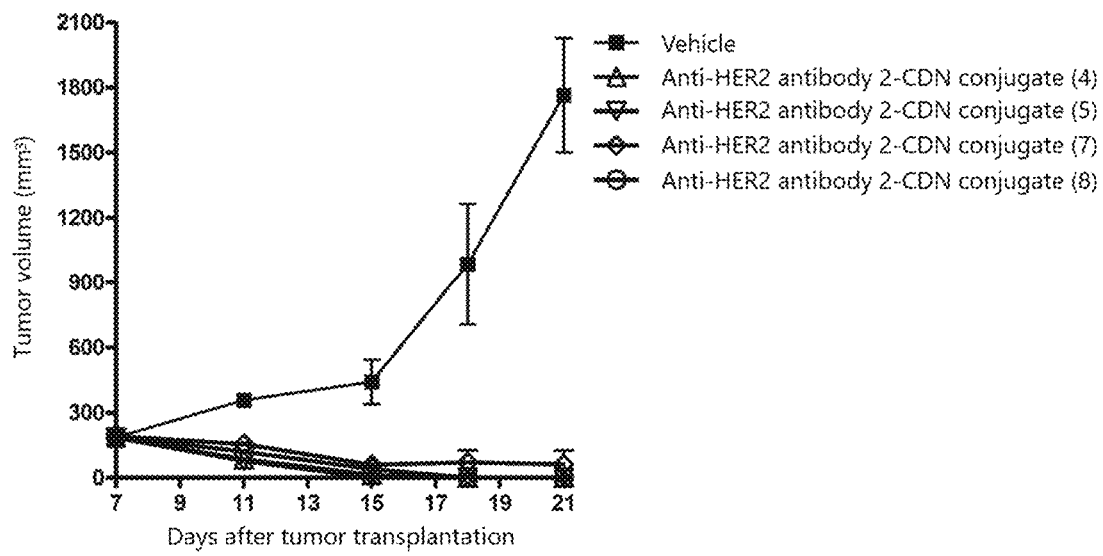
[Figure 13(c)]
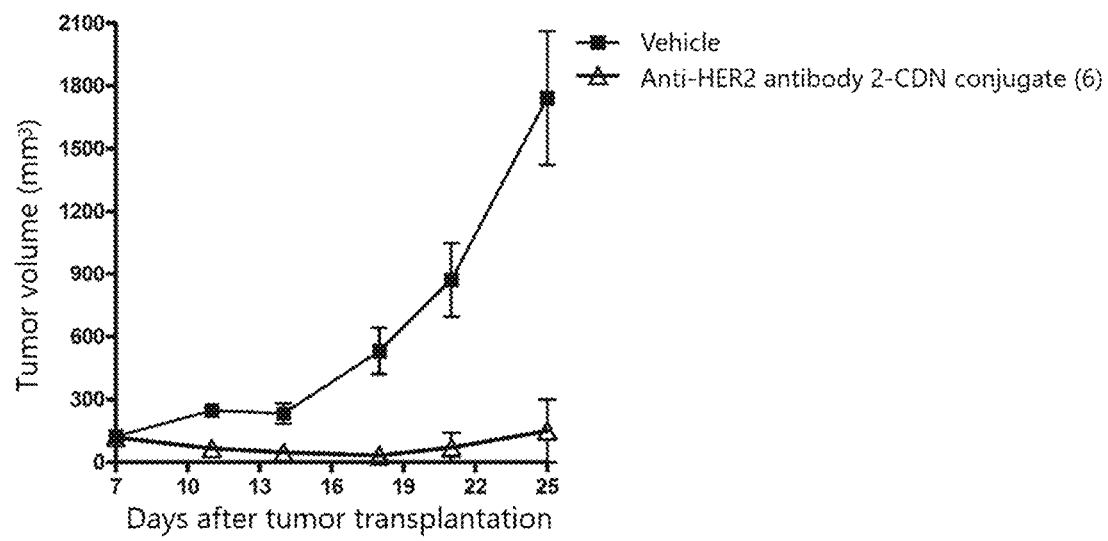

[Figure 14]
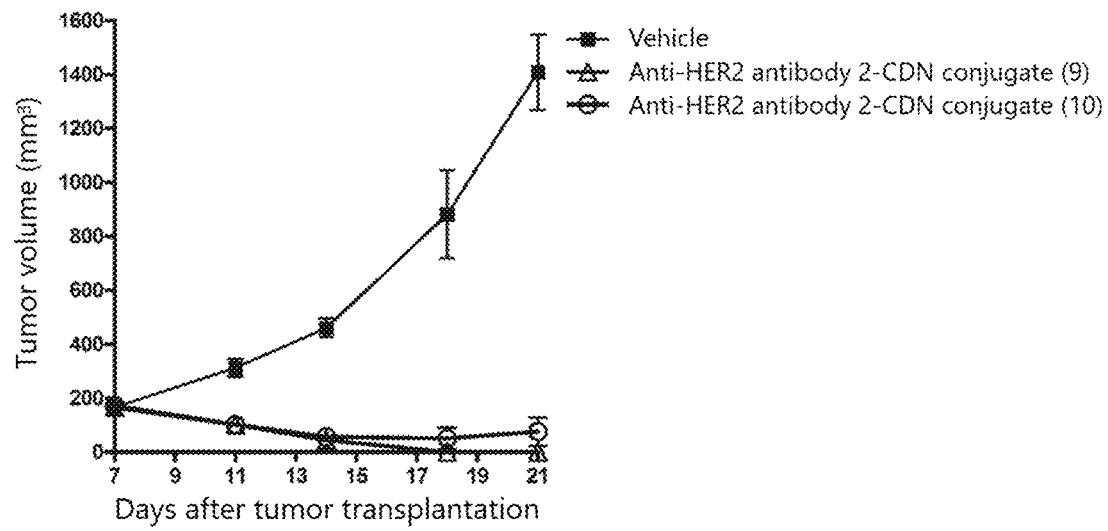
[Figure 15]
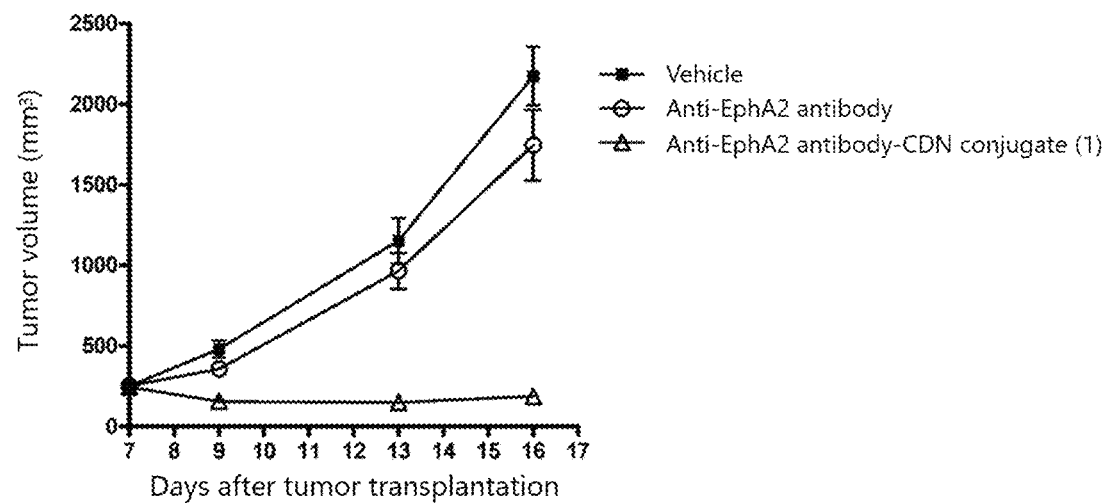

[Figure 16]

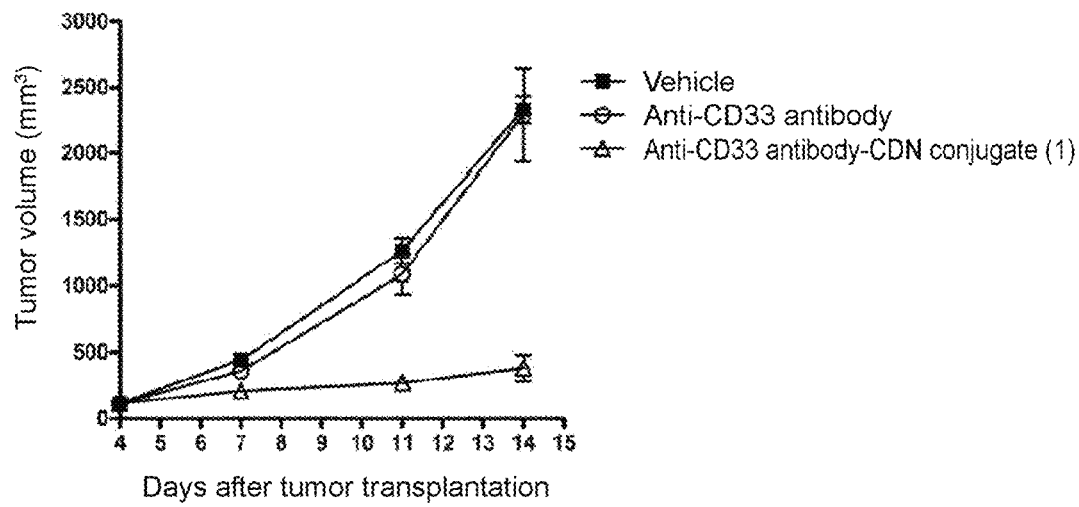

[Figure 17]

Amino acid sequence of pertuzumab light chain (SEQ ID NO: 28)

DIQMTQSPSSLSASVGDRVTITCKASQDVSIGVAWYQQKPGKAPKLLIYSASYRYTGVPS
RFSGSGSGTDFTLTISSLQPEDFATYYCQQYYIYPYTFGQGTKVEIKRTVAAPSVFIFPP
SDEQLKSGTASVVCLLNNFYPREAKVQWKVDNALQSGNSQESVTEQDSKDSTYSLSSTLT
LSKADYEKHKVYACEVTHQGLSSPVTKSFNRGEC

Amino acid sequence of pertuzumab heavy chain (SEQ ID NO: 29)

EVQLVESGGGLVQPGGSLRLSCAASGFTFTDYTMDWVRQAPGKGLEWVADVNPNSGGSIY
NQRFKGRFTLSVDRSKNTLYLQMNSLRAEDTAVYYCARNLGPSFYFDYWGQGTLVTVSSA
STKGPSVFPLAPSSKSTSGGTAALGCLVKDYFPEPVTVSWNSGALTSGVHTFPAVLQSSG
LYSLSSVVTVPSSSLGTQTYICNVNHKPSNTKVDKKVEPKSCDKTHTCPPCPAPELLGGP
SVFLFPPKPKDTLMISRTPEVTCVVVDVSHEDPEVKFNWYVDGVEVHNAKTKPREEQYNS
TYRVVSVLTVLHQDWLNGKEYKCKVSNKALPAPIEKTISKAKGQPREPQVYTLPPSREEM
TKNQVSLTCLVKGFYPSDIAVEWESNGQPENNYKTTPPVLDSDGSFFLYSKLTVDKSRWQ
QGNVFSCSVMHEALHNHYTQKSLSLSPGK

[Figure 18]

Amino acid sequence of light chain of modified anti-HER2 antibody 2 (SEQ ID NO: 28)

DIQMTQSPSSLSASVGDRVTITCKASQDVSIGVAWYQQKPGKAPKLLIYSASYRYTGVPS
RFSGSGSGTDFTLTISSLQPEDFATYYCQQYYIYPYTFGQGTKVEIKRTVAAPSVFIFPP
SDEQLKSGTASVVCLLNNFYPREAKVQWKVDNALQSGNSQESVTEQDSKDSTYSLSSTLT
LSKADYEKHKVYACEVTHQGLSSPVTKSFNRGEC

Amino acid sequence of heavy chain of modified anti-HER2 antibody 2 (SEQ ID NO: 30)
EVQLVESGGGLVQPGGSLRLSCAASGFTFTDYTMDWVRQAPGKGLEWVADVNPNSGGSIY
NQRFKGRFTLSVDRSKNTLYLQMNSLRAEDTAVYYCARNLGPSFYFDYWGQGTLVTVSSA
STKGPSVFPLAPSSKSTSGGTAALGCLVKDYFPEPVTVSWNSGALTSGVHTFPAVLQSSG
LYSLSSVVTVPSSSLGTQTYICNVNHKPSNTKVDKRVEPKSCDKTHTCPPCPAPEAAGG
PSVFLFPPKPKDTLMISRTPEVTCVVVDVSHEDPEVKFNWYVDGVEVHNAKTKPREEQYN
STYRVVSVLTVLHQDWLNGKEYKCKVSNKALPAPIEKTISKAKGQPREPQVYTLPPSREE
MTKNQVSLTCLVKGFYPSDIAVEWESNGQPENNYKTTPPVLDSDGSFFLYSKLTVDKSRW
QQGNVFSCSVMHEALHNHYTQKSLSLSPGK (The underlines indicate positions of K214R mutation and LALA mutation.)

[Figure 19]

Amino acid sequence of light chain of anti-CD33 antibody (SEQ ID NO: 31)

DIQLTQSPSTLSASVGDRVTITCRASESLDNYGIRFLTWFQQKPGKAPKLLMYAASNQGS
GVPSRFSGSGSGTEFTLTISSLQPDDFATYYCQQTKEVPWSFGQGTKVEVKRTVAAPSVF
IFPPSDEQLKSGTASVVCLLNNFYPREAKVQWKVDNALQSGNSQESVTEQDSKDSTYSLS
STLTLSKADYEKHKVYACEVTHQGLSSPVTKSFNRGEC

Amino acid sequence of heavy chain of anti-CD33 antibody (SEQ ID NO: 32)
EVQLVQSGAEVKKPGSSVKVSCKASGYTITDSNIHWVRQAPGQSLEWIGYIYPYNGGTDY
NQKFKNRATLTVDNPTNTAYMELSSLRSEDTAFYYCVNGNPWLAYWGQGTLVTVSSASTK
GPSVFPLAPSSKSTSGGTAALGCLVKDYFPEPVTVSWNSGALTSGVHTFPAVLQSSGLYS
LSSVVTVPSSSLGTQTYICNVNHKPSNTKVDKRVEPKSCDKTHTCPPCPAPEAAGGPSVF
LFPPKPKDTLMISRTPEVTCVVVDVSHEDPEVKFNWYVDGVEVHNAKTKPREEQYNSTYR
VVSVLTVLHQDWLNGKEYKCKVSNKALPAPIEKTISKAKGQPREPQVYTLPPSREEMTKN
QVSLTCLVKGFYPSDIAVEWESNGQPENNYKTTPPVLDSDGSFFLYSKLTVDKSRWQQGN
VFSCSVMHEALHNHYTQKSLSLSPGK

[Figure 20]

Amino acid sequence of light chain of anti-EphA2 antibody (SEQ ID NO: 33)

DIVMTQSPLSLPVTPGEPASISCRSSQSIVHSSGITYLEWYLQKPGQSPQLLIYKVSNRF
SGVPDRFSGSGSGTDFTLKISRVEAEDVGVYYCFQGSHVPYTFGQGTKVEIKRTVAAPSV
FIFPPSDEQLKSGTASVVCLLNNFYPREAKVQWKVDNALQSGNSQESVTEQDSKDSTYSL
SSTLTLSKADYEKHKVYACEVTHQGLSSPVTKSFNRGEC

Amino acid sequence of heavy chain of anti-EphA2 antibody (SEQ ID NO: 34)

QVQLVQSGAEVKKPGASVKVSCKASGYTFIDYSMHWVRQAPGQGLEWMGWINTYTGEPTY
SDDFKGRVTITADTSTSTAYLELSSLRSEDTAVYYCATYYRYERDFDYWGQGTLVTVSSA
STKGPSVFPLAPSSKSTSGGTAALGCLVKDYFPEPVTVSWNSGALTSGVHTFPAVLQSSG
LYSLSSVVTVPSSSLGTQTYICNVNHKPSNTKVDKRVEPKSCDKTHTCPPCPAPELLGGP
SVFLFPPKPKDTLMISRTPEVTCVVVDVSHEDPEVKFNWYVDGVEVHNAKTKPREEQYNS
TYRVVSVLTVLHQDWLNGKEYKCKVSNKALPAPIEKTISKAKGQPREPQVYTLPPSREEM
TKNQVSLTCLVKGFYPSDIAVEWESNGQPENNYKTTPPVLDSDGSFFLYSKLTVDKSRWQ
QGNVFSCSVMHEALHNHYTQKSLSLSPGK

[Figure 21]

Amino acid sequence of light chain of anti-CDH6 antibody (SEQ ID NO: 35)

DIQMTQSPSSLSASVGDRVTITCKASQNIYKNLAWYQQKPGKAPKLLIYDANTLQTGVPS
RFSGSGSGSDFTLTISSLQPEDFATYFCQQYYSGWAFGQGTKVEIKRTVAAPSVFIFPPS
DEQLKSGTASVVCLLNNFYPREAKVQWKVDNALQSGNSQESVTEQDSKDSTYSLSSTLTL
SKADYEKHKVYACEVTHQGLSSPVTKSFNRGEC

Amino acid sequence of heavy chain of anti-CDH6 antibody (SEQ ID NO: 36)
EVQLVQSGAEVKKPGASVKVSCKASGYTFTRNFMHWVRQAPGQGLEWMGWIYPGDGETEY
AQKFQGRVTITADTSTSTAYMELSSLRSEDTAVYYCARGVYGGFAGGYFDFWGQGTLVTV
SSASTKGPSVFPLAPSSKSTSGGTAALGCLVKDYFPEPVTVSWNSGALTSGVHTFPAVLQ
SSGLYSLSSVVTVPSSSLGTQTYICNVNHKPSNTKVDKRVEPKSCDKTHTCPPCPAPEAA
GGPSVFLFPPKPKDTLMISRTPEVTCVVVDVSHEDPEVKFNWYVDGVEVHNAKTKPREEQ
YNSTYRVVSVLTVLHQDWLNGKEYKCKVSNKALGAPIEKTISKAKGQPREPQVYTLPPSR
EEMTKNQVSLTCLVKGFYPSDIAVEWESNGQPENNYKTTPPVLDSDGSFFLYSKLTVDKS
RWQQGNVFSCSVMHEALHNHYTQKSLSLSPGK

[Figure 22]
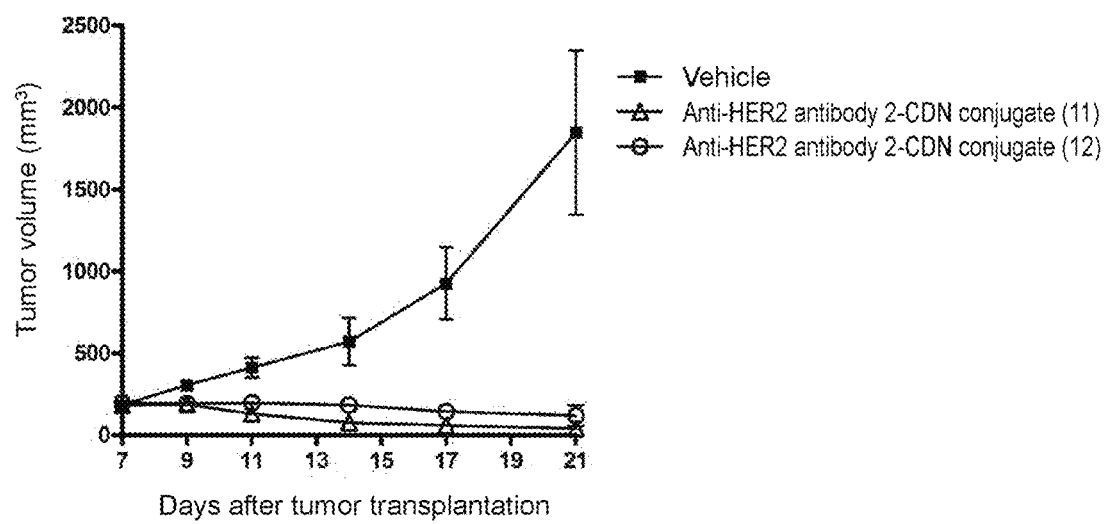

Anti-EphA2 antibody → Step 1 → (Fucα1,6)GlcNAc-anti-EphA2 antibody → Step 2 → Anti-EphA2 antibody-[SG-(N$_3$)$_2$]$_2$ Anti-CDH6 antibody → Step 1 → (Fucα1,6)GlcNAc-anti-CDH6 antibody → Step 2 → Anti-CDH6 antibody-[SG-(N$_3$)$_2$]$_2$ Modified anti-HER2 antibody 2 → Step 1 → (Fucα1,6)GlcNAc-modified anti-HER2 antibody 2 → Step 2 → Modified anti-HER2 antibody 2-[MSG1-(N$_3$)]$_2$

CYCLIC DINUCLEOTIDE DERIVATIVE BASED ANTIBODY-DRUG CONJUGATES

CROSS-REFERENCE TO RELATED APPLICATIONS

The present application claims priority under 35 U.S.C. § 371 to International Patent Application No. PCT/JP2019/035198, filed Sep. 6, 2019, which claims priority to and the benefit of Japanese Patent Application No. 2018-167369, filed on Sep. 6, 2018. The contents of these applications are hereby incorporated by reference in their entireties.

SEQUENCE LISTING

The instant application contains a Sequence Listing which has been submitted in ASCII format via EFS-Web and is hereby incorporated by reference in its entirety. Said ASCII copy, is named 122763-0103_SL.txt and is 72 kb in size.

TECHNICAL FIELD

The present invention relates to cyclic dinucleotide derivatives having novel structures with STING agonist activity, antibody-drug conjugates formed by conjugating the novel cyclic dinucleotide derivatives and antibodies against target cells together via a linker, and a pharmaceutical composition containing the antibody-drug conjugates, and so on.

BACKGROUND ART

STING (Stimulator of Interferon Genes) is a transmembrane adaptor protein localized in the endoplasmic reticulum (Non Patent Literature 1). STING functions as a central molecule for innate immune stimulation in mammals, and plays a role on the front line of defense against the invasion of pathogens such as bacteria and viruses. Activation of STING is known to be caused by a signal emitted when a plurality of cytoplasmic DNA sensors senses an exogenous or endogenous DNA. Among cytoplasmic DNA sensors, cGAS (Cyclic GMP-AMP Synthase) is expected to be an important DNA sensor. When cGAS senses a DNA, a cyclic dinucleotide (2',3'-cGAMP) is produced, and this 2',3'-cGAMP directly bonds to STING to activate it (Non Patent Literature 2). The activated STING moves to the Golgi apparatus, and promotes the autophosphorylation of TBK1 (Tank-binding kinase 1). The TBK-1 activated through autophosphorylation activates both the IRF3 (Interferon regulatory factor 3) transcription pathway (Non Patent Literature 3) and the NFκB transcription pathway (Non Patent Literature 4), increasing the production of inflammatory proteins called interferons and cytokines (type I IFN (Interferon), IL-6 (Interleukin-6), TNF-α (Tumor Necrosis Factor-α)). These proteins trigger the adaptive immune system including T cells through complex cascades, which break pathogens and cancer cells.

Recent studies have demonstrated that STING promotes, not only host defense against microorganisms, but also anti-tumor immunity. For instance, immunogenic tumors transplanted into STING-deficient mice more rapidly grow than those transplanted into wild-type mice and TRIF (Toll/Interleukin-1 (IL-1) receptor domain containing adaptor-inducing interferon-β)-deficient mice. In contrast to TLR (Toll-like receptor)-, MyD88 (Myeloid differentiation primary response 88)-, and MAVS (Mitochondrial antiviral-signaling protein)-deficient mice, spontaneous priming of CD8$^+$ T cells against tumors also disappeared in STING-deficient mice. This suggests that the STING pathway that is triggered by cytoplasmic DNA sensing involves in control of tumor growth (Non Patent Literature 5). In addition, other studies have demonstrated that STING is needed for anti-tumor effect in radiotherapy (Non Patent Literature 6) and anti-CD47 antibody therapy (Non Patent Literature 7). DNAs derived from killed tumor cells after being treated with radiation or an anti-CD47 antibody move to the cytoplasm of dendritic cells to activate the cGAS-STING pathway, and then induce IFN production to activate adaptive immunity through the innate immunity. These studies suggest that cross-priming via dendritic cells activated by the STING pathway is important to cause adaptive immunity against tumors.

The flavonoid small molecule compound DMXAA, which is known as a vascular disrupting agent, has been demonstrated to induce type I IFN production in macrophages and thus have potent anti-tumor activity in mouse tumor models (Non Patent Literature 8). DMXAA had been expected to serve as an immunotherapeutic drug for non-small cell lung cancer because of the superior anti-tumor effect in preclinical studies; however, DMXAA failed in clinical trials (Non Patent Literature 9). A recent study has revealed that DMXAA is an agonist specific to mouse STING, and exhibits no interspecies cross-reactivity to human STING, and thus is incapable of binding thereto (Non Patent Literature 10). After all, DMXAA was found to be ineffective in humans; however, studies with mouse models have suggested that small molecule drugs are capable of enhancing anti-tumor immunity by effectively priming CD8$^+$ T cells via STING.

It has been demonstrated that when a cyclic dinucleotide (CDN), another small molecule compound, is administered to tumor-bearing mice, it enhances anti-tumor immune response mediated by STING to significantly inhibit tumor growth, improving the survival rate of the mice (Non Patent Literature 11). CDNs are classified into bacterial CDNs with canonical two 3'-5' phosphate bonds (cyclic-di-GMP, cyclic-di-AMP, 3',3'-cGAMP), and non-canonical, mixed linkage CDNs with a 2'-5' phosphate bond (2',3'-cGAMP), which are produced by mammalian cGAS. A recent study has demonstrated that mixed linkage CDNs rather than canonical CDNs are capable of universally activating various types of STING (Non Patent Literature 12).

Natural type CDNs are quickly decomposed by nucleases in the blood like most nucleic acid molecules, and hence cannot be administered in the original form. Therefore, synthesized small molecule compounds having STING agonist activity in vivo have been developed (e.g., Patent Literatures 1 to 26).

The STING agonist MIW-815 (alternatively called ADU-S100, ML RR-S2 CDA, or ML-RR-CDA·2Na$^+$), which is an anti-tumor agent currently under clinical trials, is directly administered into a tumor. Such a method of directly administering a STING agonist into a tumor only allows administration of the drug in a restricted region of a tumor, and has difficulty in directly administering the drug to every distant-metastasized tumor, disadvantageously limiting the type of treatable tumors. Although Non Patent Literature 13 discloses that anti-tumor effect was exhibited through administration of ML RR-S2 CDA, examination was made only on intratumoral administration, and anti-tumor effect through systemic administration (e.g., intravenous administration) is not demonstrated. Non Patent Literature 14 discloses that anti-tumor effect was exhibited through intravenous administration of the STING agonist SB11285 to mouse tumor models, but does not clarify what structure the compound SB11285 specifically has. Patent Literature 14 describes a conjugate including an immune-stimulating compound, an antibody construct, and a linker, but does not describe any specific example of a conjugate using a STING agonist as an immune-stimulating compound. Patent Literature 26 describes a conjugate formed by conjugating a CDN having a specific structure and an antibody together via a linker, but does not describe administration of the conjugate in vivo in Examples, and thus anti-tumor effect of the conjugate has not been confirmed.

CITATION LIST

Patent Literature

Patent Literature 1: WO 2014/099824
Patent Literature 2: WO2014/179335
Patent Literature 3: WO2014/189805
Patent Literature 4: WO2014/189806
Patent Literature 5: WO2015/074145
Patent Literature 6: WO2015/185565
Patent Literature 7: WO2016/096714
Patent Literature 8: WO2016/012305
Patent Literature 9: WO2016/145102
Patent Literature 10: WO2017/027646
Patent Literature 11: WO2017/027645
Patent Literature 12: WO2017/075477
Patent Literature 13: WO2017/093933
Patent Literature 14: WO2017/100305
Patent Literature 15: WO2017/123669
Patent Literature 16: WO2017/161349
Patent Literature 17: WO2017/175147
Patent Literature 18: WO2017/175156
Patent Literature 19: WO2018/009466
Patent Literature 20: WO2018/045204
Patent Literature 21: WO2018/060323
Patent Literature 22: WO2018/067423
Patent Literature 23: WO2018/065360
Patent Literature 24: WO2014/093936
Patent Literature 25: WO2018/009648
Patent Literature 26: WO2018/100558

Non Patent Literature

Non Patent Literature 1: Nature 2008, 455, 674-678
Non Patent Literature 2: Mol. Cell, 2013, 51, 226-235
Non Patent Literature 3: Science 2015a, 347, aaa2630
Non Patent Literature 4: J. Virol. 2014, 88, 5328-5341
Non Patent Literature 5: Immunity 2014, 41, 830-842
Non Patent Literature 6: Immunity 2014, 41, 843-852
Non Patent Literature 7: Nat. Med. 2015, 21, 1209-1215
Non Patent Literature 8: J. Immunol. 1994, 153, 4684-4693
Non Patent Literature 9: J. Clin. Oncol. 2011, 29, 2965-2971
Non Patent Literature 10: J. Immunol. 2013, 190, 5216-5225
Non Patent Literature 11: Sci. Rep. 2016, 6, 19049
Non Patent Literature 12: Mol. Cell, 2015, 59, 891-903
Non Patent Literature 13: Cell Rep. 2015, 11, 1018-1030
Non Patent Literature 14: AACR Tumor Immunology and Immunotherapy, 2017, Poster #A25

SUMMARY OF INVENTION

Technical Problem

Desired is development of CDN derivatives with a novel backbone that has STING agonist activity and increases the production of inflammatory proteins such as interferons and cytokines to activate immune cells; and a therapeutic agents and/or therapeutic methods using the novel CDN derivatives for diseases associated with STING agonist activity, for example, diseases treatable with immune activation (e.g., cancer). Further desired is antibody-drug conjugates that are formed by conjugating the novel CDN derivative and an antibody against target cells together via a linker, and that allows systemic administration and is capable of delivering the STING agonist specifically to targeted cells and organs (e.g., tumor sites); and therapeutic agents and/or therapeutic methods using the antibody-drug conjugates for diseases associated with STING agonist activity, for example, diseases treatable with immune activation (e.g., cancer).

Solution to Problem

To solve the above problems, the present inventors devised novel CDN derivatives having a fused tricyclic substituent, and found that the novel CDN derivatives have potent STING agonist activity and exhibit potent anti-tumor activity. In addition, the present inventors devised antibody-drug conjugates formed by conjugating the present novel CDN derivatives and an antibody together via a linker, and found that the antibody-drug conjugates when being systemically administered exhibit anti-tumor effect in tumors expressing an antigen, thus completing the present invention.

Specifically, the present invention relates to the following.

[1] An antibody-drug conjugate represented by formula (II):

wherein
m$^1$ is in the range of 1 to 10;
Ab represents an antibody or a functional fragment of the antibody, where a glycan of the antibody is optionally remodeled;
L represents a linker linking Ab and D;
Ab bonds directly from an amino acid residue of Ab to L, or optionally bonds via a glycan or remodeled glycan of Ab to L; and
D represents a compound represented by formula (I):

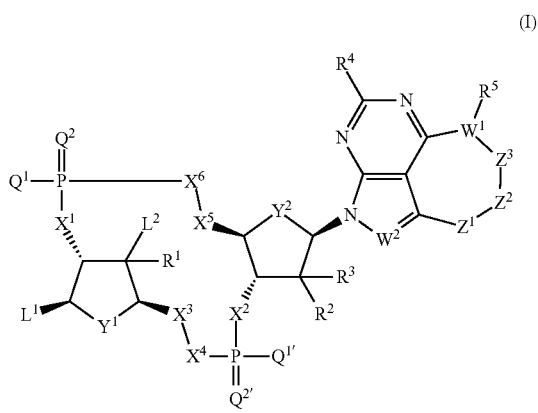

wherein
L bonds to any —NH₂ or hydroxy group included in L¹ or L²;

L¹ represents a group selected from the group consisting of the following formulas:

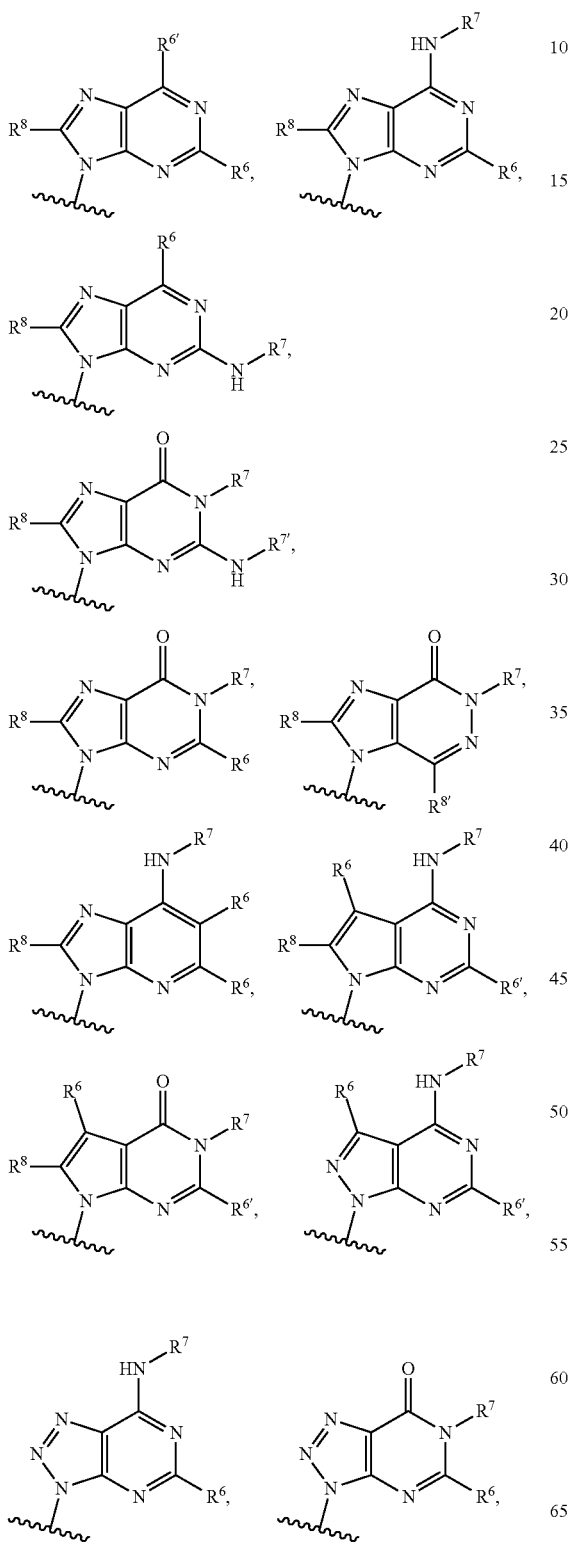

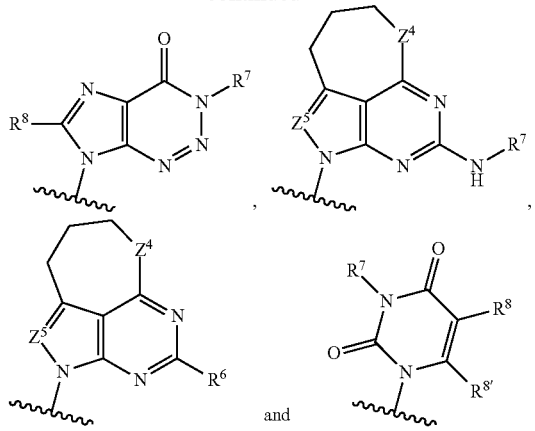

and optionally substituted at any position with one to three groups selected from the group consisting of a hydroxy group, —NH₂, a 2-hydroxyacetylaminomethyl group, and a 2-[(2-hydroxyacetyl)amino]ethyl group, wherein
$R^6$ and $R^{6'}$ each independently represent a hydrogen atom, a halogen atom, a hydroxy group, —NH₂, a C1-C6 alkyl group, a C2-C6 alkenyl group, or a C2-C6 alkynyl group;

$R^7$ and $R^{7'}$ each independently represent a hydrogen atom or a C1-C6 alkyl group, wherein the C1-C6 alkyl group is optionally substituted with one or two substituents selected from the group consisting of a halogen atom and an oxo group;

$R^8$ and $R^{8'}$ each independently represent a hydrogen atom or a halogen atom;

$Z^4$ represents —CH₂—, —NH—, or an oxygen atom; and $Z^5$ represents a nitrogen atom or —CH=, L² represents a group selected from (i) and (ii):
(i) when bonding to L, L² represents —NHR', a hydroxy C1-C6 alkyl group, or an amino C1-C6 alkyl group, wherein R' represents a hydrogen atom, a C1-C6 alkyl group, a C2-C6 alkenyl group, a C2-C6 alkynyl group, or a C3-C6 cycloalkyl group, and the C1-C6 alkyl group, C2-C6 alkenyl group, or C2-C6 alkynyl group is optionally substituted with one to six halogen atoms; and
(ii) when not bonding to L, L² represents a hydrogen atom or a halogen atom;

$Q^1$ and $Q^{1'}$ each independently represent a hydroxy group, a thiol group, or a borano group ($BH_3^-$);

$Q^2$ and $Q^{2'}$ each independently represent an oxygen atom or a sulfur atom;

$X^1$ and $X^2$ each independently represent an oxygen atom, a sulfur atom, or —CH₂—;

$Y^1$ and $Y^2$ each represent an oxygen atom or —CH₂—;

$X^3$ and $X^4$ represent a group selected from (iii) and (iv):
(iii) when $Y^1$ is an oxygen atom, $X^3$-$X^4$ represents —CH₂—O—, —CH₂—S—, —CH₂—CH₂—, or —CH₂—CF₂—; and
(iv) when $Y^1$ is —CH₂—, $X^3$-$X^4$ represents —O—CH₂—;

$X^5$ and $X^6$ represent a group selected from (v) and (vi):
(v) when $Y^2$ is an oxygen atom, $X^5$-$X^6$ represents —CH₂—O—, —CH₂—S—, —CH₂—CH₂—, or —CH₂—CF₂—; and (vi) when $Y^2$ is $-CH_2-$, $X^5$-$X^6$ represents $-O-CH_2-$;

$R^1$, $R^2$ and $R^3$ each independently represent a hydrogen atom, a halogen atom, $-OR'$, $-OC(=O)R'$, $-N_3$, $-NHR'$, $-NR'R''$, or $-NHC(=O)R'$, wherein R' is as defined above, and R'' represents a C1-C6 alkyl group, a C2-C6 alkenyl group, a C2-C6 alkynyl group, or a C3-C6 cycloalkyl group;

$W^1$ represents a nitrogen atom, an oxygen atom, a sulfur atom, or $-CH-$;

$W^2$ represents a nitrogen atom or $-CH=$;

$R^4$ represents a hydrogen atom, a halogen atom, or $-NH_2$;

$R^5$ represents a group selected from (vii) to (x):
(vii) when $W^1$ is a nitrogen atom, $R^5$ represents a hydrogen atom, a C1-C6 alkyl group, a hydroxy C1-C6 alkyl group, or an amino C1-C6 alkyl group;
(viii) when $W^1$ is an oxygen atom, $R^5$ is absent;
(ix) when $W^1$ is a sulfur atom, $R^5$ is absent; and
(x) when $W^1$ is $-CH-$, $R^5$ represents a hydrogen atom, a halogen atom, a hydroxy group, $-NH_2$, or a C1-C6 alkyl group;

$Z^1-Z^2-Z^3$ together represents $-CH_2-CH_2-CH_2-$, $-CH_2-CH_2-R'''-$, $-CH=CH-CH_2-$, $-CH=CX-CH_2-$, $-CX=CH-CH_2-$, $-CX=CX-CH_2-$, $-C(=O)-CH_2-CH_2-$, $-CH_2-CH_2-C(=O)-$, $-CH_2-CH(CH_3)-CH_2-$, or $-CH_2-CH_2-CH(CH_3)-$, wherein R''' represents $-O-$ or $-CH_2-CH_2-$ and X represents a halogen atom, or a group represented by either one of the following formulas:

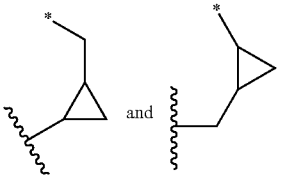

and wherein
each asterisk indicates bonding to $W^1$, and each wavy line indicates bonding to the carbon atom of $=C-$;

[2] The antibody-drug conjugate according to [1], wherein $W^1$ is a nitrogen atom;

[3] The antibody-drug conjugate according to [2], wherein $W^1$ is a nitrogen atom, and $R^5$ is a hydrogen atom;

[4] The antibody-drug conjugate according to [1], wherein $W^1$ is an oxygen atom;

[5] The antibody-drug conjugate according to [1], wherein $W^1$ is a sulfur atom;

[6] The antibody-drug conjugate according to [1], wherein $W^1$ is $-CH-$;

[7] The antibody-drug conjugate according to [6], wherein $W^1$ is $-CH-$, and $R^5$ is a hydrogen atom;

[8] The antibody-drug conjugate according to any one of [1] to [7], wherein $Z^1$, $Z^2$ and $Z^3$ together form $-CH_2-CH_2-CH_2-$ or $-CH=CH-CH_2-$;

[9] The antibody-drug conjugate according to any one of [1] to [7], wherein $Z^1$, $Z^2$ and $Z^3$ together form $-CH_2-CH(CH_3)-CH_2-$ or $-CH_2-CH_2-CH(CH_3)-$;

[10] The antibody-drug conjugate according to any one of [1] to [7], wherein $Z^1$, $Z^2$ and $Z^3$ together form $-CH_2-CH_2-R'''-$, wherein R''' represents $-O-$ or $-CH_2-CH_2-$;

[11] The antibody-drug conjugate according to any one of [1] to [10], wherein $W^2$ is $-CH=$;

[12] The antibody-drug conjugate according to any one of [1] to [10], wherein $W^2$ is a nitrogen atom;

[13] The antibody-drug conjugate according to any one of [1] to [12], wherein $R^4$ represents a hydrogen atom;

[14] The antibody-drug conjugate according to any one of [1] to [12], wherein $R^4$ represents a fluorine atom;

[15] The antibody-drug conjugate according to any one of [1] to [14], wherein $R^8$ and $R^{8'}$ in $L^1$ are each independently a hydrogen atom;

[16] The antibody-drug conjugate according to any one of [1] to [15], wherein $L^1$ is a group selected from the group consisting of the following formulas:

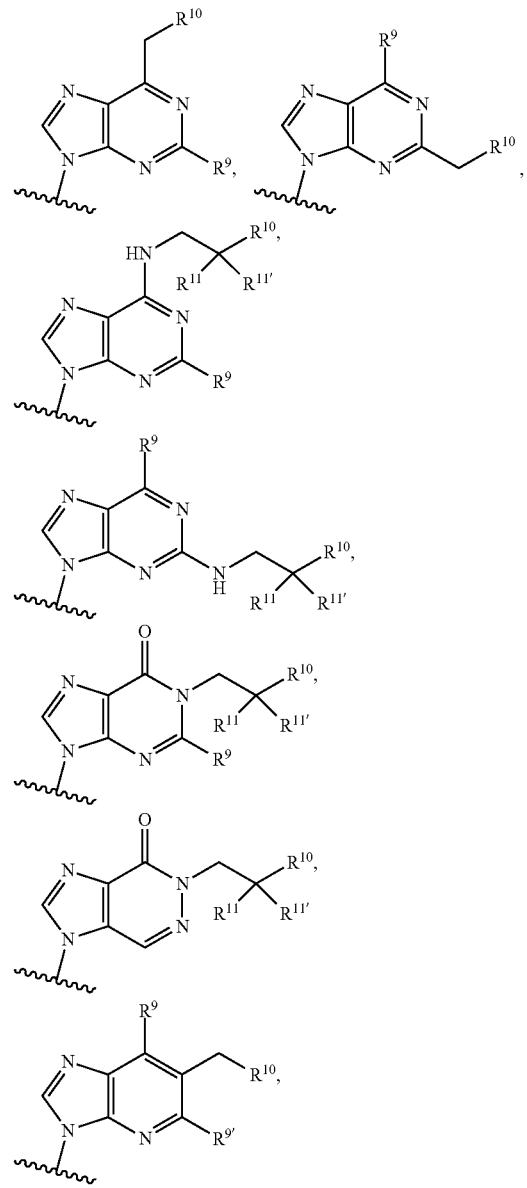

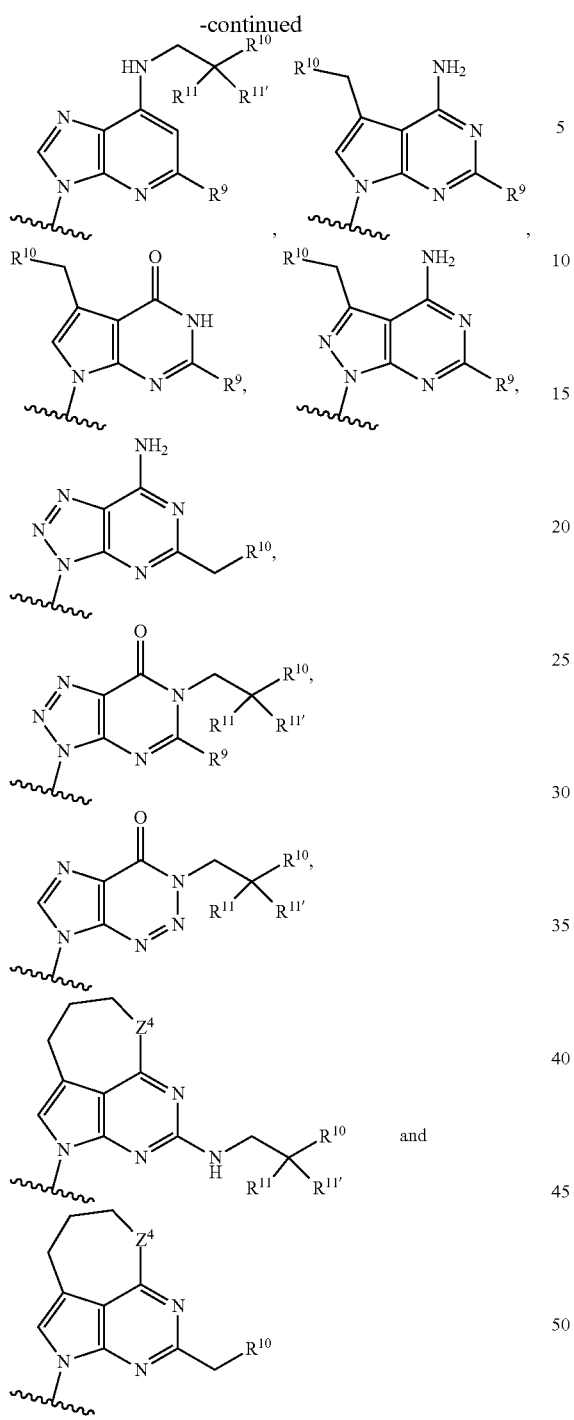

wherein
R⁹ and R⁹' each represent a hydrogen atom, a halogen atom, a hydroxy group, or —NH₂;
R¹⁰ represents a hydroxy group, —NH₂, —NHC(=O)CH₂OH, —CH₂NHC(=O)CH₂OH, —CH₂CH₂NHC(=O)CH₂OH, a hydroxy C1-C3 alkyl group, or an amino C1-C3 alkyl group;
R¹¹ and R¹¹' each independently represent a hydrogen atom, a fluorine atom, or a methyl group, or R¹¹ and R¹¹' bond together to form cyclopropane; and
Z⁴ represents —CH₂—, —NH—, or an oxygen atom;

[17] The antibody-drug conjugate according to any one of [1] to [15], wherein L¹ is a group selected from the group consisting of the following formulas:

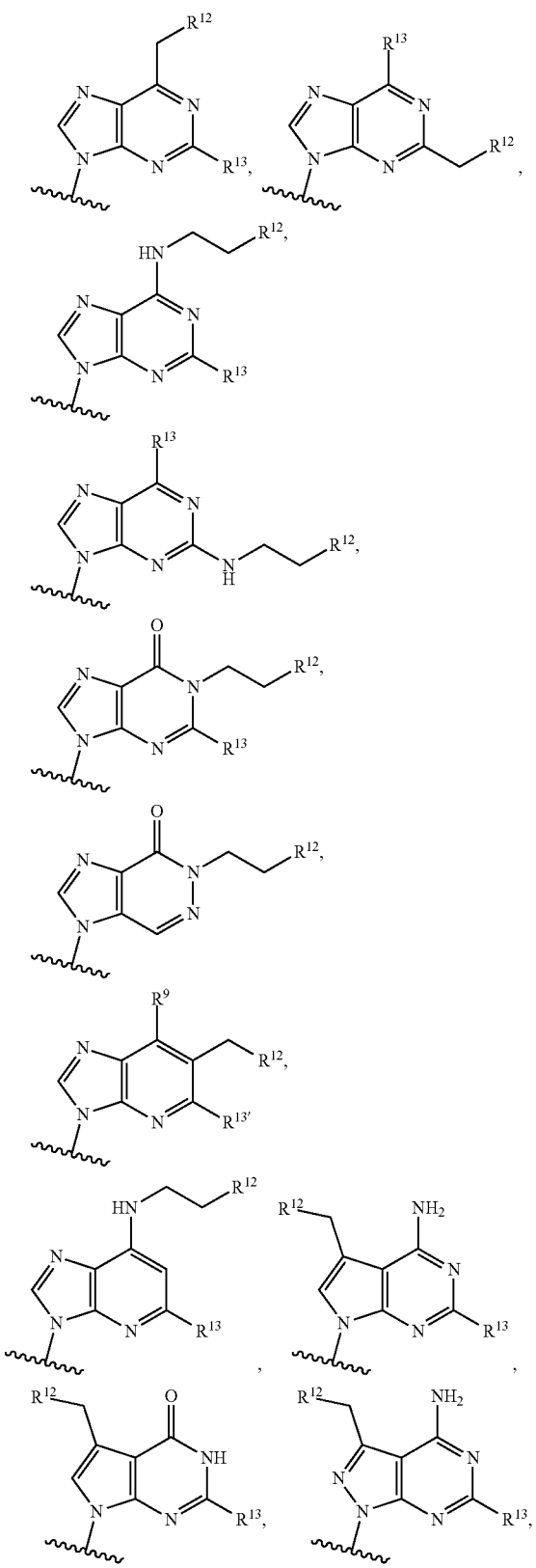

-continued

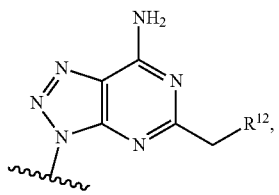

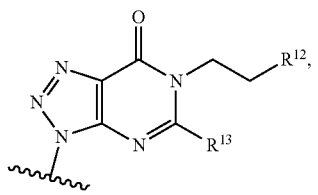

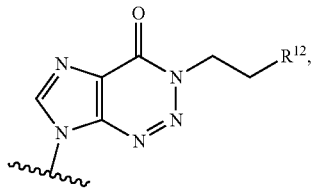

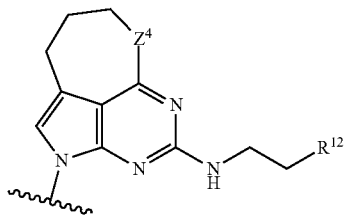

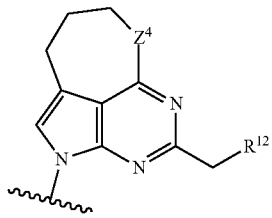

wherein
R$^{13}$ and R$^{13'}$ each independently represent a hydrogen atom, a hydroxy group, or —NH$_2$;
R$^{12}$ represents a hydroxy group, —NH$_2$, —CH$_2$OH, —NHC(=O)CH$_2$OH, —CH$_2$NHC(=O)CH$_2$OH, or —CH$_2$CH$_2$NHC(=O)CH$_2$OH; and
Z$^4$ is as defined above;

[18] The antibody-drug conjugate according to any one of [1] to [15], wherein L$^1$ is a group selected from the group consisting of the following formulas:

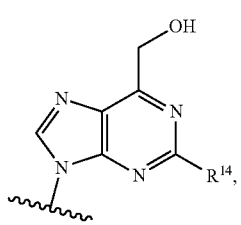 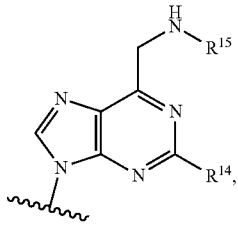

-continued

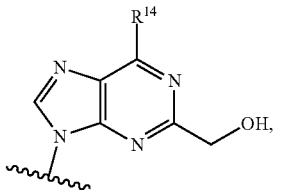

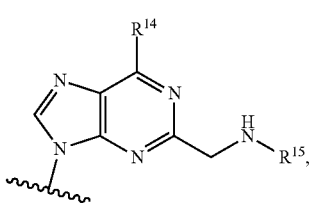

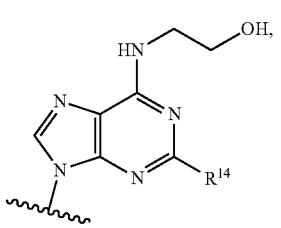

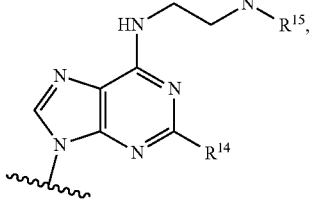

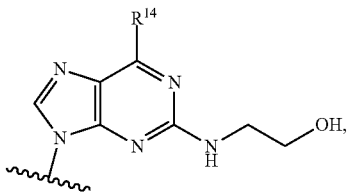

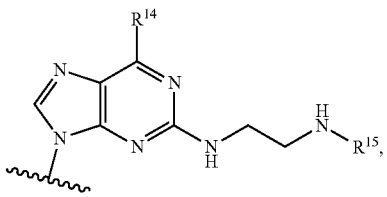

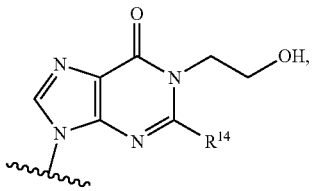

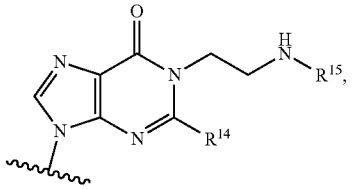

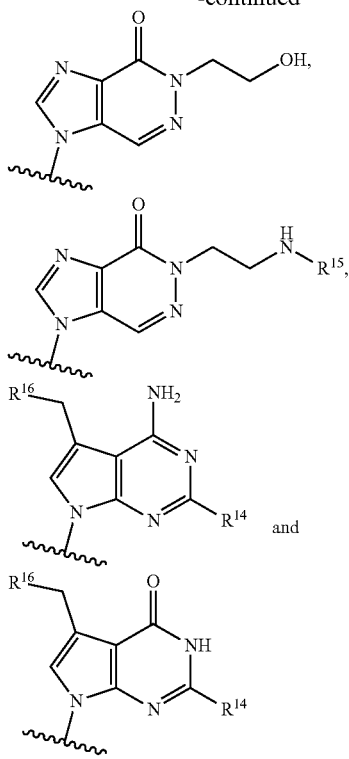

wherein
- $R^{14}$ represents a hydrogen atom or —NH$_2$;
- $R^{15}$ represents a hydrogen atom or —C(=O)CH$_2$OH; and
- $R^{16}$ represents a hydroxy group, —NH$_2$, —CH$_2$OH, —CH$_2$CH$_2$OH, —CH$_2$NH$_2$, or —CH$_2$CH$_2$NH$_2$;

[19] The antibody-drug conjugate according to any one of [1] to [18], wherein L² bonds to L and represents —NH$_2$, —CH$_2$NH$_2$, or —CH$_2$OH;

[20] The antibody-drug conjugate according to any one of [1] to [18], wherein L² does not bond to L and represents a hydrogen atom or a fluorine atom;

[21] The antibody-drug conjugate according to any one of [1] to [20], wherein Q¹ and Q¹' each independently represent a hydroxy group or a thiol group;

[22] The antibody-drug conjugate according to any one of [1] to [21], wherein X¹ and X² each represent an oxygen atom;

[23] The antibody-drug conjugate according to any one of [1] to [22], wherein Y¹ and Y² each represent an oxygen atom;

[24] The antibody-drug conjugate according to any one of [1] to [23], wherein X³ and X⁴ represent —CH$_2$—O—;

[25] The antibody-drug conjugate according to any one of [1] to [24], wherein X⁵ and X⁶ represent —CH$_2$—O—;

[26] The antibody-drug conjugate according to any one of [1] to [25], wherein R¹, R², and R³ are each independently a hydrogen atom, a hydroxy group, or a fluorine atom;

[27] The antibody-drug conjugate according to any one of [1] to [26], wherein D is represented by either one of the following two formulas:

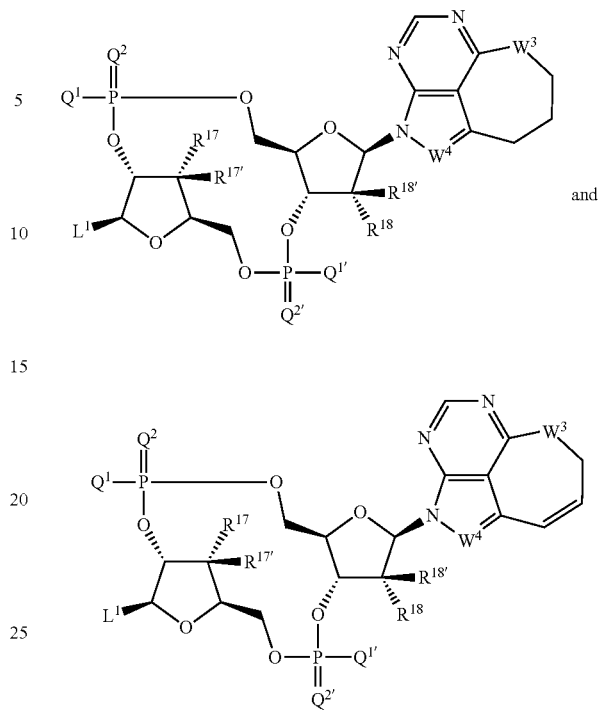

wherein
- L¹, Q¹, Q¹', Q², and Q²' are as defined above;
- $R^{17}$, $R^{17'}$, $R^{18}$, and $R^{18'}$ each independently represent a hydrogen atom, a halogen atom, a hydroxy group, or —NH$_2$;
- W³ represents —NH—, an oxygen atom, a sulfur atom, or —CH$_2$—; and
- W⁴ represents —CH= or a nitrogen atom;

[28] The antibody-drug conjugate according to [27], wherein D is represented by either one of the following two formulas:

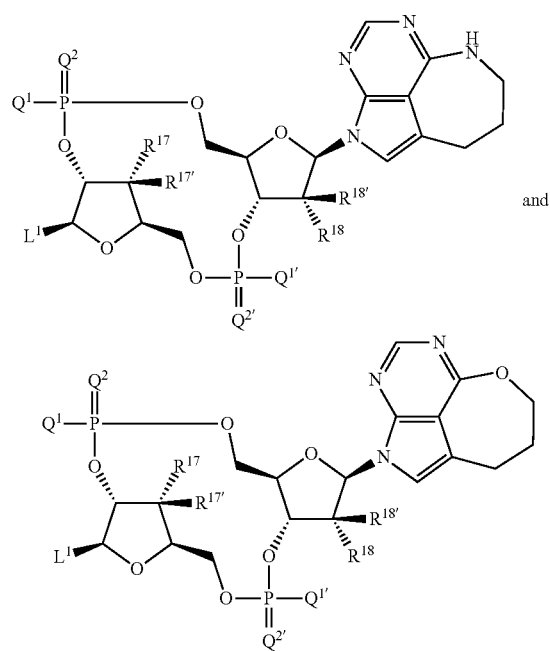

wherein
L¹, Q¹, Q¹', Q², Q²', R¹⁷, R¹⁷', R¹⁸, and R¹⁸' are as defined above;
[29] The antibody-drug conjugate according to [27] or [28], wherein D is represented by any one of the following eight formulas:
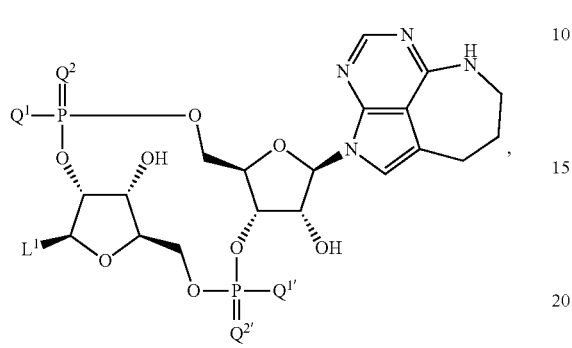
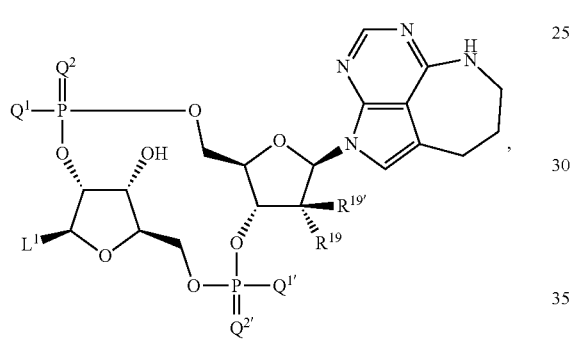
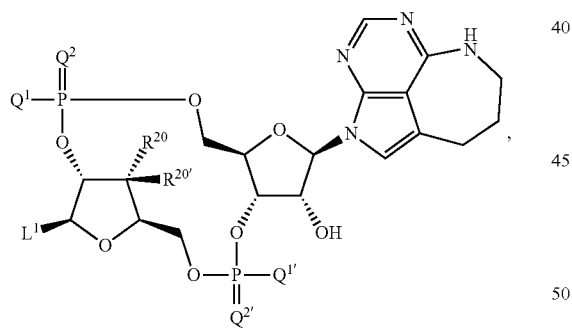
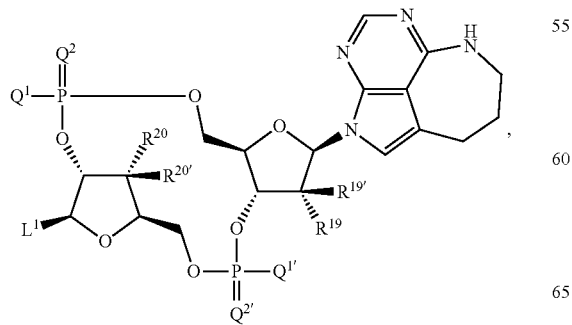
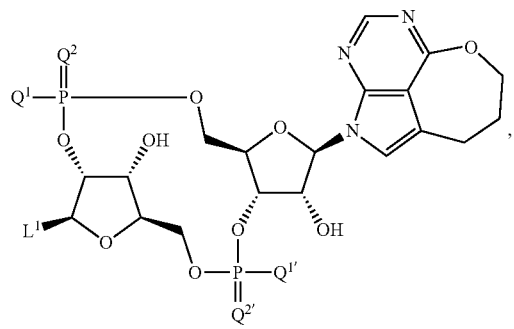
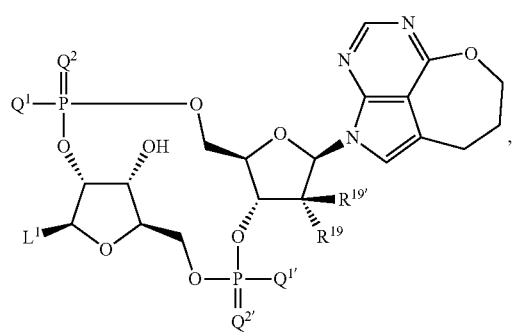
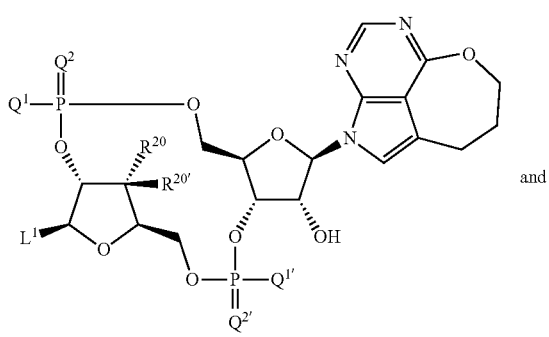
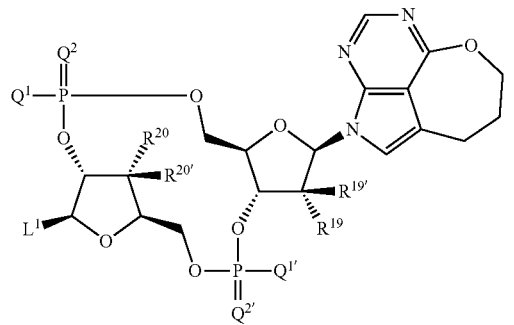
wherein
L¹, Q¹, Q¹', Q², and Q²' are as defined above; and
R¹⁹, R¹⁹', R²⁰, and R²⁰' each independently represent a hydrogen atom or a fluorine atom;

[30] The antibody-drug conjugate according to any one of [27] to [29], wherein D is represented by any one of the following four formulas:
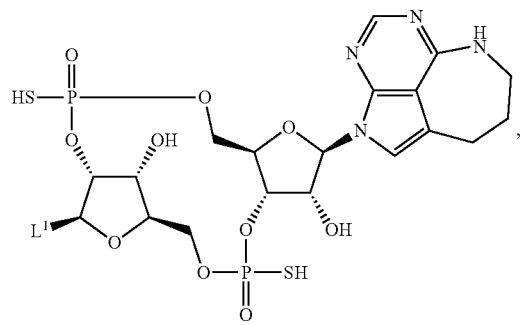
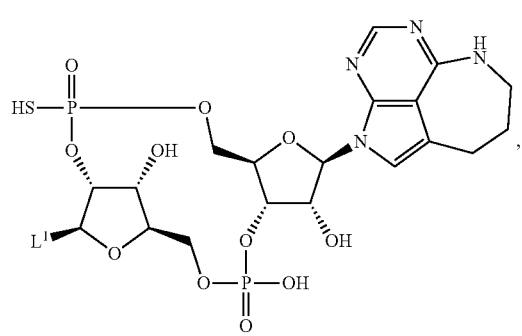
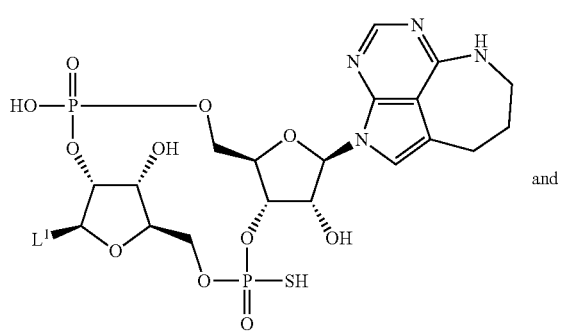
and
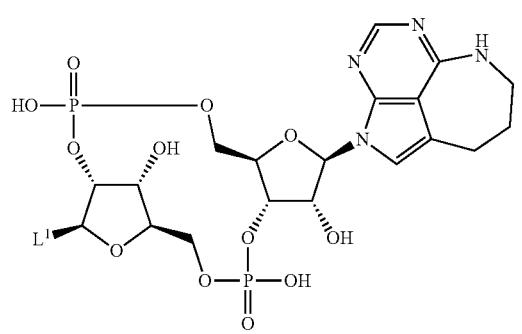
wherein
L¹ is as defined above;
[31] The antibody-drug conjugate according to any one of [27] to [30], wherein D is represented by any one of the following four formulas:
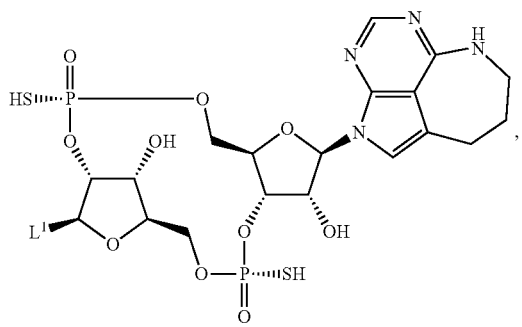
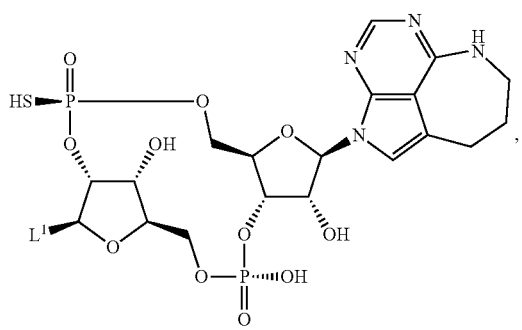
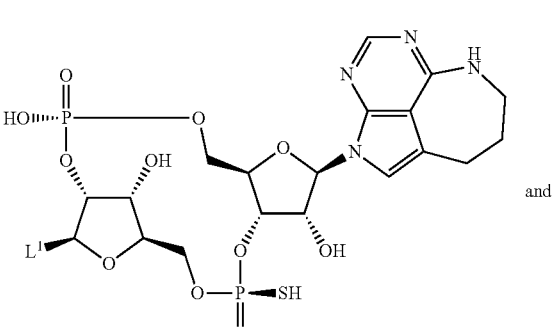
and
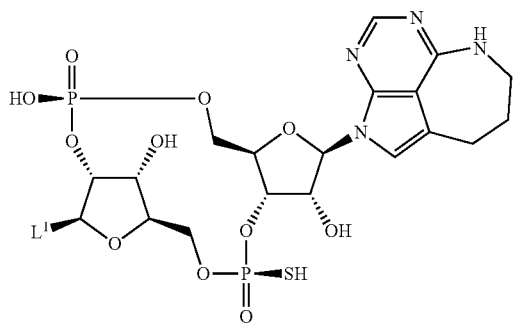

wherein

L$^1$ is as defined above;

[32] The antibody-drug conjugate according to any one of [27] to [30], wherein D is represented by any one of the following four formulas:

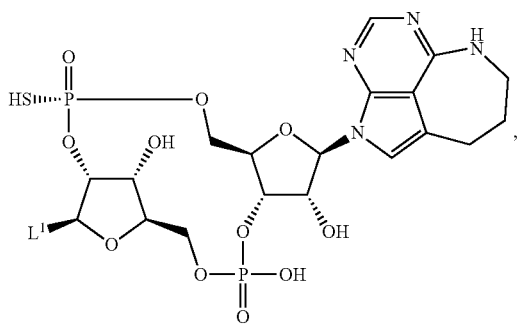

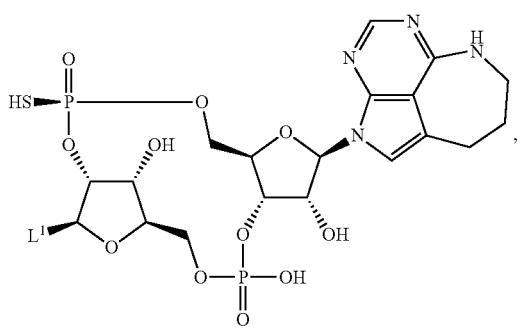

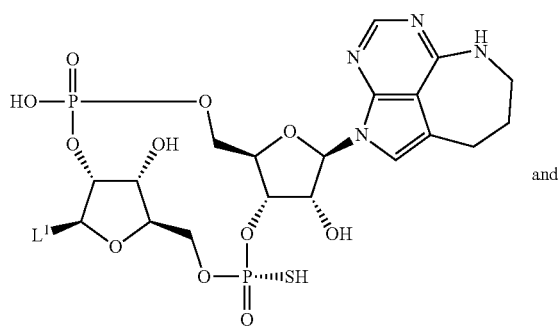

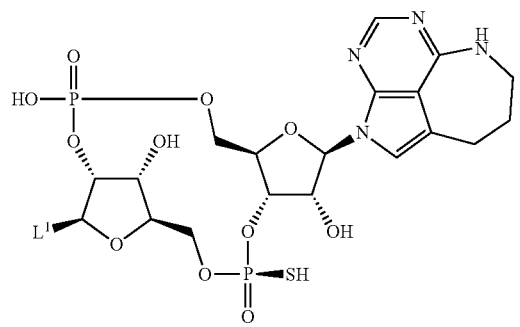

wherein

L$^1$ is as defined above;

[33] The antibody-drug conjugate according to any one of [1] to [26], wherein D is represented by the following formula:

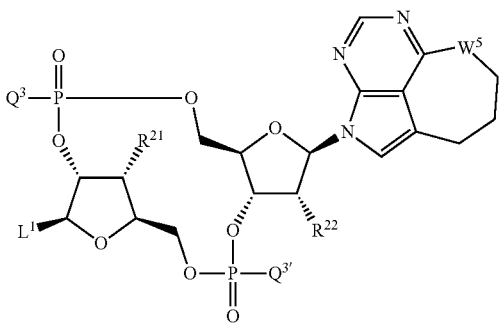

wherein

L$^1$ is as defined above;

Q$^3$ and Q$^{3'}$ each independently represent a hydroxy group or a thiol group;

R$^{21}$ and R$^{22}$ each independently represent a hydroxy group or a fluorine atom; and W$^5$ represents —NH— or a sulfur atom;

[34] The antibody-drug conjugate according to [33], wherein D is represented by either one of the following two formulas:

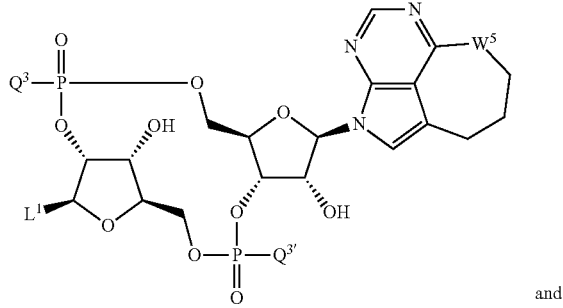

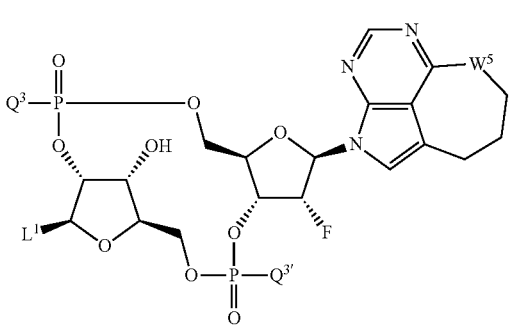

wherein

L$^1$, Q$^3$, Q$^{3'}$, and W$^5$ are as defined above;

[35] The antibody-drug conjugate according to any one of [1] to [34], wherein $L^1$ is represented by any one of the following four formulas:

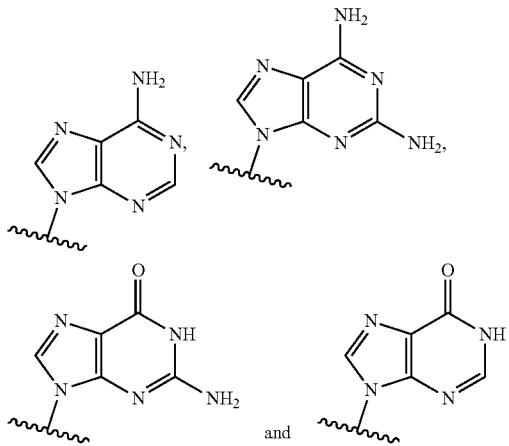

[36] The antibody-drug conjugate according to any one of [1] to [34], wherein $L^1$ is represented by any one of the following four formulas:

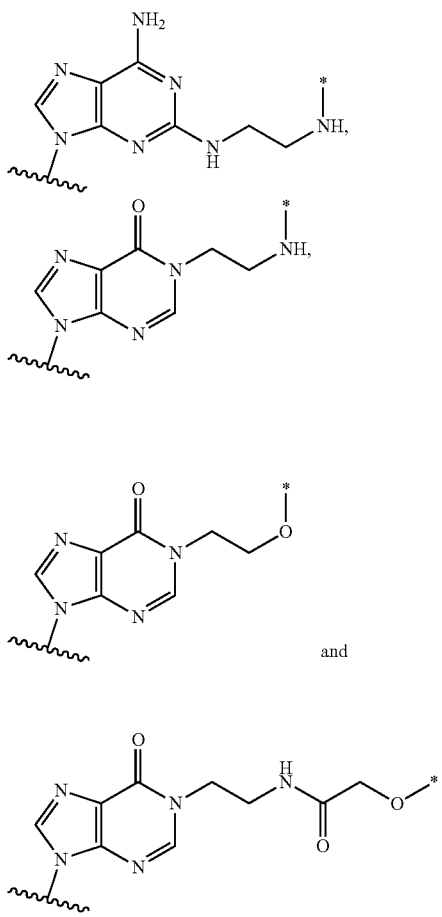

wherein each asterisk indicates bonding to L;

[37] The antibody-drug conjugate according to any one of [33], [34], and [36], wherein D is represented by any one of the following four formulas:

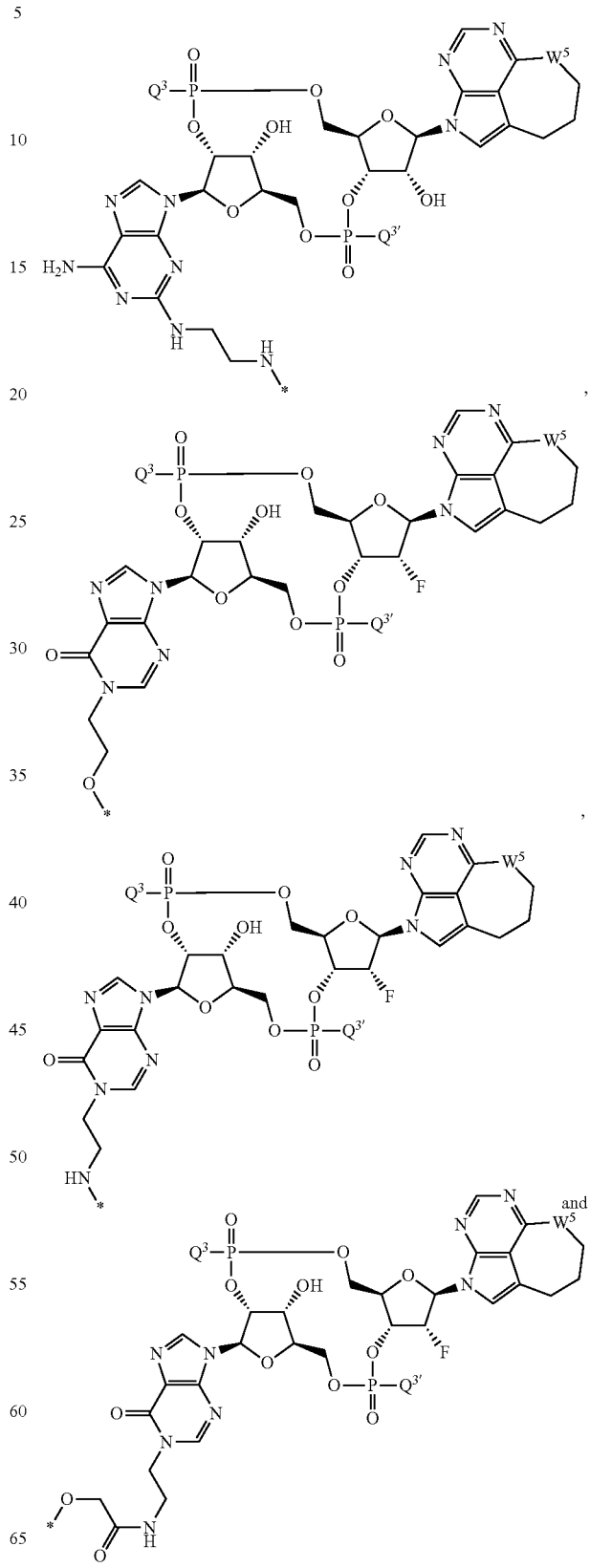

wherein
    each asterisk indicates bonding to L; and
    $Q^3$, $Q^{3'}$, and $W^5$ are as defined above;

[38] The antibody-drug conjugate according to any one of [33], [34], [36], and [37], wherein D is represented by any one of the following four formulas:

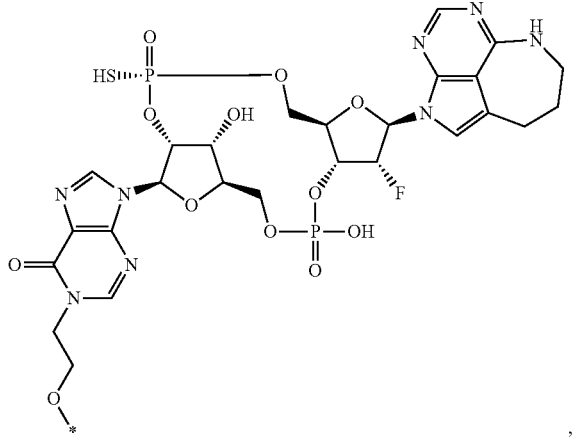

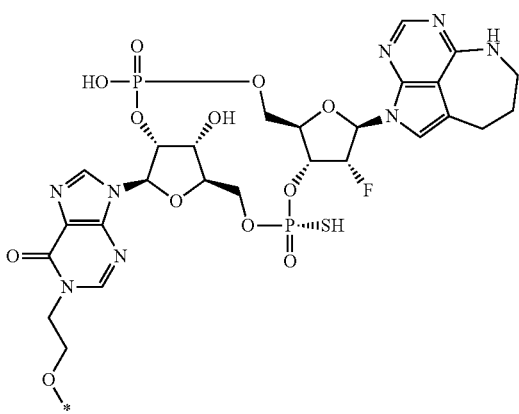

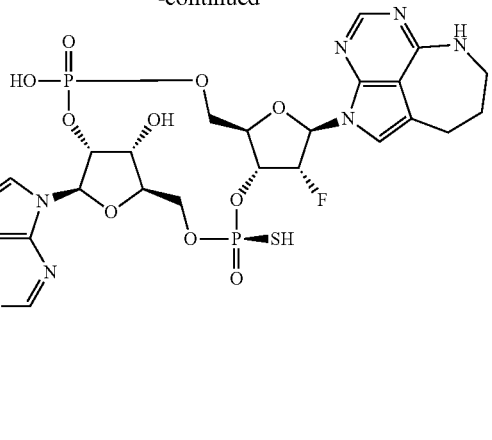

wherein
    each asterisk indicates bonding to L;

[39] The antibody-drug conjugate according to any one of [33], [34], [36], and [37], wherein D is represented by any one of the following three formulas:

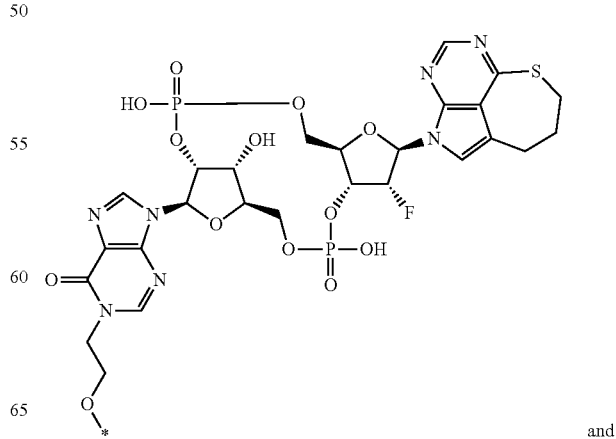

and and

25
-continued

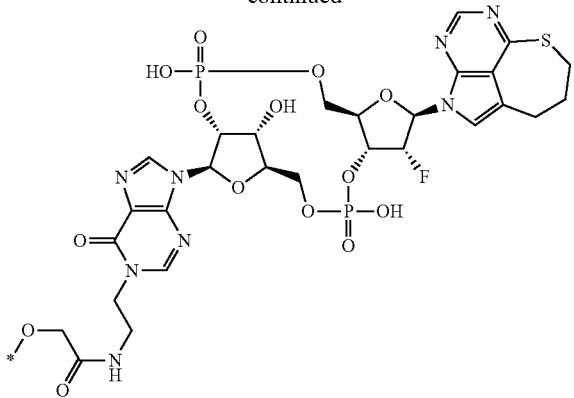

wherein
each asterisk indicates bonding to L;

[40] The antibody-drug conjugate according to any one of [33], [34], [36], and [37], wherein D is represented by any one of the following four formulas:

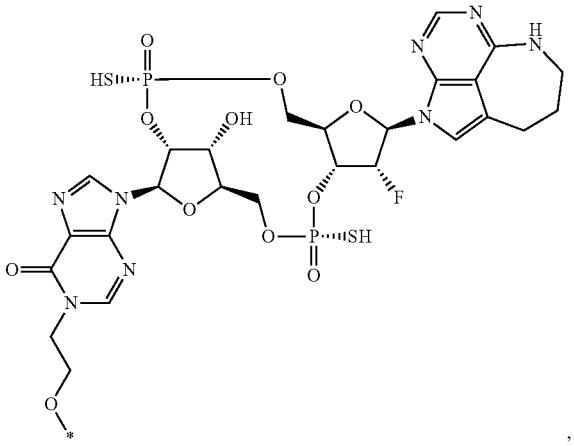

,

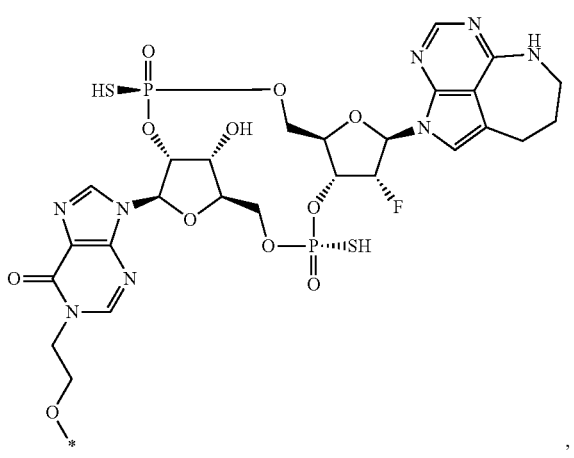

,

26
-continued

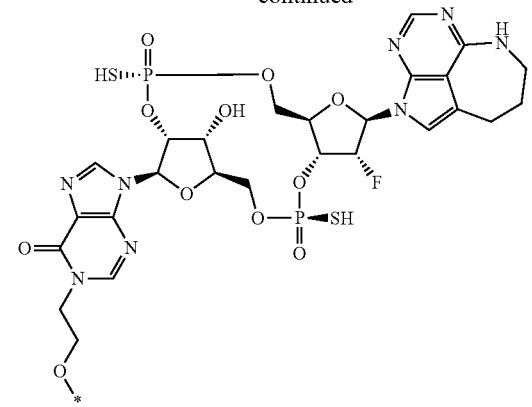

and

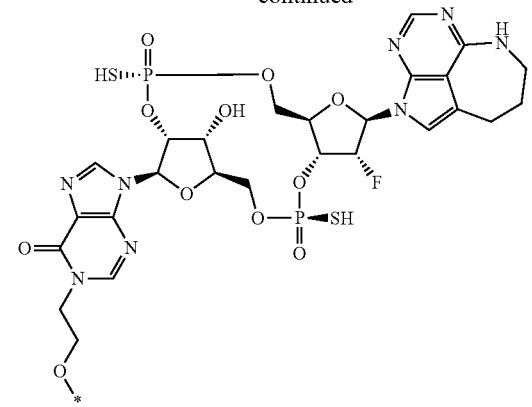

wherein
each asterisk indicates bonding to L;

[41] The antibody-drug conjugate according to any one of [1] to [40], wherein linker L is represented by -Lb-La-Lp-Lc-*, wherein
the asterisk indicates bonding to drug D;
Lp represents a linker consisting of an amino acid sequence cleavable in a target cell, or is absent;
La represents any one selected from the following group:
—C(=O)—(CH$_2$CH$_2$)n$^2$-C(=O)—,
—C(=O)—(CH$_2$CH$_2$)n$^2$-CH$_2$—C(=O)—,
—C(=O)—(CH$_2$CH$_2$)n$^2$-C(=O)—NH—(CH$_2$CH$_2$)n$^3$-C(=O)—,
—C(=O)—(CH$_2$CH$_2$)n$^2$-C(=O)—NH—(CH$_2$CH$_2$)n$^3$-CH$_2$—C(=O)—,
—C(=O)—(CH$_2$CH$_2$)n$^2$-C(=O)—NH—(CH$_2$CH$_2$O)n$^3$-CH$_2$—C(=O)—,
(CH$_2$)n$^4$-O—C(=O)—, and
(CH$_2$)n$^9$—C(=O)—, wherein
n$^2$ represents an integer of 1 to 3, n$^3$ represents an integer of 1 to 5, n$^4$ represents an integer of 0 to 2, and n$^9$ represents an integer of 2 to 7;
Lb represents a spacer bonding La and a glycan or remodeled glycan of Ab or a spacer bonding La and a cysteine residue of Ab; and
Lc represents —NH—CH$_2$—, —NH-phenyl group —CH$_2$—O(C=O)—, or —NH-heteroaryl group —CH$_2$—O(C=O)—, or is absent;

[42] The antibody-drug conjugate according to [41], wherein Lc is absent;

[43] The antibody-drug conjugate according to [41], wherein Lc is —NH—CH$_2$—;

[44] The antibody-drug conjugate according to any one of [41] to [43], wherein Lp represents any one selected from the group consisting of:

-GGVA-, -VA-, -GGFG-, -FG-, -GGPI-, -PI-, -GGVCit-, -VCit-, -GGVK-, -VK-, -GGFCit-, -FCit-, -GGFM-, -FM-, -GGLM-, -LM-, -GGICit-, and -ICit-;

[45] The antibody-drug conjugate according to [44], wherein Lp is any one of -GGVA-, -VA-, -GGFG-, -FG-, -GGVCit-, -VCit-, -GGFCit-, and -FCit-;

[46] The antibody-drug conjugate according to any one of [41] to [43], wherein Lp is any one of -GGFG-, -GGPI-, -GGVA-, -GGFM-, -GGVCit-, -GGFCit-, -GGICit-, -GGPL-, -GGAQ-, and -GGPP-;

[47] The antibody-drug conjugate according to [46], wherein Lp is -GGFG- or -GGPI-;

[48] The antibody-drug conjugate according to any one of [41] to [47], wherein La represents any one selected from the group consisting of:

—C(=O)—CH$_2$CH$_2$—C(=O)—,

—C(=O)—CH$_2$CH$_2$—C(=O)—NH—(CH$_2$CH$_2$O)$_3$—CH$_2$—C(=O)—,

—C(=O)—CH$_2$CH$_2$—C(=O)—NH—(CH$_2$CH$_2$O)$_4$—CH$_2$—C(=O)—, and (CH$_2$)$_5$—C(=O)—;

[49] The antibody-drug conjugate according to any one of [41] to [48], wherein Lb is represented by any one of the following formulas:

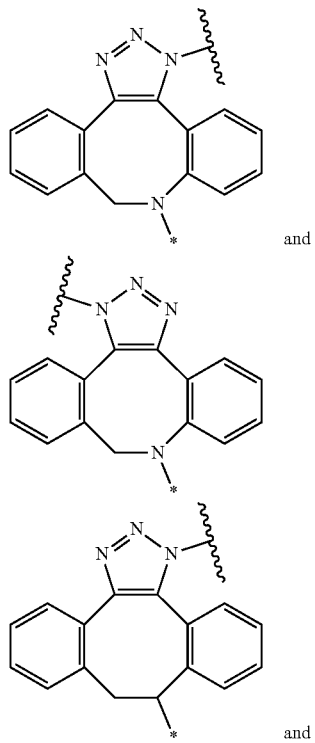

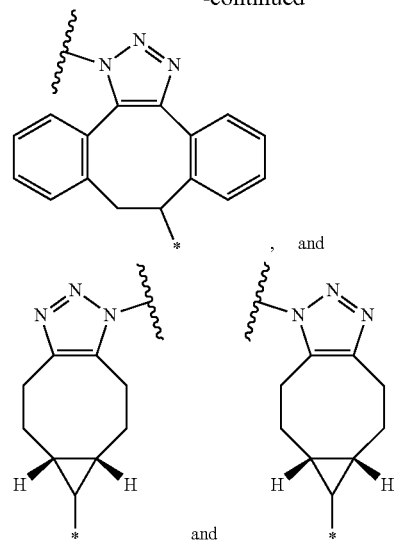

wherein, in the structural formulas for Lb shown above,
each asterisk indicates bonding to La, and each wavy line indicates bonding to a glycan or remodeled glycan of Ab;

[50] The antibody-drug conjugate according to any one of [41] to [48], wherein Lb is-(succinimid-3-yl-N)—, wherein-(succinimid-3-yl-N)-represents the following structural formula:

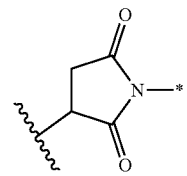

wherein the asterisk indicates bonding to La, and the wavy line indicates bonding to a side chain of a cysteine residue of the antibody through forming thioether;

[51] The antibody-drug conjugate according to any one of [41] and [46] to [49], wherein linker L is represented by -Lb-La-Lp-Lc-*, wherein the asterisk indicates bonding to drug D;

Lp is -GGFG- or -GGPI-;

La represents —C(=O)—CH$_2$CH$_2$—C(=O)—;

Lb represents the following formula:

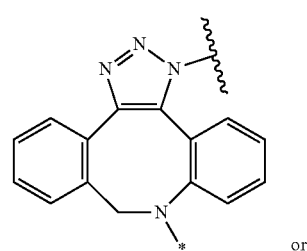

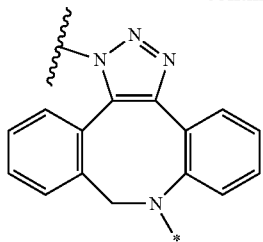

wherein, in the structural formulas for Lb shown above, each asterisk indicates bonding to La, and each wavy line indicates bonding to a glycan or remodeled glycan of Ab; and Lc represents —NH—CH$_2$—;

[52] The antibody-drug conjugate according to any one of [1] to [51], wherein the average number of conjugated drug molecules per antibody molecule in the antibody-drug conjugate is in the range of 1 to 10;

[53] The antibody-drug conjugate according to [52], wherein the average number of conjugated drug molecules per antibody molecule in the antibody-drug conjugate is in the range of 1 to 5;

[54] The antibody-drug conjugate according to any one of [1] to [53], wherein the antibody bonds via a glycan bonding to Asn297 of the antibody (N297 glycan) to L;

[55] The antibody-drug conjugate according to [54], wherein the N297 glycan is a remodeled glycan;

[56] The antibody-drug conjugate according to [54] or [55], wherein the N297 glycan is N297-(Fuc) MSG1 or N297-(Fuc) SG;

[57] The antibody-drug conjugate according to any one of [1] to [56], wherein the antibody is an anti-HER2 antibody, an anti-HER3 antibody, an anti-DLL3 antibody, an anti-FAP antibody, an anti-CDH11 antibody, an anti-CDH6 antibody, an anti-A33 antibody, an anti-CanAg antibody, an anti-CD19 antibody, an anti-CD20 antibody, an anti-CD22 antibody, an anti-CD30 antibody, an anti-CD33 antibody, an anti-CD56 antibody, an anti-CD70 antibody, an anti-CD98 antibody, an anti-TROP2 antibody, an anti-CEA antibody, an anti-Cripto antibody, an anti-EphA2 antibody, an anti-G250 antibody, an anti-MUC1 antibody, an anti-GPNMB antibody, an anti-Integrin antibody, an anti-PSMA antibody, an anti-Tenascin-C antibody, an anti-SLC44A4 antibody, an anti-Mesothelin antibody, an anti-ENPP3 antibody, an anti-CD47 antibody, an anti-EGFR antibody, an anti-GPR20 antibody, or an anti-DR5 antibody;

[58] The antibody-drug conjugate according to [57], wherein the antibody is an anti-HER2 antibody;

[59] The antibody-drug conjugate according to [58], wherein the antibody is an antibody comprising a light chain consisting of an amino acid sequence represented by SEQ ID NO: 1 and a heavy chain consisting of an amino acid sequence represented by SEQ ID NO: 2, or an antibody comprising a light chain consisting of an amino acid sequence represented by SEQ ID NO: 1 and a heavy chain consisting of an amino acid sequence represented by SEQ ID NO: 3;

[60] The antibody-drug conjugate according to [58], wherein the antibody is an antibody comprising a light chain consisting of an amino acid sequence represented by SEQ ID NO: 28 and a heavy chain consisting of an amino acid sequence represented by SEQ ID NO: 29, or an antibody comprising a light chain consisting of an amino acid sequence represented by SEQ ID NO: 28 and a heavy chain consisting of an amino acid sequence represented by SEQ ID NO: 30;

[61] The antibody-drug conjugate according to [57], wherein the antibody is an antibody comprising a light chain consisting of an amino acid sequence represented by SEQ ID NO: 31 and a heavy chain consisting of an amino acid sequence represented by SEQ ID NO: 32, an antibody comprising a light chain consisting of an amino acid sequence represented by SEQ ID NO: 33 and a heavy chain consisting of an amino acid sequence represented by SEQ ID NO: 34, or an antibody comprising a light chain consisting of an amino acid sequence represented by SEQ ID NO: 35 and a heavy chain consisting of an amino acid sequence represented by SEQ ID NO: 36;

[62] A compound or a pharmacologically acceptable salt of the compound, wherein the compound is represented by formula (Ia):

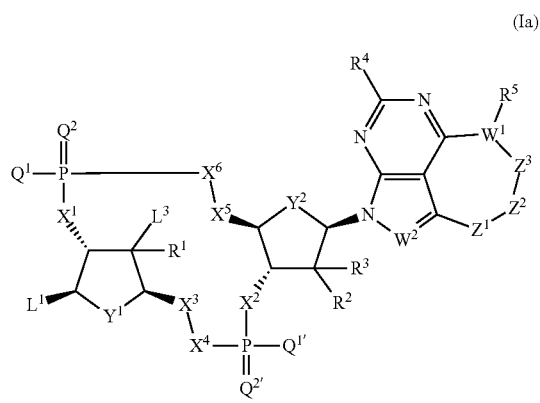

wherein

L$^1$ represents a group selected from the group consisting of the following formulas:

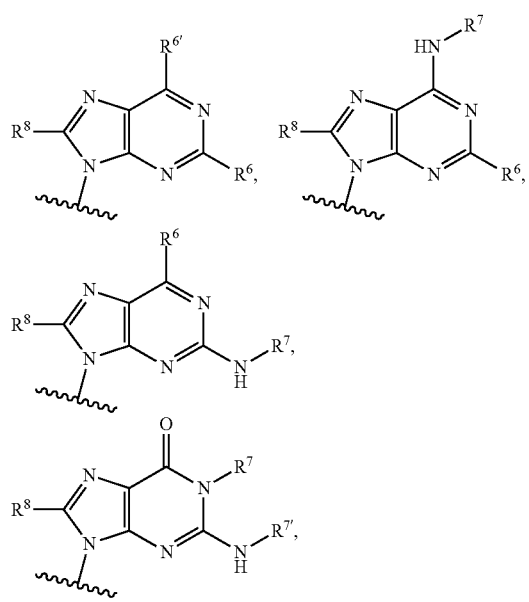

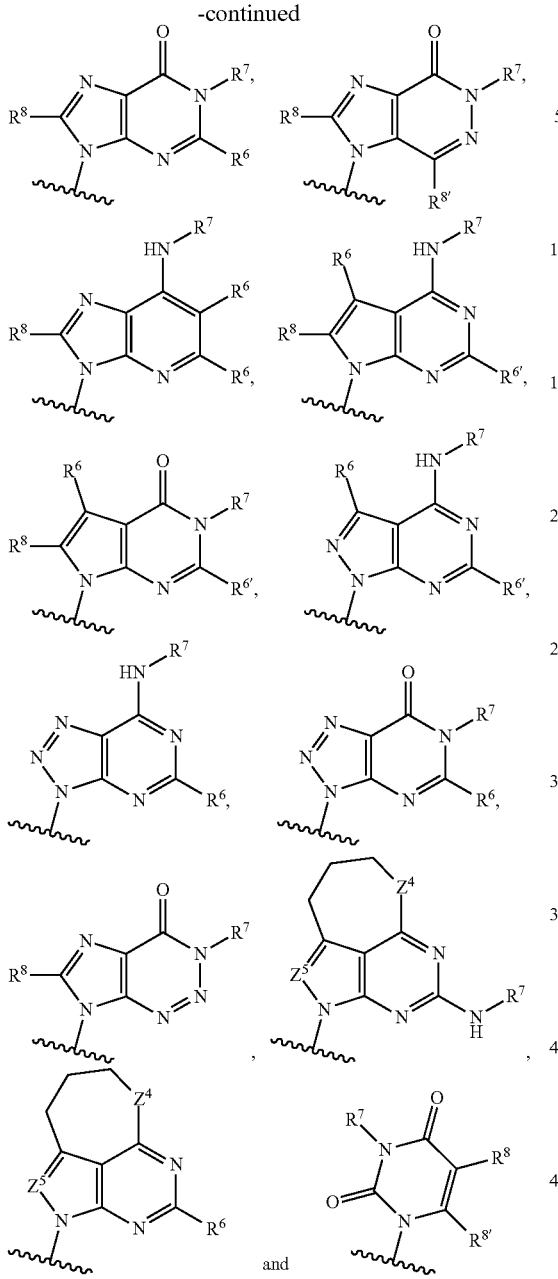

and optionally substituted at any position with one to three groups selected from the group consisting of a hydroxy group, —NH$_2$, a 2-hydroxyacetylaminomethyl group, and a 2-[(2-hydroxyacetyl)amino]ethyl group,
wherein
$R^6$ and $R^{6'}$ each independently represent a hydrogen atom, a halogen atom, a hydroxy group, —NH$_2$, a C1-C6 alkyl group, a C2-C6 alkenyl group, or a C2-C6 alkynyl group;
$R^7$ and $R^{7'}$ each independently represent a hydrogen atom or a C1-C6 alkyl group, wherein the C1-C6 alkyl group is optionally substituted with one or two substituents selected from the group consisting of a halogen atom and an oxo group;
$R^8$ and $R^{8'}$ each independently represent a hydrogen atom or a halogen atom;

$Z^4$ represents —CH$_2$—, —NH—, or an oxygen atom; and $Z^5$ represents a nitrogen atom or —CH=, $L^3$ represents a hydrogen atom, a halogen atom, —NH$_2$, a hydroxy C1-C3 alkyl group, or an amino C1-C3 alkyl group;

$Q^1$ and $Q^{1'}$ each independently represent a hydroxy group, a thiol group, or a borano group (BH$_3$);

$Q^2$ and $Q^{2'}$ each independently represent an oxygen atom or a sulfur atom;

$X^1$ and $X^2$ each independently represent an oxygen atom, a sulfur atom, or —CH$_2$—;

$Y^1$ and $Y^2$ each represent an oxygen atom or —CH$_2$—;

$X^3$ and $X^4$ represent a group selected from (iii) and (iv):
  (iii) when $Y^1$ is an oxygen atom, $X^3$-$X^4$ represents —CH$_2$—O—, —CH$_2$—S—, —CH$_2$—CH$_2$—, or —CH$_2$—CF$_2$—; and
  (iv) when $Y^1$ is —CH$_2$—, $X^3$-$X^4$ represents —O—CH$_2$—;

$X^5$ and $X^6$ represent a group selected from (v) and (vi):
  (v) when $Y^2$ is an oxygen atom, $X^5$-$X^6$ represents —CH$_2$—O—, —CH$_2$—S—, —CH$_2$—CH$_2$—, or —CH$_2$—CF$_2$—; and
  (vi) when $Y^2$ is —CH$_2$—, $X^5$-$X^6$ represents —O—CH$_2$—;

$R^1$, $R^2$, and $R^3$ each independently represent a hydrogen atom, a halogen atom, —OR', —OC(=O)R', —N$_3$, —NHR', —NR'R'', or —NHC(=O)R', wherein R' represents a hydrogen atom, a C1-C6 alkyl group, a C2-C6 alkenyl group, a C2-C6 alkynyl group, or a C3-C6 cycloalkyl group, the C1-C6 alkyl group, C2-C6 alkenyl group, or C2-C6 alkynyl group is optionally substituted with one to six halogen atoms, and R'' represents a C1-6 alkyl group, a C2-6 alkenyl group, a C2-6 alkynyl group, or a C3-C6 cycloalkyl group;

$W^1$ represents a nitrogen atom, an oxygen atom, a sulfur atom, or —CH—;

$W^2$ represents a nitrogen atom or —CH=;

$R^4$ represents a hydrogen atom, a halogen atom, or —NH$_2$;

$R^5$ represents a group selected from (vii) to (x):
  (vii) when $W^1$ is a nitrogen atom, $R^5$ represents a hydrogen atom, a C1-C6 alkyl group, a hydroxy C1-C6 alkyl group, or an amino C1-C6 alkyl group;
  (viii) when $W^1$ is an oxygen atom, $R^5$ is absent;
  (ix) when $W^1$ is a sulfur atom, $R^5$ is absent; and
  (x) when $W^1$ is —CH—, $R^5$ represents a hydrogen atom, a halogen atom, a hydroxy group, —NH$_2$, or a C1-C6 alkyl group;

$Z^1$-$Z^2$-$Z^3$ together represents a group —CH$_2$—CH$_2$—CH$_2$—, —CH$_2$—CH$_2$—R'''—, —CH=CH—CH$_2$—, —CH=CX—CH$_2$—, —CX=CH—CH$_2$—, —CX=CX—CH$_2$—, —C(=O)—CH$_2$—CH$_2$—, —CH$_2$—CH$_2$—C(=O)—, —CH$_2$—CH(CH$_3$)—CH$_2$—, or —CH$_2$—CH$_2$—CH(CH$_3$)—, wherein R''' represents —O— or —CH$_2$—CH$_2$— and X represents a halogen atom, or a group represented by either one of the following formulas:

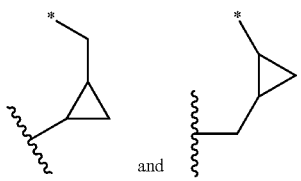 [SMILES: *CC1CC1* ; *CC1CC1*]

wherein
  each asterisk indicates bonding to $W^1$, and each wavy line indicates bonding to the carbon atom of =C—;

[63] The compound according to [62] or a pharmacologically acceptable salt of the compound, wherein $W^1$ is a nitrogen atom;

[64] The compound according to [63] or a pharmacologically acceptable salt of the compound, wherein $W^1$ is a nitrogen atom, and $R^5$ is a hydrogen atom;

[65] The compound according to [62] or a pharmacologically acceptable salt of the compound, wherein $W^1$ is an oxygen atom;

[66] The compound according to [62] or a pharmacologically acceptable salt of the compound, wherein $W^1$ is a sulfur atom;

[67] The compound according to [62] or a pharmacologically acceptable salt of the compound, wherein $W^1$ is —CH—;

[68] The compound according to [67] or a pharmacologically acceptable salt of the compound, wherein $W^1$ is —CH—, and $R^5$ is a hydrogen atom;

[69] The compound according to any one of [62] to [68] or a pharmacologically acceptable salt of the compound, wherein $Z^1$, $Z^2$, and $Z^3$ together form —CH$_2$—CH$_2$—CH$_2$— or —CH=CH—CH$_2$—;

[70] The compound according to any one of [62] to [68] or a pharmacologically acceptable salt of the compound, wherein $Z^1$, $Z^2$, and $Z^3$ together form —CH$_2$—CH(CH$_3$)—CH$_2$— or —CH$_2$—CH$_2$—CH(CH$_3$)—;

[71] The compound according to any one of [62] to [68] or a pharmacologically acceptable salt of the compound, wherein $Z^1$, $Z^2$, and $Z^3$ together form —CH$_2$—CH$_2$—R'''—, wherein R''' represents —O— or —CH$_2$—CH$_2$—;

[72] The compound according to any one of [62] to [71] or a pharmacologically acceptable salt of the compound, wherein $W^2$ is —CH=;

[73] The compound according to any one of [62] to [71] or a pharmacologically acceptable salt of the compound, wherein $W^2$ is a nitrogen atom;

[74] The compound according to any one of [62] to [73] or a pharmacologically acceptable salt of the compound, wherein $R^4$ represents a hydrogen atom;

[75] The compound according to any one of [62] to [73] or a pharmacologically acceptable salt of the compound, wherein $R^4$ represents a fluorine atom;

[76] The compound according to any one of [62] to [75] or a pharmacologically acceptable salt of the compound, wherein $R^8$ and $R^{8'}$ in $L^1$ are each independently a hydrogen atom;

[77] The compound according to any one of [62] to [76] or a pharmacologically acceptable salt of the compound, wherein $L^1$ is a group selected from the group consisting of the following formulas:

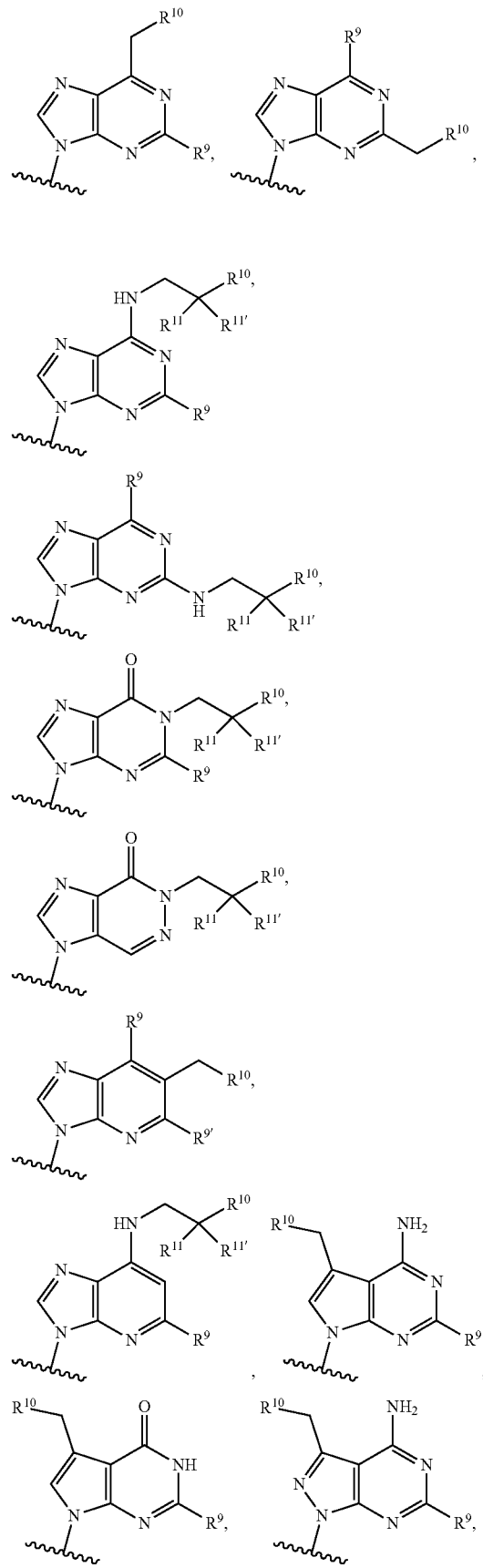

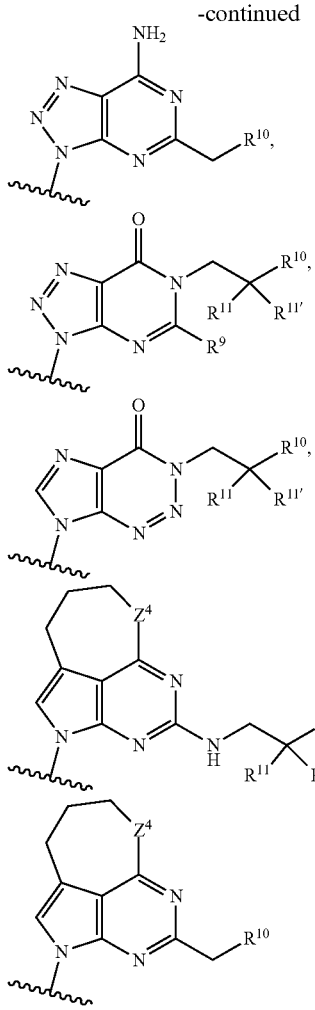

wherein
- $R^9$ and $R^{9'}$ each represent a hydrogen atom, a halogen atom, a hydroxy group, or —NH$_2$;
- $R^{10}$ represents a hydroxy group, —NH$_2$, —NHC(=O)CH$_2$OH, —CH$_2$NHC(=O)CH$_2$OH, —CH$_2$CH$_2$NHC(=O)CH$_2$OH, a hydroxy C1-C3 alkyl group, or an amino C1-C3 alkyl group;
- $R^{11}$ and $R^{11'}$ each independently represent a hydrogen atom, a fluorine atom, or a methyl group, or $R^{11}$ and $R^{11'}$ bond together to form cyclopropane; and
- $Z^4$ represents —CH$_2$—, —NH—, or an oxygen atom;

[78] The compound according to any one of [62] to [76] or a pharmacologically acceptable salt of the compound, wherein $L^1$ is a group selected from the group consisting of the following formulas:

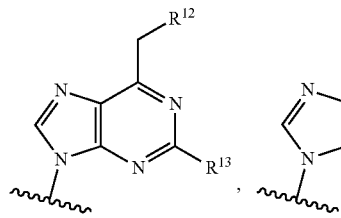

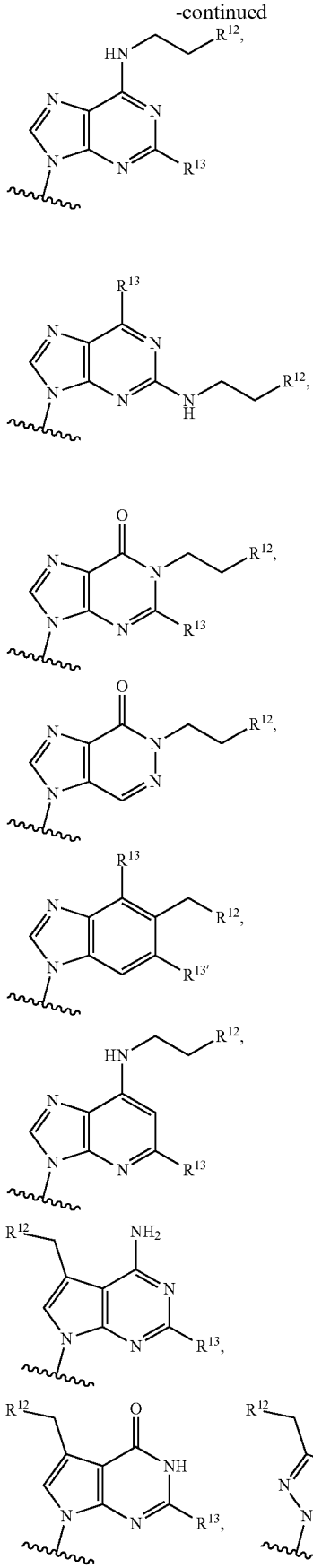

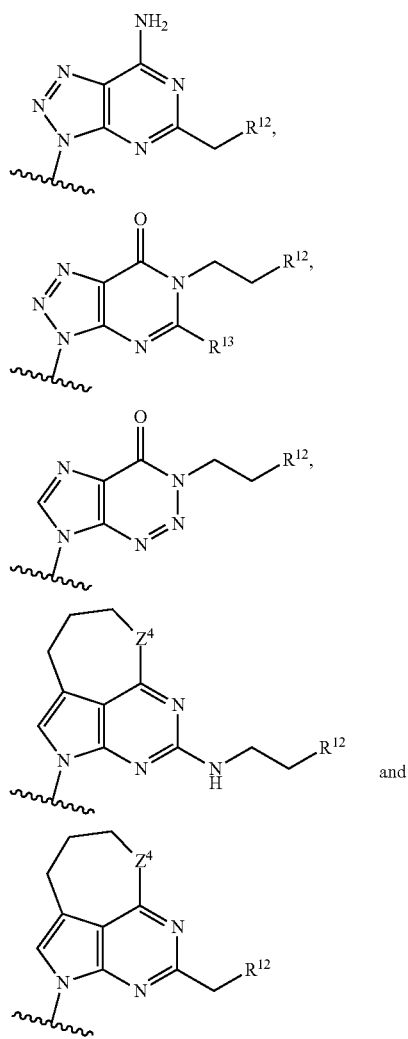

wherein

R[13] and R[13'] each independently represent a hydrogen atom, a hydroxy group, or —NH$_2$;

R[12] represents a hydroxy group, —NH$_2$, —CH$_2$OH, —NHC(=O)CH$_2$OH, —CH$_2$NHC(=O)CH$_2$OH, or —CH$_2$CH$_2$NHC(=O)CH$_2$OH; and Z[4] is as defined above;

[79] The compound according to any one of [62] to [76] or a pharmacologically acceptable salt of the compound, wherein L[1] is a group selected from the group consisting of the following formulas:

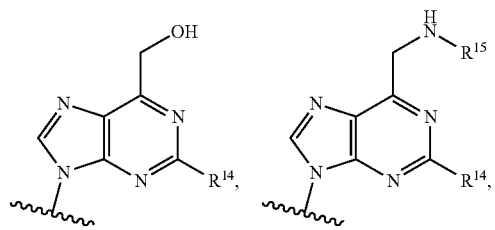

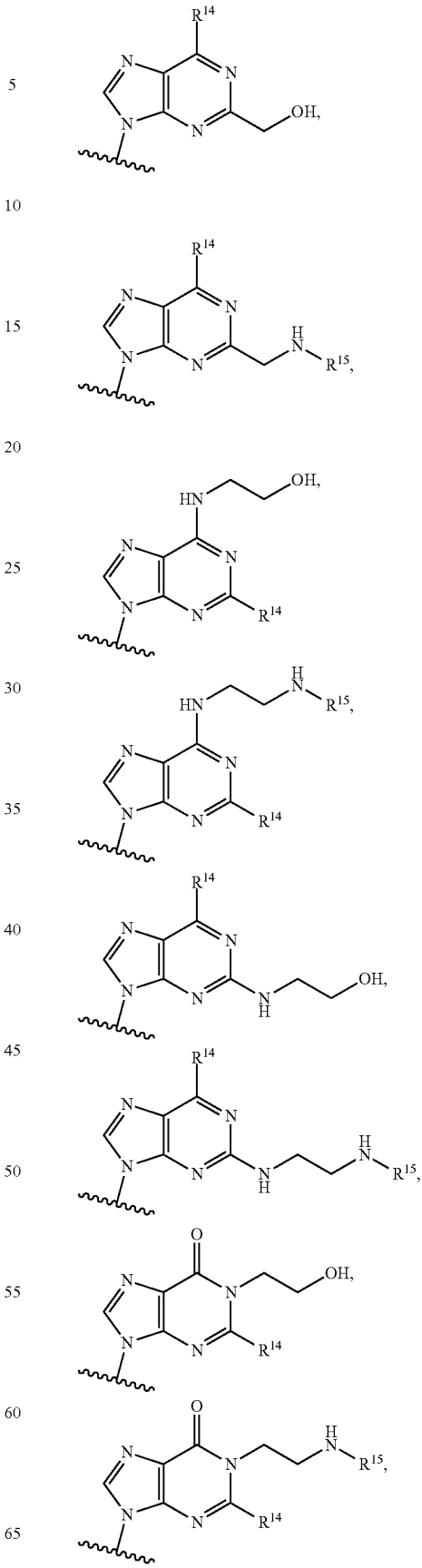

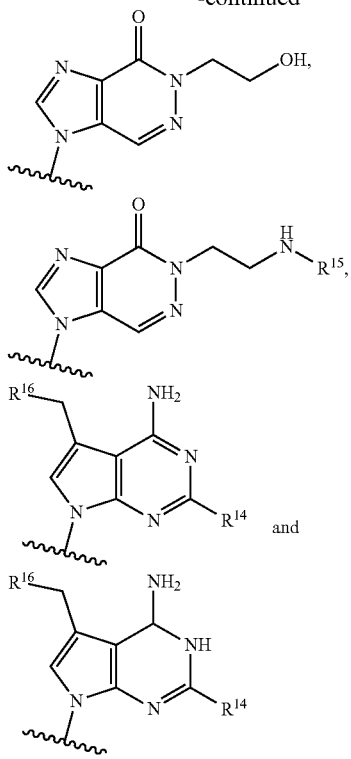

wherein
R$^{14}$ represents a hydrogen atom or —NH$_2$;
R$^{15}$ represents a hydrogen atom or —C(=O)CH$_2$OH; and
R$^{16}$ represents a hydroxy group, —NH$_2$, —CH$_2$OH, —CH$_2$CH$_2$OH, —CH$_2$NH$_2$, or —CH$_2$CH$_2$NH$_2$;

[80] The compound according to any one of [62] to [79] or a pharmacologically acceptable salt of the compound, wherein L$^3$ represents a hydrogen atom, a fluorine atom, —NH$_2$, —CH$_2$OH, or —CH$_2$NH$_2$;

[81] The compound according to any one of [62] to [80] or a pharmacologically acceptable salt of the compound, wherein Q$^1$ and Q$^{1'}$ each independently represent a hydroxy group or a thiol group;

[82] The compound according to any one of [62] to [81] or a pharmacologically acceptable salt of the compound, wherein X$^1$ and X$^2$ each represent an oxygen atom;

[83] The compound according to any one of [62] to [82] or a pharmacologically acceptable salt of the compound, wherein Y$^1$ and Y$^2$ each represent an oxygen atom;

[84] The compound according to any one of [62] to [83] or a pharmacologically acceptable salt of the compound, wherein X$^3$ and X$^4$ represent —CH$_2$—O—;

[85] The compound according to any one of [62] to [84] or a pharmacologically acceptable salt of the compound, wherein X$^5$ and X$^6$ represent —CH$_2$—O—;

[86] The compound according to any one of [62] to [85] or a pharmacologically acceptable salt of the compound, wherein R$^1$, R$^2$, and R$^3$ are each independently a hydrogen atom, a hydroxy group, or a fluorine atom;

[87] The compound according to any one of [62] to [86] or a pharmacologically acceptable salt of the compound, wherein the compound is represented by either one of the following two formulas:

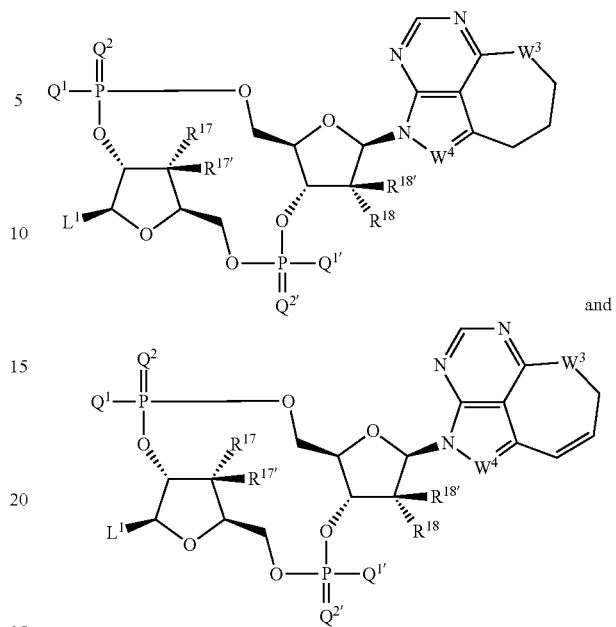

wherein
L$^1$, Q$^1$, Q$^{1'}$, Q$^2$, and Q$^{2'}$ are as defined above;
R$^{17}$, R$^{17'}$, R$^{18}$, and R$^{18'}$ each independently represent a hydrogen atom, a halogen atom, a hydroxy group, or —NH$_2$;
W$^3$ represents —NH—, an oxygen atom, a sulfur atom, or —CH$_2$—; and
W$^4$ represents —CH= or a nitrogen atom;

[88] The compound according to [87] or a pharmacologically acceptable salt of the compound, wherein the compound is represented by either one of the following two formulas:

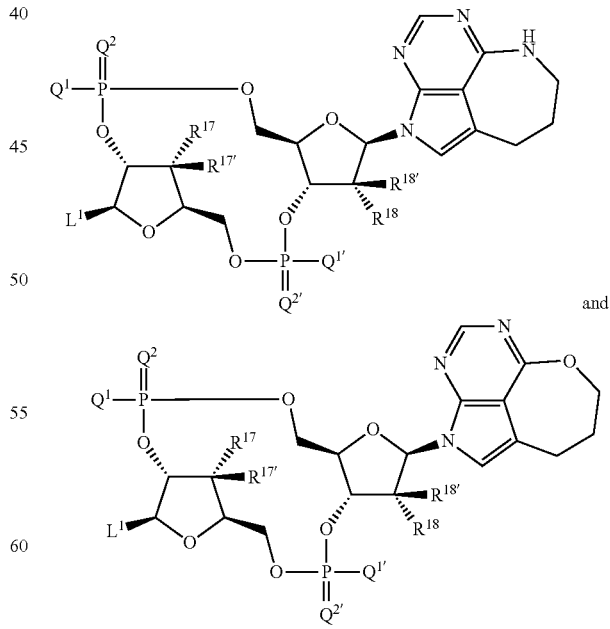

wherein
L$^1$, Q$^1$, Q$^{1'}$, Q$^2$, Q$^{1'}$, R$^{17}$, R$^{17'}$, R$^{18}$, and R$^{18'}$ are as defined above;

[89] The compound according to [87] or [88] or a pharmacologically acceptable salt of the compound, wherein the compound is represented by any one of the following eight formulas:

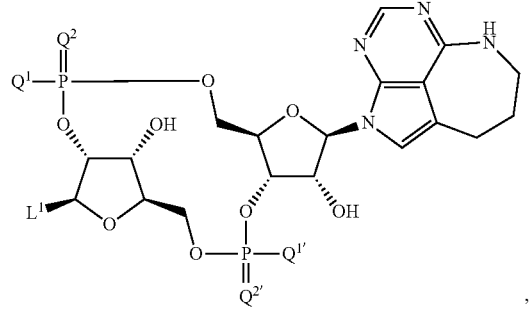

,

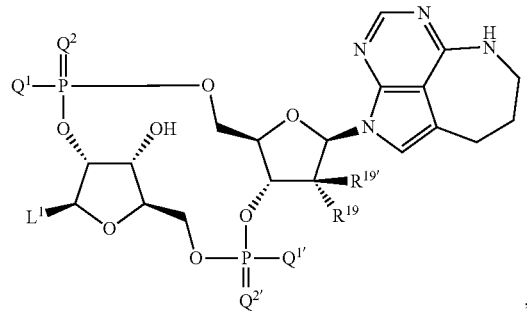

,

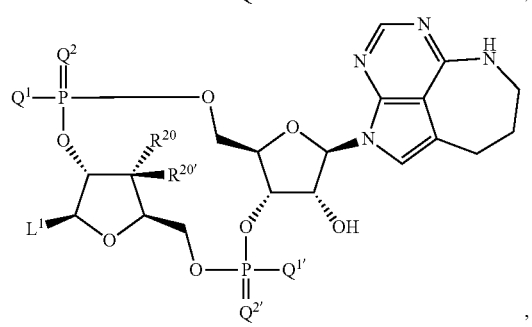

,

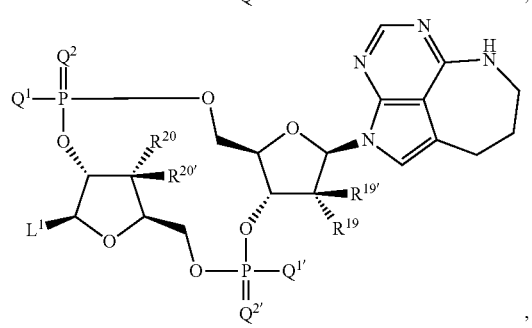

,

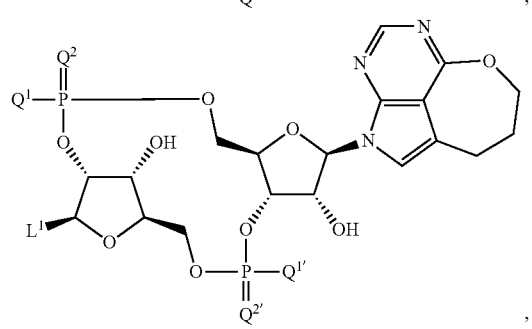

,

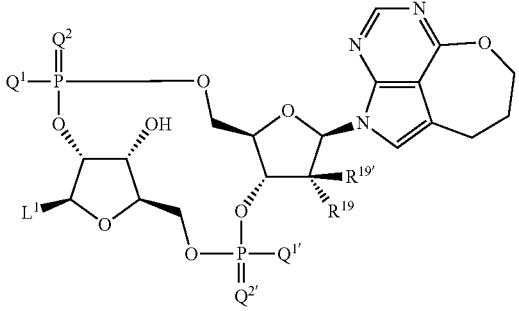

,

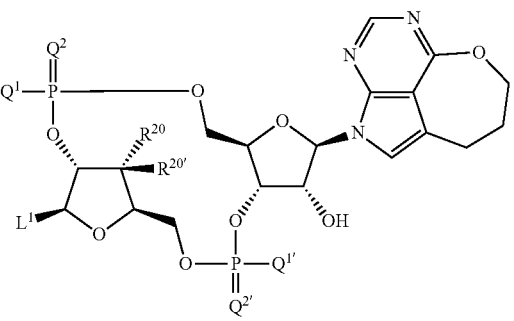

and

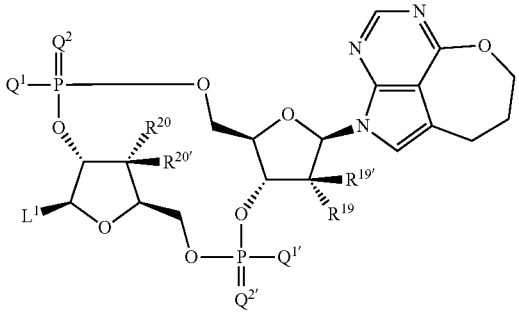

, wherein
L$^1$, Q$^1$, Q$^{1'}$, Q$^2$, and Q$^{2'}$ are as defined above; and
R$^{19}$, R$^{19'}$, R$^{20}$, and R$^{20'}$ each independently represent a hydrogen atom or a fluorine atom;

[90] The compound according to any one of [87] to [89] or a pharmacologically acceptable salt of the compound, wherein the compound is represented by any one of the following four formulas:

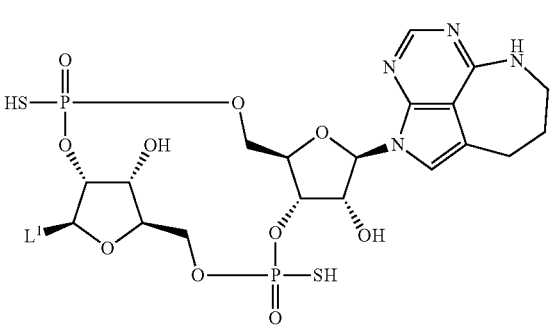

,

43

-continued

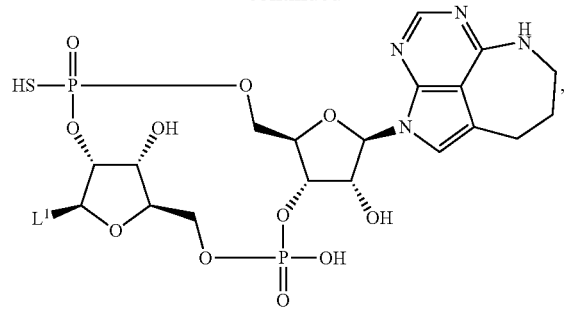

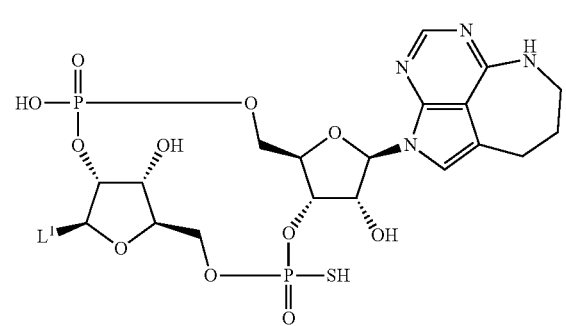

and

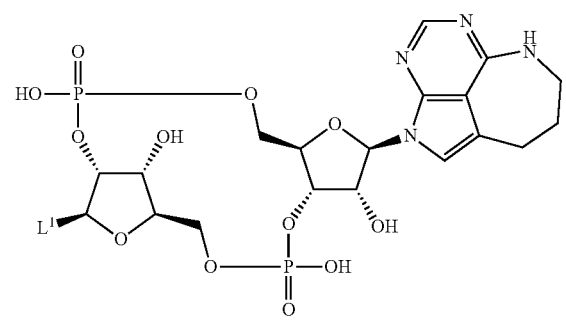

wherein
L¹ is as defined above;

[91] The compound according to any one of [87] to [90] or a pharmacologically acceptable salt of the compound, wherein the compound is represented by any one of the following four formulas:

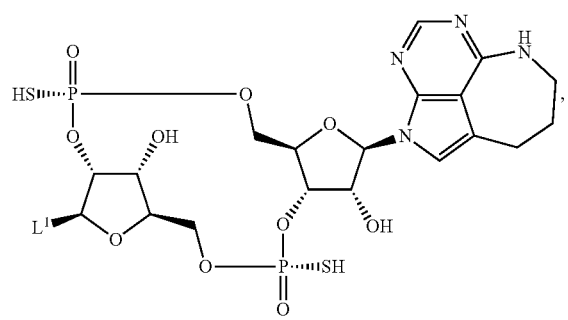

44

-continued

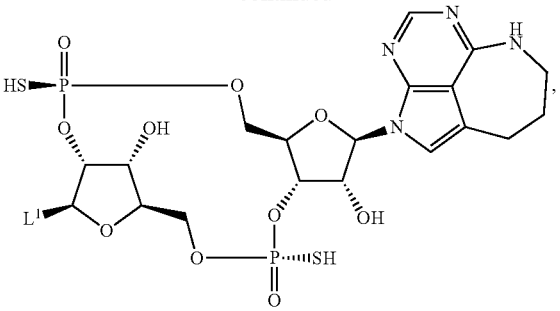

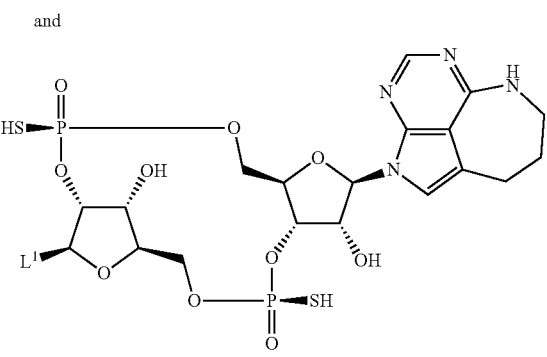

and wherein
L¹ is as defined above;

[92] The compound according to any one of [87] to [90] or a pharmacologically acceptable salt of the compound, wherein the compound is represented by any one of the following four formulas:

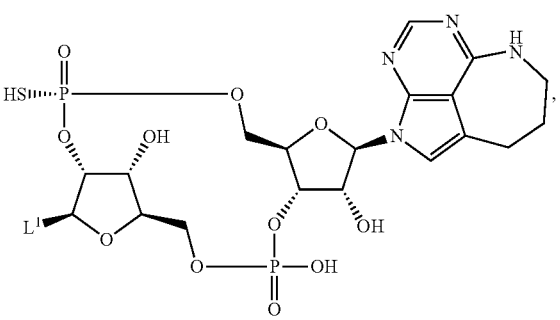

-continued

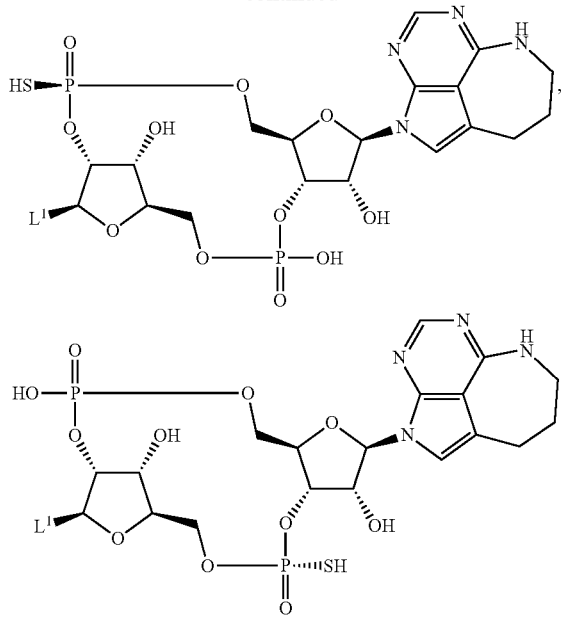

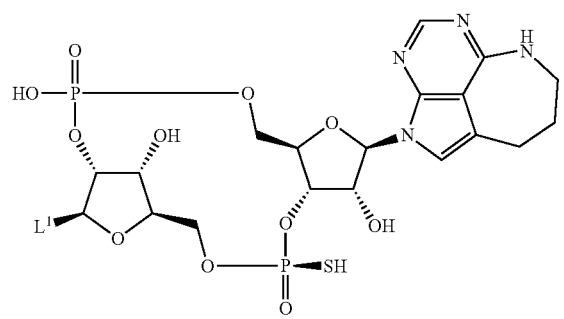

and

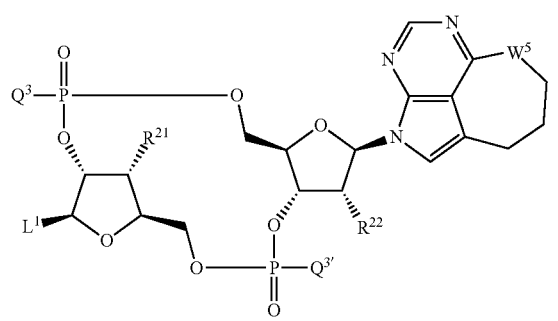

wherein
L¹ is as defined above;

[93] The compound according to any one of [62] to [86] or a pharmacologically acceptable salt of the compound, wherein the compound is represented by the following formula:

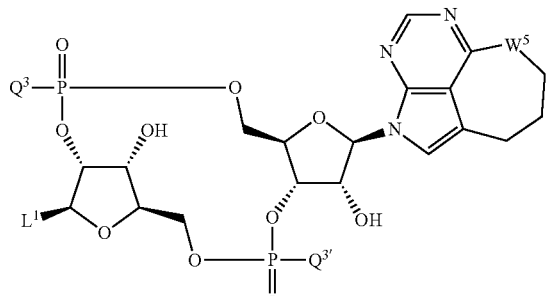

wherein
L¹ is as defined above;
Q³ and Q³' each independently represent a hydroxy group or a thiol group;
R²¹ and R²² each independently represent a hydroxy group or a fluorine atom; and
W⁵ represents —NH— or a sulfur atom;

[94] The compound according to [93] or a pharmacologically acceptable salt of the compound, wherein the compound is represented by either one of the following two formulas:

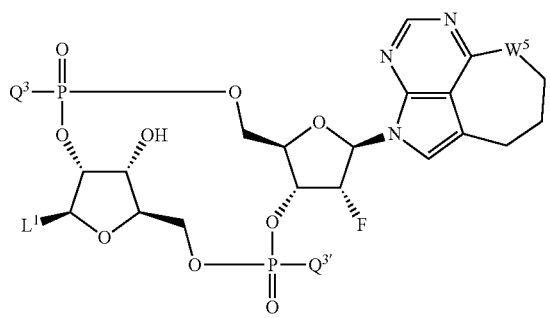

and

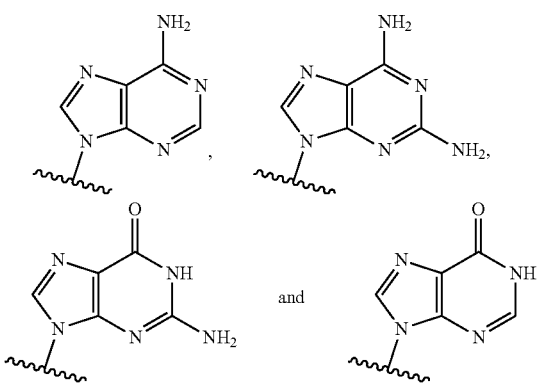

wherein
L¹, Q³, Q³', and W⁵ are as defined above;

[95] The compound according to any one of [62] to [94] or a pharmacologically acceptable salt of the compound, wherein L¹ is represented by any one of the following:

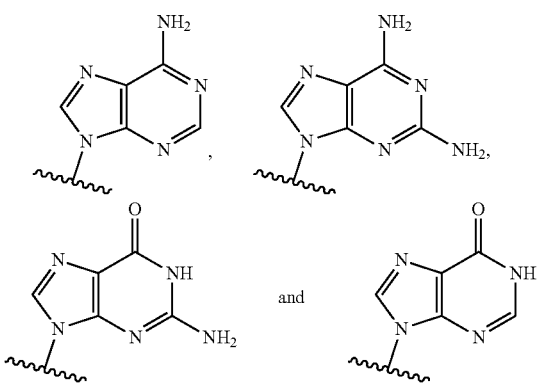

[96] The compound according to any one of [62] to [94] or a pharmacologically acceptable salt of the compound, wherein L¹ is represented by any one of the following four formulas:

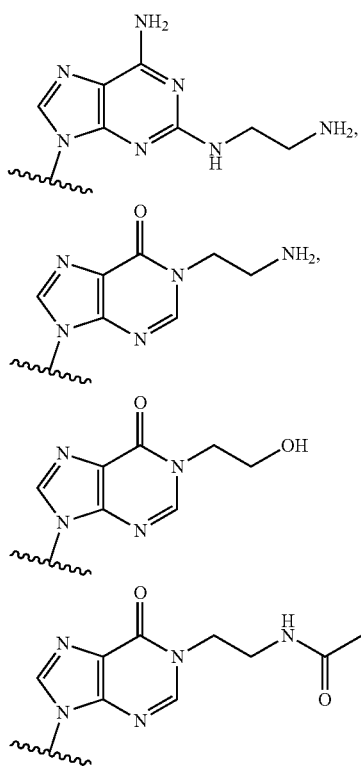

[97] The compound according to any one of [93], [94], and [96] or a pharmacological acceptable salt of the compound, wherein D is represented by any one of the following four formulas:

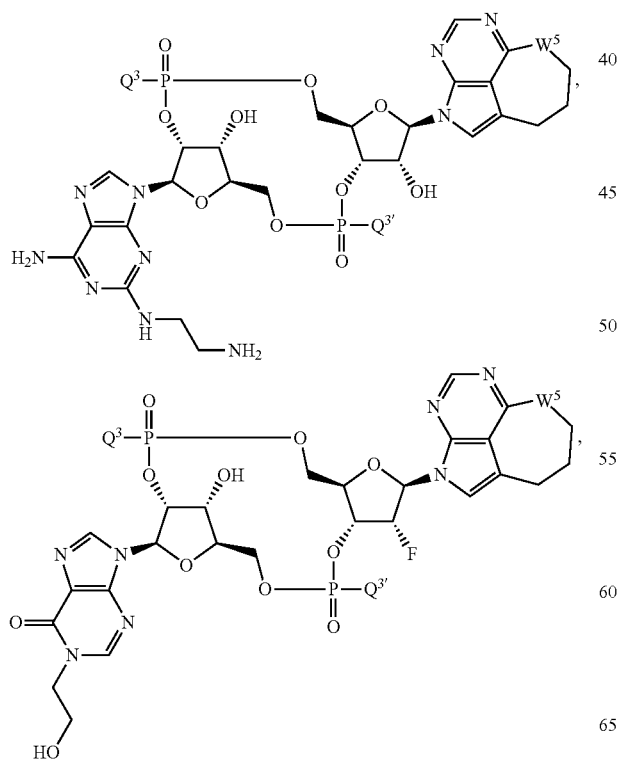

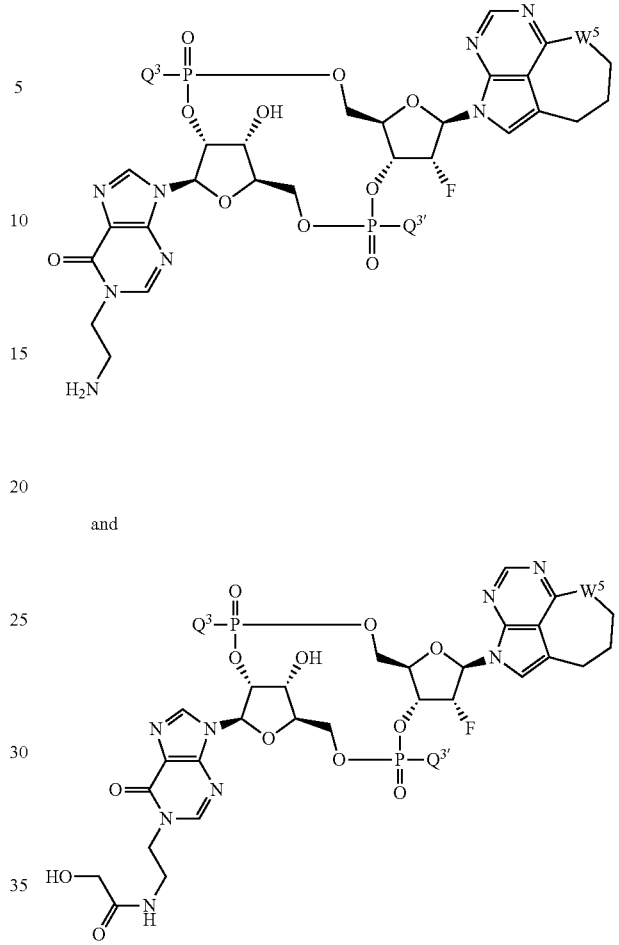

wherein
Q$^3$, Q$^{3'}$, and W$^5$ are as defined above;

[98] The compound according to any one of [93], [94], [96], and [97] or a pharmacologically acceptable salt of the compound, wherein D is represented by any one of the following four formulas:

49
-continued
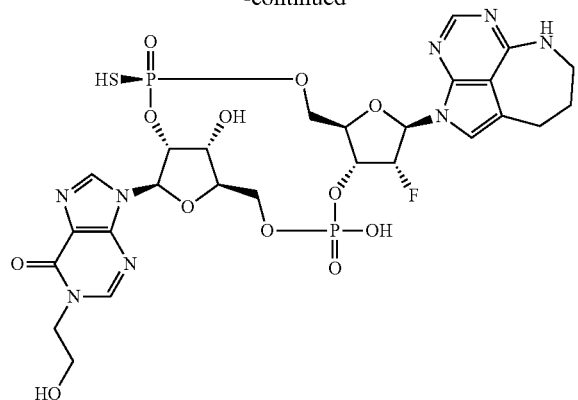
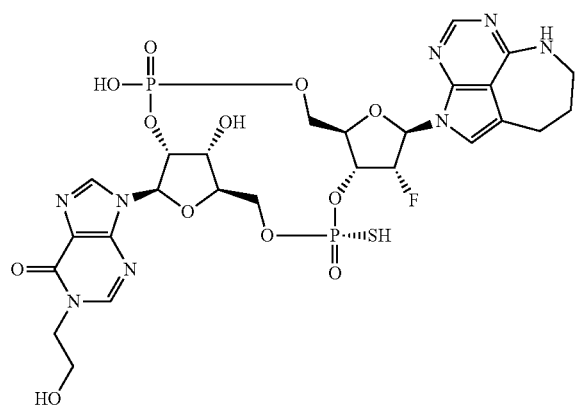
and
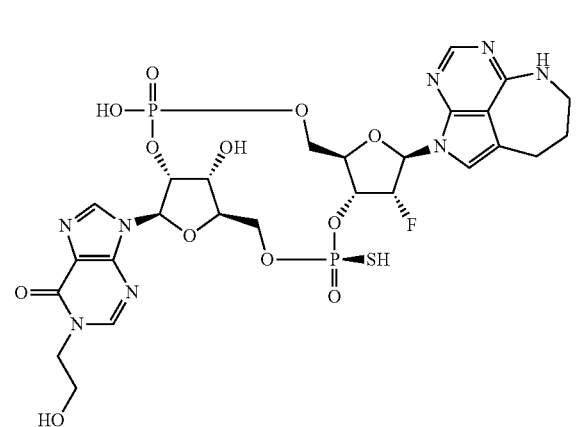
and
50
[99] The compound according to any one of [93], [94], [96], and [97] or a pharmacologically acceptable salt of the compound, wherein D is represented by any one of the following three formulas:
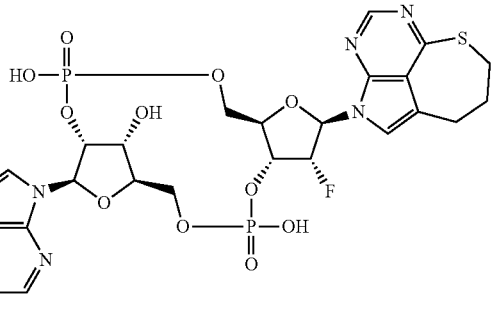
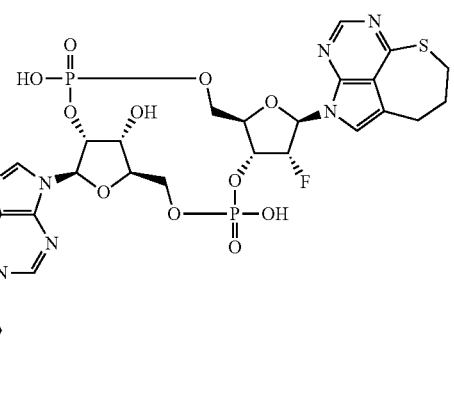

[100] The compound according to any one of [93], [94], [96], and [97] or a pharmacologically acceptable salt of the compound, wherein D is represented by any one of the following four formulas:

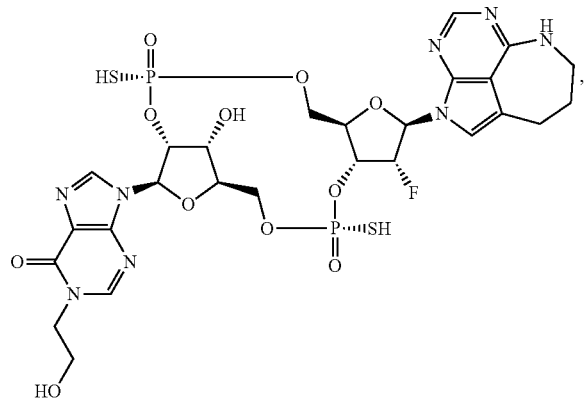

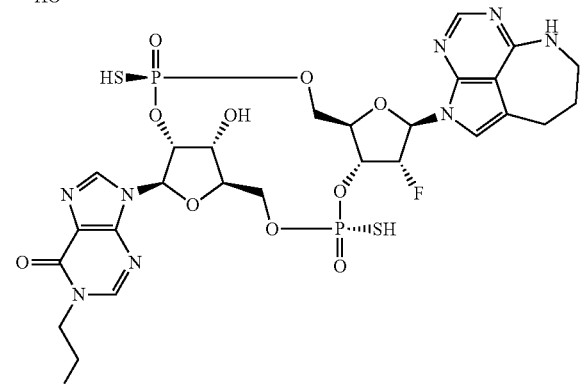

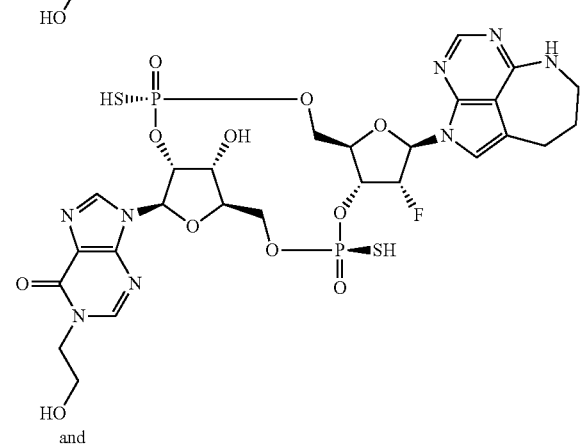

and

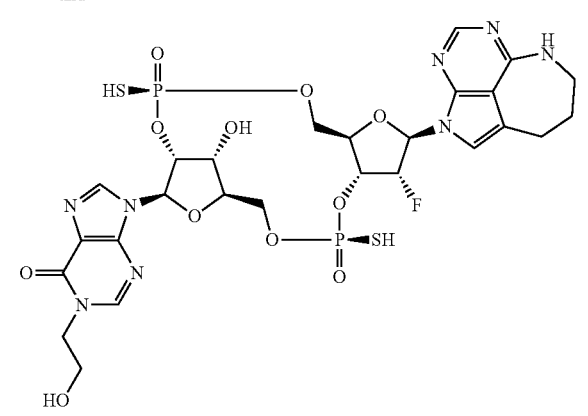

[101] A STING agonist comprising any one selected from the group consisting of the antibody-drug conjugate according to any one of [1] to [61] and the compound according to any one of [62] to [100] or a pharmacologically acceptable salt of the compound;

[102] A pharmaceutical composition comprising any one selected from the group consisting of the antibody-drug conjugate according to any one of [1] to [61] and the compound according to any one of [62] to [100] or a pharmacologically acceptable salt of the compound;

[103] An anti-tumor agent comprising any one selected from the group consisting of the antibody-drug conjugate according to any one of [1] to [61] and the compound according to any one of [62] to [100] or a pharmacologically acceptable salt of the compound;

[104] The anti-tumor agent according to [103], wherein the tumor is lung cancer, kidney cancer, urothelial cancer, colorectal cancer, prostate cancer, glioblastoma multiforme, ovarian cancer, pancreatic cancer, breast cancer, melanoma, liver cancer, bladder cancer, gastric cancer, esophageal cancer, endometrial cancer, testicular cancer, uterine cervix cancer, placental choriocarcinoma, glioblastoma multiforme, brain tumor, head-and-neck cancer, thyroid cancer, mesothelioma, gastrointestinal stromal tumor (GIST), gallbladder cancer, bile duct cancer, adrenal cancer, squamous cell carcinoma, leukemia, malignant lymphoma, plasmacytoma, myeloma, or sarcoma;

[105] A method for treating cancer, the method comprising administering any one selected from the group consisting of the antibody-drug conjugate according any one of [1] to [61], the compound according to any one of [62] to [100] or a pharmacologically acceptable salt of the compound, the STING agonist according to [101], the pharmaceutical composition according to [102], and the anti-tumor agent according to [103] or [104];

[106] The method according to [105], wherein the cancer is lung cancer, kidney cancer, urothelial cancer, colorectal cancer, prostate cancer, glioblastoma multiforme, ovarian cancer, pancreatic cancer, breast cancer, melanoma, liver cancer, bladder cancer, gastric cancer, esophageal cancer, endometrial cancer, testicular cancer, uterine cervix cancer, placental choriocarcinoma, glioblastoma multiforme, brain tumor, head-and-neck cancer, thyroid cancer, mesothelioma, gastrointestinal stromal tumor (GIST), gallbladder cancer, bile duct cancer, adrenal cancer, squamous cell carcinoma, leukemia, malignant lymphoma, plasmacytoma, myeloma, or sarcoma.

Advantageous Effects of Invention

The present invention provides novel CDN derivatives. The novel CDN derivatives of the present invention have potent STING agonist activity, and exhibit high anti-tumor activity. In addition, the present invention provides novel antibody-CDN derivative conjugates that allow systemic administration and exhibit anti-tumor effect in tumors expressing an antigen.

BRIEF DESCRIPTION OF DRAWINGS

FIG. 1 schematically shows a drug conjugate form obtained from an SG-type glycan-remodeled antibody (the molecule of (II) in A of FIG. 1), and a drug conjugate form obtained from an MSG-type glycan-remodeled antibody (the molecule of (II) in B of FIG. 1), each being the drug conjugate form of the present invention (the molecule of (II)). (a) indicates drug D, (b) indicates linker L, (c) indicates a PEG linker (L(PEG)), and (d) indicates N297 glycan, wherein each open circle represents NeuAc (Sia), each open hexagon represents Man, each solid hexagon represents GlcNAc, each open rhombus represents Gal, and each open inverted triangle represents Fuc. Each open pentagon represents a triazole ring formed through reaction between an alkyne derived from linker L and an azide group derived from a PEG linker. Each Y-shape represents antibody Ab. Each PEG linker is bonding to the carboxyl group at position 2 of a sialic acid positioned at a non-reducing terminus via an amide bond. Unless otherwise stated, such a manner of illustration is applied throughout the present specification.

FIG. 2 shows schematic diagrams illustrating the structures of a (Fucα1,6)GlcNAc-antibody (the molecule of (III) in A of FIG. 2), an SG-type glycan-remodeled antibody (the molecule of (IV) in B of FIG. 2), and an MSG-type glycan-remodeled antibody (the molecule of (IV) in C of FIG. 2), each being a production intermediate for the drug conjugate form of the present invention. In each of the diagrams, the Y-shape represents antibody Ab as in FIG. 1. (e) in A of FIG. 2 indicates N297 glycan consisting of a disaccharide in which position 1 of Fuc and position 6 of GlcNAc bond together via an α-glycosidic bond. In B and C of FIG. 2, (d) indicates N297 glycan as in FIG. 1, and (f) indicates a PEG linker having an azide group, wherein an azide group to be subjected to bonding to linker L is shown at an end. The bonding mode of each PEG linker having an azide group is the same as those of PEG linkers in FIG. 1.

FIG. 3 shows schematic diagrams illustrating steps for production of an SG-type glycan-remodeled antibody and MSG-type glycan-remodeled antibody from an antibody produced in animal cells. As in FIG. 2, molecules (III) and (IV) in the diagrams represent a (Fucα1,6)GlcNAc-antibody and an SG-type glycan-remodeled antibody or MSG-type glycan-remodeled antibody, respectively. The molecule of (V) is an antibody produced in animal cells, and a mixture of molecules with heterogeneous N297 glycans. FIG. 3A illustrates the step of producing homogeneous molecules of (Fucα1,6)GlcNAc-antibody (III) by treating heterogeneous N297 glycans of (V) with hydrolase such as EndoS. FIG. 3B illustrates the step of producing the SG-type glycan-remodeled antibody of (IV) by subjecting GlcNAc of N297 glycan in antibody (III) to transglycosylation with SG-type glycan donor molecules with use of glycosyltransferase such as an EndoS D233Q/Q303L mutant. FIG. 3C illustrates the step of producing the MSG-type glycan-remodeled antibody of (IV) by subjecting antibody (III) to transglycosylation with MSG-type glycan donor molecules in the same manner as in FIG. 3B. Each of the SG-type glycan donor molecule and MSG-type glycan donor molecule to be used here is such a molecule that a sialic acid at its non-reducing terminus is modified with a PEG linker having an azide group, and a sialic acid at each non-reducing terminus of an SG-type N297 glycan-remodeled antibody or MSG-type N297 glycan-remodeled antibody to be produced is modified in the same manner as shown in FIGS. 2B and 2C.

FIG. 4 shows the amino acid sequences of the light chain (SEQ ID NO: 1) and heavy chain (SEQ ID NO: 2) of trastuzumab.

FIG. 5 shows the amino acid sequences of the light chain (SEQ ID NO: 1) and heavy chain (SEQ ID NO: 3) of a modified anti-HER2 antibody.

FIG. 6 shows the amino acid sequences of (a) wild-type human STING, (b) REF-mutated (R232H) human STING, and (c) HAQ-mutated (R71H, G230A, R293Q) human STING.

FIG. 7 demonstrates anti-tumor effect of intratumoral administration of CDN derivatives. In each graph, the line with solid squares corresponds to a group with a vehicle, the line with open squares to a group with administration of compound No. 6a, the line with open inverted triangles to a group with administration of compound No. 8b, and the line with open circles to a group with administration of compound No. 9b. The vertical axis represents tumor volume (mm$^3$), and the horizontal axis represents days after tumor transplantation.

FIG. 8 demonstrates anti-tumor effect of intravenous administration of anti-HER2 antibody-CDN conjugate (1) and anti-LPS antibody-CDN conjugate (1). In each graph, the line with solid squares corresponds to a group with a vehicle, the line with open triangles to a group with administration of anti-HER2 antibody-CDN conjugate (1), which was formed by conjugating the compound of Example 8b to a modified anti-HER2 antibody produced in Reference Example 1, and the line with solid triangles to a group with administration of anti-LPS antibody-CDN conjugate (1), which was similarly formed by conjugating the compound of Example 8b to a modified anti-LPS antibody produced in Reference Example 2. The vertical axis represents tumor volume (mm$^3$), and the horizontal axis represents days after tumor transplantation.

FIG. 9 demonstrates anti-tumor effect of intravenous administration of anti-HER2 antibody-CDN conjugates (2) and (3). In the graph, the line with solid squares corresponds to a group with a vehicle, the line with open squares to a group with administration of anti-HER2 antibody-CDN conjugate (2), and the line with open triangles to a group with administration of anti-HER2 antibody-CDN conjugate (3). The vertical axis represents tumor volume (mm$^3$), and the horizontal axis represents days after tumor transplantation.

FIG. 10 demonstrates anti-tumor effect of intravenous administration of anti-HER2 antibody-CDN conjugate (19). In the graph, the line with solid squares corresponds to a group with a vehicle, and the line with open triangles to a group with administration of anti-HER2 antibody-CDN conjugate (19). In anti-HER2 antibody-CDN conjugate (19), a drug-linker is conjugated to the antibody through cysteine conjugation. The vertical axis represents tumor volume (mm$^3$), and the horizontal axis represents days after tumor transplantation.

FIG. 11 demonstrates anti-tumor effect of intravenous administration of anti-HER2 antibody-CDN conjugates (1) and (9) to (12). In the graph, the line with solid squares corresponds to a group with a vehicle, the line with open triangles to a group with administration of anti-HER2 antibody-CDN conjugate (9), the line with open inverted triangles to a group with administration of anti-HER2 antibody-CDN conjugate (10), the line with open rhombuses to a group with administration of anti-HER2 antibody-CDN conjugate (11), the line with open circles to a group with administration of anti-HER2 antibody-CDN conjugate (12), and the line with open squares to a group with administration of anti-HER2 antibody-CDN conjugate (1). In each of anti-HER2 antibody-CDN conjugates (9), (10), (11), (12), and (1), the compound of Example 8b is conjugated via a linker, where the linkers are different from each other. The vertical axis represents tumor volume (mm$^3$), and the horizontal axis represents days after tumor transplantation.

FIG. 12 demonstrates anti-tumor effect of intravenous administration of anti-HER2 antibody 2-CDN conjugate (1), anti-HER2 antibody 2, and compound No. 8b. In the graph, the line with solid squares corresponds to a group with a vehicle, the line with open triangles to a group with administration of 60 µg of anti-HER2 antibody 2-CDN conjugate (1), the line with solid inverted triangles to a group with administration of 59 µg of anti-HER2 antibody 2, and the line with solid circles to a group with administration of 1.2 µg of compound No. 8b. Each dose of anti-HER2 antibody 2 and compound No. 8b is the equivalent of the corresponding component constituting anti-HER2 antibody 2-CDN conjugate (1). The vertical axis represents tumor volume (mm$^3$), and the horizontal axis represents days after tumor transplantation.

FIG. 13 (a) demonstrates anti-tumor effect of intravenous administration of anti-HER2 antibody 2-CDN conjugates (2) and (3). FIG. 13 (b) demonstrates anti-tumor effect of intravenous administration of anti-HER2 antibody 2-CDN conjugates (4), (5), (7), and (8). FIG. 13 (c) demonstrates anti-tumor effect of intravenous administration of anti-HER2 antibody 2-CDN conjugate (6). In each graph, the line with solid squares corresponds to a group with a vehicle, and each line with open symbols to a group with administration of an evaluated subject of anti-HER2 antibody 2-CDN conjugates (2) to (8). The vertical axis represents tumor volume (mm$^3$), and the horizontal axis represents days after tumor transplantation.

FIG. 14 demonstrates anti-tumor effect of intravenous administration of anti-HER2 antibody 2-CDN conjugates (9) and (10). In the graph, the line with solid squares corresponds to a group with a vehicle, the line with open triangles to a group with administration of anti-HER2 antibody 2-CDN conjugate (9), and the line with open circles to a group with administration of anti-HER2 antibody 2-CDN conjugate (10). Anti-HER2 antibody 2-CDN conjugates (9) and (10) are antibody-CDN conjugates using an MSG-type glycan-remodeled antibody with the average number of conjugated drug molecules being approximately 2. The vertical axis represents tumor volume (mm$^3$), and the horizontal axis represents days after tumor transplantation.

FIG. 15 demonstrates anti-tumor effect of intravenous administration of an anti-EphA2 antibody and anti-EphA2 antibody-CDN conjugate (1). In the graph, the line with solid squares corresponds to a group with a vehicle, the line with open circles to a group with administration of an anti-EphA2 antibody, and the line with open triangles to a group with administration of anti-EphA2 antibody-CDN conjugate (1). The vertical axis represents tumor volume (mm$^3$), and the horizontal axis represents days after tumor transplantation.

FIG. 16 demonstrates anti-tumor effect of intravenous administration of an anti-CD33 antibody and anti-CD33 antibody-CDN conjugate (1). In the graph, the line with solid squares corresponds to a group with a vehicle, the line with open circles to a group with administration of an anti-CD33 antibody, and the line with open triangles to a group with administration of anti-CD33 antibody-CDN conjugate (1). The vertical axis represents tumor volume (mm$^3$), and the horizontal axis represents days after tumor transplantation.

FIG. 17 shows the amino acid sequences of the light chain (SEQ ID NO: 28) and heavy chain (SEQ ID NO: 29) of pertuzumab.

FIG. 18 shows the amino acid sequences of the light chain (SEQ ID NO: 28) and heavy chain (SEQ ID NO: 30) of modified anti-HER2 antibody 2.

FIG. 19 shows the amino acid sequences of the light chain (SEQ ID NO: 31) and heavy chain (SEQ ID NO: 32) of an anti-CD33 antibody.

FIG. 20 shows the amino acid sequences of the light chain (SEQ ID NO: 33) and heavy chain (SEQ ID NO: 34) of an anti-EphA2 antibody.

FIG. 21 shows the amino acid sequences of the light chain (SEQ ID NO: 35) and heavy chain (SEQ ID NO: 36) of an anti-CDH6 antibody.

FIG. 22 demonstrates anti-tumor effect of intravenous administration of anti-HER2 antibody 2-CDN conjugates (11) and (12). In the graph, the line with solid squares corresponds to a group with a vehicle, the line with open triangles to a group with administration of anti-HER2 antibody 2-CDN conjugate (11), and the line with open circles to a group with administration of anti-HER2 antibody 2-CDN conjugate (12).

DESCRIPTION OF EMBODIMENTS

Figure 23:
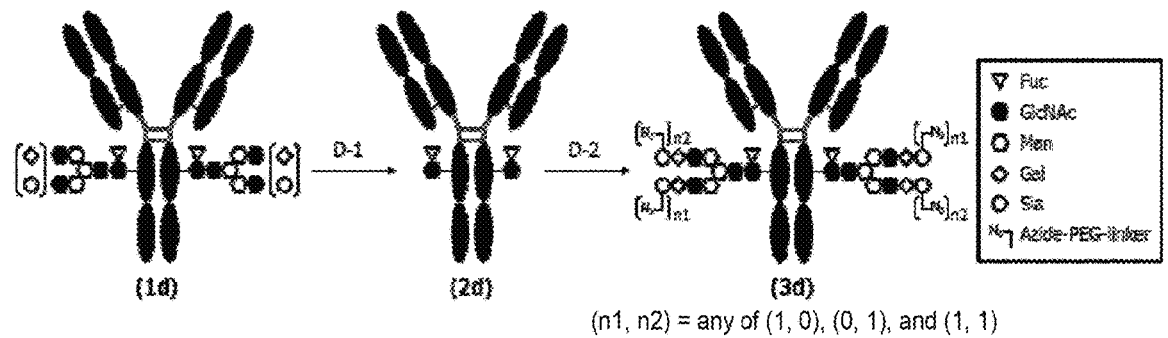
FIG. 23 shows the Formula for Scheme D: Production of Glycan-Remodeled Antibody, wherein the Glycan-remodeled antibodies may be produced by using a method shown in the formula, for example, on the basis of a method described in WO 2018/003983.

The present invention relates to novel CDN derivatives having STING agonist activity and antibody-drug conjugates thereof, and use of any of them. The novel CDN derivatives of the present invention have STING agonist activity, and activate immune cells to induce production of interferons and cytokines. The novel CDN derivatives of the present invention exert anti-tumor effect through the activation of immune cells. The novel CDN derivatives may be directly administered to targeted tissue whose immune functions are intended to be activated, or linked to an antibody capable of recognizing and binding to target cells (e.g., tumor cells or immune cells) via any linker and systemically administered.

STING (Stimulator of Interferon Genes) is a transmembrane adaptor protein localized in endoplasmic reticula. STING is known to exhibit congenital polymorphism with high frequency (PLOS One, 2013 Oct. 21, 8 (10), e77846). Known as mutated forms of STING are, for example, R232H mutation, which is mutation of the amino acid at position 232 from arginine (R) to histidine (H), and HAQ mutation, which is mutation of arginine (R) at position 71 to histidine (H), glycine (G) at position 230 to alanine (A), and arginine (R) at position 293 to glutamine (Q). Such STING polymorphs are known to cause difference in the intensity of response induced by STING agonist stimulation such as cytokine production levels (Genes and Immunity, 2011, 12, 263-269). Therefore, possession of activities against different types of STING is desired for stable action of a STING agonist in humans.

Herein, "cancer", "carcinoma", and "tumor" are used for the same meaning.

In the present invention, "immune activation activity" refers to causing in some form of activation of immune cells involved in anti-tumor immunity such as monocytes, macrophages, dendritic cells, T cells, B cells, NK cells, and neutrophils, for example, causing any structural or functional change to immune cells, including production of cytokines and chemokines, increased expression of immunostimulatory markers, decreased expression of immunosuppressive markers, the alteration of the intracellular signaling system such as phosphorylation, and altered gene expression. The meaning of the term also encompasses the phenomenon that tumor cells cause a change to induce anti-tumor immunity, such as induction of production of cytokines and chemokines that induce activation or migration of immune cells, enhancement of sensitivity to immune cells, and so on.

In the present invention, "anti-tumor effect" refers to inducing the decrease or regression of tumor by the direct or indirect influence of a drug on tumor cells. Referred to as anti-tumor effect are, for example, causing reduction of the number of tumor cells, injury of tumor cells, or regression of tumor, for example, through the phenomenon that a drug directly causes injury to tumor cells, that tumor cells activate anti-tumor immunity through stimulation by a drug, or that a drug delivered to a tumor cell is, for example, released out of the cell and activates anti-tumor immunity around the tumor cell.

In the present invention, "cytotoxicactivity" refers to causing a pathological change in some form to cells, specifically, causing, not only direct damages, but also any structural or functional damage to cells, such as cleavage of DNA, formation of nucleotide dimers, cleavage of chromosomes, damage of the mitotic apparatus, and lowered activity of enzymes.

In the present invention, "cells" include cells in animals and cultured cells.

Herein, "halogen atom", refers to a fluorine atom, a chlorine atom, a bromine atom, or an iodine atom.

Herein, "C1-C6 alkyl group" refers to a linear or branched alkyl group having one to six carbon atoms. "C1-C6 alkyl group" may include cyclopropane on the alkyl group, unless the total number of carbon atoms exceeds six. Examples of "C1-C6 alkyl group" may include, but are not limited to, the following structures:

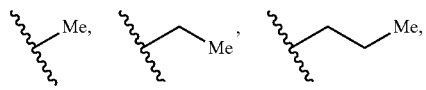

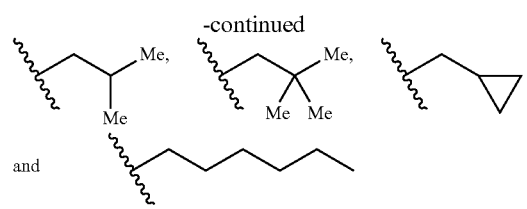

wherein each wavy line indicates a position of substitution.

Herein, "C2-C6 alkenyl group" refers to a linear or branched alkenyl group having two to six carbon atoms.

Herein, "C2-C6 alkynyl group" refers to a linear or branched alkynyl group having two to six carbon atoms.

Herein, "C3-C6 cycloalkyl group" refers to a saturated cyclic hydrocarbon group having three to six carbon atoms. "C3-C6 cycloalkyl group" may be substituted with a plurality of alkyl groups, unless the total number of carbon atoms exceeds six. Examples of "C3-C6 cycloalkyl group" may include, but are not limited to, the following structures:

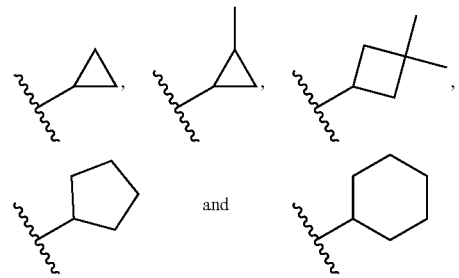

wherein each wavy line indicates a position of substitution.

Herein, "hydroxy C1-C6 alkyl group" refers to an alkyl group in which a linear or branched alkyl group having one to six carbon atoms is substituted with one or two hydroxy groups at any position. "Hydroxy C1-C6 alkyl group" may include cyclopropane on the alkyl group, unless the total number of carbon atoms exceeds six. Examples of "hydroxy C1-C6 alkyl group" may include, but are not limited to, the following structures:

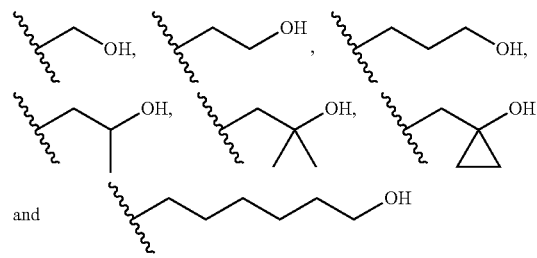

wherein each wavy line indicates a position of substitution.

In the present invention, "amino C1-C6 alkyl group" refers to an alkyl group in which a linear or branched alkyl group having one to six carbon atoms is substituted with one or two amino groups at any position. "Amino C1-C6 alkyl group" may include cyclopropane on the alkyl group, unless the total number of carbon atoms exceeds six. Examples of "amino C1-C6 alkyl group" may include, but are not limited to, the following structures:

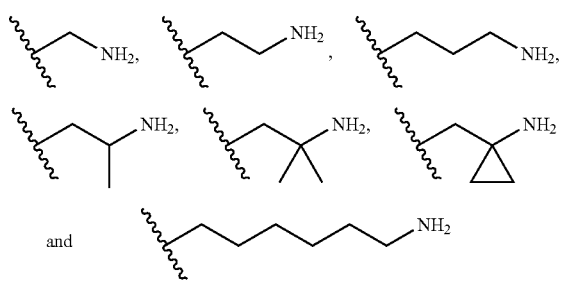

wherein each wavy line indicates a position of substitution.

<1. Novel CDN Derivative>

The novel CDN derivative of the present invention has a structure represented by formula (Ia):

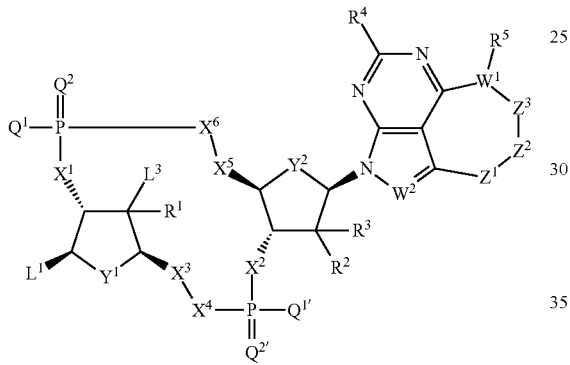

$L^1$ represents a group selected from the group consisting of the following formulas:

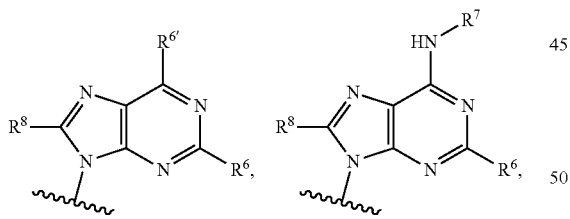

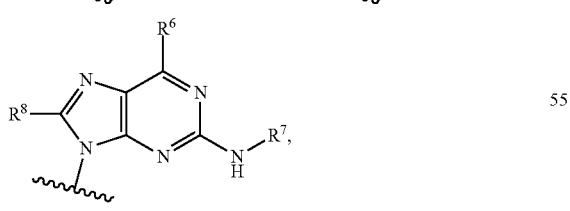

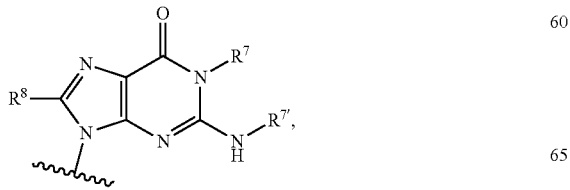

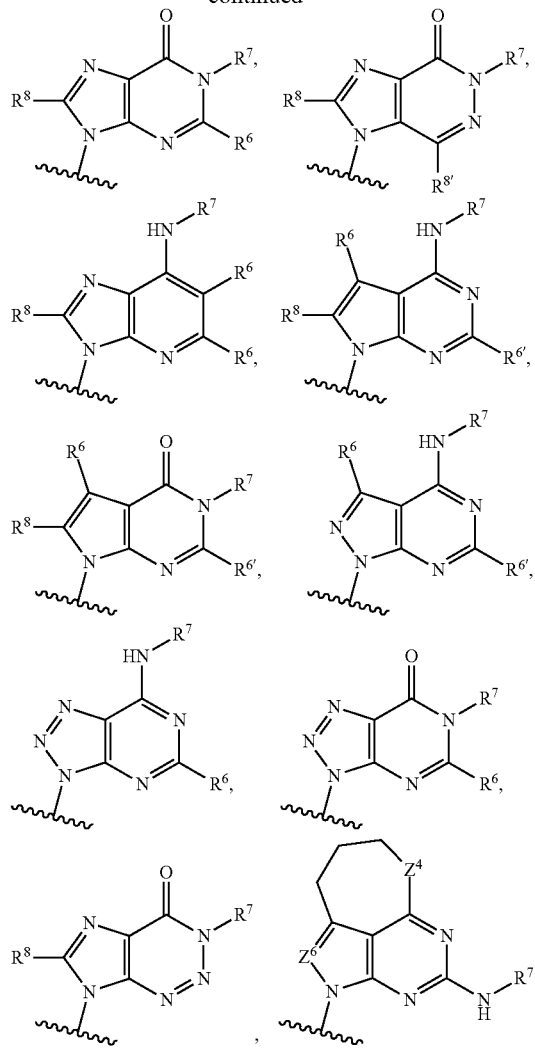

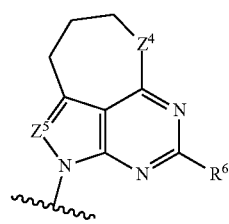

and and optionally substituted at any position with one to three groups selected from the group consisting of a hydroxy group, —NH$_2$, a 2-hydroxyacetylaminomethyl group, and a 2-[(2-hydroxyacetyl)amino]ethyl group, wherein $R^6$ and $R^{6'}$ each independently represent a hydrogen atom, a halogen atom, a hydroxy group, —NH$_2$, a C1-C6 alkyl group, a C2-C6 alkenyl group, or a C2-C6 alkynyl group;

$R^7$ and $R^{7'}$ each independently represent a hydrogen atom or a C1-C6 alkyl group, wherein the C1-C6 alkyl group is optionally substituted with one or two substituents selected from the group consisting of a halogen atom and an oxo group;

$R^8$ and $R^{8'}$ each independently represent a hydrogen atom or a halogen atom;

$Z^4$ represents —$CH_2$—, —NH—, or an oxygen atom; and $Z^5$ represents a nitrogen atom or —CH=.

$L^1$ represents a group selected from the group consisting of the following formulas:

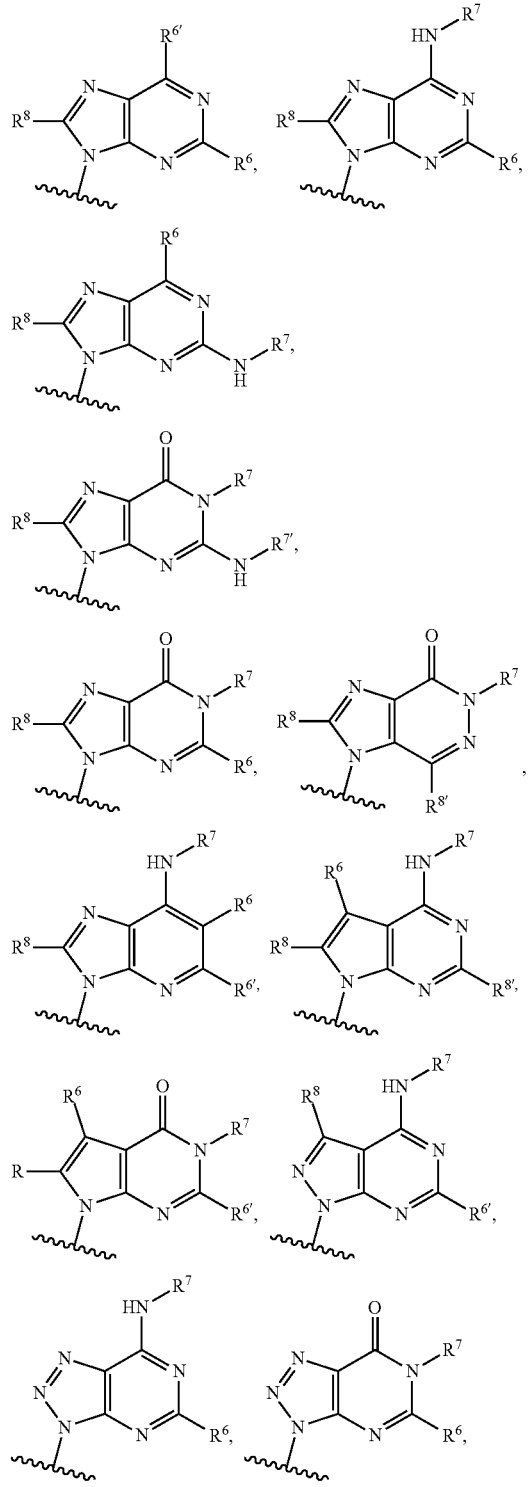

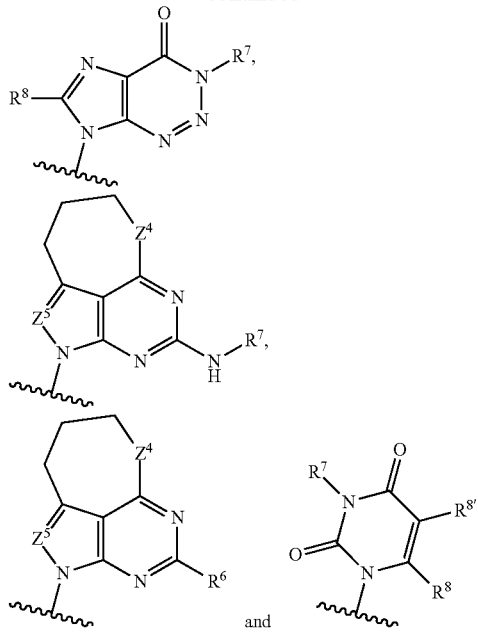

and optionally substituted at any position with one to three groups selected from the group consisting of a hydroxy group, —$NH_2$, a 2-hydroxyacetylaminomethyl group, and a 2-[(2-hydroxyacetyl)amino]ethyl group, wherein $R^6$ and $R^{6'}$ each independently represent a hydrogen atom, a halogen atom, a hydroxy group, —$NH_2$, a C1-C6 alkyl group, a C2-C6 alkenyl group, or a C2-C6 alkynyl group;

$R^7$ and $R^{7'}$ each independently represent a hydrogen atom or a C1-C6 alkyl group, wherein the C1-C6 alkyl group is optionally substituted with one or two substituents selected from the group consisting of a halogen atom and an oxo group;

$R^8$ and $R^{8'}$ each independently represent a hydrogen atom or a halogen atom;

$Z^4$ represents —$CH_2$—, —NH—, or an oxygen atom; and $Z^5$ represents a nitrogen atom or —CH=.

$L^1$ is preferably a group selected from the group consisting of the following formulas:

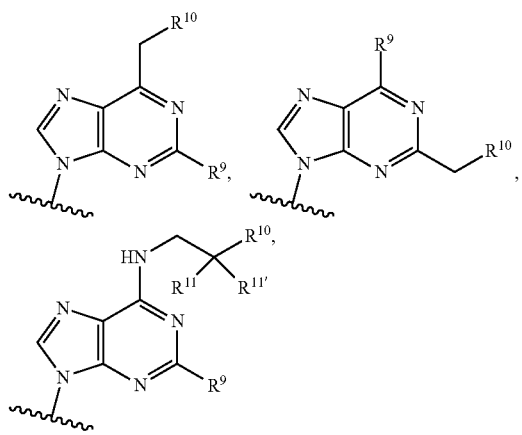

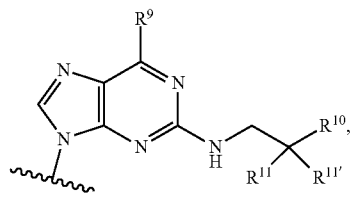
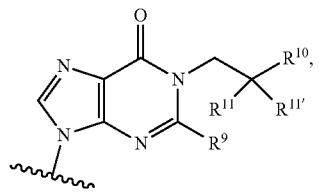
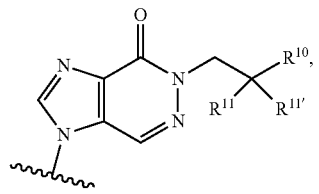
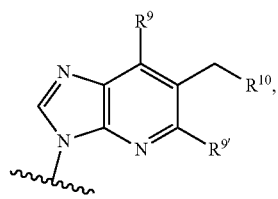
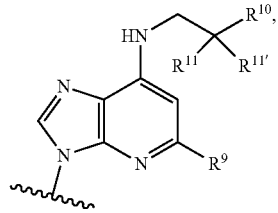
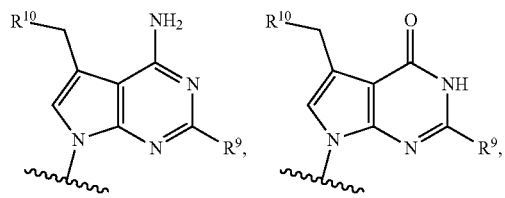
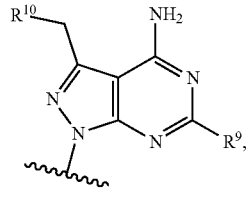
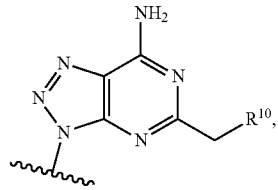

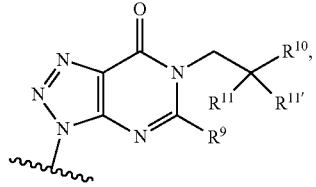
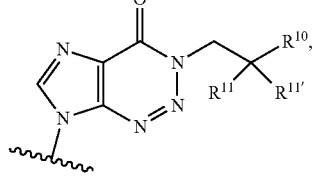
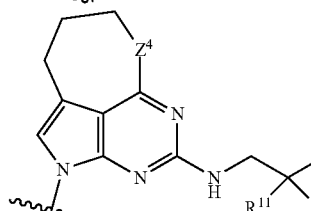
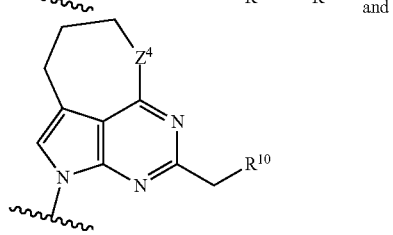

wherein $R^9$ and $R^{9'}$ each represent a hydrogen atom, a halogen atom, a hydroxy group, or $-NH_2$;

$R^{10}$ represents a hydroxy group, $-NH_2$, $-NHC(=O)CH_2OH$, $-CH_2NHC(=O)CH_2OH$, $-CH_2CH_2NHC(=O)CH_2OH$, a hydroxy C1-C3 alkyl group, or an amino C1-C3 alkyl group;

$R^{11}$ and $R^{11'}$ each independently represent a hydrogen atom, a fluorine atom, or a methyl group, or $R^{11}$ and $R^{11'}$ bond together to form cyclopropane; and $Z^4$ represents $-CH_2-$, $-NH-$, or an oxygen atom.

$L^1$ is preferably a group selected from the group consisting of the following formulas:

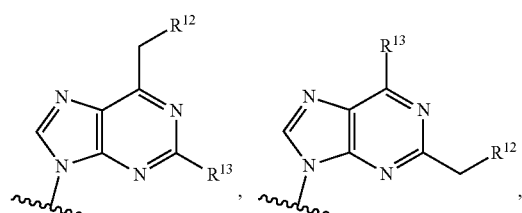
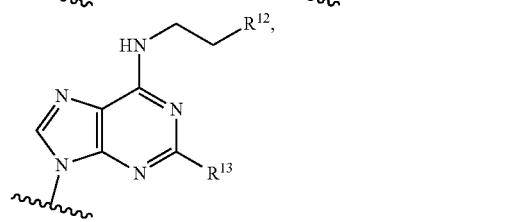

-continued
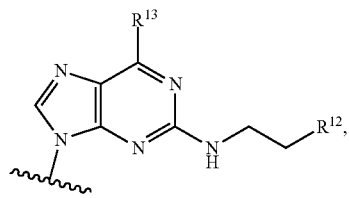
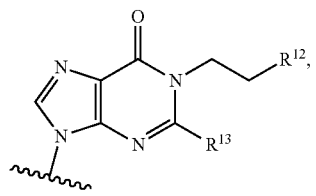
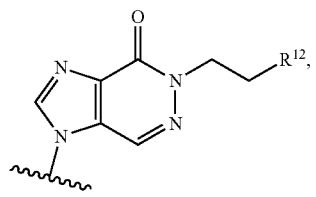
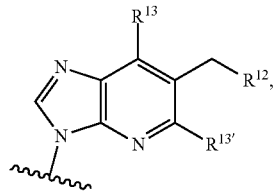
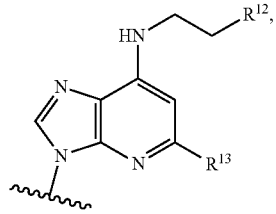
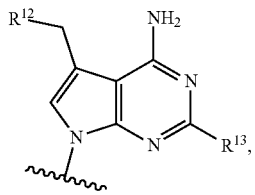
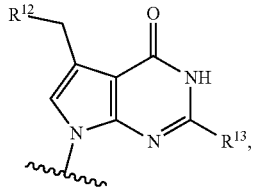
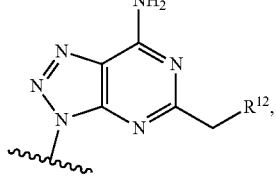
-continued
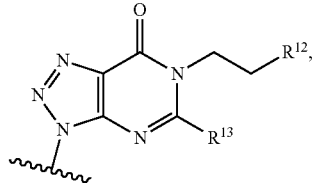
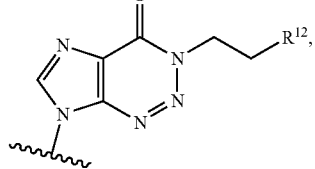
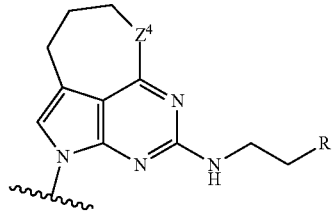
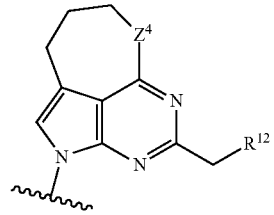
wherein
$R^{13}$ and $R^{13'}$ each independently represent a hydrogen atom, a hydroxy group, or —NH$_2$;
$R^{12}$ represents a hydroxy group, —NH$_2$, —CH$_2$OH, —NHC(=O)CH$_2$OH, —CH$_2$NHC(=O)CH$_2$OH, or —CH$_2$CH$_2$NHC(=O)CH$_2$OH; and
$Z^4$ is as defined above.
Further, $L^1$ is preferably a group selected from the group consisting of the following formulas:
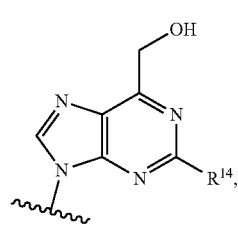 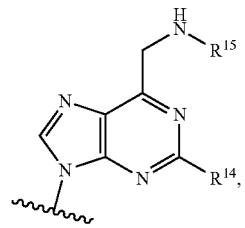
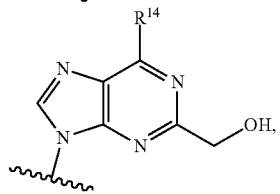
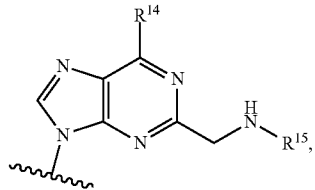

-continued

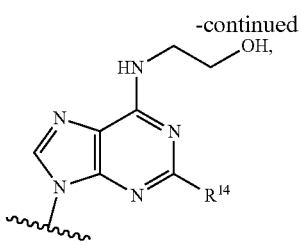

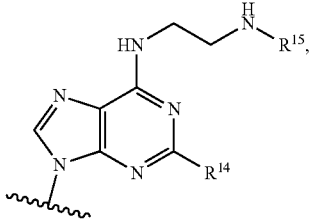

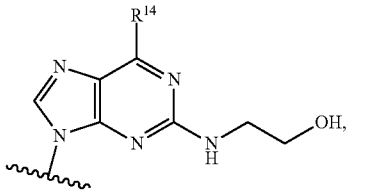

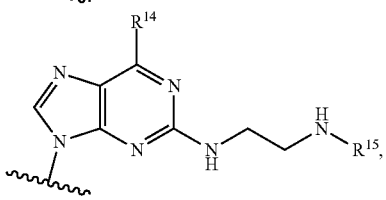

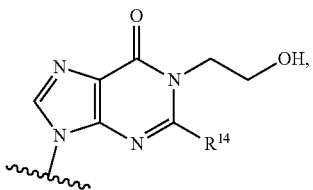

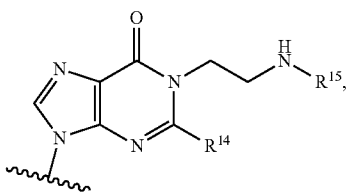

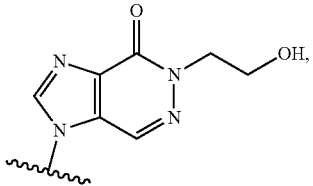

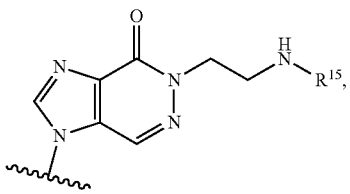

-continued

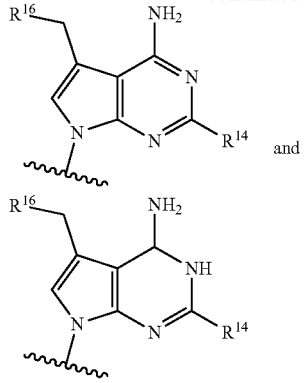

wherein
$R^{14}$ represents a hydrogen atom or —$NH_2$;
$R^{15}$ represents a hydrogen atom or —C(=O)$CH_2OH$; and
$R^{16}$ represents a hydroxy group, —$NH_2$, —$CH_2OH$, —$CH_2CH_2OH$, —$CH_2NH_2$, or —$CH_2CH_2NH_2$.

$L^1$ is more preferably a group selected from the group consisting of the following formulas:

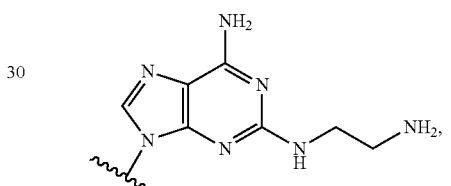

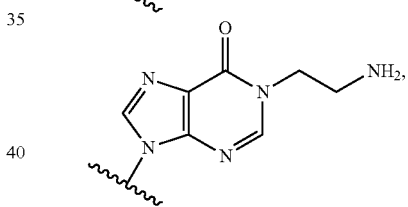

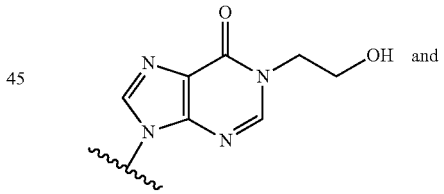

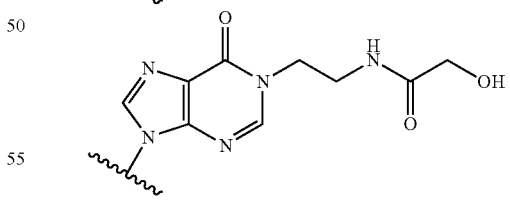

$L^3$ is selected from a hydrogen atom, a halogen atom, —$NH_2$, a hydroxy C1-C3 alkyl group, and an amino C1-C3 alkyl group.

$Q^1$ and $Q^{1'}$ each independently represent a hydroxy group, a thiol group, or a borano group ($BH_3^-$). $Q^1$ is preferably a hydroxy group or a thiol group. $Q^{1'}$ is preferably a hydroxy group or a thiol group. More preferably, the combination of $Q^1$ and $Q^{1'}$ is such that $Q^1$ and $Q^{1'}$ are each a thiol group, or such that $Q^1$ and $Q^{1'}$ are each a hydroxy group.

$Q^2$ and $Q^{2'}$ each independently represent an oxygen atom or a sulfur atom. Preferably, $Q^2$ and $Q^{2'}$ are each an oxygen atom, or each a sulfur atom.

The combination of $Q^1$ and $Q^2$ is preferably such that $Q^1$ is a thiol group and $Q^2$ is an oxygen atom, or such that $Q^1$ is a thiol group and $Q^2$ is a sulfur atom.

The combination of $Q^{1'}$ and $Q^{2'}$ is preferably such that $Q^{1'}$ is a thiol group and $Q^{2'}$ is an oxygen atom, or such that $Q^{1'}$ is a hydroxy group and $Q^{2'}$ is an oxygen atom, or such that $Q^{1'}$ is a thiol group and $Q^{2'}$ is a sulfur atom.

$X^1$ and $X^2$ each independently represent an oxygen atom, a sulfur atom, or —$CH_2$—. $X^1$ is preferably an oxygen atom. $X^2$ is preferably an oxygen atom. More preferably, $X^1$ and $X^2$ are each an oxygen atom.

$Y^1$ and $Y^2$ each represent an oxygen atom or —$CH_2$—. $Y^1$ is preferably an oxygen atom. $Y^2$ is preferably an oxygen atom. More preferably, $Y^1$ and $Y^2$ are each an oxygen atom.

$X^3$ and $X^4$ represent a group selected from (iii) and (iv):
(iii) when $Y^1$ is an oxygen atom, $X^3$-$X^4$ represents —$CH_2$—O—, —$CH_2$—S—, —$CH_2$—$CH_2$—, or —$CH_2$—$CF_2$—; and
(iv) when $Y^1$ is —$CH_2$—, $X^3$-$X^4$ represents —O—$CH_2$—.

$X^3$ and $X^4$ are preferably -$CH_2$—O— in (iii).

$X^5$ and $X^6$ represent a group selected from (v) and (vi):
(v) when $Y^2$ is an oxygen atom, $X^5$-$X^6$ represents —$CH_2$—O—, —$CH_2$—S—, —$CH_2$—$CH_2$—, or —$CH_2$—$CF_2$—; and
(vi) when $Y^2$ is —$CH_2$—, $X^3$-$X^6$ represents —O—$CH_2$—.

$X^5$ and $X^6$ are preferably -$CH_2$—O— in (v).

$R^1$, $R^2$ and $R^3$ each independently represent a hydrogen atom, a halogen atom, —OR', —OC(=O)R', —$N_3$, —NHR', —NR'R", or —NHC(=O)R', wherein R' represents a hydrogen atom, a C1-C6 alkyl group, a C2-C6 alkenyl group, a C2-C6 alkynyl group, or a C3-C6 cycloalkyl group, the C1-C6 alkyl group, C2-C6 alkenyl group, or C2-C6 alkynyl group is optionally substituted with one to six halogen atoms, and R" represents a C1-C6 alkyl group, a C2-C6 alkenyl group, a C2-C6 alkynyl group, or a C3-C6 cycloalkyl group.

$R^1$ is preferably a hydrogen atom, a hydroxy group, or a fluorine atom.

$R^2$ is preferably a hydrogen atom, a hydroxy group, or a fluorine atom.

$R^3$ is preferably a hydrogen atom, a hydroxy group, or a fluorine atom.

$W^1$ represents a nitrogen atom, an oxygen atom, a sulfur atom, or —CH—.

$R^5$ represents a group selected from (vii) to (x):
(vii) when $W^1$ is a nitrogen atom, $R^5$ represents a hydrogen atom, a C1-C6 alkyl group, a hydroxy C1-C6 alkyl group, or an amino C1-C6 alkyl group;
(viii) when $W^1$ is an oxygen atom, $R^5$ is absent;
(ix) when $W^1$ is a sulfur atom, $R^5$ is absent; and
(x) when $W^1$ is —CH—, $R^5$ represents a hydrogen atom, a halogen atom, a hydroxy group, —$NH_2$, or a C1-C6 alkyl group.

When $W^1$ is a nitrogen atom, $R^5$ is preferably a hydrogen atom. When $W^1$ is —CH—, $R^5$ is preferably a hydrogen atom.

$W^2$ represents a nitrogen atom or —CH=. $W^2$ is preferably -CH=.

$R^4$ represents a hydrogen atom, a halogen atom, or —$NH_2$. $R^4$ is preferably a hydrogen atom.

$Z^1$—$Z^2$—$Z^3$ together represents —$CH_2$—$CH_2$—$CH_2$—, —$CH_2$—$CH_2$—R'''—, —CH=CH—$CH_2$—, —CH=CX—$CH_2$—, —CX=CH—$CH_2$—, —CX=CX—$CH_2$—, —C(=O)—$CH_2$—$CH_2$—, —$CH_2$—$CH_2$—C(=O)—, —$CH_2$—CH($CH_3$)—$CH_2$—, or —$CH_2$—CH($CH_3$)—, wherein R" represents —O— or —$CH_2$—$CH_2$— and X represents a halogen atom, or a group represented by either one of the following formulas:

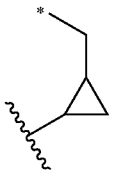 and 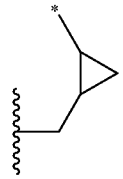

wherein
each asterisk indicates bonding to $W^1$, and each wavy line indicates bonding to the carbon atom of =C—.

$Z^1$, $Z^2$, and $Z^3$ preferably together form —$CH_2$—$CH_2$—$CH_2$—, —CH=CH—$CH_2$—, —$CH_2$—CH($CH_3$)—$CH_2$—, —$CH_2$—$CH_2$—CH($CH_3$)—, or —$CH_2$—$CH_2$—R'''—, wherein R''' represents —O— or —$CH_2$—$CH_2$—.

The novel CDN derivative of the present invention preferably has a structure represented by the following formula:

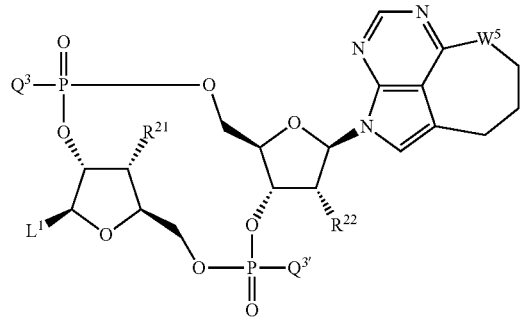

$L^1$ is as defined above.

$Q^3$ and $Q^{3'}$ each independently represent a hydroxy group or a thiol group. Preferably, $Q^3$ and $Q^{3'}$ are each a thiol group.

$R^{21}$ and $R^{22}$ each independently represent a hydroxy group or a fluorine atom. $R^{21}$ is preferably a hydroxy group. $R^{22}$ is preferably a fluorine atom.

$W^5$ represents —NH— or a sulfur atom.

Methods for producing the novel CDN derivative of the present invention are described later in <3. Production Methods>.

<2. Antibody-Drug Conjugate>

The novel CDN derivative of the present invention may be directly administered to targeted tissue (e.g., intratumoral administration), or administered as an antibody-drug conjugate in which the CDN derivative is linked to an antibody capable of recognizing and binding to target cells (e.g., tumor cells or immune cells) via any linker.

The antibody-drug conjugate of the present invention is represented by formula (II):

(II)

Ab—[L—D]$_{m1}$ $m^1$ represents the number of conjugated drug molecules per antibody molecule in the antibody-drug conjugate; Ab represents an antibody or a functional fragment of the antibody; L represents a linker linking Ab and D; D represents the above-described novel CDN derivative (herein, when used as a part of an antibody-drug conjugate, the novel CDN derivative is also referred to as "drug", simply).

Drug D is a compound having an activity to activate immune cells, specifically, STING agonist activity. When a part or the whole of the linker is cleaved off in a target cell (e.g., a tumor cell or an immune cell), drug D in the original structure is liberated to exert immune activation effect. An intended function is exerted through enhancement of the sensitivity of the target cell to immune cells or activation of immune cells via the target cell. The intended function is not limited to a particular function as long as it may be any function relating to STING agonist activity. However, it is preferably anti-tumor activity. That is, drug D linked to an antibody targeting tumor (e.g., an anti-HER2 antibody) via any linker is delivered to targeted cells or tissue, where a part or the whole of the linker is cleaved off, and drug D exerts anti-tumor effect through enhancement of the sensitivity of target cells to immune cells or activation of immune cells via target cells (e.g., production of interferons or cytokines).

Drug D to be conjugated to the antibody-drug conjugate of the present invention is represented by formula (I):

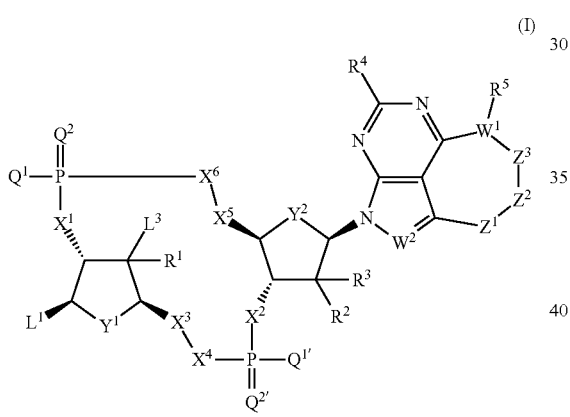

(I)

wherein

L bonds to any-$NH_2$ or hydroxy group included in $L^1$ or $L^2$;

$L^1$ is as specified in <1. Novel CDN Derivative> above;

$L^2$ represents a group selected from (i) and (ii):
  (i) when bonding to L, $L^2$ represents —NHR', a hydroxy C1-C6 alkyl group, or an amino C1-C6 alkyl group, wherein R' represents a hydrogen atom, a C1-C6 alkyl group, a C2-C6 alkenyl group, a C2-C6 alkynyl group, or a C3-C6 cycloalkyl group, and the C1-C6 alkyl group, C2-C6 alkenyl group, or C2-C6 alkynyl group is optionally substituted with one to six halogen atoms; and
  (ii) when not bonding to L, $L^2$ represents a hydrogen atom or a halogen atom;

$Q^1, Q^{1'}, Q^2, Q^{2'}, X^1, X^2, X^3, X^4, X^5, X^6, Y^1, Y^2, R^1, R^2, R^3, R^4, R^5, W^1, W^2, Z^1, Z^2$, and $Z^3$ are as specified in <1. Novel CDN Derivative> above.

When bonding to L, $L^2$ is preferably-$NH_2$, —$CH_2NH_2$, or —$CH_2OH$. When not bonding to L, $L^2$ is preferably a hydrogen atom or a fluorine atom.

Drug D to be used for the novel CDN derivative of the present invention or the antibody-drug conjugate of the present invention is preferably represented by either one of the following two formulas:

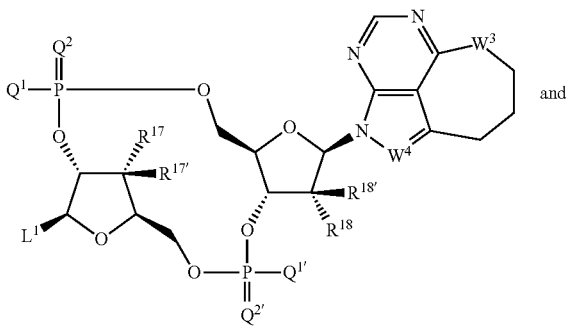

and

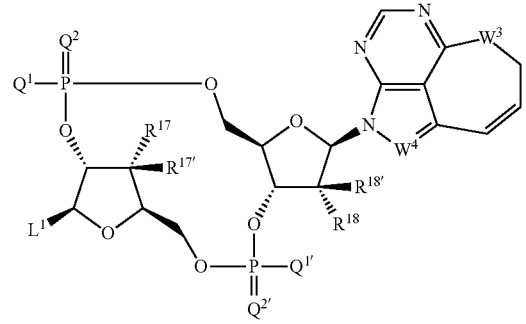

wherein $L^1, Q^1, Q^{1'}, Q^2$, and $Q^{2'}$ are as defined above;

$R^{17}, R^{17'}, R^{18}$, and $R^{18'}$ each independently represent a hydrogen atom, a halogen atom, a hydroxy group, or —$NH_2$;

$W^3$ represents —NH—, an oxygen atom, a sulfur atom, or —$CH_2$—; and $W^4$ represents —CH= or a nitrogen atom.

Drug D to be used for the novel CDN derivative of the present invention or the antibody-drug conjugate of the present invention is preferably represented by either one of the following two formulas:

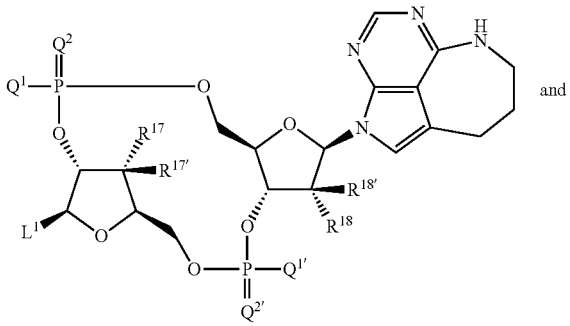

and

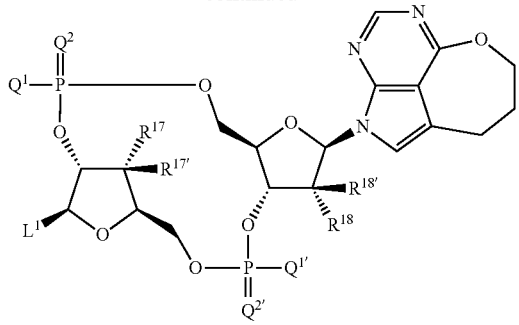

wherein $L^1$, $Q^1$, $Q^{1'}$, $Q^2$, $Q^{1'}$, $R^{17}$, $R^{17'}$, $R^{18}$, and $R^{18'}$ are as defined above.

Drug D to be used for the novel CDN derivative of the present invention or the antibody-drug conjugate of the present invention is preferably represented by any one of the following eight formulas:

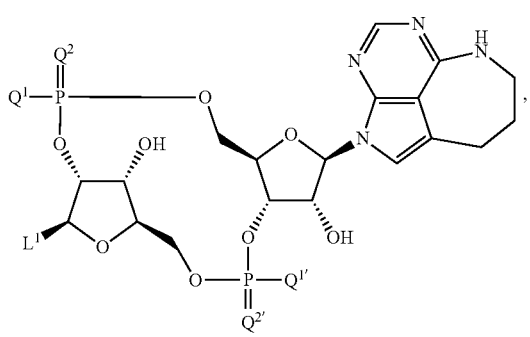

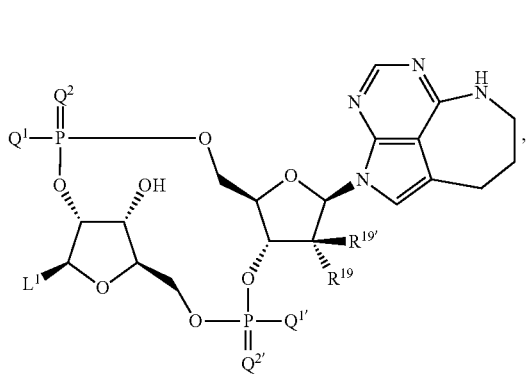

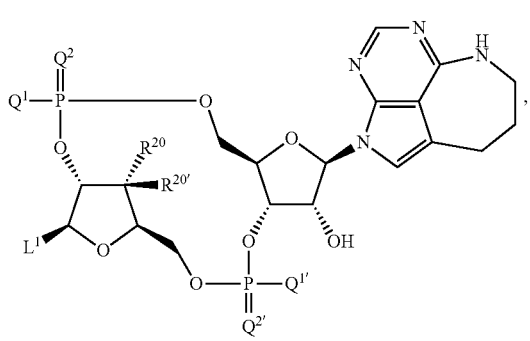

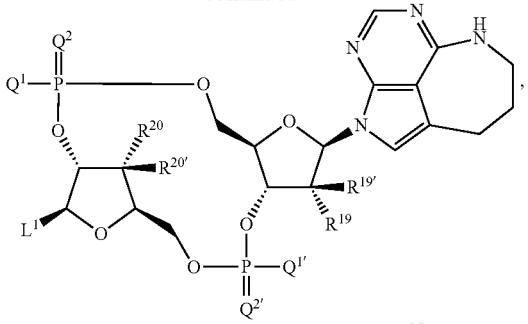

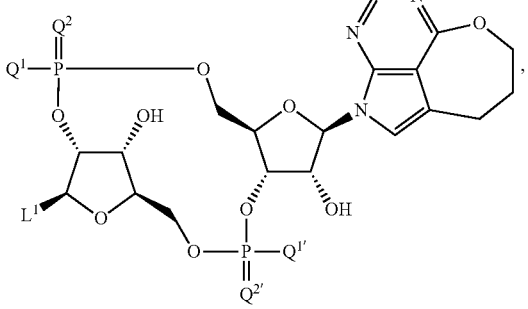

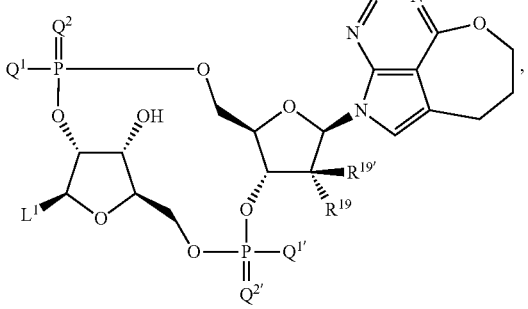

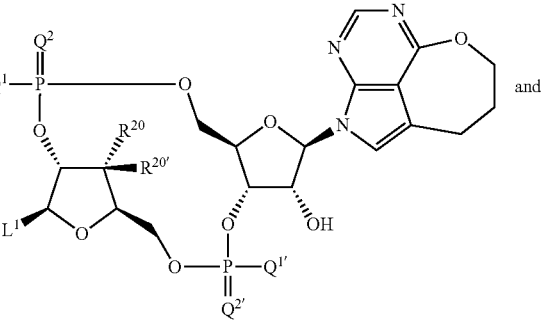

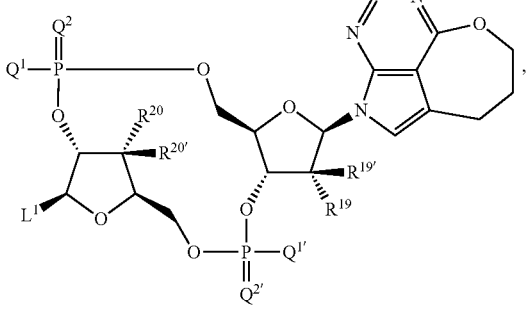

wherein
$L^1$, $Q^1$, $Q^{1'}$, $Q^2$, and $Q^{2'}$ are as defined above; and
$R^{19}$, $R^{19'}$, $R^{20}$, and $R^{20'}$ each independently represent a hydrogen atom or a fluorine atom.

Drug D to be used for the novel CDN derivative of the present invention or the antibody-drug conjugate of the present invention is preferably represented by any one of the following four formulas:

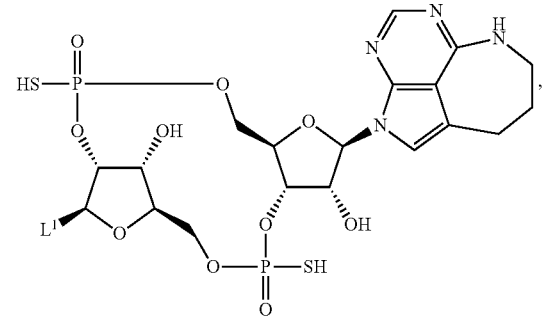

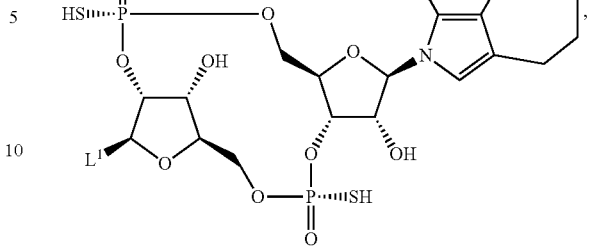

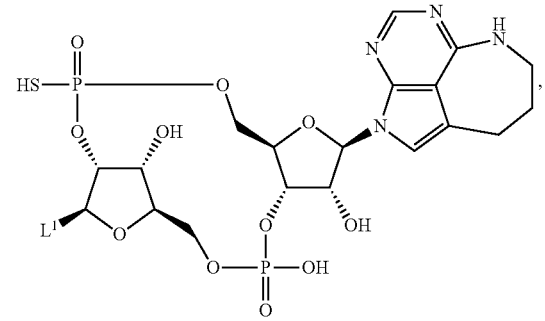

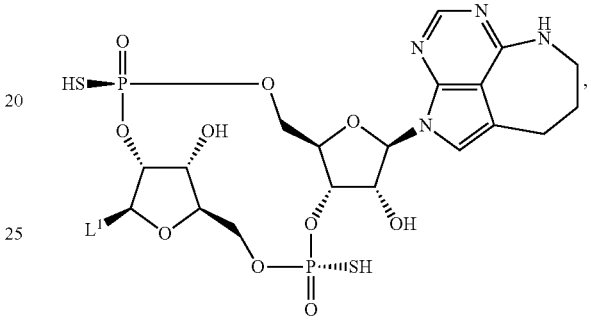

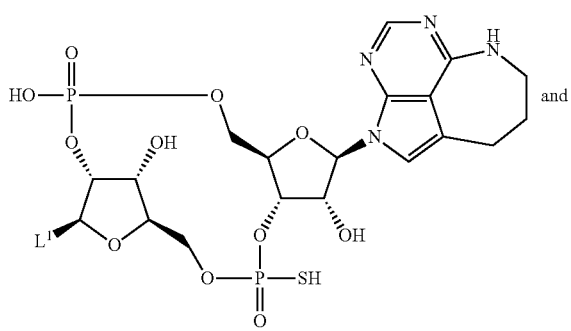

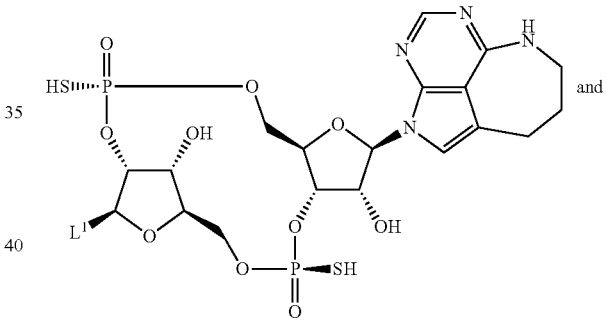

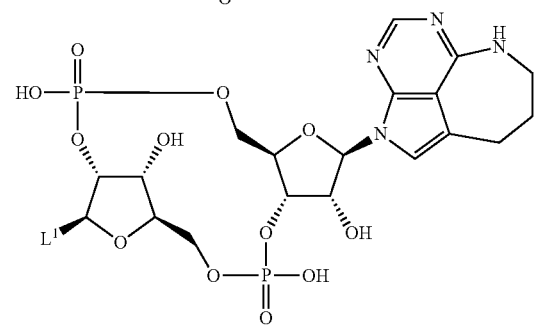

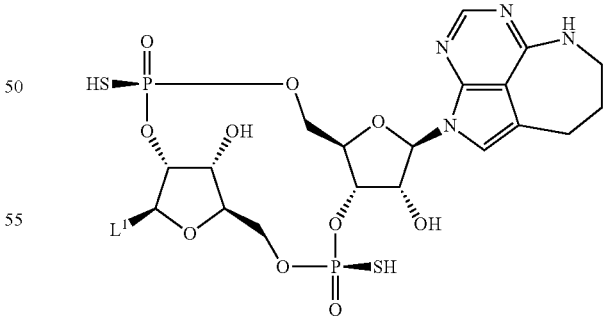

wherein

L¹ is as defined above.

Further, drug D to be used for the novel CDN derivative of the present invention or the antibody-drug conjugate of the present invention is preferably represented by any one of the following four formulas:

wherein

L¹ is as defined above.

Drug D to be used for the novel CDN derivative of the present invention or the antibody-drug conjugate of the present invention is preferably represented by any one of the following four formulas:

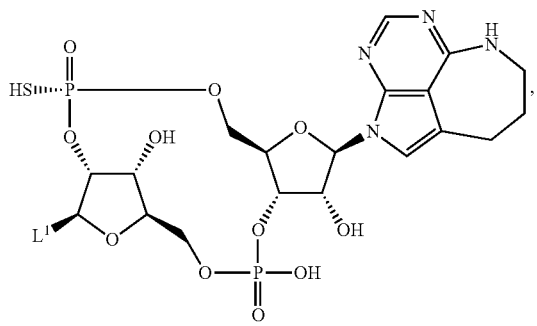

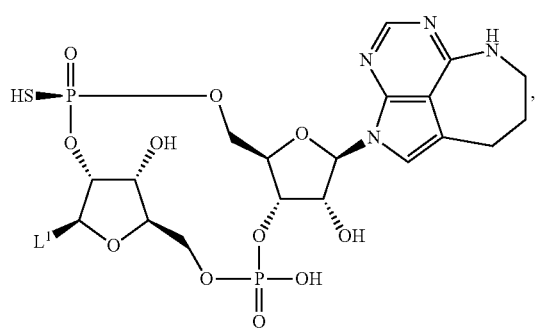

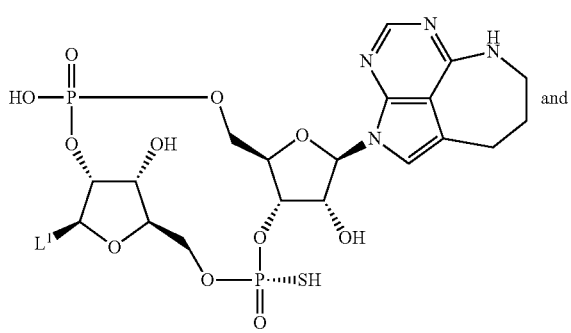

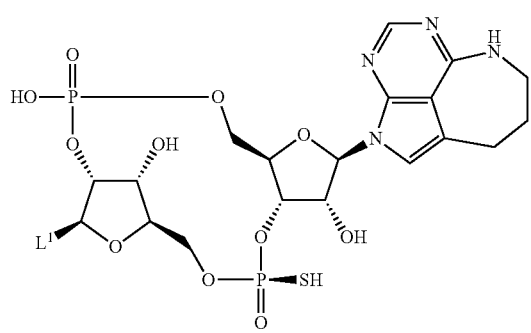

wherein

L¹ is as defined above.

Drug D to be used for the novel CDN derivative of the present invention or the antibody-drug conjugate of the present invention is preferably represented by the following formula:

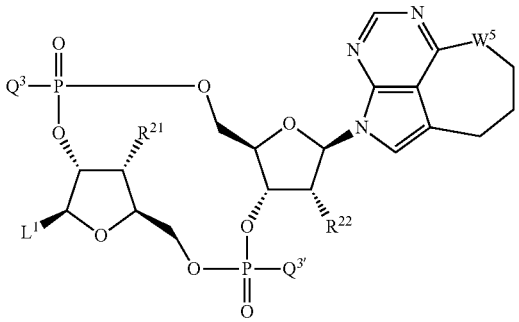

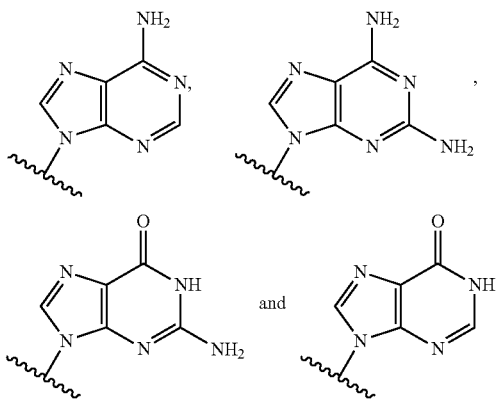

wherein $L^1$, $Q^3$, $Q^{3'}$, $R^{21}$, $R^{22}$, and $W^5$ are as specified in <1. Novel CDN Derivative> above.

In drug D to be used for the novel CDN derivative of the present invention or the antibody-drug conjugate of the present invention, $L^1$ is preferably represented by any one of the following:

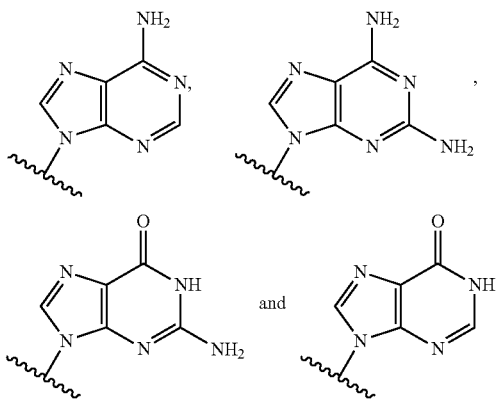

In drug D to be used for the novel CDN derivative of the present invention or the antibody-drug conjugate of the present invention, $L^1$ is preferably represented by any one of the following four formulas:

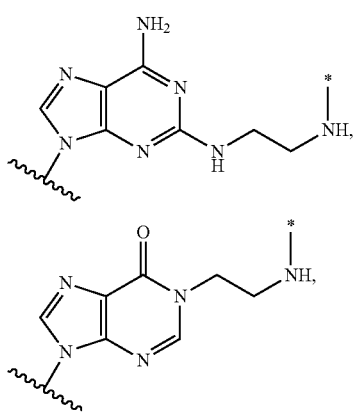

-continued

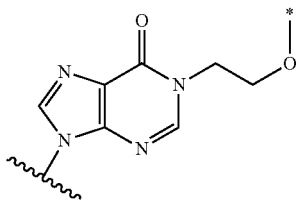
and

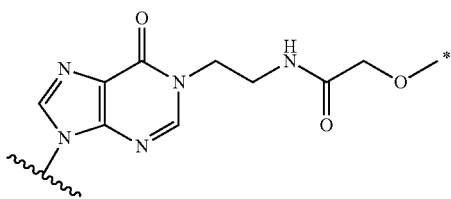

wherein
each asterisk indicates bonding to L.

Drug D to be used for the novel CDN derivative of the present invention or the antibody-drug conjugate of the present invention is preferably represented by any one of the following four formulas:

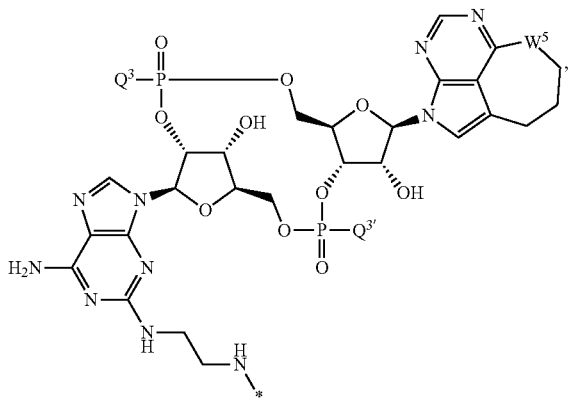
,

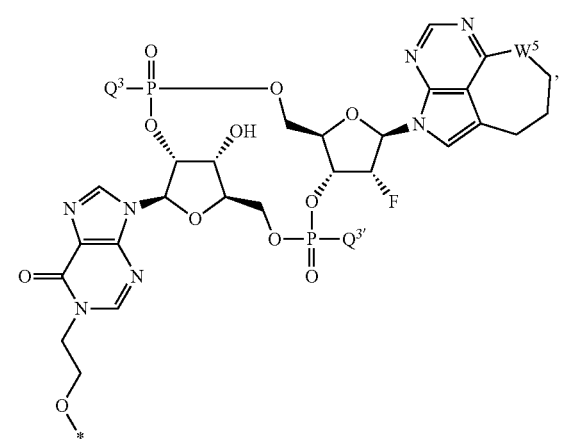
,

-continued

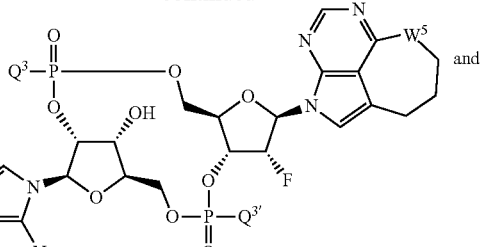
and

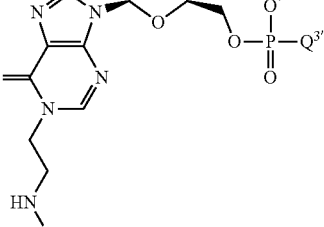

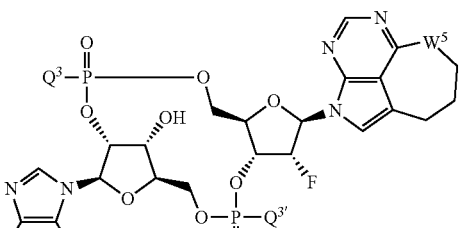

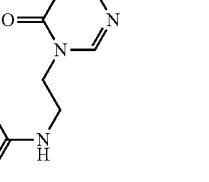

wherein
each asterisk indicates bonding to L; and
$Q^3$, $Q^{3'}$, and $W^5$ are as specified in <1. Novel CDN Derivative> above.

<2.1. Linker Structure>

The linker structure to conjugate the drug to an antibody in the antibody-drug conjugate of the present invention will be described. The linker to be used for the antibody-drug conjugate of the present invention is not limited to a particular linker as long as it may be any linker understood by those skilled in the art as a linker that links an antibody and a drug. Examples of the linker to be used for the antibody-drug conjugate of the present invention may include, but are not limited to, linkers described in Protein Cell, 2018, 9 (1): 33-46, Pharm Res, 2015, 32:3526-3540, and Int. J. Mol. Sci., 2016, 17, 561. The linker may be a linker that is cleaved in vivo, or a linker that is not cleaved in vivo, but is preferably a linker that is cleaved in vivo.

Examples of the linker to be used for the antibody-drug conjugate of the present invention may include, but are not limited to, a linker that binds a drug to a glycan or remodeled glycan in the Fc part of an antibody (hereinafter, occasionally referred to as "glycan conjugation") (e.g., described in WO 2018/003983) and a linker that binds a drug to any amino acid residue (e.g., a cysteine residue or a lysine residue) of an antibody (e.g., described in WO 2014/057687). Examples of modes of the linker that binds a drug to any amino acid residue of an antibody may include, but are not limited to, bonding to the sulfhydryl group (SH group) of cysteine in Ab via a thioether bond (herein, occasionally referred to as "cysteine conjugation"), and bonding to the amino group ($NH_2$ group) of lysine in Ab via an amide bond (hereinafter, occasionally referred to as "lysine conjugation"), and the linker is preferably in the mode of cysteine conjugation.

Preferred linker L in the present invention is represented by the following formula:

-Lb-La-Lp-Lc-* wherein
the asterisk indicates bonding to any amino group or hydroxy group included in $L^1$ or $L^2$ of drug D.

First, Lp will be described.

Lp represents a linker consisting of an amino acid sequence cleavable in vivo or in a target cell (hereinafter, occasionally referred to as a peptide linker), or is absent.

Lp is cleaved off, for example, by the action of an enzyme such as peptidase and esterase. Lp is a peptide composed of two to seven (preferably two to four) amino acids. Lp forms an amide bond at the N terminus with the carbonyl group at the right end of La, and forms an amide bond at the C terminus with an amino group (—NH—) of Lc. The amide bond in the C-terminal side of Lp is cleaved by the enzyme such as peptidase.

The amino acids constituting Lp are not limited to particular amino acids, and, for example, are L- or D-amino acids, and preferably are L-amino acids. The amino acids may be not only α-amino acids, but may include an amino acid with structure, for example, of β-alanine, ε-aminocaproic acid, or γ-aminobutyric acid, and may further include a non-natural amino acid such as an N-methylated amino acid. The amino acid sequence of Lp is not limited to a particular amino acid sequence, and examples of amino acids that constitute Lp may include glycine (Gly; G), valine (Val; V), alanine (Ala; A), phenylalanine (Phe; F), glutamic acid (Glu; E), isoleucine (Ile; I), proline (Pro; P), citrulline (Cit), leucine (Leu; L), methionine (Met; M), serine (Ser; S), lysine (Lys; K), and aspartic acid (Asp; D). Preferred among them are glycine (Gly; G), valine (Val; V), alanine (Ala; A), phenylalanine (Phe: F), and citrulline (Cit). Any of these amino acids may appear multiple times, and Lp has an amino acid sequence including freely selected amino acids. The pattern of drug liberation may be controlled via amino acid type.

Specific examples of Lp may include -GGVA-, -VA-, -GGFG-, -FG-, -GGPI-, -PI-, -GGVCit-, -VCit-, -GGVK-, -VK-, -GGFCit-, -FCit-, -GGFM-, -FM-, -GGLM-, -LM-, -GGICit-, and -ICit-. Linker Lp is preferably-GGVA-, -VA-, -GGFG-, -FG-, -GGVCit-, -VCit-, -GGFCit-, or -Fcit-. Linker Lp is more preferably-GGVA-, -GGFG, or -GGVCit-. Linker Lp is preferably-GGFG- or -GGPI-.

Next, La will be described.

La represents any one selected from the group consisting of the following:
—C(=O)—(CH$_2$CH$_2$)n$^2$-C(=O)—,
—C(=O)—(CH$_2$CH$_2$)n$^2$-CH$_2$—C(=O)—,
—C(=O)—(CH$_2$CH$_2$)n$^2$-C(=O)—NH—(CH$_2$CH$_2$)n$^3$-C(=O)—,
—C(=O)—(CH$_2$CH$_2$)n$^2$-C(=O)—NH—(CH$_2$CH$_2$)n$^3$-CH$_2$—C(=O)—,
—C(=O)—(CH$_2$CH$_2$)n$^2$-C(=O)—NH—(CH$_2$CH$_2$O) n$^3$-CH$_2$—C(=O)—,
(CH$_2$)n$^4$-O—C(=O)—, and
(CH$_2$)n$^o$—C(=O)— wherein
$n^2$ represents an integer of 1 to 3 (preferably 1 or 2), $n^3$ represents an integer of 1 to 5 (preferably an integer of 2 to 5, more preferably 3 or 4), $n^4$ represents an integer of 0 to 2 (preferably 0 or 1), and $n^o$ represents an integer of 2 to 7 (preferably an integer of 2 to 5, more preferably 2, 3, or 5).

La preferably represents any one selected from the group consisting of the following:
—C(=O)—CH$_2$CH$_2$—C(=O)—,
—C(=O)—CH$_2$CH$_2$—C(=O)—NH—(CH$_2$CH$_2$O)$_3$—CH$_2$—C(=O)—,
—C(=O)—CH$_2$CH$_2$—C(=O)—NH—(CH$_2$CH$_2$O)$_4$—CH$_2$—C(=O)—,
—C(=O)—(CH$_2$CH$_2$)$_2$—C(=O)—,
—C(=O)—CH$_2$CH$_2$—C(=O)—NH—(CH$_2$CH$_2$)$_2$—C(=O)—,
—C(=O)—CH$_2$CH$_2$—C(=O)—NH—(CH$_2$CH$_2$)$_2$—CH$_2$—C(=O)—,
—CH$_2$—OC(=O)—,
—OC(=O)—, and
(CH$_2$)$_5$—C(=O)—.

La is more preferably
—C(=O)—CH$_2$CH$_2$—C(=O)—,
—C(=O)—CH$_2$CH$_2$—C(=O)—NH—(CH$_2$CH$_2$O)$_3$—CH$_2$—C(=O)—,
or
(CH$_2$)$_5$—C(=O)—.

La is even more preferably-C(=O)—CH$_2$CH$_2$—C(=O)—.

Next, Lb will be described.

Lb represents a spacer to be used for the linker of glycan conjugation (herein, also referred to as a "spacer for linker of glycan conjugation"), or a spacer to be used for cysteine conjugation (herein, also referred to as a "spacer for linker of cysteine conjugation").

<When Lb is "Spacer for Linker of Glycan Conjugation">

When Lb is "spacer for linker of glycan conjugation", examples of Lb may include, but are not limited to, a spacer represented by the following formula:

(Lb-1)

or (Lb-2)

or

-continued

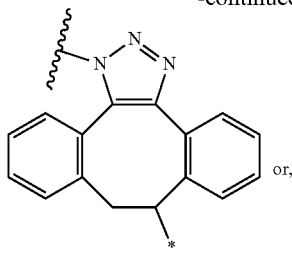
or,

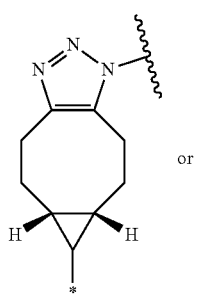
or (Lb-3)

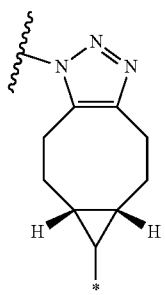

In each structural formula shown above, each asterisk (*) indicates bonding to —(C=O)— or —CH$_2$— at the left end of La, and each wavy line indicates bonding to a glycan or remodeled glycan of Ab.

When any one of Lb-1, Lb-2, and Lb-3 is selected for Lb, the triazole ring site provides structures of geometric isomers, and the Lb moieties include either one of the two structures or a mixture of them. The antibody-drug conjugate of the present invention is capable of bonding a plurality of drug molecules to one antibody molecule. When a plurality of drug molecules is to be bonded to one antibody molecule, it follows that there is a plurality of Lb moieties (e.g., see schematic diagram (1e) of an antibody-drug conjugate shown in Scheme E described later in <3. Production Methods>). When any one of Lb-1, Lb-2, and Lb-3 is selected for Lb and a plurality of Lb moieties is present per antibody molecule (e.g., when m$^2$, which is described later, is 1 or 2), the triazole ring site in each Lb moiety provides structures of geometric isomers, and the Lb moieties include either one of the two structures or a mixture of them.

<When Lb is "Spacer for Linker of Cysteine Conjugation">

When Lb is "spacer for linker of cysteine conjugation", examples of Lb may include, but are not limited to, -(succinimid-3-yl-N)—. In the present invention, "-(succinimid-3-yl-N)—" has a structure represented by the following formula:

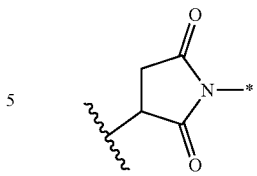

In the structural formula shown above, the asterisk indicates bonding to La, and the wavy line indicates bonding to a side chain of a cysteine residue of an antibody through forming thioether.

Next, Lc will be described.
Lc represents —NH—CH$_2$—, —NH-phenyl group —CH$_2$—O(C=O)—, or —NH-heteroaryl group —CH$_2$—O(C=O)—, or is absent. Here, the phenyl group is preferably a 1,4-phenyl group, and the heteroaryl group is preferably a 2,5-pyridyl group, a 3,6-pyridyl group, a 2,5-pyrimidyl group, or a 2,5-thienyl group. Lc is preferably —NH—CH$_2$— or absent.

More preferred linker L in the present invention is, when the bonding mode of the drug and antibody is "glycan conjugation", $Z^{L1}$—C(=O)—CH$_2$CH$_2$—C(=O)-GGFG-,
$Z^{L1}$—C(=O)—CH$_2$CH$_2$—C(=O)-GGVA-,
ZL$^{L1}$-C(=O)—CH$_2$CH$_2$—C(=O)-GGVCit-,
ZL$^{L1}$-C(=O)—CH$_2$CH$_2$—C(=O)-GGFCit-,
$Z^{L1}$—C(=O)—CH$_2$CH$_2$—C(=O)-GGICit-,
ZL$^{L1}$-C(=O)—CH$_2$CH$_2$—C(=O)-GGFM-,
ZL$^{L1}$-C(=O)—CH$_2$CH$_2$—C(=O)-GGPI-,
$Z^{L1}$—C(=O)—CH$_2$CH$_2$—C(=O)-GGLM-,
ZL$^{L1}$-C(=O)—CH$_2$CH$_2$—C(=O)—FG-,
ZL$^{L1}$-C(=O)—CH$_2$CH$_2$—C(=O)—VA-,
ZL$^{L1}$-C(=O)—CH$_2$CH$_2$—C(=O)-GGFG-NH—CH$_2$—,
ZL$^{L1}$-C(=O)—CH$_2$CH$_2$—C(=O)-GGVA-NH—CH$_2$—,
$Z^{L1}$—C(=O)—CH$_2$CH$_2$—C(=O)-GGVCit-NH—CH$_2$—,
ZL$^{L1}$-C(=O)—CH$_2$CH$_2$—C(=O)-GGFCit-NH—CH$_2$—,
ZL$^{L1}$-C(=O)—CH$_2$CH$_2$—C(=O)—NH—(CH$_2$CH$_2$O)$_3$—CH$_2$—C(=O)—, or
ZL$^{L1}$-C(=O)—CH$_2$CH$_2$—C(=O)—NH—(CH$_2$CH$_2$O)$_4$—CH$_2$—C(=O)—,
wherein $Z^{L1}$1 represents the following structural formula for Lb:

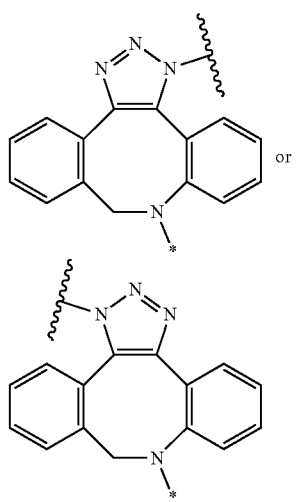

or,
when the bonding mode of the drug and antibody is "cysteine conjugation",
$Z^{L2}$—(CH$_2$)$_5$—C(=O)-GGFG-,
$Z^{L2}$—(CH$_2$)$_5$—C(=O)-GGVA-,
$Z^{L2}$—(CH$_2$)$_5$—C(=O)-GGVCit-,
$Z^{L2}$—(CH$_2$)$_5$—C(=O)-GGFCit-,
$Z^{L2}$—(CH$_2$)$_5$—C(=O)-GGICit-,
$Z^{L2}$—(CH$_2$)$_5$—C(=O)-GGFM-,
$Z^{L2}$—(CH$_2$)$_5$—C(=O)-GGPI-,
$Z^{L2}$—(CH$_2$)$_5$—C(=O)-GGLM-,
$Z^{L2}$—(CH$_2$)$_5$—C(=O)—FG-,
$Z^{L2}$—(CH$_2$)$_5$—C(=O)—VA-,
$Z^{L2}$—(CH$_2$)$_5$—C(=O)-GGFG-NH—CH$_2$—,
$Z^{L2}$—(CH$_2$)$_5$—C(=O)-GGVA-NH—CH$_2$—,
$Z^{L2}$—(CH$_2$)$_5$—C(=O)-GGVCit-NH—CH$_2$—,
$Z^{L2}$—(CH$_2$)$_5$—C(=O)-GGFCit-NH—CH$_2$—,
$Z^{L2}$—(CH$_2$)$_5$—C(=O)—NH—(CH$_2$CH$_2$O)$_3$—CH$_2$—C(=O)—, or
$Z^{L2}$—(CH$_2$)$_5$—C(=O)—NH—(CH$_2$CH$_2$O)$_4$—CH$_2$—C(=O)—,
wherein $Z^{L2}$ represents -(succinimid-3-yl-N)-represented by the following structural formula for Lb:

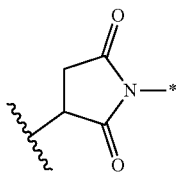 [SMILES: *C1CC(=O)N(*)C1=O]

More preferred linker L in the present invention is such that the bonding mode of the drug and antibody is "glycan conjugation", and linker L is
$Z^{L1}$—C(=O)—CH$_2$CH$_2$—C(=O)-GGFG-NH—CH$_2$—, or
$Z^{L1}$—C(=O)—CH$_2$CH$_2$—C(=O)-GGPI—NH—CH$_2$—,
wherein $Z^{L1}$ represents the following structural formula for Lb:

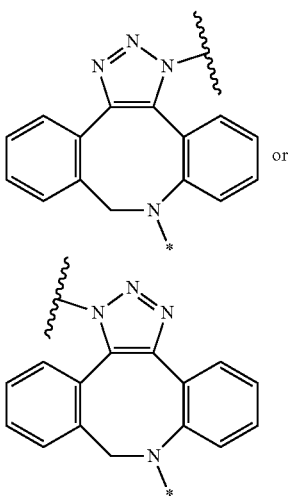

The right end in each of "preferred linker L" and "more preferred linker L" is bonding to any-NH$_2$ or hydroxy group included in L$^1$ or L$^2$ in formula (I).

<2.2. Antibody and Glycan Modification Thereof>
<2.2.1 Antibody>

Herein, "gene" refers to nucleotides including a nucleotide sequence encoding amino acids of protein, or a nucleotide sequence encoding amino acids of protein, or a complementary strand thereof, and the meaning of "gene" encompasses, for example, a polynucleotide, oligonucleotide, DNA, mRNA, cDNA, and RNA as a nucleotide sequence including a nucleotide sequence encoding amino acids of protein or a complementary strand thereof.

Herein, "nucleotides", "polynucleotide", and "nucleotide sequence" have the same meaning as that of "nucleic acid", and the meaning of "nucleotides" or "nucleotide sequence" encompasses, for example, a DNA, RNA, probe, oligonucleotide, polynucleotide, and primer.

Herein, "polypeptide", "peptide", and "protein" are used without any distinction.

Herein, a "functional fragment of an antibody" is also referred to as an "antigen-binding fragment of an antibody", and means a partial fragment of an antibody with binding activity to an antigen, and examples thereof may include, but not limited to, Fab, F(ab')$_2$, Fv, scFv, diabodies, linear antibodies, and multispecific antibodies formed from antibody fragments. In addition, the meaning of an antigen-binding fragment of an antibody encompasses Fab', a monovalent fragment of a variable region of an antibody obtained by treating F(ab')2 under reducing conditions. However, there is no limitation to those molecules and any molecule having binding ability to an antigen is acceptable. Those antigen-binding fragments include not only those obtained by treating a full-length molecule of an antibody protein with an appropriate enzyme, but also proteins produced in appropriate host cells by using an antibody gene which is modified by genetic engineering.

The concept of the functional fragment of the present invention includes a functional fragment that retains well-preserved asparagine (Asn297) to be modified with an N-linked glycan and amino acids around Asn297 in the IgG heavy chain Fc region, and has binding activity to an antigen.

The antibody to be used for the antibody-drug conjugate of the present invention refers to immunoglobulin, and is a molecule including an antigen-binding site that immunospecifically binds to an antigen. The antibody of the present invention may be of any class of IgG, IgE, IgM, IgD, IgA, and IgY, and preferred is IgG. The subclass may be any of IgG1, IgG2, IgG3, IgG4, IgA1, and IgA2, and preferred are IgG1, IgG2, and IgG4 (including antibodies having mutation that affects activities of ADCC and ADCP in the Fc region of an IgG heavy chain).

If IgG1 is used as the isotype of the antibody of the present invention, the effector function may be adjusted by substituting some amino acid residues in the constant region (see WO 88/07089, WO 94/28027, WO 94/29351). Examples of mutants of IgG1 may include, but not limited to, those with IgG1 LALA mutation (IgG1-L234A, L235A). The L234A, L$^{235}$A indicates substitution of leucine with alanine at positions 234 and 235 specified by EU Index numbering (Proceedings of the National Academy of Sciences of the United States of America, Vol. 63, No. 1 (May 15, 1969), pp. 78-85).

The antibody may be derived from any species, and preferred examples of the origin may include, but not limited to, a human, a rat, a mouse, and a rabbit. If the antibody is derived from a species other than the human species, it is preferred to chimeric or humanized antibody by using a well-known technique. The antibody of the present invention may be a polyclonal antibody or a monoclonal antibody, and is preferably a monoclonal antibody. Examples of monoclonal antibodies may include, but not limited to, monoclonal antibodies derived from non-human animals such as rat antibodies, mouse antibodies, and rabbit antibodies; chimeric antibodies; humanized antibodies; human antibodies; functional fragments of them; and modified forms of them.

The antibody is preferably, but not limited to, an antibody targeting tumor cells or immune cells. The antibody is more preferably an antibody targeting tumor cells.

If an antibody targeting tumor cells is used, it is preferred for the antibody to have one or more properties of a property of being capable of recognizing tumor cells, a property of being capable of binding to tumor cells, a property of being incorporated and internalizing in tumor cells, and a property of causing injury to tumor cells. The drug of the present invention to be conjugated to an antibody via a linker has STING agonist activity. The drug of the present invention induces interferon by activating signaling of the interferon regulatory factor-3 (IRF3). Therefore, if an antibody targeting tumor cells is used for the antibody-drug conjugate of the present invention, the antibody-drug conjugate after being administered into the body is delivered to a tumor site and incorporated in cells in tumors, and the linker portion is then cleaved off by peptidase or the like and the drug portion is liberated. The drug portion liberated is inferred to activate anti-tumor immunity and exert anti-tumor effect through STING agonist activity.

The binding ability of the antibody to tumor cells can be confirmed by using flow cytometry. The incorporation of the antibody into tumor cells can be confirmed by using (1) an assay of visualizing an antibody incorporated in cells under a fluorescence microscope with a secondary antibody (fluorescently labeled) that binds to the therapeutic antibody (Cell Death and Differentiation (2008) 15, 751-761), (2) an assay of measuring the intensity of fluorescence incorporated in cells with a secondary antibody (fluorescently labeled) that binds to the therapeutic antibody (Molecular Biology of the Cell, Vol. 15, 5268-5282 December 2004), or (3) a Mab-ZAP assay using an immunotoxin that binds to the therapeutic antibody, wherein the toxin is released upon being incorporated into cells to suppress cell growth (Bio Techniques 28:162-165, January 2000). As the immunotoxin, a recombinant complex protein of a diphtheria toxin catalytic domain and protein G may be used.

In the present invention, "high internalization ability" refers to the situation that the survival rate of targeted antigen-expressing cells (e.g., HER2-expressing cells if an anti-HER2 antibody is used) with addition of an antibody of interest and a saporin-labeled anti-mouse or rat IgG antibody (represented as a relative rate to the cell survival rate without addition of the antibody as 100%) is preferably 70% or less, and more preferably 60% or less.

If an antibody targeting tumor cells is used for the antibody-drug conjugate of the present invention, it is preferred but not essential that the antibody itself should have anti-tumor effect. It is preferable that the antibody to be used for the antibody-drug conjugate of the present invention have a characteristic of internalization, which involves migration into tumor cells.

The anti-tumor activity of the drug or antibody-drug conjugate refers to cytotoxic activity or anti-cellular effect against tumor cells, or regression of tumor volume. The anti-tumor activity can be confirmed by using any known in vitro or in vivo evaluation system.

The immune activation activity of the drug and antibody-drug conjugate refers to enhancement of sensitivity of tumor cells against immune cells or activation of immune cells via tumor cells. The immune activation activity can be confirmed by using any known in vitro or in vivo evaluation system.

Examples of the antibody to be used in the present invention may include, but not limited to an anti-HER2 antibody, an anti-HER3 antibody, an anti-DLL3 antibody, an anti-FAP antibody, an anti-CDH11 antibody, an anti-CDH6 antibody, an anti-A33 antibody, an anti-CanAg antibody, an anti-CD19 antibody, an anti-CD20 antibody, an anti-CD22 antibody, an anti-CD30 antibody, an anti-CD33 antibody, an anti-CD56 antibody, an anti-CD70 antibody, an anti-CD98 antibody, an anti-TROP2 antibody, an anti-CEA antibody, an anti-Cripto antibody, an anti-EphA2 antibody, an anti-G250 antibody, an anti-MUC1 antibody, an anti-GPNMB antibody, an anti-Integrin antibody, an anti-PSMA antibody, an anti-Tenascin-C antibody, an anti-SLC44A4 antibody, an anti-Mesothelin antibody, an anti-ENPP3 antibody, an anti-CD47 antibody, an anti-EGFR antibody, an anti-GPR20 antibody, and an anti-DR5 antibody. The antibody of the present invention is preferably an anti-HER2 antibody (e.g., trastuzumab or pertuzumab), an anti-CDH6 antibody, an anti-CD33 antibody, or an anti-EphA2 antibody, and more preferably an anti-HER2 antibody.

The antibody of the present invention may be obtained by using a method usually carried out in the art, which involves immunizing an animal with a polypeptide antigen and collecting and purifying an antibody produced in the body. The origin of the antigen is not limited to humans, and animals may be immunized with an antigen derived from non-human animals such as a mouse and a rat. In this case, the cross-reactivity of the resulting antibody that binds to the heterologous antigen with the corresponding human antigen can be tested to screen for an antibody applicable to a human disease.

Alternatively, a monoclonal antibody may be obtained from a hybridoma established by fusing an antibody-producing cell that produces an antibody against the antigen with a myeloma cell in accordance with a method known in the art (e.g., Kohler and Milstein, Nature (1975)256, p. 495-497, Kennett, R. ed., Monoclonal Antibodies, p. 365-367, Plenum Press, N.Y. (1980)).

The antigen may be obtained through gene engineering to allow host cells to produce a gene encoding the antigen protein.

The humanized antibody of the present invention may be obtained in accordance with a known method (e.g., Proc. Natl. Acad. Sci. U.S.A., 81, 6851-6855, (1984), Nature (1986) 321, p. 522-525, WO 90/07861).

For example, an anti-HER2 antibody (U.S. Pat. No. 5,821,337, WO 2004/008099, etc.), an anti-CD33 antibody (WO 2014/057687, etc.), an anti-CD70 antibody (WO 2004/073656, etc.), an anti-EphA2 antibody (WO 2009/028639, etc.), and an anti-CDH6 antibody (WO 2018/212136, etc.) may be each obtained in accordance with a known method.

For example, it is desirable that the anti-HER2 antibody of the present invention has any of the following properties, but the anti-HER2 antibody is not limited thereto.

(1) An anti-HER2 antibody having the following properties:
   (a) being capable of specifically binding to HER2; and
   (b) having activity to internalize into HER2-expressing cells by binding to HER2.
(2) The antibody according to (1), being capable of binding to the extracellular domain of HER2.

(3) The antibody according to (1) or (2), being a monoclonal antibody.
(4) The antibody according to any one of (1) to (3), having activities or activity of antibody-dependent cellular cytotoxicity (ADCC) and/or complement-dependent cytotoxicity (CDC).
(5) The antibody according to any one of (1) to (4), being a mouse monoclonal antibody, a chimeric monoclonal antibody, or a humanized monoclonal antibody.
(6) The antibody according to any one of (1) to (3), wherein the heavy chain constant region is a heavy chain constant region of human IgG1, and includes a mutation that causes lowering of activities of ADCC and ADCP.
(7) The antibody according to any one of (1) to (4), being a humanized monoclonal antibody including a heavy chain consisting of an amino acid sequence represented by SEQ ID NO: 2 and a light chain consisting of an amino acid sequence represented by SEQ ID NO: 1.
(8) The antibody according to (5), wherein the heavy chain constant region is a heavy chain constant region of human IgG1, and leucine is substituted with alanine at positions 234 and 235 specified by EU Index numbering.
(9) The antibody according to (8), being a humanized monoclonal antibody including a heavy chain consisting of an amino acid sequence represented by SEQ ID NO: 3 and a light chain consisting of an amino acid sequence represented by SEQ ID NO: 1.
(10) The antibody according to any one of (1) to (4), being a humanized monoclonal antibody including a heavy chain consisting of an amino acid sequence represented by SEQ ID NO: 29 and a light chain consisting of an amino acid sequence represented by SEQ ID NO: 28.
(11) The antibody according to any one of (1) to (4), being a humanized monoclonal antibody including a heavy chain consisting of an amino acid sequence represented by SEQ ID NO: 30 and a light chain consisting of an amino acid sequence represented by SEQ ID NO: 28.
(12) The antibody according to any one of (1) to (11), wherein one or two amino acids are deleted at the carboxyl terminus of the heavy chain.
(13) An antibody obtained by using a method for producing the antibody according to any one of (1) to (12), the method including the steps of: culturing a host cell transformed with an expression vector containing a polynucleotide encoding the antibody; and collecting the targeted antibody from a culture obtained from the step of culturing.

<2.2.2 Glycan Remodeling for Antibody>

A method for remodeling heterogeneous glycans of an antibody by enzymatic reaction to introduce homogeneous glycans having a functional group has recently been reported (ACS Chem. Biol. 2012, 7, 110-122, ACS Med. Chem. Lett. 2016, 7, 1005-1008). An attempt with use of this glycan remodeling technique has been made to site-specifically introduce a drug to synthesize a homogeneous ADC (Bioconjugate Chem. 2015, 26, 2233-2242, Angew. Chem. Int. Ed. 2016, 55, 2361-2367, US2016361436).

The glycan remodeling first uses hydrolase to cleave off heterogeneous glycans added to a protein (e.g., an antibody) with only GlcNAc at each terminus left as it is, preparing a homogenous protein moiety including GlcNAc added thereto (hereinafter, referred to as an "acceptor"). Subsequently, any glycan separately prepared (hereinafter, referred to as a "donor") is provided, and the acceptor and the donor are linked together by using glycosyltransferase. Thereby, a homogeneous glycoprotein with any glycan structure can be synthesized.

In the present invention, a "glycan" refers to a structural unit of two or more monosaccharides bonded together via glycosidic bonds. Specific monosaccharides and glycans are occasionally expressed as abbreviations such as "GlcNAc-" and "SG-". When any of these abbreviations is used in a structural formula, the abbreviation is shown with an intention that an oxygen atom or nitrogen atom involved in a glycosidic bond at the reducing terminus to another structural unit is not included in the abbreviation indicating the glycan, unless particularly defined.

In the present invention, each monosaccharide as a basic unit of a glycan is expressed for convenience with the definition that in the ring structure, the position of a carbon atom bonding to an oxygen atom constituting the ring and directly bonding to a hydroxy group (or an oxygen atom involved in a glycosidic bond) is position 1 (position 2 only for sialic acids), unless otherwise specified. The names of compounds of Examples are each provided in view of the entire chemical structure, and that rule is not necessarily applied.

When a glycan is expressed as a sign (e.g., SG, MSG, GlcNAc) in the present invention, the sign is intended, unless otherwise defined, to include carbon atoms ranging to the reducing terminus and not to include N or O involved in an N- or O-glycosidic bond.

The antibody-drug conjugate of the present invention is represented by the following formula:

wherein antibody Ab or a functional fragment of the antibody bonds from a side chain of an amino acid residue thereof (e.g., cysteine, lysine) directly to L, or bonds via a glycan or remodeled glycan of Ab to L.

Glycans in Ab of the present invention are N-linked glycans or O-linked glycans, and preferably N-linked glycans.

N-linked glycans and O-linked glycans bond to an amino acid side chain of an antibody via an N-glycosidic bond and an O-glycosidic bond, respectively.

Ab of the present invention is IgG, and preferably IgG1, IgG2, or IgG4.

IgG includes a well-preserved N-linked glycan on an asparagine residue at position 297 of the Fc region of the heavy chain (hereinafter, referred to as "Asn297 or N297"), and the N-linked glycan is known to contribute to the activity, kinetics, and so on of the antibody molecule (Eon-Duval, A. et al., Biotechnol. Prog. 2012, 28, 608-622, Sanglier-Cianferani, S., Anal. Chem. 2013, 85, 715-736).

The amino acid sequence in the constant region of IgG is well-preserved, and each of the amino acids has been specified by EU Index numbering in a report by Edelman et al. (Proc. Natl. Acad. Sci. U.S.A., 63, 78-85, (1969)). For example, Asn297, to which an N-linked glycan is added in the Fc region, corresponds to position 297 specified by EU Index numbering, and each amino acid is uniquely specified by expression with EU Index numbering, even if the actual position of the amino acid has varied through fragmentation of the molecule or deletion of a region.

The following formula illustrates a case where the antibody-drug conjugate of the present invention is bonding via N297 glycan of an antibody or a functional fragment of the antibody to L.

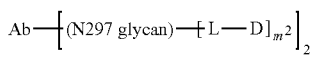

The antibody having a remodeled glycan is referred to as a glycan-remodeled antibody.

SGP (α2,6-SGP), an abbreviation for sialyl glycopeptide, is a representative N-linked glycopeptide. SGP can be separated/purified from the yolk of a hen egg, for example, in accordance with a method described in WO 2011/027868. Purified products of SGP are sold by Tokyo Chemical Industry Co., Ltd. and FUSHIMI Pharmaceutical Co., Ltd. Herein, the glycan moiety of SGP is expressed as SG, and a glycan formed by deleting one GlcNAc moiety at the reducing terminus in SG is expressed as SG(10). SG(10) may be prepared by enzymatic hydrolysis of SGP, for example, with reference to a report by Umekawa et al. (Biochim. Biophys. Acta 2010, 1800, 1203-1209). Alternatively, SG(10) may be purchased from Tokyo Chemical Industry Co., Ltd. or FUSHIMI Pharmaceutical Co., Ltd.

Herein, a glycan structure formed by deleting a sialic acid at a non-reducing terminus only in either one of the branched chains of β-Man in SG(10) is expressed as MSG(9), and a structure including a sialic acid only in the 1-3 glycan of the branched chains is expressed as MSG1, and a structure including a sialic acid only in the 1-6 glycan of the branched chains is expressed as MSG2.

The remodeled glycan of the present invention is N297-(Fuc) SG, N297-(Fuc) MSG1, N297-(Fuc) MSG2, or a mixture of N297-(Fuc) MSG1 and N297-(Fuc) MSG2, preferably N297-(Fuc) SG, N297-(Fuc) MSG1, or N297-(Fuc) MSG2, and more preferably N297-(Fuc) SG or N297-(Fuc) MSG1.

N297-(Fuc) SG is represented by the following structural formula or sequence formula:

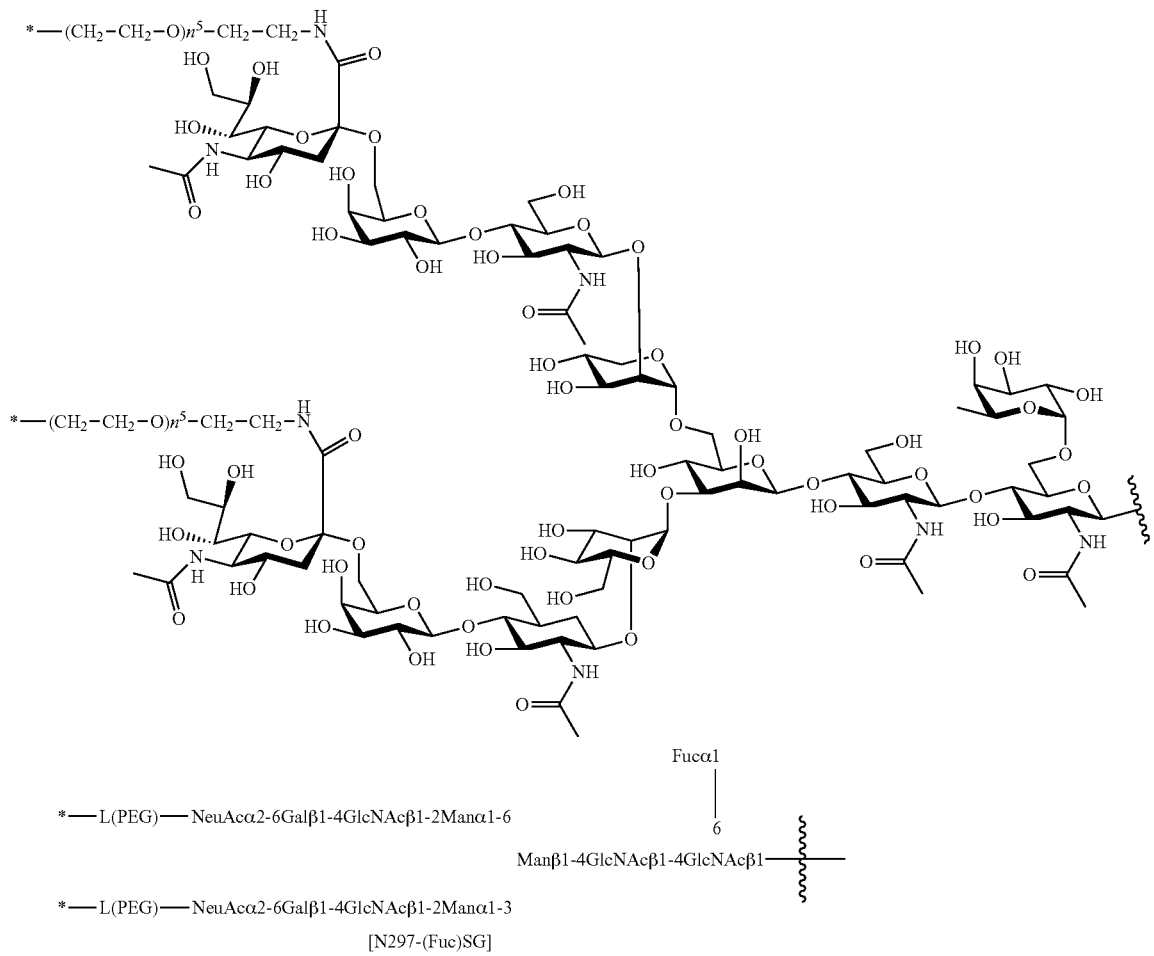

[N297-(Fuc)SG]

In the formulas, each wavy line indicates bonding to Asn297 of the antibody;

L(PEG) represents —(CH$_2$—CH$_2$—O)n$^5$-CH$_2$—CH$_2$—NH—, wherein the amino group at the right end indicates amide-bonding to the carboxyl group at position 2 of a sialic acid at the non-reducing terminus in each of the 1-3 chain and 1-6 chain of the branched chains of β-Man in N297 glycan, and each asterisk indicates bonding to linker L, in particular, a nitrogen atom at position 1 or 3 of the 1,2,3-triazole ring of Lb in linker L; and n$^5$ is an integer of 2 to 10, and preferably an integer of 2 to 5.

N297-(Fuc) MSG1 is represented by the following structural formula or sequence formula:

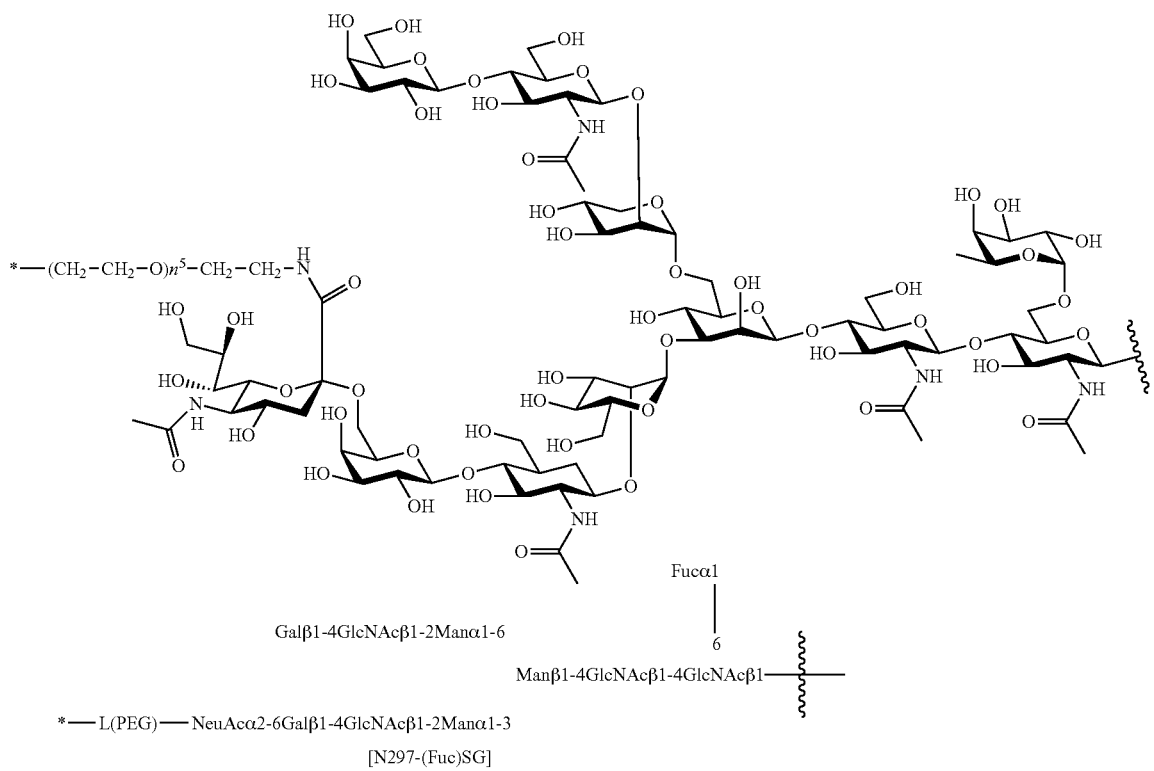

Gal β1-4GlcNAcβ1-2Manα1-6

*—L(PEG)—NeuAcα2-6Galβ1-4GlcNAcβ1-2Manα1-3

Manβ1-4GlcNAcβ1-4GlcNAcβ1—

Fucα1
|
6

[N297-(Fuc)SG]

In the formulas, each wavy line indicates bonding to Asn297 of the antibody;

L(PEG) represents —(CH$_2$—CH$_2$—O)$n^5$-CH$_2$—CH$_2$—NH—, wherein the amino group at the right end indicates amide-bonding to the carboxyl group at position 2 of a sialic acid at the non-reducing terminus in the 1-3 chain of the branched chains of β-Man in N297 glycan;

each asterisk indicates bonding to linker L, in particular, a nitrogen atom at position 1 or 3 of the 1,2,3-triazole ring of Lb in linker L; and $n^5$ is an integer of 2 to 10, and preferably an integer of 2 to 5.

N297-(Fuc) MSG2 is represented by the following structural formula or sequence formula:

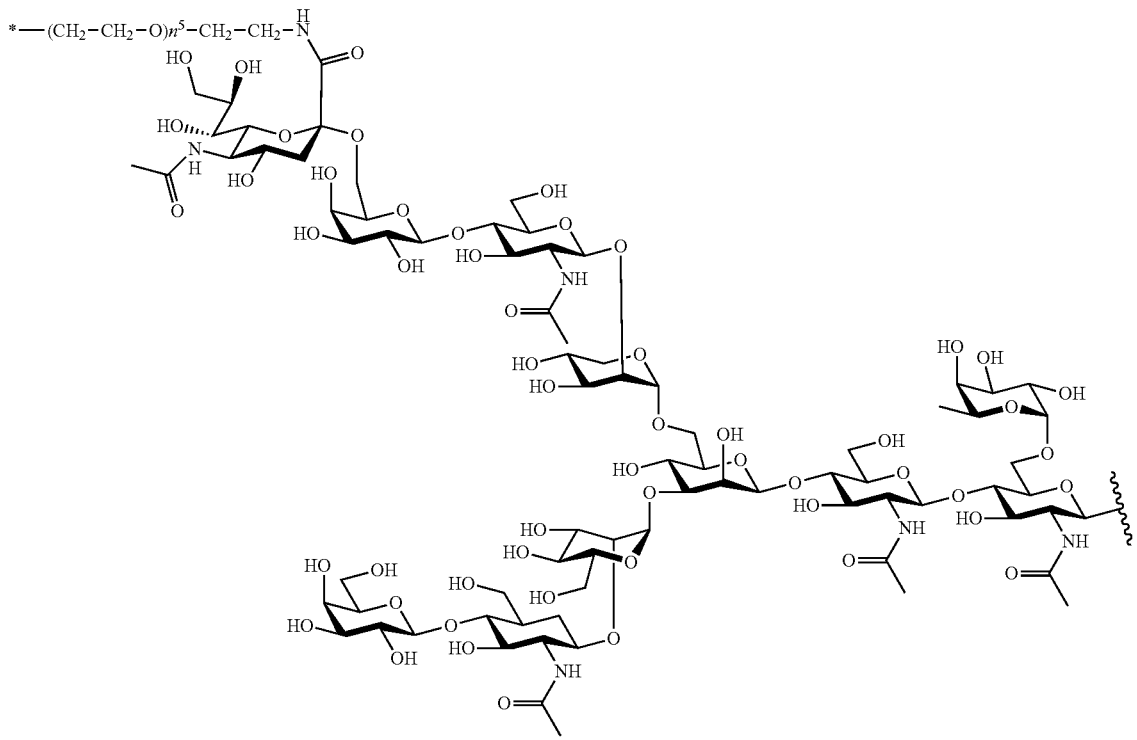

-continued

\*—L(PEG)—NeuAcα2-6Galβ1-4GlcNAcβ1-2Manα1-6

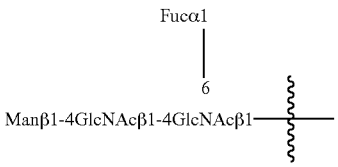

Galβ1-4GlcNAcβ1-2Manα1-3

[N297-(Fuc)SG]

In the formulas, each wavy line indicates bonding to Asn297 of the antibody;

L(PEG) represents —(CH$_2$—CH$_2$—O)n$^5$-CH$_2$—CH$_2$—NH—, wherein the amino group at the right end indicates amide-bonding to the carboxyl group at position 2 of a sialic acid at the non-reducing terminus in the 1-6 chain of the branched chains of β-Man in N297 glycan, and each asterisk indicates bonding to linker L, in particular, a nitrogen atom at position 1 or 3 of the 1,2,3-triazole ring of Lb in linker L; and n$^5$ is an integer of 2 to 10, and preferably an integer of 2 to 5.

If N297 glycan of the antibody in the antibody-drug conjugate of the present invention is N297-(Fuc) SG, the antibody-drug conjugate is a molecule to which four molecules of linker L and four molecules of drug D have been conjugated together (m$^2$=2) since the antibody is a dimer.

If N297 glycan of the antibody in the antibody-drug conjugate of the present invention is N297-(Fuc) MSG1, N297-(Fuc) MSG2, or a mixture of them, the antibody-drug conjugate is a molecule to which two molecules of linker L and two molecules of drug D have been conjugated together (m$^2$=1)since the antibody is a dimer (see FIG. 1).

N297 glycan is preferably N297-(Fuc) SG, N297-(Fuc) MSG1, or N297-(Fuc) MSG2, and more preferably N297-(Fuc) SG.

If N297 glycan of the antibody in the antibody-drug conjugate of the present invention is N297-(Fuc) SG, N297-(Fuc) MSG1, or N297-(Fuc) MSG2, a highly homogeneous ADC can be obtained.

<3. Production Methods>

Representative methods for producing the novel CDN derivative of the present invention or production intermediates thereof will be described. In the following, compound numbers shown in reaction formulas are used to identify compounds from each other. Specifically, reference in the form of "compound of formula (1)", "compound (1)", and so on will be made. Compounds with the other numbers will be expressed in the same manner.

In scheme A to scheme E in the following, the substituents R$^1$ to R$^5$, L$^1$, L$^2$, W$^1$, W$^2$, and Z$^1$ to Z$^3$ are synonymous with those in the above. The substituents R$^a$, R$^c$, R$^e$, and R$^g$ each represent a side chain of a natural α-amino acid. Examples thereof may include a methyl group, an isopropyl group, a sec-butyl group, an isobutyl group, and a benzyl group. PRO$^1$ represents a protective group for primary alcohol. PRO$^1$ is preferably a 4,4'-dimethoxytrityl group, a 4-methoxytrityl group, or the like. PRO$^2$, PRO$^3$, PRO$^7$, and PRO$^8$ each represent a protective group for secondary alcohol. Preferably, PRO$^2$, PRO$^3$, PRO$^7$, and PRO$^8$ are each a tert-butyldimethylsilyl group, a triisopropylsilyloxymethyl group, a benzoyl group, a 2-nitrobenzyl group, a 4-methoxytetrahydropyran-4-yl group, or the like. PRO$^6$ represents a protective group for carboxylic acid. PRO$^6$ is preferably a tert-butyl group, a benzyl group, or the like. PRO$^5$ and PRO$^9$ each represent a protective group for amine. PRO$^5$ is preferably a tert-butyloxycarbonyl group, a 9-fluorenylmethyloxycarbonyl group, an allyloxycarbonyl group, a 2,2,2-trichloroethoxycarbonyl group, a benzyloxycarbonyl group, or the like, and PRO$^9$ is preferably a 9-fluorenylmethyloxycarbonyl group or a 2-(trimethylsilyl) ethoxycarbonyl group. PRO$^4$ represents a protective group for alcohol or amine. PRO$^4$ is preferably a tert-butyldimethylsilyl group, a benzoyl group, or the like for alcohol, and preferably a 2-(trimethylsilyl) ethoxycarbonyl group, an allyloxycarbonyl group, a tert-butyloxycarbonyl group, or the like for amine. Q$^a$ represents an oxygen atom or a sulfur atom, and Q$^b$ represents a hydroxy group or a thiol group. Q$^{a'}$ and Q$^{b'}$ each independently represent a negatively charged oxygen atom (O—) or sulfur atom (S$^-$). R$^x$ and R$^y$ each independently represent a halogen atom or —O—PRO$^2$. n represents an integer of 1 to 3.

Scheme A

The CDN derivative of the present invention represented by (1) may be produced in accordance with scheme A described in the following.

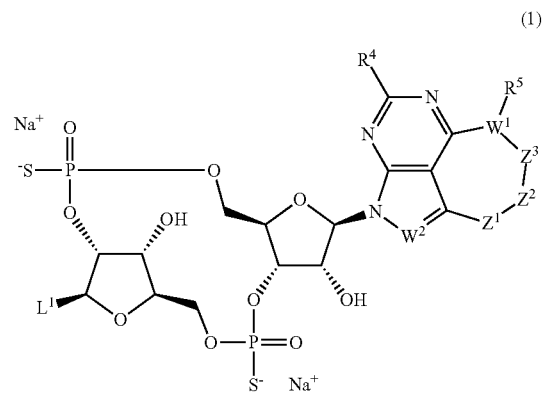

The present production method is a method for producing the compound represented by general formula (1). One-pot synthesis is applicable from steps A-1 to A-5 of the present production method, and this may be performed with reference to a report by Gaffney et al. (Org. Lett. 2010, 12, 3269-3271).

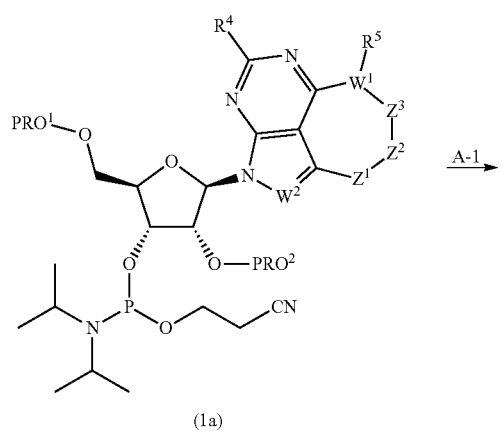
(1a)
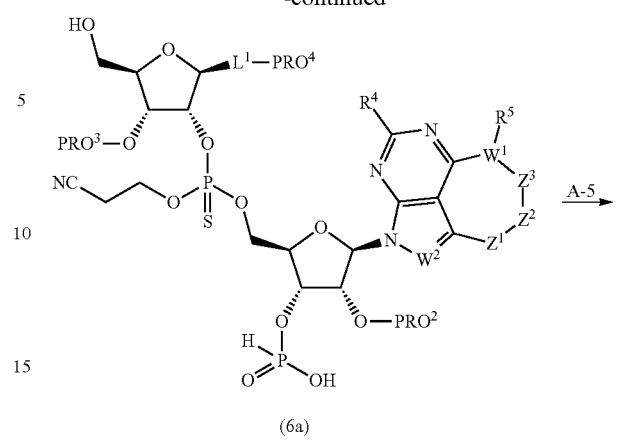
(6a)
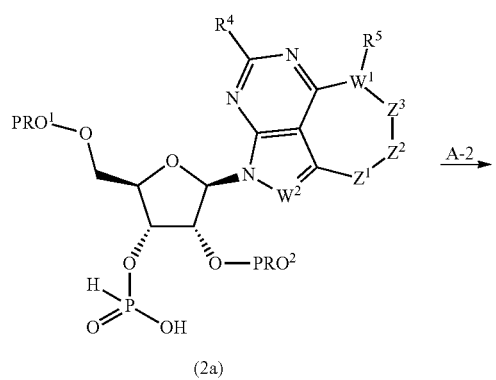
(2a)
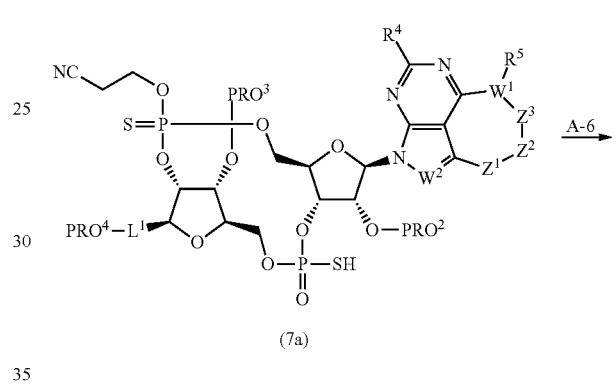
(7a)
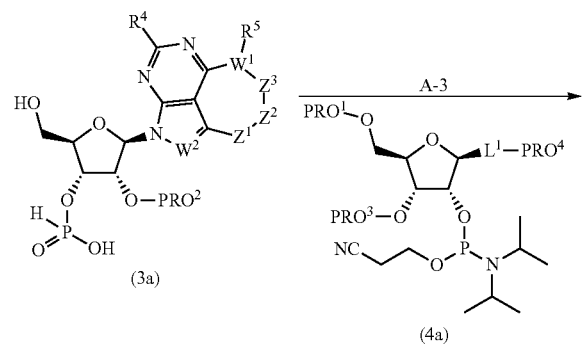
(3a) (4a)
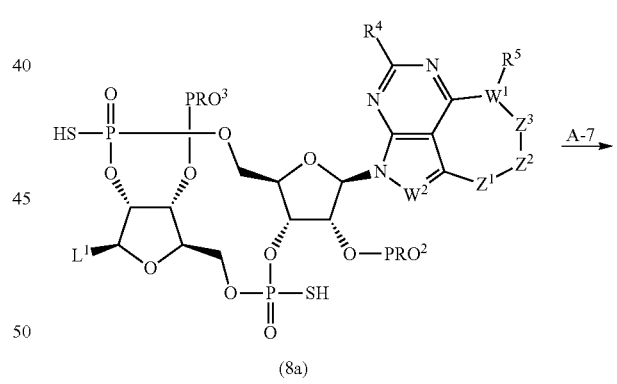
(8a)
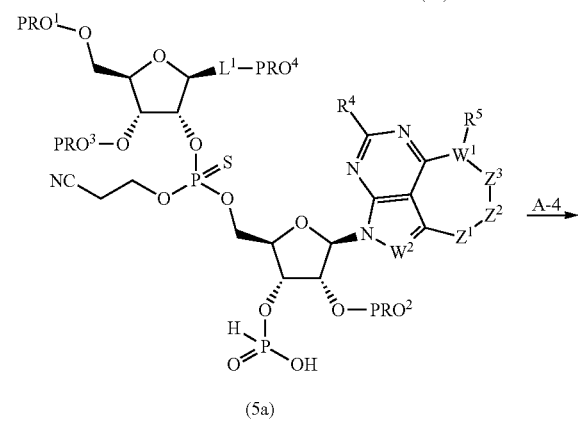
(5a)
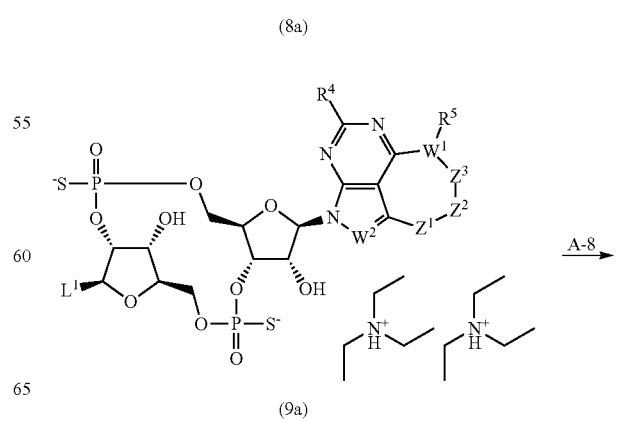
(9a)

-continued

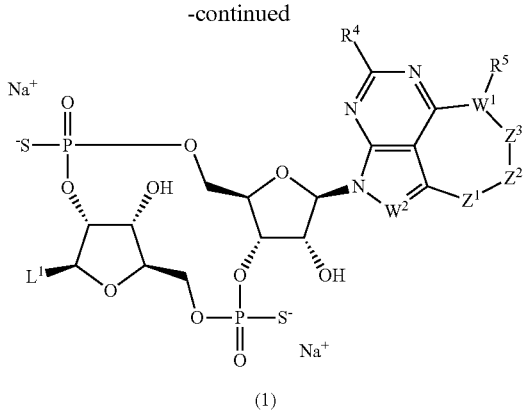

(1)

(Step A-1)
This step is a step of producing the compound of formula (2a) by sequentially performing hydrolysis reaction of the compound of formula (Ia) and removal of a cyanoethyl group from the resultant with use of a known technique of organic chemistry.

Hydrolysis reaction was performed by treating compound (1a) in a solvent (acetonitrile, tetrahydrofuran, N,N-dimethylformamide, or a mixed solvent of them) with water and an acid (pyridine trifluoroacetate, 4,5-dicyanoimidazole, 1H-tetrazole, etc.) at a temperature of from −10° C. to the boiling point of the solvent used for the reaction, preferably 15° C. to 35° C. The amount of moles of water used was 2 mol to an excessive amount of moles, preferably 2 mol to 10 mol, to 1 mol of compound (1a), and that of the acid used was 1 mol to an excessive amount of moles, preferably 1 mol to 5 mol, to 1 mol of compound (1a). The reaction time is 1 minute to 3 hours, and preferably 5 minutes to 30 minutes. To this reaction mixture, a base (tert-butylamine, etc.) was then added to remove the cyanoethyl group. The amount of moles of the base used was an excessive amount of moles, preferably 30 mol to 50 mol, to 1 mol of compound (1a). The reaction time is 5 minutes to 6 hours, and preferably 15 minutes to 1 hour. The reaction mixture was concentrated under reduced pressure to afford a crude product (2a). The crude product (2a) may be sent to the subsequent step without purification.

(Step A-2)
This step is a step of producing the compound of formula (3a) by removing a protective group for a hydroxy group from the compound of formula (2a) with use of a known technique of organic chemistry. Before the initiation of the reaction of this step, the crude form of formula (2a) was azeotroped once to three times with acetonitrile, as necessary, for drying.

When PRO$^1$ was a 4,4'-dimethoxytrityl group, the 4,4'-dimethoxytrityl group was removed by treating compound (2a) in a solvent (dichloromethane, chloroform, dichloroethane, etc.) with water and an acid (dichloroacetic acid, trifluoroacetic acid, etc.) at a temperature of from −10° C. to the boiling point of the solvent used for the reaction, preferably 15° C. to 35° C. The amount of moles of water used was an excessive amount of moles, preferably 10 mol to 20 mol, to 1 mol of compound (2a), and the acid was diluted with the solvent used for the reaction to a concentration of from 1% to 50% (v/v), preferably to 5% to 10% (v/v), and an excessive amount of moles, preferably 5 mol to 15 mol, of the diluted solution was used. The reaction time is 1 minute to 3 hours, and preferably 5 minutes to 30 minutes. Pyridine was added to the reaction mixture for quenching. The amount of moles of pyridine used was an amount enough to neutralize the acid used, preferably 2 mol to 10 mol, to 1 mol of the acid. The reaction mixture was concentrated under reduced pressure to afford a crude product (3a). The crude product (3a) was azeotroped three to five times with dehydrated acetonitrile. Acetonitrile was allowed to remain after the last azeotropic operation, and thus 0.01 M to 1 M acetonitrile solution of compound (3a) was obtained. The acetonitrile solution obtained was directly sent to the subsequent step.

(Step A-3)
This step is a step of producing the compound of formula (5a) by sequentially performing coupling reaction of the compound of formula (3a) with the compound of formula (4a) and sulfidation reaction of the resulting coupled form with use of a known technique of organic chemistry.

Before the initiation of the reaction of this step, compound (4a) was azeotroped three to five times with dehydrated acetonitrile. Acetonitrile was allowed to remain after the last azeotropic operation, and thus 0.01 M to 1 M acetonitrile solution of compound (4a) was prepared. To this solution, a drying agent (the molecular sieves 3A or the molecular sieves 4A in powder or pellets) was added, and the solution was stored until use under the nitrogen or argon atmosphere.

Coupling reaction was performed by adding azeotropically dried compound (4a) to the acetonitrile solution of compound (3a) at a temperature of from 5° C. to 35° C. The reaction time is 1 minute to 24 hours, and preferably 5 minutes to 6 hours. To this reaction mixture, a sulfiding agent (N,N-dimethyl-N'-(3-sulfanylidene-3H-1,2,4-dithiazol-5-yl) methaneimidamide, 3H-1,2-benzodithiol-3-one, etc.) was then added to perform sulfidation reaction. The amount of moles of the sulfiding agent used was 1 mol to 5 mol, preferably 1 mol to 2 mol, to 1 mol of compound (3a). The reaction time is 5 minutes to 24 hours, and preferably 30 minutes to 6 hours. The reaction mixture was concentrated under reduced pressure to afford a crude product (5a). The crude product (5a) obtained was directly sent to the subsequent step.

(Step A-4)
This step is a step of producing the compound of formula (6a) by removing a protective group for a hydroxy group from the compound of formula (5a) with use of a known technique of organic chemistry.

When PRO$^1$ was a 4,4'-dimethoxytrityl group, the 4,4'-dimethoxytrityl group was removed by treating the compound of compound (5a) in a solvent (dichloromethane, chloroform, dichloroethane, etc.) with water and an acid (dichloroacetic acid, trifluoroacetic acid, etc.) at a temperature of from −10° C. to the boiling point of the solvent used for the reaction, preferably 15° C. to 35° C. The amount of moles of water used was an excessive amount of moles, preferably 10 to 20 mol, to 1 mol of compound (5a), and the acid was diluted with the solvent used for the reaction to a concentration of from 1% to 50% (v/v), preferably to 5% to 10% (v/v), and an excessive amount of moles, preferably 5 mol to 15 mol, of the diluted solution was used. The reaction time is 1 minute to 3 hours, and preferably 5 minutes to 30 minutes. Pyridine was added to the reaction mixture for quenching. The amount of moles of pyridine used was an amount enough to neutralize the acid used, preferably 10 mol to 200 mol, to 1 mol of the acid. The reaction mixture was concentrated under reduced pressure to afford a crude product (6a). The crude product (6a) obtained was directly sent to the subsequent step.

(Step A-5)

This step is a step of producing the compound of formula (7a) by sequentially performing cyclization reaction and sulfidation reaction of the compound of formula (6a) with use of a known technique of organic chemistry.

Compound (6a) was dissolved in pyridine, and the resultant was then concentrated under reduced pressure to prepare a 0.01 M to 0.5 M pyridine solution. Cyclization reaction was performed by adding a dehydration-condensation agent (2-chloro-5,5-dimethyl-1,3,225-dioxaphosphinan-2-one, etc.) to this pyridine solution at a temperature of from 5° C. to 35° C. The amount of moles of the dehydration-condensation agent used was 1 mol to an excessive amount of moles, preferably 3 mol to 5 mol, to 1 mol of compound (6a). The reaction time is 1 minute to 6 hours, and preferably 5 minutes to 1 hour. Sulfidation reaction was then performed by adding water and a sulfiding agent (3H-1,2-benzodithiol-3-one, N,N-dimethyl-N'-(3-sulfanylidene-3H-1,2,4-dithiazol-5-yl) methaneimidamide, etc.) to this reaction mixture. The amount of moles of water used was an excessive amount of moles, preferably 30 mol to 50 mol, to 1 mol of compound (6a), and that of the sulfiding agent used was 1 mol to 5 mol, preferably 1 mol to 2 mol, to 1 mol of compound (6a). The reaction time is 5 minutes to 12 hours, and preferably 30 minutes to 3 hours. The reaction mixture was added to an aqueous solution (0.1 M to 1 M) of sodium hydrogen carbonate, and the resultant was then stirred for a period of time of 15 minutes to 24 hours for quenching. After the reaction mixture was subjected to extraction once to five times with an organic solvent (ethyl acetate, diethyl ether, toluene, or a mixed solvent of them), the extracts were combined and dried over an anhydrous salt (anhydrous sodium sulfate or anhydrous magnesium sulfate). The drying agent was removed through filtration, and the filtrate was concentrated under reduced pressure. The resulting residue was purified by silica gel column chromatography [dichloromethane/methanol, ethyl acetate/methanol, hexane/ethyl acetate, etc.], C18 silica gel column chromatography [buffer/acetonitrile], or combination of them to afford compound (7a) as a mixture of two or more diastereomers or two or more pure diastereomers. While two diastereomers are obtained in this step in many cases, additionally one or two diastereomers may be obtained for some types of raw materials (1a) and (4a). Even when compound (7a) obtained is in the form of a mixture of a plurality of diastereomers, the mixture may be sent to the subsequent step without additional purification.

(Step A-6)

This step is a step of producing the compound of formula (8a) by simultaneously removing a cyanoethyl group and all acyl protective groups from the compound of formula (7a) with use of a known technique of organic chemistry. This step was performed in an autoclave or in a shield tube, as necessary.

When $PRO^4$ was a benzoyl group, the cyanoethyl group and the benzoyl group were removed by treating the compound of compound (7a) in a solvent (methanol, ethanol, tetrahydrofuran, or a mixed solvent of them) with 28% (v/v) ammonia water at a temperature of from 5° C. to the boiling point of the solvent used for the reaction. The amount of moles of ammonia used was an excessive amount of moles, preferably 300 mol to 3000 mol, to 1 mol of compound (7a). The reaction time is 30 minutes to 96 hours, and preferably 2 hours to 48 hours. The reaction mixture was concentrated, as necessary, and the residue was purified by preparative HPLC [buffer/acetonitrile, buffer/methanol, etc.], C18 silica gel column chromatography [buffer/acetonitrile, buffer/methanol, etc.], or combination of them to afford compound (8a). Even when compound (8a) obtained is in the form of a mixture of diastereomers, the mixture may be sent to the subsequent step without additional purification. In this step, compound (8a) may be sent to the subsequent step without purification.

(Step A-7)

This step is a step of producing the compound of formula (9a) by simultaneously removing all the silyl protective groups from the compound of formula (8a) with use of a known technique of organic chemistry.

When $PRO^2$ and $PRO^3$ were each a tert-butyldimethylsilyl group, the tert-butyldimethylsilyl groups were removed by directly treating compound (8a) with triethylamine trihydrofluoride at a temperature of from 5° C. to 100° C., preferably 35° C. to 60° C. The amount of moles of triethylamine trihydrofluoride used was an excessive amount of moles, preferably 100 to 200 mol, to 1 mol of compound (8a). The reaction time is 30 minutes to 24 hours, and preferably 2 hours to 12 hours. After the reaction mixture was cooled to room temperature, an ice-cooled 3:1 to 10:1 (v/v) mixed solution of 1 M aqueous solution of triethylammonium hydrogen carbonate and triethylamine was poured in small portions into the reaction mixture for quenching. As necessary, the reaction mixture may be poured into an ice-cooled mixed solution of 1 M aqueous solution of triethylammonium hydrogen carbonate and triethylamine. In this case, the reaction vessel was washed with acetonitrile and water. The amount of moles of triethylamine to be used is an amount enough to change the condition of the reaction mixture to weakly basic condition, preferably approximately 2 mol, to 1 mol of triethylamine trihydrofluoride. After the organic solvent component of the reaction mixture was distilled off under reduced pressure, the remaining aqueous solution was purified by preparative HPLC [buffer/acetonitrile, buffer/methanol, etc.], C18 silica gel column chromatography [buffer/acetonitrile, buffer/methanol, etc.], or combination of them to afford compound (9a) as a single diastereomer.

(Step A-8)

This step is a step of producing the compound of formula (1) by ion exchange of the compound of formula (9a) with use of a known technique of organic chemistry.

A cation exchange resin (BT AG® 50W-X2 resin, 100-200 mesh, hydrogen type) was suspended in pure water, and an empty column cartridge was filled therewith. The amount of the cation exchange resin used was 10 times to 50 times as large as that of compound (9a) in a weight ratio. After an excessive portion of pure water was allowed to gravitationally flow down, a 3×column volume of 1 M aqueous solution of sodium hydroxide was allowed to gravitationally flow down, and a 6×column volume of pure water was then allowed to gravitationally flow down. Compound (9a) was dissolved in an approximately 3×column volume of pure water, and the column was charged therewith. If the compound is poorly dissolved in pure water, a mixture with a small amount of an organic solvent (acetonitrile, methanol, etc.) may be used. The solution allowed to gravitationally flow down was separated and collected, and then further eluted with a 6×column volume of pure water or the like, and fractions were separated and collected. Fractions containing the targeted product were combined and lyophilized to give compound (1) as a single diastereomer.

Scheme A'

The CDN derivative of the present invention represented by (1') may be produced in accordance with scheme A' described in the following.

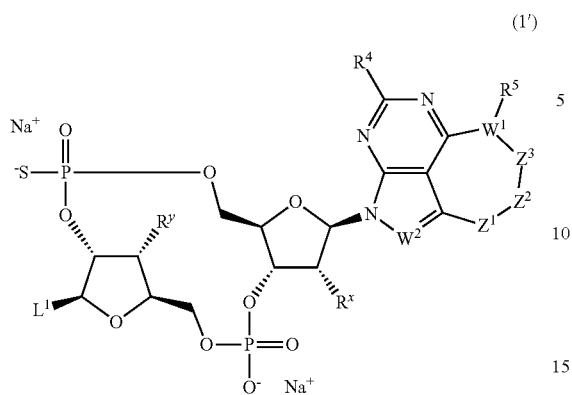

(1')

The present production method is a method for producing the compound represented by general formula (1'), the method being a partially modified form of scheme A. Specifically, the compound of general formula (1') can be produced with replacement of step A-5 of scheme A with step A'-5 shown below. When the substituents $R^x$ and $R^y$ are each a halogen atom, step A-7 may be omitted.

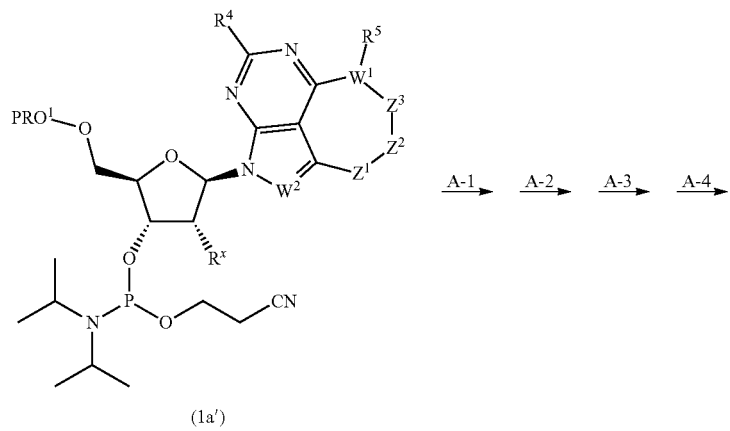

(1a')

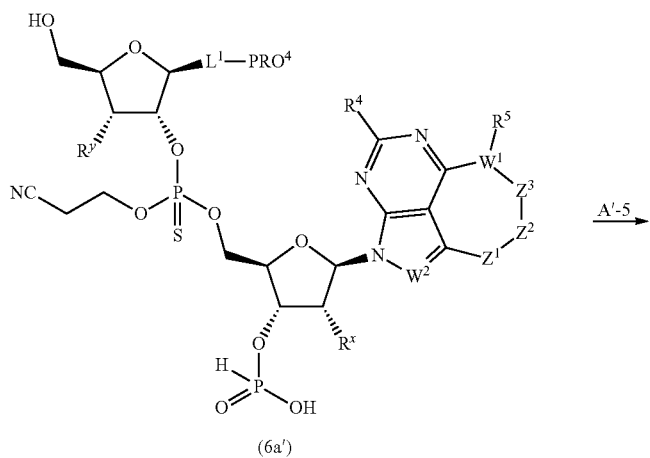

(6a')

-continued

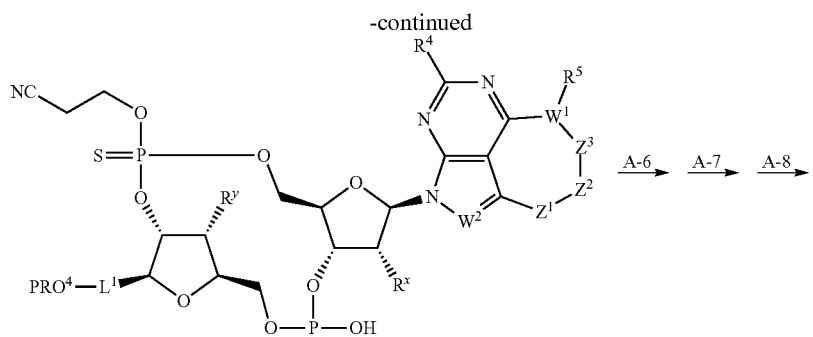
(7a')

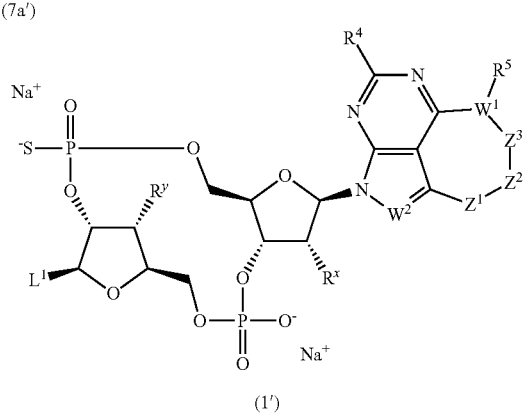
(1')

(Step A'-5)

This step is a step of producing the compound of formula (7a') by sequentially performing cyclization reaction and oxidation reaction of the compound of formula (6a') with use of a known technique of organic chemistry.

Compound (6a') was dissolved in pyridine, and the resultant was then concentrated under reduced pressure to prepare a 0.01 M to 0.5 M pyridine solution. Cyclization reaction was performed by adding a dehydration-condensation agent (2-chloro-5,5-dimethyl-1,3,2$\lambda^5$-dioxaphosphinan-2-one, etc.) to this pyridine solution at a temperature of from 5° C. to 35° C. The amount of moles of the dehydration-condensation agent used was 1 mol to an excessive amount of moles, preferably 3 mol to 5 mol, to 1 mol of compound (6a'). The reaction time is 1 minute to 6 hours, and preferably 5 minutes to 1 hour. Subsequently, oxidation reaction was performed by adding water and an oxidizing agent (iodine, etc.) to this reaction mixture. The amount of moles of water used was 0 mol to an excessive amount of moles, preferably 30 mol to 50 mol, to 1 mol of compound (6a'), and that of the oxidizing agent used was 2 mol to 10 mol, preferably 3 mol to 5 mol, to 1 mol of compound (6a'). The reaction time is 5 minutes to 12 hours, and preferably 30 minutes to 3 hours. The reaction mixture was added to an aqueous solution (0.1 M to 1 M) of sodium hydrogen carbonate, and the resultant was stirred for a period of time of from 15 minutes to 24 hours for quenching. After the reaction mixture was subjected to extraction once to five tomes with an organic solvent (ethyl acetate, diethyl ether, toluene, or a mixed solvent of them), the extracts were combined and dried over an anhydrous salt (anhydrous sodium sulfate or anhydrous magnesium sulfate). The drying agent was removed through filtration, and the filtrate was concentrated under reduced pressure. The resulting residue was purified by silica gel column chromatography [dichloromethane/methanol, ethyl acetate/methanol, hexane/ethyl acetate, etc.], C18 silica gel column chromatography [buffer/acetonitrile], or combination of them to afford compound (7a').

Scheme A"

The CDN derivative of the present invention represented by (1") may be produced in accordance with scheme A" described in the following.

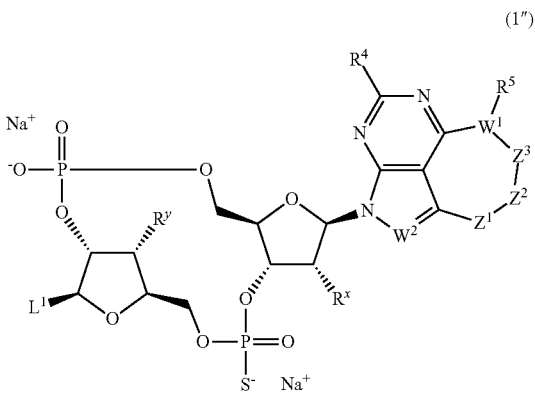
(1")

The present production method is a method for producing the compound represented by general formula (1"), the method being a partially modified form of scheme A. Specifically, the compound of general formula (1") can be produced with replacement of step A-3 of scheme A with step A"-3 shown below. When the substituents $R^x$ and $R^y$ are each a halogen atom, step A-7 may be omitted.

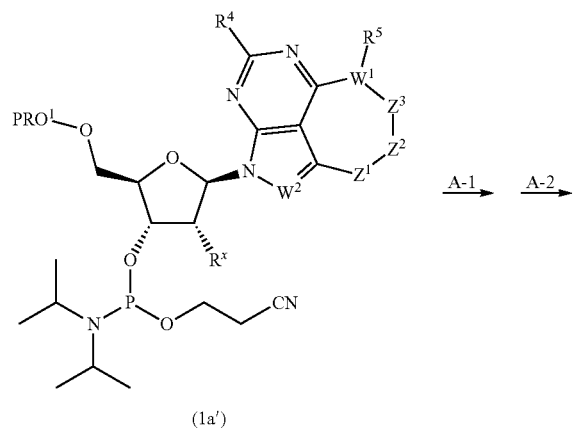
(1a′)
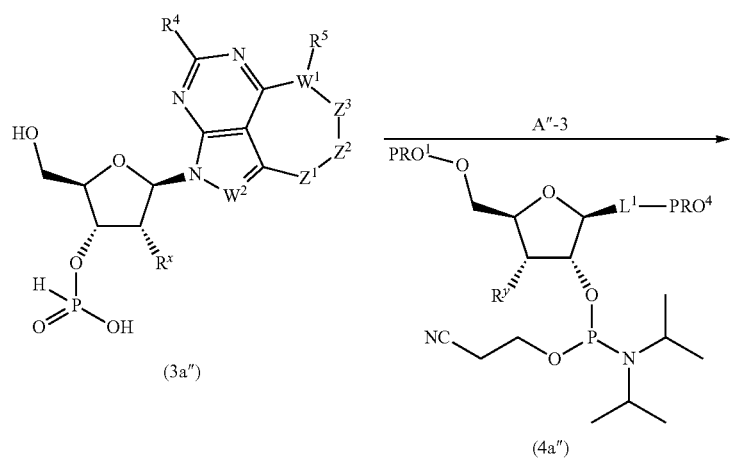
(3a″)  (4a″)
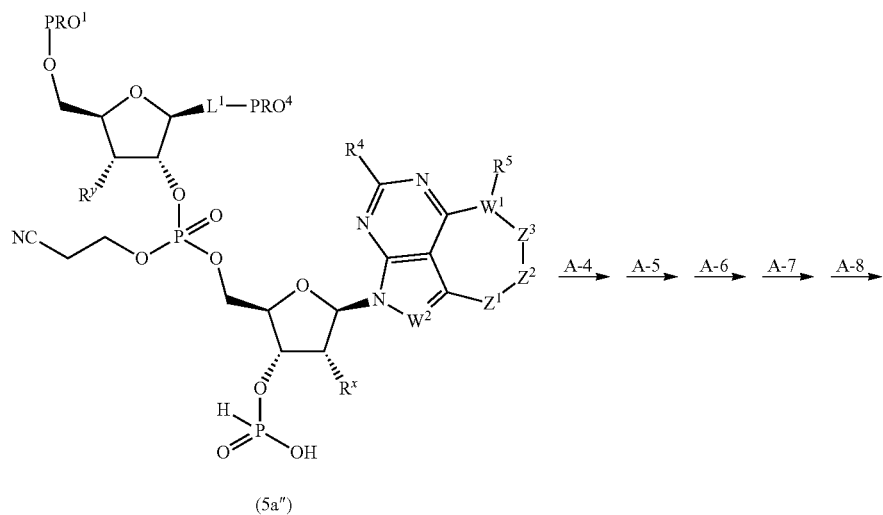
(5a″)

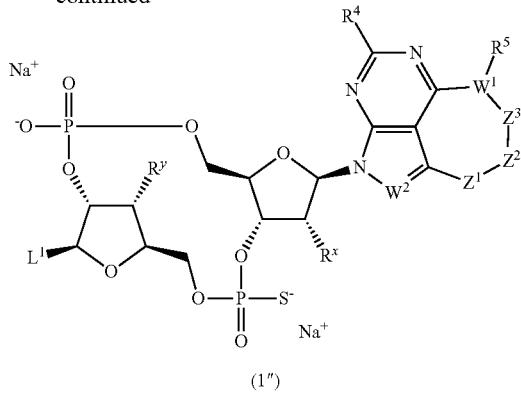

(1″)

(Step A″-3)

This step is a step of producing the compound of formula (5a″) by sequentially performing coupling reaction of the compound of formula (3a″) with the compound of formula (4a″) and oxidation reaction of the resulting coupled form with use of a known technique of organic chemistry.

Before the initiation of the reaction of this step, compound (4a″) was azeotroped three to five times with dehydrated acetonitrile. Acetonitrile was allowed to remain after the last azeotropic operation, and thus 0.01 M to 1 M acetonitrile solution of compound (4a″) was prepared. To this solution, a drying agent (the molecular sieves 3A or the molecular sieves 4A in powder or pellets) was added, and the solution was stored until use under the nitrogen or argon atmosphere.

Coupling reaction was performed by adding the acetonitrile solution of azeotropically dried compound (4a″) to the acetonitrile solution of compound (3a″) at a temperature of from 5° C. to 35° C. The reaction time is 1 minute to 24 hours, and preferably 5 minutes to 6 hours. To this reaction mixture, an oxidizing agent (tert-butyl hydroperoxide, etc.) was then added to perform oxidation reaction. The amount of moles of the oxidizing agent used was 1 mol to 5 mol, preferably 2 mol to 3 mol, to 1 mol of compound (3a″). The reaction time is 5 minutes to 24 hours, and preferably 30 minutes to 6 hours. A saturated aqueous solution of sodium thiosulfate was added to the reaction mixture, and the resultant was stirred for a period of time of from 10 minutes to 12 hours for quenching. After the reaction mixture was subjected to extraction once to five times with an organic solvent (a mixed solvent of dichloromethane and methanol, etc.), the extracts were combined and dried over an anhydrous salt (anhydrous sodium sulfate or anhydrous magnesium sulfate). The drying agent was removed through filtration, and the filtrate was concentrated under reduced pressure to afford a crude product (5a″). The crude product (5a″) obtained was directly sent to the subsequent step.

Scheme A″

The CDN derivative of the present invention represented by (1″) may be produced in accordance with scheme A″ described in the following.

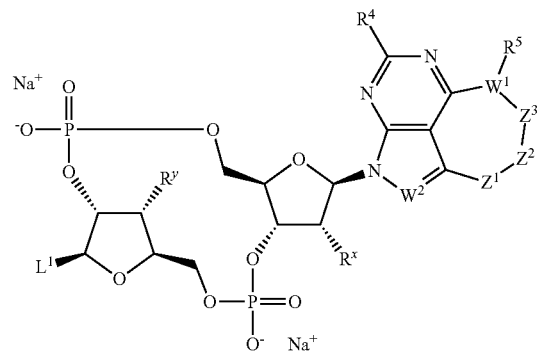

(1‴)

The present production method is a method for producing the compound represented by general formula (1‴), the method being a partially modified form of scheme A. Specifically, the compound of general formula (1‴) can be produced with replacement of step A-3 and step A-5 of scheme A respectively with step A″-3 and step A′-5. When the substituents $R^x$ and $R^y$ are each a halogen atom, step A-7 may be omitted.

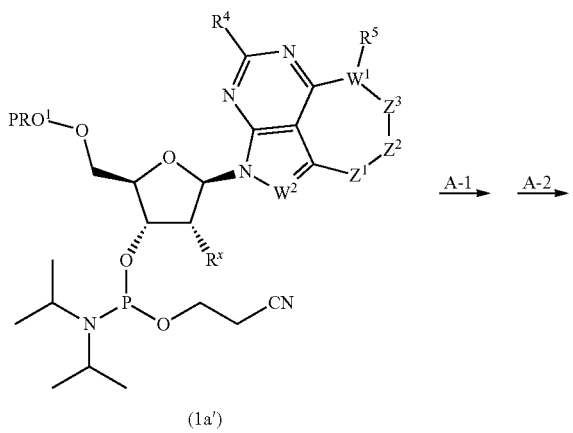

(1a′)

-continued
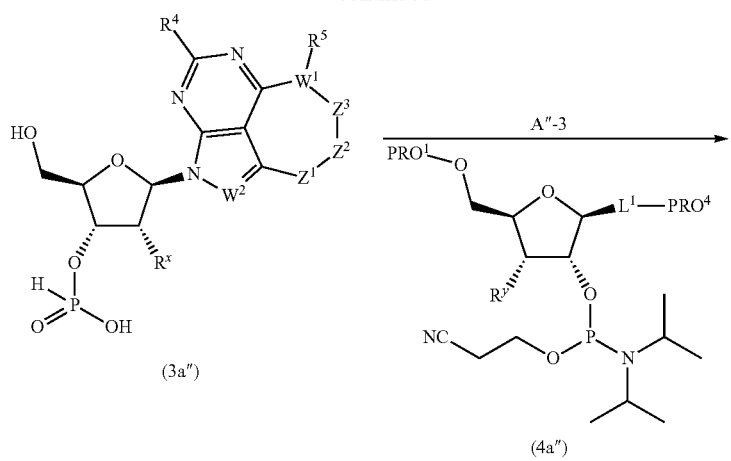
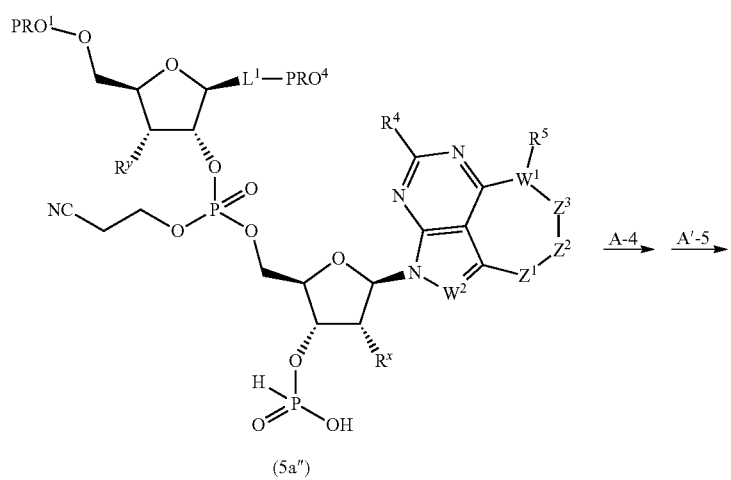
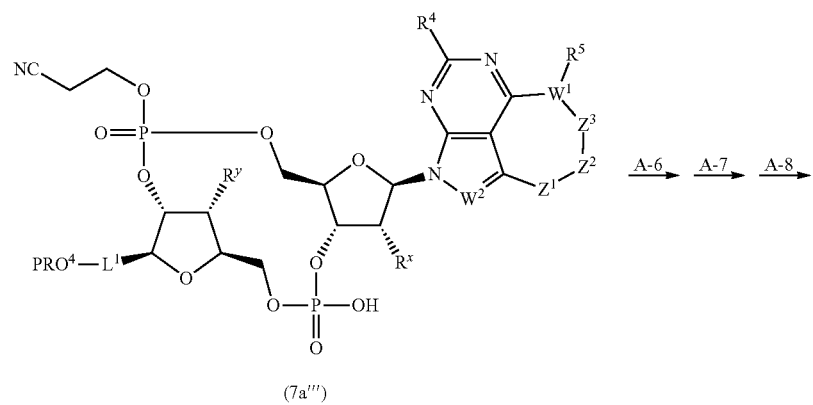

-continued
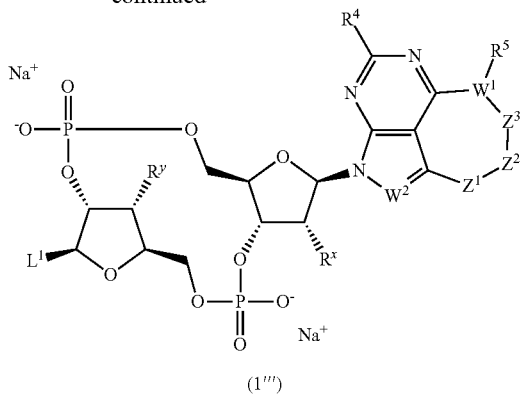
(1''')
Scheme B: Conjugate precursor (Glycan Conjugation)
The conjugate precursor of the present invention represented by (2) may be produced in accordance with scheme B described in the following.
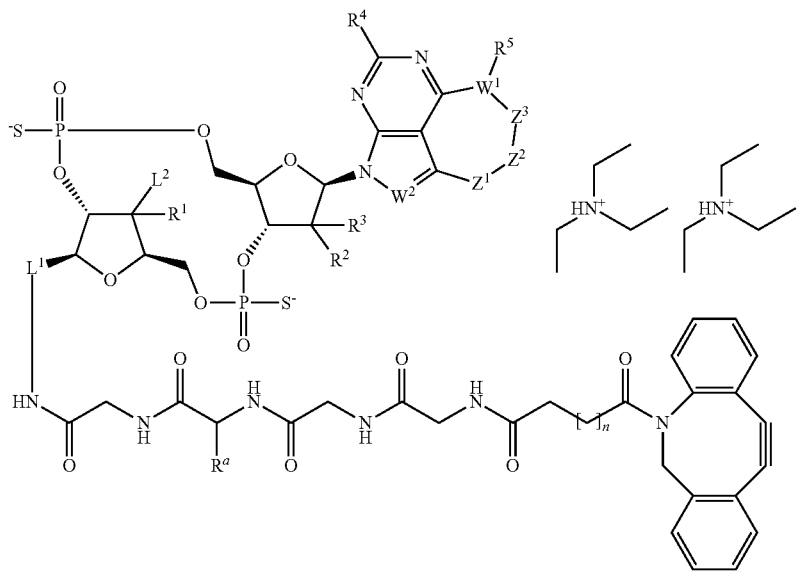
(2)
The present production method is a method for producing conjugate precursor (2) when $L^1$ is substituted with —$NH_2$ at any position.
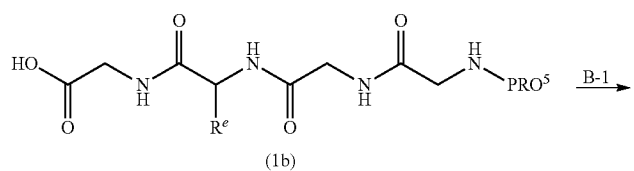
(1b)

115 116
-continued
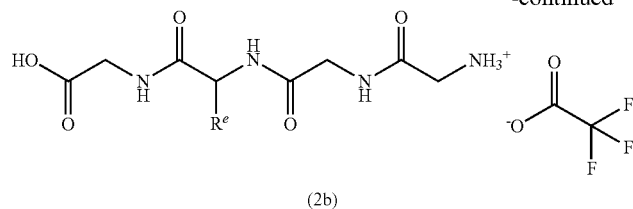
(2b)
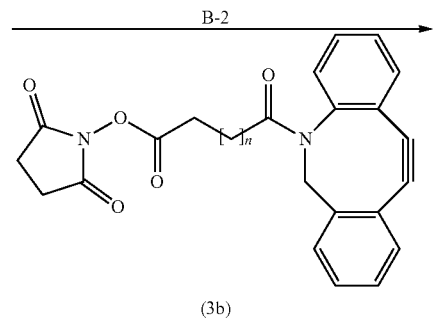
(3b)
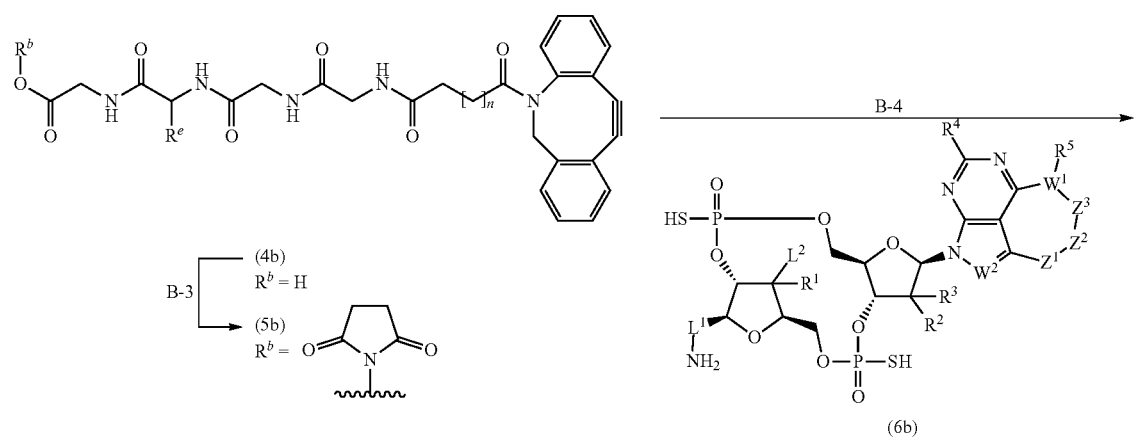
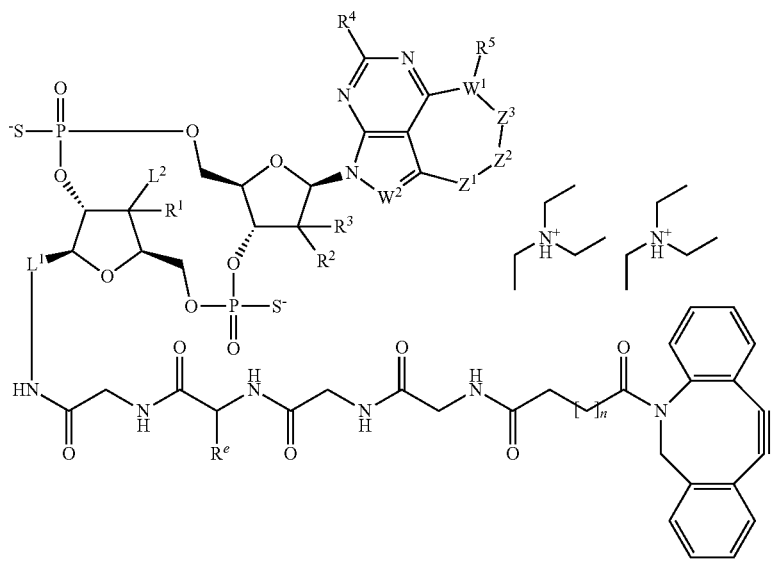
(2)

(Step B-1)

This step is a step of producing the compound of formula (2b) by removing a protective group from the compound of formula (1b) with use of a known technique of organic chemistry.

When PRO$^5$ was a tert-butyloxycarbonyl group, the protective group was removed by treating compound (1b) in a solvent (dichloromethane, dioxane, acetonitrile, ethyl acetate, tetrahydrofuran, or a mixed solvent of them) with trifluoroacetic acid at a temperature of from −10° C. to the boiling point of the solvent used for the reaction, preferably 15° C. to 35° C. The amount of moles of trifluoroacetic acid used was an excessive amount of moles, preferably 20 mol to 50 mol, to 1 mol of compound (1b). The reaction time is 5 minutes to 24 hours, and preferably 30 minutes to 6 hours. The reaction mixture was concentrated under reduced pressure, and then suspended in toluene and the resultant suspension was again concentrated under reduced pressure. This operation was repeated twice to five times. A solvent (diethyl ether, diisopropyl ether, hexane, dichloromethane, ethyl acetate, or a mixed solvent of them) was added to make a slurry, and the solid was then collected through filtration to give a crude product (2b). The crude product (2b) was sent to the subsequent step without any additional purification.

(Step B-2)

This step is a step of producing the compound of formula (4b) by performing amidation of the compound of formula (2b) with the compound of formula (3b) with use of a known technique of organic chemistry.

Amidation was performed by reacting compound (2b) in a solvent (N,N-dimethylformamide, N-methylpyrrolidone, N,N-dimethylacetamide, acetonitrile, etc.) with a base (triethylamine, N,N-diisopropylethylamine, etc.) and compound (3b) at a temperature of from 5° C. to 35° C. The amount of moles of the base used was 1 mol to 5 mol to 1 mol of compound (2b), and that of compound (3b) used was 0.5 mol to 1.5 mol to 1 mol of compound (2b). The reaction time is 10 minutes to 72 hours, and preferably 1 hour to 24 hours. The reaction mixture was poured into a two-layer mixture of an organic solvent (dichloromethane, chloroform, ethyl acetate, methanol, or a mixed solvent of them) and water or an acidic aqueous solution (0.1 to 1 M hydrochloric acid, aqueous solution of citric acid, etc.), and the resultant was subjected to extraction once to five times with the organic solvent. The extracts were combined and washed with brine, and then dried over an anhydrous salt (anhydrous sodium sulfate or anhydrous magnesium sulfate). The drying agent was removed through filtration, and the filtrate was concentrated under reduced pressure. Alternatively, the reaction mixture may be directly concentrated under reduced pressure, with the liquid separation operation omitted, and sent to the subsequent silica gel column purification. The residue obtained was purified by silica gel column chromatography [dichloromethane/methanol, ethyl acetate/methanol, etc.] to afford compound (4b). As necessary, the purity of compound (4b) may be increased by dissolving compound (4b) in a good solvent (ethyl acetate, acetonitrile, dichloromethane, methanol, or a mixed solvent of them), then reprecipitating compound (4b) with addition of a poor solvent (diethyl ether, diisopropyl ether, hexane, etc.), and collecting the solid through filtration.

(Step B-3)

This step is a step of producing the compound of formula (5b) by performing esterification of the compound of formula (4b) with use of a known technique of organic chemistry.

Esterification was performed by reacting compound (4b) in a solvent (N,N-dimethylformamide, N,N-dimethylacetamide, N-methylpyrrolidone, acetonitrile, etc.) with N-hydroxysuccinimide and a condensing agent (1-ethyl-3-(3-dimethylaminopropyl) carbodiimide hydrochloride, etc.) at a temperature of from 5° C. to 35° C. The amount of moles of N-hydroxysuccinimide used and that of the condensing agent used were each 1 mol to 3 mol to 1 mol of compound (4b). The reaction time is 30 minutes to 72 hours, and preferably 2 hours to 24 hours. The reaction mixture was diluted with an organic solvent (dichloromethane, chloroform, ethyl acetate, or a mixed solvent of them), and then washed three to five times with iced water. The organic layer was dried by using an anhydrous salt (anhydrous sodium sulfate or anhydrous magnesium sulfate). The drying agent was removed through filtration, and the filtrate was then concentrated under reduced pressure to afford a crude product (5b). As necessary, compound (5b) obtained may be purified by C18 silica gel column chromatography [acetonitrile only]. The purity of compound (5b) obtained may be increased by dissolving compound (5b) in a good solvent (ethyl acetate, acetonitrile, dichloromethane, or a mixed solvent of them), then reprecipitating compound (5b) with addition of a poor solvent (diethyl ether, diisopropyl ether, hexane, etc.), and collecting the solid through filtration.

(Step B-4)

This step is a step of producing the compound of formula (2) by performing condensation reaction of the compound of formula (5b) with the compound of formula (6b) with use of a known technique of organic chemistry.

Condensation reaction was performed by reacting compound (6b) in a solvent (N,N-dimethylformamide, N,N-dimethylacetamide, N-methylpyrrolidone, acetonitrile, etc.) with a base (triethylamine, N,N-diisopropylethylamine, etc.) and compound (5b) at a temperature of from −10° C. to 100° C., preferably 15° C. to 35° C. The amount of moles of the base used was 2 mol to 5 mol to 1 mol of compound (6b), and that of compound (5b) used was 1 mol to 2 mol to 1 mol of compound (6b). The reaction time is 5 minutes to 24 hours, and preferably 1 hour to 6 hours. Benzylamine was added to the reaction mixture for quenching. The amount of moles of benzylamine used was 4 mol to 10 mol to 1 mol of compound (6b). The reaction mixture was partially concentrated under reduced pressure, as necessary, and the remaining solution was purified by preparative HPLC [buffer/acetonitrile, buffer/methanol, etc.], C18 silica gel column chromatography [buffer/acetonitrile, buffer/methanol, etc.], or combination of them to afford compound (2).

Scheme B': Conjugate precursor (Cysteine Conjugation)

Scheme B'

The conjugate precursor of the present invention represented by (2') may be produced in accordance with scheme B' described in the following.

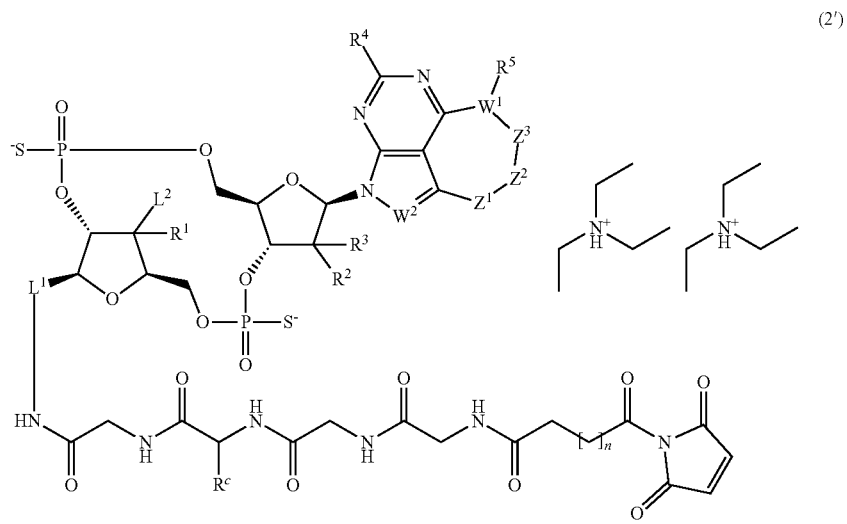
(2')
The present production method is a method for producing conjugate precursor (2') when $L^1$ is substituted with —$NH_2$ at any position.
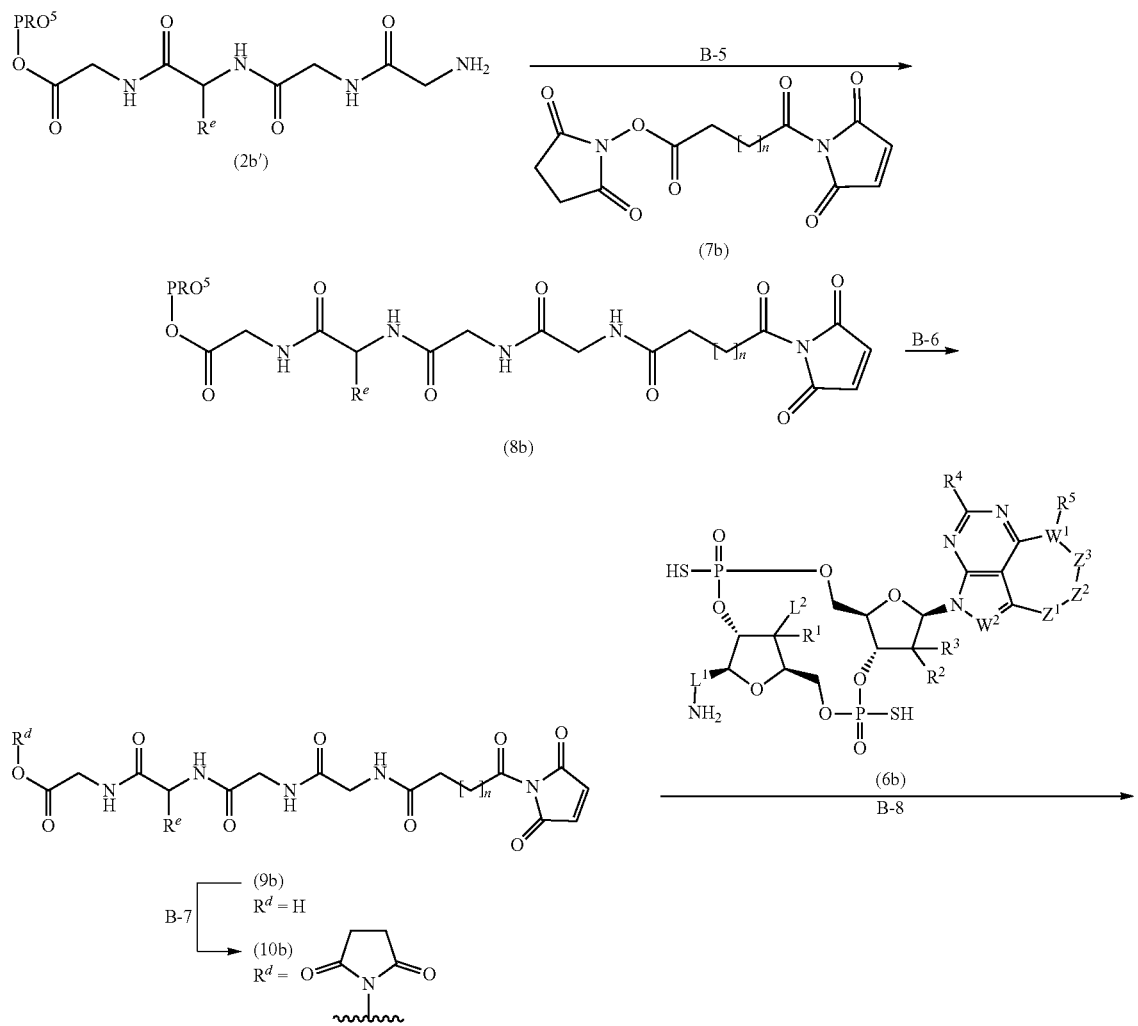

-continued

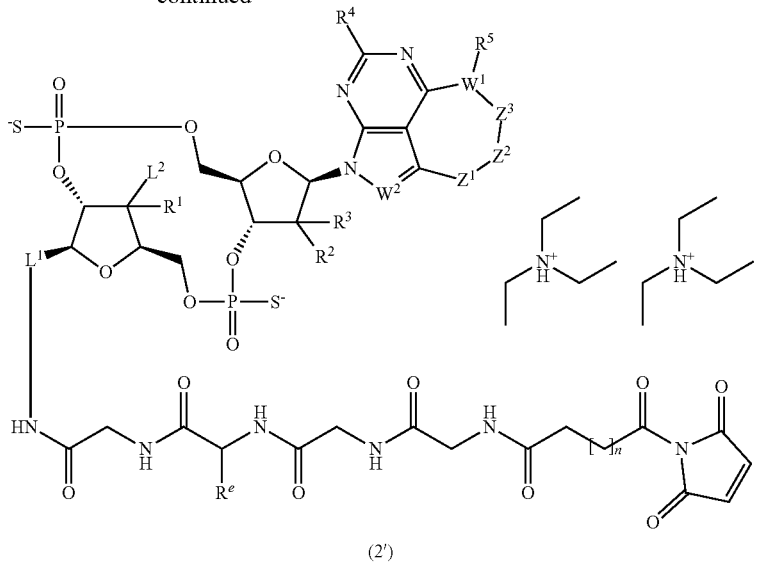

(2')

(Step B-5)

This step is a step of producing the compound of formula (8b) by performing amidation of the compound of formula (2b') with the compound of formula (7b) with use of a known technique of organic chemistry. Compound (8b) was obtained in accordance with the procedure described in step B-2 of scheme B, except that no base was used.

(Step B-6)

This step is a step of producing the compound of formula (9b) by removing a protective group from the compound of formula (8b) with use of a known technique of organic chemistry. Compound (9b) was obtained in accordance with the procedure described in step B-1 of scheme B, except that when $PRO^6$ was a tert-butyl group, silica gel column chromatography [dichloromethane/methanol] was used in the purification operation.

(Step B-7)

This step is a step of producing the compound of formula (10b) by performing esterification of the compound of formula (9b) with use of a known technique of organic chemistry. Compound (10b) was obtained in accordance with the procedure described in step B-3 of scheme B.

(Step B-8)

This step is a step of producing the compound of formula (2') by performing condensation reaction of the compound of formula (6b) with the compound of formula (10b) with use of a known technique of organic chemistry. Compound (2') was obtained in accordance with the procedure described in step B-4 of scheme B.

Scheme C

The conjugate precursor of the present invention represented by (3) may be produced in accordance with scheme C described in the following.

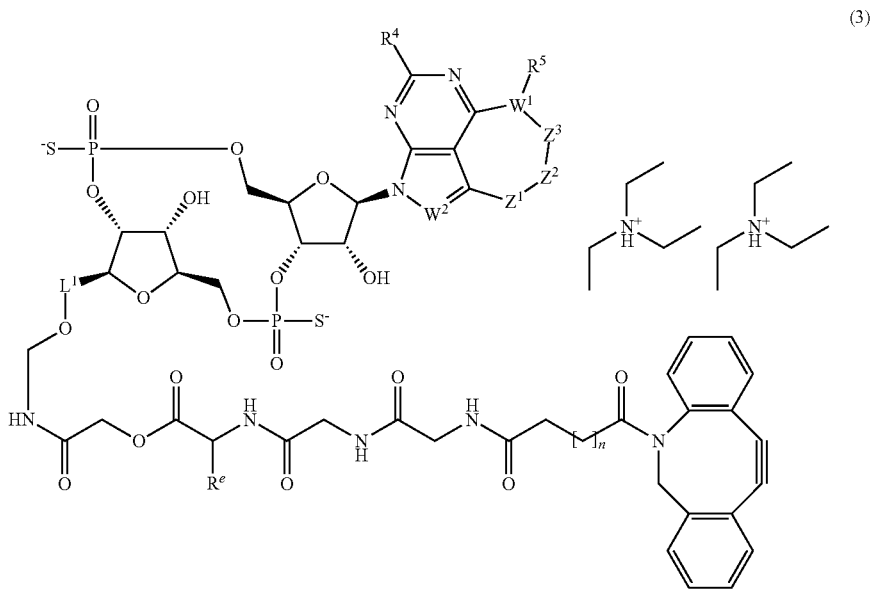

(3)

The present production method is a method for producing conjugate precursor (3) when L¹ is substituted with a hydroxy group at any position.
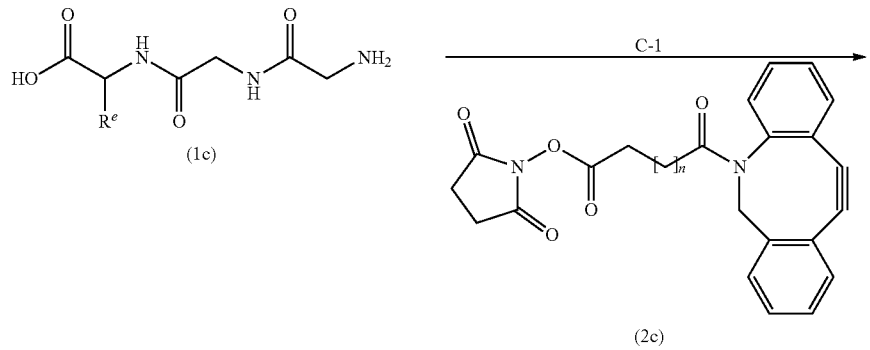
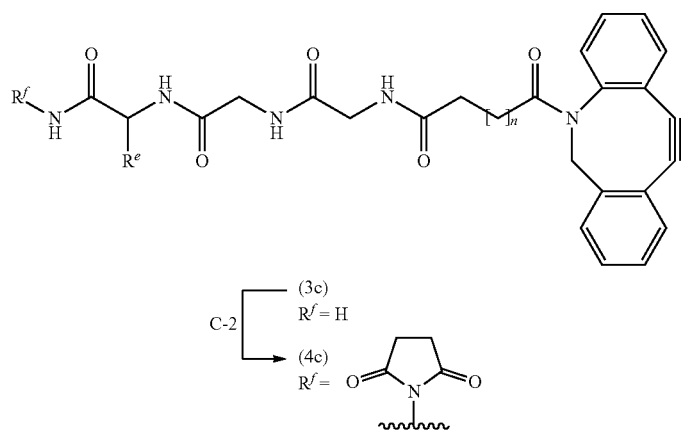
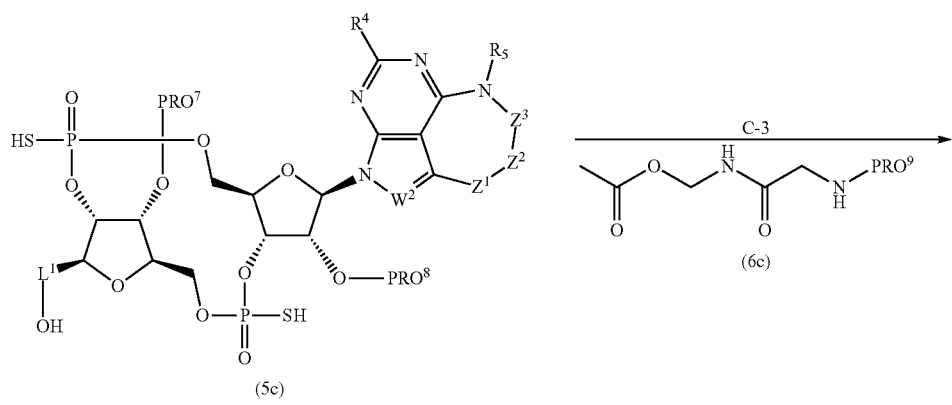

-continued
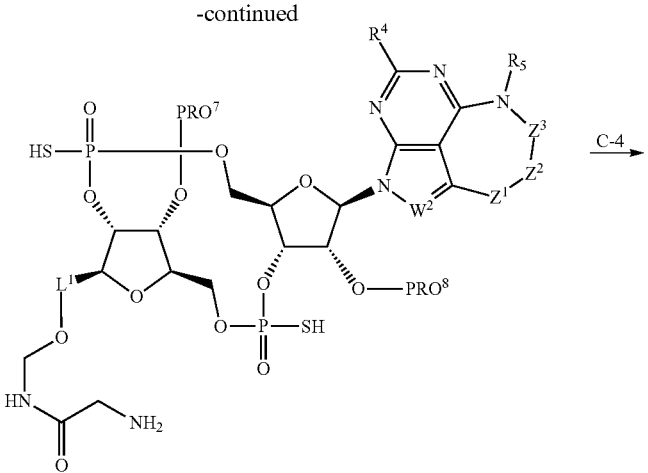
(7c)
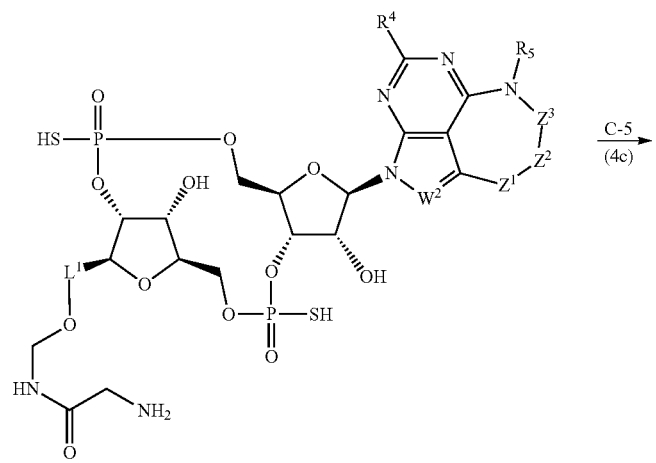
(8c)
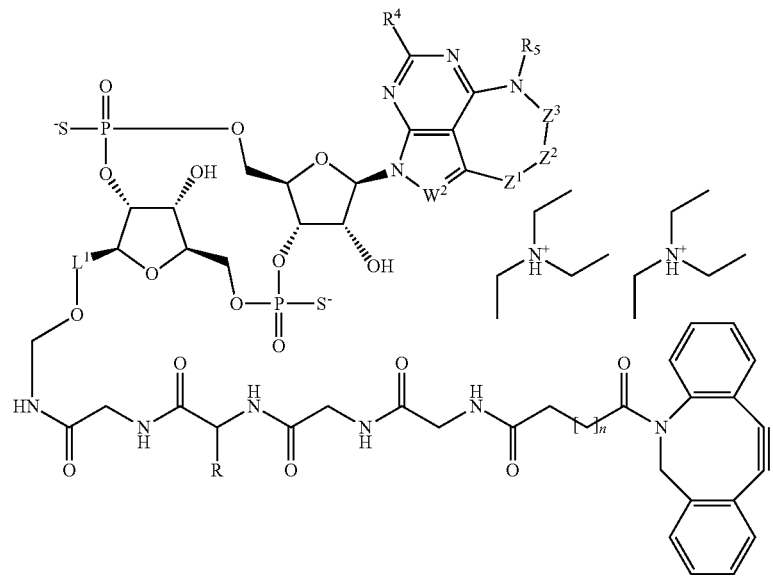
(3)

(Step C—1)

This step is a step of producing the compound of formula (3c) by performing amidation of the compound of formula (1c) with the compound of formula (2c) with use of a known technique of organic chemistry. Compound (3c) was obtained in accordance with the procedure described in step B-2 of scheme B.

(Step C—2)

This step is a step of producing the compound of formula (4c) by performing esterification of the compound of formula (3c) with use of a known technique of organic chemistry. Compound (4c) was obtained in accordance with the procedure described in step B-3 of scheme B.

(Step C—3)

This step is a step of producing the compound of formula (7c) by sequentially performing coupling reaction (aminomethylenation) of the compound of formula (5c) with the compound of formula (6c) and deprotection of the resulting coupled form with use of a known technique of organic chemistry.

When PRO$^9$ was a 9-fluorenylmethyloxycarbonyl group, aminomethylenation was performed by reacting compound (5c) in tetrahydrofuran with compound (6c) and an acid (p-toluenesulfonic acid, etc.) at a temperature of from 5° C. to 35° C. The amount of moles of compound (6c) used was 1 mol to 20 mol, preferably 2 mol to 10 mol, to 1 mol of compound (5c), and that of the acid used was 0.05 mol to an excessive amount of moles, preferably 0.1 mol to 3 mol, to 1 mol of compound (5c). The reaction time is 30 minutes to 72 hours, and preferably 2 hours to 24 hours. Subsequently, deprotection was performed by adding a base (1,8-diazabicyclo [5.4.0]-7-undecene, etc.) to the reaction mixture. When the reaction mixture contains a suspension, a solvent (N,N-dimethylformamide, etc.) may be further added to dissolve the suspension, as necessary, before reaction. The amount of moles of the base used was an excessive amount of moles, preferably 5 mol to 20 mol, to 1 mol of compound (5c). The reaction time is 10 minutes to 24 hours, and preferably 2 hours to 12 hours. Water was added to the reaction mixture, and the resultant was directly purified by C18 silica gel column chromatography [buffer/acetonitrile, etc.] to afford compound (7c).

(Step C—4)

This step is a step of producing the compound of formula (8c) by removing protective groups from the compound of formula (7c) with use of a known technique of organic chemistry. When PRO$^7$ and PRO$^8$ were each a tert-butyldimethylsilyl group, compound (8c) was obtained in accordance with the procedure described in step A-7 of scheme A.

(Step C—5)

This step is a step of producing the compound of formula (3) by performing condensation reaction of the compound of formula (8c) with the compound of formula (4c) with use of a known technique of organic chemistry. Compound (3) was obtained in accordance with the procedure described in step B-4 of scheme B.

Scheme C'

The conjugate precursor of the present invention represented by (3') may be produced in accordance with scheme C' described in the following.

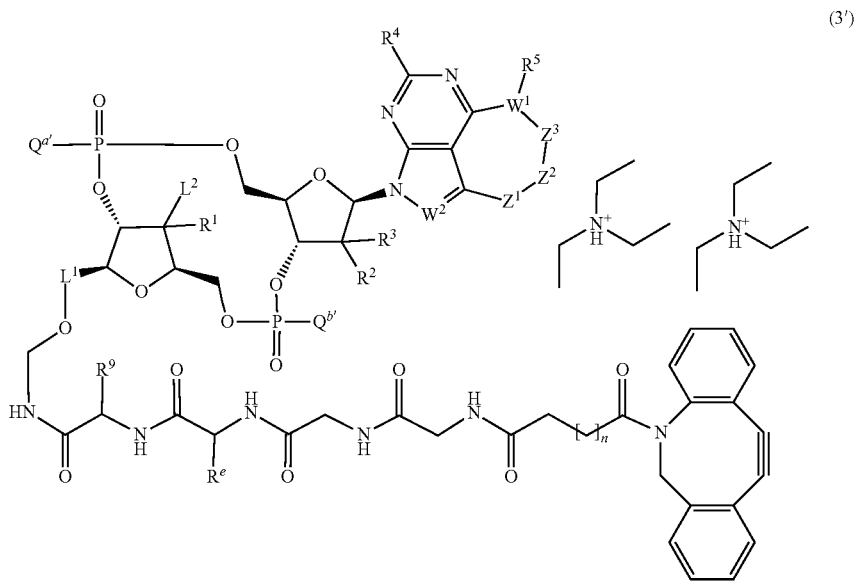

(3')

The present production method is a method for producing conjugate precursor (3') when $L^1$ is substituted with a hydroxy group at any position.
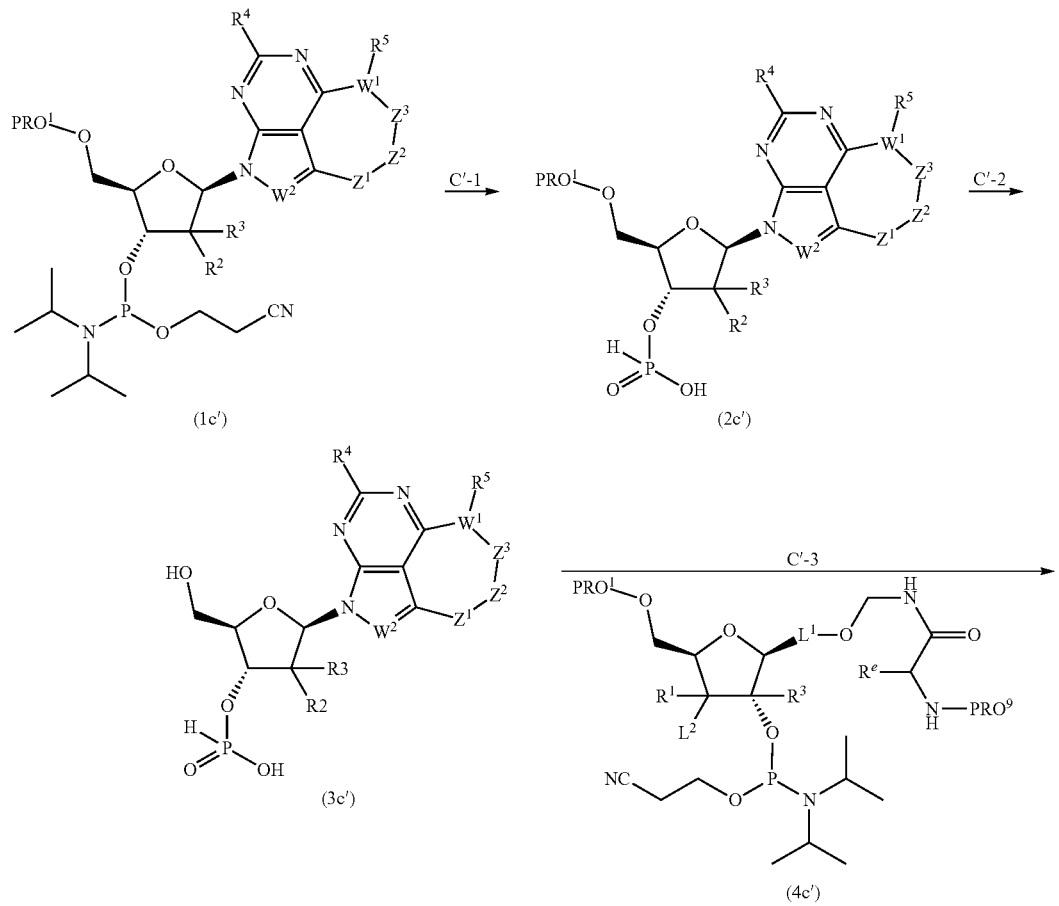
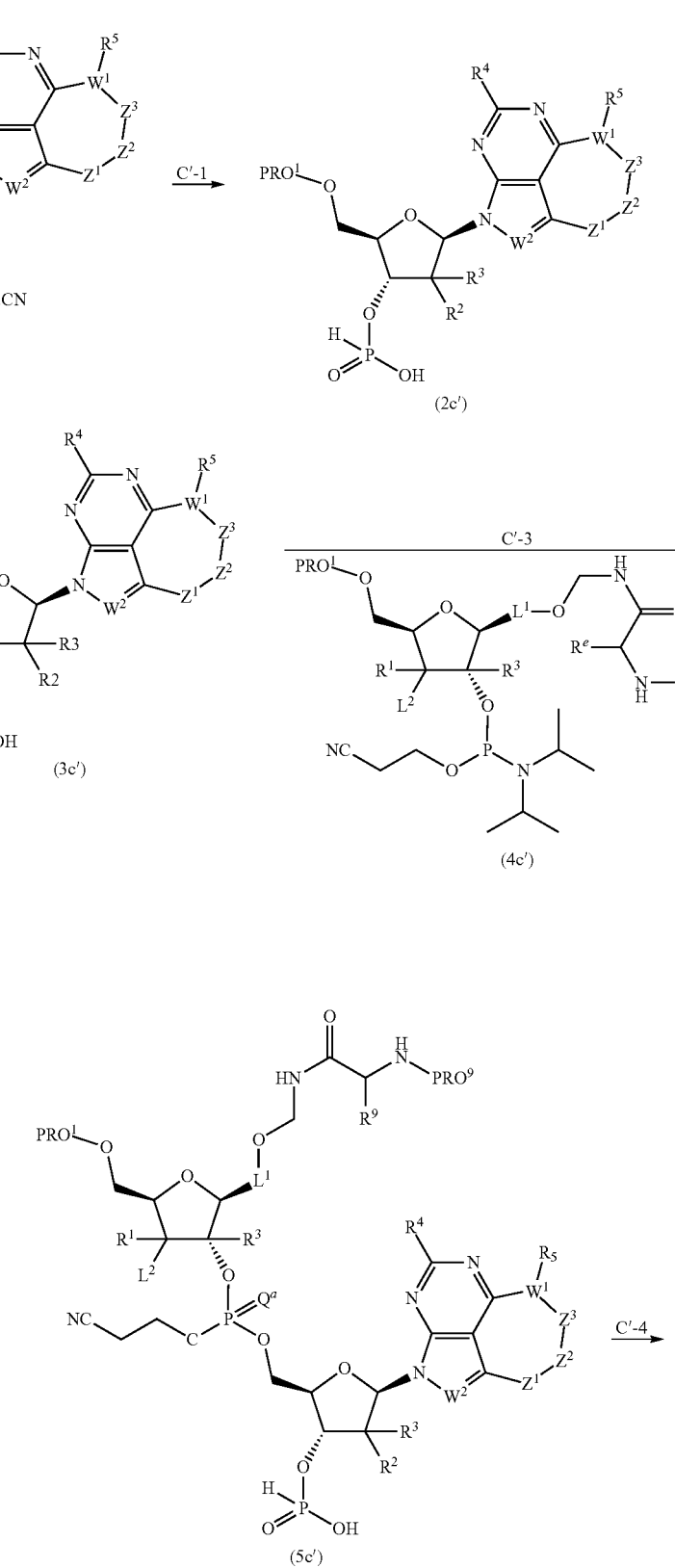

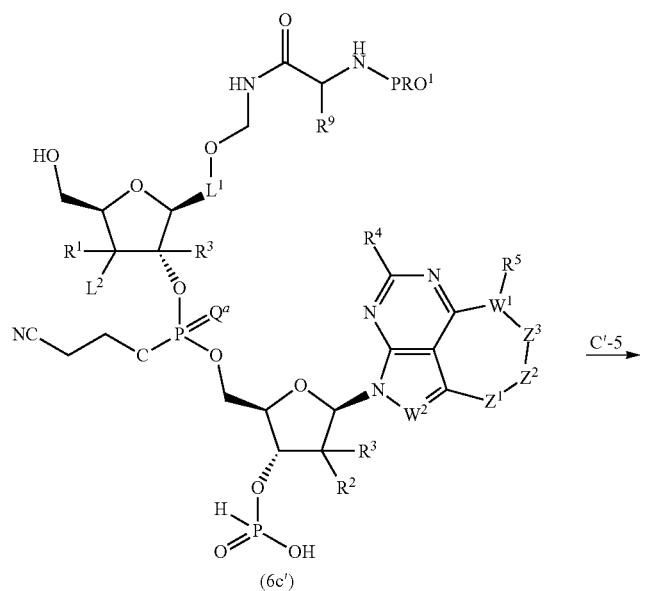
(6c′)
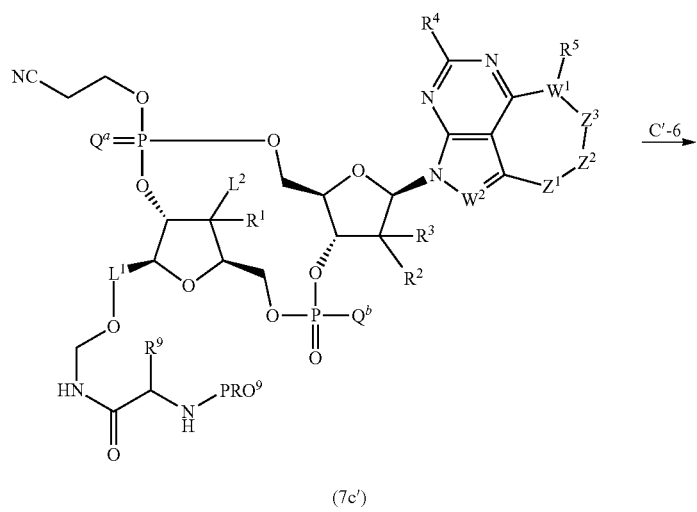
(7c′)
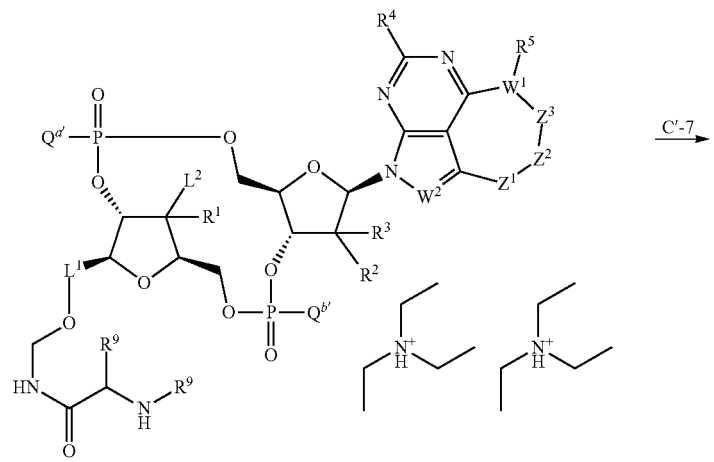
(8c′)

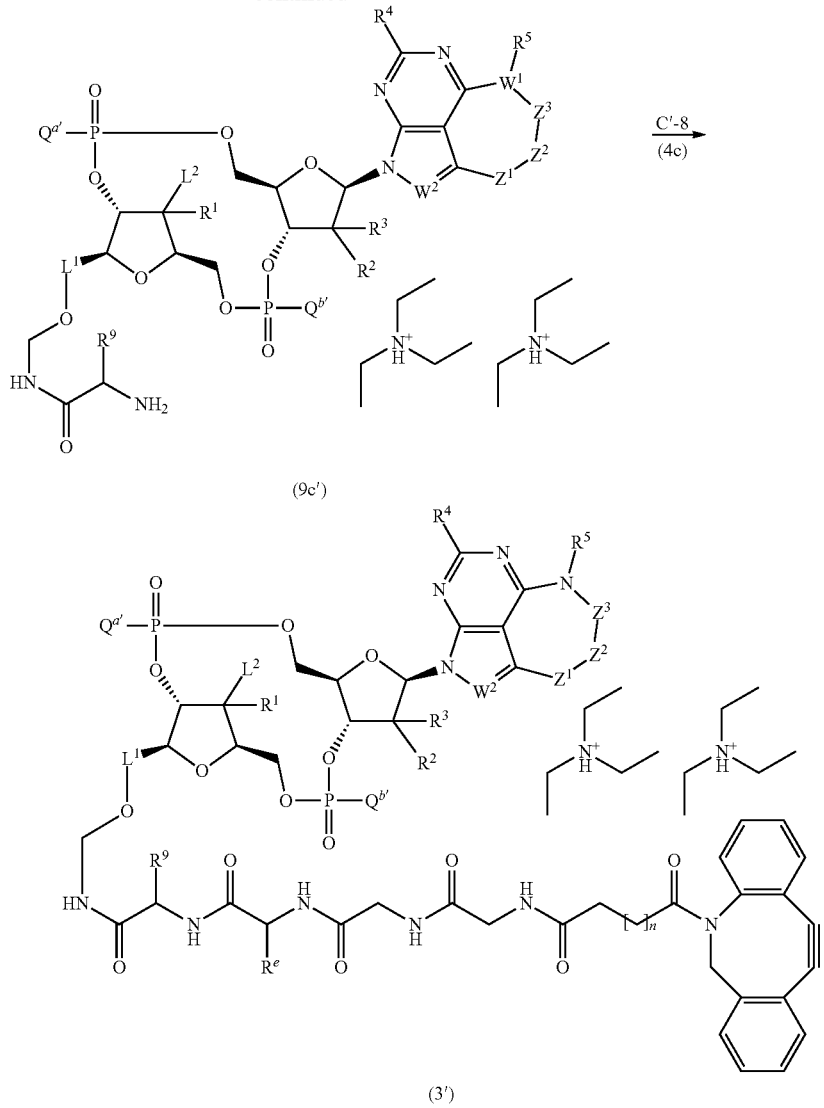

(Step C'-1)

This step is a step of producing the compound of formula (2c') by sequentially performing hydrolysis reaction of the compound of formula (1c') and removal of a cyanoethyl group from the resultant with use of a known technique of organic chemistry. Compound (2c') was obtained in accordance with the procedure described in step A-1 of scheme A.

(Step C'-2)

This step is a step of producing the compound of formula (3c') by removing a protective group for a hydroxy group from compound (2c') with use of a known technique of organic chemistry. Compound (3c') was obtained in accordance with the procedure described in step A-2 of scheme A.

(Step C'-3)

This step is a step of producing the compound of formula (5c') by sequentially performing coupling reaction of the compound of formula (3c') with the compound of formula (4c') and sulfidation reaction or oxidation reaction of the resulting coupled form with use of a known technique of organic chemistry. Compound (5c') was obtained in accordance with the procedure described in step A-3 of scheme A or step A"-3 of scheme A".

(Step C'-4)

This step is a step of producing the compound of formula (6c') by removing a protective group for a hydroxy group from the compound of formula (5c') with use of a known technique of organic chemistry. Compound (6c') was obtained in accordance with the procedure described in step A-4 of scheme A.

(Step C'-5)

This step is a step of producing the compound of formula (7c') by sequentially performing cyclization reaction of the compound of formula (6c') and sulfidation reaction or oxidation reaction of the resultant with use of a known technique of organic chemistry. Compound (7c') was obtained in accordance with the procedure described in step A-5 of scheme A or step A'-5 of scheme A'.

(Step C'-6)

This step is a step of producing the compound of formula (8c') by simultaneously removing a cyanoethyl group and all acyl protective groups from the compound of formula (7c') with use of a known technique of organic chemistry. Compound (8c') was obtained in accordance with the procedure described in step A-6 of scheme A.

(Step C'-7)

This step is a step of producing the compound of formula (9c') by simultaneously removing all silyl protective groups from the compound of formula (8c') with use of a known technique of organic chemistry. When PRO$^9$ was a 2-(trimethylsilyl) ethoxycarbonyl group, the 2-(trimethylsilyl) ethoxycarbonyl group was removed by treating compound (8c') with a tetrahydrofuran solution of tetrabutylammonium fluoride at a temperature of from 5° C. to 100° C., preferably 35° C. to 60° C. The amount of moles of tetrabutylammonium fluoride used was an excessive amount of moles, preferably 10 to 30 mol, to 1 mol of compound (8c'). The reaction time is 1 hour to 48 hours, and preferably 4 hours to 24 hours. After the reaction mixture was diluted with addition of buffer thereto, the organic solvent component was distilled off under reduced pressure, as necessary. The residue was purified by preparative HPLC [buffer/acetonitrile, buffer/methanol, etc.], C18 silica gel column chromatography [buffer/acetonitrile, buffer/methanol, etc.], or combination of them to afford compound (9c').

(Step C'-8)

This step is a step of producing the compound of formula (3') by performing condensation reaction of the compound of formula (9c') with the compound of formula (4c) with use of a known technique of organic chemistry. Compound (3') was obtained in accordance with the procedure described in step B-4 of scheme B.

Scheme D: Production of Glycan-Remodeled Antibody

Glycan-remodeled antibodies may be produced by using a method shown in the formula on FIG. 23, for example, on the basis of a method described in WO 2018/003983.

(Step D-1)

This step is a step of producing a glycan-truncated antibody by hydrolytically cleaving the glycosidic bond at GlcNAcβ1-4GlcNAc of the chitobiose structure at a reducing terminus of N-linked glycan bonding to asparagine at position 297 of the amino acid sequence of a targeted antibody (N297-linked glycan) with use of a known enzymatic reaction.

Targeted antibody (1d) (10 mg/mL) in buffer (e.g., phosphate buffer) was subjected to hydrolysis reaction of the glycosidic bond between GlcNAcβ1 and 4GlcNAc in the chitobiose structure at a reducing terminus with use of hydrolase such as the enzyme wild-type EndoS at a temperature of from 0° C. to 40° C. The reaction time is 10 minutes to 72 hours, and preferably 1 hour to 6 hours. The amount of the enzyme wild-type EndoS used was 0.1 to 10 mg, preferably 0.1 to 3 mg, to 100 mg of antibody (1d). After the completion of the reaction, the resultant was purified by affinity chromatography (HiTrap rProtein A FF (5 mL) (produced by GE Healthcare)) and/or a hydroxyapatite column (Bio-Scale Mini CHT Type I Cartridge (5 mL) (produced by Bio-Rad Laboratories, Inc.)) to afford (Fucα1,6)GlcNAc antibody (2d).

(Step D-2)

This step is a step of producing glycan-remodeled antibody (3d) by bonding an SG-type or MSG(MSG1, MSG2)-type glycan oxazoline form (hereinafter, referred to as "azide glycan oxazoline form") having a PEG linker including an azide group to (Fucα1,6)GlcNAc antibody (2d) obtained in step D-1 with use of a known enzymatic reaction.

Antibody (2d) in buffer (e.g., phosphate buffer) was subjected to transglycosylation reaction by reacting with an azide glycan oxazoline form in the presence of glycosyltransferase such as EndoS (D233Q/Q303L) at a temperature of from 0° C. to 40° C. The reaction time is 10 minutes to 72 hours, and preferably 1 hour to 6 hours. The amount of the enzyme EndoS (D233Q/Q303L) used was 1 to 10 mg, preferably 1 to 3 mg, to 100 mg of the antibody, and that of the azide glycan oxazoline form used was 2 equivalents to an excessive equivalent, preferably 4 equivalents to 20 equivalents. After the completion of the reaction, the resultant was purified by affinity chromatography (HiTrap rProtein A FF (5 mL) (produced by GE Healthcare)) and/or a hydroxyapatite column (Bio-Scale Mini CHT Type I Cartridge (5 mL) (produced by Bio-Rad Laboratories, Inc.)) to afford glycan-remodeled antibody (3d).

In preparing the glycan-remodeled antibody, concentration of an aqueous solution of an antibody, measurement of concentration, and buffer exchange may be performed in accordance with Common Operations A to C described later.

An SG-type azide glycan oxazoline form was synthesized on the basis of a method describe in WO 2018/003983. As an example, a method for synthesizing [N$_3$-PEG (3)]$_2$-SG (10)-Ox (compound 1-10 described in WO 2018/003983) is shown in the following formula.

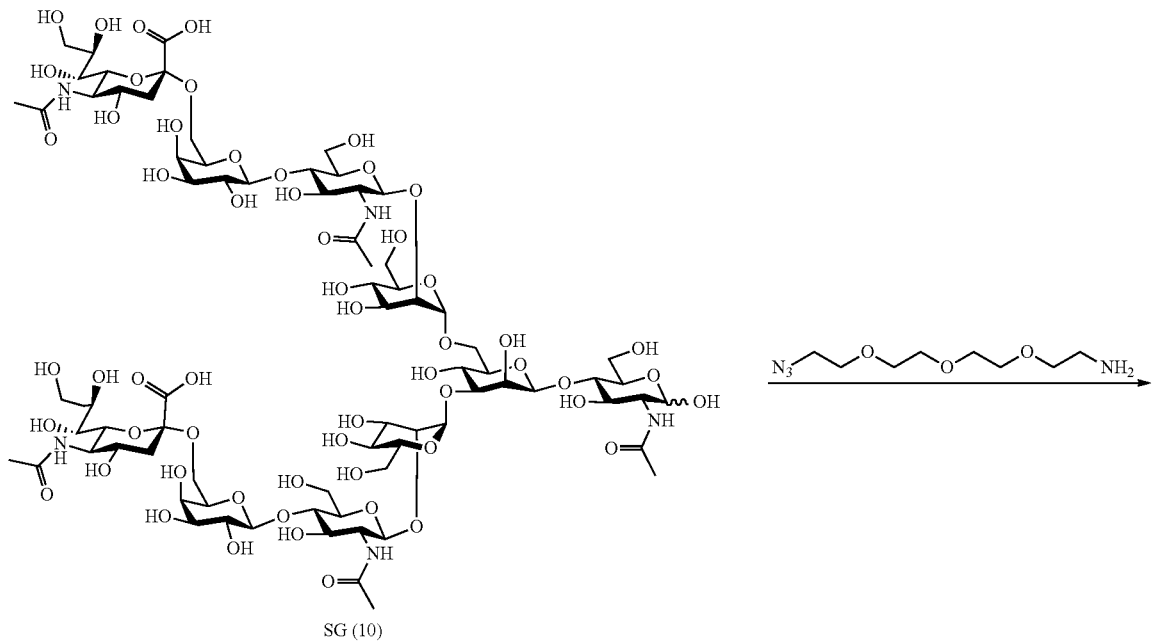

SG (10)

-continued
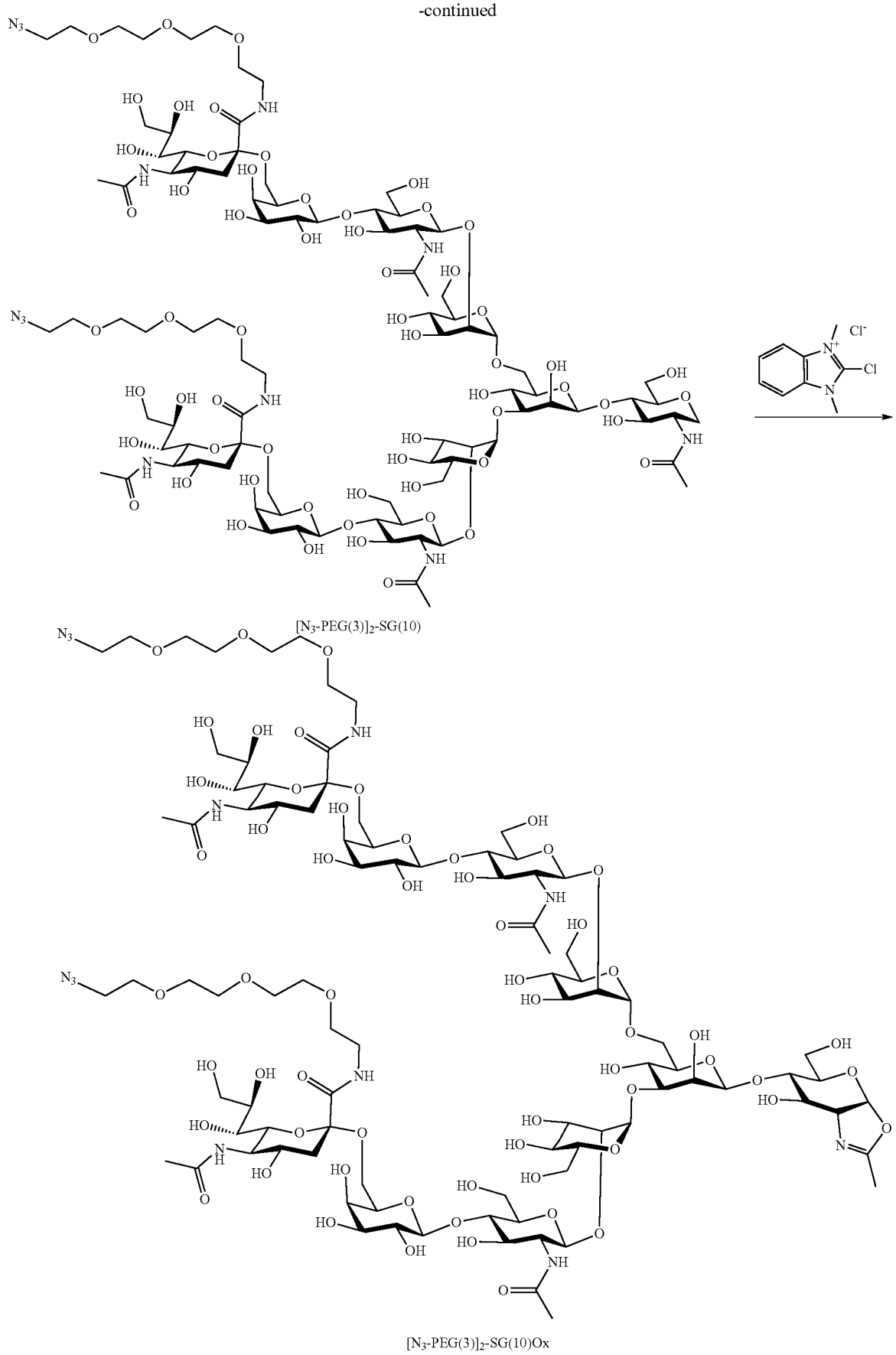
[N₃-PEG(3)]₂-SG(10)Ox

Similarly, an MSG-type azide glycan oxazoline form was synthesized on the basis of a method described in WO 2018/003983. As an example, a method for synthesizing [$N_3$-PEG (3)]-MSG1 (9)-Ox (compound 1-11 described in WO 2018/003983) is shown in the following formula.

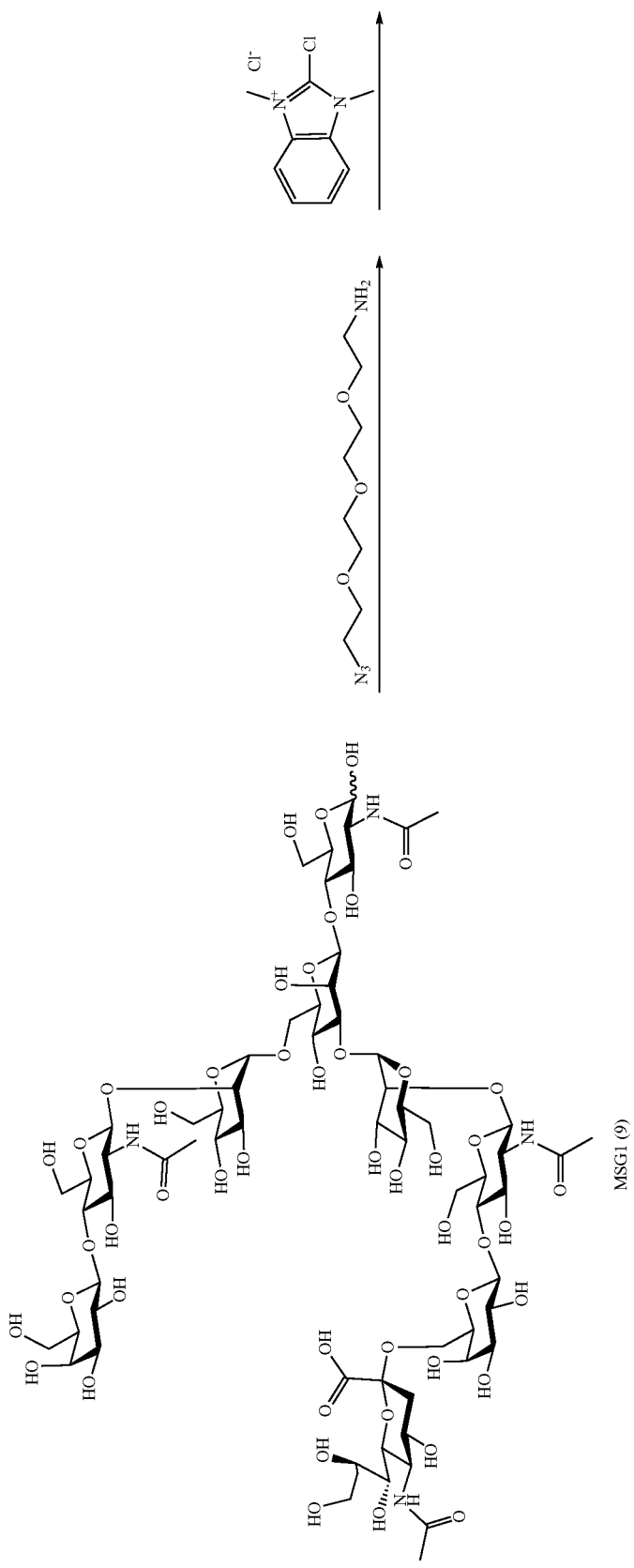

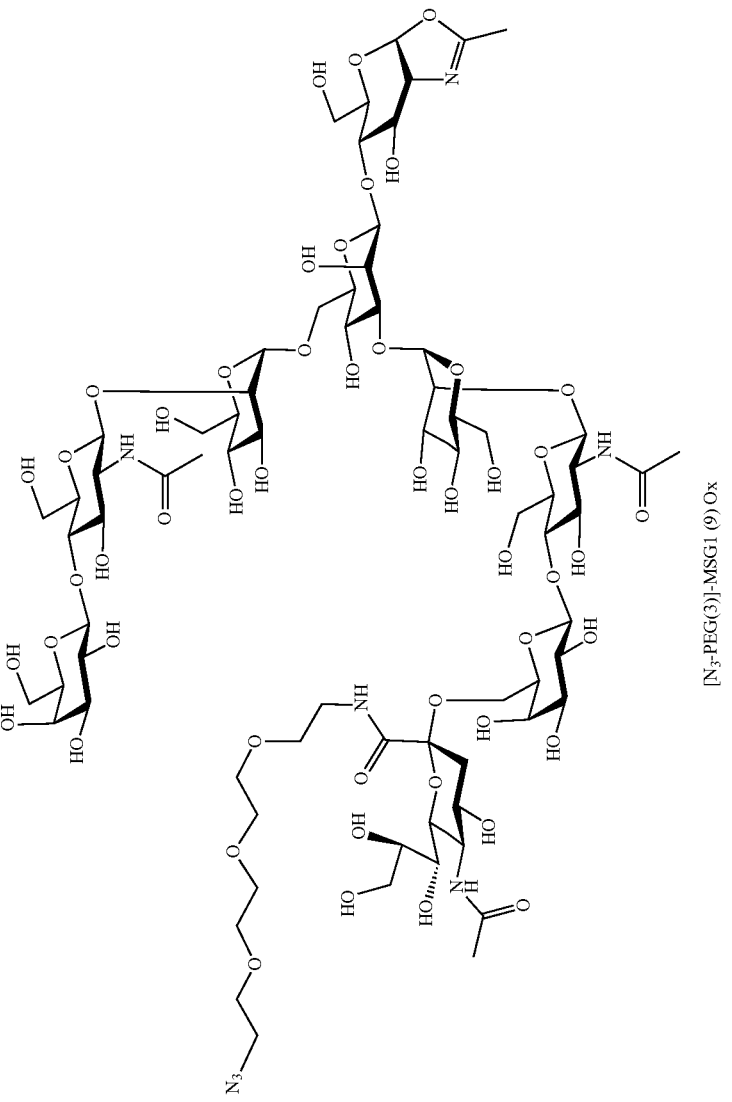

Scheme E: Conjugation of Antibody and Drug (Glycan Conjugation 1)

Figure 24:
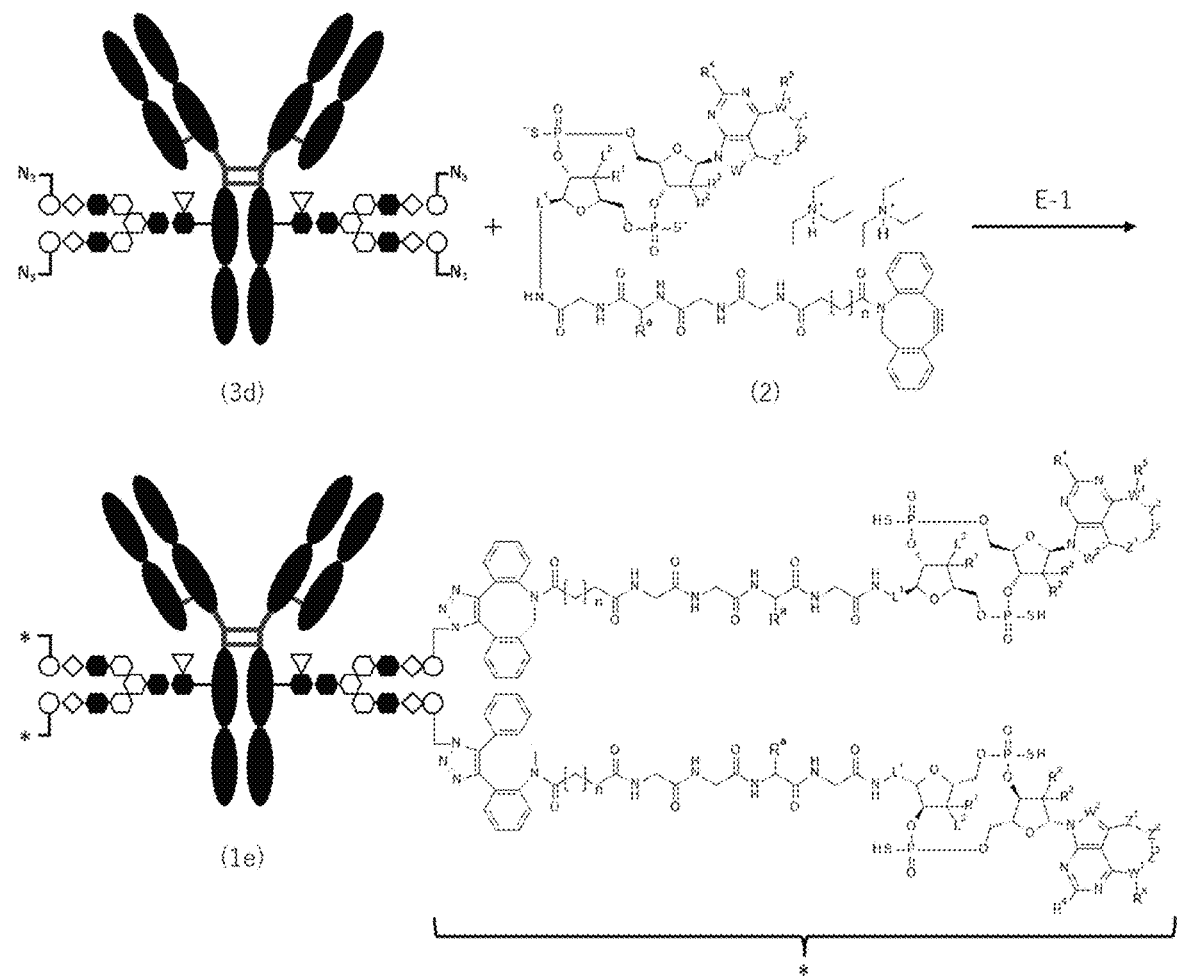
FIG. 24 shows the Formula representing Scheme E: Conjugation of Antibody and Drug (Glycan Conjugation 1).

See FIG. 24. In the formula, the two asterisks (*) in the left side of antibody-drug conjugate (1e) indicate the drug-linker moiety specified by the asterisk in the right side.

The present production method is a method for producing antibody-drug conjugate (1e) by bonding glycan-remodeled antibody (3d) obtained in step D-2 of scheme D and conjugate precursor (2) obtained in step B-4 of scheme B through SPAAC (strain-promoted azide-alkyne cycloaddition: J. Am. Chem. Soc. 2004, 126, 15046-15047) reaction. (Step E-1)

SPAAC reaction was performed by mixing a buffer solution (phosphate buffer, acetate buffer, borate buffer, etc.) of glycan-remodeled antibody (3d) and a solution of conjugate precursor (2) dissolved in an appropriate solvent (dimethyl sulfoxide, N,N-dimethylformamide, N,N-dimethylacetamide, N-methylpyrrolidone, propylene glycol, or a mixed solvent of them). The amount of moles of conjugate precursor (2) is 2 mol to an excessive amount of moles, preferably 4 mol to 30 mol, to 1 mol of glycan-remodeled antibody (3d), and the ratio of the organic solvent is preferably 1% to 200% (v/v) to the buffer solution of the antibody. The reaction temperature is 0° C. to 37° C., and preferably 15° C. to 25° C., and the reaction time is 1 hour to 150 hours, and preferably 6 hours to 72 hours. The pH of the reaction mixture is preferably 5 to 9. The reaction mixture was purified in accordance with a method described later in Common Operation D to afford antibody-drug conjugate (1e).

Scheme E': Conjugation of Antibody and Drug (Cysteine Conjugation)

The antibody-drug conjugate of the present invention with cysteine conjugation may be produced, for example, on the basis of a method described in WO 2014/057687 with use of a targeted antibody prepared, for example, in accordance with Reference Example 1 and conjugate precursor (2') having a maleimide group obtained in step B-8 of scheme B'.

Scheme E'': Conjugation of Antibody and Drug (Glycan Conjugation 2)

Figure 25:
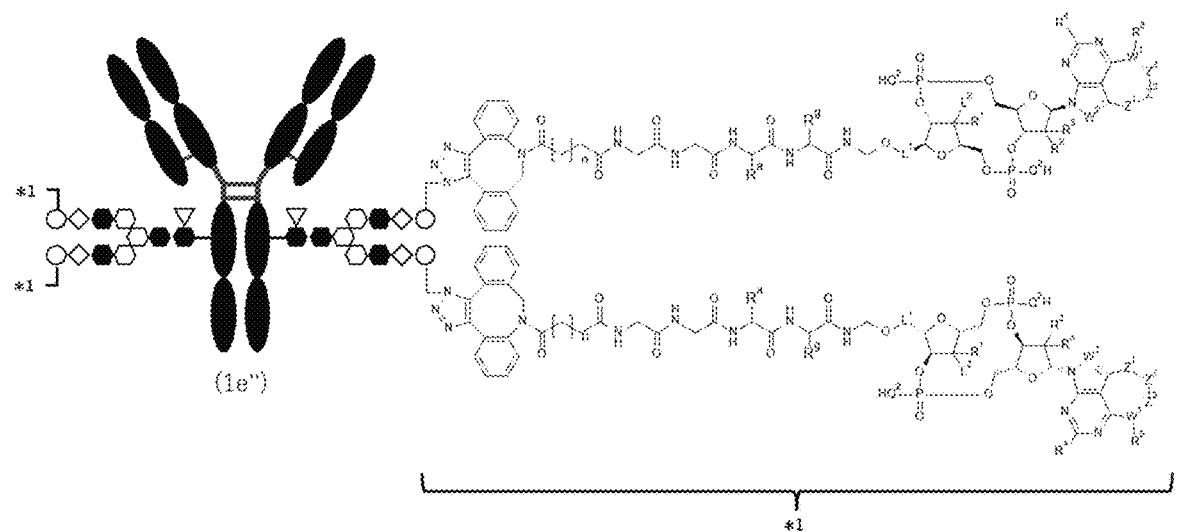
FIG. 25 shows the Formula representing Scheme E'': Conjugation of Antibody and Drug (Glycan Conjugation 2), with the replacement of conjugate precursor (2) with conjugate precursor (3') obtained in step C'-8 of scheme C', antibody-drug conjugate (1e'') shown in the formula was obtained.

With replacement of conjugate precursor (2) with conjugate precursor (3') obtained in step C'-8 of scheme C', antibody-drug conjugate (1e'') shown in the formula on FIG. 25 was obtained.

See FIG. 25. In the formula, the two asterisks (*1) in the left side of antibody-drug conjugate (1e'') indicate the drug-linker moiety specified by the asterisk in the right side.

Antibody-drug conjugates can be identified from each other through buffer exchange, purification, measurement of antibody concentration, and measurement of the average number of conjugated drug molecules per antibody molecule in accordance with Common operations D to G described later.

Common Operation A: Concentration of Aqueous Solution of Antibody

A solution of an antibody or antibody-drug conjugate was placed in an Amicon® Ultra Centrifugal Filter Device (50,000 NMWL, Merck Millipore Ltd.), and the solution of an antibody or antibody-drug conjugate was concentrated through a centrifugation operation (centrifugation at 2000 G to 4000 G for 5 to 20 minutes) using a centrifuge (Allegra X-15R, Beckman Coulter, Inc.).

Common Operation B: Measurement of Antibody Concentration

Measurement of antibody concentration was performed by using a UV measurement apparatus (Nanodrop 1000, Thermo Fisher Scientific) in accordance with a method specified by the manufacturer. In measurement, 280 nm absorption coefficients, being different among antibodies (1.3 mL mg-1 cm-1 to 1.8 mL mg-1 cm-1), were used.

Common Operation C: Buffer Exchange for Antibody

A buffer (phosphate-buffered saline (pH 6.0), phosphate buffer (pH 6.0), etc.) was added to an aqueous solution of an antibody, and the resultant was concentrated in accordance with the method described in Common Operation A. This operation was performed several times, and the antibody concentration was then measured in accordance with the method described in Common Operation B. To this antibody buffer solution, a buffer (phosphate-buffered saline (pH 6.0), phosphate buffer (pH 6.0), etc.) was appropriately added to prepare an antibody buffer solution with an intended concentration (e.g., approximately 10 mg/mL).

Common Operation D: Purification of Antibody-Drug Conjugate (Gel Filtration Chromatography)

An NAP column (NAP-5, NAP-10, NAP-25 (produced by GE Healthcare)) was equilibrated with acetate buffer (10 mM Acetate Buffer, 5% Sorbitol, pH 5.5; herein, referred to as ABS) or another appropriate buffer. This NAP column was charged with a reaction mixture of an antibody-drug conjugate, and a buffer in an amount specified by the manufacturer was allowed to gravitationally flow down to separate and collect an antibody fraction. The NAP column was again charged with this fraction, and a buffer in an amount specified by the manufacturer was allowed to gravitationally flow down to separate and collect an antibody fraction. This operation was repeated twice or three times in total to afford the antibody-drug conjugate with an unbound drug-linker, dimethyl sulfoxide, and propylene glycol removed. As necessary, the concentration of the solution of the antibody-drug conjugate was adjusted through Common Operations A and C.

Common Operation E: Measurement of Antibody Concentration and Average Number of Conjugated Drug molecules Per Antibody Molecule in Antibody-Drug Conjugate (UV Method)

The concentration of a conjugated drug in an antibody-drug conjugate can be calculated by measuring absorbance of an aqueous solution of the antibody-drug conjugate at two wavelengths of 280 nm and 260 nm (occasionally, a wavelength other than 260 nm is used) with use of an absorptiometer (UV/VIS Spectrometer Lambda 25, PerkinElmer, Inc.), followed by performing calculation shown below. The total absorbance at any wavelength is equal to the sum of the absorbances of all light-absorbing chemical species present in the system (additivity of absorbance), and hence with the assumption that the molar absorption coefficients of the antibody and the drug are unchanged before and after conjugation between the antibody and the drug, the antibody concentration and the drug concentration in the antibody-drug conjugate are expressed by the following expressions:

$$A_{280}=A_{D,280}+A_{A,280}=\varepsilon_{D,280}C_D+\varepsilon_{A,280}C_A \quad \text{Expression(I)}$$

$$A_{260}=A_{D,260}+A_{A,260}=\varepsilon_{D,260}C_D+\varepsilon_{A,260}C_A \quad \text{Expression (II)}$$

wherein $A_{280}$ denotes the absorbance of an aqueous solution of the antibody-drug conjugate at 280 nm, $A_{260}$ denotes the absorbance of an aqueous solution of the antibody-drug conjugate at 260 nm, $A_{A,280}$ denotes the absorbance of the antibody at 280 nm, $A_{A,260}$ denotes the absorbance of the antibody at 260 nm, $A_{D,280}$ denotes the absorbance of the conjugate precursor at 280 nm, $A_{D,260}$ denotes the absorbance of the conjugate precursor at 260 nm, $\varepsilon_{A,280}$ denotes the molar absorption coefficient of the antibody at 280 nm, $\varepsilon_{A,260}$ denotes the molar absorption coefficient of an antibody at 260 nm, $\varepsilon_{D,280}$ denotes the molar absorption coefficient of the conjugate precursor at 280 nm, $\varepsilon_{D,260}$ denotes the molar absorption coefficient of the conjugate precursor at 260 nm, CA denotes the antibody concentration of the antibody-drug conjugate, and $C_D$ denotes the drug concentration of the antibody-drug conjugate. For $\varepsilon_{A,280}$, $\varepsilon_{A,260}$, $\varepsilon_{D,280}$, and $\varepsilon_{D,260}$ in the above, values prepared in advance (estimates based on calculation or measured values) are used. For example, $\varepsilon_{A,280}$ can be estimated from the amino acid sequence of an antibody by using a known calculation method (Protein Science, 1995, vol. 4, 2411-2423). For $\varepsilon_{A,260}$, values calculated from a measured value obtained by UV measurement of an antibody and an estimate for $\varepsilon_{A,280}$ were used. In Examples, $\varepsilon_{A,280}$=215380 and $\varepsilon_{A,260}$=110117 were used as molar absorption coefficients of a modified anti-HER2 antibody. $\varepsilon_{A,280}$=227300 and $\varepsilon_{A,260}$=110710 were used as molar absorption coefficients of a modified anti-LPS antibody. $\varepsilon_{D,280}$ and $\varepsilon_{D,260}$ can be obtained on the basis of the Lambert-Beer's law (Absorbance=Molarity×Molar absorption coefficient×Cell optical path length) by measuring the absorbance of a solution in which a conjugate precursor to be used is dissolved at a certain molarity. The molar absorption coefficient of a conjugate precursor in Examples was obtained each time in UV measurement. $C_A$ and $C_D$ can be determined by measuring $A_{280}$ and $A_{260}$ of an aqueous solution of an antibody-drug conjugate and substituting them into expressions (I) and (II) to solve the simultaneous equations. Further, the average number of conjugated drug molecules per antibody molecule can be determined by dividing $C_D$ by $C_A$.

Common Operation F: Measurement of Antibody Concentration and Average Number of Conjugated Drug Molecules Per Antibody Molecule in Antibody-Drug Conjugate (Reverse-Phase High-Performance Liquid Chromatography: RP-HPLC)

In addition to Common Operation E described above, high-performance liquid chromatography analysis using the following method can determine antibody concentration and the average number of conjugated drug molecules per antibody molecule in an antibody-drug conjugate.

[F-1. Preparation of Sample for HPLC Analysis (Reduction of Antibody-Drug Conjugate)]

A solution of an antibody-drug conjugate (approximately 1 mg/mL, 60 μL) was mixed with an aqueous solution of dithiothreitol (DTT) (100 mM, 15 μL). The mixture was incubated at 37° C. for 30 minutes to cleave the disulfide bond between the L chain and H chain of the antibody-drug conjugate. This reaction mixture was directly used for HPLC analysis.

[F-2. HPLC Analysis]

Representative analysis conditions are as follows.

HPLC system: Agilent 1290 HPLC system (Agilent Technologies)

Detector: ultraviolet absorptiometer (measurement wavelength: 280 nm)

Column: Acquity BEH Phenyl (2.1×50 mm, 1.7 μm, produced by Waters Corporation)

Column temperature: 75° C.

Flow rate: 0.8 mL/min

Sample injection volume: 10 μL

Mobile phase A: 0.1% trifluoroacetic acid (TFA)/15% isopropyl alcohol aqueous solution Mobile Phase B: 0.075% TFA/15% isopropyl alcohol acetonitrile solution Gradient program (mobile phase B): 14%-36% (0 min-15 min), 36%-80% (15-17 min), 80%-14% (17 min-17.1 min), 14%-14% (17.1 min-23 min)

[F-3. Data Analysis]

[F-3-1] As compared with the L chain (L0) and H chain (H0) of an antibody without any conjugated drug molecule, an H chain with a conjugated drug molecule(s) (H chain with one conjugated drug molecule: H1, H chain with two conjugated drug molecules: H2) has hydrophobicity increased in proportion to the number of conjugated drug molecules and gives prolonged retention time, and hence L0, H0, H1, and H2 are eluted in this order, in principle. Through comparison of retention time of each of L0 and H0, each peak detected can be assigned to any one of L0, H0, H1, and H2.

[F-3-2] Since each drug-linker absorbs UV, peak area values were corrected by using the following expression with the molar absorption coefficients of an H chain and drug-linker according to the number of conjugated drug-linker molecules.

Corrected $H$ chain peak area $(HPA_i) =$ [Expression 1]

$$\text{Peak area} \times \frac{\text{Molar absorption coefficient of } H \text{ chain}}{\text{Molar absorption coefficient of } H \text{ chain} + \text{Number of conjugated drug molecules} \times \text{Molar absorption coefficient of drug-linker}}$$

Here, estimates calculated by using the known calculation method described in Common Operation E were used for Molar absorption coefficients (280 nm) of L chain and H chain for each antibody. For a modified anti-HER2 antibody, 26213 and 81478 were used as Molar absorption coefficient of L chain and Molar absorption coefficient of H chain, respectively. For a modified anti-LPS antibody, similarly, 27703 and 85948 were used as Molar absorption coefficient of L chain and Molar absorption coefficient of H chain, respectively. For Molar absorption coefficient (280 nm) of drug-linker, a measured value for the conjugate precursor was used in the case of conjugation through SPAAC reaction, and, in the case of cysteine conjugation, a measured value for a compound in which the maleimide group had been converted to succinimide thioether by the reaction of the conjugate precursor with mercaptoethanol or N-acetylcysteine was used.

[F-3-3] The peak area ratio (%) of each chain to the total of corrected peak area values was calculated by using the following expression.

$H$ peak chain area ratio (% $HPA_i$) = [Expression 2]

$$\frac{HPA_i}{HPA_0 + HPA_1 + HPA_2} \times 100$$

[F-3-4] The average number of conjugated drug molecules per antibody molecule (DAR) in an antibody-drug conjugate was calculated by using the following expression.

Average number of conjugated drug molecules $(DAR) =$ [Expression 3]

$$\frac{0 \times \% \, HPA_0 + 1 \times \% \, HPA_1 + 2 \times \% \, HPA_2}{100} \times 2$$

[F-3-5] Antibody concentration in an antibody-drug conjugate was calculated by using the following expression.

$$\text{Antibody concentration } (C_A) \text{ [mg/mL]} = \quad \text{[Expression 4]}$$

$$\frac{\text{Absorbance of antibody-drug complex} \times \text{Dilution ratio} \times \text{Molecular weight of antibody}}{\text{Molar absorption coefficient of antibody} + \text{Average number of conjugated drug molecules} \times \text{Molar absorption coefficient of drug-linker}}$$

Here, a measured value for an aqueous solution of an antibody-drug conjugate was used for Absorbance (280 nm) of antibody-drug complex. Dilution ratio indicates how many folds an aqueous solution of an antibody-drug conjugate was diluted in measurement of absorbance, and typically four-fold dilution is applied. For Molar absorption coefficient (280 nm) of antibody, an estimate calculated by using the known calculation method described in Common Operation E was used. For Average number of conjugated drug molecules, a value obtained in [F-3-4] was used. For Molar absorption coefficient (280 nm) of drug-linker, a measured value for a conjugate precursor was used in the case of conjugation through SPAAC reaction, and, in the case of cysteine conjugation, a measured value for a compound in which the maleimide group had been converted to succinimide thioether by the reaction of the drug-linker with mercaptoethanol or N-acetylcysteine was used.

Common Operation G: Measurement of Antibody Concentration and Average Number of Conjugated Drug Molecules Per Antibody Molecule in Antibody-Drug Conjugate (Hydrophobic Interaction-High-Performance Liquid Chromatography: HI-HPLC)

In addition to Common Operations E and F described above, high-performance liquid chromatography analysis using the following method can determine antibody concentration and the average number of conjugated drug molecules per antibody molecule in an antibody-drug conjugate.

[G-1. Preparation of Sample for HPLC Analysis]

A solution of an antibody-drug conjugate (approximately 1 mg/mL, 60 μL) was directly used for HPLC analysis.

[G-2. HPLC Analysis]

Representative analysis conditions are the following two.
HPLC system: SHIMADZU CBM-20A (Shimadzu Corporation)
Detector: ultraviolet absorptiometer (measurement wavelength: 280 nm)
Column: TSK-gel Butyl-NPR (4.6×100 mm, 2.5 μm, produced by Tosoh Corporation)
Column temperature: constant temperature around 25° C.
Mobile phase A: 1.5 M ammonium sulfate-containing 25 mM phosphate buffer (pH=7.0)
Mobile phase B: 25 mM phosphate buffer (pH=7.0)/isopropyl alcohol (3:1)
Flow rate: 0.8 mL/min
Sample injection volume: 15 μL
Gradient program (mobile phase B): 10%-15% (0 min-5 min), 15%-65% (5 min-20 min) or
HPLC system: SHIMADZU CBM-20A (Shimadzu Corporation)
Detector: ultraviolet absorptiometer (measurement wavelength: 280 nm)
Column: PolyPROPYL A (4.6×100 mm, 3 μm, 1500 angstroms, produced by PolyLC Inc.)
Column temperature: constant temperature around 40° C.
Mobile phase A: 1.5 M ammonium sulfate-containing 20 mM phosphate buffer (pH=7.4)
Mobile phase B: 20 mM phosphate buffer (pH=7.4)
Flow rate: 0.8 mL/min
Sample injection volume: 15 μL
Gradient program (mobile phase B): 40%-80% (0 min-20 min)

[G-3. Data Analysis]

[G-3-1] Hydrophobicity increases in proportion to the number of drug molecules conjugated to an antibody molecule and prolonged retention time is given, and hence, in the case of conjugation through SPAAC reaction, products with DAR=0, DAR=2, and DAR=4 are eluted in this order, in principle. Through comparison of retention time of a product with DAR=0, each peak detected can be assigned to either one of a product with DAR=2 and that with DAR=4. For some types of antibodies or drug-linkers, peaks for a product with DAR=1 and that with DAR=3 may be detected. DAR for a detected peak is estimated in some cases by fractionating the peak through HI-HPLC and then measuring the mass spectrum.

[G-3-2] Since each drug-linker absorbs UV, peak area values were corrected by using the following expression with the molar absorption coefficients of an antibody and drug-linker according to the number of conjugated drug-linker molecules.

$$\text{Corrected antibody peak area } (WPA_i) = \quad \text{[Expression 5]}$$

$$\text{Peak area} \times \frac{\text{Molar absorption coefficient of antibody}}{\text{Molar absorption coefficient of antibody} + \text{Number of conjugated drug molecules} \times \text{Molar absorption coefficient of drug-linker}}$$

Here, estimates calculated by using the known calculation method described in Common Operation E were used for Molar absorption coefficient (280 nm) of antibody. For Molar absorption coefficient (280 nm) of drug-linker, a measured value for the conjugate precursor was used.

[G-3-3] The peak area ratio (%) of an antibody to the total of corrected peak area values was calculated by using the following expression.

$$\text{Antibody peak area ratio } (\% \ WPA_i) = \quad \text{[Expression 6]}$$

$$\frac{WPA_i}{WPA_0 + WPA_1 + WPA_2 + WPA_3 + WPA_4} \times 100$$

[G-3-4] The average number of conjugated drug molecules per antibody molecule in an antibody-drug conjugate was calculated by using the following expression.

$$\text{Average number of conjugated drug molecules } (DAR) = \quad \text{[Expression 7]}$$

$$\frac{0 \times \% \ WPA_0 + 1 \times \% \ WPA_1 + 2 \times \% \ WPA_2 + 3 \times \% \ WPA_3 + 4 \times \% \ WPA_4}{100}$$

[G-3-5] Antibody concentration in an antibody-drug conjugate was calculated by using the expression shown in [F-3-5]. Then, a value obtained in [G-3-4] was used for the average number of conjugated drug molecules.

There may exist stereoisomers, optical isomers due to an asymmetric carbon atom, geometric isomers, tautomers, or optical isomers such as d-forms, l-forms, and atropisomers for the novel CDN derivative and antibody-drug conjugate of the present invention, and a production intermediate of any of them. These isomers, optical isomers, and mixtures of them are all included in the present invention.

The number of conjugated drug molecules per antibody molecule is an important factor having influence on efficacy and safety for the antibody-drug conjugate of the present invention. Antibody-drug conjugates are produced with reaction conditions, such as the amounts of raw materials and reagents to be reacted, specified so as to give a constant number of conjugated drug molecules; however, in contrast to chemical reaction of small molecule compounds, a mixture with different numbers of conjugated drug molecules is typically obtained. Numbers of conjugated drug molecules per antibody molecule are specified as the average value, namely, the average number of conjugated drug molecules (DAR). The number of cyclic dinucleotide derivative molecules conjugated to an antibody molecule is controllable, and 1 to 10 cyclic dinucleotide derivative molecules can be conjugated in terms of the average number of conjugated drug molecules per antibody molecule, but preferably the number is one to eight, and more preferably one to five.

When antibody Ab is bonding via a remodeled glycan of antibody Ab to L in the antibody-drug conjugate of the present invention, the number of conjugated drug molecules per antibody molecule in the antibody-drug conjugate, $m^2$, is an integer of 1 or 2. When the glycan is N297 glycan and the glycan is N297-(Fuc) SG, $m^2$ is 2 and DAR is in the range of 3 to 5 (preferably, in the range of 3.2 to 4.8, more preferably, in the range of 3.5 to 4.2). When N297 glycan is N297-(Fuc) MSG1, N297-(Fuc) MSG2, or a mixture of N297-(Fuc) MSG1 and N297-(Fuc) MSG2, $m^2$ is 1 and DAR is in the range of 1 to 3 (preferably, in the range of 1.0 to 2.5, more preferably, in the range of 1.2 to 2.2).

Those skilled in the art could design reaction to conjugate a required number of drug molecules to each antibody molecule on the basis of the description in Examples in the present application, and obtain an antibody with a controlled number of conjugated cyclic dinucleotide derivative molecules.

The CDN derivative and antibody-drug conjugate of the present invention, and a production intermediate of any of them may absorb moisture, allow adhesion of adsorbed water, or become a hydrate when being left to stand in the atmosphere or recrystallized. Such compounds and salts containing water are also included in the present invention.

The CDN derivative and antibody-drug conjugate of the present invention, and a production intermediate of any of them may be each converted into a pharmaceutically acceptable salt, as desired, when having a basic group such as an amino group. Examples of such salts may include hydrogen halide salts such as hydrochlorides and hydroiodides; inorganic acid salts such as nitrates, perchlorates, sulfates, and phosphates; lower alkanesulfonates such as methanesulfonates, trifluoromethanesulfonates, and ethanesulfonates; arylsufonates such as benzenesulfonates and p-toluenesulfonates; organic acid salts such as formates, acetates, malates, fumarates, succinates, citrates, tartrates, oxalates, and maleates; and amino acid salts such as ornithinates, glutamates, and aspartates.

Because the CDN derivative or antibody-drug conjugate of the present invention includes a phosphate group and/or thiophosphate group in the structure, a base addition salt can be generally formed. When a production intermediate thereof includes an acidic group such as a carboxy group, a base addition salt can be generally formed, similarly. Examples of pharmaceutical acceptable salts may include alkali metal salts such as sodium salts, potassium salts, and lithium salts; alkaline earth metal salts such as calcium salts and magnesium salts; inorganic salts such as ammonium salts; and organic amine salts such as dibenzylamine salts, morpholine salts, phenylglycine alkyl ester salts, ethylenediamine salts, N-methylglucamine salts, diethylamine salts, triethylamine salts, cyclohexylamine salts, dicyclohexylamine salts, N,N'-dibenzylethylenediamine salts, diethanolamine salts, N-benzyl-N-(2-phenylethoxy)amine salts, piperazine salts, tetramethylammonium salts, and tris(hydroxymethyl)aminomethane salts.

The CDN derivative and antibody-drug conjugate of the present invention, and a production intermediate of any of them may each exist as a hydrate, for example, formed by absorbing moisture in the air. The solvate of the present invention is not limited to a particular solvate as long as it may be any pharmaceutically acceptable solvate. Specifically hydrates, ethanol solvates, 2-propanol solvates, and so on are preferred. The CDN derivative and antibody-drug conjugate of the present invention, and a production intermediate of any of them may be each in the N-oxide form when a nitrogen atom is present therein. These solvates and N-oxide forms are included in the scope of the present invention. The CDN derivative and antibody-drug conjugate of the present invention, and a production intermediate of any of them may be each in the sulfoxide form when a sulfur atom is present therein. These solvates and sulfoxide forms are included in the scope of the present invention.

The present invention includes compounds labeled with various radioactive or nonradioactive isotopes. The CDN derivative and antibody-drug conjugate of the present invention, and a production intermediate of any of them may each contain one or more constituent atoms with non-natural ratios of atomic isotopes. Examples of atomic isotopes may include deuterium (2H), tritium (3H), iodine-125 (125I), and carbon-14 (14C). The compound of the present invention may be radiolabeled with a radioactive isotope such as tritium (3H), iodine-125 (125I), and carbon-14 (14C). The radiolabeled compound is useful as a therapeutic or prophylactic agent, a reagent for research such as an assay reagent, and a diagnostic agent such as a diagnostic agent for in vivo imaging. Isotopic variants of the antibody-drug conjugate of the present invention are all included in the scope of the present invention, regardless of whether they are radioactive or not.

<4. Medicine>

The CDN derivative or antibody-drug conjugate of the present invention exhibits anti-tumor immune activity or cytotoxic activity to cancer cells, and hence may be used as a medicine, in particular, a therapeutic agent and/or prophylactic agent for cancer, or an anti-tumor agent.

Examples of cancers to which the CDN derivative or antibody-drug conjugate of the present invention is applied may include lung cancer (non-small cell lung cancer, small cell lung cancer, etc.), kidney cancer, urothelial cancer, colorectal cancer, prostate cancer, glioblastoma multiforme, ovarian cancer (surface epithelial tumor, stromal tumor, germ cell tumor, etc.), pancreatic cancer, breast cancer, melanoma, liver cancer, bladder cancer, gastric cancer, esophageal cancer, endometrial cancer, testicular cancer (seminoma, non-seminoma), uterine cervix cancer, placental choriocarcinoma, glioblastoma multiforme, brain tumor, head-and-neck cancer, thyroid cancer, mesothelioma, gastrointestinal stromal tumor (GIST), gallbladder cancer, bile duct cancer, adrenal cancer, squamous cell carcinoma, leukemia, malignant lymphoma, plasmacytoma, myeloma, and sarcoma. However, applications of the antibody-drug conjugate are not limited thereto as long as cancer cells as a therapeutic target are expressing a protein recognizable for the antibody in the antibody-drug conjugate.

The CDN derivative or antibody-drug conjugate of the present invention can be preferably administered to mammals, and are more preferably administered to humans.

Substances to be used in a pharmaceutical composition containing the CDN derivative or antibody-drug conjugate of the present invention may be suitably selected for application from formulation additives and the like that are generally used in the art in view of the dose or administration concentration.

The CDN derivative or antibody-drug conjugate of the present invention may be administered as a pharmaceutical composition containing one or more pharmaceutically compatible components. For example, the pharmaceutical composition typically contains one or more pharmaceutical carriers (e.g., sterilized liquid (including water and oil (petroleum and oil of animal origin, plant origin, or synthetic origin (such as peanut oil, soybean oil, mineral oil, and sesame oil)) Water is a more typical carrier when the pharmaceutical composition is intravenously administered. Saline solution, an aqueous solution of dextrose, and an aqueous solution of glycerol can also be used as a liquid carrier, in particular, for an injection solution. Suitable pharmaceutical excipients are known in the art. If desired, the composition above may also contain a trace amount of a moisturizing agent, an emulsifying agent, or a pH buffering agent. Examples of suitable pharmaceutical carriers are disclosed in "Remington's Pharmaceutical Sciences" by E. W. Martin. Formulation of them depends on the mode of administration.

Various delivery systems are known and may be used for administering the CDN derivative or antibody-drug conjugate of the present invention. Examples of the introduction method may include, but are not limited to, intradermal, intramuscular, intraperitoneal, intravenous, and subcutaneous routes. The administration may be made, for example, by injection or bolus injection. In a specific preferred embodiment, administration of the CDN derivative or antibody-drug conjugate is performed by injection. Parenteral administration is a preferred route of administration.

In a representative embodiment, the pharmaceutical composition containing the above antibody-drug conjugate is formulated as a pharmaceutical composition suitable for intravenous administration to humans according to conventional procedures. The composition for intravenous administration is typically a solution in a sterile and isotonic aqueous buffer. If necessary, the medicine may contain a solubilizing agent and a local anesthetic to alleviate pain at an injection site (e.g., lignocaine). Generally, the components above are provided either individually as a dried lyophilized powder or anhydrous concentrate in a tightly sealed container such as an ampoule or sachet with indication of the amount of the active agent, or as a mixture in a unit dosage form. When the pharmaceutical composition is to be administered by infusion, it may be administered from an infusion bottle containing water or saline of sterile pharmaceutical grade. When the pharmaceutical composition is administered by injection, an ampoule containing sterile water or saline for injection may be provided so that the aforementioned components are mixed with each other before administration. The pharmaceutical composition may be provided as a solution.

The pharmaceutical composition of the present invention may be a pharmaceutical composition containing only the present CDN derivative or antibody-drug conjugate, or a pharmaceutical composition containing the CDN derivative or antibody-drug conjugate and at least one cancer treating agent other than the CDN derivative or antibody-drug conjugate. The CDN derivative or antibody-drug conjugate of the present invention may be administered in combination with other cancer treating agents, providing enhanced anticancer effect. Other anticancer agents to be used for such purpose may be administered to an individual simultaneously with, separately from, or subsequently to administration of the CDN derivative or antibody-drug conjugate, and may be administered at different intervals of administration. Examples of such cancer treating agents may include abraxane, carboplatin, cisplatin, gemcitabine, irinotecan (CPT-11), paclitaxel, pemetrexed, sorafenib, vinblastin, agents described in International Publication No. WO 2003/038043, LH-RH analogues (leuprorelin, goserelin, etc.), estramustine phosphate, estrogen antagonists (tamoxifen, raloxifene, etc.), aromatase inhibitors (anastrozole, letrozole, exemestane, etc.), and immune checkpoint inhibitors (nivolumab, ipilimumab, etc.), but are not limited thereto and any agent having an anti-tumor activity is acceptable.

The pharmaceutical composition as described can be formulated into a lyophilized formulation or a liquid formulation as a formulation having the selected composition and required purity. In formulating as a lyophilized formulation, the pharmaceutical composition may be formulated into a formulation containing appropriate formulation additives that are used in the art. Also for a liquid, the pharmaceutical composition may be formulated as a liquid formulation containing various formulation additives that are used in the art.

The components and concentration of the pharmaceutical composition may vary among administration methods; however, the antibody-drug conjugate contained in the pharmaceutical composition of the present invention can exhibit pharmaceutical effect even at a smaller dose, as the affinity of the antibody-drug conjugate with an antigen is higher, that is, as the affinity of the antibody-drug conjugate in terms of the dissociation constant (Kd value) with the antigen is higher (lower Kd value). Thus, in determining the dose of the antibody-drug conjugate, the dose may be set in view of the situation relating to the affinity of the antibody-drug conjugate with the antigen. When the CDN derivative or antibody-drug conjugate of the present invention is administered to a human, for example, approximately 0.001 to 100 mg/kg can be administered once, or in several portions at intervals of 1 to 180 days.

Hereinafter, the present invention will be described with reference to Examples; however, the present invention is not limited to Examples.

EXAMPLES

In Examples below, room temperature refers to a temperature of from 15° C. to 35° C. Dehydrated acetonitrile used was acetonitrile (dehydrated)-Super-sold by KANTO CHEMICAL CO., INC. or acetonitrile (super-dehydrated) sold by Wako Pure Chemical Industries, Ltd. Pyridine used was pyridine (dehydrated)-Super-sold by KANTO CHEMICAL CO., INC. Silica gel chromatography was performed by using a Biotage SNAP Ultra (produced by Biotage), Chromatorex Q-Pack SI (produced by FUJI SILYSIA CHEMICAL LTD.), or Purif-Pack-Ex SI (produced by Shoko Science Co., Ltd.). DIOL silica gel column chromatography was performed by using a Chromatorex Q-pack DIOL (produced by FUJI SILYSIA CHEMICAL LTD.). C18 silica gel column chromatography was performed by using a Biotage SNAP Ultra C18 (produced by Biotage). Amino-silica gel column chromatography was performed by using a Biotage SNAP Isolute NH₂ (produced by Biotage). Preparative HPLC was performed by using a SHIMADZU SPD-M10A HPLC system (Shimadzu Corporation) or the like. Used as a preparative column was a Kinetex (5 μm, C18, 100 angstroms, 250×30.0 mm, produced by Phenomenex) or Kinetex (5 μm, C18, 100 angstroms, 250×21.2 mm, produced by Phenomenex).

The following apparatuses were used for measurement of spectral data. Measurement for $^1$H-NMR spectra was performed by using a JEOL ECS-400 (400 MHZ), Varian 400-MR (400 MHZ), or Varian Unity Inova 500 (500 MHZ). Measurement for $^{31}$P-NMR spectra was performed by using a JEOL ECS-400 (160 MHz). Measurement for mass spectra was performed by using an Agilent 6130 Quadrupole LC/MS system (Agilent Technologies). LC/MS measurement was performed under the following conditions [column: Develosil Combi-RP, 5 μm, 50×2.0 mm (produced by Nomura Chemical Co., Ltd.), mobile phase: 0.1 vol % formic acid-acetonitrile/0.1 vol % formic acid-distilled water, 0.1 vol % formic acid-acetonitrile: 2%-100% (0 min-5 min or 0 min-10 min)].

Example 1: Synthesis of CDN1

(5R,7R,8R,12aR,14R,15R,15aS,16R)-7-(6-Amino-9H-purin-9-yl)-15,16-dihydroxy-2,10-bis(sulfanyl)-14-(6,7,8,9-tetrahydro-2H-2,3,5,6-tetraazabenzo[cd]azulen-2-yl)octahydro-2H,10H,12H-5,8-methano-2λ$^5$,10λ$^5$-furo[3,2-l][1,3,6,9,11,2,10]pentaoxadiphosphacyclotetradecine-2,10-dione

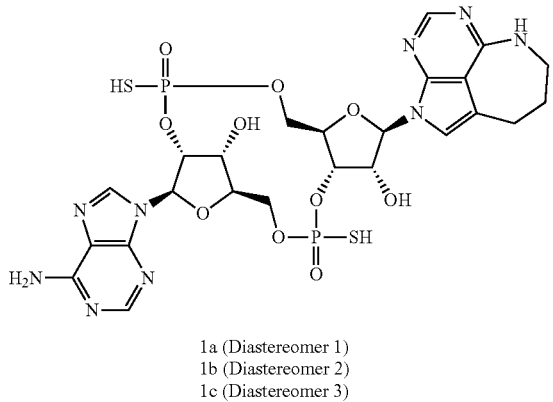

1a (Diastereomer 1)
1b (Diastereomer 2)
1c (Diastereomer 3)

[Synthesis Scheme]

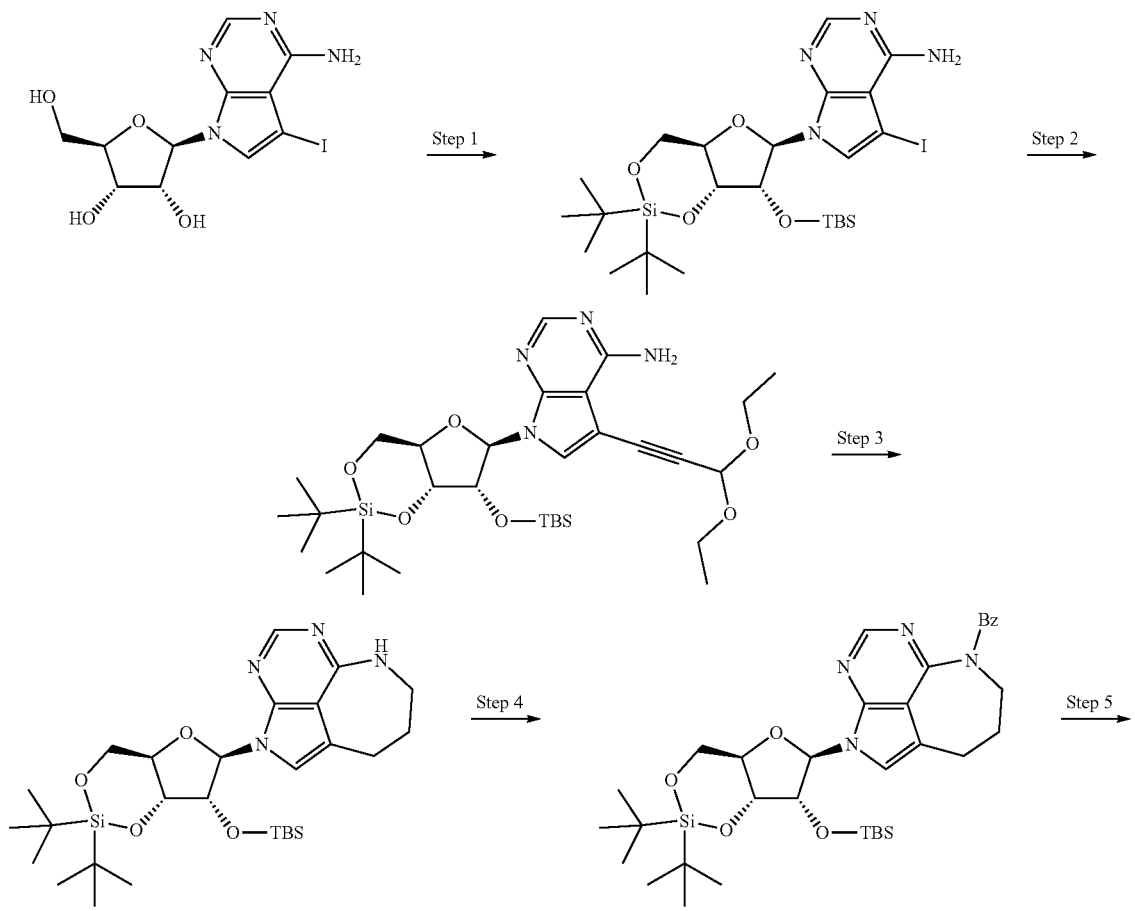

-continued
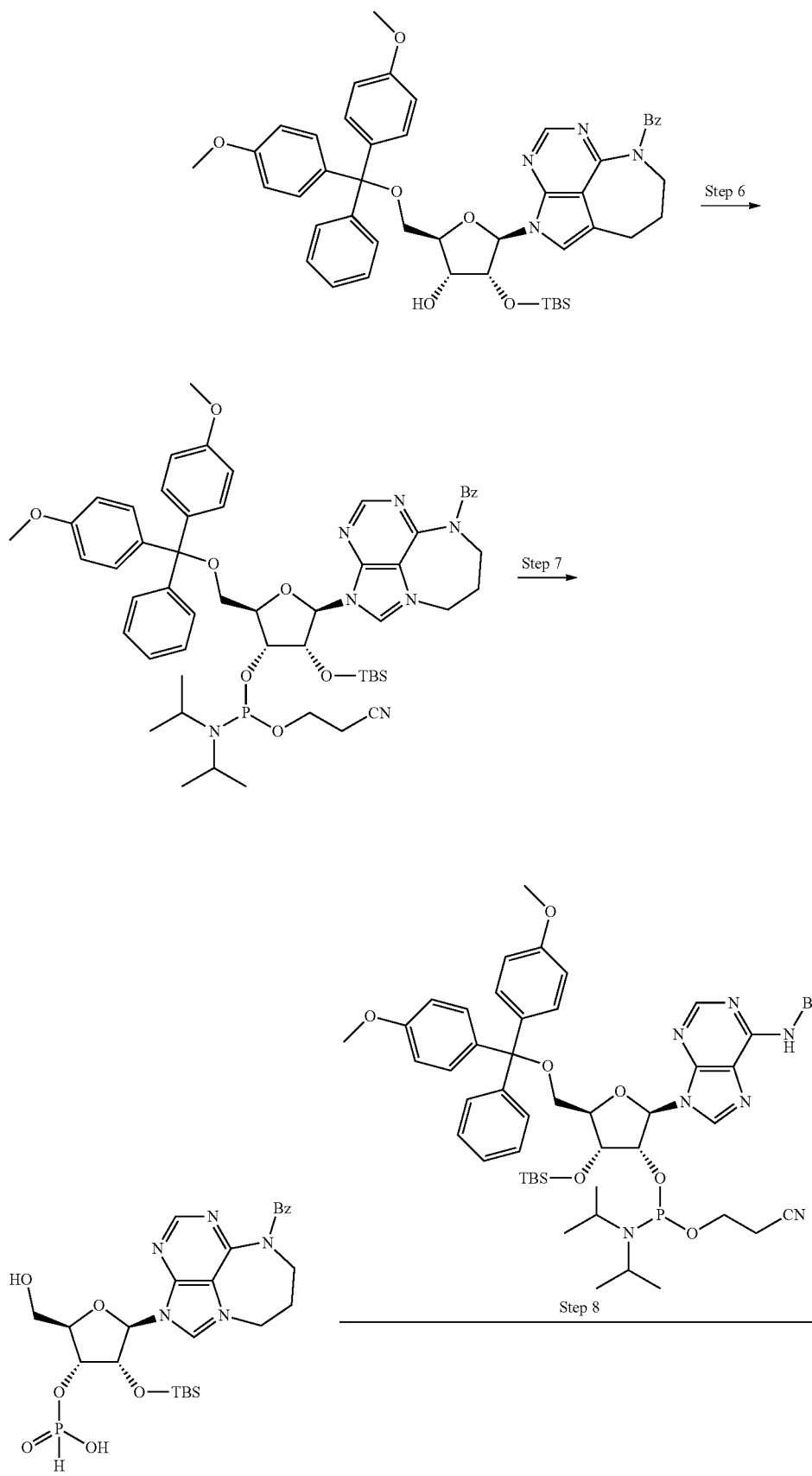

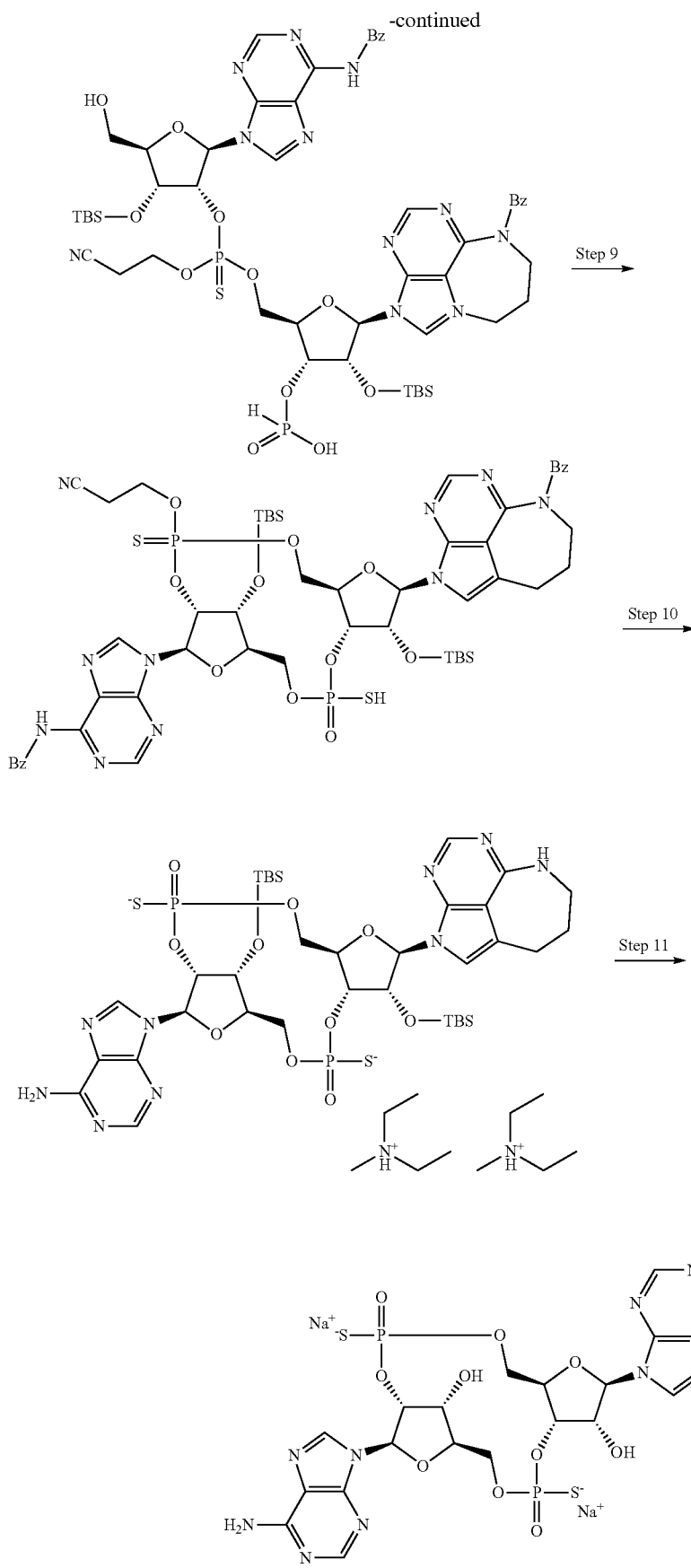

(Step 1)

7-{2-O-[tert-Butyl(dimethyl)silyl]-3,5-O-(di-tert-butylsilylidene)-β-D-ribofuranosyl}-5-iodo-7H-pyrrolo[2,3-d]pyrimidin-4-amine

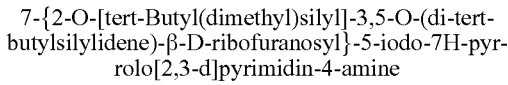

To a solution of 5-iodotubercidin (1.0 g) as a compound known in the literature (Tetrahedron 2007, 63, 9850-9861) in N,N-dimethylformamide (10 mL), di-tert-butylsilyl bis(trifluoromethanesulfonate) (1.24 mL) was slowly added dropwise at 0° C., and the reaction mixture was then stirred at the same temperature for 30 minutes. Imidazole (868 mg) was added thereto at 0° C., the temperature was then increased to room temperature, and the reaction mixture was stirred for 30 minutes. At room temperature, tert-butyldimethylchlorosilane was added thereto, and the reaction mixture was stirred at the same temperature overnight. A saturated aqueous solution of sodium hydrogen carbonate was added to the reaction mixture to quench the reaction, and the resultant was then subjected to extraction with ethyl acetate. The organic layer was washed with brine, and then dried over anhydrous sodium sulfate. The drying agent was removed through filtration, and the filtrate was concentrated under reduced pressure. The residue was purified by silica gel column chromatography [hexane/ethyl acetate] to afford the title compound (910 mg).

MS(ESI)m/z: 647 (M+H)⁺.

¹H-NMR (CDCl₃) δ: 8.25 (1H, s), 7.03 (1H, s), 6.10 (1H, s), 5.63 (2H, brs), 4.49-4.44 (2H, m), 4.26 (1H, dd, J=9.7, 4.8 Hz), 4.17 (1H, m), 4.00 (1H, t, J=9.7 Hz), 1.09 (9H, s), 1.04 (9H, s), 0.91 (9H, s), 0.13 (3H, s), 0.11 (3H, s).

(Step 2)

7-{2-O-[tert-Butyl(dimethyl)silyl]-3,5-O-(di-tert-butylsilylidene)-β-D-ribofuranosyl}-5-(3,3-diethoxyprop-1-yn-1-yl)-7H-pyrrolo[2,3-d]pyrimidin-4-amine

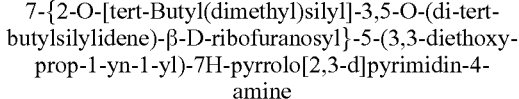

To a mixed solution of the compound obtained in step 1 (910 mg) in N,N-dimethylformamide (3.0 mL)-tetrahydrofuran (9.0 mL), propargylaldehyde dimethyl acetal (1.01 mL), triethylamine (0.392 mL), tetrakis(triphenylphosphine)palladium (0) (163 mg), and copper (I) iodide (53.6 mg) were added in this order, and the reaction mixture was stirred at 40° C. for 18 hours. A saturated aqueous solution of sodium hydrogen carbonate and ethyl acetate were added to the reaction mixture, which was subjected to extraction with ethyl acetate. The organic layer was washed with brine, and then dried over anhydrous sodium sulfate. The drying agent was removed through filtration, and the filtrate was concentrated under reduced pressure. The residue was purified by silica gel column chromatography [hexane/ethyl acetate] to afford the title compound (878 mg).

MS(ESI)m/z: 647 (M+H)⁺.

¹H-NMR (CDCl₃) δ: 8.27 (1H, s), 7.17 (1H, s), 6.09 (1H, s), 5.56 (2H, brs), 5.50 (1H, s), 4.48 (1H, dd, J=9.1, 4.9 Hz), 4.42 (1H, d, J=4.9 Hz), 4.25 (1H, dd, J=9.4, 4.6 Hz), 4.17 (1H, m), 4.00 (1H, t, J=9.7 Hz), 3.85-3.77 (2H, m), 3.66 (2H, m), 1.28 (6H, t, J=7.3 Hz), 1.08 (9H, s), 1.04 (9H, s), 0.91 (9H, s), 0.13 (3H, s), 0.11 (3H, s).

(Step 3)

2-{2-O-[tert-Butyl(dimethyl)silyl]-3,5-O-(di-tert-butylsilylidene)-β-D-ribofuranosyl}-6,7,8,9-tetrahydro-2H-2,3,5,6-tetraazabenzo[cd]azulene

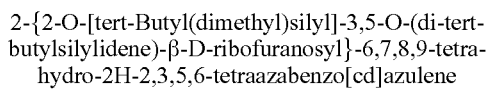

To a solution of the compound obtained in step 2 (878 mg) in ethanol (8.8 mL), 10% palladium-carbon (M) wet (500 mg) was added, and the reaction mixture was stirred under the hydrogen atmosphere at room temperature for 9 hours. The catalyst was removed through filtration and then washed with dichloromethane, and the filtrate was concentrated under reduced pressure. To a solution of the residue in acetic acid (8.8 mL), 10% palladium-carbon (M) wet (500 mg) was added, and the reaction mixture was stirred under the hydrogen atmosphere at 40° C. for 2 days. The catalyst was removed through filtration and then washed with dichloromethane, and the filtrate was concentrated under reduced pressure. The residue was purified by silica gel column chromatography [hexane/ethyl acetate/0.1% triethylamine] to afford the title compound (603 mg).

MS(ESI)m/z: 561 (M+H)⁺.

¹H-NMR (CDCl₃) δ: 8.47 (1H, brs), 8.07 (1H, s), 6.70 (1H, s), 6.14 (1H, s), 4.47-4.43 (2H, m), 4.29 (1H, dd, J=9.1, 4.8 Hz), 4.15 (1H, m), 3.99 (1H, t, J=9.7 Hz), 3.55 (2H, m), 2.89 (2H, t, J=5.4 Hz), 2.04 (2H, m), 1.09 (9H, s), 1.04 (9H, s), 0.90 (9H, s), 0.10 (3H, s), 0.10 (3H, s).

(Step 4)

6-Benzoyl-2-{2-O-[tert-butyl(dimethyl)silyl]-3,5-O-(di-tert-butylsilylidene)-β-D-ribofuranosyl}-6,7,8,9-tetrahydro-2H-2,3,5,6-tetraazabenzo[cd]azulene

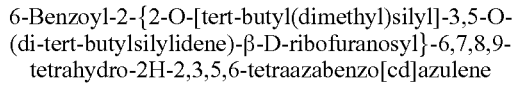

To a solution of the compound obtained in step 3 (2.17 g) in dichloromethane (21.7 mL), pyridine (1.56 mL), N,N-dimethylaminopyridine (94.5 mg), and benzoyl chloride (0.898 mL) were added in this order at room temperature, and the reaction mixture was stirred at 50° C. for 15 hours. A saturated aqueous solution of sodium hydrogen carbonate was added to the reaction mixture to quench the reaction. After extraction with dichloromethane, the organic layer was dried over anhydrous sodium sulfate. The drying agent was removed through filtration, and the filtrate was concentrated under reduced pressure. The residue was purified by silica gel column chromatography [hexane/ethyl acetate/0.1% triethylamine] to afford the title compound (1.91 g).

MS(ESI)m/z: 665 (M+H)⁺.

¹H-NMR (CDCl₃) δ: 8.08 (1H, s), 7.37-7.33 (3H, m), 7.23 (2H, t, J=7.6 Hz), 6.97 (1H, s), 6.21 (1H, s), 4.50-4.46 (2H, m), 4.37-4.30 (2H, m), 4.28-4.09 (2H, m), 4.02 (1H, t, J=10.0 Hz), 3.03 (2H, t, J=6.3 Hz), 2.29-2.17 (2H, m), 1.10 (9H, s), 1.05 (9H, s), 0.90 (9H, s), 0.10 (6H, s).

(Step 5)

6-Benzoyl-2-{5-O-[bis(4-methoxyphenyl)(phenyl)methyl]-2-O-[tert-butyl(dimethyl)silyl]-β-D-ribofuranosyl}-6,7,8,9-tetrahydro-2H-2,3,5,6-tetraazabenzo[cd]azulene

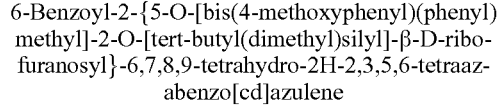

To a solution of the compound obtained in step 4 (1.91 g) in dichloromethane (15 mL), a mixture of hydrogen fluoride-pyridine (0.30 mL) and pyridine (1.88 mL) prepared at 0° C. was added, and the reaction mixture was stirred at 0° C. for 2 hours. A saturated aqueous solution of sodium hydrogen carbonate was added to the reaction mixture to quench the reaction. After the reaction mixture was subjected to extraction with dichloromethane, the organic layer was dried over anhydrous sodium sulfate. The drying agent was removed through filtration, and the filtrate was concentrated under reduced pressure. The residue was dissolved in pyridine (15 mL), 4,4'-dimethoxytrityl chloride (1.17 g) was added thereto, and the reaction mixture was stirred at 0° C. for 12 hours. Methanol was added thereto, the reaction mixture was stirred for 30 minutes, and a saturated aqueous solution of sodium hydrogen carbonate was then added thereto to quench the reaction. After the reaction mixture was subjected to extraction with dichloromethane, the organic layer was dried over anhydrous sodium sulfate. The drying agent was removed through filtration, and the filtrate was concentrated under reduced pressure. The residue was purified by silica gel column chromatography [hexane/ethyl acetate/0.1% triethylamine] to afford the title compound (1.98 g).

MS(ESI)m/z: 827 (M+H)$^+$.

$^1$H-NMR (CDCl$_3$) δ: 8.07 (1H, s), 7.47 (2H, m), 7.37-7.19 (13H, m), 6.84 (4H, m), 6.37 (1H, d, J=5.5 Hz), 4.75 (1H, t, J=5.2 Hz), 4.38-4.20 (4H, m), 3.80 (6H, s), 3.53 (1H, dd, J=10.7, 2.8 Hz), 3.40 (1H, dd, J=11.0, 3.1 Hz), 2.83 (1H, d, J=3.7 Hz), 2.78 (2H, t, J=6.4 Hz), 2.17 (2H, m), 0.81 (9H, s), −0.03 (3H, s), −0.21 (3H, s).

(Step 6)

6-Benzoyl-2-(5-O-[bis(4-methoxyphenyl)(phenyl) methyl]-2-O-[tert-butyl(dimethyl)silyl]-3-O-{(2-cyanoethoxy)[di(propan-2-yl)amino]phosphanyl}-β-D-ribofuranosyl)-6,7,8,9-tetrahydro-2H-2,3,5,6-tetraazabenzo[cd]azulene To a solution of the compound obtained in step 5 (1.98 g) in dichloromethane (23.9 mL), N,N-diisopropylethylamine (1.02 mL) and 2-cyanoethyl N,N-diisopropylchlorophosphoramidite (1.07 mL) were added, and the reaction mixture was stirred at room temperature for 15 hours. A saturated aqueous solution of sodium hydrogen carbonate was added to the reaction mixture to quench the reaction. After the reaction mixture was subjected to extraction with dichloromethane, the organic layer was dried over anhydrous sodium sulfate. The drying agent was removed through filtration, and the filtrate was concentrated under reduced pressure. The residue was purified by silica gel column chromatography [hexane/ethyl acetate] to afford the title compound (2.06 g) as a mixture of diastereomers at the phosphorus atom (diastereomer ratio=7:3).

MS(ESI)m/z: 1027 (M+H)$^+$.

$^1$H-NMR (CDCl$_3$) δ: 8.06 (0.3H, s), 8.04 (0.7H, s), 7.50-7.16 (15H, m), 6.85-6.79 (4H, m), 6.35 (0.7H, d, J=6.7 Hz), 6.31 (0.3H, d, J=6.1 Hz), 4.84 (0.7H, dd, J=7.0, 4.6 Hz), 4.78 (0.3H, t, J=5.8 Hz), 4.43-4.17 (4H, m), 4.04-3.85 (1.3H, m), 3.80-3.76 (6H, m), 3.69-3.43 (3H, m), 3.50 (0.7H, dd, J=10.6, 3.3 Hz), 3.33-3.26 (1H, m), 2.87-2.76 (2H, m), 2.74-2.60 (1.4H, m), 2.31 (0.6H, t, J=6.7 Hz), 2.23-2.11 (2H, m), 1.21-1.13 (7.8H, m), 1.04 (4.2H, d, J=6.7 Hz), 0.73 (2.7H, s), 0.72 (6.3H, s), −0.03 (0.9H, s), −0.06 (2.1H, s), −0.24 (3H, s).

(Step 7)

6-Benzoyl-2-{2-O-[tert-butyl(dimethyl)silyl]-3-O-[hydroxy (oxo)-λ$^5$-phosphanyl]-β-D-ribofuranosyl}-6,7,8,9-tetrahydro-2H-2,3,5,6-tetraazabenzo[cd]azulene To a solution of the compound obtained in step 6 (1.37 g) in acetonitrile (6.67 mL), water (48 μL) and a pyridine salt of trifluoroacetic acid (335 mg) were added, and the reaction mixture was stirred at room temperature for 15 minutes. To the reaction mixture, tert-butylamine (6.67 mL) was added, and the reaction mixture was stirred at room temperature for 15 minutes. After the reaction mixture was concentrated under reduced pressure, the residue was azeotroped twice with acetonitrile (5 mL). Water (0.240 mL) was added to a solution of the residue in dichloromethane (16.7 mL), to which a solution of dichloroacetic acid (0.953 mL) in dichloromethane (16.7 mL) was added, and the reaction mixture was stirred at room temperature for 15 minutes. Pyridine (1.82 mL) was added thereto to quench the reaction, and the reaction mixture was then concentrated under reduced pressure. The residue was azeotroped three times with dehydrated acetonitrile (10 mL), with about 5 mL of acetonitrile allowed to remain after the last operation. The resulting acetonitrile solution of the title compound was directly used for the subsequent reaction.

(Step 8)

Commercially available (ChemGenes Corporation) N-benzoyl-5'-O-[bis(4-methoxyphenyl)(phenyl)methyl]-3'-O-[tert-butyl(dimethyl)silyl]-2'-O-{(2-cyanoethoxy)[di(propan-2-yl)amino]phosphanyl}adenosine (1.31 g) was azeotroped three times with dehydrated acetonitrile (10 mL), with about 5 mL of acetonitrile allowed to remain after the last operation, and the molecular sieves 3A, 1/16 (5 pellet-like particles) were added thereto. This acetonitrile solution was added to the solution synthesized in step 7, and the reaction mixture was stirred under the nitrogen atmosphere at room temperature for 20 minutes. To the reaction mixture, N,N-dimethyl-N'-(3-sulfanylidene-3H-1,2,4-dithiazol-5-yl) methaneimidamide (300 mg) was added, and the reaction mixture was stirred at room temperature for 30 minutes, and then concentrated under reduced pressure. Water (0.240 mL) was added to a solution of the residue in dichloromethane (19.0 mL), a solution of dichloroacetic acid (1.20 mL) in dichloromethane (19.0 mL) was added thereto, and the reaction mixture was stirred at room temperature for 15 minutes. After pyridine (13.2 mL) was added thereto to quench the reaction, the resultant was concentrated under reduced pressure. The resulting crude product was directly used for the subsequent reaction.

(Step 9)

N-{9-[(5R,7R,8R,12aR,14R,15R,15aR,16R)-14-(6-Benzoyl-6,7,8,9-tetrahydro-2H-2,3,5,6-tetraazabenzo [cd]azulen-2-yl)-15,16-bis{[tert-butyl(dimethyl)silyl]oxy}-10-(2-cyanoethoxy)-2-oxo-2-sulfanyl-10-sulfanylideneoctahydro-2H,10H,12H-5,8-methano-2λ$^5$,10λ$^5$-furo[3,2-1][1,3,6,9,11,2,10] pentaoxadiphosphacyclotetradecin-7-yl]-9H-purin-6-yl}benzamide After a solution of the crude product obtained in step 8 in pyridine (39.6 mL) was concentrated to about 25 mL, 2-chloro-5,5-dimethyl-1,3,2λ$^5$-dioxaphosphinan-2-one (908 mg) was added thereto, and the reaction mixture was stirred at room temperature for 30 minutes. Water (0.84 mL) and 3H-1,2-benzodithiol-3-one (336 mg) were added thereto, and the reaction mixture was stirred at room temperature for 15 minutes. The reaction mixture was poured into an aqueous solution (180 mL) of sodium hydrogen carbonate (5.25 g), and the resultant was stirred at room temperature for 30 minutes, and then subjected to extraction with ethyl acetate. After the organic layer was dried over anhydrous sodium sulfate, the drying agent was removed through filtration and the filtrate was concentrated under reduced pressure. The residue was purified by silica gel column chromatography [hexane/ethyl acetate/methanol] to afford the title compound (507 mg) as a mixture of diastereomers at the phosphorus atom.

MS(ESI)m/z: 1219 (M+H)$^+$.

(Step 10)

Bis(N,N-diethylethaneaminium) (5R,7R,8R,12aR, 14R,15R,15aR,16R)-7-(6-amino-9H-purin-9-yl)-15, 16-bis{[tert-butyl(dimethyl)silyl]oxy}-2,10-dioxo-14-(6,7,8,9-tetrahydro-2H-2,3,5,6-tetraazabenzo[cd] azulen-2-yl)octahydro-2H,10H,12H-5,8-methano-2$\lambda^5$,10$\lambda^5$-furo[3,2-1][1,3,6,9,11,2,10] pentaoxadiphosphacyclotetradecine-2,10-bis (thiolate)

To a solution of the compound obtained in step 9 (507 mg) in methanol (5 mL), 28% ammonia water (5 mL) was added, and the reaction mixture was stirred at room temperature for 14 hours. After the reaction mixture was concentrated, the residue was purified by C18 silica gel column chromatography [10 mM aqueous solution of triethylammonium acetate/acetonitrile] to afford the title compound (301 mg) as a mixture of diastereomers at the phosphorus atom.

MS(ESI)m/z: 958 (M+H)$^+$.

(Step 11)

Disodium (5R,7R,8R,12aR,14R,15R,15aS,16R)-7-(6-amino-9H-purin-9-yl)-15,16-dihydroxy-2,10-dioxo-14-(6,7,8,9-tetrahydro-2H-2,3,5,6-tetraazabenzo[cd]azulen-2-yl)octahydro-2H,10H,12H-5,8-methano-2$\lambda^5$,10$\lambda^5$-furo[3,2-1][1,3,6,9,11,2,10] pentaoxadiphosphacyclotetradecine-2,10-bis (thiolate)

Triethylamine trihydrofluoride (3.84 mL) was added to the compound obtained in step 10 (301 mg), and the reaction mixture was stirred at 45° C. for 3 hours. To the reaction mixture, an ice-cooled mixture of 1 M aqueous solution of triethylammonium hydrogen carbonate (20 mL) and triethylamine (4 mL) was added at room temperature. After the reaction mixture was concentrated under reduced pressure, the reaction mixture was purified by C18 silica gel column chromatography [10 mM aqueous solution of triethylammonium acetate/acetonitrile] and preparative HPLC [10 mM aqueous solution of triethylammonium acetate/acetonitrile, acetonitrile: 0%-25% (0 min-40 min)] to separate diastereomers at the phosphorus atom. The resulting compound (triethylamine salt) was converted into a sodium salt with the following procedure.

[Conversion to Sodium Salt]

BT AG® 50W-X2 Resin (biotechnology grade, 100-200 mesh, hydrogen form) (500 mg) was suspended in pure water, and an empty column was filled therewith. After an excessive portion of pure water was allowed to gravitationally flow down, 1 M aqueous solution of sodium hydroxide (5 mL) and pure water (10 mL) were allowed to gravitationally flow down in this order. The compound obtained above was dissolved in pure water (5 mL), and a column was charged therewith. A solution allowed to gravitationally flow down was separated, and then further eluted with pure water (10 mL). Fractions containing the targeted product were combined and freeze-dried to give diastereomer 1 (83.4 mg), diastereomer 2 (44.8 mg), and diastereomer 3 (13.1 mg) of the title compound (retention time in HPLC: diastereomer 1>2, 3).

Diastereomer 1

MS(ESI)m/z: 730 (M+H)$^+$.

$^1$H-NMR (CD$_3$OD) δ: 8.74 (1H, s), 8.17 (1H, s), 8.02 (1H, s), 7.10 (1H, s), 6.34 (1H, d, J=8.5 Hz), 6.30 (1H, d, J=4.8 Hz), 5.41-5.34 (1H, m), 5.19-5.13 (1H, m), 4.85 (1H, d, J=3.6 Hz), 4.79 (1H, t, J=4.5 Hz), 4.52-4.41 (2H, m), 4.40-4.31 (2H, m), 4.07-3.97 (2H, m), 3.52-3.47 (2H, m), 2.90-2.76 (2H, m), 2.05-1.95 (2H, m).

$^{31}$P-NMR (CD$_3$OD) δ: 57.9 (s), 54.5 (s).

Diastereomer 2

MS(ESI)m/z: 730 (M+H)$^+$.

$^1$H-NMR (CD$_3$OD) δ: 8.82 (1H, s), 8.17 (1H, s), 8.02 (1H, s), 7.13 (1H, s), 6.35 (1H, d, J=2.4 Hz), 6.33 (1H, s), 5.50-5.43 (2H, m), 4.80 (1H, dd, J=6.7, 4.2 Hz), 4.52-4.28 (5H, m), 4.02 (1H, d, J=12.1 Hz), 3.93-3.86 (1H, m), 3.54-3.47 (2H, m), 2.95-2.88 (2H, m), 2.05-1.97 (2H, m).

$^{31}$P-NMR (CD$_3$OD) δ: 63.0 (s), 60.2 (s).

Diastereomer 3

MS(ESI)m/z: 730 (M+H)$^+$.

$^1$H-NMR (CD$_3$OD) δ: 9.16 (1H, s), 8.17 (1H, s), 8.02 (1H, s), 7.12 (1H, s), 6.35 (1H, d, J=8.5 Hz), 6.29 (1H, d, J=6.7 Hz), 5.63-5.56 (1H, m), 5.54-5.46 (1H, m), 4.79 (1H, dd, J=6.7, 4.8 Hz), 4.53-4.43 (2H, m), 4.36-4.28 (2H, m), 4.26-4.19 (1H, m), 4.16-4.09 (1H, m), 3.93-3.86 (1H, m), 3.52-3.47 (2H, m), 2.92-2.87 (2H, m), 2.04-1.95 (2H, m).

$^{31}$P-NMR (CD$_3$OD) δ: 62.8 (s), 58.7 (s).

Example 2: Synthesis of CDN2

(5R,7R,8R,12aR,14R,15R,15aS,16R)-7-(6-Amino-9H-purin-9-yl)-15,16-dihydroxy-2,10-bis(sulfanyl)-14-(6,7,8,9-tetrahydro-2H-2,3,5,6-tetraazabenzo[cd] azulen-2-yl)octahydro-2H,10H,12H-5,8-methano-2$\lambda^5$,10$\lambda^5$-furo[3,2-1][1,3,6,9,11,2,10] pentaoxadiphosphacyclotetradecine-2,10-dione (Diastereomer 4 of Compound 1 Described in Example 1)

2a (Diastereomer 4 of 1)

[Synthesis Scheme]
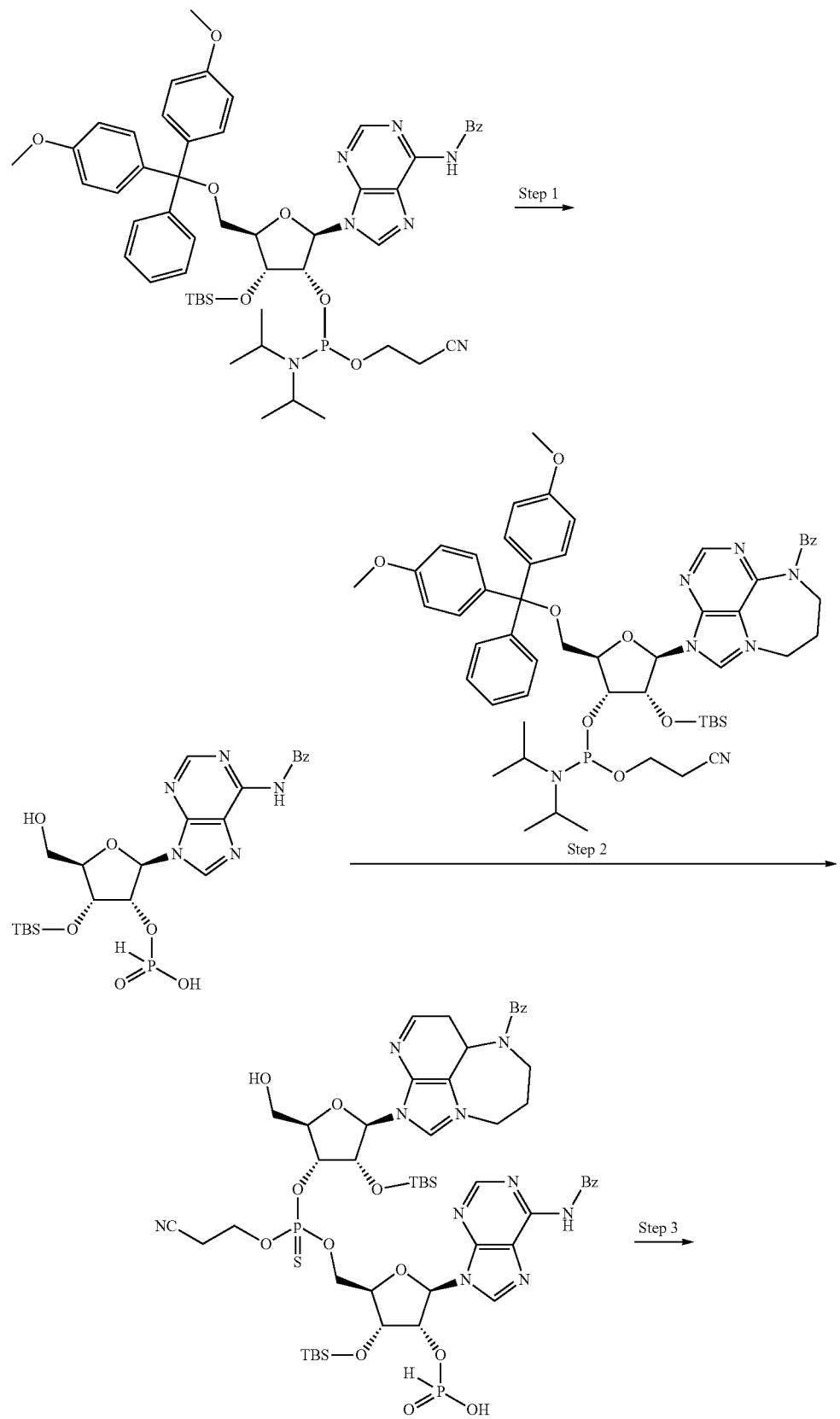

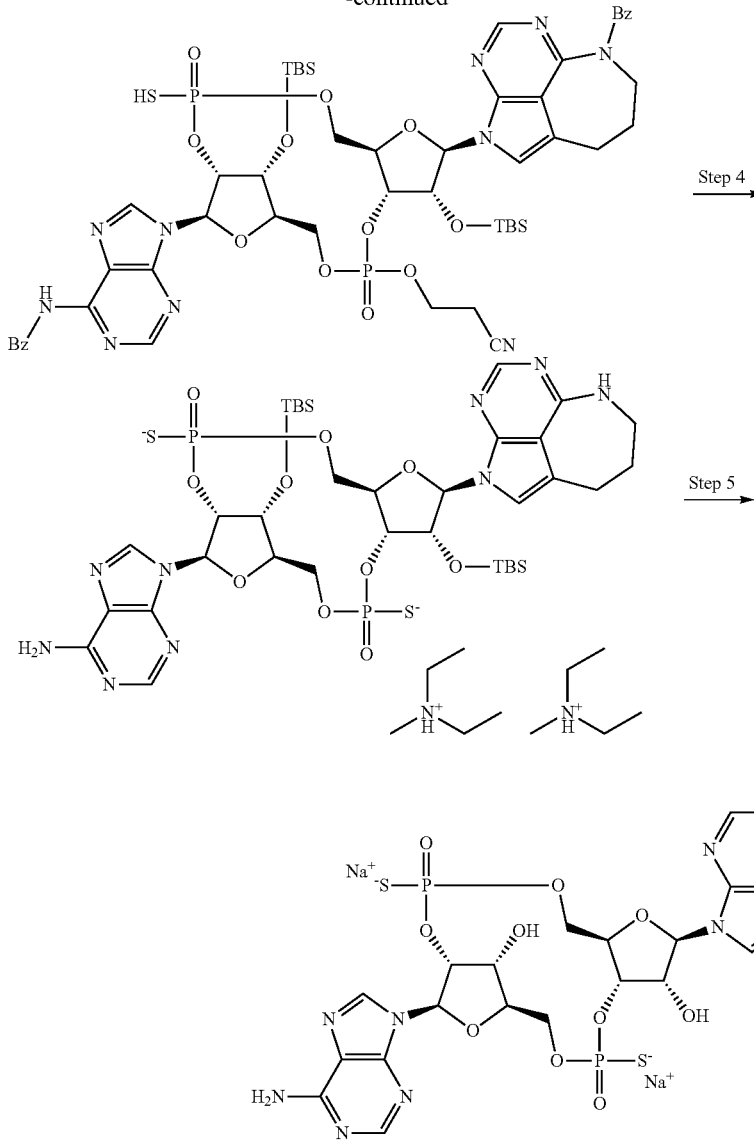

(Step 1)

N-Benzoyl-3'-O-[tert-butyl(dimethyl)silyl]-2'-O-[hydroxy (oxo)-λ5-phosphanyl]adenosine With use of Commercially available (ChemGenes Corporation) N-benzoyl-5'-O-[bis(4-methoxyphenyl)(phenyl)methyl]-3'-O-[tert-butyl(dimethyl)silyl]-2'-O-{(2-cyanoethoxy)[di(propan-2-yl)amino]phosphanyl}adenosine (962 mg), the reaction was performed in the same manner as in step 7 of Example 1 to afford an acetonitrile solution of the title compound. This acetonitrile solution was directly used for the subsequent reaction.

(Step 2)

With use of the compound obtained in step 1 and the compound obtained in step 6 of Example 1 (1.00 g), the reaction was performed in the same manner as in step 8 of Example 1. The resulting crude product was directly used for the subsequent reaction.

(Step 3)

N-{9-[(5R,7R,8R,12aR,14R,15R,15aR,16R)-14-(6-Benzoyl-6,7,8,9-tetrahydro-2H-2,3,5,6-tetraazabenzo[cd]azulen-2-yl)-15,16-bis{[tert-butyl(dimethyl)silyl]oxy}-2-(2-cyanoethoxy)-10-oxo-10-sulfanyl-2-sulfanylideneoctahydro-2H,10H,12H-5,8-methano-2λ$^5$,10λ$^5$-furo[3,2-1][1,3,6,9,11,2,10]pentaoxadiphosphacyclotetradecin-7-yl]-9H-purin-6-yl}benzamide With use of the crude product obtained in step 2, the reaction was performed in the same manner as in step 9 of Example 1 to afford the title compound (367 mg) as a mixture of diastereomers at the phosphorus atom.

MS(ESI)m/z: 1219 (M+H)$^+$.

(Step 4)

Bis(N,N-diethylethaneaminium) (5R,7R,8R,12aR,14R,15R,15aR,16R)-7-(6-amino-9H-purin-9-yl)-15,16-bis{[tert-butyl(dimethyl)silyl]oxy}-2,10-dioxo-14-(6,7,8,9-tetrahydro-2H-2,3,5,6-tetraazabenzo[cd]azulen-2-yl)octahydro-2H,10H,12H-5,8-methano-2λ⁵,10λ⁵-furo[3,2-1][1,3,6,9,11,2,10]pentaoxadiphosphacyclotetradecine-2,10-bis(thiolate)

With use of the compound obtained in step 3 (367 mg), the reaction was performed in the same manner as in step 10 of Example 1 to afford diastereomer 1 (115 mg: with impurities) and diastereomer 4 (101 mg: with impurities) of the title compound.

Diastereomer 1 (Less Polar)

MS(ESI)m/z: 958 (M+H)⁺.

Diastereomer 4 (More Polar)

MS(ESI)m/z: 958 (M+H)⁺.

(Step 5)

Disodium (5R,7R,8R,12aR,14R,15R,15aS,16R)-7-(6-amino-9H-purin-9-yl)-15,16-dihydroxy-2,10-dioxo-14-(6,7,8,9-tetrahydro-2H-2,3,5,6-tetraazabenzo[cd]azulen-2-yl)octahydro-2H,10H,12H-5,8-methano-2λ⁵,10λ⁵-furo[3,2-1][1,3,6,9,11,2,10]pentaoxadiphosphacyclotetradecine-2,10-bis(thiolate)

(Diastereomer 4 of Compound 1)

With use of the compound obtained in step 4 (diastereomer 4) (101 mg: with impurities), the reaction was performed in the same manner as in step 11 of Example 1, and purification was then performed under the following [Purification Conditions] to afford the title compound as a triethylamine salt.

[Purification Conditions] C18 silica gel column chromatography [10 mM aqueous solution of triethylammonium acetate/acetonitrile], preparative HPLC [10 mM aqueous solution of triethylammonium acetate/acetonitrile, acetonitrile: 5%-25% (0 min-40 min)], and preparative HPLC [10 mM aqueous solution of triethylammonium acetate/methanol, methanol: 5%-100% (0 min-40 min)].

The triethylamine salt obtained was subjected to salt exchange in the same manner as in [Conversion to Sodium Salt] described in step 11 of Example 1 to afford the title compound (28.5 mg).

MS(ESI)m/z: 730 (M+H)⁺.

¹H-NMR (CD₃OD) δ: 9.11 (1H, s), 8.19 (1H, s), 8.02 (1H, s), 7.08 (1H, s), 6.35 (1H, d, J=8.5 Hz), 6.27 (1H, d, J=4.8 Hz), 5.43-5.36 (1H, m), 5.29-5.21 (1H, m), 4.95-4.88 (1H, m), 4.80 (1H, dd, J=4.5, 2.3 Hz), 4.50-4.43 (1H, m), 4.42-4.33 (2H, m), 4.30-4.22 (1H, m), 4.20-4.03 (2H, m), 3.52-3.46 (2H, m), 2.85-2.66 (2H, m), 2.05-1.90 (2H, m).

³¹P-NMR (CD₃OD) δ: 58.1 (s), 54.1 (s).

Example 3: Synthesis of CDN3

(5R,7R,8R,12aR,14R,15R,15aS,16R)-7-(6-Amino-9H-purin-9-yl)-2,10,15,16-tetrahydroxy-14-(6,7,8,9-tetrahydro-2H-2,3,5,6-tetraazabenzo[cd]azulen-2-yl)octahydro-2H,10H,12H-5,8-methano-2λ⁵,10λ⁵-furo[3,2-1][1,3,6,9,11,2,10]pentaoxadiphosphacyclotetradecine-2,10-dione

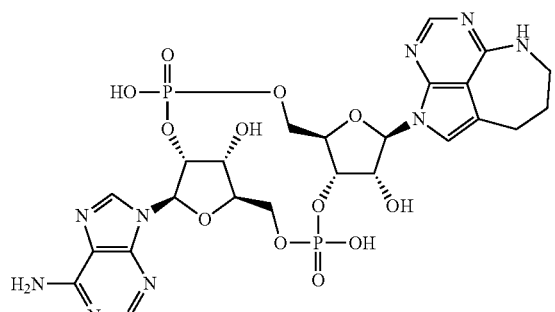

3

[Synthesis Scheme]

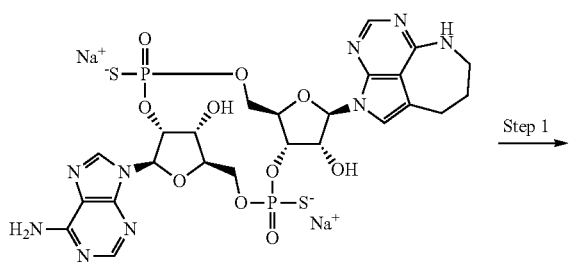

Step 1

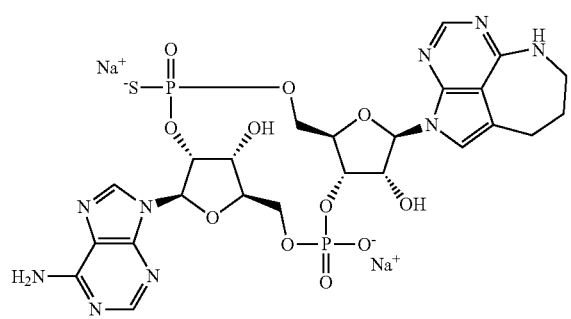

(Step 1)

Disodium (5R,7R,8R,12aR,14R,15R,15aS,16R)-7-(6-amino-9H-purin-9-yl)-15,16-dihydroxy-2,10-dioxo-14-(6,7,8,9-tetrahydro-2H-2,3,5,6-tetraazabenzo[cd]azulen-2-yl)octahydro-2H,10H,12H-5,8-methano-2$\lambda^5$,10$\lambda^5$-furo[3,2-1][1,3,6,9,11,2,10]pentaoxadiphosphacyclotetradecine-2,10-bis(olate)

To a solution of the compound obtained in step 11 of Example 1 (diastereomer 1) (30.0 mg) in acetone (0.5 mL)-water (0.2 mL), triethylamine (0.27 mL) and iodomethane (60 μL) were added, and the reaction mixture was stirred for 1 day. After the reaction mixture was concentrated under reduced pressure, the reaction mixture was purified by preparative HPLC [10 mM aqueous solution of triethylammonium acetate/acetonitrile, acetonitrile: 0%-20% (0 min-40 min)]. The compound obtained was subjected to salt exchange in the same manner as in [Conversion to Sodium Salt] described in step 11 of Example 1 to afford the title compound (21.2 mg).

MS(ESI)m/z: 698 (M+H)$^+$.

$^1$H-NMR (CD$_3$OD) δ: 8.55 (1H, s), 8.18 (1H, s), 8.01 (1H, s), 7.32 (1H, s), 6.26 (1H, s), 6.13 (1H, s), 5.00-4.85 (2H, m), 4.68-4.64 (1H, m), 4.48-4.23 (5H, m), 4.15-4.04 (2H, m), 3.49-3.39 (2H, m), 2.90-2.66 (2H, m), 1.98-1.83 (2H, m).

$^{31}$P-NMR (CD$_3$OD) δ: −0.22 (s).

Example 4: Synthesis of CDN4

(5R,7R,8R,12aR,14R,15R,15aS,16R)-7-(2-Amino-6-oxo-1,6-dihydro-9H-purin-9-yl)-15,16-dihydroxy-2,10-bis(sulfanyl)-14-(6,7,8,9-tetrahydro-2H-2,3,5,6-tetraazabenzo[cd]azulen-2-yl)octahydro-2H,10H,12H-5,8-methano-2$\lambda^5$,10$\lambda^5$-furo[3,2-1][1,3,6,9,11,2,10]pentaoxadiphosphacyclotetradecine-2,10-dione

4

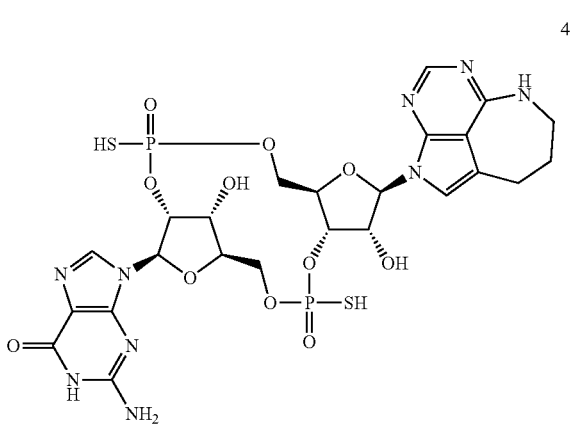

4a (Diastereomer 1)
4b (Diastereomer 2)

[Synthesis Scheme]

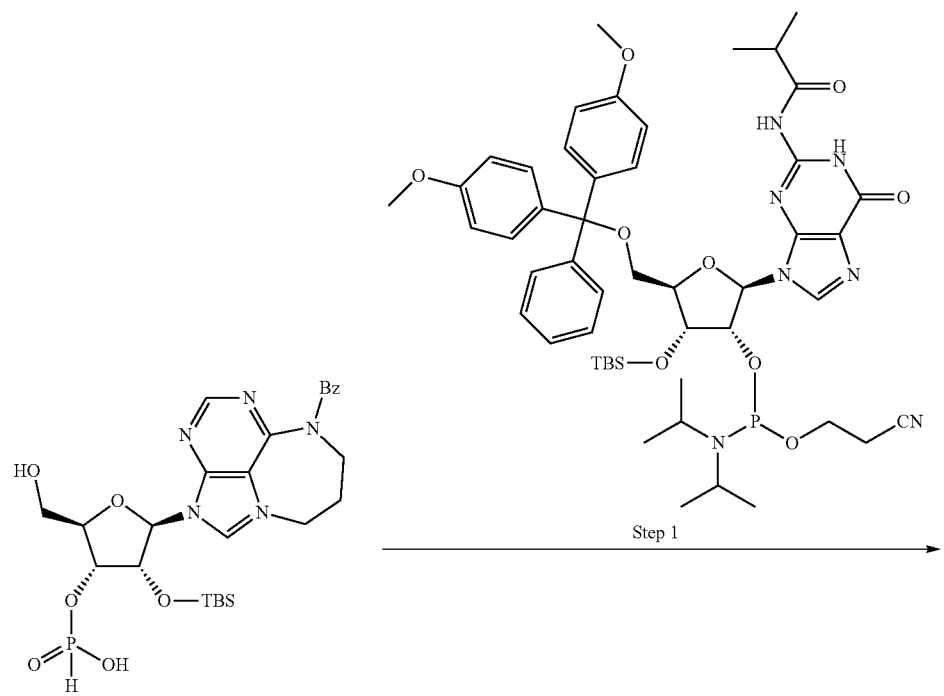

Step 1

-continued
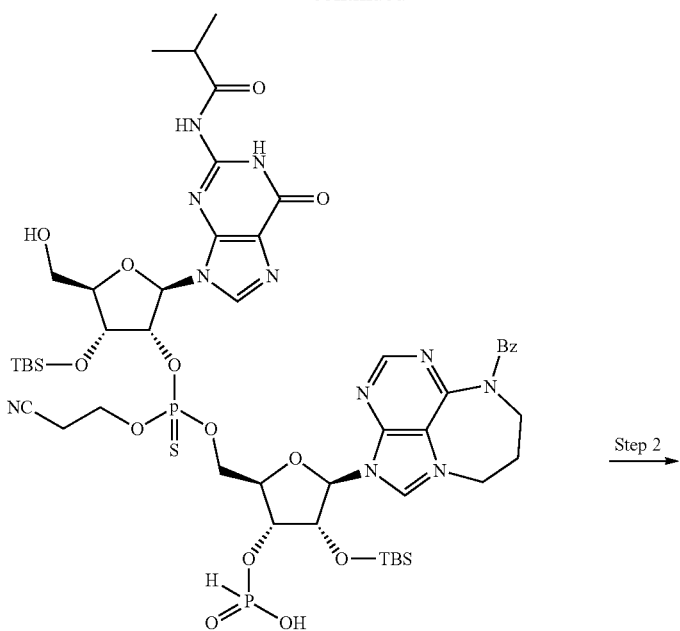
Step 2
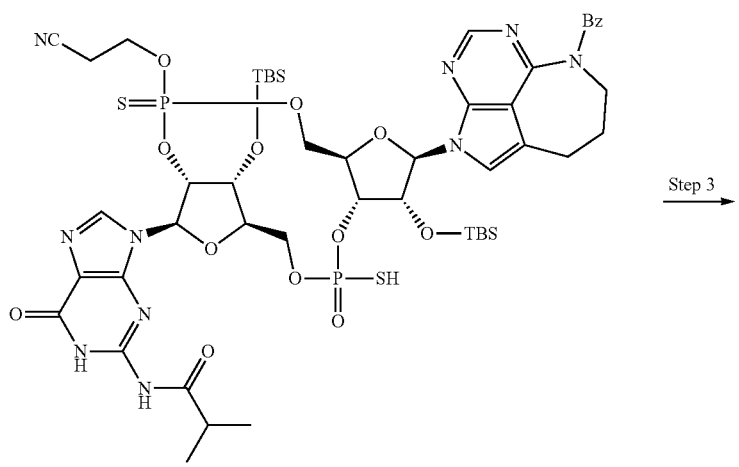
Step 3
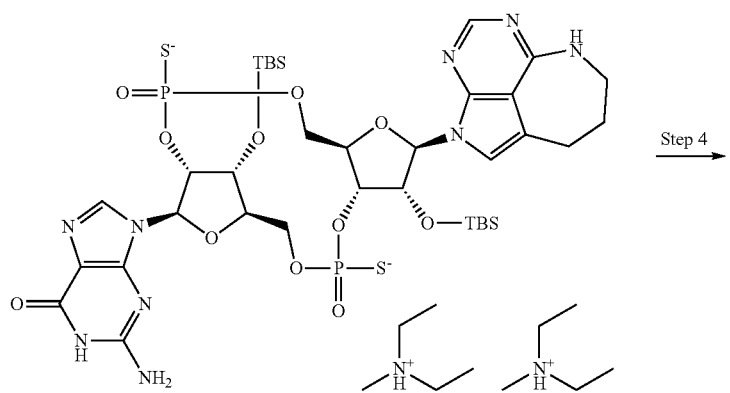
Step 4

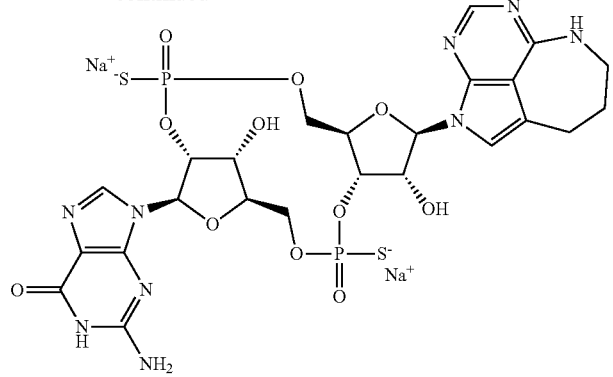

(Step 1)

The reaction of step 7 of Example 1 was performed in the following scale (raw material: 1.01 g). With use of an acetonitrile solution of the compound obtained and commercially available (Wuhu Nuowei Chemistry Co., Ltd.) 5'-O-[bis(4-methoxyphenyl)(phenyl)methyl]-3'-O-[tert-butyl(dimethyl)silyl]-2'-O-{(2-cyanoethoxy)[di(propan-2-yl)amino]phosphanyl}-N-(2-methylpropanoyl)guanosine (954 mg), the reaction was performed in the same manner as in step 8 of Example 1. The resulting crude product was directly used for the subsequent reaction.

(Step 2)

N-{9-[(5R,7R,8R,12aR,14R,15R,15aR,16R)-14-(6-Benzoyl-6,7,8,9-tetrahydro-2H-2,3,5,6-tetraazabenzo[cd]azulen-2-yl)-15,16-bis{[tert-butyl(dimethyl)silyl]oxy}-10-(2-cyanoethoxy)-2-oxo-2-sulfanyl-10-sulfanylideneoctahydro-2H,10H,12H-5,8-methano-2λ⁵,10λ⁵-furo[3,2-1][1,3,6,9,11,2,10]pentaoxadiphosphacyclotetradecin-7-yl]-6-oxo-6,9-dihydro-1H-purin-2-yl}-2-methylpropanamide With use of the crude product obtained in step 1, the reaction was performed in the same manner as in step 9 of Example 1 to afford the title compound (357 mg) as a mixture of diastereomers at the phosphorus atom.

MS(ESI)m/z: 1201 (M+H)⁺.

(Step 3)

Bis(N,N-diethylethaneaminium) (5R,7R,8R,12aR,14R,15R,15aR,16R)-7-(2-amino-6-oxo-1,6-dihydro-9H-purin-9-yl)-15,16-bis{[tert-butyl(dimethyl)silyl]oxy}-2,10-dioxo-14-(6,7,8,9-tetrahydro-2H-2,3,5,6-tetraazabenzo[cd]azulen-2-yl)octahydro-2H,10H,12H-5,8-methano-2λ⁵,10λ⁵-furo[3,2-1][1,3,6,9,11,2,10]pentaoxadiphosphacyclotetradecine-2,10-bis(thiolate)

With use of the compound obtained in step 3 (357 mg), the reaction was performed in the same manner as in step 10 of Example 1 to afford the title compound (241 mg) as a mixture of diastereomers at the phosphorus atom.

MS(ESI)m/z: 974 (M+H)⁺.

(Step 4)

Disodium (5R,7R,8R,12aR,14R,15R,15aS,16R)-7-(2-amino-6-oxo-1,6-dihydro-9H-purin-9-yl)-15,16-dihydroxy-2,10-dioxo-14-(6,7,8,9-tetrahydro-2H-2,3,5,6-tetraazabenzo[cd]azulen-2-yl)octahydro-2H,10H,12H-5,8-methano-2λ⁵,10λ⁵-furo[3,2-1][1,3,6,9,11,2,10]pentaoxadiphosphacyclotetradecine-2,10-bis(thiolate)

With use of the compound obtained in step 3 (241 mg), the reaction was performed in the same manner as in step 11 of Example 1, and diastereomers at the phosphorus atom were separated under the following [Purification Conditions] to afford two diastereomers of the title compound as triethylamine salts.

[Purification Conditions] C18 silica gel column chromatography [10 mM aqueous solution of triethylammonium acetate/acetonitrile] and preparative HPLC [10 mM aqueous solution of triethylammonium acetate/acetonitrile, acetonitrile: 5%-20% (0 min-40 min)].

The triethylamine salts obtained were each subjected to salt exchange in the same manner as in [Conversion to Sodium Salt] described in step 11 of Example 1 to afford diastereomer 1 (56.7 mg) and diastereomer 2 (25.9 mg) of the title compound (retention time in HPLC: diastereomer 1>2).

Diastereomer 1 (Less Polar)

MS(ESI)m/z: 746 (M+H)⁺.

¹H-NMR (CD₃OD) δ: 8.03 (1H, s), 8.00 (1H, s), 7.11 (1H, s), 6.27 (1H, d, J=3.0 Hz), 5.99 (1H, d, J=8.5 Hz), 5.67-5.61 (1H, m), 5.27-5.21 (1H, m), 4.85 (1H, d, J=3.6 Hz), 4.73 (1H, dd, J=3.9, 2.0 Hz), 4.48-4.39 (2H, m), 4.38-4.30 (2H, m), 4.18-4.08 (2H, m), 3.51-3.45 (2H, m), 2.80-2.71 (1H, m), 2.63-2.53 (1H, m), 2.02-1.84 (2H, m).

³¹P-NMR (CD₃OD) δ: 57.6 (s), 53.5 (s).

Diastereomer 2 (More Polar)

MS(ESI)m/z: 746 (M+H)⁺.

¹H-NMR (CD₃OD) δ: 8.20 (1H, s), 8.01 (1H, s), 7.19 (1H, s), 6.32 (1H, d, J=6.0 Hz), 6.05 (1H, d, J=8.5 Hz), 5.67-5.53 (1H, m), 5.47-5.40 (1H, m), 4.77-4.71 (1H, m), 4.51-4.46 (1H, m), 4.45-4.30 (3H, m), 4.28-4.25 (1H, m), 4.19-4.08 (1H, m), 3.96-3.89 (1H, m), 3.53-3.46 (2H, m), 2.92-2.79 (2H, m), 2.05-1.93 (2H, m).

³¹P-NMR (CD₃OD) δ: 61.7 (s), 59.5 (s).

Example 5: Synthesis of CDN5
(5R,7R,8R,12aR,14R,15R,15aS,16R)-7-[1-(2-Aminoethyl)-6-oxo-1,6-dihydro-9H-purin-9-yl]-15,16-dihydroxy-2,10-bis(sulfanyl)-14-(6,7,8,9-tetrahydro-2H-2,3,5,6-tetraazabenzo[cd]azulen-2-yl)octahydro-2H,10H,12H-5,8-methano-2$\lambda^5$,10$\lambda^5$-furo[3,2-l][1,3,6,9,11,2,10]pentaoxadiphosphacyclotetradecine-2,10-dione
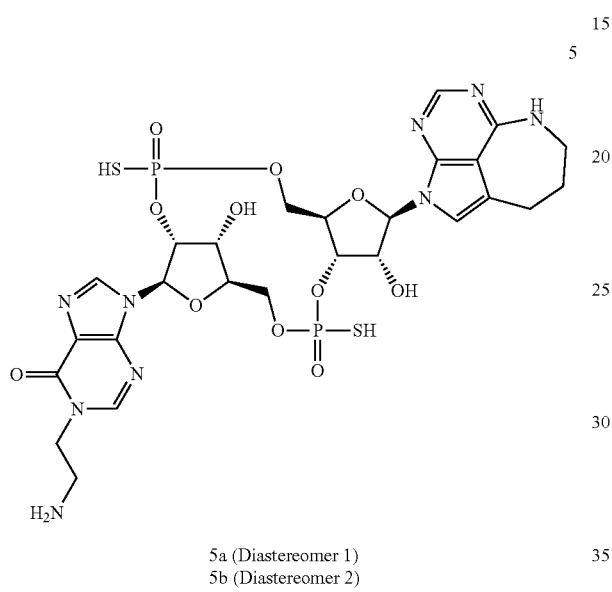
5a (Diastereomer 1)
5b (Diastereomer 2)
[Synthesis Scheme]
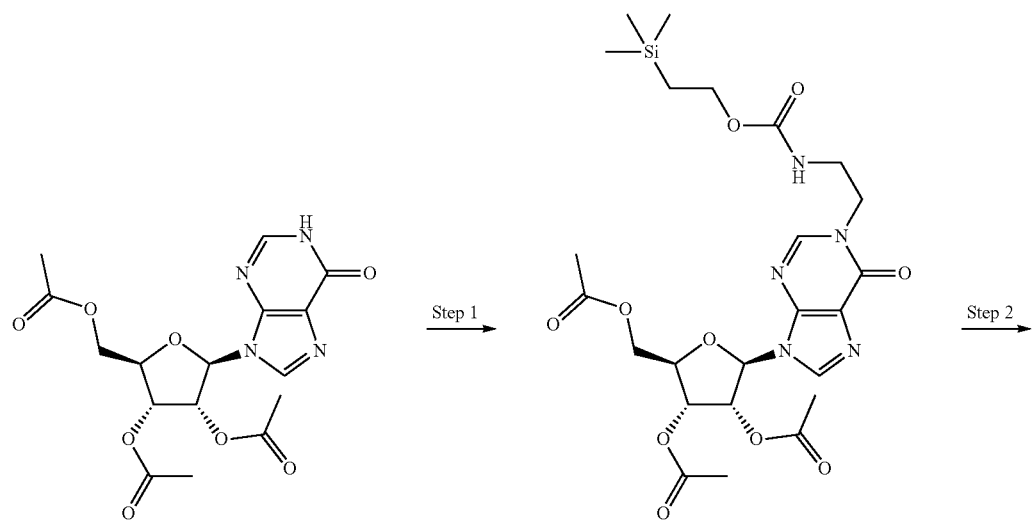

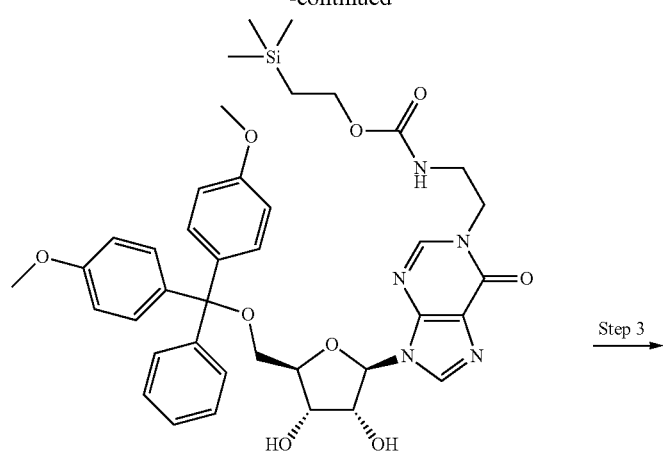
Step 3 →
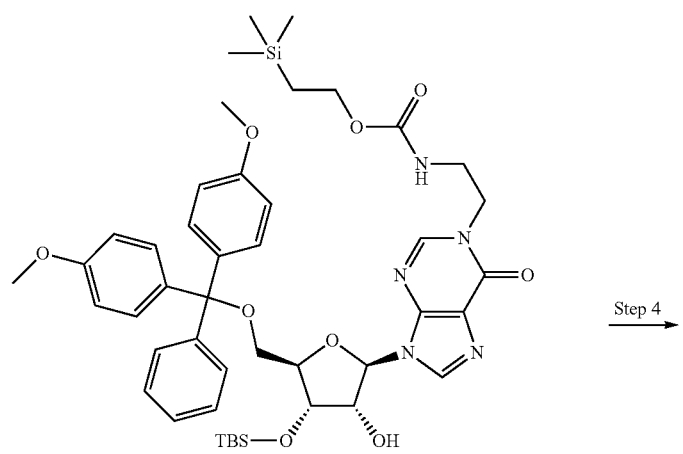
Step 4 →
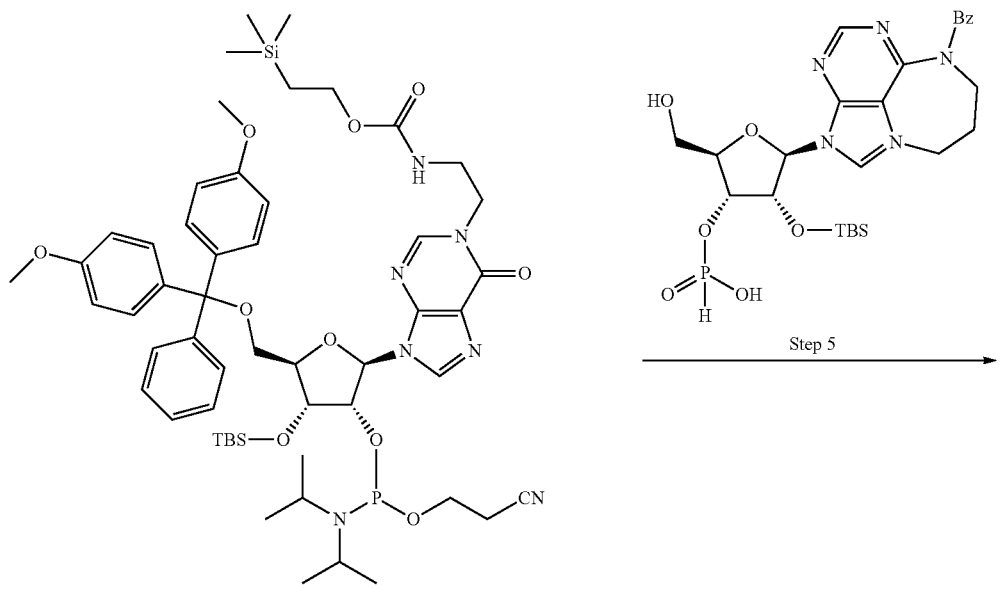
Step 5 →

-continued
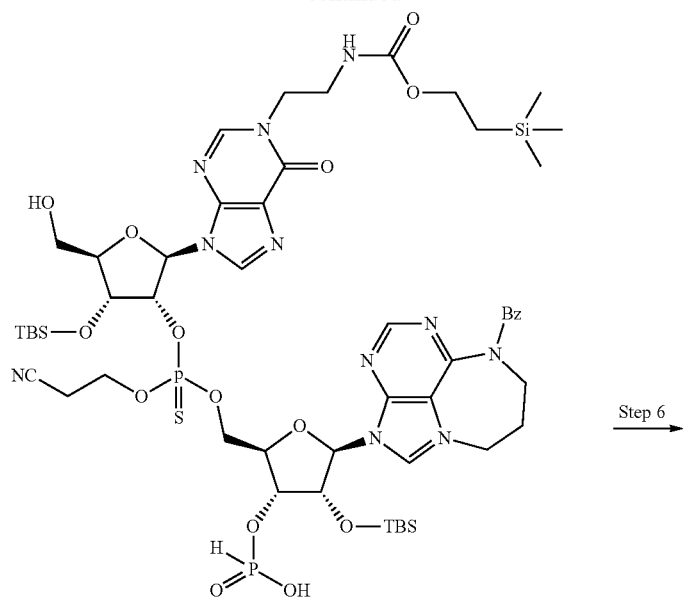
Step 6
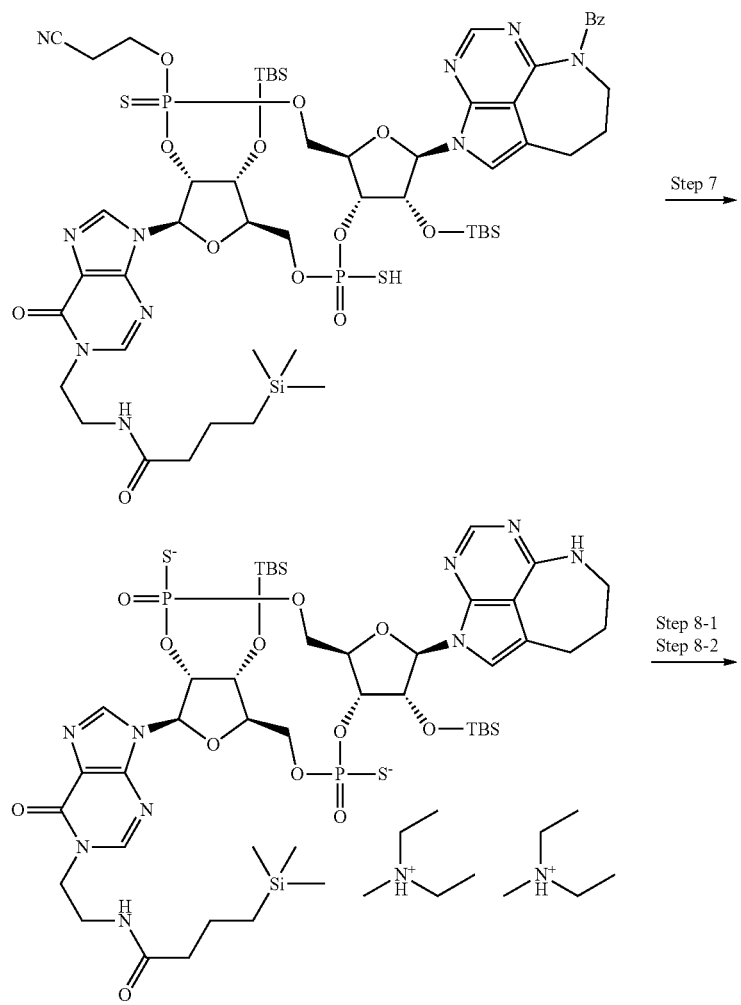
Step 7
Step 8-1
Step 8-2

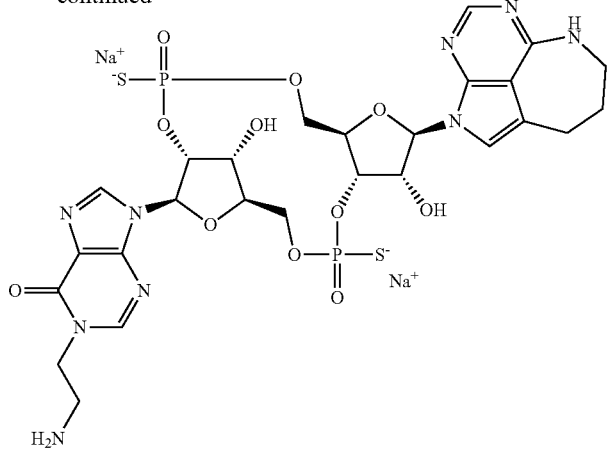

(Step 1)

2',3',5'-Tri-O-acetyl-1-[2-({[2-(trimethylsilyl)ethoxy]carbonyl}amino)ethyl]inosine To a suspension of 2',3',5'-tri-O-acetylinosine (5.00 g) in tetrahydrofuran (90 mL), 2-(trimethylsilyl)ethyl (2-hydroxyethyl)carbamate (3.12 g) and triphenylphosphine (3.99 g) were added, and a solution of dipropan-2-yl(E)-diazene-1,2-dicarboxylate (3.05 mL) in tetrahydrofuran (10 mL) was added thereto, and the reaction mixture was stirred at room temperature for 15 hours. After the reaction mixture was concentrated under reduced pressure, the residue was purified by silica gel column chromatography [hexane/ethyl acetate/methanol] to afford the title compound (3.01 g).

MS(ESI)m/z: 582 (M+H)$^+$.

$^1$H-NMR (CDCl$_3$) δ: 7.96 (1H, s), 7.93 (1H, s), 6.10 (1H, d, J=4.8 Hz), 5.86 (1H, t, J=5.4 Hz), 5.58 (1H, t, J=5.1 Hz), 4.96 (1H, t, J=7.3 Hz), 4.47-4.40 (2H, m), 4.36 (1H, dd, J=13.0, 5.1 Hz), 4.24 (2H, t, J=5.4 Hz), 4.15 (2H, t, J=8.8 Hz), 3.55 (2H, q, J=6.0 Hz), 2.15 (3H, s), 2.13 (3H, s), 2.10 (3H, s), 0.97 (2H, t, J=8.8 Hz), 0.03 (9H, s).

(Step 2)

5'-O-[Bis(4-methoxyphenyl)(phenyl)methyl]-1-[2-({[2-(trimethylsilyl)ethoxy]carbonyl}amino)ethyl]inosine To a solution of the compound obtained in step 1 (3.01 g) in tetrahydrofuran (15 mL)-methanol (15 mL), potassium carbonate (100 mg) was added, and the reaction mixture was stirred at room temperature for 2 hours. Acetic acid (83 µL) was added to the reaction mixture, which was concentrated under reduced pressure, and the residue was azeotroped with pyridine. The resultant was again dissolved in pyridine (30 mL), to which 4,4'-dimethoxytrityl chloride (2.10 g) was added at 0° C., and the reaction mixture was stirred for 30 minutes and then stored in a refrigerator overnight. Methanol (1 mL) was added to the reaction mixture, which was stirred for 30 minutes, and then concentrated under reduced pressure. The residue was purified by silica gel column chromatography [hexane/ethyl acetate/methanol/0.1% triethylamine] to afford the title compound (3.61 g).

MS(ESI)m/z: 758 (M+H)$^+$.

$^1$H-NMR (CDCl$_3$) δ: 7.92 (1H, s), 7.76 (1H, s), 7.37 (2H, d, J=7.3 Hz), 7.29-7.14 (7H, m), 6.78 (4H, d, J=8.5 Hz), 5.94 (1H, d, J=5.4 Hz), 5.63 (1H, br s), 4.81-4.74 (1H, m), 4.46-4.41 (1H, m), 4.36-4.31 (1H, m), 4.19-4.05 (4H, m), 3.76 (6H, s), 3.52-3.44 (2H, m), 3.44-3.31 (2H, m), 0.99-0.91 (2H, m), 0.02 (9H, s). (only observable peaks are shown)

(Step 3)

5'-O-[Bis(4-methoxyphenyl)(phenyl)methyl]-3'-O-[tert-butyl(dimethyl)silyl]-1-[2-({[2-(trimethylsilyl)ethoxy]carbonyl}amino)ethyl]inosine To a solution of the compound obtained in step 2 (3.61 g) in dichloromethane (18 mL), imidazole (811 mg) and tert-butyl(chloro)dimethylsilane (861 mg) were added, and the reaction mixture was stirred at room temperature for 17 hours. A saturated aqueous solution of sodium hydrogen carbonate was added to the reaction mixture, which was subjected to extraction with dichloromethane. After the organic layer was dried over anhydrous sodium sulfate, the drying agent was removed through filtration, and the filtrate was concentrated under reduced pressure. The residue was purified by silica gel column chromatography [hexane/ethyl acetate/0.1% triethylamine] to afford the title compound (1.61 g) and 5'-O-[bis(4-methoxyphenyl)(phenyl)methyl]-2'-O-[tert-butyl(dimethyl)silyl]-1-[2-({[2-(trimethylsilyl)ethoxy]carbonyl}amino)ethyl]inosine (1.31 g) as a regioisomer of the title compound.

MS(ESI)m/z: 872 (M+H)$^+$.

$^1$H-NMR (CDCl$_3$) δ: 7.98 (1H, s), 7.85 (1H, s), 7.39 (2H, d, J=7.9 Hz), 7.32-7.15 (7H, m), 6.78 (4H, d, J=9.1 Hz), 5.93 (1H, d, J=4.8 Hz), 5.22-5.11 (1H, m), 4.60 (1H, q, J=5.6 Hz), 4.47 (1H, t, J=4.2 Hz), 4.28-4.08 (5H, m), 3.77 (6H, s), 3.59-3.49 (2H, m), 3.45 (1H, dd, J=10.3, 3.0 Hz), 3.26 (1H, dd, J=10.3, 3.9 Hz), 3.15-3.08 (1H, m), 0.95 (2H, t, J=8.5 Hz), 0.88 (9H, s), 0.07 (3H, s), 0.02 (9H, s), 0.00 (3H, s).

Regioisomer (2'-O-TBS form)

MS(ESI)m/z: 872 (M+H)$^+$.

$^1$H-NMR (CDCl$_3$) δ: 7.99 (1H, s), 7.82 (1H, s), 7.46-7.41 (2H, m), 7.35-7.19 (7H, m), 6.84-6.78 (4H, m), 5.98 (1H, d, J=5.4 Hz), 5.06-4.96 (1H, m), 4.84 (1H, t, J=5.4 Hz), 4.34-4.08 (6H, m), 3.78 (6H, s), 3.54 (2H, q, J=5.8 Hz), 3.48 (1H, dd, J=10.6, 2.7 Hz), 3.39 (1H, dd, J=10.6, 3.9 Hz), 2.71 (1H, d, J=4.2 Hz), 0.99-0.91 (2H, m), 0.85 (9H, s), 0.03 (9H, s), 0.02 (3H, s), −0.12 (3H, s).

(Step 4)

5'-O-[Bis(4-methoxyphenyl)(phenyl)methyl]-3'-O-[tert-butyl(dimethyl)silyl]-2'-O-{(2-cyanoethoxy)[di(propan-2-yl)amino]phosphanyl}-1-[2-({[2-(trimethylsilyl)ethoxy]carbonyl}amino)ethyl]inosine

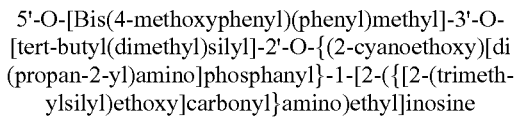

To a solution of the compound obtained in step 3 (1.61 g) in dichloromethane (18.5 mL), 4,5-dicyanoimidazole (240 mg) and 2-cyanoethyl N,N,N',N'-tetraisopropylphosphorodiamidite (0.703 mL) were added, and the reaction mixture was stirred at room temperature for 15 hours. A saturated aqueous solution of sodium hydrogen carbonate was added to the reaction mixture to quench the reaction. After the reaction mixture was subjected to extraction with dichloromethane, the organic layer was dried over anhydrous sodium sulfate. The drying agent was removed through filtration, and the filtrate was concentrated under reduced pressure. The residue was purified by DIOL silica gel column chromatography [hexane/ethyl acetate] to afford the title compound (1.95 g) as a mixture of diastereomers at the phosphorus atom (diastereomer ratio=61:39).

MS(ESI)m/z: 1072 (M+H)$^+$.

$^1$H-NMR (CDCl$_3$) δ: 8.04 (0.39H, s), 7.99 (0.61H, s), 7.83 (0.39H, s), 7.82 (0.61H, s), 7.42 (2H, d, J=7.3 Hz), 7.35-7.15 (7H, m), 6.85-6.77 (4H, m), 6.15 (0.61H, d, J=6.0 Hz), 6.09 (0.39H, d, J=4.8 Hz), 5.34-5.24 (0.61H, m), 5.12-5.03 (0.39H, m), 4.86-4.76 (0.39H, m), 4.72-4.62 (0.61H, m), 4.47-4.42 (0.39H, m), 4.42-4.36 (0.69H, m), 4.31-4.05 (6H, m), 3.78 (6H, s), 3.78-3.65 (1H, m), 3.61-3.39 (7H, m), 3.35 (0.61H, dd, J=10.6, 3.9 Hz), 3.28 (0.39H, dd, J=10.9, 4.2 Hz), 2.49 (0.78H, t, J=6.0 Hz), 2.29 (1.22H, t, J=5.7 Hz), 1.30-0.94 (12H, m), 0.85 (5.49H, s), 0.84 (3.51H, s), 0.09 (1.17H, s), 0.08 (1.83H, s), 0.03 (9H, s), 0.02 (1.83H, s), 0.00 (1.17H, s).

(Step 5)

The same reaction as in step 7 of Example 1 was performed in the following scale (raw material: 910 mg). With use of an acetonitrile solution of the compound obtained and the compound obtained in step 4 (950 mg), the reaction was performed in the same manner as in step 8 of Example 1. The resulting crude product was directly used for the subsequent reaction.

(Step 6)

2-(Trimethylsilyl)ethyl (2-{9-[(5R,7R,8R,12aR,14R,15R,15aR,16R)-14-(6-benzoyl-6,7,8,9-tetrahydro-2H-2,3,5,6-tetraazabenzo[cd]azulen-2-yl)-15,16-bis{[tert-butyl(dimethyl)silyl]oxy}-10-(2-cyanoethoxy)-2-oxo-2-sulfanyl-10-sulfanylideneoctahydro-2H,10H,12H-5,8-methano-2λ$^5$,10λ$^5$-furo[3,2-1][1,3,6,9,11,2,10]pentaoxadiphosphacyclotetradecin-7-yl]-6-oxo-6,9-dihydro-1H-purin-1-yl}ethyl)carbamate

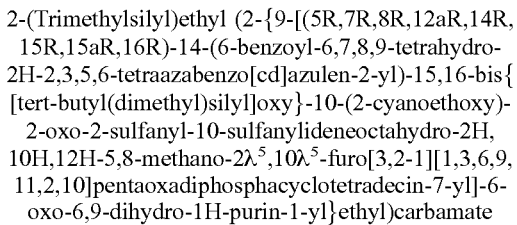

With use of the crude product obtained in step 5, the reaction was performed in the same manner as in step 9 of Example 1 to afford the title compound (602 mg) as a mixture of diastereomers at the phosphorus atom.

MS(ESI)m/z: 1303 (M+H)$^+$.

(Step 7)

Bis(N,N-diethylethaneaminium) (5R,7R,8R,12aR,14R,15R,15aR,16R)-15,16-bis{[tert-butyl(dimethyl)silyl]oxy}-2,10-dioxo-7-{6-oxo-1-[2-({[2-(trimethylsilyl)ethoxy]carbonyl}amino)ethyl]-1,6-dihydro-9H-purin-9-yl}-14-(6,7,8,9-tetrahydro-2H-2,3,5,6-tetraazabenzo[cd]azulen-2-yl)octahydro-2H,10H,12H-5,8-methano-2λ$^5$,10λ$^5$-furo[3,2-1][1,3,6,9,11,2,10]pentaoxadiphosphacyclotetradecine-2,10-bis(thiolate)

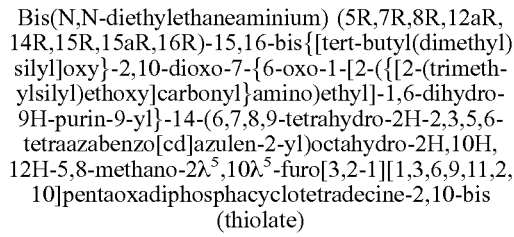

With use of the compound obtained in step 6 (602 mg), the reaction was performed in the same manner as in step 10 of Example 1 to afford diastereomer 1 (205 mg: with impurities) and diastereomer 2 (244 mg: with impurities) of the title compound.

Diastereomer 1 (Less Polar)
 MS(ESI)m/z: 1146 (M+H)$^+$.
Diastereomer 2 (More Polar)
 MS(ESI)m/z: 1146 (M+H)$^+$.

(Step 8-1)

Disodium (5R,7R,8R,12aR,14R,15R,15aS,16R)-7-[1-(2-aminoethyl)-6-oxo-1,6-dihydro-9H-purin-9-yl]-15,16-dihydroxy-2,10-dioxo-14-(6,7,8,9-tetrahydro-2H-2,3,5,6-tetraazabenzo[cd]azulen-2-yl)octahydro-2H,10H,12H-5,8-methano-2λ$^5$,10λ$^5$-furo[3,2-1][1,3,6,9,11,2,10]pentaoxadiphosphacyclotetradecine-2,10-bis(thiolate)

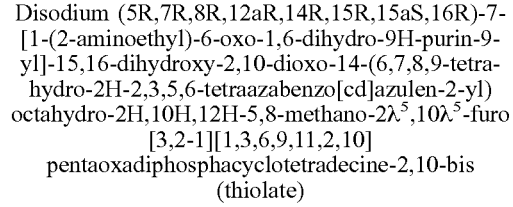

(Diastereomer 1)

Triethylamine trihydrofluoride (1.31 mL) was added to the compound obtained in step 7 (diastereomer 1) (145 mg: with impurities), and the reaction mixture was stirred at 45° C. for 3 hours. To the reaction mixture, an ice-cooled mixture of 1 M solution of triethylammonium hydrogen carbonate (10 mL) and triethylamine (2 mL) was added. The reaction mixture was concentrated under reduced pressure, and then purified by C18 silica gel column chromatography [10 mM aqueous solution of triethylammonium acetate/acetonitrile]. To a solution of the compound obtained in tetrahydrofuran (4 mL), a tetrahydrofuran solution of tetrabutylammonium fluoride (approximately 1 M, 2 mL) was added, and the reaction mixture was stirred at room temperature for 39 hours. To the reaction mixture, 10 mM aqueous solution of triethylammonium acetate (4 mL) was added, and the reaction mixture was concentrated under reduced pressure. The residue was purified by C18 silica gel column chromatography [10 mM aqueous solution of triethylammonium acetate/acetonitrile] and preparative HPLC [10 mM aqueous solution of triethylammonium acetate/acetonitrile, acetonitrile: 5%-50% (0 min-40 min)]. Salt exchange was performed in the same manner as in [Conversion to Sodium Salt] described in step 11 of Example 1, except that in salt exchange for the compound obtained (triethylamine salt), a mixed solution of acetonitrile-methanol-pure water (1:1:1) was used for the solvent and eluent to dissolve the compound, to afford the title compound (72.5 mg).

MS(ESI)m/z: 774 (M+H)$^+$.

$^1$H-NMR (CD$_3$OD) δ: 8.60 (1H, s), 8.15 (1H, s), 8.02 (1H, s), 7.11 (1H, s), 6.26 (1H, d, J=4.8 Hz), 6.24 (1H, t, J=5.1 Hz), 5.47 (1H, dt, J=8.2, 4.2 Hz), 5.23-5.17 (1H, m), 4.77-4.73 (2H, m), 4.52-4.44 (2H, m), 4.36-4.19 (3H, m), 4.14-4.02 (3H, m), 3.48 (2H, t, J=4.8 Hz), 3.31-3.26 (2H, m), 2.90-2.74 (2H, m), 2.01-1.93 (2H, m).

$^{31}$P-NMR (CD$_3$OD) δ: 57.7 (s), 54.7 (s).

(Step 8-2)

Disodium (5R,7R,8R,12aR,14R,15R,15aS,16R)-7-[1-(2-aminoethyl)-6-oxo-1,6-dihydro-9H-purin-9-yl]-15,16-dihydroxy-2,10-dioxo-14-(6,7,8,9-tetrahydro-2H-2,3,5,6-tetraazabenzo[cd]azulen-2-yl)octahydro-2H,10H,12H-5,8-methano-2λ$^5$,10λ$^5$-furo[3,2-l][1,3,6,9,11,2,10]pentaoxadiphosphacyclotetradecine-2,10-bis(thiolate)

(Diastereomer 2)

With use of the compound obtained in step 7 (diastereomer 2) (133 mg: with impurities), reaction and salt exchange were performed in the same manner as in step 8-1 to afford the title compound (55.4 mg).

MS(ESI)m/z: 774 (M+H)$^+$.

$^1$H-NMR (CD$_3$OD) δ: 8.72 (1H, s), 8.25 (1H, s), 8.02 (1H, s), 7.11 (1H, s), 6.31 (1H, d, J=6.7 Hz), 6.28 (1H, d, J=8.5 Hz), 5.47-5.38 (2H, m), 4.77 (1H, dd, J=6.7, 4.2 Hz), 4.48 (1H, d, J=4.2 Hz), 4.46-4.37 (2H, m), 4.37-4.29 (3H, m), 4.27-4.18 (1H, m), 4.08-4.02 (1H, m), 3.92-3.85 (1H, m), 3.53-3.46 (2H, m), 3.28-3.23 (2H, m), 2.93-2.86 (2H, m), 2.04-1.96 (2H, m). 31P-NMR (CD$_3$OD) δ: 62.6 (s), 60.0 (s).

Example 6: Synthesis of CDN6

(5R,7R,8R,12aR,14R,15R,15aS,16R)-15,16-Dihydroxy-7-[1-(2-hydroxyethyl)-6-oxo-1,6-dihydro-9H-purin-9-yl]-2,10-bis(sulfanyl)-14-(6,7,8,9-tetrahydro-2H-2,3,5,6-tetraazabenzo[cd]azulen-2-yl)octahydro-2H,10H,12H-5,8-methano-2λ$^5$,10λ$^5$-furo[3,2-l][1,3,6,9,11,2,10]pentaoxadiphosphacyclotetradecine-2,10-dione

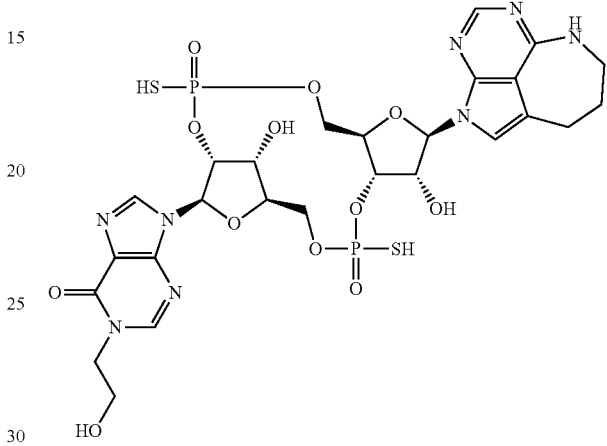

6
6a (Diastereomer 1)
6b (Diastereomer 2)

[Synthesis Scheme]

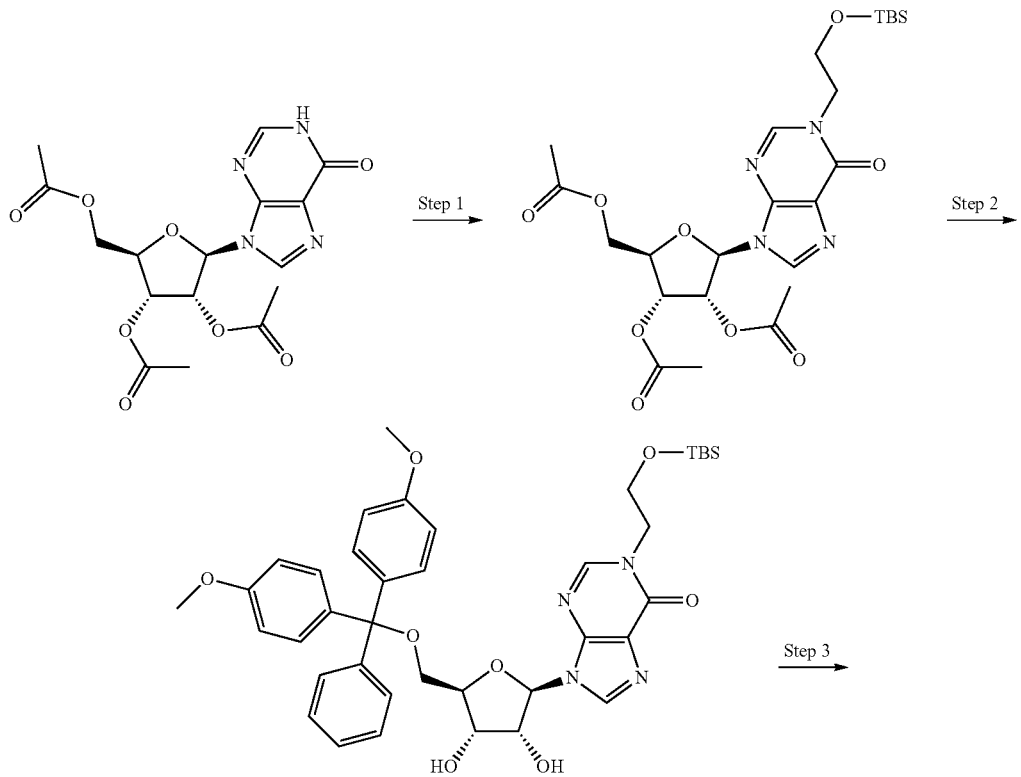

191 192
-continued
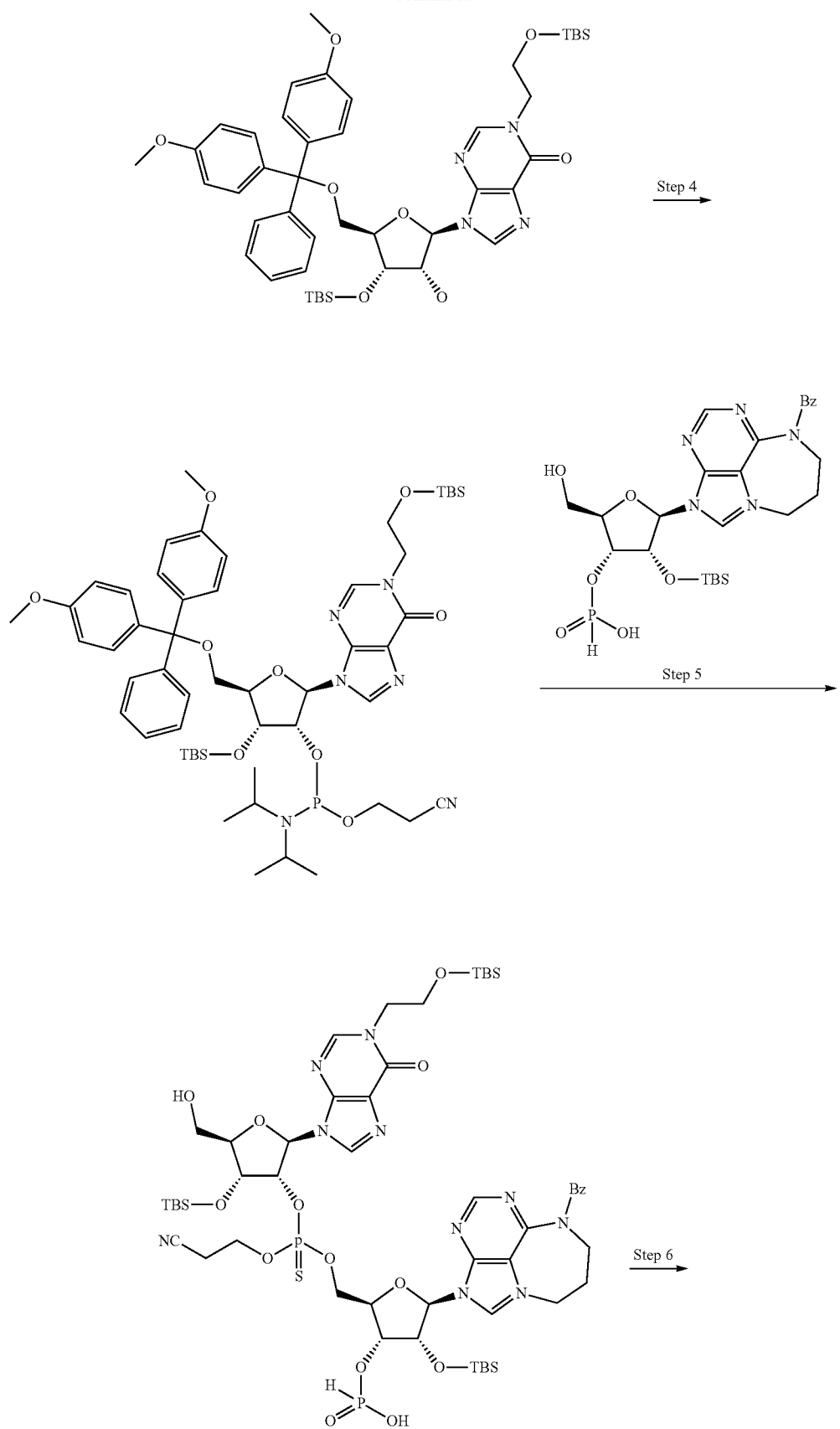

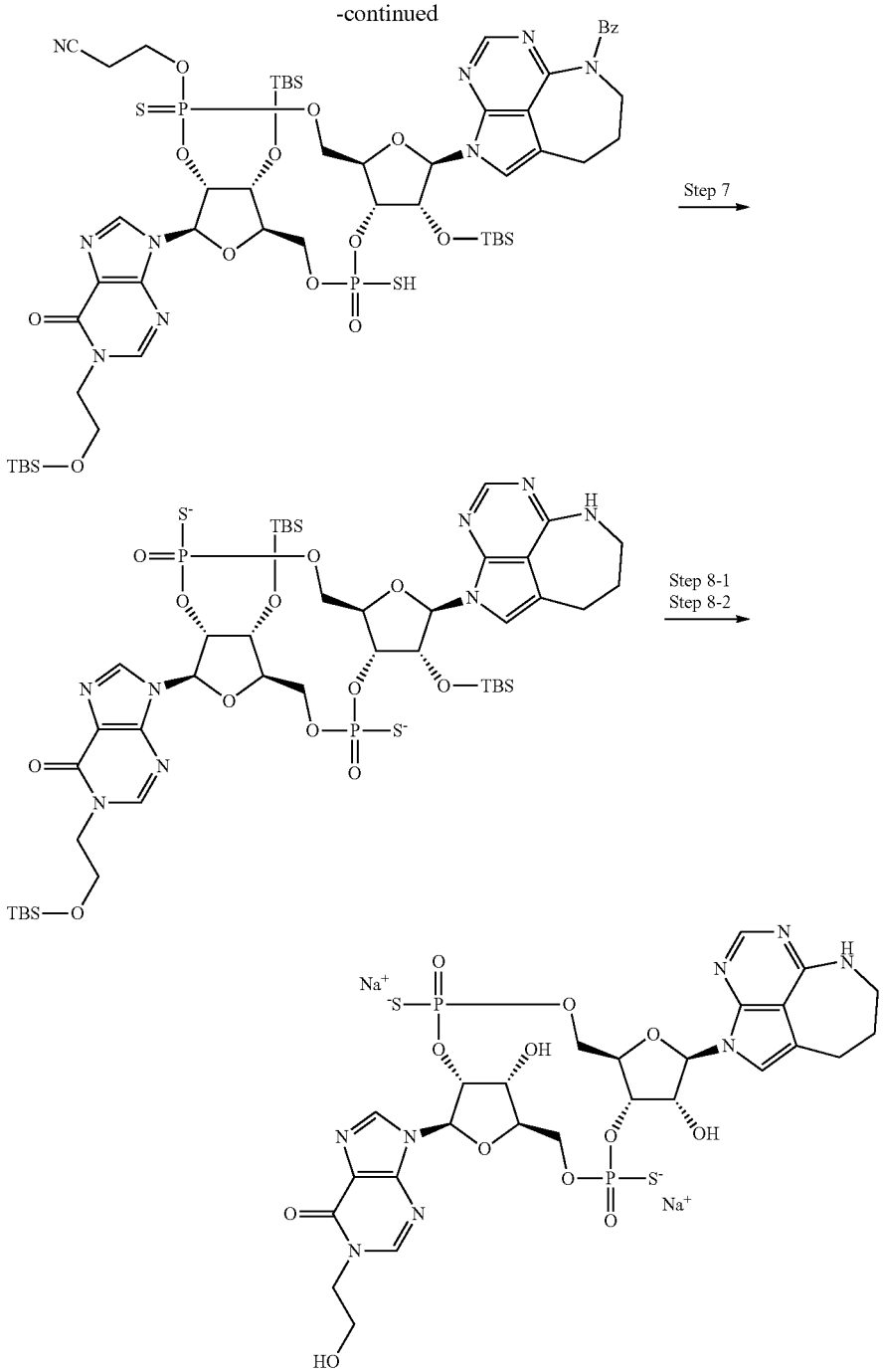

(Step 1)

2',3',5'-Tri-O-acetyl-1-(2-{[tert-butyl(dimethyl)silyl]oxy}ethyl)inosine

To a suspension of commercially available (Ark Pharm, Inc.) 2',3',5'-tri-O-acetylinosine (10.0 g) in tetrahydrofuran (100 mL), 2-{[tert-butyl(dimethyl)silyl]oxy}ethan-1-ol (5.37 g) and triphenylphosphine (7.69 g) were added, and dipropan-2-yl (E)-diazene-1,2-dicarboxylate (6.10 mL) was then added thereto, and the reaction mixture was stirred at room temperature for 6 hours. After the reaction mixture was concentrated under reduced pressure, the residue was purified by silica gel column chromatography [hexane/ethyl acetate/dichloromethane] to afford the title compound as a mixture (10.6 g) with triphenylphosphine oxide.

MS(ESI)m/z: 553 (M+H)⁺.

¹H-NMR (CDCl₃) δ: 8.05 (1H, s), 7.92 (1H, s), 6.12 (1H, d, J=5.4 Hz), 5.86 (1H, t, J=5.4 Hz), 5.59 (1H, dd, J=5.4, 4.2 Hz), 4.47-4.41 (2H, m), 4.38-4.31 (1H, m), 4.22-4.17 (2H, m), 3.89 (2H, t, J=4.8 Hz), 2.15 (3H, s), 2.14 (3H, s), 2.08 (3H, s), 0.83 (9H, s), −0.06 (3H, s), −0.06 (3H, s).

(Step 2)

5'-O-[Bis(4-methoxyphenyl)(phenyl)methyl]-1-(2-{[tert-butyl(dimethyl)silyl]oxy}ethyl)inosine With use of the compound obtained in step 1 (10.6 g), the reaction was performed in the same manner as in step 2 of Example 5 to afford the title compound as a mixture (7.21 g) with triphenylphosphine oxide.

MS(ESI)m/z: 729 (M+H)$^+$.

$^1$H-NMR (CDCl$_3$) δ: 8.01 (1H, s), 7.97 (1H, s), 7.35-7.30 (2H, m), 7.25-7.17 (7H, m), 6.81-6.76 (4H, m), 5.95 (1H, d, J=5.4 Hz), 5.13 (1H, brs), 4.68-4.61 (1H, m), 4.43-4.36 (2H, m), 4.31-4.23 (1H, m), 4.15-4.08 (1H, m), 3.89 (2H, t, J=4.5 Hz), 3.77 (6H, s), 3.42 (1H, dd, J=10.3, 3.6 Hz), 3.34 (1H, dd, J=10.3, 3.6 Hz), 3.10 (1H, brs), 0.83 (9H, s), −0.06 (3H, s), —0.07 (3H, s).

(Step 3)

5'-O-[Bis(4-methoxyphenyl)(phenyl)methyl]-3'-O-[tert-butyl(dimethyl)silyl]-1-(2-{[tert-butyl(dimethyl)silyl]oxy}ethyl)inosine With use of the compound obtained in step 2 (7.21 g), the reaction was performed in the same manner as in step 3 of Example 5 to afford the title compound (2.17 g) and 5'-O-[bis(4-methoxyphenyl)(phenyl)methyl]-2'-O-[tert-butyl(dimethyl)silyl]-1-(2-{[tert-butyl(dimethyl)silyl]oxy}ethyl)inosine (2.55 g) as a regioisomer of the title compound.

MS(ESI)m/z: 843 (M+H)$^+$.

$^1$H-NMR (CDCl$_3$) δ: 7.99 (1H, s), 7.97 (1H, s), 7.43-7.39 (2H, m), 7.33-7.19 (7H, m), 6.83-6.77 (4H, m), 5.96 (1H, d, J=4.2 Hz), 4.56-4.50 (2H, m), 4.33-4.25 (1H, m), 4.19-4.02 (2H, m), 3.89 (2H, t, J=4.8 Hz), 3.78 (6H, s), 3.45 (1H, dd, J=10.9, 4.2 Hz), 3.27 (1H, dd, J=10.9, 4.2 Hz), 3.03 (1H, d, J=6.0 Hz), 0.88 (9H, s), 0.82 (9H, s), 0.07 (3H, s), −0.01 (3H, s), −0.07 (3H, s), −0.07 (3H, s).

Regioisomer (2'-O-TBS form)

MS(ESI)m/z: 843 (M+H)$^+$.

$^1$H-NMR (CDCl$_3$) δ: 7.98 (1H, s), 7.94 (1H, s), 7.46-7.42 (2H, m), 7.35-7.20 (7H, m), 6.85-6.79 (4H, m), 5.99 (1H, d, J=5.4 Hz), 4.83 (1H, t, J=5.1 Hz), 4.33-4.29 (1H, m), 4.27-4.24 (1H, m), 4.24-4.12 (2H, m), 3.90 (2H, t, J=4.5 Hz), 3.79 (3H, s), 3.78 (3H, s), 3.48 (1H, dd, J=10.3, 3.0 Hz), 3.40 (1H, dd, J=10.3, 3.0 Hz), 2.71 (1H, d, J=3.6 Hz), 0.86 (9H, s), 0.83 (9H, s), 0.01 (3H, s), −0.07 (3H, s), −0.07 (3H, s), −0.11 (3H, s).

(Step 4)

5'-O-[Bis(4-methoxyphenyl)(phenyl)methyl]-3'-O-[tert-butyl(dimethyl)silyl]-1-(2-{[tert-butyl(dimethyl)silyl]oxy}ethyl)-2'-O-{(2-cyanoethoxy)[di(propan-2-yl)amino]phosphanyl}inosine With use of the compound obtained in step 3 (2.17 g), the reaction was performed in the same manner as in step 4 of Example 5 to afford the title compound (2.65 g) as a mixture of diastereomers at the phosphorus atom.

MS(ESI)m/z: 1043 (M+H)$^+$.

$^1$H-NMR (CDCl$_3$): 8.03 (0.53H, s), 8.01 (0.47H, s), 7.97 (0.53H, s), 7.93 (0.47H, s), 7.45-7.41 (2H, m), 7.35-7.19 (7H, m), 6.83-6.78 (4H, m), 6.17 (0.53H, d, J=4.2 Hz), 6.05 (0.47H, d, J=4.2 Hz), 4.87-4.80 (0.47H, m), 4.64-4.58 (0.53H, m), 4.46-4.40 (1H, m), 4.30-4.05 (3H, m), 3.92-3.87 (2H, m), 3.78 (6H, s), 3.86-3.40 (5H, m), 3.33-3.24 (1H, m), 2.54 (0.94H, t, J=6.0 Hz), 2.43 (1.06H, t, J=6.7 Hz), 1.16-1.09 (9H, m), 1.01-0.97 (3H, m), 0.83 (4.23H, s), 0.83 (4.77H, s), 0.82 (9H, s), 0.07 (1.41H, s), 0.04 (1.59H, s), −0.02 (3H, s), −0.07 (1.41H, s), −0.08 (1.59H, s), −0.08 (3H, s).

(Step 5)

The same reaction as in step 7 of Example 1 was performed in the following scale (raw material: 935 mg). With use of an acetonitrile solution of the compound obtained and the compound obtained in step 4 (950 mg), the reaction was performed in the same manner as in step 8 of Example 1. The resulting crude product was directly used for the subsequent reaction.

(Step 6)

3-({(5R,7R,8R,12aR,14R,15R,15aR,16R)-14-(6-Benzoyl-6,7,8,9-tetrahydro-2H-2,3,5,6-tetraazabenzo[cd]azulen-2-yl)-15,16-bis{[tert-butyl(dimethyl)silyl]oxy}-7-[1-(2-{[tert-butyl(dimethyl)silyl]oxy}ethyl)-6-oxo-1,6-dihydro-9H-purin-9-yl]-2-oxo-2-sulfanyl-10-sulfanylideneoctahydro-2H,10H,12H-5,8-methano-2λ$^5$,10λ$^5$-furo[3,2-1][1,3,6,9,11,2,10]pentaoxadiphosphacyclotetradecin-10-yl}oxy)propanenitrile With use of the crude product obtained in step 5, the reaction was performed in the same manner as in step 9 of Example 1 to afford the title compound (494 mg) as a mixture of diastereomers at the phosphorus atom.

MS(ESI)m/z: 1274 (M+H)$^+$.

(Step 7)

Bis(N,N-diethylethaneaminium) (5R,7R,8R,12aR,14R,15R,15aR,16R)-15,16-bis{[tert-butyl(dimethyl)silyl]oxy}-7-[1-(2-{[tert-butyl(dimethyl)silyl]oxy}ethyl)-6-oxo-1,6-dihydro-9H-purin-9-yl]-2,10-dioxo-14-(6,7,8,9-tetrahydro-2H-2,3,5,6-tetraazabenzo[cd]azulen-2-yl)octahydro-2H,10H,12H-5,8-methano-2λ$^5$,10λ$^5$-furo[3,2-1][1,3,6,9,11,2,10]pentaoxadiphosphacyclotetradecine-2,10-bis(thiolate)

With use of the compound obtained in step 6 (494 mg), the reaction was performed in the same manner as in step 10 of Example 1 to afford diastereomer 1 (88.5 mg: with impurities) and diastereomer 2 (70.7 mg: with impurities) of the title compound.

Diastereomer 1 (Less Polar)

MS(ESI)m/z: 1003 (M−C$_6$H$_{15}$Si+2H)$^+$.

Diastereomer 2 (More Polar)

MS(ESI)m/z: 1003 (M−C$_6$H$_{15}$Si+2H)$^+$.

(Step 8-1)

Disodium (5R,7R,8R,12aR,14R,15R,15aS,16R)-15,16-dihydroxy-7-[1-(2-hydroxyethyl)-6-oxo-1,6-dihydro-9H-purin-9-yl]-2,10-dioxo-14-(6,7,8,9-tetrahydro-2H-2,3,5,6-tetraazabenzo[cd]azulen-2-yl)octahydro-2H,10H,12H-5,8-methano-2λ$^5$,10λ$^5$-furo[3,2-1][1,3,6,9,11,2,10]pentaoxadiphosphacyclotetradecine-2,10-bis(thiolate)

(Diastereomer 1)

With use of the compound obtained in step 7 (diastereomer 1) (88.5 mg: with impurities), the reaction was performed in the same manner as in step 11 of Example 1, and purification was then performed under the following [Purification Conditions] to afford the title compound as a triethylamine salt.

[Purification Conditions] C18 silica gel column chromatography [10 mM aqueous solution of triethylammonium acetate/acetonitrile] and preparative HPLC [10 mM aqueous solution of triethylammonium acetate/acetonitrile, acetonitrile: 5%-30% (0 min-40 min)].

The triethylamine salt obtained was subjected to salt exchange in the same manner as in [Conversion to Sodium Salt] described in step 11 of Example 1 to afford the title compound (25.7 mg).

MS(ESI)m/z: 775 (M+H)$^+$.

$^1$H-NMR (CD$_3$OD) δ: 8.63 (1H, s), 8.22 (1H, s), 8.02 (1H, s), 7.11 (1H, s), 6.30-6.24 (2H, m), 5.46-5.37 (1H, m), 5.23-5.15 (1H, m), 4.83-4.79 (1H, m), 4.78-4.74 (1H, m), 4.53-4.42 (2H, m), 4.35-4.16 (3H, m), 4.16-3.97 (3H, m), 3.83-3.78 (2H, m), 3.52-3.47 (2H, m), 2.88-2.81 (2H, m), 2.03-1.95 (2H, m).

$^{31}$P-NMR (CD$_3$OD) δ: 57.8 (s), 54.4 (s).

(Step 8-2)

Disodium (5R,7R,8R,12aR,14R,15R,15aS,16R)-15,16-dihydroxy-7-[1-(2-hydroxyethyl)-6-oxo-1,6-dihydro-9H-purin-9-yl]-2,10-dioxo-14-(6,7,8,9-tetrahydro-2H-2,3,5,6-tetraazabenzo[cd]azulen-2-yl)octahydro-2H,10H,12H-5,8-methano-2λ$^5$,10λ$^5$-furo[3,2-l][1,3,6,9,11,2,10]pentaoxadiphosphacyclotetradecine-2,10-bis(thiolate)

(Diastereomer 2)

With use of the compound obtained in step 7 (diastereomer 2) (70.7 mg: with impurities), the reaction was performed in the same manner as in step 11 of Example 1, and purification was then performed under the following [Purification Conditions] to afford the title compound as a triethylamine salt.

[Purification Conditions] C18 silica gel column chromatography [10 mM aqueous solution of triethylammonium acetate/acetonitrile], preparative HPLC [10 mM aqueous solution of triethylammonium acetate/acetonitrile, acetonitrile: 5%-25% (0 min-40 min)], and preparative HPLC [10 mM aqueous solution of triethylammonium acetate/methanol, methanol: 15%-70% (0 min-40 min)].

The triethylamine salt obtained was subjected to salt exchange in the same manner as in [Conversion to Sodium Salt] described in step 11 of Example 1 to afford the title compound (17.8 mg).

MS(ESI)m/z: 775 (M+H)$^+$.

$^1$H-NMR (CD$_3$OD) δ: 8.72 (1H, s), 8.23 (1H, s), 8.02 (1H, s), 7.11 (1H, s), 6.30 (2H, dd, J=13.6, 7.6 Hz), 5.48-5.39 (2H, m), 4.78 (1H, dd, J=6.7, 4.2 Hz), 4.51-4.28 (5H, m), 4.26-4.13 (2H, m), 4.06-4.00 (1H, m), 3.93-3.86 (1H, m), 3.85-3.80 (2H, m), 3.52-3.47 (2H, m), 2.94-2.88 (2H, m), 2.05-1.97 (2H, m).

$^{31}$P-NMR (CD$_3$OD) δ: 62.9 (s), 60.0 (s).

Example 7: Synthesis of CDN7

N-(2-{9-[(5R,7R,8R,12aR,14R,15R,15aS,16R)-15,16-Dihydroxy-2,10-dioxo-2,10-bis(sulfanyl)-14-(6,7,8,9-tetrahydro-2H-2,3,5,6-tetraazabenzo[cd]azulen-2-yl)octahydro-2H,10H,12H-5,8-methano-2λ$^5$,10λ$^5$-furo[3,2-l][1,3,6,9,11,2,10]pentaoxadiphosphacyclotetradecin-7-yl]-6-oxo-6,9-dihydro-1H-purin-1-yl}ethyl)-2-hydroxyacetamide

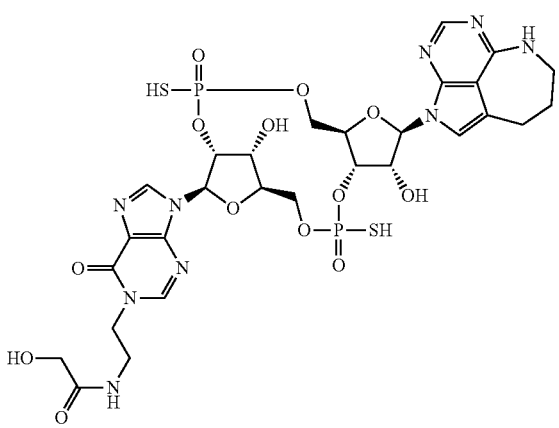

7a (Diastereomer 1)
7b (Diastereomer 2)

[Synthesis Scheme]

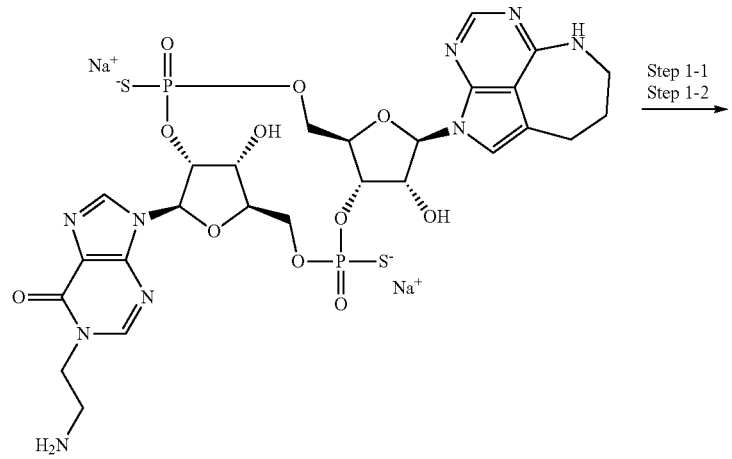

Step 1-1
Step 1-2

-continued

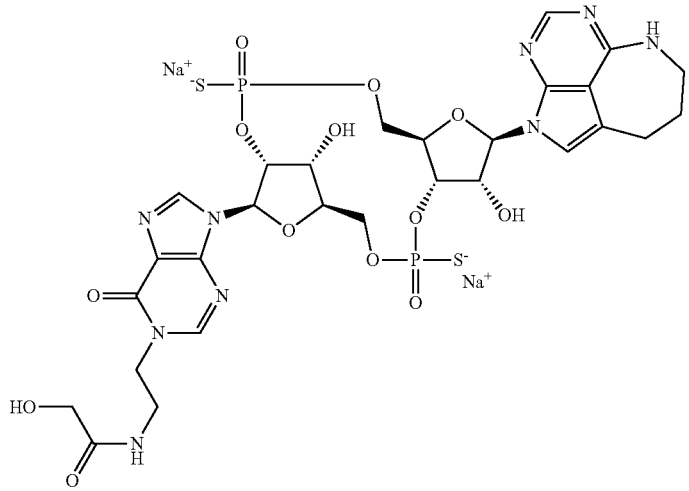

(Step 1-1)

Disodium (5R,7R,8R,12aR,14R,15R,15aS,16R)-15,
16-dihydroxy-7-{1-[2-(2-hydroxyacetamide)ethyl]-
6-oxo-1,6-dihydro-9H-purin-9-yl}-2,10-dioxo-14-(6,
7,8,9-tetrahydro-2H-2,3,5,6-tetraazabenzo[cd]
azulen-2-yl)octahydro-2H,10H,12H-5,8-methano-
2$\lambda^5$,10$\lambda^5$-furo[3,2-1][1,3,6,9,11,2,10]
pentaoxadiphosphacyclotetradecine-2,10-bis
(thiolate)

(Diastereomer 1)

To a solution of the compound obtained in step 8-1 of Example 5 (10.0 mg) in N,N-dimethylformamide (0.5 mL), triethylamine (8 µL) and 1-[(hydroxyacetyl)oxy]-2,5-dione (5.3 mg) were added, and the reaction mixture was stirred at room temperature for 2 hours. The reaction mixture was diluted with 10 mM aqueous solution of triethylammonium acetate, and purified by C18 silica gel column chromatography [10 mM aqueous solution of triethylammonium acetate/acetonitrile] and preparative HPLC [10 mM aqueous solution of triethylammonium acetate/acetonitrile, acetonitrile: 0%-30% (0 min-40 min)]. The compound obtained (triethylamine salt) was subjected to salt exchange in the same manner as in [Conversion to Sodium Salt] described in step 11 of Example 1 to afford the title compound (10.5 mg).

MS(ESI)m/z: 832 (M+H)$^+$.

$^1$H-NMR (CD$_3$OD) δ: 8.57 (1H, s), 8.04 (1H, s), 8.03 (1H, s), 7.13 (1H, s), 6.26 (1H, d, J=4.2 Hz), 6.24-6.19 (1H, m), 5.57-5.49 (1H, m), 5.26-5.18 (1H, m), 4.80 (1H, d, J=3.6 Hz), 4.76 (1H, t, J=4.5 Hz), 4.51-4.41 (2H, m), 4.35-4.17 (3H, m), 4.11-3.95 (3H, m), 3.91 (2H, s), 3.62-3.55 (2H, m), 3.52-3.45 (2H, m), 2.89-2.65 (2H, m), 2.02-1.91 (2H, m).

$^{31}$P-NMR (CD$_3$OD) δ: 57.6 (s), 54.3 (s).

(Step 1-2)

Disodium (5R,7R,8R,12aR,14R,15R,15aS,16R)-15,
16-dihydroxy-7-{1-[2-(2-hydroxyacetamide)ethyl]-
6-oxo-1,6-dihydro-9H-purin-9-yl}-2,10-dioxo-14-(6,
7,8,9-tetrahydro-2H-2,3,5,6-tetraazabenzo[cd]
azulen-2-yl)octahydro-2H,10H,12H-5,8-methano-
2$\lambda^5$,10$\lambda^5$-furo[3,2-1][1,3,6,9,11,2,10]
pentaoxadiphosphacyclotetradecine-2,10-bis
(thiolate)

(Diastereomer 2)

With use of the compound obtained in step 8-2 (30.0 mg) of Example 5, the reaction was performed in the same manner as in step 1-1, and purification was then performed under the following [Purification Conditions] to afford the title compound as a triethylamine salt.

[Purification Conditions] C18 silica gel column chromatography [10 mM aqueous solution of triethylammonium acetate/acetonitrile] and preparative HPLC [10 mM aqueous solution of triethylammonium acetate/acetonitrile, acetonitrile: 5%-30% (0 min-40 min)].

The triethylamine salt obtained was subjected to salt exchange in the same manner as in [Conversion to Sodium Salt] described in step 11 of Example 1 to afford the title compound (23.6 mg).

MS(ESI)m/z: 832 (M+H)$^+$.

$^1$H-NMR (CD$_3$OD) δ: 8.69 (1H, s), 8.14 (1H, s), 8.02 (1H, s), 7.11 (1H, s), 6.31 (1H, d, J=6.7 Hz), 6.26 (1H, d, J=7.9 Hz), 5.49-5.40 (2H, m), 4.77 (1H, dd, J=6.7, 4.8 Hz), 4.48 (1H, d, J=4.2 Hz), 4.46-4.28 (4H, m), 4.22 (2H, t, J=5.4 Hz), 4.06-4.00 (1H, m), 3.94 (2H, s), 3.92-3.86 (1H, m), 3.70-3.55 (2H, m), 3.52-3.47 (2H, m), 2.92-2.86 (2H, m), 2.04-1.96 (2H, m).

$^{31}$P-NMR (CD$_3$OD) δ: 62.7 (s), 59.9 (s).

Example 8: Synthesis of CDN8
(5R,7R,8R,12aR,14R,15R,15aS,16R)-7-{6-Amino-2-[(2-aminoethyl)amino]-9H-purin-9-yl}-15,16-dihydroxy-2,10-bis(sulfanyl)-14-(6,7,8,9-tetrahydro-2H-2,3,5,6-tetraazabenzo[cd]azulen-2-yl)octahydro-2H,10H,12H-5,8-methano-2$\lambda^5$,10$\lambda^5$-furo[3,2-l][1,3,6,9,11,2,10]pentaoxadiphosphacyclotetradecine-2,10-dione
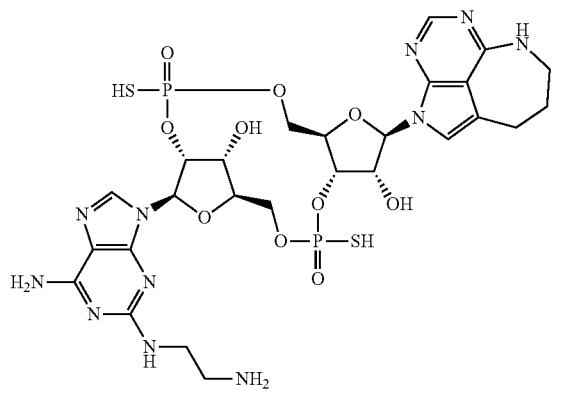
8a (Diastereomer 1)
8b (Diastereomer 2)
[Synthesis Scheme]
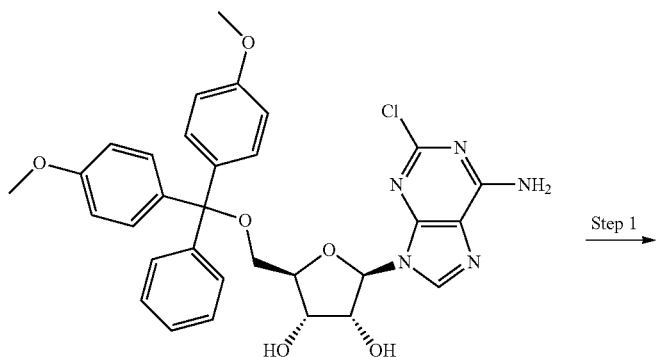
Step 1
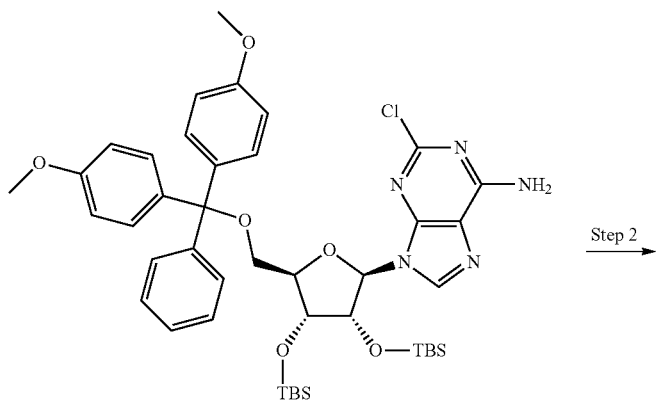
Step 2

-continued
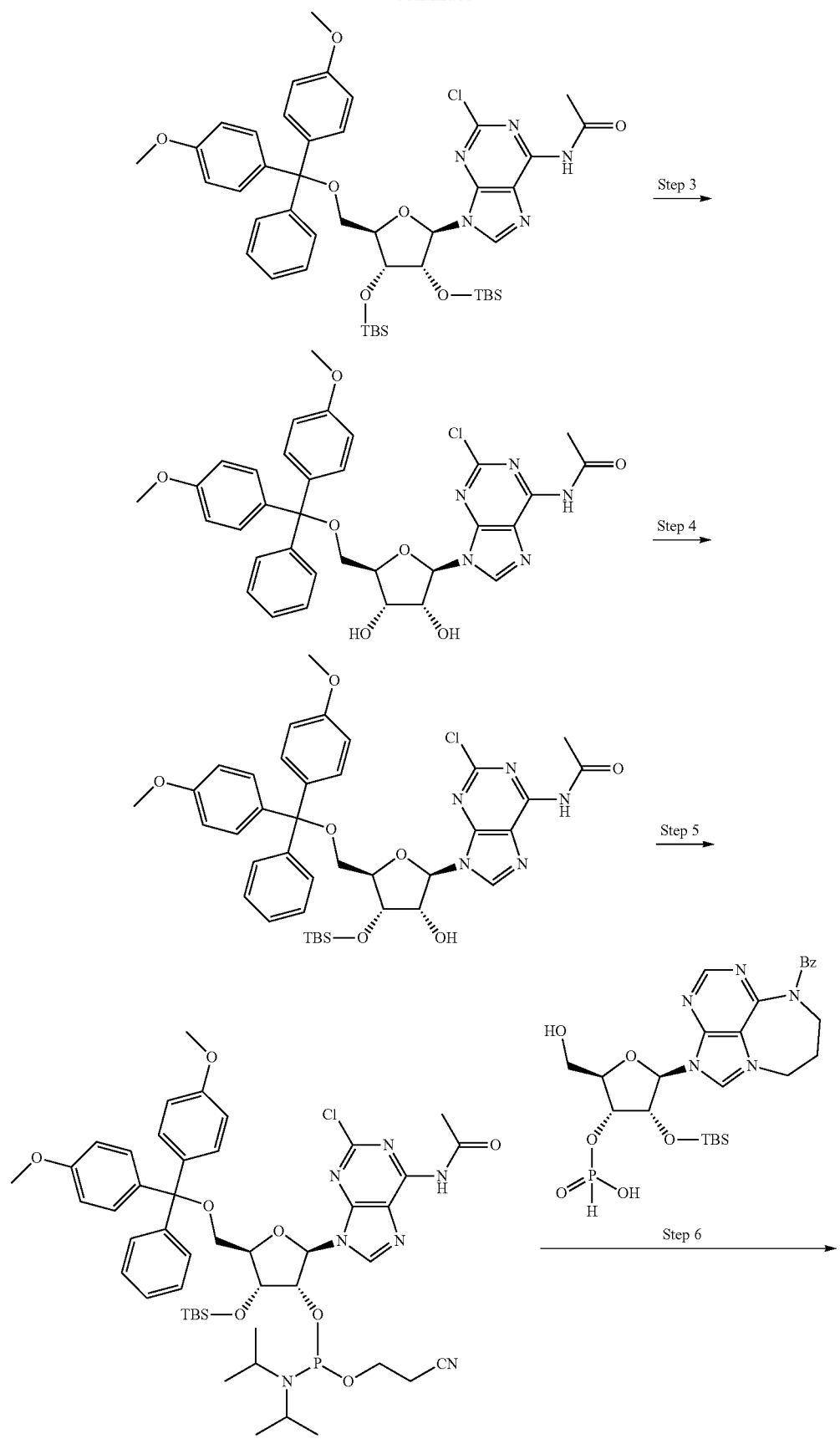

-continued

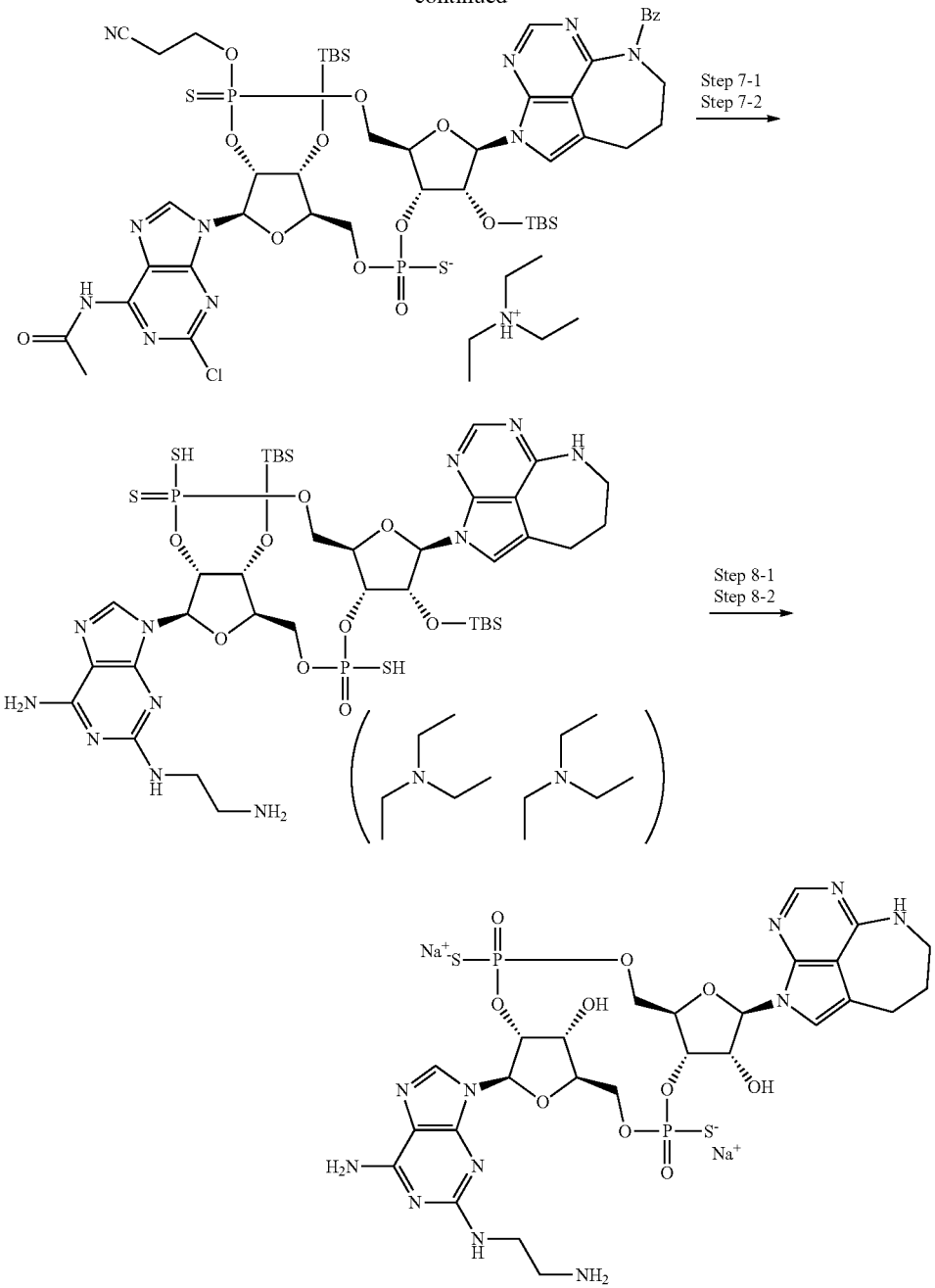

(Step 1)

5'-O-[Bis(4-methoxyphenyl)(phenyl)methyl]-2',3'-bis-O-[tert-butyl(dimethyl)silyl]-2-chloroadenosine To a solution of 5'-O-[bis(4-methoxyphenyl)(phenyl)methyl]-2-chloroadenosine (29.1 g) as a compound known in the literature (J. Med. Chem. 1989, 32, 1135-1140) in N,N-dimethylformamide (145 mL), imidazole (16.4 g) and tert-butyldimethylchlorosilane (18.2 g) were added, and the reaction mixture was stirred at room temperature for 18 hours. After water was added to the reaction mixture to quench the reaction, the resultant was subjected to extraction with ethyl acetate. The organic layer was washed with brine, and then dried over anhydrous sodium sulfate. The drying agent was removed through filtration, and the filtrate was concentrated under reduced pressure. The residue was purified by silica gel column chromatography [hexane/ethyl acetate/0.1% triethylamine] to afford the title compound (34.9 g).

MS(ESI)m/z: 832 (M+H)$^+$.

$^1$H-NMR (CDCl$_3$) δ: 8.02 (1H, s), 7.47-7.42 (2H, m), 7.36-7.32 (4H, m), 7.31-7.18 (3H, m), 6.84-6.79 (4H, m), 5.90 (1H, d, J=4.8 Hz), 5.72 (2H, brs), 4.74 (1H, dd, J=4.5, 2.3 Hz), 4.25 (1H, dd, J=4.2, 2.3 Hz), 4.21 (1H, q, J=4.2 Hz), 3.78 (6H, s), 3.58 (1H, dd, J=10.9, 4.2 Hz), 3.33 (1H, dd, J=10.9, 4.2 Hz), 0.84 (9H, s), 0.82 (9H, s), 0.04 (3H, s), −0.01 (3H, s), −0.02 (3H, s), −0.17 (3H, s).

(Step 2)

N-Acetyl-5'-O-[bis(4-methoxyphenyl)(phenyl)methyl]-2',3'-bis-O-[tert-butyl(dimethyl)silyl]-2-chloroadenosine To a solution of the compound obtained in step 1 (34.9 g) in pyridine (210 mL), acetic anhydride (140 mL) and 4-dimethylaminopyridine (515 mg) were added, and the reaction mixture was stirred under the nitrogen atmosphere at room temperature for 21 hours. After the reaction mixture was diluted with dichloromethane (100 mL), a saturated aqueous solution of sodium hydrogen carbonate was added thereto, and the reaction mixture was subjected to extraction with dichloromethane. After the organic layer was dried over anhydrous sodium sulfate, the drying agent was removed through filtration, and the filtrate was concentrated under reduced pressure. Dichloromethane (210 mL) and morpholine (7.30 mL) were added to the residue, and the resultant was stirred at room temperature for 1 hour. A saturated aqueous solution of ammonium chloride was added to the reaction mixture, which was subjected to extraction with dichloromethane. After the organic layer was dried over anhydrous sodium sulfate, the drying agent was removed through filtration, and the filtrate was concentrated under reduced pressure. The residue was purified by silica gel column chromatography [hexane/ethyl acetate/0.1% triethylamine] to afford the title compound (45.4 g: with impurities). The compound obtained was directly used for the subsequent reaction, without additional purification.

$^1$H-NMR (CDCl$_3$) δ: 8.95 (1H, brs), 8.22 (1H, s), 7.45-7.42 (2H, m), 7.34-7.20 (7H, m), 6.82 (4H, dq, J=9.4, 2.7 Hz), 5.96 (1H, d, J=4.8 Hz), 4.72-4.69 (1H, m), 4.23 (2H, brs), 3.79 (6H, S), 3.59 (1H, dd, J=10.9, 3.6 Hz), 3.35 (1H, dd, J=10.3, 3.6 Hz), 2.73 (3H, s), 0.83 (9H, s), 0.82 (9H, s), 0.04 (3H, s), 0.00 (3H, s), −0.03 (3H, s), −0.18 (3H, s).

(Step 3)

N-Acetyl-5'-O-[bis(4-methoxyphenyl)(phenyl)methyl]-2-chloroadenosine

To a solution of the compound obtained in step 2 (45.4 g: with impurities) in tetrahydrofuran (200 mL), a tetrahydrofuran solution of tetrabutylammonium fluoride (approximately 1.0 M, 100 mL) was added, and the reaction mixture was stirred under the nitrogen atmosphere at room temperature for 3 hours. A saturated aqueous solution of ammonium chloride was added to the reaction mixture, which was subjected to extraction with dichloromethane. After the organic layer was dried over anhydrous sodium sulfate, the drying agent was removed through filtration, and the filtrate was concentrated under reduced pressure. The residue was purified by silica gel column chromatography [dichloromethane/acetone/0.1% triethylamine] to afford the title compound (23.0 g). $^1$H-NMR (CDCl$_3$) δ: 8.71 (1H, brs), 8.16 (1H, s), 7.28-7.16 (9H, m), 6.78-6.73 (4H, m), 5.99 (1H, d, J=5.4 Hz), 4.86 (1H, t, J=5.1 Hz), 4.49 (1H, dd, J=5.1, 2.7 Hz), 4.39 (1H, q, J=3.2 Hz), 3.78 (3H, s), 3.77 (3H, s), 3.42 (1H, dd, J=10.9, 3.6 Hz), 3.35 (1H, dd, J=10.6, 3.3 Hz), 2.66 (3H, s).

(Step 4)

N-Acetyl-5'-O-[bis(4-methoxyphenyl)(phenyl)methyl]-3'-O-[tert-butyl(dimethyl)silyl]-2-chloroadenosine To a solution of the compound obtained in step 3 (23.0 g) in N,N-dimethylformamide (178 mL), imidazole (5.94 g) and tert-butyldimethylchlorosilane (6.44 g) were added, and the reaction mixture was stirred under the nitrogen atmosphere at room temperature for 18 hours. A saturated aqueous solution of sodium hydrogen carbonate was added to the reaction mixture, which was subjected to extraction with dichloromethane. After the organic layer was dried over anhydrous sodium sulfate, the drying agent was removed through filtration, and the filtrate was concentrated under reduced pressure. The residue was purified by silica gel column chromatography [hexane/ethyl acetate/0.1% triethylamine] to afford the title compound (9.01 g).

$^1$H-NMR (CDCl$_3$) δ: 8.42 (1H, brs), 8.14 (1H, s), 7.38-7.35 (2H, m), 7.29-7.18 (7H, m), 6.80-6.76 (4H, m), 5.99 (1H, d, J=4.2 Hz), 4.71-4.66 (2H, m), 4.17-4.14 (1H, m), 3.78 (6H, s), 3.49 (1H, dd, J=10.6, 3.3 Hz), 3.29 (1H, dd, J=10.9, 4.2 Hz), 3.02 (1H, d, J=5.4 Hz), 2.67 (3H, s), 0.89 (9H, s), 0.11 (3H, s), 0.02 (3H, s).

(Step 5)

N-Acetyl-5'-O-[bis(4-methoxyphenyl)(phenyl)methyl]-3'-O-[tert-butyl(dimethyl)silyl]-2-chloro-2'-O-{(2-cyanoethoxy)[di(propan-2-yl)amino]phosphanyl}adenosine With use of the compound obtained in step 4 (9.01 g), the reaction was performed in the same manner as in step 6 of Example 1 to afford the title compound (10.6 g) as a mixture of diastereomers at the phosphorus atom (diastereomer ratio=65:35). 1H-NMR (CDCl$_3$) δ: 8.40 (1H, brs), 8.31 (0.35H, s), 8.25 (0.65H, s), 7.38 (2H, d, J=7.3 Hz), 7.29-7.19 (7H, m), 6.80 (4H, dd, J=9.1, 2.4 Hz), 6.27 (0.35H, d, J=3.0 Hz), 6.13 (0.65H, d, J=3.6 Hz), 4.88-4.83 (0.65H, m), 4.69-4.65 (0.35H, m), 4.56 (1H, t, J=4.8 Hz), 4.23-4.17 (1H, m), 3.93-3.78 (1H, m), 3.78 (6H, s), 3.64-3.54 (4H, m), 3.33-3.28 (1H, m), 2.67 (3H, s), 2.56 (1.3H, t, J=6.3 Hz), 2.52 (0.7H, t, J=6.3 Hz), 1.16 (2.1H, d, J=7.3 Hz), 1.14 (3.9H, d, J=6.0 Hz), 1.12 (3.9H, d, J=6.0 Hz), 1.02 (2.1H, d, J=6.7 Hz), 0.83 (5.9H, s), 0.82 (3.1H, s), 0.10 (1.9H, s), 0.07 (1.1H, s), 0.01H (3H, s).

(Step 6)

N,N-Diethylethaneaminium (5R,7R,8R,12aR,14R,15R,15aR,16R)-7-(6-acetamido-2-chloro-9H-purin-9-yl)-14-(6-benzoyl-6,7,8,9-tetrahydro-2H-2,3,5,6-tetraazabenzo[cd]azulen-2-yl)-15,16-bis{[tert-butyl(dimethyl)silyl]oxy}-10-(2-cyanoethoxy)-2-oxo-10-sulfanylideneoctahydro-2H,10H,12H-5,8-methano-2λ$^5$,10λ$^5$-furo[3,2-l][1,3,6,9,11,2,10]pentaoxadiphosphacyclotetradecine-2-thiolate The same reaction as in step 7 of Example 1 was performed in the following scale (raw material: 2.06 g). With use of an acetonitrile solution of the compound obtained and the compound obtained in step 5 (1.98 g), the reaction was performed in the same manner as in step 8 of Example 1 and step 9 of Example 1 to afford diastereomer 1 (180 mg) and diastereomer 2 (167 mg: with impurities) of the title compound.

Diastereomer 1 (Less Polar)

MS(ESI)m/z: 1191 (M+H)$^+$.

$^1$H-NMR (CD$_3$OD) δ: 9.10 (1H, s), 8.00 (1H, s), 7.40-7.36 (2H, m), 7.30-7.23 (4H, m), 6.38 (1H, d, J=8.5 Hz), 6.35 (1H, d, J=3.0 Hz), 5.67-5.60 (1H, m), 5.09-5.04 (1H, m), 4.72 (1H, d, J=3.6 Hz), 4.50-4.29 (8H, m), 4.07 (1H, dd, J=12.4, 4.5 Hz), 3.91-3.83 (1H, m), 3.54-3.45 (1H, m), 3.17 (6H, q, J=7.3 Hz), 3.08 (2H, t, J=6.0 Hz), 2.45-2.42 (2H, m), 2.42 (3H, s), 2.28-2.23 (2H, m), 1.29 (9H, t, J=7.3 Hz), 1.01 (9H, s), 0.90 (9H, s), 0.29 (3H, s), 0.28 (3H, s), 0.25 (3H, s), 0.10 (3H, s).

Diastereomer 2 (More Polar)

MS(ESI)m/z: 1191 (M+H)$^+$.

(Step 7-1)

(5R,7R,8R,12aR,14R,15R,15aR,16R)-7-{6-Amino-2-[(2-aminoethyl)amino]-9H-purin-9-yl}-15,16-bis{[tert-butyl(dimethyl)silyl]oxy}-2,10-bis(sulfanyl)-14-(6,7,8,9-tetrahydro-2H-2,3,5,6-tetraazabenzo[cd]azulen-2-yl)octahydro-2H,10H,12H-5,8-methano-2$\lambda^5$,10$\lambda^5$-furo[3,2-1][1,3,6,9,11,2,10]pentaoxadiphosphacyclotetradecine-2,10-dione To a solution of the compound obtained in step 6 (diastereomer 1) (49.6 mg) in methanol (1.28 mL), ethylenediamine (256 μL) was added, and the reaction mixture was stirred at 60° C. for 2 hours, and then reacted by using a microwave reactor at 120° C. for 2 hours. The resultant was purified by preparative HPLC [10 mM aqueous solution of triethylammonium acetate/acetonitrile, acetonitrile: 40%-70% (0 min-30 min)] to afford the title compound (37.2 mg).

MS(ESI)m/z: 1016 (M+H)$^+$.

$^1$H-NMR (CD$_3$OD) δ: 8.27 (1H, s), 7.99 (1H, s), 7.16 (1H, s), 6.25 (1H, d, J=4.2 Hz), 6.09 (1H, d, J=8.5 Hz), 5.41-5.35 (1H, m), 5.12-5.08 (1H, m), 4.86-4.80 (2H, m), 4.69 (1H, t, J=4.5 Hz), 4.51-4.45 (1H, m), 4.29-4.23 (2H, m), 4.11-4.03 (2H, m), 3.51-3.44 (4H, m), 3.13-3.04 (2H, m), 2.80-2.76 (2H, m), 2.02-1.92 (2H, m), 0.99 (9H, s), 0.84 (9H, s), 0.32 (3H, s), 0.29 (3H, s), 0.24 (3H, s), 0.07 (3H, s).

(Step 7-2)

Bis(N,N-diethylethaneaminium) (5R,7R,8R,12aR,14R,15R,15aR,16R)-7-{6-amino-2-[(2-aminoethyl)amino]-9H-purin-9-yl}-15,16-bis{[tert-butyl(dimethyl)silyl]oxy}-2,10-dioxo-14-(6,7,8,9-tetrahydro-2H-2,3,5,6-tetraazabenzo[cd]azulen-2-yl)octahydro-2H,10H,12H-5,8-methano-2$\lambda^5$,10$\lambda^5$-furo[3,2-1][1,3,6,9,11,2,10]pentaoxadiphosphacyclotetradecine-2,10-bis(thiolate)

To a solution of the compound obtained in step 6 (diastereomer 2) (50.0 mg: with impurities) in methanol (1.29 mL), ethylenediamine (25.8 μL) was added, and the reaction mixture was stirred at 60° C. for 2 hours, and then reacted by using a microwave reactor at 120° C. for 2 hours. The resultant was purified by preparative HPLC [10 mM aqueous solution of triethylammonium acetate/acetonitrile, acetonitrile: 30%-50% (0 min-30 min)] to afford the title compound (23.7 mg).

MS(ESI)m/z: 1016 (M+H)$^+$.

$^1$H-NMR (CD$_3$OD) δ: 8.16 (1H, s), 8.00 (1H, s), 7.08 (1H, s), 6.33 (1H, d, J=7.3 Hz), 6.13 (1H, d, J=8.5 Hz), 5.51-5.48 (1H, m), 5.30 (1H, t, J=4.8 Hz), 5.13-5.06 (1H, m), 4.95 (1H, d, J=4.2 Hz), 4.66-4.55 (2H, m), 4.24 (1H, s), 4.08 (1H, dd, J=12.4, 4.5 Hz), 3.89-3.83 (1H, m), 3.69-3.61 (1H, m), 3.50-3.33 (4H, m), 3.12-3.01 (14H, m), 2.89 (2H, t, J=5.4 Hz), 2.03-1.96 (2H, m), 1.25 (18H, t, J=7.3 Hz), 0.99 (9H, s), 0.74 (9H, s), 0.27 (6H, s), 0.18 (3H, s), −0.08 (3H, s).

(Step 8-1)

Disodium (5R,7R,8R,12aR,14R,15R,15aS,16R)-7-{6-amino-2-[(2-aminoethyl)amino]-9H-purin-9-yl}-15,16-dihydroxy-2,10-dioxo-14-(6,7,8,9-tetrahydro-2H-2,3,5,6-tetraazabenzo[cd]azulen-2-yl)octahydro-2H,10H,12H-5,8-methano-2$\lambda^5$,10$\lambda^5$-furo[3,2-1][1,3,6,9,11,2,10]pentaoxadiphosphacyclotetradecine-2,10-bis(thiolate)

(Diastereomer 1)

With use of the compound obtained in step 7-1 (37.2 mg), the reaction was performed in the same manner as in step 11 of Example 1, and the resultant was then purified by preparative HPLC [10 mM aqueous solution of triethylammonium acetate/acetonitrile, acetonitrile: 2%-20% (0 min-30 min)] to afford the title compound as a triethylamine salt.

The triethylamine salt obtained was subjected to salt exchange in the same manner as in [Conversion to Sodium Salt] described in step 11 of Example 1 to afford the title compound (16.5 mg).

MS(ESI)m/z: 788 (M+H)$^+$.

$^1$H-NMR (CD$_3$OD) δ: 8.21 (1H, brs), 8.01 (1H, s), 7.07 (1H, s), 6.27 (1H, d, J=3.6 Hz), 6.10 (1H, d, J=8.5 Hz), 5.51-5.41 (1H, m), 5.16-5.11 (1H, m), 4.83 (1H, d, J=3.6 Hz), 4.73 (1H, t, J=4.2 Hz), 4.50-4.45 (2H, m), 4.35-4.29 (2H, m), 4.16-4.04 (2H, m), 3.50-3.42 (4H, m), 3.17-3.05 (2H, m), 2.82-2.66 (2H, m), 2.04-1.92 (2H, m).

$^{31}$P-NMR (CD$_3$OD) δ: 57.9 (s), 54.2 (s).

(Step 8-2)

Disodium (5R,7R,8R,12aR,14R,15R,15aS,16R)-7-{6-amino-2-[(2-aminoethyl)amino]-9H-purin-9-yl}-15,16-dihydroxy-2,10-dioxo-14-(6,7,8,9-tetrahydro-2H-2,3,5,6-tetraazabenzo[cd]azulen-2-yl)octahydro-2H,10H,12H-5,8-methano-2$\lambda^5$,10$\lambda^5$-furo[3,2-1][1,3,6,9,11,2,10]pentaoxadiphosphacyclotetradecine-2,10-bis(thiolate)

(Diastereomer 2)

With use of the compound obtained in step 7-2 (23.7 mg), the reaction was performed in the same manner as in step 11 of Example 1, and the resultant was then purified by preparative HPLC [10 mM aqueous solution of triethylammonium acetate/acetonitrile, acetonitrile: 2%-20% (0 min-30 min)] to afford the title compound as a triethylamine salt.

The triethylamine salt obtained was subjected to salt exchange in the same manner as in [Conversion to Sodium Salt] described in step 11 of Example 1 to afford the title compound (14.9 mg).

MS(ESI)m/z: 788 (M+H)$^+$.

$^1$H-NMR (CD$_3$OD) δ: 8.27 (1H, brs), 8.02 (1H, s), 7.15 (1H, s), 6.31 (1H, d, J=6.0 Hz), 6.12 (1H, d, J=8.5 Hz), 5.45-5.33 (2H, m), 4.75 (1H, dd, J=5.7, 4.5 Hz), 4.50 (1H, d, J=4.2 Hz), 4.47-4.30 (4H, m), 4.17-4.13 (1H, brm), 3.94-3.89 (1H, m), 3.69-3.59 (1H, brm), 3.51-3.44 (3H, m), 3.21-3.07 (2H, m), 2.88-2.85 (2H, m), 2.03-1.97 (2H, m).

$^{31}$P-NMR (CD$_3$OD) δ: 62.2 (s), 59.8 (s).

Example 9: Synthesis of CDN9
(5R,7R,8R,12aR,14R,15R,15aS,16R)-7-{6-Amino-2-[(2-hydroxyethyl)amino]-9H-purin-9-yl}-15,16-dihydroxy-2,10-bis(sulfanyl)-14-(6,7,8,9-tetrahydro-2H-2,3,5,6-tetraazabenzo[cd]azulen-2-yl)octahydro-2H,10H,12H-5,8-methano-2λ$^5$,10λ$^5$-furo[3,2-1][1,3,6,9,11,2,10]pentaoxadiphosphacyclotetradecine-2,10-dione
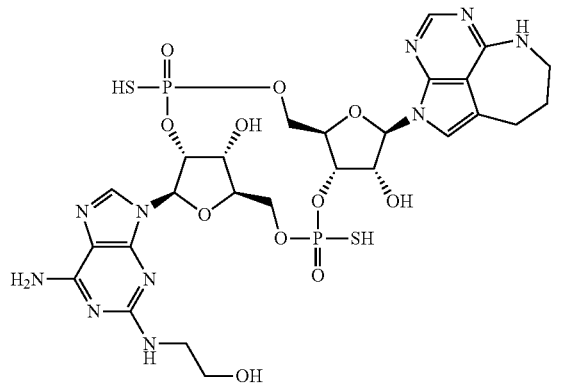
9a (Diastereomer 1)
9b (Diastereomer 2)
[Synthesis Scheme]
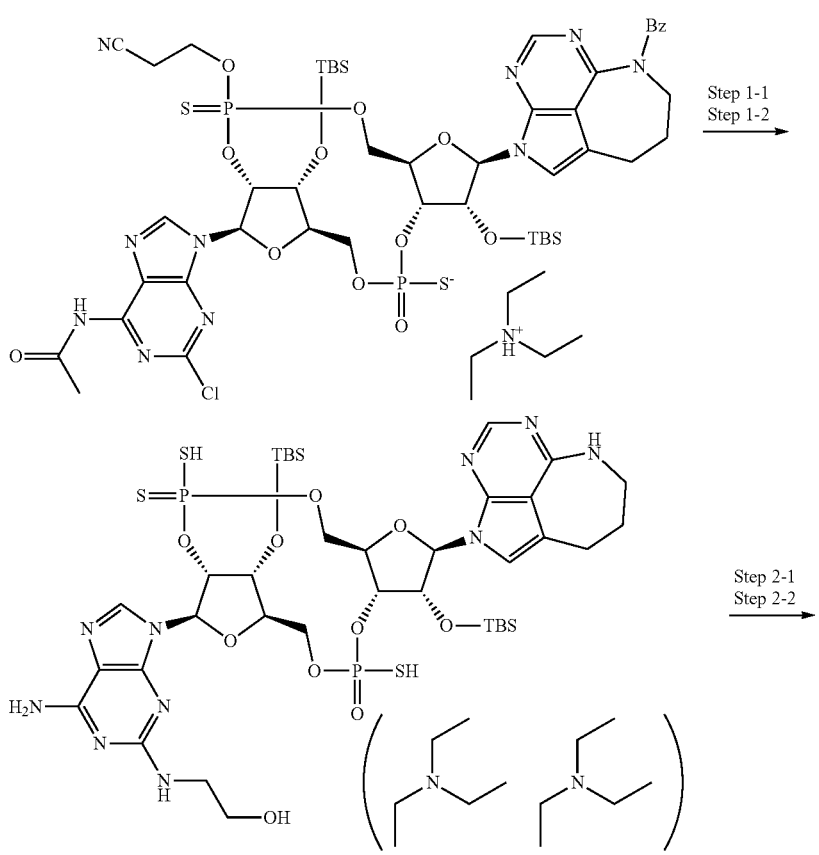
Step 1-1
Step 1-2
Step 2-1
Step 2-2

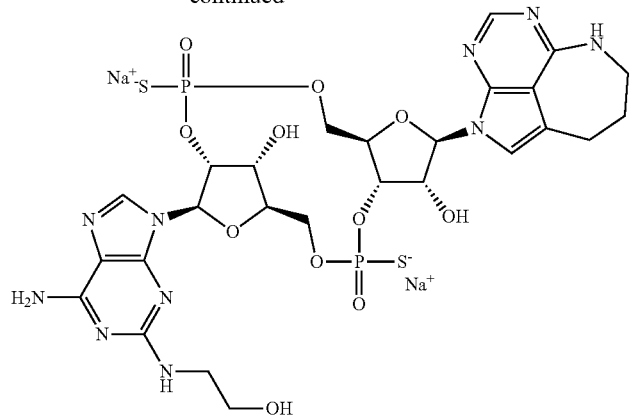

(Step 1-1)

(5R,7R,8R,12aR,14R,15R,15aR,16R)-7-{6-Amino-2-[(2-hydroxyethyl)amino]-9H-purin-9-yl}-15,16-bis{[tert-butyl(dimethyl)silyl]oxy}-2,10-bis(sulfanyl)-14-(6,7,8,9-tetrahydro-2H-2,3,5,6-tetraazabenzo[cd]azulen-2-yl)octahydro-2H,10H,12H-5,8-methano-2λ$^5$,10λ$^5$-furo[3,2-l][1,3,6,9,11,2,10]pentaoxadiphosphacyclotetradecine-2,10-dione To a solution of the compound obtained in step 6 of Example 8 (diastereomer 1) (50.1 mg) in methanol (1.29 mL), 2-aminoethanol (258 µL) was added, and the reaction mixture was stirred at 60° C. for 2 hours, and then reacted by using a microwave reactor at 120° C. for 2 hours. The resultant was purified by preparative HPLC [10 mM solution of triethylammonium acetate/acetonitrile, acetonitrile: 20%-60% (0 min-30 min)] to afford the title compound (39.4 mg) as a mixture containing a compound derived from ethanolamine.

MS(ESI)m/z: 1017 (M+H)$^+$.

$^1$H-NMR (CD$_3$OD) δ: 8.32 (1H, s), 8.01 (1H, s), 7.16 (1H, s), 6.28 (1H, d, J=5.4 Hz), 6.13 (1H, d, J=9.1 Hz), 5.44-5.38 (1H, m), 5.19-5.14 (1H, m), 4.98-4.83 (2H, m), 4.78-4.75 (1H, m), 4.45-4.39 (1H, m), 4.28-4.22 (1H, m), 4.18 (1H, s), 4.13-4.07 (1H, m), 4.04-3.99 (1H, m), 3.67 (2H, t, J=5.4 Hz), 3.51-3.42 (4H, m), 2.86 (2H, t, J=5.4 Hz), 2.04-1.98 (2H, m), 0.98 (9H, s), 0.82 (9H, s), 0.31 (3H, s), 0.27 (3H, s), 0.22 (3H, s), 0.05 (3H, s).

(Step 1-2)

Bis(N,N-diethylethaneaminium) (5R,7R,8R,12aR,14R,15R,15aR,16R)-7-{6-amino-2-[(2-hydroxyethyl)amino]-9H-purin-9-yl}-15,16-bis{[tert-butyl(dimethyl)silyl]oxy}-2,10-dioxo-14-(6,7,8,9-tetrahydro-2H-2,3,5,6-tetraazabenzo[cd]azulen-2-yl)octahydro-2H,10H,12H-5,8-methano-2λ$^5$,10λ$^5$-furo[3,2-l][1,3,6,9,11,2,10]pentaoxadiphosphacyclotetradecine-2,10-bis(thiolate)

To a solution of the compound obtained in step 6 of Example 8 (diastereomer 2) (49.3 mg: with impurities) in methanol (1.27 mL), 2-aminoethanol (254 µL) was added, and the reaction mixture was stirred at 60° C. for 2 hours, and then reacted by using a microwave reactor at 120° C. for 3 hours. The resultant was purified by preparative HPLC [10 mM solution of triethylammonium acetate/acetonitrile, acetonitrile: 20%-60% (0 min-30 min)] to afford the title compound (26.1 mg).

MS(ESI)m/z: 1017 (M+H)$^+$.

$^1$H-NMR (CD$_3$OD) δ: 8.25 (1H, s), 8.01 (1H, s), 7.10 (1H, s), 6.36 (1H, d, J=7.3 Hz), 6.17 (1H, d, J=7.9 Hz), 5.59-5.53 (1H, m), 5.41 (1H, t, J=4.5 Hz), 5.21-5.14 (1H, m), 5.02-4.95 (2H, m), 4.70-4.61 (2H, m), 4.18 (1H, s), 4.03 (1H, dd, J=12.1, 4.8 Hz), 3.91-3.86 (1H, m), 3.75-3.69 (2H, m), 3.52-3.43 (4H, m), 3.14 (12H, q, J=7.3 Hz), 2.93-2.91 (2H, m), 2.04-1.99 (2H, m), 1.28 (18H, t, J=7.6 Hz), 0.99 (9H, s), 0.75 (9H, s), 0.27 (6H, s), 0.21 (3H, s), −0.05 (3H, s).

(Step 2-1)

Disodium (5R,7R,8R,12aR,14R,15R,15aS,16R)-7-{6-amino-2-[(2-hydroxyethyl)amino]-9H-purin-9-yl}-15,16-dihydroxy-2,10-dioxo-14-(6,7,8,9-tetrahydro-2H-2,3,5,6-tetraazabenzo[cd]azulen-2-yl)octahydro-2H, 10H,12H-5,8-methano-2λ$^5$,10λ$^5$-furo[3,2-l][1,3,6,9,11,2,10]pentaoxadiphosphacyclotetradecine-2,10-bis(thiolate)

(Diastereomer 1)

With use of the mixture obtained in step 1-1 (39.4 mg), the reaction was performed in the same manner as in step 11 of Example 1, and purification was then performed under the following [Purification Conditions] to afford the title compound as a triethylamine salt.

[Purification Conditions] preparative HPLC [10 mM aqueous solution of triethylammonium acetate/acetonitrile, acetonitrile: 2%-20% (0 min-30 min)].

The triethylamine salt obtained was subjected to salt exchange in the same manner as in [Conversion to Sodium Salt] described in step 11 of Example 1 to afford the title compound (16.8 mg).

MS(ESI)m/z: 789 (M+H)$^+$.

$^1$H-NMR (CD$_3$OD) δ: 8.25 (1H, s), 8.02 (1H, s), 7.10 (1H, s), 6.30 (1H, d, J=3.6 Hz), 6.15 (1H, d, J=8.5 Hz), 5.49-5.42 (1H, m), 5.21-5.16 (1H, m), 4.87-4.85 (1H, m), 4.77 (1H, t, J=4.2 Hz), 4.50-4.35 (3H, m), 4.31 (1H, s), 4.12-4.10 (2H, m), 3.64 (2H, t, J=5.4 Hz), 3.51-3.38 (4H, m), 2.85-2.70 (2H, m), 2.02-1.94 (2H, m).

$^{31}$P-NMR (CD$_3$OD) δ: 57.8 (s), 53.9 (s).

(Step 2-2)

Disodium (5R,7R,8R,12aR,14R,15R,15aS,16R)-7-{6-amino-2-[(2-hydroxyethyl)amino]-9H-purin-9-yl}-15,16-dihydroxy-2,10-dioxo-14-(6,7,8,9-tetrahydro-2H-2,3,5,6-tetraazabenzo[cd]azulen-2-yl)octahydro-2H,10H,12H-5,8-methano-2λ$^5$,10λ$^5$-furo[3,2-1][1,3,6,9,11,2,10]pentaoxadiphosphacyclotetradecine-2,10-bis(thiolate)

(Diastereomer 2)

With use of the compound obtained in step 1-2 (26.1 mg), the reaction was performed in the same manner as in step 11 of Example 1, and purification was then performed under the following [Purification Conditions] to afford the title compound as a triethylamine salt.

[Purification Conditions] preparative HPLC [10 mM aqueous solution of triethylammonium acetate/acetonitrile, acetonitrile: 2%-20% (0 min-30 min)].

The triethylamine salt obtained was subjected to salt exchange in the same manner as in [Conversion to Sodium Salt] described in step 11 of Example 1 to afford the title compound (18.6 mg).

MS(ESI)m/z: 789 (M+H)$^+$.

$^1$H-NMR (CD$_3$OD) δ: 8.35 (1H, s), 8.03 (1H, s), 7.17 (1H, s), 6.33 (1H, d, J=6.0 Hz), 6.16 (1H, d, J=8.5 Hz), 5.49-5.41 (2H, m), 4.80 (1H, t, J=5.4 Hz), 4.51-4.26 (5H, m), 4.07 (1H, d, J=12.7 Hz), 3.94-3.89 (1H, m), 3.67 (2H, 5, J=5.7 Hz), 3.53-3.39 (4H, m), 2.89 (2H, t, J=5.4 Hz), 2.03-1.99 (2H, m).

$^{31}$P-NMR (CD$_3$OD) δ: 62.8 (s), 60.3 (s).

Example 10: Synthesis of CDN10

(5R,7R,8R,12aR,14R,15R,15aS,16R)-7-{6-Amino-2-[(2-amino-2-methylpropyl)amino]-9H-purin-9-yl}-15,16-dihydroxy-2,10-bis(sulfanyl)-14-(6,7,8,9-tetrahydro-2H-2,3,5,6-tetraazabenzo[cd]azulen-2-yl)octahydro-2H,10H,12H-5,8-methano-2λ$^5$,10λ$^5$-furo[3,2-1][1,3,6,9,11,2,10]pentaoxadiphosphacyclotetradecine-2,10-dione

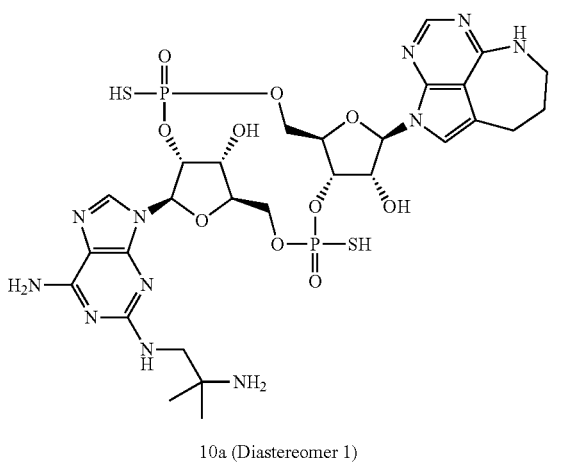

10a (Diastereomer 1)

[Synthesis Scheme]

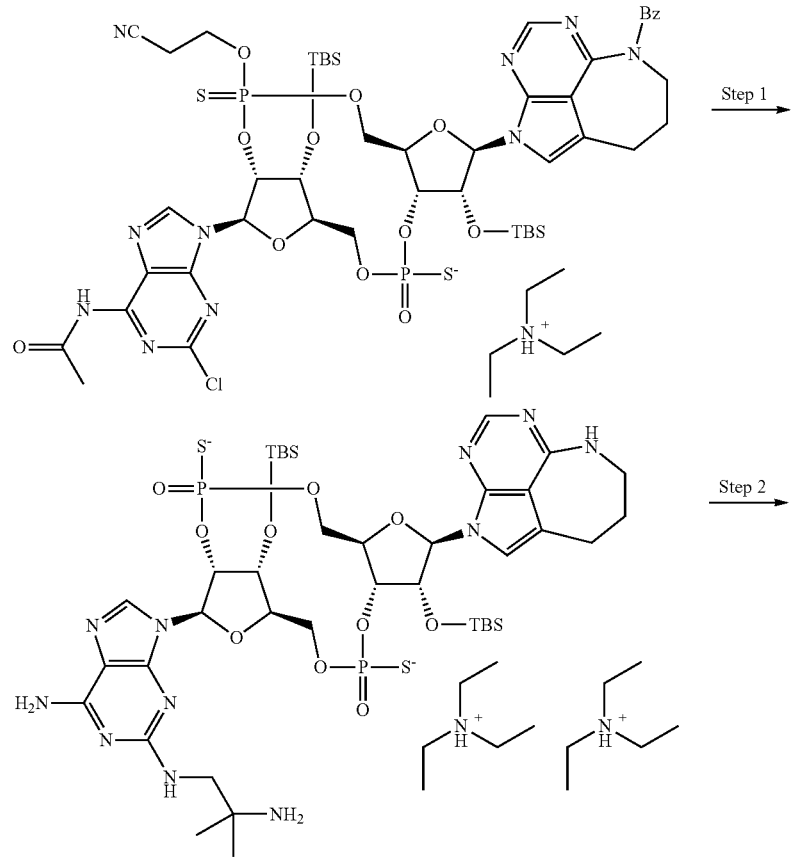

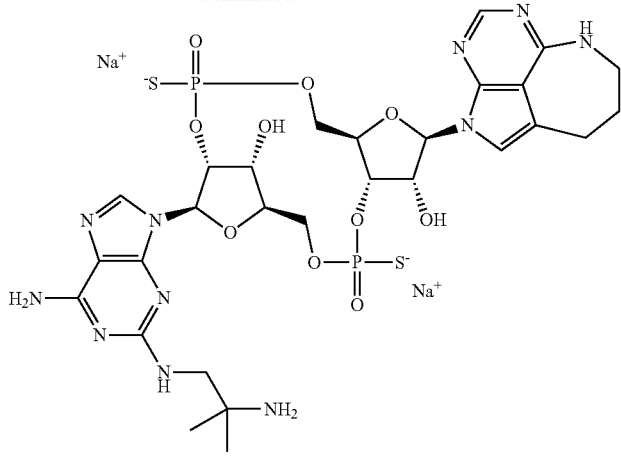

(Step 1)

Bis(N,N-diethylethaneaminium) (5R,7R,8R,12aR,14R,15R,15aR,16R)-7-{6-amino-2-[(2-amino-2-methylpropyl)amino]-9H-purin-9-yl}-15,16-bis{[tert-butyl(dimethyl)silyl]oxy}-2,10-dioxo-14-(6,7,8,9-tetrahydro-2H-2,3,5,6-tetraazabenzo[cd]azulen-2-yl)octahydro-2H,10H,12H-5,8-methano-2λ⁵,10λ⁵-furo[3,2-l][1,3,6,9,11,2,10]pentaoxadiphosphacyclotetradecine-2,10-bis(thiolate)

To a solution of the compound obtained in step 6 of Example 8 (diastereomer 1) (41.0 mg) in methanol (1.10 mL), 1,2-diamino-2-methylpropane (210 μL) was added, and the reaction mixture was stirred at 60° C. for 2 hours, and then reacted by using a microwave reactor at 120° C. for 6 hours. The resultant was simply purified by preparative HPLC [10 mM solution of triethylammonium acetate/acetonitrile, acetonitrile: 20%-60% (0 min-30 min)] to afford the title compound (16.3 mg: with impurities). The compound obtained was directly used for the subsequent reaction, without additional purification.

MS(ESI)m/z: 1044 (M+H)⁺.

(Step 2)

Disodium (5R,7R,8R,12aR,14R,15R,15aS,16R)-7-{6-amino-2-[(2-amino-2-methylpropyl)amino]-9H-purin-9-yl}-15,16-dihydroxy-2,10-dioxo-14-(6,7,8,9-tetrahydro-2H-2,3,5,6-tetraazabenzo[cd]azulen-2-yl)octahydro-2H,10H,12H-5,8-methano-2λ⁵,10λ⁵-furo[3,2-l][1,3,6,9,11,2,10]pentaoxadiphosphacyclotetradecine-2,10-bis(thiolate)

With use of the compound obtained in step 1 (16.3 mg: with impurities), the reaction was performed in the same manner as in step 11 of Example 1, and purification was then performed under the following [Purification Conditions] to afford the title compound as a triethylamine salt.

[Purification Conditions] preparative HPLC [10 mM aqueous solution of triethylammonium acetate/acetonitrile, acetonitrile: 5%-25% (0 min-30 min)].

The triethylamine salt obtained was subjected to salt exchange in the same manner as in [Conversion to Sodium Salt] described in step 11 of Example 1 to afford the title compound (6.4 mg).

MS(ESI)m/z: 816 (M+H)⁺.

¹H-NMR (CD₃OD) δ: 8.28 (1H, brs), 8.01 (1H, s), 7.05 (1H, s), 6.27 (1H, d, J=4.2 Hz), 6.15 (1H, d, J=7.9 Hz), 5.41-5.27 (1H, m), 5.13-5.08 (1H, m), 4.84 (1H, d, J=3.6 Hz), 4.73 (1H, t, J=4.5 Hz), 4.50-4.44 (2H, m), 4.36-4.31 (2H, m), 4.16-4.00 (2H, m), 3.49 (2H, dd, J=6.3, 3.3 Hz), 3.31-3.25 (2H, m), 2.84-2.70 (2H, m), 2.03-1.91 (2H, m), 1.34 (3H, s), 1.30 (3H, s).

³¹P-NMR (CD₃OD) δ: 57.9 (s), 54.5 (s).

Example 11: Synthesis of CDN11

(5R,7R,8R,12aR,14R,15R,15aS,16R)-7-[6-Amino-2-(aminomethyl)-9H-purin-9-yl]-15,16-dihydroxy-2,10-bis(sulfanyl)-14-(6,7,8,9-tetrahydro-2H-2,3,5,6-tetraazabenzo[cd]azulen-2-yl)octahydro-2H,10H,12H-5,8-methano-2λ⁵,10λ⁵-furo[3,2-l][1,3,6,9,11,2,10]pentaoxadiphosphacyclotetradecine-2,10-dione

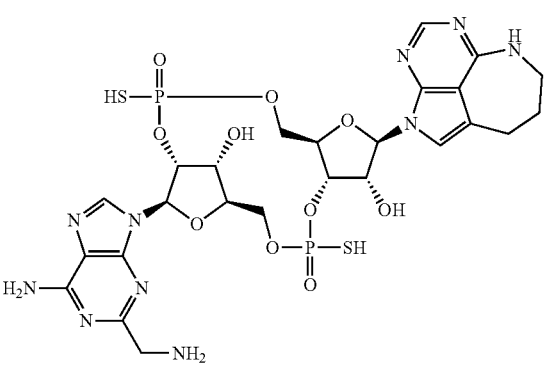

11a (Diastereomer 1)
11b (Diastereomer 2)

[Synthesis Scheme]
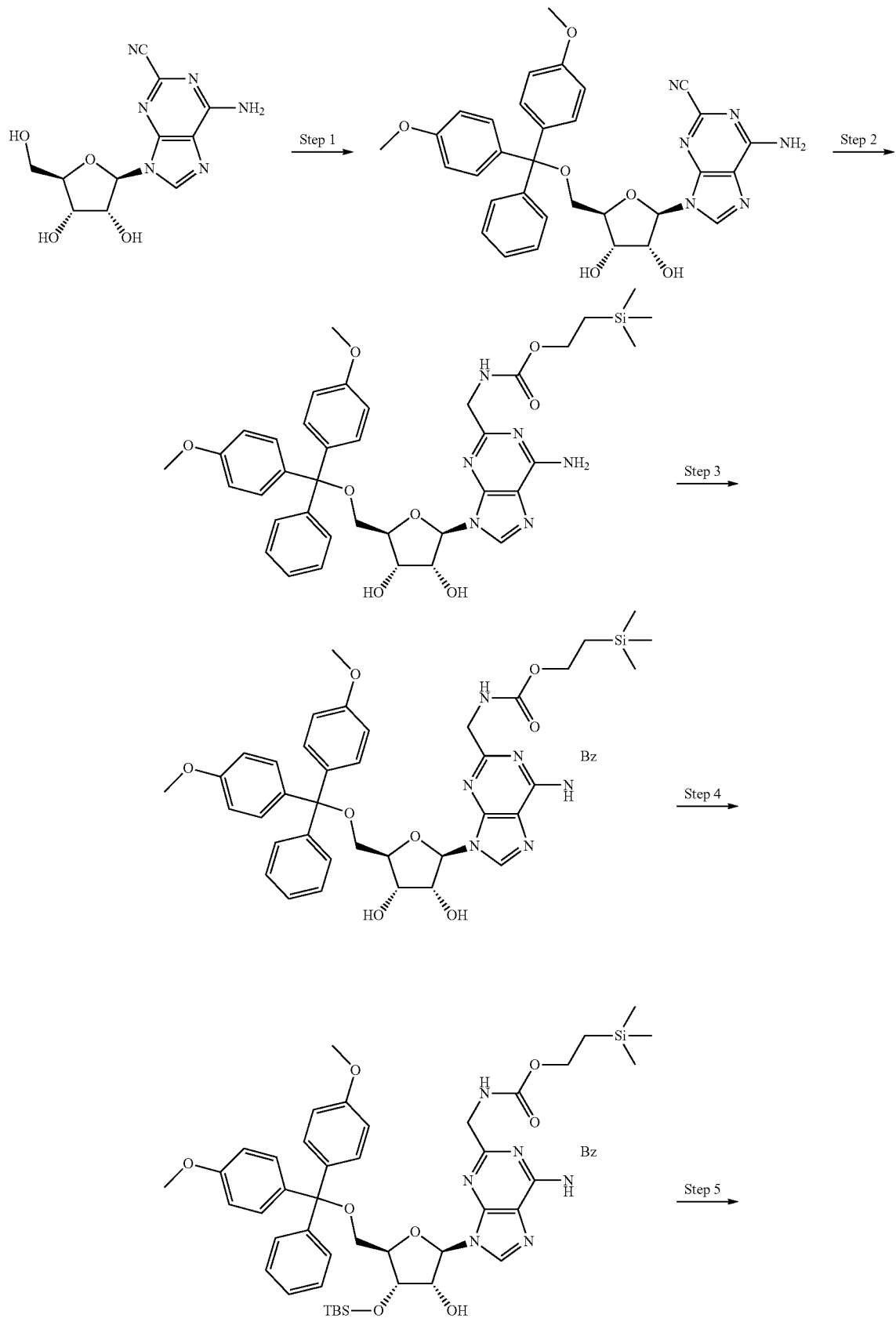

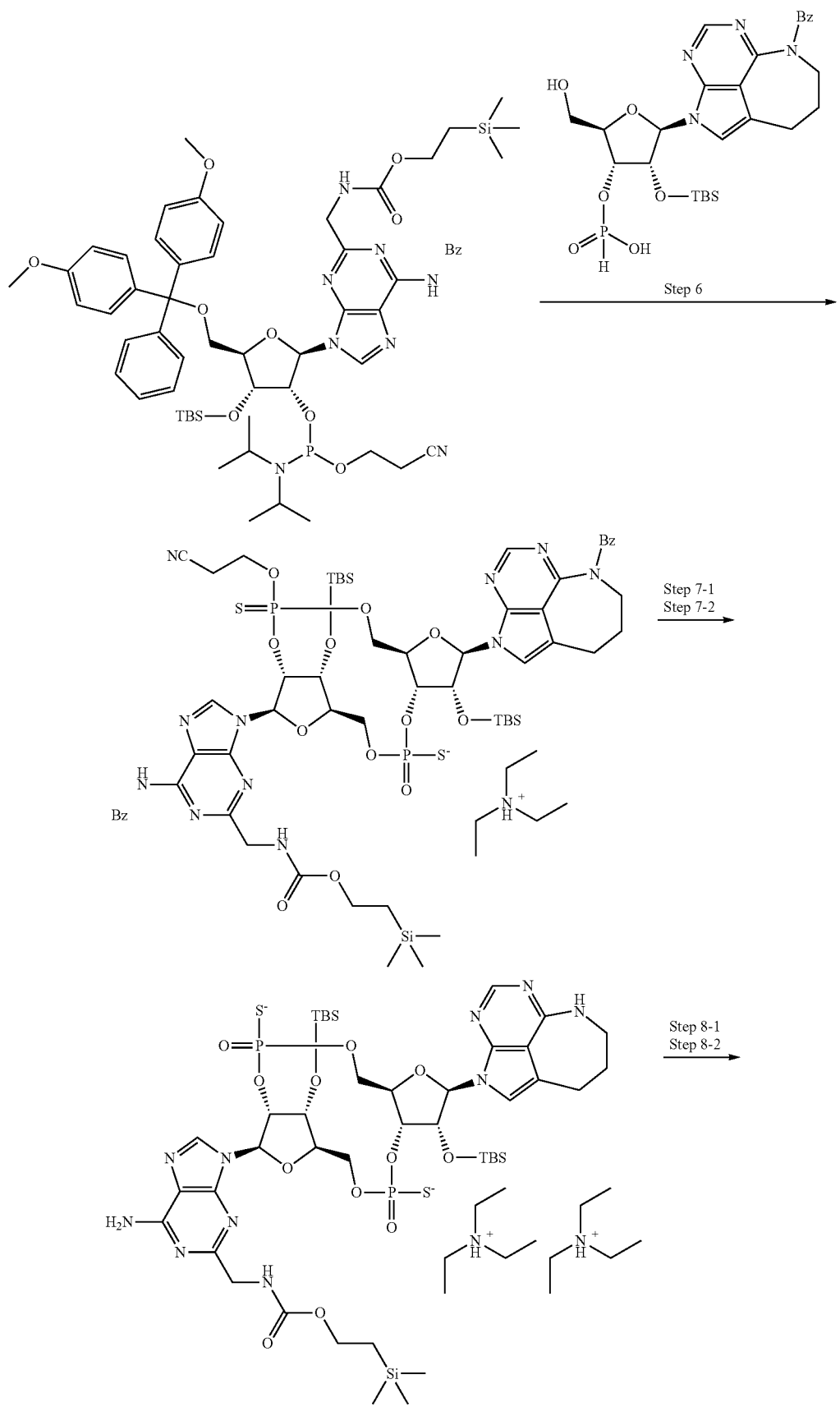

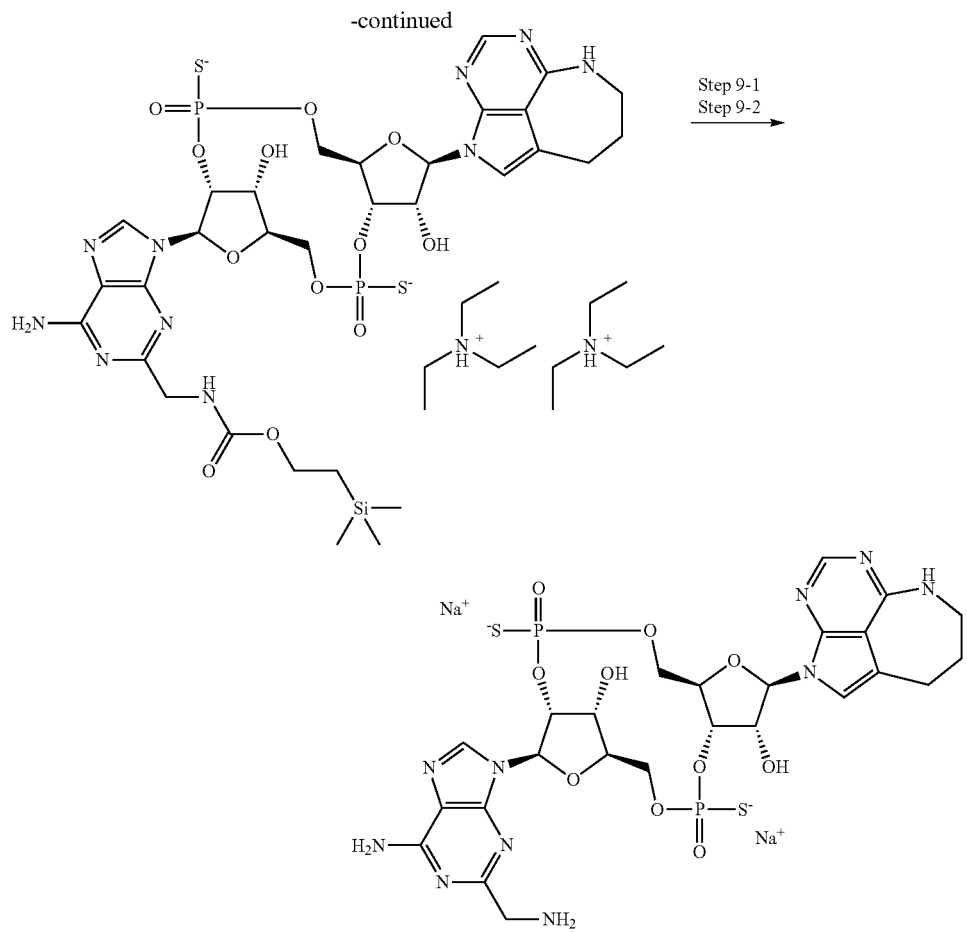

(Step 1)

5'-O-[Bis(4-methoxyphenyl)(phenyl)methyl]-2-cyanoadenosine

To a solution of 2-cyanoadenosine (440 mg) as a compound known in the literature (J. Am. Chem. Soc. 1989, 111, 8502-8504) in pyridine (8.00 mL), 4,4'-dimethoxytrityl chloride (642 mg) was added, and the reaction mixture was stirred under the nitrogen atmosphere at room temperature for 4 hours. After methanol (10 mL) was added to the reaction mixture to quench the reaction, the resultant was concentrated under reduced pressure. The residue was purified by silica gel column chromatography [hexane/ethyl acetate/methanol/0.1% triethylamine] to afford the title compound (528 mg).

$^1$H-NMR (CDCl$_3$) δ: 8.21 (1H, s), 7.31-7.17 (9H, m), 6.79-6.70 (4H, m), 5.99 (1H, d, J=5.4 Hz), 5.86 (2H, brs), 4.86 (1H, q, J=4.6 Hz), 4.65 (1H, t, J=3.6 Hz), 4.48-4.45 (1H, m), 4.41 (1H, q, J=3.0 Hz), 3.79 (6H, s), 3.46 (1H, dd, J=10.9, 3.6 Hz), 3.34 (1H, dd, J=10.6, 3.3 Hz), 2.93 (1H, d, J=2.4 Hz).

(Step 2)

5'-O-[Bis(4-methoxyphenyl)(phenyl)methyl]-2-[({[2-(trimethylsilyl)ethoxy]carbonyl}amino)methyl]adenosine To a solution of the compound obtained in step 1 (14.3 g) in tetrahydrofuran (500 mL), a tetrahydrofuran solution of lithium aluminum hydride (approximately 2.5 M, 29.0 mL) was added, and the reaction mixture was stirred under the nitrogen atmosphere at 40° C. for 2 hours. The reaction mixture was ice-cooled, to which a saturated aqueous solution of sodium hydrogen carbonate (450 mL) was added, and the reaction mixture was stirred for 10 minutes, and then 1-({[2-(trimethylsilyl)ethoxy]carbonyl}oxy) pyrrolidine-2,5-dione (25.0 g) was added thereto to react at room temperature for 18 hours. A saturated aqueous solution of the Rochelle salt was added thereto, and the reaction mixture was stirred for 2.5 hour, and then subjected to extraction with a mixture of dichloromethane/methanol. After the organic layer was dried over anhydrous sodium sulfate, the drying agent was removed through filtration, and the filtrate was concentrated under reduced pressure. The residue was purified by silica gel column chromatography [hexane/ethyl acetate/0.1% triethylamine] to afford the title compound (10.8 g).

$^1$H-NMR (CDCl$_3$) δ: 8.01 (1H, s), 7.26-7.15 (9H, m), 6.75-6.71 (4H, m), 6.37 (1H, brs), 5.93 (1H, d, J=6.0 Hz), 5.67 (2H, brs), 5.59 (1H, brs), 4.77-4.74 (1H, m), 4.46-4.37 (4H, m), 4.21 (2H, t, J=8.5 Hz), 3.76 (3H, s), 3.76 (3H, s), 3.42 (1H, dd, J=10.6, 3.3 Hz), 3.25 (1H, dd, J=10.6, 3.3 Hz), 3.16 (1H, brs), 1.03 (2H, t, J=8.5 Hz), 0.05 (9H, s).

(Step 3)

N-Benzoyl-5'-O-[bis(4-methoxyphenyl)(phenyl)methyl]-2-[({[2-(trimethylsilyl)ethoxy]carbonyl}amino)methyl]adenosine To a solution of the compound obtained in step 2 (10.8 g) in pyridine (70.0 mL), chlorotrimethylsilane (15.0 mL) was added, and the reaction mixture was stirred under the nitrogen atmosphere at room temperature for 2 hours. Benzoyl chloride (8.44 mL) was added to the reaction mixture, which was further stirred for 2 hours. The reaction mixture was cooled to 0° C. and stirred for 10 minutes with addition of water (21.0 mL), and then further stirred at the same temperature for 20 minutes with addition of 28% ammonia water (31.4 mL). The temperature was increased to room temperature and the reaction mixture was further stirred for 3 hours, and then concentrated under reduced pressure. The residue was suspended in ethyl acetate, and the solid was removed through filtration. The filtrate was concentrated under reduced pressure. The residue was purified by silica gel column chromatography [hexane/ethyl acetate/methanol/0.1% triethylamine] to afford the title compound (9.47 g).

MS(ESI)m/z: 847 (M+H)$^+$.

$^1$H-NMR (CDCl$_3$) δ: 9.54 (1H, brs), 8.17 (2H, d, J=6.7 Hz), 7.91 (1H, brs), 7.66-7.52 (3H, m), 7.35-7.10 (9H, m), 6.75 (4H, d, J=8.5 Hz), 6.45 (1H, brs), 6.23 (1H, brs), 6.03 (1H, d, J=6.7 Hz), 4.70-4.65 (2H, m), 4.45-4.19 (5H, m), 3.73 (6H, s), 3.38-3.32 (2H, m), 2.65 (1H, brs), 1.05 (2H, t, J=8.8 Hz), 0.00 (9H, s).

(Step 4)

N-Benzoyl-5'-O-[bis(4-methoxyphenyl)(phenyl)methyl]-3'-O-[tert-butyl(dimethyl)silyl]-2-[({[2-(trimethylsilyl)ethoxy]carbonyl}amino)methyl]adenosine With use of the compound obtained in step 3 (9.47 g), the reaction was performed in the same manner as in step 4 of Example 8 to afford the title compound (3.13 g).

MS(ESI)m/z: 961 (M+H)$^+$.

$^1$H-NMR (CDCl$_3$) δ: 8.87 (1H, brs), 8.24 (1H, brs), 8.02 (2H, d, J=7.3 Hz), 7.64-7.51 (3H, m), 7.40-7.18 (9H, m), 6.81-6.77 (4H, m), 6.08 (1H, d, J=4.8 Hz), 5.85 (1H, brs), 4.70-4.52 (4H, m), 4.23-4.17 (3H, m), 3.77 (6H, s), 3.50 (1H, dd, J=10.9, 3.0 Hz), 3.29 (1H, dd, J=10.9, 4.2 Hz), 3.21 (1H, d, J=6.0 Hz), 1.06-1.02 (2H, m), 0.89 (9H, s), 0.09 (3H, s), 0.05 (9H, s), 0.01 (3H, s).

(Step 5)

N-Benzoyl-5'-O-[bis(4-methoxyphenyl)(phenyl)methyl]-3'-O-[tert-butyl(dimethyl)silyl]-2'-O-{(2-cyanoethoxy)[di(propan-2-yl)amino]phosphanyl}-2-[({[2-(trimethylsilyl)ethoxy]carbonyl}amino)methyl]adenosine To a solution of the compound obtained in step 4 (1.49 g) in dichloromethane (15.5 mL), N,N-diisopropylethylamine (1.58 mL) and 2-cyanoethyl N,N-diisopropylchlorophosphoramidite (1.04 mL) were added, and the reaction mixture was stirred under the nitrogen atmosphere at room temperature for 2 hours. The reaction mixture was concentrated under reduced pressure, and the residue was purified by silica gel column chromatography [hexane/ethyl acetate/0.1% triethylamine] and C18 silica gel column chromatography [acetonitrile: 100%] to afford the title compound (1.39 g) as a mixture of diastereomers at the phosphorus atom (diastereomer ratio=6:4).

$^1$H-NMR (CDCl$_3$) δ8.84 (1H, s), 8.33 (0.6H, s), 8.28 (0.4H, s), 8.02-7.99 (2H, m), 7.64-7.59 (1H, m), 7.55-7.51 (2H, m), 7.42-7.20 (9H, m), 6.82-6.79 (4H, m), 6.30 (0.4H, d, J=4.2 Hz), 6.25 (0.6H, d, J=4.2 Hz), 5.95-5.88 (1H, m), 4.89-4.77 (1H, m), 4.60-4.58 (2H, m), 4.51-4.45 (1H, m), 4.25-4.18 (3H, m), 3.86-3.46 (5H, m), 3.78 (6H, s), 3.35-3.29 (1H, m), 2.53 (1.2H, t, J=6.3 Hz), 2.38 (0.8H, t, J=6.3 Hz), 1.16-0.98 (14H, m), 0.85 (3.6H, s), 0.84 (5.4H, s), 0.10 (1.8H, s), 0.08 (1.2H, s), 0.05 (9H, s), 0.01 (1.2H, s), −0.01 (1.8H, s).

(Step 6)

N,N-Diethylethaneaminium (5R,7R,8R,12aR,14R,15R,15aR,16R)-7-{6-benzamido-2-[({[2-(trimethylsilyl)ethoxy]carbonyl}amino)methyl]-9H-purin-9-yl}-14-(6-benzoyl-6,7,8,9-tetrahydro-2H-2,3,5,6-tetraazabenzo[cd]azulen-2-yl)-15,16-bis{[tert-butyl(dimethyl)silyl]oxy}-10-(2-cyanoethoxy)-2-oxo-10-sulfanylideneoctahydro-2H,10H,12H-5,8-methano-2λ$^5$,10λ$^5$-furo[3,2-1][1,3,6,9,11,2,10]pentaoxadiphosphacyclotetradecine-2-thiolate The same reaction as in step 7 of Example 1 was performed in the following scale (raw material: 1.94 g). With use of an acetonitrile solution of the compound obtained and the compound obtained in step 5 (2.19 g), the reaction was performed in the same manner as in step 8 of Example 1 and step 9 of Example 1 to afford diastereomer 1 (138 mg) and diastereomer 2 (82.8 mg) of the title compound.

Diastereomer 1 (Less Polar)

$^1$H-NMR (CD$_3$OD) δ: 9.08 (1H, s), 8.11 (2H, d, J=7.3 Hz), 7.98 (1H, s), 7.67 (1H, t, J=7.6 Hz), 7.57 (2H, t, J=7.9 Hz), 7.37 (2H, d, J=7.9 Hz), 7.28-7.22 (4H, m), 6.54 (1H, d, J=8.5 Hz), 6.36 (1H, d, J=1.8 Hz), 5.66-5.59 (1H, m), 5.07-5.02 (1H, m), 4.85-4.83 (1H, m), 4.72 (1H, d, J=3.6 Hz), 4.58-4.08 (12H, m), 3.88-3.78 (1H, m), 3.49-3.38 (1H, m), 3.21 (6H, q, J=7.3 Hz), 3.05-3.00 (2H, m), 2.49-2.40 (1H, m), 2.34-2.26 (1H, m), 2.09-2.03 (2H, m), 1.31 (9H, t, J=7.6 Hz), 1.21-1.09 (2H, m), 1.02 (9H, s), 0.91 (9H, s), 0.30 (3H, s), 0.29 (3H, s), 0.26 (3H, s), 0.12 (3H, s), 0.05 (9H, s).

Diastereomer 2 (More Polar)

MS(ESI)m/z: 1392 (M+H)$^+$.

$^1$H-NMR (CD$_3$OD) δ: 8.91 (1H, s), 8.10-8.07 (2H, m), 7.94 (1H, s), 7.67-7.63 (1H, m), 7.59-7.54 (2H, m), 7.41-7.20 (6H, m), 6.54 (1H, d, J=8.5 Hz), 6.22 (1H, d, J=5.4 Hz), 5.36-5.30 (1H, m), 3.20 (6H, q, J=7.3 Hz), 3.04-3.00 (2H, m), 2.85-2.75 (2H, m), 2.23-2.13 (2H, m), 1.30 (9H, t, J=7.3 Hz), 1.03 (9H, s), 0.79 (9H, s), 0.05 (9H, s). (only observable peaks are shown)

(Step 7-1)

Bis(N,N-diethylethaneaminium) (5R,7R,8R,12aR,14R,15R,15aR,16R)-7-{6-amino-2-[({[2-(trimethylsilyl)ethoxy]carbonyl}amino)methyl]-9H-purin-9-yl}-15,16-bis{[tert-butyl(dimethyl)silyl]oxy}-2,10-dioxo-14-(6,7,8,9-tetrahydro-2H-2,3,5,6-tetraazabenzo[cd]azulen-2-yl)octahydro-2H,10H,12H-5,8-methano-215,105-furo[3,2-1][1,3,6,9,11,2,10]pentaoxadiphosphacyclotetradecine-2,10-bis(thiolate)

With use of the compound obtained in step 6 (diastereomer 1) (42.3 mg), the reaction was performed in the same manner as in step 10 of Example 1 to afford the title compound (25.9 mg).

MS(ESI)m/z: 1131 (M+H)$^+$.

$^1$H-NMR (CD$_3$OD) δ: 8.72 (1H, s), 8.00 (1H, s), 7.26 (1H, s), 6.35 (1H, d, J=9.1 Hz), 6.26 (1H, d, J=4.8 Hz), 5.42-5.36

(1H, m), 5.20-5.15 (1H, m), 4.91-4.87 (2H, m), 4.80-4.78 (1H, m), 4.43 (1H, t, J=11.2 Hz), 4.36-4.28 (3H, m), 4.20-4.15 (3H, m), 4.09-3.99 (2H, m), 3.51 (2H, d, J=6.7 Hz), 3.13 (12H, q, J=7.3 Hz), 2.85 (2H, brs), 2.01-1.97 (2H, m), 1.25 (18H, t, J=7.3 Hz), 1.07-1.00 (2H, m), 1.00 (9H, s), 0.82 (9H, s), 0.32 (3H, s), 0.28 (3H, s), 0.25 (3H, s), 0.07 (12H, s).

(Step 7-2)

Bis(N,N-diethylethaneaminium) (5R,7R,8R,12aR,14R,15R,15aR,16R)-7-{6-amino-2-[({[2-(trimethylsilyl)ethoxy]carbonyl}amino)methyl]-9H-purin-9-yl}-15,16-bis{[tert-butyl(dimethyl)silyl]oxy}-2,10-dioxo-14-(6,7,8,9-tetrahydro-2H-2,3,5,6-tetraazabenzo[cd]azulen-2-yl)octahydro-2H,10H,12H-5,8-methano-2λ$^5$,10λ$^5$-furo[3,2-1][1,3,6,9,11,2,10]pentaoxadiphosphacyclotetradecine-2,10-bis (thiolate)

With use of the compound obtained in step 6 (diastereomer 2) (82.8 mg), the reaction was performed in the same manner as in step 10 of Example 1 to afford the title compound (45.2 mg).

$^1$H-NMR (CD$_3$OD) δ: 8.61 (1H, s), 8.01 (1H, s), 7.08 (1H, s), 6.34 (2H, t, J=7.9 Hz), 5.49 (1H, dd, J=10.6, 4.5 Hz), 5.42 (1H, t, J=5.1 Hz), 5.24-5.17 (1H, m), 5.00-4.95 (2H, m), 4.69-4.57 (2H, m), 4.36 (2H, t, J=17.8 Hz), 4.22-4.15 (3H, m), 4.05 (1H, dd, J=12.4, 5.1 Hz), 3.90-3.85 (1H, m), 3.51 (2H, d, J=9.1 Hz), 3.17 (12H, q, J=7.3 Hz), 2.92 (2H, t, J=5.4 Hz), 2.04-1.99 (2H, m), 1.29 (18H, t, J=7.3 Hz), 1.07-0.98 (2H, m), 1.00 (9H, s), 0.74 (9H, s), 0.28 (3H, s), 0.28 (3H, s), 0.21 (3H, s), 0.07 (9H, s), −0.06 (3H, s).

(Step 8-1)

Bis(N,N-diethylethaneaminium) (5R,7R,8R,12aR,14R,15R,15aS,16R)-7-{6-amino-2-[({[2-(trimethylsilyl)ethoxy]carbonyl}amino)methyl]-9H-purin-9-yl}-15,16-dihydroxy-2,10-dioxo-14-(6,7,8,9-tetrahydro-2H-2,3,5,6-tetraazabenzo[cd]azulen-2-yl)octahydro-2H,10H,12H-5,8-methano-2λ$^5$,10λ$^5$-furo[3,2-1][1,3,6,9,11,2,10]pentaoxadiphosphacyclotetradecine-2,10-bis (thiolate)

Triethylamine trihydrofluoride (700 µL) was added to the compound (25.9 mg) obtained in step 7-1, and the reaction mixture was stirred at 55° C. for 2 hours. An ice-cooled mixture of 1 M aqueous solution of triethylammonium carbonate (3.5 mL) and triethylamine (1.10 mL) was added to the reaction mixture, which was purified by preparative HPLC [10 mM aqueous solution of triethylammonium acetate/acetonitrile, acetonitrile: 10%-40% (0 min-30 min)] to afford the title compound (19.1 mg).

MS(ESI)m/z: 903 (M+H)$^+$.

$^1$H-NMR (CD$_3$OD) δ: 8.71 (1H, s), 8.03 (1H, s), 7.10 (1H, s), 6.37 (1H, d, J=7.9 Hz), 6.28 (1H, d, J=4.2 Hz), 5.38-5.33 (1H, m), 5.18-5.13 (1H, m), 4.84-4.80 (2H, m), 4.50-4.40 (2H, m), 4.35-4.40 (4H, m), 4.21-4.16 (2H, m), 4.07-4.00 (2H, m), 3.51-3.49 (2H, m), 3.07 (12H, q, J=7.3 Hz), 2.85 (2H, t, J=5.4 Hz), 2.02-1.97 (2H, m), 1.23 (18H, t, J=7.3 Hz), 1.04 (2H, t, J=8.2 Hz), 0.07 (9H, s).

(Step 8-2)

Bis(N,N-diethylethaneaminium) (5R,7R,8R,12aR,14R,15R,15aS,16R)-7-{6-amino-2-[({[2-(trimethylsilyl)ethoxy]carbonyl}amino)methyl]-9H-purin-9-yl}-15,16-dihydroxy-2,10-dioxo-14-(6,7,8,9-tetrahydro-2H-2,3,5,6-tetraazabenzo[cd]azulen-2-yl)octahydro-2H,10H,12H-5,8-methano-2λ$^5$,10λ$^5$-furo[3,2-1][1,3,6,9,11,2,10]pentaoxadiphosphacyclotetradecine-2,10-bis (thiolate)

With use of the compound obtained step 7-2 (45.2 mg), the reaction was performed in the same manner as in step 8-1 to afford the title compound (37.1 mg).

MS(ESI)m/z: 903 (M+H)$^+$.

$^1$H-NMR (CD$_3$OD) δ: 8.75 (1H, s), 8.02 (1H, s), 7.13 (1H, s), 6.36 (1H, d, J=9.1 Hz), 6.33 (1H, d, J=6.7 Hz), 5.51-5.42 (2H, m), 4.81 (1H, dd, J=6.7, 4.8 Hz), 4.51-4.28 (7H, m), 4.18 (2H, dt, J=8.3, 2.6 Hz), 4.02 (1H, d, J=12.7 Hz), 3.92-3.87 (1H, m), 3.51-3.47 (2H, m), 3.13 (12H, q, J=7.3 Hz), 2.93-2.90 (2H, m), 2.04-1.98 (2H, m), 1.27 (18H, t, J=7.3 Hz), 1.06-0.99 (2H, m), 0.06 (9H, s).

(Step 9-1)

Disodium (5R,7R,8R,12aR,14R,15R,15aS,16R)-7-[6-amino-2-(aminomethyl)-9H-purin-9-yl]-15,16-dihydroxy-2,10-dioxo-14-(6,7,8,9-tetrahydro-2H-2,3,5,6-tetraazabenzo[cd]azulen-2-yl)octahydro-2H,10H,12H-5,8-methano-2λ$^5$,10λ$^5$-furo[3,2-1][1,3,6,9,11,2,10]pentaoxadiphosphacyclotetradecine-2,10-bis (thiolate)

(Diastereomer 1)

To a solution of the compound obtained in step 8-1 (19.1 mg) in tetrahydrofuran (576 µL), a tetrahydrofuran solution of tetrabutylammonium fluoride (approximately 1 M, 288 µL) was added, and the reaction mixture was stirred under the nitrogen atmosphere at room temperature overnight, and purification was then performed under the following [Purification Conditions] to afford the title compound as a triethylamine salt.

[Purification Conditions] preparative HPLC [10 mM aqueous solution of triethylammonium acetate/acetonitrile, acetonitrile: 0%-30% (0 min-40 min)] and Sep-Pak® C18 [water/acetonitrile].

The triethylamine salt obtained was subjected to salt exchange in the same manner as in [Conversion to Sodium Salt] described in step 11 of Example 1 to afford the title compound (8.4 mg).

MS(ESI)m/z: 759 (M+H)$^+$.

$^1$H-NMR (CD$_3$OD) δ: 8.48 (1H, s), 8.03 (1H, s), 7.04 (1H, s), 6.27 (1H, d, J=3.6 Hz), 6.24 (1H, d, J=8.5 Hz), 5.98-5.93 (1H, m), 5.04-4.99 (1H, m), 4.81-4.79 (2H, m), 4.45-4.39 (2H, m), 4.31-4.27 (2H, m), 4.12-3.99 (4H, m), 3.54-3.44 (2H, m), 2.88-2.85 (2H, m), 2.02-1.97 (2H, m).

$^{31}$P-NMR (CD$_3$OD) δ: 57.6, 55.5.

(Step 9-2)

Disodium (5R,7R,8R,12aR,14R,15R,15aS,16R)-7-[6-amino-2-(aminomethyl)-9H-purin-9-yl]-15,16-dihydroxy-2,10-dioxo-14-(6,7,8,9-tetrahydro-2H-2,3,5,6-tetraazabenzo[cd]azulen-2-yl)octahydro-2H,10H,12H-5,8-methano-2λ$^5$,10λ$^5$-furo[3,2-1][1,3,6,9,11,2,10]pentaoxadiphosphacyclotetradecine-2,10-bis (thiolate)

(Diastereomer 2)

With use of the compound obtained in step 8-2 (37.1 mg), the reaction was performed in the same manner as in step 9-1 to afford the title compound (12.8 mg).

MS(ESI)m/z: 759 (M+H)$^+$.
$^1$H-NMR (CD$_3$OD) δ: 8.61 (1H, s), 8.02 (1H, s), 7.13 (1H, s), 6.31 (1H, d, J=6.0 Hz), 6.28 (1H, d, J=8.5 Hz), 5.61-5.55 (1H, m), 5.38-5.35 (1H, m), 4.80 (1H, t, J=5.1 Hz), 4.54 (1H, d, J=4.2 Hz), 4.48-4.28 (4H, m), 4.13 (2H, s), 4.08-4.04 (1H, m), 3.94-3.90 (1H, m), 3.52-3.49 (2H, m), 2.90-2.88 (2H, m), 2.03-1.98 (2H, m).
$^{31}$P-NMR (CD$_3$OD) δ: 62.2 (s), 60.0 (s).

Example 12: Synthesis of CDN12

(5R,7R,8R,12aR,14R,15R,15aS,16R)-7-[6-Amino-2-(hydroxymethyl)-9H-purin-9-yl]-15,16-dihydroxy-2,10-bis(sulfanyl)-14-(6,7,8,9-tetrahydro-2H-2,3,5,6-tetraazabenzo[cd]azulen-2-yl)octahydro-2H,10H,12H-5,8-methano-2λ$^5$,10λ$^5$-furo[3,2-l][1,3,6,9,11,2,10]pentaoxadiphosphacyclotetradecine-2,10-dione

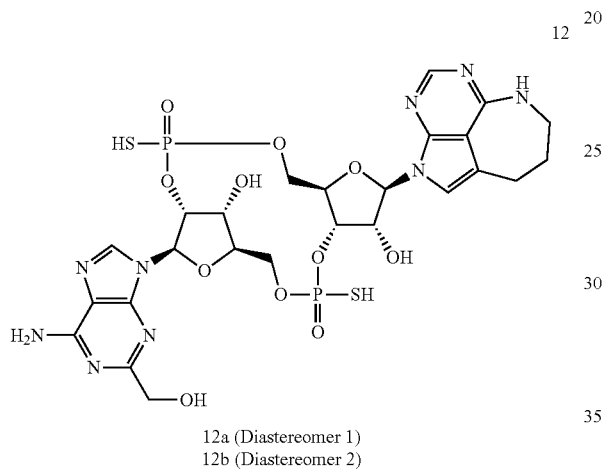

12a (Diastereomer 1)
12b (Diastereomer 2)

[Synthesis Scheme]

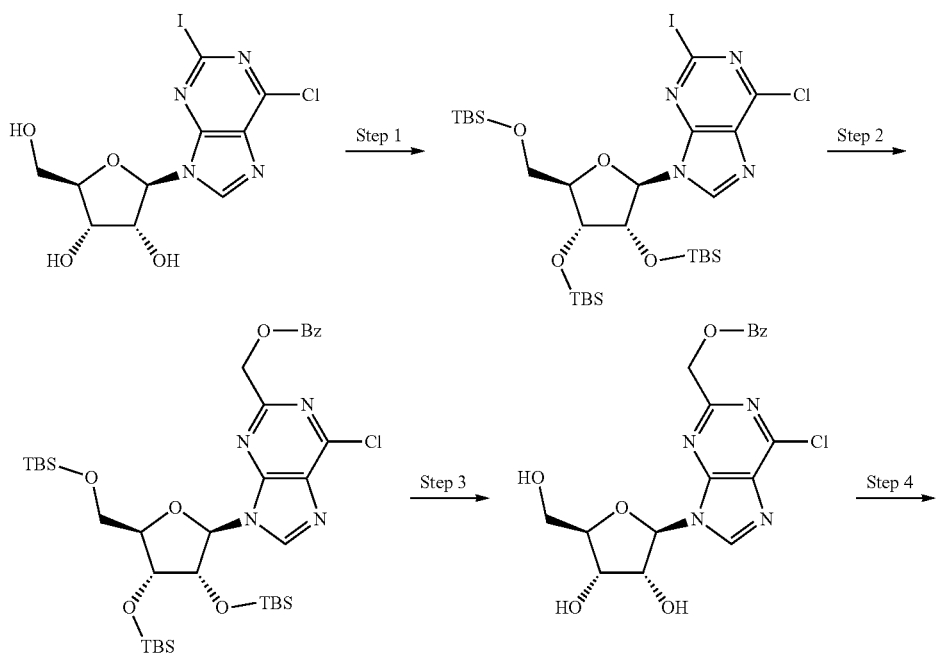

-continued
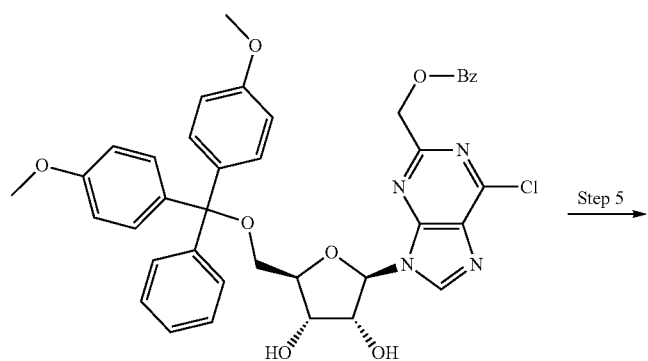
Step 5
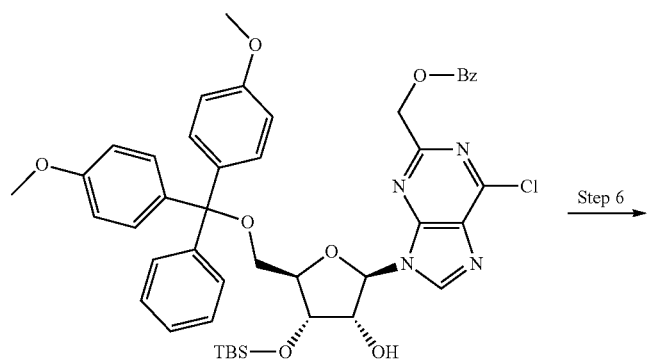
Step 6
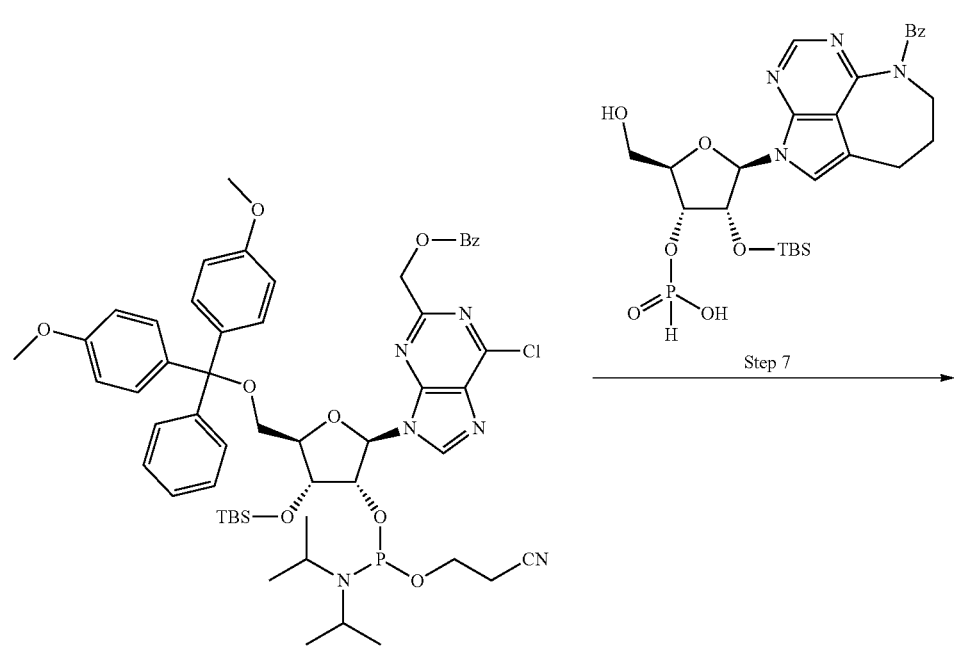
Step 7

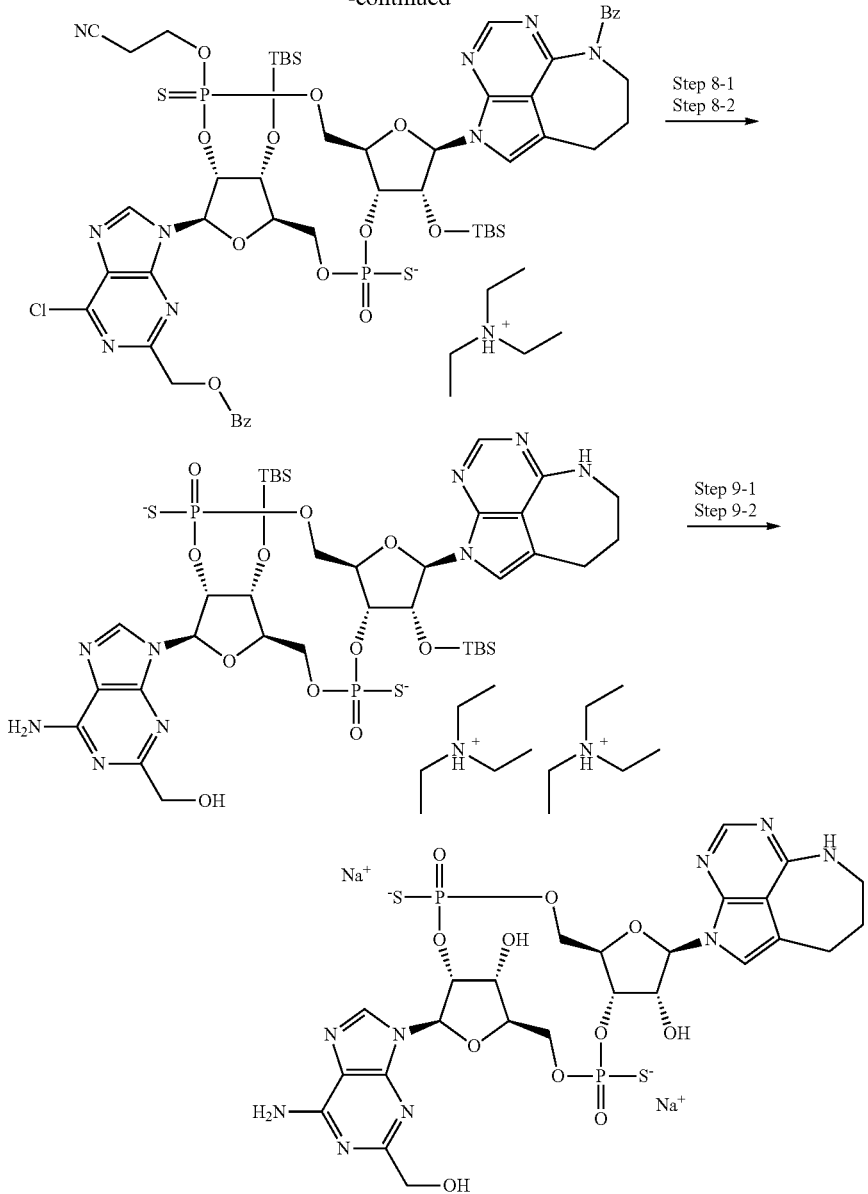

(Step 1)

6-Chloro-2-iodo-9-{2,3,5-tris-O-[tert-butyl(dimethyl)silyl]-β-D-ribofuranosyl}-9H-purine To a solution of commercially available (Amadis Chemical Company Limited) 6-chloro-2-iodo-9-β-D-ribofuranosyl-9H-purine (9.65 g) in ethylene glycol dimethyl ether (120 mL), N,N-diisopropylethylamine (40.7 mL) and tert-butyldimethylsilyl trifluoromethanesulfonate (26.9 mL) were added at 0° C., and the temperature was increased to room temperature under the nitrogen atmosphere, and the reaction mixture was stirred for 19 hours. The reaction mixture was cooled to 0° C., and a saturated aqueous solution of sodium hydrogen carbonate was added to the reaction mixture to quench the reaction, and the reaction mixture was then subjected to extraction with dichloromethane. After the organic layer was dried over anhydrous sodium sulfate, the drying agent was removed through filtration, and the filtrate was concentrated under reduced pressure. The residue was purified by silica gel column chromatography [hexane/ethyl acetate] to afford the title compound (13.7 g).

$^1$H-NMR (CDCl$_3$) δ: 8.48 (1H, s), 6.02 (1H, d, J=4.2 Hz), 4.54 (1H, t, J=4.5 Hz), 4.29 (1H, t, J=4.5 Hz), 4.18-4.15 (1H, m), 4.04 (1H, dd, J=11.5, 4.2 Hz), 3.80 (1H, dd, J=11.5, 2.4 Hz), 0.96 (9H, s), 0.93 (9H, s), 0.84 (9H, s), 0.17 (3H, s), 0.16 (3H, s), 0.10 (3H, s), 0.09 (3H, s), 0.01 (3H, s), −0.16 (3H, s).

(Step 2)

2-[(Benzoyloxy)methyl]-6-chloro-9-{2,3,5-tris-O-[tert-butyl(dimethyl)silyl]-β-D-ribofuranosyl}-9H-purine To a solution of the compound obtained in step 1 (13.7 g) in tetrahydrofuran (121 mL), tetrakis(triphenylphosphine)

palladium (0) (2.10 g) and (benzyloxymethyl) zinc iodide prepared in the manner described below (approximately 0.9 M, 30.2 mL) were added under the nitrogen atmosphere, and the reaction mixture was stirred at room temperature for 20 hours. After a saturated aqueous solution of ammonium chloride was added to the reaction mixture to quench the reaction, the resultant was subjected to extraction with dichloromethane. After the organic layer was dried over anhydrous sodium sulfate, the drying agent was removed through filtration, and the filtrate was concentrated under reduced pressure. The residue was purified by silica gel column chromatography [hexane/ethyl acetate] to afford the title compound (7.29 g).

[Preparation of (Benzyloxymethyl) zinc Iodide]

After a suspension of zinc powder (5.99 g) in tetrahydrofuran (17.1 mL) was ultrasonicated under the nitrogen atmosphere, a solution of iodomethyl benzoate (12.0 g) in tetrahydrofuran (21.3 mL) was added thereto at 10 to 15° C., and the reaction mixture was stirred at the same temperature for 1.5 hours to afford a tetrahydrofuran solution of (benzyloxymethyl) zinc iodide (approximately 0.9 M, 38.4 mL).

MS(ESI)m/z: 763 (M+H)$^+$.

$^1$H-NMR (CDCl$_3$) δ: 8.58 (1H, s), 8.13 (1H, dd, J=8.5, 1.2 Hz), 7.60-7.56 (1H, m), 7.47-7.43 (2H, m), 6.09 (1H, d, J=4.8 Hz), 5.60 (1H, d, J=13.9 Hz,), 5.56 (1H, d, J=13.9 Hz), 4.48 (1H, t, J=4.5 Hz), 4.27 (1H, t, J=4.2 Hz), 4.15-4.11 (1H, m), 4.03 (1H, dd, J=11.5, 3.0 Hz), 3.80 (1H, dd, J=11.5, 2.4 Hz) 0.96 (9H, s), 0.90 (9H, s), 0.76 (9H, s), 0.16 (3H, s), 0.15 (3H, s), 0.08 (3H, s), 0.06 (3H, s), −0.07 (3H, s), −0.27 (3H, s).

(Step 3)

2-[(Benzoyloxy)methyl]-6-chloro-9-β-D-ribofuranosyl-9H-purine

To a solution of the compound obtained in step 2 (7.29 g) in tetrahydrofuran (47.7 mL), a tetrahydrofuran solution of tetrabutylammonium fluoride (approximately 1 M, 38 mL) was added under the nitrogen atmosphere at 0° C., and the reaction mixture was stirred at the same temperature for 2.5 hours. After a saturated aqueous solution of ammonium chloride was added to the reaction mixture to quench the reaction, the resultant was subjected to extraction with dichloromethane. After the organic layer was dried over anhydrous sodium sulfate, the drying agent was removed through filtration, and the filtrate was concentrated under reduced pressure. The residue was purified by silica gel column chromatography [hexane/ethyl acetate] to afford the title compound (3.69 g).

$^1$H-NMR (CDCl$_3$) δ: 8.23 (1H, s), 8.15 (2H, dd, J=8.5, 1.2 Hz), 7.63-7.59 (1H, m), 7.48 (2H, t, J=7.9 Hz), 5.89 (1H, d, J=6.0 Hz), 5.61 (1H, d, J=13.9 Hz), 5.56 (1H, d, J=14.5 Hz), 4.90 (1H, q, J=5.6 Hz), 4.46-4.43 (1H, m), 4.28 (1H, q, J=2.2 Hz), 4.02 (1H, dd, J=10.0, 2.7 Hz), 3.84-3.79 (1H, m), 3.71-3.65 (1H, m), 3.56-3.53 (1H, m), 2.70 (1H, d, J=2.4 Hz).

(Step 4)

2-[(Benzoyloxy)methyl]-9-{5-O-[bis(4-methoxyphenyl)(phenyl)methyl]-β-D-ribofuranosyl}-6-chloro-9H-purine To a solution of the compound obtained in step 3 (2.36 g) in pyridine (56 mL), 4,4'-dimethoxytrityl chloride (2.30 g) was added, and the reaction mixture was stirred under the nitrogen atmosphere at room temperature for 17 hours. Ethanol (20 mL) was added to the reaction mixture, which was further stirred for about 10 minutes, and then concentrated under reduced pressure. The residue was purified by silica gel column chromatography [hexane/ethyl acetate] to afford the title compound (1.41 g).

MS(ESI)m/z: 745 (M+Na)$^+$.

$^1$H-NMR (CDCl$_3$) δ: 8.32 (1H, s), 8.14-8.11 (2H, m), 7.64-7.59 (1H, m), 7.49-7.44 (2H, m), 7.23-7.12 (9H, m), 6.72 (4H, d, J=7.9 Hz), 5.94 (1H, d, J=5.4 Hz), 5.64 (1H, d, J=15.1 Hz), 5.59 (1H, d, J=14.5 Hz), 4.83-4.77 (2H, m), 4.37-4.33 (2H, m), 3.77 (6H, s), 3.35 (1H, dd, J=10.6, 3.3 Hz), 3.28 (1H, dd, J=10.9, 3.6 Hz), 2.64 (1H, s).

(Step 5)

2-[(Benzoyloxy)methyl]-9-{5-O-[bis(4-methoxyphenyl)(phenyl)methyl]-3-O-[tert-butyl(dimethyl)silyl]-β-D-ribofuranosyl}-6-chloro-9H-purine To a solution of the compound obtained in step 4 (2.61 g) in ethylene glycol dimethyl ether (72.0 mL), N,N-diisopropylethylamine (1.89 mL) and tert-butyldimethylsilyl trifluoromethanesulfonate (1.24 mL) were added, and the reaction mixture was stirred under the nitrogen atmosphere at room temperature for 1.5 hours. A saturated aqueous solution of sodium hydrogen carbonate was added the reaction mixture to quench the reaction, and the resultant was then subjected to extraction with dichloromethane. After the organic layer was dried over anhydrous sodium sulfate, the drying agent was removed through filtration, and the filtrate was concentrated under reduced pressure. The residue was purified by silica gel column chromatography [hexane/ethyl acetate/ 0.1% triethylamine] to afford the title compound (1.10 g).

$^1$H-NMR (CDCl$_3$) δ: 8.35 (1H, s), 8.12-8.10 (2H, m), 7.60-7.56 (1H, m), 7.46-7.42 (2H, m), 7.37-7.35 (2H, m), 7.28-7.20 (7H, m), 6.81-6.75 (4H, m), 6.00 (1H, d, J=4.8 Hz), 5.50 (2H, s), 4.69 (1H, q, J=5.6 Hz), 4.39 (1H, dd, J=5.1, 3.9 Hz), 4.16 (1H, q, J=3.8 Hz), 3.77 (6H, s), 3.45 (1H, dd, J=10.6, 3.3 Hz), 3.31 (1H, dd, J=10.9, 4.2 Hz), 3.06 (1H, d, J=6.7 Hz), 0.86 (9H, s), 0.04 (3H, s), −0.02 (3H, s).

(Step 6)

2-[(Benzoyloxy)methyl]-9-(5-O-[bis(4-methoxyphenyl)(phenyl)methyl]-3-O-[tert-butyl(dimethyl)silyl]-2-O-{(2-cyanoethoxy)[di(propan-2-yl)amino]phosphanyl}-β-D-ribofuranosyl)-6-chloro-9H-purine With use of the compound obtained in step 5 (511 mg), the reaction was performed in the same manner as in step 6 of Example 1 to afford the title compound (569 mg) as a mixture of diastereomers at the phosphorus atom (diastereomer ratio=6:4).

$^1$H-NMR (CDCl$_3$) δ: 8.43 (0.6H, s), 8.39 (0.4H, s), 8.10 (2H, d, J=7.9 Hz), 7.58 (1H, t, J=7.6 Hz), 7.47-7.38 (4H, m), 7.31-7.18 (7H, m), 6.82-6.78 (4H, m), 6.25 (0.4H, d, J=4.8 Hz), 6.21 (0.6H, d, J=4.8 Hz), 5.49 (1H, d, J=13.9 Hz), 5.45 (1H, d, 13.9 Hz), 4.98-4.93 (0.6H, m), 4.83-4.78 (0.4H, m), 4.45 (0.6H, t, J=4.2 Hz), 4.36 (0.4H, t, J=4.2 Hz), 4.21-4.17 (1H, m), 3.78 (6H, s), 3.76-3.32 (6H, m), 2.46 (1.2H, t, J=6.3 Hz), 2.30 (0.8H, t, J=6.3 Hz), 1.28-0.86 (12H, m), 0.825 (5.4H, s), 0.815 (3.6H, s), 0.08 (1.8H, s), 0.04 (1.2H, s), −0.01 (1.8H, s), —0.02 (1.2H, s).

(Step 7)

N,N-Diethylethaneaminium (5R,7R,8R,12aR,14R, 15R,15aR,16R)-7-{2-[(benzoyloxy)methyl]-6-chloro-9H-purin-9-yl}-14-(6-benzoyl-6,7,8,9-tetrahydro-2H-2,3,5,6-tetraazabenzo[cd]azulen-2-yl)-15, 16-bis{[tert-butyl(dimethyl)silyl]oxy}-10-(2-cyanoethoxy)-2-oxo-10-sulfanylideneoctahydro-2H, 10H,12H-5,8-methano-2$\lambda^5$,10$\lambda^5$-furo[3,2-1][1,3,6,9, 11,2,10]pentaoxadiphosphacyclotetradecine-2-thiolate The same reaction as in step 7 of Example 1 was performed in the following scale (raw material: 2.72 g). With use of an acetonitrile solution of the compound obtained and the compound obtained in step 6 (3.03 g), the reaction was performed in the same manner as in step 8 of Example 1 and step 9 of Example 1 to afford diastereomer 1 (351 mg) and diastereomer 2 (351 mg) of the title compound.

Diastereomer 1 (Less Polar)

MS(ESI)m/z: 1268 (M+H)$^+$.

$^1$H-NMR (CD$_3$OD) δ: 9.30 (1H, s), 8.14 (2H, d, J=7.3 Hz), 7.99 (1H, s), 7.64 (1H, t, J=7.3 Hz), 7.52 (2H, t, J=7.9 Hz), 7.40-7.36 (2H, m), 7.30-7.23 (4H, m), 6.43 (1H, d, J=8.5 Hz), 6.37 (1H, d, J=3.0 Hz), 5.62-5.56 (1H, m), 5.62 (2H, s), 5.06-5.01 (1H, m), 4.83 (1H, dd, J=4.5, 2.7 Hz), 4.69 (1H, d, J=4.2 Hz), 4.49-4.28 (7H, m), 4.08 (1H, dd, J=12.1, 4.8 Hz), 3.81-3.70 (1H, m), 3.46-3.38 (1H, m), 3.17-3.10 (8H, m), 2.29-2.23 (4H, m), 1.28 (9H, t, J=7.3 Hz), 0.91 (9H, s), 0.90 (9H, s), 0.29 (3H, s), 0.20 (3H, s), 0.16 (3H, s), 0.11 (3H, s).

Diastereomer 2 (More Polar)

MS(ESI)m/z: 1268 (M+H)$^+$.

$^1$H-NMR (CD$_3$OD) δ: 8.97 (1H, s), 8.14 (2H, d, J=8.5 Hz), 7.94 (1H, s), 7.68-7.63 (1H, m), 7.55-7.50 (2H, m), 7.39-7.36 (2H, m), 7.26-7.21 (4H, m), 6.41 (1H, d, J=7.9 Hz), 6.21 (1H, d, J=5.4 Hz), 5.64 (1H, d, J=15.1 Hz), 5.57 (1H, d, J=15.1 Hz), 5.25-5.18 (2H, m), 5.13-5.10 (1H, m), 5.04-5.01 (1H, m), 4.94-4.78 (3H, m), 4.51 (1H, t, J=10.9 Hz), 4.33-4.06 (6H, m), 3.15 (6H, q, J=7.3 Hz), 3.08-2.96 (2H, m), 2.84-2.71 (2H, m), 2.25-2.19 (2H, m), 1.28 (9H, t, J=7.3 Hz), 0.91 (9H, s), 0.79 (9H, s), 0.19 (6H, s), 0.14 (3H, s)-0.07 (3H, s).

(Step 8-1)

Bis(N,N-diethylethaneaminium) (5R,7R,8R,12aR, 14R,15R,15aR,16R)-7-[6-amino-2-(hydroxymethyl)-9H-purin-9-yl]-15,16-bis{[tert-butyl(dimethyl)silyl]oxy}-2,10-dioxo-14-(6,7,8,9-tetrahydro-2H-2,3,5,6-tetraazabenzo[cd]azulen-2-yl)octahydro-2H,10H, 12H-5,8-methano-2$\lambda^5$,10$\lambda^5$-furo[3,2-1][1,3,6,9,11,2, 10]pentaoxadiphosphacyclotetradecine-2,10-bis (thiolate)

To a solution of the compound obtained in step 7 (diastereomer 1) (37.3 mg) in methanol (0.500 mL), 28% aqueous solution of ammonia (0.500 mL) was added, and the reaction mixture was stirred in a shield tube at 60° C. for 3 hours. The reaction mixture was directly purified by preparative HPLC [10 mM aqueous solution of triethylammonium acetate/acetonitrile, acetonitrile: 35%-55% (0 min-30 min)] to afford the title compound (22.0 mg: with impurities).

MS(ESI)m/z: 988 (M+H)$^+$.

(Step 8-2)

Bis(N,N-diethylethaneaminium) (5R,7R,8R,12aR, 14R,15R,15aR,16R)-7-[6-amino-2-(hydroxymethyl)-9H-purin-9-yl]-15,16-bis{[tert-butyl(dimethyl)silyl] oxy}-2,10-dioxo-14-(6,7,8,9-tetrahydro-2H-2,3,5,6-tetraazabenzo[cd]azulen-2-yl)octahydro-2H,10H, 12H-5,8-methano-2$\lambda^5$,10$\lambda^5$-furo[3,2-1][1,3,6,9,11,2, 10]pentaoxadiphosphacyclotetradecine-2,10-bis (thiolate)

To a solution of the compound obtained in step 7 (diastereomer 2) (37.7 mg) in tetrahydrofuran (0.500 mL), 28% aqueous solution of ammonia (0.500 mL) was added, and the reaction mixture was stirred in a shield tube at 60° C. for 3 hours. Thereto, 28% aqueous solution of ammonia (0.500 mL) was further added, and the reaction mixture was further stirred for 3 hours. Thereto, 28% aqueous solution of ammonia (0.500 mL) was further added, and the reaction mixture was further stirred overnight. The reaction mixture was directly purified by preparative HPLC [10 mM aqueous solution of triethylammonium acetate/acetonitrile, acetonitrile: 20%-50% (0 min-30 min)] to afford the title compound (19.3 mg).

MS(ESI)m/z: 988 (M+H)$^+$.

$^1$H-NMR (CD$_3$OD) δ: 8.64 (1H, s), 8.02 (1H, s), 7.09 (1H, s), 6.35 (2H, d, J=7.9 Hz), 5.48-5.41 (2H, m), 5.26-5.19 (1H, m), 5.00-4.95 (2H, m), 4.70-4.53 (4H, m), 4.22 (1H, s), 4.06 (1H, dd, J=12.1, 4.8 Hz), 3.91-3.86 (1H, m), 3.53-3.48 (2H, m), 3.18 (12H, q, J=7.3 Hz), 2.92 (2H, t, J=5.4 Hz), 2.04-1.99 (2H, m), 1.29 (18H, t, J=7.3 Hz), 1.00 (9H, s), 0.74 (9H, s), 0.28 (6H, s), 0.21 (3H, s), –0.06 (3H, s).

(Step 9-1)

Disodium (5R,7R,8R,12aR,14R,15R,15aS,16R)-7-[6-amino-2-(hydroxymethyl)-9H-purin-9-yl]-15,16-dihydroxy-2,10-dioxo-14-(6,7,8,9-tetrahydro-2H-2, 3,5,6-tetraazabenzo[cd]azulen-2-yl)octahydro-2H, 10H,12H-5,8-methano-2$\lambda^5$,10$\lambda^5$-furo[3,2-1][1,3,6,9, 11,2,10]pentaoxadiphosphacyclotetradecine-2,10-bis (thiolate)

With use of the compound obtained in step 8-1 (22.0 mg: with impurities), the reaction was performed in the same manner as in step 11 of Example 1, and purification was then performed under the following [Purification Conditions] to afford the title compound as a triethylamine salt.

[Purification Conditions] preparative HPLC [10 mM aqueous solution of triethylammonium acetate/acetonitrile, acetonitrile: 2%-30% (0 min-30 min)].

The triethylamine salt obtained was subjected to salt exchange in the same manner as in [Conversion to Sodium Salt] described in step 11 of Example 1 to afford the title compound (8.0 mg).

MS(ESI)m/z: 760 (M+H)$^+$.

$^1$H-NMR (CD$_3$OD) δ: 8.70 (1H, s), 8.03 (1H, s), 7.14 (1H, s), 6.39 (1H, d, J=8.5 Hz), 6.29 (1H, d, J=3.6 Hz), 5.40-5.35 (1H, m), 5.15 (1H, dt, J=9.1, 3.8 Hz), 4.84 (1H, d, J=3.6 Hz), 4.80 (1H, t, J=4.5 Hz), 4.57 (2H, s), 4.51-4.43 (2H, m), 4.38-4.31 (2H, m), 4.09-4.00 (2H, m), 3.52-3.48 (2H, m), 2.89-2.76 (2H, m), 2.01-1.97 (2H, m).

$^{31}$P-NMR (CD$_3$OD) δ: 58.1 (s), 54.4 (s).

(Step 9-2)

Disodium (5R,7R,8R,12aR,14R,15R,15aS,16R)-7-[6-amino-2-(hydroxymethyl)-9H-purin-9-yl]-15,16-dihydroxy-2,10-dioxo-14-(6,7,8,9-tetrahydro-2H-2,3,5,6-tetraazabenzo[cd]azulen-2-yl)octahydro-2H,10H,12H-5,8-methano-2λ⁵,10λ⁵-furo[3,2-1][1,3,6,9,11,2,10]pentaoxadiphosphacyclotetradecine-2,10-bis(thiolate)

With use of the compound obtained in step 8-2 (19.3 mg), the reaction was performed in the same manner as in step 11 of Example 1, and purification was then performed under the following [Purification Conditions] to afford the title compound as a triethylamine salt.

[Purification Conditions] preparative HPLC [10 mM aqueous solution of triethylammonium acetate/acetonitrile, acetonitrile: 2%-30% (0 min-30 min)].

The triethylamine salt obtained was subjected to salt exchange in the same manner as in [Conversion to Sodium Salt] described in step 11 of Example 1 to afford the title compound (6.5 mg).

MS(ESI)m/z: 760 (M+H)⁺.

¹H-NMR (CD₃OD) δ: 8.76 (1H, s), 8.05 (1H, s), 7.18 (1H, s), 6.38 (1H, d, J=8.5 Hz), 6.33 (1H, d, J=6.7 Hz), 5.49-5.43 (2H, m), 4.81 (1H, dd, J=6.3, 4.5 Hz), 4.58 (2H, s), 4.51-4.29 (5H, m), 4.04 (1H, d, J=12.1 Hz), 3.93-3.88 (1H, m), 3.54-3.52 (2H, m), 2.92 (2H, t, J=5.4 Hz), 2.05-2.00 (2H, m).

³¹P-NMR (CD₃OD) δ: 63.0 (s), 60.3 (s).

Example 13: Synthesis of CDN13

(5R,7R,8R,12aR,14R,15R,15aS,16R)-7-{6-[(2-aminoethyl)amino]-9H-purin-9-yl}-15,16-dihydroxy-2,10-bis(sulfanyl)-14-(6,7,8,9-tetrahydro-2H-2,3,5,6-tetraazabenzo[cd]azulen-2-yl)octahydro-2H,10H,12H-5,8-methano-2λ⁵,10λ⁵-furo[3,2-1][1,3,6,9,11,2,10]pentaoxadiphosphacyclotetradecine-2,10-dione

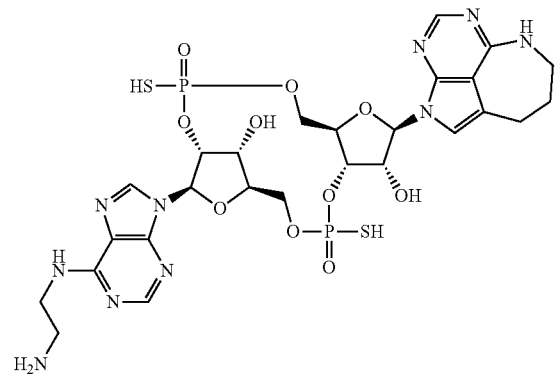

13a (Diastereomer 1)
13b (Diastereomer 2)

[Synthesis Scheme]

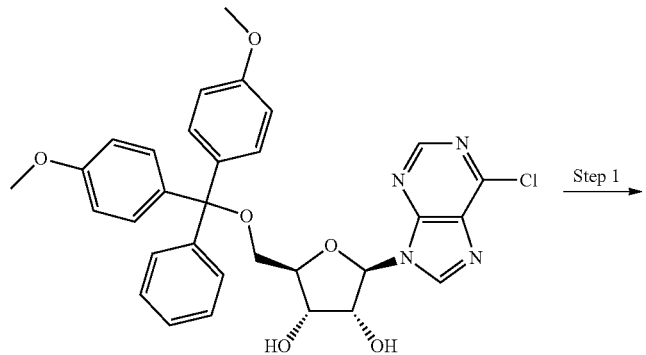

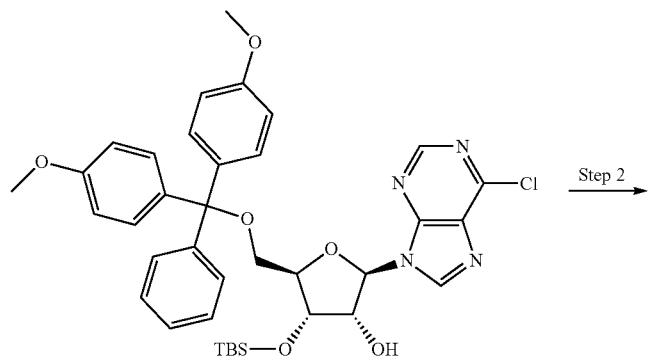

-continued
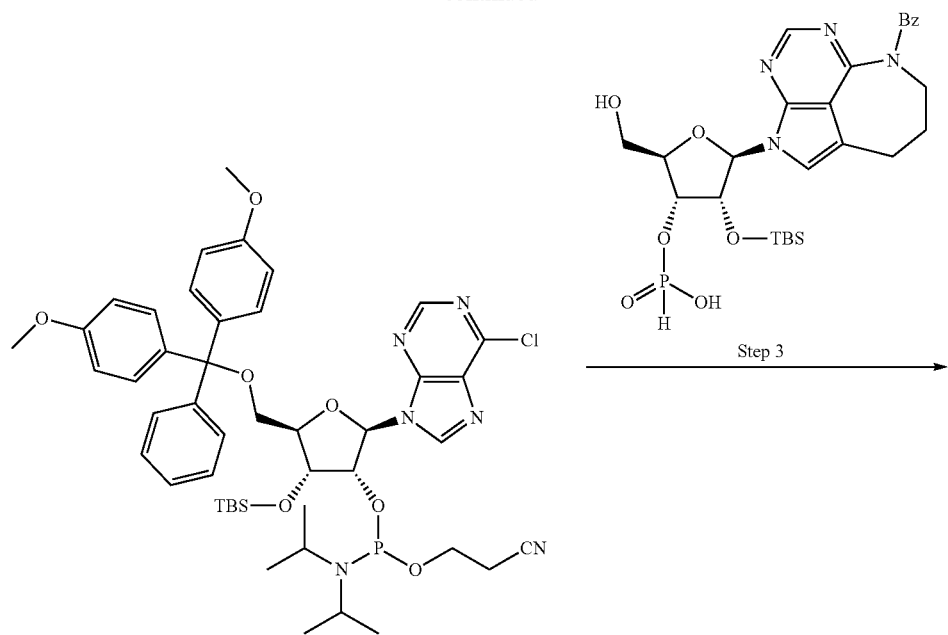
Step 3
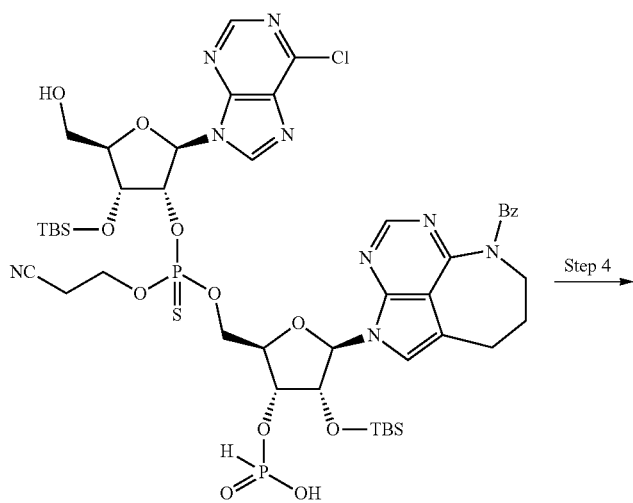
Step 4
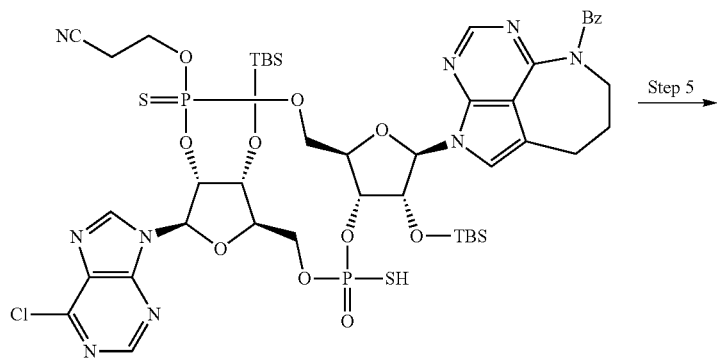
Step 5

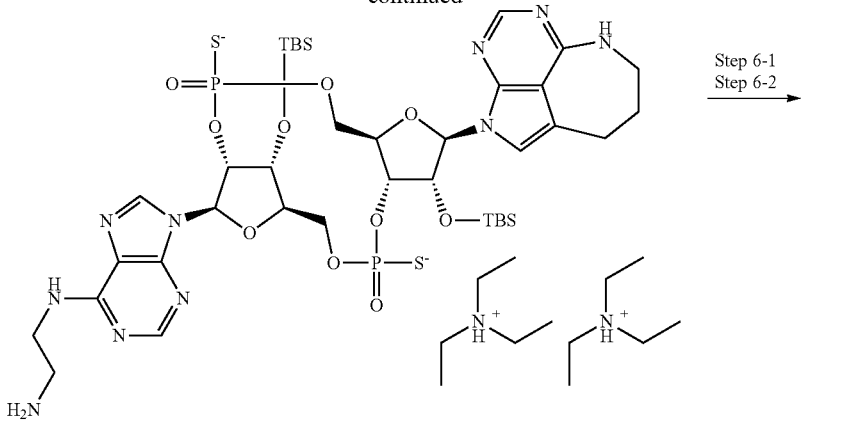

(Step 1)

9-{5-O-[Bis(4-methoxyphenyl)(phenyl)methyl]-3-O-[tert-butyl(dimethyl)silyl]-β-D-ribofuranosyl}-6-chloro-9H-purine With use of 9-{5-O-[bis(4-methoxyphenyl)(phenyl)methyl]-β-D-ribofuranosyl}-6-chloro-9H-purine (15.3 g) as a compound known in the literature (J. Org. Chem. 2000, 65, 5104-5113), the reaction was performed in the same manner as in step 3 of Example 5 to afford the title compound (8.44 g) and 9-{5-O-[bis(4-methoxyphenyl)(phenyl)methyl]-2-O-[tert-butyl(dimethyl)silyl]-β-D-ribofuranosyl}-6-chloro-9H-purine (5.77 g) as a regioisomer of the title compound.

MS(ESI)m/z: 703 (M+H)$^+$.

$^1$H-NMR (CDCl$_3$) δ: 8.71 (1H, s), 8.37 (1H, s), 7.40-7.37 (2H, m), 7.31-7.19 (7H, m), 6.82-6.78 (4H, m), 6.06 (1H, d, J=4.9 Hz), 4.79-4.74 (1H, m), 4.59 (1H, dd, J=4.9, 3.9 Hz), 4.20 (1H, dd, J=3.9, 1.9 Hz), 3.79 (3H, s), 3.78 (3H, s), 3.52 (1H, dd, J=10.7, 3.4 Hz), 3.29 (1H, dd, J=10.7, 3.9 Hz), 3.08 (1H, d, J=6.8 Hz), 0.90 (9H, s), 0.10 (3H, s), 0.03 (3H, s).

Regioisomer (2'-O-TBS form)

MS(ESI)m/z: 703 (M+H)$^+$.

$^1$H-NMR (CDCl$_3$) δ: 8.67 (1H, s), 8.36 (1H, s), 7.46-7.42 (2H, m), 7.36-7.20 (7H, m), 6.84-6.80 (4H, m), 6.11 (1H, d, J=5.4 Hz), 5.00-4.97 (1H, m), 4.40-4.35 (1H, m), 4.31-4.28 (1H, m), 3.79 (3H, s), 3.79 (3H, s), 3.52 (1H, dd, J=10.7, 2.9 Hz), 3.42 (1H, dd, J=10.7, 3.9 Hz), 2.68 (1H, d, J=3.9 Hz), 0.84 (9H, s), 0.00 (3H, s), -0.16 (3H, s).

(Step 2)

9-(5-O-[Bis(4-methoxyphenyl)(phenyl)methyl]-3-O-[tert-butyl(dimethyl)silyl]-2-O-{(2-cyanoethoxy)[di(propan-2-yl)amino]phosphanyl}-β-D-ribofuranosyl)-6-chloro-9H-purine With use of the compound obtained in step 1 (5.39 g), the reaction was performed in the same manner as in step 4 of Example 5 to afford the title compound (5.78 g) as a mixture of diastereomers at the phosphorus atom (diastereomer ratio=1:1).

MS(ESI)m/z: 903 (M+H)$^+$.

$^1$H-NMR (CDCl$_3$) δ: 8.69 (0.5H, s), 8.67 (0.5H, s), 8.43 (0.5H, s), 8.41 (0.5H, s), 7.43-7.37 (2H, m), 7.32-7.19 (7H, m), 6.83-6.78 (4H, m), 6.30 (0.5H, d, J=4.4 Hz), 6.21 (0.5H, d, J=4.9 Hz), 5.06-5.00 (0.5H, m), 4.86-4.80 (0.5H, m), 4.56-4.50 (1H, m), 4.27-4.20 (1H, m), 3.79 (6H, s), 3.75-3.62 (1H, m), 3.57-3.46 (4H, m), 3.30 (1H, dt, J=10.7, 3.9 Hz), 2.50 (1H, t, J=6.3 Hz), 2.37 (1H, t, J=6.6 Hz), 1.13-1.06 (9H, m), 0.90 (1.5H, s), 0.89 (1.5H, s), 0.86 (4.5H, s), 0.85 (4.5H, s), 0.12 (1.5H, s), 0.08 (1.5H, s), 0.02 (1.5H, s), 0.02 (1.5H, s).

(Step 3)

The same reaction as in step 7 of Example 1 was performed in the following scale (raw material: 1.84 g). With use of an acetonitrile solution of the compound obtained and the compound obtained in step 2 (1.62 g), the reaction was performed in the same manner as in step 8 of Example 1. The resulting crude product was directly used for the subsequent reaction.

(Step 4)

3-{[(5R,7R,8R,12aR,14R,15R,15aR,16R)-14-(6-Benzoyl-6,7,8,9-tetrahydro-2H-2,3,5,6-tetraazabenzo[cd]azulen-2-yl)-15,16-bis{[tert-butyl(dimethyl)silyl]oxy}-7-(6-chloro-9H-purin-9-yl)-2-oxo-2-sulfanyl-10-sulfanylideneoctahydro-2H,10H,12H-5,8-methano-2$\lambda^5$,10$\lambda^5$-furo[3,2-1][1,3,6,9,11,2,10]pentaoxadiphosphacyclotetradecin-10-yl]oxy}propanenitrile

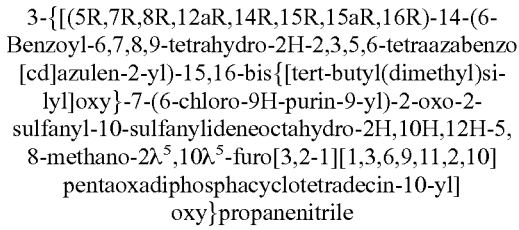

With use of the crude product obtained in step 3, the reaction was performed in the same manner as in step 9 of Example 1 to afford the title compound (626 mg) as a mixture of diastereomers at the phosphorus atom.

MS(ESI)m/z: 1134 (M+H)$^+$.

(Step 5)

Bis(N,N-diethylethaneaminium) (5R,7R,8R,12aR,14R,15R,15aR,16R)-7-{6-[(2-aminoethyl)amino]-9H-purin-9-yl}-15,16-bis{[tert-butyl(dimethyl)silyl]oxy}-2,10-dioxo-14-(6,7,8,9-tetrahydro-2H-2,3,5,6-tetraazabenzo[cd]azulen-2-yl)octahydro-2H,10H,12H-5,8-methano-2$\lambda^5$,10$\lambda^5$-furo[3,2-1][1,3,6,9,11,2,10]pentaoxadiphosphacyclotetradecine-2,10-bis(thiolate)

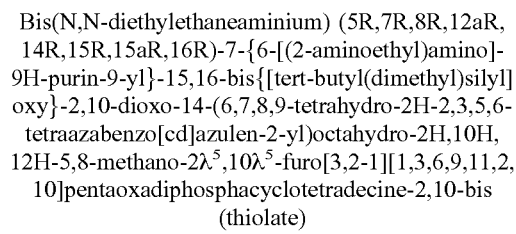

To a solution of the compound obtained in step 4 (299 mg: a mixture of diastereomers) in ethanol (10 mL), ethylenediamine (0.352 mL) and triethylamine (0.735 mL) were added, and the reaction mixture was stirred at 60° C. for 15 hours. After the reaction mixture was concentrated under reduced pressure, the residue was purified by C18 silica gel column chromatography [10 mM aqueous solution of triethylammonium acetate/acetonitrile] to afford diastereomer 1 (122 mg: with impurities) and diastereomer 2 (111 mg: with impurities) of the title compound.

Diastereomer 1 (Less Polar)

MS(ESI)m/z: 1001 (M+H)$^+$.

Diastereomer 2 (More Polar)

MS(ESI)m/z: 1001 (M+H)$^+$.

(Step 6-1)

Disodium (5R,7R,8R,12aR,14R,15R,15aS,16R)-7-{6-[(2-aminoethyl)amino]-9H-purin-9-yl}-15,16-dihydroxy-2,10-dioxo-14-(6,7,8,9-tetrahydro-2H-2,3,5,6-tetraazabenzo[cd]azulen-2-yl)octahydro-2H,10H,12H-5,8-methano-2$\lambda^5$,10$\lambda^5$-furo[3,2-1][1,3,6,9,11,2,10]pentaoxadiphosphacyclotetradecine-2,10-bis(thiolate)

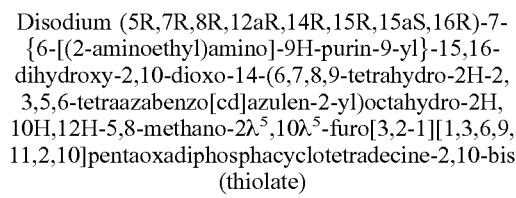

(Diastereomer 1)

With use of the compound obtained in step 5 (diastereomer 1) (122 mg: with impurities), the reaction was performed in the same manner as in step 11 of Example 1, and purification was then performed under the following [Purification Conditions] to afford the title compound as a triethylamine salt.

[Purification Conditions] C18 silica gel column chromatography [10 mM aqueous solution of triethylammonium acetate/acetonitrile] and preparative HPLC [10 mM aqueous solution of triethylammonium acetate/acetonitrile, acetonitrile: 5%-30% (0 min-40 min)].

The triethylamine salt obtained was subjected to salt exchange in the same manner as in [Conversion to Sodium Salt] described in step 11 of Example 1 to afford the title compound (29.6 mg).

MS(ESI)m/z: 773 (M+H)$^+$.

$^1$H-NMR (CD$_3$OD) δ: 8.77 (1H, s), 8.27 (1H, s), 8.03 (1H, s), 7.10 (1H, s), 6.35 (1H, d, J=8.5 Hz), 6.27 (1H, d, J=4.8 Hz), 5.41 (1H, ddd, J=7.9, 4.2, 2.1 Hz), 5.21-5.14 (1H, m), 4.84-4.77 (2H, m), 4.49-4.38 (2H, m), 4.35-4.26 (2H, m), 4.09-3.99 (2H, m), 3.92-3.80 (2H, m), 3.51-3.45 (2H, m), 3.22 (2H, t, J=6.0 Hz), 2.89-2.81 (2H, m), 2.02-1.94 (2H, m).

$^{31}$P-NMR (CD$_3$OD) δ: 57.8 (s), 55.0 (s).

(Step 6-2)

Disodium (5R,7R,8R,12aR,14R,15R,15aS,16R)-7-{6-[(2-aminoethyl)amino]-9H-purin-9-yl}-15,16-dihydroxy-2,10-dioxo-14-(6,7,8,9-tetrahydro-2H-2,3,5,6-tetraazabenzo[cd]azulen-2-yl)octahydro-2H,10H,12H-5,8-methano-2$\lambda^5$,10$\lambda^5$-furo[3,2-1][1,3,6,9,11,2,10]pentaoxadiphosphacyclotetradecine-2,10-bis(thiolate)

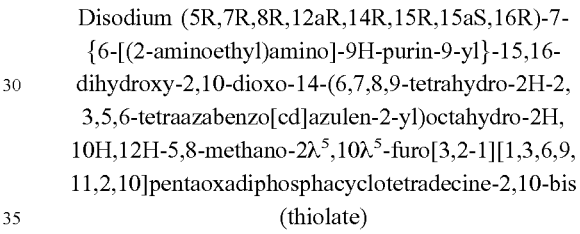

(Diastereomer 2)

With use of the compound obtained in step 5 (diastereomer 2) (119 mg: with impurities), the reaction was performed in the same manner as in step 11 of Example 1, and purification was then performed under the following [Purification Conditions] to afford the title compound as a triethylamine salt.

[Purification Conditions] C18 silica gel column chromatography [10 mM aqueous solution of triethylammonium acetate/acetonitrile] and preparative HPLC [10 mM aqueous solution of triethylammonium acetate/acetonitrile, acetonitrile: 5%-25% (0 min-40 min)].

The triethylamine salt obtained was subjected to salt exchange in the same manner as in [Conversion to Sodium Salt] described in step 11 of Example 1 to afford the title compound (15.6 mg).

MS(ESI)m/z: 773 (M+H)$^+$.

$^1$H-NMR (CD$_3$OD) δ: 8.83 (1H, s), 8.27 (1H, s), 8.02 (1H, s), 7.10 (1H, s), 6.35 (1H, d, J=7.9 Hz), 6.32 (1H, d, J=6.7 Hz), 5.55-5.43 (2H, m), 4.81 (1H, dd, J=7.0, 4.5 Hz), 4.52-4.29 (5H, m), 4.06-4.00 (1H, m), 3.93-3.80 (3H, m), 3.52-3.47 (2H, m), 3.21 (2H, t, J=5.7 Hz), 2.94-2.88 (2H, m), 2.05-1.96 (2H, m).

$^{31}$P-NMR (CD$_3$OD) δ: 63.1 (s), 60.1 (s).

Example 14: Synthesis of CDN14
(5R,7R,8R,12aR,14R,15R,15aS,16R)-15,16-Dihydroxy-7-{6-[(2-hydroxyethyl)amino]-9H-purin-9-yl}-2,10-bis(sulfanyl)-14-(6,7,8,9-tetrahydro-2H-2,3,5,6-tetraazabenzo[cd]azulen-2-yl)octahydro-2H,10H,12H-5,8-methano-2λ$^5$,10λ$^5$-furo[3,2-1][1,3,6,9,11,2,10]pentaoxadiphosphacyclotetradecine-2,10-dione
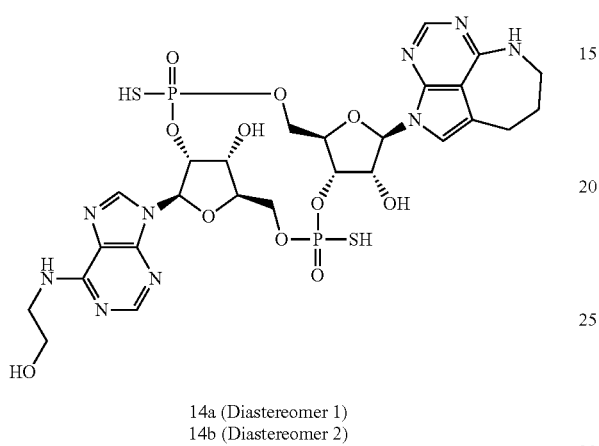
14a (Diastereomer 1)
14b (Diastereomer 2)
[Synthesis Scheme]
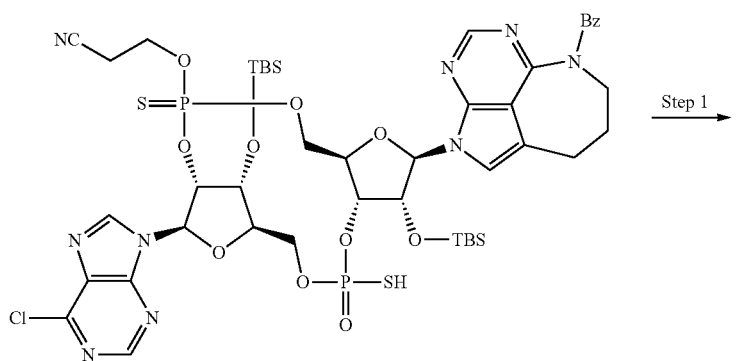
Step 1
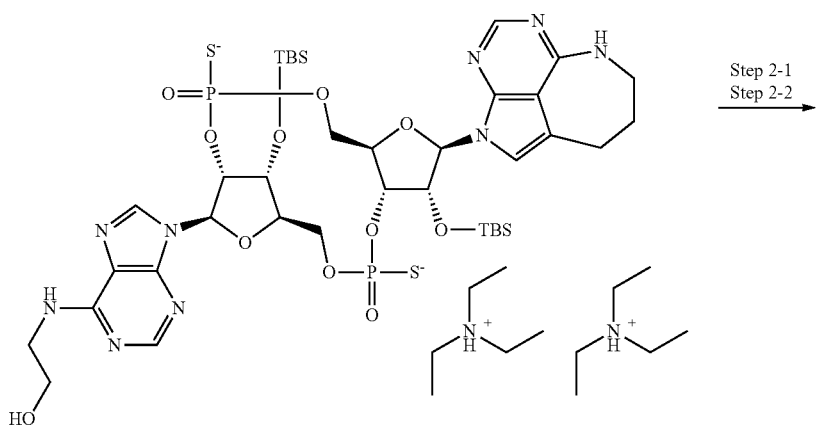
Step 2-1
Step 2-2

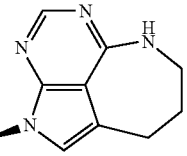
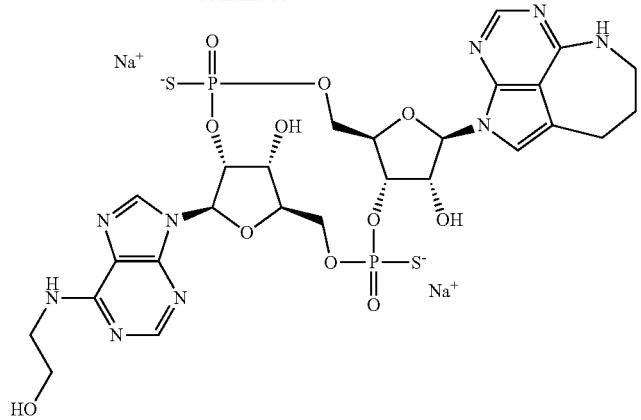

(Step 1)

Bis(N,N-diethylethaneaminium) (5R,7R,8R,12aR, 14R,15R,15aR,16R)-15,16-bis{[tert-butyl(dimethyl) silyl]oxy}-7-{6-[(2-hydroxyethyl)amino]-9H-purin-9-yl}-2,10-dioxo-14-(6,7,8,9-tetrahydro-2H-2,3,5,6-tetraazabenzo[cd]azulen-2-yl)octahydro-2H,10H, 12H-5,8-methano-2$\lambda^5$,10$\lambda^5$-furo[3,2-1][1,3,6,9,11,2, 10]pentaoxadiphosphacyclotetradecine-2,10-bis (thiolate)

To a solution of the compound obtained in step 4 of Example 13 (313 mg) in ethanol (10 mL), 2-aminoethanol (0.330 mL) and triethylamine (0.769 mL) were added, and the reaction mixture was stirred at 60° C. for 15 hours. After the reaction mixture was concentrated under reduced pressure, the residue was purified by C18 silica gel column chromatography [10 mM aqueous solution of triethylammonium acetate/acetonitrile] to afford diastereomer 1 (111 mg: with impurities) and diastereomer 2 (102 mg: with impurities) of the title compound.

Diastereomer 1 (Less Polar)
MS(ESI)m/z: 1002 (M+H)$^+$.
Diastereomer 2 (More Polar)
MS(ESI)m/z: 1002 (M+H)$^+$.

(Step 2-1)

Disodium (5R,7R,8R,12aR,14R,15R,15aS,16R)-15, 16-dihydroxy-7-{6-[(2-hydroxyethyl)amino]-9H-purin-9-yl}-2,10-dioxo-14-(6,7,8,9-tetrahydro-2H-2, 3,5,6-tetraazabenzo[cd]azulen-2-yl)octahydro-2H, 10H,12H-5,8-methano-2$\lambda^5$,10$\lambda^5$-furo[3,2-1][1,3,6,9, 11,2,10]pentaoxadiphosphacyclotetradecine-2,10-bis (thiolate)

(Diastereomer 1)

With use of the compound obtained in step 1 (diastereomer 1) (111 mg: with impurities), the reaction was performed in the same manner as in step 11 of Example 1, and purification was then performed under the following [Purification Conditions] to afford the title compound as a triethylamine salt.

[Purification Conditions] C18 silica gel column chromatography [10 mM aqueous solution of triethylammonium acetate/acetonitrile] and preparative HPLC [10 mM aqueous solution of triethylammonium acetate/acetonitrile, acetonitrile: 5%-30% (0 min-40 min)].

The triethylamine salt obtained was subjected to salt exchange in the same manner as in [Conversion to Sodium Salt] described in step 11 of Example 1 to afford the title compound (47.1 mg).

MS(ESI)m/z: 774 (M+H)$^+$.

$^1$H-NMR (CD$_3$OD) δ: 8.70 (1H, s), 8.22 (1H, s), 8.03 (1H, s), 7.10 (1H, s), 6.34 (1H, d, J=8.5 Hz), 6.29 (1H, d, J=4.8 Hz), 5.41-5.34 (1H, m), 5.19-5.13 (1H, m), 4.84 (1H, d, J=4.2 Hz), 4.79 (1H, dd, J=4.8, 2.4 Hz), 4.52-4.41 (2H, m), 4.39-4.31 (2H, m), 4.07-3.96 (2H, m), 3.81-3.66 (4H, m), 3.52-3.47 (2H, m), 2.90-2.77 (2H, m), 2.03-1.95 (2H, m).

$^{31}$P-NMR (CD$_3$OD) δ: 57.9 (s), 54.4 (s).

(Step 2-2)

Disodium (5R,7R,8R,12aR,14R,15R,15aS,16R)-15, 16-dihydroxy-7-{6-[(2-hydroxyethyl)amino]-9H-purin-9-yl}-2,10-dioxo-14-(6,7,8,9-tetrahydro-2H-2, 3,5,6-tetraazabenzo[cd]azulen-2-yl)octahydro-2H, 10H,12H-5,8-methano-2$\lambda^5$,10$\lambda^5$-furo[3,2-1][1,3,6,9, 11,2,10]pentaoxadiphosphacyclotetradecine-2,10-bis (thiolate)

(Diastereomer 2)

With use of the compound obtained in step 1 (diastereomer 2) (102 mg: with impurities), the reaction was performed in the same manner as in step 11 of Example 1, and purification was then performed under the following [Purification Conditions] to afford the title compound as a triethylamine salt.

[Purification Conditions] C18 silica gel column chromatography [10 mM aqueous solution of triethylammonium acetate/acetonitrile] and preparative HPLC [10 mM aqueous solution of triethylammonium acetate/acetonitrile, acetonitrile: 5%-25% (0 min-40 min)].

The triethylamine salt obtained was subjected to salt exchange in the same manner as in [Conversion to Sodium Salt] described in step 11 of Example 1 to afford the title compound (27.1 mg).

MS(ESI)m/z: 774 (M+H)$^+$.

$^1$H-NMR (CD$_3$OD) δ: 8.78 (1H, s), 8.22 (1H, s), 8.02 (1H, s), 7.12 (1H, s), 6.34 (1H, d, J=1.8 Hz), 6.32 (1H, s), 5.52-5.42 (2H, m), 4.80 (1H, dd, J=6.7, 4.8 Hz), 4.50-4.28 (5H, m), 4.05-3.98 (1H, m), 3.93-3.86 (1H, m), 3.81-3.68 (4H, m), 3.53-3.47 (2H, m), 2.95-2.88 (2H, m), 2.05-1.98 (2H, m).

$^{31}$P-NMR (CD$_3$OD) δ: 63.0 (s), 60.2 (s).

Example 15: Synthesis of CDN15

N-[2-({9-[(5R,7R,8R,12aR,14R,15R,15aS,16R)-15,16-Dihydroxy-2,10-dioxo-2,10-bis(sulfanyl)-14-(6,7,8,9-tetrahydro-2H-2,3,5,6-tetraazabenzo[cd]azulen-2-yl)octahydro-2H,10H,12H-5,8-methano-2$\lambda^5$,10$\lambda^5$-furo[3,2-1][1,3,6,9,11,2,10]pentaoxadiphosphacyclotetradecin-7-yl]-9H-purin-6-yl}amino)ethyl]-2-hydroxyacetamide

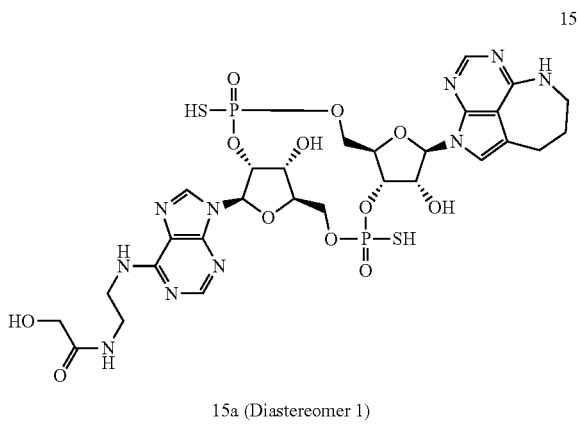 [SMILES: O=C(CO)NCCNc1ncnc2c1ncn2[C@@H]1O[C@@H]2COP(=O)(S)O[C@H]3[C@@H](O)[C@H](n4cc5c6c(ncnc64)NCCC5)O[C@@H]3COP(=O)(S)O[C@@H]1[C@@H]2O]

15a (Diastereomer 1)

[Synthesis Scheme]

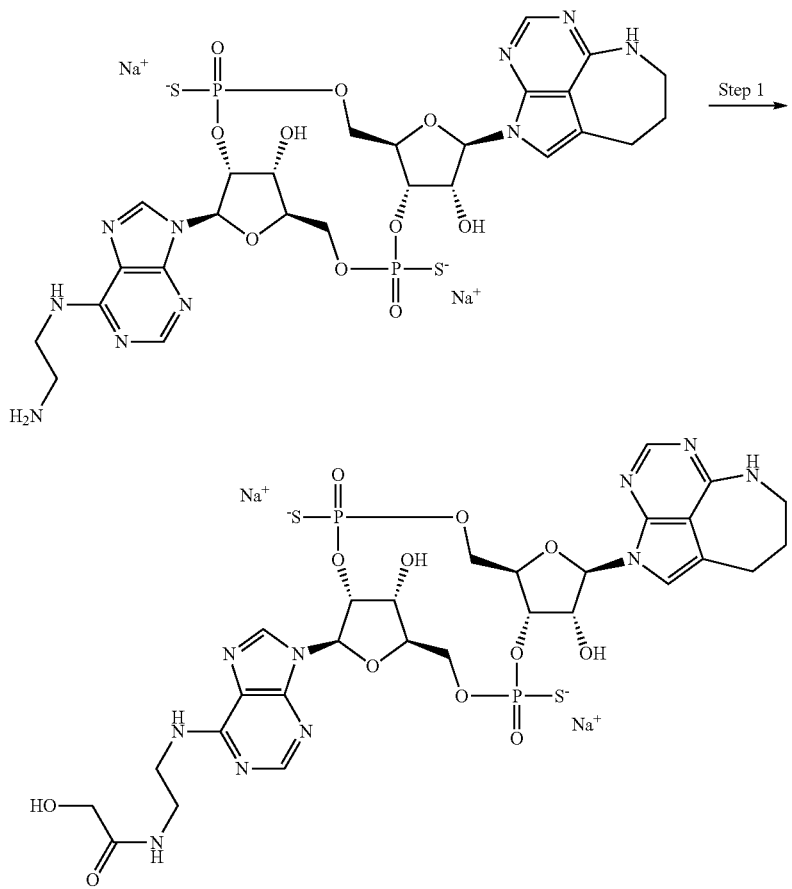

(Step 1)

Disodium (5R,7R,8R,12aR,14R,15R,15aS,16R)-15,16-dihydroxy-7-(6-{[2-(2-hydroxyacetamide)ethyl]amino}-9H-purin-9-yl)-2,10-dioxo-14-(6,7,8,9-tetrahydro-2H-2,3,5,6-tetraazabenzo[cd]azulen-2-yl)octahydro-2H,10H,12H-5,8-methano-2$\lambda^5$,10$\lambda^5$-furo[3,2-1][1,3,6,9,11,2,10]pentaoxadiphosphacyclotetradecine-2,10-bis(thiolate)

With use of the compound obtained in step 6-2 of Example 13 (10.0 mg), the reaction was performed in the same manner as in step 1-1 of Example 7, and purification was then performed under the following [Purification Conditions] to afford the title compound as a triethylamine salt.

[Purification Conditions] C18 silica gel column chromatography [10 mM aqueous solution of triethylammonium acetate/acetonitrile], preparative HPLC [10 mM aqueous solution of triethylammonium acetate/acetonitrile, acetonitrile: 5%-35% (0 min-40 min)].

The triethylamine salt obtained was subjected to salt exchange in the same manner as in [Conversion to Sodium Salt] described in step 11 of Example 1 to afford the title compound (6.6 mg).

MS(ESI)m/z: 831 (M+H)$^+$.

$^1$H-NMR (CD$_3$OD) δ: 8.78 (1H, s), 8.24 (1H, s), 8.02 (1H, s), 7.12 (1H, s), 6.33 (2H, d, J=6.7 Hz), 5.52-5.42 (2H, m), 4.80 (1H, dd, J=6.7, 4.2 Hz), 4.50-4.27 (5H, m), 4.04-3.98

(1H, m), 3.95 (2H, s), 3.93-3.86 (1H, m), 3.83-3.73 (2H, m), 3.58-3.46 (4H, m), 2.95-2.88 (2H, m), 2.05-1.98 (2H, m).
$^{31}$P-NMR (CD$_3$OD) δ: 63.1 (s), 60.4 (s).
Example 16: Synthesis of CDN16
(5R,7R,8R,12aR,14R,15R,15aS,16R)-7-{2-Amino-6-[(2-hydroxyethyl)amino]-9H-purin-9-yl}-15,16-dihydroxy-2,10-bis(sulfanyl)-14-(6,7,8,9-tetrahydro-2H-2,3,5,6-tetraazabenzo[cd]azulen-2-yl)octahydro-2H,10H,12H-5,8-methano-2λ$^5$,10λ$^5$-furo[3,2-l][1,3,6,9,11,2,10]pentaoxadiphosphacyclotetradecine-2,10-dione
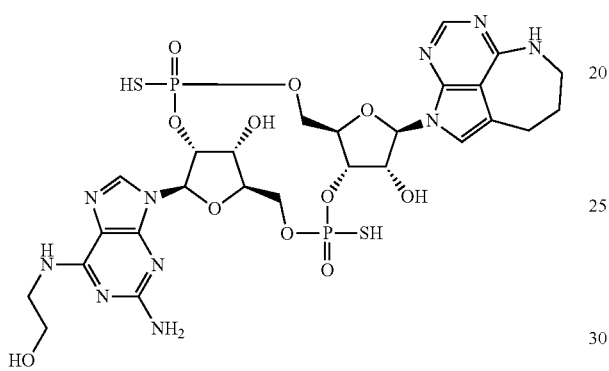
16a (Diastereomer 1)
16b (Diastereomer 2)
[Synthesis Scheme]
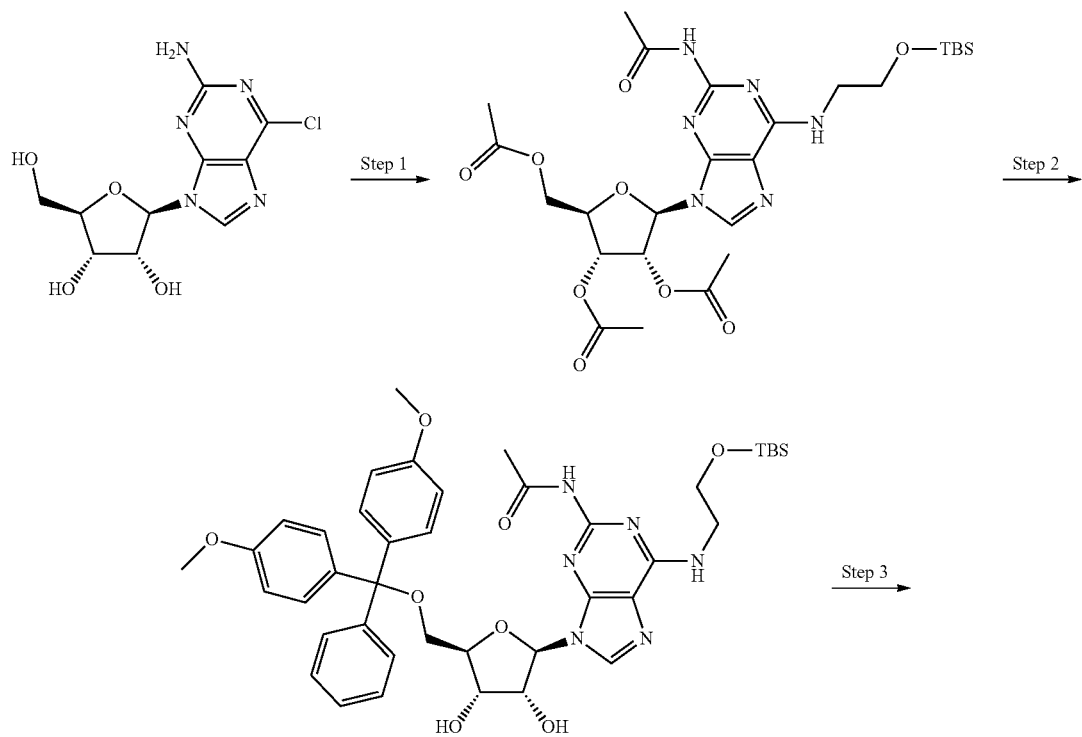

-continued
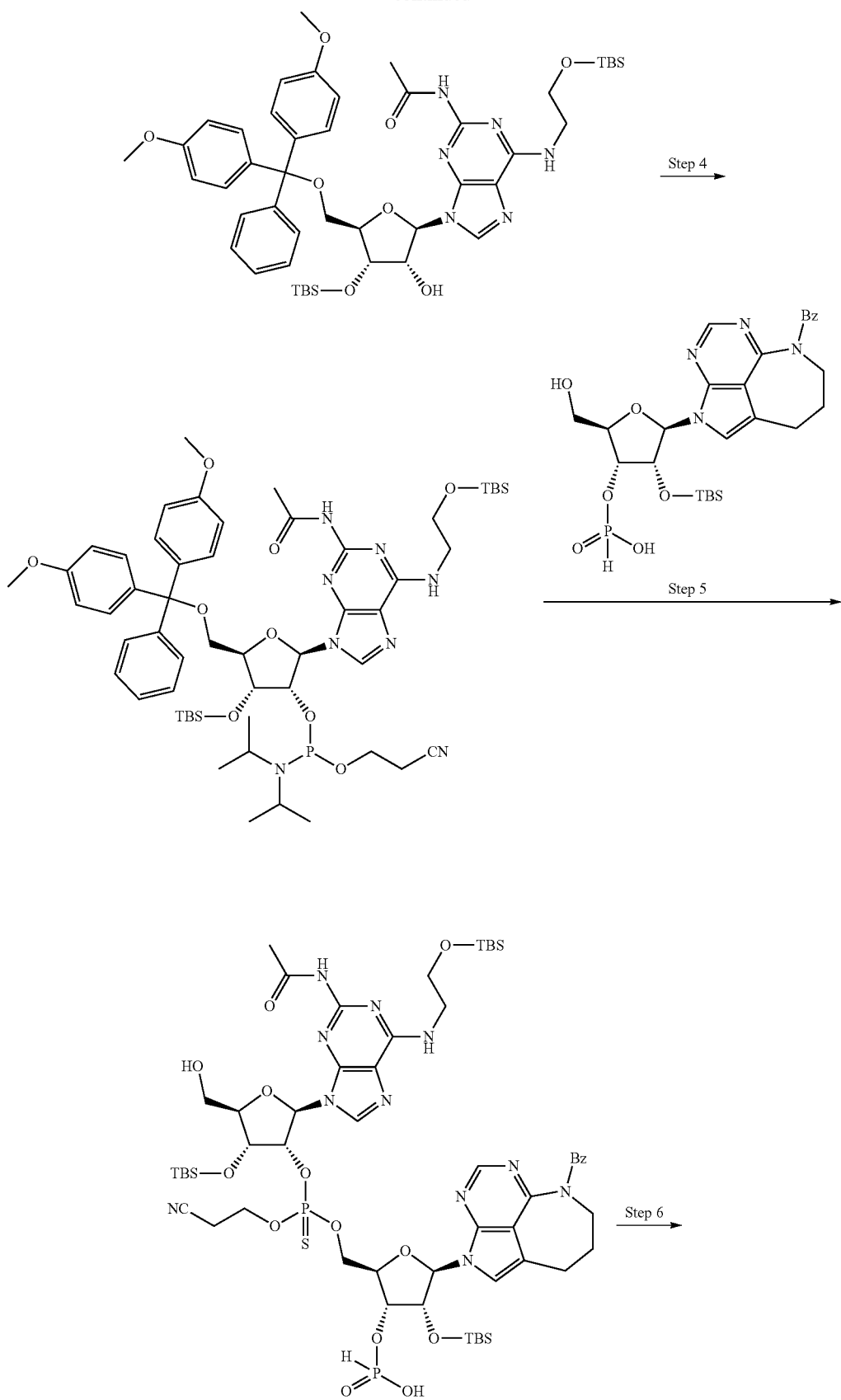

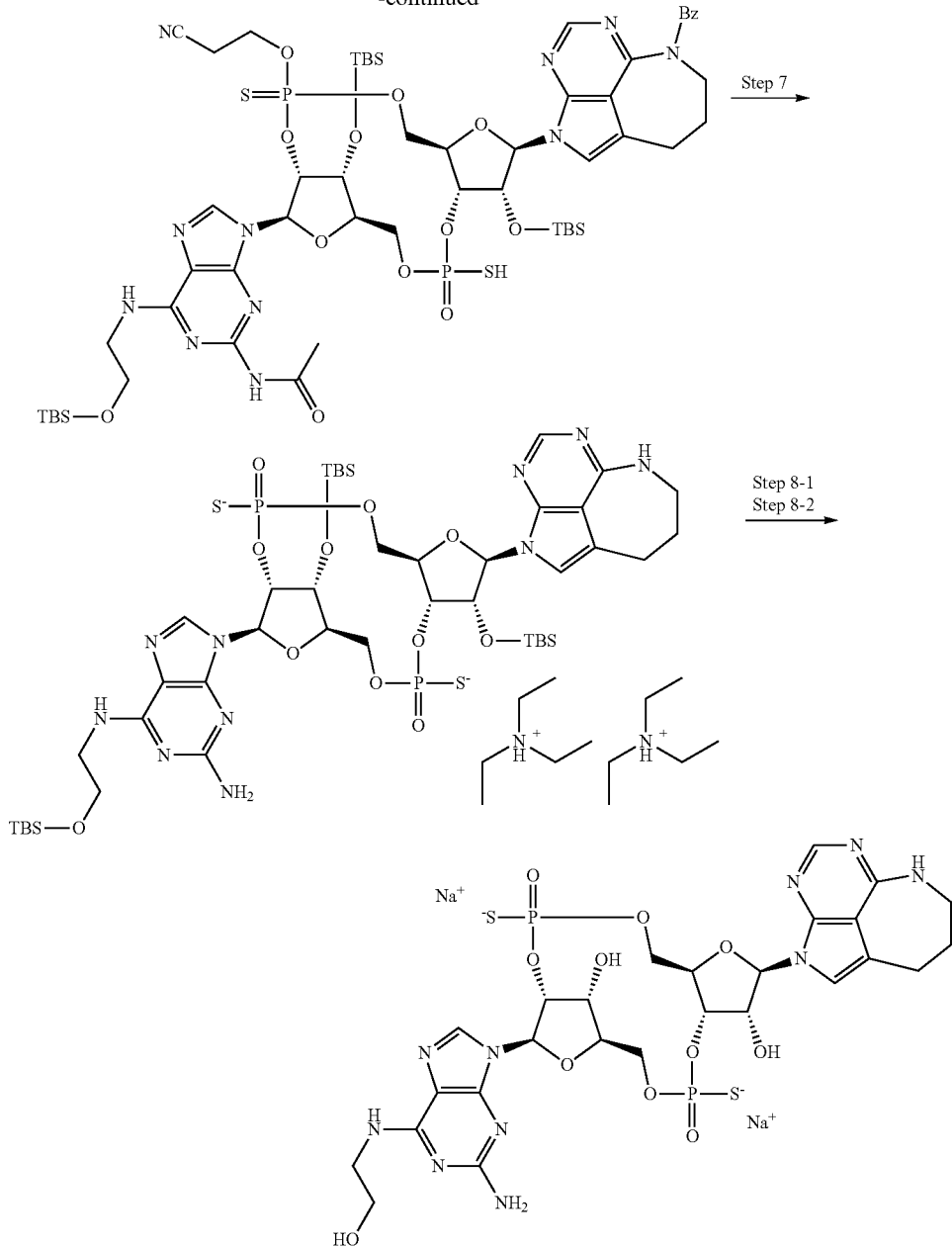

(Step 1)

2-Acetamido-2',3',5'-tri-O-acetyl-N-(2-{[tert-butyl(dimethyl)silyl]oxy}ethyl) adenosine To a solution of commercially available (Tokyo Chemical Industry Co., Ltd.) 6-chloro-9-β-D-ribofuranosyl-9H-purin-2-amine (5.00 g) in ethanol (30 mL), 2-{[tert-butyl(dimethyl)silyl]oxy}ethan-1-amine (3.49 g) and N,N-diisopropylethylamine (4.33 mL) were added, and the reaction mixture was stirred at 80° C. for 65 hours. After the reaction mixture was concentrated under reduced pressure, pyridine (15 mL) and acetic anhydride (15 mL) were added to the residue, and the reaction mixture was stirred at 70° C. for 4 hours. After the reaction mixture was concentrated under reduced pressure, saturated aqueous solution of sodium hydrogen carbonate was added to the reaction mixture, which was subjected to extraction with ethyl acetate. After the organic layer was dried over anhydrous sodium sulfate, the drying agent was removed through filtration, and the filtrate was concentrated under reduced pressure. The residue was purified by silica gel column chromatography [hexane/ethyl acetate] to afford the title compound (8.91 g).

MS(ESI)m/z: 609 (M+H)$^+$.

$^1$H-NMR (CDCl$_3$) δ: 7.84 (1H, s), 7.77 (1H, s), 6.14 (1H, brs), 6.03 (1H, d, J=4.8 Hz), 5.92 (1H, t, J=5.1 Hz), 5.72 (1H, t, J=5.1 Hz), 4.50-4.40 (2H, m), 4.35 (1H, dd, J=11.8, 4.5 Hz), 3.83 (2H, t, J=5.1 Hz), 3.76-3.63 (2H, m), 2.54 (3H, s), 2.14 (3H, s), 2.10 (6H, s), 0.91 (9H, s), 0.07 (6H, s).

(Step 2)

2-Acetamido-5'-O-[bis(4-methoxyphenyl)(phenyl)methyl]-N-(2-{[tert-butyl(dimethyl)silyl]oxy}ethyl) adenosine To a solution of the compound obtained in step 1 (4.00 g) in dichloromethane (40 mL), a methanol solution of sodium methoxide (1.0 M, 6.64 mL) were added, and the reaction mixture was stirred at 0° C. for 1 hour. After acetic acid (0.413 mL) and pyridine (0.5 mL) were added to the reaction mixture to quench the reaction, the reaction mixture was concentrated under reduced pressure. Pyridine was added to the residue, and the resultant was then partially concentrated under reduced pressure to prepare a pyridine solution (approximately 20 mL). To this solution, 4,4'-dimethoxytrityl chloride (4.68 g) was added at 0° C., and the reaction mixture was stirred at the same temperature for 30 minutes, and then stored at 4° C. overnight. Methanol (2 mL) was added to the reaction mixture, which was stirred for 30 minutes, and then concentrated under reduced pressure. The residue was purified by silica gel column chromatography [hexane/ethyl acetate/methanol/0.1% triethylamine] to afford the title compound (4.41 g).

MS(ESI)m/z: 785 (M+H)$^+$.

$^1$H-NMR (CDCl$_3$) δ: 7.97 (1H, s), 7.90 (1H, s), 7.21-7.08 (9H, m), 6.73-6.67 (4H, m), 6.14 (1H, s), 5.88 (1H, d, J=6.7 Hz), 4.91-4.85 (1H, m), 4.46 (1H, t, J=3.0 Hz), 4.32 (1H, d, J=5.4 Hz), 3.86-3.80 (2H, m), 3.76 (3H, s), 3.76 (3H, s), 3.70-3.66 (1H, m), 3.42-3.34 (2H, m), 3.13 (1H, dd, J=10.6, 2.7 Hz), 2.24 (3H, s), 0.90 (9H, s), 0.07 (3H, s), 0.07 (3H, s). (only observable peaks are shown)

(Step 3)

2-Acetamido-5'-O-[bis(4-methoxyphenyl)(phenyl)methyl]-3'-O-[tert-butyl(dimethyl)silyl]-N-(2-{[tert-butyl(dimethyl)silyl]oxy}ethyl) adenosine With use of the compound obtained in step 2 (4.41 g), the reaction was performed in the same manner as in step 3 of Example 5 to afford the title compound (1.75 g) and 2-acetamido-5'-O-[bis(4-methoxyphenyl)(phenyl)methyl]-2'-O-[tert-butyl(dimethyl)silyl]-N-(2-{[tert-butyl(dimethyl)silyl]oxy}ethyl) adenosine (1.31 g) as a regioisomer of the title compound.

MS(ESI)m/z: 899 (M+H)$^+$.

$^1$H-NMR (CDCl$_3$) δ: 7.89 (1H, s), 7.69 (1H, brs), 7.39-7.34 (2H, m), 7.29-7.18 (7H, m), 6.80-6.75 (4H, m), 6.11 (1H, brs), 5.89 (1H, d, J=5.4 Hz), 4.65 (1H, dd, J=5.4, 2.7 Hz), 4.43 (1H, dd, J=5.1, 3.3 Hz), 4.19-4.15 (1H, m), 3.83 (2H, dd, J=5.4, 2.7 Hz), 3.77 (6H, s), 3.74-3.63 (2H, m), 3.40 (1H, dd, J=10.9, 3.6 Hz), 3.22 (1H, dd, J=10.9, 3.9 Hz), 2.43 (3H, s), 0.90 (9H, s), 0.88 (9H, s), 0.10 (3H, s), 0.06 (6H, s), 0.03 (3H, s). (only observable peaks are shown)

Regioisomer (2'-O-TBS form)

MS(ESI)m/z: 899 (M+H)$^+$.

$^1$H-NMR (CDCl$_3$) δ: 7.84 (1H, s), 7.52 (1H, brs), 7.48-7.44 (2H, m), 7.37-7.32 (4H, m), 7.29-7.18 (3H, m), 6.83-6.78 (4H, m), 6.12 (1H, brs), 5.89 (1H, d, J=6.0 Hz), 4.96-4.89 (1H, m), 4.32-4.27 (1H, m), 4.24 (1H, dd, J=3.2, 1.6 Hz), 3.84 (2H, dd, J=5.4, 2.7 Hz), 3.78 (6H, s), 3.75-3.65 (2H, m), 3.48 (1H, dd, J=10.6, 2.7 Hz), 3.35 (1H, dd, J=10.6, 3.6 Hz), 2.72 (1H, d, J=3.0 Hz), 2.37 (3H, s), 0.91 (9H, s), 0.84 (9H, s), 0.07 (6H, s), −0.01 (3H, s), −0.17 (3H, s).

(Step 4)

2-Acetamido-5'-O-[bis(4-methoxyphenyl)(phenyl)methyl]-3'-O-[tert-butyl(dimethyl)silyl]-N-(2-{[tert-butyl(dimethyl)silyl]oxy}ethyl)-2'-O-{(2-cyanoethoxy)[di(propan-2-yl)amino]phosphanyl}adenosine With use of the compound obtained in step 3 (1.75 g), the reaction was performed in the same manner as in step 4 of Example 5 to afford the title compound (2.08 g) as a mixture of diastereomers at the phosphorus atom (diastereomer ratio=6:4).

MS(ESI)m/z: 1099 (M+H)$^+$.

$^1$H-NMR (CDCl$_3$) δ: 7.90 (0.6H, s), 7.88 (0.4H, s), 7.61 (1H, d, J=7.3 Hz), 7.45-7.18 (9H, m), 6.81 (4H, m), 6.10 (0.6H, d, J=5.4 Hz), 6.09 (1H, brs), 6.06 (0.4H, d, J=4.8 Hz), 4.95-4.85 (0.6H, m), 4.76-4.69 (0.4H, s), 4.45-4.41 (0.6H, m), 4.40-4.36 (0.4H, m), 4.19-4.13 (1H, m), 3.86-3.80 (2H, m), 3.78 (6H, s), 3.75-3.41 (8H, m), 3.32-3.22 (1H, m), 2.55-2.45 (3H, m), 2.36-2.30 (1H, m), 1.30-1.10 (9H, m), 0.92 (1.2H, d, J=6.7 Hz), 0.90 (9H, s), 0.85 (9H, s), 0.76 (1.8H, d, J=6.7 Hz), 0.10 (1.8H, s), 0.07 (1.2H, s), 0.06 (6H, s), 0.00 (3H, s).

(Step 5)

The same reaction as in step 7 of Example 1 was performed in the following scale (raw material: 981 mg). With use of an acetonitrile solution of the compound obtained and the compound obtained in step 4 (1.05 g), the reaction was performed in the same manner as in step 8 of Example 1. The resulting crude product was directly used for the subsequent reaction.

(Step 6)

N-{9-[(5R,7R,8R,12aR,14R,15R,15aR,16R)-14-(6-Benzoyl-6,7,8,9-tetrahydro-2H-2,3,5,6-tetraazabenzo[cd]azulen-2-yl)-15,16-bis{[tert-butyl(dimethyl)silyl]oxy}-10-(2-cyanoethoxy)-2-oxo-2-sulfanyl-10-sulfanylideneoctahydro-2H,10H,12H-5,8-methano-2λ$^5$,10λ$^5$-furo[3,2-1][1,3,6,9,11,2,10]pentaoxadiphosphacyclotetradecin-7-yl]-6-[(2-{[tert-butyl(dimethyl)silyl]oxy}ethyl)amino]-9H-purin-2-yl}acetamide With use of the crude product obtained in step 5, the reaction was performed in the same manner as in step 9 of Example 1 to afford the title compound (413 mg) as a mixture of diastereomers at the phosphorus atom.

MS(ESI)m/z: 1330 (M+H)$^+$.

(Step 7)

Bis(N,N-diethylethaneaminium) (5R,7R,8R,12aR,14R,15R,15aR,16R)-7-{2-amino-6-[(2-{[tert-butyl(dimethyl)silyl]oxy}ethyl)amino]-9H-purin-9-yl}-15,16-bis{[tert-butyl(dimethyl)silyl]oxy}-2,10-dioxo-14-(6,7,8,9-tetrahydro-2H-2,3,5,6-tetraazabenzo[cd]azulen-2-yl)octahydro-2H,10H,12H-5,8-methano-2λ$^5$,10λ$^5$-furo[3,2-1][1,3,6,9,11,2,10]pentaoxadiphosphacyclotetradecine-2,10-bis(thiolate)

The compound obtained in step 6 (413 mg) was dissolved in methanol (5 mL) and 28% ammonia water (5 mL), and the reaction mixture was stirred at room temperature for 63 hours. After the reaction mixture was concentrated under reduced pressure, the residue was simply purified by C18 silica gel column chromatography [10 mM aqueous solution of triethylammonium acetate/acetonitrile], and diastereomer 1 with less polar and diastereomer 2 with more polar were separated from each other. The diastereomers were each again dissolved in methanol (5 mL) and 28% ammonia water (5 mL), and each reaction mixture was stirred at 100° C. for 2 days. After each reaction mixture was concentrated under reduced pressure, each residue was purified by C18 silica gel column chromatography [10 mM aqueous solution of triethylammonium acetate/acetonitrile] to afford diastereomer 1 (70.4 mg: with impurities) and diastereomer 2 (65.1 mg: with impurities) of the title compound.

Diastereomer 1 (Less Polar)

MS(ESI)m/z: 1131 (M+H)$^+$.

Diastereomer 2 (More Polar)

MS(ESI)m/z: 1131 (M+H)$^+$.

(Step 8-1)

Disodium (5R,7R,8R,12aR,14R,15R,15aS,16R)-7-{2-amino-6-[(2-hydroxyethyl)amino]-9H-purin-9-yl}-15,16-dihydroxy-2,10-dioxo-14-(6,7,8,9-tetrahydro-2H-2,3,5,6-tetraazabenzo[cd]azulen-2-yl)octahydro-2H,10H,12H-5,8-methano-2$\lambda^5$,10$\lambda^5$-furo[3,2-1][1,3,6,9,11,2,10]pentaoxadiphosphacyclotetradecine-2,10-bis(thiolate)

(Diastereomer 1)

With use of the compound obtained in step 7 (diastereomer 1) (70.4 mg: with impurities), the reaction was performed in the same manner as in step 11 of Example 1, and purification was then performed under the following [Purification Conditions] to afford the title compound as a triethylamine salt.

[Purification Conditions] C18 silica gel column chromatography [10 mM aqueous solution of triethylammonium acetate/acetonitrile] and preparative HPLC [10 mM aqueous solution of triethylammonium acetate/acetonitrile, acetonitrile: 5%-30% (0 min-40 min)].

The triethylamine salt obtained was subjected to salt exchange in the same manner as in [Conversion to Sodium Salt] described in step 11 of Example 1 to afford the title compound (20.8 mg).

MS(ESI)m/z: 789 (M+H)$^+$.

$^1$H-NMR (CD$_3$OD) δ: 8.24 (1H, s), 8.02 (1H, s), 7.09 (1H, s), 6.29 (1H, d, J=4.2 Hz), 6.12 (1H, d, J=8.5 Hz), 5.46-5.39 (1H, m), 5.22-5.15 (1H, m), 4.84 (1H, d, J=3.6 Hz), 4.80 (1H, t, J=4.5 Hz), 4.50-4.32 (3H, m), 4.32-4.28 (1H, m), 4.12-3.98 (2H, m), 3.74 (2H, t, J=5.4 Hz), 3.68-3.60 (2H, m), 3.48 (2H, t, J=5.4 Hz), 2.87-2.70 (2H, m), 2.01-1.93 (2H, m).

$^{31}$P-NMR (CD$_3$OD) δ: 57.8 (s), 54.1 (s).

(Step 8-2)

Disodium (5R,7R,8R,12aR,14R,15R,15aS,16R)-7-{2-amino-6-[(2-hydroxyethyl)amino]-9H-purin-9-yl}-15,16-dihydroxy-2,10-dioxo-14-(6,7,8,9-tetrahydro-2H-2,3,5,6-tetraazabenzo[cd]azulen-2-yl)octahydro-2H, 10H,12H-5,8-methano-2$\lambda^5$,10$\lambda^5$-furo[3,2-1][1,3,6,9,11,2,10]pentaoxadiphosphacyclotetradecine-2,10-bis(thiolate)

(Diastereomer 2)

With use of the compound obtained in step 7 (diastereomer 2) (65.1 mg: with impurities), the reaction was performed in the same manner as in step 11 of Example 1, and purification was then performed under the following [Purification Conditions] to afford the title compound as a triethylamine salt.

[Purification Conditions] C18 silica gel column chromatography [10 mM aqueous solution of triethylammonium acetate/acetonitrile], preparative HPLC [10 mM aqueous solution of triethylammonium acetate/acetonitrile, acetonitrile: 5%-30% (0 min-40 min)], and preparative HPLC [10 mM aqueous solution of triethylammonium acetate/methanol, methanol: 0%-60% (0 min-40 min)].

The triethylamine salt obtained was subjected to salt exchange in the same manner as in [Conversion to Sodium Salt] described in step 11 of Example 1 to afford the title compound (7.9 mg).

MS(ESI)m/z: 789 (M+H)$^+$.

$^1$H-NMR (CD$_3$OD) δ: 8.39 (1H, s), 8.02 (1H, s), 7.13 (1H, s), 6.33 (1H, d, J=6.7 Hz), 6.13 (1H, d, J=8.5 Hz), 5.51-5.40 (2H, m), 4.83-4.78 (1H, m), 4.51-4.29 (4H, m), 4.28-4.23 (1H, m), 4.07-4.00 (1H, m), 3.94-3.87 (1H, m), 3.75 (2H, t, J=5.7 Hz), 3.69-3.62 (2H, m), 3.53-3.47 (2H, m), 2.91 (2H, t, J=5.7 Hz), 2.05-1.97 (2H, m).

$^{31}$P-NMR (CD$_3$OD) δ: 62.9 (s), 60.3 (s).

Example 17: Synthesis of CDN17

(5R,7R,8R,12aR,14R,15R,15aS,16R)-15,16-Dihydroxy-7-[6-(hydroxymethyl)-9H-purin-9-yl]-2,10-bis(sulfanyl)-14-(6,7,8,9-tetrahydro-2H-2,3,5,6-tetraazabenzo[cd]azulen-2-yl)octahydro-2H,10H,12H-5,8-methano-2$\lambda^5$,10$\lambda^5$-furo[3,2-1][1,3,6,9,11,2,10]pentaoxadiphosphacyclotetradecine-2,10-dione

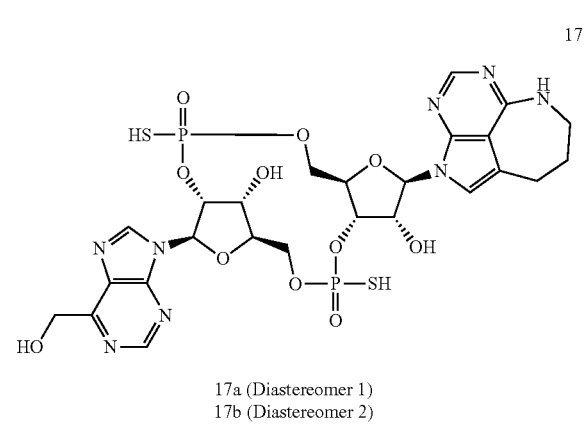 [SMILES: O=P1(S)OC[C@H]2O[C@@H](n3cc4c5c(ncnc53)NCCC4)[C@H](O)[C@@H]2OP(=O)(S)OC[C@H]2O[C@@H](n3cnc4c(CO)ncnc43)[C@H](O1)[C@@H]2O]

17

17a (Diastereomer 1)
17b (Diastereomer 2)

[Synthesis Scheme]
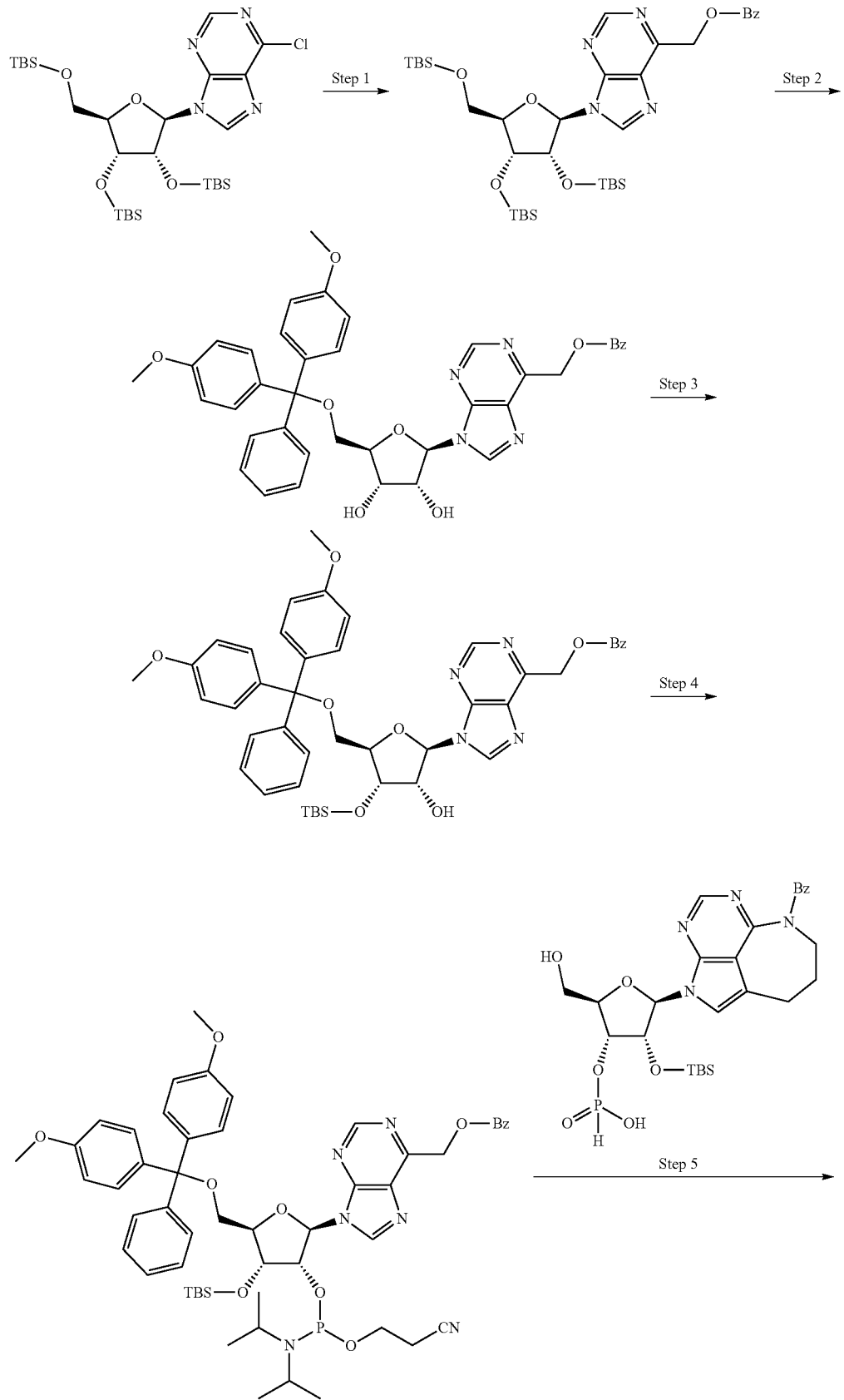

-continued
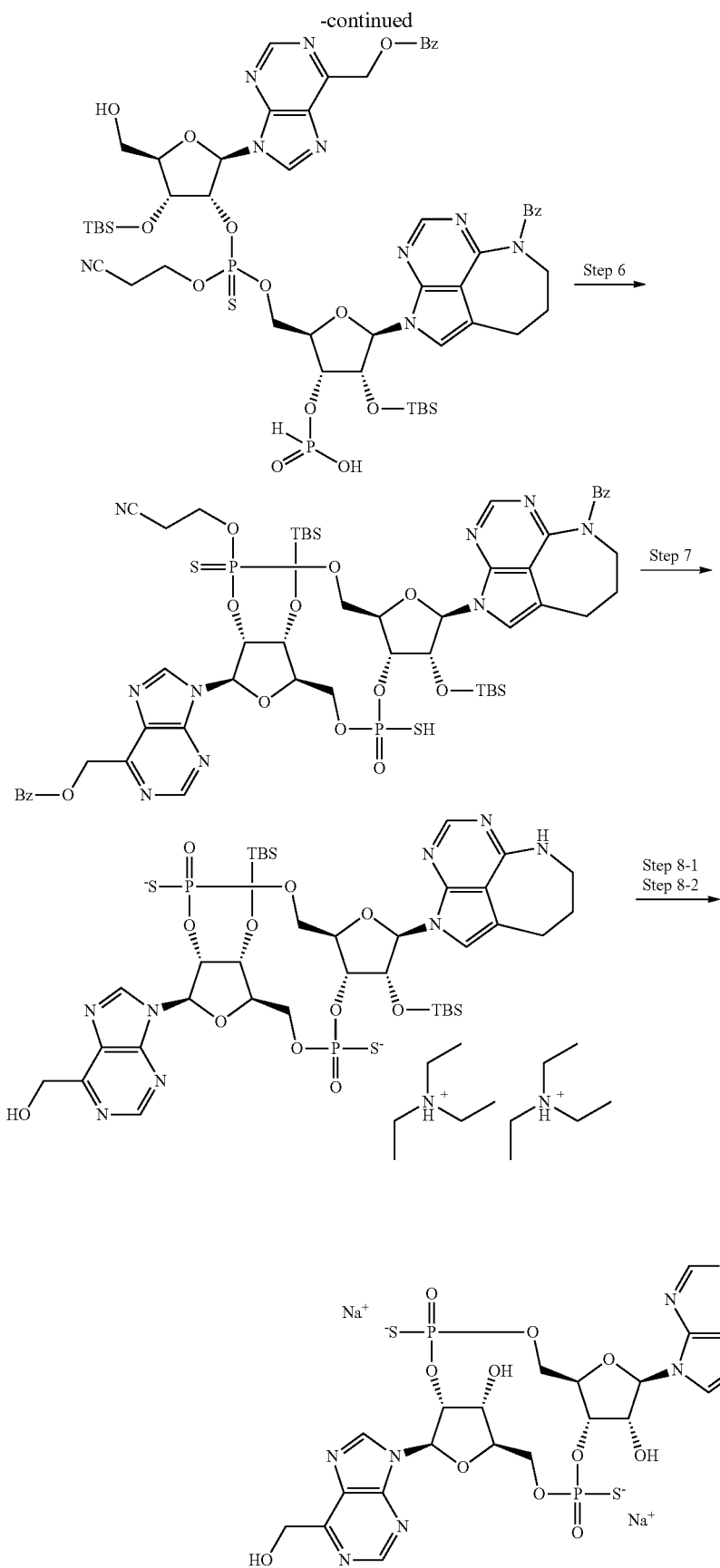

(Step 1)

6-[(Benzoyloxy)methyl]-9-{2,3,5-tris-O-[tert-butyl(dimethyl)silyl]-β-D-ribofuranosyl}-9H-purine With use of 6-chloro-9-{2,3,5-tris-O-[tert-butyl(dimethyl)silyl]-β-D-ribofuranosyl}-9H-purine (10.7 g) as a compound known in the literature (J. Org. Chem. 1997, 62, 6833-6841), the reaction was performed in the same manner as in step 2 of Example 12 to afford the title compound (10.4 g).

MS(ESI)m/z: 729 (M+H)$^+$.

$^1$H-NMR (CDCl$_3$) δ: 8.94 (1H, s), 8.50 (1H, s), 8.18-8.13 (2H, m), 7.60-7.54 (1H, m), 7.48-7.41 (2H, m), 6.13 (1H, d, J=4.2 Hz), 5.88 (2H, s), 4.63 (1H, dd, J=4.5, 2.1 Hz), 4.34 (1H, dd, J=4.2, 2.1 Hz), 4.17-4.14 (1H, m), 4.04 (1H, dd, J=11.5, 3.6 Hz), 3.80 (1H, dd, J=11.5, 2.4 Hz), 0.94 (9H, s), 0.93 (9H, s), 0.80 (9H, s), 0.14 (3H, s), 0.13 (3H, s), 0.11 (3H, s), 0.10 (3H, s), −0.02 (3H, s), −0.20 (3H, s).

(Step 2)

6-[(Benzoyloxy)methyl]-9-{5-O-[bis(4-methoxyphenyl)(phenyl)methyl]-β-D-ribofuranosyl}-9H-purine To a solution of the compound obtained in step 1 (10.3 g) in tetrahydrofuran (50 mL), a tetrahydrofuran solution of tetrabutylammonium fluoride (approximately 1 M, 49.4 mL) was added, and the reaction mixture was stirred at 0° C. for 4 hours. Acetic acid (2.83 mL) was added to the reaction mixture, which was then concentrated under reduced pressure. The residue was partially purified by silica gel column chromatography [dichloromethane/methanol]. To a solution of the crude product in pyridine (50 mL), 4,4'-dimethoxytrityl chloride (10.1 g) was added at 0° C., and the reaction mixture was stirred at 4° C. overnight. Methanol (2 mL) was added to the reaction mixture, which was stirred for 1 hour. Saturated aqueous solution of sodium hydrogen carbonate was added to the reaction mixture, which was subjected to extraction with dichloromethane. After the organic layer was dried over anhydrous sodium sulfate, the drying agent was removed through filtration, and the filtrate was concentrated under reduced pressure. The residue was purified by silica gel column chromatography [hexane/ethyl acetate/0.1% triethylamine] to afford the title compound (4.62 g).

MS(ESI)m/z: 689 (M+H)$^+$.

$^1$H-NMR (CDCl$_3$) δ: 8.91 (1H, s), 8.33 (1H, s), 8.15-8.11 (2H, m), 7.60-7.54 (1H, m), 7.46-7.40 (2H, m), 7.27-7.12 (9H, m), 6.75-6.70 (4H, m), 6.04 (1H, d, J=6.0 Hz), 5.88 (2H, s), 5.43 (1H, brs), 4.90-4.84 (1H, m), 4.48-4.41 (2H, m), 3.76 (6H, s), 3.44 (1H, dd, J=10.6, 3.3 Hz), 3.30 (1H, dd, J=10.6, 3.3 Hz), 3.09 (1H, brs).

(Step 3)

6-[(Benzoyloxy)methyl]-9-{5-O-[bis(4-methoxyphenyl)(phenyl)methyl]-3-O-[tert-butyl(dimethyl)silyl]-β-D-ribofuranosyl}-9H-purine With use of the compound obtained in step 2 (4.53 g), the reaction was performed in the same manner as in step 3 of Example 5 to afford the title compound (2.09 g) and 6-[(benzoyloxy)methyl]-9-{5-O-[bis(4-methoxyphenyl)(phenyl)methyl]-2-O-[tert-butyl(dimethyl)silyl]-β-D-ribofuranosyl}-9H-purine (1.81 g) as a regioisomer of the title compound.

MS(ESI)m/z: 803 (M+H)$^+$.

$^1$H-NMR (CDCl$_3$) δ: 8.92 (1H, s), 8.32 (1H, s), 8.16-8.12 (2H, m), 7.60-7.54 (1H, m), 7.47-7.36 (4H, m), 7.31-7.17 (7H, m), 6.81-6.76 (4H, m), 6.07 (1H, d, J=4.8 Hz), 5.87 (2H, s), 4.81-4.74 (1H, m), 4.62-4.57 (1H, m), 4.22-4.17 (1H, m), 3.77 (6H, s), 3.52 (1H, dd, J=10.9, 3.6 Hz), 3.26 (1H, dd, J=10.9, 3.6 Hz), 3.12 (1H, d, J=6.7 Hz), 0.89 (9H, s), 0.09 (3H, s), 0.02 (3H, s).

Regioisomer (2'-O-TBS form)

MS(ESI)m/z: 803 (M+H)$^+$.

$^1$H-NMR (CDCl$_3$) δ: 8.87 (1H, s), 8.31 (1H, s), 8.17-8.13 (2H, m), 7.60-7.55 (1H, m), 7.48-7.42 (4H, m), 7.35-7.31 (4H, m), 7.28-7.17 (3H, m), 6.83-6.78 (4H, m), 6.12 (1H, d, J=5.4 Hz), 5.88 (2H, s), 4.99 (1H, dd, J=5.1, 2.6 Hz), 4.40-4.34 (1H, m), 4.28 (1H, dd, J=3.6, 2.0 Hz), 3.77 (6H, s), 3.53 (1H, dd, J=10.9, 3.0 Hz), 3.40 (1H, dd, J=10.9, 3.9 Hz), 2.68 (1H, d, J=4.8 Hz), 0.84 (9H, s), 0.00 (3H, s), −0.14 (3H, s).

(Step 4)

6-[(Benzoyloxy)methyl]-9-(5-O-[bis(4-methoxyphenyl)(phenyl)methyl]-3-O-[tert-butyl(dimethyl)silyl]-2-O-{(2-cyanoethoxy)[di(propan-2-yl)amino]phosphanyl}-β-D-ribofuranosyl)-9H-purine With use of the compound obtained in step 3 (2.04 g), the reaction was performed in the same manner as in step 4 of Example 5 to afford the title compound (2.37 g) as a mixture of diastereomers at the phosphorus atom (diastereomer ratio=56:44).

MS(ESI)m/z: 1003 (M+H)$^+$.

$^1$H-NMR (CDCl$_3$) δ: 8.88 (0.44H, s), 8.87 (0.56H, s), 8.37 (0.44H, s), 8.35 (0.56H, s), 8.16-8.11 (2H, m), 7.60-7.54 (1H, m), 7.47-7.38 (4H, m), 7.33-7.16 (7H, m), 6.83-6.76 (4H, m), 6.31 (0.44H, d, J=4.8 Hz), 6.21 (0.56H, d, J=4.8 Hz), 5.87 (0.88H, s), 5.86 (1.12H, s), 5.08-5.01 (0.56H, m), 4.86-4.80 (0.44H, m), 4.56-4.50 (1H, m), 4.27-4.20 (1H, m), 3.85-3.54 (2H, m), 3.78 (6H, s), 3.54-3.44 (3H, m), 3.34-3.25 (1H, m), 2.51 (1.12H, t, J=6.3 Hz), 2.34 (0.88H, t, J=6.3 Hz), 1.14-1.05 (9H, m), 0.90 (3H, d, J=6.7 Hz), 0.85 (5.04H, s), 0.85 (3.96H, s), 0.11 (1.68H, s), 0.08 (1.32H, s), 0.01 (3H, s).

(Step 5)

The same reaction as in step 7 of Example 1 was performed in the following scale (raw material: 783 mg). With use of an acetonitrile solution of the compound obtained and the compound obtained in step 4 (765 mg), the reaction was performed in the same manner as in step 8 of Example 1. The resulting crude product was directly used for the subsequent reaction.

(Step 6)

{9-[(5R,7R,8R,12aR,14R,15R,15aR,16R)-14-(6-Benzoyl-6,7,8,9-tetrahydro-2H-2,3,5,6-tetraazabenzo[cd]azulen-2-yl)-15,16-bis{[tert-butyl(dimethyl)silyl]oxy}-10-(2-cyanoethoxy)-2-oxo-2-sulfanyl-10-sulfanylideneoctahydro-2H,10H,12H-5,8-methano-2λ$^5$,10λ$^5$-furo[3,2-l][1,3,6,9,11,2,10]pentaoxadiphosphacyclotetradecin-7-yl]-9H-purin-6-yl}methyl benzoate With use of the crude product obtained in step 5, the reaction was performed in the same manner as in step 9 of Example 1 to afford the title compound (345 mg) as a mixture of diastereomers at the phosphorus atom.

MS(ESI)m/z: 1234 (M+H)$^+$.

(Step 7)

Bis(N,N-diethylethaneaminium) (5R,7R,8R,12aR,14R,15R,15aS,16R)-15,16-bis{[tert-butyl(dimethyl)silyl]oxy}-7-[6-(hydroxymethyl)-9H-purin-9-yl]-2,10-dioxo-14-(6,7,8,9-tetrahydro-2H-2,3,5,6-tetraazabenzo[cd]azulen-2-yl)octahydro-2H,10H,12H-5,8-methano-2λ$^5$,10λ$^5$-furo[3,2-1][1,3,6,9,11,2,10]pentaoxadiphosphacyclotetradecine-2,10-bis(thiolate)

With use of the compound obtained in step 6 (345 mg), the reaction was performed in the same manner as in step 10 of Example 1 to afford diastereomer 1 (101 mg: with impurities) and diastereomer 2 (89.9 mg: with impurities) of the title compound.

Diastereomer 1 (Less Polar)

MS(ESI)m/z: 973 (M+H)$^+$.

Diastereomer 2 (More Polar)

MS(ESI)m/z: 973 (M+H)$^+$.

(Step 8-1)

Disodium (5R,7R,8R,12aR,14R,15R,15aS,16R)-15,16-dihydroxy-7-[6-(hydroxymethyl)-9H-purin-9-yl]-2,10-dioxo-14-(6,7,8,9-tetrahydro-2H-2,3,5,6-tetraazabenzo[cd]azulen-2-yl)octahydro-2H,10H,12H-5,8-methano-2λ$^5$,10λ$^5$-furo[3,2-1][1,3,6,9,11,2,10]pentaoxadiphosphacyclotetradecine-2,10-bis(thiolate)

(Diastereomer 1)

With use of the compound obtained in step 7 (diastereomer 1) (101 mg: with impurities), the reaction was performed in the same manner as in step 11 of Example 1, and purification was then performed under the following [Purification Conditions] to afford the title compound as a triethylamine salt.

[Purification Conditions] C18 silica gel column chromatography [10 mM aqueous solution of triethylammonium acetate/acetonitrile], preparative HPLC [10 mM aqueous solution of triethylammonium acetate/acetonitrile, acetonitrile: 5%-30% (0 min-40 min)].

The triethylamine salt obtained was subjected to salt exchange in the same manner as in [Conversion to Sodium Salt] described in step 11 of Example 1 to afford the title compound (59.2 mg).

MS(ESI)m/z: 745 (M+H)$^+$.

$^1$H-NMR (CD$_3$OD) δ: 9.07 (1H, s), 8.88 (1H, s), 8.03 (1H, s), 7.10 (1H, s), 6.48 (1H, d, J=8.5 Hz), 6.29 (1H, d, J=4.8 Hz), 5.46 (1H, dt, J=7.9, 4.2 Hz), 5.21-5.15 (1H, m), 5.10 (2H, s), 4.84-4.80 (1H, m), 4.79 (1H, t, J=4.5 Hz), 4.51-4.42 (2H, m), 4.37-4.34 (1H, m), 4.33-4.24 (1H, m), 4.09-3.97 (2H, m), 3.52-3.47 (2H, m), 2.89-2.82 (2H, m), 2.03-1.95 (2H, m).

$^{31}$P-NMR (CD$_3$OD) δ: 57.9 (s), 54.8 (s).

(Step 8-2)

Disodium (5R,7R,8R,12aR,14R,15R,15aS,16R)-15,16-dihydroxy-7-[6-(hydroxymethyl)-9H-purin-9-yl]-2,10-dioxo-14-(6,7,8,9-tetrahydro-2H-2,3,5,6-tetraazabenzo[cd]azulen-2-yl)octahydro-2H,10H,12H-5,8-methano-2λ$^5$,10λ$^5$-furo[3,2-1][1,3,6,9,11,2,10]pentaoxadiphosphacyclotetradecine-2,10-bis(thiolate)

(Diastereomer 2)

With use of the compound obtained in step 7 (diastereomer 2) (88.5 mg: with impurities), the reaction was performed in the same manner as in step 11 of Example 1, and purification was then performed under the following [Purification Conditions] to afford the title compound as a triethylamine salt.

[Purification Conditions] C18 silica gel column chromatography [10 mM aqueous solution of triethylammonium acetate/acetonitrile], preparative HPLC [10 mM aqueous solution of triethylammonium acetate/acetonitrile, acetonitrile: 5%-30% (0 min-40 min)], and preparative HPLC [10 mM aqueous solution of triethylammonium acetate/methanol, methanol: 10%-70% (0 min-40 min)].

The triethylamine salt obtained was subjected to salt exchange in the same manner as in [Conversion to Sodium Salt] described in step 11 of Example 1 to afford the title compound (27.7 mg).

MS(ESI)m/z: 745 (M+H)$^+$.

$^1$H-NMR (CD$_3$OD) δ: 9.16 (1H, s), 8.87 (1H, s), 8.03 (1H, s), 7.11 (1H, s), 6.51 (1H, d, J=8.5 Hz), 6.33 (1H, d, J=6.7 Hz), 5.58-5.45 (2H, m), 5.12-5.09 (2H, m), 4.81-4.76 (1H, m), 4.53-4.49 (1H, m), 4.48-4.36 (2H, m), 4.34 (2H, s), 4.09-4.02 (1H, m), 3.92-3.85 (1H, m), 3.53-3.47 (2H, m), 2.94-2.87 (2H, m), 2.05-1.97 (2H, m).

$^{31}$P-NMR (CD$_3$OD) δ: 63.1 (s), 60.1 (s).

Example 18: Synthesis of CDN18

(5R,7R,8R,12aR,14R,15R,15aS,16R)-7-[4-Amino-5-(3-aminopropyl)-7H-pyrrolo[2,3-d]pyrimidin-7-yl]-15,16-dihydroxy-2,10-bis(sulfanyl)-14-(6,7,8,9-tetrahydro-2H-2,3,5,6-tetraazabenzo[cd]azulen-2-yl)octahydro-2H,10H,12H-5,8-methano-2λ$^5$,10λ$^5$-furo[3,2-1][1,3,6,9,11,2,10]pentaoxadiphosphacyclotetradecine-2,10-dione

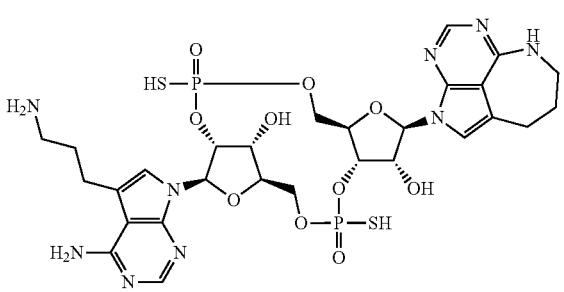

18

18a (Diastereomer 1)
18b (Diastereomer 2)

[Synthesis Scheme]
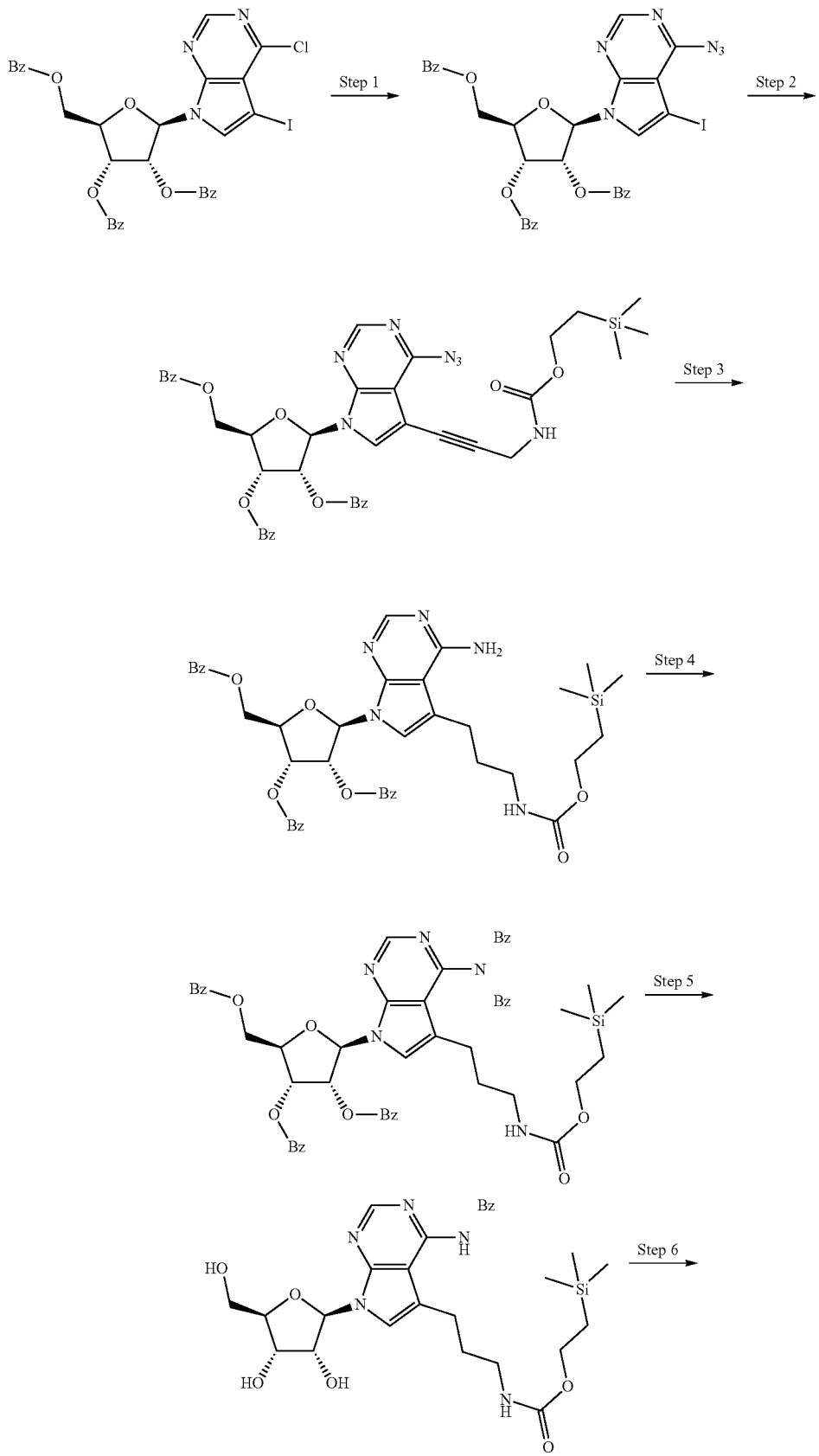

-continued
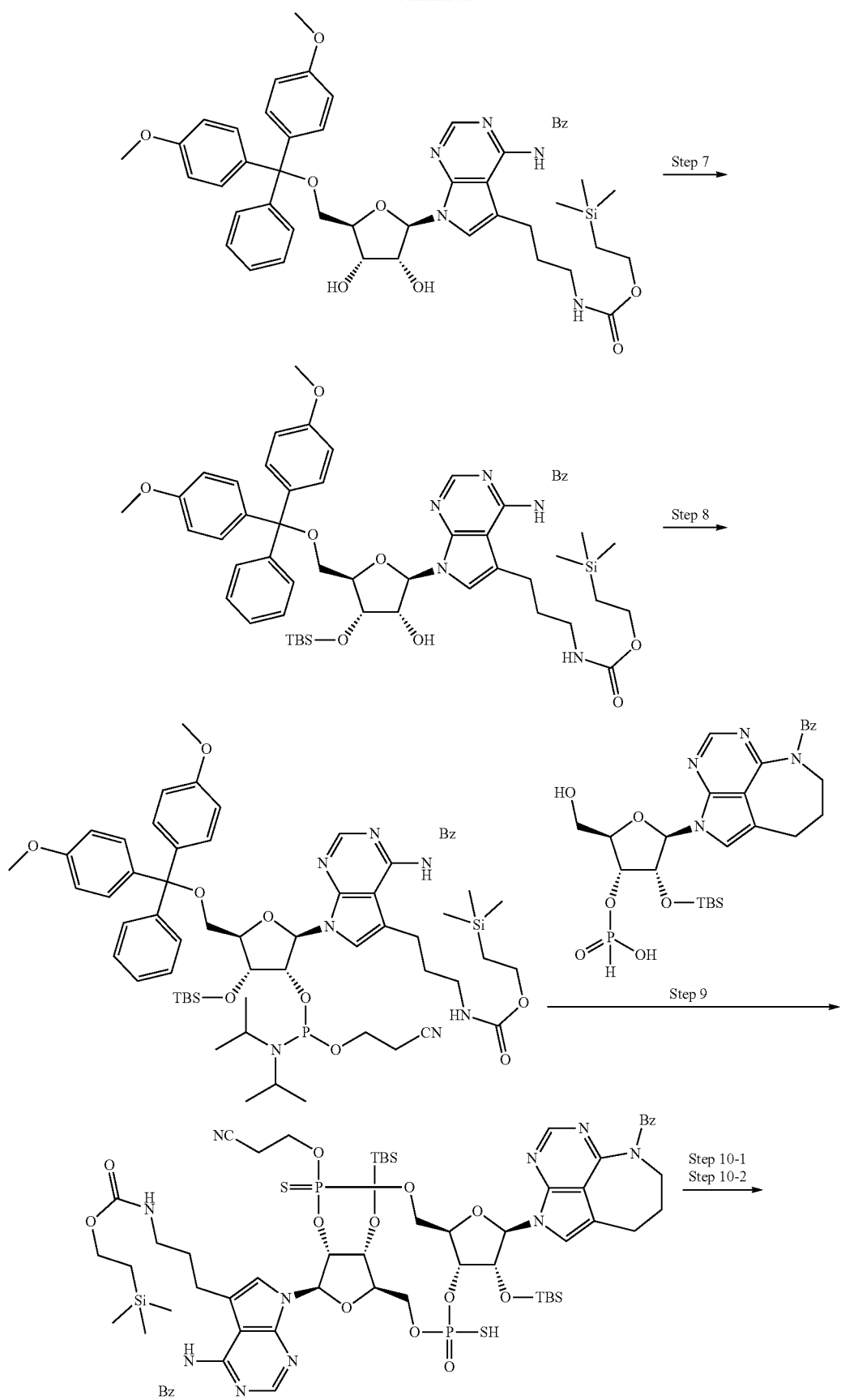

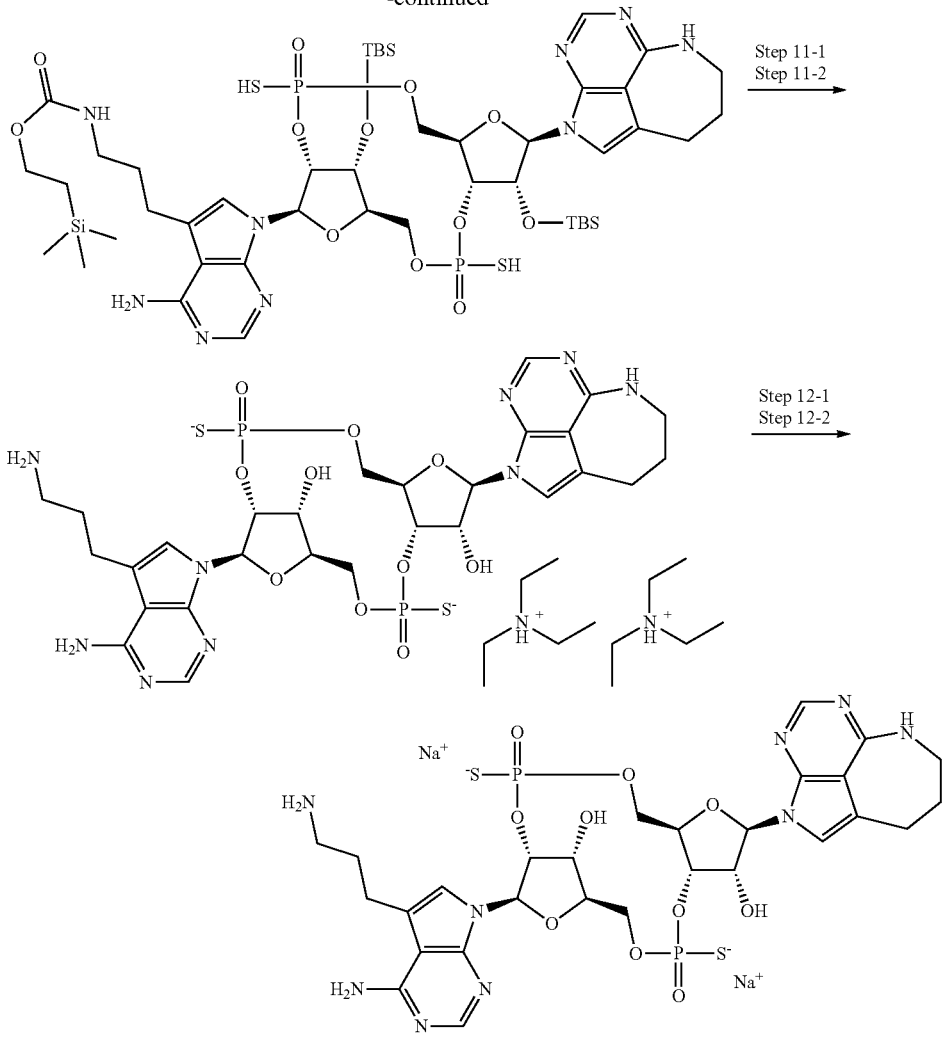

(Step 1)

4-Azido-5-iodo-7-(2,3,5-tri-O-benzoyl-β-D-ribofuranosyl)-7H-pyrrolo[2,3-d]pyrimidine To a solution of 4-chloro-5-iodo-7-(2,3,5-tri-O-benzoyl-β-D-ribofuranosyl)-7H-pyrrolo[2,3-d]pyrimidine (17.96 g) as a compound known in the literature (Synth. Commun. 2012, 42, 358-374) in N,N-dimethylformamide (90 mL), tetrabutylammonium azide (10.1 g) was added, and the reaction mixture was stirred at 80° C. for 30 minutes. The temperature of the reaction mixture was returned to room temperature, and a saturated aqueous solution of sodium hydrogen carbonate and ethyl acetate were added to the reaction mixture, which was subjected to extraction with ethyl acetate. The organic layer was washed with brine, and then dried over anhydrous sodium sulfate. The drying agent was removed through filtration and the filtrate was concentrated under reduced pressure. The residue was purified by silica gel column chromatography [hexane/ethyl acetate] to afford the title compound (17.66 g).

$^1$H-NMR (CDCl$_3$) δ: 9.18 (1H, s), 8.13-8.09 (2H, m), 8.03-7.99 (2H, m), 7.95-7.90 (2H, m), 7.64-7.34 (10H, m), 6.71 (1H, d, J=5.1 Hz), 6.20 (1H, t, J=5.5 Hz), 6.11 (1H, t, J=5.3 Hz), 4.96 (1H, dd, J=12.2, 3.2 Hz), 4.88-4.84 (1H, m), 4.70 (1H, dd, J=12.2, 3.2 Hz).

(Step 2)

4-Azido-7-(2,3,5-tri-O-benzoyl-β-D-ribofuranosyl)-5-[3-({[2-(trimethylsilyl)ethoxy]carbonyl}amino)prop-1-yn-1-yl]-7H-pyrrolo[2,3-d]pyrimidine To a mixed solution of the compound obtained in step 1 (9.64 g) in N,N-dimethylformamide (30 mL)-tetrahydrofuran (100 mL), 2-(trimethylsilyl)ethylprop-2-yn-1-yl carbamate (6.58 g), triethylamine (4.57 mL), tetrakis(triphenylphosphine) palladium (0) (763 mg), and copper (I) iodide (251 mg) were added in this order, and the reaction mixture was stirred at room temperature overnight. Water was added to the reaction mixture, which was subjected to extraction with ethyl acetate. The organic layer was washed with brine, and then dried over anhydrous sodium sulfate. The drying agent was removed through filtration, and the filtrate was concentrated under reduced pressure. The residue was purified by silica gel column chromatography [hexane/ethyl acetate] to afford the title compound (7.20 g).

$^1$H-NMR (CDCl$_3$) δ: 9.16 (1H, s), 8.14-8.08 (2H, m), 8.03-7.99 (2H, m), 7.94-7.90 (2H, m), 7.66 (1H, s), 7.65-

7.35 (9H, m), 6.66 (1H, d, J=5.1 Hz), 6.22 (1H, t, J=5.5 Hz), 6.10 (1H, t, J=5.3 Hz), 5.07 (1H, brs), 4.95 (1H, dd, J=12.3, 2.9 Hz), 4.88-4.84 (1H, m), 4.70 (1H, dd, J=12.3, 3.7 Hz), 4.29 (2H, d, J=5.5 Hz), 4.21 (2H, t, J=8.6 Hz), 1.02 (2H, t, J=8.6 Hz), 0.05 (9H, s).
(Step 3)

7-(2,3,5-Tri-O-benzoyl-β-D-ribofuranosyl)-5-[3-({[2-(trimethylsilyl)ethoxy]carbonyl}amino) propyl]-7H-pyrrolo[2,3-d]pyrimidin-4-amine To a mixed solution of the compound obtained in step 2 (7.20 g) in methanol (70 mL)-tetrahydrofuran (70 mL), 20% palladium hydroxide-carbon (2 g) was added, and the reaction mixture was stirred under the hydrogen atmosphere at room temperature for 2 hours. After the catalyst was removed through filtration, the filtrate was concentrated under reduced pressure. The residue was purified by silica gel column chromatography [hexane/ethyl acetate] to afford the title compound (5.45 g).
$^{1}$H-NMR (CDCl$_3$) δ: 8.26 (1H, s), 8.19-8.15 (2H, m), 8.02-7.97 (2H, m), 7.96-7.92 (2H, m), 7.65-7.48 (5H, m), 7.43-7.32 (4H, m), 6.82 (1H, s), 6.73 (1H, d, J=6.3 Hz), 6.17 (1H, t, J=5.9 Hz), 6.11 (1H, dd, J=5.9, 3.9 Hz), 5.23 (2H, s), 4.90 (1H, dd, J=12.2, 3.4 Hz), 4.77-4.70 (2H, m), 4.63 (1H, dd, J=12.2, 3.4 Hz), 4.15 (2H, t, J=8.6 Hz), 3.20-3.10 (2H, m), 2.62 (2H, t, J=7.6 Hz), 1.72-1.62 (2H, m), 1.01-0.94 (2H, m), 0.04 (9H, s).
(Step 4)

N,N-Dibenzoyl-7-(2,3,5-tri-O-benzoyl-β-D-ribofuranosyl)-5-[3-({[2-(trimethylsilyl)ethoxy]carbonyl}amino) propyl]-7H-pyrrolo[2,3-d]pyrimidin-4-amine To a solution of the compound obtained in step 3 (5.45 g) in dichloromethane (60 mL), pyridine (1.69 mL) and benzoyl chloride (2.01 mL) were added in this order at 0° C., and the reaction mixture was stirred at 0° C. for 5 minutes, to which triethylamine (2.91 mL) was further added, and the reaction mixture was stirred at room temperature for 2 hours. A saturated aqueous solution of sodium hydrogen carbonate and dichloromethane were added to the reaction mixture, which was subjected to extraction with dichloromethane. After the organic layer was dried over anhydrous sodium sulfate, the drying agent was removed through filtration and the filtrate was concentrated under reduced pressure. The residue was purified by silica gel column chromatography [hexane/ethyl acetate], and further powdered with ethyl acetate and hexane. The resulting solid was collected through filtration to give the title compound (6.16 g).
$^{1}$H-NMR (CDCl$_3$) δ: 8.54 (1H, s), 8.20-8.16 (2H, m), 8.02-7.98 (2H, m), 7.96-7.92 (2H, m), 7.82-7.76 (4H, m), 7.65-7.32 (15H, m), 7.18 (1H, brs), 6.82 (1H, d, J=5.9 Hz), 6.17 (1H, t, J=6.1 Hz), 6.13 (1H, dd, J=5.9, 3.5 Hz), 4.94 (1H, dd, J=12.2, 3.2 Hz), 4.79-4.75 (1H, m), 4.65 (1H, dd, J=12.2, 3.2 Hz), 4.41 (1H, brs), 4.08 (2H, t, J=8.6 Hz), 2.95-2.87 (2H, m), 2.58-2.50 (2H, m), 1.54-1.52 (2H, m), 0.97-0.91 (2H, m), 0.02 (9H, s).
(Step 5)

N-Benzoyl-7-β-D-ribofuranosyl-5-[3-({[2-(trimethylsilyl)ethoxy]carbonyl}amino) propyl]-7H-pyrrolo[2,3-d]pyrimidin-4-amine To a solution of the compound obtained in step 4 (6.16 g) in tetrahydrofuran (250 mL), a methanol solution of sodium methoxide (1.0 M, 12.0 mL) was added dropwise at 0° C., and the reaction mixture was stirred at room temperature for 1 hour. Acetic acid (1.07 mL) was added to the reaction mixture at 0° C., and the reaction mixture was then concentrated under reduced pressure. The residue was purified by silica gel column chromatography [ethyl acetate/methanol], and further powdered with ethyl acetate and hexane. The resulting solid was collected through filtration to give the title compound (3.35 g).
$^{1}$H-NMR (CD$_3$OD) δ: 8.62 (1H, s), 8.04 (2H, d, J=7.0 Hz), 7.69-7.62 (1H, m), 7.60-7.54 (3H, m), 6.26 (1H, d, J=6.3 Hz), 4.59 (1H, t, J=5.7 Hz), 4.31 (1H, dd, J=5.1, 3.5 Hz), 4.12-4.01 (3H, m), 3.86 (1H, dd, J=12.3, 2.9 Hz), 3.76 (1H, dd, J=12.1, 3.5 Hz), 3.01 (2H, t, J=6.7 Hz), 2.76 (2H, t, J=7.4 Hz), 1.86-1.76 (2H, m), 0.93 (2H, t, J=8.2 Hz), 0.03 (9H, s).
(Step 6)

N-Benzoyl-7-{5-O-[bis(4-methoxyphenyl)(phenyl)methyl]-β-D-ribofuranosyl}-5-[3-({[2-(trimethylsilyl)ethoxy]carbonyl}amino) propyl]-7H-pyrrolo[2,3-d]pyrimidin-4-amine The compound obtained in step 5 (3.35 g) was azeotroped with pyridine, and 4,4'-dimethoxytrityl chloride (2.38 g) was added to a solution of the residue in anhydrous pyridine (50 mL) at 0° C., and the reaction mixture was stirred at room temperature overnight. After ethanol (5 mL) was added to the reaction mixture to quench the reaction, and the resultant was then concentrated under reduced pressure. The residue was purified by silica gel column chromatography [hexane/ethyl acetate] to afford the title compound (4.34 g).
$^{1}$H-NMR (CDCl$_3$) δ: 8.51 (1H, brs), 8.30 (1H, brs), 8.05-7.90 (1H, m), 7.56-7.42 (3H, m), 7.39-7.31 (2H, m), 7.29-7.16 (10H, m), 6.81-6.75 (4H, m), 6.22 (1H, d, J=5.9 Hz), 4.91 (1H, brs), 4.76-4.67 (2H, m), 4.45-4.41 (1H, m), 4.38-4.29 (1H, m), 4.05-3.95 (2H, m), 3.77 (6H, s), 3.50 (1H, dd, J=10.6, 3.1 Hz), 3.37-3.27 (1H, m), 3.19-2.94 (4H, m), 2.66 (1H, brs), 1.82 (1H, brs), 0.93-0.76 (2H, m), −0.01 (9H, s).
(Step 7)

N-Benzoyl-7-{5-O-[bis(4-methoxyphenyl)(phenyl)methyl]-3-O-[tert-butyl(dimethyl)silyl]-β-D-ribofuranosyl}-5-[3-({[2-(trimethylsilyl)ethoxy]carbonyl}amino) propyl]-7H-pyrrolo[2,3-d]pyrimidin-4-amine (3'-O-TBS Form)

With use of the compound obtained in step 6 (4.34 g), the reaction was performed in the same manner as in step 4 of Example 8 to afford the title compound (1.51 g) and N-benzoyl-7-{5-O-[bis(4-methoxyphenyl)(phenyl)methyl]-2-O-[tert-butyl(dimethyl)silyl]-β-D-ribofuranosyl}-5-[3-({[2-(trimethylsilyl)ethoxy]carbonyl}amino) propyl]-7H-pyrrolo[2,3-d]pyrimidin-4-amine (2'-O-TBS form) (2.01 g) as a regioisomer of the title compound.
(3'-OTBS Form) (More Polar)
$^{1}$H-NMR (CDCl$_3$) δ: 8.38-8.26 (2H, m), 8.10-8.03 (1H, m), 7.58-7.40 (5H, m), 7.36-7.20 (10H, m), 6.86-6.77 (4H, m), 6.30-6.22 (1H, m), 5.02-4.89 (1H, m), 4.63-4.45 (2H, m), 4.17-4.10 (1H, m), 4.04-3.92 (2H, m), 3.79 (3H, s), 3.79 (3H, s), 3.59-3.52 (1H, m), 3.32-3.23 (1H, m), 3.17-2.80 (4H, m), 1.86-1.64 (2H, m), 0.89 (9H, s), 0.86-0.72 (2H, m), 0.09 (3H, s), 0.01 (3H, s), −0.01 (9H, s).
(2'-OTBS Form) (Less Polar)
$^{1}$H-NMR (CDCl$_3$) δ: 8.39-8.25 (2H, m), 8.04 (1H, s), 7.57-7.42 (5H, m), 7.37-7.18 (10H, m), 6.87-6.80 (4H, m), 6.33 (1H, d, J=5.1 Hz), 5.01 (1H, brs), 4.78 (1H, t, J=5.7 Hz), 4.40-4.33 (1H, m), 4.29-4.25 (1H, m), 4.05-3.92 (2H, m), 3.80 (3H, s), 3.79 (3H, s), 3.59-3.51 (1H, m), 3.44-3.37 (1H, m), 3.16-3.03 (1H, m), 2.99-2.81 (3H, m), 1.74-1.61 (2H, m), 0.83 (9H, s), 0.80-0.70 (2H, m), 0.00-0.03 (12H, m), −0.20 (3H, s).

(Step 8)

N-Benzoyl-7-(5-O-[bis(4-methoxyphenyl)(phenyl)methyl]-3-O-[tert-butyl(dimethyl)silyl]-2-O-{(2-cyanoethoxy)[di(propan-2-yl)amino]phosphanyl}-β-D-ribofuranosyl)-5-[3-({[2-(trimethylsilyl)ethoxy]carbonyl}amino) propyl]-7H-pyrrolo[2,3-d]pyrimidin-4-amine With use of the compound obtained in step 7 (3'-OTBS form) (1.51 g), the reaction was performed in the same manner as in step 6 of Example 1 to afford diastereomer 1 (0.77 g) and diastereomer 2 (0.48 g) of the title compound, as diastereomers at the phosphorus atom.

Diastereomer 1 (Less Polar)

$^1$H-NMR (CDCl$_3$) δ: 8.36-8.27 (2H, m), 8.02 (1H, brs), 7.57-7.40 (5H, m), 7.37-7.21 (10H, m), 6.87-6.77 (4H, m), 6.39 (1H, d, J=5.1 Hz), 4.98 (1H, brs), 4.85-4.73 (1H, m), 4.56-4.47 (1H, m), 4.20-4.15 (1H, m), 4.05-3.92 (2H, m), 3.88-3.67 (8H, m), 3.63-3.47 (3H, m), 3.33-3.23 (1H, m), 3.15-2.82 (3H, m), 2.60-2.45 (2H, m), 1.83-1.64 (2H, m), 1.10 (6H, d, J=6.7 Hz), 0.92 (6H, d, J=6.7 Hz), 0.87 (9H, s), 0.81-0.71 (2H, m), 0.12 (3H, s), 0.03 (3H, s), −0.01 (9H, s).

Diastereomer 2 (More Polar)

$^1$H-NMR (CDCl$_3$) δ: 8.36-8.28 (2H, m), 8.05 (1H, brs), 7.57-7.38 (5H, m), 7.36-7.19 (10H, m), 6.84-6.79 (4H, m), 6.48-6.40 (1H, m), 5.02 (1H, brs), 4.65-4.42 (2H, m), 4.19-4.15 (1H, m), 4.06-3.90 (2H, m), 3.80-3.48 (11H, m), 3.32-3.24 (1H, m), 3.17-3.03 (2H, m), 2.99-2.86 (1H, m), 2.51-2.40 (2H, m), 1.86-1.69 (2H, m), 1.18-1.02 (12H, m), 0.85 (9H, s), 0.81-0.71 (2H, m), 0.08 (3H, s), 0.02 (3H, s), −0.01 (9H, s).

(Step 9)

2-(Trimethylsilyl)ethyl (3-{4-benzamido-7-[(5R,7R,8R,12aR,14R,15R,15aR,16R)-14-(6-benzoyl-6,7,8,9-tetrahydro-2H-2,3,5,6-tetraazabenzo[cd]azulen-2-yl)-15,16-bis{[tert-butyl(dimethyl)silyl]oxy}-10-(2-cyanoethoxy)-2-oxo-2-sulfanyl-10-sulfanylideneoctahydro-2H,10H,12H-5,8-methano-2λ$^5$,10λ$^5$-furo[3,2-1][1,3,6,9,11,2,10]pentaoxadiphosphacyclotetradecin-7-yl]-7H-pyrrolo[2,3-d]pyrimidin-5-yl}propyl)carbamate The same reaction as in step 7 of Example 1 was performed in the following scale (raw material: 1.08 g). With use of an acetonitrile solution of the compound obtained and the compound obtained in step 8 (1.25 g: a mixture of diastereomers), the reaction was performed in the same manner as in step 8 of Example 1 and step 9 of Example 1 to afford the title compound as a mixture of diastereomers at the phosphorus atom. The diastereomers at the phosphorus atom were separated by preparative HPLC [10 mM aqueous solution of triethylammonium acetate/acetonitrile, acetonitrile: 10%-50% (0 min-35 min)] to afford diastereomer 1 (0.19 g) and diastereomer 2 (0.043 g) of the title compound.

Diastereomer 1 (Less Polar)
MS(ESI)m/z: 1419 (M+H)$^+$.

Diastereomer 2 (More Polar)
MS(ESI)m/z: 1419 (M+H)$^+$.

(Step 10-1)

2-(Trimethylsilyl)ethyl (3-{4-amino-7-[(5R,7R,8R,12aR,14R,15R,15aR,16R)-15,16-bis{[tert-butyl(dimethyl)silyl]oxy}-2,10-dioxo-2,10-bis(sulfanyl)-14-(6,7,8,9-tetrahydro-2H-2,3,5,6-tetraazabenzo[cd]azulen-2-yl)octahydro-2H,10H,12H-5,8-methano-2λ$^5$,10λ$^5$-furo[3,2-1][1,3,6,9,11,2,10]pentaoxadiphosphacyclotetradecin-7-yl]-7H-pyrrolo[2,3-d]pyrimidin-5-yl}propyl)carbamate With use of the compound obtained in step 9 (diastereomer 1) (0.19 g), the reaction was performed in the same manner as in step 8-1 of Example 12. The resultant was purified by preparative HPLC [10 mM aqueous solution of triethylammonium acetate/acetonitrile, acetonitrile: 40%-70% (0 min-35 min)] to afford the title compound (58 mg).

MS(ESI)m/z: 1158 (M+H)$^+$.

(Step 10-2)

2-(Trimethylsilyl)ethyl (3-{4-amino-7-[(5R,7R,8R,12aR,14R,15R,15aR,16R)-15,16-bis{[tert-butyl(dimethyl)silyl]oxy}-2,10-dioxo-2,10-bis(sulfanyl)-14-(6,7,8,9-tetrahydro-2H-2,3,5,6-tetraazabenzo[cd]azulen-2-yl)octahydro-2H,10H,12H-5,8-methano-2λ$^5$,10λ$^5$-furo[3,2-1][1,3,6,9,11,2,10]pentaoxadiphosphacyclotetradecin-7-yl]-7H-pyrrolo[2,3-d]pyrimidin-5-yl}propyl)carbamate With use of the compound obtained in step 9 (diastereomer 2) (43 mg), the reaction was performed in the same manner as in step 8-1 of Example 12. The resultant was purified by preparative HPLC [10 mM aqueous solution of triethylammonium acetate/acetonitrile, acetonitrile: 30%-60% (0 min-35 min)] to afford the title compound (15 mg).

MS(ESI)m/z: 1158 (M+H)$^+$.

(Step 11-1)

Bis(N,N-diethylethaneaminium) (5R,7R,8R,12aR,14R,15R,15aS,16R)-7-[4-amino-5-(3-aminopropyl)-7H-pyrrolo[2,3-d]pyrimidin-7-yl]-15,16-dihydroxy-2,10-dioxo-14-(6,7,8,9-tetrahydro-2H-2,3,5,6-tetraazabenzo[cd]azulen-2-yl)octahydro-2H,10H,12H-5,8-methano-2λ$^5$,10λ$^5$-furo[3,2-1][1,3,6,9,11,2,10]pentaoxadiphosphacyclotetradecine-2,10-bis(thiolate)

To a solution of the compound obtained in step 10-1 (58 mg) in tetrahydrofuran (1 mL), a tetrahydrofuran solution of tetrabutylammonium fluoride (approximately 1 M, 5 mL) was added, and the reaction mixture was stirred at room temperature overnight. Because the reaction had not completed yet, the reaction mixture was further stirred at 40° C. for 3 hours. The reaction mixture was concentrated under reduced pressure, and then purified by preparative HPLC [10 mM aqueous solution of triethylammonium acetate/acetonitrile, acetonitrile: 10%-40% (0 min-35 min)]. The resultant was further purified with a Sep-Pak® C18 [0.1% aqueous solution of triethylamine/acetonitrile, acetonitrile: 0%-30%] to afford the title compound (25 mg).

MS(ESI)m/z: 786 (M+H)$^+$.

(Step 11-2)

Bis(N,N-diethylethaneaminium) (5R,7R,8R,12aR,14R,15R,15aS,16R)-7-[4-amino-5-(3-aminopropyl)-7H-pyrrolo[2,3-d]pyrimidin-7-yl]-15,16-dihydroxy-2,10-dioxo-14-(6,7,8,9-tetrahydro-2H-2,3,5,6-tetraazabenzo[cd]azulen-2-yl)octahydro-2H,10H,12H-5,8-methano-2$\lambda^5$,10$\lambda^5$-furo[3,2-1][1,3,6,9,11,2,10]pentaoxadiphosphacyclotetradecine-2,10-bis(thiolate)

With use of the compound obtained in step 10-2 (15 mg), the reaction was performed in the same manner as in step 11-1 to afford the title compound (7.2 mg).
MS(ESI)m/z: 786 (M+H)$^+$.
(Step 12-1)

Disodium (5R,7R,8R,12aR,14R,15R,15aS,16R)-7-[4-amino-5-(3-aminopropyl)-7H-pyrrolo[2,3-d]pyrimidin-7-yl]-15,16-dihydroxy-2,10-dioxo-14-(6,7,8,9-tetrahydro-2H-2,3,5,6-tetraazabenzo[cd]azulen-2-yl)octahydro-2H,10H,12H-5,8-methano-2$\lambda^5$,10$\lambda^5$-furo[3,2-1][1,3,6,9,11,2,10]pentaoxadiphosphacyclotetradecine-2,10-bis(thiolate)

(Diastereomer 1)
With use of the compound obtained in step 11-1 (25 mg), salt exchange was performed in the same manner as in [Conversion to Sodium Salt] described in step 11 of Example 1 to afford the title compound (17 mg).
MS(ESI)m/z: 786 (M+H)$^+$.
$^1$H-NMR (CD$_3$OD) δ: 8.028 (1H, s), 8.025 (1H, s), 7.71 (1H, s), 7.09 (1H, s), 6.51 (1H, d, J=8.2 Hz), 6.26 (1H, d, J=5.1 Hz), 5.38-5.29 (1H, m), 5.17-5.10 (1H, m), 4.85-4.80 (1H, m), 4.75 (1H, d, J=3.9 Hz), 4.44-4.37 (1H, m), 4.33-4.23 (3H, m), 4.09-3.97 (2H, m), 3.52-3.46 (2H, m), 3.00-2.72 (6H, m), 2.13-2.02 (2H, m), 2.02-1.93 (2H, m).
$^{31}$P-NMR (CD$_3$OD) δ: 56.65 (s), 55.31 (s).
(Step 12-2)

Disodium (5R,7R,8R,12aR,14R,15R,15aS,16R)-7-[4-amino-5-(3-aminopropyl)-7H-pyrrolo[2,3-d]pyrimidin-7-yl]-15,16-dihydroxy-2,10-dioxo-14-(6,7,8,9-tetrahydro-2H-2,3,5,6-tetraazabenzo[cd]azulen-2-yl)octahydro-2H,10H,12H-5,8-methano-2$\lambda^5$,10$\lambda^5$-furo[3,2-1][1,3,6,9,11,2,10]pentaoxadiphosphacyclotetradecine-2,10-bis(thiolate)

(Diastereomer 2)
With use of the compound obtained in step 11-2 (7.2 mg), salt exchange was performed in the same manner as in [Conversion to Sodium Salt] described in step 11 of Example 1 to afford the title compound (6.0 mg).
MS(ESI)m/z: 786 (M+H)$^+$.
$^1$H-NMR (CD$_3$OD) δ: 8.02 (1H, s), 8.01 (1H, s), 7.75 (1H, s), 7.07 (1H, s), 6.52 (1H, d, J=8.6 Hz), 6.29 (1H, d, J=7.4 Hz), 5.61-5.55 (1H, m), 5.47-5.37 (1H, m), 4.86-4.83 (1H, m), 4.56-4.43 (2H, m), 4.31-4.21 (3H, m), 4.06-3.99 (1H, m), 3.91-3.84 (1H, m), 3.54-3.46 (3H, m), 3.00-2.87 (5H, m), 2.29-2.07 (2H, m), 2.06-1.95 (2H, m).
$^{31}$P-NMR (CD$_3$OD) δ: 63.08 (s), 58.68 (s).

Example 19: Synthesis of CDN19

(5R,7R,8R,12aR,14R,15R,15aS,16R)-7-(6-Amino-9H-purin-9-yl)-15,16-dihydroxy-2,10-bis(sulfanyl)-14-(6,7,8,9-tetrahydro-2H-1,2,3,5,6-pentaazabenzo[cd]azulen-2-yl)octahydro-2H,10H,12H-5,8-methano-2$\lambda^5$,10$\lambda^5$-furo[3,2-1][1,3,6,9,11,2,10]pentaoxadiphosphacyclotetradecine-2,10-dione

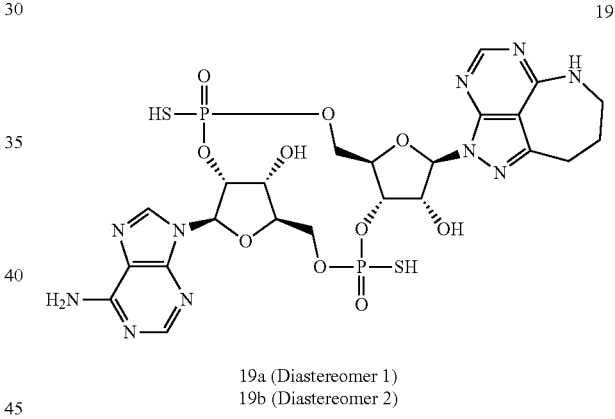

19a (Diastereomer 1)
19b (Diastereomer 2)

[Synthesis Scheme]

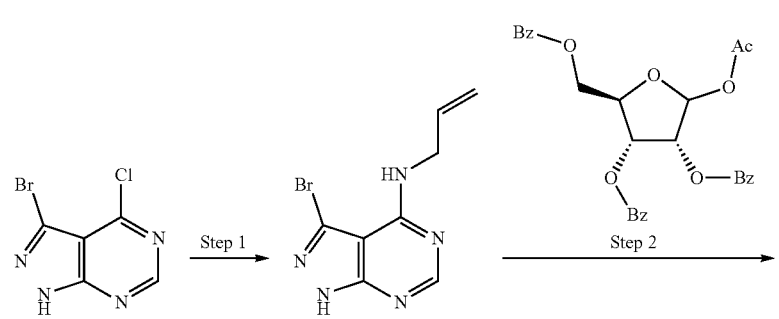

283  284
-continued
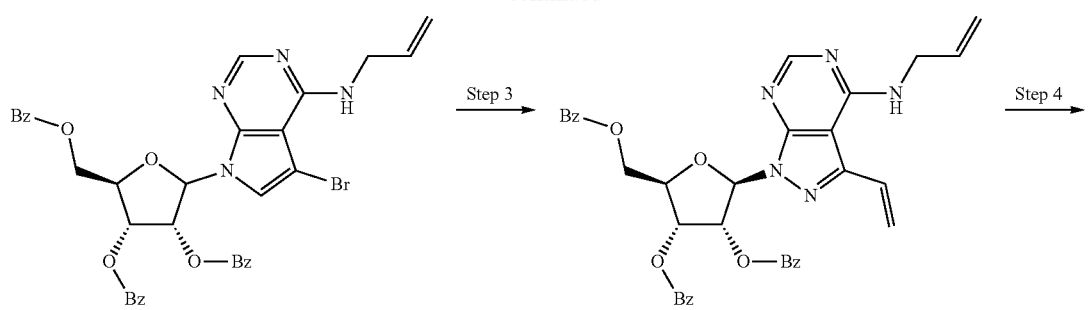
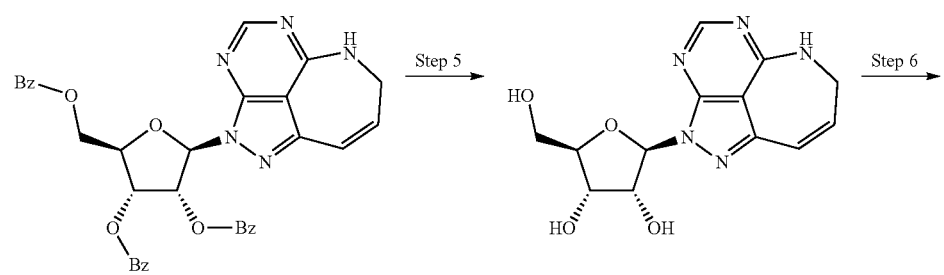
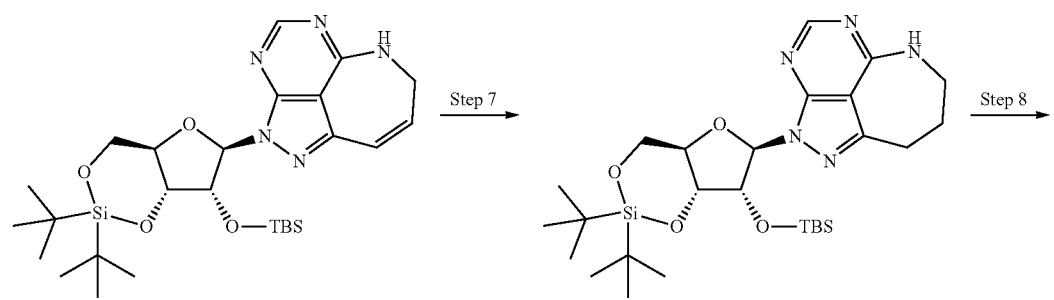
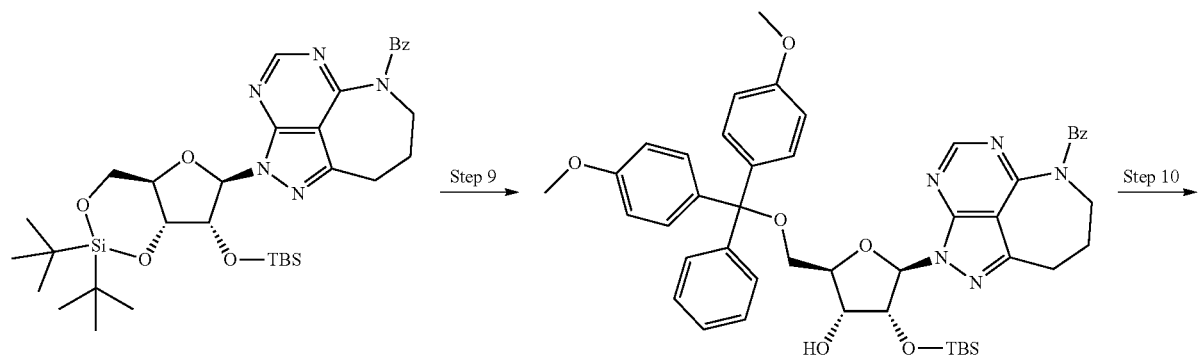

285 286
-continued
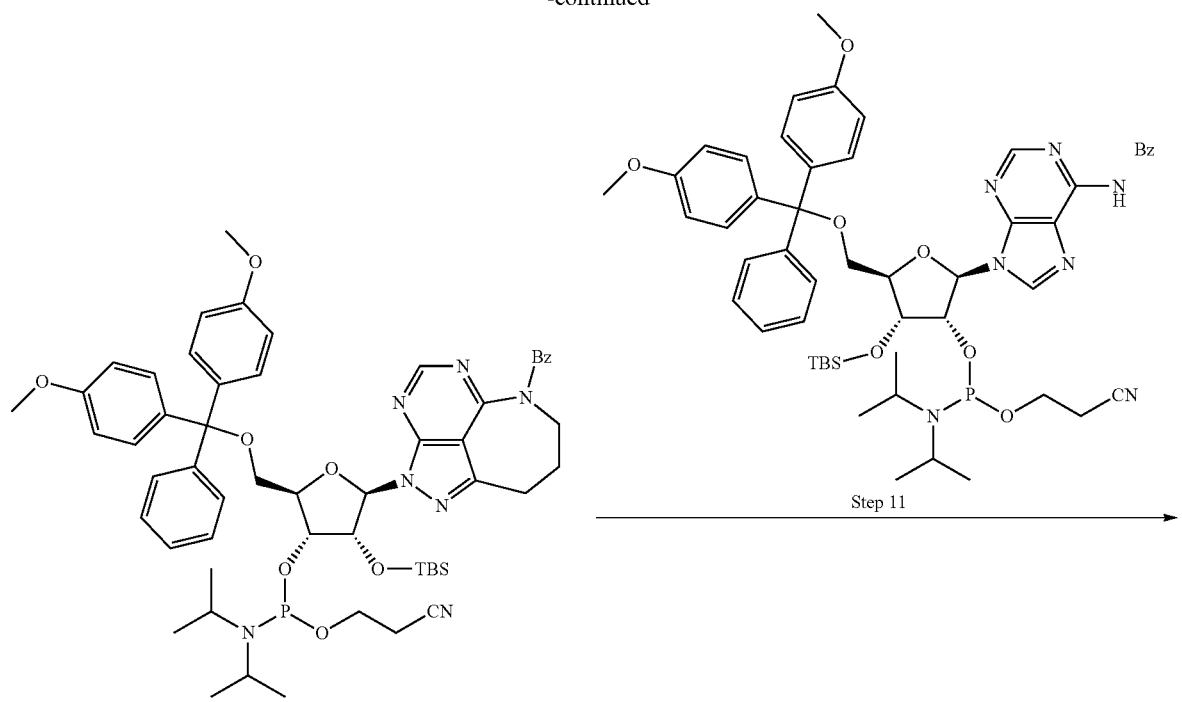
Step 11
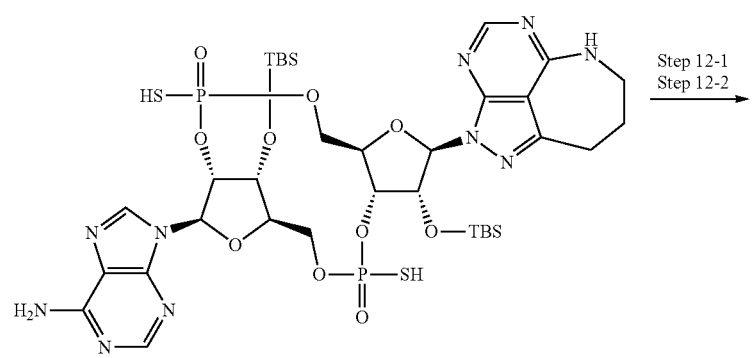
Step 12-1
Step 12-2
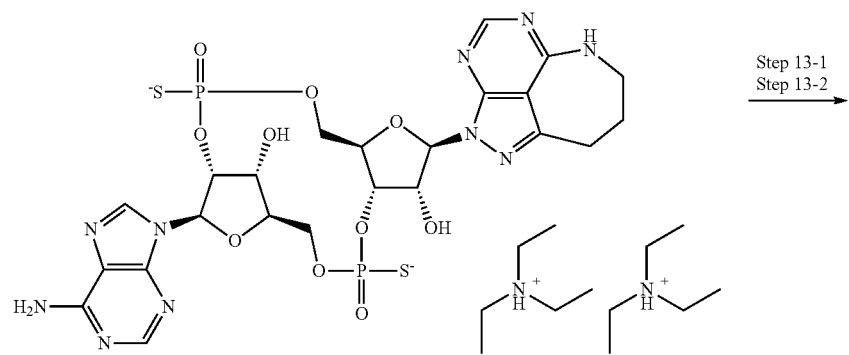
Step 13-1
Step 13-2

-continued

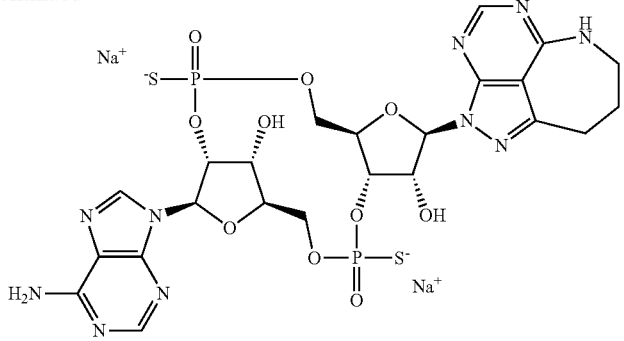

(Step 1)

3-Bromo-N-(prop-2-en-1-yl)-1H-pyrazolo[3,4-d]pyrimidin-4-amine

Commercially available (BePharm Ltd.) 3-bromo-4-chloro-1H-pyrazolo[3,4-d]pyrimidine (8.50 g) was suspended in dioxane (140 mL), to which N,N,-diisopropylethylamine (12.5 mL) and allylamine (11 mL) were added at room temperature, and the reaction mixture was stirred at the same temperature for 70 hours. The reaction mixture was concentrated under reduced pressure, and the residue was made into a slurry with dichloromethane and ethyl acetate, from which the solid was then collected through filtration (solid 1). After the filtrate was concentrated under reduced pressure, the same operation was repeated twice to afford solid 2 and solid 3. The final filtrate was purified with a silica gel column [hexane/ethyl acetate] to afford solid 4. Further, solid 1 was purified with a silica gel column [hexane/ethyl acetate] to afford solid 5. Solid 4 and solid 5 were combined to give the title compound (4.48 g). Solid 2 and solid 3 were combined to give the title compound with impurities (3.78 g).

MS(ESI)m/z: 254 (M+H)$^+$.

$^1$H-NMR (DMSO-d$_6$) δ: 13.82 (1H, s), 8.26 (1H, s), 7.23 (1H, t, J=5.9 Hz), 5.96 (1H, m), 5.18 (1H, dd, J=17.1, 1.5 Hz), 5.10 (1H, dd, J=10.3, 1.5 Hz), 4.19 (2H, m).

(Step 2)

3-Bromo-N-(prop-2-en-1-yl)-1-(2,3,5-tri-O-benzoyl-β-D-ribofuranosyl)-1H-pyrazolo[3,4-d]pyrimidin-4-amine The compound obtained in step 1 (1.00 g) and commercially available (Ark Pharm) 1-O-acetyl-2,3,5-tri-O-benzoyl-β-D-ribofuranose (2.58 g) were suspended in nitromethane (50 mL), and then dissolved by heating. A boron trifluoride-diethyl ether complex (0.63 mL) was added thereto with heating to reflux, and the reaction mixture was stirred at the same temperature for 1 hour. Thereto, 1-O-acetyl-2,3,5-tri-O-benzoyl-β-D-ribofuranose (0.40 g) and a boron trifluoride-diethyl ether complex (0.10 mL) were further added, and the reaction mixture was further stirred for 3 hours. After the reaction mixture was concentrated under reduced pressure, the residue was purified by silica gel column chromatography [hexane/ethyl acetate] to afford the title compound (1.80 g).

MS(ESI)m/z: 698 (M+H)$^+$.

$^1$H-NMR (CDCl$_3$): 8.40 (1H, s), 8.13 (2H, m), 7.96 (4H, m), 7.59-7.32 (9H, m), 6.79 (1H, d, J=3.4 Hz), 6.39 (1H, dd, J=5.1, 3.7 Hz), 6.25 (1H, t, J=5.6 Hz), 6.17 (1H, t, J=5.6 Hz), 6.00 (1H, m), 5.31 (1H, dd, J=17.1, 1.0 Hz), 5.24 (1H, dd, J=10.5, 1.2 Hz), 4.81 (1H, m), 4.75 (1H, dd, J=12.0, 3.7 Hz), 4.63 (1H, dd, J=12.2, 4.4 Hz), 4.30 (2H, m).

(Step 3)

3-Ethenyl-N-(prop-2-en-1-yl)-1-(2,3,5-tri-O-benzoyl-β-D-ribofuranosyl)-1H-pyrazolo[3,4-d]pyrimidin-4-amine A solution of the compound obtained in step 2 (11.65 g) in toluene (120 mL) was ultrasonicated to degas under reduced pressure. Tributylvinyltin (12.8 mL) and tetrakis(triphenylphosphine) palladium (0) (2.73 g) were added to the reaction mixture under the nitrogen atmosphere, and the reaction mixture was heated to reflux for 2 hours. After the reaction mixture was concentrated under reduced pressure, the residue was purified by silica gel column chromatography [dichloromethane/ethyl acetate] to afford the title compound (10.07 g).

MS(ESI)m/z: 646 (M+H)$^+$.

$^1$H-NMR (CDCl$_3$) δ: 8.42 (1H, s), 8.09 (2H, m), 7.99 (2H, m), 7.95 (2H, m), 7.59-7.50 (3H, m), 7.42-7.33 (6H, m), 6.90-6.84 (2H, m), 6.43 (1H, dd, J=5.4, 3.4 Hz), 6.32 (1H, t, J=5.9 Hz), 6.00 (1H, m), 5.94 (1H, dd, J=17.6, 1.0 Hz), 5.67 (1H, dd, J=11.2, 1.0 Hz), 5.56 (1H, t, J=5.6 Hz), 5.27 (1H, dd, J=17.1, 1.0 Hz), 5.22 (1H, dd, J=10.3, 1.0 Hz), 4.82 (1H, m), 4.77 (1H, dd, J=12.2, 3.9 Hz), 4.62 (1H, dd, J=11.7, 4.9 Hz), 4.29 (2H, m).

(Step 4)

2-(2,3,5-Tri-O-benzoyl-β-D-ribofuranosyl)-6,7-dihydro-2H-1,2,3,5,6-pentaazabenzo[cd]azulene The compound obtained in step 3 (9.0 g) was azeotroped twice with benzene. To a solution of the residue in dichloromethane (480 mL), (+)-10-camphorsulfonic acid (4.2 g) and benzylidene [1,3-bis(2,4,6-trimethylphenyl) imidazolidin-2-ylidene] dichloride (tricyclohexyl-λ$^5$-phosphanyl) ruthenium (Grubbs second-generation catalyst) (360 mg) were added, and the reaction mixture was heated to reflux for 3 hours. The Grubbs second-generation catalyst (360 mg) was further added thereto, and the reaction mixture was further heated to reflux for 1 hour. The reaction mixture was cooled to room temperature, washed with a saturated aqueous solution of sodium hydrogen carbonate and brine in this order, and then dried over anhydrous sodium sulfate. The drying agent was removed through filtration, and the filtrate was concentrated under reduced pressure. The residue was purified by silica gel column chromatography [hexane/ethyl acetate] to afford the title compound (6.39 g).

MS(ESI)m/z: 618 (M+H)+.

$^1$H-NMR (CDCl$_3$) δ: 8.39 (1H, s), 8.11 (2H, m), 7.99 (2H, m), 7.96 (2H, m), 7.57-7.52 (3H, m), 7.42-7.35 (6H, m), 6.83 (1H, d, J=2.9 Hz), 6.76 (1H, d, J=10.7 Hz), 6.43 (1H, dd, J=5.1, 3.2 Hz), 6.33 (1H, t, J=5.9 Hz), 6.12 (1H, m), 5.61 (1H, brs), 4.83 (1H, m), 4.78 (1H, dd, J=12.2, 3.9 Hz), 4.63 (1H, dd, J=12.0, 4.6 Hz), 4.16 (2H, m).

(Step 5)

2-β-D-Ribofuranosyl-6,7-dihydro-2H-1,2,3,5,6-pentaazabenzo[cd]azulene

To a mixed solution of the compound obtained in step 4 (620 mg) in methanol (10 mL)-tetrahydrofuran (5.0 mL), a methanol solution of sodium methoxide (1.0 M, 0.10 mL) was added at room temperature, and the reaction mixture was stirred at the same temperature for 18 hours. The reaction mixture was neutralized with 1 N hydrochloric acid, and then concentrated under reduced pressure. The residue was purified by silica gel column chromatography [dichloromethane/methanol] to afford the title compound (279 mg).

MS(ESI)m/z: 306 (M+H)+.

$^1$H-NMR (CD$_3$OD) δ: 8.23 (1H, s), 6.79 (1H, m), 6.22-6.17 (2H, m), 4.74 (1H, t, J=5.1 Hz), 4.42 (1H, t, J=4.6 Hz), 4.14 (2H, dd, J=5.9, 1.5 Hz), 4.11 (1H, q, J=4.1 Hz), 3.81 (1H, dd, J=12.4, 3.2 Hz), 3.68 (1H, dd, J=12.4, 4.6 Hz).

(Step 6)

2-{2-O-[tert-Butyl(dimethyl)silyl]-3,5-O-(di-tert-butylsilylidene)-β-D-ribofuranosyl}-6,7-dihydro-2H-1,2,3,5,6-pentaazabenzo[cd]azulene With use of the compound obtained in step 5 (2.81 g), the reaction was performed in the same manner as in step 1 of Example 1 to afford the title compound (4.72 g).

$^1$H-NMR (CDCl$_3$) δ: 8.38 (1H, s), 6.85 (1H, dt, J=11.0, 1.4 Hz), 6.28 (1H, s), 6.16-6.08 (1H, m), 5.78 (1H, brs), 4.71-4.63 (2H, m), 4.39 (1H, dd, J=9.0, 5.1 Hz), 4.22-4.10 (3H, m), 3.96 (1H, dd, J=10.6, 9.0 Hz), 1.11 (9H, s), 1.05 (9H, s), 0.90 (9H, s), 0.11 (3H, s), 0.09 (3H, s).

(Step 7)

2-{2-O-[tert-Butyl(dimethyl)silyl]-3,5-O-(di-tert-butylsilylidene)-β-D-ribofuranosyl}-6,7,8,9-tetrahydro-2H-1,2,3,5,6-pentaazabenzo[cd]azulene To a solution of the compound obtained in step 6 (2.12 g) in tetrahydrofuran (20 mL), acetic acid (three drops with a Pasteur pipette) and 10% palladium-carbon (AD) wet (0.82 g) were added, and the reaction mixture was stirred under the hydrogen atmosphere at room temperature for 3 hours. The catalyst was removed through filtration and then washed with tetrahydrofuran, and the filtrate was concentrated under reduced pressure. The residue was purified by silica gel column chromatography [hexane/ethyl acetate] to afford the title compound (2.09 g).

$^1$H-NMR (CDCl$_3$) δ: 8.29 (1H, s), 6.33 (1H, brs), 6.27 (1H, s), 4.70 (1H, d, J=4.7 Hz), 4.62 (1H, dd, J=9.6, 4.9 Hz), 4.39 (1H, dd, J=9.0, 5.1 Hz), 4.21-4.08 (1H, m), 3.95 (1H, dd, J=10.4, 9.2 Hz), 3.65-3.58 (2H, m), 3.15-2.99 (2H, m), 2.22-2.10 (2H, m), 1.11 (9H, s), 1.05 (9H, s), 0.90 (9H, s), 0.10 (3H, s), 0.09 (3H, s).

(Step 8)

6-Benzoyl-2-{2-O-[tert-butyl(dimethyl)silyl]-3,5-O-(di-tert-butylsilylidene)-β-D-ribofuranosyl}-6,7,8,9-tetrahydro-2H-1,2,3,5,6-pentaazabenzo[cd]azulene With use of the compound obtained in step 7 (2.09 g), the reaction was performed in the same manner as in step 4 of Example 1 to afford the title compound (2.23 g).

$^1$H-NMR (CDCl$_3$) δ: 8.19 (1H, s), 7.47-7.40 (3H, m), 7.33-7.28 (2H, m), 6.34 (1H, s), 4.72 (1H, d, J=4.7 Hz), 4.66 (1H, dd, J=9.4, 4.7 Hz), 4.49 (1H, dd, J=14.7, 8.0 Hz), 4.40 (1H, dd, J=9.0, 5.1 Hz), 4.24-4.09 (2H, m), 3.96 (1H, dd, J=10.6, 9.0 Hz), 3.26-3.11 (2H, m), 2.45-2.23 (2H, m), 1.12 (9H, s), 1.05 (9H, s), 0.90 (9H, s), 0.12 (3H, s), 0.10 (3H, s).

(Step 9)

6-Benzoyl-2-{5-O-[bis(4-methoxyphenyl)(phenyl)methyl]-2-O-[tert-butyl(dimethyl)silyl]-β-D-ribofuranosyl}-6,7,8,9-tetrahydro-2H-1,2,3,5,6-pentaazabenzo[cd]azulene With use of the compound obtained in step 8 (2.23 g), the reaction was performed in the same manner as in step 5 of Example 1 to afford the title compound (2.69 g).

$^1$H-NMR (CDCl$_3$) δ: 8.22 (1H, s), 7.55-7.51 (2H, m), 7.46-7.36 (7H, m), 7.32-7.26 (2H, m), 7.26-7.16 (3H, m), 6.80-6.73 (4H, m), 6.43 (1H, d, J=5.5 Hz), 5.32 (1H, t, J=5.5 Hz), 4.43 (1H, dd, J=14.3, 8.0 Hz), 4.34-4.29 (1H, m), 4.25-4.13 (2H, m), 3.78 (3H, s), 3.77 (3H, s), 3.46 (1H, dd, J=10.4, 3.3 Hz), 3.17-3.05 (3H, m), 2.79 (1H, d, J=3.5 Hz), 2.40-2.19 (2H, m), 0.82 (9H, s), 0.03 (3H, s), −0.13 (3H, s).

(Step 10)

6-Benzoyl-2-(5-O-[bis(4-methoxyphenyl)(phenyl)methyl]-2-O-[tert-butyl(dimethyl)silyl]-3-O-{(2-cyanoethoxy)[di(propan-2-yl)amino]phosphanyl}-β-D-ribofuranosyl)-6,7,8,9-tetrahydro-2H-1,2,3,5,6-pentaazabenzo[cd]azulene With use of the compound obtained in step 9 (2.69 g), the reaction was performed in the same manner as in step 4 of Example 5 to afford the title compound (2.93 g) as a mixture of diastereomers at the phosphorus atom (diastereomer ratio=6:4).

$^1$H-NMR (CDCl$_3$) δ: 8.22 (0.4H, s), 8.21 (0.6H, s), 7.56-7.50 (2H, m), 7.44-7.37 (7H, m), 7.28-7.18 (5H, m), 6.81-6.73 (4H, m), 6.44 (0.6H, d, J=6.3 Hz), 6.40 (0.4H, d, J=6.3 Hz), 5.34-5.28 (1H, m), 4.47-4.35 (2.4H, m), 4.32-4.26 (0.6H, m), 4.25-4.16 (1H, m), 4.03-3.84 (1H, m), 3.80-3.73 (6H, m), 3.69-3.44 (4H, m), 3.18-3.00 (3H, m), 2.73-2.59 (1H, m), 2.40-2.19 (3H, m), 1.22-1.14 (8.4H, m), 1.01 (3.6H, d, J=6.7 Hz), 0.76 (3.6H, s), 0.74 (5.4H, s), 0.02 (1.2H, s), 0.01 (1.8H, s), −0.12 (1.8H, s), −0.15 (1.2H, s).

(Step 11)

(5R,7R,8R,12aR,14R,15R,15aR,16R)-7-(6-Amino-9H-purin-9-yl)-15,16-bis{[tert-butyl(dimethyl)silyl]oxy}-2,10-bis(sulfanyl)-14-(6,7,8,9-tetrahydro-2H-1,2,3,5,6-pentaazabenzo[cd]azulen-2-yl)octahydro-2H,10H,12H-5,8-methano-2λ$^5$,10λ$^5$-furo[3,2-l][1,3,6,9,11,2,10]pentaoxadiphosphacyclotetradecine-2,10-dione With use of the compound obtained in step 10 (1.04 g), the reaction was performed in the same manner as in step 7 of Example 1 to afford an acetonitrile solution of 6-benzoyl-2-{2-O-[tert-butyl(dimethyl)silyl]-3-O-(dihydroxyphosphanyl)-β-D-ribofuranosyl}-6,7,8,9-tetrahydro-2H-1,2,3,5,6- pentaazabenzo[cd]azulene. With use of this acetonitrile solution and commercially available (Cool Pharm Ltd.) N-benzoyl-5'-O-[bis(4-methoxyphenyl)(phenyl)methyl]-3'-O-[tert-butyl(dimethyl)silyl]-2'-O-{(2-cyanoethoxy)[di(propan-2-yl)amino]phosphanyl}adenosine (1.20 g), the reaction was performed in the same manner as in step 8 of Example 1, step 9 of Example 1, and step 10 of Example 1 to afford the title compound as a mixture of diastereomers at the phosphorus atom. The diastereomers at the phosphorus atom were separated by preparative HPLC [10 mM aqueous solution of triethylammonium acetate/acetonitrile, acetonitrile: 25-50% (0 min-35 min)] to afford diastereomer 1 (15 mg) and diastereomer 2 (55 mg) of the title compound (retention time in HPLC: diastereomer 1>2).

Diastereomer 1 (Less Polar)

MS(ESI)m/z: 959 (M+H)$^+$.

Diastereomer 2 (More Polar)

MS(ESI)m/z: 959 (M+H)$^+$.

(Step 12-1)

Bis(N,N-diethylethaneaminium) (5R,7R,8R,12aR,14R,15R,15aS,16R)-7-(6-amino-9H-purin-9-yl)-15,16-dihydroxy-2,10-dioxo-14-(6,7,8,9-tetrahydro-2H-1,2,3,5,6-pentaazabenzo[cd]azulen-2-yl)octahydro-2H,10H,12H-5,8-methano-2$\lambda^5$,10$\lambda^5$-furo[3,2-1][1,3,6,9,11,2,10]pentaoxadiphosphacyclotetradecine-2,10-bis(thiolate)

Triethylamine trihydrofluoride (1 mL) was added to the compound obtained in step 11 (diastereomer 1) (20 mg), and the reaction mixture was stirred at 45° C. for 2 hours. The reaction mixture was added to an ice-cooled mixed solution of 1 M aqueous solution of triethylammonium hydrogen carbonate (3 mL) and triethylamine (1 mL) to quench the reaction. The resultant was purified with a Sep-Pak® C18 [0.1% triethylamine water/acetonitrile, acetonitrile: 0%-17%] to afford the title compound (15 mg).

MS(ESI)m/z: 731 (M+H)$^+$.

(Step 12-2)

Bis(N,N-diethylethaneaminium) (5R,7R,8R,12aR,14R,15R,15aS,16R)-7-(6-amino-9H-purin-9-yl)-15,16-dihydroxy-2,10-dioxo-14-(6,7,8,9-tetrahydro-2H-1,2,3,5,6-pentaazabenzo[cd]azulen-2-yl)octahydro-2H,10H,12H-5,8-methano-2$\lambda^5$,10$\lambda^5$-furo[3,2-1][1,3,6,9,11,2,10]pentaoxadiphosphacyclotetradecine-2,10-bis(thiolate)

With use of the compound obtained in step 11 (diastereomer 2) (43 mg), the reaction was performed in the same manner as in step 12-1 to afford the title compound (34 mg).

MS(ESI)m/z: 731 (M+H)$^+$.

(Step 13-1)

Disodium (5R,7R,8R,12aR,14R,15R,15aS,16R)-7-(6-amino-9H-purin-9-yl)-15,16-dihydroxy-2,10-dioxo-14-(6,7,8,9-tetrahydro-2H-1,2,3,5,6-pentaazabenzo[cd]azulen-2-yl)octahydro-2H,10H,12H-5,8-methano-2$\lambda^5$,10$\lambda^5$-furo[3,2-1][1,3,6,9,11,2,10]pentaoxadiphosphacyclotetradecine-2,10-bis(thiolate)

(Diastereomer 1)

With use of the compound obtained in step 12-1 (15 mg), salt exchange was performed in the same manner as in [Conversion to Sodium Salt] described in step 11 of Example 1 to afford a mixture of diastereomers of the title compound (12 mg).

MS(ESI)m/z: 731 (M+H)$^+$.

1H-NMR (CD$_3$OD) δ: 8.79 (1H, s), 8.18 (1H, s), 8.14 (1H, s), 6.37-6.34 (2H, m), 5.50 (1H, dd, J=10.8, 5.3 Hz), 5.40-5.33 (1H, m), 5.06 (1H, dd, J=4.5, 2.9 Hz), 4.94 (1H, d, J=3.5 Hz), 4.67-4.30 (4H, m), 4.03 (1H, ddd, J=12.5, 6.1, 2.2 Hz), 3.93 (1H, dt, J=18.1, 6.1 Hz), 3.58 (2H, d, J=7.4 Hz), 3.02 (2H, t, J=5.9 Hz), 2.18-2.04 (2H, m).

$^{31}$P-NMR (CD$_3$OD) δ: 56.5 (s), 54.2 (s).

(Step 13-2)

Disodium (5R,7R,8R,12aR,14R,15R,15aS,16R)-7-(6-amino-9H-purin-9-yl)-15,16-dihydroxy-2,10-dioxo-14-(6,7,8,9-tetrahydro-2H-1,2,3,5,6-pentaazabenzo[cd]azulen-2-yl)octahydro-2H,10H,12H-5,8-methano-2$\lambda^5$,10$\lambda^5$-furo[3,2-1][1,3,6,9,11,2,10]pentaoxadiphosphacyclotetradecine-2,10-bis(thiolate)

(Diastereomer 2)

With use of the compound obtained in step 12-2 (34 mg), salt exchange was performed in the same manner as in [Conversion to Sodium Salt] described in step 11 of Example 1 to afford a mixture of diastereomers of the title compound (28 mg: diastereomer ratio=4:1).

MS(ESI)m/z: 731 (M+H)$^+$.

$^1$H-NMR (CD$_3$OD) δ: 9.16 (0.2H, s), 8.85 (0.8H, s), 8.19 (0.2H, s), 8.17 (0.8H, s), 8.14 (0.8H, s), 8.13 (0.2H, s), 6.38-6.30 (2H, m), 5.67-5.61 (0.8H, m), 5.57-5.36 (1.2H, m), 5.22 (0.8H, dd, J=5.9, 4.3 Hz), 5.10 (0.2H, t, J=4.5 Hz), 4.64-4.26 (4.8H, m), 4.16-4.10 (0.2H, m), 4.05-3.98 (1H, m), 3.86-3.79 (1H, m), 3.62-3.54 (2H, m), 3.07 (1.6H, t, J=5.7 Hz), 2.98 (0.4H, t, J=5.9 Hz), 2.17-2.04 (2H, m).

$^{31}$P-NMR (CD$_3$OD) δ: 63.5 (s), 63.4 (s), 60.0 (s), 59.9 (s).

Example 20: Synthesis of CDN20

(5R,7R,8R,12aR,14R,15R,15aS,16R)-7-(6-Amino-9H-purin-9-yl)-14-(8,9-dihydro-6-oxa-2,3,5-triazabenzo[cd]azulen-2 (7H)-yl)-15,16-dihydroxy-2,10-bis(sulfanyl)octahydro-2H,10H,12H-5,8-methano-2$\lambda^5$,10$\lambda^5$-furo[3,2-1][1,3,6,9,11,2,10]pentaoxadiphosphacyclotetradecine-2,10-dione

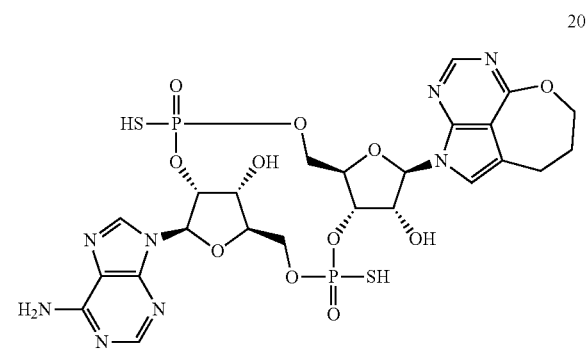

20a (Diastereomer 1)
20b (Diastereomer 2)

[Synthesis Scheme]
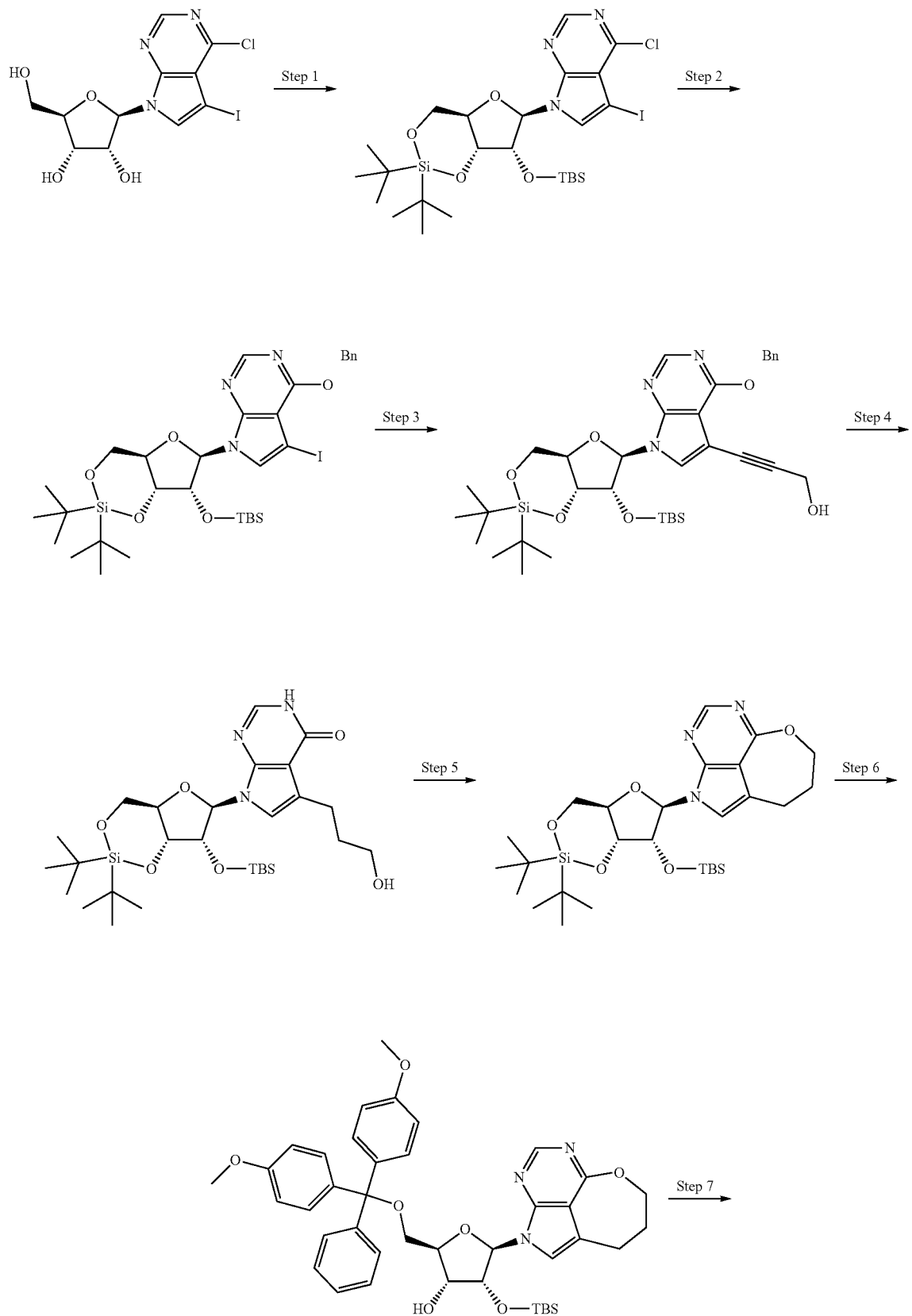

295
296
-continued
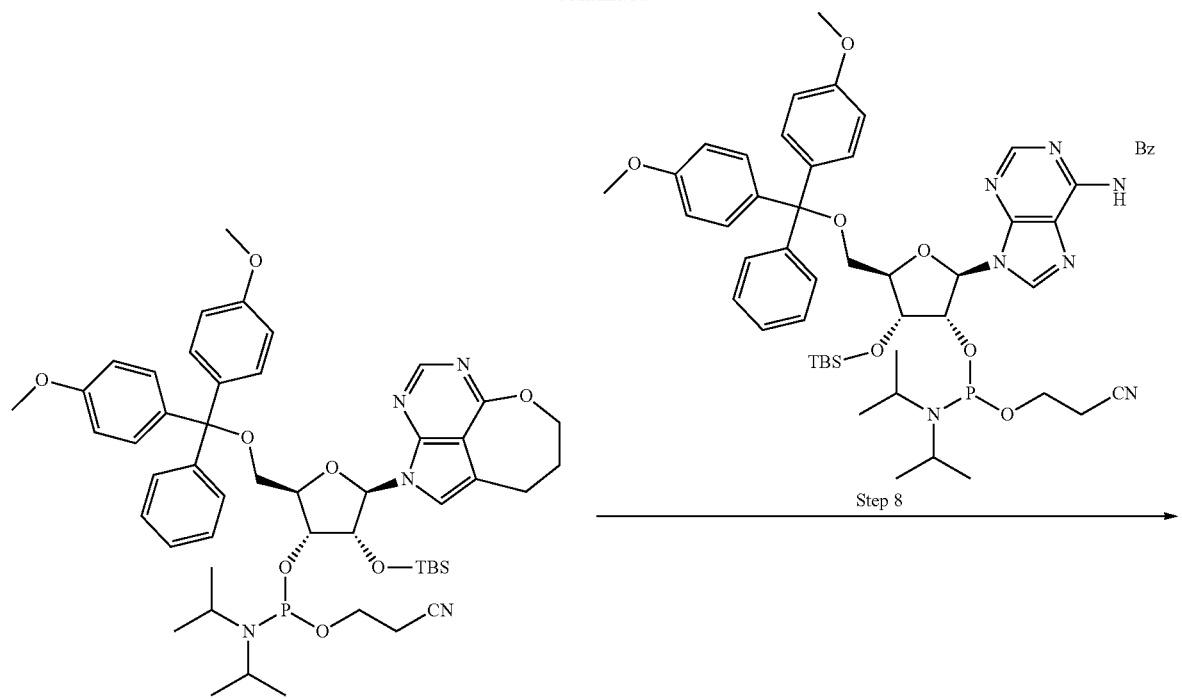
Step 8
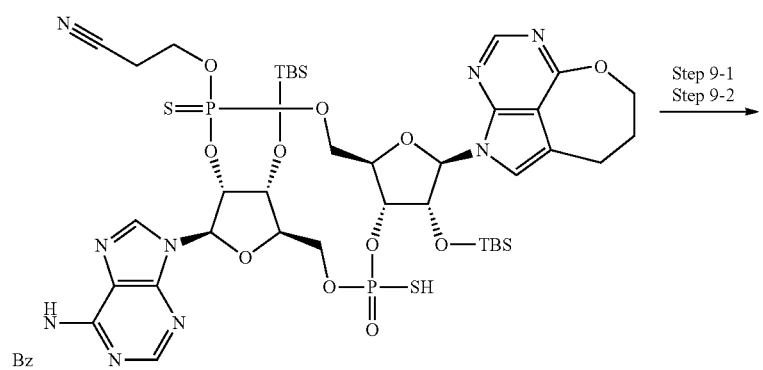
Step 9-1
Step 9-2
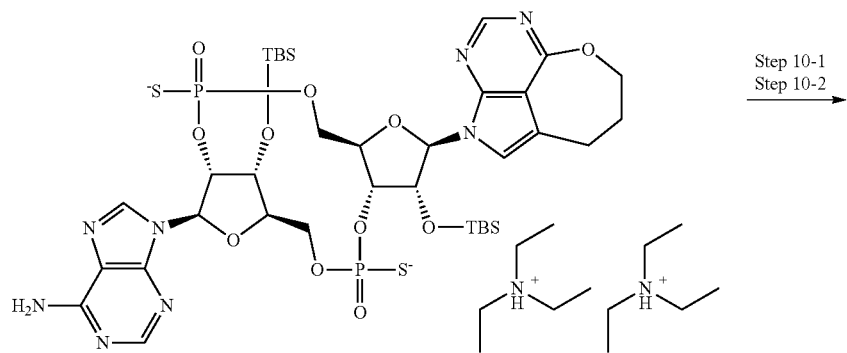
Step 10-1
Step 10-2

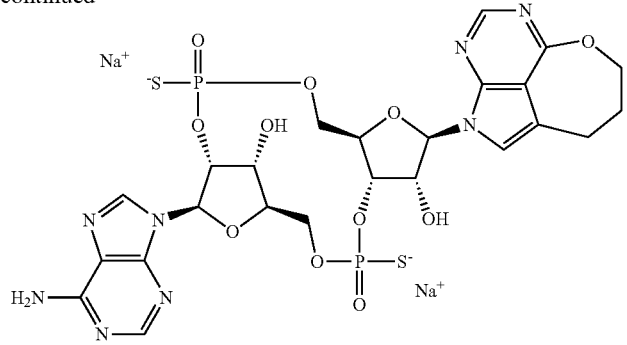

(Step 1)

7-{2-O-[tert-Butyl(dimethyl)silyl]-3,5-O-(di-tert-butylsilylidene)-β-D-ribofuranosyl}-4-chloro-5-iodo-7H-pyrrolo[2,3-d]pyrimidine With use of 4-chloro-5-iodo-7-β-D-ribofuranosyl-7H-pyrrolo[2,3-d]pyrimidine (3.15 g) as a compound known in the literature (J. Med. Chem. 2008, 51, 3934-3945), the reaction was performed in the same manner as in step 1 of Example 1 to afford the title compound (2.97 g).
$^1$H-NMR (CDCl$_3$) δ: 8.62 (1H, s), 7.38 (1H, s), 6.18 (1H, s), 4.53-4.47 (1H, m), 4.44 (1H, d, J=3.9 Hz), 4.24-4.18 (2H, m), 4.06-3.98 (1H, m), 1.09 (9H, s), 1.05 (9H, s), 0.92 (9H, s), 0.13 (3H, s), 0.12 (3H, s).

(Step 2)

4-(Benzyloxy)-7-{2-O-[tert-butyl(dimethyl)silyl]-3,5-O-(di-tert-butylsilylidene)-β-D-ribofuranosyl}-5-iodo-7H-pyrrolo[2,3-d]pyrimidine To a solution of the compound obtained in step 1 (4.97 g) and benzyl alcohol (1.0 mL) in tetrahydrofuran (50 mL), sodium hydride (containing 37% mineral oil) (426 mg) was added under ice-cooling, and the temperature was increased to room temperature and the reaction mixture was stirred overnight. A saturated aqueous solution of ammonium chloride was added to the reaction mixture under ice-cooling to quench the reaction. After the reaction mixture was subjected to extraction with ethyl acetate, the organic layer was washed with water and brine, and dried over anhydrous sodium sulfate. The drying agent was removed through filtration, and the filtrate was concentrated under reduced pressure. The residue was purified by silica gel column chromatography [hexane/ethyl acetate] to afford the title compound (3.38 g).
$^1$H-NMR (CDCl$_3$) δ: 8.43 (1H, s), 7.62-7.57 (2H, m), 7.43-7.37 (2H, m), 7.36-7.30 (1H, m), 7.13 (1H, s), 6.15 (1H, s), 5.65 (1H, d, J=13.7 Hz), 5.62 (1H, d, J=13.7 Hz), 4.50-4.43 (2H, m), 4.27 (1H, dd, J=9.2, 4.9 Hz), 4.21-4.12 (1H, m), 4.01 (1H, dd, J=10.4, 9.2 Hz), 1.09 (9H, s), 1.04 (9H, s), 0.91 (9H, s), 0.12 (3H, s), 0.11 (3H, s).

(Step 3)

4-(Benzyloxy)-7-{2-O-[tert-butyl(dimethyl)silyl]-3,5-O-(di-tert-butylsilylidene)-β-D-ribofuranosyl}-5-(3-hydroxyprop-1-yn-1-yl)-7H-pyrrolo[2,3-d]pyrimidine With use of the compound obtained in step 2 (3.38 g) and 2-propyn-1-ol (1.35 mL), the reaction was performed in the same manner as in step 2 of Example 1, except that the reaction temperature was set to room temperature, to afford the title compound (2.22 g).
$^1$H-NMR (CDCl$_3$) δ: 8.46 (1H, s), 7.59-7.55 (2H, m), 7.43-7.33 (3H, m), 7.22 (1H, s), 6.16 (1H, s), 5.60 (1H, d, J=12.7 Hz), 5.57 (1H, d, J=12.7 Hz), 4.51-4.41 (4H, m), 4.27 (1H, dd, J=9.5, 5.0 Hz), 4.19 (1H, dt, J=9.9, 5.0 Hz), 4.01 (1H, dd, J=9.9, 9.5 Hz), 1.52 (1H, t, J=6.3 Hz), 1.08 (9H, s), 1.04 (9H, s), 0.91 (9H, s), 0.13 (3H, s), 0.11 (3H, s).

(Step 4)

7-{2-O-[tert-Butyl(dimethyl)silyl]-3,5-O-(di-tert-butylsilylidene)-β-D-ribofuranosyl}-5-(3-hydroxypropyl)-3,7-dihydro-4H-pyrrolo[2,3-d]pyrimidin-4-one With use of the compound obtained in step 3 (3.38 g), the reaction was performed in the same manner as in step 7 of Example 19, except that the reaction solvent was changed to a mixture of methanol (20 mL)-tetrahydrofuran (20 mL), to afford the title compound (0.92 g).
$^1$H-NMR (CDCl$_3$) δ: 11.36 (1H, brs), 7.86 (1H, s), 6.69 (1H, s), 6.10 (1H, s), 4.48 (1H, dd, J=9.2, 4.9 Hz), 4.37 (1H, d, J=5.1 Hz), 4.23 (1H, dd, J=9.3, 4.8 Hz), 4.16 (1H, dt, J=9.8, 4.8 Hz), 4.02 (1H, dd, J=9.8, 9.3 Hz), 3.84 (1H, t, J=6.3 Hz), 3.58 (2H, dd, J=11.9, 6.1 Hz), 3.03-2.90 (2H, m), 1.86 (2H, s), 1.09 (9H, s), 1.04 (9H, s), 0.90 (9H, s), 0.10 (6H, s).

(Step 5)

2-{2-O-[tert-Butyl(dimethyl)silyl]-3,5-O-(di-tert-butylsilylidene)-β-D-ribofuranosyl}-2,7,8,9-tetrahydro-6-oxa-2,3,5-triazabenzo[cd]azulene To a solution of the compound obtained in step 4 (0.92 g) in tetrahydrofuran (32 mL), triphenylphosphine (0.62 g) and diisopropyl azodicarboxylate (0.47 mL) were added under ice-cooling, and the temperature was increased to room temperature and the reaction mixture was stirred for 1 hour. After the reaction mixture was concentrated under reduced pressure, the residue was purified by silica gel column chromatography [hexane/ethyl acetate] to afford the title compound (0.77 g).
$^1$H-NMR (CDCl$_3$) δ: 8.44 (1H, s), 6.85 (1H, s), 6.19 (1H, s), 4.56-4.51 (2H, m), 4.50-4.44 (2H, m), 4.35 (1H, dd, J=9.5, 5.0 Hz), 4.17 (1H, dt, J=10.0, 5.0 Hz), 4.00 (1H, dd, J=10.0, 9.5 Hz), 2.98-2.92 (2H, m), 2.28-2.20 (2H, m), 1.10 (9H, s), 1.05 (9H, s), 0.91 (9H, s), 0.12 (3H, s), 0.11 (3H, s).

(Step 6)

2-{5-O-[Bis(4-methoxyphenyl)(phenyl)methyl]-2-O-[tert-butyl(dimethyl)silyl]-β-D-ribofuranosyl}-2,7,8,9-tetrahydro-6-oxa-2,3,5-triazabenzo[cd]azulene With use of the compound obtained in step 5 (0.95 g), the reaction was performed in the same manner as in step 5 of Example 1 to afford the title compound (1.13 g).
$^1$H-NMR (CDCl$_3$) δ: 8.42 (1H, s), 7.48-7.43 (2H, m), 7.37-7.21 (7H, m), 7.19 (1H, s), 6.85-6.79 (4H, m), 6.35 (1H, d, J=5.4 Hz), 4.71 (1H, t, J=5.4 Hz), 4.55-4.48 (2H, m), 4.35 (1H, dd, J=8.2, 4.3 Hz), 4.22 (1H, q, J=3.0 Hz), 3.79 (3H, s), 3.79 (3H, s), 3.53 (1H, dd, J=10.6, 3.1 Hz), 3.37 (1H, dd, J=10.6, 3.1 Hz), 2.80 (1H, d, J=4.3 Hz), 2.71 (2H, t, J=5.5 Hz), 2.23-2.15 (2H, m), 0.83 (9H, s), −0.04 (3H, s), −0.16 (3H, s).

(Step 7)

2-(5-O-[Bis(4-methoxyphenyl)(phenyl)methyl]-2-O-[tert-butyl(dimethyl)silyl]-3-O-{(2-cyanoethoxy)[di(propan-2-yl)amino]phosphanyl}-β-D-ribofuranosyl)-2,7,8,9-tetrahydro-6-oxa-2,3,5-triazabenzo[cd]azulene With use of the compound obtained in step 6 (1.13 g), the reaction was performed in the same manner as in step 4 of Example 5, except that silica gel column chromatography [hexane/ethyl acetate/0.1% triethylamine] was used for purification, to afford the title compound (1.00 g) as a mixture of diastereomers at the phosphorus atom (diastereomer ratio=6:4).
$^1$H-NMR (CDCl$_3$) δ: 8.41 (0.4H, s), 8.39 (0.6H, s), 7.51-7.43 (2H, m), 7.39-7.17 (8H, m), 6.85-6.79 (4H, m), 6.34 (0.6H, d, J=6.7 Hz), 6.30 (0.4H, d, J=5.9 Hz), 4.82 (0.6H, dd, J=6.7, 4.7 Hz), 4.76 (0.4H, dd, J=5.9, 4.7 Hz), 4.55-4.47 (2H, m), 4.43-4.35 (1.2H, m), 4.30-4.25 (0.8H, m), 4.05-3.85 (1H, m), 3.81-3.76 (6H, m), 3.70-3.47 (4H, m), 3.32-3.24 (1H, m), 2.79-2.64 (3.2H, m), 2.31 (0.8H, t, J=6.5 Hz), 2.23-2.14 (2H, m), 1.20-1.15 (8.4H, m), 1.03 (3.6H, d, J=7.0 Hz), 0.75 (3.6H, s), 0.73 (5.4H, s), −0.03 (1.2H, s), −0.08 (1.8H, s), −0.20 (1.2H, s), −0.22 (1.8H, s).

(Step 8)

N-{9-[(5R,7R,8R,12aR,14R,15R,15aR,16R)-15,16-Bis{[tert-butyl(dimethyl)silyl]oxy}-10-(2-cyanoethoxy)-14-(8,9-dihydro-6-oxa-2,3,5-triazabenzo[cd]azulen-2 (7H)-yl)-2-oxo-2-sulfanyl-10-sulfanylideneoctahydro-2H,10H,12H-5,8-methano-2λ$^5$,10λ$^5$-furo[3,2-1][1,3,6,9,11,2,10]pentaoxadiphosphacyclotetradecin-7-yl]-9H-purin-6-yl}benzamide With use of the compound obtained in step 7 (1.00 g), the reaction was performed in the same manner as in step 7 of Example 1 to afford an acetonitrile solution of 2-{2-O-[tert-butyl(dimethyl)silyl]-3-O-(dihydroxyphosphanyl)-β-D-ribofuranosyl}-2,7,8,9-tetrahydro-6-oxa-2,3,5-triazabenzo[cd]azulene. With use of this acetonitrile solution and commercially available (Cool Pharm Ltd.) N-benzoyl-5'-O-[bis(4-methoxyphenyl)(phenyl)methyl]-3'-O-[tert-butyl(dimethyl)silyl]-2'-O-{(2-cyanoethoxy)[di(propan-2-yl)amino]phosphanyl}adenosine (1.28 g), the reaction was performed in the same manner as in step 8 of Example 1 and step 9 of Example 1 to afford a mixture containing diastereomer 1 of the title compound and a mixture containing diastereomer 2 of the title compound.

Diastereomer 1 (Less Polar)
MS(ESI)m/z: 1116 (M+H)$^+$.
Diastereomer 2 (More Polar)
MS(ESI)m/z: 1116 (M+H)$^+$.

(Step 9-1)

Bis(N,N-diethylethaneaminium) (5R,7R,8R,12aR,14R,15R,15aR,16R)-7-(6-amino-9H-purin-9-yl)-15,16-bis{[tert-butyl(dimethyl)silyl]oxy}-14-(8,9-dihydro-6-oxa-2,3,5-triazabenzo[cd]azulen-2 (7H)-yl)-2,10-dioxooctahydro-2H,10H,12H-5,8-methano-2λ$^5$,10λ$^5$-furo[3,2-1][1,3,6,9,11,2,10]pentaoxadiphosphacyclotetradecine-2,10-bis(thiolate)

With use of the whole quantity of the compound obtained in step 8 (the mixture containing diastereomer 1), the reaction was performed in the same manner as in step 10 of Example 1, and purification was then performed under the following [Purification Conditions] to afford the title compound (73 mg) as a triethylamine salt.
[Purification Conditions] HPLC [10 mM aqueous solution of triethylammonium acetate/acetonitrile, acetonitrile: 30%-60% (0 min-35 min)].
MS(ESI)m/z: 959 (M+H)$^+$.

(Step 9-2)

Bis(N,N-diethylethaneaminium) (5R,7R,8R,12aR,14R,15R,15aR,16R)-7-(6-amino-9H-purin-9-yl)-15,16-bis{[tert-butyl(dimethyl)silyl]oxy}-14-(8,9-dihydro-6-oxa-2,3,5-triazabenzo[cd]azulen-2 (7H)-yl)-2,10-dioxooctahydro-2H,10H,12H-5,8-methano-2λ$^5$,10λ$^5$-furo[3,2-1][1,3,6,9,11,2,10]pentaoxadiphosphacyclotetradecine-2,10-bis(thiolate)

With use of the whole quantity of the compound obtained in step 8 (the mixture containing diastereomer 2), the reaction was performed in the same manner as in step 10 of Example 1, and purification was then performed under the following [Purification Conditions] to afford the title compound (58 mg) as a triethylamine salt.
[Purification Conditions] HPLC [10 mM aqueous solution of triethylammonium acetate/acetonitrile, acetonitrile: 25%-50% (0 min-35 min)].
MS(ESI)m/z: 959 (M+H)$^+$.

(Step 10-1)

Disodium (5R,7R,8R,12aR,14R,15R,15aS,16R)-7-(6-amino-9H-purin-9-yl)-14-(8,9-dihydro-6-oxa-2,3,5-triazabenzo[cd]azulen-2 (7H)-yl)-15,16-dihydroxy-2,10-dioxooctahydro-2H,10H,12H-5,8-methano-2λ$^5$,10λ$^5$-furo[3,2-1][1,3,6,9,11,2,10]pentaoxadiphosphacyclotetradecine-2,10-bis(thiolate)

(Diastereomer 1)
With use of the compound obtained in step 9-1 (68 mg), the reaction was performed in the same manner as in step 12-1 of Example 19, and salt exchange was then performed in the same manner as in [Conversion to Sodium Salt] described in step 11 of Example 1 to afford the title compound (42 mg).
MS(ESI)m/z: 731 (M+H)$^+$.
$^1$H-NMR (CD$_3$OD) δ: 8.73 (1H, s), 8.31 (1H, s), 8.17 (1H, s), 7.36 (1H, s), 6.38 (1H, d, J=4.7 Hz), 6.34 (1H, d, J=8.2 Hz), 5.42-5.34 (1H, m), 5.24-5.16 (1H, m), 4.86-4.81 (2H, m), 4.64-4.29 (6H, m), 4.12-4.01 (2H, m), 2.98-2.81 (2H, m), 2.28-2.13 (2H, m).
$^{31}$P-NMR (CD$_3$OD) δ: 58.2 (s), 54.4 (s).

(Step 10-2)

Disodium (5R,7R,8R,12aR,14R,15R,15aS,16R)-7-(6-amino-9H-purin-9-yl)-14-(8,9-dihydro-6-oxa-2,3,5-triazabenzo[cd]azulen-2 (7H)-yl)-15,16-dihydroxy-2,10-dioxooctahydro-2H,10H,12H-5,8-methano-2λ$^5$,10λ$^5$-furo[3,2-1][1,3,6,9,11,2,10]pentaoxadiphosphacyclotetradecine-2,10-bis (thiolate)

(Diastereomer 2)

With use of the compound obtained in step 9-2 (58 mg), the reaction was performed in the same manner as in step 12-1 of Example 19, and salt exchange was then performed in the same manner as in [Conversion to Sodium Salt] described in step 11 of Example 1 to afford the title compound (35 mg).

MS(ESI)m/z: 731 (M+H)$^+$.

$^1$H-NMR (CD$_3$OD) δ: 8.81 (1H, s), 8.31 (1H, s), 8.17 (1H, s), 7.38 (1H, s), 6.41 (1H, d, J=6.7 Hz), 6.34 (1H, d, J=8.6 Hz), 5.56-5.41 (2H, m), 4.87 (1H, m), 4.64-4.27 (7H, m), 4.06-3.99 (1H, m), 3.92-3.88 (1H, m), 2.99 (2H, t, J=5.5 Hz), 2.28-2.19 (2H, m).

$^{31}$P-NMR (CD$_3$OD) δ: 63.1 (s), 60.5 (s).

Example 21: Synthesis of Drug-Linker 1

[Synthesis Scheme]

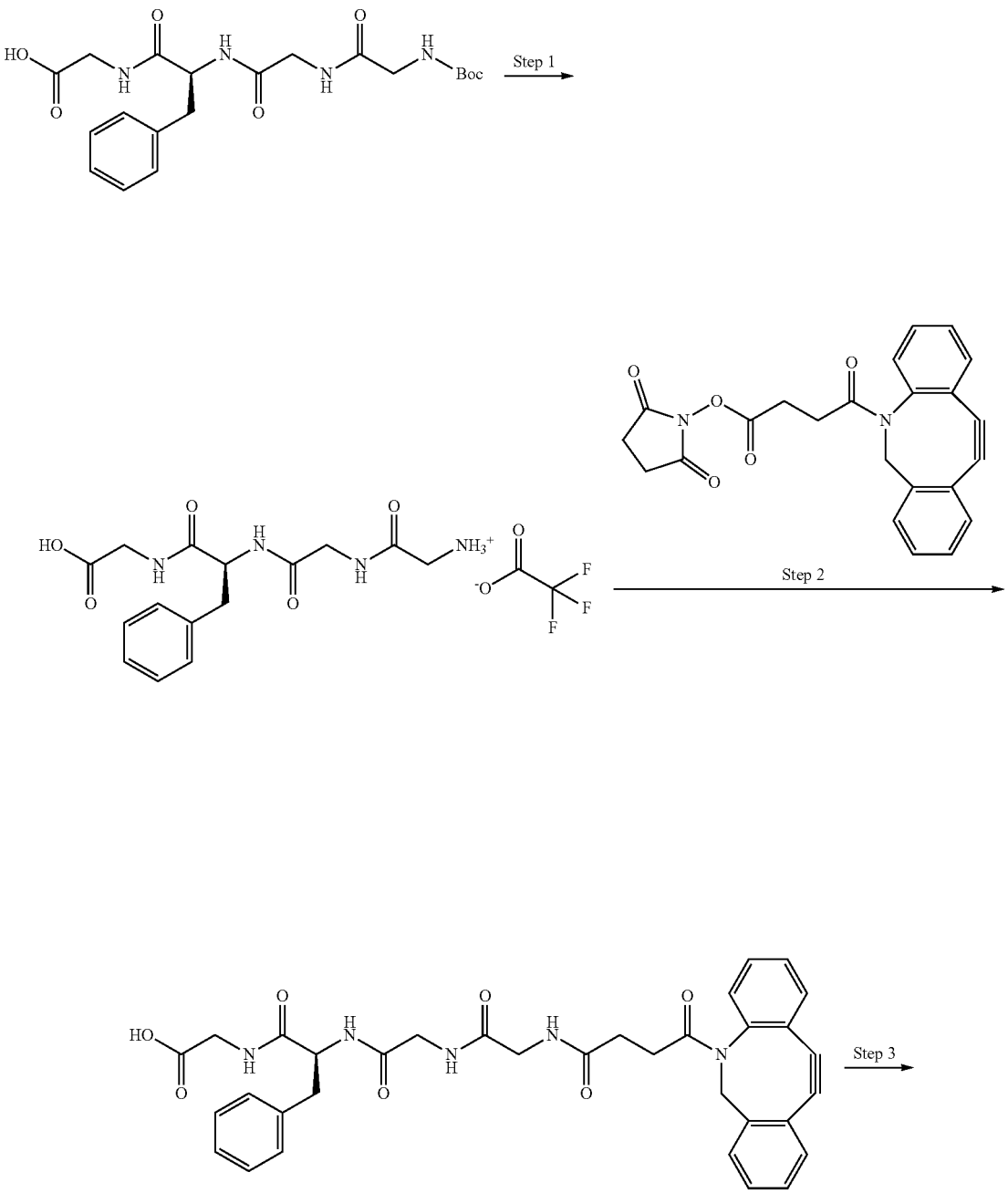

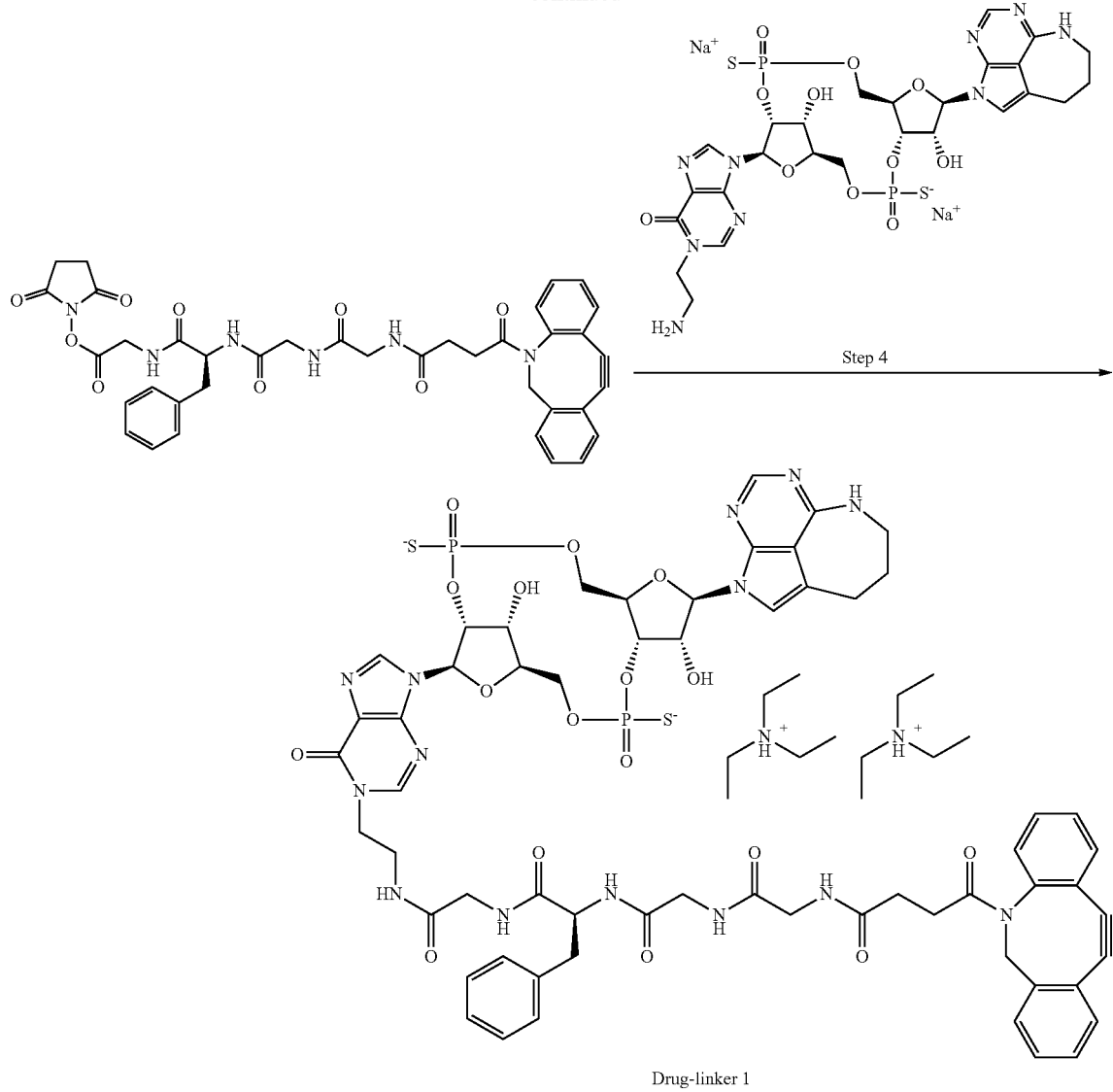

Drug-linker 1

(Step 1)

N-(Azaniumylacetyl)glycyl-L-phenylalanylglycine trifluoroacetate

To a solution of commercially available (Bachem Holding AG) N-(tert-butoxycarbonyl)glycylglycyl-L-phenylalanylglycine (3.00 g) in dichloromethane (30 mL), trifluoroacetic acid (15 mL) was added at room temperature, and the reaction mixture was stirred at the same temperature for 3 hours. The reaction mixture was concentrated under reduced pressure, and then suspended in toluene and again concentrated under reduced pressure. This concentration operation was further repeated twice. The residue was made into a slurry with diethyl ether (100 mL), and then collected through filtration to give a crude form of the title compound (3.27 g).

MS(ESI)m/z: 337 (M+H)$^+$.

$^1$H-NMR (DMSO-$d_6$) δ: 12.60 (1H, brs), 8.48 (1H, t, J=5.6 Hz), 8.44 (1H, t, J=5.9 Hz), 8.31 (1H, d, J=8.8 Hz), 7.97 (3H, brs), 7.28-7.16 (5H, m), 4.58 (1H, m), 3.87 (1H, dd, J=16.8, 5.6 Hz), 3.78 (2H, d, J=5.9 Hz), 3.67 (1H, dd, J=17.1, 5.4 Hz), 3.56 (2H, brd, J=4.4 Hz), 3.05 (1H, dd, J=13.7, 3.9 Hz), 2.74 (1H, dd, J=13.7, 10.3 Hz).

(Step 2)

N-[4-(11,12-Didehydrodibenzo[b,f]azocin-5 (6H)-yl)-4-oxobutanoyl]glycylglycyl-L-phenylalanylglycine To a solution of the compound obtained in step 1 (2.09 g) in N,N-dimethylformamide (46.4 mL), triethylamine (0.804 mL) and 1-{[4-(11,12-didehydrodibenzo[b,f]azocin-5 (6H)-yl)-4-oxobutanoyl]oxy}pyrrolidine-2,5-dione (1.87 g) were added, and the reaction mixture was stirred at room temperature for 21 hours. The reaction mixture was concentrated under reduced pressure, and the residue was purified by silica gel column chromatography [dichloromethane/methanol]. To a dichloromethane solution of the resulting compound, diethyl ether was added to make a slurry, and the compound was collected through filtration to give the title compound (2.10 g).

MS(ESI)m/z: 624 (M+H)+.

¹H-NMR (DMSO-d₆) δ: 8.20-7.91 (4H, m), 7.68-7.13 (13H, m), 4.98 (1H, dd, J=13.9, 3.2 Hz), 4.51-4.46 (1H, m), 3.73-3.47 (7H, m), 3.00 (1H, dd, J=13.9, 4.1 Hz), 2.73 (1H, t, J=11.7 Hz), 2.67-2.57 (1H, m), 2.29-2.22 (1H, m), 2.06-2.01 (1H, m), 1.80-1.73 (1H, m). (only observable peaks are shown)

(Step 3)

2,5-Dioxopyrrolidin-1-yl N-[4-(11,12-didehydrodibenzo[b,f]azocin-5 (6H)-yl)-4-oxobutanoyl]glycylglycyl-L-phenylalanylglycinate To a solution of the compound obtained in step 2 (2.10 g) in N,N-dimethylformamide (33.7 mL), N-hydroxysuccinimide (426 mg) and 1-ethyl-3-(3-dimethylaminopropyl)-carbodiimide hydrochloride (710 mg) were added, and the reaction mixture was stirred under the nitrogen atmosphere at room temperature for 16 hours. The reaction mixture was diluted with dichloromethane, and then washed three times with iced water, and dried over anhydrous sodium sulfate. The drying agent was removed through filtration, and the filtrate was concentrated under reduced pressure. Ethyl acetate was added to the oily residue to precipitate a solid. The solvent was distilled off under reduced pressure, and diethyl ether was added to the resulting solid to make a slurry, and the solid was collected through filtration to give the title compound (2.18 g).

¹H-NMR (DMSO-d₆) δ: 8.74-8.69 (1H, m), 8.16-8.08 (2H, m), 8.00-7.93 (1H, m), 7.71-7.15 (13H, m), 5.00 (1H, dd, J=13.9, 3.0 Hz), 4.55-4.49 (1H, m), 4.27 (2H, t, J=6.0 Hz), 3.77-3.68 (1H, m), 3.64-3.50 (4H, m), 3.02 (1H, dd, J=13.9, 4.2 Hz), 2.82-2.73 (5H, m), 2.69-2.58 (1H, m), 2.33-2.24 (1H, m), 2.10-2.02 (1H, m), 1.83-1.75 (1H, m).

(Step 4)

Bis(N,N-diethylethaneaminium) N-[4-(11,12-didehydrodibenzo[b,f]azocin-5 (6H)-yl)-4-oxobutanoyl]glycylglycyl-L-phenylalanyl-N-(2-{9-[(5R,7R,8R,12aR,14R,15R,15aS,16R)-15,16-dihydroxy-2,10-dioxo-2,10-disulfide-14-(6,7,8,9-tetrahydro-2H-2,3,5,6-tetraazabenzo[cd]azulen-2-yl)octahydro-2H,10H,12H-5,8-methano-2λ⁵,10λ⁵-furo[3,2-1][1,3,6,9,11,2,10]pentaoxadiphosphacyclotetradecin-7-yl]-6-oxo-6,9-dihydro-1H-purin-1-yl}ethyl)glycinamide (Drug-Linker 1)

To a solution of the compound obtained in step 8-2 of Example 5 (10.0 mg) in N,N-dimethylformamide (1 mL), triethylamine (8 μL) and the compound obtained in step 3 (17.6 mg) were added, and the reaction mixture was stirred at room temperature for 2 hours. Benzylamine (3 μL) was added to the reaction mixture, which was stirred at room temperature for 1 hour. To the reaction mixture, 10 mM aqueous solution of triethylammonium acetate and methanol were added, and the reaction mixture was purified by C18 silica gel column chromatography [10 mM aqueous solution of triethylammonium acetate/acetonitrile] and preparative HPLC [10 mM aqueous solution of triethylammonium acetate/acetonitrile, acetonitrile: 5%-50% (0 min-40 min)] to afford the title compound (10.9 mg).

MS(ESI)m/z: 1379 (M+H)+.

¹H-NMR (CD₃OD) δ: 8.72 (1H, d, J=10.0 Hz), 8.15 (1H, d, J=10.0 Hz), 8.02 (1H, s), 7.63-7.50 (2H, m), 7.42-7.37 (3H, m), 7.32-7.13 (8H, m), 7.12 (1H, s), 6.31 (1H, d, J=6.7 Hz), 6.25 (1H, d, J=8.5 Hz), 5.51-5.40 (2H, m), 5.09-4.99 (1H, m), 4.85-4.77 (1H, m), 4.53-4.42 (2H, m), 4.42-4.15 (5H, m), 4.04-3.96 (1H, m), 3.92-3.46 (12H, m), 3.18 (12H, q, J=7.3 Hz), 3.16-2.73 (5H, m), 2.40-2.23 (2H, m), 2.06-1.94 (4H, m), 1.29 (18H, t, J=7.3 Hz).

Example 22: Synthesis of Drug-Linker 2

[Synthesis Scheme]

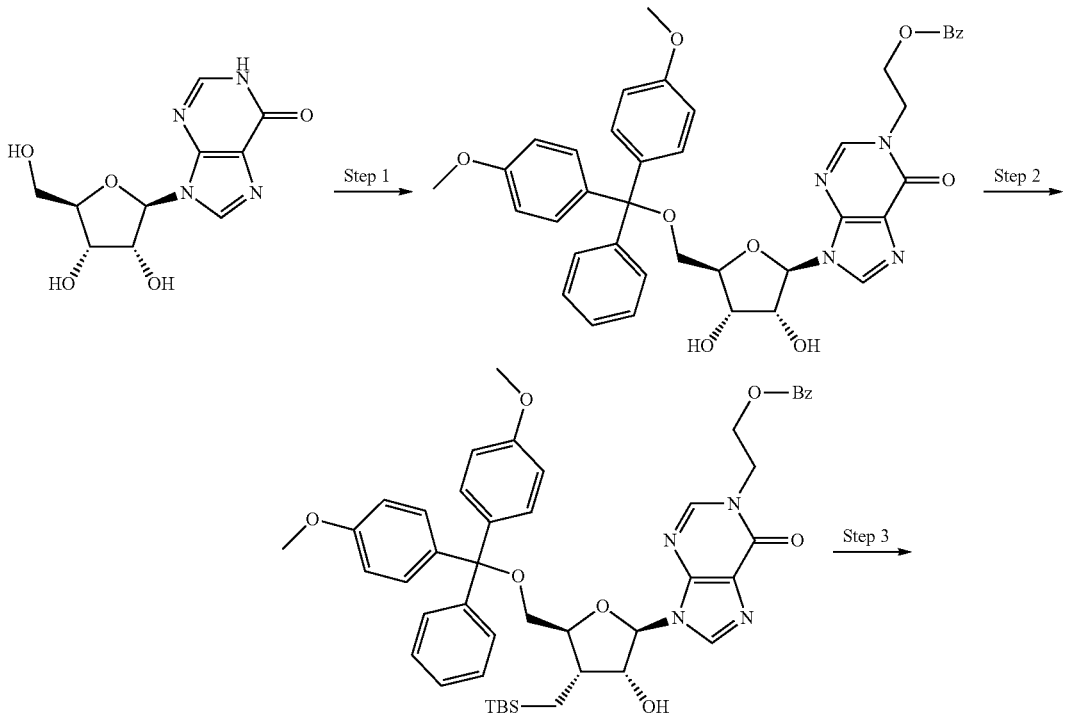

307 308
-continued
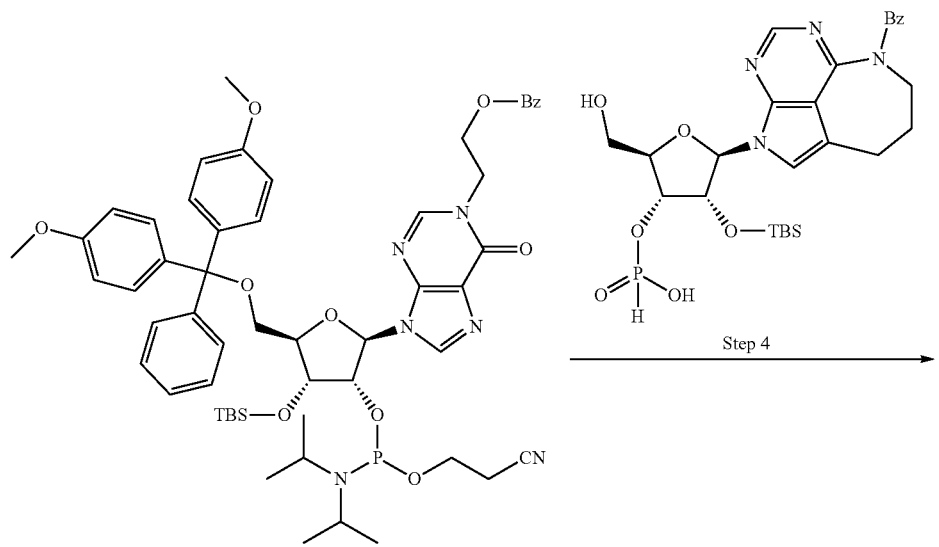
Step 4
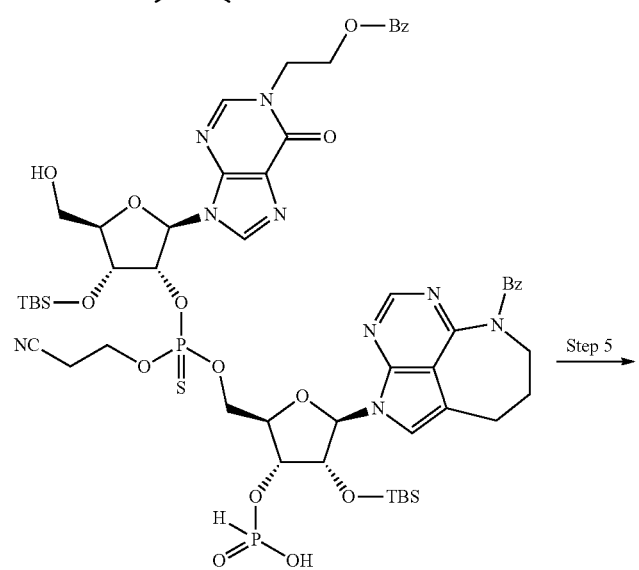
Step 5
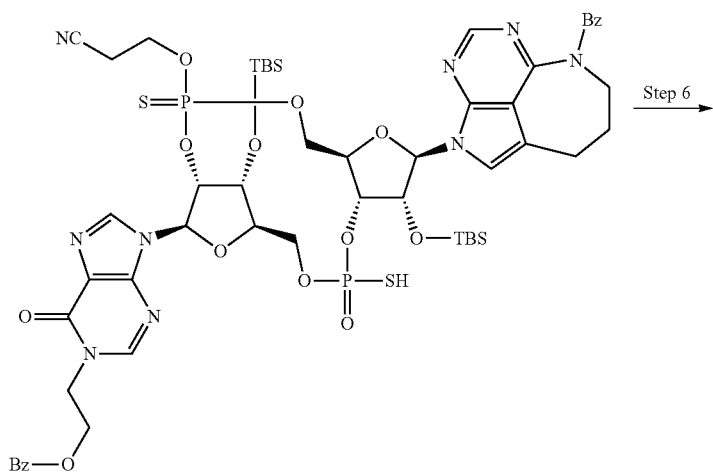
Step 6

-continued
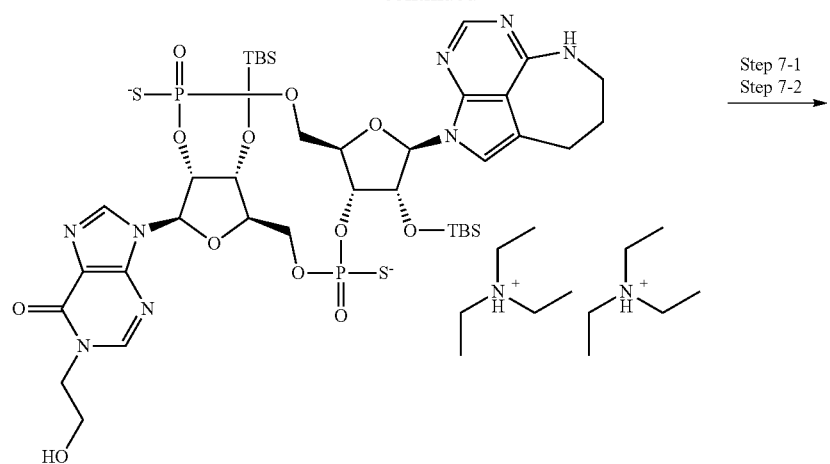
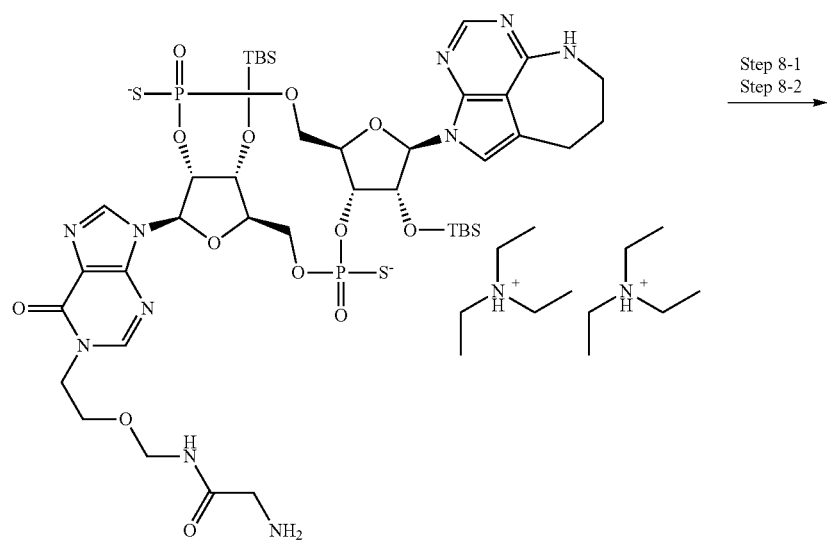
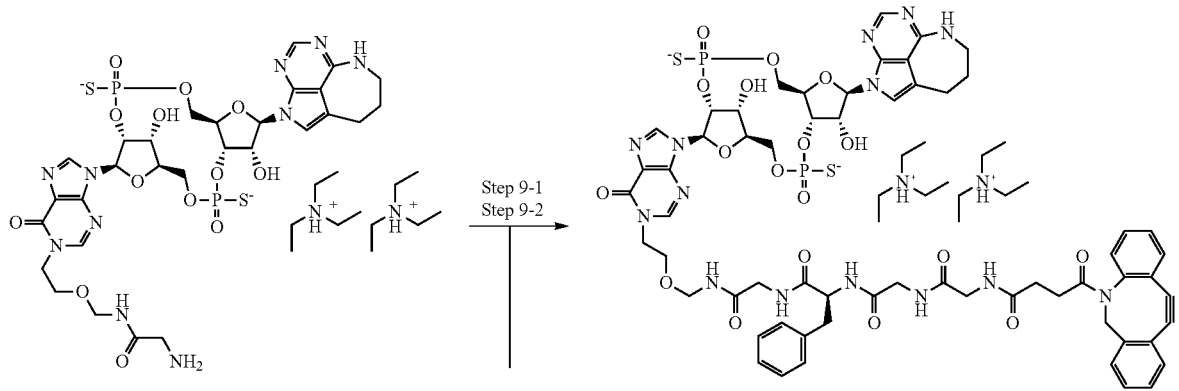
Drug-linker 2a
Drug-linker 2b

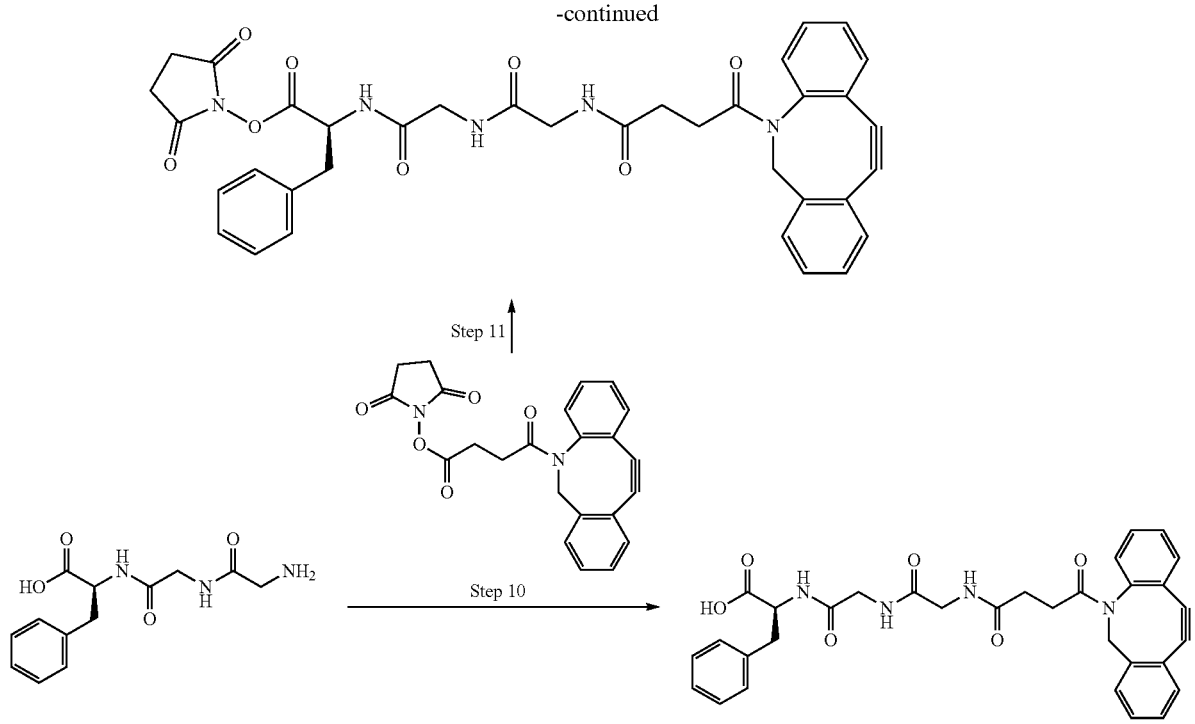

(Step 1)

1-[2-(Benzoyloxy)ethyl]-5'-O-[bis(4-methoxyphenyl)(phenyl)methyl]inosine

To a solution of inosine (10.0 g) in pyridine (50 mL) and N,N-dimethylacetamide (50 mL), 4,4'-dimethoxytrityl chloride (15.2 g) was added at 0° C., and the reaction mixture was then stirred at 4° C. for 64 hours. Methanol (2 mL) was added to the reaction mixture, which was stirred for 10 minutes, and then concentrated to about 50 mL. To the residue, 2-bromoethylbenzoate (7.02 mL) and 2,3,4,6,7,8,9,10-octahydropyrimido [1,2-a]azepine (13.9 mL) were added, and the reaction mixture was stirred at room temperature for 1 day. A saturated aqueous solution of sodium hydrogen carbonate and water were added to the reaction mixture, which was subjected to extraction with ethyl acetate. The organic layer was washed with brine, and then dried over anhydrous sodium sulfate. The drying agent was removed through filtration, and the filtrate was concentrated under reduced pressure. The residue was purified by silica gel column chromatography [hexane/ethyl acetate/methanol/0.1% triethylamine] to afford the title compound (15.2 g).

MS(ESI)m/z: 719 (M+H)$^+$.

$^1$H-NMR (CDCl$_3$) δ: 8.00 (1H, s), 7.98 (1H, s), 7.98-7.94 (2H, m), 7.62-7.15 (12H, m), 6.80-6.75 (4H, m), 5.95 (1H, d, J=5.4 Hz), 4.82-4.79 (1H, m), 4.72-4.64 (3H, m), 4.55-4.34 (5H, m), 3.77 (6H, s), 3.43 (1H, dd, J=10.6, 3.9 Hz), 3.34 (1H, dd, J=10.6, 3.6 Hz).

(Step 2)

1-[2-(Benzoyloxy)ethyl]-5'-O-[bis(4-methoxyphenyl)(phenyl)methyl]-3'-O-[tert-butyl(dimethyl)silyl]inosine With use of the compound obtained in step 1 (3.01 g), the reaction was performed in the same manner as in step 3 of Example 5 to afford the title compound (1.20 g) and 1-[2-(benzoyloxy)ethyl]-5'-O-[bis(4-methoxyphenyl)(phenyl)methyl]-2'-O-[tert-butyl(dimethyl)silyl]inosine (1.22 g) as a regioisomer of the title compound.

MS(ESI)m/z: 833 (M+H)$^+$.

$^1$H-NMR (CDCl$_3$) δ: 8.03 (1H, s), 7.98-7.96 (1H, m), 7.96 (1H, s), 7.96-7.94 (1H, m), 7.59-7.52 (1H, m), 7.44-7.38 (4H, m), 7.32-7.15 (7H, m), 6.83-6.77 (4H, m), 5.94 (1H, d, J=4.8 Hz), 4.69-4.63 (2H, m), 4.59-4.35 (4H, m), 4.16 (1H, dd, J=3.8, 1.9 Hz), 3.77 (6H, d, J=1.8 Hz), 3.47 (1H, dd, J=10.9, 3.0 Hz), 3.27 (1H, dd, J=10.9, 4.2 Hz), 3.00 (1H, d, J=6.7 Hz), 0.87 (9H, s), 0.06 (3H, s), −0.01 (3H, s).

(2'-O-TBS Form)

MS(ESI)m/z: 833 (M+H)$^+$.

$^1$H-NMR (CDCl$_3$) δ: 8.01 (1H, s), 7.97-7.93 (2H, m), 7.91 (1H, s), 7.59-7.53 (1H, m), 7.45-7.38 (4H, m), 7.35-7.17 (7H, m), 6.83-6.77 (4H, m), 5.97 (1H, d, J=6.0 Hz), 4.84 (1H, t, J=5.4 Hz), 4.71-4.60 (2H, m), 4.52-4.37 (2H, m), 4.33-4.28 (1H, m), 4.28-4.24 (1H, m), 3.78 (3H, s), 3.77 (3H, s), 3.47 (1H, dd, J=10.9, 3.0 Hz), 3.38 (1H, dd, J=10.9, 3.6 Hz), 2.71 (1H, d, J=3.0 Hz), 0.80 (9H, s), −0.03 (3H, s), −0.19 (3H, s).

(Step 3)

1-[2-(Benzoyloxy)ethyl]-5'-O-[bis(4-methoxyphenyl)(phenyl)methyl]-3'-O-[tert-butyl(dimethyl)silyl]-2'-O-{(2-cyanoethoxy)[di(propan-2-yl)amino]phosphanyl}inosine With use of the compound obtained in step 2 (1.20 g), the reaction was performed in the same manner as in step 4 of Example 5 to afford the title compound (1.41 g) as a mixture of diastereomers at the phosphorus atom (diastereomer ratio=0.55:0.45).

MS(ESI)m/z: 1033 (M+H)$^+$.

$^1$H-NMR (CDCl$_3$) δ: 8.05 (0.45H, s), 8.04 (0.55H, s), 7.99-7.95 (2H, m), 7.95 (0.55H, s), 7.92 (0.45H, s), 7.59-

7.53 (1H, m), 7.45-7.39 (4H, m), 7.35-7.10 (7H, m), 6.83-6.78 (4H, m), 6.15 (0.55H, d, J=5.4 Hz), 6.08 (0.45H, d, J=6.0 Hz), 4.86-4.49 (3H, m), 4.49-4.35 (3H, m), 4.25-4.10 (1H, m), 3.78 (6H, s), 3.72-3.41 (5H, m), 3.35-3.25 (1H, m), 2.47 (1H, t, J=6.7 Hz), 2.32 (1H, t, J=6.3 Hz), 1.33-1.24 (6H, m), 1.13-1.03 (6H, m), 0.84 (4.05H, s), 0.84 (4.95H, s), 0.08 (1.35H, s), 0.05 (1.65H, s), 0.00 (1.35H, s), −0.01 (1.65H, s).
(Step 4)

The same reaction as in step 7 of Example 1 was performed in the following scale (raw material: 1.40 g). With use of an acetonitrile solution of the compound obtained and the compound obtained in step 3 (1.41 g), the reaction was performed in the same manner as in step 8 of Example 1. The resulting crude product was directly used for the subsequent reaction.
(Step 5)

2-{9-[(5R,7R,8R,12aR,14R,15R,15aR,16R)-14-(6-Benzoyl-6,7,8,9-tetrahydro-2H-2,3,5,6-tetraazabenzo[cd]azulen-2-yl)-15,16-bis{[tert-butyl(dimethyl)silyl]oxy}-10-(2-cyanoethoxy)-2-oxo-2-sulfanyl-10-sulfanylideneoctahydro-2H,10H,12H-5,8-methano-2$\lambda^5$,10$\lambda^5$-furo[3,2-1][1,3,6,9,11,2,10]pentaoxadiphosphacyclotetradecin-7-yl]-6-oxo-6,9-dihydro-1H-purin-1-yl}ethyl benzoate With use of the crude product obtained in step 4, the reaction was performed in the same manner as in step 9 of Example 1 to afford the title compound (778 mg) as a mixture of diastereomers at the phosphorus atom.
MS(ESI)m/z: 1264 (M+H)$^+$.
(Step 6)

Bis(N,N-diethylethaneaminium) (5R,7R,8R,12aR,14R,15R,15aR,16R)-15,16-bis{[tert-butyl(dimethyl)silyl]oxy}-7-[1-(2-hydroxyethyl)-6-oxo-1,6-dihydro-9H-purin-9-yl]-2,10-dioxo-14-(6,7,8,9-tetrahydro-2H-2,3,5,6-tetraazabenzo[cd]azulen-2-yl)octahydro-2H,10H,12H-5,8-methano-2$\lambda^5$,10$\lambda^5$-furo[3,2-1][1,3,6,9,11,2,10]pentaoxadiphosphacyclotetradecine-2,10-bis(thiolate)

With use of the compound obtained in step 5 (778 mg), the reaction was performed in the same manner as in step 10 of Example 1 to afford diastereomer 1 (255 mg) and diastereomer 2 (with impurities) of the title compound. Diastereomer 2 was again purified by preparative HPLC [water/acetonitrile with 0.2% triethylamine, acetonitrile with 0.2% triethylamine: 5%-50% (0 min-40 min)] to afford diastereomer 2 (94.6 mg) of the title compound.
Diastereomer 1 (Less Polar)
MS(ESI)m/z: 1003 (M+H)$^+$.
$^1$H-NMR (CD$_3$OD) δ: 8.66 (1H, s), 8.21 (1H, s), 8.04 (1H, s), 7.33 (1H, s), 6.27 (1H, d, J=5.1 Hz), 6.25 (1H, d, J=3.6 Hz), 5.39-5.29 (1H, m), 5.18-5.11 (1H, m), 4.85-4.81 (1H, m), 4.79-4.74 (1H, m), 4.71-4.66 (1H, m), 4.50-4.42 (1H, m), 4.36-4.21 (2H, m), 4.09-3.98 (2H, m), 3.85-3.78 (2H, m), 3.78-3.69 (2H, m), 3.55-3.46 (2H, m), 3.17 (12H, q, J=7.3 Hz), 2.98-2.75 (2H, m), 2.05-1.88 (2H, m), 1.28 (18H, t, J=7.3 Hz), 0.98 (9H, s), 0.85 (9H, s), 0.31 (3H, s), 0.27 (3H, s), 0.25 (3H, s), 0.09 (3H, s).
Diastereomer 2 (More Polar)
MS(ESI)m/z: 1003 (M+H)$^+$.
$^1$H-NMR (CD$_3$OD) δ: 8.50 (1H, s), 8.22 (1H, s), 8.07 (1H, s), 7.20 (1H, s), 6.33 (1H, d, J=7.3 Hz), 6.26 (1H, d, J=9.1 Hz), 5.59-5.44 (1H, m), 5.38-5.32 (1H, m), 5.21-5.11 (1H, m), 4.99-4.89 (2H, m), 4.68-4.54 (2H, m), 4.25-4.12 (3H, m), 4.09-4.03 (1H, m), 3.90-3.80 (3H, m), 3.59-3.51 (2H, m), 3.20 (12H, q, J=7.3 Hz), 2.96-2.89 (2H, m), 2.07-1.98 (2H, m), 1.30 (18H, t, J=7.3 Hz), 0.99 (9H, s), 0.74 (9H, s), 0.27 (3H, s), 0.27 (3H, s), 0.20 (3H, s), −0.05 (3H, s).
(Step 7-1)

Bis(N,N-diethylethaneaminium) (5R,7R,8R,12aR,14R,15R,15aR,16R)-15,16-bis{[tert-butyl(dimethyl)silyl]oxy}-7-(1-{2-[(glycylamino)methoxy]ethyl}-6-oxo-1,6-dihydro-9H-purin-9-yl)-2,10-dioxo-14-(6,7,8,9-tetrahydro-2H-2,3,5,6-tetraazabenzo[cd]azulen-2-yl)octahydro-2H,10H,12H-5,8-methano-2$\lambda^5$,10$\lambda^5$-furo[3,2-1][1,3,6,9,11,2,10]pentaoxadiphosphacyclotetradecine-2,10-bis(thiolate)

(Diastereomer 1)
To a solution of the compound obtained in step 6 (diastereomer 1) (30 mg) in tetrahydrofuran (0.5 mL), [(N-{[(9H-fluoren-9-yl)methoxy]carbonyl}glycyl)amino]methyl acetate (91.7 mg) and p-toluenesulfonic acid monohydrate (11.8 mg) were added, and the reaction mixture was stirred at room temperature for 6 hours. To the reaction mixture, N,N-dimethylformamide (0.5 mL) and 1,8-diazabicyclo[5.4.0]-7-undecene (56 μL) were added, and the reaction mixture was stirred at room temperature for 3 hours. To the reaction mixture, 10 mM aqueous solution of triethylammonium acetate was added, and the reaction mixture was purified by C18 silica gel column chromatography [10 mM aqueous solution of triethylammonium acetate/acetonitrile] to afford the title compound (25.6 mg) containing the raw material as an impurity.
MS(ESI)m/z: 1089 (M+H)$^+$.
(Step 7-2)

Bis(N,N-diethylethaneaminium) (5R,7R,8R,12aR,14R,15R,15aR,16R)-15,16-bis{[tert-butyl(dimethyl)silyl]oxy}-7-(1-{2-[(glycylamino)methoxy]ethyl}-6-oxo-1,6-dihydro-9H-purin-9-yl)-2,10-dioxo-14-(6,7,8,9-tetrahydro-2H-2,3,5,6-tetraazabenzo[cd]azulen-2-yl)octahydro-2H,10H,12H-5,8-methano-2$\lambda^5$,10$\lambda^5$-furo[3,2-1][1,3,6,9,11,2,10]pentaoxadiphosphacyclotetradecine-2,10-bis(thiolate)

(Diastereomer 2)
With use of the compound obtained in step 6 (diastereomer 2) (84.6 mg), the reaction was performed in the same manner as in step 7-1 to afford the title compound (70.9 mg) containing the raw material as an impurity.
MS(ESI)m/z: 1089 (M+H)$^+$.
(Step 8-1)

Bis(N,N-diethylethaneaminium) (5R,7R,8R,12aR,14R,15R,15aS,16R)-7-(1-{2-[(glycylamino)methoxy]ethyl}-6-oxo-1,6-dihydro-9H-purin-9-yl)-15,16-dihydroxy-2,10-dioxo-14-(6,7,8,9-tetrahydro-2H-2,3,5,6-tetraazabenzo[cd]azulen-2-yl)octahydro-2H,10H,12H-5,8-methano-2$\lambda^5$,10$\lambda^5$-furo[3,2-1][1,3,6,9,11,2,10]pentaoxadiphosphacyclotetradecine-2,10-bis(thiolate) Diastereomer 1

To the compound obtained in step 7-1 (25.6 mg), triethylamine trihydrofluoride (2 mL) was added, and the reaction mixture was stirred at 45° C. for 3 hours. To the reaction mixture, an ice-cooled mixture of 1 M solution of triethylammonium hydrogen carbonate (10 mL) and triethylamine (2 mL) was added at room temperature. The reaction mixture was concentrated under reduced pressure, and then purified by C18 silica gel column chromatography (10 mM aqueous solution of triethylammonium acetate/acetonitrile) to afford the title compound (16.6 mg: with an impurity derived from the raw material in step 7-1).

MS(ESI)m/z: 861 (M+H)$^+$.

(Step 8-2)

Bis(N,N-diethylethaneaminium) (5R,7R,8R,12aR, 14R,15R,15aS,16R)-7-(1-{2-[(glycylamino) methoxy]ethyl}-6-oxo-1,6-dihydro-9H-purin-9-yl)-15,16-dihydroxy-2,10-dioxo-14-(6,7,8,9-tetrahydro-2H-2,3,5,6-tetraazabenzo[cd]azulen-2-yl)octahydro-2H,10H,12H-5,8-methano-2$\lambda^5$,10$\lambda^5$-furo[3,2-1][1,3,6,9,11,2,10]pentaoxadiphosphacyclotetradecine-2,10-bis(thiolate)

(Diastereomer 2)

With use of the compound obtained in step 7-2 (70.9 mg), the reaction was performed in the same manner as in step 8-1 to afford the title compound (51.7 mg: with an impurity derived from the raw material in step 7-2).

MS(ESI)m/z: 861 (M+H)$^+$.

(Step 9-1)

Bis(N,N-diethylethaneaminium) N-[4-(11,12-didehydrodibenzo[b,f]azocin-5 (6H)-yl)-4-oxobutanoyl] glycylglycyl-L-phenylalanyl-N-[(2-{9-[(5R,7R,8R,12aR,14R,15R,15aS,16R)-15,16-dihydroxy-2,10-dioxo-2,10-disulfide-14-(6,7,8,9-tetrahydro-2H-2,3,5,6-tetraazabenzo[cd]azulen-2-yl)octahydro-2H,10H,12H-5,8-methano-2$\lambda^5$,10$\lambda^5$-furo[3,2-1][1,3,6,9,11,2,10]pentaoxadiphosphacyclotetradecin-7-yl]-6-oxo-6,9-dihydro-1H-purin-1-yl}ethoxy)methyl] glycinamide (Drug-Linker 2a: Diastereomer 1)

To a solution of the compound obtained in step 8-1 (16.6 mg) in N,N-dimethylformamide (0.5 mL), triethylamine (6 μL) and a compound obtained in step 11 described later (15.5 mg) were added, and the reaction mixture was stirred at room temperature for 3 hours. Benzylamine (3 μL) was added to the reaction mixture, which was stirred at room temperature for 1 hour. Thereto, 10 mM aqueous solution of triethylammonium acetate and methanol were added, and the reaction mixture was purified by C18 silica gel column chromatography [10 mM aqueous solution of triethylammonium acetate/acetonitrile] and preparative HPLC [10 mM aqueous solution of triethylammonium acetate/acetonitrile, acetonitrile: 10%-45% (0 min-30 min)] to afford the title compound (5.1 mg).

MS(ESI)m/z: 1409 (M+H)$^+$.

$^1$H-NMR (CD$_3$OD) δ: 8.66-8.60 (1H, m), 8.17 (1H, s), 8.02 (1H, s), 7.65-7.48 (2H, m), 7.43-7.36 (3H, m), 7.31-7.13 (8H, m), 7.11 (1H, s), 6.30-6.21 (2H, m), 5.46-5.37 (1H, m), 5.23-5.16 (1H, m), 5.08-4.99 (1H, m), 4.86-4.81 (1H, m), 4.80-4.75 (1H, m), 4.70-4.40 (7H, m), 4.40-4.20 (3H, m), 4.10-3.97 (3H, m), 3.86-3.58 (8H, m), 3.51-3.43 (3H, m), 3.18 (12H, q, J=7.3 Hz), 3.01-2.93 (1H, m), 2.85-2.72 (3H, m), 2.37-2.15 (2H, m), 2.01-1.93 (2H, m), 1.29 (18H, t, J=7.3 Hz). (only observable peaks are shown)

(Step 9-2)

Bis(N,N-diethylethaneaminium) N-[4-(11,12-didehydrodibenzo[b,f]azocin-5 (6H)-yl)-4-oxobutanoyl] glycylglycyl-L-phenylalanyl-N-[(2-{9-[(5R,7R,8R,12aR,14R,15R,15aS,16R)-15,16-dihydroxy-2,10-dioxo-2,10-disulfide-14-(6,7,8,9-tetrahydro-2H-2,3,5,6-tetraazabenzo[cd]azulen-2-yl)octahydro-2H,10H,12H-5,8-methano-2$\lambda^5$,10$\lambda^5$-furo[3,2-1][1,3,6,9,11,2,10]pentaoxadiphosphacyclotetradecin-7-yl]-6-oxo-6,9-dihydro-1H-purin-1-yl}ethoxy)methyl] glycinamide (Drug-Linker 2b: Diastereomer 2)

With use of the compound obtained in step 8-2 (51.7 mg), the reaction was performed in the same manner as in step 9-1, and purification was then performed under the following [Purification Conditions] to afford the title compound (33.7 mg).

[Purification Conditions] C18 silica gel column chromatography [10 mM aqueous solution of triethylammonium acetate/acetonitrile], preparative HPLC [10 mM aqueous solution of triethylammonium acetate/acetonitrile, acetonitrile: 10%-50% (0 min-30 min)].

MS(ESI)m/z: 1409 (M+H)$^+$.

$^1$H-NMR (CD$_3$OD) δ: 8.73 (1H, d, J=6.7 Hz), 8.19 (1H, d, J=3.0 Hz), 8.02 (1H, s), 7.66-7.50 (2H, m), 7.43-7.37 (3H, m), 7.33-7.13 (8H, m), 7.11 (1H, s), 6.33-6.23 (2H, m), 5.51-5.38 (2H, m), 5.04 (1H, t, J=13.6 Hz), 4.83-4.77 (1H, m), 4.64-4.55 (2H, m), 4.52-4.26 (6H, m), 4.25-3.97 (2H, m), 3.93-3.45 (13H, m), 3.19 (12H, q, J=7.3 Hz), 3.17-3.11 (1H, m), 3.02-2.92 (1H, m), 2.91-2.73 (3H, m), 2.40-2.24 (2H, m), 2.07-1.95 (3H, m), 1.30 (18H, t, J=7.3 Hz).

(Step 10)

N-[4-(11,12-Didehydrodibenzo[b,f]azocin-5 (6H)-yl)-4-oxobutanoyl]glycylglycyl-L-phenylalanine To a solution of commercially available (Bachem Holding AG) (2S)-2-[[2-[(2-aminoacetyl)amino]acetyl]amino]-3-phenylpropanoic acid (2.86 g) in N,N-dimethylformamide (51.2 mL), triethylamine (2.56 mL) and commercially available (Click Chemistry Tools) 1-{[4-(11,12-didehydrodibenzo[b,f]azocin-5 (6H)-yl)-4-oxobutanoyl] oxy}pyrrolidine-2,5-dione (3.69 g) were added, and the reaction mixture was stirred at room temperature for 24 hours. An aqueous solution (500 mL) of citric acid monohydrate (24.0 g) was added to the reaction mixture, which was subjected to extraction with ethyl acetate. After the organic layer was dried over anhydrous sodium sulfate, the drying agent was removed through filtration, and the filtrate was concentrated under reduced pressure. The residue was dissolved in an ethyl acetate/acetonitrile mixed solution, and then precipitated with diisopropyl ether and collected through filtration to give the title compound (4.30 g).

$^1$H-NMR (DMSO-d$_6$) δ: 12.8 (1H, brs), 8.15-7.95 (3H, m), 7.68-7.17 (13H, m), 5.01 (1H, d, J=14.2 Hz), 4.41-4.37 (1H, m), 3.74-3.57 (5H, m), 3.05-3.01 (1H, m), 2.87 (1H, dd, J=14.2, 9.3 Hz), 2.68-2.59 (1H, m), 2.32-2.25 (1H, m), 2.09-2.03 (1H, m), 1.82-1.76 (1H, m).

(Step 11)

2,5-Dioxopyrrolidin-1-yl N-[4-(11,12-didehydrodibenzo[b,f]azocin-5 (6H)-yl)-4-oxobutanoyl] glycylglycyl-L-phenylalaninate To a solution of the compound obtained in step 10 (2.10 g) in N,N-dimethylformamide (75.9 mL), N-hydroxysuccinimide (961 mg) and 1-ethyl-3-(3-dimethylaminopropyl) carbodiimide hydrochloride (1.60 g) were added, and the reaction mixture was stirred under the nitrogen atmosphere at room temperature for 21 hours. The reaction mixture was diluted with dichloromethane, washed three times with iced water, and then dried over anhydrous sodium sulfate. The drying agent was removed through filtration, and the filtrate was concentrated under reduced pressure. Toluene was added to the residue, and the resultant was again concentrated under reduced pressure. The residue was dissolved in acetonitrile, and the resultant was purified by C18 silica gel column chromatography [acetonitrile: 100%]. Fraction containing the targeted product were concentrated under reduced pressure, and thereafter diisopropyl ether was added to the residue to make a slurry. The solid obtained was collected through filtration to give the title compound (2.59 g).

$^1$H-NMR (DMSO-$d_6$) δ: 8.58-8.51 (1H, m), 8.17-8.00 (2H, m), 7.66-7.20 (13H, m), 5.02-4.98 (1H, m), 4.90-4.85 (1H, m), 3.78-3.57 (5H, m), 3.24-3.19 (1H, m), 3.06-3.00 (1H, m), 2.82 (4H, brs), 2.67-2.58 (1H, m), 2.32-2.23 (1H, m), 2.09-2.02 (1H, m), 1.82-1.75 (1H, m).

Example 23: Synthesis of Drug-Linker 3

[Synthesis Scheme]

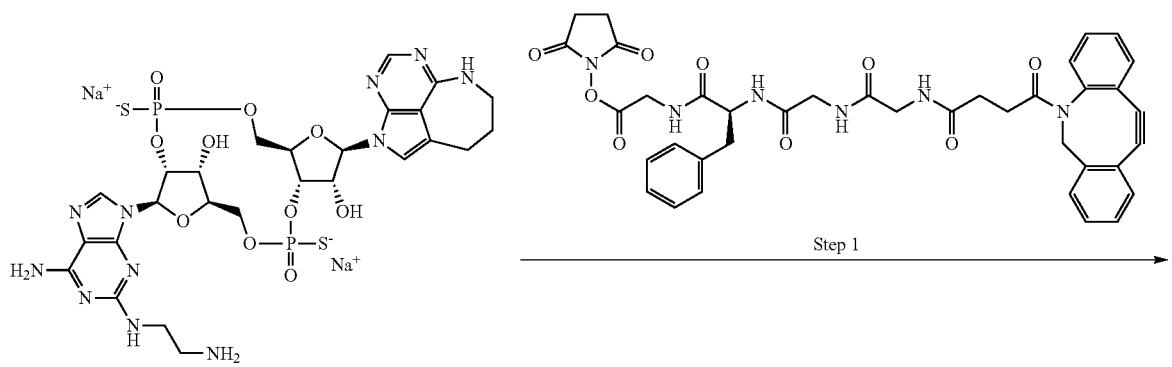

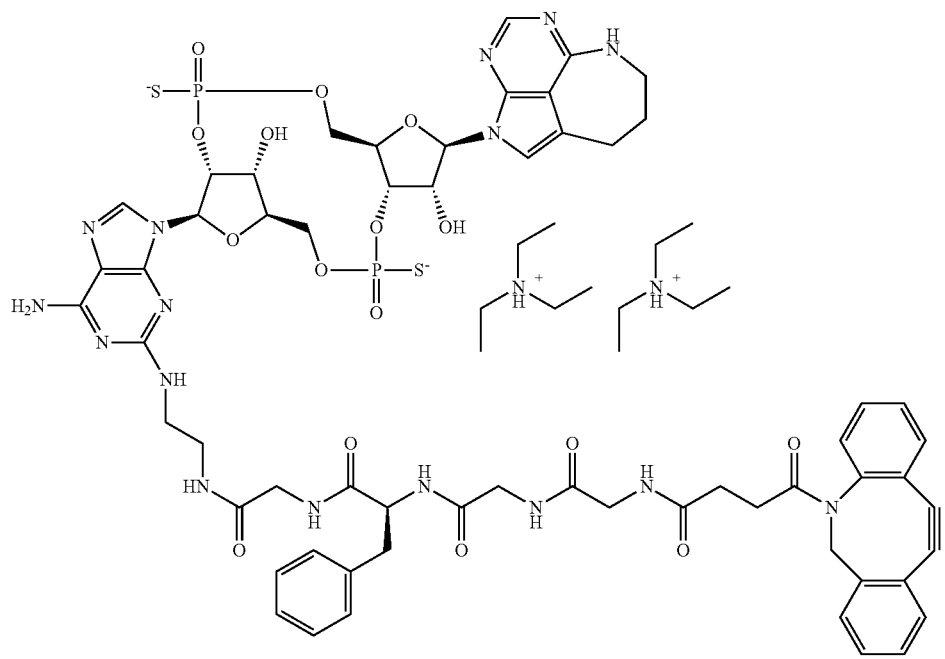

Drug-linker 3

(Step 1)

Bis(N,N-diethylethaneaminium) N-[4-(11,12-didehydrodibenzo[b,f]azocin-5 (6H)-yl)-4-oxobutanoyl]glycylglycyl-L-phenylalanyl-N-[2-({6-amino-9-[(5R,7R,8R,12aR,14R,15R,15aS,16R)-15,16-dihydroxy-2,10-dioxo-2,10-disulfide-14-(6,7,8,9-tetrahydro-2H-2,3,5,6-tetraazabenzo[cd]azulen-2-yl)octahydro-2H,10H,12H-5,8-methano-2λ⁵,10λ⁵-furo[3,2-l][1,3,6,9,11,2,10]pentaoxadiphosphacyclotetradecin-7-yl]-9H-purin-2-yl}amino)ethyl]glycinamide (Drug-Linker 3)

To a solution of the compound obtained in step 8-2 of Example 8 (4.8 mg) in N,N-dimethylformamide (0.29 mL), triethylamine (1.9 μL) and the compound obtained in step 3 of Example 21 (5.2 mg) were added, and the reaction mixture was stirred under the nitrogen atmosphere at room temperature for 1.5 hours. After benzylamine (3.2 μL) was added thereto to quench the reaction, the resultant was purified by preparative HPLC [10 mM aqueous solution of triethylammonium acetate/acetonitrile, acetonitrile: 20%-40% (0 min-30 min)] to afford the title compound (8.0 mg).

MS(ESI)m/z: 1393 (M+H)⁺.

¹H-NMR (CD₃OD) δ: 8.35 (1H, brs), 8.02 (1H, s), 7.61-7.15 (14H, m), 6.33 (1H, dd, J=6.0, 3.0 Hz), 6.15-6.09 (1H, m), 5.49-5.37 (2H, m), 5.05 (1H, dd, J=13.9, 12.1 Hz), 4.85-4.79 (1H, m), 4.53-4.21 (6H, m), 4.06-3.61 (8H, m), 3.51-3.13 (6H, m), 3.16 (12H, q, J=7.3 Hz), 3.06-2.65 (7H, m), 2.35-1.94 (4H, m), 1.28 (18H, t, J=7.6 Hz).

Example 24: Synthesis of Drug-Linker 4

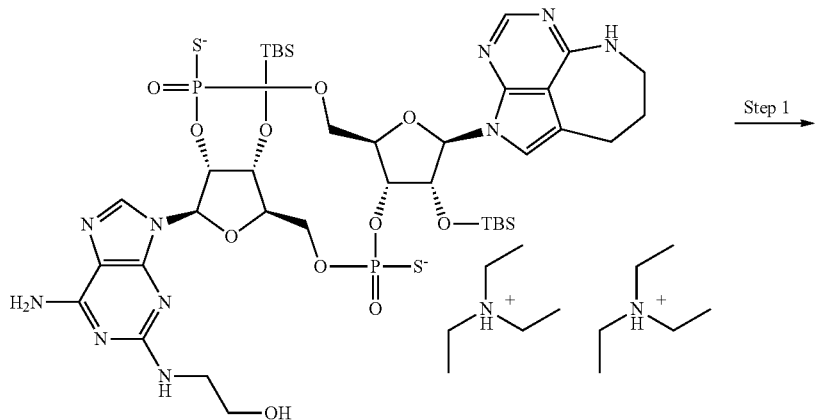

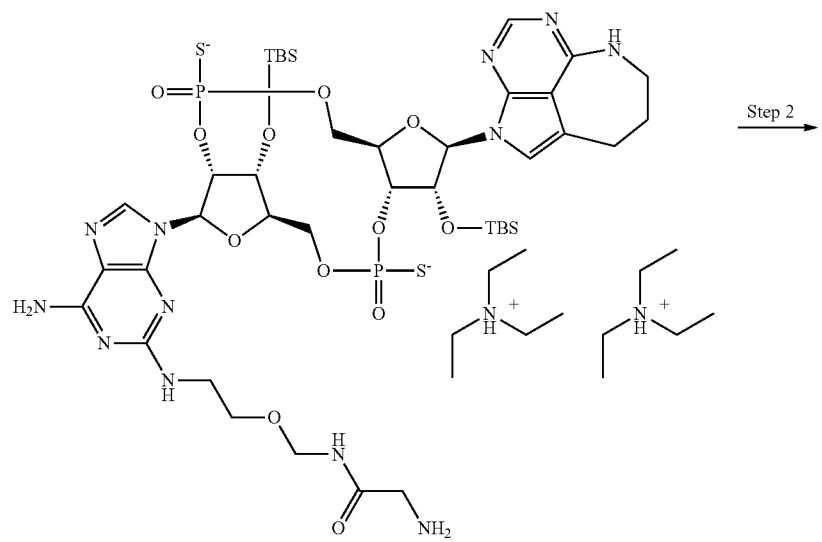

321

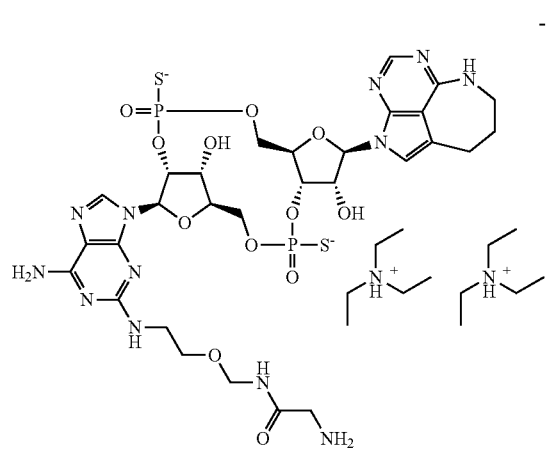

322

-continued

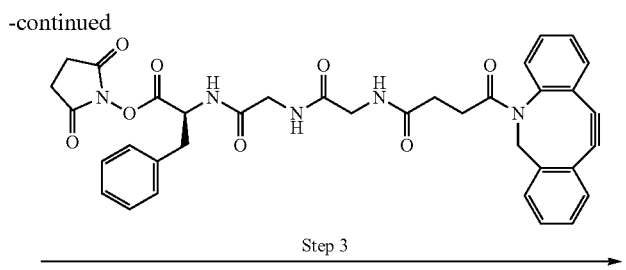

Step 3

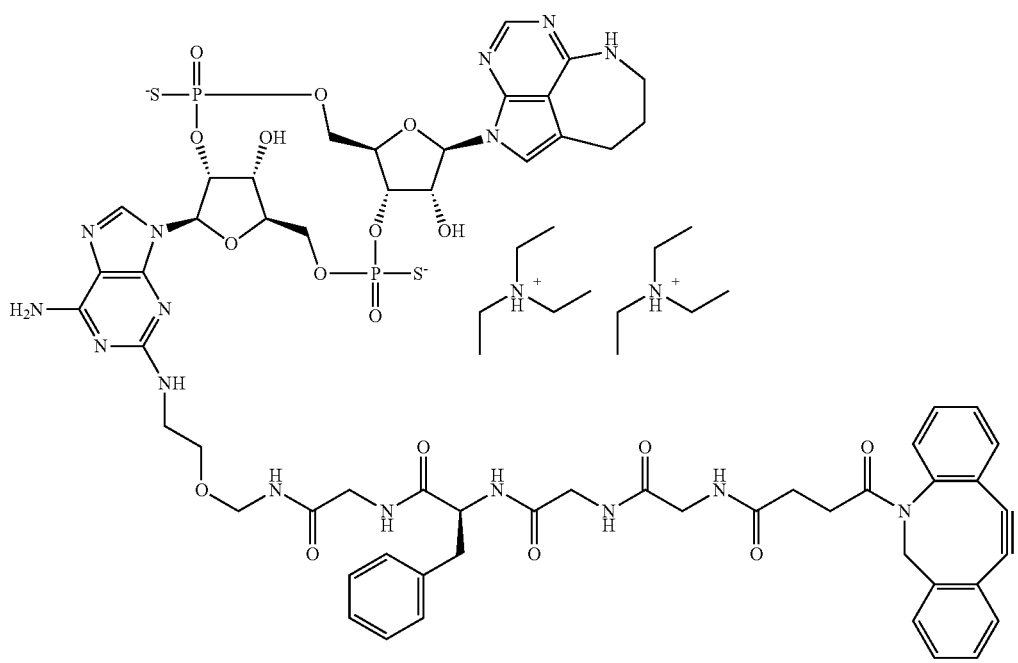

Drug-linker 4

(Step 1)

Bis(N,N-diethylethaneaminium) (5R,7R,8R,12aR, 14R,15R,15aR,16R)-7-[6-amino-2-({2-[(glycy-lamino)methoxy]ethyl}amino)-9H-purin-9-yl]-15, 16-bis{[tert-butyl(dimethyl)silyl]oxy}-2,10-dioxo-14-(6,7,8,9-tetrahydro-2H-2,3,5,6-tetraazabenzo[cd]azulen-2-yl)octahydro-2H,10H,12H-5,8-methano-2λ$^5$,10λ$^5$-furo[3,2-1][1,3,6,9,11,2,10] pentaoxadiphosphacyclotetradecine-2,10-bis(thiolate)

With use of the compound obtained in step 1-2 of Example 9 (17.6 mg), the reaction was performed in the same manner as in step 7-1 of Example 22 to afford the title compound (8.3 mg).

MS(ESI)m/z: 1103 (M+H)$^+$.

(Step 2)

Bis(N,N-diethylethaneaminium) (5R,7R,8R,12aR, 14R,15R,15aS,16R)-7-[6-amino-2-({2-[(glycy-lamino)methoxy]ethyl}amino)-9H-purin-9-yl]-15, 16-dihydroxy-2,10-dioxo-14-(6,7,8,9-tetrahydro-2H-2,3,5,6-tetraazabenzo[cd]azulen-2-yl)octahydro-2H, 10H,12H-5,8-methano-2λ$^5$,10λ$^5$-furo[3,2-1][1,3,6,9, 11,2,10]pentaoxadiphosphacyclotetradecine-2,10-bis(thiolate)

With use of the compound obtained in step 1 (10.7 mg), the reaction was performed in the same manner as in step 8-1 of Example 22 to afford the title compound (7.6 mg).

MS(ESI)m/z: 875 (M+H)$^+$.

(Step 3)

Bis(N,N-diethylethaneaminium) N-[4-(11,12-didehydrodibenzo[b,f]azocin-5 (6H)-yl)-4-oxobutanoyl]glycylglycyl-L-phenylalanyl-N-{[2-({6-amino-9-[(5R,7R,8R,12aR,14R,15R,15aS,16R)-15,16-dihydroxy-2,10-dioxo-2,10-disulfide-14-(6,7,8,9-tetrahydro-2H-2,3,5,6-tetraazabenzo[cd]azulen-2-yl)octahydro-2H,10H,12H-5,8-methano-2$\lambda^5$,10$\lambda^5$-furo[3,2-1][1,3,6,9,11,2,10]pentaoxadiphosphacyclotetradecin-7-yl]-9H-purin-2-yl}amino)ethoxy]methyl}glycinamide (Drug-Linker 4)
With use of the compound obtained in step 2 (7.6 mg), the reaction was performed in the same manner as in step 9-1 of Example 22. Purification was performed under the following [Purification Conditions] to afford the title compound (7.6 mg) as a triethylamine salt.
[Purification Conditions] preparative HPLC [10 mM aqueous solution of triethylammonium acetate/acetonitrile, acetonitrile: 20%-40% (0 min-30 min)].
MS(ESI)m/z: 1423 (M+H)$^+$.
$^1$H-NMR (CD$_3$OD) δ: 8.37 (1H, brs), 8.01 (1H, d, J=2.4 Hz), 7.63-7.11 (14H, m), 6.33 (1H, d, J=6.7 Hz), 6.17 (1H, d, J=7.3 Hz), 5.51-5.36 (2H, m), 5.09-5.03 (1H, m), 4.84-4.80 (1H, m), 4.63-4.25 (8H, m), 4.07-3.58 (9H, m), 3.50-3.41 (4H, m), 3.28-2.72 (8H, m), 3.18 (12H, q, J=7.3 Hz), 2.45-1.96 (4H, m), 1.29 (18H, t, J=7.3 Hz).

Example 25: Synthesis of Glycan-Remodeled Antibody 1

Figure 26:
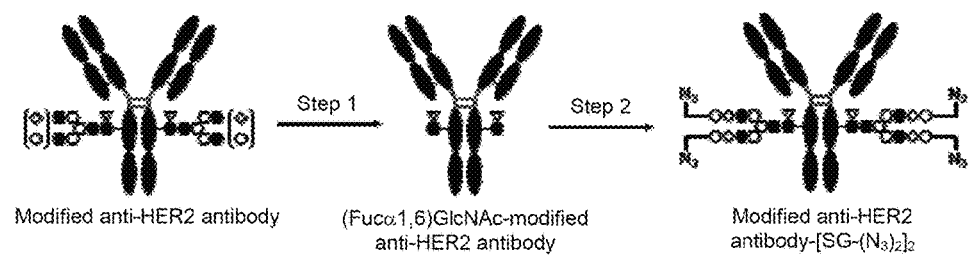
FIG. 26 shows the Synthesis Scheme representing Example 25: Synthesis of Glycan-Remodeled Antibody 1, Synthesis of Modified Anti-HER2 Antibody-[SG-(N$_3$)$_2$]$_2$.

Synthesis of Modified Anti-HER2 Antibody-[SG-(N$_3$)$_2$]$_2$
See FIG. 26. [Synthesis Scheme]
(Step 1)
Preparation of (Fucα1,6)GlcNAc-Modified Anti-HER2 Antibody
To a phosphate-buffered saline solution of a modified anti-HER2 antibody prepared in accordance with Reference Example 1 (20 mL, 12.6 mg/mL, pH 6.0), a phosphate-buffered saline solution of wild-type EndoS (0.147 mL, 7.70 mg/mL, pH 6.0) was added, and the reaction mixture was shaken at 37° C. for 2 hours and 15 minutes. The degree of progression of the reaction was checked by using an Experion electrophoresis station (produced by Bio-Rad Laboratories, Inc.). After the completion of the reaction, purification by affinity chromatography and purification by hydroxyapatite column chromatography were performed in accordance with the following methods.
(1) Purification by Affinity Chromatography
Purification apparatus: AKTA avant 25 (produced by GE Healthcare)
Column: HiTrap rProtein A FF (5 mL) (produced by GE Healthcare)
Flow rate: 5 mL/min (1.25 mL/min in charging)
The reaction mixture obtained above was purified in two separate operations. In connecting to the column, the reaction mixture was added to the column, and 2 CV of binding buffer (20 mM phosphate buffer (pH 6.0)) was flowed at 1.25 mL/min and 5 CV thereof was further flowed at 5 mL/min. In intermediate washing, 15 CV of washing solution (20 mM phosphate buffer (pH 7.0), 0.5 M sodium chloride solution) was flowed. In elution, 6 CV of elution buffer (ImmunoPure IgG Elution buffer, produced by Pierce) was flowed. The eluate was immediately neutralized with 1 M Tris buffer (pH 9.0). Fractions containing the targeted product were subjected to buffer exchange to 5 mM phosphate buffer/50 mM 2-morpholinoethanesulfonic acid (MES) solution (pH 6.8) in accordance with the method described in Common Operation C. The antibody concentration of the buffer solution obtained was measured in accordance with the method described in Common Operation B, thus providing a partially purified solution of the title antibody (26.57 mg/mL, 9.0 mL).
(2) Purification by Hydroxyapatite Chromatography
Purification apparatus: AKTA avant 25 (produced by GE Healthcare)
Column: Bio-Scale Mini CHT Type I cartridge (5 mL) (produced by Bio-Rad Laboratories, Inc.)
Flow rate: 5 mL/min (1.25 mL/min in charging)
The solution obtained in (1) was added to the column, and 2 CV of solution A (5 mM phosphate buffer, 50 mM MES solution (pH 6.8)) was flowed at 1.25 mL/min and 3 CV thereof was further flowed at 5 mL/min. Thereafter, elution was performed with solution A and solution B (5 mM phosphate buffer/50 mM MES solution (pH 6.8), 2 M sodium chloride solution). The elution conditions were solution A: solution B=100:0 to 0:100 (5 CV). Further, 5 CV of washing solution (500 mM phosphate buffer (pH 6.5)) was flowed. Fractions containing the targeted product were subjected to buffer exchange to 20 mM phosphate buffer (pH 6.0) in accordance with the method described in Common Operation C. The antibody concentration of the buffer solution obtained was measured in accordance with the method described in Common Operation B, thus providing a solution of the title antibody (17.29 mg/mL, approximately 13 mL).
(Step 2)
Preparation of Modified Anti-HER2 Antibody-[SG-(N$_3$)$_2$]$_2$
To the antibody obtained in step 1 in a 20 mM phosphate buffer solution (17.29 mg/mL, 13 mL, pH 6.0), [N$_3$-PEG(3)]$_2$-SG(10)Ox (compound 1-10 in WO2018/003983) (52 mg) in a 20 mM phosphate buffer solution (pH 6.0) (3.0 mL+1.0 mL for washing) and a phosphate-buffered saline solution of EndoS (D233Q/Q303L) (0.698 mL, 5.8 mg/mL, pH 6.0) were added, and the reaction mixture was shaken at 30° C. for 4 hours. The reaction mixture was stored at −80° C. for 15 hours and then thawed at 30° C., and [N$_3$-PEG(3)]$_2$-SG(10)Ox (7.4 mg) and a phosphate-buffered saline solution of EndoS (D233Q/Q303L) (0.155 mL, 5.8 mg/mL, pH 6.0) were further added to the reaction mixture, which was shaken at 30° C. for 2 hours. The degree of progression of the reaction was checked by using an Experion electrophoresis station (produced by Bio-Rad Laboratories, Inc.). After the completion of the reaction, purification by affinity chromatography and purification by hydroxyapatite chromatography were performed as in step 1. Fractions containing the targeted product (seven fractions in total) were separated into four former fractions and three latter fractions, and each fraction was subjected to buffer exchange to phosphate-buffered saline (pH 6.0) in accordance with the method described in Common Operation C. The antibody concentration of each buffer solution obtained was measured in accordance with the method described in Common Operation B, thus providing a solution of the title antibody (four former fractions: 14.99 mg/mL, 10 mL) and a solution of the title antibody (three latter fractions: 10.97 mg/mL, 6.2 mL).

Example 26: Synthesis of Glycan-Remodeled Antibody 2

Figure 27:
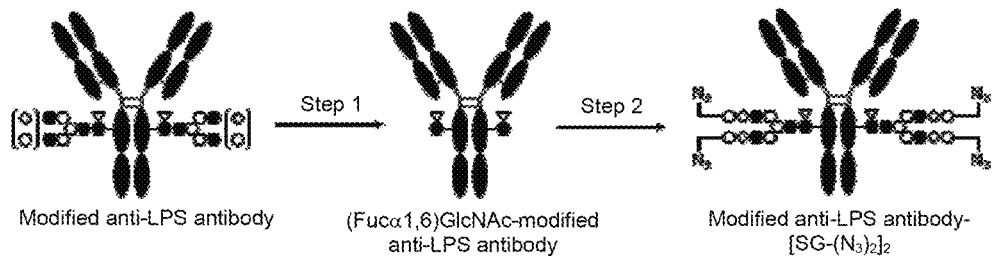
FIG. 27 shows the Synthesis Scheme representing Example 26: Synthesis of Glycan-Remodeled Antibody 2, Preparation of Modified Anti-LPS Antibody-[SG-(N$_3$)$_2$]$_2$.

Preparation of Modified Anti-LPS Antibody-[SG-(N$_3$)$_2$]$_2$
See FIG. 27. [Synthesis Scheme]
(Step 1)
Preparation of (Fucα1,6)GlcNAc-Modified Anti-LPS Antibody
With use of a phosphate-buffered saline solution of a modified anti-LPS antibody prepared in accordance with Reference Example 2 (8.5 mL, 10.96 mg/mL, pH 6.0), the same operations as in step 1 of Example 25 were performed to afford the title antibody in a 20 mM phosphate buffer solution (11.70 mg/mL, 7.5 mL, pH 6.0).

(Step 2)

Preparation of Modified Anti-LPS Antibody-[SG-($N_3$)$_2$]$_2$

With use of the antibody in a 20 mM phosphate buffer solution obtained in step 1 (11.70 mg/mL, 7.5 mL, pH 6.0) and [$N_3$-PEG (3)]$_2$-SG(10)Ox (20.3 mg), the same operations as in step 2 of Example 25 were performed to afford a phosphate-buffered saline solution of the title antibody (10.55 mg/mL, 7.5 mL, pH 6.0).

Example 27: Synthesis of Antibody-Drug Conjugate 1 (Synthesis of Anti-HER2 Antibody-CDN Conjugate 1)

A phosphate-buffered saline solution of glycan-remodeled antibody 1 (pH 6.0) (10.97 mg/mL, 0.500 mL) was diluted with propylene glycol (0.250 mL). To this solution, a mixture of a dimethyl sulfoxide solution of drug-linker 3 (10 mM, 0.0907 mL, 24 equivalents per antibody molecule) and propylene glycol (0.159 mL) was added, and the resultant was reacted with tube rotator (MTR-103, AS ONE Corporation) at room temperature for 2 days. The reaction mixture was purified in accordance with the method described in Common Operation D to afford a solution of the targeted antibody-drug conjugate in ABS (10 mM acetate buffer, 5% sorbitol, pH 5.5) (3.5 mL).

Analysis was performed in accordance with the methods described in Common Operations E and G to acquire the following results.

Antibody concentration: 0.97 mg/mL

Antibody yield: 3.41 mg (62%)

Average number of conjugated drug molecules: 3.6

Example 28: Synthesis of Antibody-Drug Conjugate 2 (Synthesis of Anti-HER2 Antibody-CDN Conjugate 2)

A phosphate-buffered saline solution of glycan-remodeled antibody 1 (pH 6.0) (10.97 mg/mL, 0.500 mL) was diluted with propylene glycol (0.250 mL). To this solution, a mixture of a dimethyl sulfoxide solution of drug-linker 4 (10 mM, 0.0907 mL, 24 equivalents per antibody molecule) and propylene glycol (0.159 mL) was added, and the resultant was reacted with a tube rotator (MTR-103, AS ONE Corporation) at room temperature for 2 days. The reaction mixture was purified in accordance with the method described in Common Operation D to afford a solution of the targeted antibody-drug conjugate in ABS (3.5 mL).

Analysis was performed in accordance with the methods described in Common Operations E and G to acquire the following results.

Antibody concentration: 1.08 mg/mL

Antibody yield: 3.78 mg (69%)

Average number of conjugated drug molecules: 3.2

Example 29: Synthesis of Antibody-Drug Conjugate 3 (Synthesis of Anti-HER2 Antibody-CDN Conjugate 3)

A phosphate-buffered saline solution of glycan-remodeled antibody 1 (pH 6.0) (10.97 mg/mL, 0.500 mL) was diluted with propylene glycol (0.250 mL). To this solution, a mixture of a dimethyl sulfoxide solution of drug-linker 2a (10 mM, 0.0907 mL, 24 equivalents per antibody molecule) and propylene glycol (0.159 mL) was added, and the resultant was reacted with a tube rotator (MTR-103, AS ONE Corporation) at room temperature for 47 hours. The reaction mixture was purified in accordance with the method described in Common Operation D to afford a solution of the targeted antibody-drug conjugate in ABS (3.5 mL).

Analysis was performed in accordance with the methods described in Common Operations E and G to acquire the following results.

Antibody concentration: 0.91 mg/mL

Antibody yield: 3.17 mg (58%)

Average number of conjugated drug molecules: 3.6

Example 30: Synthesis of Antibody-Drug Conjugate 4 (Synthesis of Anti-LPS Antibody-CDN Conjugate 1)

A phosphate-buffered saline solution of glycan-remodeled antibody 2 (pH 6.0) (10.55 mg/mL, 1.00 mL) was diluted with propylene glycol (0.500 mL). To this solution, a mixture of a dimethyl sulfoxide solution of drug-linker 3 (10 mM, 0.174 mL, 24 equivalents per antibody molecule) and propylene glycol (0.326 mL) was added, and the resultant was reacted with a tube rotator (MTR-103, AS ONE Corporation) at room temperature for 2 days. The reaction mixture was purified in accordance with the method described in Common Operation D to afford a solution of the targeted antibody-drug conjugate in ABS (6.5 mL).

Analysis was performed in accordance with the methods described in Common Operations E and G to acquire the following results.

Antibody concentration: 1.11 mg/mL

Antibody yield: 7.23 mg (69%)

Average number of conjugated drug molecules: 3.9

Example 31: Synthesis of CDN21

(5R,7R,8R,12aR,14R,15R,15aS,16R)-7-(6-Amino-9H-purin-9-yl)-15,16-dihydroxy-2,10-bis(sulfanyl)-14-(7,8,9,10-tetrahydro-2H-6-oxa-2,3,5-triazacyclooctal[1,2,3-cd]inden-2-yl)octahydro-2H,10H,12H-5,8-methano-2$\lambda^5$,10$\lambda^5$-furo[3,2-1][1,3,6,9,11,2,10]pentaoxadiphosphacyclotetradecine-2,10-dione

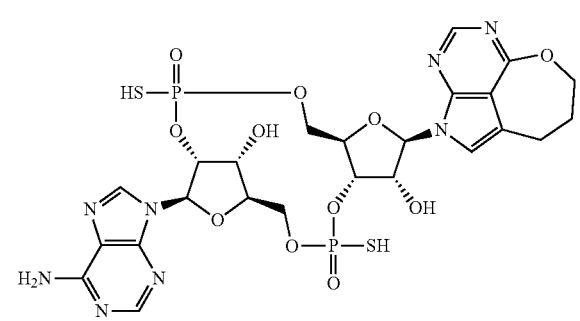

21

21a (Diastereomer 1)
21b (Diastereomer 2)

[Synthesis Scheme]
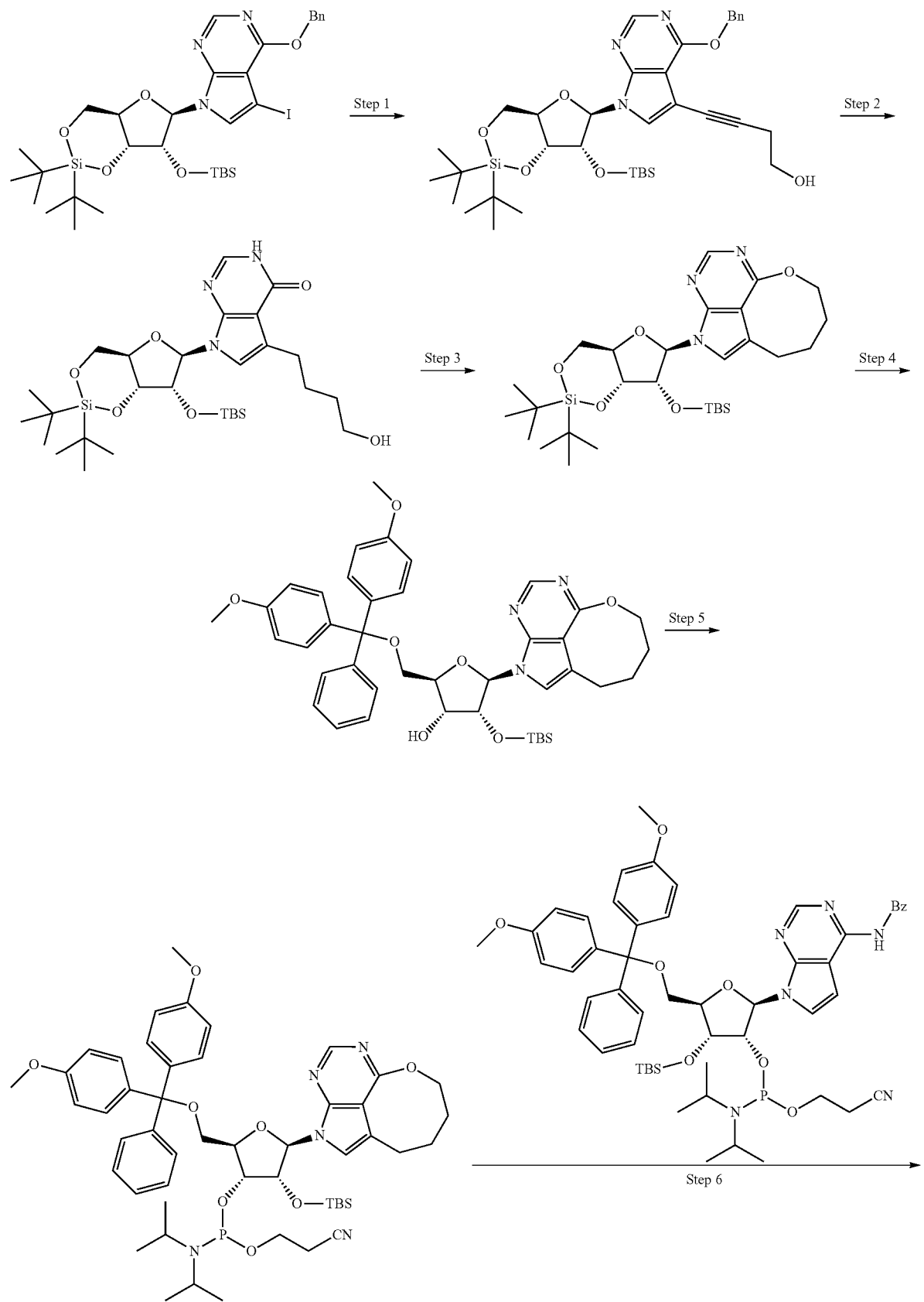

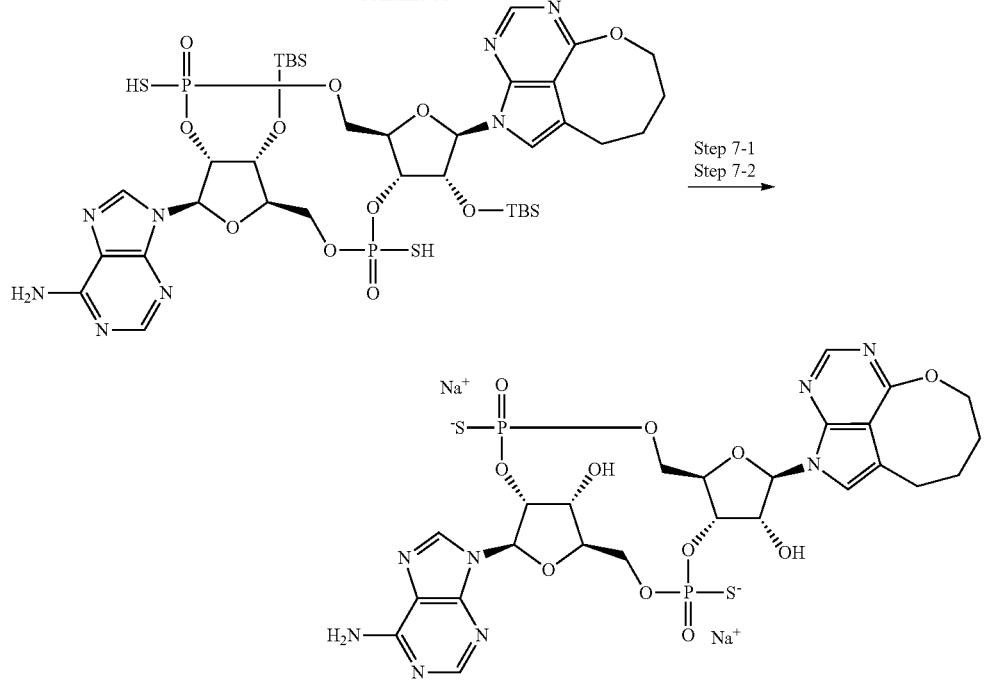

(Step 1)

4-(Benzyloxy)-7-{2-O-[tert-butyl(dimethyl)silyl]-3,5-O-(di-tert-butylsilylidene)-β-D-ribofuranosyl}-5-(4-hydroxybut-1-yn-1-yl)-7H-pyrrolo[2,3-d]pyrimidine With use of the compound obtained in step 2 of Example 20 (3.37 g) and 3-butyn-1-ol (1.72 mL), the reaction was performed in the same manner as in step 2 of Example 1, except that the reaction temperature was set to room temperature, to afford the title compound (2.74 g).

$^1$H-NMR (CDCl$_3$) δ: 8.44 (1H, s), 7.58-7.53 (2H, m), 7.42-7.31 (3H, m), 7.16 (1H, s), 6.16 (1H, s), 5.61 (2H, dd, J=14.9, 12.5 Hz), 4.47 (1H, dd, J=9.2, 4.9 Hz), 4.42 (1H, d, J=4.7 Hz), 4.26 (1H, dd, J=9.4, 4.7 Hz), 4.17 (1H, td, J=9.9, 4.8 Hz), 4.01 (1H, t, J=9.6 Hz), 3.71-3.64 (2H, m), 2.65 (2H, t, J=6.1 Hz), 1.87 (1H, t, J=6.5 Hz), 1.08 (9H, s), 1.04 (9H, s), 0.91 (9H, s), 0.11 (3H, s), 0.10 (3H, s).

(Step 2)

7-{2-O-[tert-Butyl(dimethyl)silyl]-3,5-O-(di-tert-butylsilylidene)-β-D-ribofuranosyl}-5-(4-hydroxybutyl)-3,7-dihydro-4H-pyrrolo[2,3-d]pyrimidin-4-one With use of the compound obtained in step 1 (2.74 g), the reaction was performed in the same manner as in step 7 of Example 19, except that the reaction solvent was changed to a mixed solvent of methanol (30 mL)-tetrahydrofuran (30 mL), to afford the title compound (2.21 g).

$^1$H-NMR (CDCl$_3$) δ: 11.55 (1H, brs), 7.90 (1H, s), 6.63 (1H, s), 6.09 (1H, s), 4.47 (1H, dd, J=9.0, 5.1 Hz), 4.38 (1H, d, J=4.7 Hz), 4.24 (1H, dd, J=9.4, 4.7 Hz), 4.19-4.11 (1H, m), 4.01 (1H, t, J=9.8 Hz), 3.82-3.74 (2H, m), 2.88 (1H, brs), 2.83-2.74 (2H, m), 1.85-1.75 (2H, m), 1.71-1.62 (2H, m), 1.09 (9H, s), 1.04 (9H, s), 0.90 (9H, s), 0.102 (3H, s), 0.099 (3H, s).

(Step 3)

2-{2-O-[tert-Butyl(dimethyl)silyl]-3,5-O-(di-tert-butylsilylidene)-β-D-ribofuranosyl}-7,8,9,10-tetrahydro-2H-6-oxa-2,3,5-triazacycloocta[1,2,3-cd]indene With use of the compound obtained in step 2 (1.89 g), the reaction was performed in the same manner as in step 5 of Example 20 to afford the title compound (1.40 g).

$^1$H-NMR (CDCl$_3$) δ: 8.41 (1H, s), 6.84 (1H, s), 6.21 (1H, s), 4.54-4.43 (4H, m), 4.31 (1H, dd, J=9.6, 4.9 Hz), 4.17 (1H, td, J=10.0, 5.1 Hz), 4.00 (1H, dd, J=10.4, 9.2 Hz), 2.87-2.73 (2H, m), 2.05-1.87 (4H, m), 1.10 (9H, s), 1.05 (9H, s), 0.91 (9H, s), 0.12 (3H, s), 0.10 (3H, s).

(Step 4)

2-{5-O-[Bis(4-methoxyphenyl)(phenyl)methyl]-2-O-[tert-butyl(dimethyl)silyl]-β-D-ribofuranosyl}-7,8,9,10-tetrahydro-2H-6-oxa-2,3,5-triazacycloocta[1,2,3-cd]indene With use of the compound obtained in step 3 (1.61 g), the reaction was performed in the same manner as in step 5 of Example 1 to afford the title compound (1.95 g).

$^1$H-NMR (CDCl$_3$) δ: 8.40 (1H, s), 7.49-7.43 (2H, m), 7.38-7.20 (8H, m), 6.86-6.78 (4H, m), 6.38 (1H, d, J=5.5 Hz), 4.70 (1H, t, J=5.3 Hz), 4.54-4.45 (2H, m), 4.38-4.31 (1H, m), 4.26-4.18 (1H, m), 3.79 (3H, s), 3.79 (3H, s), 3.53 (1H, dd, J=10.6, 2.3 Hz), 3.37 (1H, dd, J=10.6, 3.1 Hz), 2.81 (1H, d, J=3.9 Hz), 2.56-2.45 (2H, m), 2.00-1.91 (2H, m), 1.86-1.76 (2H, m), 0.82 (9H, s), −0.04 (3H, s), −0.17 (3H, s).

(Step 5)

2-(5-O-[Bis(4-methoxyphenyl)(phenyl)methyl]-2-O-[tert-butyl(dimethyl)silyl]-3-O-{(2-cyanoethoxy)[di(propan-2-yl)amino]phosphanyl}-β-D-ribofuranosyl)-7,8,9,10-tetrahydro-2H-6-oxa-2,3,5-triazacyclooct[1,2,3-cd]indene With use of the compound obtained in step 4 (1.95 g), operations were performed in the same manner as in step 4 of Example 5 to afford the title compound (2.20 g) as a mixture of diastereomers at the phosphorus atom (diastereomer ratio=6:4).

$^1$H-NMR (CDCl$_3$) δ: 8.39 (0.4H, s), 8.37 (0.6H, s), 7.51-7.45 (2H, m), 7.40-7.20 (8H, m), 6.86-6.78 (4H, m), 6.37 (0.6H, d, J=6.7 Hz), 6.32 (0.4H, d, J=6.3 Hz), 4.83-4.78 (0.6H, m), 4.77-4.70 (0.4H, m), 4.56-4.44 (2H, m), 4.42-4.33 (1.4H, m), 4.29-4.24 (0.6H, m), 4.07-3.86 (1H, m), 3.82-3.75 (6H, m), 3.70-3.46 (4H, m), 3.32-3.24 (1H, m), 2.76-2.65 (1H, m), 2.63-2.49 (2H, m), 2.32 (1H, t, J=6.7 Hz), 2.01-1.90 (2H, m), 1.87-1.74 (2H, m), 1.23-1.12 (8.4H, m), 1.03 (3.6H, d, J=6.7 Hz), 0.74 (3.6H, s), 0.72 (5.4H, s), −0.04 (1.2H, s), −0.08 (1.8H, s), −0.21 (1.2H, s), −0.23 (1.8H, s).

(Step 6)

(5R,7R,8R,12aR,14R,15R,15aR,16R)-7-(6-Amino-9H-purin-9-yl)-15,16-bis{[tert-butyl(dimethyl)silyl]oxy}-2,10-bis(sulfanyl)-14-(7,8,9,10-tetrahydro-2H-6-oxa-2,3,5-triazacyclooct[1,2,3-cd]inden-2-yl)octahydro-2H,10H,12H-5,8-methano-2λ$^5$,10λ$^5$-furo[3,2-l][1,3,6,9,11,2,10]pentaoxadiphosphacyclotetradecine-2,10-dione With use of the compound obtained in step 5 (1.18 g), the reaction was performed in the same manner as in step 7 of Example 1 to afford an acetonitrile solution of 2-{2-O-[tert-butyl(dimethyl)silyl]-3-O-[hydroxy (oxo)-λ$^5$-phosphanyl]-β-D-ribofuranosyl}-7,8,9,10-tetrahydro-2H-6-oxa-2,3,5-triazacyclooct[1,2,3-cd]indene. With use of this acetonitrile solution and commercially available (Cool Pharm Ltd.) N-benzoyl-5'-O-[bis(4-methoxyphenyl)(phenyl)methyl]-3'-O-[tert-butyl(dimethyl)silyl]-2'-O-{(2-cyanoethoxy)[di(propan-2-yl)amino]phosphanyl}adenosine (1.49 g), the reaction was performed in the same manner as in steps 8, 9, and 10 of Example 1 to afford the title compound as a mixture of diastereomers at the phosphorus atom. This mixture was purified by HPLC [10 mM aqueous solution of triethylammonium acetate/acetonitrile, acetonitrile: 25%-60% (0 min-35 min)] to afford diastereomer 1 (50 mg) and diastereomer 2 (34 mg) of the title compound.

Diastereomer 1 (Less Polar)

MS(ESI)m/z: 973 (M+H)$^+$.

Diastereomer 2 (More Polar)

MS(ESI)m/z: 973 (M+H)$^+$.

(Step 7-1)

Disodium (5R,7R,8R,12aR,14R,15R,15aS,16R)-7-(6-amino-9H-purin-9-yl)-15,16-dihydroxy-2,10-dioxo-14-(7,8,9,10-tetrahydro-2H-6-oxa-2,3,5-triazacyclooct[1,2,3-cd]inden-2-yl)octahydro-2H,10H,12H-5,8-methano-2λ$^5$,10λ$^5$-furo[3,2-l][1,3,6,9,11,2,10]pentaoxadiphosphacyclotetradecine-2,10-bis(thiolate)

(Diastereomer 1)

With use of the compound obtained in step 6 (diastereomer 1) (50 mg), the reaction was performed in the same manner as in step 11 of Example 1, and the resultant was then purified with a Sep-Pak® C18 [0.1% aqueous solution of triethylamine/acetonitrile=5:1] to afford a triethylamine salt of the title compound.

The triethylamine salt obtained was subjected to salt exchange in the same manner as in [Conversion to Sodium Salt] described in step 11 of Example 1 to afford the title compound (33 mg).

MS(ESI)m/z: 745 (M+H)$^+$.

$^1$H-NMR (CD$_3$OD) δ: 8.73 (1H, s), 8.30 (1H, s), 8.17 (1H, s), 7.40 (1H, s), 6.39 (1H, d, J=4.3 Hz), 6.34 (1H, d, J=8.6 Hz), 5.40-5.36 (1H, m), 5.22-5.17 (1H, m), 4.87-4.84 (1H, m), 4.80 (1H, t, J=4.5 Hz), 4.64-4.31 (6H, m), 4.11-4.03 (2H, m), 2.82 (1H, dd, J=16.4, 8.6 Hz), 2.68 (1H, dd, J=16.2, 8.8 Hz), 2.06-1.71 (4H, m).

$^{31}$P-NMR (CD$_3$OD) δ: 58.1 (s), 54.2 (s).

(Step 7-2)

Disodium (5R,7R,8R,12aR,14R,15R,15aS,16R)-7-(6-amino-9H-purin-9-yl)-15,16-dihydroxy-2,10-dioxo-14-(7,8,9,10-tetrahydro-2H-6-oxa-2,3,5-triazacyclooct[1,2,3-cd]inden-2-yl)octahydro-2H,10H,12H-5,8-methano-2λ$^5$,10λ$^5$-furo[3,2-l][1,3,6,9,11,2,10]pentaoxadiphosphacyclotetradecine-2,10-bis(thiolate)

(Diastereomer 2)

With use of the compound obtained in step 6 (diastereomer 2) (34 mg), the reaction was performed in the same manner as in step 11 of Example 1, and the resultant was then purified with a Sep-Pak® C18 [0.1% aqueous solution of triethylamine/acetonitrile=5:1] to afford a triethylamine salt of the title compound.

The triethylamine salt obtained was subjected to salt exchange in the same manner as in [Conversion to Sodium Salt] described in step 11 of Example 1 to afford the title compound (21 mg).

MS(ESI)m/z: 745 (M+H)$^+$.

$^1$H-NMR (CD$_3$OD) δ: 8.81 (1H, s), 8.30 (1H, s), 8.17 (1H, s), 7.40 (1H, s), 6.43 (1H, d, J=6.7 Hz), 6.34 (1H, d, J=8.6 Hz), 5.55-5.42 (2H, m), 4.87-4.84 (1H, m), 4.59-4.28 (7H, m), 4.06-3.99 (1H, m), 3.94-3.86 (1H, m), 2.96-2.81 (2H, m), 2.07-1.94 (2H, m), 1.93-1.80 (2H, m).

$^{31}$P-NMR (CD$_3$OD) δ: 63.1 (s), 60.5 (s).

Example 32: Synthesis of CDN22
(5R,7R,8R,12aR,14R,15R,15aS,16R)-7-(6-Amino-9H-purin-9-yl)-15,16-dihydroxy-14-[(7S)-7-methyl-8,9-dihydro-6-oxa-2,3,5-triazabenzo[cd]azulen-2(7H)-yl]-2,10-bis(sulfanyl)octahydro-2H,10H,12H-5,8-methano-2λ$^5$,10λ$^5$-furo[3,2-l][1,3,6,9,11,2,10]pentaoxadiphosphacyclotetradecine-2,10-dione
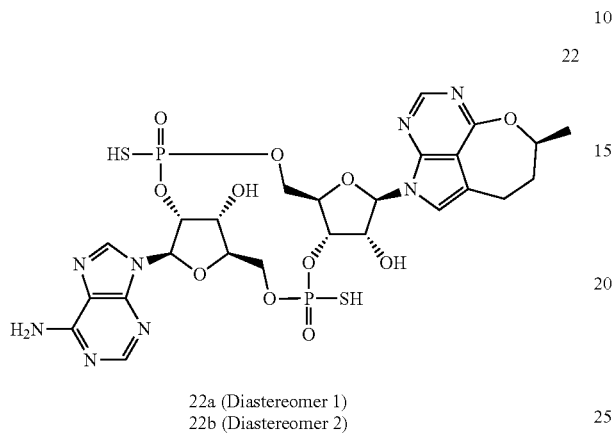
22a (Diastereomer 1)
22b (Diastereomer 2)
[Synthesis Scheme]
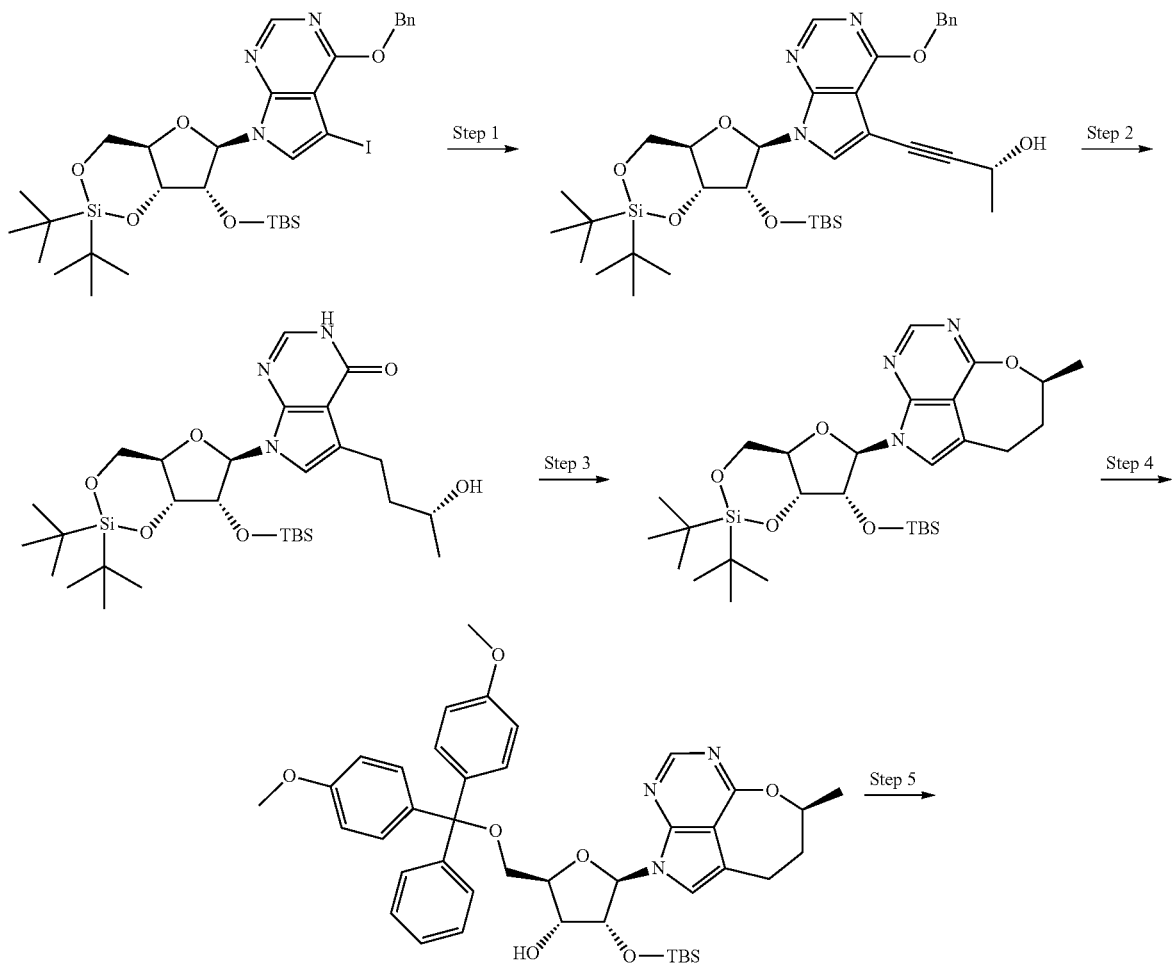

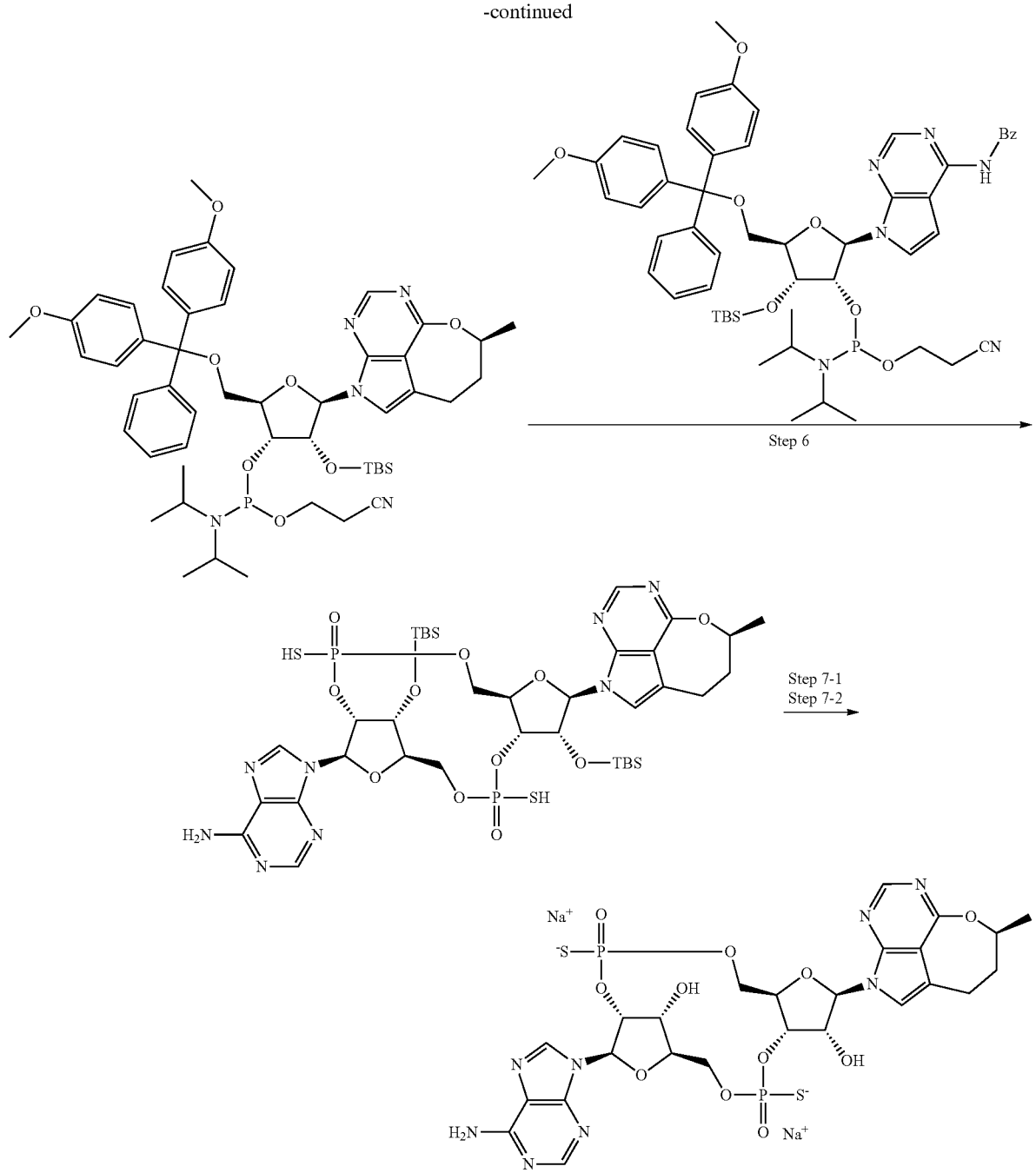

(Step 1)

4-(Benzyloxy)-7-{2-O-[tert-butyl(dimethyl)silyl]-3,5-O-(di-tert-butylsilylidene)-β-D-ribofuranosyl}-5-[(3R)-3-hydroxybut-1-yn-1-yl]-7H-pyrrolo[2,3-d]pyrimidine With use of the compound obtained in step 2 of Example 20 (2.54 g) and (R)-(+)-3-butyn-2-ol (1.36 mL), the reaction was performed in the same manner as in step 2 of Example 1, except that the reaction temperature was set to room temperature, to afford the title compound (1.85 g).

$^1$H-NMR (CDCl$_3$) δ: 8.46 (1H, s), 7.57 (2H, d, J=7.0 Hz), 7.44-7.32 (3H, m), 7.20 (1H, s), 6.16 (1H, s), 5.58 (1H, d, J=12.9 Hz), 5.55 (1H, d, J=13.7 Hz), 4.71-4.63 (1H, m), 4.48 (1H, dd, J=9.2, 4.9 Hz), 4.42 (1H, d, J=4.7 Hz), 4.26 (1H, dd, J=9.4, 4.7 Hz), 4.23-4.14 (1H, m), 4.01 (1H, t, J=9.6 Hz), 1.70 (1H, d, J=5.5 Hz), 1.42 (3H, d, J=6.7 Hz), 1.09 (9H, s), 1.04 (9H, s), 0.91 (9H, s), 0.12 (3H, s), 0.11 (3H, s).

(Step 2)

7-{2-O-[tert-Butyl(dimethyl)silyl]-3,5-O-(di-tert-butylsilylidene)-β-D-ribofuranosyl}-5-[(3R)-3-hydroxybutyl]-3,7-dihydro-4H-pyrrolo[2,3-d]pyrimidin-4-one With use of the compound obtained in step 1 (1.85 g), the reaction was performed in the same manner as in step 7 of Example 19, except that the reaction solvent was changed to a mixed solvent of methanol (15 mL)-tetrahydrofuran (15 mL), to afford the title compound (1.34 g).

$^1$H-NMR (CDCl$_3$) δ: 11.81 (1H, s), 7.89 (1H, s), 6.68 (1H, s), 6.12 (1H, s), 4.49 (1H, dd, J=9.2, 4.5 Hz), 4.34 (1H, d, J=4.3 Hz), 4.27-4.14 (3H, m), 4.03 (1H, t, J=9.6 Hz), 3.77-3.65 (1H, m), 3.17-3.06 (1H, m), 2.85-2.74 (1H, m), 1.84-1.73 (1H, m), 1.71-1.61 (1H, m), 1.15 (3H, d, J=6.3 Hz), 1.09 (9H, s), 1.04 (9H, s), 0.90 (9H, s), 0.10 (6H, s).

(Step 3)

(7S)-2-{2-O-[tert-Butyl(dimethyl)silyl]-3,5-O-(di-tert-butylsilylidene)-β-D-ribofuranosyl}-7-methyl-2,7,8,9-tetrahydro-6-oxa-2,3,5-triazabenzo[cd]azulene With use of the compound obtained in step 2 (1.34 g), the reaction was performed in the same manner as in step 5 of Example 20 to afford the title compound (0.70 g).

$^1$H-NMR (CDCl$_3$) δ: 8.43 (1H, s), 6.82 (1H, s), 6.19 (1H, s), 4.58-4.43 (3H, m), 4.33 (1H, dd, J=9.6, 5.0 Hz), 4.17 (1H, td, J=10.0, 5.0 Hz), 4.00 (1H, dd, J=10.4, 9.2 Hz), 3.06-2.97 (1H, m), 2.89-2.79 (1H, m), 2.23-2.08 (2H, m), 1.60 (3H, d, J=6.3 Hz), 1.10 (9H, s), 1.05 (9H, s), 0.91 (9H, s), 0.12 (3H, s), 0.11 (3H, s).

(Step 4)

(7S)-2-{5-O-[Bis(4-methoxyphenyl)(phenyl)methyl]-2-O-[tert-butyl(dimethyl)silyl]-β-D-ribofuranosyl}-7-methyl-2,7,8,9-tetrahydro-6-oxa-2,3,5-triazabenzo[cd]azulene With use of the compound obtained in step 3 (0.70 g), the reaction was performed in the same manner as in step 5 of Example 1 to afford the title compound (0.82 g).

$^1$H-NMR (CDCl$_3$) δ: 8.41 (1H, s), 7.49-7.43 (2H, m), 7.37-7.20 (7H, m), 7.16 (1H, s), 6.85-6.78 (4H, m), 6.35 (1H, d, J=5.5 Hz), 4.72 (1H, t, J=5.3 Hz), 4.57-4.47 (1H, m), 4.36 (1H, dd, J=9.0, 3.9 Hz), 4.22 (1H, q, J=3.1 Hz), 3.79 (3H, s), 3.79 (3H, s), 3.52 (1H, dd, J=10.6, 2.7 Hz), 3.37 (1H, dd, J=10.6, 3.1 Hz), 2.81 (1H, d, J=3.9 Hz), 2.78-2.58 (2H, m), 2.16-2.07 (2H, m), 1.59 (3H, d, J=6.7 Hz), 0.83 (9H, s), −0.03 (3H, s), −0.15 (3H, s).

(Step 5)

(7S)-2-(5-O-[Bis(4-methoxyphenyl)(phenyl)methyl]-2-O-[tert-butyl(dimethyl)silyl]-3-O-{(2-cyanoethoxy)[di(propan-2-yl)amino]phosphanyl}-β-D-ribofuranosyl)-7-methyl-2,7,8,9-tetrahydro-6-oxa-2,3,5-triazabenzo[cd]azulene With use of the compound obtained in step 4 (0.82 g), operations were performed in the same manner as in step 4 of Example 5 to afford the title compound (0.85 g) as a mixture of diastereomers at the phosphorus atom (diastereomer ratio=6:4).

$^1$H-NMR (CDCl$_3$) δ: 8.40 (0.4H, s), 8.38 (0.6H, s), 7.50-7.43 (2H, m), 7.39-7.16 (8H, m), 6.86-6.78 (4H, m), 6.34 (0.6H, d, J=6.7 Hz), 6.30 (0.4H, d, J=5.9 Hz), 4.86-4.80 (0.6H, m), 4.79-4.74 (0.4H, m), 4.55-4.46 (1H, m), 4.44-4.35 (1.4H, m), 4.29-4.24 (0.6H, m), 4.05-3.85 (1H, m), 3.82-3.75 (6H, m), 3.69-3.47 (4H, m), 3.31-3.24 (1H, m), 2.82-2.61 (3H, m), 2.31 (1H, t, J=6.7 Hz), 2.17-2.07 (2H, m), 1.58-1.55 (3H, m), 1.22-1.13 (8.4H, m), 1.03 (3.6H, d, J=6.7 Hz), 0.75 (3.6H, s), 0.74 (5.4H, s), −0.03 (1.2H, s), −0.07 (1.8H, s), −0.19 (1.2H, s), —0.21 (1.8H, s).

(Step 6)

(5R,7R,8R,12aR,14R,15R,15aR,16R)-7-(6-Amino-9H-purin-9-yl)-15,16-bis{[tert-butyl(dimethyl)silyl]oxy}-14-[(7S)-7-methyl-8,9-dihydro-6-oxa-2,3,5-triazabenzo[cd]azulen-2(7H)-yl]-2,10-bis(sulfanyl)octahydro-2H,10H,12H-5,8-methano-2λ$^5$,10λ$^5$-furo[3,2-1][1,3,6,9,11,2,10]pentaoxadiphosphacyclotetradecine-2,10-dione With use of the compound obtained in step 5 (0.85 g), the reaction was performed in the same manner as in step 7 of Example 1 to afford an acetonitrile solution of (7S)-2-{2-O-[tert-butyl(dimethyl)silyl]-3-O-[hydroxy (oxo)-λ$^5$-phosphanyl]-β-D-ribofuranosyl}-7-methyl-2,7,8,9-tetrahydro-6-oxa-2,3,5-triazabenzo[cd]azulene. With use of this acetonitrile solution and commercially available (Cool Pharm Ltd.) N-benzoyl-5'-O-[bis(4-methoxyphenyl)(phenyl)methyl]-3'-O-[tert-butyl(dimethyl)silyl]-2'-O-{(2-cyanoethoxy)[di(propan-2-yl)amino]phosphanyl}adenosine (1.12 g), the reaction was performed in the same manner as in steps 8, 9, and 10 of Example 1 to afford the title compound as a mixture of diastereomers at the phosphorus atom. This mixture was purified by HPLC [10 mM aqueous solution of triethylammonium acetate/acetonitrile, acetonitrile: 25%-60% (0 min-35 min)] to afford diastereomer 1 (95 mg) and diastereomer 2 (44 mg) of the title compound (retention time in HPLC: diastereomer 1>2).

Diastereomer 1 (Less Polar)

MS(ESI)m/z: 973 (M+H)$^+$.

Diastereomer 2 (More Polar)

MS(ESI)m/z: 973 (M+H)$^+$.

(Step 7-1)

Disodium (5R,7R,8R,12aR,14R,15R,15aS,16R)-7-(6-amino-9H-purin-9-yl)-15,16-dihydroxy-14-[(7S)-7-methyl-8,9-dihydro-6-oxa-2,3,5-triazabenzo[cd]azulen-2 (7H)-yl]-2,10-dioxooctahydro-2H,10H,12H-5,8-methano-2λ$^5$,10λ$^5$-furo[3,2-1][1,3,6,9,11,2,10]pentaoxadiphosphacyclotetradecine-2,10-bis(thiolate)

(Diastereomer 1)

With use of the compound obtained in step 6 (diastereomer 1) (95 mg), the reaction was performed in the same manner as in step 11 of Example 1, and the resultant was then purified with a Sep-Pak® C18 [0.1% aqueous solution of triethylamine/acetonitrile=5:1] to afford a triethylamine salt of the title compound.

The triethylamine salt obtained was subjected to salt exchange in the same manner as in [Conversion to Sodium Salt] described in step 11 of Example 1 to afford the title compound (57 mg).

MS(ESI)m/z: 745 (M+H)$^+$.

$^1$H-NMR (CD$_3$OD) δ: 8.72 (1H, s), 8.30 (1H, s), 8.17 (1H, s), 7.35 (1H, s), 6.37 (1H, d, J=4.3 Hz), 6.34 (1H, d, J=8.2 Hz), 5.40-5.35 (1H, m), 5.22-5.17 (1H, m), 4.85-4.81 (2H, m), 4.66-4.58 (1H, m), 4.53-4.40 (2H, m), 4.39-4.30 (2H, m), 4.12-4.01 (2H, m), 3.02-2.93 (1H, m), 2.80-2.68 (1H, m), 2.23-2.14 (1H, m), 2.12-2.00 (1H, m), 1.57 (3H, d, J=6.3 Hz).

$^{31}$P-NMR (CD$_3$OD) δ: 58.1 (s), 54.3 (s).

(Step 7-2)

Disodium (5R,7R,8R,12aR,14R,15R,15aS,16R)-7-(6-amino-9H-purin-9-yl)-15,16-dihydroxy-14-[(7S)-7-methyl-8,9-dihydro-6-oxa-2,3,5-triazabenzo[cd]azulen-2 (7H)-yl]-2,10-dioxooctahydro-2H,10H,12H-5,8-methano-2λ$^5$,10λ$^5$-furo[3,2-1][1,3,6,9,11,2,10]pentaoxadiphosphacyclotetradecine-2,10-bis(thiolate)

(Diastereomer 2)

With use of the compound obtained in step 6 (diastereomer 2) (44 mg), the reaction was performed in the same manner as in step 11 of Example 1, and the resultant was then purified with a Sep-Pak® C18 [0.1% aqueous solution of triethylamine/acetonitrile=5:1] to afford a triethylamine salt of the title compound.

The triethylamine salt obtained was subjected to salt exchange in the same manner as in [Conversion to Sodium Salt] described in step 11 of Example 1 to afford the title compound (30 mg).

MS(ESI)m/z: 745 (M+H)$^+$.

$^1$H-NMR (CD$_3$OD) δ: 8.81 (1H, s), 8.30 (1H, s), 8.17 (1H, s), 7.36 (1H, s), 6.41 (1H, d, J=6.7 Hz), 6.34 (1H, d, J=8.6 Hz), 5.55-5.42 (2H, m), 4.87-4.84 (1H, m), 4.65-4.57 (1H, m), 4.55-4.28 (5H, m), 4.06-3.99 (1H, m), 3.93-3.86 (1H, m), 3.11-3.01 (1H, m), 2.95-2.83 (1H, m), 2.29-2.19 (1H, m), 2.16-2.03 (1H, m), 1.57 (3H, d, J=6.3 Hz).

$^{31}$P-NMR (CD$_3$OD) δ: 63.7 (s), 61.2 (s).

Example 33: Synthesis of CDN23

(5R,7R,8R,12aR,14R,15R,15aS,16R)-7-(6-Amino-9H-purin-9-yl)-14-(8,9-dihydro-6-thia-2,3,5-triazabenzo[cd]azulen-2 (7H)-yl)-15,16-dihydroxy-2,10-bis(sulfanyl)octahydro-2H,10H,12H-5,8-methano-2λ$^5$,10λ$^5$-furo[3,2-1][1,3,6,9,11,2,10]pentaoxadiphosphacyclotetradecine-2,10-dione

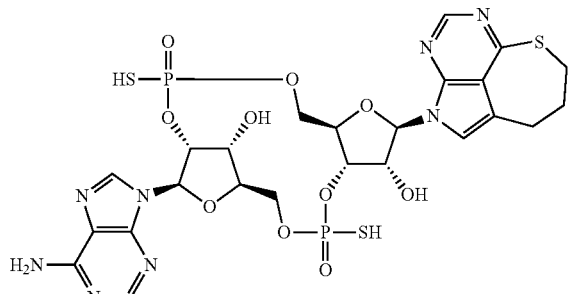

23a (Diastereomer 1)
23b (Diastereomer 2)

[Synthesis Scheme]

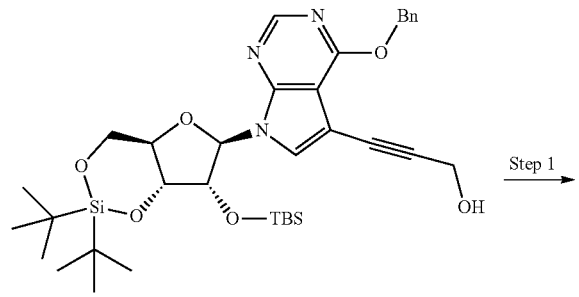

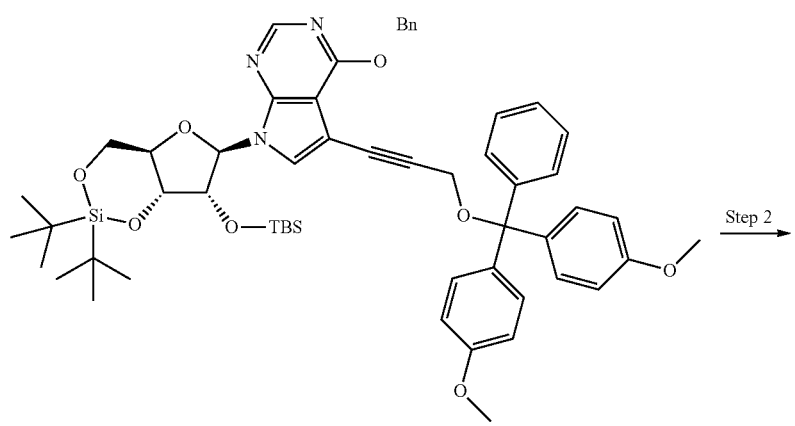

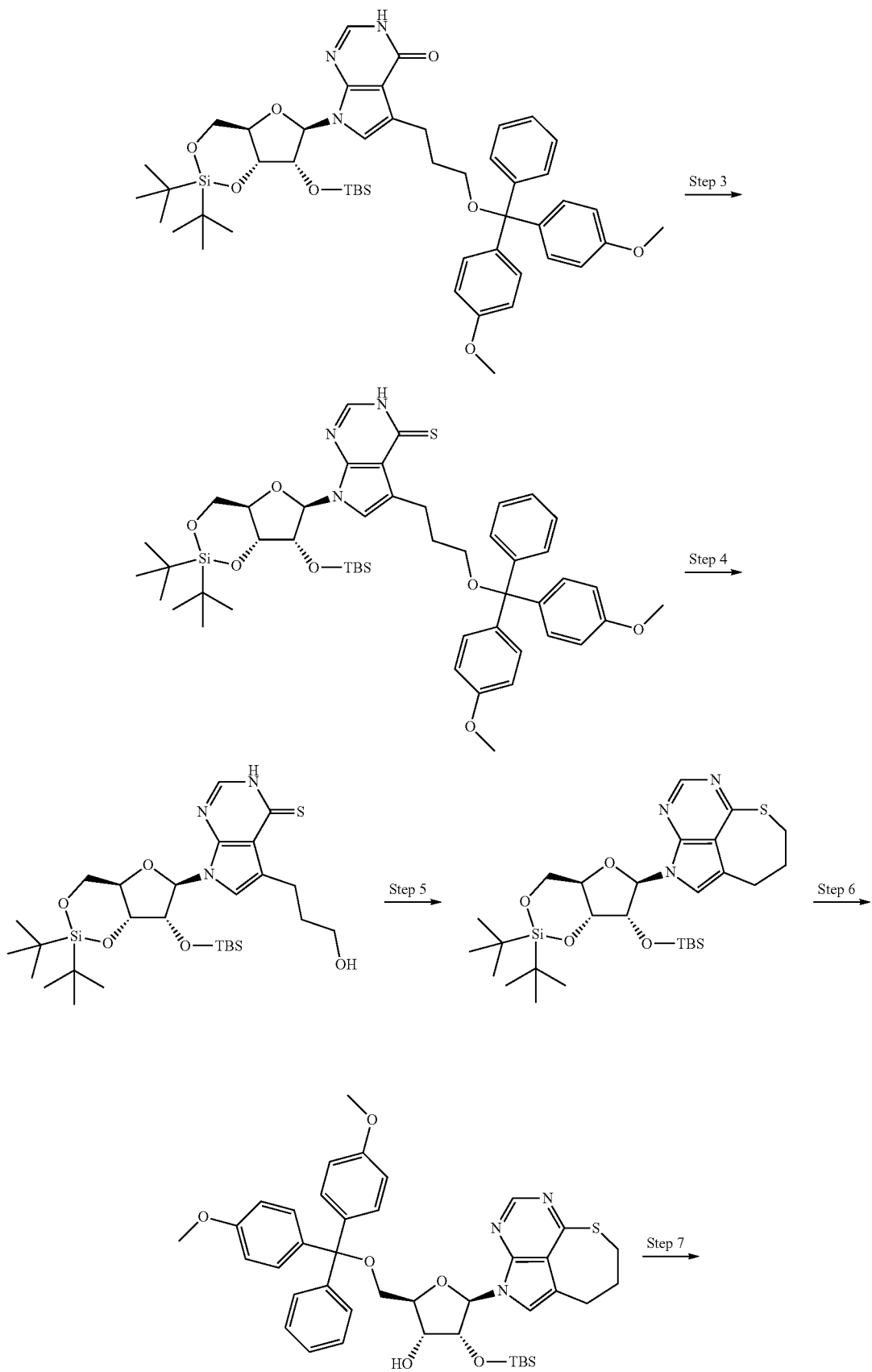

-continued
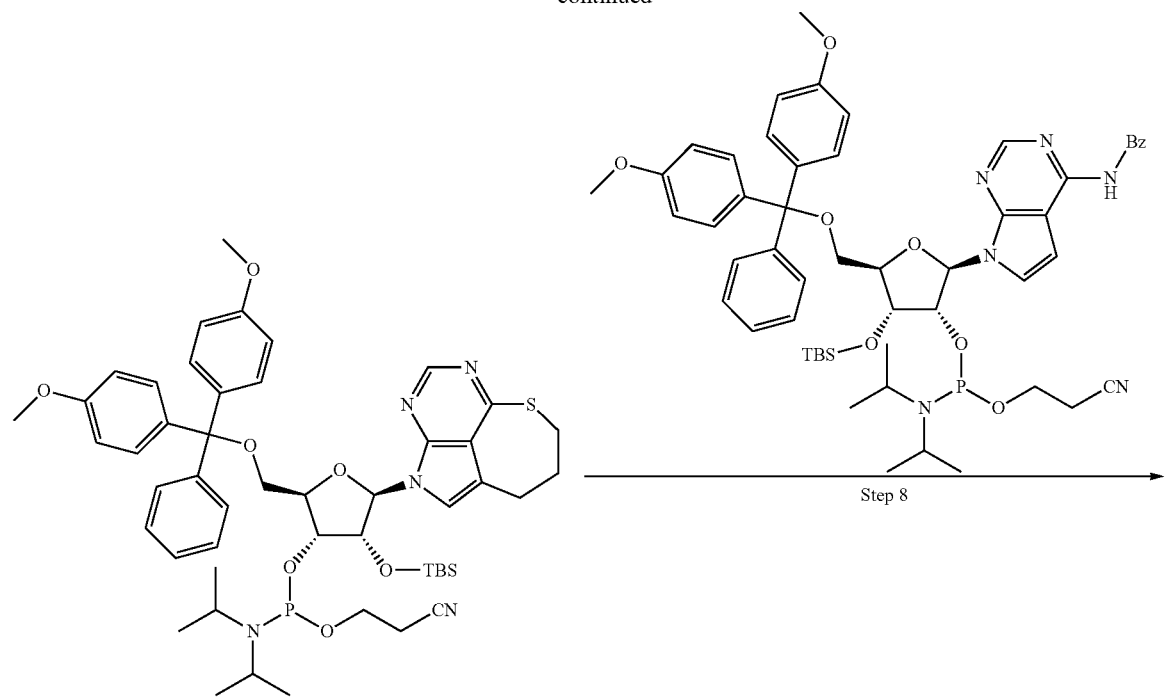
Step 8
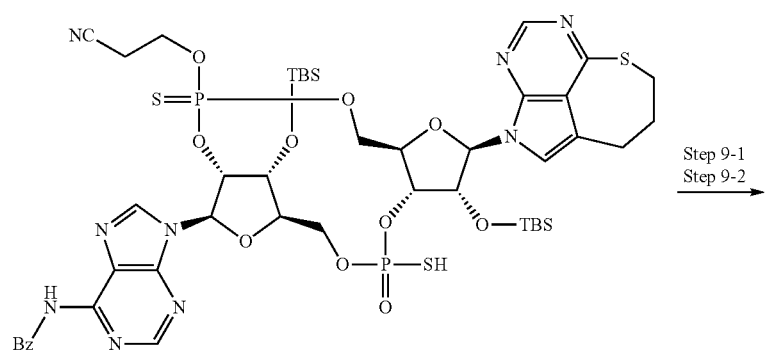
Step 9-1
Step 9-2
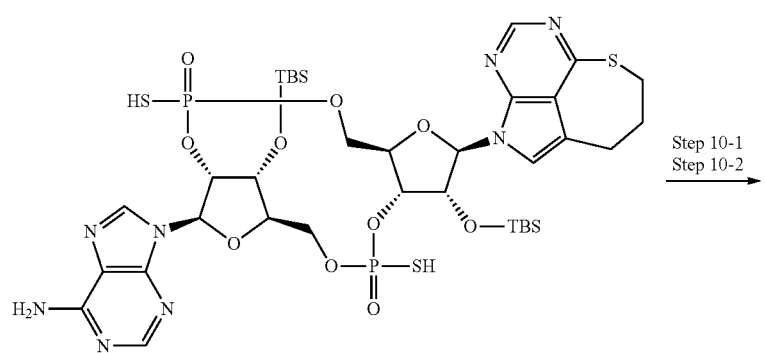
Step 10-1
Step 10-2

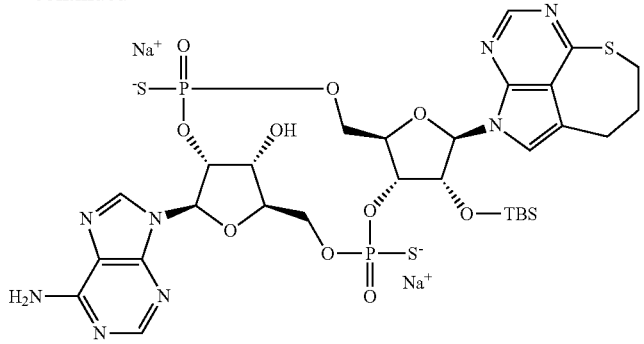

(Step 1)

4-(Benzyloxy)-5-{3-[bis(4-methoxyphenyl)(phenyl)methoxy]prop-1-yn-1-yl}-7-{2-O-[tert-butyl(dimethyl)silyl]-3,5-O-(di-tert-butylsilylidene)-β-D-ribofuranosyl}-7H-pyrrolo[2,3-d]pyrimidine With use of the compound obtained in step 3 of Example 20 (4.17 g), the reaction was performed in the same manner as in step 1 of Example 11, except that the reaction solvent was changed to a mixed solvent of dichloromethane (40 mL)-pyridine (40 mL), to afford the title compound (5.70 g).

$^1$H-NMR (CDCl$_3$) δ: 8.44 (1H, s), 7.53-7.47 (4H, m), 7.41-7.35 (4H, m), 7.33-7.11 (7H, m), 6.86-6.79 (4H, m), 6.17 (1H, s), 5.61 (1H, d, J=13.7 Hz), 5.58 (1H, d, J=13.7 Hz), 4.49 (1H, dd, J=9.0, 5.0 Hz), 4.44 (1H, d, J=4.8 Hz), 4.29 (1H, dd, J=9.6, 5.0 Hz), 4.23-4.15 (1H, m), 4.04 (1H, t, J=9.8 Hz), 3.98 (2H, s), 3.78 (6H, s), 1.10 (9H, s), 1.05 (9H, s), 0.91 (9H, s), 0.12 (3H, s), 0.11 (3H, s).

(Step 2)

5-{3-[Bis(4-methoxyphenyl)(phenyl)methoxy]propyl}-7-{2-O-[tert-butyl(dimethyl)silyl]-3,5-O-(di-tert-butylsilylidene)-β-D-ribofuranosyl}-3,7-dihydro-4H-pyrrolo[2,3-d]pyrimidin-4-one To a mixed solution of the compound obtained in step 1 (5.70 g) in methanol (100 mL)-tetrahydrofuran (50 mL), ammonium formate (3.71 g) and 10% palladium-carbon (AD) wet (2 g) were added, and the reaction mixture was stirred at room temperature for 3 hours. After the catalyst was removed through filtration, the filtrate was concentrated under reduced pressure. The residue was purified by silica gel column chromatography [hexane/ethyl acetate] to afford the title compound (4.56 g).

$^1$H-NMR (CDCl$_3$) δ: 11.61 (1H, brs), 7.75 (1H, s), 7.48-7.44 (2H, m), 7.37-7.14 (7H, m), 6.84-6.79 (4H, m), 6.57 (1H, s), 6.05 (1H, s), 4.45 (1H, dd, J=9.2, 4.9 Hz), 4.35 (1H, d, J=5.1 Hz), 4.23 (1H, dd, J=9.6, 4.9 Hz), 4.16-4.10 (1H, m), 3.97 (1H, t, J=9.8 Hz), 3.78 (6H, s), 3.19-3.08 (2H, m), 2.90 (2H, t, J=7.8 Hz), 2.07-1.98 (2H, m), 1.09 (9H, s), 1.04 (9H, s), 0.89 (9H, s), 0.09 (3H, s), 0.08 (3H, s).

(Step 3)

5-{3-[Bis(4-methoxyphenyl)(phenyl)methoxy]propyl}-7-{2-O-[tert-butyl(dimethyl)silyl]-3,5-O-(di-tert-butylsilylidene)-β-D-ribofuranosyl}-3,7-dihydro-4H-pyrrolo[2,3-d]pyrimidine-4-thione To a solution of the compound obtained in step 2 (1.01 g) in dichloromethane (10 mL), pyridine (0.461 mL) was added, and trifluoromethanesulfonic anhydride (0.385 mL) was added dropwise thereto under ice-cooling, and the reaction mixture was stirred for 30 minutes. A suspension of sodium monohydrogensulfide n-hydrate (2.54 g) in N,N-dimethylformamide (25 mL) was added to the reaction mixture at the same temperature, and the reaction mixture was stirred at room temperature for 2 hours. A saturated aqueous solution of sodium hydrogen carbonate and ethyl acetate were added to the reaction mixture, which was filtered through a Celite, and then subjected to extraction with ethyl acetate. The organic layer was washed with brine, and dried over anhydrous sodium sulfate. The drying agent was removed through filtration, and the filtrate was concentrated under reduced pressure. The residue was purified by silica gel column chromatography [hexane/ethyl acetate] to afford the title compound (0.51 g).

$^1$H-NMR (CDCl$_3$) δ: 10.83 (1H, s), 7.83 (1H, s), 7.50-7.44 (2H, m), 7.39-7.14 (7H, m), 6.87-6.79 (4H, m), 6.72 (1H, s), 6.07 (1H, s), 4.48-4.42 (1H, m), 4.31 (1H, d, J=4.3 Hz), 4.21-4.09 (2H, m), 3.99-3.92 (1H, m), 3.79 (6H, s), 3.19-3.09 (4H, m), 2.09-1.98 (2H, m), 1.08 (9H, s), 1.04 (9H, s), 0.90 (9H, s), 0.09 (3H, s), 0.09 (3H, s).

(Step 4)

7-{2-O-[tert-Butyl(dimethyl)silyl]-3,5-O-(di-tert-butylsilylidene)-β-D-ribofuranosyl}-5-(3-hydroxypropyl)-3,7-dihydro-4H-pyrrolo[2,3-d]pyrimidine-4-thione To a solution of the compound obtained in step 3 (2.79 g) in dichloromethane (80 mL), distilled water (4 mL) was added, and dichloroacetic acid (1.28 mL) was added dropwise thereto under ice-cooling, and the reaction mixture was stirred for 30 minutes. Pyridine (2.50 mL) was added to the reaction mixture at the same temperature, and the reaction mixture was then concentrated under reduced pressure. The residue was purified by silica gel column chromatography [hexane/ethyl acetate] to afford the title compound (0.96 g).

$^1$H-NMR (CDCl$_3$) δ: 11.16 (1H, s), 7.89 (1H, s), 6.83 (1H, s), 6.11 (1H, s), 4.51-4.45 (1H, m), 4.36-4.29 (1H, m), 4.22-4.13 (2H, m), 4.06-3.97 (1H, m), 3.68 (2H, t, J=6.1 Hz), 3.27-3.09 (2H, m), 2.25-2.13 (1H, brm), 2.00-1.93 (2H, m), 1.08 (9H, s), 1.04 (9H, s), 0.90 (9H, s), 0.10 (6H, s).

(Step 5)

2-{2-O-[tert-Butyl(dimethyl)silyl]-3,5-O-(di-tert-butylsilylidene)-β-D-ribofuranosyl}-2,7,8,9-tetrahydro-6-thia-2,3,5-triazabenzo[cd]azulene With use of the compound obtained in step 4 (0.35 g), the reaction was performed in the same manner as in step 5 of Example 20 to afford the title compound (0.25 g).

¹H-NMR (CDCl₃) δ: 8.53 (1H, s), 6.92 (1H, s), 6.21 (1H, s), 4.50-4.44 (2H, m), 4.30 (1H, dd, J=9.6, 4.9 Hz), 4.17 (1H, td, J=10.0, 5.0 Hz), 4.00 (1H, dd, J=10.4, 9.2 Hz), 3.18-3.12 (2H, m), 3.06-3.00 (2H, m), 2.39-2.30 (2H, m), 1.09 (9H, s), 1.05 (9H, s), 0.91 (9H, s), 0.12 (3H, s), 0.11 (3H, s).
(Step 6)

2-{5-O-[Bis(4-methoxyphenyl)(phenyl)methyl]-2-O-[tert-butyl(dimethyl)silyl]-β-D-ribofuranosyl}-2,7,8,9-tetrahydro-6-thia-2,3,5-triazabenzo[cd]azulene With use of the compound obtained in step 5 (0.41 g), the reaction was performed in the same manner as in step 5 of Example 1 to afford the title compound (0.46 g).
¹H-NMR (CDCl₃) δ: 8.52 (1H, s), 7.48-7.42 (2H, m), 7.37-7.20 (8H, m), 6.85-6.78 (4H, m), 6.36 (1H, d, J=5.1 Hz), 4.70 (1H, t, J=5.1 Hz), 4.37 (1H, dd, J=8.8, 4.1 Hz), 4.23-4.19 (1H, m), 3.79 (3H, s), 3.79 (3H, s), 3.53 (1H, dd, J=10.6, 2.7 Hz), 3.38 (1H, dd, J=10.6, 3.1 Hz), 3.16-3.09 (2H, m), 2.78 (1H, d, J=4.1 Hz), 2.76-2.70 (2H, m), 2.30-2.22 (2H, m), 0.83 (9H, s), −0.03 (3H, s), −0.14 (3H, s).
(Step 7)

2-(5-O-[Bis(4-methoxyphenyl)(phenyl)methyl]-2-O-[tert-butyl(dimethyl)silyl]-3-O-{(2-cyanoethoxy)[di(propan-2-yl)amino]phosphanyl}-β-D-ribofuranosyl)-2,7,8,9-tetrahydro-6-thia-2,3,5-triazabenzo[cd]azulene With use of the compound obtained in step 6 (0.46 g), operations were performed in the same manner as in step 4 of Example 5 to afford the title compound (0.48 g) as a mixture of diastereomers at the phosphorus atom (diastereomer ratio=6:4).
¹H-NMR (CDCl₃) δ: 8.51 (0.4H, s), 8.49 (0.6H, s), 7.50-7.43 (2H, m), 7.38-7.23 (8H, m), 6.86-6.78 (4H, m), 6.36 (0.6H, d, J=6.7 Hz), 6.32 (0.4H, d, J=5.5 Hz), 4.83-4.78 (0.6H, m), 4.76-4.71 (0.4H, m), 4.45-4.35 (1.4H, m), 4.29-4.24 (0.6H, m), 4.04-3.84 (1H, m), 3.82-3.75 (6H, m), 3.70-3.48 (4H, m), 3.32-3.25 (1H, m), 3.16-3.09 (2H, m), 2.84-2.73 (2H, m), 2.73-2.61 (1H, m), 2.36-2.20 (3H, m), 1.22-1.13 (8.4H, m), 1.03 (3.6H, d, J=7.0 Hz), 0.76 (3.6H, s), 0.75 (5.4H, s), −0.03 (1.2H, s), −0.07 (1.8H, s), −0.18 (1.2H, s), −0.20 (1.8H, s).
(Step 8)

N-{9-[(5R,7R,8R,12aR,14R,15R,15aR,16R)-15,16-Bis{[tert-butyl(dimethyl)silyl]oxy}-10-(2-cyanoethoxy)-14-(8,9-dihydro-6-thia-2,3,5-triazabenzo[cd]azulen-2 (7H)-yl)-2-oxo-2-sulfanyl-10-sulfanylideneoctahydro-2H,10H,12H-5,8-methano-2λ⁵,10λ⁵-furo[3,2-1][1,3,6,9,11,2,10]pentaoxadiphosphacyclotetradecin-7-yl]-9H-purin-6-yl}benzamide With use of the compound obtained in step 7 (0.48 g), the reaction was performed in the same manner as in step 7 of Example 1 to afford an acetonitrile solution of 2-{2-O-[tert-butyl(dimethyl)silyl]-3-O-[hydroxy (oxo)-λ⁵-phosphanyl]-β-D-ribofuranosyl}-2,7,8,9-tetrahydro-6-thia-2,3,5-triazabenzo[cd]azulene. With use of this acetonitrile solution and commercially available (Cool Pharm Ltd.) N-benzoyl-5'-O-[bis(4-methoxyphenyl)(phenyl)methyl]-3'-O-[tert-butyl(dimethyl)silyl]-2'-O-{(2-cyanoethoxy)[di(propan-2-yl)amino]phosphanyl}adenosine (0.61 g), the reaction was performed in the same manner as in steps 8 and 9 of Example 1 to afford the title compound as a mixture of diastereomers at the phosphorus atom. This mixture was purified by HPLC [10 mM aqueous solution of triethylammonium acetate/acetonitrile, acetonitrile: 40%-90% (0 min-35 min)] to afford diastereomer 1 (40 mg) and diastereomer 2 (18 mg) of the title compound.
Diastereomer 1 (Less Polar)
MS(ESI)m/z: 1132 (M+H)⁺.
Diastereomer 2 (More Polar)
MS(ESI)m/z: 1132 (M+H)⁺.
(Step 9-1)

(5R,7R,8R,12aR,14R,15R,15aR,16R)-7-(6-Amino-9H-purin-9-yl)-15,16-bis{[tert-butyl(dimethyl)silyl]oxy}-14-(8,9-dihydro-6-thia-2,3,5-triazabenzo[cd]azulen-2 (7H)-yl)-2,10-bis(sulfanyl)octahydro-2H,10H,12H-5,8-methano-2λ⁵,10λ⁵-furo[3,2-1][1,3,6,9,11,2,10]pentaoxadiphosphacyclotetradecine-2,10-dione With use of the compound obtained in step 8 (diastereomer 1) (40 mg), the reaction was performed in the same manner as in step 10 of Example 1, and the resultant was then purified by preparative HPLC [10 mM aqueous solution of triethylammonium acetate/acetonitrile, acetonitrile: 30%-60% (0 min-35 min)] to afford the title compound (35 mg).
MS(ESI)m/z: 975 (M+H)⁺.
(Step 9-2)

(5R,7R,8R,12aR,14R,15R,15aR,16R)-7-(6-Amino-9H-purin-9-yl)-15,16-bis{[tert-butyl(dimethyl)silyl]oxy}-14-(8,9-dihydro-6-thia-2,3,5-triazabenzo[cd]azulen-2 (7H)-yl)-2,10-bis(sulfanyl)octahydro-2H,10H,12H-5,8-methano-25,1025-furo[3,2-1][1,3,6,9,11,2,10]pentaoxadiphosphacyclotetradecine-2,10-dione With use of the compound obtained in step 8 (diastereomer 2) (18 mg), the reaction was performed in the same manner as in step 10 of Example 1, and the resultant was then purified by preparative HPLC [10 mM aqueous solution of triethylammonium acetate/acetonitrile, acetonitrile: 25%-50% (0 min-35 min)] to afford the title compound (15 mg).
MS(ESI)m/z: 975 (M+H)⁺.
(Step 10-1)

Disodium (5R,7R,8R,12aR,14R,15R,15aS,16R)-7-(6-amino-9H-purin-9-yl)-14-(8,9-dihydro-6-thia-2,3,5-triazabenzo[cd]azulen-2 (7H)-yl)-15,16-dihydroxy-2,10-dioxooctahydro-2H,10H,12H-5,8-methano-2λ⁵,10λ⁵-furo[3,2-1][1,3,6,9,11,2,10]pentaoxadiphosphacyclotetradecine-2,10-bis(thiolate)

(Diastereomer 1)
With use of the compound obtained in step 9-1 (35 mg), the reaction was performed in the same manner as in step 11 of Example 1, and the resultant was purified with a Sep-Pak® C18 [0.1% aqueous solution of triethylamine/acetonitrile=5:1] to afford a triethylamine salt of the title compound.
The triethylamine salt obtained was subjected to salt exchange in the same manner as in [Conversion to Sodium Salt] described in step 11 of Example 1 to afford the title compound (18 mg).
MS(ESI)m/z: 747 (M+H)⁺.
¹H-NMR (CD₃OD): 8.73 (1H, s), 8.41 (1H, s), 8.17 (1H, s), 7.48 (1H, s), 6.40 (1H, d, J=4.3 Hz), 6.34 (1H, d, J=8.6 Hz), 5.40-5.35 (1H, m), 5.23-5.17 (1H, m), 4.86-4.79 (2H, m), 4.54-4.41 (2H, m), 4.39-4.31 (2H, m), 4.12-4.01 (2H, m), 3.23-3.16 (2H, m), 3.05-2.86 (2H, m), 2.36-2.20 (2H, m).
$^{31}$P-NMR (CD$_3$OD) δ: 58.1 (s), 54.2 (s).
(Step 10-2)

Disodium (5R,7R,8R,12aR,14R,15R,15aS,16R)-7-(6-amino-9H-purin-9-yl)-14-(8,9-dihydro-6-thia-2,3,5-triazabenzo[cd]azulen-2 (7H)-yl)-15,16-dihydroxy-2,10-dioxooctahydro-2H,10H,12H-5,8-methano-2λ$^5$,10λ$^5$-furo[3,2-1][1,3,6,9,11,2,10]pentaoxadiphosphacyclotetradecine-2,10-bis(thiolate)

(Diastereomer 2)
With use of the compound obtained in step 9-2 (15 mg), the reaction was performed in the same manner as in step 11 of Example 1, and the resultant was purified with a Sep-Pak® C18 [0.1% aqueous solution of triethylamine/acetonitrile=5:1] to afford a triethylamine salt the title compound.
The triethylamine salt obtained was subjected to salt exchange in the same manner as in [Conversion to Sodium Salt] described in step 11 of Example 1 to afford the title compound (8.1 mg).
MS(ESI)m/z: 747 (M+H)$^+$.
$^1$H-NMR (CD$_3$OD) δ: 8.81 (1H, s), 8.41 (1H, s), 8.17 (1H, s), 7.49 (1H, s), 6.43 (1H, d, J=6.7 Hz), 6.34 (1H, d, J=8.2 Hz), 5.55-5.41 (2H, m), 4.87-4.82 (1H, m), 4.57-4.27 (5H, m), 4.07-3.99 (1H, m), 3.94-3.86 (1H, m), 3.24-3.16 (2H, m), 3.12-3.03 (2H, m), 2.39-2.25 (2H, m).
$^{31}$P-NMR (CD$_3$OD) δ: 63.0 (s), 60.5 (s).

Example 34: Synthesis of CDN24

1-[(5R,7R,8R,12aR,14R,15R,15aS,16R)-15,16-Dihydroxy-2,10-dioxo-2,10-bis(sulfanyl)-14-(6,7,8,9-tetrahydro-2H-2,3,5,6-tetraazabenzo[cd]azulen-2-yl)octahydro-2H,10H,12H-5,8-methano-2λ$^5$,10λ$^5$-furo[3,2-1][1,3,6,9,11,2,10]pentaoxadiphosphacyclotetradecin-7-yl]pyrimidin-2,4 (1H,3H)-dione

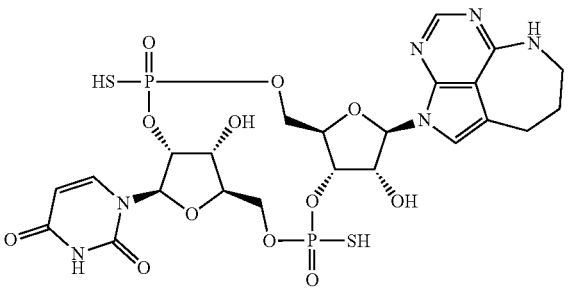

24a (Diastereomer 1)
24b (Diastereomer 2)

[Synthesis Scheme]

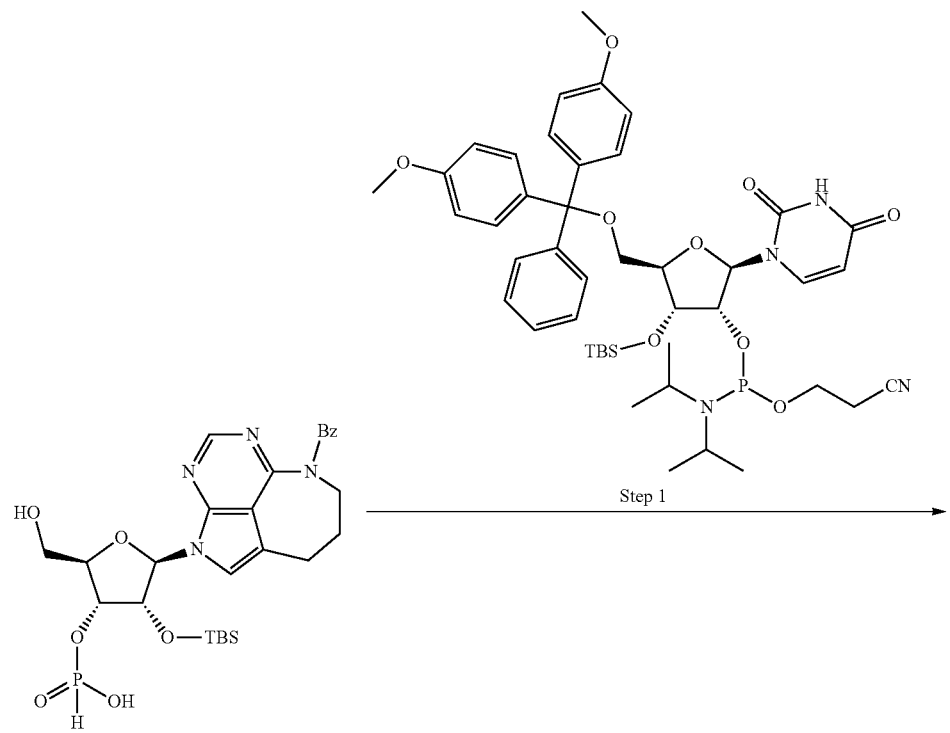

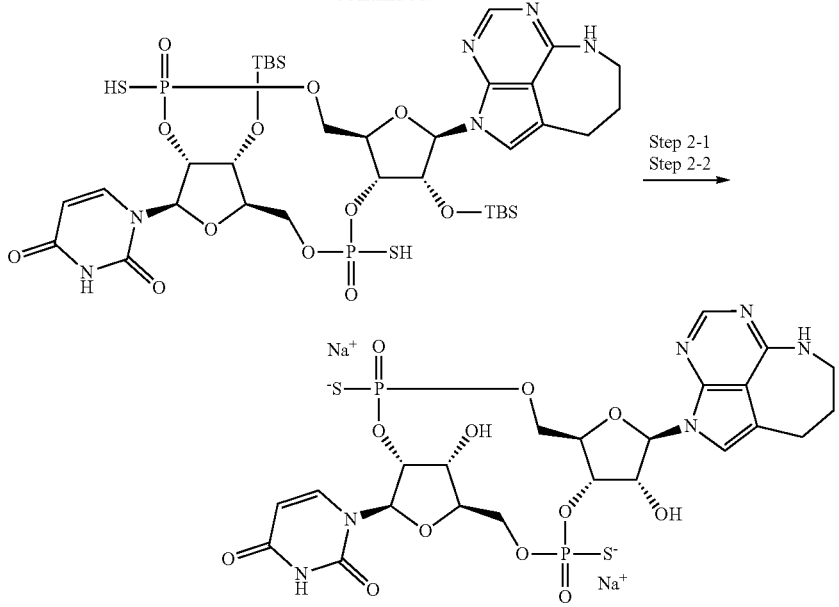

(Step 1)

1-[(5R,7R,8R,12aR,14R,15R,15aR,16R)-15,16-Bis{[tert-butyl(dimethyl)silyl]oxy}-2,10-dioxo-2,10-bis(sulfanyl)-14-(6,7,8,9-tetrahydro-2H-2,3,5,6-tetraazabenzo[cd]azulen-2-yl)octahydro-2H,10H,12H-5,8-methano-2$\lambda^5$,10$\lambda^5$-furo[3,2-1][1,3,6,9,11,2,10]pentaoxadiphosphacyclotetradecin-7-yl]pyrimidin-2,4 (1H,3H)-dione The same reaction as in step 7 of Example 1 was performed in the following scale (raw material: 1.01 g). With use of an acetonitrile solution of the compound obtained and commercially available (Angene International Limited) 5'-O-[bis(4-methoxyphenyl)(phenyl)methyl]-3'-O-[tert-butyl(dimethyl)silyl]-2'-O-{(2-cyanoethoxy)[di(propan-2-yl)amino]phosphanyl}uridine (1.03 g), the reaction was performed in the same manner as in steps 8, 9, and 10 of Example 1 to afford the title compound as a mixture of diastereomers at the phosphorus atom. This mixture was purified by HPLC [10 mM aqueous solution of triethylammonium acetate/acetonitrile, acetonitrile: 25%-60% (0 min-35 min)] to afford diastereomer 1 (50 mg) and diastereomer 2 (23 mg) of the title compound.

Diastereomer 1 (Less Polar)
  MS(ESI)m/z: 935 (M+H)$^+$.
Diastereomer 2 (More Polar)
  MS(ESI)m/z: 935 (M+H)$^+$.

(Step 2-1)

Disodium (5R,7R,8R,12aR,14R,15R,15aS,16R)-7-(2,4-dioxo-3,4-dihydropyrimidin-1 (2H)-yl)-15,16-dihydroxy-2,10-dioxo-14-(6,7,8,9-tetrahydro-2H-2,3,5,6-tetraazabenzo[cd]azulen-2-yl)octahydro-2H,10H,12H-5,8-methano-2$\lambda^5$,10$\lambda^5$-furo[3,2-1][1,3,6,9,11,2,10]pentaoxadiphosphacyclotetradecine-2,10-bis (thiolate)

(Diastereomer 1)

With use of the compound obtained in step 1 (diastereomer 1) (50 mg), the reaction was performed in the same manner as in step 11 of Example 1, and the resultant was then purified with a Sep-Pak® C18 [0.1% aqueous solution of triethylamine/acetonitrile=5:1] to afford a triethylamine salt of the title compound.

The triethylamine salt obtained was subjected to salt exchange in the same manner as in [Conversion to Sodium Salt] described in step 11 of Example 1 to afford the title compound (30 mg).

MS(ESI)m/z: 707 (M+H)$^+$.
$^1$H-NMR (CD$_3$OD) δ: 8.09 (1H, d, J=8.2 Hz), 8.03 (1H, s), 7.16 (1H, s), 6.32 (1H, d, J=8.6 Hz), 6.28 (1H, d, J=4.3 Hz), 5.82 (1H, d, J=8.2 Hz), 5.08-5.01 (1H, m), 4.93-4.84 (1H, m), 4.73 (1H, t, J=4.5 Hz), 4.68 (1H, d, J=3.9 Hz), 4.48-4.38 (2H, m), 4.33-4.24 (1H, m), 4.23 (1H, d, J=2.3 Hz), 4.09-3.99 (2H, m), 3.56-3.46 (2H, m), 2.96-2.83 (2H, m), 2.07-1.95 (2H, m).
$^{31}$P-NMR (CD$_3$OD) δ: 58.3 (s), 54.6 (s).

(Step 2-2)

Disodium (5R,7R,8R,12aR,14R,15R,15aS,16R)-7-(2,4-dioxo-3,4-dihydropyrimidin-1 (2H)-yl)-15,16-dihydroxy-2,10-dioxo-14-(6,7,8,9-tetrahydro-2H-2,3,5,6-tetraazabenzo[cd]azulen-2-yl)octahydro-2H,10H,12H-5,8-methano-2$\lambda^5$,10$\lambda^5$-furo[3,2-1][1,3,6,9,11,2,10]pentaoxadiphosphacyclotetradecine-2,10-bis (thiolate)

(Diastereomer 2)

With use of the compound obtained in step 1 (diastereomer 2) (23 mg), the reaction was performed in the same manner as in step 11 of Example 1, and the resultant was then purified with a Sep-Pak® C18 [0.1% aqueous solution of triethylamine/acetonitrile=5:1] to afford a triethylamine salt of the title compound.

The triethylamine salt obtained was subjected to salt exchange in the same manner as in [Conversion to Sodium Salt] described in step 11 of Example 1 to afford the title compound (11 mg).

MS(ESI)m/z: 707 (M+H)$^+$.
$^1$H-NMR (CD$_3$OD) δ: 8.08 (1H, d, J=7.8 Hz), 8.01 (1H, s), 7.16 (1H, s), 6.35 (1H, d, J=8.6 Hz), 6.31 (1H, d, J=6.7

Hz), 5.85 (1H, d, J=7.8 Hz), 5.38-5.33 (1H, m), 5.04-4.96 (1H, m), 4.75 (1H, dd, J=6.5, 4.5 Hz), 4.50-4.34 (3H, m), 4.33-4.26 (1H, m), 4.22-4.17 (1H, m), 4.04-3.97 (1H, m), 3.91-3.84 (1H, m), 3.53-3.46 (2H, m), 2.97-2.87 (2H, m), 2.05-1.95 (2H, m).

$^{31}$P-NMR (CD$_3$OD) δ: 63.2 (s), 60.2 (s).

Example 35: Synthesis of CDN25

(5R,7R,8R,12aR,14R,15R,15aS,16R)-15,16-Dihydroxy-7-(6-oxo-1,6-dihydro-9H-purin-9-yl)-2,10-bis(sulfanyl)-14-(6,7,8,9-tetrahydro-2H-2,3,5,6-tetraazabenzo[cd]azulen-2-yl)octahydro-2H,10H,12H-5,8-methano-2λ$^5$,10λ$^5$-furo[3,2-1][1,3,6,9,11,2,10]pentaoxadiphosphacyclotetradecine-2,10-dione

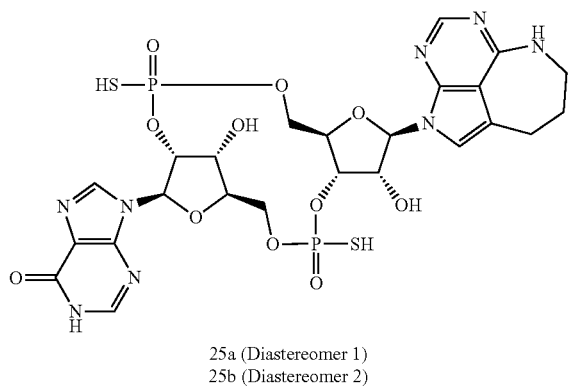

25a (Diastereomer 1)
25b (Diastereomer 2)

[Synthesis Scheme]

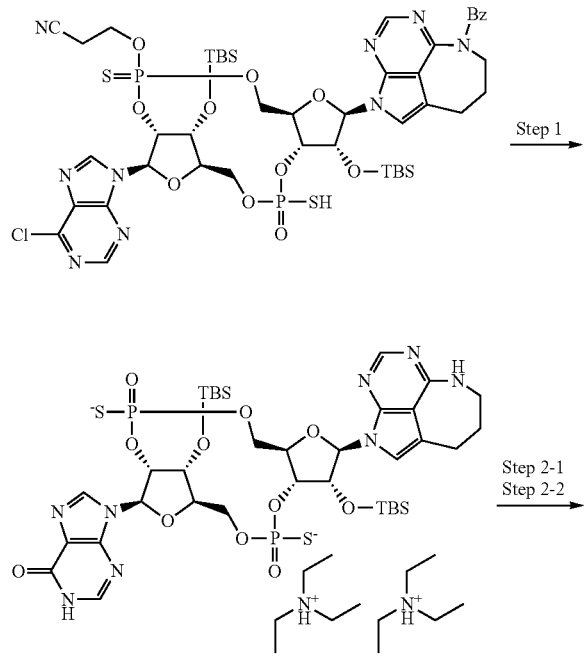

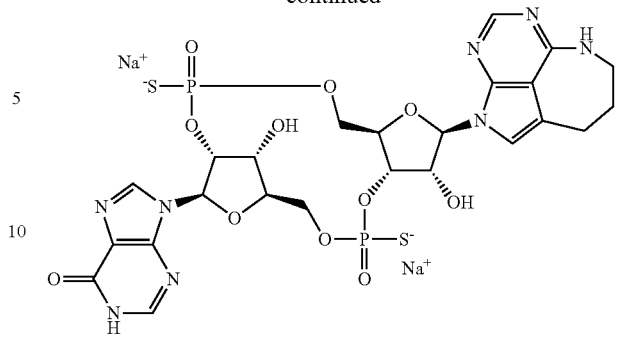

(Step 1)

Bis(N,N-diethylethaneaminium) (5R,7R,8R,12aR,14R,15R,15aR,16R)-15,16-bis{[tert-butyl(dimethyl)silyl]oxy}-2,10-dioxo-7-(6-oxo-1,6-dihydro-9H-purin-9-yl)-14-(6,7,8,9-tetrahydro-2H-2,3,5,6-tetraazabenzo[cd]azulen-2-yl)octahydro-2H,10H,12H-5,8-methano-2λ$^5$,10λ$^5$-furo[3,2-1][1,3,6,9,11,2,10]pentaoxadiphosphacyclotetradecine-2,10-bis(thiolate)

To a solution of the compound (313 mg) obtained in step 4 of Example 13 in tetrahydrofuran (5.0 mL), N-[(E)-(pyridine-2-yl)methylidene]hydroxylamine (337 mg) and N,N,N',N'-tetramethylguanidine (0.346 mL) were added, and the reaction mixture was stirred at room temperature for 1 day. Methanol (5.0 mL) and 28% ammonia water (5.0 mL) were added to the reaction mixture, which was stirred at 50° C. for 5 hours. After the reaction mixture was concentrated under reduced pressure, the residue was purified by C18 silica gel column chromatography [10 mM aqueous solution of triethylammonium acetate/acetonitrile] to afford diastereomer 1 (106 mg: with impurities) and diastereomer 2 (105 mg: with impurities) of the title compound.

Diastereomer 1 (Less Polar)
MS(ESI)m/z: 959 (M+H)$^+$.
Diastereomer 2 (More Polar)
MS(ESI)m/z: 959 (M+H)$^+$.

(Step 2-1)

Disodium (5R,7R,8R,12aR,14R,15R,15aS,16R)-15,16-dihydroxy-2,10-dioxo-7-(6-oxo-1,6-dihydro-9H-purin-9-yl)-14-(6,7,8,9-tetrahydro-2H-2,3,5,6-tetraazabenzo[cd]azulen-2-yl)octahydro-2H,10H,12H-5,8-methano-2λ$^5$,10λ$^5$-furo[3,2-1][1,3,6,9,11,2,10]pentaoxadiphosphacyclotetradecine-2,10-bis(thiolate)

(Diastereomer 1)
With use of the compound (diastereomer 1) (106 mg: with impurities) obtained in the above step 1, the reaction was performed in the same manner as in step 11 of Example 1, and purification was carried out under the following [Purification Conditions] to afford the title compound as a triethylamine salt.

[Purification Conditions] C18 silica gel column chromatography [10 mM aqueous solution of triethylammonium acetate/acetonitrile] and preparative HPLC [10 mM aqueous solution of triethylammonium acetate/acetonitrile-methanol solution (1:1), acetonitrile-methanol solution (1:1): 7%-50% (0 min-40 min)].

The triethylamine salt obtained was subjected to salt exchange in the same manner as in [Conversion to Sodium Salt] described in step 11 of Example 1 to afford the title compound (43.4 mg).

MS(ESI)m/z: 731 (M+H)$^+$.

$^1$H-NMR (CD$_3$OD) δ: 8.66 (1H, s), 8.02 (2H, s), 7.09 (1H, s), 6.30 (1H, d, J=6.8 Hz), 6.28 (1H, d, J=4.8 Hz), 5.45-5.38 (1H, m), 5.20-5.13 (1H, m), 4.82 (1H, d, J=4.2 Hz), 4.77 (1H, t, J=4.5 Hz), 4.52-4.41 (2H, m), 4.36-4.27 (2H, m), 4.08-3.97 (2H, m), 3.53-3.46 (2H, m), 2.88-2.80 (2H, m), 2.04-1.95 (2H, m).

$^{31}$P-NMR (CD$_3$OD) δ: 57.7 (s), 54.6 (s).

(Step 2-2)

Disodium (5R,7R,8R,12aR,14R,15R,15aS,16R)-15,16-dihydroxy-2,10-dioxo-7-(6-oxo-1,6-dihydro-9H-purin-9-yl)-14-(6,7,8,9-tetrahydro-2H-2,3,5,6-tetraazabenzo[cd]azulen-2-yl)octahydro-2H,10H,12H-5,8-methano-2λ$^5$,10λ$^5$-furo[3,2-1][1,3,6,9,11,2,10]pentaoxadiphosphacyclotetradecine-2,10-bis(thiolate)

(Diastereomer 2)

With use of the compound (diastereomer 2) (105 mg: with impurities) obtained in the above step 1, the reaction was performed in the same manner as in step 11 of Example 1, and purification was carried out under the following [Purification Conditions] to afford the title compound as a triethylamine salt.

[Purification Conditions] C18 silica gel column chromatography [10 mM aqueous solution of triethylammonium acetate/acetonitrile] and preparative HPLC [10 mM aqueous solution of triethylammonium acetate/acetonitrile-methanol solution (1:1), acetonitrile-methanol solution (1:1): 7%-45% (0 min-40 min)].

The triethylamine salt obtained was subjected to salt exchange in the same manner as in [Conversion to Sodium Salt] described in step 11 of Example 1 to afford the title compound (21.5 mg).

MS(ESI)m/z: 731 (M+H)$^+$.

$^1$H-NMR (CD$_3$OD) δ: 8.72 (1H, s), 8.03 (1H, s), 8.02 (1H, s), 7.11 (1H, s), 6.32 (1H, d, J=6.0 Hz), 6.30 (1H, d, J=8.0 Hz), 5.49-5.40 (2H, m), 4.77 (1H, dd, J=6.7, 4.2 Hz), 4.49 (1H, d, J=4.5 Hz), 4.47-4.29 (4H, m), 4.07-4.01 (1H, m), 3.93-3.86 (1H, m), 3.52-3.47 (2H, m), 2.90 (2H, t, J=5.4 Hz), 2.05-1.97 (2H, m).

$^{31}$P-NMR (CD$_3$OD) δ: 62.9 (s), 60.0 (s)

Example 36: Synthesis of CDN26

(5R,7R,8R,12aR,14R,15R,15aS,16R)-15,16-Dihydroxy-7-[1-(3-hydroxypropyl)-6-oxo-1,6-dihydro-9H-purin-9-yl]-2,10-bis(sulfanyl)-14-(6,7,8,9-tetrahydro-2H-2,3,5,6-tetraazabenzo[cd]azulen-2-yl)octahydro-2H,10H,12H-5,8-methano-2λ$^5$,10λ$^5$-furo[3,2-1][1,3,6,9,11,2,10]pentaoxadiphosphacyclotetradecine-2,10-dione

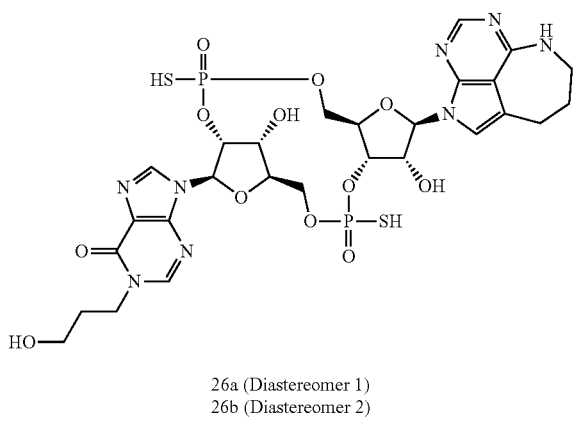

26
26a (Diastereomer 1)
26b (Diastereomer 2)

[Synthesis Scheme]

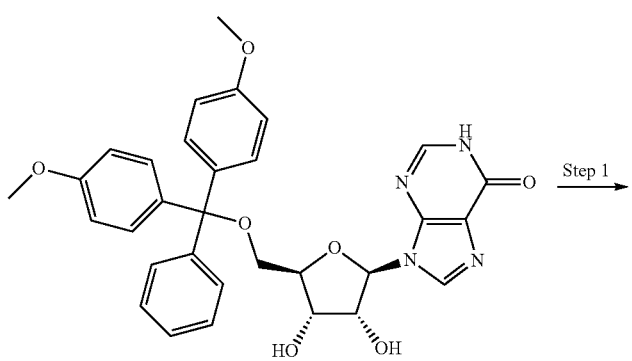

Step 1

-continued
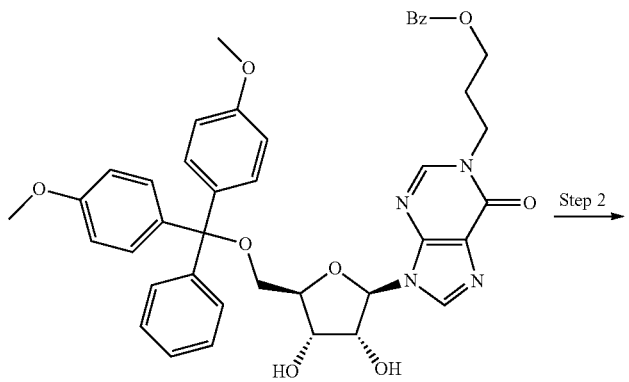
Step 2
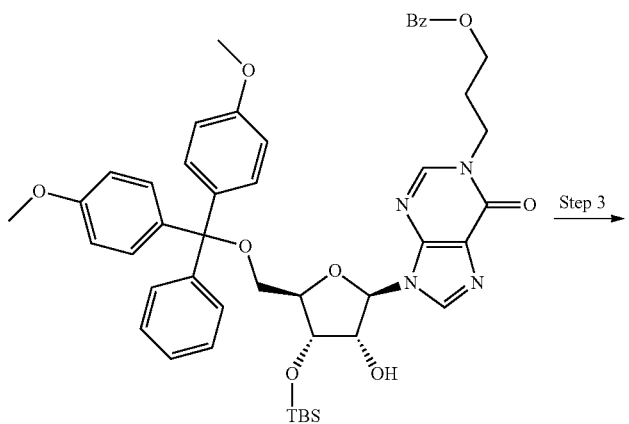
Step 3
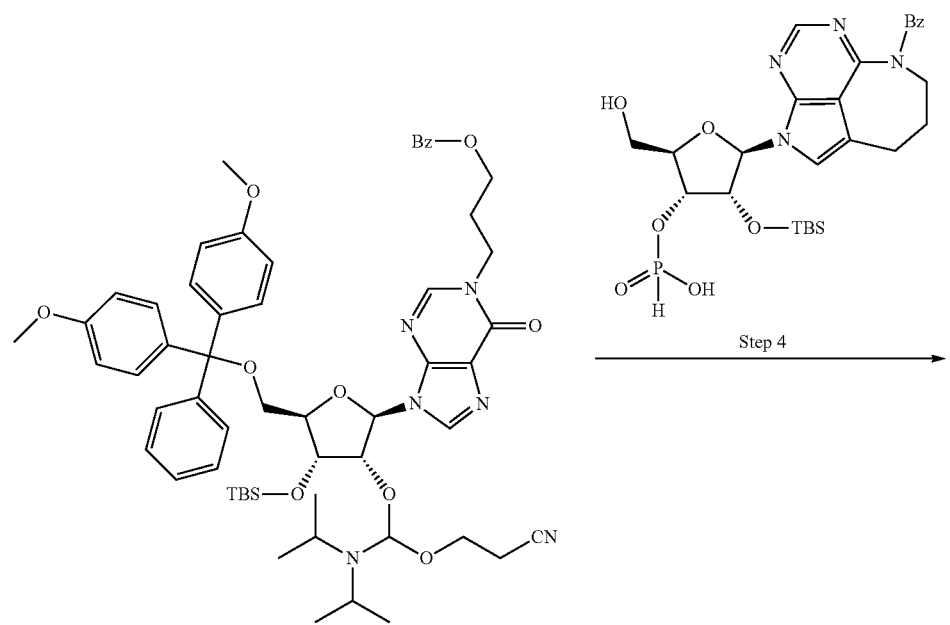
Step 4

-continued
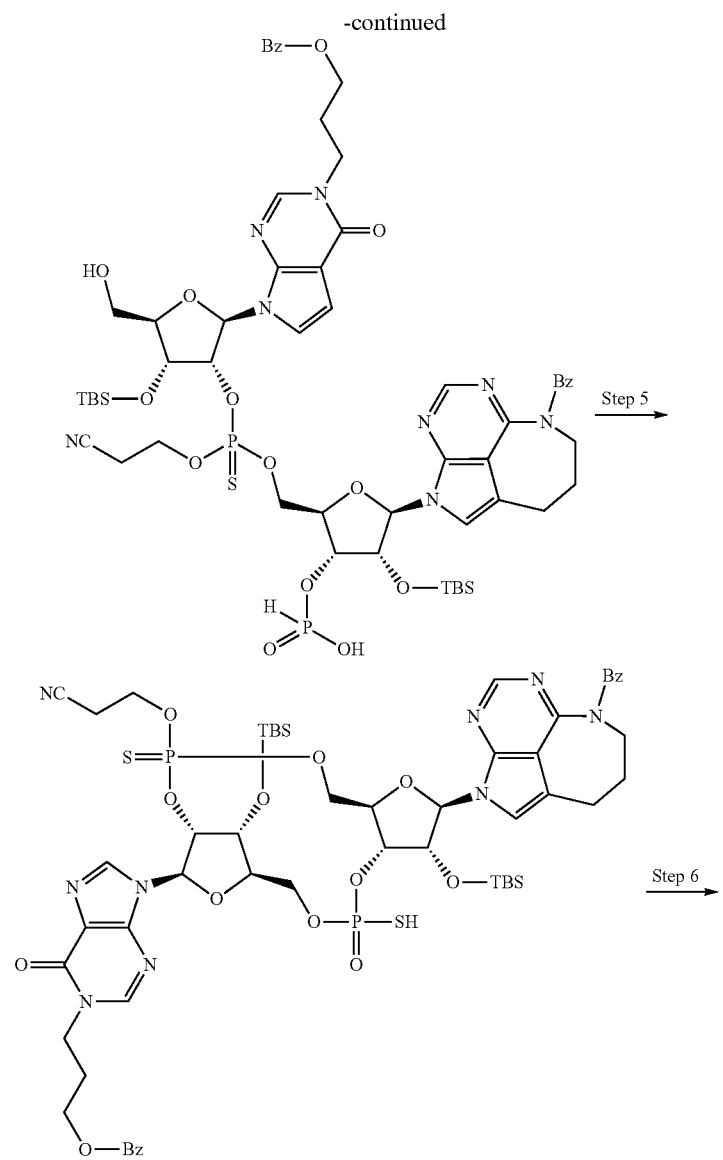
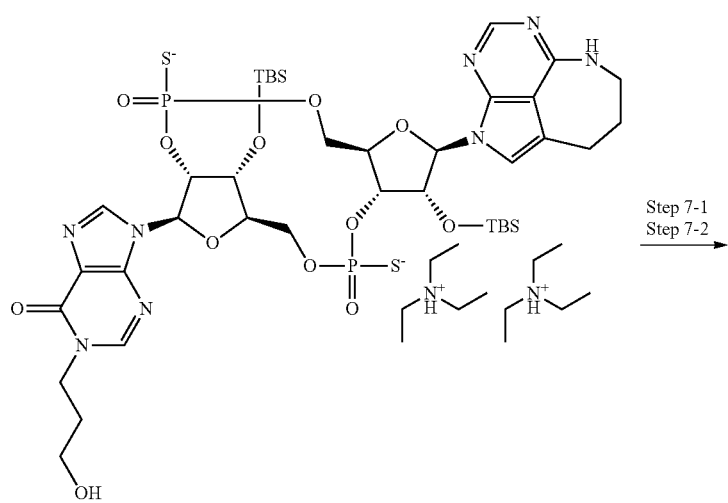

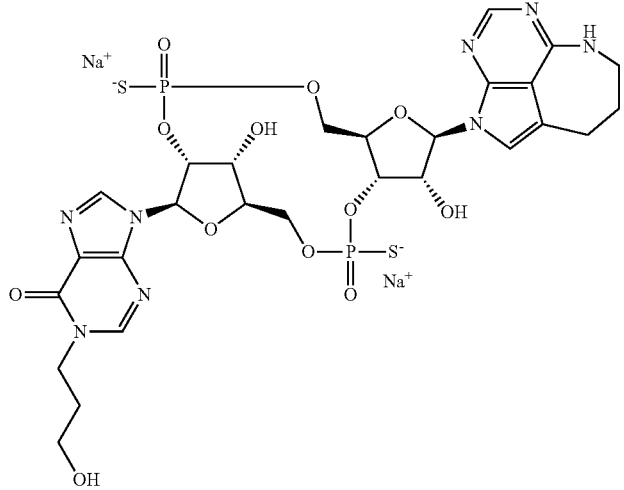

(Step 1)

1-[3-(Benzoyloxy) propyl]-5'-O-[bis(4-methoxyphenyl)(phenyl)methyl]inosine

To a solution of 3-bromopropan-1-ol (1.14 mL) in tetrahydrofuran (25 mL), triethylamine (1.83 mL) and benzoyl chloride (1.43 mL) were added, and the reaction mixture was stirred at room temperature for 6 hours. The reaction mixture was filtered and washed with tetrahydrofuran, and the filtrate was concentrated under reduced pressure. To a solution of the residue in dehydrated N,N-dimethylacetamide (25 mL), commercially available (Aamdis Chemical) 5'-O-[bis(4-methoxyphenyl)(phenyl)methyl]inosine (5.0 g) and 1,8-diazabicyclo [5.4.0]-7-undecene (2.75 mL) were added, and the reaction mixture was stirred at room temperature for 3 days. Water was added to the reaction mixture, which was subjected to extraction with ethyl acetate. The organic layer was washed with brine, and then dried over anhydrous sodium sulfate. The drying agent was removed through filtration, and the filtrate was concentrated under reduced pressure. The residue was purified by silica gel column chromatography [hexane/ethyl acetate/methanol] to afford the title compound (4.41 g).

MS(ESI)m/z: 733 (M+H)$^+$.

$^1$H-NMR (CDCl$_3$) δ: 8.00-7.98 (1H, m), 7.98-7.96 (1H, m), 7.97 (1H, s), 7.96 (1H, s), 7.58-7.52 (1H, m), 7.46-7.39 (2H, m), 7.35-7.30 (2H, m), 7.26-7.16 (7H, m), 6.81-6.75 (4H, m), 5.87 (1H, d, J=6.0 Hz), 4.85 (1H, d, J=3.6 Hz), 4.67-4.62 (1H, m), 4.43-4.34 (3H, m), 4.30-4.16 (2H, m), 3.78-3.75 (1H, m), 3.77 (6H, s), 3.42 (1H, dd, J=10.3, 3.6 Hz), 3.33 (1H, dd, J=10.3, 3.6 Hz), 3.02 (1H, d, J=2.4 Hz), 2.32 (2H, dd, J=11.8, 5.7 Hz).

(Step 2)

1-[3-(Benzoyloxy) propyl]-5'-O-[bis(4-methoxyphenyl)(phenyl)methyl]-3'-O-[tert-butyl(dimethyl)silyl] inosine With use of the compound (4.41 g) obtained in the above step 1, the reaction was performed in the same manner as in step 3 of Example 5 to afford the title compound (1.60 g) and 1-[3-(benzoyloxy) propyl]-5'-O-[bis(4-methoxyphenyl)(phenyl)methyl]-2'-O-[tert-butyl(dimethyl)silyl]inosine (1.70 g) as a regioisomer of the title compound.

MS(ESI)m/z: 847 (M+H)$^+$.

$^1$H-NMR (CDCl$_3$) δ: 8.01 (1H, d, J=1.2 Hz), 8.00 (1H, s), 7.99 (1H, d, J=1.2 Hz), 7.93 (1H, s), 7.60-7.52 (1H, m), 7.46-7.38 (4H, m), 7.33-7.16 (7H, m), 6.83-6.77 (4H, m), 5.90 (1H, d, J=4.8 Hz), 4.58-4.52 (1H, m), 4.50-4.46 (1H, m), 4.39 (2H, t, J=6.0 Hz), 4.28-4.12 (3H, m), 3.78 (3H, s), 3.77 (3H, s), 3.46 (1H, dd, J=10.6, 3.9 Hz), 3.26 (1H, dd, J=10.6, 3.9 Hz), 2.99 (1H, d, J=6.7 Hz), 2.30 (2H, dd, J=13.3, 6.0 Hz), 0.88 (9H, s), 0.07 (3H, s), 0.00 (3H, s).

Regioisomer (2'-O-TBS Form)

MS(ESI)m/z: 847 (M+H)$^+$.

$^1$H-NMR (CDCl$_3$) δ: 8.01 (1H, d, J=1.8 Hz), 7.99 (1H, d, J=1.8 Hz), 7.98 (1H, s), 7.87 (1H, s), 7.59-7.54 (1H, m), 7.47-7.40 (4H, m), 7.36-7.17 (7H, m), 6.84-6.78 (4H, m), 5.94 (1H, d, J=5.4 Hz), 4.84 (1H, t, J=5.4 Hz), 4.41-4.35 (2H, m), 4.33-4.28 (1H, m), 4.28-4.19 (3H, m), 3.78 (3H, s), 3.78 (3H, s), 3.48 (1H, dd, J=10.9, 3.0 Hz), 3.37 (1H, dd, J=10.9, 3.0 Hz), 2.68 (1H, d, J=3.6 Hz), 2.34-2.26 (2H, m), 0.84 (9H, s), 0.01 (3H, s), −0.13 (3H, s).

(Step 3)

1-[3-(Benzoyloxy) propyl]-5'-O-[bis(4-methoxyphenyl)(phenyl)methyl]-3'-O-[tert-butyl(dimethyl)silyl]-2'-O-{(2-cyanoethoxy)[di(propan-2-yl)amino]phosphanyl}inosine With use of the compound (1.60 g) obtained in the above step 2, the reaction was performed in the same manner as in step 4 of Example 5 to afford the title compound (1.91 g) as a mixture of diastereomers at the phosphorus atom (diastereomer ratio=67:33).

MS(ESI)m/z: 1047 (M+H)$^+$.

$^1$H-NMR (CDCl$_3$) δ: 8.04-8.00 (0.33H, m), 8.03 (1H, s), 8.02 (1H, s), 7.91 (0.67H, d, J=14.5 Hz), 7.60-7.53 (1H, m), 7.49-7.40 (4H, m), 7.35-7.17 (7H, m), 6.84-6.78 (4H, m), 6.14 (0.67H, d, J=5.1 Hz), 6.06 (0.33H, d, J=6.0 Hz), 4.86-4.78 (0.33H, m), 4.68-4.61 (0.67H, m), 4.44-4.35 (2H, m), 4.29-4.09 (4H, m), 3.78 (6H, s), 3.65-3.42 (6.33H, m), 3.34-3.24 (0.67H, m), 2.76 (1.34H, t, J=6.6 Hz), 2.50 (0.66H, t, J=6.6 Hz), 2.38 (1.34H, t, J=6.6 Hz), 2.30 (0.66H, t, J=6.6 Hz), 1.30-1.24 (6H, m), 1.15-1.07 (4.02H, m), 0.95 (1.98H, d, J=6.6 Hz), 0.84 (9H, s), 0.09 (0.99H, s), 0.05 (2.01H, s), 0.00 (3H, s).

(Step 4)

The same reaction as in step 7 of Example 1 was carried out in the following scale (raw material: 981 mg). With use of an acetonitrile solution of the compound obtained and the compound (1.03 g) obtained in the above step 3, the reaction was performed in the same manner as in step 8 of Example 1, and the resulting crude product was directly used for the subsequent reaction.

(Step 5)

3-{9-[(5R,7R,8R,12aR,14R,15R,15aR,16R)-14-(6-Benzoyl-6,7,8,9-tetrahydro-2H-2,3,5,6-tetraazabenzo[cd]azulen-2-yl)-15,16-bis{[tert-butyl(dimethyl)silyl]oxy}-10-(2-cyanoethoxy)-2-oxo-2-sulfanyl-10-sulfanylideneoctahydro-2H,10H,12H-5,8-methano-2$\lambda^5$,10$\lambda^5$-furo[3,2-1][1,3,6,9,11,2,10]pentaoxadiphosphacyclotetradecin-7-yl]-6-oxo-6,9-dihydro-1H-purin-1-yl}propyl benzoate

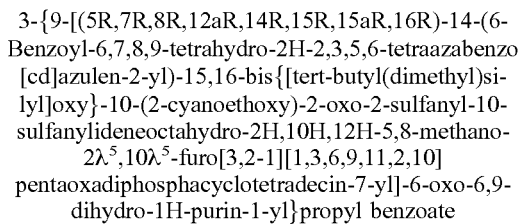

With use of the crude product obtained in the above step 4, the reaction was performed in the same manner as in step 9 of Example 1 to afford the title compound (774 mg) as a mixture of diastereomers at the phosphorus atom.

MS(ESI)m/z: 1278 (M+H)$^+$.

(Step 6)

Bis(N,N-diethylethaneaminium) (5R,7R,8R,12aR,14R,15R,15aR,16R)-15,16-bis{[tert-butyl(dimethyl)silyl]oxy}-7-[1-(3-hydroxypropyl)-6-oxo-1,6-dihydro-9H-purin-9-yl]-2,10-dioxo-14-(6,7,8,9-tetrahydro-2H-2,3,5,6-tetraazabenzo[cd]azulen-2-yl)octahydro-2H,10H,12H-5,8-methano-2$\lambda^5$,10$\lambda^5$-furo[3,2-1][1,3,6,9,11,2,10]pentaoxadiphosphacyclotetradecine-2,10-bis(thiolate)

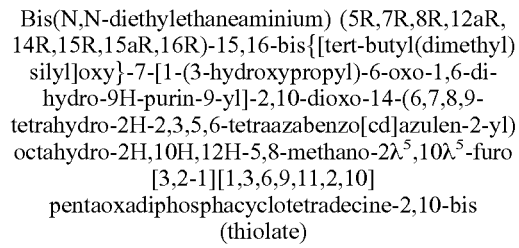

With use of the compound (774 mg) obtained in the above step 5, the reaction was performed in the same manner as in step 10 of Example 1, and the resultant was purified by C18 silica gel column chromatography [0.2% aqueous solution of triethylamine/acetonitrile] to afford diastereomer 1 (101 mg: with impurities) and diastereomer 2 (90.8 mg: with impurities) of the title compound.

Diastereomer 1 (Less Polar)
MS(ESI)m/z: 1017 (M+H)$^+$.
Diastereomer 2 (More Polar)
MS(ESI)m/z: 1017 (M+H)$^+$.

(Step 7-1)

Disodium (5R,7R,8R,12aR,14R,15R,15aS,16R)-15,16-dihydroxy-7-[1-(3-hydroxypropyl)-6-oxo-1,6-dihydro-9H-purin-9-yl]-2,10-dioxo-14-(6,7,8,9-tetrahydro-2H-2,3,5,6-tetraazabenzo[cd]azulen-2-yl)octahydro-2H,10H,12H-5,8-methano-2$\lambda^5$,10$\lambda^5$-furo[3,2-1][1,3,6,9,11,2,10]pentaoxadiphosphacyclotetradecine-2,10-bis(thiolate)

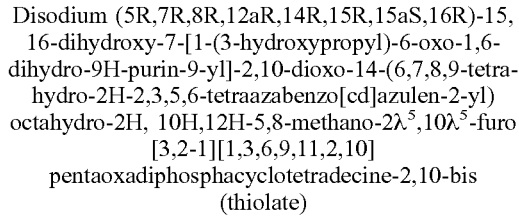

(Diastereomer 1)

With use of the compound (diastereomer 1) (101 mg: with impurities) obtained in the above step 6, the reaction was performed in the same manner as in step 11 of Example 1, and purification was carried out under the following [Purification Conditions] to afford the title compound as a triethylamine salt.

[Purification Conditions] C18 silica gel column chromatography [10 mM aqueous solution of triethylammonium acetate/acetonitrile].

The triethylamine salt obtained was subjected to salt exchange in the same manner as in [Conversion to Sodium Salt] described in step 11 of Example 1 to afford the title compound (48.8 mg).

MS(ESI)m/z: 789 (M+H)$^+$.

$^1$H-NMR (CD$_3$OD) δ: 8.65 (1H, s), 8.28 (1H, s), 8.03 (1H, s), 7.09 (1H, s), 6.28 (1H, s), 6.27 (1H, d, J=4.8 Hz), 5.46-5.38 (1H, m), 5.21-5.13 (1H, m), 4.83-4.80 (1H, m), 4.79-4.75 (1H, m), 4.52-4.39 (2H, m), 4.36-4.28 (2H, m), 4.26-4.17 (1H, m), 4.17-4.08 (1H, m), 4.08-3.97 (2H, m), 3.59 (2H, t, J=5.7 Hz), 3.49 (2H, t, J=4.8 Hz), 2.91-2.74 (2H, m), 2.02-1.92 (4H, m).

$^{31}$P-NMR (CD$_3$OD) δ: 57.6 (s), 54.6 (s).

(Step 7-2)

Disodium (5R,7R,8R,12aR,14R,15R,15aS,16R)-15,16-dihydroxy-7-[1-(3-hydroxypropyl)-6-oxo-1,6-dihydro-9H-purin-9-yl]-2,10-dioxo-14-(6,7,8,9-tetrahydro-2H-2,3,5,6-tetraazabenzo[cd]azulen-2-yl)octahydro-2H,10H,12H-5,8-methano-2$\lambda^5$,10$\lambda^5$-furo[3,2-1][1,3,6,9,11,2,10]pentaoxadiphosphacyclotetradecine-2,10-bis(thiolate)

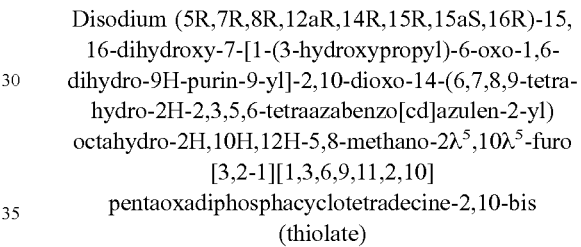

(Diastereomer 2)

With use of the compound (diastereomer 2) (90.8 mg: with impurities) obtained in the above step 6, the reaction was performed in the same manner as in step 11 of Example 1, and purification was carried out under the following [Purification Conditions] to afford the title compound as a triethylamine salt.

[Purification Conditions] C18 silica gel column chromatography [10 mM aqueous solution of triethylammonium acetate/acetonitrile] and preparative HPLC [10 mM aqueous solution of triethylammonium acetate/acetonitrile, acetonitrile: 3%-20% (0 min-40 min)].

The triethylamine salt obtained was subjected to salt exchange in the same manner as in [Conversion to Sodium Salt] described in step 11 of Example 1 to afford the title compound (22.3 mg).

MS(ESI)m/z: 789 (M+H)$^+$.

$^1$H-NMR (CD$_3$OD) δ: 8.71 (1H, s), 8.29 (1H, s), 8.02 (1H, s), 7.11 (1H, s), 6.32 (1H, d, J=6.7 Hz), 6.28 (1H, d, J=8.5 Hz), 5.48-5.38 (2H, m), 4.80-4.74 (1H, m), 4.51-4.47 (1H, m), 4.47-4.28 (4H, m), 4.27-4.14 (2H, m), 4.07-4.01 (1H, m), 3.92-3.86 (1H, m), 3.60 (2H, t, J=6.0 Hz), 3.53-3.47 (2H, m), 2.93-2.87 (2H, m), 2.06-1.94 (4H, m).

$^{31}$P-NMR (CD$_3$OD) δ: 62.8 (s), 59.9 (s).

Example 37: Synthesis of CDN27
(5R,7R,8R,12aR,14R,15R,15aS,16R)-7-[2-Amino-1-(2-hydroxyethyl)-6-oxo-1,6-dihydro-9H-purin-9-yl]-15,16-dihydroxy-2,10-bis(sulfanyl)-14-(6,7,8,9-tetrahydro-2H-2,3,5,6-tetraazabenzo[cd]azulen-2-yl)octahydro-2H,10H,12H-5,8-methano-2$\lambda^5$,10$\lambda^5$-furo[3,2-l][1,3,6,9,11,2,10]pentaoxadiphosphacyclotetradecine-2,10-dione
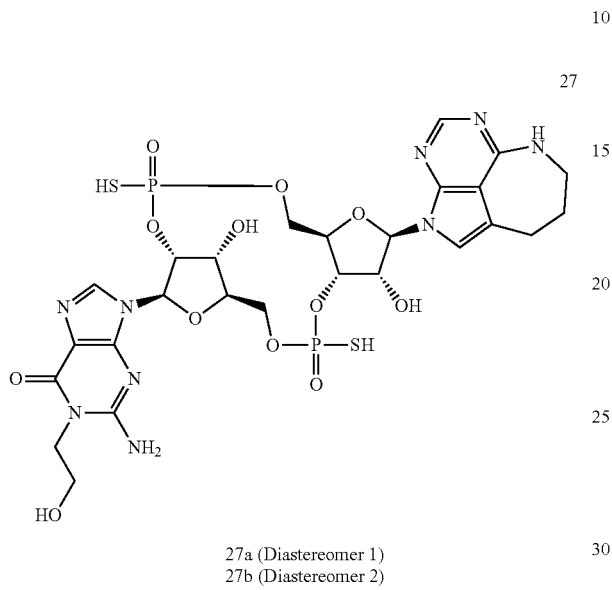
27a (Diastereomer 1)
27b (Diastereomer 2)
[Synthesis Scheme]
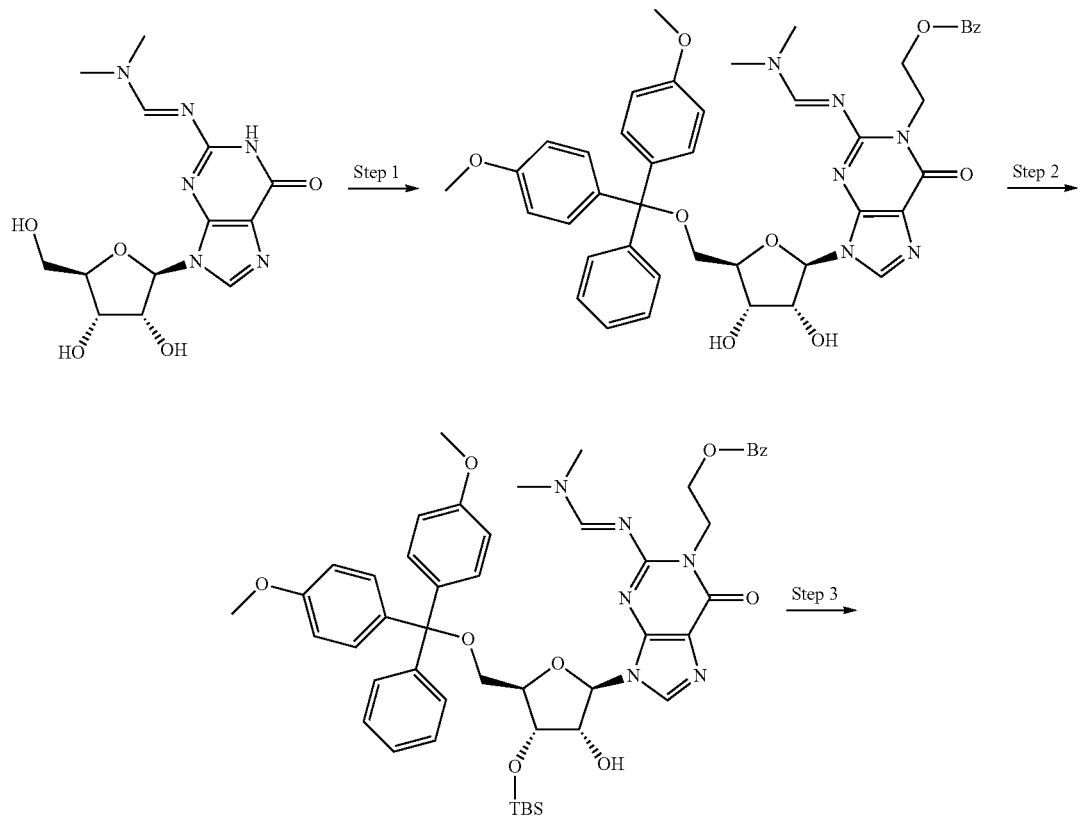

-continued
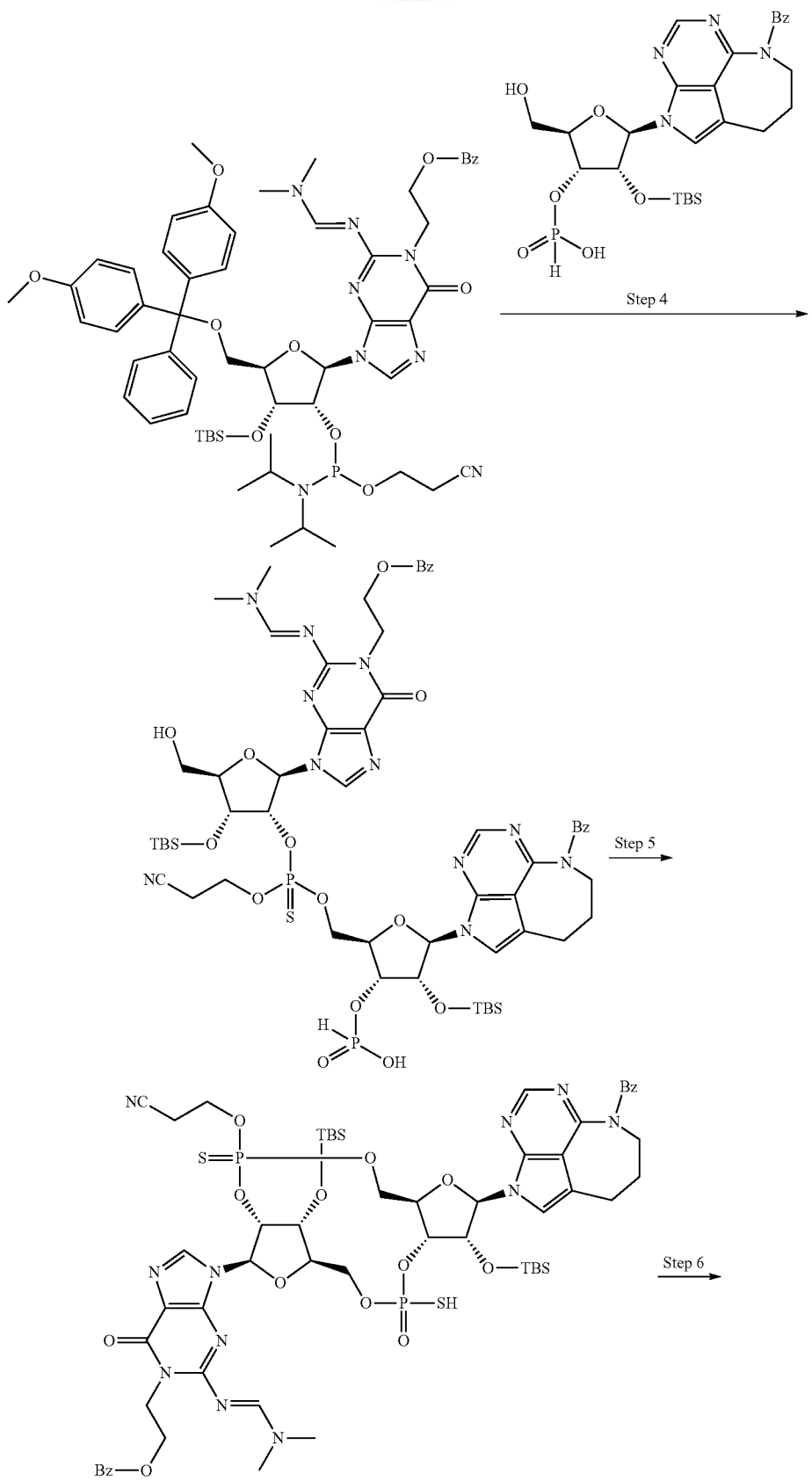

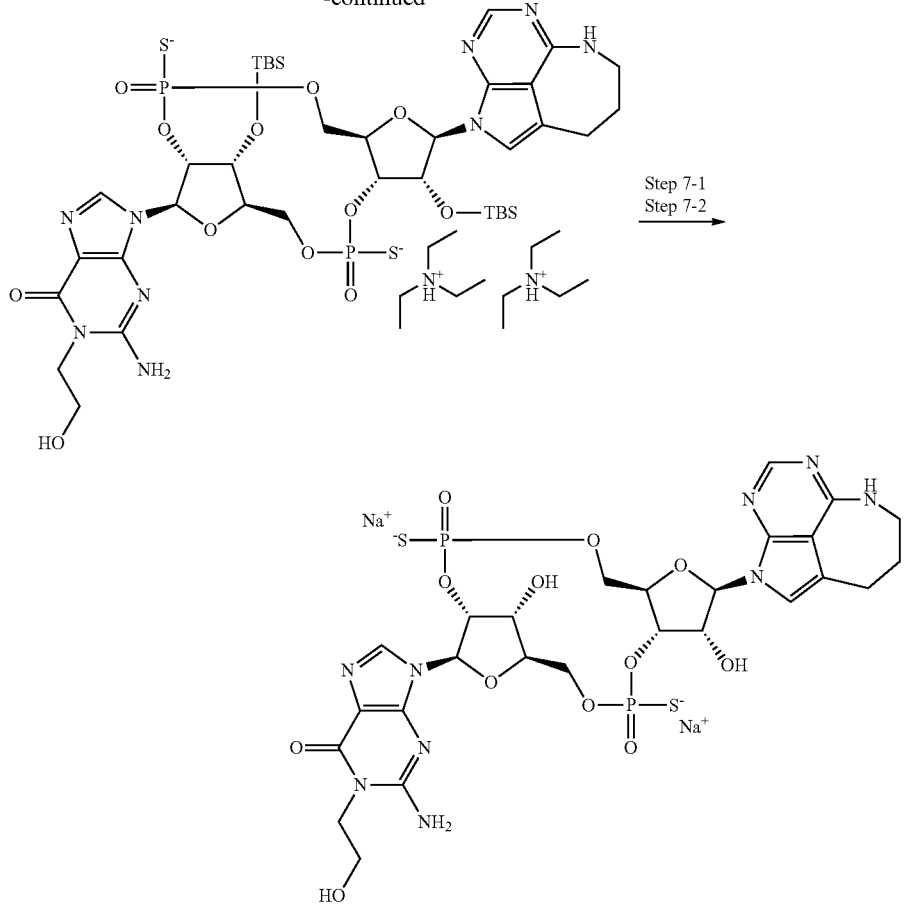

(Step 1)

1-[2-(Benzoyloxy)ethyl]-5'-O-[bis(4-methoxyphenyl)(phenyl)methyl]-N-[(dimethylamino)methylidene]guanosine To a mixed solution of N-[(dimethylamino)methylidene] guanosine (10.0 g) as a compound known in the literature (Journal of Organic Chemistry, 1994, 59, 7243-7248) in N,N-dimethylacetamide (50 mL)-pyridine (50 mL), 4,4'-dimethoxytrityl chloride (10.5 g) was added at 0° C., and the reaction mixture was stirred at 4° C. for 16 hours. To the reaction mixture, 2-bromoethyl benzoate (6.54 mL) and 1,8-diazabicyclo [5.4.0]-7-undecene (11.0 mL) were added, and the reaction mixture was stirred at room temperature for 2 days. A saturated aqueous solution of sodium hydrogen carbonate and water were added to the reaction mixture, which was subjected to extraction with ethyl acetate. The organic layer was washed with brine, and dried over anhydrous sodium sulfate. The drying agent was removed through filtration, and the filtrate was concentrated under reduced pressure. The residue was purified by silica gel column chromatography [hexane/ethyl acetate/methanol] to afford the title compound as a mixture with triphenylphosphine oxide (16.7 g).

MS(ESI)m/z: 789 (M+H)$^+$.

$^1$H-NMR (CDCl$_3$) δ: 8.17 (1H, s), 7.93-7.89 (2H, m), 7.55 (1H, s), 7.54-7.48 (1H, m), 7.42-7.36 (4H, m), 7.31-7.26 (4H, m), 7.25-7.19 (2H, m), 7.16-7.11 (1H, m), 6.82-6.76 (4H, m), 5.96 (1H, d, J=6.7 Hz), 4.79-4.70 (1H, m), 4.70-4.61 (2H, m), 4.60-4.52 (1H, m), 4.52-4.45 (1H, m), 4.41-4.38 (1H, m), 4.34-4.30 (1H, m), 3.75 (3H, s), 3.75 (3H, s), 3.39-3.36 (2H, m), 2.89 (3H, s), 2.80 (3H, s).

(Step 2)

1-[2-(Benzoyloxy)ethyl]-5'-O-[bis(4-methoxyphenyl)(phenyl)methyl]-3'-O-[tert-butyl(dimethyl)silyl]-N-[(dimethylamino)methylidene]guanosine With use of the compound (15.7 g) obtained in the above step 1, the reaction was performed in the same manner as in step 3 of Example 5 to afford the title compound (4.82 g) and 1-[2-(benzoyloxy)ethyl]-5'-O-[bis(4-methoxyphenyl)(phenyl)methyl]-2'-O-[tert-butyl(dimethyl)silyl]-N-[(dimethylamino)methylidene]guanosine (6.01 g) as a regioisomer of the title compound.

MS(ESI)m/z: 903 (M+H)$^+$.

$^1$H-NMR (CDCl$_3$) δ: 8.24 (1H, s), 7.99-7.95 (2H, m), 7.85 (1H, s), 7.56-7.50 (1H, m), 7.44-7.38 (4H, m), 7.34-7.27 (6H, m), 7.24-7.18 (1H, m), 6.84-6.79 (4H, m), 5.98 (1H, d, J=4.2 Hz), 4.87-4.77 (2H, m), 4.72-4.61 (2H, m), 4.41-4.36 (2H, m), 4.16-4.09 (1H, m), 3.78 (3H, s), 3.78 (3H, s), 3.45 (1H, dd, J=10.6, 3.9 Hz), 3.25 (1H, dd, J=10.6, 3.9 Hz), 3.05 (1H, d, J=5.4 Hz), 2.91 (3H, s), 2.78 (3H, s), 0.86 (9H, s), 0.05 (3H, s), −0.04 (3H, s).

Regioisomer (2'-O-TBS Form)

MS(ESI)m/z: 903 (M+H)$^+$.

$^1$H-NMR (CDCl$_3$) δ: 8.23 (1H, s), 7.97-7.91 (2H, m), 7.82 (1H, s), 7.56-7.50 (1H, m), 7.45-7.36 (4H, m), 7.35-7.26

(6H, m), 7.25-7.19 (1H, m), 6.85-6.79 (4H, m), 5.98 (1H, d, J=5.4 Hz), 4.88-4.77 (2H, m), 4.73-4.62 (3H, m), 4.32-4.27 (1H, m), 4.23-4.19 (1H, m), 3.79 (3H, s), 3.79 (3H, s), 3.47 (1H, dd, J=10.9, 3.6 Hz), 3.37 (1H, dd, J=10.9, 3.6 Hz), 2.90 (3H, s), 2.76 (1H, d, J=2.5 Hz), 2.75 (3H, s), 0.84 (9H, s), 0.02 (3H, s), −0.15 (3H, s).
(Step 3)

1-[2-(Benzoyloxy)ethyl]-5'-O-[bis(4-methoxyphenyl)(phenyl)methyl]-3'-O-[tert-butyl(dimethyl)silyl]-2'-O-{(2-cyanoethoxy)[di(propan-2-yl)amino]phosphanyl}-N-[(dimethylamino)methylidene]guanosine With use of the compound (4.81 g) obtained in the above step 2, the reaction was performed in the same manner as in step 4 of Example 5 to afford the title compound (5.41 g) as a mixture of diastereomers at the phosphorus atom (diastereomer ratio=7:3).
MS(ESI)m/z: 1103 (M+H)$^+$.
$^1$H-NMR (CDCl$_3$) δ: 8.33 (0.7H, s), 8.31 (0.3H, s), 7.98-7.94 (2H, m), 7.87 (0.3H, s), 7.80 (0.7H, s), 7.56-7.50 (1H, m), 7.46-7.37 (4H, m), 7.35-7.27 (6H, m), 7.24-7.18 (1H, m), 6.85-6.80 (4H, m), 6.14 (0.7H, d, J=6.0 Hz), 6.13 (0.3H, d, J=5.4 Hz), 4.92-4.59 (4H, m), 4.55-4.48 (0.7H, m), 4.33-4.29 (0.3H, m), 4.25-4.21 (0.6H, m), 4.17-4.13 (1.4H, m), 3.79 (3H, s), 3.79 (3H, s), 3.60-3.38 (5H, m), 3.33-3.23 (1H, m), 2.93 (2.1H, s), 2.92 (0.9H, s), 2.82 (2.1H, s), 2.81 (0.9H, s), 2.47-2.42 (0.6H, m), 2.34-2.27 (1.4H, m), 1.09 (4.2H, d, J=6.7 Hz), 1.07 (1.8H, d, J=7.3 Hz), 1.05 (4.2H, d, J=6.7 Hz), 0.91 (1.8H, d, J=7.3 Hz), 0.84 (9H, s), 0.07 (0.9H, s), 0.04 (2.1H, s), −0.02 (3H, s).
(Step 4)
The same reaction as in step 7 of Example 1 was carried out in the following scale (raw material: 1.68 g). With use of an acetonitrile solution of the compound obtained and the compound (1.81 g) obtained in the above step 3, the reaction was performed in the same manner as in step 8 of Example 1, and the resulting crude product was directly used for the subsequent reaction.
(Step 5)

2-(9-[(5R,7R,8R,12aR,14R,15R,15aR,16R)-14-(6-Benzoyl-6,7,8,9-tetrahydro-2H-2,3,5,6-tetraazabenzo[cd]azulen-2-yl)-15,16-bis{[tert-butyl(dimethyl)silyl]oxy}-10-(2-cyanoethoxy)-2-oxo-2-sulfanyl-10-sulfanylideneoctahydro-2H,10H,12H-5,8-methano-2λ$^5$,10λ$^5$-furo[3,2-1][1,3,6,9,11,2,10]pentaoxadiphosphacyclotetradecin-7-yl]-2-{(E)-[(dimethylamino)methylidene]amino}-6-oxo-6,9-dihydro-1H-purin-1-yl)ethyl benzoate With use of the crude product obtained in the above step 4, the reaction was performed in the same manner as in step 9 of Example 1 to afford the title compound (1.15 g) as a mixture of diastereomers at the phosphorus atom.
MS(ESI)m/z: 1334 (M+H)$^+$.
(Step 6)

Bis(N,N-diethylethaneaminium) (5R,7R,8R,12aR,14R,15R,15aR,16R)-7-[2-amino-1-(2-hydroxyethyl)-6-oxo-1,6-dihydro-9H-purin-9-yl]-15,16-bis{[tert-butyl(dimethyl)silyl]oxy}-2,10-dioxo-14-(6,7,8,9-tetrahydro-2H-2,3,5,6-tetraazabenzo[cd]azulen-2-yl)octahydro-2H,10H,12H-5,8-methano-2λ$^5$,10λ$^5$-furo[3,2-1][1,3,6,9,11,2,10]pentaoxadiphosphacyclotetradecine-2,10-bis(thiolate)

With use of the compound (1.15 g) obtained in the above step 5, the reaction was performed in the same manner as in step 10 of Example 1 to afford diastereomer 1 (134 mg: with impurities) and diastereomer 2 (127 mg: with impurities) of the title compound.
Diastereomer 1 (Less Polar)
MS(ESI)m/z: 1018 (M+H)$^+$.
Diastereomer 2 (More Polar)
MS(ESI)m/z: 1018 (M+H)$^+$.
(Step 7-1)

Disodium (5R,7R,8R,12aR,14R,15R,15aS,16R)-7-[2-amino-1-(2-hydroxyethyl)-6-oxo-1,6-dihydro-9H-purin-9-yl]-15,16-dihydroxy-2,10-dioxo-14-(6,7,8,9-tetrahydro-2H-2,3,5,6-tetraazabenzo[cd]azulen-2-yl)octahydro-2H,10H,12H-5,8-methano-2λ$^5$,10λ$^5$-furo[3,2-1][1,3,6,9,11,2,10]pentaoxadiphosphacyclotetradecine-2,10-bis(thiolate)

(Diastereomer 1)
With use of the compound (diastereomer 1) (134 mg: with impurities) obtained in the above step 6, the reaction was performed in the same manner as in step 11 of Example 1, and purification was then performed under the following [Purification Conditions] to afford the title compound as a triethylamine salt.
[Purification Conditions] C18 silica gel column chromatography [10 mM aqueous solution of triethylammonium acetate/acetonitrile] and preparative HPLC [10 mM aqueous solution of triethylammonium acetate/acetonitrile, acetonitrile: 5%-25% (0 min-40 min)].
The triethylamine salt obtained was subjected to salt exchange in the same manner as in [Conversion to Sodium Salt] described in step 11 of Example 1 to afford the title compound (36.0 mg).
MS(ESI)m/z: 790 (M+H)$^+$.
$^1$H-NMR (CD$_3$OD) δ: 8.01 (1H, s), 7.99 (1H, s), 7.17 (1H, s), 6.23 (1H, d, J=2.4 Hz), 5.96 (1H, d, J=8.5 Hz), 5.67-5.58 (1H, m), 5.29-5.22 (1H, m), 4.95-4.85 (1H, m), 4.83-4.79 (1H, m), 4.48-4.40 (2H, m), 4.39-4.31 (2H, m), 4.22-4.09 (3H, m), 3.73-3.66 (2H, m), 3.56-3.50 (1H, m), 3.50-3.44 (2H, m), 2.80-2.68 (1H, m), 2.48-2.35 (1H, m), 2.00-1.88 (1H, m), 1.87-1.77 (1H, m).
$^{31}$P-NMR (CD$_3$OD) δ: 57.6 (s), 53.1 (s).
(Step 7-2)

Disodium (5R,7R,8R,12aR,14R,15R,15aS,16R)-7-[2-amino-1-(2-hydroxyethyl)-6-oxo-1,6-dihydro-9H-purin-9-yl]-15,16-dihydroxy-2,10-dioxo-14-(6,7,8,9-tetrahydro-2H-2,3,5,6-tetraazabenzo[cd]azulen-2-yl)octahydro-2H,10H,12H-5,8-methano-2λ$^5$,10λ$^5$-furo[3,2-1][1,3,6,9,11,2,10]pentaoxadiphosphacyclotetradecine-2,10-bis(thiolate)

(Diastereomer 2)
With use of the compound (diastereomer 2) (127 mg: with impurities) obtained in the above step 6, the reaction was performed in the same manner as in step 11 of Example 1, and purification was then performed under the following [Purification Conditions] to afford the title compound as a triethylamine salt.
[Purification Conditions] C18 silica gel column chromatography [10 mM aqueous solution of triethylammonium acetate/acetonitrile] and preparative HPLC [10 mM aqueous solution of triethylammonium acetate/acetonitrile, acetonitrile: 3%-20% (0 min-40 min)].

The triethylamine salt obtained was subjected to salt exchange in the same manner as in [Conversion to Sodium Salt] described in step 11 of Example 1 to afford the title compound (20.1 mg).

MS(ESI)m/z: 790 (M+H)+.

$^1$H-NMR (CD$_3$OD) δ: 8.20 (1H, s), 8.02 (1H, s), 7.19 (1H, s), 6.31 (1H, d, J=6.0 Hz), 6.05 (1H, d, J=8.5 Hz), 5.62-5.52 (1H, m), 5.47-5.40 (1H, m), 4.80-4.75 (1H, m), 4.51-4.47 (1H, m), 4.47-4.21 (5H, m), 4.16-4.09 (1H, m), 3.99-3.89 (2H, m), 3.84-3.78 (2H, m), 3.52-3.46 (2H, m), 2.93-2.83 (1H, m), 2.82-2.72 (1H, m), 2.03-1.92 (2H, m).

$^{31}$P-NMR (CD$_3$OD) δ: 61.6 (s), 59.6 (s).

Example 38: Synthesis of CDN28

N-[2-({6-Amino-9-[(5R,7R,8R,12aR,14R,15R,15aS,16R)-15,16-dihydroxy-2,10-dioxo-2,10-bis(sulfanyl)-14-(6,7,8,9-tetrahydro-2H-2,3,5,6-tetraazabenzo[cd]azulen-2-yl)octahydro-2H,10H,12H-5,8-methano-2λ$^5$,10λ$^5$-furo[3,2-l][1,3,6,9,11,2,10]pentaoxadiphosphacyclotetradecin-7-yl]-9H-purin-2-yl}amino)ethyl]-2-hydroxyacetamide

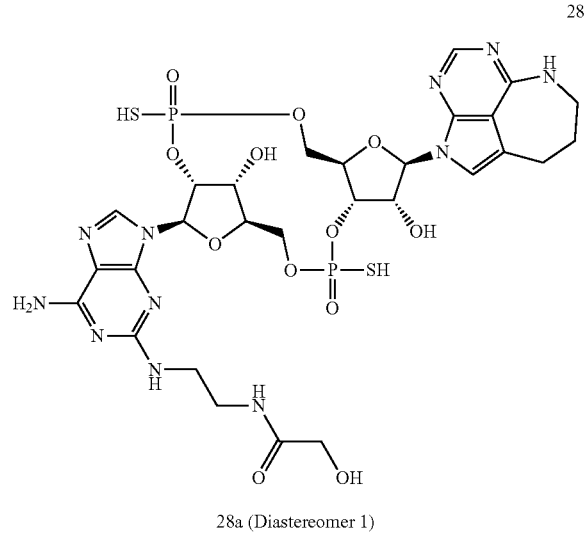 [SMILES: Nc1nc(NCCNC(=O)CO)nc2c1ncn2[C@@H]1O[C@@H]2COP(=O)(S)O[C@H]3[C@@H](O)[C@H](n4cc5c6c(ncnc64)NCCC5)O[C@@H]3COP(=O)(S)O[C@@H]1[C@@H]2O]

28a (Diastereomer 1)

[Synthesis Scheme]

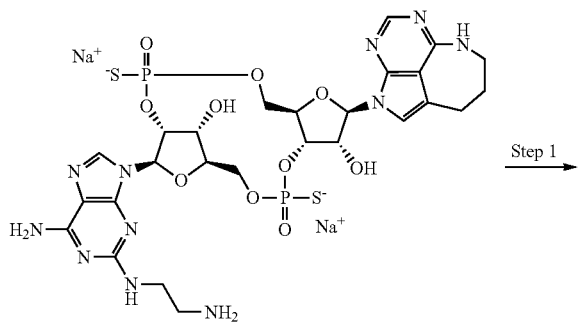

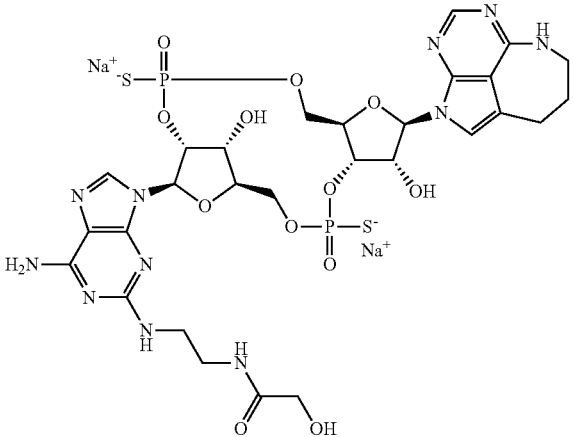

(Step 1)

Disodium (5R,7R,8R,12aR,14R,15R,15aS,16R)-7-(6-amino-2-{[2-(2-hydroxyacetamide)ethyl]amino}-9H-purin-9-yl)-15,16-dihydroxy-2,10-dioxo-14-(6,7,8,9-tetrahydro-2H-2,3,5,6-tetraazabenzo[cd]azulen-2-yl)octahydro-2H,10H,12H-5,8-methano-2λ$^5$,10λ$^5$-furo[3,2-l][1,3,6,9,11,2,10]pentaoxadiphosphacyclotetradecine-2,10-bis(thiolate)

With use of the compound (6.6 mg) obtained in step 8-2 of Example 8, the reaction was performed in the same manner as in step 1-1 of Example 7, and purification was then carried out under the following [Purification Conditions] to afford the title compound as a triethylamine salt.

[Purification Conditions] preparative HPLC [10 mM aqueous solution of triethylammonium acetate/acetonitrile, acetonitrile: 2%-30% (0 min-30 min)].

The triethylamine salt obtained was subjected to salt exchange in the same manner as in [Conversion to Sodium Salt] described in step 11 of Example 1 to afford the title compound (2.9 mg).

MS(ESI)m/z: 846 (M+H)+.

$^1$H-NMR (CD$_3$OD) δ: 8.33 (1H, s), 8.02 (1H, s), 7.16 (1H, s), 6.33 (1H, d, J=6.0 Hz), 6.18 (1H, d, J=8.5 Hz), 5.53-5.45 (2H, m), 4.79 (1H, t, J=5.1 Hz), 4.50-4.25 (5H, m), 4.10 (1H, d, J=11.5 Hz), 3.97 (2H, s), 3.94-3.89 (1H, m), 3.53-3.39 (6H, m), 2.88 (2H, t, J=5.7 Hz), 2.04-1.98 (2H, m).

$^{31}$P-NMR (CD$_3$OD) δ: 62.6, 60.1.

Example 39: Synthesis of CDN29

N-({6-Amino-9-[(5R,7R,8R,12aR,14R,15R,15aS,16R)-15,16-dihydroxy-2,10-dioxo-2,10-bis(sulfanyl)-14-(6,7,8,9-tetrahydro-2H-2,3,5,6-tetraazabenzo[cd]azulen-2-yl)octahydro-2H,10H,12H-5,8-methano-2$\lambda^5$,10$\lambda^5$-furo[3,2-l][1,3,6,9,11,2,10]pentaoxadiphosphacyclotetradecin-7-yl]-9H-purin-2-yl}methyl)-2-hydroxyacetamide

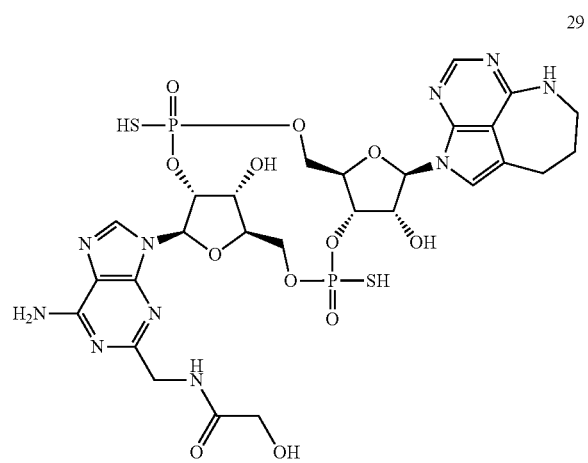

29
29a (Diastereomer 1)

[Synthesis Scheme]

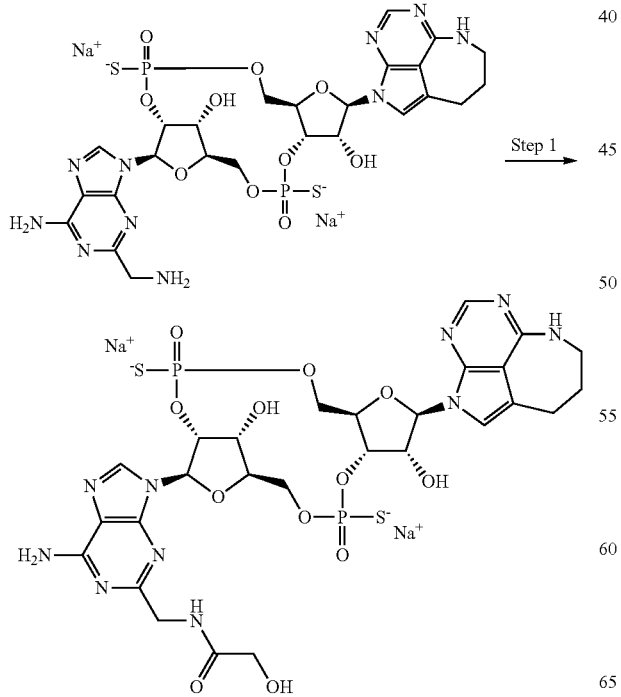

Step 1

(Step 1)

Disodium (5R,7R,8R,12aR,14R,15R,15aS,16R)-7-{6-amino-2-[(2-hydroxyacetamide)methyl]-9H-purin-9-yl}-15,16-dihydroxy-2,10-dioxo-14-(6,7,8,9-tetrahydro-2H-2,3,5,6-tetraazabenzo[cd]azulen-2-yl)octahydro-2H,10H,12H-5,8-methano-2$\lambda^5$,10$\lambda^5$-furo[3,2-l][1,3,6,9,11,2,10]pentaoxadiphosphacyclotetradecine-2,10-bis(thiolate)

With use of the compound (4.6 mg) obtained in step 9-2 of Example 11, the reaction was performed in the same manner as in step 1-1 of Example 7, and the resultant was purified by preparative HPLC [10 mM aqueous solution of triethylammonium acetate/acetonitrile, acetonitrile: 2%-30% (0 min-30 min)] to afford the title compound as a triethylamine salt.

The triethylamine salt obtained was subjected to salt exchange in the same manner as in [Conversion to Sodium Salt] described in step 11 of Example 1 to afford the title compound (4.0 mg).

MS(ESI)m/z: 817 (M+H)$^+$.

$^1$H-NMR (CD$_3$OD) δ: 8.75 (1H, s), 8.02 (1H, s), 7.12 (1H, s), 6.36 (1H, d, J=8.5 Hz), 6.33 (1H, d, J=6.7 Hz), 5.49-5.41 (2H, m), 4.80 (1H, dd, J=6.7, 4.8 Hz), 4.50-4.29 (7H, m), 4.07 (2H, s), 4.05-4.01 (1H, m), 3.92-3.87 (1H, m), 3.51-3.49 (2H, m), 2.93-2.90 (2H, m), 2.03-1.99 (2H, m).

$^{31}$P-NMR (CD$_3$OD) δ: 63.2, 60.3.

Example 40: Synthesis of CDN30

(5R,7R,8R,12aR,14R,15R,15aS,16R)-7-(6-Amino-2-{[(1-aminocyclopropyl)methyl]amino}-9H-purin-9-yl)-15,16-dihydroxy-2,10-bis(sulfanyl)-14-(6,7,8,9-tetrahydro-2H-2,3,5,6-tetraazabenzo[cd]azulen-2-yl)octahydro-2H,10H,12H-5,8-methano-2$\lambda^5$,10$\lambda^5$-furo[3,2-l][1,3,6,9,11,2,10]pentaoxadiphosphacyclotetradecine-2,10-dione 30
30a (Diastereomer 1)
30b (Diastereomer 2)

[Synthesis Scheme]
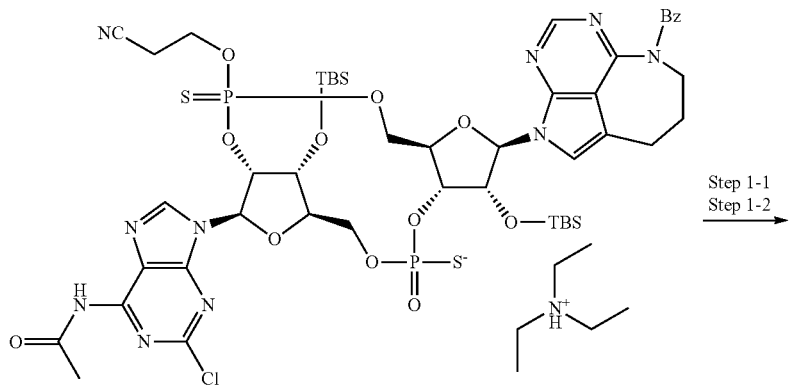
Step 1-1
Step 1-2
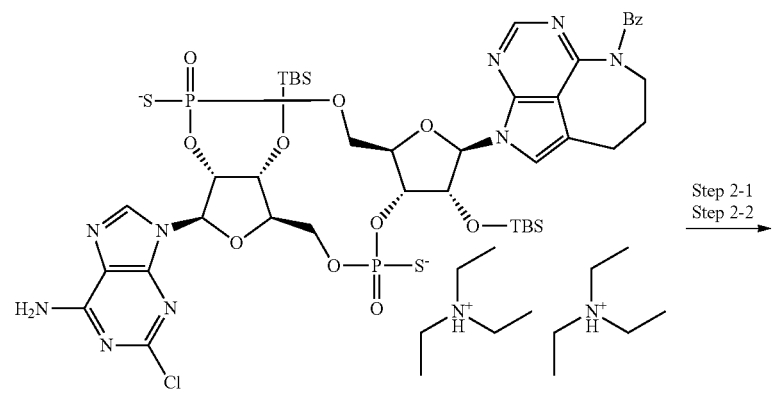
Step 2-1
Step 2-2
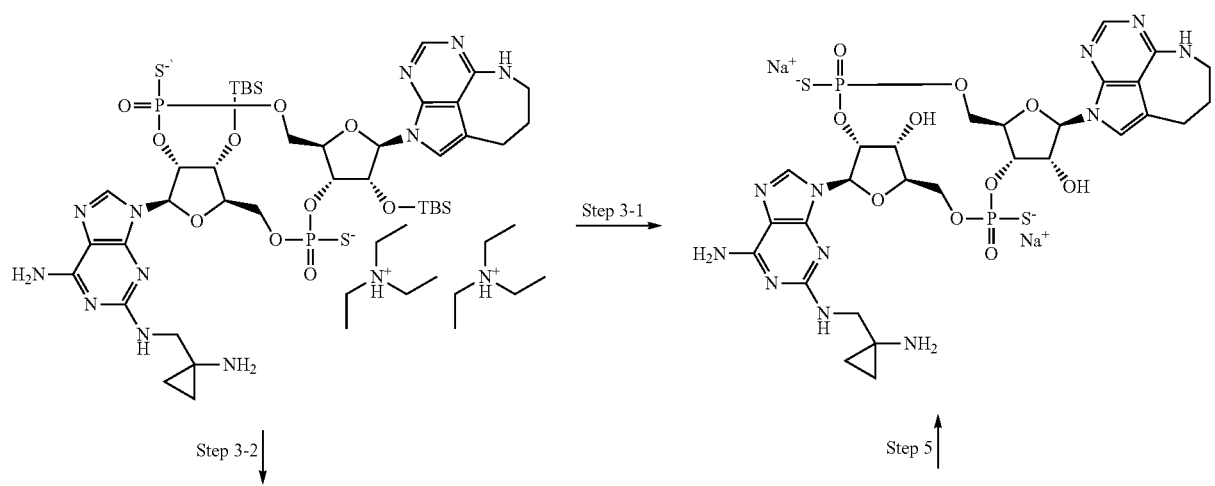
Step 3-1
Step 3-2
Step 5

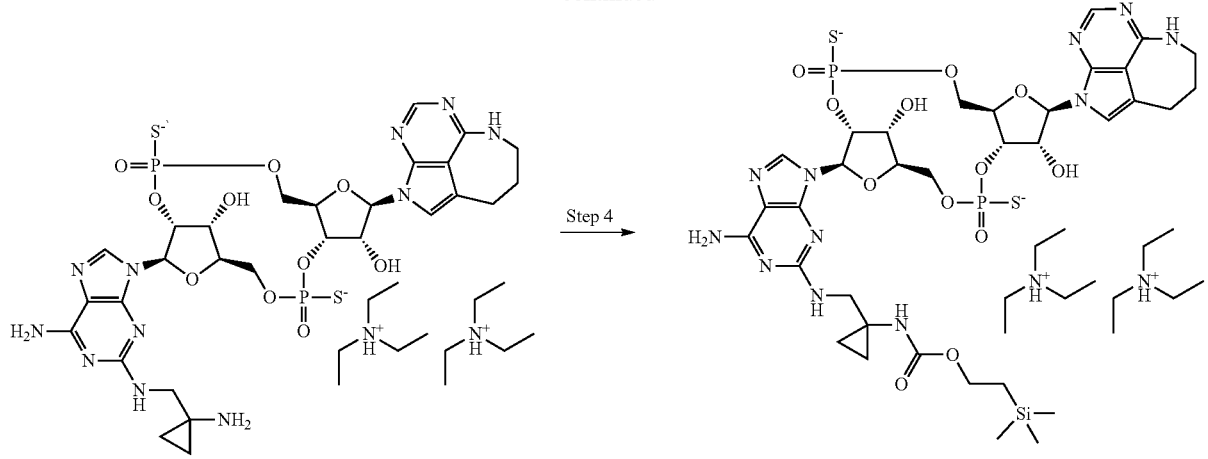

(Step 1-1)

Bis(N,N-diethylethaneaminium) (5R,7R,8R,12aR, 14R,15R,15aR,16R)-7-(6-amino-2-chloro-9H-purin-9-yl)-15,16-bis{[tert-butyl(dimethyl)silyl]oxy}-2,10-dioxo-14-(6,7,8,9-tetrahydro-2H-2,3,5,6-tetraazabenzo[cd]azulen-2-yl)octahydro-2H,10H, 12H-5,8-methano-2$\lambda^5$,10$\lambda^5$-furo[3,2-1][1,3,6,9,11,2,10]pentaoxadiphosphacyclotetradecine-2,10-bis (thiolate)

With use of the compound (diastereomer 1) (590 mg) obtained in step 6 of Example 8, the reaction was performed in the same manner as in step 10 of Example 1 to afford the title compound (420 mg).

MS(ESI)m/z: 992 (M+H)$^+$.

$^1$H-NMR (CD$_3$OD) δ: 8.76 (1H, s), 7.97 (1H, s), 7.30 (1H, s), 6.23 (1H, d, J=4.8 Hz), 6.22 (1H, d, J=7.9 Hz), 5.43-5.37 (1H, m), 5.19-5.15 (1H, m), 4.85-4.77 (3H, m), 4.44-4.31 (2H, m), 4.22 (1H, brs), 4.08-4.00 (2H, m), 3.52-3.48 (2H, m), 3.14 (12H, q, J=7.3 Hz), 2.84-2.81 (2H, m), 2.02-1.92 (2H, m), 1.26 (18H, t, J=7.3 Hz), 1.00 (9H, s), 0.85 (9H, s), 0.33 (3H, s), 0.28 (3H, s), 0.27 (3H, s), 0.10 (3H, s).

(Step 1-2)

Bis(N,N-diethylethaneaminium) (5R,7R,8R,12aR, 14R,15R,15aR,16R)-7-(6-amino-2-chloro-9H-purin-9-yl)-15,16-bis{[tert-butyl(dimethyl)silyl]oxy}-2,10-dioxo-14-(6,7,8,9-tetrahydro-2H-2,3,5,6-tetraazabenzo[cd]azulen-2-yl)octahydro-2H,10H, 12H-5,8-methano-2$\lambda^5$,10$\lambda^5$-furo[3,2-1][1,3,6,9,11,2,10]pentaoxadiphosphacyclotetradecine-2,10-bis (thiolate)

With use of the compound (diastereomer 2) (710 mg) obtained in step 6 of Example 8, the reaction was performed in the same manner as in step 10 of Example 1 to afford the title compound (452 mg).

MS(ESI)m/z: 992 (M+H)$^+$.

$^1$H-NMR (CD$_3$OD) δ: 8.55 (1H, s), 8.01 (1H, s), 7.07 (1H, s), 6.34 (1H, d, J=7.3 Hz), 6.20 (1H, d, J=8.5 Hz), 5.52-5.44 (1H, m), 5.38-5.36 (1H, m), 5.17-5.10 (1H, m), 4.98-4.95 (2H, m), 4.67-4.57 (2H, m), 4.25 (1H, brs), 4.11-4.07 (1H, m), 3.89-3.84 (1H, m), 3.52-3.49 (2H, m), 3.18 (12H, q, 7.3 Hz), 2.93-2.91 (2H, m), 2.03-1.99 (2H, m), 1.30 (18H, t, J=7.3 Hz), 1.00 (9H, s), 0.74 (9H, s), 0.27 (6H, s), 0.20 (3H, s), −0.28 (3H, s).

(Step 2-1)

Bis(N,N-diethylethaneaminium) (5R,7R,8R,12aR, 14R,15R,15aR,16R)-7-(6-amino-2-{[(1-aminocyclopropyl)methyl]amino}-9H-purin-9-yl)-15,16-bis{[tert-butyl(dimethyl)silyl]oxy}-2,10-dioxo-14-(6,7,8,9-tetrahydro-2H-2,3,5,6-tetraazabenzo[cd]azulen-2-yl)octahydro-2H,10H,12H-5,8-methano-2$\lambda^5$,10$\lambda^5$-furo[3,2-1][1,3,6,9,11,2,10]pentaoxadiphosphacyclotetradecine-2,10-bis (thiolate)

To a solution of 1-(aminomethyl)cyclopropan-1-amine·2HCl (309 mg) in methanol (40 mL), MP-Carbonate resin (5.45 g) was added, and the reaction mixture was stirred at room temperature for 2 hours. The resin was removed through filtration, and the filtrate was concentrated under reduced pressure. A solution of the residue in methanol (0.837 mL) was added to the compound (30.0 mg) obtained in the above step 1-1, and the resultant was reacted with a microwave reactor at 120° C. for 4 hours. After the reaction mixture was concentrated under reduced pressure, the residue was purified by preparative HPLC [10 mM aqueous solution of triethylammonium acetate/acetonitrile, acetonitrile: 30%-60% (0 min-30 min)] to afford a mixture containing the title compound. The mixture obtained was directly used for the subsequent step.

MS(ESI)m/z: 1042 (M+H)$^+$.

(Step 2-2)

Bis(N,N-diethylethaneaminium) (5R,7R,8R,12aR, 14R,15R,15aR,16R)-7-(6-amino-2-{[(1-aminocyclopropyl)methyl]amino}-9H-purin-9-yl)-15,16-bis{[tert-butyl(dimethyl)silyl]oxy}-2,10-dioxo-14-(6,7,8,9-tetrahydro-2H-2,3,5,6-tetraazabenzo[cd]azulen-2-yl)octahydro-2H,10H,12H-5,8-methano-2$\lambda^5$,10$\lambda^5$-furo[3,2-1][1,3,6,9,11,2,10]pentaoxadiphosphacyclotetradecine-2,10-bis (thiolate)

With use of the compound (58.6 mg) obtained in the above step 1-2, a mixture containing the title compound was obtained in the same manner as in the above step 2-1. The mixture obtained was directly used for the subsequent reaction.

MS(ESI)m/z: 1042 (M+H)$^+$.

(Step 3-1)

Disodium (5R,7R,8R,12aR,14R,15R,15aS,16R)-7-(6-amino-2-{[(1-aminocyclopropyl)methyl]amino}-9H-purin-9-yl)-15,16-dihydroxy-2,10-dioxo-14-(6,7,8,9-tetrahydro-2H-2,3,5,6-tetraazabenzo[cd]azulen-2-yl)octahydro-2H,10H,12H-5,8-methano-2$\lambda^5$,10$\lambda^5$-furo[3,2-l][1,3,6,9,11,2,10]pentaoxadiphosphacyclotetradecine-2,10-bis (thiolate)

(Diastereomer 1)

With use of the mixture obtained in the above step 2-1, the reaction was performed in the same manner as in step 11 of Example 1, and the resultant was then purified by preparative HPLC [10 mM aqueous solution of triethylammonium acetate/acetonitrile, acetonitrile: 2%-20% (0 min-30 min)] to afford the title compound as a triethylamine salt.

The triethylamine salt obtained was subjected to salt exchange in the same manner as in [Conversion to Sodium Salt] described in step 11 of Example 1 to afford the title compound (2.0 mg).

MS(ESI)m/z: 812 (M−2Na+1H)⁻.

$^1$H-NMR (CD$_3$OD) δ: 8.25 (1H, s), 8.01 (1H, s), 7.04 (1H, s), 6.28 (1H, d, J=4.2 Hz), 6.12 (1H, d, J=7.9 Hz), 5.43-5.35 (1H, m), 5.15-5.11 (1H, m), 4.75 (1H, t, J=4.2 Hz), 4.65-4.56 (1H, m), 4.49-4.43 (2H, m), 4.37-4.31 (2H, m), 4.15-4.01 (2H, m), 3.73-3.59 (1H, m), 3.50-3.47 (2H, m), 3.22-3.15 (1H, m), 2.85-2.68 (2H, m), 2.00-1.93 (2H, m), 0.87-0.80 (4H, m).

$^{31}$P-NMR (CD$_3$OD) δ: 57.7 (s), 54.3 (s).

(Step 3-2)

Bis(N,N-diethylethaneaminium) (5R,7R,8R,12aR,14R,15R,15aS,16R)-7-(6-amino-2-{[(1-aminocyclopropyl)methyl]amino}-9H-purin-9-yl)-15,16-dihydroxy-2,10-dioxo-14-(6,7,8,9-tetrahydro-2H-2,3,5,6-tetraazabenzo[cd]azulen-2-yl)octahydro-2H,10H,12H-5,8-methano-2$\lambda^5$,10$\lambda^5$-furo[3,2-l][1,3,6,9,11,2,10]pentaoxadiphosphacyclotetradecine-2,10-bis (thiolate)

With use of the mixture obtained in the above step 2-2, the reaction was performed in the same manner as in step 11 of Example 1 to afford a mixture containing the title compound. The mixture obtained was directly used for the subsequent reaction.

(Step 4)

Bis(N,N-diethylethaneaminium) (5R,7R,8R,12aR,14R,15R,15aS,16R)-7-[6-amino-2-({[1-({[2-(trimethylsilyl)ethoxy]carbonyl}amino)cyclopropyl]methyl}amino)-9H-purin-9-yl]-15,16-dihydroxy-2,10-dioxo-14-(6,7,8,9-tetrahydro-2H-2,3,5,6-tetraazabenzo[cd]azulen-2-yl)octahydro-2H,10H,12H-5,8-methano-2$\lambda^5$,10$\lambda^5$-furo[3,2-l][1,3,6,9,11,2,10]pentaoxadiphosphacyclotetradecine-2,10-bis (thiolate)

To a solution of the mixture obtained in the above step 3-2 in N,N-dimethylformamide (1.0 mL), triethylamine (40.8 μL) and 2,5-dioxopyrrolidin-1-yl (2-(trimethylsilyl)ethyl) carbonate (39.5 mg) was added, and the reaction mixture was stirred at room temperature for 1 hour. After quenching by adding water to the reaction mixture, the resultant was purified by preparative HPLC [10 mM aqueous solution of triethylammonium acetate/acetonitrile, acetonitrile: 10%-50% (0 min-30 min)] to afford the title compound (11.0 mg).

MS(ESI)m/z: 958 (M+H)⁺.

$^1$H-NMR (CD$_3$OD) δ: 8.40 (1H, s), 8.03 (1H, s), 7.12 (1H, s), 6.32 (1H, d, J=6.7 Hz), 6.18 (1H, d, J=8.5 Hz), 5.53-5.49 (1H, m), 5.46-5.39 (1H, m), 4.83 (1H, dd, J=6.3, 4.5 Hz), 4.53-4.30 (4H, m), 4.26-4.24 (1H, m), 4.13-4.08 (2H, m), 4.04-4.00 (1H, m), 3.93-3.88 (1H, m), 3.60 (1H, d, J=13.9 Hz), 3.52-3.49 (2H, m), 3.40 (1H, d, J=13.9 Hz), 3.04 (12H, q, 7.3 Hz), 2.93-2.90 (2H, m), 2.04-1.99 (2H, m), 1.23 (18H, t, J=7.3 Hz), 0.96-0.92 (2H, m), 0.84-0.80 (2H, m), 0.76-0.73 (2H, m), 0.02 (9H, s).

(Step 5)

Disodium (5R,7R,8R,12aR,14R,15R,15aS,16R)-7-(6-amino-2-{[(1-aminocyclopropyl)methyl]amino}-9H-purin-9-yl)-15,16-dihydroxy-2,10-dioxo-14-(6,7,8,9-tetrahydro-2H-2,3,5,6-tetraazabenzo[cd]azulen-2-yl)octahydro-2H,10H,12H-5,8-methano-2$\lambda^5$,10$\lambda^5$-furo[3,2-l][1,3,6,9,11,2,10]pentaoxadiphosphacyclotetradecine-2,10-bis (thiolate)

(Diastereomer 2)

To a solution of the compound (11.0 mg) obtained in the above step 4 in tetrahydrofuran (474 μL), a tetrahydrofuran solution of tetrabutylammonium fluoride (approximately 1 M, 237 μL) was added, and the reaction mixture was stirred under the nitrogen atmosphere at 40° C. for 3 hours. After quenching by adding 10 mM aqueous solution of triethylammonium acetate to the reaction mixture, the resultant was purified by preparative HPLC [10 mM aqueous solution of triethylammonium acetate/acetonitrile, acetonitrile: 2%-30% (0 min-30 min)] and a Sep-Pak® C18 [water/acetonitrile/0.1% triethylamine] to afford the title compound as a triethylamine salt.

The triethylamine salt obtained was subjected to salt exchange in the same manner as in [Conversion to Sodium Salt] described in step 11 of Example 1 to afford the title compound (4.1 mg).

MS(ESI)m/z: 812 (M−2Na+1H)⁻.

$^1$H-NMR (CD$_3$OD) δ: 8.34 (1H, s), 8.01 (1H, s), 7.14 (1H, s), 6.32 (1H, d, J=6.0 Hz), 6.16 (1H, d, J=8.5 Hz), 5.43-5.37 (2H, m), 4.78 (1H, t, J=5.4 Hz), 4.50-4.28 (5H, m), 4.12-4.08 (1H, m), 3.95-3.89 (1H, m), 3.69-3.64 (1H, m), 3.51-3.48 (2H, m), 3.26 (1H, d, J=14.5), 2.89-2.86 (2H, m), 2.03-1.98 (2H, m), 0.83-0.79 (4H, m).

$^{31}$P-NMR (CD$_3$OD) δ: 62.3 (s), 60.0 (s).

Example 41: Synthesis of CDN31

(5R,7R,8R,12aR,14R,15R,15aS,16R)-15,16-Dihydroxy-7-[2-(hydroxymethyl)-6-(methylamino)-9H-purin-9-yl]-2,10-bis(sulfanyl)-14-(6,7,8,9-tetrahydro-2H-2,3,5,6-tetraazabenzo[cd]azulen-2-yl)octahydro-2H,10H,12H-5,8-methano-2λ⁵,10λ⁵-furo[3,2-1][1,3,6,9,11,2,10]pentaoxadiphosphacyclotetradecine-2,10-dione

31

31a (Diastereomer 1)

[Synthesis Scheme]

(Step 1)

(5R,7R,8R,12aR,14R,15R,15aR,16R)-15,16-Bis{[tert-butyl(dimethyl)silyl]oxy}-7-[2-(hydroxymethyl)-6-(methylamino)-9H-purin-9-yl]-2,10-bis(sulfanyl)-14-(6,7,8,9-tetrahydro-2H-2,3,5,6-tetraazabenzo[cd]azulen-2-yl)octahydro-2H,10H,12H-5,8-methano-2λ⁵,10λ⁵-furo[3,2-1][1,3,6,9,11,2,10]pentaoxadiphosphacyclotetradecine-2,10-dione To a solution of diastereomer 2 (more polar) obtained in step 7 of Example 12 (56.5 mg) in methanol (1.00 mL), 40% aqueous solution of methylamine (1.00 mL) was added, and the reaction mixture was stirred in a sealed tube at 60° C. for 3 hours. The reaction mixture was concentrated under reduced pressure to afford a mixture containing the title compound. The mixture obtained was directly used for the subsequent reaction.

MS(ESI)m/z: 1002 (M+H)⁺.

(Step 2)

Disodium (5R,7R,8R,12aR,14R,15R,15aS,16R)-15,16-dihydroxy-7-[2-(hydroxymethyl)-6-(methylamino)-9H-purin-9-yl]-2,10-dioxo-14-(6,7,8,9-tetrahydro-2H-2,3,5,6-tetraazabenzo[cd]azulen-2-yl)octahydro-2H,10H,12H-5,8-methano-2λ⁵,10λ⁵-furo[3,2-1][1,3,6,9,11,2,10]pentaoxadiphosphacyclotetradecine-2,10-bis(thiolate)

With use of the mixture obtained in the above step 1, the reaction was performed in the same manner as in step 11 of Example 1, and the resultant was then purified by preparative HPLC [10 mM aqueous solution of triethylammonium acetate/acetonitrile, acetonitrile: 2%-20% (0 min-30 min)] to afford the title compound as a triethylamine salt.

The triethylamine salt obtained was subjected to salt exchange in the same manner as in [Conversion to Sodium Salt] described in step 11 of Example 1 to afford the title compound (16.0 mg).

MS(ESI)m/z: 774 (M+H)⁺.

¹H-NMR (CD₃OD) δ: 8.70 (1H, s), 8.02 (1H, s), 7.13 (1H, s), 6.38 (1H, d, J=9.1 Hz), 6.33 (1H, d, J=7.3 Hz), 5.49-5.42 (2H, m), 4.80 (1H, dd, J=6.7, 4.2 Hz), 4.60 (2H, s), 4.50-4.28 (5H, m), 4.05-4.00 (1H, m), 3.92-3.87 (1H, m), 3.52-3.49 (2H, m), 3.14 (3H, brs), 2.91 (2H, t, J=5.4 Hz), 2.04-1.99 (2H, m).

³¹P-NMR (CD₃OD) δ: 63.1 (s), 60.3 (s).

Example 42: Synthesis of CDN32
(5R,7R,8R,12aR,14R,15aS,16R)-16-Hydroxy-7-[1-(2-hydroxyethyl)-6-oxo-1,6-dihydro-9H-purin-9-yl]-2,10-bis(sulfanyl)-14-(6,7,8,9-tetrahydro-2H-2,3,5,6-tetraazabenzo[cd]azulen-2-yl)octahydro-2H,10H,12H-5,8-methano-2$\lambda^5$,10$\lambda^5$-furo[3,2-l][1,3,6,9,11,2,10]pentaoxadiphosphacyclotetradecine-2,10-dione
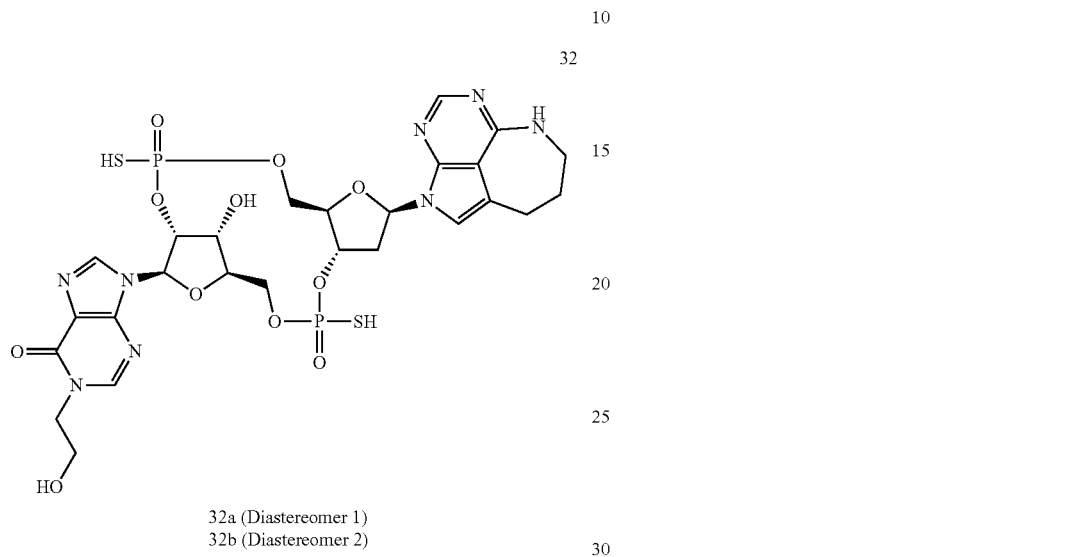
32a (Diastereomer 1)
32b (Diastereomer 2)
[Synthesis Scheme]
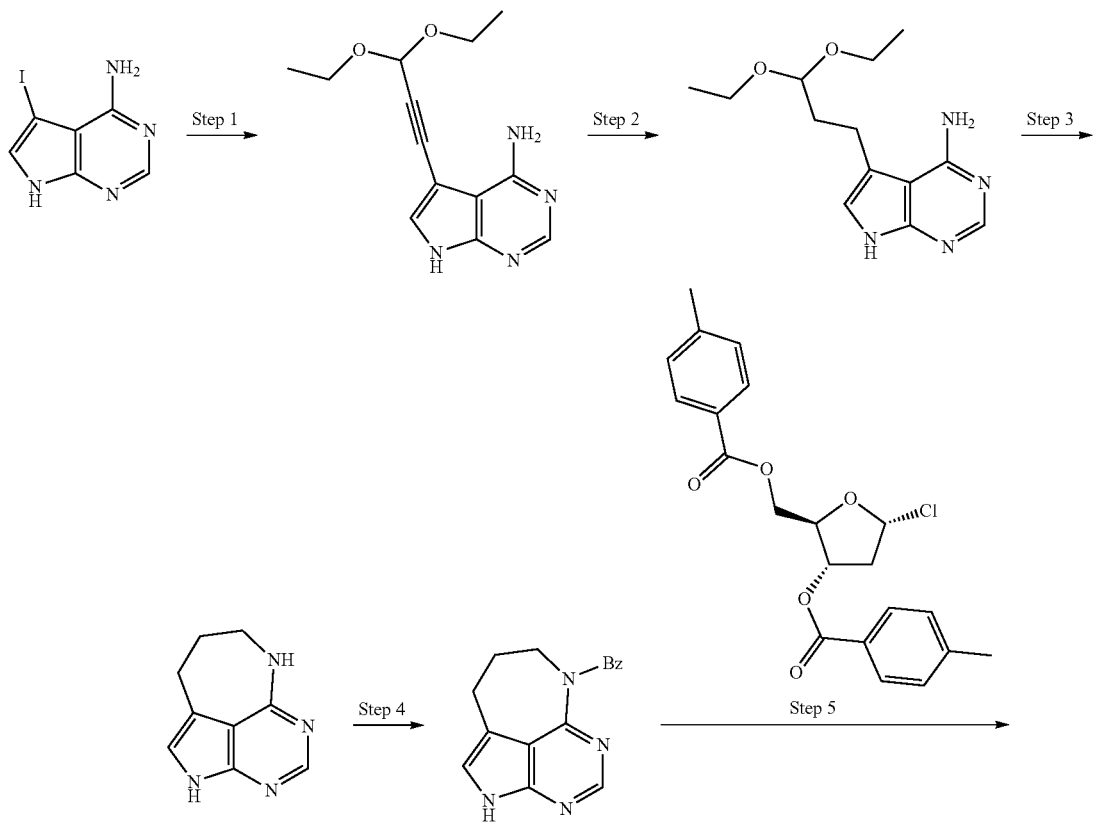

387  388
-continued
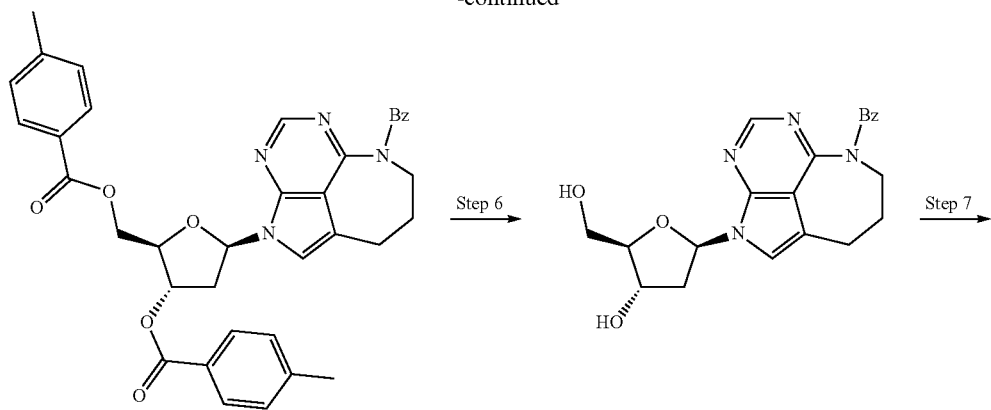
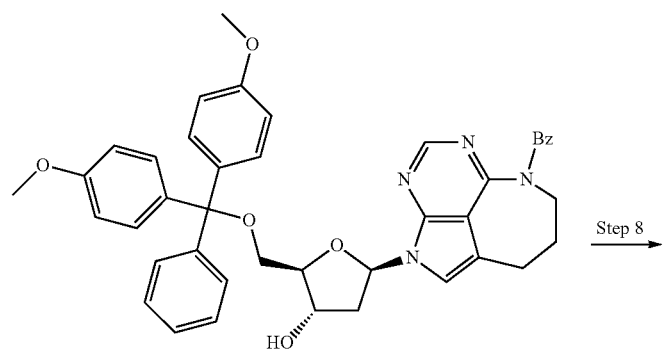
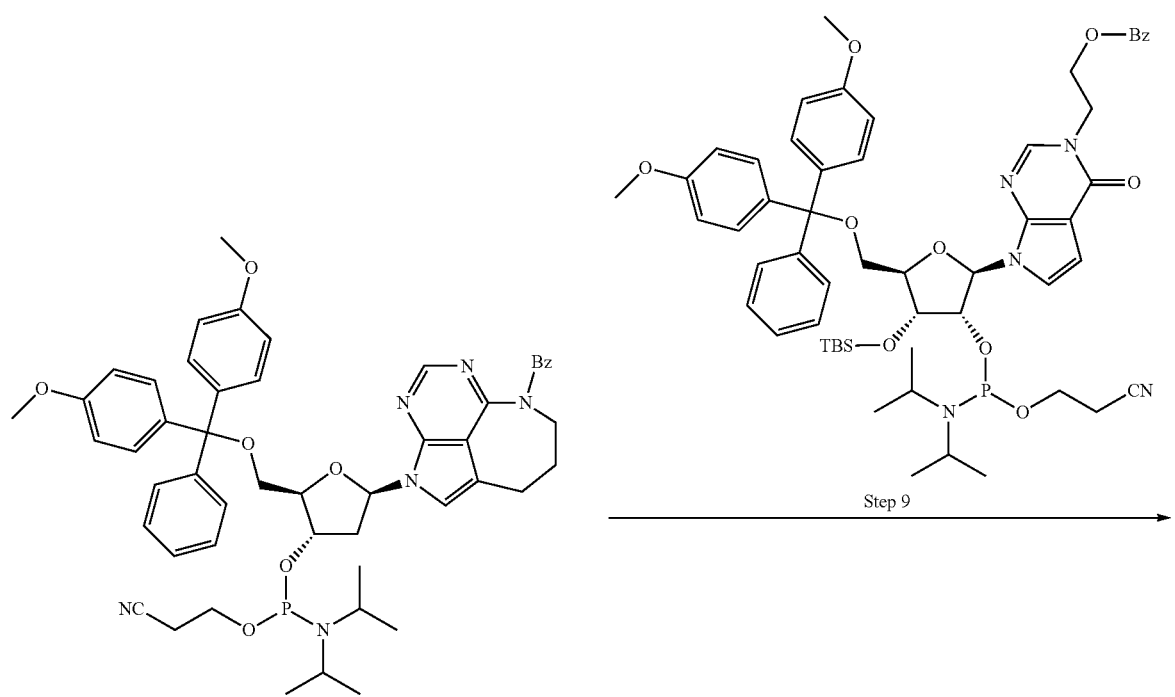

-continued
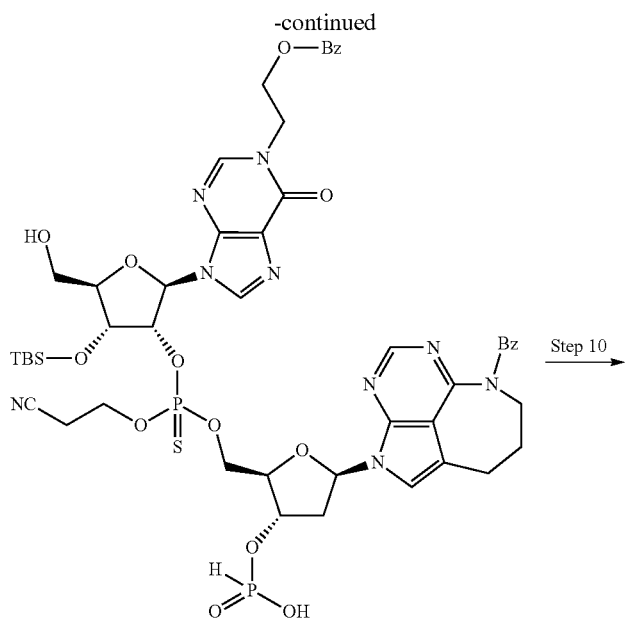
Step 10
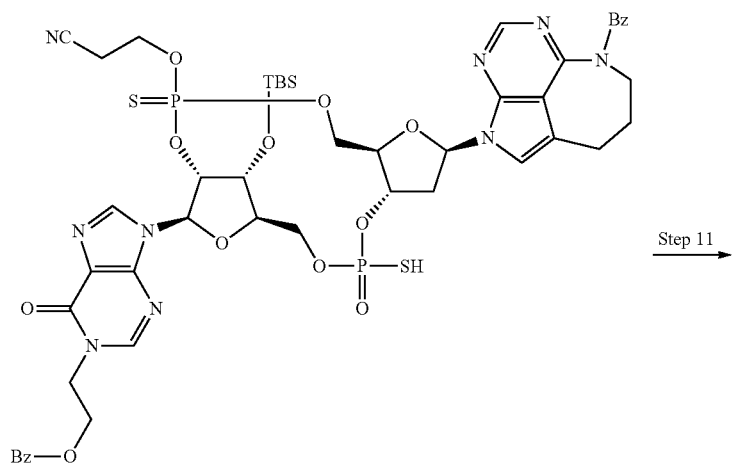
Step 11
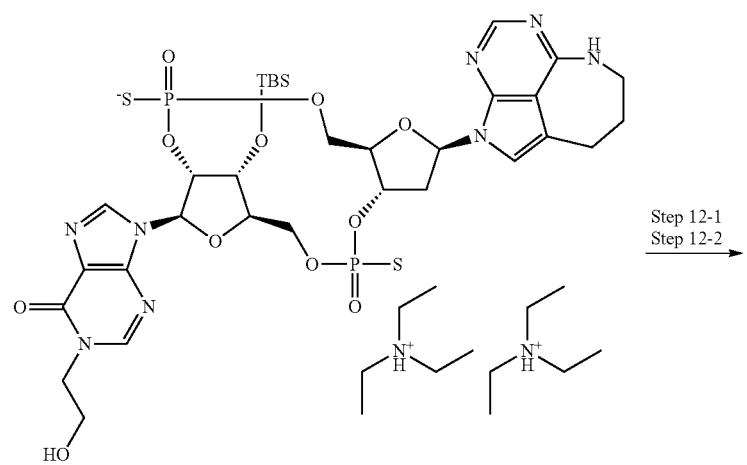
Step 12-1
Step 12-2

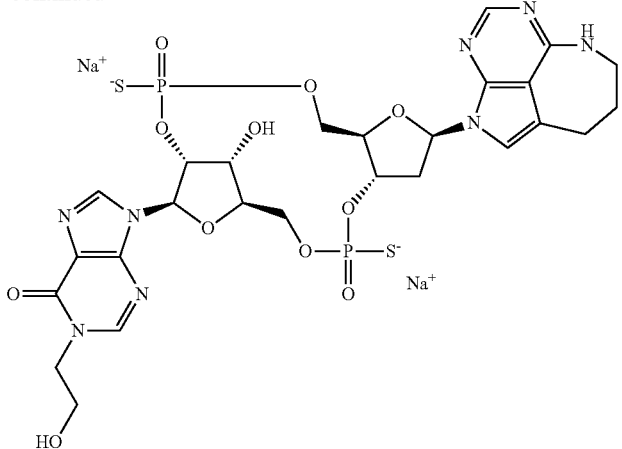

(Step 1)

5-(3,3-Diethoxyprop-1-yn-1-yl)-7H-pyrrolo[2,3-d]pyrimidin-4-amine

To a solution of commercially available (PharmaBlock Sciences (Nanjing), Inc.) 5-iodo-7H-pyrrolo[2,3-d]pyrimidin-4-amine (22 g) in N,N-dimethylformamide (70 mL), copper iodide (1.61 g), bis(triphenylphosphine) palladium dichloride (5.94 g), and triethylamine (35 mL) were added. Propargylaldehyde diethyl acetal (22 mL) was added thereto over 2 hours, and the reaction mixture was stirred at room temperature overnight. Chloroform (350 mL) was added to the reaction mixture, which was washed twice with water. After drying the organic layer with magnesium sulfate, the drying agent was removed through filtration, and the filtrate was concentrated under reduced pressure. Ethyl acetate (350 mL) was added to the residue, and the resultant was stirred overnight. A solid precipitated was collected through filtration to give the title compound (9.60 g).

MS(ESI)m/z: 261 (M+H)$^+$.

$^1$H-NMR (DMSO-d$_6$) δ: 12.04 (1H, brs), 8.11 (1H, brs), 7.57 (1H, s), 6.56 (2H, brs), 5.59 (1H, s), 3.68 (2H, m), 3.57 (2H, m), 1.17 (6H, t, J=7.3 Hz).

(Step 2)

5-(3,3-Diethoxypropyl)-7H-pyrrolo[2,3-d]pyrimidin-4-amine

To a mixed solution of the compound (17.9 g) obtained in the above step 1 in tetrahydrofuran (160 mL)-ethanol (80 mL), 10% palladium-carbon (M) wet (25.0 g) was added, and the reaction mixture was stirred under the hydrogen atmosphere at room temperature overnight. The catalyst was removed through filtration with a Celite, and the filtrate was concentrated under reduced pressure to afford a crude form of the title compound (17.0 g).

MS(ESI)m/z: 265 (M+H)$^+$.

(Step 3)

6,7,8,9-Tetrahydro-2H-2,3,5,6-tetraazabenzo[cd]azulene

The compound (50.21 g) obtained in the above step 2 was dissolved in 90% aqueous solution of acetic acid (344 mL), and the reaction mixture was stirred at 50° C. overnight. After confirming the disappearance of the raw material, palladium-carbon (M) wet (60 g) was added to the reaction mixture, which was stirred under the hydrogen atmosphere at 40° C. overnight. The catalyst was removed through filtration with a Celite, and the filtrate was concentrated under reduced pressure. A saturated aqueous solution of sodium hydrogen carbonate (350 mL) was added to the residue, and the resultant was subjected seven times to extraction with chloroform/methanol (9:1). The organic layer was concentrated under reduced pressure, and the residue was then purified by silica gel column chromatography [chloroform/methanol] to afford the title compound (18.47 g).

MS(ESI)m/z: 175 (M+H)$^+$.

$^1$H-NMR (DMSO-d$_6$) δ: 11.26 (1H, brs), 7.97 (1H, s), 7.37 (1H, brs), 6.86 (1H, brs), 3.35 (2H, m), 2.80 (2H, t, J=5.4 Hz), 1.88 (2H, m).

(Step 4)

Phenyl(2,7,8,9-tetrahydro-6H-2,3,5,6-tetraazabenzo[cd]azulen-6-yl) methanone

To a suspension of the compound (8.47 g) obtained in the above step 3 in dichloromethane (120 mL), dehydrated pyridine (39.2 mL), N,N-dimethylaminopyridine (2.38 g), and benzoyl chloride (22.6 mL) were added in this order, and the reaction mixture was stirred at room temperature for 1 hour. After the reaction mixture was concentrated under reduced pressure, chloroform (150 mL), methanol (60 mL), and triethylamine (50 mL) were added to the residue, and the resultant was stirred at room temperature for 3 hours. The reaction mixture was poured into a two-layer mixture of chloroform and water, and subjected to extraction with chloroform. The organic layer was washed twice with 25 w/v % aqueous solution of potassium hydrogen sulfate, and dried over anhydrous magnesium sulfate. The drying agent was removed through filtration, and the filtrate was concentrated under reduced pressure. Ethyl acetate (50 mL) and hexane (125 mL) were added in this order to the residue to make a slurry, which was then stirred for 1 hour. A solid precipitated was collected through filtration to give the title compound (9.89 g).

MS(ESI)m/z: 279 (M+H)$^+$.

$^1$H-NMR (CDCl$_3$) δ: 10.07 (1H, brs), 8.11 (1H, s), 7.39-7.21 (5H, m), 7.12 (1H, s), 4.32 (2H, m), 3.06 (2H, m), 2.26 (2H, m).

(Step 5)

6-Benzoyl-2-[2-deoxy-3,5-bis-O-(4-methylbenzoyl)-β-D-erythro-pentofuranosyl]-6,7,8,9-tetrahydro-2H-2,3,5,6-tetraazabenzo[cd]azulene To a suspension of the compound (7.10 g) obtained in the above step 4 in acetonitrile (80 mL), powdery potassium hydroxide (2.9 g) and tris [2-(2-methoxyethoxy)ethyl]amine (0.41 mL) were added under the nitrogen atmosphere, and the reaction mixture was stirred at room temperature for 15 minutes. Under ice-cooling, 2-deoxy-3,5-bis-O-(4-methylbenzoyl)-α-D-erythro-pentofuranosyl chloride (10.12 g) as a compound known in the literature (Synlett 2004 (2): 335-337) and acetonitrile (60 mL) were added thereto, the temperature was increased to room temperature, and the reaction mixture was stirred overnight. A saturated aqueous solution of ammonium chloride was added to the reaction mixture to quench the reaction. A solid precipitated was collected through filtration, and then washed with water to give the title compound (9.70 g).
MS(ESI)m/z: 631 (M+H)$^+$.
$^1$H-NMR (CDCl$_3$) δ: 8.10 (1H, s), 8.00-7.96 (4H, m), 7.37-7.22 (9H, m), 7.10 (1H, s), 6.88 (1H, dd, J=8.5, 5.4 Hz), 5.76 (1H, m), 4.77 (1H, dd, J=11.8, 3.9 Hz), 4.65-4.57 (2H, m), 4.32 (1H, m), 4.20 (1H, m), 2.90-2.78 (3H, m), 2.73 (1H, ddd, J=2.1, 5.7, 8.5 Hz), 2.44 (6H, s), 2.19 (2H, m).

(Step 6)

6-Benzoyl-2-(2-deoxy-β-D-erythro-pentofuranosyl)-6,7,8,9-tetrahydro-2H-2,3,5,6-tetraazabenzo[cd]azulene To a mixed solution of the compound (8.69 g) obtained in the above step 5 in methanol (45 mL)-tetrahydrofuran (135 mL), 2 N aqueous solution of sodium hydroxide (27.6 mL) was added dropwise at −10° C. over 20 minutes. After stirring at the same temperature for 2 hours, 1 N hydrochloric acid (58 mL) was added thereto to quench the reaction. After the reaction mixture was concentrated under reduced pressure, the residue was purified by silica gel column chromatography [chloroform/methanol] to afford the title compound (4.09 g).
MS(ESI)m/z: 395 (M+H)$^+$.
$^1$H-NMR (CDCl$_3$) δ: 8.04 (1H, s), 7.39-7.23 (5H, m), 7.05 (1H, s), 6.27 (1H, dd, J=9.7, 5.4 Hz), 6.00 (1H, d, J=10.9 Hz), 4.77 (1H, d, J=4.8 Hz), 4.41 (1H, dd, J=14.5, 7.9 Hz), 4.19 (1H, $), 4.15 (1H, dd, J=14.5, 7.9 Hz), 3.94 (1H, d, J=12.7 Hz), 3.74 (1H, m), 3.16-2.95 (3H, m), 2.30-2.14 (3H, m), 1.96 (1H, s).

(Step 7)

6-Benzoyl-2-{5-O-[bis(4-methoxyphenyl)(phenyl)methyl]-2-deoxy-β-D-erythro-pentofuranosyl}-6,7,8,9-tetrahydro-2H-2,3,5,6-tetraazabenzo[cd]azulene With use of the compound (4.55 g) obtained in the above step 6, the reaction was performed in the same manner as in step 1 of Example 11 to afford the title compound (6.38 g).
MS(ESI)m/z: 697 (M+H)$^+$.
$^1$H-NMR (CDCl$_3$) δ: 8.08 (1H, s), 7.43 (2H, d, J=7.9 Hz), 7.36-7.19 (13H, m), 6.84-6.76 (5H, m), 4.66 (1H, brs), 4.31 (1H, m), 4.21 (1H, m), 4.07 (1H, m), 3.79 (6H, s), 3.44 (1H, dd, J=10.0, 3.9 Hz), 3.38 (1H, dd, J=10.3, 4.8 Hz), 2.85 (2H, t, J=6.3 Hz), 2.66 (1H, m), 2.47 (1H, ddd, J=4.1, 6.5, 13.9 Hz), 2.18 (2H, m). (only observable peaks are shown)

(Step 8)

6-Benzoyl-2-(5-O-[bis(4-methoxyphenyl)(phenyl)methyl]-3-O-{(2-cyanoethoxy)[di(propan-2-yl)amino]phosphanyl}-2-deoxy-β-D-erythro-pentofuranosyl)-6,7,8,9-tetrahydro-2H-2,3,5,6-tetraazabenzo[cd]azulene With use of the compound (6.37 g) obtained in the above step 7, the reaction was performed in the same manner as in step 6 of Example 1 to afford the title compound (6.05 g) as a mixture of diastereomers (diastereomer ratio=1:1).
$^1$H-NMR (CDCl$_3$) δ: 8.09 (0.5H, s), 8.08 (0.5H, s), 7.46-7.41 (2H, m), 7.35-7.19 (13H, m), 6.84-6.75 (5H, m), 4.82-4.76 (1H, m), 4.35-4.19 (3H, m), 3.89-3.54 (4H, m), 3.79 (1.5H, s), 3.79 (1.5H, s), 3.78 (1.5H, s), 3.78 (1.5H, s), 3.42 (1H, td, J=9.8, 3.8 Hz), 3.38-3.30 (1H, m), 2.81 (2H, t, J=6.3 Hz), 2.74-2.66 (1H, m), 2.63-2.49 (1H, m), 2.62 (1H, t, J=6.0 Hz), 2.45 (1H, t, J=6.3 Hz), 2.21-2.14 (2H, m), 1.20-1.17 (9H, m), 1.11 (3H, d, J=6.7 Hz).

(Step 9)

With use of the compound (868 mg) obtained in the above step 8, the reaction was performed in the same manner as in step 7 of Example 1 to afford an acetonitrile solution of 6-benzoyl-2-{2-deoxy-3-O-[hydroxy (oxo)-λ$^5$-phosphanyl]-β-D-erythro-pentofuranosyl}-6,7,8,9-tetrahydro-2H-2,3,5,6-tetraazabenzo[cd]azulene. With use of this acetonitrile solution and the compound (1.00 g) obtained in step 3 of Example 22, the reaction was performed in the same manner as in step 8 of Example 1, and the resulting crude product was directly used for the subsequent reaction.

(Step 10)

2-{9-[(5R,7R,8R,12aR,14R,15aS,16R)-14-(6-Benzoyl-6,7,8,9-tetrahydro-2H-2,3,5,6-tetraazabenzo[cd]azulen-2-yl)-16-{[tert-butyl(dimethyl)silyl]oxy}-10-(2-cyanoethoxy)-2-oxo-2-sulfanyl-10-sulfanylideneoctahydro-2H,10H,12H-5,8-methano-2λ$^5$,10λ$^5$-furo[3,2-1][1,3,6,9,11,2,10]pentaoxadiphosphacyclotetradecin-7-yl]-6-oxo-6,9-dihydro-1H-purin-1-yl}ethyl benzoate With use of the crude product obtained in step 9, the reaction was performed in the same manner as in the above step 9 of Example 1 to afford the title compound (702 mg) as a mixture of diastereomers at the phosphorus atom.
MS(ESI)m/z: 1134 (M+H)$^+$.

(Step 11)

Bis(N,N-diethylethaneaminium) (5R,7R,8R,12aR,14R,15aS,16R)-16-{[tert-butyl(dimethyl)silyl]oxy}-7-[1-(2-hydroxyethyl)-6-oxo-1,6-dihydro-9H-purin-9-yl]-2,10-dioxo-14-(6,7,8,9-tetrahydro-2H-2,3,5,6-tetraazabenzo[cd]azulen-2-yl)octahydro-2H,10H,12H-5,8-methano-2λ$^5$,10λ$^5$-furo[3,2-1][1,3,6,9,11,2,10]pentaoxadiphosphacyclotetradecine-2,10-bis(thiolate)

With use of the compound (702 mg) obtained in the above step 10, the reaction was performed in the same manner as in step 10 of Example 1 to afford diastereomer 1 (119 mg: with impurities) and diastereomer 2 (113 mg: with impurities) of the title compound.
Diastereomer 1 (Less Polar)
MS(ESI)m/z: 873 (M+H)$^+$.
Diastereomer 2 (More Polar)
MS(ESI)m/z: 873 (M+H)$^+$.

(Step 12-1)

Disodium (5R,7R,8R,12aR,14R,15aS,16R)-16-hydroxy-7-[1-(2-hydroxyethyl)-6-oxo-1,6-dihydro-9H-purin-9-yl]-2,10-dioxo-14-(6,7,8,9-tetrahydro-2H-2,3,5,6-tetraazabenzo[cd]azulen-2-yl)octahydro-2H,10H,12H-5,8-methano-2λ$^5$,10λ$^5$-furo[3,2-1][1,3,6,9,11,2,10]pentaoxadiphosphacyclotetradecine-2,10-bis(thiolate)

(Diastereomer 1)

With use of the compound (diastereomer 1) (119 mg: with impurities) obtained in the above step 11, the reaction was performed in the same manner as in step 11 of Example 1, and purification was then performed under the following [Purification Conditions] to afford the title compound as a triethylamine salt.

[Purification Conditions] C18 silica gel column chromatography [10 mM aqueous solution of triethylammonium acetate/acetonitrile] and preparative HPLC [10 mM aqueous solution of triethylammonium acetate/acetonitrile, acetonitrile: 5%-30% (0 min-40 min)].

The triethylamine salt obtained was subjected to salt exchange in the same manner as in [Conversion to Sodium Salt] described in step 11 of Example 1 to afford the title compound (51.8 mg).

MS(ESI)m/z: 759 (M+H)$^+$.

$^1$H-NMR (CD$_3$OD) δ: 8.69 (1H, s), 8.24 (1H, s), 8.02 (1H, s), 7.09 (1H, s), 6.68 (1H, t, J=7.0 Hz), 6.29 (1H, d, J=8.5 Hz), 5.36-5.27 (2H, m), 4.75-4.71 (1H, m), 4.41-4.30 (3H, m), 4.28-4.12 (3H, m), 4.06-4.00 (1H, m), 3.94-3.84 (1H, m), 3.82 (2H, t, J=4.8 Hz), 3.52-3.47 (2H, m), 2.91-2.69 (4H, m), 2.04-1.96 (2H, m).

$^{31}$P-NMR (CD$_3$OD) δ: 57.3 (s), 54.9 (s).

(Step 12-2)

Disodium (5R,7R,8R,12aR,14R,15aS,16R)-16-hydroxy-7-[1-(2-hydroxyethyl)-6-oxo-1,6-dihydro-9H-purin-9-yl]-2,10-dioxo-14-(6,7,8,9-tetrahydro-2H-2,3,5,6-tetraazabenzo[cd]azulen-2-yl)octahydro-2H,10H,12H-5,8-methano-2λ$^5$,10λ$^5$-furo[3,2-1][1,3,6,9,11,2,10]pentaoxadiphosphacyclotetradecine-2,10-bis(thiolate)

(Diastereomer 2)

With use of the compound (diastereomer 2) (113 mg: with impurities) obtained in the above step 11, the reaction was performed in the same manner as in step 11 of Example 1, and purification was then performed under the following [Purification Conditions] to afford the title compound as a triethylamine salt.

[Purification Conditions] C18 silica gel column chromatography [10 mM aqueous solution of triethylammonium acetate/acetonitrile] and preparative HPLC [10 mM aqueous solution of triethylammonium acetate/acetonitrile, acetonitrile: 5%-25% (0 min-40 min)].

The triethylamine salt obtained was subjected to salt exchange in the same manner as in [Conversion to Sodium Salt] described in step 11 of Example 1 to afford the title compound (65.4 mg).

MS(ESI)m/z: 759 (M+H)$^+$.

$^1$H-NMR (CD$_3$OD) δ: 8.78 (1H, s), 8.24 (1H, s), 8.02 (1H, s), 7.08 (1H, s), 6.73 (1H, dd, J=9.1, 5.4 Hz), 6.29 (1H, d, J=8.5 Hz), 5.59-5.52 (1H, m), 5.45-5.37 (1H, m), 4.45 (1H, d, J=4.2 Hz), 4.40-4.16 (6H, m), 4.01 (1H, d, J=12.7 Hz), 3.87-3.75 (3H, m), 3.53-3.46 (2H, m), 2.93-2.88 (2H, m), 2.87-2.65 (2H, m), 2.06-1.96 (2H, m).

$^{31}$P-NMR (CD$_3$OD) δ: 63.1 (s), 57.3 (s).

Example 43: Synthesis of CDN33

(5R,7R,8R,12aR,14R,15S,15aR,16R)-15-Fluoro-16-hydroxy-7-[1-(2-hydroxyethyl)-6-oxo-1,6-dihydro-9H-purin-9-yl]-2,10-bis(sulfanyl)-14-(6,7,8,9-tetrahydro-2H-2,3,5,6-tetraazabenzo[cd]azulen-2-yl)octahydro-2H,10H,12H-5,8-methano-2λ$^5$,10λ$^5$-furo[3,2-1][1,3,6,9,11,2,10]pentaoxadiphosphacyclotetradecine-2,10-dione

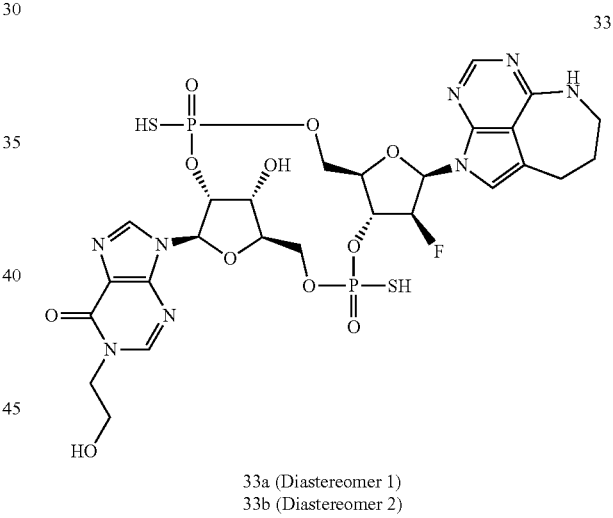

33
33a (Diastereomer 1)
33b (Diastereomer 2)

[Synthesis Scheme]

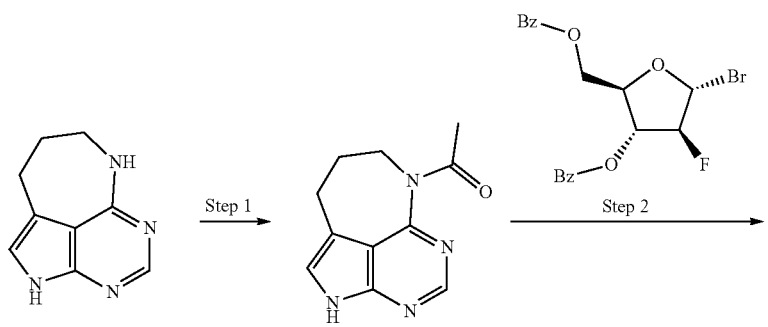

-continued
397          398
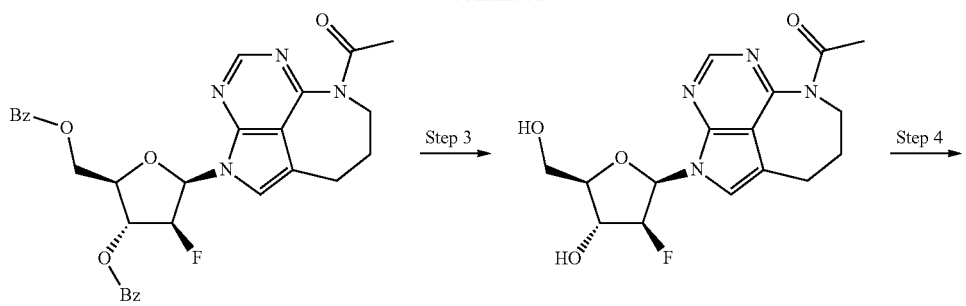
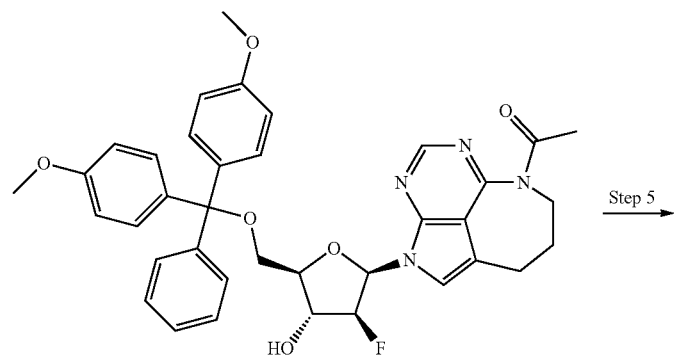
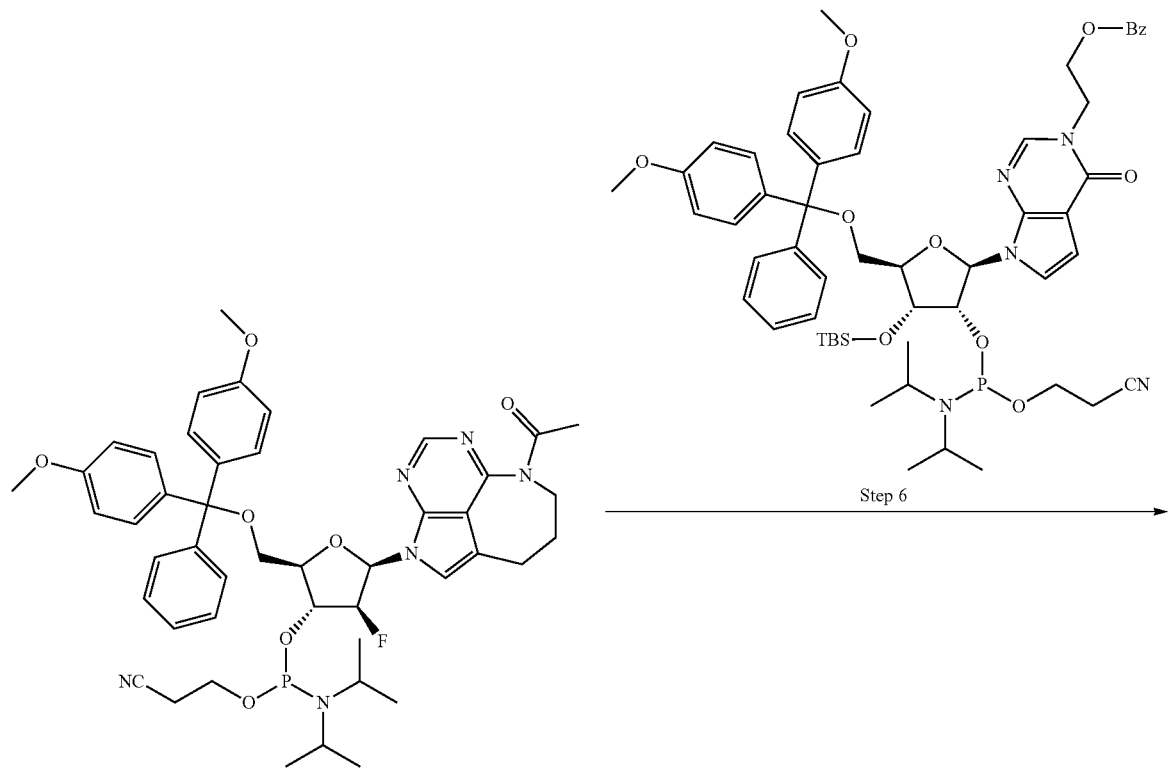

-continued
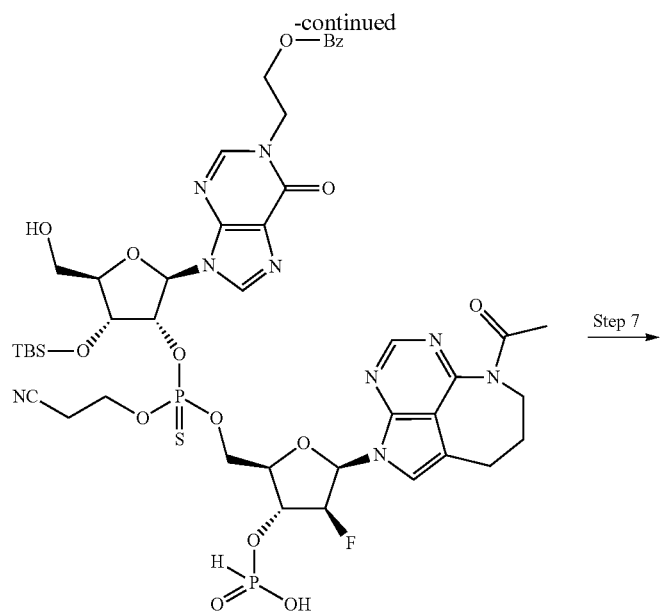
Step 7
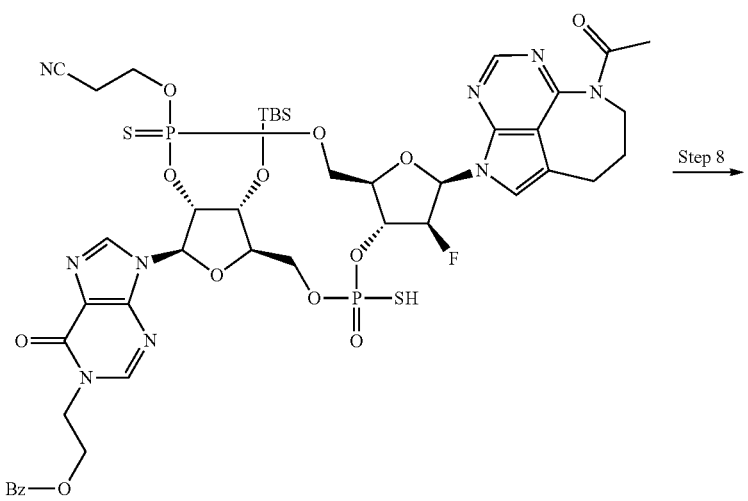
Step 8
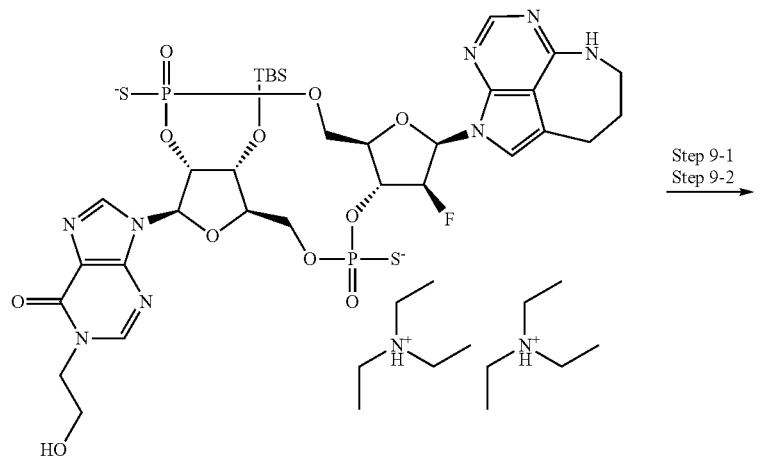
Step 9-1
Step 9-2

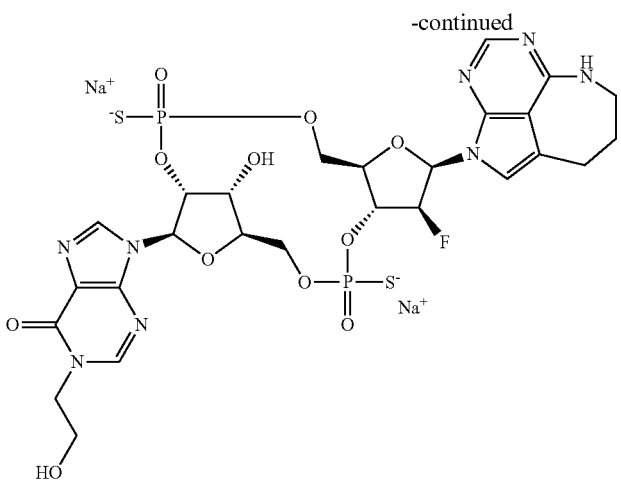

(Step 1)

1-(2,7,8,9-Tetrahydro-6H-2,3,5,6-tetraazabenzo[cd]azulen-6-yl) ethan-1-one

The compound (6.88 g) obtained in step 3 of Example 42 was dissolved in acetic anhydride (48 mL), and the reaction mixture was stirred at 90° C. The reaction mixture was concentrated under reduced pressure, and the residue was dissolved in a mixture of chloroform (100 mL)-methanol (50 mL)-triethylamine (30 mL). After stirring at room temperature for 4 hours, the reaction mixture was poured into a two-layer mixture of chloroform and water, and subjected to extraction with chloroform. After the organic layer was dried over magnesium sulfate, the drying agent was removed through filtration, and the filtrate was concentrated under reduced pressure. Hexane/ethyl acetate (1:2) was added to the residue to make a slurry, and the solid was then collected through filtration to give the title compound (7.18 g).

MS(ESI)m/z: 217 (M+H)$^+$.

$^1$H-NMR (CD$_3$OD) δ: 8.47 (1H, s), 7.21 (1H, s), 4.11 (2H, d, J=8.5 Hz), 2.97 (2H, t, J=6.3 Hz), 2.46 (3H, s), 2.06 (2H, m).

(Step 2)

6-Acetyl-2-(3,5-di-O-benzoyl-2-deoxy-2-fluoro-β-D-arabinofuranosyl)-6,7,8,9-tetrahydro-2H-2,3,5,6-tetraazabenzo[cd]azulene With use of the compound (6.00 g) obtained in the above step 1 and commercially available (Carbosynth Limited) [(2R,3R,4S,5R)-3-benzoyloxy-5-bromo-4-fluoro-tetrahydrofuran-2-yl]methyl benzoate (14.1 g), the reaction was performed in the same manner as in step 5 of Example 42 to afford the title compound (11.45 g).

MS(ESI)m/z: 559 (M+H)$^+$.

$^1$H-NMR (CDCl$_3$) δ: 8.58 (1H, s), 8.12 (4H, t, J=7.3 Hz), 7.69-7.44 (6H, m), 7.28 (1H, d, J=2.4 Hz), 6.92 (1H, dd, J=23.3, 2.7 Hz), 5.77 (1H, dd, J=17.5, 3.0 Hz), 5.34 (1H, dd, J=50.2, 3.0 Hz), 4.83 (2H, dd, J=11.8, 4.5 Hz), 4.76 (2H, dd, J=11.8, 5.1 Hz), 4.56 (1H, m), 4.14 (2H, m), 2.90 (2H, t, J=6.7 Hz), 2.07 (3H, s).

(Step 3)

6-Acetyl-2-(2-deoxy-2-fluoro-β-D-arabinofuranosyl)-6,7,8,9-tetrahydro-2H-2,3,5,6-tetraazabenzo[cd]azulene To a mixed solution of the compound (8.70 g) obtained in the above step 2 in methanol (58 mL)-tetrahydrofuran (117 mL), 2 N aqueous solution of sodium hydroxide (32 mL) was added dropwise at −20° C. over 12 minutes. After stirring at the same temperature for 3 hours, 1 N hydrochloric acid (66 mL) was added thereto to quench the reaction. The reaction mixture was concentrated under reduced pressure, and the residue was then purified by silica gel column chromatography [chloroform/methanol] to afford the title compound (3.27 g).

MS(ESI)m/z: 351 (M+H)$^+$.

$^1$H-NMR (CDCl$_3$) δ: 8.54 (1H, s), 7.20 (1H, d, J=1.8 Hz), 6.68 (1H, dd, J=17.5, 4.2 Hz), 5.16 (1H, ddd, J=52.0, 2.4, 1.2 Hz), 4.75 (1H, ddd, J=19.2, 2.6, 1.3 Hz), 4.16 (1H, m), 4.08 (2H, m), 3.99 (1H, dd, J=12.1, 3.6 Hz), 3.92 (1H, dd, J=12.1, 4.2 Hz), 2.93 (2H, m), 2.52 (3H, s), 2.07 (2H, m). (only observable peaks are shown)

(Step 4)

6-Acetyl-2-{5-O-[bis(4-methoxyphenyl)(phenyl)methyl]-2-deoxy-2-fluoro-β-D-arabinofuranosyl}-6,7,8,9-tetrahydro-2H-2,3,5,6-tetraazabenzo[cd]azulene With use of the compound (3.95 g) obtained in the above step 3 (3.95 g), the reaction was performed in the same manner as in step 1 of Example 11 to afford the title compound (5.66 g).

MS(ESI)m/z: 653 (M+H)$^+$.

$^1$H-NMR (CDCl$_3$) δ: 8.56 (1H, s), 7.50-7.20 (10H, m), 6.85-6.78 (5H, m), 5.07 (1H, dt, J=51.8, 3.2 Hz), 4.59 (1H, brd, J=18.1 Hz), 4.21-4.02 (3H, m), 3.80 (3H, s), 3.79 (3H, s), 3.50 (1H, dd, J=10.3, 5.4 Hz), 3.44 (1H, dd, J=10.0, 5.1 Hz), 2.88 (2H, m), 2.54 (3H, s), 2.42 (1H, brs), 2.07 (2H, m).

(Step 5)

6-Acetyl-2-(5-O-[bis(4-methoxyphenyl)(phenyl)methyl]-3-O-{(2-cyanoethoxy)[di(propan-2-yl)amino]phosphanyl}-2-deoxy-2-fluoro-β-D-arabinofuranosyl)-6,7,8,9-tetrahydro-2H-2,3,5,6-tetraazabenzo[cd]azulene With use of the compound (5.68 g) obtained in the above step 4, the reaction was performed in the same manner as in step 6 of Example 1 to afford the title compound (5.08 g) as a mixture of diastereomers at the phosphorus atom (diastereomer ratio=1:1).

MS(ESI)m/z: 853 (M+H)$^+$.

$^1$H-NMR (CDCl$_3$) δ: 8.58 (0.5H, s), 8.57 (0.5H, s), 7.51-7.20 (10H, m), 6.85-6.76 (5H, m), 5.24-5.02 (1H, m), 4.76-4.60 (1H, m), 4.21-4.05 (3H, m), 3.91-3.74 (1H, m), 3.80 (1.5H, s), 3.79 (1.5H, s), 3.79 (1.5H, s), 3.79 (1.5H, s), 3.69-3.55 (3H, m), 3.49-3.37 (2H, m), 2.95-2.80 (2H, m), 2.61 (1H, t, J=6.3 Hz), 2.54 (3H, s), 2.43 (1H, t, J=6.7 Hz), 2.11-2.03 (2H, m), 1.21-1.17 (9H, m), 1.11 (3H, d, J=7.3 Hz).

(Step 6)

With use of the compound (1.00 g) obtained in the above step 5, the reaction was performed in the same manner as in step 7 of Example 1 to afford an acetonitrile solution of 6-acetyl-2-{2-deoxy-2-fluoro-3-O-[hydroxy (oxo)-λ$^5$-phosphanyl]-β-D-arabinofuranosyl}-6,7,8,9-tetrahydro-2H-2,3,5,6-tetraazabenzo[cd]azulene. With use of this acetonitrile solution and the compound (1.21 g) obtained in step 3 of Example 22, the reaction was performed in the same manner as in step 8 of Example 1, and the resulting crude product was directly used for the subsequent reaction.

(Step 7)

2-{9-[(5R,7R,8R,12aR,14R,15S,15aR,16R)-14-(6-Acetyl-6,7,8,9-tetrahydro-2H-2,3,5,6-tetraazabenzo[cd]azulen-2-yl)-16-{[tert-butyl(dimethyl)silyl]oxy}-10-(2-cyanoethoxy)-15-fluoro-2-oxo-2-sulfanyl-10-sulfanylideneoctahydro-2H, 10H,12H-5,8-methano-2λ$^5$,10λ$^5$-furo[3,2-1][1,3,6,9,11,2,10]pentaoxadiphosphacyclotetradecin-7-yl]-6-oxo-6,9-dihydro-1H-purin-1-yl}ethyl benzoate With use of the crude product obtained in the above step 6, the reaction was performed in the same manner as in step 9 of Example 1 to afford the title compound (757 mg) as a mixture of diastereomers at the phosphorus atom.

MS(ESI)m/z: 1090 (M+H)$^+$.

(Step 8)

Bis(N,N-diethylethaneaminium) (5R,7R,8R,12aR,14R,15S,15aR,16R)-16-{[tert-butyl(dimethyl)silyl]oxy}-15-fluoro-7-[1-(2-hydroxyethyl)-6-oxo-1,6-dihydro-9H-purin-9-yl]-2,10-dioxo-14-(6,7,8,9-tetrahydro-2H-2,3,5,6-tetraazabenzo[cd]azulen-2-yl)octahydro-2H,10H,12H-5,8-methano-2λ$^5$,10λ$^5$-furo[3,2-1][1,3,6,9,11,2,10]pentaoxadiphosphacyclotetradecine-2,10-bis(thiolate)

With use of the compound (757 mg) obtained in the above step 7, the reaction was performed in the same manner as in step 10 of Example 1 to afford diastereomer 1 (113 mg: with impurities) and diastereomer 2 (108 mg: with impurities) of the title compound.

Diastereomer 1 (Less Polar)

MS(ESI)m/z: 891 (M+H)$^+$.

Diastereomer 2 (More Polar)

MS(ESI)m/z: 891 (M+H)$^+$.

(Step 9-1)

Disodium (5R,7R,8R,12aR,14R,15S,15aR,16R)-15-fluoro-16-hydroxy-7-[1-(2-hydroxyethyl)-6-oxo-1,6-dihydro-9H-purin-9-yl]-2,10-dioxo-14-(6,7,8,9-tetrahydro-2H-2,3,5,6-tetraazabenzo[cd]azulen-2-yl)octahydro-2H,10H,12H-5,8-methano-2λ$^5$,10λ$^5$-furo[3,2-1][1,3,6,9,11,2,10]pentaoxadiphosphacyclotetradecine-2,10-bis(thiolate)

(Diastereomer 1)

With use of the compound (diastereomer 1) (113 mg: with impurities) obtained in the above step 8, the reaction was performed in the same manner as in step 11 of Example 1, and purification was then performed under the following [Purification Conditions] to afford the title compound as a triethylamine salt.

[Purification Conditions] C18 silica gel column chromatography [10 mM aqueous solution of triethylammonium acetate/acetonitrile] and preparative HPLC [10 mM aqueous solution of triethylammonium acetate/acetonitrile, acetonitrile: 5%-30% (0 min-30 min)].

The triethylamine salt obtained was subjected to salt exchange in the same manner as in [Conversion to Sodium Salt] described in step 11 of Example 1 to afford the title compound (28.8 mg).

MS(ESI)m/z: 777 (M+H)$^+$.

$^1$H-NMR (CD$_3$OD) δ: 8.67 (1H, s), 8.24 (1H, s), 8.04 (1H, s), 7.05 (1H, s), 6.73 (1H, dd, J=23.9, 2.7 Hz), 6.28 (1H, d, J=8.5 Hz), 5.43-5.24 (3H, m), 4.77-4.72 (1H, m), 4.51-4.32 (4H, m), 4.26-4.12 (2H, m), 4.06-3.91 (2H, m), 3.82 (2H, t, J=5.1 Hz), 3.50 (2H, t, J=5.1 Hz), 2.92-2.85 (2H, m), 2.06-1.97 (2H, m).

$^{31}$P-NMR (CD$_3$OD) δ: 57.8 (s), 54.7 (s).

(Step 9-2)

Disodium (5R,7R,8R,12aR,14R,15S,15aR,16R)-15-fluoro-16-hydroxy-7-[1-(2-hydroxyethyl)-6-oxo-1,6-dihydro-9H-purin-9-yl]-2,10-dioxo-14-(6,7,8,9-tetrahydro-2H-2,3,5,6-tetraazabenzo[cd]azulen-2-yl)octahydro-2H,10H,12H-5,8-methano-2λ$^5$,10λ$^5$-furo[3,2-1][1,3,6,9,11,2,10]pentaoxadiphosphacyclotetradecine-2,10-bis(thiolate)

(Diastereomer 2)

With use of the compound (diastereomer 2) (108 mg: with impurities) obtained in the above step 8, the reaction was performed in the same manner as in step 11 of Example 1, and purification was then performed under the following [Purification Conditions] to afford the title compound as a triethylamine salt.

[Purification Conditions] C18 silica gel column chromatography [10 mM aqueous solution of triethylammonium acetate/acetonitrile] and preparative HPLC [10 mM aqueous solution of triethylammonium acetate/acetonitrile, acetonitrile: 5%-20% (0 min-30 min)].

The triethylamine salt obtained was subjected to salt exchange in the same manner as in [Conversion to Sodium Salt] described in step 11 of Example 1 to afford the title compound (3.2 mg).

MS(ESI)m/z: 777 (M+H)$^+$.

$^1$H-NMR (CD$_3$OD) δ: 8.76 (1H, s), 8.23 (1H, s), 8.04 (1H, s), 7.06 (1H, s), 6.73 (1H, dd, J=24.5, 2.1 Hz), 6.28 (1H, d, J=8.5 Hz), 5.53-5.45 (1H, m), 5.43-5.27 (2H, m), 4.62-4.49 (1H, m), 4.45-4.41 (1H, m), 4.40-4.27 (2H, m), 4.27-4.15

(3H, m), 4.03-3.92 (2H, m), 3.87-3.78 (2H, m), 3.51 (2H, t, J=5.6 Hz), 2.90 (2H, t, J=5.6 Hz), 2.08-1.96 (2H, m).
$^{31}$P-NMR (CD$_3$OD) δ: 63.0 (s), 57.8 (s).
Example 44: Synthesis of CDN34
(5R,7R,8R,12aR,14R,15R,15aR,16R)-15-Fluoro-16-hydroxy-7-[1-(2-hydroxyethyl)-6-oxo-1,6-dihydro-9H-purin-9-yl]-2,10-bis(sulfanyl)-14-(6,7,8,9-tetrahydro-2H-2,3,5,6-tetraazabenzo[cd]azulen-2-yl)octahydro-2H,10H,12H-5,8-methano-2λ$^5$,10λ$^5$-furo[3,2-l][1,3,6,9,11,2,10]pentaoxadiphosphacyclotetradecine-2,10-dione
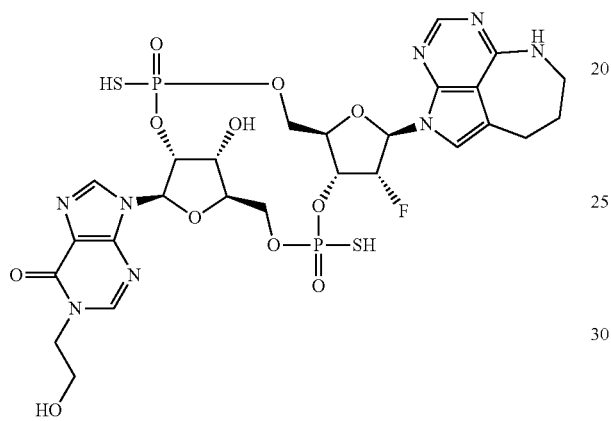
34a (Diastereomer 1)
34b (Diastereomer 2)
[Synthesis Scheme]
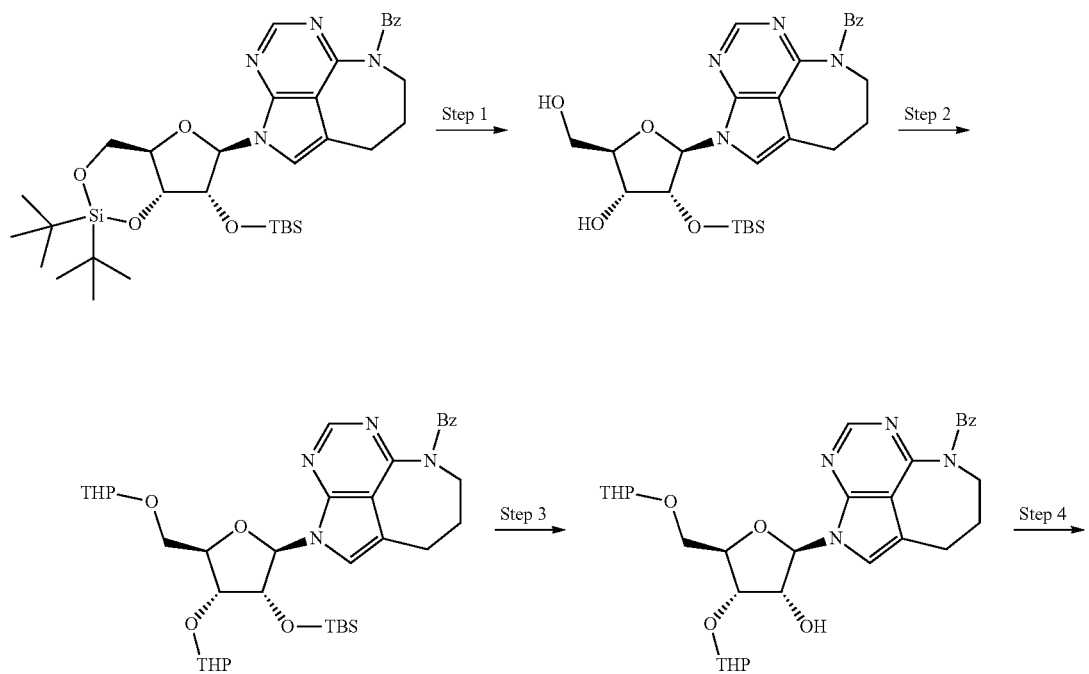

407           408
-continued
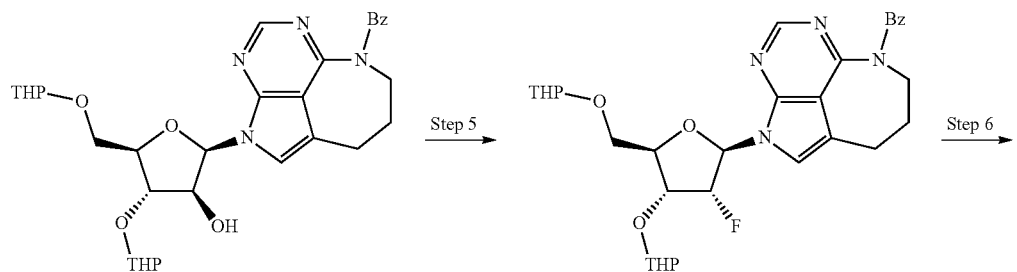
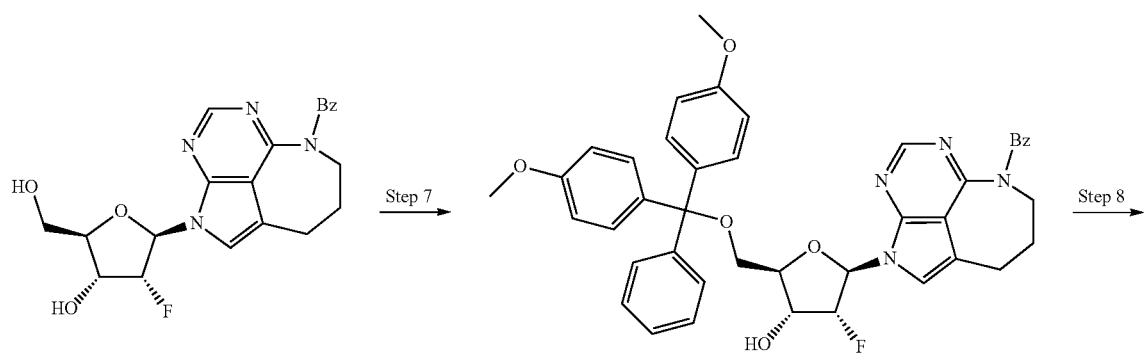
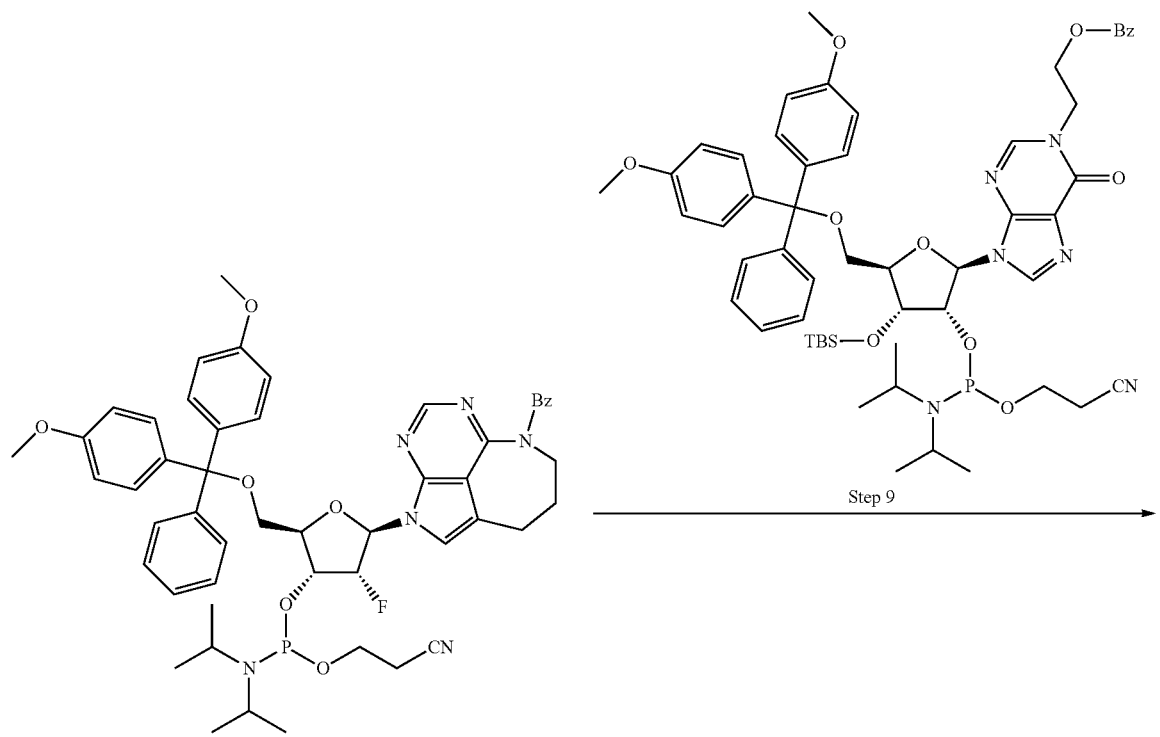

-continued
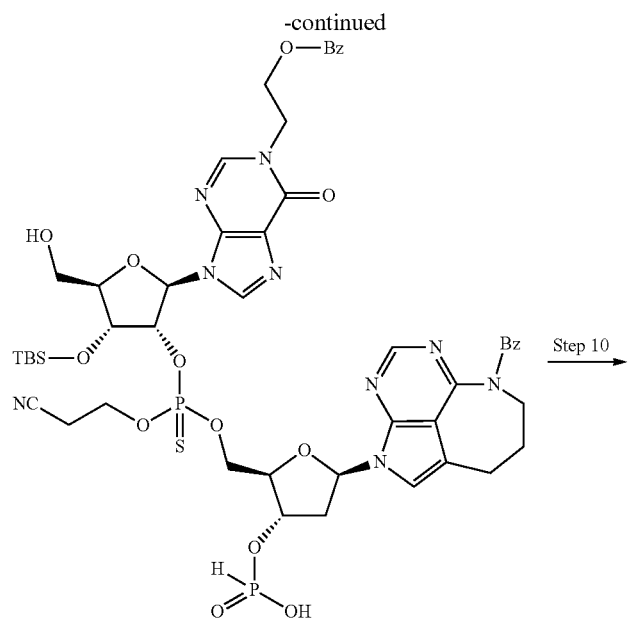
Step 10
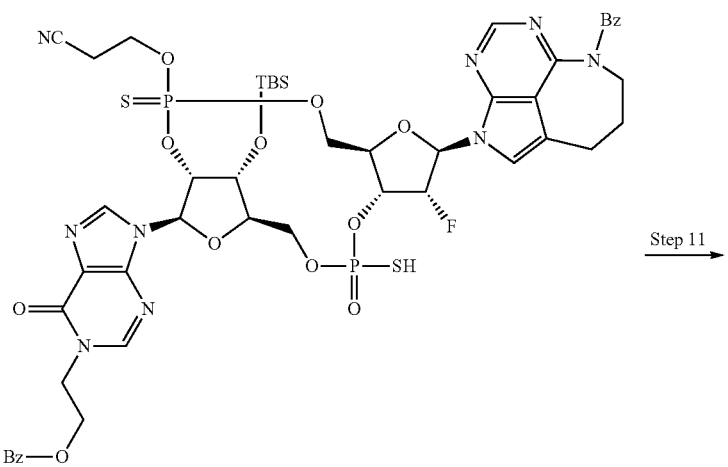
Step 11
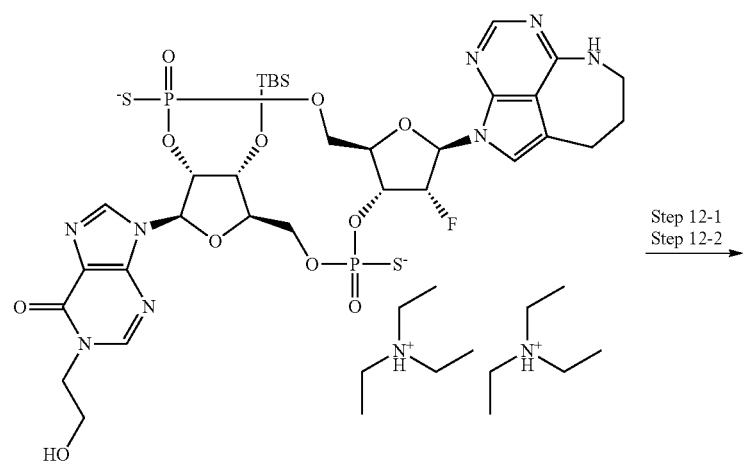
Step 12-1
Step 12-2

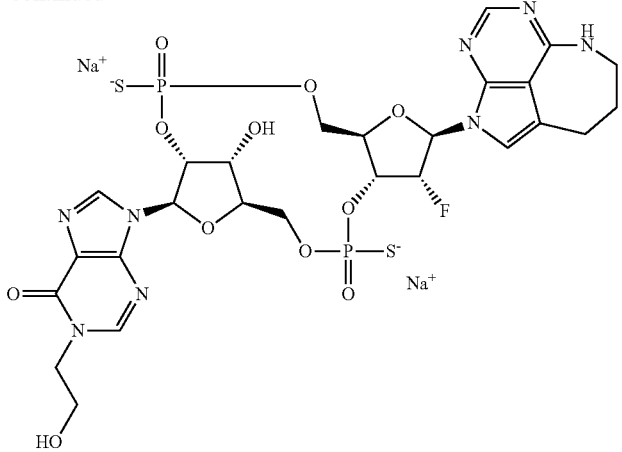

(Step 1)

6-Benzoyl-2-{2-O-[tert-butyl(dimethyl)silyl]-β-D-ribofuranosyl}-6,7,8,9-tetrahydro-2H-2,3,5,6-tetraazabenzo[cd]azulene To a mixed solution of the compound (35.80 g) obtained in step 4 of Example 1 in dichloromethane (322 mL)-pyridine (35 mL), a solution of hydrogen fluoride-pyridine (6.33 g) in dichloromethane (36 mL) was added under ice-cooling over 5 minutes, and the reaction mixture was stirred at the same temperature for 3 hours. A saturated aqueous solution of sodium hydrogen carbonate (268 mL) and brine (143 mL) were added to the reaction mixture in this order to quench the reaction, and the resultant was subjected to extraction with ethyl acetate. After the organic layer was dried over anhydrous sodium sulfate, the drying agent was removed through filtration, and the filtrate was concentrated under reduced pressure. Hexane/ethyl acetate (1:1) (108 mL) was added to the residue to make a slurry, which was then stirred 50° C. for 30 minutes, and hexane (161 mL) was further added thereto and the resultant was further stirred for 2 hours. A solid precipitated was collected through filtration, and washed with hexane/ethyl acetate (4:1) (143 mL) to give the title compound (26.81 g).

MS(ESI)m/z: 525 (M+H)$^+$.

$^1$H-NMR (DMSO-d$_6$) δ: 7.98 (1H, s), 7.65 (1H, s), 7.39 (1H, m), 7.26-7.20 (4H, m), 6.19 (1H, d, J=6.5 Hz), 5.15 (1H, t, J=5.6 Hz), 5.00 (1H, d, J=4.8 Hz) 4.48 (1H, t, J=5.6 Hz), 4.27 (1H, m), 4.11-4.02 (2H, m), 3.97 (1H, m), 3.67-3.57 (2H, m), 2.99 (2H, m), 2.23-2.07 (2H, m), 0.68 (9H, s), −0.11 (3H, s), −0.26 (3H, s).

(Step 2)

6-Benzoyl-2-{2-O-[tert-butyl(dimethyl)silyl]-3,5-bis-O-(oxan-2-yl)-β-D-ribofuranosyl}-6,7,8,9-tetrahydro-2H-2,3,5,6-tetraazabenzo[cd]azulene To a solution of the compound (19.93 g) obtained in the above step 1 and 3,4-dihydro-2H-pyran (35 mL) in N,N-dimethylformamide (200 mL), p-toluenesulfonic acid monohydrate (7.25 g) was added under ice-cooling, and the reaction mixture was stirred at room temperature for 3 hours. A saturated aqueous solution of sodium hydrogen carbonate was added to the reaction mixture under ice-cooling to quench the reaction, and the reaction mixture was subjected to extraction with ethyl acetate. The organic layer was washed with water and brine in this order, and dried over anhydrous sodium sulfate. The drying agent was removed through filtration, and the filtrate was concentrated under reduced pressure. The residue was purified by silica gel column chromatography [hexane/ethyl acetate] to afford the title compound (24.73 g).

$^1$H-NMR (CDCl$_3$): 8.10-8.07 (1H, m), 7.59-7.35 (1H, m), 7.35-7.27 (3H, m), 7.25-7.17 (2H, m), 6.44-6.36 (1H, m), 4.90-3.36 (13H, m), 3.06-2.96 (2H, m), 2.31-2.15 (2H, m), 2.01-1.43 (12H, m), 0.84-0.73 (9H, m), 0.04-(−0.35) (6H, m).

(Step 3)

6-Benzoyl-2-[3,5-bis-O-(oxan-2-yl)-β-D-ribofuranosyl]-6,7,8,9-tetrahydro-2H-2,3,5,6-tetraazabenzo[cd]azulene To a solution of the compound (24.73 g) obtained in the above step 2 and acetic acid (3.1 mL) in tetrahydrofuran (250 mL), a tetrahydrofuran solution of tetrabutylammonium fluoride (approximately 1 M, 55 mL) was added under ice-cooling, and the reaction mixture was stirred at room temperature overnight. The reaction mixture was concentrated under reduced pressure, ethyl acetate was added to the residue, and the resultant was washed with water and brine in this order. After the organic layer was dried over anhydrous sodium sulfate, the drying agent was removed through filtration, and the filtrate was concentrated under reduced pressure. The residue was purified by silica gel column chromatography [hexane/ethyl acetate] to afford the title compound (18.74 g).

$^1$H-NMR (CDCl$_3$) δ: 8.12-8.09 (1H, m), 7.49-7.30 (4H, m), 7.28-7.20 (2H, m), 6.41-6.30 (1H, m), 4.83-4.18 (7H, m), 4.12-3.50 (7H, m), 3.06-2.97 (2H, m), 2.31-2.17 (2H, m), 1.96-1.47 (12H, m).

(Step 4)

6-Benzoyl-2-[3,5-bis-O-(oxan-2-yl)-β-D-arabinofuranosyl]-6,7,8,9-tetrahydro-2H-2,3,5,6-tetraazabenzo[cd]azulene To a solution of the compound (18.74 g) obtained in the above step 3 and pyridine (13.1 mL) in dichloromethane (300 mL), trifluoromethanesulfonic anhydride (11 mL) was added dropwise under ice-cooling, and the reaction mixture was stirred for 10 minutes. Brine was added to the reaction mixture to quench the reaction, the resultant was subjected to extraction with dichloromethane, and the organic layer was dried over anhydrous sodium sulfate. The drying agent was removed through filtration, and the filtrate was concentrated under reduced pressure. The residue was dissolved in tetrahydrofuran (300 mL), a solution of tetrabutylammonium nitrite (28.34 g) in tetrahydrofuran (150 mL) was added dropwise under ice-cooling, and the reaction mixture was stirred at room temperature overnight. The reaction mixture was concentrated under reduced pressure, ethyl acetate was added to the residue, and the resultant was washed with water and brine in this order. After the organic layer was dried over anhydrous sodium sulfate, the drying agent was removed through filtration, and the filtrate was concentrated under reduced pressure. The residue was purified by silica gel column chromatography [hexane/ethyl acetate] to afford the title compound (10.46 g).

$^1$H-NMR (CDCl$_3$) δ: 8.13-8.06 (1H, m), 7.63-7.30 (4H, m), 7.29-7.18 (2H, m), 6.79-6.55 (1H, m), 4.93-3.45 (14H, m), 3.11-2.95 (2H, m), 2.32-2.14 (2H, m), 1.98-1.44 (12H, m).

(Step 5)

6-Benzoyl-2-[2-deoxy-2-fluoro-3,5-bis-O-(oxan-2-yl)-β-D-ribofuranosyl]-6,7,8,9-tetrahydro-2H-2,3,5,6-tetraazabenzo[cd]azulene To a solution of the compound (10.46 g) obtained in the above step 4 and pyridine (7.3 mL) in dichloromethane (200 mL), trifluoromethanesulfonic anhydride (6.1 mL) was added dropwise under ice-cooling, and the reaction mixture was stirred for 10 minutes. Brine was added to the reaction mixture to quench the reaction, the resultant was subjected to extraction with dichloromethane, and the organic layer was dried over anhydrous sodium sulfate. The drying agent was removed through filtration, and the filtrate was concentrated under reduced pressure. The residue was dissolved in tetrahydrofuran (200 mL), a tetrahydrofuran solution of tetrabutylammonium fluoride (approximately 1 M, 150 mL) was added thereto, and the resultant was stirred at the same temperature for 3 hours. A saturated aqueous solution of ammonium chloride was added to the reaction mixture, which was subjected to extraction with ethyl acetate. The organic layer was washed with brine, and dried over anhydrous sodium sulfate, and the drying agent was then removed through filtration, and the filtrate was concentrated under reduced pressure. The residue was purified by silica gel column chromatography [hexane/ethyl acetate] to afford the title compound (7.65 g).

$^1$H-NMR (CDCl$_3$) δ: 8.13-8.08 (1H, m), 7.53-7.31 (4H, m), 7.26-7.22 (2H, m), 6.68-6.53 (1H, m), 5.42-5.08 (1H, m), 4.93-4.18 (6H, m), 4.10-3.76 (3H, m), 3.71-3.47 (3H, m), 3.06-2.96 (2H, m), 2.29-2.18 (2H, m), 1.96-1.47 (12H, m).

(Step 6)

6-Benzoyl-2-(2-deoxy-2-fluoro-β-D-ribofuranosyl)-6,7,8,9-tetrahydro-2H-2,3,5,6-tetraazabenzo[cd]azulene To a solution of the compound (7.65 g) obtained in above step 5 in ethanol (150 mL), pyridinium p-toluenesulfonate (6.62 g) was added, and the reaction mixture was stirred at 50° C. for 3 hours. The reaction mixture was concentrated under reduced pressure, ethyl acetate was added to the residue, and the resultant was washed with a saturated aqueous solution of sodium hydrogen carbonate and brine in this order. After the organic layer was dried over anhydrous sodium sulfate, the drying agent was removed through filtration, and the filtrate was concentrated under reduced pressure. The residue was purified by silica gel column chromatography [hexane/ethyl acetate] to afford the title compound (3.55 g).

$^1$H-NMR (CDCl$_3$) δ: 8.05 (1H, s), 7.41-7.35 (3H, m), 7.30-7.24 (2H, m), 7.06 (1H, s), 6.07-6.00 (2H, m), 5.85 (1H, ddd, J=52.8, 6.7, 4.7 Hz), 4.66 (1H, d, J=3.9 Hz), 4.42-4.31 (2H, m), 4.20 (1H, m), 3.93 (1H, dd, J=12.9, 1.6 Hz), 3.74 (1H, td, J=12.3, 1.6 Hz), 3.12-2.96 (2H, m), 2.51 (1H, s), 2.33-2.15 (2H, m).

(Step 7)

6-Benzoyl-2-{5-O-[bis(4-methoxyphenyl)(phenyl)methyl]-2-deoxy-2-fluoro-β-D-ribofuranosyl}-6,7,8,9-tetrahydro-2H-2,3,5,6-tetraazabenzo[cd]azulene With use of the compound (3.55 g) obtained in the above step 6, the reaction was performed in the same manner as in step 1 of Example 11 to afford the title compound (5.77 g).

$^1$H-NMR (CDCl$_3$) δ: 8.09 (1H, s), 7.45-7.41 (2H, m), 7.36-7.17 (13H, m), 6.85-6.79 (4H, m), 6.53 (1H, dd, J=17.2, 2.3 Hz), 5.40 (1H, ddd, J=53.2, 4.8, 2.3 Hz), 4.83-4.72 (1H, m), 4.32-4.21 (2H, m), 4.19-4.14 (1H, m), 3.79 (3H, s), 3.79 (3H, s), 3.59 (1H, dd, J=11.0, 2.7 Hz), 3.45 (1H, dd, J=11.0, 3.5 Hz), 2.79 (2H, t, J=6.3 Hz), 2.45 (1H, s), 2.24-2.11 (2H, m).

(Step 8)

6-Benzoyl-2-(5-O-[bis(4-methoxyphenyl)(phenyl)methyl]-3-O-{(2-cyanoethoxy)[di(propan-2-yl)amino]phosphanyl}-2-deoxy-2-fluoro-β-D-ribofuranosyl)-6,7,8,9-tetrahydro-2H-2,3,5,6-tetraazabenzo[cd]azulene With use of the compound (5.77 g) obtained in the above step 7, the reaction was performed in the same manner as in step 6 of Example 1 to afford the title compound (5.95 g) as a mixture of diastereomers at the phosphorus atom (diastereomer ratio=1:1).

$^1$H-NMR (CDCl$_3$) δ: 8.10 (0.5H, s), 8.09 (0.5H, s), 7.45-7.12 (15H, m), 6.84-6.75 (4H, m), 6.57-6.46 (1H, m), 5.61-5.33 (1H, m), 5.07-4.83 (1H, m), 4.34-4.18 (3H, m), 3.93-3.72 (7H, m), 3.69-3.49 (4H, m), 3.38-3.27 (1H, m), 2.87-2.68 (2H, m), 2.61 (1H, td, J=6.3, 1.6 Hz), 2.40 (1H, td, J=6.4, 2.1 Hz), 2.21-2.12 (2H, m), 1.21-1.13 (9H, m), 1.03 (3H, d, J=6.7 Hz).

(Step 9)

With use of the compound (1.02 g) obtained in the above step 8, the reaction was performed in the same manner as in step 7 of Example 1 to afford an acetonitrile solution of 6-benzoyl-2-{2-deoxy-2-fluoro-3-O-[hydroxy (oxo)-λ$^5$-phosphanyl]-β-D-ribofuranosyl}-6,7,8,9-tetrahydro-2H-2,3,5,6-tetraazabenzo[cd]azulene. With use of the acetonitrile solution obtained and the compound (1.15 g) obtained in step 3 of Example 22, the reaction was performed in the same manner as in step 8 of Example 1, and the resulting crude product was directly used for the subsequent reaction.

(Step 10)

2-{9-[(5R,7R,8R,12aR,14R,15R,15aR,16R)-14-(6-Benzoyl-6,7,8,9-tetrahydro-2H-2,3,5,6-tetraazabenzo[cd]azulen-2-yl)-16-{[tert-butyl(dimethyl)silyl]oxy}-10-(2-cyanoethoxy)-15-fluoro-2-oxo-2-sulfanyl-10-sulfanylideneoctahydro-2H,10H,12H-5,8-methano-2$\lambda^5$,10$\lambda^5$-furo[3,2-1][1,3,6,9,11,2,10]pentaoxadiphosphacyclotetradecin-7-yl]-6-oxo-6,9-dihydro-1H-purin-1-yl}ethyl benzoate With use of the crude product obtained in the above step 9, the reaction was performed in the same manner as in step 9 of Example 1 to afford the title compound (818 mg: with impurities) as a mixture of diastereomers at the phosphorus atom.

MS(ESI)m/z: 1152 (M+H)$^+$.

(Step 11)

Bis(N,N-diethylethaneaminium) (5R,7R,8R,12aR,14R,15R,15aR,16R)-16-{[tert-butyl(dimethyl)silyl]oxy}-15-fluoro-7-[1-(2-hydroxyethyl)-6-oxo-1,6-dihydro-9H-purin-9-yl]-2,10-dioxo-14-(6,7,8,9-tetrahydro-2H-2,3,5,6-tetraazabenzo[cd]azulen-2-yl)octahydro-2H,10H,12H-5,8-methano-2$\lambda^5$,10$\lambda^5$-furo[3,2-1][1,3,6,9,11,2,10]pentaoxadiphosphacyclotetradecine-2,10-bis(thiolate)

With use of the compound (818 mg) obtained in the above step 10, the reaction was performed in the same manner as in step 10 of Example 1 to afford diastereomer 1 (107 mg: with impurities) and diastereomer 2 (101 mg: with impurities) of the title compound.

Diastereomer 1 (Less Polar)

MS(ESI)m/z: 891 (M+H)$^+$.

Diastereomer 2 (More Polar)

MS(ESI)m/z: 891 (M+H)$^+$.

(Step 12-1)

Disodium (5R,7R,8R,12aR,14R,15R,15aR,16R)-15-fluoro-16-hydroxy-7-[1-(2-hydroxyethyl)-6-oxo-1,6-dihydro-9H-purin-9-yl]-2,10-dioxo-14-(6,7,8,9-tetrahydro-2H-2,3,5,6-tetraazabenzo[cd]azulen-2-yl)octahydro-2H,10H,12H-5,8-methano-2$\lambda^5$,10$\lambda^5$-furo[3,2-1][1,3,6,9,11,2,10]pentaoxadiphosphacyclotetradecine-2,10-bis(thiolate)

(Diastereomer 1)

With use of the compound (diastereomer 1) (107 mg: with impurities) obtained in the above step 11, the reaction was performed in the same manner as in step 11 of Example 1, and purification was then performed under the following [Purification Conditions] to afford the title compound as a triethylamine salt.

[Purification Conditions] C18 silica gel column chromatography [10 mM aqueous solution of triethylammonium acetate/acetonitrile] and preparative HPLC [10 mM aqueous solution of triethylammonium acetate/acetonitrile, acetonitrile: 5%-30% (0 min-30 min)].

The triethylamine salt obtained was subjected to salt exchange in the same manner as in [Conversion to Sodium Salt] described in step 11 of Example 1 to afford the title compound (29.1 mg).

MS(ESI)m/z: 777 (M+H)$^+$.

$^1$H-NMR (CD$_3$OD) δ: 8.58 (1H, m), 8.11 (1H, m), 8.03 (1H, s), 7.11 (1H, s), 6.47 (1H, d, J=17.5 Hz), 6.26 (1H, d, J=8.5 Hz), 5.53-5.36 (2H, m), 5.29-5.17 (1H, m), 4.77 (1H, d, J=4.2 Hz), 4.54-4.46 (1H, m), 4.44-4.38 (1H, m), 4.35-4.32 (1H, m), 4.30-4.25 (2H, m), 4.25-4.16 (1H, m), 4.06-3.99 (1H, m), 3.96-3.85 (1H, m), 3.82-3.71 (2H, m), 3.54-3.42 (2H, m), 2.77-2.68 (1H, m), 2.66-2.55 (1H, m), 2.02-1.81 (2H, m).

$^{31}$P-NMR (CD$_3$OD) δ: 57.5 (s), 53.0 (s).

(Step 12-2)

Disodium (5R,7R,8R,12aR,14R,15R,15aR,16R)-15-fluoro-16-hydroxy-7-[1-(2-hydroxyethyl)-6-oxo-1,6-dihydro-9H-purin-9-yl]-2,10-dioxo-14-(6,7,8,9-tetrahydro-2H-2,3,5,6-tetraazabenzo[cd]azulen-2-yl)octahydro-2H,10H,12H-5,8-methano-2$\lambda^5$,10$\lambda^5$-furo[3,2-1][1,3,6,9,11,2,10]pentaoxadiphosphacyclotetradecine-2,10-bis(thiolate)

(Diastereomer 2)

With use of the compound (diastereomer 2) (101 mg: with impurities) obtained in the above step 11, the reaction was performed in the same manner as in step 11 of Example 1, and purification was then performed under the following [Purification Conditions] to afford the title compound as a triethylamine salt.

[Purification Conditions] C18 silica gel column chromatography [10 mM aqueous solution of triethylammonium acetate/acetonitrile] and preparative HPLC [10 mM aqueous solution of triethylammonium acetate/acetonitrile, acetonitrile: 5%-20% (0 min-30 min)].

The triethylamine salt obtained was subjected to salt exchange in the same manner as in [Conversion to Sodium Salt] described in step 11 of Example 1 to afford the title compound (11.2 mg).

MS(ESI)m/z: 777 (M+H)$^-$.

$^1$H-NMR (CD$_3$OD) δ: 8.61 (1H, m), 8.16 (1H, m), 8.02 (1H, m), 7.36 (III, s), 6.49 (1H, dd, J=16.0, 2.1 Hz), 6.28 (1H, d, J=8.5 Hz), 5.56-5.33 (3H, m), 4.58-4.49 (2H, m), 4.45-4.37 (2H, m), 4.31-4.27 (1H, m), 4.25-4.16 (1H, m), 4.10-3.98 (3H, m), 3.80 (2H, t, J=5.1 Hz), 3.48 (2H, dd, J=6.7, 3.6 Hz), 2.90-2.72 (2H, m), 2.00-1.90 (2H, m).

$^{31}$P-NMR (CD$_3$OD) δ: 59.5 (s), 57.7 (s).

Example 45: Synthesis of CDN35
(5R,7R,8R,12aR,14R,15R,15aR,16R)-7-[1-(2-Aminoethyl)-6-oxo-1,6-dihydro-9H-purin-9-yl]-15-fluoro-16-hydroxy-2,10-bis(sulfanyl)-14-(6,7,8,9-tetrahydro-2H-2,3,5,6-tetraazabenzo[cd]azulen-2-yl)octahydro-2H,10H,12H-5,8-methano-2$\lambda^5$,10$\lambda^5$-furo[3,2-l][1,3,6,9,11,2,10]pentaoxadiphosphacyclotetradecine-2,10-dione
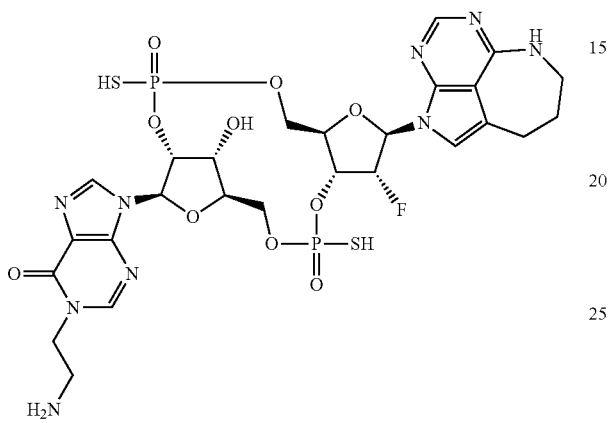
35a (Diastereomer 1)
35b (Diastereomer 2)
[Synthesis Scheme]
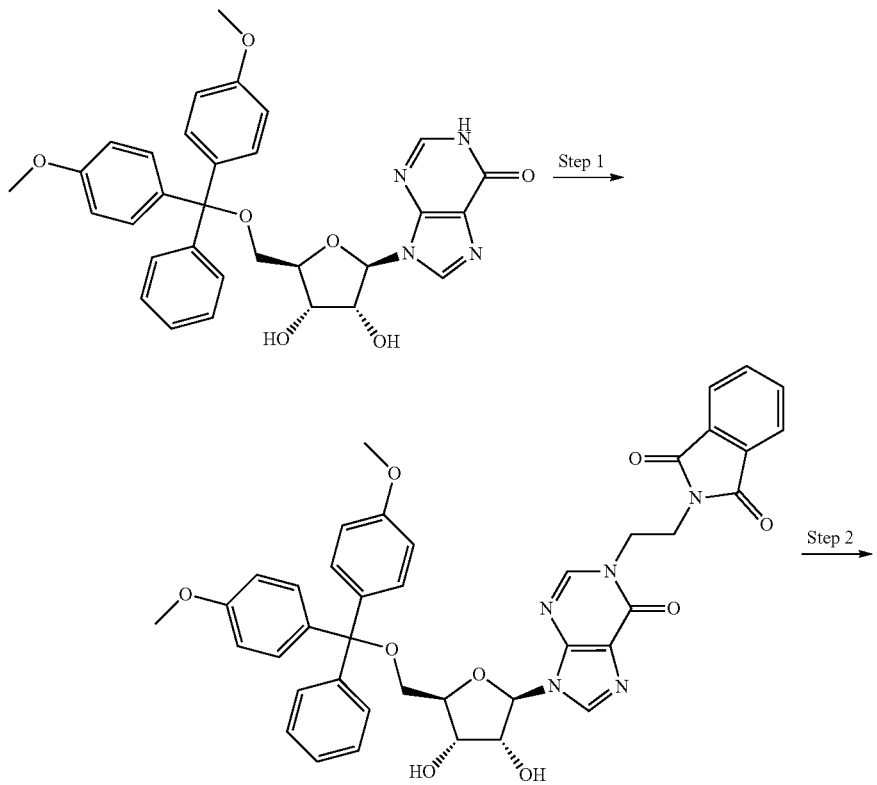

-continued
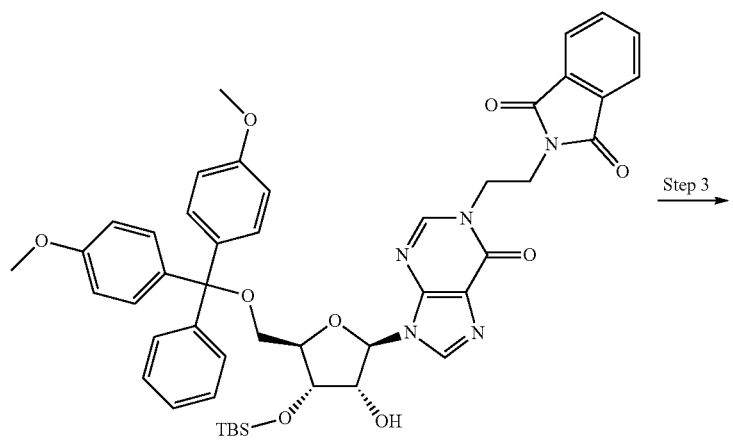
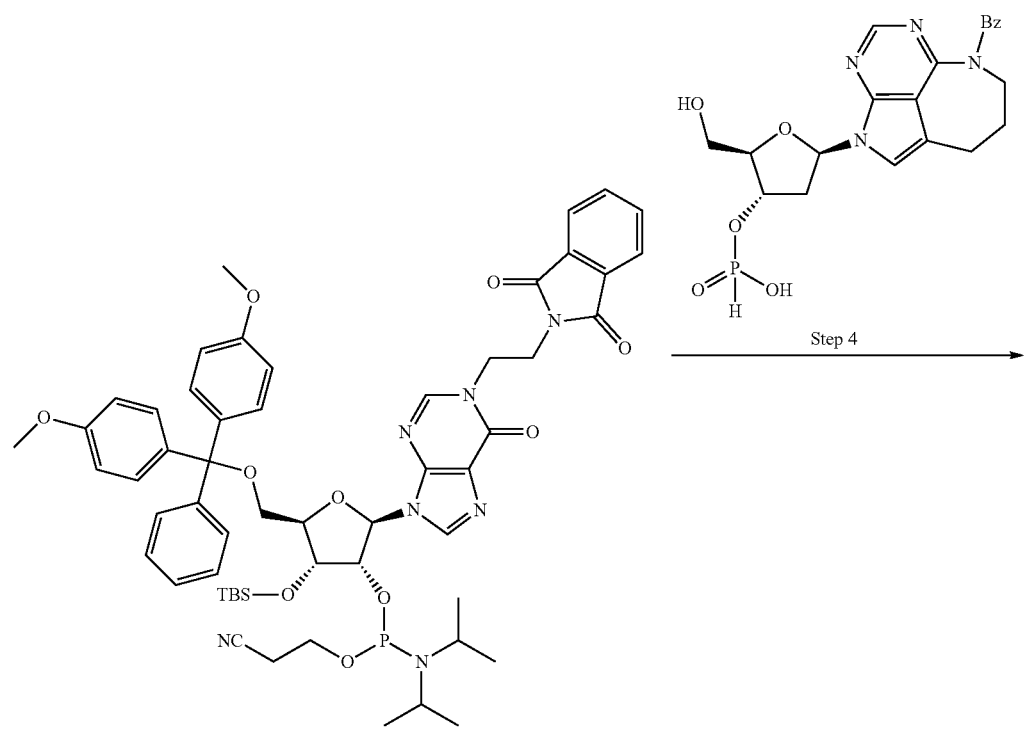

-continued
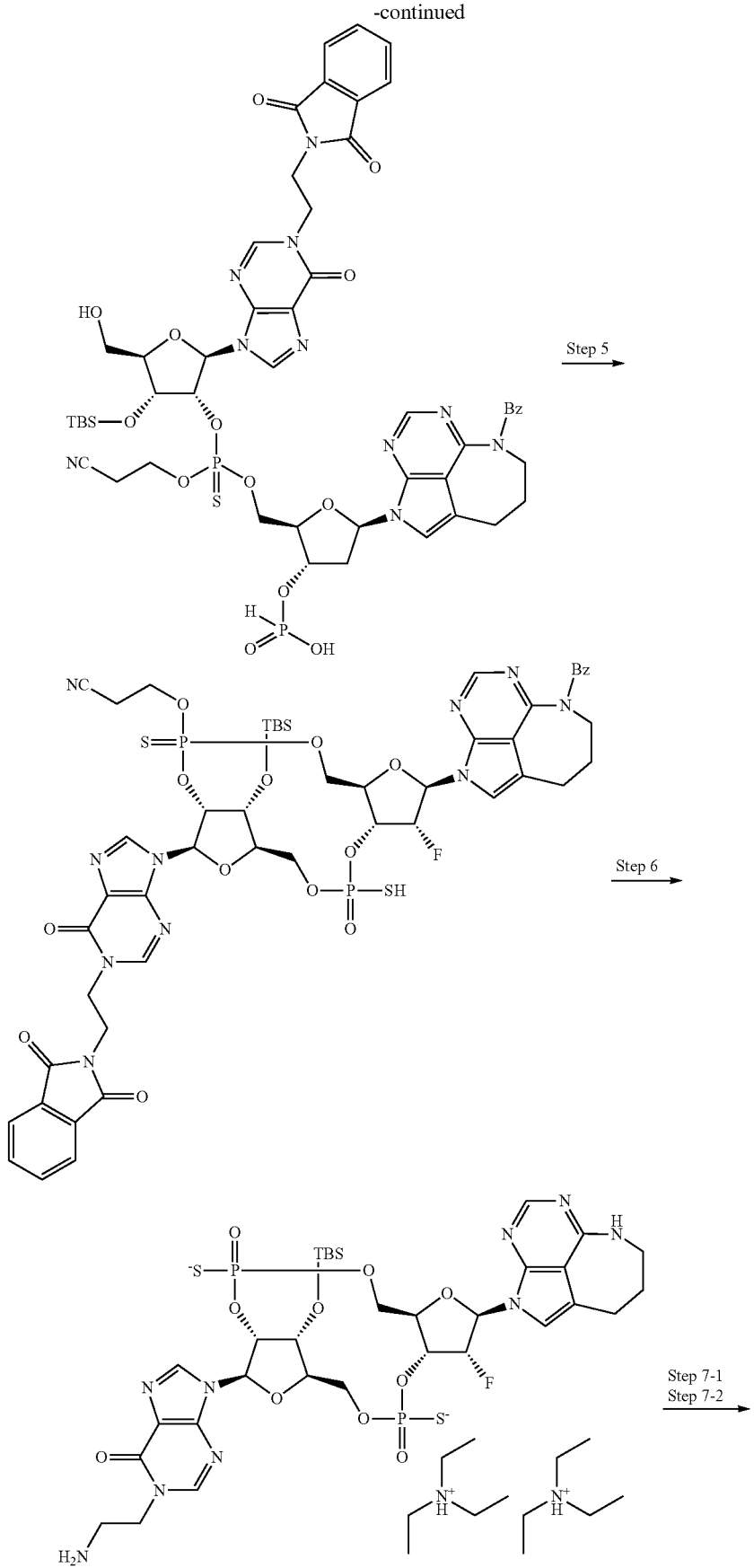

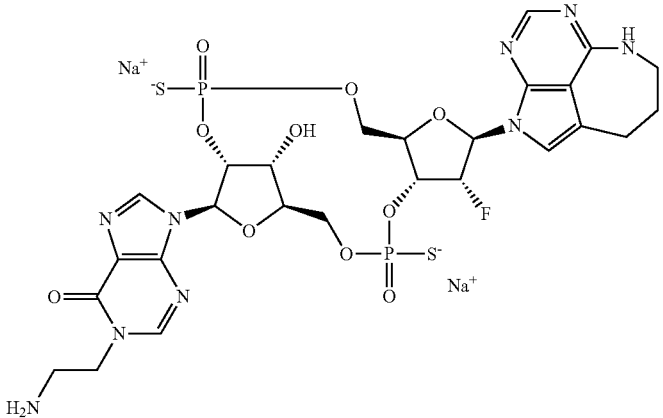

(Step 1)

5'-O-[Bis(4-methoxyphenyl)(phenyl)methyl]-1-[2-(1,3-dioxo-1,3-dihydro-2H-isoindol-2-yl)ethyl]inosine To a suspension of commercially available (Aamdis Chemical) 5'-O-[bis(4-methoxyphenyl)(phenyl)methyl]inosine (13.0 g) in N,N-dimethylacetamide (60 mL), N-(2-bromoethyl) phthalimide (7.02 g) and 1,8-diazabicyclo[5.4.0]-7-undecene (4.1 mL) were added, and the reaction mixture was stirred at room temperature overnight. Thereto, N-(2-Bromoethyl) phthalimide (1.75 g) and 1,8-diazabicyclo [5.4.0]-7-undecene (1.1 mL) were further added, and the reaction mixture was further stirred for 1 day. Water was added to the reaction mixture to quench the reaction, and the resultant was subjected to extraction with dichloromethane. After the organic layer was dried over anhydrous sodium sulfate, the drying agent was removed through filtration, and the filtrate was concentrated under reduced pressure. The residue was purified by silica gel column chromatography [ethyl acetate/methanol] to afford the title compound (12.4 g).

$^1$H-NMR (CDCl$_3$) δ: 7.83 (1H, s), 7.76-7.67 (4H, m), 7.64 (1H, s), 7.35-7.33 (2H, m), 7.25-7.11 (7H, m), 6.74-6.70 (4H, m), 5.93 (1H, d, J=5.1 Hz), 5.68 (1H, d, J=3.9 Hz), 4.71 (1H, q, J=4.8 Hz), 4.43 (1H, m), 4.37-4.18 (3H, m), 4.10-4.06 (2H, m), 3.730 (3H, s), 3.728 (3H, s), 3.51 (1H, m), 3.36 (1H, dd, J=10.6, 3.9 Hz), 3.32 (1H, dd, J=11.0, 5.5 Hz).

(Step 2)

5'-O-[Bis(4-methoxyphenyl)(phenyl)methyl]-3'-O-[tert-butyl(dimethyl)silyl]-1-[2-(1,3-dioxo-1,3-dihydro-2H-isoindol-2-yl)ethyl]inosine With use of the compound (12.4 g) obtained in the above step 1, the reaction was performed in the same manner as in step 3 of Example 5 to afford the title compound (4.18 g) and 5'-O-[bis(4-methoxyphenyl)(phenyl)methyl]-2'-O-[tert-butyl(dimethyl)silyl]-1-[2-(1,3-dioxo-1,3-dihydro-2H-isoindol-2-yl)ethyl]inosine (6.31 g) as a regioisomer of the title compound.

$^1$H-NMR (CDCl$_3$) δ: 8.00 (1H, s), 7.82-7.77 (2H, m), 7.74 (1H, s), 7.72-7.67 (2H, m), 7.41-7.39 (2H, m), 7.32-7.19 (7H, m), 6.83-6.78 (4H, m), 5.90 (1H, d, J=5.1 Hz), 4.53-4.41 (3H, m), 4.32-4.25 (1H, m), 4.19-4.11 (3H, m), 3.79 (3H, s), 3.78 (3H, s), 3.46 (1H, dd, J=10.6, 3.1 Hz), 3.24 (1H, dd, J=10.8, 4.1 Hz), 2.98 (1H, d, J=6.7 Hz), 0.85 (9H, s), 0.04 (3H, s), —0.03 (3H, s).

Regioisomer (2'-O-TBS Form)

$^1$H-NMR (CDCl$_3$) δ: 7.97 (1H, s), 7.82-7.78 (2H, m), 7.73-7.69 (2H, m), 7.66 (1H, s), 7.44-7.41 (2H, m), 7.33-7.18 (7H, m), 6.81 (4H, d, J=7.8 Hz), 5.91 (1H, d, J=5.9 Hz), 4.82 (1H, t, J=5.5 Hz), 4.43 (1H, m), 4.34-4.23 (3H, m), 4.18-4.08 (2H, m), 3.79 (6H, s), 3.46 (1H, dd, J=10.6, 2.7 Hz), 3.36 (1H, dd, J=10.6, 3.5 Hz), 2.70 (1H, d, J=3.1 Hz), 0.83 (9H, s), −0.04 (3H, s), −0.19 (3H, s).

(Step 3)

5'-O-[Bis(4-methoxyphenyl)(phenyl)methyl]-3'-O-[tert-butyl(dimethyl)silyl]-2'-O-{(2-cyanoethoxy)[di(propan-2-yl)amino]phosphanyl}-1-[2-(1,3-dioxo-1,3-dihydro-2H-isoindol-2-yl)ethyl]inosine With use of the compound (8.89 g) obtained in the above step 2, the reaction was performed in the same manner as in step 6 of Example 1 to afford the title compound (9.45 g) as a mixture of diastereomers at the phosphorus atom (diastereomer ratio=1:1).

$^1$H-NMR (CDCl$_3$) δ: 8.01 (0.5H, s), 8.00 (0.5H, s), 7.82-7.77 (2H, m), 7.74 (0.5H, s), 7.72-7.67 (2.5H, m), 7.42 (2H, d, J=7.8 Hz), 7.33-7.18 (7H, m), 6.81 (4H, d, J=8.6 Hz), 6.10 (0.5H, d, J=5.5 Hz), 6.04 (0.5H, d, J=5.1 Hz), 4.75 (0.5H, m), 4.60 (0.5H, m), 4.49-4.41 (1H, m), 4.38-4.23 (2H, m), 4.22-4.05 (3H, m), 3.79 (6H, s), 3.78-3.65 (1H, m), 3.62-3.39 (4H, m), 3.33-3.23 (1H, m), 2.49 (1H, t, J=6.3 Hz), 2.34 (1H, t, J=6.7 Hz), 1.12-1.08 (9H, m), 0.91 (3H, d, J=7.0 Hz), 0.82 (9H, s), 0.06 (1.5H, s), 0.03 (1.5H, s), −0.03 (3H, s).

(Step 4)

With use of the compound (1.30 g) obtained in step 8 of Example 44, the reaction was performed in the same manner as in step 7 of Example 1 to afford an acetonitrile solution of 6-benzoyl-2-{2-deoxy-2-fluoro-3-O-[hydroxy (oxo)-λ$^5$-phosphanyl]-β-D-ribofuranosyl}-6,7,8,9-tetrahydro-2H-2,3,5,6-tetraazabenzo[cd]azulene. With use of the acetonitrile solution obtained and the compound (1.50 g) obtained in the above step 3, the reaction was performed in the same manner as in step 8 of Example 1, and the resulting crude product was directly used for the subsequent reaction.

(Step 5)

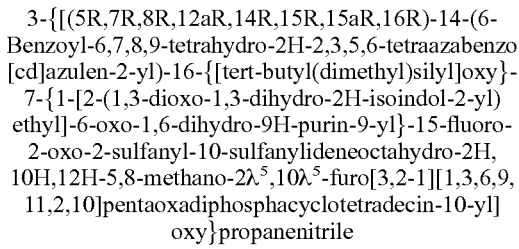

3-{[(5R,7R,8R,12aR,14R,15R,15aR,16R)-14-(6-Benzoyl-6,7,8,9-tetrahydro-2H-2,3,5,6-tetraazabenzo[cd]azulen-2-yl)-16-{[tert-butyl(dimethyl)silyl]oxy}-7-{1-[2-(1,3-dioxo-1,3-dihydro-2H-isoindol-2-yl)ethyl]-6-oxo-1,6-dihydro-9H-purin-9-yl}-15-fluoro-2-oxo-2-sulfanyl-10-sulfanylideneoctahydro-2H,10H,12H-5,8-methano-2$\lambda^5$,10$\lambda^5$-furo[3,2-1][1,3,6,9,11,2,10]pentaoxadiphosphacyclotetradecin-10-yl]oxy}propanenitrile With use of the crude product obtained in the above step 4, the reaction was performed in the same manner as in step 9 of Example 1 to afford the title compound (828 mg) as a mixture of diastereomers at the phosphorus atom.

MS(ESI)m/z: 1177 (M+H)$^+$.

(Step 6)

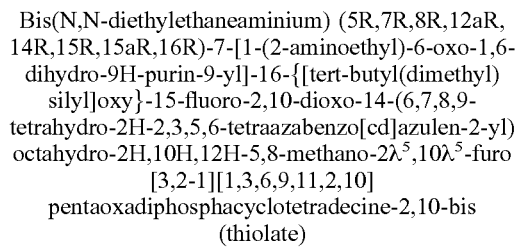

Bis(N,N-diethylethaneaminium) (5R,7R,8R,12aR,14R,15R,15aR,16R)-7-[1-(2-aminoethyl)-6-oxo-1,6-dihydro-9H-purin-9-yl]-16-{[tert-butyl(dimethyl)silyl]oxy}-15-fluoro-2,10-dioxo-14-(6,7,8,9-tetrahydro-2H-2,3,5,6-tetraazabenzo[cd]azulen-2-yl)octahydro-2H,10H,12H-5,8-methano-2$\lambda^5$,10$\lambda^5$-furo[3,2-1][1,3,6,9,11,2,10]pentaoxadiphosphacyclotetradecine-2,10-bis(thiolate)

To a mixed solution of the compound (828 mg) obtained in the above step 5 in ethanol (5.0 mL)-tetrahydrofuran (5.0 mL), hydrazine monohydrate (0.342 mL) was added, and the reaction mixture was stirred at 50° C. for 6 hours. After the reaction mixture was concentrated under reduced pressure, the residue was purified by C18 silica gel column chromatography [10 mM aqueous solution of triethylammonium acetate/acetonitrile] to afford diastereomer 1 (90.9 mg: with impurities) and diastereomer 2 (91.1 mg: with impurities) of the title compound.

Diastereomer 1 (Less Polar)
MS(ESI)m/z: 890 (M+H)$^+$.

Diastereomer 2 (More Polar)
MS(ESI)m/z: 890 (M+H)$^+$.

(Step 7-1)

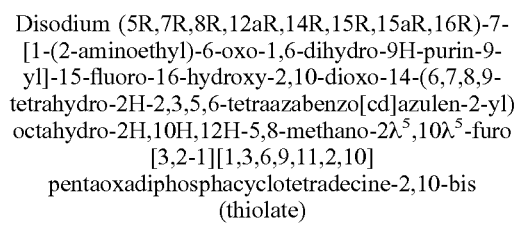

Disodium (5R,7R,8R,12aR,14R,15R,15aR,16R)-7-[1-(2-aminoethyl)-6-oxo-1,6-dihydro-9H-purin-9-yl]-15-fluoro-16-hydroxy-2,10-dioxo-14-(6,7,8,9-tetrahydro-2H-2,3,5,6-tetraazabenzo[cd]azulen-2-yl)octahydro-2H,10H,12H-5,8-methano-2$\lambda^5$,10$\lambda^5$-furo[3,2-1][1,3,6,9,11,2,10]pentaoxadiphosphacyclotetradecine-2,10-bis(thiolate)

(Diastereomer 1)

With use of the compound (90.9 mg: with impurities) obtained in the above step 6 (diastereomer 1), the reaction was performed in the same manner as in step 11 of Example 1, and purification was then performed under the following [Purification Conditions] to afford the title compound as a triethylamine salt.

[Purification Conditions] C18 silica gel column chromatography [10 mM aqueous solution of triethylammonium acetate/acetonitrile] and preparative HPLC [10 mM aqueous solution of triethylammonium acetate/acetonitrile-methanol solution (1:1), acetonitrile-methanol solution (1:1): 10%-50% (0 min-40 min)].

The triethylamine salt obtained was subjected to salt exchange in the same manner as in [Conversion to Sodium Salt] described in step 11 of Example 1 to afford the title compound (20.2 mg).

MS(ESI)m/z: 776 (M+H)$^+$.

$^1$H-NMR (CD$_3$OD): 8.54 (1H, s), 8.03 (1H, s), 7.99 (1H, s), 7.13 (1H, s), 6.44 (1H, d, J=18.1 Hz), 6.22 (1H, d, J=7.9 Hz), 5.56-5.38 (2H, m), 5.33-5.21 (1H, m), 4.72 (1H, d, J=4.2 Hz), 4.58-4.49 (1H, m), 4.41-4.24 (4H, m), 4.24-4.17 (1H, m), 4.05-3.98 (1H, m), 3.86-3.76 (1H, m), 3.50-3.42 (2H, m), 3.27-3.16 (2H, m), 2.78-2.68 (1H, m), 2.59-2.49 (1H, m), 1.98-1.80 (2H, m).

$^{31}$P-NMR (CD$_3$OD) δ: 57.5 (s), 53.1 (s).

(Step 7-2)

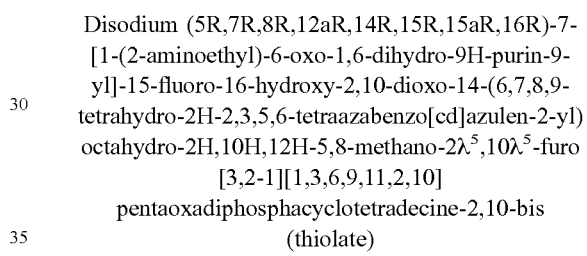

Disodium (5R,7R,8R,12aR,14R,15R,15aR,16R)-7-[1-(2-aminoethyl)-6-oxo-1,6-dihydro-9H-purin-9-yl]-15-fluoro-16-hydroxy-2,10-dioxo-14-(6,7,8,9-tetrahydro-2H-2,3,5,6-tetraazabenzo[cd]azulen-2-yl)octahydro-2H,10H,12H-5,8-methano-2$\lambda^5$,10$\lambda^5$-furo[3,2-1][1,3,6,9,11,2,10]pentaoxadiphosphacyclotetradecine-2,10-bis(thiolate)

(Diastereomer 2)

With use of the compound (diastereomer 2) (91.1 mg: with impurities) obtained in the above step 6, the reaction was performed in the same manner as in step 11 of Example 1, and purification was then performed under the following [Purification Conditions] to afford the title compound as a triethylamine salt.

[Purification Conditions] C18 silica gel column chromatography [10 mM aqueous solution of triethylammonium acetate/acetonitrile] and preparative HPLC [10 mM aqueous solution of triethylammonium acetate/acetonitrile-methanol solution (1:1), acetonitrile-methanol solution (1:1): 10%-45% (0 min-40 min)].

The triethylamine salt obtained was subjected to salt exchange in the same manner as in [Conversion to Sodium Salt] described in step 11 of Example 1 to afford the title compound (26.3 mg).

MS(ESI)m/z: 776 (M+H)$^+$.

$^1$H-NMR (CD$_3$OD): 8.56 (1H, s), 8.08 (1H, s), 8.02 (1H, s), 7.37 (1H, s), 6.48 (1H, d, J=16.2 Hz), 6.23 (1H, d, J=7.9 Hz), 5.58-5.32 (3H, m), 4.65-4.27 (6H, m), 4.07-3.96 (3H, m), 3.48-3.42 (2H, m), 3.38-3.23 (2H, m), 2.85-2.75 (1H, m), 2.69-2.59 (1H, m), 1.99-1.81 (2H, m).

$^{31}$P-NMR (CD$_3$OD) δ: 59.0 (s), 57.6 (s).

Example 46: Synthesis of CDN36

N-(2-{9-[(5R,7R,8R,12aR,14R,15R,15aR,16R)-15-Fluoro-16-hydroxy-2,10-dioxo-2,10-bis(sulfanyl)-14-(6,7,8,9-tetrahydro-2H-2,3,5,6-tetraazabenzo[cd]azulen-2-yl)octahydro-2H,10H,12H-5,8-methano-2λ⁵,10λ⁵-furo[3,2-1][1,3,6,9,11,2,10]pentaoxadiphosphacyclotetradecin-7-yl]-6-oxo-6,9-dihydro-1H-purin-1-yl}ethyl)-2-hydroxyacetamide

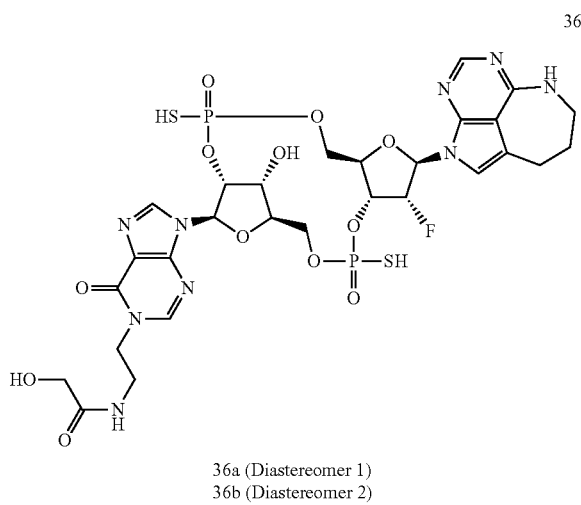 [SMILES: O=C(CO)NCCn1cnc2c(ncn2[C@@H]2O[C@@H]3COP(=O)(S)O[C@H]4[C@@H](F)[C@H](n5cc6c7c(ncnc75)NCCC6)O[C@@H]4COP(=O)(S)O[C@@H]2[C@@H]3O)c1=O]

36a (Diastereomer 1)
36b (Diastereomer 2)

[Synthesis Scheme]

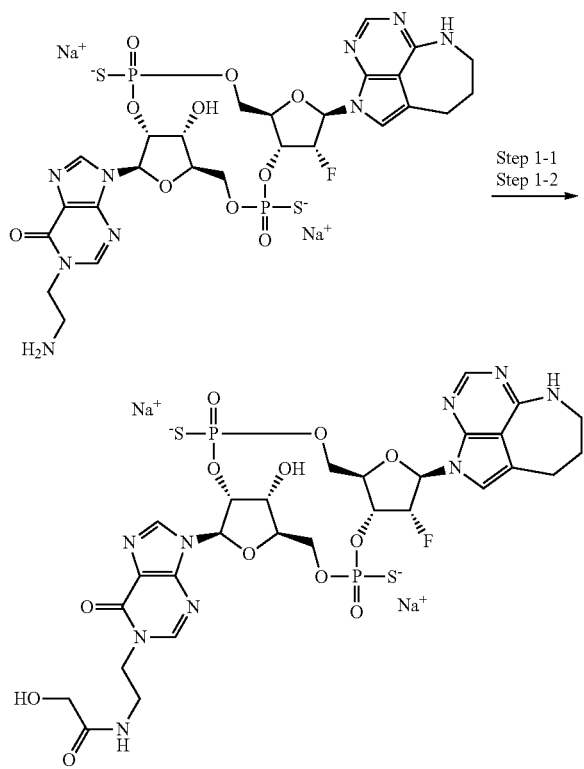

(Step 1-1)

Disodium (5R,7R,8S,12aR,14R,15R,15aS,16R)-16-fluoro-15-hydroxy-7-{1-[2-(2-hydroxyacetamide)ethyl]-6-oxo-1,6-dihydro-9H-purin-9-yl}-2,10-dioxo-14-(6,7,8,9-tetrahydro-2H-2,3,5,6-tetraazabenzo[cd]azulen-2-yl)octahydro-2H,10H,12H-5,8-methano-2λ⁵,10λ⁵-furo[3,2-1][1,3,6,9,11,2,10]pentaoxadiphosphacyclotetradecine-2,10-bis(thiolate)

(Diastereomer 1)

With use of the compound (15.0 mg) obtained in step 7-1 of Example 45, the reaction was performed in the same manner as in step 1-1 of Example 7, and purification was then performed under the following [Purification Conditions] to afford the title compound as a triethylamine salt.

[Purification Conditions] C18 silica gel column chromatography [10 mM aqueous solution of triethylammonium acetate/acetonitrile] and preparative HPLC [10 mM aqueous solution of triethylammonium acetate/acetonitrile-methanol solution (1:1), acetonitrile-methanol solution (1:1): 10%-45% (0 min-40 min)].

The triethylamine salt obtained was subjected to salt exchange in the same manner as in [Conversion to Sodium Salt] described in step 11 of Example 1 to afford the title compound (10.3 mg).

MS(ESI)m/z: 834 (M+H)⁺.

¹H-NMR (CD₃OD) δ: 8.46 (1H, brm), 8.04 (1H, s), 7.82 (1H, brm), 7.15 (1H, brm), 6.43 (1H, d, J=16.9 Hz), 6.17 (1H, dd, J=9.1, 4.5 Hz), 5.70-5.24 (3H, m), 4.81-4.75 (1H, m), 4.52-4.44 (1H, m), 4.43-4.26 (4H, m), 4.24-3.94 (2H, m), 3.89-3.84 (2H, m), 3.72-3.37 (5H, m), 2.75-2.65 (1H, m), 2.48-2.32 (1H, m), 1.98-1.76 (2H, m).

³¹P-NMR (CD₃OD) δ: 57.0 (s), 53.0 (s).

(Step 1-2)

Disodium (5R,7R,8S,12aR,14R,15R,15aS,16R)-16-fluoro-15-hydroxy-7-{1-[2-(2-hydroxyacetamide)ethyl]-6-oxo-1,6-dihydro-9H-purin-9-yl}-2,10-dioxo-14-(6,7,8,9-tetrahydro-2H-2,3,5,6-tetraazabenzo[cd]azulen-2-yl)octahydro-2H,10H,12H-5,8-methano-2λ⁵,10λ⁵-furo[3,2-1][1,3,6,9,11,2,10]pentaoxadiphosphacyclotetradecine-2,10-bis(thiolate)

(Diastereomer 2)

With use of the compound (15.0 mg) obtained in step 7-2 of Example 45, the reaction was performed in the same manner as in step 1-1 of Example 7, and purification was then performed under the following [Purification Conditions] to afford the title compound as a triethylamine salt.

[Purification Conditions] C18 silica gel column chromatography [10 mM aqueous solution of triethylammonium acetate/acetonitrile] and preparative HPLC [10 mM aqueous solution of triethylammonium acetate/acetonitrile-methanol solution (1:1), acetonitrile-methanol solution (1:1): 10%-45% (0 min-40 min)].

The triethylamine salt obtained was subjected to salt exchange in the same manner as in [Conversion to Sodium Salt] described in step 11 of Example 1 to afford the title compound (10.6 mg).

MS(ESI)m/z: 834 (M+H)⁺.

¹H-NMR (CD₃OD) δ: 8.54 (1H, brs), 8.03 (1H, s), 7.97 (1H, brs), 7.35 (1H, brs), 6.48 (1H, d, J=15.7 Hz), 6.23 (1H, d, J=8.5 Hz), 5.65-5.39 (3H, m), 4.57-4.47 (2H, m), 4.46-4.36 (2H, m), 4.31-4.19 (2H, m), 4.07-3.96 (2H, m), 3.95-3.78 (3H, m), 3.67-3.43 (4H, m), 2.85-2.75 (1H, m), 2.71-2.59 (1H, m), 2.00-1.84 (2H, m).

³¹P-NMR (CD₃OD) δ: 59.1 (s), 57.5 (s).

Example 47: Synthesis of CDN37
(5R,7R,8R,12aR,14R,15R,15aR,16R)-7-{6-Amino-2-[(2-aminoethyl)amino]-9H-purin-9-yl}-15-fluoro-16-hydroxy-2,10-bis(sulfanyl)-14-(6,7,8,9-tetrahydro-2H-2,3,5,6-tetraazabenzo[cd]azulen-2-yl)octahydro-2H,10H,12H-5,8-methano-2λ$^5$,10λ$^5$-furo[3,2-l][1,3,6,9,11,2,10]pentaoxadiphosphacyclotetradecine-2,10-dione
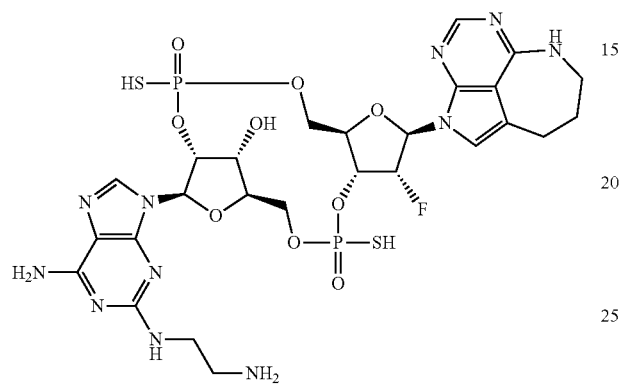
37a (Diastereomer 1)
37b (Diastereomer 2)
[Synthesis Scheme]
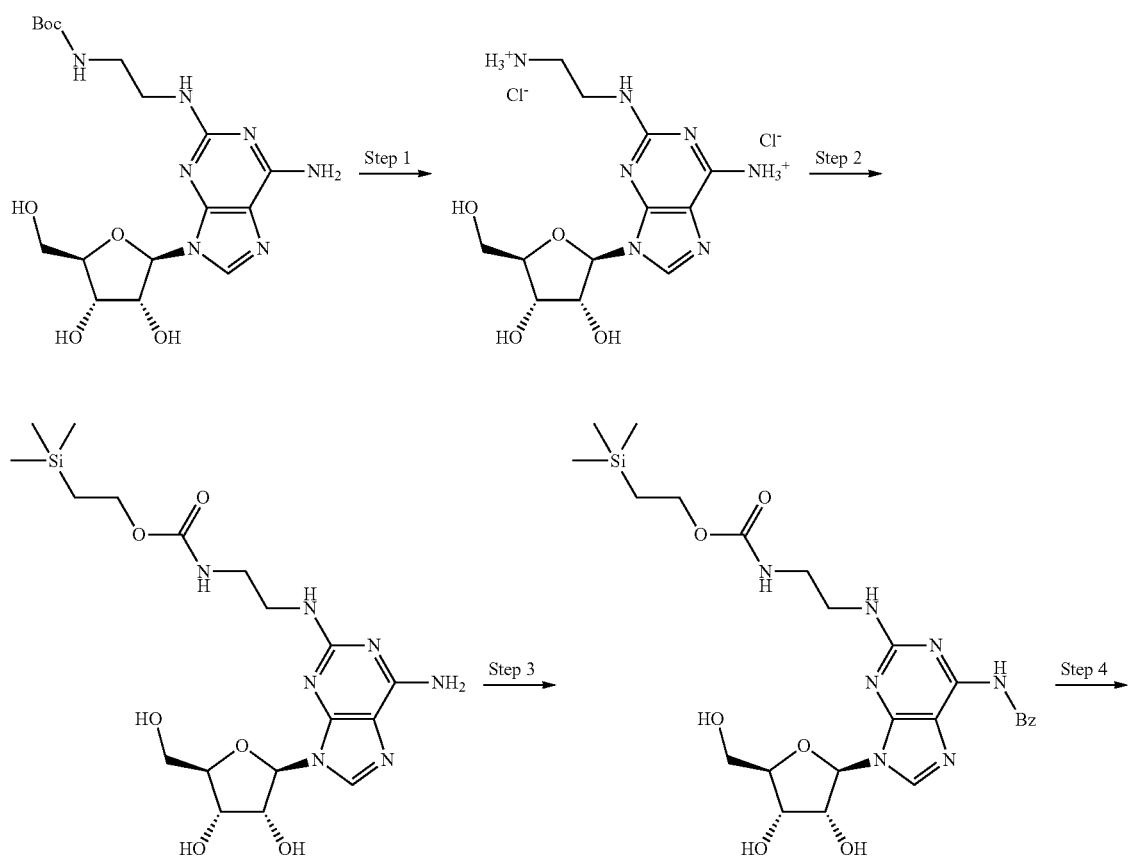

-continued
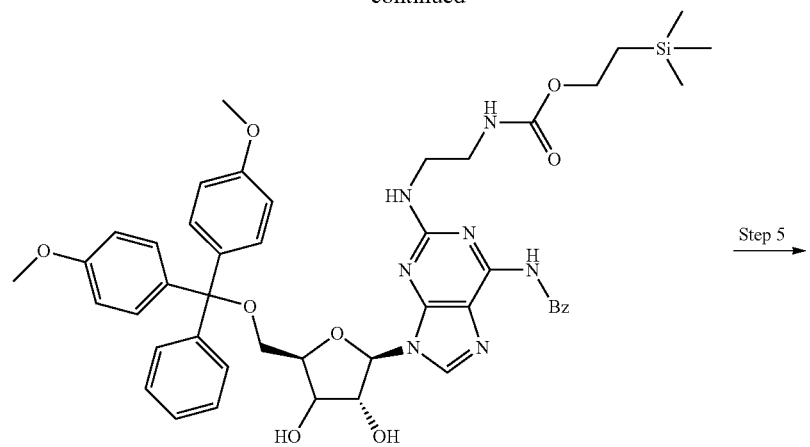
Step 5
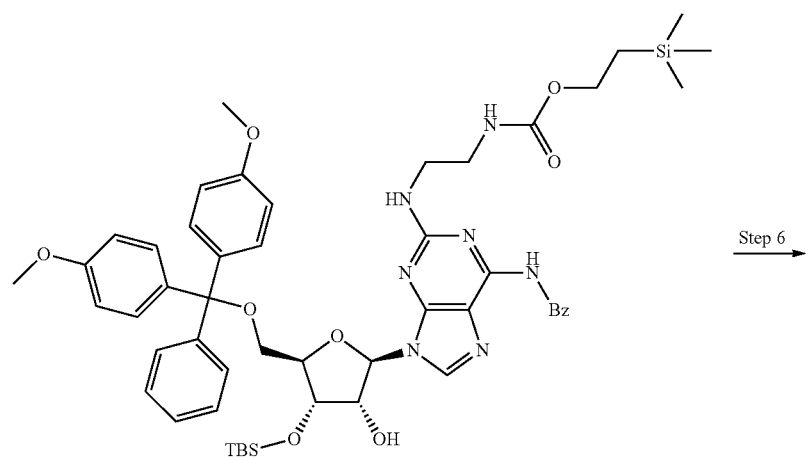
Step 6
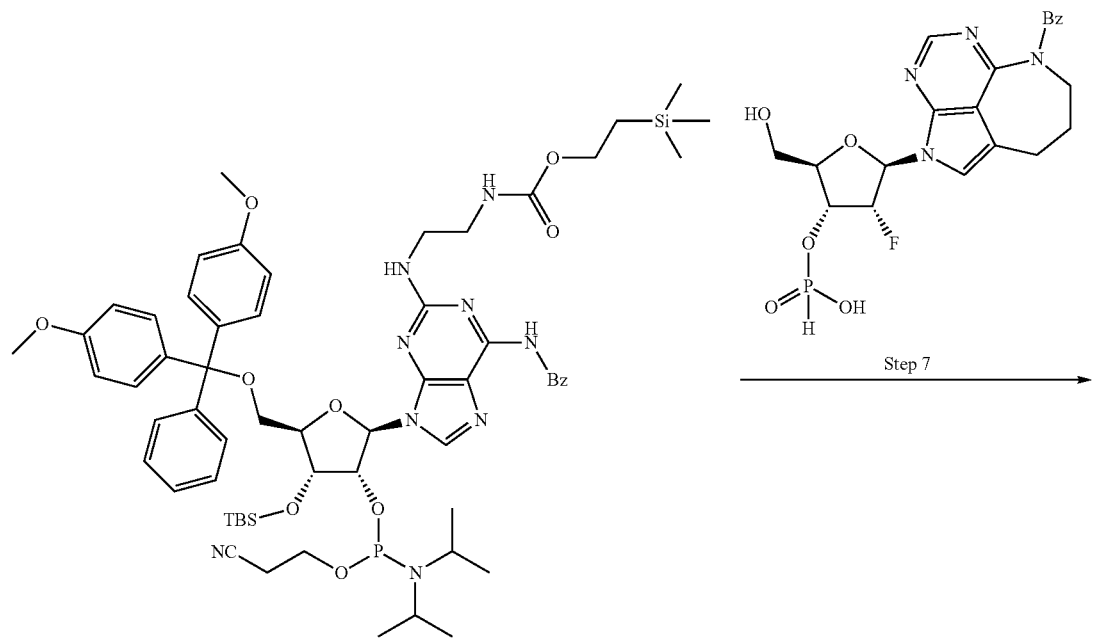
Step 7

-continued
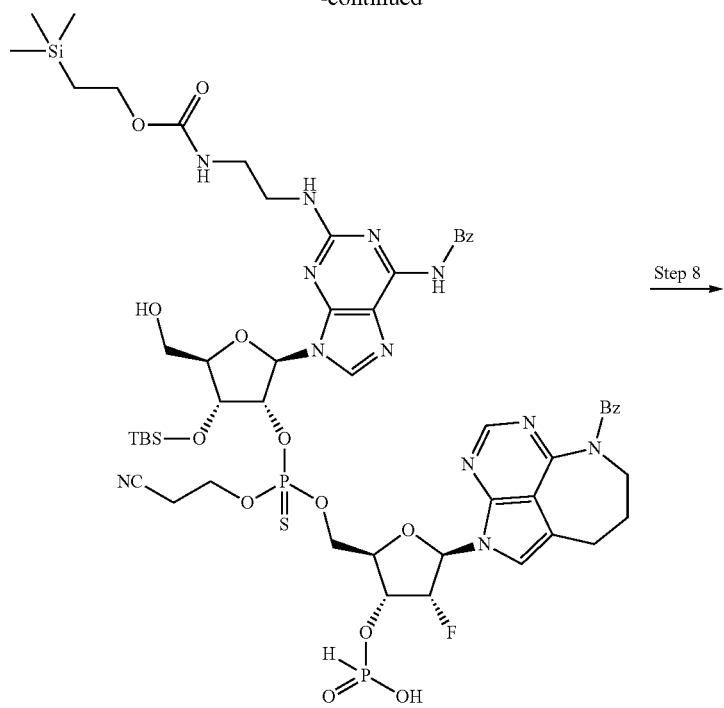
Step 8 →
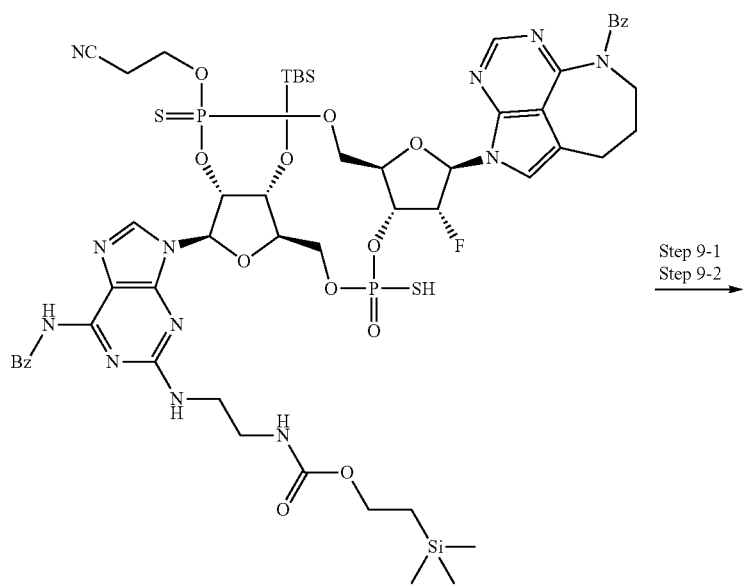
Step 9-1
Step 9-2 →

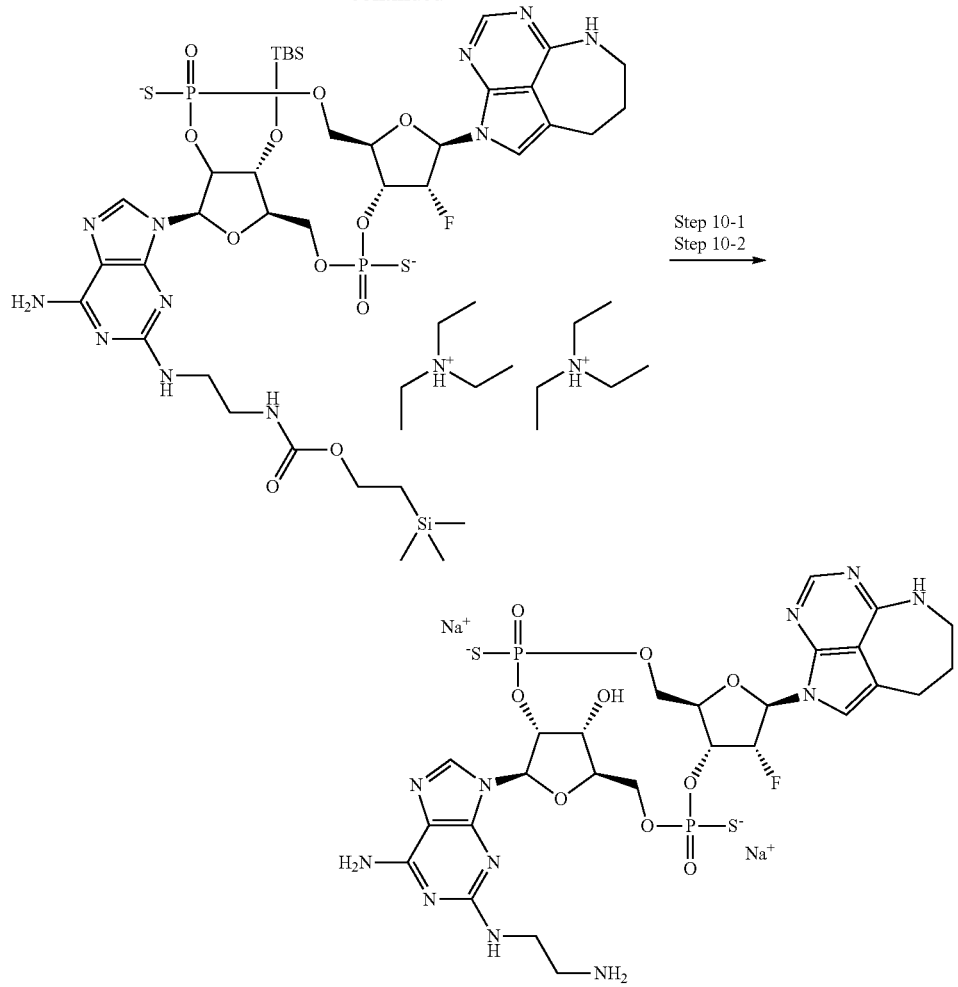

(Step 1)

2-[(2-Azaniumylethyl)amino]adenosine dichloride

To a solution of 2-({2-[(tert-butoxycarbonyl)amino]ethyl}amino) adenosine (28.7 g) as a compound known in the literature (WO 2012/159072) in methanol (240 mL), a dioxane solution of hydrogen chloride (approximately 4 M, 240 mL) was added, and the reaction mixture was stirred at room temperature overnight. The reaction mixture was concentrated to about 50 mL under reduced pressure, and a solid precipitated was then suspended in diethyl ether, and collected through filtration to give the title compound (28.8 g).

$^1$H-NMR (CD$_3$OD) δ: 8.32 (1H, s), 5.98 (1H, d, J=6.0 Hz), 4.51 (1H, t, J=5.4 Hz), 4.30 (1H, dd, J=5.1, 3.3 Hz), 4.14-4.11 (1H, m), 3.86-3.72 (4H, m), 3.23 (2H, t, J=6.0 Hz).

(Step 2)

2-{[2-({[2-(Trimethylsilyl)ethoxy]carbonyl}amino)ethyl]amino}adenosine

To a mixture of the compound (28.8 g) obtained in the above step 1 in tetrahydrofuran (330 mL)-water (70 mL), triethylamine (37 mL) and 1-({[2-(trimethylsilyl)ethoxy]carbonyl}oxy) pyrrolidine-2,5-dione (18.4 g) were added, and the reaction mixture was stirred at room temperature for 3 hours. The reaction mixture was concentrated under reduced pressure, and azeotroped with toluene. The residue was suspended in toluene, and the solid was collected through filtration. The solid obtained was dissolved in dichloromethane and methanol, and the resultant was concentrated under reduced pressure. Tetrahydrofuran was added to the residue, a solid precipitated was removed through filtration, and the filtrate was concentrated under reduced pressure. The residue was dissolved in dichloromethane and methanol, and the resultant was concentrated under reduced pressure. A solid precipitated was suspended in dichloromethane, and collected through filtration to give the title compound (22.5 g).

$^1$H-NMR (CD$_3$OD) δ: 7.92 (1H, s), 5.83 (1H, d, J=6.0 Hz), 4.77 (1H, t, J=5.4 Hz), 4.33 (1H, dd, J=4.8, 3.0 Hz), 4.14-4.10 (3H, m), 3.87 (1H, dd, J=12.4, 2.7 Hz), 3.73 (1H, dd, J=12.1, 3.0 Hz), 3.50-3.42 (2H, m), 3.32-3.29 (2H, m), 0.98-0.86 (2H, m), 0.03 (9H, s).

(Step 3)

N-Benzoyl-2-{[2-({[2-(trimethylsilyl)ethoxy]carbonyl}amino)ethyl]amino}adenosine With use of the compound (24.7 g) obtained in the above step 2, the reaction was performed in the same manner as in step 3 of Example 11 to afford the title compound (22.1 g).

¹H-NMR (CD₃OD) δ: 8.19 (1H, s), 8.05 (2H, d, J=7.9 Hz), 7.63 (1H, t, J=7.6 Hz), 7.54 (2H, t, J=7.6 Hz), 5.95 (1H, d, J=5.4 Hz), 4.75 (1H, t, J=5.4 Hz), 4.36 (1H, t, J=4.5 Hz), 4.11-4.07 (3H, m), 3.86 (1H, dd, J=12.4, 3.3 Hz), 3.75 (1H, dd, J=12.1, 3.6 Hz), 3.59-3.47 (2H, m), 3.36-3.33 (2H, m), 0.92 (2H, t, J=8.2 Hz), 0.00 (9H, s).
(Step 4)

N-Benzoyl-5'-O-[bis(4-methoxyphenyl)(phenyl)methyl]-2-{[2-({[2-(trimethylsilyl)ethoxy]carbonyl}amino)ethyl]amino}adenosine With use of the compound (22.1 g) obtained in the above step 3, the reaction was performed in the same manner as in step 1 of Example 11 to afford the title compound (29.5 g).
¹H-NMR (DMSO-d₆) δ: 10.7 (1H, s), 8.09 (1H, s), 8.01-7.99 (2H, m), 7.64-7.60 (1H, m), 7.52 (2H, t, J=7.6 Hz), 7.36-7.34 (2H, m), 7.26-7.17 (7H, m), 7.05-7.02 (1H, m), 6.95-6.92 (1H, m), 6.85-6.80 (4H, m), 5.88 (1H, d, J=4.8 Hz), 5.53 (1H, d, J=5.4 Hz), 5.20 (1H, d, J=5.4 Hz), 4.72-4.63 (1H, m), 4.34-4.26 (1H, m), 4.05-3.99 (3H, m), 3.72-3.71 (6H, m), 3.31-3.10 (6H, m), 0.89 (2H, t, J=8.5 Hz), 0.00 (9H, s).
(Step 5)

N-Benzoyl-5'-O-[bis(4-methoxyphenyl)(phenyl)methyl]-3'-O-[tert-butyl(dimethyl)silyl]-2-{[2-({[2-(trimethylsilyl)ethoxy]carbonyl}amino)ethyl]amino}adenosine With use of the compound (29.5 g) obtained in the above step 4, the reaction was performed in the same manner as in step 3 of Example 5 to afford the title compound (6.85 g).
¹H-NMR (DMSO-d₆, 90° C.) δ: 10.3 (1H, brs), 8.02 (1H, s), 7.99 (2H, d, J=7.3 Hz), 7.60 (1H, t, J=7.3 Hz), 7.51 (2H, t, J=7.6 Hz), 7.37 (2H, d, J=7.3 Hz), 7.28-7.20 (7H, m), 6.85-6.82 (4H, m), 6.69-6.53 (2H, m), 5.86 (1H, d, J=5.4 Hz), 5.07-5.04 (1H, m), 4.80-4.74 (1H, m), 4.36-4.33 (1H, m), 4.08-3.99 (3H, m), 3.74 (6H, s), 3.37-3.15 (6H, m), 0.89 (2H, t, J=7.9 Hz), 0.86 (9H, s), 0.09 (3H, s), 0.04 (3H, s), 0.01 (9H, s).
(Step 6)

N-Benzoyl-5'-O-[bis(4-methoxyphenyl)(phenyl)methyl]-3'-O-[tert-butyl(dimethyl)silyl]-2'-O-{(2-cyanoethoxy)[di(propan-2-yl)amino]phosphanyl}-2-{[2-({[2-(trimethylsilyl)ethoxy]carbonyl}amino)ethyl]amino}adenosine With use of the compound (6.22 g) obtained in the above step 5, the reaction was performed in the same manner as in step 6 of Example 1 to afford the title compound (6.18 g) as a mixture of diastereomers at the phosphorus atom (diastereomer ratio=1:1).
¹H-NMR (CD₃Cl) δ: 8.82 (1H, s), 8.00-7.97 (2H, m), 7.88 (0.5H, s), 7.85 (0.5H, s), 7.59 (1H, t, J=7.0 Hz), 7.51 (2H, t, J=7.6 Hz), 7.43 (2H, d, J=7.3 Hz), 7.33-7.20 (7H, m), 6.81 (4H, d, J=8.5 Hz), 6.08-6.01 (1H, m), 5.19-4.88 (2H, m), 4.51-4.42 (1H, m), 4.20-4.08 (3H, m), 3.82-3.24 (11H, m), 3.78 (6H, s), 2.52 (1H, 5, J=6.3 Hz), 2.38-2.34 (1H, m), 1.14-1.09 (9H, m), 0.90-0.85 (2H, m), 0.87 (9H, s), 0.12 (1.5H, s), 0.09 (1.5H, s), 0.03 (3H, s), −0.01 (9H, s).
(Step 7)

With use of the compound (1.03 g) obtained in step 8 of Example 44, the reaction was performed in the same manner as in step 7 of Example 1 to afford an acetonitrile solution of 6-benzoyl-2-{2-deoxy-2-fluoro-3-O-[hydroxy (oxo)-λ⁵-phosphanyl]-β-D-ribofuranosyl}-6,7,8,9-tetrahydro-2H-2,3,5,6-tetraazabenzo[cd]azulene. With use of the acetonitrile solution obtained and the compound (999 mg) obtained in the above step 6, the reaction was performed in the same manner as in step 8 of Example 1, and the resulting crude product was directly used for the subsequent reaction.
(Step 8)

2-(Trimethylsilyl)ethyl [2-({6-benzamido-9-[(5R,7R,8R,12aR,14R,15R,15aR,16R)-14-(6-benzoyl-6,7,8,9-tetrahydro-2H-2,3,5,6-tetraazabenzo[cd]azulen-2-yl)-16-{[tert-butyl(dimethyl)silyl]oxy}-10-(2-cyanoethoxy)-15-fluoro-2-oxo-2-sulfanyl-10-sulfanylideneoctahydro-2H,10H,12H-5,8-methano-2λ⁵,10λ⁵-furo[3,2-l][1,3,6,9,11,2,10]pentaoxadiphosphacyclotetradecin-7-yl]-9H-purin-2-yl}amino)ethyl]carbamate With use of the mixture obtained in the above step 7, the reaction was performed in the same manner as in step 9 of Example 1 to afford diastereomer 1 (370 mg: with impurities) and diastereomer 2 (201 mg: with impurities) of the title compound.
Diastereomer 1 (Less Polar)
MS(ESI)m/z: 1307 (M−H)⁻.
Diastereomer 2 (More Polar)
MS(ESI)m/z: 1307 (M−H)⁻.
(Step 9-1)

Bis(N,N-diethylethaneaminium) (5R,7R,8R,12aR,14R,15R,15aR,16R)-7-(6-amino-2-{[2-({[2-(trimethylsilyl)ethoxy]carbonyl}amino)ethyl]amino}-9H-purin-9-yl)-16-{[tert-butyl(dimethyl)silyl]oxy}-15-fluoro-2,10-dioxo-14-(6,7,8,9-tetrahydro-2H-2,3,5,6-tetraazabenzo[cd]azulen-2-yl)octahydro-2H,10H,12H-5,8-methano-2λ⁵,10λ⁵-furo[3,2-l][1,3,6,9,11,2,10]pentaoxadiphosphacyclotetradecine-2,10-bis(thiolate)

With use of the compound (370 mg: with impurities) obtained in the above step 8 (diastereomer 1), the reaction was performed in the same manner as in step 10 of Example 1 to afford the title compound (134 mg: with impurities).
MS(ESI)m/z: 1048 (M+H)⁺.
(Step 9-2)

Bis(N,N-diethylethaneaminium) (5R,7R,8R,12aR,14R,15R,15aR,16R)-7-(6-amino-2-{[2-({[2-(trimethylsilyl)ethoxy]carbonyl}amino)ethyl]amino}-9H-purin-9-yl)-16-{[tert-butyl(dimethyl)silyl]oxy}-15-fluoro-2,10-dioxo-14-(6,7,8,9-tetrahydro-2H-2,3,5,6-tetraazabenzo[cd]azulen-2-yl)octahydro-2H,10H,12H-5,8-methano-2λ⁵,10λ⁵-furo[3,2-l][1,3,6,9,11,2,10]pentaoxadiphosphacyclotetradecine-2,10-bis(thiolate)

With use of the compound (diastereomer 2) (201 mg: with impurities) obtained in the above step 8, the reaction was performed in the same manner as in step 10 of Example 1 to afford the title compound (49.1 mg: with impurities).
MS(ESI)m/z: 1048 (M+H)⁺.

(Step 10-1)

Disodium (5R,7R,8R,12aR,14R,15R,15aR,16R)-7-
{6-amino-2-[(2-aminoethyl)amino]-9H-purin-9-yl}-
15-fluoro-16-hydroxy-2,10-dioxo-14-(6,7,8,9-tetra-
hydro-2H-2,3,5,6-tetraazabenzo[cd]azulen-2-yl)
octahydro-2H,10H,12H-5,8-methano-2λ$^5$,10λ$^5$-furo
[3,2-l][1,3,6,9,11,2,10]
pentaoxadiphosphacyclotetradecine-2,10-bis
(thiolate)

(Diastereomer 1)

With use of the compound (134 mg) obtained in the above step 9-1, the reaction was performed in the same manner as in step 5 of Example 40, and the resultant was then purified by C18 silica gel column chromatography [10 mM aqueous solution of triethylammonium acetate/acetonitrile] to afford the title compound as a triethylamine salt.

The triethylamine salt obtained was subjected to salt exchange in the same manner as in [Conversion to Sodium Salt] described in step 11 of Example 1 to afford the title compound (22 mg).

MS(ESI)m/z: 790 (M+H)$^+$.

$^1$H-NMR (CD$_3$OD) δ: 8.04 (1H, brs), 8.01 (1H, s), 7.06 (1H, s), 6.43 (1H, d, J=16.9 Hz), 6.00 (1H, d, J=7.3 Hz), 5.78-5.55 (1H, m), 5.39 (1H, dd, J=51.7, 3.9 Hz), 5.31-5.18 (1H, m), 4.80 (1H, d, J=3.6 Hz), 4.50-4.44 (1H, m), 4.40-4.32 (4H, m), 4.14-4.10 (1H, m), 3.52-3.40 (2H, m), 3.35-3.23 (2H, m), 3.06-2.90 (2H, m), 2.63-2.53 (1H, m), 2.40-2.20 (1H, m), 1.99-1.76 (2H, m).

$^{31}$P-NMR (CD$_3$OD) δ: 57.2 (s), 52.6 (s).

(Step 10-2)

Disodium (5R,7R,8R,12aR,14R,15R,15aR,16R)-7-
{6-amino-2-[(2-aminoethyl)amino]-9H-purin-9-yl}-
15-fluoro-16-hydroxy-2,10-dioxo-14-(6,7,8,9-tetra-
hydro-2H-2,3,5,6-tetraazabenzo[cd]azulen-2-yl)
octahydro-2H,10H,12H-5,8-methano-2λ$^5$,10λ$^5$-furo
[3,2-l][1,3,6,9,11,2,10]
pentaoxadiphosphacyclotetradecine-2,10-bis
(thiolate)

(Diastereomer 2)

With use of the compound (49.1 mg: with impurities) obtained in the above step 9-2, the reaction was performed in the same manner as in step 5 of Example 40, and the resultant was then purified by C18 silica gel column chromatography [10 mM aqueous solution of triethylammonium acetate/acetonitrile] to afford the title compound as a triethylamine salt.

The triethylamine salt obtained was subjected to salt exchange in the same manner as in [Conversion to Sodium Salt] described in step 11 of Example 1 to afford the title compound (21 mg).

MS(ESI)m/z: 790 (M+H)$^+$.

$^1$H-NMR (CD$_3$OD) δ: 8.02 (1H, brs), 8.01 (1H, s), 7.40 (1H, s), 6.48 (1H, d, J=16.3 Hz), 6.01 (1H, d, J=7.9 Hz), 5.80-5.63 (1H, m), 5.45-5.28 (2H, m), 4.54-4.48 (2H, m), 4.41-4.36 (2H, m), 4.28-4.20 (2H, m), 4.08-4.03 (1H, m), 3.54-3.41 (2H, m), 3.40-2.52 (6H, m), 2.03-1.84 (2H, m).

$^{31}$P-NMR (CD$_3$OD) δ: 57.8 (s).

Example 48: Synthesis of CDN38

(5S,7R,8R,12aR,14R,15R,15aS)-15-Hydroxy-7-[1-
(2-hydroxyethyl)-6-oxo-1,6-dihydro-9H-purin-9-yl]-
2,10-bis(sulfanyl)-14-(6,7,8,9-tetrahydro-2H-2,3,5,6-
tetraazabenzo[cd]azulen-2-yl)octahydro-2H,10H,
12H-5,8-methano-2λ$^5$,10λ$^5$-furo[3,2-l][1,3,6,9,11,2,
10]pentaoxadiphosphacyclotetradecine-2,10-dione

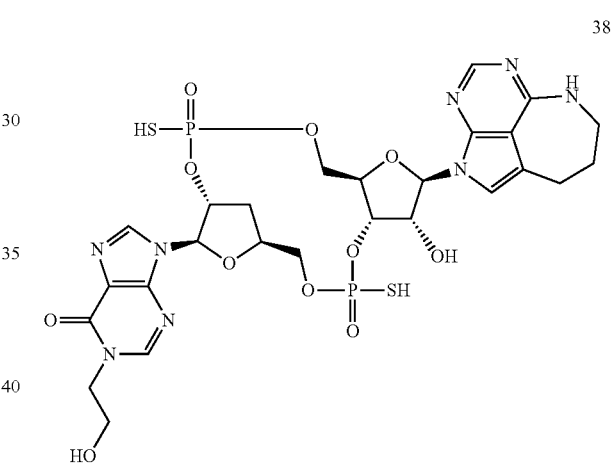

38
38a (Diastereomer 1)
38b (Diastereomer 2)

[Synthesis Scheme]

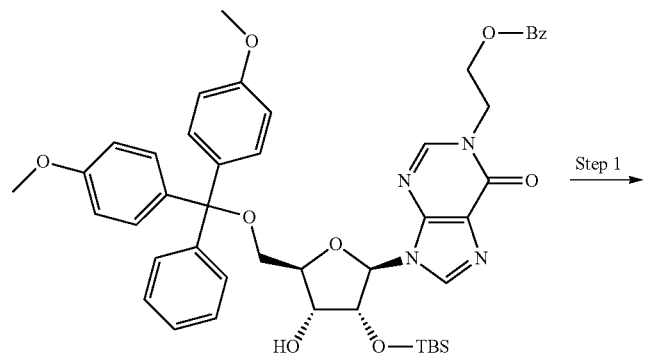

Step 1

-continued
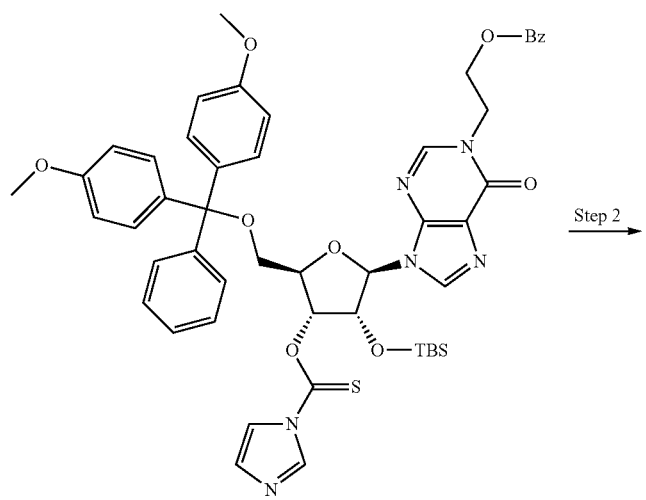
Step 2
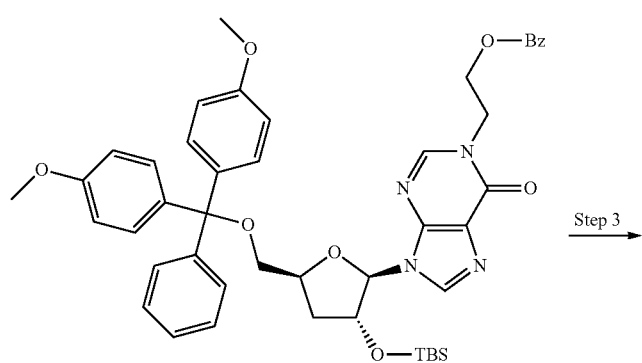
Step 3
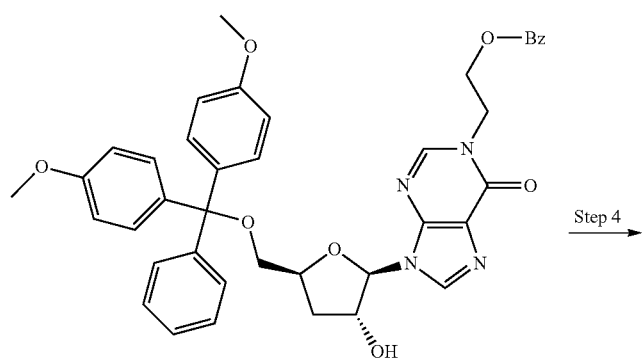
Step 4

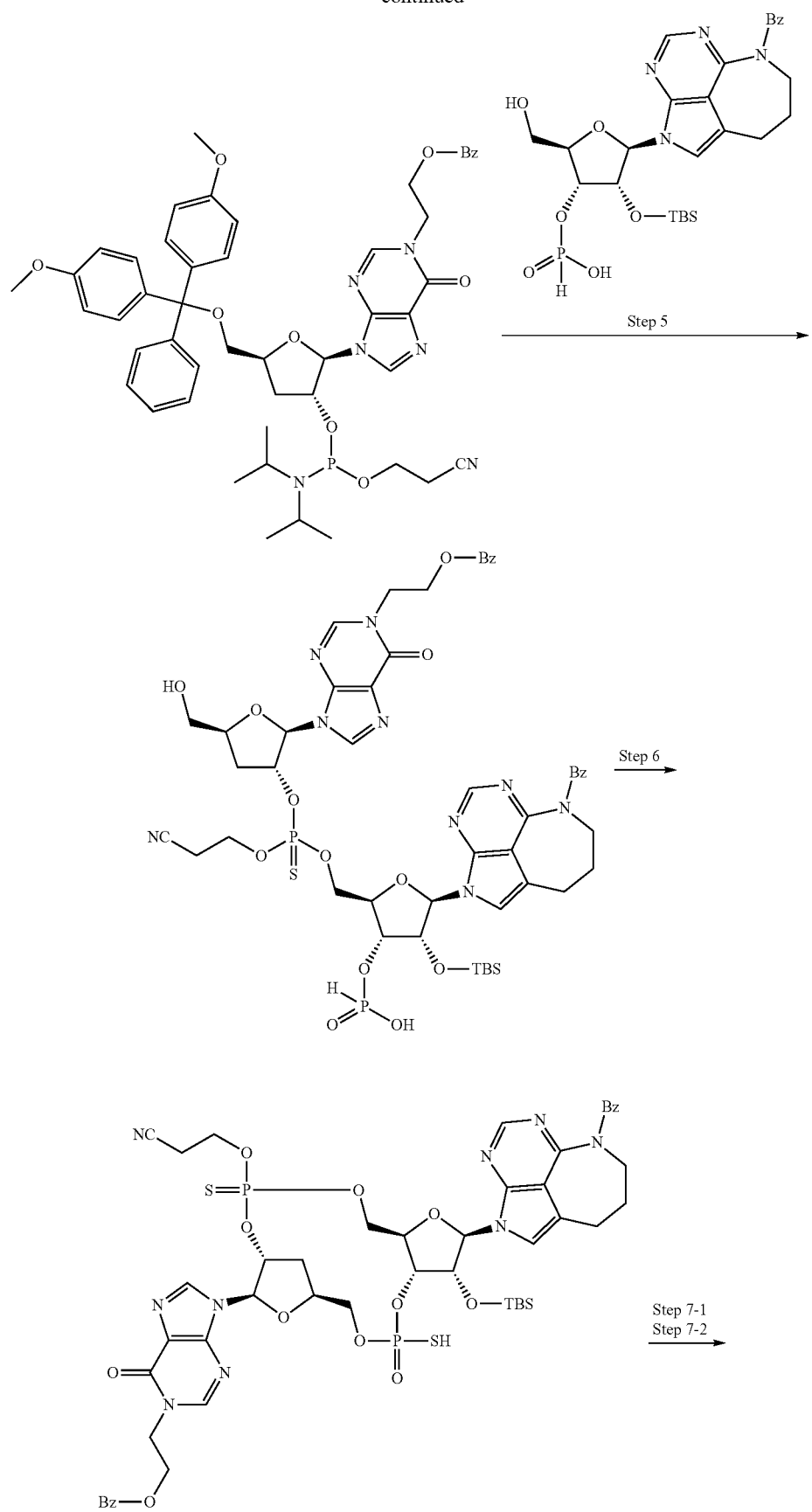

-continued

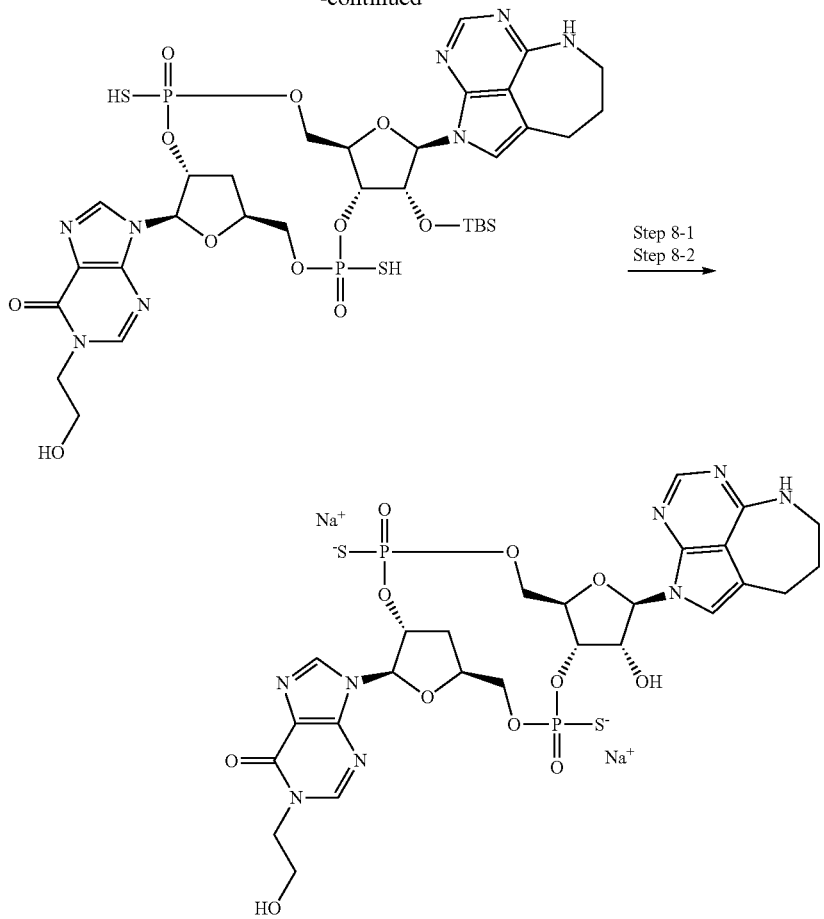

Step 8-1
Step 8-2

(Step 1)

1-[2-(Benzoyloxy)ethyl]-5'-O-[bis(4-methoxyphenyl)(phenyl)methyl]-2'-O-[tert-butyl(dimethyl)silyl]-3'-O-(1H-imidazole-1-carbothioyl)inosine To a solution of the compound (2'-O-TBS form) (1.45 g) obtained in step 2 of Example 22 in N,N-dimethylformamide (8.7 mL), N,N-dimethyl-4-aminopyridine (213 mg), and di(1H-imidazol-1-yl) methanethione (1.55 g) were added at room temperature, and the reaction mixture was stirred for 20 hours. The reaction mixture was diluted with ethyl acetate, and washed with a saturated aqueous solution of sodium hydrogen carbonate and brine in this order. After the organic layer was dried over anhydrous sodium sulfate, the drying agent was removed through filtration, and the filtrate was concentrated under reduced pressure. The residue was purified by silica gel column chromatography [hexane/ethyl acetate] to afford the title compound (1.58 g).

MS(ESI)m/z: 943 (M+H)$^+$.

$^1$H-NMR (CDCl$_3$) δ: 8.38 (1H, s), 8.05 (1H, s), 8.02-7.94 (3H, m), 7.93 (1H, s), 7.66-7.65 (1H, m), 7.60-7.52 (1H, m), 7.46-7.18 (10H, m), 7.08 (1H, s), 6.83-6.80 (4H, m), 6.07 (1H, dd, J=5.4, 3.0 Hz), 6.02 (1H, d, J=6.0 Hz), 5.20 (1H, dd, J=6.7, 5.4 Hz), 4.72-4.63 (2H, m), 4.55-4.38 (3H, m), 3.78 (3H, s), 3.77 (3H, s), 3.57-3.56 (2H, m), 0.65 (9H, s), −0.11 (3H, s), —0.26 (3H, s).

(Step 2)

1-[2-(Benzoyloxy)ethyl]-5'-O-[bis(4-methoxyphenyl)(phenyl)methyl]-2'-O-[tert-butyl(dimethyl)silyl]-3'-deoxyinosine To a solution of the compound (1.69 g) obtained in the above step 1 in benzene (10 mL), tributyltin hydride (1.42 mL) and 2,2'-azobis(isobutyronitrile) (29.4 mg) were added at room temperature, and the reaction mixture was stirred at 80° C. for 4 hours. The reaction mixture was concentrated under reduced pressure, and the residue was purified by silica gel column chromatography [hexane/ethyl acetate] to afford the title compound (1.12 g).

MS(ESI)m/z: 817 (M+H)$^+$.

$^1$H-NMR (CDCl$_3$) δ: 7.99-7.96 (4H, m), 7.60-7.55 (1H, m), 7.46-7.19 (11H, m), 6.83-6.81 (4H, m), 5.94 (1H, d, J=1.2 Hz), 4.68-4.60 (4H, m), 4.52-4.39 (2H, m), 3.79 (6H, s), 3.42-3.34 (2H, m), 2.15-2.08 (1H, m), 1.94-1.89 (1H, m), 0.86 (9H, s), 0.06 (3H, s), 0.04 (3H, s).

(Step 3)

1-[2-(Benzoyloxy)ethyl]-5'-O-[bis(4-methoxyphenyl)(phenyl)methyl]-3'-deoxyinosine To a solution of the compound (1.75 g) obtained in the above step 2 in tetrahydrofuran (11 mL), a tetrahydrofuran solution of tetrabutylammonium fluoride (approximately 1

M, 2.6 mL) was added at 0° C., and the reaction mixture was stirred at room temperature for 3 hours. The reaction mixture was concentrated under reduced pressure, and the residue was purified by silica gel column chromatography [hexane/ethyl acetate] to afford the title compound (1.29 g).

MS(ESI)m/z: 703 (M+H)$^+$.

$^1$H-NMR (CDCl$_3$) δ: 7.99-7.95 (4H, m), 7.60-7.55 (1H, m), 7.45-7.37 (4H, m), 7.29-7.17 (7H, m), 6.81-6.78 (4H, m), 5.88 (1H, d, J=3.0 Hz), 4.76-4.63 (4H, m), 4.52-4.40 (2H, m), 3.78 (6H, s), 3.36 (1H, dd, J=10.3, 3.0 Hz), 3.29 (1H, dd, J=10.3, 4.8 Hz), 2.30-2.23 (1H, m), 2.18-2.12 (1H, m). (only observable peaks are shown)

(Step 4)

1-[2-(Benzoyloxy)ethyl]-5'-O-[bis(4-methoxyphenyl)(phenyl)methyl]-2'-O-{(2-cyanoethoxy)[di(propan-2-yl)amino]phosphanyl}-3'-deoxyinosine With use of the compound (1.28 g), obtained in the above step 3 the reaction was performed in the same manner as in step 4 of Example 5 to afford the title compound (1.47 g) as a mixture of diastereomers at the phosphorus atom (diastereomer ratio=1:1).

MS(ESI)m/z: 820 (M–C$_6$H14N+OH+H)$^+$.

$^1$H-NMR (CDCl$_3$) δ: 7.99-7.94 (4H, m), 7.59-7.56 (1H, m), 7.46-7.42 (4H, m), 7.33-7.18 (7H, m), 6.81 (4H, d, J=8.5 Hz), 6.13 (0.5H, br s), 6.07 (0.5H, br s), 4.84-4.39 (6H, m), 3.84-3.52 (10H, m), 3.42-3.34 (2H, m), 2.59 (1H, t, J=6.3 Hz), 2.52 (1H, t, J=6.3 Hz), 2.30-2.07 (2H, m), 1.18-1.07 (12H, m).

(Step 5)

The same reaction as in step 7 of Example 1 was carried out in the following scale (raw material: 836 mg). With use of an acetonitrile solution of the compound obtained and the compound (735 mg) obtained in the above step 4, the reaction was performed in the same manner as in step 8 of Example 1, and the resulting crude product was directly used for the subsequent reaction.

(Step 6)

2-{9-[(5S,7R,8R,12aR,14R,15R,15aR)-14-(6-Benzoyl-6,7,8,9-tetrahydro-2H-2,3,5,6-tetraazabenzo[cd]azulen-2-yl)-15-{[tert-butyl(dimethyl)silyl]oxy}-10-(2-cyanoethoxy)-2-oxo-2-sulfanyl-10-sulfanylideneoctahydro-2H,10H,12H-5,8-methano-2λ$^5$,10λ$^5$-furo[3,2-1][1,3,6,9,11,2,10]pentaoxadiphosphacyclotetradecin-7-yl]-6-oxo-6,9-dihydro-1H-purin-1-yl}ethyl benzoate With use of the crude product obtained in the above step 5, the reaction was performed in the same manner as in step 9 of Example 1 to afford diastereomer 1 (67.6 mg) and diastereomer 2 (91.6 mg) of the title compound (retention time in HPLC: diastereomer 1>2).

Diastereomer 1 (Less Polar)

MS(ESI)m/z: 1134 (M+H)$^+$.

Diastereomer 2 (More Polar)

MS(ESI)m/z: 1134 (M+H)$^+$.

(Step 7-1)

(5S,7R,8R,12aR,14R,15R,15aR)-15-{[tert-Butyl(dimethyl)silyl]oxy}-7-[1-(2-hydroxyethyl)-6-oxo-1,6-dihydro-9H-purin-9-yl]-2,10-bis(sulfanyl)-14-(6,7,8,9-tetrahydro-2H-2,3,5,6-tetraazabenzo[cd]azulen-2-yl)octahydro-2H,10H,12H-5,8-methano-2λ$^5$,10λ$^5$-furo[3,2-1][1,3,6,9,11,2,10]pentaoxadiphosphacyclotetradecine-2,10-dione With use of the compound (diastereomer 1) (67.6 mg) obtained in the above step 6, the reaction was performed in the same manner as in step 10 of Example 1, and the resultant was purified by preparative HPLC [10 mM aqueous solution of triethylammonium acetate/acetonitrile, acetonitrile: 0%-50% (0 min-30 min)] to afford the title compound (34.9 mg).

MS(ESI)m/z: 873 (M+H)$^+$.

(Step 7-2)

(5S,7R,8R,12aR,14R,15R,15aR)-15-{[tert-Butyl(dimethyl)silyl]oxy}-7-[1-(2-hydroxyethyl)-6-oxo-1,6-dihydro-9H-purin-9-yl]-2,10-bis(sulfanyl)-14-(6,7,8,9-tetrahydro-2H-2,3,5,6-tetraazabenzo[cd]azulen-2-yl)octahydro-2H,10H,12H-5,8-methano-2λ$^5$,10λ$^5$-furo[3,2-1][1,3,6,9,11,2,10]pentaoxadiphosphacyclotetradecine-2,10-dione With use of the compound (diastereomer 2) (91.6 mg) obtained in the above step 6, the reaction was performed in the same manner as in step 10 of Example 1, and the resultant was purified by preparative HPLC [10 mM aqueous solution of triethylammonium acetate/acetonitrile, acetonitrile: 0%-50% (0 min-30 min)] to afford the title compound (44.2 mg).

MS(ESI)m/z: 873 (M+H)$^+$.

(Step 8-1)

Disodium (5S,7R,8R,12aR,14R,15R,15aS)-15-Hydroxy-7-[1-(2-hydroxyethyl)-6-oxo-1,6-dihydro-9H-purin-9-yl]-2,10-dioxo-14-(6,7,8,9-tetrahydro-2H-2,3,5,6-tetraazabenzo[cd]azulen-2-yl)octahydro-2H,10H,12H-5,8-methano-2λ$^5$,10λ$^5$-furo[3,2-1][1,3,6,9,11,2,10]pentaoxadiphosphacyclotetradecine-2,10-bis(thiolate)

(Diastereomer 1)

With use of the compound (34.9 mg) obtained in the above step 7-1, the reaction was performed in the same manner as in step 11 of Example 1, and the resultant was then purified with a Sep-Pak® C18 [0.1% aqueous solution of triethylamine/acetonitrile] to afford the title compound as a triethylamine salt.

The triethylamine salt obtained was subjected to salt exchange in the same manner as in [Conversion to Sodium Salt] described in step 11 of Example 1 to afford the title compound (21.9 mg).

MS(ESI)m/z: 759 (M+H)$^-$.

$^1$H-NMR (CD$_3$OD) δ: 8.34 (1H, brs), 8.23 (1H, s), 8.02 (1H, s), 7.24 (1H, brs), 6.28 (1H, d, J=3.6 Hz), 6.15 (1H, d, J=3.0 Hz), 5.37-5.32 (1H, m), 4.99-4.93 (1H, m), 4.74-4.58 (3H, m), 4.36-4.29 (2H, m), 4.24-4.13 (3H, m), 4.00-3.91 (1H, m), 3.82 (2H, t, J=4.8 Hz), 3.51-3.49 (2H, m), 3.00-2.90 (3H, m), 2.57-2.51 (1H, m), 2.02-1.97 (2H, m).

$^{31}$P-NMR (CD$_3$OD) δ: 59.7 (s), 56.2 (s).

(Step 8-2)

Disodium (5S,7R,8R,12aR,14R,15R,15aS)-15-hydroxy-7-[1-(2-hydroxyethyl)-6-oxo-1,6-dihydro-9H-purin-9-yl]-2,10-dioxo-14-(6,7,8,9-tetrahydro-2H-2,3,5,6-tetraazabenzo[cd]azulen-2-yl)octahydro-2H,10H,12H-5,8-methano-2$\lambda^5$,10$\lambda^5$-furo[3,2-1][1,3,6,9,11,2,10]pentaoxadiphosphacyclotetradecine-2,10-bis(thiolate)

(Diastereomer 2)

With use of the compound (44.2 mg) obtained in the above step 7-2, the reaction was performed in the same manner as in step 11 of Example 1, and the resultant was then purified with a Sep-Pak® C18 [0.1% aqueous solution of triethylamine/acetonitrile] to afford the title compound as a triethylamine salt.

The triethylamine salt obtained was subjected to salt exchange in the same manner as in [Conversion to Sodium Salt] described in step 11 of Example 1 to afford the title compound (26.5 mg).

MS(ESI)m/z: 759 (M+H)$^+$.

$^1$H-NMR (CD$_3$OD) δ: 8.48-8.46 (1H, brm), 8.24 (1H, s), 8.03 (1H, s), 7.41-7.38 (1H, brm), 6.32 (1H, d, J=4.8 Hz), 6.15 (1H, d, J=4.2 Hz), 5.46-5.41 (1H, m), 5.21-5.17 (1H, m), 4.68-4.65 (1H, m), 4.59-4.54 (2H, m), 4.50-4.44 (1H, m), 4.35-4.32 (1H, m), 4.21-4.18 (2H, m), 4.02-3.92 (2H, m), 3.84-3.81 (2H, m), 3.52-3.50 (2H, m), 2.96-2.83 (3H, m), 2.54-2.48 (1H, m), 2.03-1.98 (2H, m).

$^{31}$P-NMR (CD$_3$OD) δ: 60.3 (s), 59.1 (s).

Example 49: Synthesis of CDN39

(5R,7R,8R,12aR,14R,15R,15aS,16R)-16-Fluoro-15-hydroxy-7-[1-(2-hydroxyethyl)-6-oxo-1,6-dihydro-9H-purin-9-yl]-2,10-bis(sulfanyl)-14-(6,7,8,9-tetrahydro-2H-2,3,5,6-tetraazabenzo[cd]azulen-2-yl)octahydro-2H,10H,12H-5,8-methano-2$\lambda^5$,10$\lambda^5$-furo[3,2-1][1,3,6,9,11,2,10]pentaoxadiphosphacyclotetradecine-2,10-dione

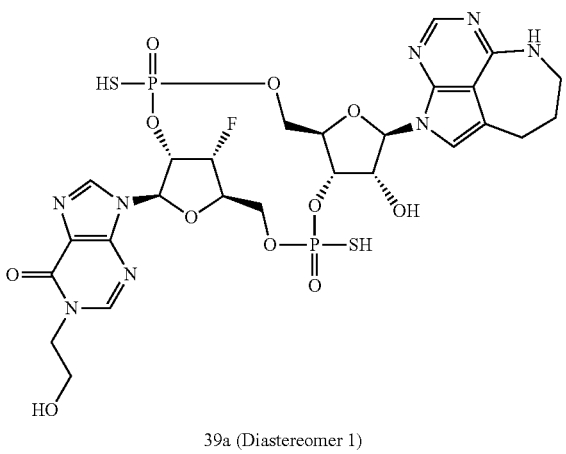

39a (Diastereomer 1)
39b (Diastereomer 2)

[Synthesis Scheme]

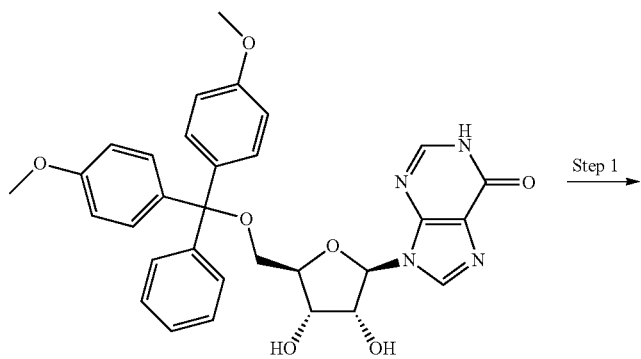

Step 1

-continued
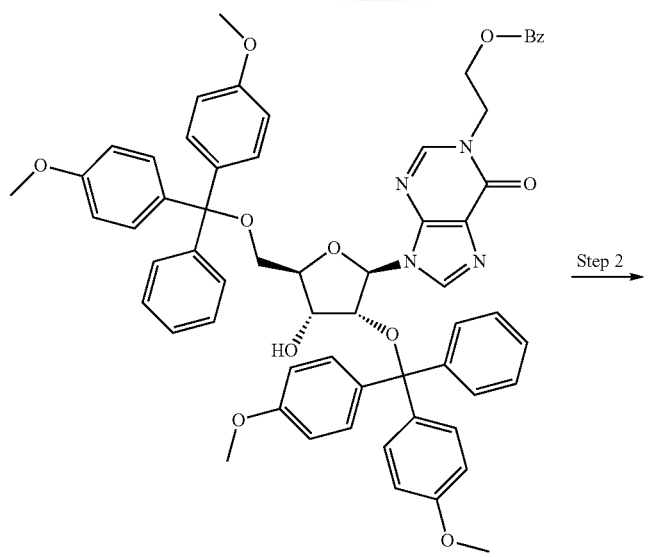
Step 2
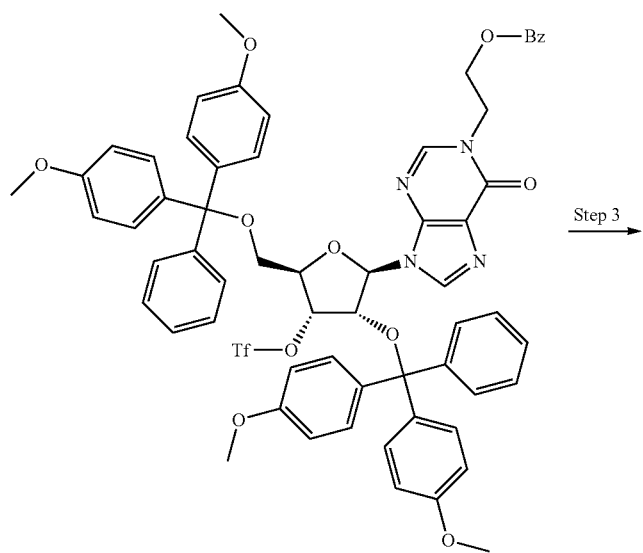
Step 3
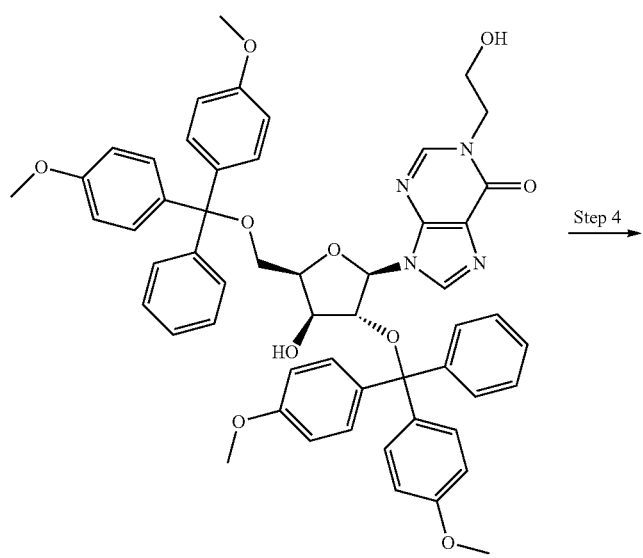
Step 4

-continued
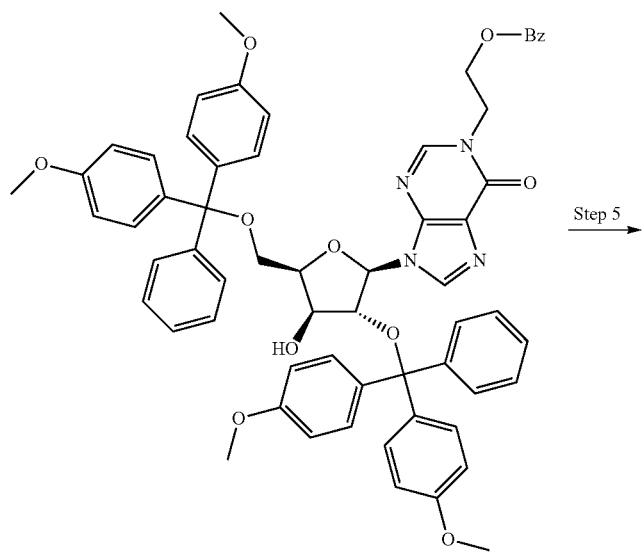
Step 5
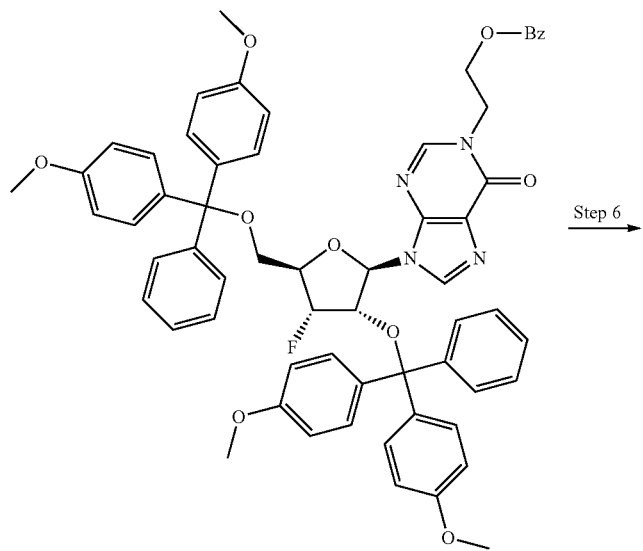
Step 6
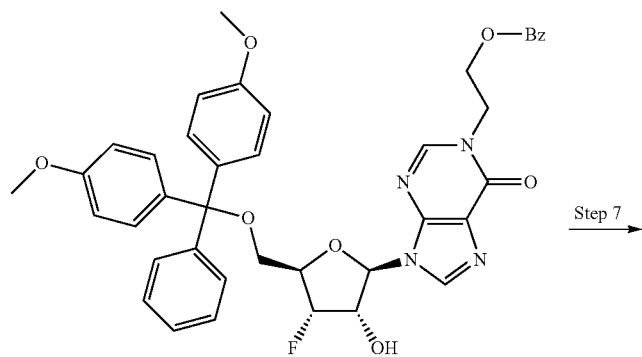
Step 7

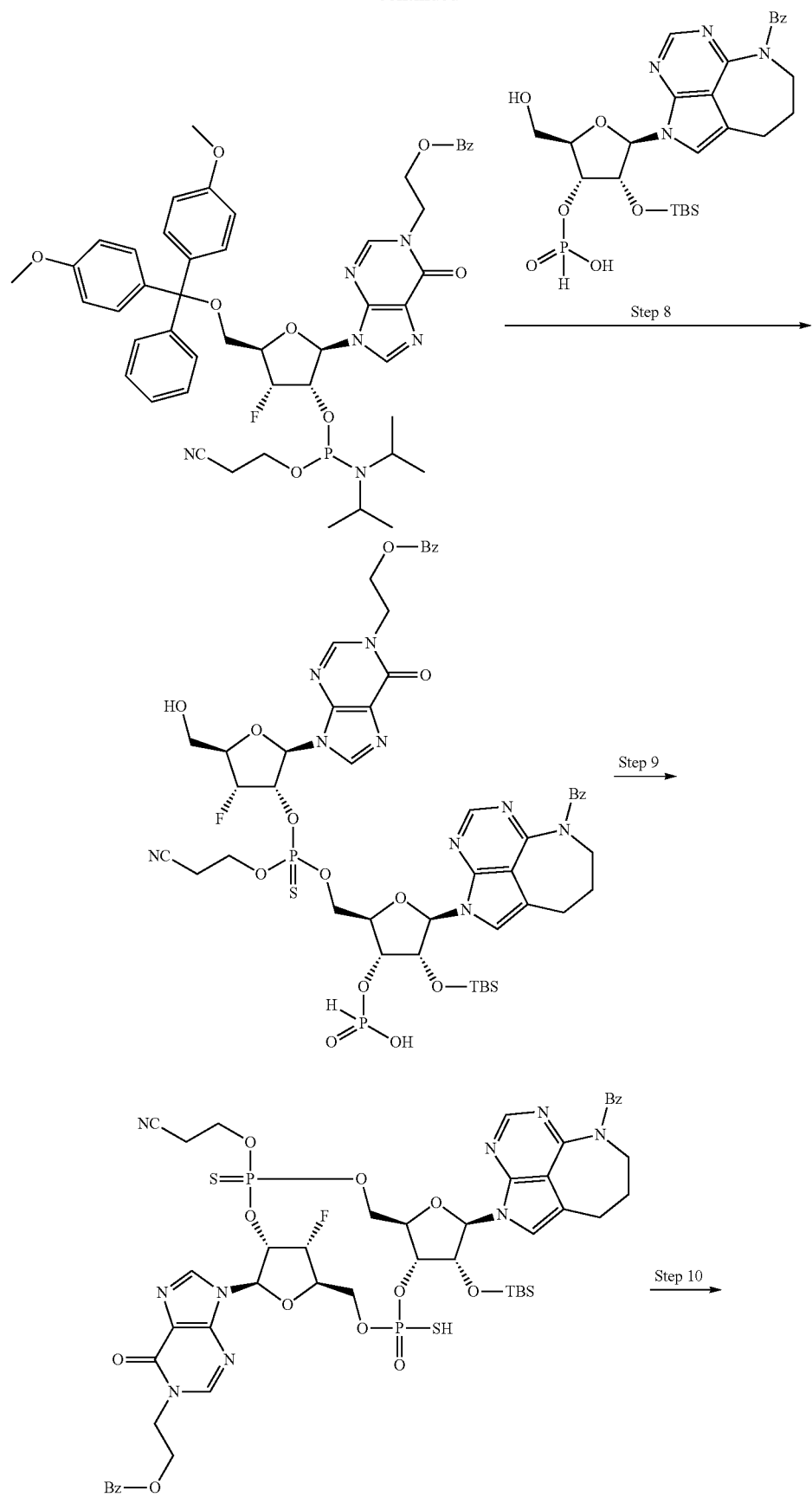

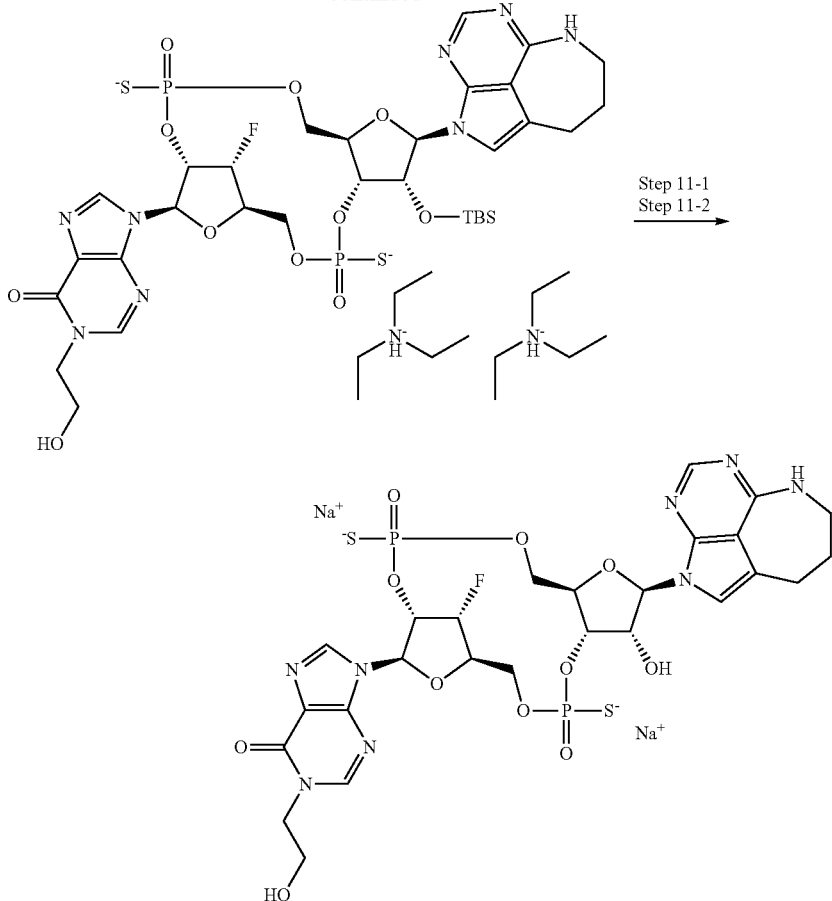

(Step 1)

1-[2-(Benzoyloxy)ethyl]-2',5'-bis-O-[bis(4-methoxyphenyl)(phenyl)methyl]inosine

To a mixed solution of commercially available (Amadis Chemical Company Limited) 5'-O-[bis(4-methoxyphenyl)(phenyl)methyl]inosine (20.0 g) in pyridine (50 mL)-N,N-dimethylacetamide (70.1 mL), 4,4'-dimethoxytrityl chloride (12.5 g), 2-bromoethyl benzoate (6.60 mL), and 1,8-diazabicyclo [5.4.0]-7-undecene (13.1 mL) were added, and the reaction mixture was stirred at room temperature for 20 hours. A saturated aqueous solution of sodium hydrogen carbonate and water were added to the reaction mixture to quench the reaction, and the resultant was then subjected to extraction with ethyl acetate. The organic layer was washed with brine, and dried over anhydrous sodium sulfate. The drying agent was removed through filtration, and the filtrate was concentrated under reduced pressure. The residue was purified by silica gel column chromatography [hexane/ethyl acetate/0.1% triethylamine] to afford the title compound (24.1 g: with impurities).

MS(ESI)m/z: 1121 (M+H)$^+$.

(Step 2)

1-[2-(Benzoyloxy)ethyl]-2',5'-bis-O-[bis(4-methoxyphenyl)(phenyl)methyl]-3'-O-(trifluoromethanesulfonyl)inosine To a solution of the compound (24.1 g) obtained in the above step 1 in dichloromethane (120 mL), pyridine (19.0 mL) was added, and trifluoromethanesulfonic anhydride (5.96 mL) was slowly added dropwise thereto at 0° C., and the reaction mixture was stirred at the same temperature for 1 hour. A saturated aqueous solution of sodium hydrogen carbonate and water were added to the reaction mixture to quench the reaction, and the resultant was then subjected to extraction with dichloromethane, and the organic layer was dried over anhydrous sodium sulfate. The drying agent was removed through filtration, and the filtrate was concentrated under reduced pressure. The residue was purified by silica gel column chromatography [hexane/ethyl acetate/0.1% triethylamine] to afford the title compound (19.7 g: with impurities).

MS(ESI)m/z: 1153 (M+H)$^+$.

(Step 3)

9-{2,5-Bis-O-[bis(4-methoxyphenyl)(phenyl)methyl]-β-D-xylofuranosyl}-1-(2-hydroxyethyl)-1,9-dihydro-6H-purin-6-one To a solution of the compound (19.7 g) obtained in the above step 2 in N,N-dimethylformamide (85.4 mL), cesium acetate (8.20 g) was added, and the reaction mixture was stirred at room temperature for 16 hours. Methanol (85.4 mL) and potassium carbonate (4.72 g) were added to the reaction mixture, which was stirred at room temperature for 2 hours. Water was added to the reaction mixture to quench the reaction, and the resultant was then subjected to extraction with ethyl acetate. The organic layer was washed with brine, and dried over anhydrous sodium sulfate. The drying agent was removed through filtration, and the filtrate was concentrated under reduced pressure. The residue was purified by silica gel column chromatography [hexane/ethyl acetate/methanol/0.1% triethylamine] to afford the title compound (12.2 g: with impurities).

MS(ESI)m/z: 917 (M+H)$^+$.

(Step 4)

1-[2-(Benzoyloxy)ethyl]-9-{2,5-bis-O-[bis(4-methoxyphenyl)(phenyl)methyl]-β-D-xylofuranosyl}-1,9-dihydro-6H-purin-6-one To a solution of the compound (12.2 g) obtained in the above step 3 in dichloromethane (48.8 mL), pyridine (1.61 mL) and benzoic anhydride (3.16 g) were added, and the reaction mixture was stirred at room temperature for 64 hours. A saturated aqueous solution of sodium hydrogen carbonate and water were added to the reaction mixture to quench the reaction, and the resultant was subjected to extraction with ethyl acetate. The organic layer was washed with brine, and then dried over anhydrous sodium sulfate. The drying agent was removed through filtration, and the filtrate was concentrated under reduced pressure. The residue was purified by silica gel column chromatography [hexane/ethyl acetate/methanol/0.1% triethylamine] to afford the title compound (7.36 g: with impurities).

MS(ESI)m/z: 1021 (M+H)$^+$.

(Step 5)

1-[2-(Benzoyloxy)ethyl]-2',5'-bis-O-[bis(4-methoxyphenyl)(phenyl)methyl]-3'-deoxy-3'-fluoroinosine To a solution of the compound (7.36 g) obtained in the above step 4 in dichloromethane (37.0 mL), 2,6-lutidine (3.34 mL) was added, to which N,N-diethylaminosulfur trifluoride (1.42 g) was then added at −78° C., and the temperature was gradually increased to room temperature under the nitrogen atmosphere, and thereafter the reaction mixture was stirred overnight. A saturated aqueous solution of sodium hydrogen carbonate was slowly added to the reaction mixture to quench the reaction, water was added thereto, and the resultant was subjected to extraction with ethyl acetate. The organic layer was washed with brine, and then dried over anhydrous sodium sulfate. The drying agent was removed through filtration, and the filtrate was concentrated under reduced pressure. The residue was purified by silica gel column chromatography [hexane/ethyl acetate 0.1% triethylamine] to afford the title compound (6.89 g: with impurities).

MS(ESI)m/z: 1023 (M+H)$^+$.

(Step 6)

1-[2-(Benzoyloxy)ethyl]-5'-O-[bis(4-methoxyphenyl)(phenyl)methyl]-3'-deoxy-3'-fluoroinosine To a solution of the compound (6.89 g) obtained in the above step 5 in dichloromethane (25.0 mL), water (0.303 mL) and dichloroacetic acid (1.39 mL) were added, and the reaction mixture was stirred at room temperature for 63 hours. Pyridine (2.0 mL) was added to the reaction mixture, which was concentrated under reduced pressure. The residue was partially purified by silica gel column chromatography [hexane/ethyl acetate/methanol] and DIOL silica gel column chromatography [hexane/ethyl acetate]. To a solution of the compound (25.0 mL) obtained in pyridine,4,4'-dimethoxytrityl chloride (1.83 g) was added at 0° C., and the reaction mixture was stirred at 4° C. for 21 hours. Methanol (1.0 mL) was added to the reaction mixture, which was stirred at 4° C. for 1 hour, and then concentrated under reduced pressure. The residue was purified by silica gel column chromatography [hexane/ethyl acetate/methanol/0.1% triethylamine] to afford the title compound (1.33 g).

MS(ESI)m/z: 721 (M+H)$^+$.

$^1$H-NMR (CDCl$_3$) δ: 7.99 (1H, s), 7.95 (1H, d, J=1.2 Hz), 7.93 (1H, s), 7.93 (1H, d, J=1.5 Hz), 7.58-7.51 (1H, m), 7.43-7.37 (2H, m), 7.35-7.30 (2H, m), 7.26-7.13 (7H, m), 6.82-6.75 (4H, m), 5.98 (1H, d, J=7.3 Hz), 5.13 (1H, dd, J=54.7, 4.1 Hz), 5.05-4.92 (1H, m), 4.63 (2H, t, J=5.1 Hz), 4.56-4.25 (4H, m), 3.76 (3H, s), 3.76 (3H, s), 3.45 (1H, dd, J=10.9, 3.6 Hz), 3.34 (1H, dd, J=10.9, 3.6 Hz).

(Step 7)

1-[2-(Benzoyloxy)ethyl]-5'-O-[bis(4-methoxyphenyl)(phenyl)methyl]-2'-O-{(2-cyanoethoxy)[di(propan-2-yl)amino]phosphanyl}-3'-deoxy-3'-fluoroinosine With use of the compound (1.33 g) obtained in the above step 6, the reaction was performed in the same manner as in step 4 of Example 5 to afford the title compound (1.49 g) as a mixture of diastereomers at the phosphorus atom (diastereomer ratio=1:1).

MS(ESI)m/z: 921 (M+H)$^+$.

$^1$H-NMR (CDCl$_3$) δ: 7.99 (0.5H, s), 7.98-7.93 (3H, m), 7.88 (0.5H, s), 7.58-7.52 (1H, m), 7.45-7.37 (4H, m), 7.33-7.18 (7H, m), 6.85-6.77 (4H, m), 6.14 (0.5H, d, J=7.3 Hz), 6.10 (0.5H, d, J=7.9 Hz), 5.27-5.01 (2H, m), 4.70-4.61 (2H, m), 4.57-4.30 (3H, m), 3.78 (3H, s), 3.77 (3H, s), 3.62-3.33 (6H, m), 2.56 (1H, t, J=6.3 Hz), 2.32 (1H, t, J=6.3 Hz), 1.12 (6H, d, J=6.3 Hz), 1.04 (3H, d, J=6.3 Hz), 0.76 (3H, d, J=6.3 Hz).

(Step 8)

The same reaction as in step 7 of Example 1 was carried out in the following scale (raw material: 948 mg). With use of an acetonitrile solution of the compound obtained and the compound (850 mg) obtained in the above step 7, the reaction was performed in the same manner as in step 8 of Example 1, and the resulting crude product was directly used for the subsequent reaction.

(Step 9)

2-{9-[(5R,7R,8S,12aR,14R,15R,15aR,16R)-14-(6-Benzoyl-6,7,8,9-tetrahydro-2H-2,3,5,6-tetraazabenzo [cd]azulen-2-yl)-15-{[tert-butyl(dimethyl)silyl]oxy}-10-(2-cyanoethoxy)-16-fluoro-2-oxo-2-sulfanyl-10-sulfanylideneoctahydro-2H,10H,12H-5,8-methano-2λ$^5$,10λ$^5$-furo[3,2-1][1,3,6,9,11,2,10] pentaoxadiphosphacyclotetradecin-7-yl]-6-oxo-6,9-dihydro-1H-purin-1-yl}ethyl benzoate With use of the crude product obtained in the above step 8, the reaction was performed in the same manner as in step 9 of Example 1 to afford the title compound (709 mg) as a mixture of diastereomers at the phosphorus atom.

MS(ESI)m/z: 1152 (M+H)$^+$.

(Step 10)

Bis(N,N-diethylethaneaminium) (5R,7R,8S,12aR,14R,15R,15aR,16R)-15-{[tert-butyl(dimethyl)silyl]oxy}-16-fluoro-7-[1-(2-hydroxyethyl)-6-oxo-1,6-dihydro-9H-purin-9-yl]-2,10-dioxo-14-(6,7,8,9-tetrahydro-2H-2,3,5,6-tetraazabenzo[cd]azulen-2-yl)octahydro-2H,10H,12H-5,8-methano-2λ$^5$,10λ$^5$-furo[3,2-l][1,3,6,9,11,2,10]pentaoxadiphosphacyclotetradecine-2,10-bis(thiolate)

With use of the compound (709 mg) obtained in the above step 9, the reaction was performed in the same manner as in step 10 of Example 1 to afford diastereomer 1 (108 mg: with impurities) and diastereomer 2 (102 mg: with impurities) of the title compound.
Diastereomer 1 (Less Polar)
MS(ESI)m/z: 891 (M+H)$^+$.
Diastereomer 2 (More Polar)
MS(ESI)m/z: 891 (M+H)$^+$.
(Step 11-1)

Disodium (5R,7R,8S,12aR,14R,15R,15aS,16R)-16-fluoro-15-hydroxy-7-[1-(2-hydroxyethyl)-6-oxo-1,6-dihydro-9H-purin-9-yl]-2,10-dioxo-14-(6,7,8,9-tetrahydro-2H-2,3,5,6-tetraazabenzo[cd]azulen-2-yl)octahydro-2H,10H,12H-5,8-methano-2λ$^5$,10λ$^5$-furo[3,2-l][1,3,6,9,11,2,10]pentaoxadiphosphacyclotetradecine-2,10-bis(thiolate)

(Diastereomer 1)
With use of the compound (diastereomer 1) (108 mg: with impurities) obtained in the above step 10, the reaction was performed in the same manner as in step 11 of Example 1, and purification was then performed under the following [Purification Conditions] to afford the title compound as a triethylamine salt.
[Purification Conditions] C18 silica gel column chromatography [10 mM aqueous solution of triethylammonium acetate/acetonitrile] and preparative HPLC [10 mM aqueous solution of triethylammonium acetate/acetonitrile, acetonitrile: 3%-30% (0 min-40 min)].
The triethylamine salt obtained was subjected to salt exchange in the same manner as in [Conversion to Sodium Salt] described in step 11 of Example 1 to afford the title compound (40.1 mg).
MS(ESI)m/z: 777 (M+H)$^+$.
$^1$H-NMR (CD$_3$OD) δ: 8.66 (1H, m), 8.26 (1H, s), 8.02 (1H, s), 7.09 (1H, s), 6.29-6.24 (2H, m), 5.68-5.45 (2H, m), 5.26-5.18 (1H, m), 4.78-4.73 (1H, m), 4.62-4.42 (3H, m), 4.26-3.98 (5H, m), 3.85-3.78 (2H, m), 3.53-3.47 (2H, m), 2.91-2.84 (2H, m), 2.04-1.96 (2H, m).
$^{31}$P-NMR (CD$_3$OD) δ: 58.0 (s), 56.9 (s).
(Step 11-2)

Disodium (5R,7R,8S,12aR,14R,15R,15aS,16R)-16-fluoro-15-hydroxy-7-[1-(2-hydroxyethyl)-6-oxo-1,6-dihydro-9H-purin-9-yl]-2,10-dioxo-14-(6,7,8,9-tetrahydro-2H-2,3,5,6-tetraazabenzo[cd]azulen-2-yl)octahydro-2H,10H,12H-5,8-methano-2λ$^5$,10λ$^5$-furo[3,2-l][1,3,6,9,11,2,10]pentaoxadiphosphacyclotetradecine-2,10-bis(thiolate)

(Diastereomer 2)
With use of the compound (diastereomer 2) (102 mg: with impurities) obtained in the above step 10, the reaction was performed in the same manner as in step 11 of Example 1, and purification was then performed under the following [Purification Conditions] to afford the title compound as a triethylamine salt.
[Purification Conditions] C18 silica gel column chromatography [10 mM aqueous solution of triethylammonium acetate/acetonitrile] and preparative HPLC [10 mM aqueous solution of triethylammonium acetate/acetonitrile, acetonitrile: 3%-25% (0 min-40 min)].

The triethylamine salt obtained was subjected to salt exchange in the same manner as in [Conversion to Sodium Salt] described in step 11 of Example 1 to afford the title compound (26.7 mg).
MS(ESI)m/z: 777 (M+H)$^+$.
$^1$H-NMR (CD$_3$OD) δ: 8.73 (1H, m), 8.25 (1H, s), 8.02 (1H, s), 7.10 (1H, brs), 6.33 (1H, d, J=6.7 Hz), 6.28 (1H, d, J=9.1 Hz), 5.65-5.50 (1H, m), 5.49-5.43 (1H, m), 5.31 (1H, dd, J=54.4, 3.6 Hz), 4.79 (1H, dd, J=6.3, 4.5 Hz), 4.62-4.34 (4H, m), 4.27-4.14 (2H, m), 4.08-4.01 (1H, m), 3.93-3.87 (1H, m), 3.86-3.80 (2H, m), 3.53-3.47 (2H, m), 2.95-2.89 (2H, m), 2.06-1.97 (2H, m).
$^{31}$P-NMR (CD$_3$OD) δ: 63.1 (s), 59.7 (s).

Example 50: Synthesis of CDN40

(5R,7R,8S,12aR,14R,15R,15aS,16R)-7-[1-(2-Aminoethyl)-6-oxo-1,6-dihydro-9H-purin-9-yl]-16-fluoro-15-hydroxy-2,10-bis(sulfanyl)-14-(6,7,8,9-tetrahydro-2H-2,3,5,6-tetraazabenzo[cd]azulen-2-yl)octahydro-2H,10H,12H-5,8-methano-2λ$^5$,10λ$^5$-furo[3,2-l][1,3,6,9,11,2,10]pentaoxadiphosphacyclotetradecine-2,10-dione

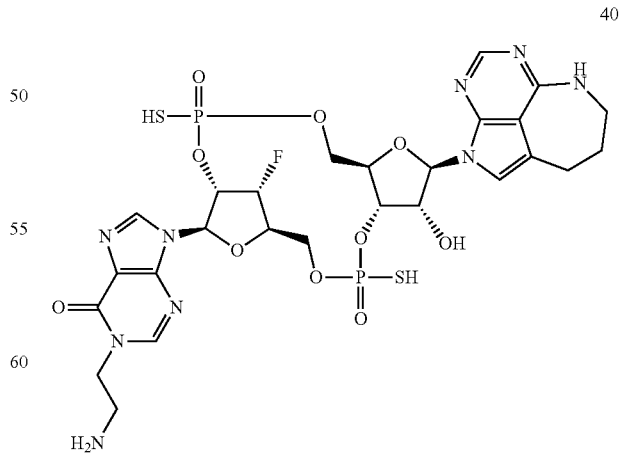

40

40a (Diastereomer 1)
40b (Diastereomer 2)

[Synthesis Scheme]
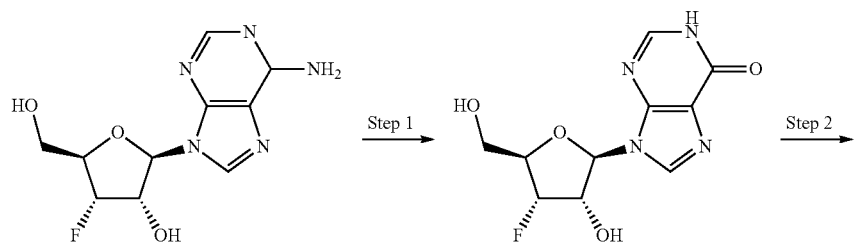
Step 1 → Step 2 →
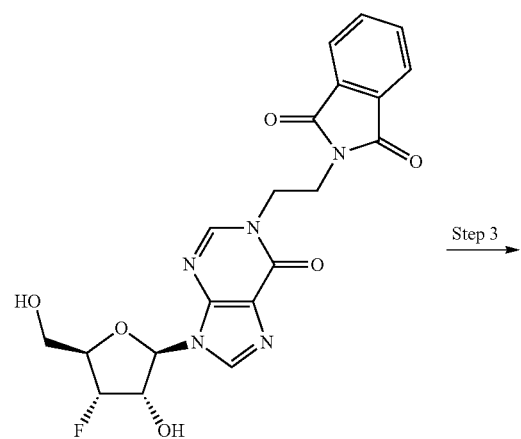
Step 3 →
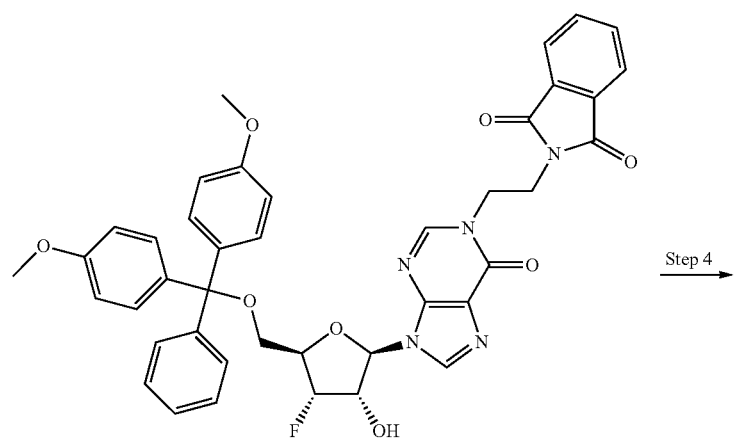
Step 4 →

465 466
-continued
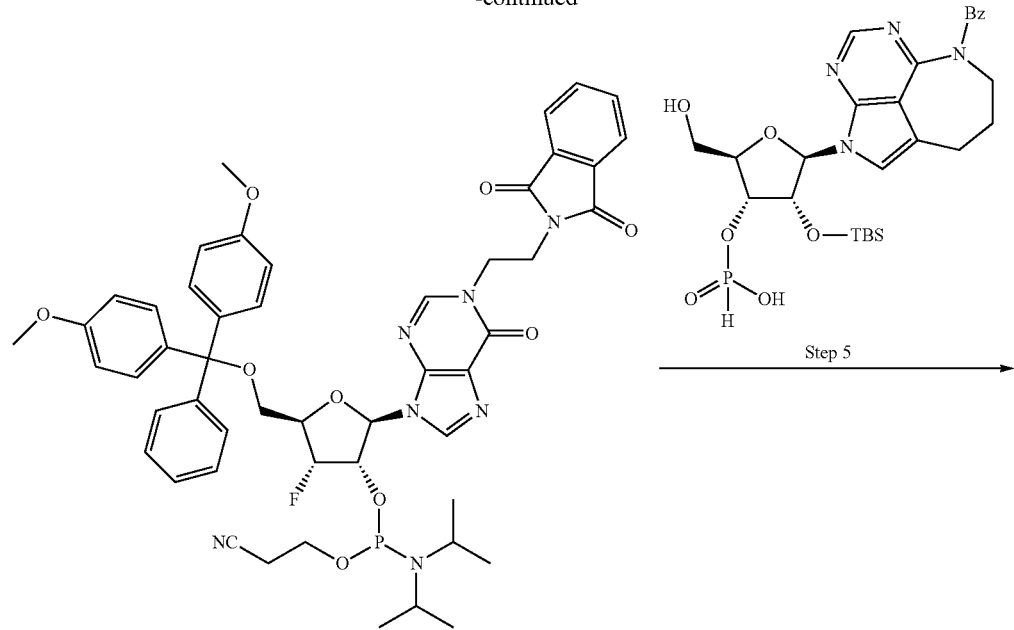
Step 5
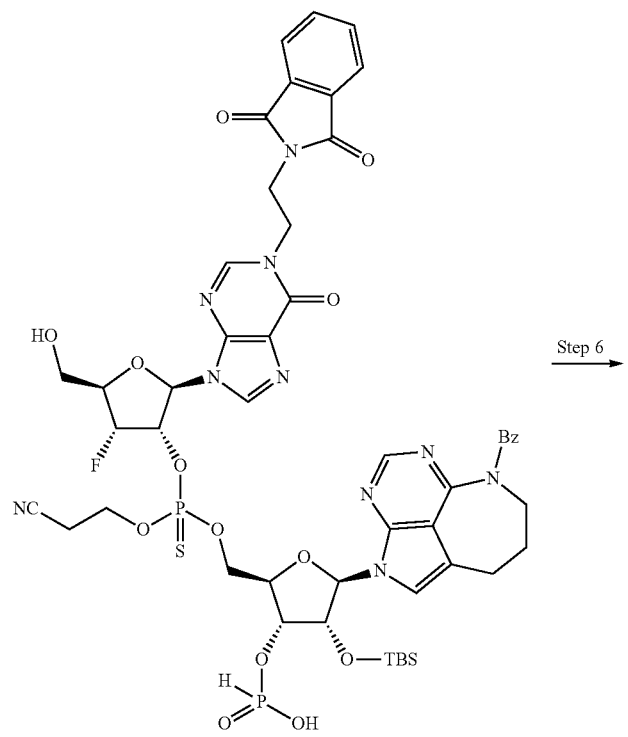
Step 6

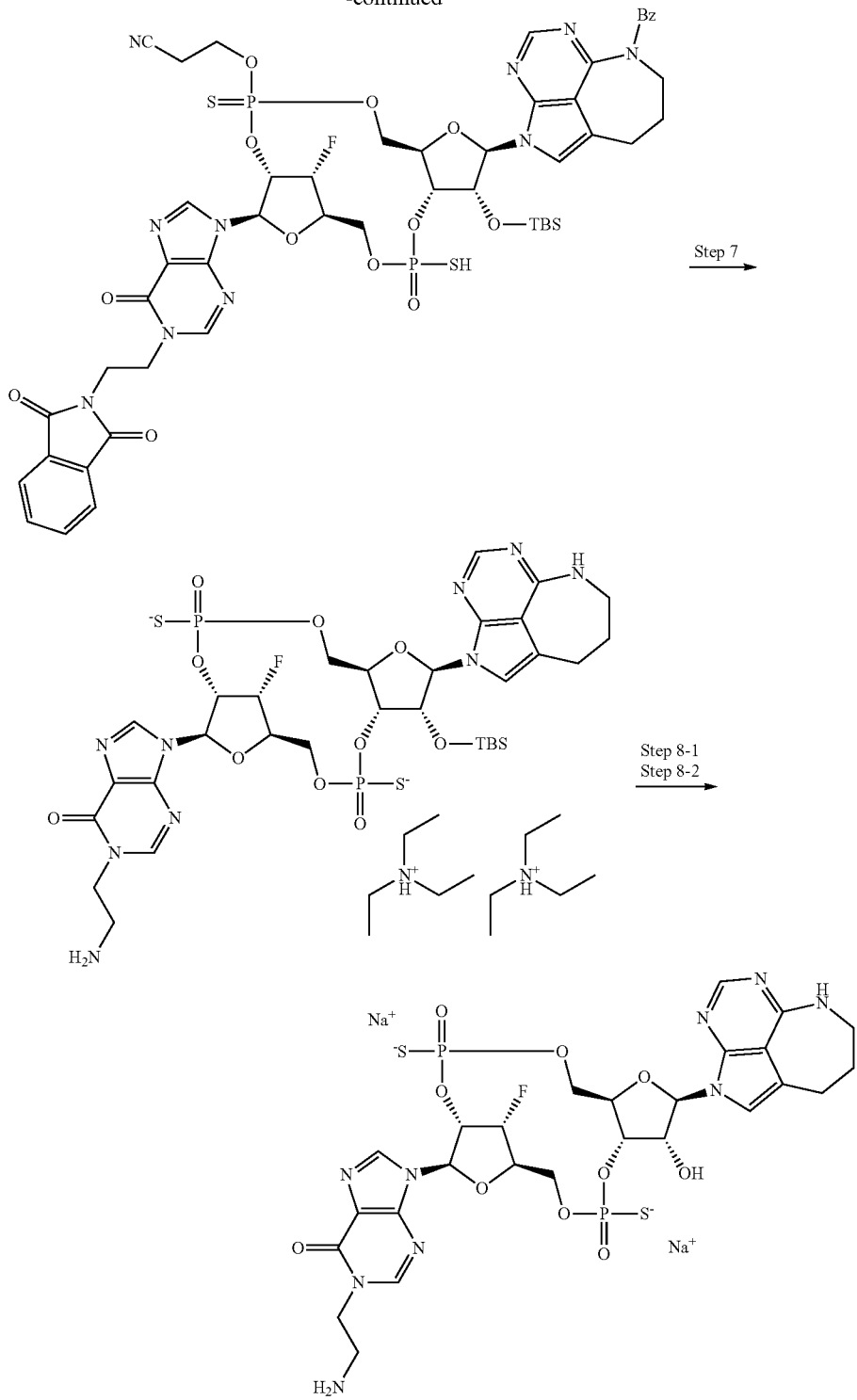

(Step 1)

3'-Deoxy-3'-fluoroinosine

To a solution of commercially available (Angene International Limited) 3'-deoxy-3'-fluoroadenosine (2.38 g) in acetic acid (120 mL), an aqueous solution (48 mL) of sodium nitrite (6.10 g) was added in small portions, and the reaction mixture was stirred at room temperature for 43 hours. The reaction mixture was concentrated under reduced pressure, and azeotroped twice with toluene. The residue was purified by silica gel column chromatography [dichloromethane/methanol] to afford the title compound (3.76 g).

MS(ESI)m/z: 271 (M+H)$^+$.

¹H-NMR (CD₃OD) δ: 8.30 (1H, s), 8.05 (1H, s), 6.03 (1H, d, J=7.8 Hz), 5.08 (1H, dd, J=54.4, 4.1 Hz), 4.89-4.85 (1H, m), 4.38 (1H, dt, J=26.8, 3.2 Hz), 3.82-3.73 (2H, m).
(Step 2)

3'-Deoxy-1-[2-(1,3-dioxo-1,3-dihydro-2H-isoindol-2-yl)ethyl]-3'-fluoroinosine

To a solution of the compound (3.76 g) obtained in the above step 1 in N,N-dimethylacetamide (37.6 mL), 2-(2-bromoethyl)-1H-isoindole-1,3 (2H)-dione (6.60 mL) and 1,8-diazabicyclo [5.4.0]-7-undecene (3.12 mL) were added, and the reaction mixture was stirred at room temperature for 3 days. The reaction mixture was concentrated under reduced pressure, and the residue was purified by silica gel column chromatography [hexane/ethyl acetate/methanol] to afford the title compound (3.51 g: with impurities).
MS(ESI)m/z: 444 (M+H)⁺.
¹H-NMR (CDCl₃) δ: 7.87 (1H, s), 7.84 (1H, s), 7.81 (2H, dd, J=5.4, 3.0 Hz), 7.73 (2H, dd, J=5.4, 3.0 Hz), 5.83 (1H, d, J=7.9 Hz), 5.28 (1H, dd, J=11.5, 2.4 Hz), 5.18 (1H, dd, J=55.0, 4.2 Hz), 5.01-4.87 (1H, m), 4.49 (1H, d, J=28.4 Hz), 4.43-4.28 (2H, m), 4.19-4.08 (2H, m), 3.95 (1H, d, J=8.2 Hz), 3.91-3.84 (1H, m), 3.76 (1H, d, J=13.3 Hz).
(Step 3)

5'-O-[Bis(4-methoxyphenyl)(phenyl)methyl]-3'-deoxy-1-[2-(1,3-dioxo-1,3-dihydro-2H-isoindol-2-yl)ethyl]-3'-fluoroinosine With use of the compound (3.51 g) obtained in the above step 2, the reaction was performed in the same manner as in step 1 of Example 11 to afford the title compound (4.05 g).
MS(ESI)m/z: 746 (M+H)⁺.
¹H-NMR (CDCl₃) δ: 7.95 (1H, s), 7.79 (2H, dd, J=5.4, 3.0 Hz), 7.73 (1H, s), 7.70 (2H, dd, J=5.4, 3.0 Hz), 7.34-7.29 (2H, m), 7.25-7.18 (7H, m), 6.81-6.76 (4H, m), 5.92 (1H, d, J=7.3 Hz), 5.12 (1H, dd, J=54.4, 4.2 Hz), 4.97-4.85 (1H, m), 4.55-4.40 (2H, m), 4.30-4.22 (1H, m), 4.21-4.01 (2H, m), 3.77 (6H, s), 3.73 (1H, d, J=10.3 Hz), 3.43 (1H, dd, J=10.9, 3.6 Hz), 3.32 (1H, dd, J=10.9, 3.6 Hz).
(Step 4)

5'-O-[Bis(4-methoxyphenyl)(phenyl)methyl]-2'-O-{(2-cyanoethoxy)[di(propan-2-yl)amino]phosphanyl}-3'-deoxy-1-[2-(1,3-dioxo-1,3-dihydro-2H-isoindol-2-yl)ethyl]-3'-fluoroinosine With use of the compound (4.05 g) obtained in the above step 3, the reaction was performed in the same manner as in step 4 of Example 5 to afford the title compound (4.35 g) as a mixture of diastereomers at the phosphorus atom (diastereomer ratio=1:1).
MS(ESI)m/z: 946 (M+H)⁺.
¹H-NMR (CDCl₃) δ: 7.95 (0.5H, s), 7.94 (0.5H, s), 7.84-7.78 (2H, m), 7.73-7.68 (2H, m), 7.65 (1H, s), 7.43-7.41 (2H, m), 7.32-7.15 (7H, m), 6.84-6.77 (4H, m), 6.09 (0.5H, d, J=7.9 Hz), 6.05 (0.5H, d, J=7.9 Hz), 5.31-5.16 (1H, m), 5.15-4.98 (1H, m), 4.51-4.21 (3H, m), 4.20-4.05 (2H, m), 3.793 (1.5H, s), 3.789 (3H, s), 3.784 (1.5H, s), 3.66-3.55 (2H, m), 3.50-3.30 (4H, m), 2.56 (1H, t, J=6.3 Hz), 2.41 (1H, t, J=6.3 Hz), 1.16 (3H, d, J=7.3 Hz), 1.14 (3H, d, J=7.3 Hz), 1.10 (3H, d, J=7.3 Hz), 0.83 (3H, d, J=7.3 Hz).
(Step 5)
The same reaction as in step 7 of Example 1 was carried out in the following scale (raw material: 1.47 g). With use of an acetonitrile solution of the compound obtained and the compound (1.35 g) obtained in the above step 4, the reaction was performed in the same manner as in step 8 of Example 1, and the resulting crude product was directly used for the subsequent reaction.
(Step 6)

3-{[(5R,7R,8S,12aR,14R,15R,15aR,16R)-14-(6-Benzoyl-6,7,8,9-tetrahydro-2H-2,3,5,6-tetraazabenzo[cd]azulen-2-yl)-15-{[tert-butyl(dimethyl)silyl]oxy}-7-{1-[2-(1,3-dioxo-1,3-dihydro-2H-isoindol-2-yl)ethyl]-6-oxo-1,6-dihydro-9H-purin-9-yl}-16-fluoro-2-oxo-2-sulfanyl-10-sulfanylideneoctahydro-2H,10H,12H-5,8-methano-2λ⁵,10λ⁵-furo[3,2-1][1,3,6,9,11,2,10]pentaoxadiphosphacyclotetradecin-10-yl]oxy}propanenitrile With use of the crude product obtained in the above step 5, the reaction was performed in the same manner as in step 9 of Example 1 to afford the title compound (1.25 g) as a mixture of diastereomers at the phosphorus atom.
MS(ESI)m/z: 1177 (M+H)⁺.
(Step 7)

Bis(N,N-diethylethaneaminium) (5R,7R,8S,12aR,14R,15R,15aR,16R)-7-[1-(2-aminoethyl)-6-oxo-1,6-dihydro-9H-purin-9-yl]-15-{[tert-butyl(dimethyl)silyl]oxy}-16-fluoro-2,10-dioxo-14-(6,7,8,9-tetrahydro-2H-2,3,5,6-tetraazabenzo[cd]azulen-2-yl)octahydro-2H,10H,12H-5,8-methano-2λ⁵,10λ⁵-furo[3,2-1][1,3,6,9,11,2,10]pentaoxadiphosphacyclotetradecine-2,10-bis(thiolate)

To a mixed solution of the compound (1.25 g) obtained in the above step 6 in ethanol (7.5 mL)-tetrahydrofuran (7.5 mL), hydrazine monohydrate (0.599 mL) was added, and the reaction mixture was stirred at 50° C. for 6 hours. After the reaction mixture was concentrated under reduced pressure, the residue was purified by C18 silica gel column chromatography [10 mM aqueous solution of triethylammonium acetate/acetonitrile] to afford diastereomer 1 (145 mg: with impurities) and diastereomer 2 (198 mg: with impurities) of the title compound (retention time in HPLC: diastereomer 1>2).
Diastereomer 1 (Less Polar)
MS(ESI)m/z: 890 (M+H)⁺.
Diastereomer 2 (More Polar)
MS(ESI)m/z: 890 (M+H)⁺.
(Step 8-1)

Disodium (5R,7R,8S,12aR,14R,15R,15aS,16R)-7-[1-(2-aminoethyl)-6-oxo-1,6-dihydro-9H-purin-9-yl]-16-fluoro-15-hydroxy-2,10-dioxo-14-(6,7,8,9-tetrahydro-2H-2,3,5,6-tetraazabenzo[cd]azulen-2-yl)octahydro-2H,10H,12H-5,8-methano-2λ⁵,10λ⁵-furo[3,2-1][1,3,6,9,11,2,10]pentaoxadiphosphacyclotetradecine-2,10-bis(thiolate)

(Diastereomer 1)
With use of the compound (diastereomer 1) (145 mg: with impurities) obtained in the above step 7, the reaction was performed in the same manner as in step 11 of Example 1, and purification was then performed under the following [Purification Conditions] to afford the title compound as a triethylamine salt.

[Purification Conditions] C18 silica gel column chromatography [10 mM aqueous solution of triethylammonium acetate/acetonitrile] and preparative HPLC [10 mM aqueous solution of triethylammonium acetate/acetonitrile-methanol solution (1:1), acetonitrile-methanol solution (1:1): 5%-50% (0 min-40 min)].

The triethylamine salt obtained was subjected to salt exchange in the same manner as in [Conversion to Sodium Salt] described in step 11 of Example 1 to afford the title compound (70.7 mg).

MS(ESI)m/z: 776 (M+H)$^+$.

$^1$H-NMR (CD$_3$OD) δ: 8.64 (1H, s), 8.23 (1H, s), 8.02 (1H, s), 7.07 (1H, s), 6.27 (1H, d, J=4.5 Hz), 6.25 (1H, d, J=6.7 Hz), 5.67-5.43 (2H, m), 5.23-5.16 (1H, m), 4.76 (1H, t, J=5.1 Hz), 4.63-4.45 (3H, m), 4.31-4.03 (5H, m), 3.51-3.46 (2H, m), 3.31-3.26 (2H, m), 2.90-2.83 (2H, m), 2.03-1.94 (2H, m).

$^{31}$P-NMR (CD$_3$OD) δ: 57.9 (s), 56.9 (s).

(Step 8-2)

Disodium (5R,7R,8S,12aR,14R,15R,15aS,16R)-7-[1-(2-aminoethyl)-6-oxo-1,6-dihydro-9H-purin-9-yl]-16-fluoro-15-hydroxy-2,10-dioxo-14-(6,7,8,9-tetrahydro-2H-2,3,5,6-tetraazabenzo[cd]azulen-2-yl)octahydro-2H,10H,12H-5,8-methano-2λ$^5$,10λ$^5$-furo[3,2-1][1,3,6,9,11,2,10]pentaoxadiphosphacyclotetradecine-2,10-bis(thiolate)

(Diastereomer 2)

With use of the compound (diastereomer 2) (198 mg: with impurities) obtained in the above step 7, the reaction was performed in the same manner as in step 11 of Example 1, and purification was then performed under the following [Purification Conditions] to afford the title compound as a triethylamine salt.

[Purification Conditions] C18 silica gel column chromatography [10 mM aqueous solution of triethylammonium acetate/acetonitrile] and preparative HPLC [10 mM aqueous solution of triethylammonium acetate/acetonitrile-methanol solution (1:1), acetonitrile-methanol solution (1:1): 5%-50% (0 min-40 min)].

The triethylamine salt obtained was subjected to salt exchange in the same manner as in [Conversion to Sodium Salt] described in step 11 of Example 1 to afford the title compound (69.7 mg).

MS(ESI)m/z: 776 (M+H)$^+$.

$^1$H-NMR (CD$_3$OD) δ: 8.73 (1H, s), 8.27 (1H, s), 8.02 (1H, s), 7.09 (1H, s), 6.31 (1H, d, J=6.7 Hz), 6.26 (1H, d, J=8.5 Hz), 5.62-5.47 (1H, m), 5.47-5.41 (1H, m), 5.30 (1H, dd, J=53.8, 3.6 Hz), 4.78 (1H, dd, J=6.7, 4.2 Hz), 4.58 (1H, d, J=26.0 Hz), 4.51-4.41 (2H, m), 4.40-4.23 (3H, m), 4.11-4.05 (1H, m), 3.93-3.86 (1H, m), 3.53-3.46 (2H, m), 3.36-3.28 (2H, m), 2.90 (2H, t, J=5.7 Hz), 2.05-1.96 (2H, m).

$^{31}$P-NMR (CD$_3$OD) δ: 62.8 (s), 59.4 (s).

Example 51: Synthesis of CDN41

N-(2-{9-[(5R,7R,8S,12aR,14R,15R,15aS,16R)-16-Fluoro-15-hydroxy-2,10-dioxo-2,10-bis(sulfanyl)-14-(6,7,8,9-tetrahydro-2H-2,3,5,6-tetraazabenzo[cd]azulen-2-yl)octahydro-2H,10H,12H-5,8-methano-2λ$^5$,10λ$^5$-furo[3,2-1][1,3,6,9,11,2,10]pentaoxadiphosphacyclotetradecin-7-yl]-6-oxo-6,9-dihydro-1H-purin-1-yl}ethyl)-2-hydroxyacetamide

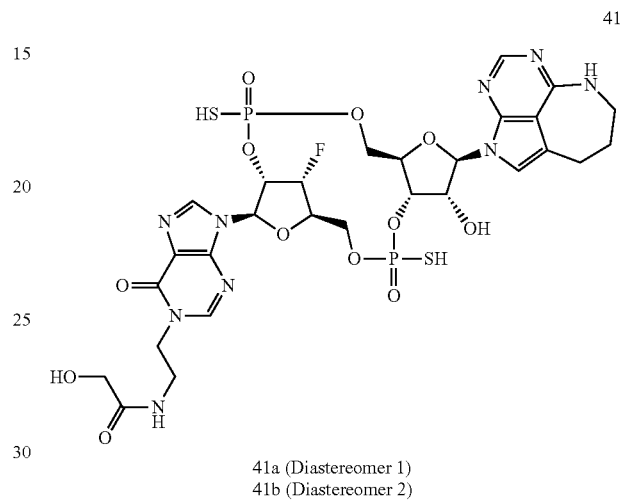

41a (Diastereomer 1)
41b (Diastereomer 2)

[Synthesis Scheme]

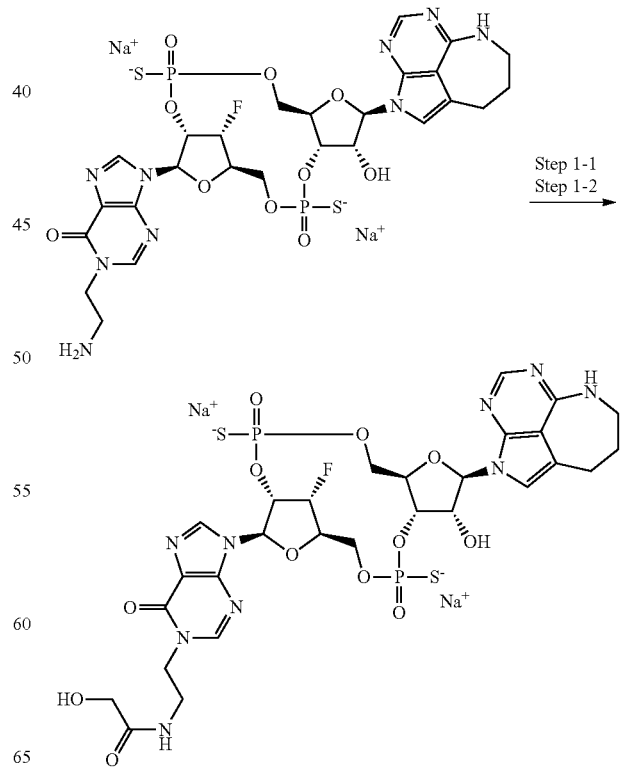

Step 1-1
Step 1-2

(Step 1-1)

Disodium (5R,7R,8S,12aR,14R,15R,15aS,16R)-16-fluoro-15-hydroxy-7-{1-[2-(2-hydroxyacetamide)ethyl]-6-oxo-1,6-dihydro-9H-purin-9-yl}-2,10-dioxo-14-(6,7,8,9-tetrahydro-2H-2,3,5,6-tetraazabenzo[cd]azulen-2-yl)octahydro-2H,10H,12H-5,8-methano-2$\lambda^5$,10$\lambda^5$-furo[3,2-1][1,3,6,9,11,2,10]pentaoxadiphosphacyclotetradecine-2,10-bis(thiolate)

(Diastereomer 1)

With use of the compound (25.0 mg) obtained in step 8-1 of Example 50, the reaction was performed in the same manner as in step 1-1 of Example 7, and purification was then performed under the following [Purification Conditions] to afford the title compound as a triethylamine salt.

[Purification Conditions] C18 silica gel column chromatography [10 mM aqueous solution of triethylammonium acetate/acetonitrile] and preparative HPLC [10 mM aqueous solution of triethylammonium acetate/acetonitrile, acetonitrile: 5%-30% (0 min-40 min)].

The triethylamine salt obtained was subjected to salt exchange in the same manner as in [Conversion to Sodium Salt] described in step 11 of Example 1 to afford the title compound (18.6 mg).

MS(ESI)m/z: 834 (M+H)$^+$.

$^1$H-NMR (CD$_3$OD) δ: 8.60 (1H, m), 8.12 (1H, m), 8.02 (1H, s), 7.11 (1H, brs), 6.27 (1H, d, J=4.9 Hz), 6.23 (1H, d, J=9.1 Hz), 5.75-5.58 (1H, m), 5.54 (1H, dd, J=53.5, 3.0 Hz), 5.28-5.20 (1H, m), 4.75 (1H, t, J=5.2 Hz), 4.62-4.52 (1H, m), 4.52-4.42 (2H, m), 4.29-4.01 (5H, m), 3.92 (2H, s), 3.64-3.58 (2H, m), 3.53-3.47 (2H, m), 2.93-2.76 (2H, m), 2.06-1.93 (2H, m).

$^{31}$P-NMR (CD$_3$OD) δ: 57.9 (s), 56.7 (s).

(Step 1-2)

Disodium (5R,7R,8S,12aR,14R,15R,15aS,16R)-16-fluoro-15-hydroxy-7-{1-[2-(2-hydroxyacetamide)ethyl]-6-oxo-1,6-dihydro-9H-purin-9-yl}-2,10-dioxo-14-(6,7,8,9-tetrahydro-2H-2,3,5,6-tetraazabenzo[cd]azulen-2-yl)octahydro-2H,10H,12H-5,8-methano-2$\lambda^5$,10$\lambda^5$-furo[3,2-1][1,3,6,9,11,2,10]pentaoxadiphosphacyclotetradecine-2,10-bis(thiolate)

(Diastereomer 2)

With use of the compound (diastereomer 2) (15.0 mg) obtained in step 8-2 of Example 50, the reaction was performed in the same manner as in step 1-1 of Example 7, and purification was then performed under the following [Purification Conditions] to afford the title compound as a triethylamine salt.

[Purification Conditions] C18 silica gel column chromatography [10 mM aqueous solution of triethylammonium acetate/acetonitrile] and preparative HPLC [10 mM aqueous solution of triethylammonium acetate/acetonitrile, acetonitrile: 5%-30% (0 min-40 min)].

The triethylamine salt obtained was subjected to salt exchange in the same manner as in [Conversion to Sodium Salt] described in step 11 of Example 1 to afford the title compound (7.4 mg).

MS(ESI)m/z: 834 (M+H)$^+$.

$^1$H-NMR (CD$_3$OD) δ: 8.69 (1H, m), 8.16 (1H, s), 8.02 (1H, s), 7.11 (1H, s), 6.32 (1H, d, J=6.7 Hz), 6.26 (1H, d, J=8.6 Hz), 5.67-5.51 (1H, m), 5.48-5.43 (1H, m), 5.29 (1H, dd, J=54.0, 3.7 Hz), 4.77 (1H, dd, J=6.4, 4.6 Hz), 4.62-4.33 (2H, m), 4.25-4.17 (2H, m), 4.08-4.01 (1H, m), 3.94 (2H, s), 3.93-3.85 (1H, m), 3.70-3.56 (2H, m), 3.52-3.46 (2H, m), 2.93-2.86 (2H, m), 2.04-1.97 (4H, m).

$^{31}$P-NMR (CD$_3$OD) δ: 62.8 (s), 59.5 (s).

Example 52: Synthesis of CDN42

(5R,7R,8S,12aR,14R,15R,15aS,16R)-7-{6-Amino-2-[(2-aminoethyl)amino]-9H-purin-9-yl}-16-fluoro-15-hydroxy-2,10-bis(sulfanyl)-14-(6,7,8,9-tetrahydro-2H-2,3,5,6-tetraazabenzo[cd]azulen-2-yl)octahydro-2H,10H,12H-5,8-methano-2$\lambda^5$,10$\lambda^5$-furo[3,2-1][1,3,6,9,11,2,10]pentaoxadiphosphacyclotetradecine-2,10-dione

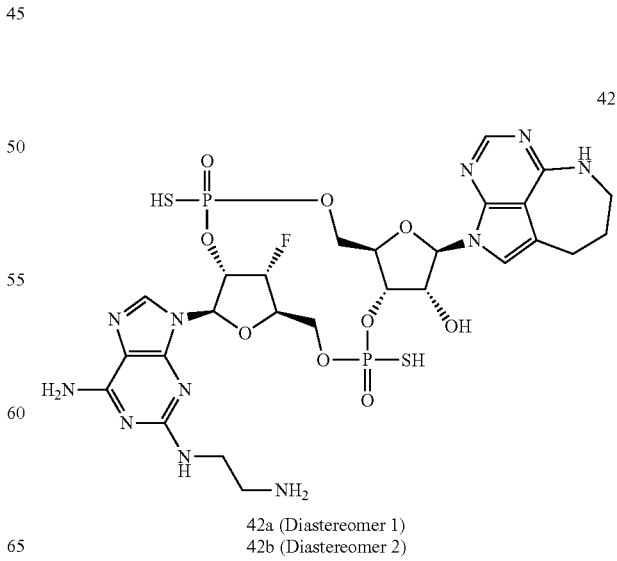

42
42a (Diastereomer 1)
42b (Diastereomer 2)

[Synthesis Scheme]
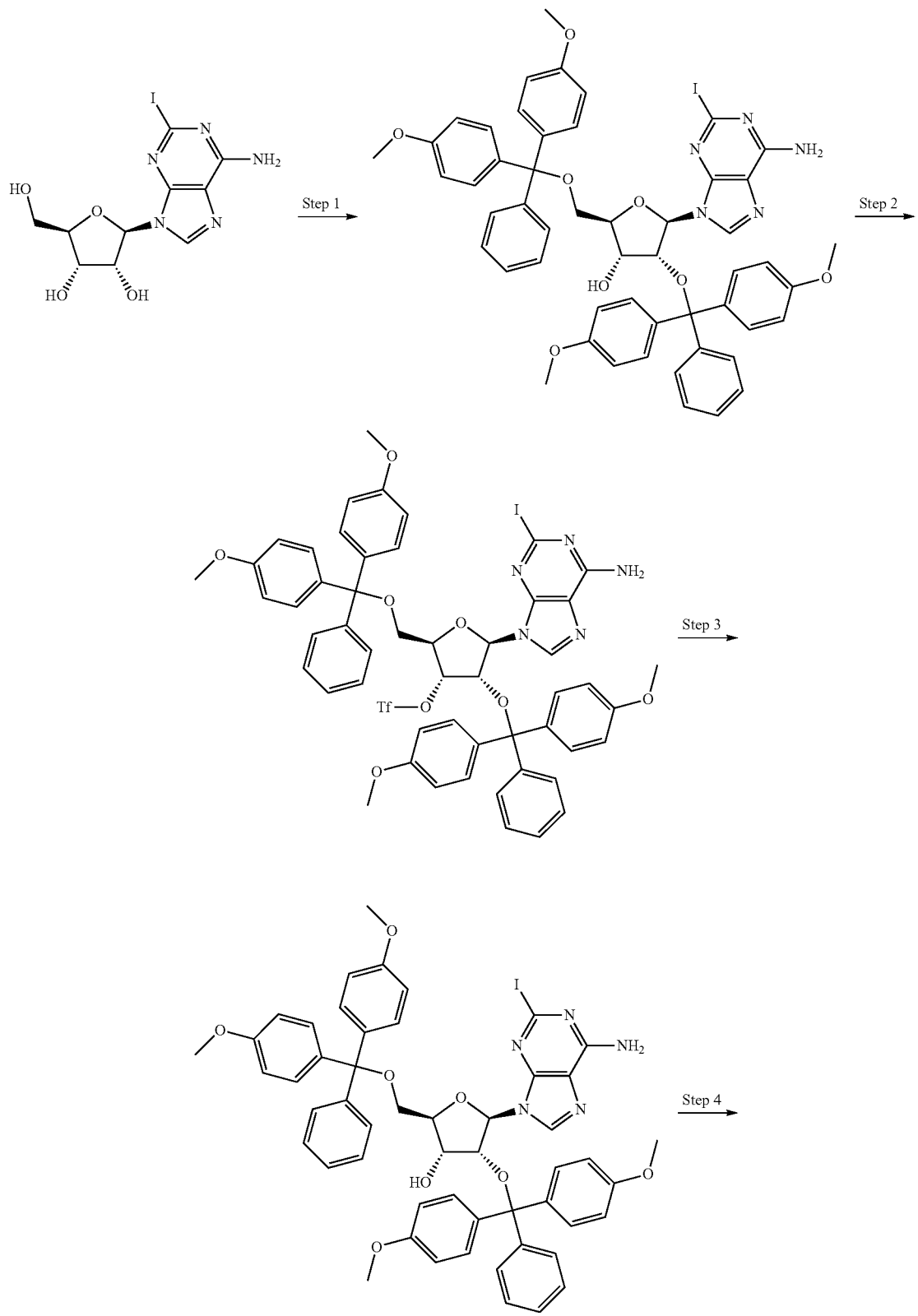

477 478
-continued
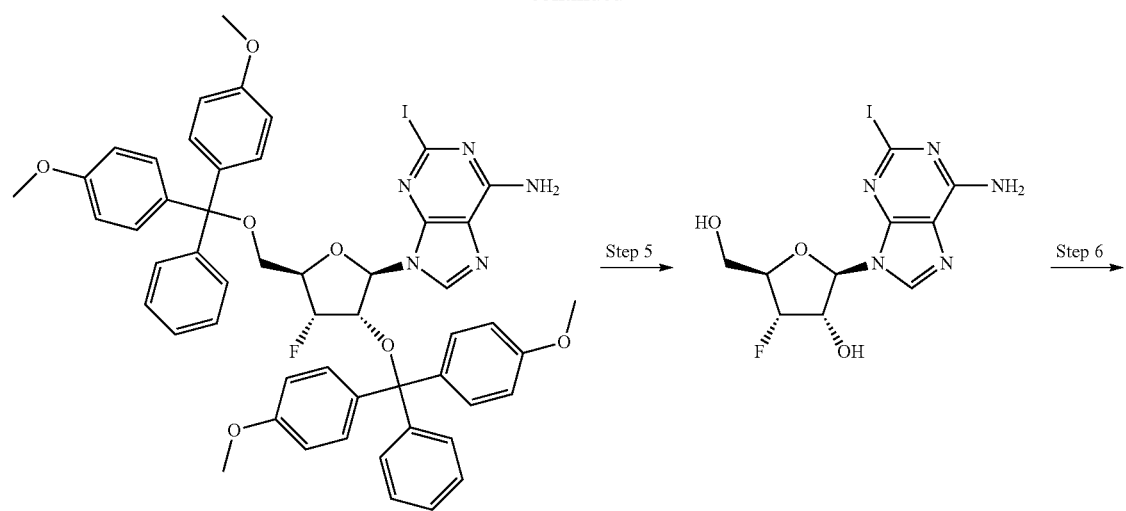
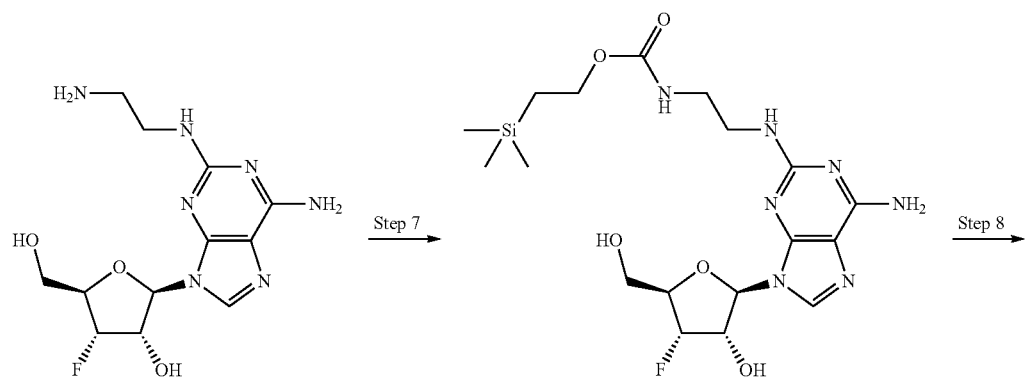
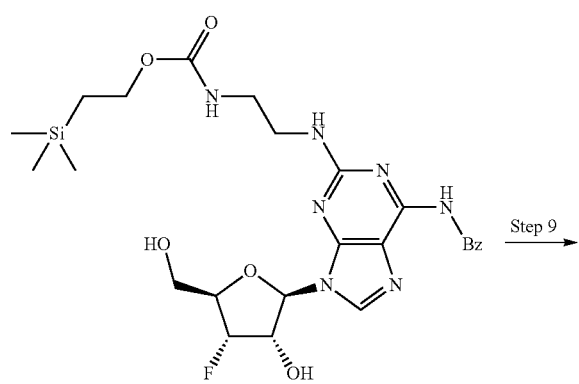

-continued
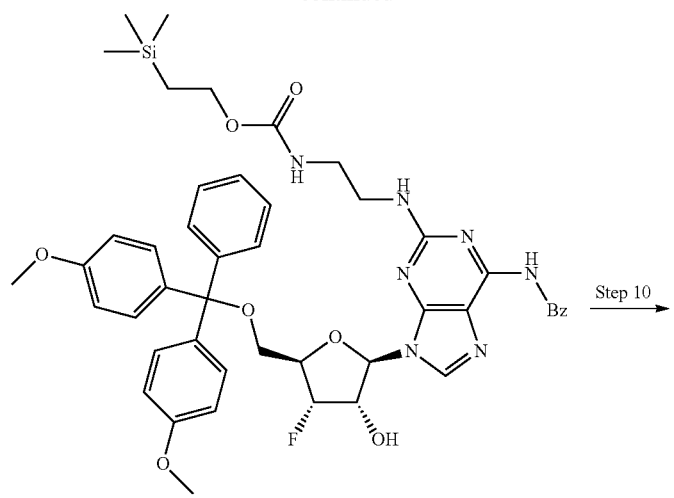
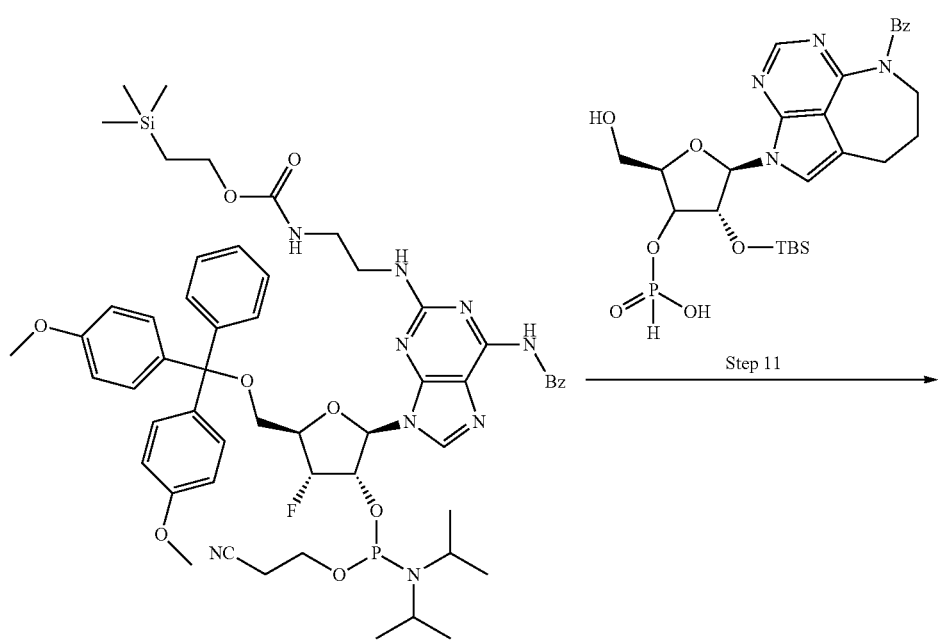

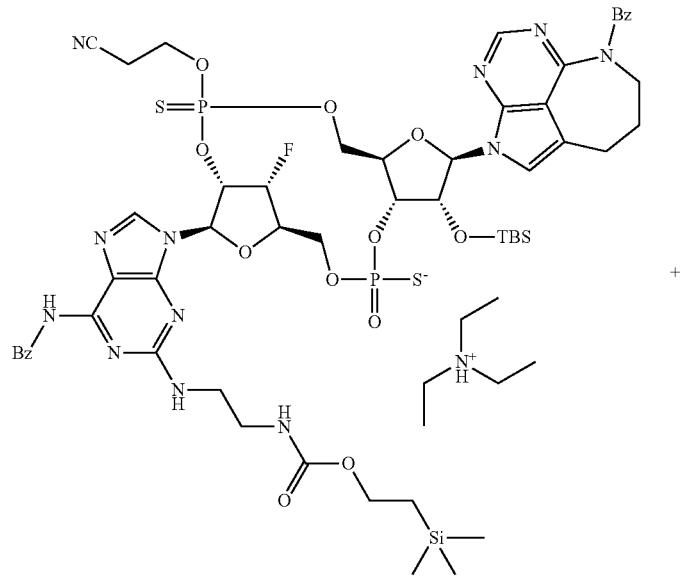
A
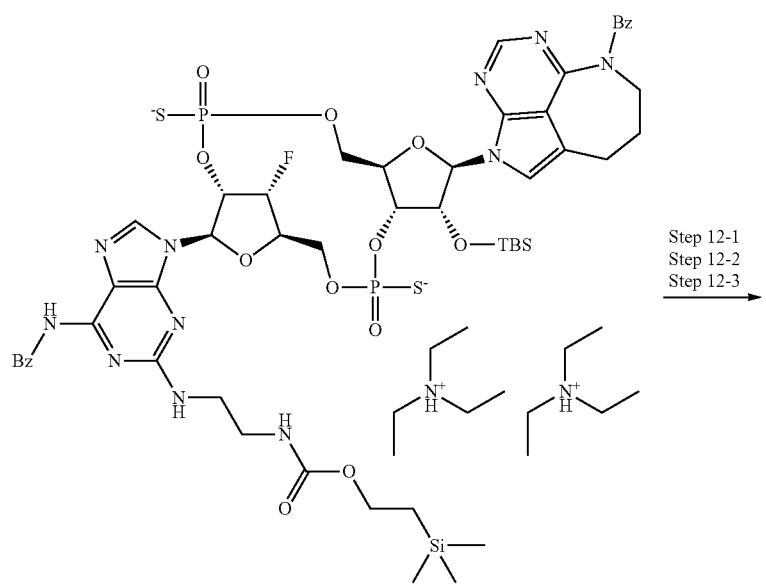
B
Step 12-1
Step 12-2
Step 12-3

-continued
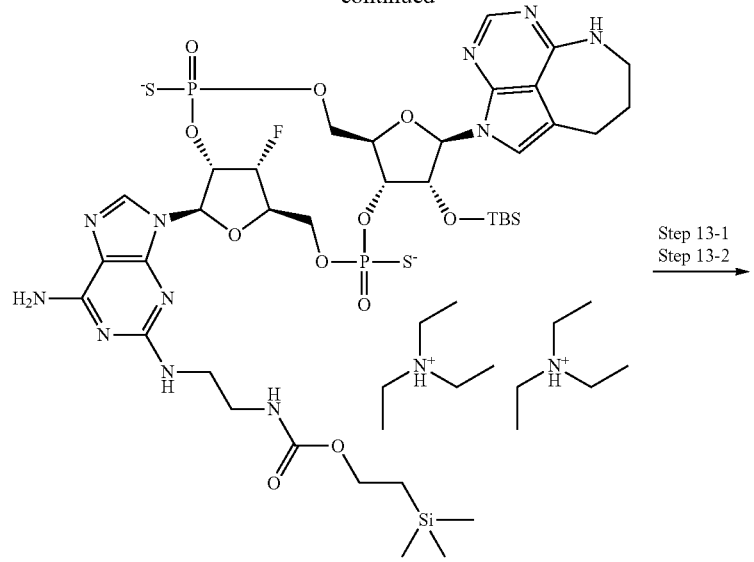
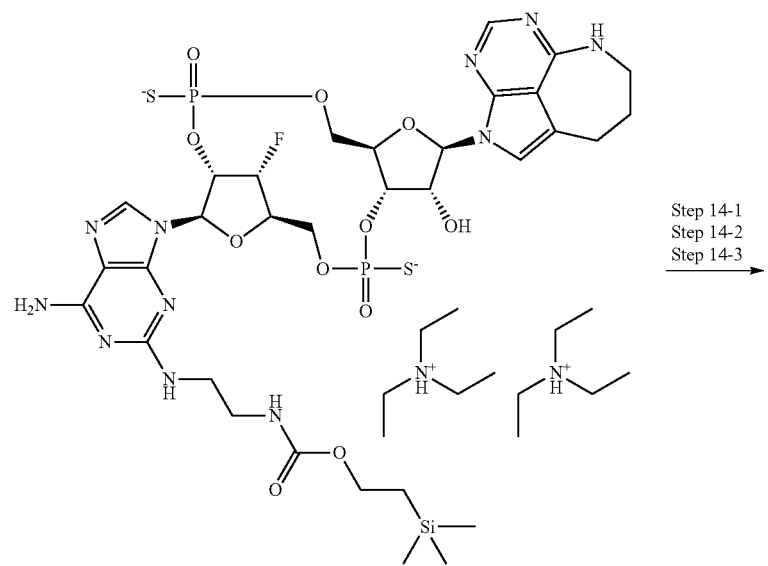
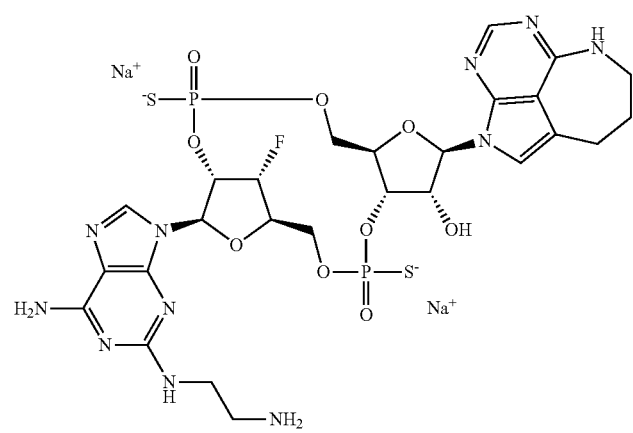

(Step 1)

2',5'-Bis-O-[bis(4-methoxyphenyl)(phenyl)methyl]-2-iodoadenosine

Commercially available (Amadis Chemical Company Limited)$_2$-iodoadenosine (1.35 g) was azeotroped three times with pyridine. To a solution of the residue in dehydrated pyridine (17.0 mL), 4,4'-dimethoxytrityl chloride (2.35 g) was added, and the reaction mixture was stirred under the nitrogen atmosphere at room temperature overnight. Methanol (5.00 mL) was added to the reaction mixture to quench the reaction, and the resultant was then concentrated under reduced pressure. The residue was purified by silica gel column chromatography [hexane/ethyl acetate/0.1% triethylamine] to afford the title compound (1.96 g: with impurities).
MS(ESI)m/z: 998 (M+H)$^+$.
$^1$H-NMR (CDCl$_3$) δ: 7.88 (1H, s), 7.29-7.12 (18H, m), 6.73-6.60 (8H, m), 6.31 (1H, d, J=7.9 Hz), 5.69 (2H, brs), 5.13 (1H, dd, J=7.6, 4.5 Hz), 4.07 (1H, t, J=3.3 Hz), 3.77 (6H, s), 3.76 (3H, s), 3.74 (3H, s), 3.14 (2H, d, J=3.6 Hz), 2.87 (1H, d, J=4.2 Hz), 2.28 (1H, s).

(Step 2)

2',5'-Bis-O-[bis(4-methoxyphenyl)(phenyl)methyl]-2-iodo-3'-O-(trifluoromethanesulfonyl) adenosine The compound (100 mg) obtained in the above step 1 was azeotroped three times with toluene. To a solution of the residue in dehydrated dichloromethane (1.0 mL), pyridine (0.20 mL) and trifluoromethanesulfonic anhydride (27.0 μL) were added under the nitrogen atmosphere at 0° C., and the reaction mixture was stirred at the same temperature for 80 minutes. Trifluoromethanesulfonic anhydride (27.0 μL) was further added thereto, and the reaction mixture was further stirred for 80 minutes. A saturated aqueous solution of sodium hydrogen carbonate was added to the reaction mixture to quench the reaction, and the resultant was then subjected to extraction with dichloromethane. After the organic layer was dried over anhydrous sodium sulfate, the drying agent was removed through filtration, and the filtrate was concentrated under reduced pressure. The residue was purified by silica gel column chromatography [hexane/ethyl acetate/0.1% triethylamine] to afford the title compound (57.2 mg).
MS(ESI)m/z: 1130 (M+H)$^+$.
$^1$H-NMR (CDCl$_3$) δ: 7.73 (1H, s), 7.32-7.09 (18H, m), 6.79-6.70 (6H, m), 6.60-6.56 (2H, m), 6.19 (1H, dd, J=8.2, 3.9 Hz), 6.01 (1H, d, J=7.9 Hz), 5.59 (2H, brs), 4.05 (1H, d, J=3.6 Hz), 3.98 (1H, t, J=6.7 Hz), 3.78 (3H, s), 3.77 (3H, s), 3.71 (3H, s), 3.70 (3H, s), 3.39 (1H, dd, J=10.9, 6.0 Hz), 3.17 (1H, dd, J=10.6, 7.0 Hz).

(Step 3)

9-{2,5-Bis-O-[bis(4-methoxyphenyl)(phenyl)methyl]-β-D-xylofuranosyl}-2-iodo-9H-purin-6-amine To a solution of the compound (2.76 g) obtained in the above step 2 in N,N-dimethylformamide (24.4 mL), cesium acetate (1.20 g) was added, and the reaction mixture was stirred at room temperature for 3 hours. Methanol (24.4 mL) and potassium carbonate (675 mg) were added to the reaction mixture, which was further stirred for 2 hours. Water was added to the reaction mixture to precipitate a solid, and the methanol component was then distilled off under reduced pressure. The resulting solid was collected through filtration to give the title compound (2.38 g).
$^1$H-NMR (CDCl$_3$) δ: 8.02 (1H, s), 7.42-7.13 (18H, m), 6.79-6.72 (8H, m), 5.68 (2H, brs), 5.55 (1H, d, J=1.2 Hz), 5.49 (1H, d, J=9.1 Hz), 4.48 (1H, s), 4.41-4.37 (1H, m), 4.06 (1H, dd, J=9.1, 3.6 Hz), 3.77 (9H, s), 3.76 (3H, s), 3.56-3.48 (2H, m).

(Step 4)

2',5'-Bis-O-[bis(4-methoxyphenyl)(phenyl)methyl]-3'-deoxy-3'-fluoro-2-iodoadenosine To a solution of the compound (2.54 g) obtained in the above step 3 in dichloromethane (17.0 mL), pyridine (1.13 mL) was added, and N,N-diethylaminosulfur trifluoride (0.397 mL) was added thereto under ice-cooling, and the reaction mixture was stirred under the nitrogen atmosphere at room temperature for 40 minutes. A saturated aqueous solution of sodium hydrogen carbonate was added to the reaction mixture to quench the reaction, and the resultant was then subjected to extraction with dichloromethane. After the organic layer was dried over anhydrous sodium sulfate, the drying agent was removed through filtration, and the filtrate was concentrated under reduced pressure. The residue was purified by silica gel column chromatography [hexane/ethyl acetate/0.1% triethylamine] to afford the title compound (2.02 g: with impurities).
MS(ESI)m/z: 1000 (M+H)$^+$.

(Step 5)

3'-Deoxy-3'-fluoro-2-iodoadenosine

To a solution of the mixture (2.02 g) obtained in the above step 4 in dichloromethane (20.2 mL), water (0.364 mL) and dichloroacetic acid (0.996 mL) were added under ice-cooling, and the reaction mixture was stirred at room temperature for 15 minutes. Pyridine (1.95 mL) was added to the reaction mixture to quench the reaction, and the resultant was concentrated under reduced pressure. The residue was purified by silica gel column chromatography [hexane/ethyl acetate] to afford the title compound (1.34 g: with impurities).
$^1$H-NMR (CD$_3$OD) δ: 5.94 (1H, d, J=7.9 Hz), 5.09 (1H, dd, J=54.7, 4.3 Hz), 4.95-4.89 (1H, m), 4.40 (1H, d, J=27.3 Hz), 3.87-3.76 (2H, m). (only observable peaks are shown)

(Step 6)

2-[(2-Aminoethyl)amino]-3'-deoxy-3'-fluoroadenosine

Ethylenediamine (1.35 mL) was added to the compound (1.34 g) obtained in the above step 5, and the reaction mixture was stirred at 110° C. for 1 hour. The reaction mixture was concentrated under reduced pressure, and the residue was purified by C18 silica gel column chromatography [10 mM aqueous solution of triethylammonium acetate/acetonitrile] to afford the title compound (543 mg: with impurities).
$^1$H-NMR (CD$_3$OD) δ: 7.94 (1H, s), 5.88 (1, d, J=7.9 Hz), 5.09 (1H, dd, J=54.7, 4.5 Hz), 4.95 (1H, dq, J=25.1, 4.2 Hz), 4.38 (1H, dt, J=27.6, 2.7 Hz), 3.84-3.76 (2H, m), 3.56-3.53 (2H, m), 3.01 (2H, t, J=5.7 Hz).

(Step 7)

3'-Deoxy-3'-fluoro-2-{[2-({[2-(trimethylsilyl)ethoxy]carbonyl}amino)ethyl]amino}adenosine To a solution of the compound (543 mg) obtained in the above step 6 in tetrahydrofuran (10 mL), 1-({[2-(trimethylsilyl)ethoxy]carbonyl}oxy) pyrrolidine-2,5-dione (961 mg), N,N-dimethylformamide (5.0 mL), and methanol (5.0 mL) were added, and the reaction mixture was stirred at room temperature for 1.5 hours. Thereto, 1-({[2-(trimethylsilyl)ethoxy]carbonyl}oxy) pyrrolidine-2,5-dione (800 mg) was further added, and the reaction mixture was further stirred for 40 minutes. After the reaction mixture was concentrated under reduced pressure, the residue was purified by silica gel column chromatography [hexane/ethyl acetate] to afford the title compound (483 mg).

$^1$H-NMR (CD$_3$OD) δ: 7.87 (1H, s), 5.83 (1H, d, J=7.9 Hz), 5.15-4.96 (2H, m), 4.35 (1H, dt, J=27.4, 2.7 Hz), 4.11-4.04 (2H, m), 3.84-3.73 (2H, m), 3.48-3.38 (2H, m), 2.96-2.83 (2H, m), 0.95-0.83 (2H, m), 0.00 (9H, s).

(Step 8)

N-Benzoyl-3'-deoxy-3'-fluoro-2-{[2-({[2-(trimethylsilyl)ethoxy]carbonyl}amino)ethyl]amino}adenosine With use of the compound (483 mg) obtained in the above step 7, the reaction was performed in the same manner as in step 3 of Example 11 to afford the title compound (374 mg).

$^1$H-NMR (CDCl$_3$) δ: 9.16-9.03 (1H, m), 8.01 (2H, d, J=7.3 Hz), 7.63-7.33 (4H, m), 5.85-5.60 (2H, m), 5.21-4.91 (2H, m), 4.45 (1H, d, J=27.8 Hz), 4.19-4.06 (2H, m), 3.92 (1H, d, J=12.7 Hz), 3.77-3.34 (6H, m), 1.05-0.87 (2H, m), −0.02 (9H, s). (only observable peaks are shown)

(Step 9)

N-Benzoyl-5'-O-[bis(4-methoxyphenyl)(phenyl)methyl]-3'-deoxy-3'-fluoro-2-{[2-({[2-(trimethylsilyl)ethoxy]carbonyl}amino)ethyl]amino}adenosine With use of the compound (374 mg) obtained in the above step 8, the reaction was performed in the same manner as in step 1 of Example 11 to afford the title compound (398 mg).

MS(ESI)m/z: 878 (M+H)$^+$.

$^1$H-NMR (CDCl$_3$) δ: 8.94 (1H, brs), 8.01-7.98 (2H, m), 7.88-7.81 (1H, m), 7.62-7.49 (3H, m), 7.40-7.20 (9H, m), 6.83-6.78 (4H, m), 6.12-5.48 (2H, m), 5.22-4.98 (2H, m), 4.52 (1H, d, J=27.8 Hz), 4.24-4.10 (2H, m), 3.77 (6H, s), 3.65-3.29 (8H, m), 1.04-0.88 (2H, m), 0.01 (9H, brs).

(Step 10)

N-Benzoyl-5'-O-[bis(4-methoxyphenyl)(phenyl)methyl]-2'-O-{(2-cyanoethoxy)[di(propan-2-yl)amino]phosphanyl}-3'-deoxy-3'-fluoro-2-{[2-({[2-(trimethylsilyl)ethoxy]carbonyl}amino)ethyl]amino}adenosine With use of the compound (398 mg) obtained in the above step 9, the reaction was performed in the same manner as in step 6 of Example 1 to afford the title compound (434 mg) as a mixture of diastereomers at the phosphorus atom (diastereomer ratio=1:1).

$^1$H-NMR (CDCl$_3$) δ: 8.79-8.75 (1H, m), 8.00-7.97 (2H, m), 7.83 (0.5H, s), 7.77 (0.5H, s), 7.61-7.21 (12H, m), 6.84-6.79 (4H, m), 6.07-5.96 (1H, m), 5.58-5.10 (3H, m), 4.50-4.40 (1H, m), 4.11-4.06 (2H, m), 3.87-3.80 (1H, m), 3.79 (3H, s), 3.78 (3H, s), 3.65-3.20 (10H, m), 2.63-2.59 (1H, m), 2.39 (1H, t, J=6.3 Hz), 1.17 (3H, d, J=6.7 Hz), 1.15 (3H, d, J=6.7 Hz), 1.10 (3H, d, J=6.7 Hz), 0.92-0.86 (2H, m), 0.81 (3H, d, J=6.7 Hz), −0.01 (9H, s).

(Step 11)

Compound A:

N,N-diethylethaneaminium (5R,7R,8S,12aR,14R,15R,15aR,16R)-7-(6-benzamido-2-{[2-({[2-(trimethylsilyl)ethoxy]carbonyl}amino)ethyl]amino}-9H-purin-9-yl)-14-(6-benzoyl-6,7,8,9-tetrahydro-2H-2,3,5,6-tetraazabenzo[cd]azulen-2-yl)-15-{[tert-butyl(dimethyl)silyl]oxy}-10-(2-cyanoethoxy)-16-fluoro-2-oxo-10-sulfanylideneoctahydro-2H,10H,12H-5,8-methano-2λ$^5$,10λ$^5$-furo[3,2-1][1,3,6,9,11,2,10]pentaoxadiphosphacyclotetradecine-2-thiolate Compound B:

bis(N,N-diethylethaneaminium) (5R,7R,8S,12aR,14R,15R,15aR,16R)-7-(6-benzamido-2-{[2-({[2-(trimethylsilyl)ethoxy]carbonyl}amino)ethyl]amino}-9H-purin-9-yl)-14-(6-benzoyl-6,7,8,9-tetrahydro-2H-2,3,5,6-tetraazabenzo[cd]azulen-2-yl)-15-{[tert-butyl(dimethyl)silyl]oxy}-16-fluoro-2,10-dioxooctahydro-2H,10H,12H-5,8-methano-2λ$^5$,10λ$^5$-furo[3,2-1][1,3,6,9,11,2,10]pentaoxadiphosphacyclotetradecine-2,10-bis(thiolate)

The same reaction as in step 7 of Example 1 was carried out in the following scale (raw material: 502 mg). With use of an acetonitrile solution of the compound obtained and the compound (434 mg) obtained in the above step 10, the reaction was performed in the same manner as in step 8 of Example 1 and step 9 of Example 1 to afford diastereomer 1 (43.9 mg) and diastereomer 2 (27.0 mg) of title compound A, and diastereomer 1 (55.0 mg) and diastereomer 2 (121 mg) of title compound B (each with impurities).

Diastereomer 1 of Compound A (Less Polar)

MS(ESI)m/z: 1309 (M+H)$^+$.

Diastereomer 2 of Compound A (More Polar)

MS(ESI)m/z: 1309 (M+H)$^+$.

Diastereomer 1 of Compound B (Less Polar)

MS(ESI)m/z: 1256 (M+H)$^+$.

Diastereomer 2 of Compound B (More Polar)

MS(ESI)m/z: 1256 (M+H)$^+$.

(Step 12-1)

Bis(N,N-diethylethaneaminium) (5R,7R,8S,12aR,14R,15R,15aR,16R)-7-(6-amino-2-{[2-({[2-(trimethylsilyl)ethoxy]carbonyl}amino)ethyl]amino}-9H-purin-9-yl)-15-{[tert-butyl(dimethyl)silyl]oxy}-16-fluoro-2,10-dioxo-14-(6,7,8,9-tetrahydro-2H-2,3,5,6-tetraazabenzo[cd]azulen-2-yl)octahydro-2H,10H,12H-5,8-methano-2λ$^5$,10λ$^5$-furo[3,2-1][1,3,6,9,11,2,10]pentaoxadiphosphacyclotetradecine-2,10-bis(thiolate)

With use of compound A (diastereomer 1) (43.9 mg) obtained in the above step 11, the reaction was performed in the same manner as in step 10 of Example 1 to afford the title compound.

MS(ESI)m/z: 1048 (M+H)$^+$.

(Step 12'-1)

Bis(N,N-diethylethaneaminium) (5R,7R,8S,12aR, 14R,15R,15aR,16R)-7-(6-amino-2-{[2-({[2-(trimethylsilyl)ethoxy]carbonyl}amino)ethyl]amino}-9H-purin-9-yl)-15-{[tert-butyl(dimethyl)silyl]oxy}-16-fluoro-2,10-dioxo-14-(6,7,8,9-tetrahydro-2H-2,3,5,6-tetraazabenzo[cd]azulen-2-yl)octahydro-2H,10H,12H-5,8-methano-2λ$^5$,10λ$^5$-furo[3,2-1][1,3,6,9,11,2,10]pentaoxadiphosphacyclotetradecine-2,10-bis(thiolate)

With use of compound B (diastereomer 1) (55.0 mg) obtained in the above step 11, the reaction was performed in the same manner as in step 10 of Example 1 to afford the title compound.
MS(ESI)m/z: 1048 (M+H)$^+$.

(Step 12-2)

Bis(N,N-diethylethaneaminium) (5R,7R,8S,12aR, 14R,15R,15aR,16R)-7-(6-amino-2-{[2-({[2-(trimethylsilyl)ethoxy]carbonyl}amino)ethyl]amino}-9H-purin-9-yl)-15-{[tert-butyl(dimethyl)silyl]oxy}-16-fluoro-2,10-dioxo-14-(6,7,8,9-tetrahydro-2H-2,3,5,6-tetraazabenzo[cd]azulen-2-yl)octahydro-2H,10H,12H-5,8-methano-2λ$^5$,10λ$^5$-furo[3,2-1][1,3,6,9,11,2,10]pentaoxadiphosphacyclotetradecine-2,10-bis(thiolate)

With use of compound A (diastereomer 2) (27.0 mg: with impurities) obtained in the above step 11, the reaction was performed in the same manner as in step 10 of Example 1 to afford the title compound.
MS(ESI)m/z: 1048 (M+H)$^+$.

(Step 13-1)

Bis(N,N-diethylethaneaminium) (5R,7R,8S,12aR, 14R,15R,15aS,16R)-7-(6-amino-2-{[2-({[2-(trimethylsilyl)ethoxy]carbonyl}amino)ethyl]amino}-9H-purin-9-yl)-16-fluoro-15-hydroxy-2,10-dioxo-14-(6,7,8,9-tetrahydro-2H-2,3,5,6-tetraazabenzo[cd]azulen-2-yl)octahydro-2H,10H,12H-5,8-methano-2λ$^5$,10λ$^5$-furo[3,2-1][1,3,6,9,11,2,10]pentaoxadiphosphacyclotetradecine-2,10-bis(thiolate)

The compound obtained in the above step 12-1 and the compound obtained in step 12'-1 were combined, and the reaction was performed in the same manner as in step 11 of Example 1 to afford the title compound (36.4 mg).
MS(ESI)m/z: 934 (M+H)$^+$.

(Step 13-2)

Bis(N,N-diethylethaneaminium) (5R,7R,8S,12aR, 14R,15R,15aS,16R)-7-(6-amino-2-{[2-({[2-(trimethylsilyl)ethoxy]carbonyl}amino)ethyl]amino}-9H-purin-9-yl)-16-fluoro-15-hydroxy-2,10-dioxo-14-(6,7,8,9-tetrahydro-2H-2,3,5,6-tetraazabenzo[cd]azulen-2-yl)octahydro-2H,10H,12H-5,8-methano-2λ$^5$,10λ$^5$-furo[3,2-1][1,3,6,9,11,2,10]pentaoxadiphosphacyclotetradecine-2,10-bis(thiolate)

With use of the compound obtained in the above step 12-2, the reaction was performed in the same manner as in step 11 of Example 1 to afford the title compound (12.4 mg).
MS(ESI)m/z: 934 (M+H)$^+$.

(Step 14-1)

Disodium (5R,7R,8S,12aR,14R,15R,15aS,16R)-7-{6-amino-2-[(2-aminoethyl)amino]-9H-purin-9-yl}-16-fluoro-15-hydroxy-2,10-dioxo-14-(6,7,8,9-tetrahydro-2H-2,3,5,6-tetraazabenzo[cd]azulen-2-yl)octahydro-2H,10H,12H-5,8-methano-2λ$^5$,10λ$^5$-furo[3,2-1][1,3,6,9,11,2,10]pentaoxadiphosphacyclotetradecine-2,10-bis(thiolate)

(Diastereomer 1)

With use of the compound (36.4 mg) obtained in the above step 13-1, the reaction was performed in the same manner as in step 5 of Example 40, and purification was then performed under the following [Purification Conditions] to afford the title compound as a triethylamine salt.

[Purification Conditions] preparative HPLC [10 mM aqueous solution of triethylammonium acetate/acetonitrile, acetonitrile: 2%-30% (0 min-40 min)] and Sep-Pak® C18 [water/acetonitrile/0.1% triethylamine].

The triethylamine salt obtained was subjected to salt exchange in the same manner as in [Conversion to Sodium Salt] described in step 11 of Example 1 to afford the title compound (21.0 mg).
MS(ESI)m/z: 790 (M+H)$^+$.
$^1$H-NMR (CD$_3$OD) δ: 8.26 (1H, brs), 8.01 (1H, s), 7.04 (1H, s), 6.27 (1H, d, J=4.8 Hz), 6.13 (1H, d, J=7.9 Hz), 5.69-5.50 (1H, m), 5.57 (1H, dd, J=53.5, 2.7 Hz), 5.14-5.10 (1H, m), 4.73 (1H, t, J=4.8 Hz), 4.62-4.53 (1H, m), 4.50-4.44 (2H, m), 4.24-4.01 (3H, m), 3.67-3.58 (1H, m), 3.50-3.44 (3H, m), 3.20-3.04 (2H, m), 2.83-2.81 (2H, m), 2.04-1.94 (2H, m).
$^{31}$P-NMR (CD$_3$OD) δ: 58.4 (s), 56.5 (s).

(Step 14-2)

Bis(N,N,N-tributylbutan-1-aminium) (5R,7R,8S, 12aR,14R,15R,15aS,16R)-7-{6-amino-2-[(2-aminoethyl)amino]-9H-purin-9-yl}-16-fluoro-15-hydroxy-2,10-dioxo-14-(6,7,8,9-tetrahydro-2H-2,3,5,6-tetraazabenzo[cd]azulen-2-yl)octahydro-2H,10H,12H-5,8-methano-2λ$^5$,10λ$^5$-furo[3,2-1][1,3,6,9,11,2,10]pentaoxadiphosphacyclotetradecine-2,10-bis(thiolate)

With use of the compound (29.5 mg) obtained in the above step 13-2, the reaction was performed in the same manner as in step 5 of Example 40, and purification was then performed under the following [Purification Conditions] to afford the title compound (24.2 mg: with impurities).

[Purification Conditions] preparative HPLC [10 mM aqueous solution of triethylammonium acetate/acetonitrile, acetonitrile: 2%-30% (0 min-30 min)], Sep-Pak® C18 [water/acetonitrile/0.1% triethylamine], and preparative HPLC [10 mM aqueous solution of triethylammonium acetate/acetonitrile, acetonitrile: 10%-25% (0 min-30 min)].
$^1$H-NMR (CD$_3$OD) δ: 8.27 (1H, s), 8.02 (1H, s), 7.13 (1H, s), 6.32 (1H, d, J=6.0 Hz), 6.15 (1H, d, J=7.9 Hz), 5.63-5.51 (1H, m), 5.39-5.35 (1H, m), 5.30 (1H, dd, J=54.4, 3.6 Hz), 4.77 (1H, t, J=5.1 Hz), 4.60-4.34 (4H, m), 4.19-4.13 (1H, m), 3.92-3.88 (1H, m), 3.70-3.62 (1H, m), 3.51-3.45 (3H, m), 3.26-3.07 (18H, m), 2.98-2.87 (2H, m), 2.03-1.99 (2H, m), 1.70-1.62 (16H, m), 1.47-1.37 (16H, m), 1.03 (24H, t, J=7.3 Hz).

(Step 14-2')

Disodium (5R,7R,8S,12aR,14R,15R,15aS,16R)-7-{6-amino-2-[(2-aminoethyl)amino]-9H-purin-9-yl}-16-fluoro-15-hydroxy-2,10-dioxo-14-(6,7,8,9-tetrahydro-2H-2,3,5,6-tetraazabenzo[cd]azulen-2-yl)octahydro-2H,10H,12H-5,8-methano-2λ⁵,10λ⁵-furo[3,2-l][1,3,6,9,11,2,10]pentaoxadiphosphacyclotetradecine-2,10-bis(thiolate)

(Diastereomer 2)

The compound (19.0 mg: with impurities) obtained in the above step 14-2 was purified by preparative HPLC [10 mM aqueous solution of triethylammonium acetate/acetonitrile, acetonitrile: 10%-25% (0 min-30 min)].

The resulting compound was subjected to salt exchange in the same manner as in [Conversion to Sodium Salt] described in step 11 of Example 1 to afford the title compound (8.4 mg).

MS(ESI)m/z: 790 (M+H)⁺.

$^1$H-NMR (CD$_3$OD) δ: 8.27 (1H, s), 8.01 (1H, s), 7.12 (1H, s), 6.31 (1H, d, J=6.0 Hz), 6.15 (1H, d, J=8.5 Hz), 5.65-5.49 (1H, m), 5.38-5.34 (1H, m), 5.30 (1H, dd, J=55.0, 3.0 Hz), 4.77 (1H, dd, J=5.7, 4.5 Hz), 4.60-4.34 (4H, m), 4.19-4.13 (1H, m), 3.92-3.88 (1H, m), 3.68-3.61 (1H, m), 3.51-3.45 (3H, m), 3.22-3.07 (2H, m), 2.89-2.87 (2H, m), 2.03-1.98 (2H, m).

$^{31}$P-NMR (CD$_3$OD) δ: 62.6 (s), 59.5 (s).

Example 53: Synthesis of CDN43

(5S,7R,8R,12aR,14R,15R,15aS,16R)-16-Amino-7-(2-amino-6-oxo-1,6-dihydro-9H-purin-9-yl)-15-hydroxy-2,10-bis(sulfanyl)-14-(6,7,8,9-tetrahydro-2H-2,3,5,6-tetraazabenzo[cd]azulen-2-yl)octahydro-2H,10H,12H-5,8-methano-2λ⁵,10λ⁵-furo[3,2-l][1,3,6,9,11,2,10]pentaoxadiphosphacyclotetradecine-2,10-dione

43

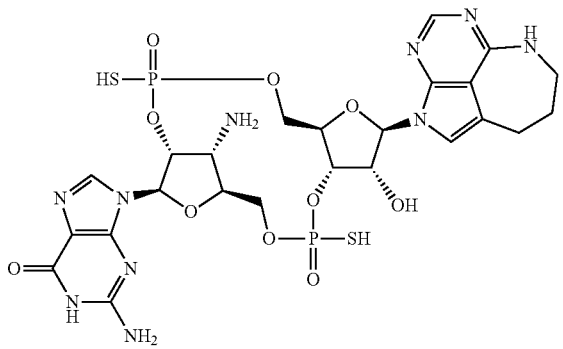

43a (Diastereomer 1)
43b (Diastereomer 2)

[Synthesis Scheme]

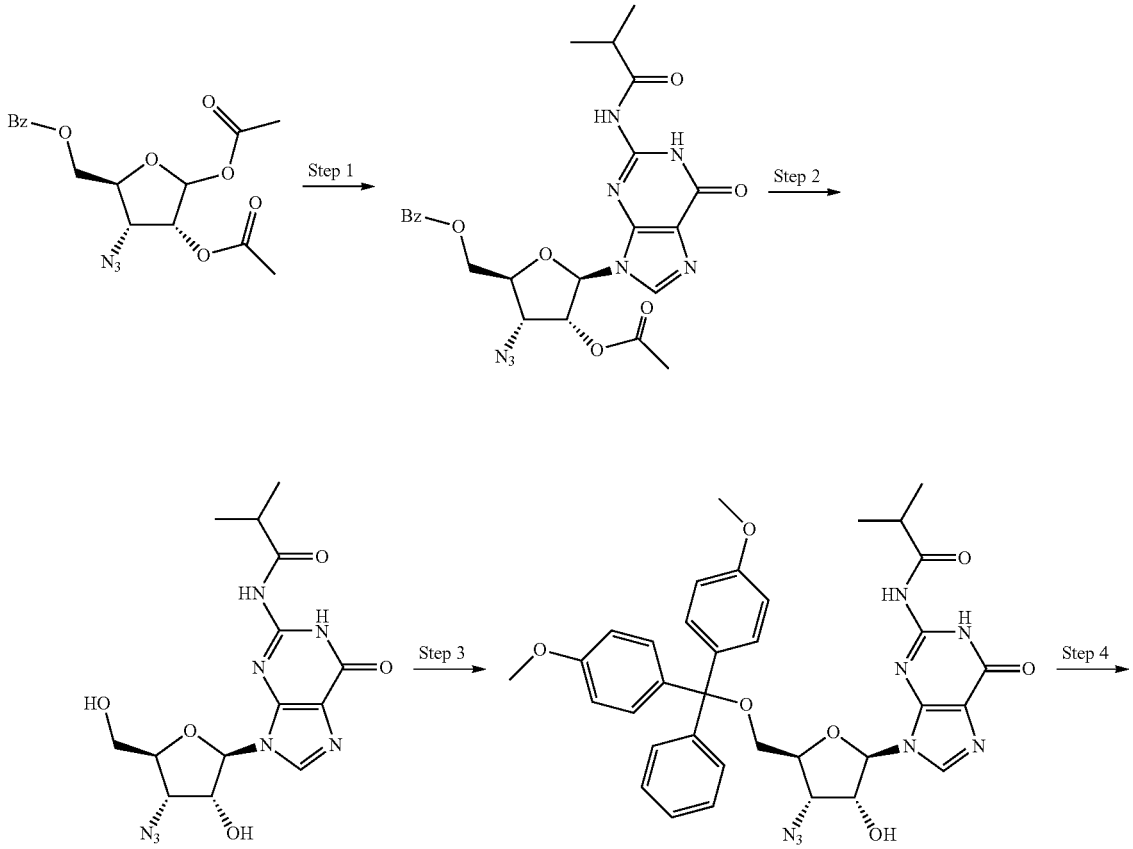

493
-continued
494
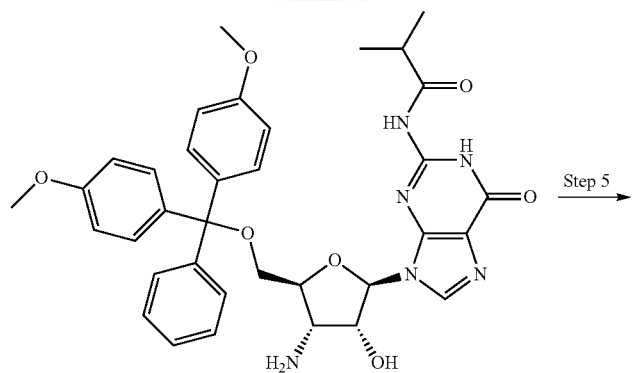
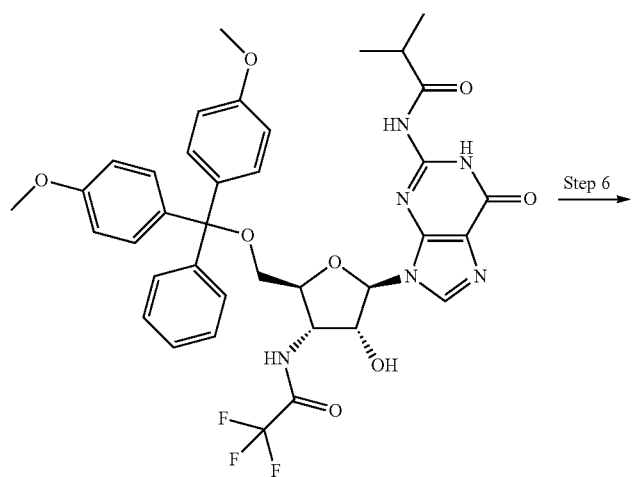
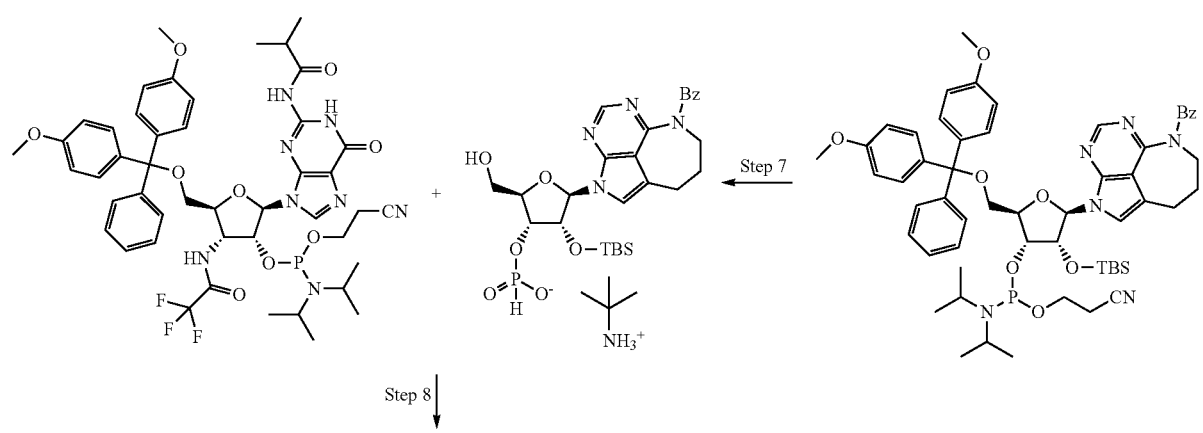

-continued
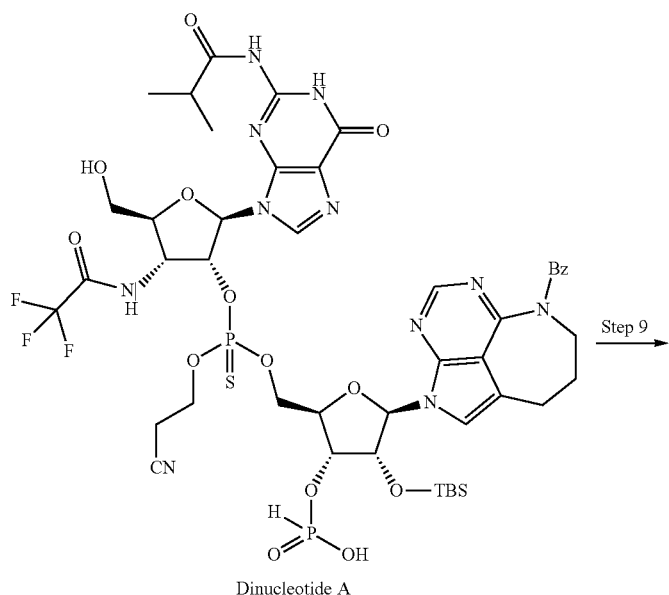
Dinucleotide A
Step 9
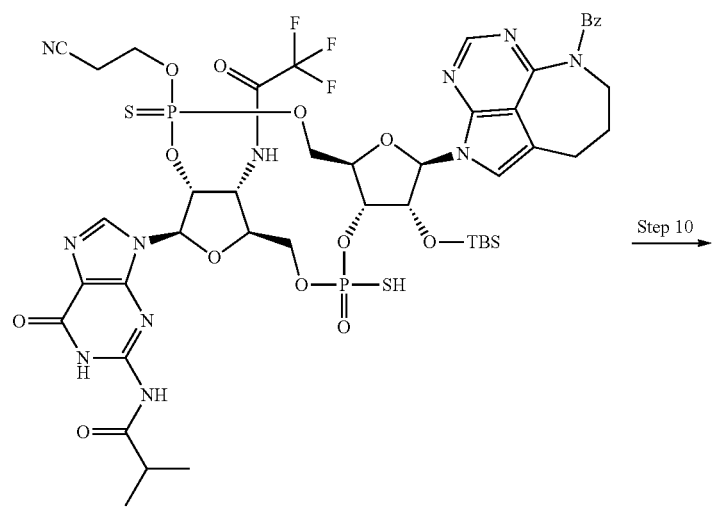
Step 10
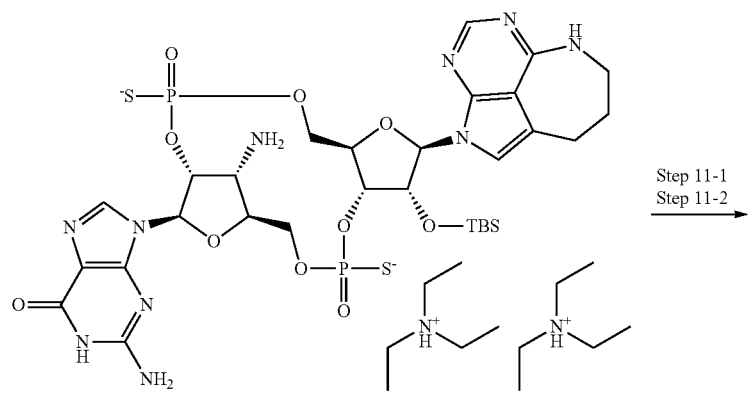
Step 11-1
Step 11-2

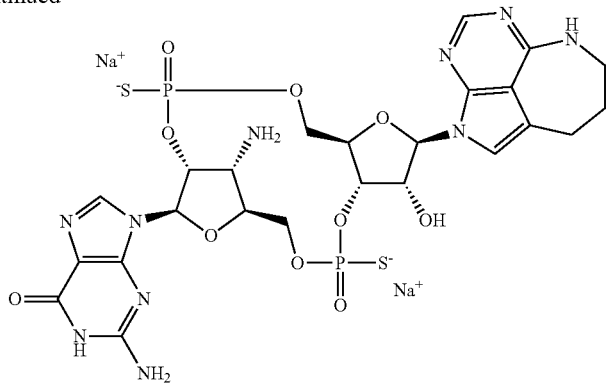

(Step 1)

2'-O-Acetyl-3'-azido-5'-O-benzoyl-3'-deoxy-N-(2-methylpropanoyl)guanosine

To a solution of 1,2-di-O-acetyl-3-azido-5-O-benzoyl-3-deoxy-D-ribofuranose (4.0 g) as a compound known in the literature (Recl. Trav. Chim. Pay-Bas 1986, 105, 85-91) in acetonitrile (60 mL), N2-isobutyrylguanine (3.65 g) and N,O-bis(trimethylsilyl) acetamide (8.08 mL) were added at room temperature, and the reaction mixture was stirred at 70° C. for 3 hours. Trimethylsilyl trifluoromethanesulfonate (2.98 mL) was added thereto at 70° C., and the reaction mixture was stirred at the same temperature for 1 day. After the reaction mixture was cooled, a saturated aqueous solution of sodium hydrogen carbonate was added thereto to quench the reaction, and the resultant was subjected to extraction with ethyl acetate. The organic layer was washed with brine, and dried over anhydrous sodium sulfate. The drying agent was removed through filtration, and the filtrate was concentrated under reduced pressure. The residue was purified by silica gel column chromatography [hexane/ethyl acetate] to afford the title compound (4.82 g).

$^1$H-NMR (CDCl$_3$) δ: 12.2 (1H, s), 9.42 (1H, s), 8.02 (2H, m), 7.71 (1H, s), 7.63 (1H, m), 7, 48 (2H, m), 5.97 (1H, d, J=3.9 Hz), 5.87 (1H, dd, J=5.5, 3.9 Hz), 5.10 (1H, dd, J=11.7, 5.5 Hz), 4.93 (1H, t, J=5.9 Hz), 4.66 (1H, dd, J=11.7, 5.5 Hz), 4.14 (1H, q, J=7.2 Hz), 2.77 (1H, m), 2.21 (3H, s), 1.31 (6H, m).

(Step 2)

3'-Azido-3'-deoxy-N-(2-methylpropanoyl)guanosine

To a mixed solution of the compound (5.48 g) obtained in the above step 1 in tetrahydrofuran (64 mL)-methanol (32 mL), 5 M sodium hydroxide (17 mL) was added at 0° C., and the reaction mixture was stirred for 15 minutes. Acetic acid (5.08 mL) was added to the reaction mixture to quench the reaction, and the reaction mixture was concentrated under reduced pressure. The residue was purified by silica gel column chromatography [dichloromethane/methanol] to afford the title compound (3.8 g).

$^1$H-NMR (CD$_3$OD) δ: 8.29 (1H, s), 5.97 (1H, d, J=5.7 Hz), 4.86 (1H, t, J=5.3 Hz), 4.29 (1H, t, J=5.3 Hz), 4.10 (1H, dt, J=5.9, 2.4 Hz), 3.87 (1H, dd, J=12.1, 3.1 Hz), 3.76 (1H, dd, J=12.3, 3.3 Hz), 2.74 (1H, m), 1.24 (6H, d, J=6.7 Hz).

(Step 3)

3'-Azido-5'-O-[bis(4-methoxyphenyl)(phenyl)methyl]-3'-deoxy-N-(2-methylpropanoyl)guanosine With use of the compound (3.8 g) obtained in the above step 2, the reaction was performed in the same manner as in step 1 of Example 11 to afford the title compound (5.78 g).

$^1$H-NMR (CDCl$_3$) δ: 11.9 (1H, s), 7.68 (2H, d, J=7.4 Hz), 7.60 (1H, s), 7.57 (2H, d, J=8.6 Hz), 7.51 (2H, d, J=8.6 Hz), 7.39-7.18 (3H, m), 7.02 (1H, d, J=4.7 Hz), 6.95 (2H, d, J=9.0 Hz), 6.89 (2H, d, J=9.0 Hz), 5.84 (1H, m), 5.63 (1H, d, J=7.8 Hz), 4.58 (1H, dd, J=6.7, 2.3 Hz), 3.99 (1H, m), 3.83 (3H, s), 3.81 (3H, s), 3.63 (1H, dd, J=11.0, 1.6 Hz), 2.92 (1H, dd, J=10.8, 2.5 Hz), 0.91 (1H, m), 69 (3H, d, J=6.7 Hz), 0.21 (3H, d, J=7.0 Hz).

(Step 4)

3'-Amino-5'-O-[bis(4-methoxyphenyl)(phenyl)methyl]-3'-deoxy-N-(2-methylpropanoyl)guanosine To a solution of the compound (5.17 g) obtained in the above step 3 in methanol (60 mL), triphenylphosphine (3.98 g) was added, and the reaction mixture was stirred at room temperature for 4 hours. The reaction mixture was concentrated under reduced pressure, and the residue was purified by silica gel column chromatography [hexane/ethyl acetate] to afford the title compound (2.22 g).

$^1$H-NMR (CDCl$_3$) δ: 7.77 (2H, d, J=6.7 Hz), 7.49-7.17 (8H, m), 6.86-6.77 (4H, m), 5.93 (1H, d, J=2.7 Hz), 5.85 (1H, d, J=3.5 Hz), 5.02 (1H, dd, J=6.7, 2.7 Hz), 4.74 (1H, m), 4.32 (1H, m), 4.06 (1H, m), 3.79 (3H, s), 3.78 (3H, s), 3.72 (1H, t, J=5.9 Hz), 3.49 (1H, dd, J=10.4, 3.3 Hz), 3.33 (1H, dd, J=10.4, 3.7 Hz), 2.26 (1H, m), 1.21-0.95 (6H, m).

(Step 5)

5'-O-[Bis(4-methoxyphenyl)(phenyl)methyl]-3'-deoxy-N-(2-methylpropanoyl)-3'-(2,2,2-trifluoroacetamide)guanosine To a solution of the compound (2.22 g) obtained in the above step 4 in N,N-dimethylformamide (20 mL), ethyl trifluoroacetate (4.0 mL) was added, and the reaction mixture was stirred at 50° C. for 2 days. After the reaction mixture was cooled, a saturated aqueous solution of sodium hydrogen carbonate was added thereto to quench the reaction, and the resultant was subjected to extraction with ethyl acetate. The organic layer was washed with brine, and then dried over anhydrous sodium sulfate. The drying agent was removed through filtration, and the filtrate was concentrated under reduced pressure. The residue was purified by silica gel column chromatography [dichloromethane/methanol] to afford the title compound (2.06 g).

MS(ESI)m/z: 751 (M+H)⁺.

$^1$H-NMR (CDCl$_3$) δ: 12.0 (1H, brs), 7.81 (1H, brs), 7.65 (1H, s), 7.59 (2H, d, J=7.4 Hz), 7.47 (2H, d, J=9.0 Hz), 7.43 (2H, d, J=8.6 Hz), 7.27-7.18 (3H, m), 6.87 (2H, d, J=9.0 Hz), 6.82 (2H, d, J=9.0 Hz), 5.72 (1H, d, J=6.3 Hz), 5.67 (1H, m), 5.02 (1H, m), 4.33 (1H, m), 3.80 (3H, s), 3.78 (3H, s), 3.60 (1H, dd, J=10.6, 1.6 Hz), 3.29 (1H, dd, J=10.6, 2.7 Hz), 1.36 (1H, m), 0.82 (3H, d, J=7.0 Hz), 0.44 (3H, d, J=6.7 Hz).
(Step 6)

5'-O-[Bis(4-methoxyphenyl)(phenyl)methyl]-2'-O-{(2-cyanoethoxy)[di(propan-2-yl)amino]phosphanyl}-3'-deoxy-N-(2-methylpropanoyl)-3'-(2,2,2-trifluoroacetamide)guanosine With use of the compound (1.0 g) obtained in the above step 5, the reaction was performed in the same manner as in step 4 of Example 5 to afford the title compound (780 mg) as a mixture of diastereomers at the phosphorus atom.
(Step 7)

2-Methylpropan-2-aminium 6-benzoyl-2-{2-O-[tert-butyl(dimethyl)silyl]-3-O-[oxide(oxo)-λ$^5$-phosphanyl]-β-D-ribofuranosyl}-6,7,8,9-tetrahydro-2H-2,3,5,6-tetraazabenzo[cd]azulene To a solution of the compound (5.0 g) obtained in the above step 6 of Example 1 in acetonitrile (30 mL), water (0.18 mL) and a pyridine salt of trifluoroacetic acid (1.2 g) were added, and the reaction mixture was stirred at room temperature for 30 minutes. To the reaction mixture, tert-butylamine (30 mL) was added, and the reaction mixture was stirred at room temperature for 30 minutes. After the reaction mixture was concentrated under reduced pressure, the residue was azeotroped twice with acetonitrile. To a solution of the residue in dichloromethane (50 mL), water (0.88 mL) and a solution of dichloroacetic acid (3.2 mL) in dichloromethane (50 mL) were added in this order, and the reaction mixture was stirred at room temperature for 1 hour. Methanol (5 mL) and pyridine (6.3 mL) were added thereto to quench the reaction, and the reaction mixture was concentrated under reduced pressure. The residue was purified by DIOL silica gel column chromatography [hexane/ethyl acetate→dichloromethane/methanol] to afford the title compound (3.0 g).

MS(ESI)m/z: 589 (M+H)⁺.

$^1$H-NMR (CD$_3$OD) δ: 8.01 (1H, s), 7.65 (1H, s), 7.44 (1H, m), 7.34-7.26 (4H, m), 7.02 (1H, d, J=639.3 Hz), 6.24 (1H, s), 4.89 (1H, m), 4.81 (1H, ddd, J=10.6, 5.1, 1.6 Hz), 4.43-4.27 (3H, m), 3.90 (2H, m), 3.14 (2H, m), 2.30 (2H, m), 1.42 (9H, s), 0.80 (9H, s), −0.27 (6H, s).
(Step 8)
Dinucleotide A To a mixed solution of the compound (543 mg) obtained in the above step 7 in dichloromethane (6.0 mL)-acetonitrile (6.0 mL), the molecular sieves 3A, 1/16 (500 mg) and 4,5-dicyanoimidazole (126 mg) were added, and the reaction mixture was stirred at room temperature for 15 minutes. The compound (780 mg) obtained in the above step 6 was added to the reaction mixture, which was stirred for 5 hours, and N,N-dimethyl-N'-(3-sulfanylidene-3H-1,2,4-dithiazol-5-yl)methaneimidamide (219 mg) was added thereto, and the reaction mixture was further stirred for 2 hours. The molecular sieves 3A were removed from the reaction mixture through filtration, and a saturated aqueous solution of sodium hydrogen carbonate was added to the filtrate, which was subjected to extraction with ethyl acetate. After the organic layer was dried over anhydrous sodium sulfate, the drying agent was removed through filtration, and the filtrate was concentrated under reduced pressure. The residue was purified by silica gel column chromatography [hexane/ethyl acetate]. To a solution of the resulting compound (740 mg) in dichloromethane (6.0 mL), water (0.086 mL) and a solution of dichloroacetic acid (0.158 mL) in dichloromethane (6.0 mL) were added in this order, and the reaction mixture was stirred at room temperature for 1.5 hours. Pyridine (0.31 mL) was added thereto to quench the reaction, and the reaction mixture was then concentrated under reduced pressure. The residue was purified by silica gel column chromatography [dichloromethane/methanol] to afford the title compound (520 mg) as a mixture of diastereomers at the phosphorus atom.

MS(ESI)m/z: 1168 (M+H)⁺.
(Step 9)

N-{9-[(5S,7R,8R,12aR,14R,15R,15aR,16R)-14-(6-Benzoyl-6,7,8,9-tetrahydro-2H-2,3,5,6-tetraazabenzo[cd]azulen-2-yl)-15-{[tert-butyl(dimethyl)silyl]oxy}-10-(2-cyanoethoxy)-2-oxo-2-sulfanyl-10-sulfanylidene-16-(2,2,2-trifluoroacetamide)octahydro-2H,10H,12H-5,8-methano-2λ$^5$,10λ$^5$-furo[3,2-1][1,3,6,9,11,2,10]pentaoxadiphosphacyclotetradecin-7-yl]-6-oxo-6,9-dihydro-1H-purin-2-yl}-2-methylpropanamide With use of the compound (270 mg) obtained in the above step 8, the reaction was performed in the same manner as in step 9 of Example 1 to afford the title compound (110 mg) as a mixture of diastereomers at the phosphorus atom.

MS(ESI)m/z: 1182 (M+H)⁺.
(Step 10)

Bis(N,N-diethylethaneaminium) (5S,7R,8R,12aR,14R,15R,15aR,16R)-16-amino-7-(2-amino-6-oxo-1,6-dihydro-9H-purin-9-yl)-15-{[tert-butyl(dimethyl)silyl]oxy}-2,10-dioxo-14-(6,7,8,9-tetrahydro-2H-2,3,5,6-tetraazabenzo[cd]azulen-2-yl)octahydro-2H,10H,12H-5,8-methano-2λ$^5$,10λ$^5$-furo[3,2-1][1,3,6,9,11,2,10]pentaoxadiphosphacyclotetradecine-2,10-bis(thiolate)

With use of the compound (110 mg) obtained in the above step 9, the reaction was performed in the same manner as in step 10 of Example 1 to afford diastereomer 1 (34.2 mg) and diastereomer 2 (19.3 mg) of the title compound.
Diastereomer 1 (Less Polar)
 MS(ESI)m/z: 859 (M+H)⁺.
Diastereomer 2 (More Polar)
 MS(ESI)m/z: 859 (M+H)⁺.
(Step 11-1)

Disodium (5S,7R,8R,12aR,14R,15R,15aS,16R)-16-amino-7-(2-amino-6-oxo-1,6-dihydro-9H-purin-9-yl)-15-hydroxy-2,10-dioxo-14-(6,7,8,9-tetrahydro-2H-2,3,5,6-tetraazabenzo[cd]azulen-2-yl)octahydro-2H,10H,12H-5,8-methano-2λ$^5$,10λ$^5$-furo[3,2-1][1,3,6,9,11,2,10]pentaoxadiphosphacyclotetradecine-2,10-bis(thiolate)

(Diastereomer 1)
With use of the compound (34.2 mg) obtained in the above step 10 (diastereomer 1), the reaction was performed in the same manner as in step 11 of Example 1, and the resultant was then purified by C18 silica gel column chromatography [10 mM aqueous solution of triethylammonium acetate/acetonitrile] to afford the title compound as a triethylamine salt.

The triethylamine salt obtained was subjected to salt exchange in the same manner as in [Conversion to Sodium Salt] described in step 11 of Example 1 to afford the title compound (8.9 mg).

MS(ESI)m/z: 745 (M+H)+.

$^1$H-NMR (CD$_3$OD) δ: 8.01 (1H, s), 7.93 (1H, s), 7.01 (1H, s), 6.20 (1H, d, J=3.9 Hz), 6.01 (1H, d, J=8.6 Hz), 5.65 (1H, m), 5.19 (1H, dt, J=9.5, 4.0 Hz), 4.68 (1H, t, J=4.3 Hz), 4.40-4.28 (2H, m), 4.23 (1H, m), 4.17 (1H, m), 4.11-4.01 (3H, m), 3.41 (2H, m), 2.75-2.53 (2H, m), 1.98-1.78 (2H, m).

$^{31}$P-NMR (CD$_3$OD) δ: 58.0 (s), 54.3 (s).

(Step 11-2)

Disodium (5S,7R,8R,12aR,14R,15R,15aS,16R)-16-amino-7-(2-amino-6-oxo-1,6-dihydro-9H-purin-9-yl)-15-hydroxy-2,10-dioxo-14-(6,7,8,9-tetrahydro-2H-2,3,5,6-tetraazabenzo[cd]azulen-2-yl)octahydro-2H,10H,12H-5,8-methano-2λ$^5$,10λ$^5$-furo[3,2-1][1,3,6,9,11,2,10]pentaoxadiphosphacyclotetradecine-2,10-bis(thiolate)

(Diastereomer 2)

With use of the compound (diastereomer 2) (19.3 mg) obtained in the above step 10, the reaction was performed in the same manner as in step 11 of Example 1, and the resultant was then purified by C18 silica gel column chromatography [10 mM aqueous solution of triethylammonium acetate/acetonitrile] to afford the title compound as a triethylamine salt.

The triethylamine salt obtained was subjected to salt exchange in the same manner as in [Conversion to Sodium Salt] described in step 11 of Example 1 to afford the title compound (5.6 mg).

MS(ESI)m/z: 745 (M+H)+.

$^1$H-NMR (DMSO-d$_6$) δ: 10.7 (1H, s), 8.40 (2H, brs), 8.09 (1H, s), 8.03 (1H, s), 7.74 (1H, brs), 7.22 (1H, s), 6.95 (1H, brs), 6.53 (2H, brs), 61.6 (2H, t, J=8.2 Hz), 5.57 (1H, q, J=8.0 Hz), 5.25 (1H, dd, J=7.8, 4.3 Hz), 4.61 (1H, dd, J=7.6, 4.5 Hz), 4.38 (1H, s), 4.27-4.11 (3H, m), 3.85-3.71 (3H, m), 3.35 (2H, m), 2.80 (2H, m), 1.93 (2H, m).

$^{31}$P-NMR (DMSO-d$_6$) δ: 60.3 (s), 58.3 (s).

Example 54: Synthesis of CDN44

(5R,7R,8S,12aR,14R,15R,15aR,16R)-15,16-Difluoro-7-[1-(2-hydroxyethyl)-6-oxo-1,6-dihydro-9H-purin-9-yl]-2,10-bis(sulfanyl)-14-(6,7,8,9-tetrahydro-2H-2,3,5,6-tetraazabenzo[cd]azulen-2-yl)octahydro-2H,10H,12H-5,8-methano-2λ$^5$,10λ$^5$-furo[3,2-1][1,3,6,9,11,2,10]pentaoxadiphosphacyclotetradecine-2,10-dione

44

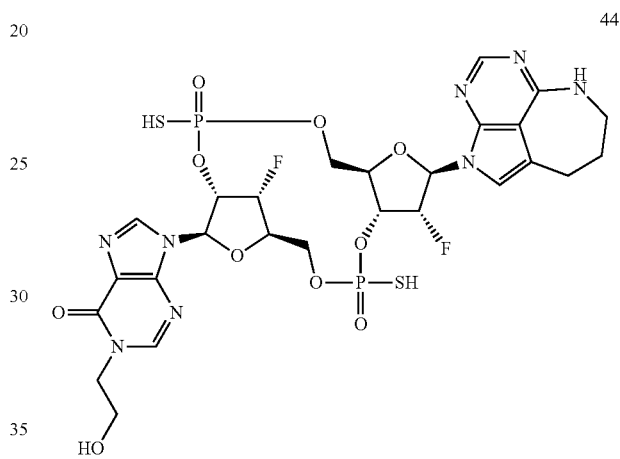

44a (Diastereomer 1)
44b (Diastereomer 2)

[Synthesis Scheme]

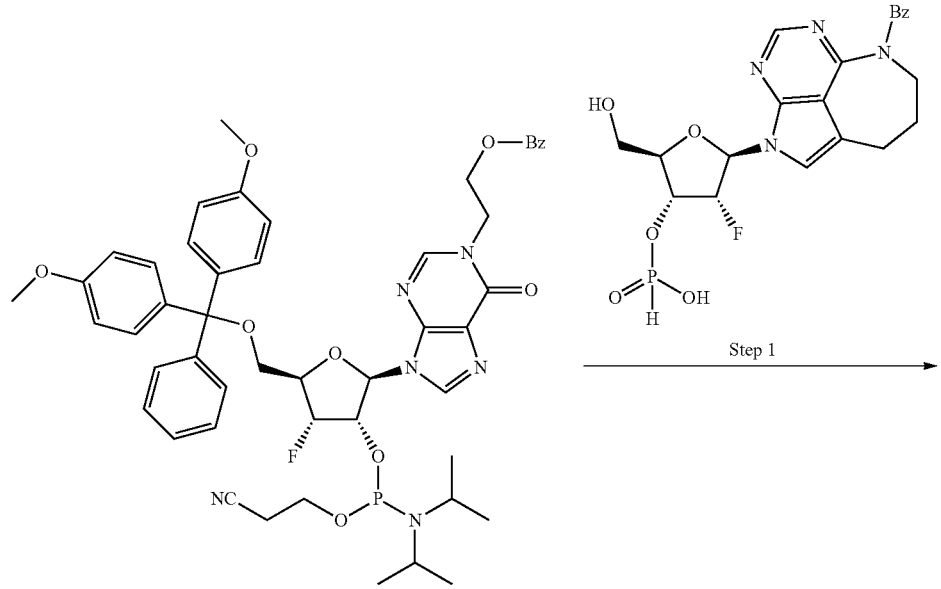

Step 1

-continued
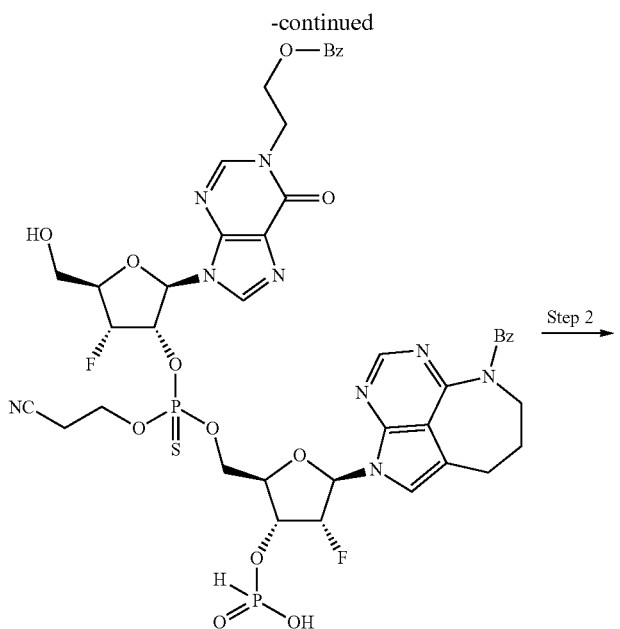
Step 2
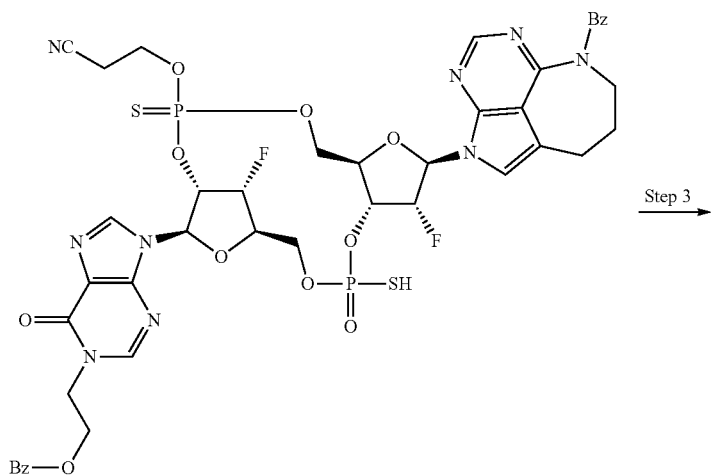
Step 3
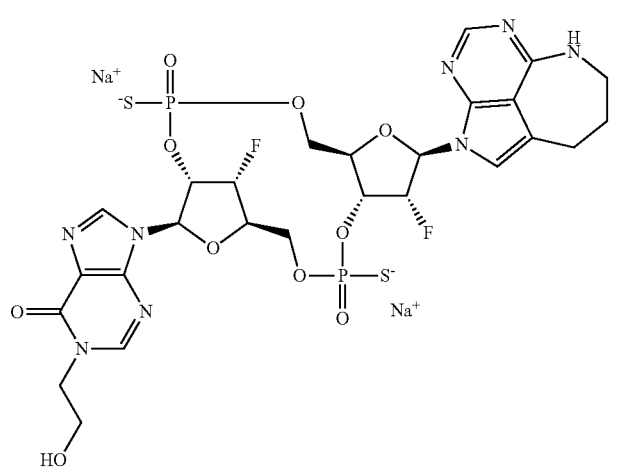

(Step 1)

With use of the compound (636 mg) obtained in step 8 of Example 44, the reaction was performed in the same manner as in step 7 of Example 1 to afford an acetonitrile solution of 6-benzoyl-2-{2-deoxy-2-fluoro-3-O-[hydroxy (oxo)-$\lambda^5$-phosphanyl]-β-D-ribofuranosyl}-6,7,8,9-tetrahydro-2H-2,3,5,6-tetraazabenzo[cd]azulene. With use of the acetonitrile solution obtained and the compound obtained in step 7 of Example 49 (640 mg), the reaction was performed in the same manner as in step 8 of Example 1, and the resulting crude product was directly used for the subsequent reaction.

(Step 2)

2-{9-[(5R,7R,8S,12aR,14R,15R,15aR,16R)-14-(6-Benzoyl-6,7,8,9-tetrahydro-2H-2,3,5,6-tetraazabenzo[cd]azulen-2-yl)-10-(2-cyanoethoxy)-15,16-difluoro-2-oxo-2-sulfanyl-10-sulfanylideneoctahydro-2H,10H,12H-5,8-methano-2$\lambda^5$,10$\lambda^5$-furo[3,2-l][1,3,6,9,11,2,10]pentaoxadiphosphacyclotetradecin-7-yl]-6-oxo-6,9-dihydro-1H-purin-1-yl}ethyl benzoate With use of the crude product obtained in the above step 1, the reaction was performed in the same manner as in step 9 of Example 1 to afford the title compound (228 mg: with impurities) as a mixture of diastereomers at the phosphorus atom.

MS(ESI)m/z: 1040 (M+H)$^+$.

(Step 3)

Disodium (5R,7R,8S,12aR,14R,15R,15aR,16R)-15,16-difluoro-7-[1-(2-hydroxyethyl)-6-oxo-1,6-dihydro-9H-purin-9-yl]-2,10-dioxo-14-(6,7,8,9-tetrahydro-2H-2,3,5,6-tetraazabenzo[cd]azulen-2-yl)octahydro-2H,10H,12H-5,8-methano-2$\lambda^5$,10$\lambda^5$-furo[3,2-l][1,3,6,9,11,2,10]pentaoxadiphosphacyclotetradecine-2,10-bis(thiolate)

The compound (228 mg) obtained in the above step 2 was dissolved in methanol (5 mL) and 28% aqueous solution of ammonia (5 mL), and the reaction mixture was stirred at 60° C. for 12 hours. The reaction mixture was concentrated under reduced pressure, and then purified by C18 silica gel column chromatography [10 mM aqueous solution of triethylammonium acetate/acetonitrile], preparative HPLC [10 mM aqueous solution of triethylammonium acetate/acetonitrile, acetonitrile: 5%-30% (0 min-40 min)], and preparative HPLC [10 mM aqueous solution of triethylammonium acetate/acetonitrile-methanol solution (1:1), acetonitrile-methanol solution (1:1): 7%-50% (0 min-40 min)] in this order to afford diastereomer 1 and diastereomer 2 of the title compound as triethylamine salts (retention time in HPLC: diastereomer 1>2).

The triethylamine salts obtained were each subjected to salt exchange in the same manner as in [Conversion to Sodium Salt] described in step 11 of Example 1 to afford diastereomer 1 (12.5 mg) and diastereomer 2 (15.8 mg) of the title compound.

Diastereomer 1 (Less Polar)

MS(ESI)m/z: 779 (M+H)$^+$.

$^1$H-NMR (CD$_3$OD) δ: 8.63 (1H, s), 8.16 (1H, s), 8.03 (1H, s), 7.08 (1H, s), 6.47 (1H, dd, J=17.5, 1.8 Hz), 6.27 (1H, d, J=7.9 Hz), 5.64-5.36 (3H, m), 5.31-5.20 (1H, m), 4.62-4.50 (2H, m), 4.44-4.39 (1H, m), 4.32-4.12 (3H, m), 4.10-4.03 (1H, m), 3.99-3.91 (1H, m), 3.83-3.72 (2H, m), 3.52-3.46 (2H, m), 2.78-2.72 (2H, m), 2.04-1.85 (2H, m).

$^{31}$P-NMR (CD$_3$OD) δ: 57.5 (s), 55.0 (s).

Diastereomer 2 (More Polar)

MS(ESI)m/z: 779 (M+H)$^+$.

$^1$H-NMR (CD$_3$OD) δ: 8.69 (1H, s), 8.21 (1H, s), 8.03 (1H, s), 7.25 (1H, s), 6.49 (1H, dd, J=15.1, 3.0 Hz), 6.28 (1H, d, J=9.1 Hz), 5.64-5.28 (4H, m), 4.61-4.39 (4H, m), 4.26-4.17 (1H, m), 4.13-3.95 (3H, m), 3.84-3.77 (2H, m), 3.53-3.45 (2H, m), 2.92-2.77 (2H, m), 2.02-1.92 (2H, m).

$^{31}$P-NMR (CD$_3$OD) δ: 60.7 (s), 57.4 (s).

Example 55: Synthesis of CDN45

(5R,7R,8S,12aR,14R,15R,15aR,16R)-7-{6-Amino-2-[(2-aminoethyl)amino]-9H-purin-9-yl}-15,16-difluoro-2,10-bis(sulfanyl)-14-(6,7,8,9-tetrahydro-2H-2,3,5,6-tetraazabenzo[cd]azulen-2-yl)octahydro-2H,10H,12H-5,8-methano-2$\lambda^5$,10$\lambda^5$-furo[3,2-l][1,3,6,9,11,2,10]pentaoxadiphosphacyclotetradecine-2,10-dione

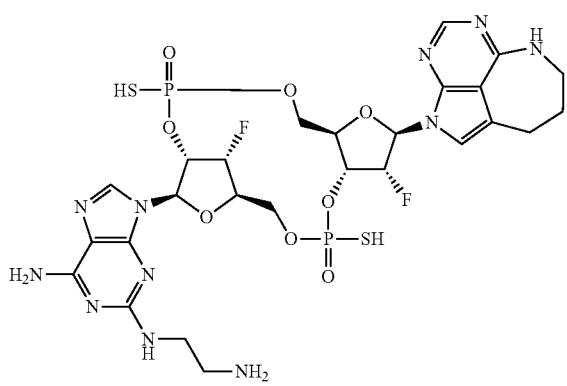

45

45a (Diastereomer 1)
45b (Diastereomer 2)

[Synthesis Scheme]
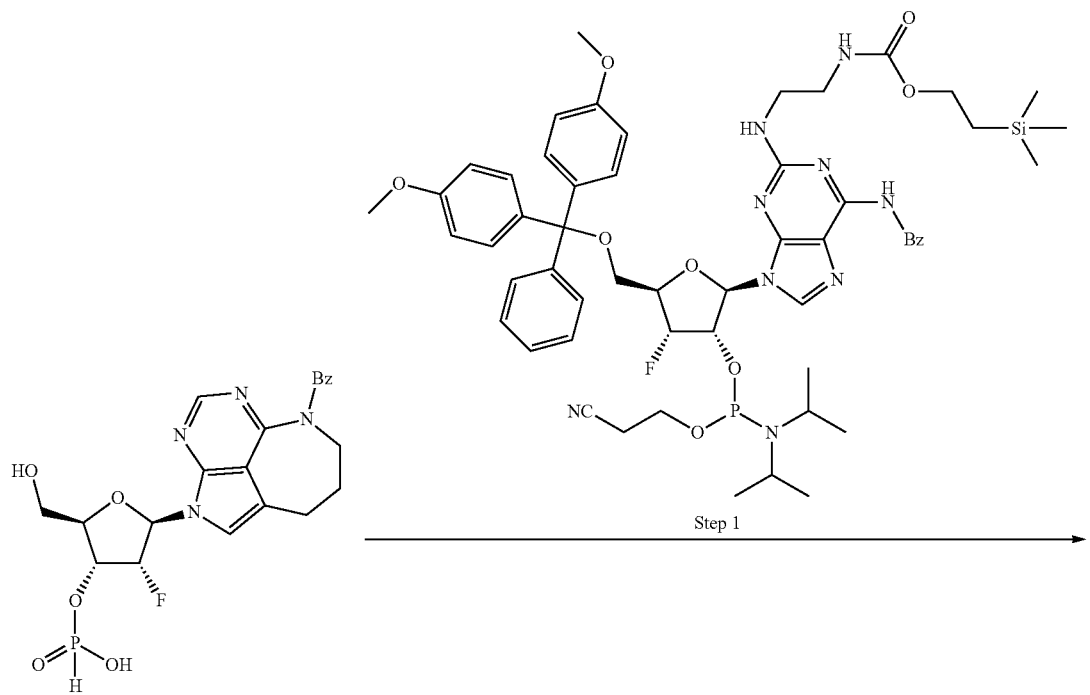
Step 1
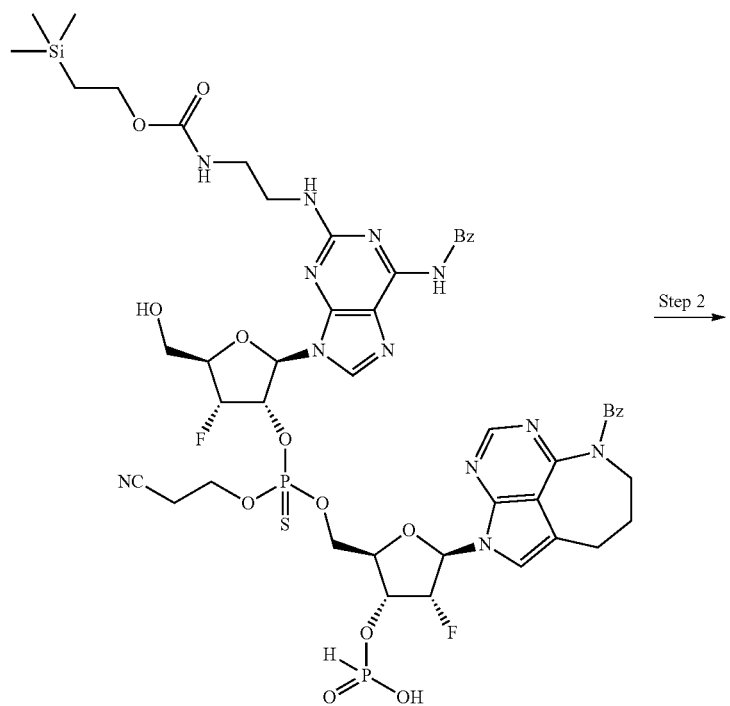
Step 2

-continued

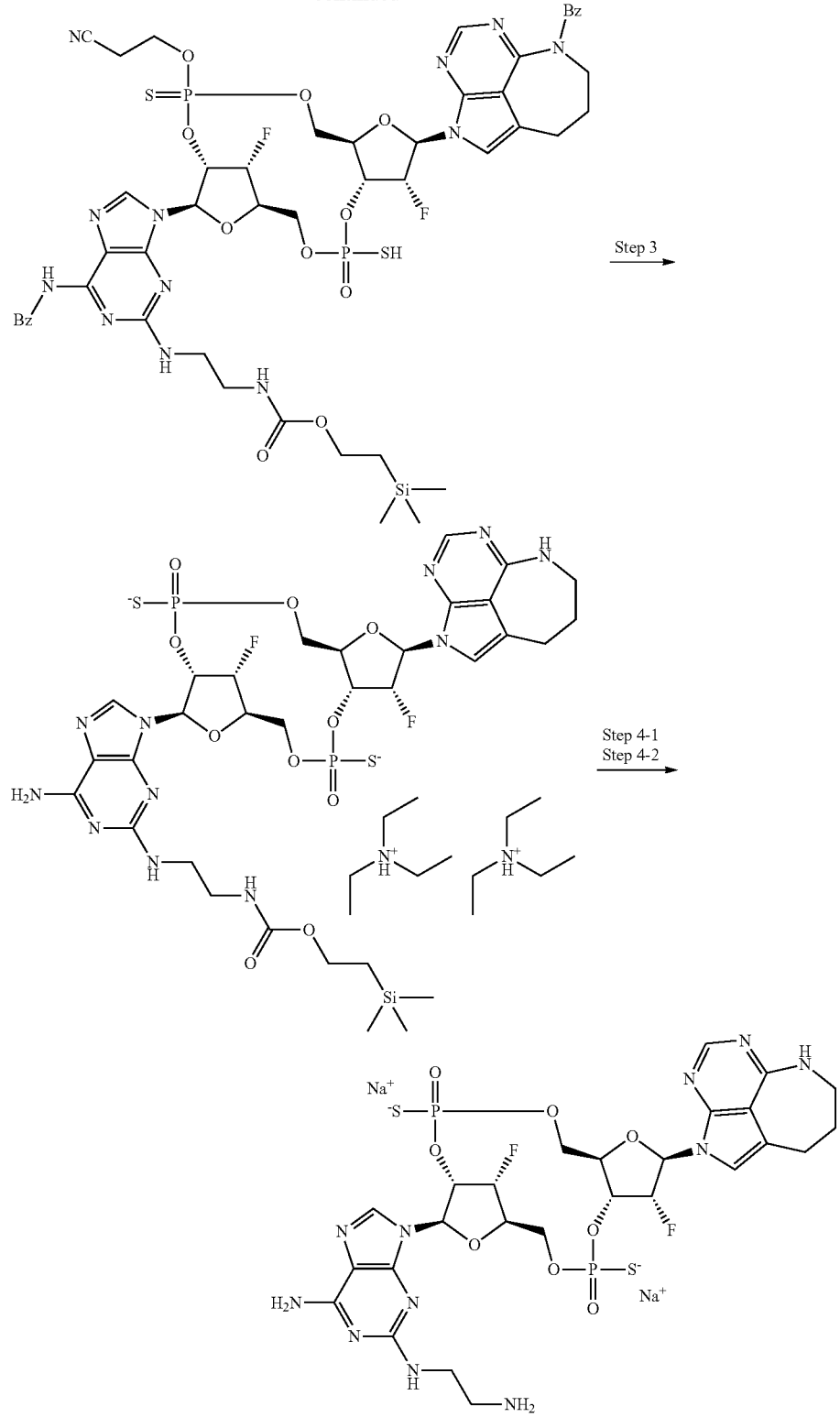

(Step 1)

With use of the compound (696 mg) obtained in step 8 of Example 44, the reaction was performed in the same manner as in step 7 of Example 1 to afford an acetonitrile solution of 6-benzoyl-2-{2-deoxy-2-fluoro-3-O-[hydroxy (oxo)-$\lambda^5$-phosphanyl]-β-D-ribofuranosyl}-6,7,8,9-tetrahydro-2H-2,3,5,6-tetraazabenzo[cd]azulene. With use of the acetonitrile solution obtained and the compound (738 mg) obtained in step 10 of Example 52, the reaction was performed in the same manner as in step 8 of Example 1, and the resulting crude product was directly used for the subsequent reaction.
(Step 2)

2-(Trimethylsilyl)ethyl [2-({6-benzamido-9-[(5R,7R,8S,12aR,14R,15R,15aR,16R)-14-(6-benzoyl-6,7,8,9-tetrahydro-2H-2,3,5,6-tetraazabenzo[cd]azulen-2-yl)-10-(2-cyanoethoxy)-15,16-difluoro-2-oxo-2-sulfanyl-10-sulfanylideneoctahydro-2H,10H,12H-5,8-methano-2$\lambda^5$,10$\lambda^5$-furo[3,2-l][1,3,6,9,11,2,10]pentaoxadiphosphacyclotetradecin-7-yl]-9H-purin-2-yl}amino)ethyl]carbamate With use of the mixture obtained in the above step 1, the reaction was performed in the same manner as in step 9 of Example 1 to afford a mixture containing the title compound (1.31 g). The mixture obtained was directly used for the subsequent reaction.

MS(ESI)m/z: 1195 (M−H)⁻.
(Step 3)

Bis(N,N-diethylethaneaminium) (5R,7R,8S,12aR,14R,15R,15aR,16R)-7-(6-amino-2-{[2-({[2-(trimethylsilyl)ethoxy]carbonyl}amino)ethyl]amino}-9H-purin-9-yl)-15,16-difluoro-2,10-dioxo-14-(6,7,8,9-tetrahydro-2H-2,3,5,6-tetraazabenzo[cd]azulen-2-yl)octahydro-2H,10H,12H-5,8-methano-2$\lambda^5$,10$\lambda^5$-furo[3,2-1][1,3,6,9,11,2,10]pentaoxadiphosphacyclotetradecine-2,10-bis(thiolate)

With use of the mixture (1.31 g) obtained in the above step 2, the reaction was performed in the same manner as in step 10 of Example 1 to afford diastereomer 1 (249 mg: with impurities) and diastereomer 2 (344 mg: with impurities) of the title compound.
Diastereomer 1 (Less Polar)
MS(ESI)m/z: 936 (M+H)⁺.
Diastereomer 2 (More Polar)
MS(ESI)m/z: 936 (M+H)⁺.
(Step 4-1)

Disodium (5R,7R,8S,12aR,14R,15R,15aR,16R)-7-{6-amino-2-[(2-aminoethyl)amino]-9H-purin-9-yl}-15,16-difluoro-2,10-dioxo-14-(6,7,8,9-tetrahydro-2H-2,3,5,6-tetraazabenzo[cd]azulen-2-yl)octahydro-2H,10H,12H-5,8-methano-2$\lambda^5$,10$\lambda^5$-furo[3,2-1][1,3,6,9,11,2,10]pentaoxadiphosphacyclotetradecine-2,10-bis(thiolate)

(Diastereomer 1)
With use of the compound (diastereomer 1) (249 mg: with impurities) obtained in the above step 3, the reaction was performed in the same manner as in step 5 of Example 40, and purification was then performed under the following [Purification Conditions] to afford the title compound as a triethylamine salt.
[Purification Conditions] preparative HPLC [10 mM aqueous solution of triethylammonium acetate/acetonitrile, acetonitrile: 10%-40% (0 min-30 min)], and preparative HPLC [10 mM aqueous solution of triethylammonium acetate/acetonitrile, acetonitrile: 0%-30% (0 min-30 min)].
The triethylamine salt obtained was subjected to salt exchange in the same manner as in [Conversion to Sodium Salt] described in step 11 of Example 1 to afford the title compound (9.2 mg).

MS(ESI)m/z: 792 (M+H)⁺.
¹H-NMR (CD₃OD) δ: 8.17 (1H, brs), 8.01 (1H, s), 7.01 (1H, s), 6.45 (1H, d, J=17.5 Hz), 6.07 (1H, d, J=8.5 Hz), 5.84-5.64 (1H, m), 5.61 (1H, dd, J=53.5, 3.3 Hz), 5.40 (1H, dd, J=52.0, 4.2 Hz), 5.30-5.18 (1H, m), 4.59-4.17 (6H, m), 3.54-3.42 (2H, m), 3.39-3.31 (2H, m), 3.05-2.98 (2H, m), 2.69-2.51 (2H, m), 2.02-1.83 (2H, m).
³¹P-NMR (CD₃OD) δ: 57.3 (s), 54.8 (s).
(Step 4-2)

Disodium (5R,7R,8S,12aR,14R,15R,15aR,16R)-7-{6-amino-2-[(2-aminoethyl)amino]-9H-purin-9-yl}-15,16-difluoro-2,10-dioxo-14-(6,7,8,9-tetrahydro-2H-2,3,5,6-tetraazabenzo[cd]azulen-2-yl)octahydro-2H,10H,12H-5,8-methano-2$\lambda^5$,10$\lambda^5$-furo[3,2-1][1,3,6,9,11,2,10]pentaoxadiphosphacyclotetradecine-2,10-bis(thiolate)

(Diastereomer 2)
With use of the compound (diastereomer 2) (344 mg: with impurities) obtained in the above step 3, the reaction was performed in the same manner as in step 5 of Example 40, and purification was then performed under the following [Purification Conditions] to afford the title compound as a triethylamine salt.
[Purification Conditions] preparative HPLC [10 mM aqueous solution of triethylammonium acetate/acetonitrile, acetonitrile: 10%-40% (0 min-30 min)], and preparative HPLC [10 mM aqueous solution of triethylammonium acetate/acetonitrile, acetonitrile: 10%-30% (0 min-30 min)].
The triethylamine salt obtained was subjected to salt exchange in the same manner as in [Conversion to Sodium Salt] described in step 11 of Example 1 to afford the title compound (4.7 mg).

MS(ESI)m/z: 792 (M+H)⁺.
¹H-NMR (CD₃OD) δ: 8.05 (1H, brs), 8.01 (1H, s), 7.35 (1H, s), 6.50 (1H, d, J=16.3 Hz), 6.06 (1H, d, J=8.5 Hz), 5.98-5.75 (1H, m), 5.48-5.28 (3H, m), 4.59-4.28 (3H, m), 4.29-4.22 (1H, m), 4.04-3.98 (1H, m), 3.56-3.42 (2H, m), 3.36-2.61 (6H, m), 2.05-1.86 (2H, m).
³¹P-NMR (CD₃OD) δ: 58.4 (brs), 57.6 (s).

Example 56: Synthesis of CDN46

(5R,7R,8R,12aR,14R,15S,15aR,16R)-7-(6-Amino-9H-purin-9-yl)-15,16-dihydroxy-2,10-bis(sulfanyl)-14-(6,7,8,9-tetrahydro-2H-2,3,5,6-tetraazabenzo[cd]azulen-2-yl) decahydro-2H,10H-5,8-methano-2$\lambda^5$,10$\lambda^5$-cyclopenta[1][1,3,6,9,11,2,10]pentaoxadiphosphacyclotetradecine-2,10-dione

46

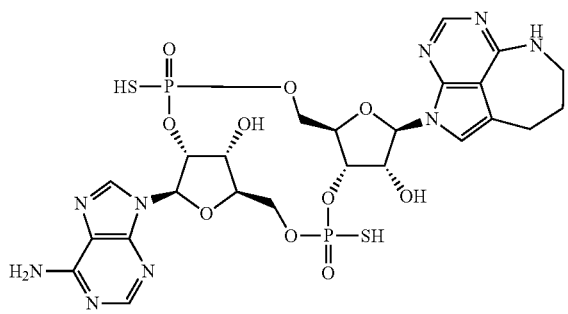

46a (Diastereomer 1)
46b (Diastereomer 2)

[Synthesis Scheme]
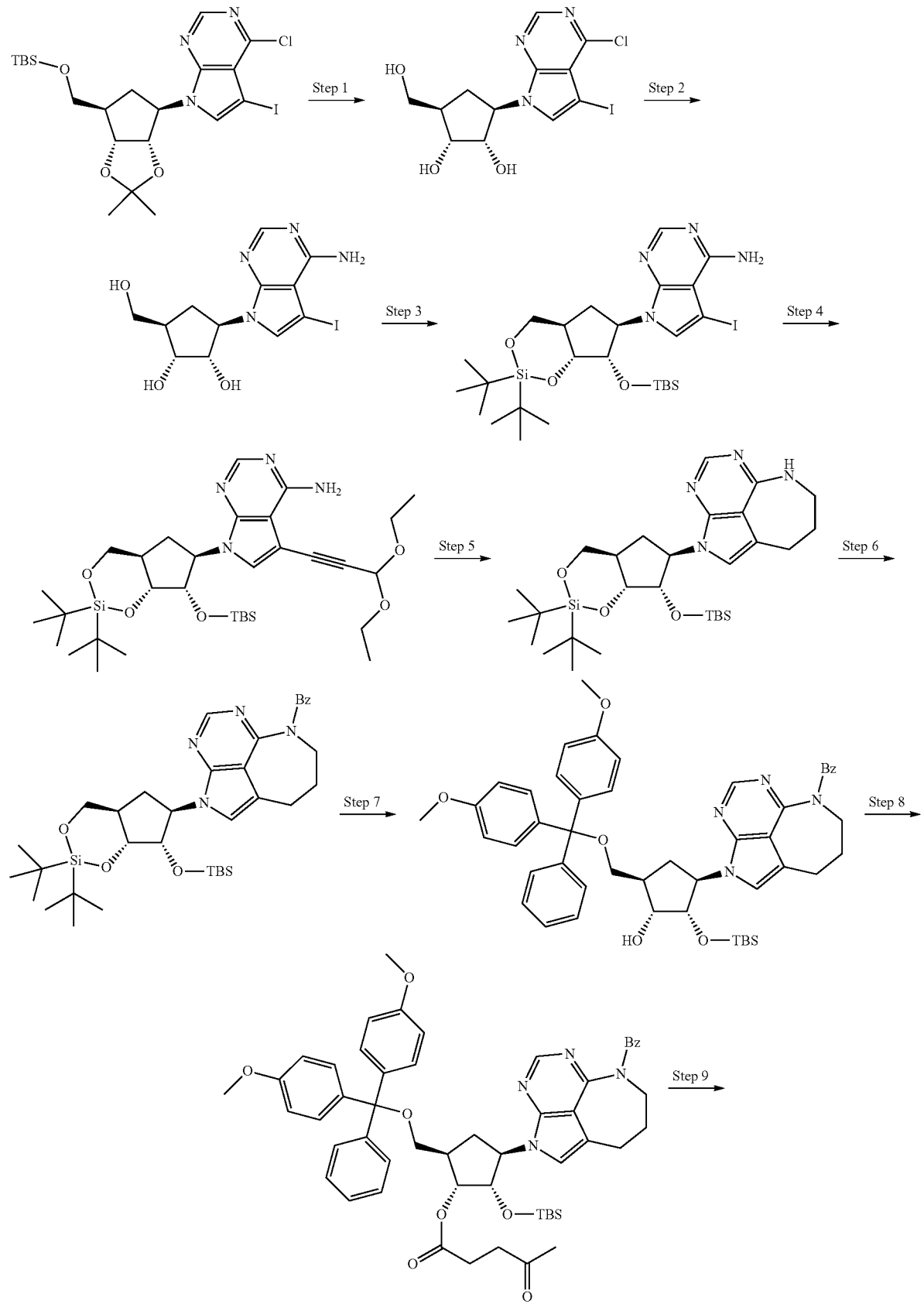

-continued
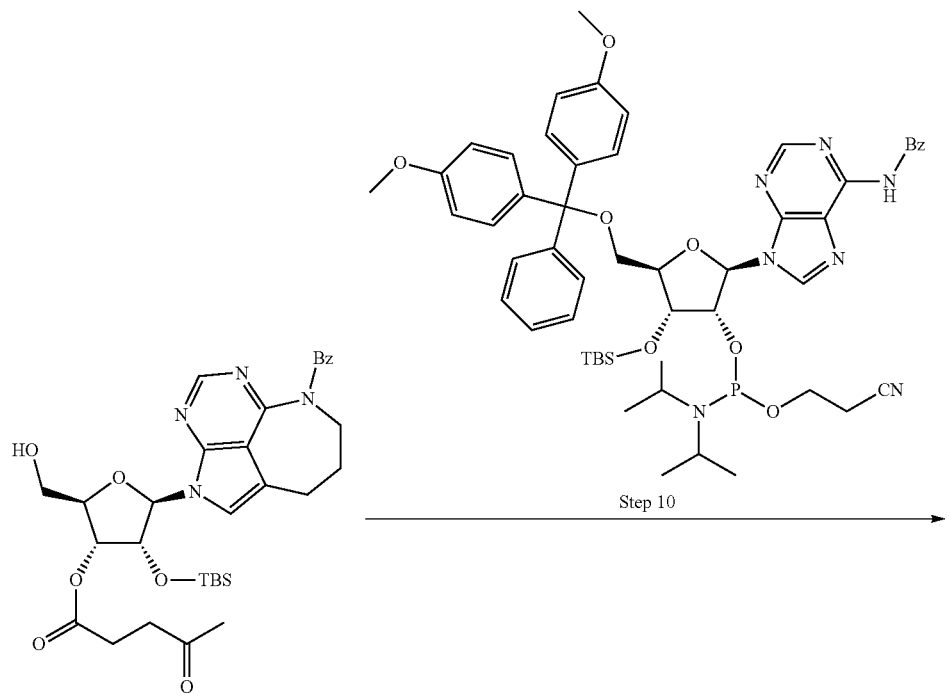
Step 10
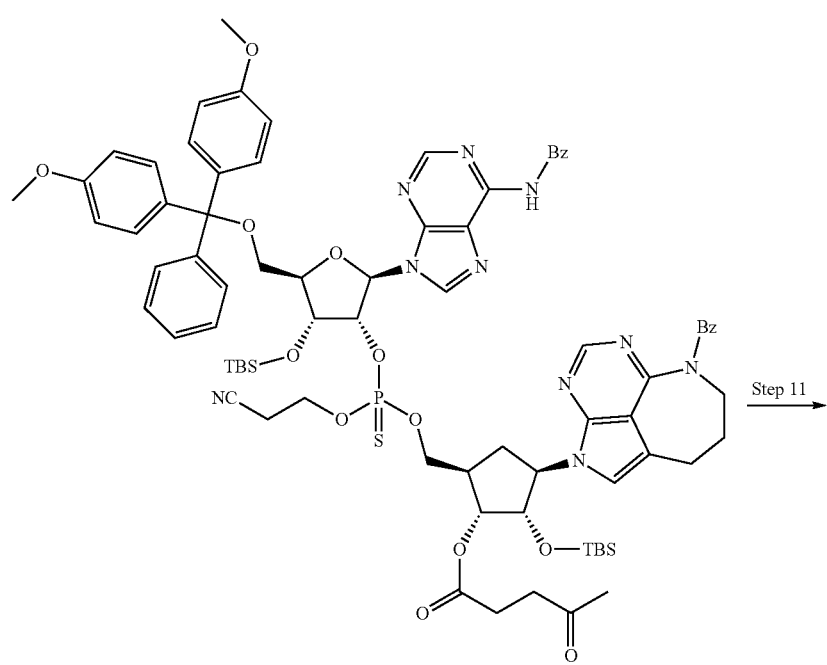
Step 11

-continued
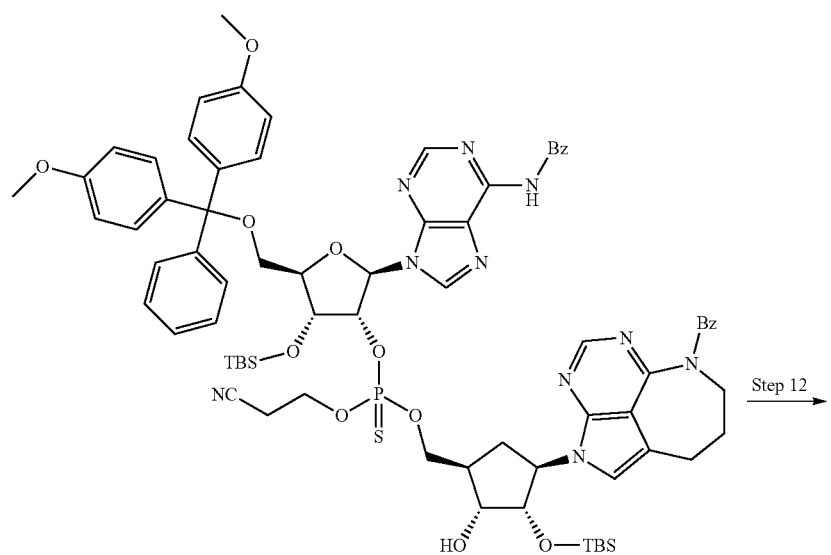
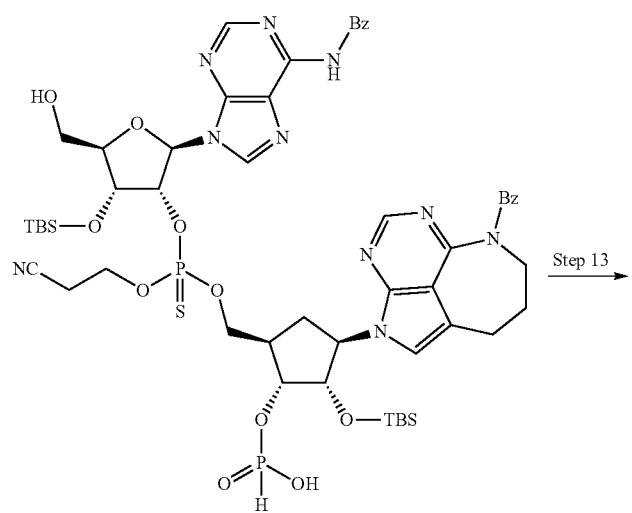
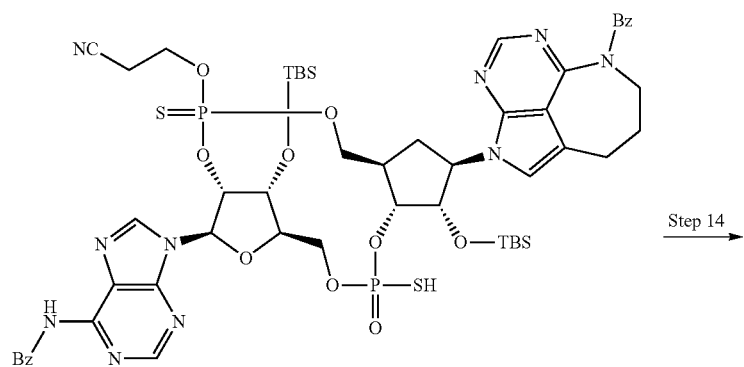

-continued

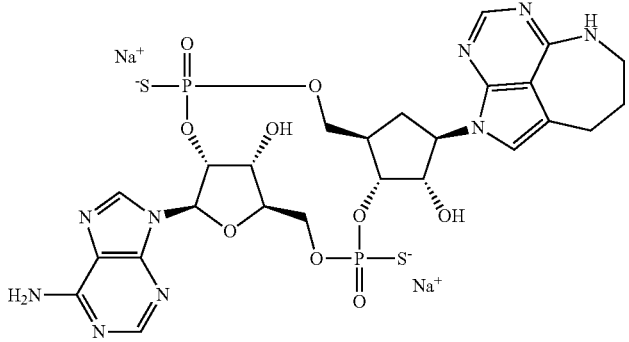

(Step 1)

(1R,2S,3R,5R)-3-(4-Chloro-5-iodo-7H-pyrrolo[2,3-d]pyrimidin-7-yl)-5-(hydroxymethyl)cyclopentane-1,2-diol To 7-[(3aS,4R,6R,6aR)-6-({[tert-butyl(dimethyl)silyl]oxy}methyl)-2,2-dimethyltetrahydro-2H,3aH-cyclopenta[d][1,3]dioxol-4-yl]-4-chloro-5-iodo-7H-pyrrolo[2,3-d]pyrimidine (6.0 g) as a compound known in the literature (WO 2015/199136), trifluoroacetic acid (36 mL) and water (12 mL) were added in this order, and the reaction mixture was stirred at room temperature for 3 hours. The reaction mixture was concentrated under reduced pressure to afford a crude form of the title compound. The crude product obtained was directly used for the subsequent reaction.

(Step 2)

(1R,2S,3R,5R)-3-(4-Amino-5-iodo-7H-pyrrolo[2,3-d]pyrimidin-7-yl)-5-(hydroxymethyl)cyclopentane-1,2-diol To a solution of the compound (4.4 g) obtained in the above step 1 in 1,4-dioxane (40 mL), 28% ammonia water (40 mL) was added, and the reaction mixture was stirred at 90° C. for 72 hours. After the reaction mixture was concentrated under reduced pressure, the residue was purified by C18 silica gel column chromatography [water/methanol] to afford the title compound (3.4 g).

$^1$H-NMR (CD$_3$OD) δ: 8.07 (1H, s), 7.56 (1H, s), 6.57 (1H, brs), 4.89 (1H, dd, J=19.2, 8.6 Hz), 4.79 (1H, d, 6.7 Hz), 4.70 (1H, t, J=5.3 Hz), 4.59 (1H, d, J=4.3 Hz), 4.15 (1H, m), 3.78 (1H, m), 3.45 (2H, m), 2.14 (1H, m), 2.03 (1H, m), 1.48 (1H, m).

(Step 3)

7-[(4aR,6R,7S,7aR)-2,2-Di-tert-butyl-7-{[tert-butyl(dimethyl)silyl]oxy}hexahydro-2H-cyclopenta[d][1,3,2]dioxasilin-6-yl]-5-iodo-7H-pyrrolo[2,3-d]pyrimidin-4-amine With use of the compound (3.3 g) obtained in the above step 2, the reaction was performed in the same manner as in step 1 of Example 1 to afford the title compound (4.6 g).

$^1$H-NMR (CDCl$_3$) δ: 8.27 (1H, s), 7.00 (1H, s), 5.69 (1H, brs), 4.92 (1H, dt, J=9.0, 1.2 Hz), 4.32 (3H, m), 3.98 (1H, t, J=10.8 Hz), 2.58 (1H, m), 2.26 (1H, m), 1.74 (1H, brs), 1.49 (1H, dt, J=12.5, 8.6 Hz), 1.13 (9H, s), 1.09 (9H, s), 0.86 (9H, s), 0.06 (3H, s), 0.00 (3H, s).

(Step 4)

7-[(4aR,6R,7S,7aR)-2,2-Di-tert-butyl-7-{[tert-butyl(dimethyl)silyl]oxy}hexahydro-2H-cyclopenta[d][1,3,2]dioxasilin-6-yl]-5-(3,3-diethoxyprop-1-yn-1-yl)-7H-pyrrolo[2,3-d]pyrimidin-4-amine With use of the compound (4.6 g) obtained in the above step 3, the reaction was performed in the same manner as in step 2 of Example 1 to afford the title compound (3.6 g).

$^1$H-NMR (CDCl$_3$) δ: 8.30 (1H, s), 7.15 (1H, s), 5.61 (1H, brs), 5.55 (1H, s), 4.90 (1H, dt, J=9.0, 1.2 Hz), 4.32 (3H, m), 3.97 (1H, t, J=10.8 Hz), 3.86 (2H, m), 3.71 (2H, m), 2.58 (1H, m), 2.28 (1H, m), 1.68 (1H, s), 1.48 (1H, m), 1.32 (6H, t, J=7.0 Hz), 1.13 (9H, s), 1.09 (9H, s), 0.86 (9H, s), 0.05 (3H, s), 0.04 (3H, s).

(Step 5)

2-[(4aR,6R,7S,7aR)-2,2-Di-tert-butyl-7-{[tert-butyl(dimethyl)silyl]oxy}hexahydro-2H-cyclopenta[d][1,3,2]dioxasilin-6-yl]-6,7,8,9-tetrahydro-2H-2,3,5,6-tetraazabenzo[cd]azulene With use of the compound (3.60 g) obtained in the above step 4, the reaction was performed in the same manner as in step 3 of Example 1 to afford the title compound (2.44 g).

MS(ESI)m/z: 589 (M+H)$^+$.

$^1$H-NMR (CDCl$_3$) δ: 8.18 (1H, s), 6.66 (1H, s), 6.55 (1H, brs), 4.94 (1H, m), 4.36-4.25 (3H, m), 3.97 (1H, t, J=10.8 Hz), 3.57 (2H, m), 2.93 (2H, t, J=5.5 Hz), 2.58 (1H, m), 2.27 (1H, m), 2.09 (1H, m), 1.46 (1H, dt, J=12.5, 8.6 Hz), 1.29 (1H, m), 1.12 (9H, s), 1.08 (9H, s), 0.86 (9H, s), 0.04 (3H, s), 0.03 (3H, s).

(Step 6)

{2-[(4aR,6R,7S,7aR)-2,2-Di-tert-butyl-7-{[tert-butyl(dimethyl)silyl]oxy}hexahydro-2H-cyclopenta[d][1,3,2]dioxasilin-6-yl]-2,7,8,9-tetrahydro-6H-2,3,5,6-tetraazabenzo[cd]azulen-6-yl}(phenyl) methanone With use of the compound (2.44 g) obtained in the above step 5, the reaction was performed in the same manner as in step 4 of Example 1 to afford the title compound (2.01 g).

MS(ESI)m/z: 663 (M+H)$^+$.

$^1$H-NMR (CDCl$_3$) δ: 8.12 (1H, s), 7.42-7.25 (5H, m), 6.97 (1H, s), 5.04 (1H, t, J=9.0 Hz), 4.44 (1H, m), 4.38 (1H, dd, J=10.0, 4.9 Hz), 4.33-4.23 (3H, m), 4.00 (1H, t, J=10.8 Hz), 3.06 (2H, m), 2.60 (1H, m), 2.29 (3H, m), 1.57 (1H, m), 1.14 (9H, s), 1.10 (9H, s), 0.84 (9H, s), 0.06 (3H, s), 0.05 (3H, s).

(Step 7)

{2-[(1R,2S,3R,4R)-4-{[Bis(4-methoxyphenyl)(phenyl)methoxy]methyl}-2-{[tert-butyl(dimethyl)silyl]oxy}-3-hydroxycyclopentyl]-2,7,8,9-tetrahydro-6H-2,3,5,6-tetraazabenzo[cd]azulen-6-yl}(phenyl)methanone With use of the compound (2.01 g) obtained in the above step 6, the reaction was performed in the same manner as in step 5 of Example 1 to afford the title compound (2.13 g).
$^1$H-NMR (CDCl$_3$) δ: 8.03 (1H, s), 7.49 (2H, m), 7.38-7.19 (13H, m), 7.02 (1H, s), 6.83 (4H, m), 5.07 (1H, m), 4.60 (1H, dd, J=8.6, 5.1 Hz), 4.29 (2H, m), 3.99 (1H, m), 3.79 (6H, s), 3.33 (1H, dd, J=9.4, 3.9 Hz), 3.22 (1H, dd, J=9.2, 4.1 Hz), 2.97 (2H, t, J=6.5 Hz), 2.68 (1H, d, J=1.6 Hz), 2.37-2.18 (5H, m), 0.73 (9H, s), −0.18 (3H, s), −0.47 (3H, s).

(Step 8)

(1R,2S,3R,5R)-3-(6-Benzoyl-6,7,8,9-tetrahydro-2H-2,3,5,6-tetraazabenzo[cd]azulen-2-yl)-5-{[bis(4-methoxyphenyl)(phenyl)methoxy]methyl}-2-{[tert-butyl(dimethyl)silyl]oxy}cyclopentyl 4-oxopentanoate To a solution of levulinic acid (2.96 g) in tetrahydrofuran (20 mL), N,N-dicyclohexylcarbodiimide (2.63 g) was added, and the reaction mixture was stirred at room temperature for 12 hours. After a precipitate was removed through filtration, the filtrate was concentrated under reduced pressure. To a solution of the residue in dichloromethane (20 mL), the compound (2.10 g) obtained in the above step 7 and 4-dimethylaminopyridine (155 mg) were added, and the reaction mixture was stirred at room temperature for 1 hour. After a saturated aqueous solution of sodium hydrogen carbonate was added to the reaction mixture to quench the reaction, the resultant was subjected to extraction with ethyl acetate, and the organic layer was dried over anhydrous sodium sulfate. The drying agent was removed through filtration, and the filtrate was concentrated under reduced pressure. The residue was purified by silica gel column chromatography [hexane/ethyl acetate] to afford the title compound (2.35 g).
$^1$H-NMR (CDCl$_3$) δ: 8.02 (1H, s), 7.49 (2H, m), 7.40-7.19 (13H, m), 7.04 (1H, s), 6.84 (4H, m), 5.26 (1H, dd, J=5.1, 2.0 Hz), 5.06 (1H, q, J=9.0 Hz), 4.61 (1H, dd, J=8.8, 4.9 Hz), 4.28 (2H, m), 3.79 (6H, s), 3.39 (1H, dd, J=9.2, 3.7 Hz), 3.19 (1H, dd, J=9.4, 3.9 Hz), 3.00-1.85 (14H, m), 0.64 (9H, s), −0.13 (3H, s), −0.45 (3H, s).

(Step 9)

(1R,2S,3R,5R)-3-(6-Benzoyl-6,7,8,9-tetrahydro-2H-2,3,5,6-tetraazabenzo[cd]azulen-2-yl)-2-{[tert-butyl(dimethyl)silyl]oxy}-5-(hydroxymethyl)cyclopentyl-4-oxopentanoate To a solution of the compound (2.35 g) obtained in the above step 8 in dichloromethane (25 mL), water (0.24 mL) and a solution of dichloroacetic acid (1.05 mL) in dichloromethane (25 mL) were added in this order, and the reaction mixture was stirred at room temperature for 1 hour. After methanol (1.0 mL) and a saturated aqueous solution of sodium hydrogen carbonate were added to the reaction mixture to quench the reaction, the resultant was subjected to extraction with ethyl acetate, and the organic layer was dried over anhydrous sodium sulfate. The drying agent was removed through filtration, and the filtrate was concentrated under reduced pressure. The residue was purified by silica gel column chromatography [hexane/ethyl acetate] to afford the title compound (1.15 g).
MS(ESI)m/z: 621 (M+H)$^+$.
$^1$H-NMR (CDCl$_3$) δ: 8.05 (1H, s), 7.38-7.17 (5H, m), 7.04 (1H, s), 5.19 (1H, dd, J=4.5, 1.4 Hz), 4.82-4.69 (2H, m), 4.47 (1H, dd, J=14.5, 7.4 Hz), 4.31 (1H, d, J=7.8 Hz), 4.15-4.08 (1H, m), 3.83 (1H, m), 3.75 (1H, d, J=10.8 Hz), 3.11-2.95 (2H, m), 2.90-2.51 (4H, m), 2.47-2.32 (2H, m), 2.32-2.11 (3H. m), 2.22 (3H, s), 0.68 (9H, s), −0.16 (3H, s), −0.50 (3H, s).

(Step 10)

N-Benzoyl-2'-O-[({(1R,2R,3S,4R)-4-(6-benzoyl-6,7,8,9-tetrahydro-2H-2,3,5,6-tetraazabenzo[cd]azulen-2-yl)-3-{[tert-butyl(dimethyl)silyl]oxy}-2-[(4-oxopentanoyl)oxy]cyclopentyl}methoxy)(2-cyanoethoxy)phosphorothioyl]-5'-O-[bis(4-methoxyphenyl)(phenyl)methyl]-3'-O-[tert-butyl(dimethyl)silyl]adenosine To a solution of the compound (550 mg) obtained in the above step 9 in acetonitrile (12 mL), the molecular sieves 3A, 1/16 (500 mg) and N-benzoyl-5'-O-[bis(4-methoxyphenyl)(phenyl)methyl]-3'-O-[tert-butyl(dimethyl)silyl]-2'-O-{(2-cyanoethoxy)[di(propan-2-yl)amino]phosphanyl}adenosine (1.23 g) were added, and the reaction mixture was stirred at room temperature for 15 minutes. To the reaction mixture, 4,5-dicyanoimidazole was added and the reaction mixture was stirred for 1 hour, and thereafter 3H-1,2-benzothiol-3-one 1,1-dioxide (355 mg) was added thereto, and the reaction mixture was further stirred for 1 hour. The molecular sieves 3A were removed from the reaction mixture through filtration, and a saturated aqueous solution of sodium hydrogen carbonate was added to the filtrate, which was subjected to extraction with ethyl acetate. After the organic layer was dried over anhydrous sodium sulfate, the drying agent was removed through filtration, and the filtrate was concentrated under reduced pressure. The residue was purified by silica gel column chromatography [hexane/ethyl acetate] to afford the title compound (1.17 g) as a mixture of diastereomers at the phosphorus atom.
MS(ESI)m/z: 1539 (M+H)$^+$.

(Step 11)

N-Benzoyl-2'-O-[{[(1R,2R,3S,4R)-4-(6-benzoyl-6,7,8,9-tetrahydro-2H-2,3,5,6-tetraazabenzo[cd]azulen-2-yl)-3-{[tert-butyl(dimethyl)silyl]oxy}-2-hydroxycyclopentyl]methoxy}(2-cyanoethoxy)phosphorothioyl]-5'-O-[bis(4-methoxyphenyl)(phenyl)methyl]-3'-O-[tert-butyl(dimethyl)silyl]adenosine To a solution of the compound (1.22 g) obtained in the above step 10 in acetonitrile (2.0 mL), a mixed solution of hydrazine monohydrate (0.25 mL) in acetic acid (5.0 mL)-pyridine (7.5 mL) was added, and the reaction mixture was stirred at room temperature for 30 minutes. After water was added to the reaction mixture to quench the reaction, the resultant was subjected to extraction with ethyl acetate, and the organic layer was dried over anhydrous sodium sulfate. The drying agent was removed through filtration, and the filtrate was concentrated under reduced pressure. The residue was purified by silica gel column chromatography [hexane/ethyl acetate] to afford the title compound (770 mg) as a mixture of diastereomers at the phosphorus atom.
MS(ESI)m/z: 1442 (M+H)$^+$.

(Step 12)

N-Benzoyl-2'-O-[{[(1R,2R,3S,4R)-4-(6-benzoyl-6,7,
8,9-tetrahydro-2H-2,3,5,6-tetraazabenzo[cd]azulen-
2-yl)-3-{[tert-butyl(dimethyl)silyl]oxy}-2-{[hydroxy
(oxo)-$\lambda^5$-phosphanyl]oxy}cyclopentyl]methoxy}(2-
cyanoethoxy)phosphorothioyl]-3'-O-[tert-butyl(dim-
ethyl)silyl]adenosine To a solution of the compound (770 mg) obtained in the above step 11 in pyridine (8.0 mL), diphenyl phosphite (0.61 mL) was added, and the reaction mixture was stirred at room temperature for 2 hours. Water (20 mL), acetonitrile (8.0 mL), and aqueous solution of triethylammonium acetate (2 M, 1.6 mL) were added to the reaction mixture, which was stirred for 1 hour, and the reaction mixture was then concentrated under reduced pressure. To a solution of the residue in dichloromethane (5.0 mL), water (0.096 mL) and a solution of dichloroacetic acid (0.22 mL) in dichloromethane (5.0 mL) were added in this order, and the reaction mixture was stirred for 30 minutes. Pyridine (0.43 mL) was added thereto to quench the reaction, and the reaction mixture was then concentrated under reduced pressure. The residue was purified by silica gel column chromatography [hexane/ethyl acetate] to afford the title compound (400 mg) as a mixture of diastereomers at the phosphorus atom.
MS(ESI)m/z: 1203 (M+H)$^+$.

(Step 13)

N-{9-[(5R,7R,8R,12aR,14R,15S,15aR,16R)-14-(6-
Benzoyl-6,7,8,9-tetrahydro-2H-2,3,5,6-tetraazabenzo
[cd]azulen-2-yl)-15,16-bis{[tert-butyl(dimethyl)si-
lyl]oxy}-10-(2-cyanoethoxy)-2-oxo-2-sulfanyl-10-
sulfanylidenedecahydro-2H,10H-5,8-methano-2$\lambda^5$,
10$\lambda^5$-cyclopenta[1][1,3,6,9,11,2,10]
pentaoxadiphosphacyclotetradecin-7-yl]-9H-purin-6-
yl}benzamide With use of the compound (400 mg) obtained in the above step 12, the reaction was performed in the same manner as in step 9 of Example 1 to afford the title compound (300 mg) as a mixture of diastereomers at the phosphorus atom.
MS(ESI)m/z: 1217 (M+H)$^+$.

(Step 14)

Disodium (5R,7R,8R,12aR,14R,15S,15aR,16R)-7-
(6-amino-9H-purin-9-yl)-15,16-dihydroxy-2,10-
dioxo-14-(6,7,8,9-tetrahydro-2H-2,3,5,6-tetraaz-
abenzo[cd]azulen-2-yl) decahydro-2H,10H-5,8-
methano-2$\lambda^5$,10$\lambda^5$-cyclopenta[1][1,3,6,9,11,2,10]
pentaoxadiphosphacyclotetradecine-2,10-bis
(thiolate)

To a solution of the compound (300 mg) obtained in the above step 13 in methanol (10 mL), 28% ammonia water (10 mL) was added, and the reaction mixture was stirred at room temperature for 12 hours. After the reaction mixture was concentrated under reduced pressure, triethylamine trihydrofluoride (3.0 mL) was added to the residue, and the resultant was stirred at 45° C. for 2 hours. The reaction mixture was added dropwise to an ice-cooled mixed solution of 1 M solution of triethylammonium hydrogen carbonate (18 mL)-triethylamine (6.0 mL) to quench the reaction. The reaction mixture was concentrated under reduced pressure, and then purified by C18 silica gel column chromatography [10 mM aqueous solution of triethylammonium acetate/acetonitrile] to afford diastereomer 1 and diastereomer 2 of the title compound as triethylamine salts.

The triethylamine salts obtained were each subjected to salt exchange in the same manner as in [Conversion to Sodium Salt] described in step 11 of Example 1 to afford diastereomer 1 (45.6 mg) and diastereomer 2 (12.6 mg) of the title compound.

Diastereomer 1 (Less Polar)

MS(ESI)m/z: 728 (M+H)$^+$.

$^1$H-NMR (CD$_3$OD) δ: 8.69 (1H, s), 8.10 (1H, s), 7.93 (1H, s), 7.10 (1H, s), 6.29 (1H, d, J=8.2 Hz), 5.38 (1H, dq, J=9.7.2.7 Hz), 4.99 (2H, m), 4.79 (1H, d, J=3.9 Hz), 4.61 (1H, dd, J=7.2, 4.9 Hz), 4.36 (1H, m), 4.29 (1H, m), 4.19 (1H, m), 3.99 (1H, m), 3.89 (1H, q, J=9.9 Hz), 3.47 (2H, t, J=4.9 Hz), 2.80 (2H. q, J=5.7 Hz), 2.72 (1H, m), 2.37 (1H, dt, J=16.4, 6.7 Hz), 1.94 (2H, m), 1.61 (1H, dt, J=16.4, 6.7 Hz).

$^{31}$P-NMR (CD$_3$OD) δ: 58.3 (s), 54.0 (s).

Diastereomer 2 (More Polar)

MS(ESI)m/z: 728 (M+H)$^+$.

$^1$H-NMR (CD$_3$OD) δ: 8.74 (1H, s), 8.10 (1H, s), 7.95 (1H, s), 7.09 (1H, s), 6.26 (1H, d, J=8.6 Hz), 5.44 (1H, m), 5.24 (1H, m), 5.06 (1H, q, J=9.3 Hz), 4.59 (1H, dd, J=9.4, 4.3 Hz), 4.51 (1H, d, J=4.3 Hz), 4.34-4.21 (3H, m), 3.94 (1H, m), 3.74 (1H, m), 3.47 (2H, m), 2.85 (2H, t, J=5.5 Hz), 2.54 (1H, m), 2.45 (1H, dt, J=17.1, 6.7 Hz), 1.95 (2H, m), 1.38 (1H, ddd, J=14.6, 8.3, 5.0 Hz).

$^{31}$P-NMR (CD$_3$OD) δ: 62.7 (s), 60.1 (s).

Example 57: Synthesis of CDN47

(5R,7R,8R,12aR,14R,15R,15aS,16R)-7-(6-Amino-
9H-purin-9-yl)-15,16-dihydroxy-2,10-bis(sulfanyl)-
10-sulfanylidene-14-(6,7,8,9-tetrahydro-2H-2,3,5,6-
tetraazabenzo[cd]azulen-2-yl)octahydro-2H,10H,
12H-5,8-methano-2$\lambda^5$,10$\lambda^5$-furo[3,2-1][1,3,6,9,11,2,
10]pentaoxadiphosphacyclotetradecine-2-one

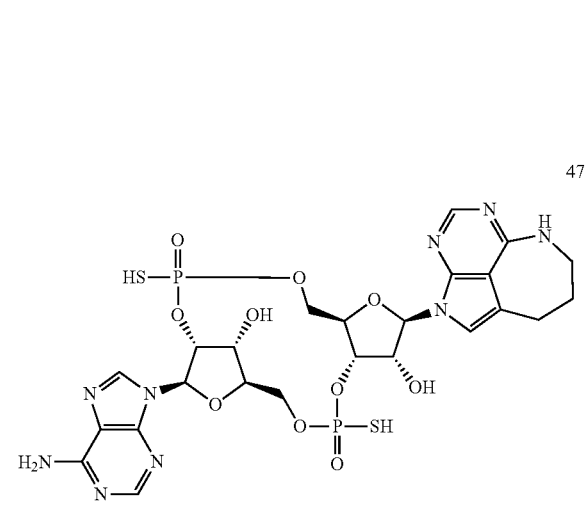

47a (Diastereomer 1)

[Synthesis Scheme]
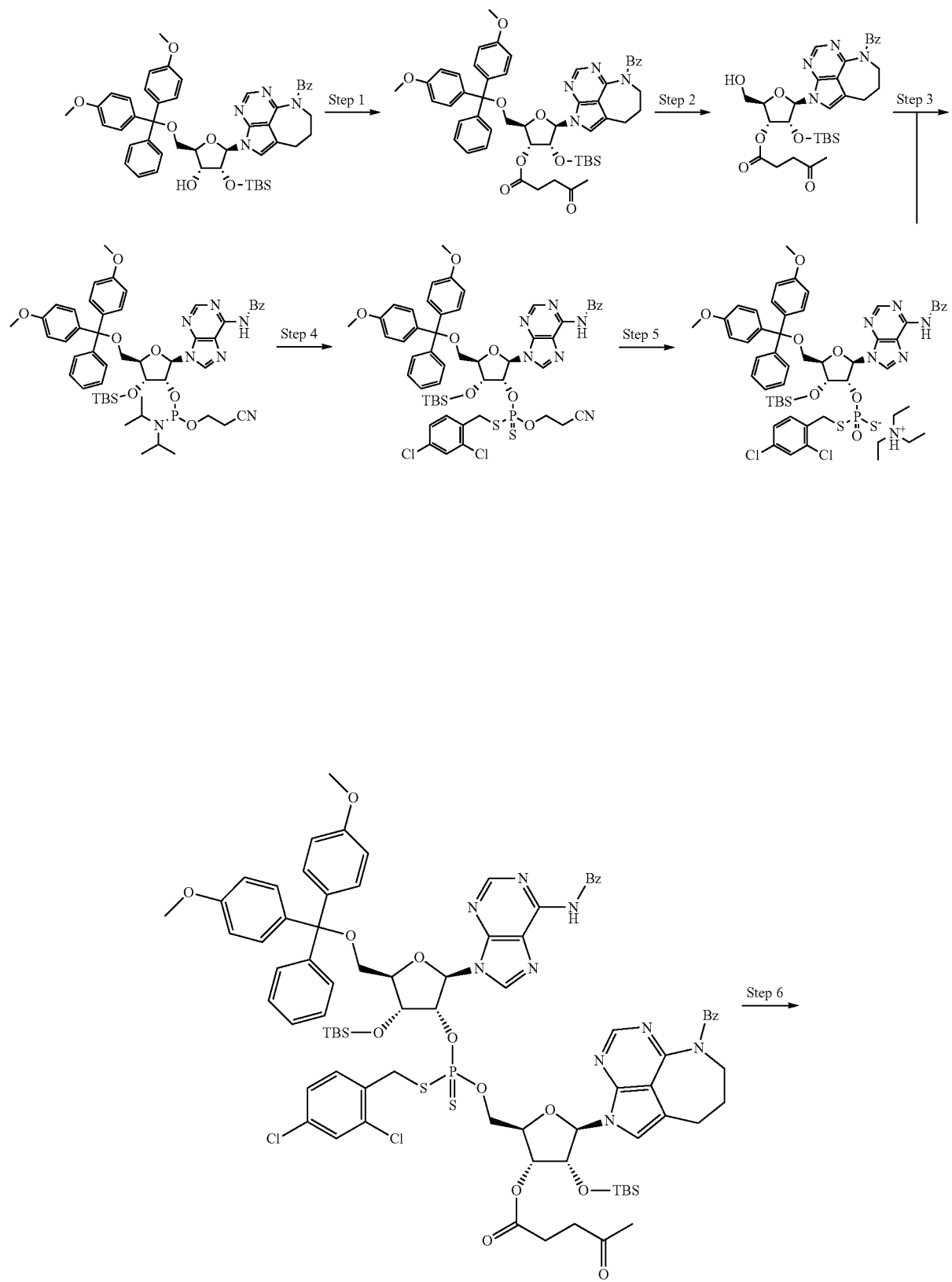
Dinucleotide B

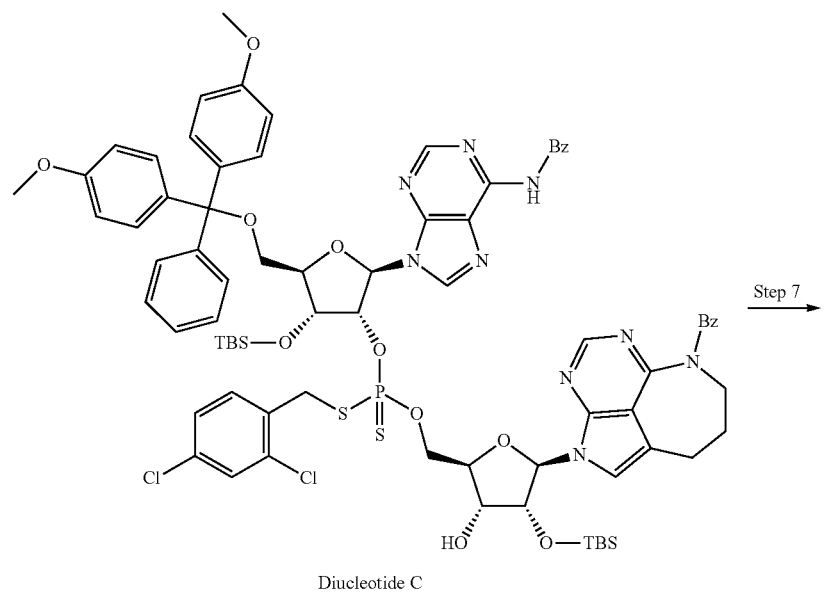
Diucleotide C
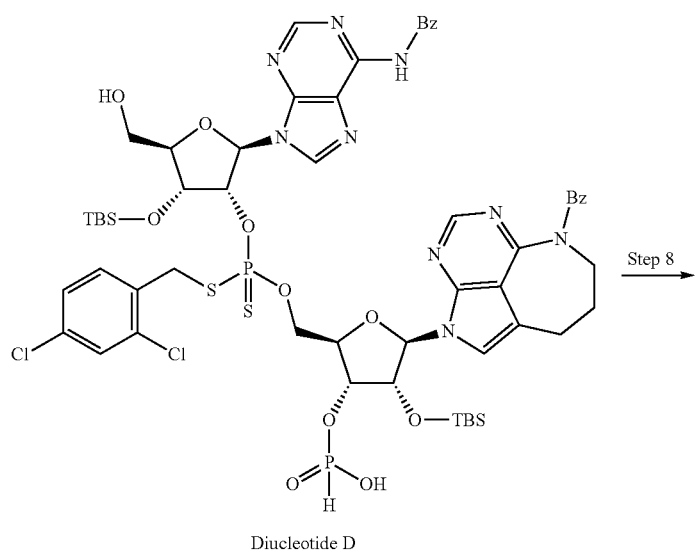
Diucleotide D
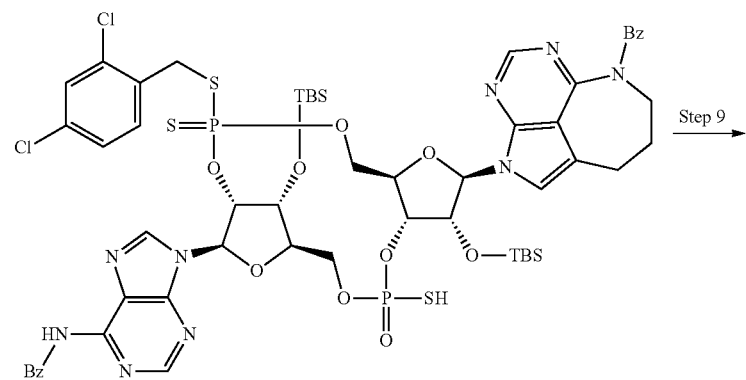

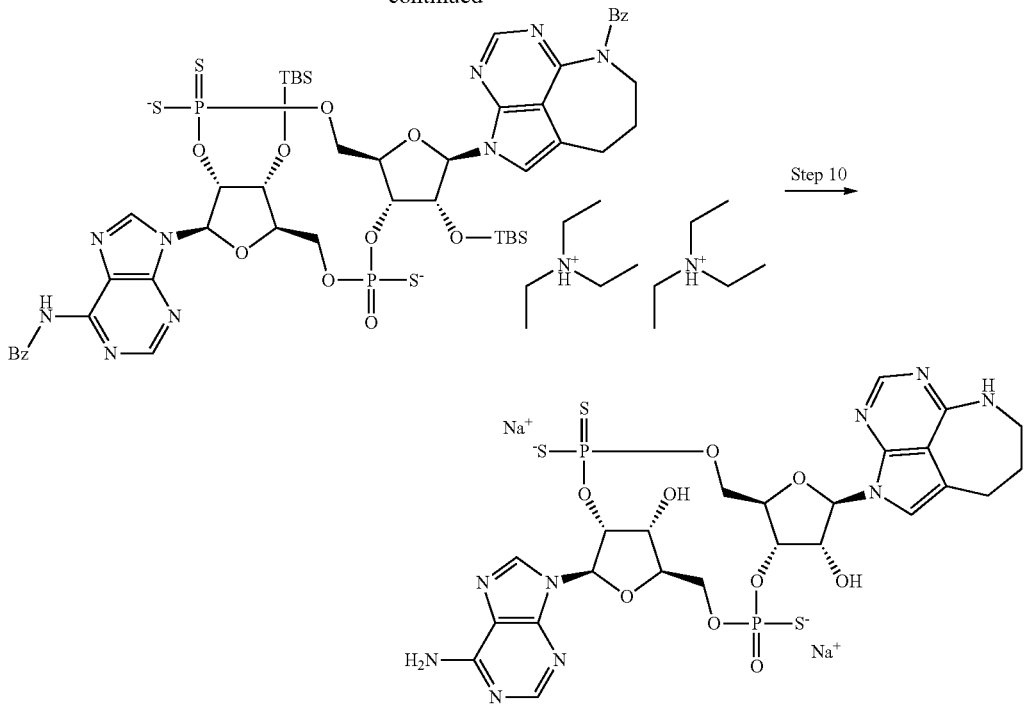

(Step 1)

6-Benzoyl-2-{5-O-[bis(4-methoxyphenyl)(phenyl)methyl]-2-O-[tert-butyl(dimethyl)silyl]-3-O-(4-oxopentanoyl)-β-D-ribofuranosyl}-6,7,8,9-tetrahydro-2H-2,3,5,6-tetraazabenzo[cd]azulene With use of the compound obtained in step 5 of Example 1, the reaction was performed in the same manner as in step 8 of Example 56 to afford the title compound (2.8 g).

$^1$H-NMR (CDCl$_3$) δ: 8.08 (1H, s), 7.48-7.19 (15H, m), 6.37 (4H, d, J=6.7 Hz), 5.48 (1H, dd, J=5.1, 2.3 Hz), 4.83 (1H, dd, J=6.7, 5.1 Hz), 4.37-4.00 (3H, m), 3.80 (3H, s), 3.79 (3H, s), 3.69 (1H, m), 3.54 (1H, dd, J=10.6, 2.7 Hz), 3.39 (1H, dd, J=11.0, 2.7 Hz), 2.90-2.57 (6H, m), 2.20 (3H, s), 2.20-2.11 (2H, m), 0.69 (9H, s), −0.03 (3H, s), −0.29 (3H, s).

(Step 2)

6-Benzoyl-2-{2-O-[tert-butyl(dimethyl)silyl]-3-O-(4-oxopentanoyl)-β-D-ribofuranosyl}-6,7,8,9-tetrahydro-2H-2,3,5,6-tetraazabenzo[cd]azulene With use of the compound (2.8 g) obtained in the above step 1, the reaction was performed in the same manner as in step 9 of Example 56 to afford the title compound (1.74 g).

$^1$H-NMR (CDCl$_3$) δ: 8.06 (1H, s), 7.38-7.20 (5H, m), 7.04 (1H, s), 6.32 (1H, dd, J=12.1, 1.6 Hz), 5.64 (1H, d, J=7.8 Hz), 5.47 (1H, d, J=5.1 Hz), 5.16 (1H, dd, J=7.8, 5.1 Hz), 4.40 (1H, m), 4.29 (1H, s), 4.17 (1H, m), 3.91 (1H, m), 3.75 (1H, m), 3.02 (2H, m), 2.90-2.60 (4H, m), 2.30-2.14 (2H, m), 2, 22 (3H, s), 0.68 (9H, s), −0.15 (3H, s), −0.46 (3H, s).

(Step 3)

N-Benzoyl-5'-O-[bis(4-methoxyphenyl)(phenyl)methyl]-3'-O-[tert-butyl(dimethyl)silyl]-2'-O-[(2-cyanoethoxy){[(2,4-dichlorophenyl)methyl]sulfanyl}phosphorothioyl]adenosine To a solution of commercially available (ChemGenes Corporation) N-benzoyl-5'-O-[bis(4-methoxyphenyl)(phenyl)methyl]-3'-O-[tert-butyl(dimethyl)silyl]-2'-O-{(2-cyanoethoxy)[di(propan-2-yl)amino]phosphanyl}adenosine (3.73 g) in acetonitrile (30 mL), the molecular sieves 3A, 1/16 (1.0 g) and 2,4-dichlorobenzylmercaptan (1.8 mL) were added, and the reaction mixture was stirred at room temperature for 10 minutes. Imidazole perchlorate (3.18 g) was added to the reaction mixture, which was stirred for 2.5 hours, and sulfur (242 mg) was then added thereto, and the reaction mixture was further stirred for 1 hour. The molecular sieves 3A were removed from the reaction mixture through filtration, and a saturated aqueous solution of sodium hydrogen carbonate was added to the filtrate, which was subjected to extraction with ethyl acetate. After the organic layer was dried over anhydrous sodium sulfate, the drying agent was removed through filtration, and the filtrate was concentrated under reduced pressure. The residue was purified by silica gel column chromatography [hexane/ethyl acetate] to afford the title compound (2.73 g) as a mixture of diastereomers at the phosphorus atom.

MS(ESI)m/z: 1111 (M+H)$^+$.

$^1$H-NMR (CDCl$_3$) δ: 8.89 (1H, s), 8.74 (1H, d, J=1.8 Hz), 8.32 (0.5H s), 8.26 (0.5H, s), 8.02 (2H, m), 7.64-7.61 (15H, m), 6.82 (4H, d, J=9.0), 6.45 (0.5H, d, J=6.7 Hz), 6.38 (0.5H, d, J=6.3 Hz), 5.88 (0.5H, ddd, J=14.2, 6.6, 4.8 Hz), 5.74 (0.5H, ddd, J=14.4, 6.4, 4.8 Hz), 4.75 (0.5H, dd, J=4.7, 2.7 Hz), 4.64 (0.5H, dd, J=4.7, 2.3 Hz), 4.22-3.82 (5H, m), 3.78 (6H, s), 3.58-3.53 (2H, m), 3.34-3.29 (2H, m), 2, 57 (1H, t, J=6.3 Hz), 2.48 (1H, t, J=6.3 Hz), 0.90 (4.5H, s), 0.88 (4.5H, s), 0.16 (1.5H, s), 0.11 (1.5H, s), 0.07 (1.5H, s), 0.04 (1.5H, s).

(Step 4)

N,N-Diethylethaneaminium N-benzoyl-5'-O-[bis(4-methoxyphenyl)(phenyl)methyl]-3'-O-[tert-butyl(dimethyl)silyl]-2'-O-[{[(2,4-dichlorophenyl)methyl]sulfanyl}(sulfide)phosphoryl]adenosine To a solution of the compound (2.66 g) obtained in the above step 3 in acetonitrile (30 mL), triethylamine (30 mL)

was added, and the reaction mixture was stirred at room temperature for 4 hours. The reaction mixture was concentrated under reduced pressure, and the residue was purified by DIOL silica gel column chromatography [hexane/ethyl acetate] to afford the title compound (2.5 g) as a mixture of diastereomers at the phosphorus atom.

MS(ESI)m/z: 1058 (M+H)+.

(Step 5)
Dinucleotide B

To a solution of the compound (2.5 g) obtained in the above step 4 in dichloromethane (10 mL), the molecular sieves 4A, 1/16 (1.0 g), the compound (930 mg) obtained in the above step 2, and 1-methylimidazole (1.18 mL) were added in this order, and the reaction mixture was stirred at room temperature for 20 minutes. To the reaction mixture, 2,4,6-triisopropylbenzelsulfonyl chloride (905 mg) was added, and the reaction mixture was further stirred for 4 hours. The molecular sieves 4A were removed from the reaction mixture through filtration, and a saturated aqueous solution of sodium hydrogen carbonate was added to the filtrate, which was subjected to extraction with ethyl acetate. After the organic layer was dried over anhydrous sodium sulfate, the drying agent was removed through filtration, and the filtrate was concentrated under reduced pressure. The residue was purified by silica gel column chromatography [hexane/ethyl acetate] to afford the title compound (1.04 g) as a mixture of diastereomers at the phosphorus atom.

MS(ESI)m/z: 1662 (M+H)+.

(Step 6)
Dinucleotide C

With use of the compound (1.04 g) obtained in the above step 5, the reaction was performed in the same manner as in step 11 of Example 56 to afford the title compound (820 mg) as a mixture of diastereomers at the phosphorus atom.

MS(ESI)m/z: 1564 (M+H)+.

(Step 7)
Dinucleotide D

With use of the compound (820 mg) obtained in the above step 6, the reaction was performed in the same manner as in step 12 of Example 56 to afford the title compound (440 mg) as a mixture of diastereomers at the phosphorus atom.

(Step 8)

N-{9-[(5R,7R,8R,12aR,14R,15R,15aR,16R)-14-(6-Benzoyl-6,7,8,9-tetrahydro-2H-2,3,5,6-tetraazabenzo[cd]azulen-2-yl)-15,16-bis{[tert-butyl(dimethyl)silyl]oxy}-10-{[(2,4-dichlorophenyl)methyl]sulfanyl}-2-oxo-2-sulfanyl-10-sulfanylideneoctahydro-2H,10H,12H-5,8-methano-2$\lambda^5$,10$\lambda^5$-furo[3,2-1][1,3,6,9,11,2,10]pentaoxadiphosphacyclotetradecin-7-yl]-9H-purin-6-yl}benzamide With use of the compound (440 mg) obtained in the above step 7, the reaction was performed in the same manner as in step 9 of Example 1 to afford the title compound (360 mg).

MS(ESI)m/z: 1340 (M+H)+.

(Step 9)

Bis(N,N-diethylethaneaminium) (5R,7R,8R,12aR,14R,15R,15aR,16R)-7-(6-benzamido-9H-purin-9-yl)-14-(6-benzoyl-6,7,8,9-tetrahydro-2H-2,3,5,6-tetraazabenzo[cd]azulen-2-yl)-15,16-bis{[tert-butyl(dimethyl)silyl]oxy}-2-oxo-10-sulfanylideneoctahydro-2H,10H,12H-5,8-methano-2$\lambda^5$,10$\lambda^5$-furo[3,2-1][1,3,6,9,11,2,10]pentaoxadiphosphacyclotetradecine-2,10-bis(thiolate)

To a dimethyl sulfoxide solution of the compound (360 mg) obtained in the above step 8, 1-dodecanethiol (434 mg) and 1,8-diazabicyclo [5.4.0]-7-undecene (0.40 mL) were added, and the reaction mixture was stirred at room temperature for 6 hours. The reaction mixture was directly purified by C18 silica gel column chromatography [10 mM aqueous solution of triethylammonium acetate/acetonitrile] to afford the title compound (130 mg).

MS(ESI)m/z: 1182 (M+H)+.

(Step 10)

Disodium (2S,5R,7R,8R,12aR,14R,15R,15aS,16R)-7-(6-amino-9H-purin-9-yl)-15,16-dihydroxy-2-oxo-10-sulfanylidene-14-(6,7,8,9-tetrahydro-2H-2,3,5,6-tetraazabenzo[cd]azulen-2-yl)octahydro-2H,10H,12H-5,8-methano-2$\lambda^5$,10$\lambda^5$-furo[3,2-1][1,3,6,9,11,2,10]pentaoxadiphosphacyclotetradecine-2,10-bis (thiolate)

With use of the compound (130 mg) obtained in the above step 9, the reaction was performed in the same manner as in step 14 of Example 56, and the resultant was then purified by C18 silica gel column chromatography [10 mM aqueous solution of triethylammonium acetate/acetonitrile] to afford the title compound as a triethylamine salt.

The triethylamine salt obtained was subjected to salt exchange in the same manner as in [Conversion to Sodium Salt] described in step 11 of Example 1 to afford the title compound (62.8 mg).

MS(ESI)m/z: 746 (M+H)+.

$^1$H-NMR (CD$_3$OD) δ: 8.70 (1H, s), 8.07 (1H, s), 8.03 (1H, s), 7.25 (1H, s), 6.26 (1H, d, J=8.6 Hz), 6.21 (1H, d, J=5.9 Hz), 5.52 (1H, dq, J=14.1, 5.2 Hz), 5.36 (1H, m), 4.70 (1H, dd, J=5.7, 4.5 Hz), 4.42 (1H, d, J=4.3 Hz), 4.37-4.26 (3H, m), 4.21 (1H, m), 3.96 (1H, m), 3.84 (1H, m), 3.50 (2H, m), 2.81 (2H, m), 1.93 (2H, m).

$^{31}$P-NMR (CD$_3$OD) δ: 119.8 (s), 59.4 (s).

Example 58: Synthesis of CDN48

(5R,7R,8R,12aR,14R,15R,15aR,16R)-14-(8,9-Dihydro-6-thia-2,3,5-triazabenzo[cd]azulen-2 (7H)-yl)-15-fluoro-16-hydroxy-7-[1-(2-hydroxyethyl)-6-oxo-1,6-dihydro-9H-purin-9-yl]-2,10-bis(sulfanyl)octahydro-2H,10H,12H-5,8-methano-2$\lambda^5$,10$\lambda^5$-furo[3,2-1][1,3,6,9,11,2,10]pentaoxadiphosphacyclotetradecine-2,10-dione

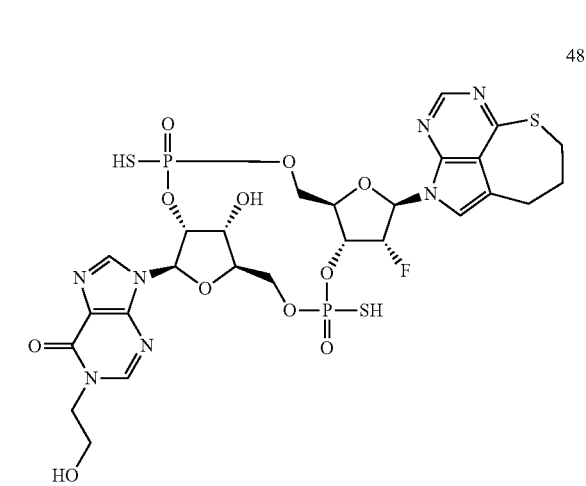

48

48a (Diastereomer 1)
48b (Diastereomer 2)

[Synthesis Scheme]
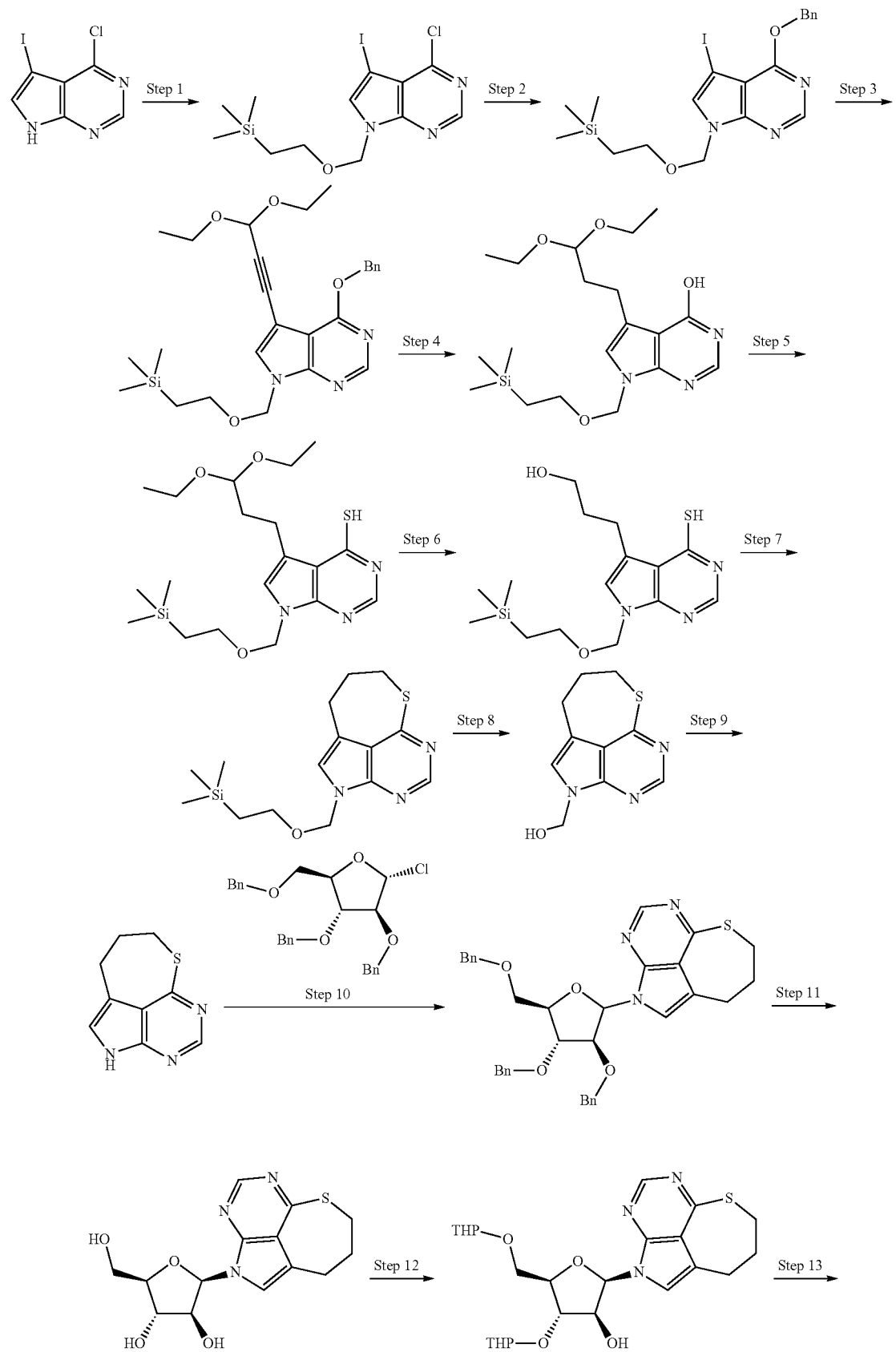

535
536
-continued
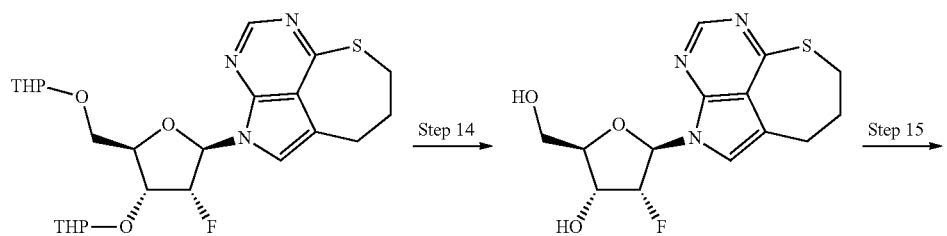
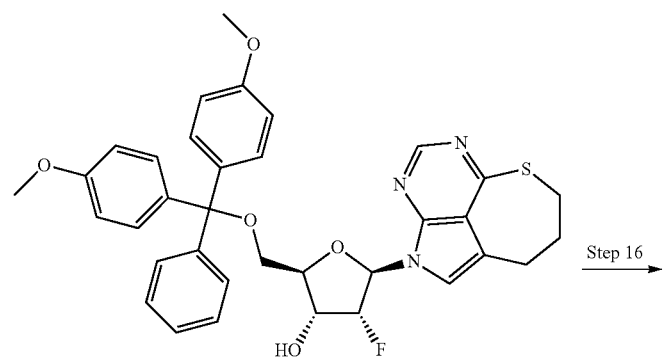
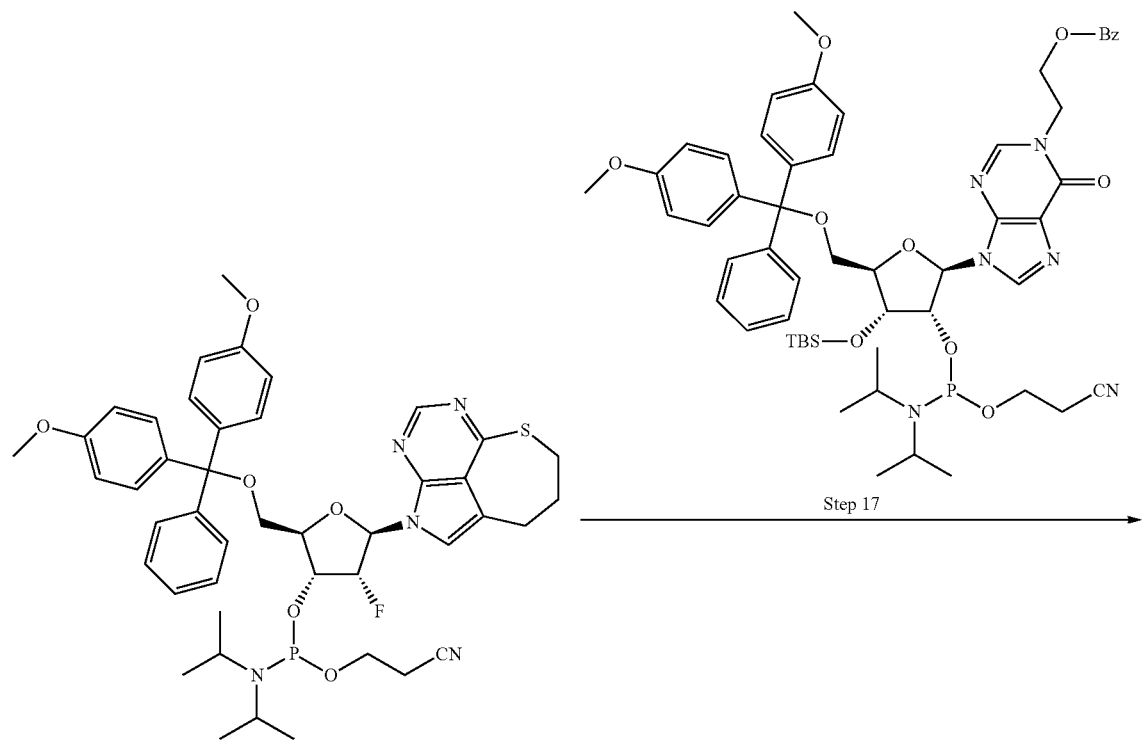

-continued
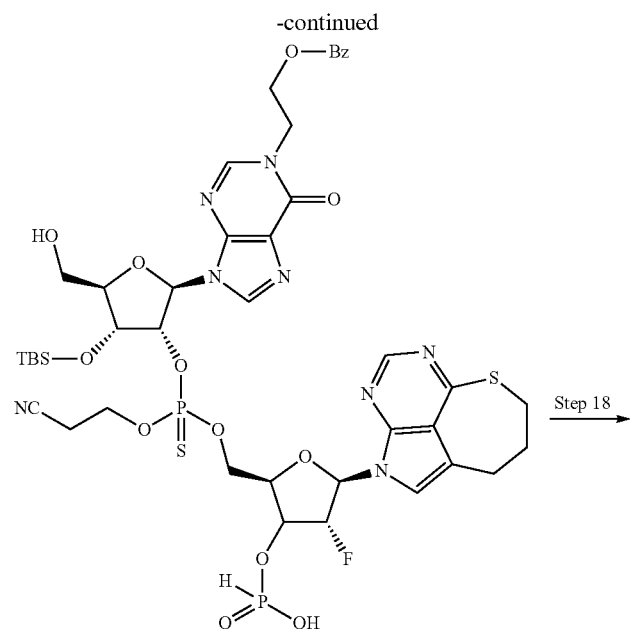
Step 18
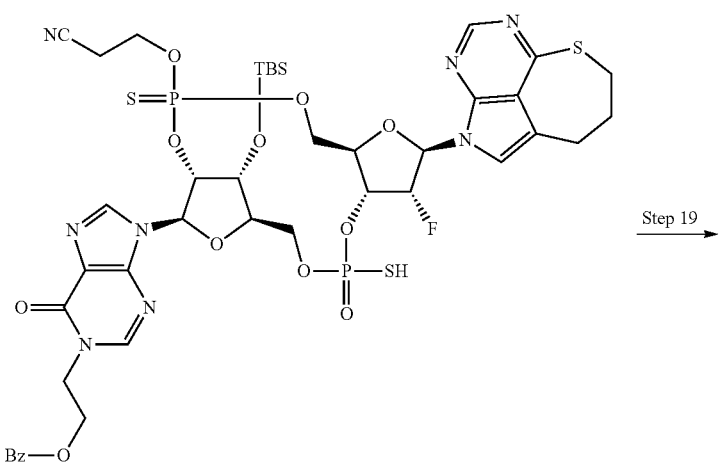
Step 19
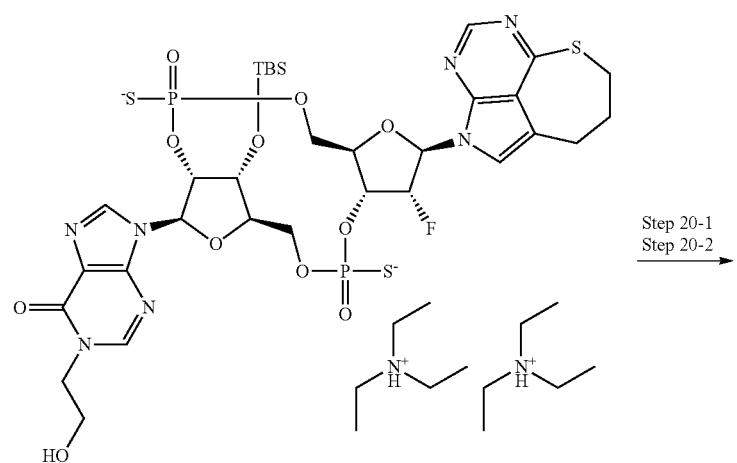
Step 20-1
Step 20-2

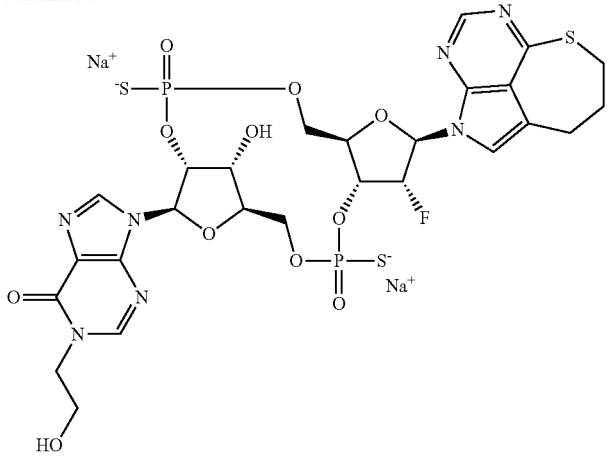

(Step 1)

4-Chloro-5-iodo-7-{[2-(trimethylsilyl)ethoxy]methyl}-7H-pyrrolo[2,3-d]pyrimidine To a solution of commercially available (PharmaBlock Sciences (Nanjing), Inc.) 4-chloro-5-iodo-7H-pyrrolo[2,3-d]pyrimidine (73.8 g) in N,N-dimethylformamide (10 mL), sodium hydride (containing 45% mineral oil) (13.3 g) was added under ice-cooling, and the reaction mixture was stirred for 40 minutes with increasing the temperature to room temperature. The reaction mixture was again ice-cooled, [2-(chloromethoxy)ethyl] (trimethyl)silane (51.0 mL) was added thereto over 10 minutes, and the reaction mixture was then stirred at the same temperature for 30 minutes. To the mostly solidified reaction mixture, water (260 mL) was added in small portions to quench the reaction. The solid was collected through filtration, washed with water (1500 mL) and hexane (600 mL), and dried under reduced pressure at 40° C. to afford the title compound (97.63 g).

MS(ESI)m/z: 410 (M+H)$^+$.

$^1$H-NMR (CDCl$_3$) δ: 8.64 (1H, s), 7.54 (1H, s), 5.61 (2H, s), 3.52 (2H, t, J=8.3 Hz), 0.92 (2H, t, J=8.3 Hz), −0.04 (9H, s).

(Step 2)

4-(Benzyloxy)-5-iodo-7-{[2-(trimethylsilyl)ethoxy]methyl}-7H-pyrrolo[2,3-d]pyrimidine To a solution of benzyl alcohol (27 mL) in N,N-dimethylformamide (170 mL), sodium hydride (containing 45% mineral oil) (12 g) was added under ice-cooling, and the reaction mixture was stirred for 40 minutes with increasing the temperature to room temperature. The reaction mixture was again ice-cooled, a suspension of the compound (97.63 g) obtained in the above step 1 in N,N-dimethylformamide (360 mL) was added thereto over 40 minutes, and the reaction mixture was stirred at the same temperature for 35 minutes. Ice chips and a saturated aqueous solution of ammonium chloride were added to the reaction mixture to quench the reaction. The reaction mixture was poured into a two-layer mixture of a saturated aqueous solution of ammonium chloride and ethyl acetate, and subjected to extraction with ethyl acetate:toluene (9:1). The organic layer was washed twice with water and twice with brine, and then dried over anhydrous sodium sulfate. The drying agent was removed through filtration, and the filtrate was concentrated under reduced pressure. The residue was purified by silica gel column chromatography [hexane/ethyl acetate] to afford the title compound (107.7 g).

MS(ESI)m/z: 482 (M+H)$^+$.

$^1$H-NMR (CDCl$_3$) δ: 8.47 (1H, s), 7.61 (2H, d, J=7.3 Hz), 7.41 (2H, t, J=7.6 Hz), 7.36-7.30 (1H, m), 7.30 (1H, s), 5.65 (2H, s), 5.57 (2H, s), 3.52 (2H, t, J=8.3 Hz), 0.91 (2H, t, J=8.3 Hz), −0.05 (9H, s).

(Step 3)

4-(Benzyloxy)-5-(3,3-diethoxyprop-1-yn-1-yl)-7-{[2-(trimethylsilyl)ethoxy]methyl}-7H-pyrrolo[2,3-d]pyrimidine To a mixed solution of the compound (113.4 g) obtained in the above step 2 in acetonitrile (1000 mL)-triethylamine (98 mL), copper iodide (4.49 g), tetrakistriphenylphosphinepalladium (0) (8.17 g), and 3,3-diethoxyprop-1-yne (104 mL) were added under the nitrogen atmosphere at room temperature, and the reaction mixture was stirred at the same temperature for 4.5 hours. After the reaction mixture was concentrated under reduced pressure, ethyl acetate and hexane were added to the residue, and a solid precipitated was removed through filtration. The solid was washed with a mixture of ethyl acetate:hexane (1:1), and the filtrate was then concentrated under reduced pressure. The residue was purified by silica gel column chromatography [hexane/ethyl acetate] to afford the title compound (145.5 g: with impurities).

MS(ESI)m/z: 482 (M+H)$^+$.

(Step 4)

5-(3,3-Diethoxypropyl)-7-{[2-(trimethylsilyl)ethoxy]methyl}-7H-pyrrolo[2,3-d]pyrimidin-4-ol To a solution of the compound (145.5 g) obtained in the above step 3 in ethanol (900 mL), a 10% palladium-carbon catalyst (M) wet (50.2 g) was added, and the reaction mixture was stirred under the hydrogen atmosphere at room temperature for 5 hours. Dichloromethane (500 mL) was added to the reaction mixture, the catalyst was removed through filtration with a Celite, and the filtrate was concentrated under reduced pressure.

The residue was purified twice by silica gel column chromatography [hexane/ethyl acetate] to afford the title compound (59.6 g).

MS(ESI)m/z: 418 (M+Na)$^+$, 394 [M−H]$^−$.

$^1$H-NMR (CDCl$_3$) δ: 11.23 (1H, brs), 7.85 (1H, s), 6.79 (1H, s), 5.47 (2H, s), 4.58 (1H, t, J=5.9 Hz), 3.69 (2H, m), 3.57-3.49 (4H, m), 2.90 (2H, t, J=7.8 Hz), 2.07 (2H, m), 1.23 (6H, t, J=7.1 Hz), 0.91 (2H, t, J=8.1 Hz), −0.04 (9H, s).
(Step 5)

5-(3,3-Diethoxypropyl)-7-{[2-(trimethylsilyl)ethoxy]methyl}-7H-pyrrolo[2,3-d]pyrimidin-4-thiol To a solution of the compound (59.6 g) obtained in the above step 4 in dehydrated dichloromethane (300 mL), 2,6-lutidine (42 mL) was added under the nitrogen atmosphere. Trifluoromethanesulfonic anhydride (31 mL) was added dropwise thereto at −20° C. over 20 minutes, and the reaction mixture was stirred at the same temperature for 20 minutes. Thereto, N,N-dimethylformamide (500 mL) and sodium monohydrogensulfide hydrate (33.5 g) were added under ice-cooling, the temperature was increased to room temperature, and the reaction mixture was then stirred for 2.5 hours. The reaction mixture was concentrated under reduced pressure to distill off low-boiling-point components. The residue was poured into a two-layer mixture of ethyl acetate and an ice-cooled saturated aqueous solution of ammonium chloride, and subjected to extraction with a mixture of ethyl acetate:toluene (9:1). The organic layer was washed once with a saturated aqueous solution of ammonium chloride, and twice with brine, and then dried over anhydrous sodium sulfate. The drying agent was removed through filtration, and the filtrate was concentrated under reduced pressure. The residue was purified by silica gel column chromatography [hexane/ethyl acetate] to afford a mixture of the title compound and 2,6-lutidine. The mixture obtained was poured into a two-layer mixture of ethyl acetate and 1 N hydrochloric acid, and subjected twice to extraction with ethyl acetate. The organic layer was washed three times with brine, and then dried over anhydrous sodium sulfate. The drying agent was removed through filtration, and the filtrate was concentrated under reduced pressure to afford the title compound (57.6 g).

MS(ESI)m/z: 410 [M−H]$^−$.

$^1$H-NMR (CDCl$_3$) δ: 11.69 (1H, brs), 7.90 (1H, s), 6.96 (1H, s), 5.49 (2H, s), 4.61 (1H, t, J=5.9 Hz), 3.71 (2H, m), 3.55 (2H, m), 3.49 (2H, t, J=8.1 Hz), 3.14 (2H, t, J=7.8 Hz), 2.08 (2H, m), 1.23 (6H, t, J=7.1 Hz), 0.90 (2H, t, J=8.3 Hz), −0.04 (9H, s).
(Step 6)

3-(4-Sulfanyl-7-{[2-(trimethylsilyl)ethoxy]methyl}-7H-pyrrolo[2,3-d]pyrimidin-5-yl) propan-1-ol The compound (31.62 g) obtained in the above step 5 was dissolved in 80% aqueous solution of acetic acid (300 mL), and the reaction mixture was stirred at room temperature for 30 minutes. After confirming the disappearance of the raw material, the reaction mixture was ice-cooled, sodium borohydride (1.45 g) was carefully added in small portions thereto, and the reaction mixture was stirred at the same temperature for 30 minutes. Subsequently, sodium triacetoxyborohydride (24.4 g) was added thereto over 15 minutes, and the reaction mixture was stirred at the same temperature for 1.5 hours. The reaction mixture was concentrated to about ⅓ of the original volume under reduced pressure. Sodium hydrogen carbonate (solid) was carefully added to the residue to neutralize to some degree, the reaction mixture was subjected to extraction with ethyl acetate. The organic layer was washed with saturated sodium hydrogen carbonate and brine in this order, and dried over anhydrous sodium sulfate. The drying agent was removed through filtration, and the filtrate was concentrated under reduced pressure. The residue was purified by silica gel column chromatography [hexane/ethyl acetate] to afford the title compound (17.93 g).

MS(ESI)m/z: 340 [M+H]$^+$.

$^1$H-NMR (CDCl$_3$) δ: 11.92 (1H, brs), 7.95 (1H, s), 7.01 (1H, s), 5.51 (2H, s), 3.70 (2H, t, J=5.9 Hz), 3.50 (2H, t, J=8.1 Hz), 3.23 (2H, t, J=7.3 Hz), 2.33 (1H, brs), 1.99 (2H, m), 0.91 (2H, t, J=8.3 Hz), −0.04 (9H, s).
(Step 7)

2-{[2-(Trimethylsilyl)ethoxy]methyl}-2,7,8,9-tetrahydro-6-thia-2,3,5-triazabenzo[cd]azulene To a solution of the compound (31.31 g) obtained in the above step 6 in dehydrated tetrahydrofuran (600 mL), triphenylphosphine (25.4 g) and diisopropyl azodicarboxylate (21.8 g) were added under the nitrogen atmosphere at 0° C., and the reaction mixture was stirred at the same temperature for 1 hour. After the reaction mixture was concentrated under reduced pressure, the residue was purified by silica gel column chromatography [dichloromethane/ethyl acetate] and silica gel column chromatography [hexane/ethyl acetate] in this order to afford the title compound (35.93 g: with impurities).

MS(ESI)m/z: 322 [M+H]$^+$.

$^1$H-NMR (CDCl$_3$) δ: 8.57 (1H, s), 7.08 (1H, s), 5.58 (2H, s), 3.52 (2H, t, J=8.3 Hz), 3.17 (2H, m), 3.06 (2H, t, J=5.6 Hz), 2.36 (2H, m), 0.92 (2H, t, J=8.3 Hz), −0.05 (9H, s).
(Step 8)

(8,9-Dihydro-6-thia-2,3,5-triazabenzo[cd]azulen-2(7H)-yl) methanol

To a solution of the compound (35.93 g) obtained in the above step 7 in dichloromethane (150 mL), trifluoroacetic acid (150 mL) was added at room temperature, and the reaction mixture was stirred at the same temperature for 1.5 hours. The reaction mixture was concentrated under reduced pressure, and then azeotroped four times with toluene. A mixture of dichloromethane:hexane (1:2) was added to the reside, and a solid precipitated was collected through filtration (solid 1). After the filtrate was concentrated under reduced pressure, the residue was purified by silica gel column chromatography [hexane/ethyl acetate→ethyl acetate/methanol] to afford solid 2. Solid 1 and solid 2 were combined to give the title compound (20.13 g).

MS(ESI)m/z: 222 [M+H]$^+$.

$^1$H-NMR (CDCl$_3$) δ: 8.60 (1H, s), 7.19 (1H, s), 5.71 (2H, s), 3.21 (2H, m), 3.07 (2H, m), 2.38 (2H, m). (only observable peaks are shown)
(Step 9)

2,7,8,9-Tetrahydro-6-thia-2,3,5-triazabenzo[cd]azulene

To a suspension of the compound (20.13 g) obtained in the above step 8 in methanol (250 mL), 28% aqueous solution of ammonia (150 mL) was added, and the reaction mixture was stirred at room temperature for 1.5 hours. The reaction mixture was concentrated to about half the volume under reduced pressure. A solid precipitated was collected through filtration, and washed with ethanol to afford solid 1. The filtrate was concentrated under reduced pressure, and solid 2 was obtained through the same procedure. The filtrate was applied to silica gel, and then purified by silica gel column chromatography [dichloromethane/methanol]. Fractions containing the targeted product were concentrated under reduced pressure, the slurry was washed with ethanol, and the solid was then collected through filtration (solid 3). Solid 1, solid 2, and solid 3 were combined to give the title compound (12.36 g).

MS(ESI)m/z: 192 [M+H]$^+$.

$^1$H-NMR (CDCl$_3$) δ: 10.53 (1H, brs), 8.57 (1H, s), 7.10 (1H, s), 3.18 (2H, m), 3.08 (2H, t, J=5.6 Hz), 2.37 (2H, m).
(Step 10)

2-(2,3,5-Tri-O-benzyl-β-D-arabinofuranosyl)-2,7,8, 9-tetrahydro-6-thia-2,3,5-triazabenzo[cd]azulene To a suspension of the compound (13.47 g) obtained in the above step 9 in dehydrated acetonitrile (350 mL), powdery potassium hydroxide (10.3 g) and tris [2-(2-methoxyethoxy)ethyl]amine (1.13 mL) were added under the nitrogen atmosphere, and the reaction mixture was stirred at room temperature for 1.5 hours. A solution of 2,3,5-tri-O-benzyl-α-D-arabinofuranosyl chloride (40.2 g) as a compound known in the literature (J. Med. Chem. 1976, 19, 6, 814-816) in acetonitrile (100 mL) was added in small portions thereto under ice-cooling, and the temperature was increased to room temperature and the reaction mixture was stirred for 4 hours. Undissolved matters were removed through filtration, and washed with acetonitrile. The filtrate was concentrated under reduced pressure, and the residue was purified twice by silica gel column chromatography [hexane/ethyl acetate] to afford the title compound (26.19 g).

MS(ESI)m/z: 594 [M+H]$^+$.

$^1$H-NMR (CDCl$_3$) δ: 8.51 (1H, s), 7.37-7.17 (14H, m), 6.86 (2H, m), 6.82 (1H, d, J=4.9 Hz), 4.68 (1H, d, J=11.7 Hz), 4.59 (1H, d, J=11.7 Hz), 4.54 (1H, d, J=13.2 Hz), 4.52 (1H, d, J=11.7 Hz), 4.36-4.33 (2H, m), 4.22 (1H, d, J=11.7 Hz), 4.14-4.08 (2H, m), 3.77 (1H, dd, J=10.7, 3.9 Hz), 3.72 (1H, dd, J=10.5, 4.1 Hz), 3.13 (2H, m), 2.81 (2H, m), 2.27 (2H, m).
(Step 11)

2-β-D-Arabinofuranosyl-2,7,8,9-tetrahydro-6-thia-2, 3,5-triazabenzo[cd]azulene

To a solution of the compound (26.19 g) obtained in the above step 10 in dehydrated dichloromethane (300 mL), a dichloromethane solution of boron trichloride (1 M, 200 mL) was added under the nitrogen atmosphere at −78° C., and the reaction mixture was stirred at the same temperature for 2 hours, and the temperature was then increased to 0° C. and the reaction mixture was further stirred for 4 hours. The reaction mixture was again cooled to −78° C., a solution of methanol (80 mL) in dichloromethane (160 mL) was added thereto, and the reaction mixture was stirred for 30 minutes with increasing the temperature to room temperature. The reaction mixture was concentrated under reduced pressure, and azeotroped twice with ethanol. Ethanol (200 mL) and diethyl ether (100 mL) were added to the residue to make a slurry, and the solid was collected through filtration (solid 1). The filtrate was concentrated under reduced pressure, and the residue was purified by silica gel column chromatography [dichloromethane/methanol]. Fractions containing the targeted product were concentrated under reduced pressure, ethanol was added thereto to make a slurry, and the solid was collected through filtration (solid 2). Solid 1 and solid 2 were combined to give the title compound (13.2 g).

MS(ESI)m/z: 324 [M+H]$^+$.

$^1$H-NMR (CD$_3$OD) δ: 8.73 (1H, s), 7.96 (1H, s), 6.70 (1H, d, J=4.9 Hz), 4.32 (1H, t, J=4.6 Hz), 4.25 (1H, t, J=4.6 Hz), 3.97 (1H, m), 3.90 (1H, dd, J=12.0, 3.2 Hz), 3.85 (1H, dd, J=12.0, 4.6 Hz), 3.53 (2H, m), 3.17 (2H, m), 2.43 (2H, m).
(Step 12)

2-[3,5-Bis-O-(oxan-2-yl)-β-D-arabinofuranosyl]-2,7, 8,9-tetrahydro-6-thia-2,3,5-triazabenzo[cd]azulene To a solution of the compound (15.35 g) obtained in the above step 11 in dehydrated dimethyl sulfoxide (160 mL), 3,4-dihydro-2H-pyran (17.2 mL) and p-toluenesulfonic acid monohydrate (9.02 g) were added at 0° C., and the reaction mixture was stirred at room temperature for 3 hours. Thereto, 3,4-dihydro-2H-pyran (8.6 mL) was further added, and the reaction mixture was stirred for 45 minutes, and immediately thereafter triethylamine (13 mL) was added thereto to quench the reaction. The reaction mixture was poured into a two-layer mixture of ethyl acetate and a saturated aqueous solution of sodium hydrogen carbonate, and subjected to extraction with ethyl acetate. The organic layer was washed once with water, and twice with brine, and then dried over anhydrous sodium sulfate. The drying agent was removed through filtration, and the filtrate was concentrated under reduced pressure. The residue was purified by silica gel column chromatography [hexane/ethyl acetate] to afford the title compound (10.81 g) as a mixture of four diastereomers.

MS(ESI)m/z: 492 [M+H]$^+$.

$^1$H-NMR (CDCl$_3$) δ: 8.548 (0.2H, s), 8.546 (0.3H, s), 8.54 (0.3H, s), 8.53 (0.2H, s), 7.54 (0.2H, s), 7.53 (0.3H, s), 7.51 (0.2H, s), 7.44 (0.3H, s), 6.75 (0.2H, d, J=5.4 Hz), 6.71 (0.2H, d, J=5.9 Hz), 6.57 (0.3H, d, J=5.9 Hz), 6.56 (0.3H, d, J=5.9 Hz), 4.87-4.69 (2H, m), 4.55-3.54 (10H, m), 3.18-3.12 (2H, m), 3.10-2.96 (2H, m), 2.40-2.30 (2H, m), 1.92-1.51 (12H, m).
(Step 13)

2-[2-Deoxy-2-fluoro-3,5-bis-O-(oxan-2-yl)-β-D-ribofuranosyl]-2,7,8,9-tetrahydro-6-thia-2,3,5-triazabenzo[cd]azulene To a solution of the compound (10.81 g) obtained in the above step 12 in dehydrated dichloromethane (150 mL), pyridine (5.3 mL) and trifluoromethanesulfonic anhydride (5.6 mL) were added under the nitrogen atmosphere at 0° C., and the reaction mixture was stirred at the same temperature for 1 hour. After ice chips were added to the reaction mixture to quench the reaction, the reaction mixture was poured into a two-layer mixture of ethyl acetate and a saturated aqueous solution of sodium hydrogen carbonate, and subjected to extraction with ethyl acetate. The organic layer was washed twice with brine, and dried over anhydrous sodium sulfate. The drying agent was removed through filtration, and the filtrate was concentrated under reduced pressure to afford a crude form of triflate as an amorphous form. The crude form of triflate obtained was dissolved in dehydrated tetrahydrofuran (150 mL), to which a tetrahydrofuran solution of tetrabutylammonium fluoride (approximately 1 M, 154 mL) was added in small portions under ice-cooling, and the reaction mixture was stirred at the same temperature overnight. A saturated aqueous solution of ammonium chloride was added to the reaction mixture to quench the reaction. The reaction mixture was concentrated to about half the volume under reduced pressure. The residue was poured into a two-layer mixture of ethyl acetate and a saturated aqueous solution of ammonium chloride, and subjected to extraction with ethyl acetate. The organic layer was washed once with a saturated aqueous solution of ammonium chloride, and twice with brine. The aqueous layer was again subjected to extraction with ethyl acetate, and the extract was washed with brine. The organic layers were combined and dried over anhydrous sodium sulfate. The drying agent was removed through filtration, and the filtrate was concentrated under reduced pressure to afford a crude form of the title compound (40.37 g).

MS(ESI)m/z: 494 [M+H]$^+$.

(Step 14)

2-(2-Deoxy-2-fluoro-β-D-ribofuranosyl)-2,7,8,9-tetrahydro-6-thia-2,3,5-triazabenzo[cd]azulene To a solution of the compound (40.37 g) obtained in the above step 13 in methanol (400 mL), p-toluenesulfonic acid monohydrate (2.09 g) was added, and the reaction mixture was stirred at 60° C. for 4 hours. Triethylamine (16 mL) was added to the reaction mixture to quench the reaction. The reaction mixture was concentrated under reduced pressure, and the residue was purified by silica gel column chromatography [hexane/ethyl acetate→ethyl acetate/methanol]. Fractions containing the targeted product was concentrated under reduced pressure until the fractions became a slurry, and the solid was collected through filtration. The solid obtained was washed with hexane/ethyl acetate (1:1) to afford solid 1. The filtrate was concentrated under reduced pressure, and the residue was purified by silica gel column chromatography [dichloromethane/methanol] to afford solid 2. Solid 1 and solid 2 were combined to give the title compound (5.32 g).

MS(ESI)m/z: 326 [M+H]$^+$.

$^1$H-NMR (CDCl$_3$) δ: 8.51 (1H, s), 7.01 (1H, s), 6.00 (1H, dd, J=13.7, 6.3 Hz), 5.95 (1H, dd, J=11.7, 2.0 Hz), 5.87 (1H, ddd, J=52.7, 6.3, 4.9 Hz), 4.69 (1H, m), 4.32 (1H, brs), 3.96 (1H, d, J=12.7 Hz), 3.77 (1H, m), 3.17 (2H, m), 3.04 (2H, m), 2.41-2.31 (3H, m).

(Step 15)

2-{5-O-[Bis(4-methoxyphenyl)(phenyl)methyl]-2-deoxy-2-fluoro-β-D-ribofuranosyl}-2,7,8,9-tetrahydro-6-thia-2,3,5-triazabenzo[cd]azulene With use of the compound (5.32 g) obtained in the above step 14, the reaction was performed in the same manner as in step 1 of Example 11 to afford the title compound (10.1 g).

MS(ESI)m/z: 628 [M+H]$^+$.

$^1$H-NMR (CDCl$_3$) δ: 8.54 (1H, s), 7.42 (2H, d, J=7.3 Hz), 7.32-7.21 (8H, m), 6.81 (4H, m), 6.52 (1H, dd, J=17.3, 2.2 Hz), 5.37 (1H, ddd, J=53.3, 4.4, 2.4 Hz), 4.76 (1H, m), 4.16 (1H, m), 3.789 (3H, s), 3.786 (3H, s), 3.59 (1H, dd, J=10.7, 2.4 Hz), 3.44 (1H, dd, J=10.7, 3.4 Hz), 3.12 (2H, m), 2.76 (2H, t, J=5.6 Hz), 2.27 (2H, m), 2.18 (1H, dd, J=7.8, 2.9 Hz).

(Step 16)

2-(5-O-[Bis(4-methoxyphenyl)(phenyl)methyl]-3-O-{(2-cyanoethoxy)[di(propan-2-yl)amino]phosphanyl}-2-deoxy-2-fluoro-β-D-ribofuranosyl)-2,7,8,9-tetrahydro-6-thia-2,3,5-triazabenzo[cd]azulene With use of the compound (10.1 g) obtained in the above step 15, the reaction was performed in the same manner as in step 6 of Example 1 to afford the title compound (12.6 g) as a mixture of diastereomers at the phosphorus atom (diastereomer ratio=1:1).

$^1$H-NMR (CDCl$_3$) δ: 8.53 (1H, s), 7.40 (2H, m), 7.34-7.17 (8H, m), 6.84-6.74 (4H, m), 6.53 (0.5H, dd, J=17.3, 2.2 Hz), 6.48 (0.5H, dd, J=17.6, 1.5 Hz), 5.50-5.31 (1H, m), 4.99 (0.5H, m), 4.85 (0.5H, m), 4.31-4.26 (1H, m), 3.93-3.76 (1H, m), 3.792 (1.5H, s), 3.789 (1.5H, s), 3.779 (1.5H, s), 3.776 (1.5H, s), 3.67-3.51 (4H, m), 3.34-3.30 (1H, m), 3.13-3.10 (2H, m), 2.76-2.69 (2H, m), 2.61 (1H, td, J=6.3, 2.4 Hz), 2.39 (1H, m), 2.28-2.21 (2H, m), 1.19-1.15 (9H, m), 1.03 (3H, d, J=6.8 Hz).

(Step 17)

With use of the compound (740 mg) obtained in the above step 16, the reaction was performed in the same manner as in step 7 of Example 1 to afford an acetonitrile solution of 2-{2-deoxy-2-fluoro-3-O-[hydroxy (oxo)-λ$^5$-phosphanyl]-β-D-ribofuranosyl}-2,7,8,9-tetrahydro-6-thia-2,3,5-triazabenzo[cd]azulene. With use of the acetonitrile solution obtained and the compound obtained in step 3 of Example 22 (924 mg), the reaction was performed in the same manner as in step 8 of Example 1, and the resulting crude product was directly used for the subsequent reaction.

(Step 18)

2-{9-[(5R,7R,8R,12aR,14R,15R,15aR,16R)-16-{[tert-Butyl(dimethyl)silyl]oxy}-10-(2-cyanoethoxy)-14-(8,9-dihydro-6-thia-2,3,5-triazabenzo[cd] azulen-2 (7H)-yl)-15-fluoro-2-oxo-2-sulfanyl-10-sulfanylideneoctahydro-2H,10H,12H-5,8-methano-2λ$^5$,10λ$^5$-furo[3,2-1][1,3,6,9,11,2,10]pentaoxadiphosphacyclotetradecin-7-yl]-6-oxo-6,9-dihydro-1H-purin-1-yl}ethyl benzoate With use of the crude product obtained in the above step 17, the reaction was performed in the same manner as in step 9 of Example 1 to afford the title compound (502 mg: with impurities) as a mixture of diastereomers at the phosphorus atom.

MS(ESI)m/z: 1065 (M+H)$^+$.

(Step 19)

Bis(N,N-diethylethaneaminium) (5R,7R,8R,12aR,14R,15R,15aR,16R)-16-{[tert-butyl(dimethyl)silyl]oxy}-14-(8,9-dihydro-6-thia-2,3,5-triazabenzo[cd]azulen-2 (7H)-yl)-15-fluoro-7-[1-(2-hydroxyethyl)-6-oxo-1,6-dihydro-9H-purin-9-yl]-2,10-dioxooctahydro-2H,10H,12H-5,8-methano-2λ$^5$, 10λ$^5$-furo[3,2-1][1,3,6,9,11,2,10]pentaoxadiphosphacyclotetradecine-2,10-bis (thiolate)

With use of the compound (502 mg) obtained in the above step 18, the reaction was performed in the same manner as in step 10 of Example 1 to afford diastereomer 1 (67.8 mg: with impurities) and diastereomer 2 (69.5 mg: with impurities) of the title compound.

Diastereomer 1 (Less Polar)

MS(ESI)m/z: 908 (M+H)$^+$.

Diastereomer 2 (More Polar)

MS(ESI)m/z: 908 (M+H)$^+$.

(Step 20-1)

Disodium (5R,7R,8R,12aR,14R,15R,15aR,16R)-14-(8,9-dihydro-6-thia-2,3,5-triazabenzo[cd]azulen-2(7H)-yl)-15-fluoro-16-hydroxy-7-[1-(2-hydroxyethyl)-6-oxo-1,6-dihydro-9H-purin-9-yl]-2,10-dioxooctahydro-2H,10H,12H-5,8-methano-2λ$^5$,10λ$^5$-furo[3,2-1][1,3,6,9,11,2,10]pentaoxadiphosphacyclotetradecine-2,10-bis(thiolate)

(Diastereomer 1)

With use of the compound obtained in step 19 above (diastereomer 1) (67.8 mg: with impurities), the reaction was performed in the same manner as in step 11 of Example 1, and the purification was then performed under the following [Purification Conditions] to afford the title compound as a triethylamine salt.

[Purification Conditions] C18 silica gel column chromatography [10 mM aqueous solution of triethylammonium acetate/acetonitrile], preparative HPLC [10 mM aqueous solution of triethylammonium acetate/acetonitrile-methanol solution (1:1), acetonitrile-methanol solution (1:1): 10%-45% (0 min-40 min)], and preparative HPLC [10 mM aqueous solution of triethylammonium acetate/methanol, methanol: 25%-75% (0 min-40 min)].

The obtained triethylamine salt was subjected to salt exchange in the same manner as in [Conversion to Sodium Salt] described in step 11 of Example 1 to afford the title compound (21.2 mg).

MS(ESI)m/z: 794 (M+H)$^+$.

$^1$H-NMR (CD$_3$OD) δ: 8.55 (1H, brs), 8.41 (1H, s), 8.09 (1H, brs), 7.51 (1H, s), 6.58 (1H, d, J=16.9 Hz), 6.25 (1H, d, J=7.9 Hz), 5.55-5.34 (2H, m), 5.30-5.17 (1H, m), 4.74 (1H, d, J=4.2 Hz), 4.55-4.47 (1H, m), 4.46-4.40 (1H, m), 4.37-4.30 (2H, m), 4.28-4.16 (2H, m), 4.05-3.99 (1H, m), 3.90-3.70 (3H, m), 3.28-3.20 (1H, m), 3.18-3.10 (1H, m), 2.91-2.82 (1H, m), 2.76-2.64 (1H, m), 2.33-2.22 (1H, m), 2.21-2.09 (1H, m).

$^{31}$P-NMR (CD$_3$OD) δ: 57.6 (s), 52.7 (s).

(Step 20-2)

Disodium (5R,7R,8R,12aR,14R,15R,15aR,16R)-14-(8,9-dihydro-6-thia-2,3,5-triazabenzo[cd]azulen-2(7H)-yl)-15-fluoro-16-hydroxy-7-[1-(2-hydroxyethyl)-6-oxo-1,6-dihydro-9H-purin-9-yl]-2,10-dioxooctahydro-2H,10H,12H-5,8-methano-2λ$^5$,10λ$^5$-furo[3,2-1][1,3,6,9,11,2,10]pentaoxadiphosphacyclotetradecine-2,10-bis(thiolate)

(Diastereomer 2)

With use of the compound obtained in step 19 above (diastereomer 2) (69.5 mg: with impurities), the reaction was performed in the same manner as in step 11 of Example 1, and purification was then performed under the following [Purification Conditions] to afford the title compound as a triethylamine salt.

[Purification Conditions] C18 silica gel column chromatography [10 mM aqueous solution of triethylammonium acetate/acetonitrile], preparative HPLC [10 mM aqueous solution of triethylammonium acetate/acetonitrile-methanol solution (1:1), acetonitrile-methanol solution (1:1): 10%-45% (0 min-40 min)], and preparative HPLC [10 mM aqueous solution of triethylammonium acetate/methanol, methanol: 25%-75% (0 min-40 min)].

The obtained triethylamine salt was subjected to salt exchange in the same manner as in [Conversion to Sodium Salt] described in step 11 of Example 1 to afford the title compound (14.9 mg).

MS(ESI)m/z: 794 (M+H)$^+$.

$^1$H-NMR (CD$_3$OD) δ: 8.60 (1H, s), 8.41 (1H, s), 8.16 (1H, s), 7.72 (1H, s), 6.60 (1H, d, J=15.7 Hz), 6.28 (1H, d, J=7.9 Hz), 5.61-5.33 (3H, m), 4.59-4.49 (2H, m), 4.48-4.39 (2H, m), 4.34-4.27 (1H, m), 4.25-4.16 (1H, m), 4.11-3.99 (3H, m), 3.86-3.75 (2H, m), 3.25-3.11 (2H, m), 3.05-2.90 (2H, m), 2.35-2.17 (2H, m).

$^{31}$P-NMR (CD$_3$OD) δ: 59.1 (s), 57.9 (s).

Example 59: Synthesis of CDN49

(5R,7R,8R,12aR,14R,15R,15aR,16R)-7-[1-(2-Aminoethyl)-6-oxo-1,6-dihydro-9H-purin-9-yl]-14-(8,9-dihydro-6-thia-2,3,5-triazabenzo[cd]azulen-2(7H)-yl)-15-fluoro-16-hydroxy-2,10-bis(sulfanyl)octahydro-2H,10H,12H-5,8-methano-2λ$^5$,10λ$^5$-furo[3,2-1][1,3,6,9,11,2,10]pentaoxadiphosphacyclotetradecine-2,10-dione

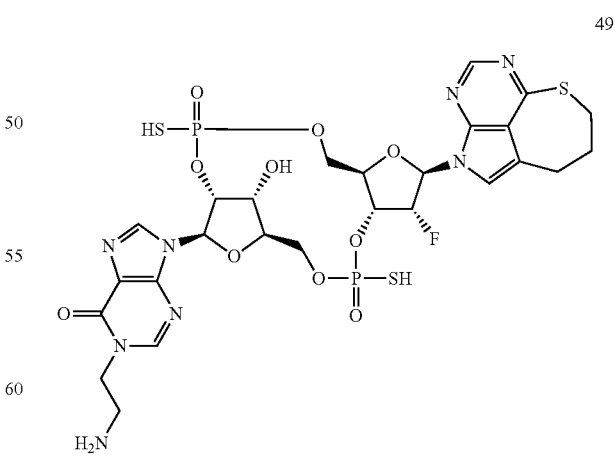

49

49a (Diastereomer 1)
49b (Diastereomer 2)

[Synthesis Scheme]
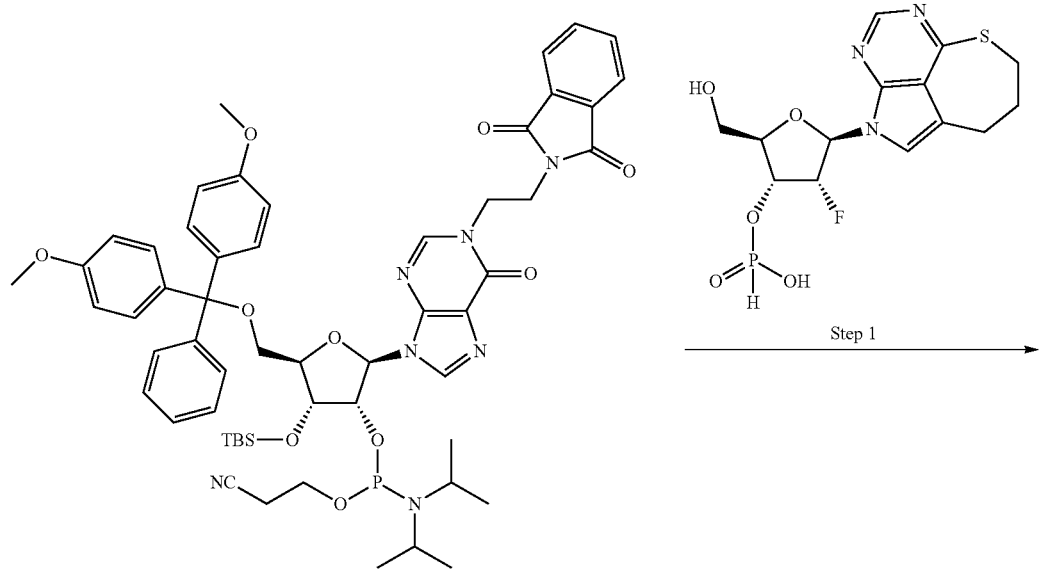
Step 1
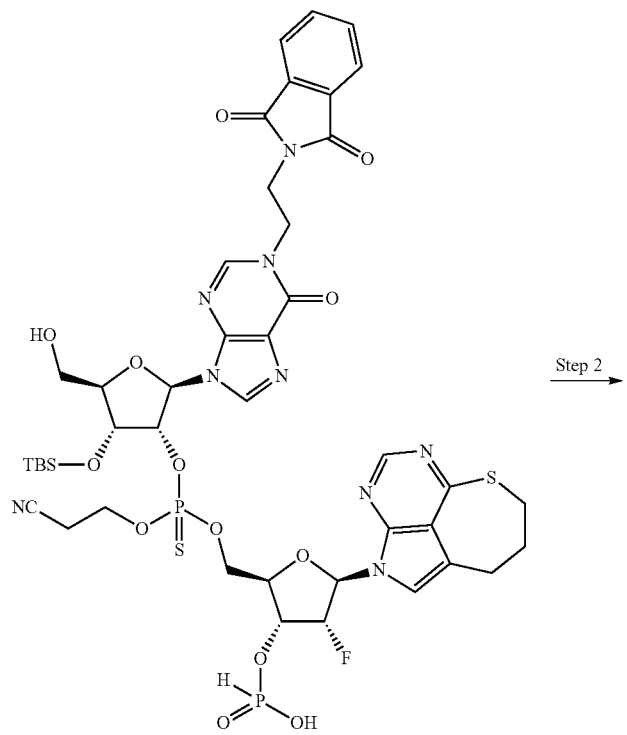
Step 2

551
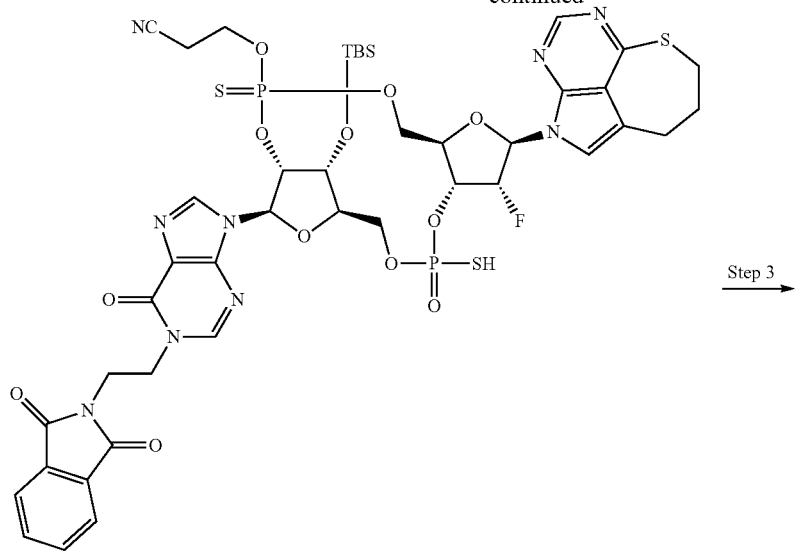
-continued
Step 3
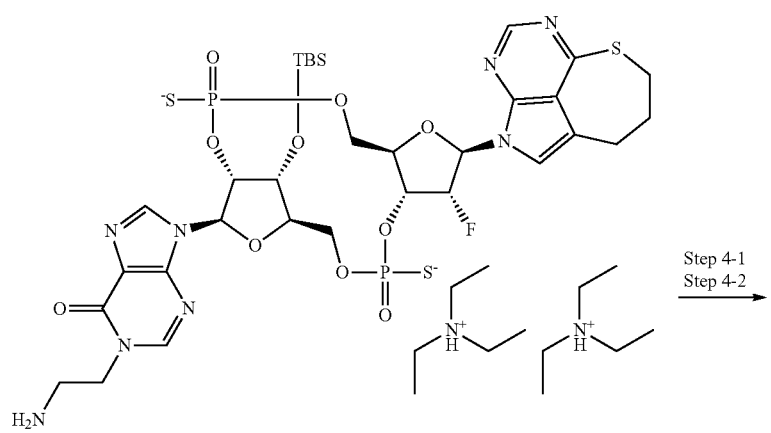
Step 4-1
Step 4-2
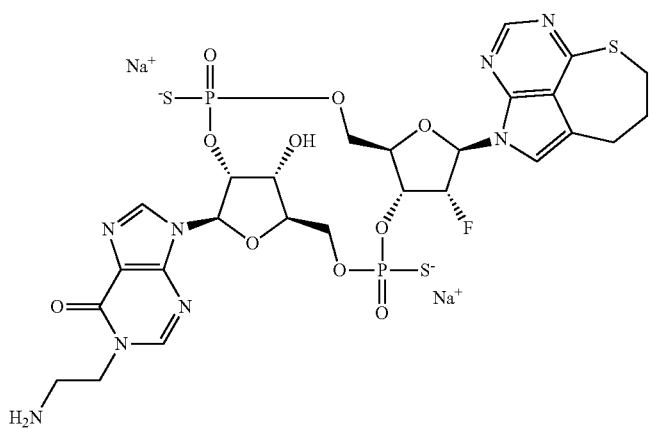

(Step 1)

With use of the compound obtained in step 16 of Example 58 (1.80 g), the reaction was performed in the same manner as in step 7 of Example 1 to afford an acetonitrile solution of 2-{2-deoxy-2-fluoro-3-O-[hydroxy (oxo)-λ⁵-phosphanyl]-β-D-ribofuranosyl}-2,7,8,9-tetrahydro-6-thia-2,3,5-triazabenzo[cd]azulene. With use of the obtained acetonitrile solution and the compound obtained in step 3 of Example 45 (2.30 g), the reaction was performed in the same manner as in step 8 of Example 1, and the resulting crude product was directly used for the subsequent reaction.

(Step 2)

3-{[(5R,7R,8R,12aR,14R,15R,15aR,16R)-16-{[tert-Butyl(dimethyl)silyl]oxy}-14-(8,9-dihydro-6-thia-2,3,5-triazabenzo[cd]azulen-2 (7H)-yl)-7-{1-[2-(1,3-dioxo-1,3-dihydro-2H-isoindol-2-yl)ethyl]-6-oxo-1,6-dihydro-9H-purin-9-yl}-15-fluoro-2-oxo-2-sulfanyl-10-sulfanylideneoctahydro-2H,10H,12H-5,8-methano-2λ⁵,10λ⁵-furo[3,2-1][1,3,6,9,11,2,10]pentaoxadiphosphacyclotetradecin-10-yl]oxy}propanenitrile

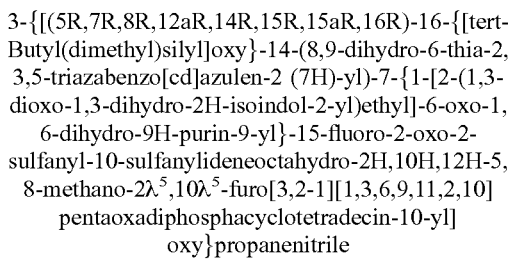

With use of the crude product obtained in step 1 above, the reaction was performed in the same manner as in step 9 of Example 1 to afford the title compound (1.22 g) as a mixture of diastereomers at the phosphorus atom.

MS(ESI)m/z: 1090 (M+H)⁺.

(Step 3)

Bis(N,N-diethylethaneaminium) (5R,7R,8R,12aR,14R,15R,15aR,16R)-7-[1-(2-aminoethyl)-6-oxo-1,6-dihydro-9H-purin-9-yl]-16-{[tert-butyl(dimethyl)silyl]oxy}-14-(8,9-dihydro-6-thia-2,3,5-triazabenzo[cd]azulen-2 (7H)-yl)-15-fluoro-2,10-dioxooctahydro-2H,10H,12H-5,8-methano-2λ⁵,10λ⁵-furo[3,2-1][1,3,6,9,11,2,10]pentaoxadiphosphacyclotetradecine-2,10-bis (thiolate)

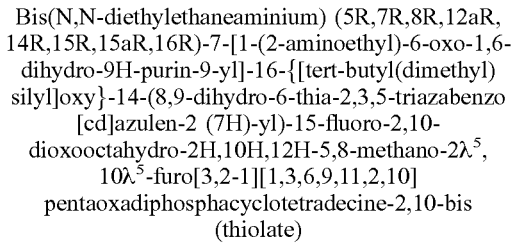

With use of the compound obtained in step 2 above (1.22 g), the reaction was performed in the same manner as in step 6 of Example 45, and the resultant was then purified by C18 silica gel column chromatography [10 mM aqueous solution of triethylammonium acetate/acetonitrile] to afford diastereomer 1 (108 mg: with impurities) and diastereomer 2 (111 mg: with impurities) of the title compound.

Diastereomer 1 (Less Polar)
MS(ESI)m/z: 907 (M+H)⁺.
Diastereomer 2 (More Polar)
MS(ESI)m/z: 907 (M+H)⁺.

(Step 4-1)

Disodium (5R,7R,8R,12aR,14R,15R,15aR,16R)-7-[1-(2-aminoethyl)-6-oxo-1,6-dihydro-9H-purin-9-yl]-14-(8,9-dihydro-6-thia-2,3,5-triazabenzo[cd]azulen-2 (7H)-yl)-15-fluoro-16-hydroxy-2,10-dioxooctahydro-2H,10H,12H-5,8-methano-2λ⁵,10λ⁵-furo[3,2-1][1,3,6,9,11,2,10]pentaoxadiphosphacyclotetradecine-2,10-bis (thiolate)

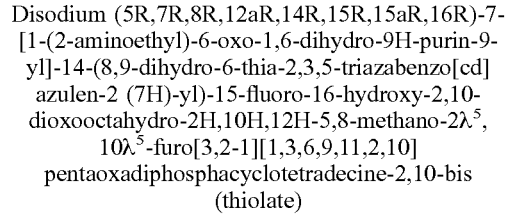

(Diastereomer 1)

With use of the compound obtained in step 3 above (diastereomer 1) (108 mg: with impurities), the reaction was performed in the same manner as in step 11 of Example 1, and the purification was then performed under the following [Purification Conditions] to afford the title compound as a triethylamine salt.

[Purification Conditions] C18 silica gel column chromatography [10 mM aqueous solution of triethylammonium acetate/acetonitrile] and preparative HPLC [10 mM aqueous solution of triethylammonium acetate/acetonitrile-methanol solution (1:1), acetonitrile-methanol solution (1:1): 10%-50% (0 min-40 min)].

The obtained triethylamine salt was subjected to salt exchange in the same manner as in [Conversion to Sodium Salt] described in step 11 of Example 1 to afford the title compound (44.4 mg).

MS(ESI)m/z: 793 (M+H)⁺.

¹H-NMR (CD₃OD) δ: 8.50 (1H, s), 8.42 (1H, s), 7.92 (1H, s), 7.56 (1H, s), 6.56 (1H, d, J=16.3 Hz), 6.21 (1H, d, J=6.0 Hz), 5.57-5.40 (2H, m), 5.35-5.22 (1H, m), 4.73-4.67 (1H, m), 4.58-4.49 (1H, m), 4.45-4.26 (4H, m), 4.24-4.15 (1H, m), 4.05-3.96 (1H, m), 3.78-3.51 (1H, m), 3.26-3.06 (4H, m), 2.93-2.82 (1H, m), 2.70-2.51 (1H, m), 2.29-2.07 (2H, m).

³¹P-NMR (CD₃OD) δ: 57.5 (s), 52.9 (s).

(Step 4-2)

Disodium (5R,7R,8R,12aR,14R,15R,15aR,16R)-7-[1-(2-aminoethyl)-6-oxo-1,6-dihydro-9H-purin-9-yl]-14-(8,9-dihydro-6-thia-2,3,5-triazabenzo[cd]azulen-2 (7H)-yl)-15-fluoro-16-hydroxy-2,10-dioxooctahydro-2H,10H,12H-5,8-methano-2λ⁵,10λ⁵-furo[3,2-1][1,3,6,9,11,2,10]pentaoxadiphosphacyclotetradecine-2,10-bis (thiolate)

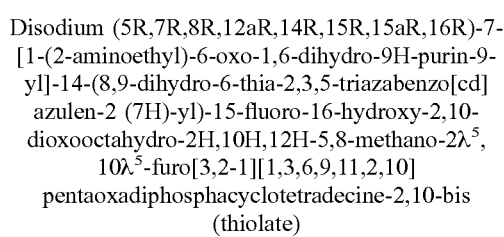

(Diastereomer 2)

With use of the compound obtained in step 3 (diastereomer 2) (111 mg: with impurities), the reaction was performed in the same manner as in step 11 of Example 1, and the purification was then performed under the following [Purification Conditions] to afford the title compound as a triethylamine salt.

[Purification Conditions] C18 silica gel column chromatography [10 mM aqueous solution of triethylammonium acetate/acetonitrile], preparative HPLC [10 mM aqueous solution of triethylammonium acetate/acetonitrile, acetonitrile: 5%-25% (0 min-40 min)], and preparative HPLC [10 mM aqueous solution of triethylammonium acetate/methanol, methanol: 20%-60% (0 min-40 min)].

The obtained triethylamine salt was subjected to salt exchange in the same manner as in [Conversion to Sodium Salt] described in step 11 of Example 1 to afford the title compound (40.6 mg).

MS(ESI)m/z: 793 (M+H)⁺.

¹H-NMR (CD₃OD) δ: 8.57 (1H, s), 8.41 (1H, s), 8.13 (1H, s), 7.72 (1H, s), 6.59 (1H, dd, J=15.7, 1.8 Hz), 6.26 (1H, d, J=8.5 Hz), 5.61-5.34 (3H, m), 4.57-4.48 (2H, m), 4.48-4.38 (2H, m), 4.38-4.28 (2H, m), 4.08-3.98 (3H, m), 3.29-3.21 (2H, m), 3.20-3.12 (2H, m), 3.02-2.92 (1H, m), 2.92-2.81 (1H, m), 2.29-2.15 (2H, m).

³¹P-NMR (CD₃OD) δ: 58.7 (s), 57.8 (s).

Example 60: Synthesis of CDN50

N-(2-{9-[(5R,7R,8R,12aR,14R,15R,15aR,16R)-14-(8,9-Dihydro-6-thia-2,3,5-triazabenzo[cd]azulen-2(7H)-yl)-15-fluoro-16-hydroxy-2,10-dioxo-2,10-bis(sulfanyl)octahydro-2H,10H,12H-5,8-methano-2λ$^5$,10λ$^5$-furo[3,2-l][1,3,6,9,11,2,10]pentaoxadiphosphacyclotetradecin-7-yl]-6-oxo-6,9-dihydro-1H-purin-1-yl}ethyl)-2-hydroxyacetamide

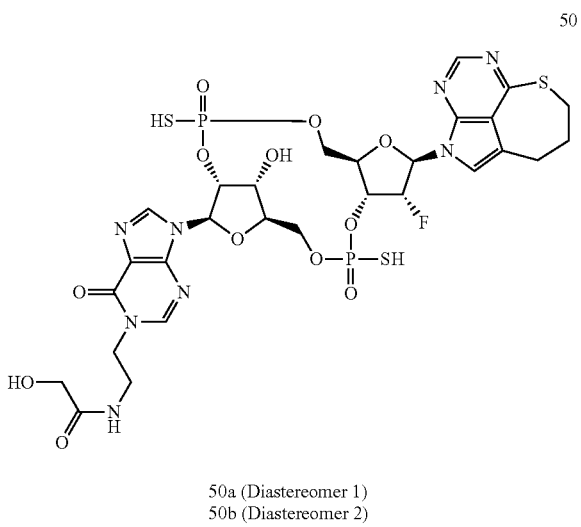 [SMILES: O=C(CO)NCCn1cnc2c(ncn2[C@@H]2O[C@@H]3COP(=O)(S)O[C@H]4[C@@H](F)[C@H](n5cc6c7c(ncnc75)SCCC6)O[C@@H]4COP(=O)(S)O[C@@H]2[C@@H]3O)c1=O]

50a (Diastereomer 1)
50b (Diastereomer 2)

[Synthesis Scheme]

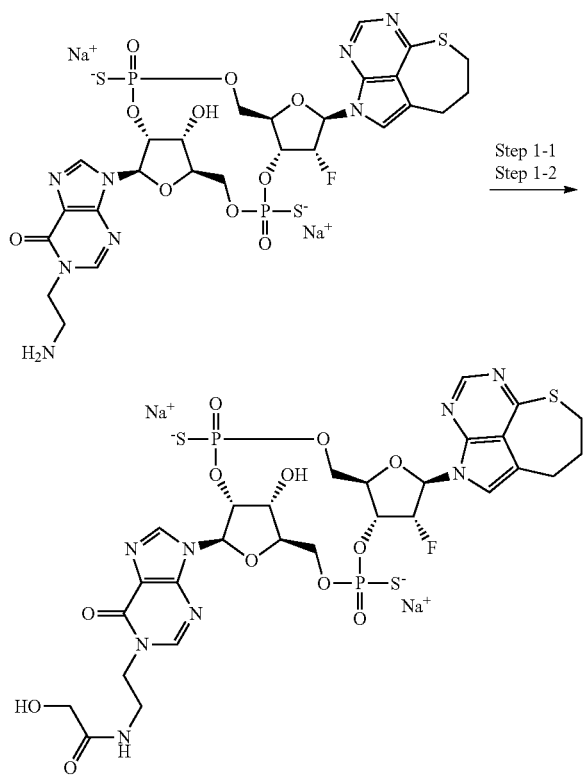

(Step 1-1)

Disodium (5R,7R,8R,12aR,14R,15R,15aR,16R)-14-(8,9-dihydro-6-thia-2,3,5-triazabenzo[cd]azulen-2(7H)-yl)-15-fluoro-16-hydroxy-7-{1-[2-(2-hydroxyacetamide)ethyl]-6-oxo-1,6-dihydro-9H-purin-9-yl}-2,10-dioxooctahydro-2H,10H,12H-5,8-methano-2λ$^5$,10λ$^5$-furo[3,2-l][1,3,6,9,11,2,10]pentaoxadiphosphacyclotetradecine-2,10-bis(thiolate)

(Diastereomer 1)

With use of the compound obtained in step 4-1 of Example 59 (20.0 mg), the reaction was performed in the same manner as in step 1-1 of Example 7, and the purification was then performed under the following [Purification Conditions] to afford the title compound as a triethylamine salt.

[Purification Conditions] C18 silica gel column chromatography [10 mM aqueous solution of triethylammonium acetate/acetonitrile] and preparative HPLC [10 mM aqueous solution of triethylammonium acetate/acetonitrile, acetonitrile: 10%-30% (0 min-40 min)].

The obtained triethylamine salt was subjected to salt exchange in the same manner as in [Conversion to Sodium Salt] described in step 11 of Example 1 to afford the title compound (15.6 mg).

MS(ESI)m/z: 851 (M+H)$^+$.

$^1$H-NMR (CD$_3$OD) δ: 8.43 (1H, s), 8.40 (1H, brs), 7.66 (1H, brs), 7.58 (1H, s), 6.53 (1H, d, J=16.3 Hz), 6.14 (1H, d, J=8.5 Hz), 5.73-5.64 (1H, m), 5.59-5.42 (1H, m), 5.42-5.29 (1H, m), 4.80-4.74 (1H, m), 4.53-4.26 (5H, m), 4.21-4.12 (1H, m), 3.99-3.92 (1H, m), 3.83 (2H, s), 3.66-3.56 (1H, m), 3.43-3.26 (2H, m), 3.23-3.06 (2H, m), 2.89-2.79 (1H, m), 2.49-2.33 (1H, m), 2.27-2.15 (1H, m), 2.15-2.02 (1H, m).

$^{31}$P-NMR (CD$_3$OD) δ: 57.0 (s), 52.6 (s).

(Step 1-2)

Disodium (5R,7R,8R,12aR,14R,15R,15aR,16R)-14-(8,9-dihydro-6-thia-2,3,5-triazabenzo[cd]azulen-2(7H)-yl)-15-fluoro-16-hydroxy-7-{1-[2-(2-hydroxyacetamide)ethyl]-6-oxo-1,6-dihydro-9H-purin-9-yl}-2,10-dioxooctahydro-2H,10H,12H-5,8-methano-2λ$^5$,10λ$^5$-furo[3,2-l][1,3,6,9,11,2,10]pentaoxadiphosphacyclotetradecine-2,10-bis(thiolate)

(Diastereomer 2)

With use of the compound obtained in step 4-2 of Example 59 (10.0 mg), the reaction was performed in the same manner as in step 1-1 of Example 7, and the purification was then performed under the following [Purification Conditions] to afford the title compound as a triethylamine salt.

[Purification Conditions] C18 silica gel column chromatography [10 mM aqueous solution of triethylammonium acetate/acetonitrile] and preparative HPLC [10 mM aqueous solution of triethylammonium acetate/acetonitrile, acetonitrile: 7%-25% (0 min-40 min)].

The obtained triethylamine salt was subjected to salt exchange in the same manner as in [Conversion to Sodium Salt] described in step 11 of Example 1 to afford the title compound (6.6 mg).

MS(ESI)m/z: 851 (M+H)$^+$.

$^1$H-NMR (CD$_3$OD) δ: 8.46 (1H, s), 8.42 (1H, s), 7.84 (1H, s), 7.78 (1H, s), 6.59 (1H, d, J=15.1 Hz), 6.20 (1H, d, J=7.9

Hz), 5.69-5.38 (3H, m), 4.60-4.50 (2H, m), 4.48-4.38 (2H, m), 4.31-4.20 (2H, m), 4.10-3.93 (2H, m), 3.87 (2H, s), 3.73-3.57 (2H, m), 3.52-3.41 (1H, m), 3.25-3.10 (2H, m), 3.01-2.90 (1H, m), 2.83-2.71 (1H, m), 2.30-2.11 (2H, m).
$^{31}$P-NMR (CD$_3$OD) δ: 58.2 (s), 57.6 (s).
Example 61: Synthesis of CDN51
(5R,7R,8R,12aR,14R,15R,15aR,16R)-7-{6-Amino-2-[(2-aminoethyl)amino]-9H-purin-9-yl}-14-(8,9-dihydro-6-thia-2,3,5-triazabenzo[cd]azulen-2 (7H)-yl)-15-fluoro-16-hydroxy-2,10-bis(sulfanyl)octahydro-2H,10H,12H-5,8-methano-2λ$^5$,10λ$^5$-furo[3,2-l][1,3,6,9,11,2,10]pentaoxadiphosphacyclotetradecine-2,10-dione
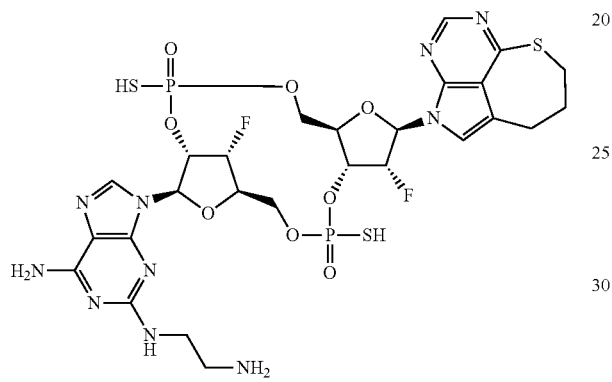
51a (Diastereomer 1)
51b (Diastereomer 2)
[Synthesis Scheme]
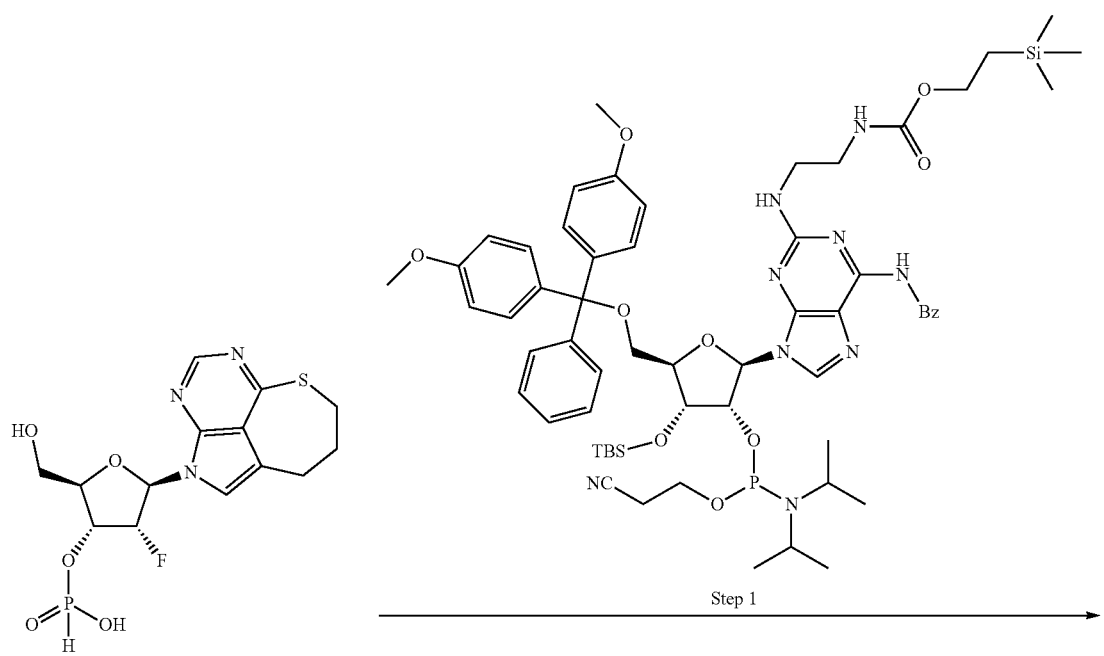
Step 1

-continued
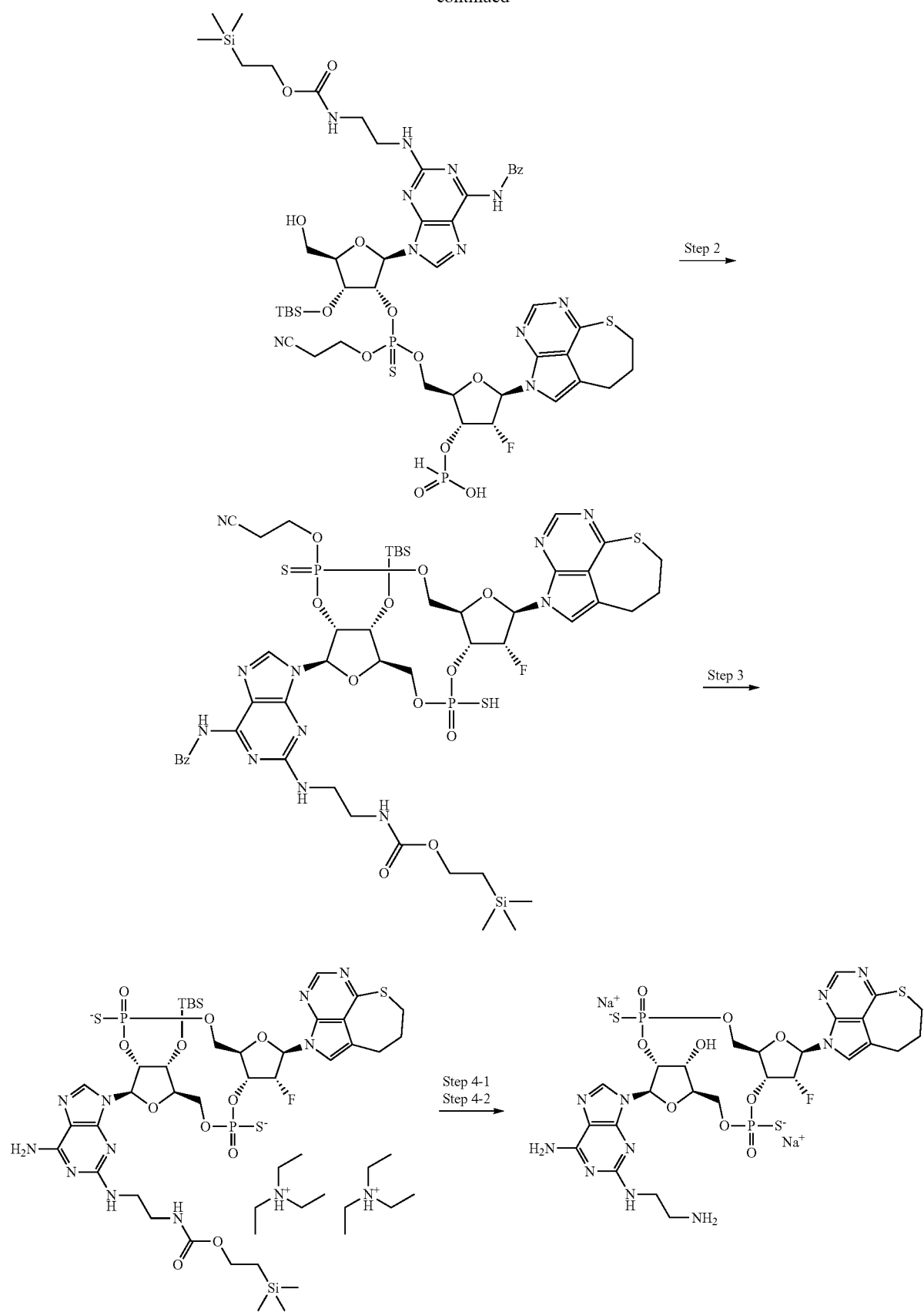

(Step 1)

With use of the compound obtained in step 16 of Example 58 (1.80 g), the reaction was performed in the same manner as in step 7 of Example 1 to afford an acetonitrile solution of 2-{2-deoxy-2-fluoro-3-O-[hydroxy (oxo)-$\lambda^5$-phosphanyl]-β-D-ribofuranosyl}-2,7,8,9-tetrahydro-6-thia-2,3,5-triazabenzo[cd]azulene. With use of the obtained acetonitrile solution and the compound obtained in step 6 of Example 47 (3.10 g), the reaction was performed in the same manner as in step 8 of Example 1, and the resulting crude product was directly used for the subsequent reaction.

(Step 2)

2-(Trimethylsilyl)ethyl [2-({6-benzamido-9-[(5R,7R,8R,12aR,14R,15R,15aR,16R)-16-{[tert-butyl(dimethyl)silyl]oxy}-10-(2-cyanoethoxy)-14-(8,9-dihydro-6-thia-2,3,5-triazabenzo[cd]azulen-2 (7H)-yl)-15-fluoro-2-oxo-2-sulfanyl-10-sulfanylideneoctahydro-2H,10H,12H-5,8-methano-2$\lambda^5$,10$\lambda^5$-furo[3,2-1][1,3,6,9,11,2,10]pentaoxadiphosphacyclotetradecin-7-yl]-9H-purin-2-yl}amino)ethyl]carbamate With use of the crude product obtained in step 1 above, the reaction was performed in the same manner as in step 9 of Example 1 to afford the title compound (1.83 g: with impurities).

MS(ESI)m/z: 1222 (M+H)$^+$.

(Step 3)

Bis(N,N-diethylethancaminium) (5R,7R,8R,12aR,14R,15R,15aR,16R)-7-(6-amino-2-{[2-({[2-(trimethylsilyl)ethoxy]carbonyl}amino)ethyl]amino}-9H-purin-9-yl)-16-{[tert-butyl(dimethyl)silyl]oxy}-14-(8,9-dihydro-6-thia-2,3,5-triazabenzo[cd]azulen-2 (7H)-yl)-15-fluoro-2,10-dioxooctahydro-2H,10H,12H-5,8-methano-2$\lambda^5$,10$\lambda^5$-furo[3,2-1][1,3,6,9,11,2,10]pentaoxadiphosphacyclotetradecine-2,10-bis(thiolate)

With use of the mixture obtained in step 2 above (1.83 g), the reaction was performed in the same manner as in step 10 of Example 1 to afford diastereomer 1 (151 mg: with impurities) and diastereomer 2 (103 mg: with impurities) of the title compound.

Diastereomer 1 (Less Polar)

MS(ESI)m/z: 1065 (M+H)$^+$.

Diastereomer 2 (More Polar)

MS(ESI)m/z: 1065 (M+H)$^+$.

(Step 4-1)

Disodium (5R,7R,8R,12aR,14R,15R,15aR,16R)-7-{6-amino-2-[(2-aminoethyl)amino]-9H-purin-9-yl}-14-(8,9-dihydro-6-thia-2,3,5-triazabenzo[cd]azulen-2 (7H)-yl)-15-fluoro-16-hydroxy-2,10-dioxooctahydro-2H,10H,12H-5,8-methano-2$\lambda^5$,10$\lambda^5$-furo[3,2-1][1,3,6,9,11,2,10]pentaoxadiphosphacyclotetradecine-2,10-bis(thiolate)

(Diastereomer 1)

With use of the compound obtained in step 3 above (diastereomer 1) (151 mg: with impurities), the reaction was performed in the same manner as in step 5 of Example 40, and the purification was then performed under the following [Purification Conditions] to afford the title compound as a triethylamine salt.

[Purification Conditions] C18 silica gel column chromatography [10 mM aqueous solution of triethylammonium acetate/acetonitrile] and preparative HPLC [10 mM aqueous solution of triethylammonium acetate/acetonitrile, acetonitrile: 2%-30% (0 min-30 min)].

The obtained triethylamine salt was subjected to salt exchange in the same manner as in [Conversion to Sodium Salt] described in step 11 of Example 1 to afford the title compound (10.6 mg).

MS(ESI)m/z: 807 (M+H)$^+$.

$^1$H-NMR (CD$_3$OD) δ: 8.39 (1H, s), 7.97 (1H, brs), 7.55 (1H, s), 6.51 (1H, d, J=16.3 Hz), 6.00-5.92 (1H, m), 5.83-5.65 (1H, m), 5.44 (1H, dd, J=52.0, 3.6 Hz), 5.34-5.20 (1H, m), 4.77 (1H, d, J=3.6 Hz), 4.49-4.31 (5H, m), 4.11-4.07 (1H, m), 3.28-2.72 (8H, m), 2.29-1.99 (2H, m).

$^{31}$P-NMR (CD$_3$OD) δ: 57.3 (s), 52.3 (s).

(Step 4-2)

Disodium (5R,7R,8R,12aR,14R,15R,15aR,16R)-7-{6-amino-2-[(2-aminoethyl)amino]-9H-purin-9-yl}-14-(8,9-dihydro-6-thia-2,3,5-triazabenzo[cd]azulen-2 (7H)-yl)-15-fluoro-16-hydroxy-2,10-dioxooctahydro-2H,10H,12H-5,8-methano-2$\lambda^5$,10$\lambda^5$-furo[3,2-1][1,3,6,9,11,2,10]pentaoxadiphosphacyclotetradecine-2,10-bis(thiolate)

(Diastereomer 2)

With use of the compound obtained in step 3 above (diastereomer 2) (103 mg: with impurities), the reaction was performed in the same manner as in step 5 of Example 40, and the purification was then performed under the following [Purification Conditions] to afford the title compound as a triethylamine salt.

[Purification Conditions] C18 silica gel column chromatography [10 mM aqueous solution of triethylammonium acetate/acetonitrile] and preparative HPLC [10 mM aqueous solution of triethylammonium acetate/acetonitrile, acetonitrile: 10%-30% (0 min-30 min)].

The obtained triethylamine salt was subjected to salt exchange in the same manner as in [Conversion to Sodium Salt] described in step 11 of Example 1 to afford the title compound (12.1 mg).

MS(ESI)m/z: 807 (M+H)$^+$.

$^1$H-NMR (CD$_3$OD) δ: 8.39 (1H, s), 7.95 (1H, brs), 7.82 (1H, s), 6.58 (1H, d, J=15.1 Hz), 6.00-5.95 (1H, m), 5.90-5.71 (1H, m), 5.40 (1H, dd, J=51.7, 3.3 Hz), 5.38-5.25 (1H, m), 4.53-4.39 (4H, m), 4.28-4.18 (2H, m), 4.10-4.05 (1H, m), 3.27-2.54 (8H, m), 2.34-2.10 (2H, m).

$^{31}$P-NMR (CD$_3$OD) δ: 57.9 (s), 57.3 (s).

Example 62: Synthesis of CDN52
(5R,7R,8R,12aR,14R,15R,15aR,16R)-15-Fluoro-2,16-dihydroxy-7-[1-(2-hydroxyethyl)-6-oxo-1,6-dihydro-9H-purin-9-yl]-10-sulfanyl-14-(6,7,8,9-tetrahydro-2H-2,3,5,6-tetraazabenzo[cd]azulen-2-yl)octahydro-2H,10H,12H-5,8-methano-2λ$^5$,10λ$^5$-furo[3,2-1][1,3,6,9,11,2,10]pentaoxadiphosphacyclotetradecine-2,10-dione
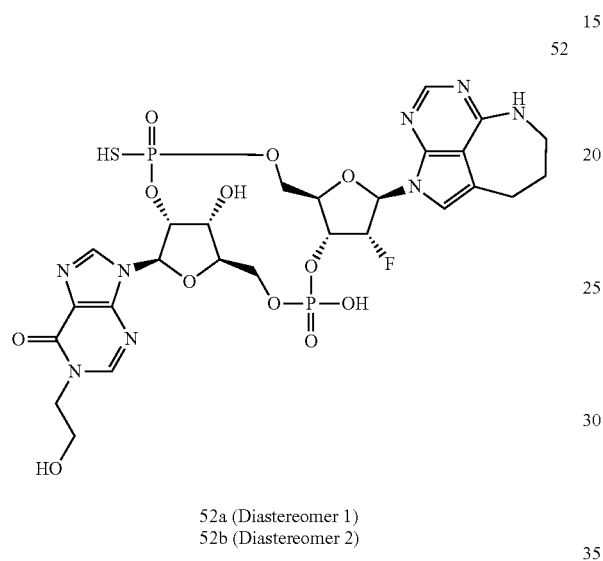
52a (Diastereomer 1)
52b (Diastereomer 2)
[Synthesis Scheme]
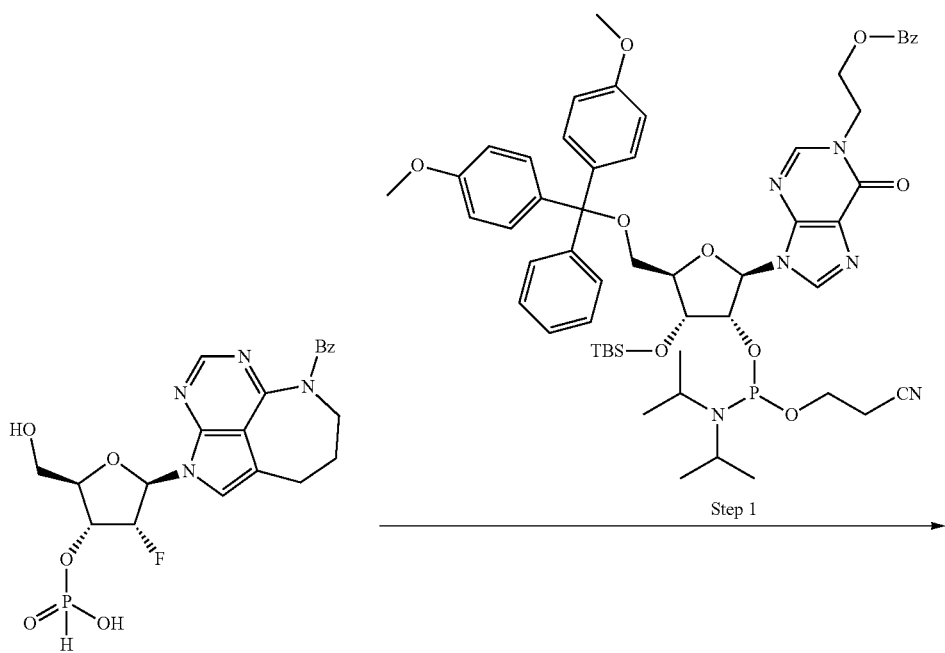

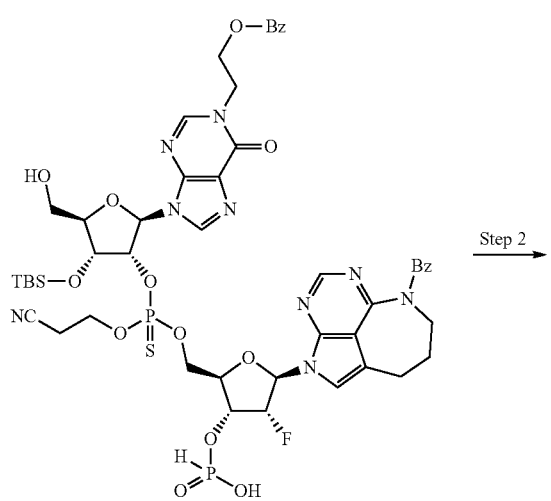

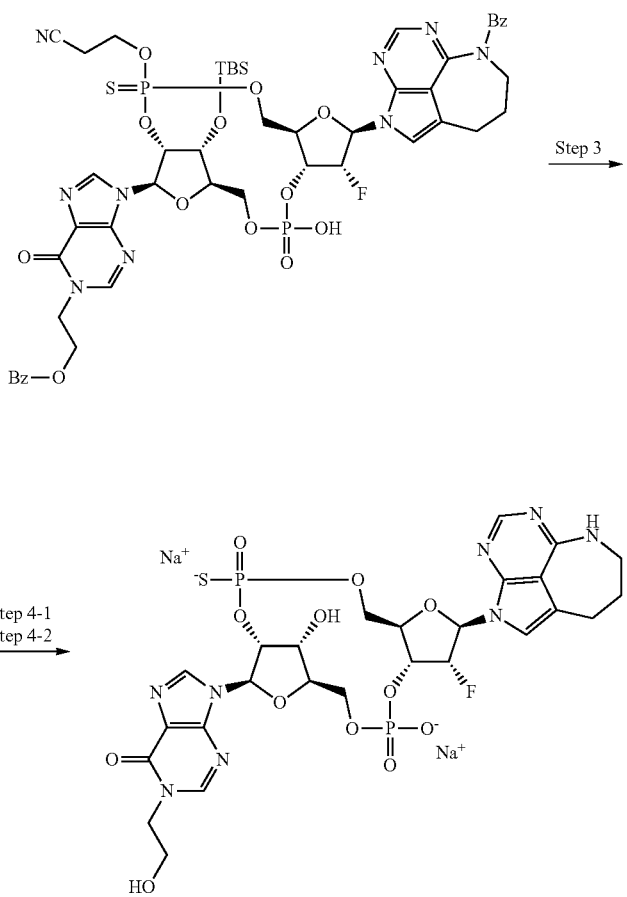

(Step 1)

With use of the compound obtained in step 8 of Example 44 (1.00 g), the reaction was performed in the same manner as in step 7 of Example 1 to afford an acetonitrile solution of 6-benzoyl-2-{2-deoxy-2-fluoro-3-O-[hydroxy (oxo)-$\lambda^5$-phosphanyl]-β-D-ribofuranosyl}-6,7,8,9-tetrahydro-2H-2,3,5,6-tetraazabenzo[cd]azulene. With use of the obtained acetonitrile solution and the compound obtained in step 3 of Example 22 (1.13 g), the reaction was performed in the same manner as in step 8 of Example 1, and the resulting crude product was directly used for the subsequent reaction.

(Step 2)

2-{9-[(5R,7R,8R,12aR,14R,15R,15aR,16R)-14-(6-Benzoyl-6,7,8,9-tetrahydro-2H-2,3,5,6-tetraazabenzo[cd]azulen-2-yl)-16-{[tert-butyl(dimethyl)silyl]oxy}-10-(2-cyanoethoxy)-15-fluoro-2-hydroxy-2-oxo-10-sulfanylideneoctahydro-2H,10H,12H-5,8-methano-2$\lambda^5$,10$\lambda^5$-furo[3,2-1][1,3,6,9,11,2,10]pentaoxadiphosphacyclotetradecin-7-yl]-6-oxo-6,9-dihydro-1H-purin-1-yl}ethyl benzoate A solution of the crude product obtained in step 1 above in pyridine (32.5 mL) was concentrated to about 25 mL, and 2-chloro-5,5-dimethyl-1,3,225-dioxaphosphinan-2-one (945 mg) was then added thereto, and the reaction mixture was stirred at room temperature for 30 minutes. Iodine (1.11 g) was added to the reaction mixture, which was stirred for 1 hour. The reaction mixture was poured into an aqueous solution (150 mL) of sodium hydrogen carbonate (4.30 g), and the resultant was stirred for 30 minutes, and then subjected to extraction with ethyl acetate. After the organic layer was dried over anhydrous sodium sulfate, the drying agent was removed through filtration, and the filtrate was concentrated under reduced pressure. The residue was purified by silica gel column chromatography [hexane/ethyl acetate/methanol] to afford the title compound (671 mg: with impurities) as a mixture of diastereomers at the phosphorus atom.

MS(ESI)m/z: 1136 (M+H)$^+$.

(Step 3)

Bis(N,N-diethylethaneaminium) (5R,7R,8R,12aR,14R,15R,15aR,16R)-16-{[tert-butyl(dimethyl)silyl]oxy}-15-fluoro-7-[1-(2-hydroxyethyl)-6-oxo-1,6-dihydro-9H-purin-9-yl]-2,10-dioxo-10-sulfide-14-(6,7,8,9-tetrahydro-2H-2,3,5,6-tetraazabenzo[cd]azulen-2-yl)octahydro-2H,10H,12H-5,8-methano-2$\lambda^5$,10$\lambda^5$-furo[3,2-1][1,3,6,9,11,2,10]pentaoxadiphosphacyclotetradecin-2-olate With use of the compound obtained in step 2 above (671 mg), the reaction was performed in the same manner as in step 10 of Example 1 to afford diastereomer 1 (55.6 mg: with impurities) and diastereomer 2 (65.7 mg: with impurities) of the title compound.

Diastereomer 1 (Less Polar)

MS(ESI)m/z: 875 (M+H)⁺.

Diastereomer 2 (More Polar)

MS(ESI)m/z: 875 (M+H)⁺.

(Step 4-1)

Disodium (5R,7R,8R,12aR,14R,15R,15aR,16R)-15-fluoro-16-hydroxy-7-[1-(2-hydroxyethyl)-6-oxo-1,6-dihydro-9H-purin-9-yl]-2,10-dioxo-10-sulfide-14-(6,7,8,9-tetrahydro-2H-2,3,5,6-tetraazabenzo[cd]azulen-2-yl)octahydro-2H,10H,12H-5,8-methano-2λ⁵,10λ⁵-furo[3,2-l][1,3,6,9,11,2,10]pentaoxadiphosphacyclotetradecin-2-olate (Diastereomer 1)

With use of the compound obtained in step 3 above (diastereomer 1) (55.6 mg: with impurities), the reaction was performed in the same manner as in step 11 of Example 1, and the purification was then performed under the following [Purification Conditions] to afford the title compound as a triethylamine salt.

[Purification Conditions] C18 silica gel column chromatography [10 mM aqueous solution of triethylammonium acetate/acetonitrile] and preparative HPLC [10 mM aqueous solution of triethylammonium acetate/acetonitrile, acetonitrile: 5%-25% (0 min-30 min)].

The obtained triethylamine salt was subjected to salt exchange in the same manner as in [Conversion to Sodium Salt] described in step 11 of Example 1 to afford the title compound (11.3 mg).

MS(ESI)m/z: 761 (M+H)⁺.

¹H-NMR (CD₃OD): 8.55 (1H, m), 8.15 (1H, m), 8.03 (1H, s), 7.14 (1H, d, J=4.8 Hz), 6.46 (1H, d, J=18.1 Hz), 6.28 (1H, d, J=7.9 Hz), 5.50-5.29 (2H, m), 5.16-5.04 (1H, m), 4.74-4.69 (1H, m), 4.40-4.18 (6H, m), 4.13-4.07 (1H, m), 4.02-3.91 (1H, m), 3.84-3.74 (2H, m), 3.53-3.43 (2H, m), 2.81-2.63 (2H, m), 2.02-1.85 (2H, m).

³¹P-NMR (CD₃OD) δ: 53.4 (s), −0.86 (s).

(Step 4-2)

Disodium (5R,7R,8R,12aR,14R,15R,15aR,16R)-15-fluoro-16-hydroxy-7-[1-(2-hydroxyethyl)-6-oxo-1,6-dihydro-9H-purin-9-yl]-2,10-dioxo-10-sulfide-14-(6,7,8,9-tetrahydro-2H-2,3,5,6-tetraazabenzo[cd]azulen-2-yl)octahydro-2H,10H,12H-5,8-methano-25,1015-furo[3,2-l][1,3,6,9,11,2,10]pentaoxadiphosphacyclotetradecin-2-olate (Diastereomer 2)

With use of the compound obtained in step 3 above (diastereomer 2) (65.7 mg: with impurities), the reaction was performed in the same manner as in step 11 of Example 1, and the purification was then performed under the following [Purification Conditions] to afford the title compound as a triethylamine salt.

[Purification Conditions] C18 silica gel column chromatography [10 mM aqueous solution of triethylammonium acetate/acetonitrile] and preparative HPLC [10 mM aqueous solution of triethylammonium acetate/acetonitrile, acetonitrile: 3%-20% (0 min-30 min)].

The obtained triethylamine salt was subjected to salt exchange in the same manner as in [Conversion to Sodium Salt] described in step 11 of Example 1 to afford the title compound (23.5 mg).

MS(ESI)m/z: 761 (M+H)⁺.

¹H-NMR (CD₃OD) δ: 8.58 (1H, d, J=3.0 Hz), 8.19 (1H, d, J=2.4 Hz), 8.03 (1H, s), 7.40 (1H, $), 6.49 (1H, dd, J=16.3, 1.8 Hz), 6.29 (1H, d, J=8.5 Hz), 5.51-5.22 (3H, m), 4.59-4.55 (1H, m), 4.43-4.17 (5H, m), 4.14-4.01 (3H, m), 3.85-3.78 (2H, m), 3.51-3.44 (2H, m), 2.90-2.75 (2H, m), 1.99-1.90 (2H, m).

³¹P-NMR (CD₃OD) δ: 59.7 (s), −0.75 (s).

Example 63: Synthesis of CDN53

(5R,7R,8R,12aR,14R,15R,15aR,16R)-15-Fluoro-10,16-dihydroxy-7-[1-(2-hydroxyethyl)-6-oxo-1,6-dihydro-9H-purin-9-yl]-2-sulfanyl-14-(6,7,8,9-tetrahydro-2H-2,3,5,6-tetraazabenzo[cd]azulen-2-yl)octahydro-2H,10H,12H-5,8-methano-2λ⁵,10λ⁵-furo[3,2-l][1,3,6,9,11,2,10]pentaoxadiphosphacyclotetradecine-2,10-dione

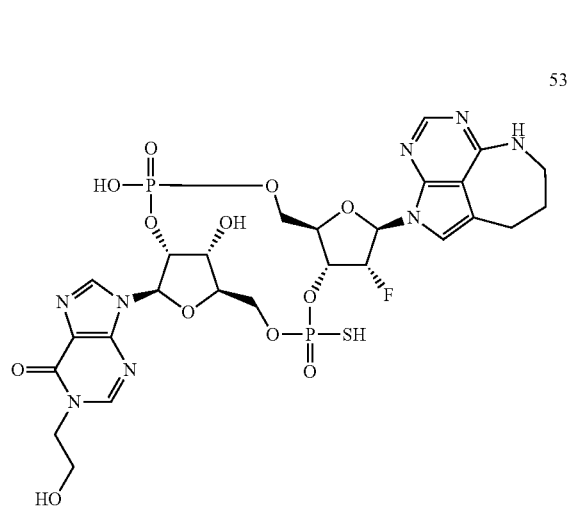 [SMILES: O=c1c2ncn([C@@H]3O[C@@H]4COP(=O)(O)O[C@H]5[C@@H](F)[C@H](n6cc7c8c(ncnc86)NCCC7)O[C@@H]5COP(=O)(O)O[C@@H]3[C@@H]4O)c2ncn1CCO]

53a (Diastereomer 1)

[Synthesis Scheme]
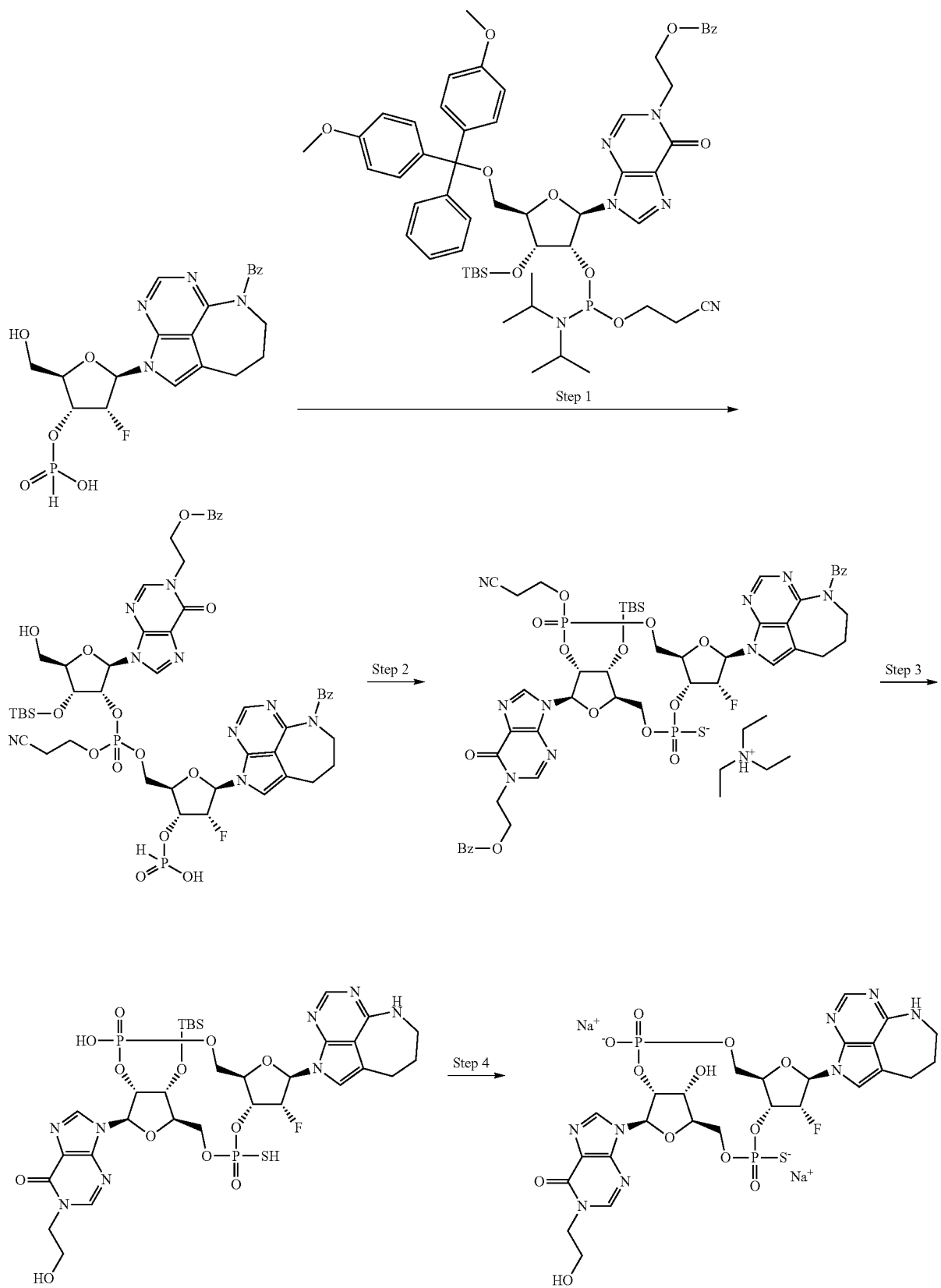

(Step 1)

With use of the compound obtained in step 8 of Example 44 (1.02 g), the reaction was performed in the same manner as in step 7 of Example 1 to afford an acetonitrile solution of 6-benzoyl-2-{2-deoxy-2-fluoro-3-O-[hydroxy (oxo)-$\lambda^5$-phosphanyl]-β-D-ribofuranosyl}-6,7,8,9-tetrahydro-2H-2,3,5,6-tetraazabenzo[cd]azulene (acetonitrile solution A). The compound obtained in step 3 of Example 22 (1.23 g) was azeotropically dehydrated three times with dehydrated acetonitrile (10 mL). After the last operation, about 7 mL of acetonitrile was allowed to remain, and the molecular sieves 3A, 1/16 (5 pellet-like particles) were added thereto (acetonitrile solution B). Acetonitrile solution A and acetonitrile solution B were mixed together, and the mixture was stirred under the nitrogen atmosphere at room temperature for 15 minutes. A decane solution of tert-butyl hydroperoxide (5.5 M, 0.50 mL) was added to the reaction mixture, which was stirred for 40 minutes, and the reaction mixture was ice-cooled, to which an aqueous solution (1.1 mL) of sodium thiosulfate pentahydrate (826 mg) was added, and the reaction mixture was stirred for 10 minutes. Water (20 mL) was added to the reaction mixture, which was subjected to extraction with a mixture of dichloromethane-methanol. After the organic layer was dried over anhydrous sodium sulfate, the drying agent was removed through filtration, and the filtrate was concentrated under reduced pressure. To a solution of the residue in dichloromethane (15.9 mL), water (0.200 mL) and a solution of dichloroacetic acid (1.00 mL) in dichloromethane (15.9 mL) were added in this order, and the reaction mixture was stirred at room temperature for 15 minutes. After pyridine (11.0 mL) was added to the reaction mixture to quench the reaction, the reaction mixture was concentrated under reduced pressure. The resulting crude product was directly used for the subsequent reaction.

(Step 2)

N,N-Diethylethaneaminium (5R,7R,8R,12aR,14R,15R,15aR,16R)-7-{1-[2-(benzoyloxy)ethyl]-6-oxo-1,6-dihydro-9H-purin-9-yl}-14-(6-benzoyl-6,7,8,9-tetrahydro-2H-2,3,5,6-tetraazabenzo[cd]azulen-2-yl)-16-{[tert-butyl(dimethyl)silyl]oxy}-10-(2-cyanoethoxy)-15-fluoro-2,10-dioxooctahydro-2H,10H,12H-5,8-methano-2$\lambda^5$,10$\lambda^5$-furo[3,2-1][1,3,6,9,11,2,10]pentaoxadiphosphacyclotetradecine-2-thiolate The crude product obtained in step 1 was reacted in the same manner as in step 9 of Example 1 to afford the title compound (122 mg: with impurities).

MS(ESI)m/z: 1136 (M+H)⁺.

(Step 3)

(5R,7R,8R,12aR,14R,15R,15aR,16R)-16-{[tert-Butyl(dimethyl)silyl]oxy}-15-fluoro-10-hydroxy-7-[1-(2-hydroxyethyl)-6-oxo-1,6-dihydro-9H-purin-9-yl]-2-sulfanyl-14-(6,7,8,9-tetrahydro-2H-2,3,5,6-tetraazabenzo[cd]azulen-2-yl)octahydro-2H,10H,12H-5,8-methano-2$\lambda^5$,10$\lambda^5$-furo[3,2-1][1,3,6,9,11,2,10]pentaoxadiphosphacyclotetradecine-2,10-dione With use of the compound obtained in step 2 above (122 mg, with impurities), the reaction was performed in the same manner as in step 10 of Example 1, and the resulting crude product was directly used for the subsequent reaction.

MS(ESI)m/z: 875 (M+H)⁺.

(Step 4)

Disodium (5R,7R,8R,12aR,14R,15R,15aR,16R)-15-fluoro-16-hydroxy-7-[1-(2-hydroxyethyl)-6-oxo-1,6-dihydro-9H-purin-9-yl]-2,10-dioxo-2-sulfide-14-(6,7,8,9-tetrahydro-2H-2,3,5,6-tetraazabenzo[cd]azulen-2-yl)octahydro-2H,10H,12H-5,8-methano-2$\lambda^5$,10$\lambda^5$-furo[3,2-1][1,3,6,9,11,2,10]pentaoxadiphosphacyclotetradecin-10-olate With use of the crude product obtained in step 3 above, the reaction was performed in the same manner as in step 11 of Example 1, and the resultant was then purified by preparative HPLC [10 mM aqueous solution of triethylammonium acetate/acetonitrile, acetonitrile: 2%-30% (0 min-30 min)] to afford the title compound as a triethylamine salt. The obtained triethylamine salt was subjected to salt exchange in the same manner as in [Conversion to Sodium Salt] described in step 11 of Example 1 to afford the title compound (30 mg).

MS(ESI)m/z: 761 (M+H)⁺.

¹H-NMR (CD₃OD) δ: 8.58 (1H, s), 8.12 (1H, s), 8.02 (1H, s), 7.13 (1H, s), 6.47 (1H, d, J=18.1 Hz), 6.27 (1H, d, J=8.5 Hz), 5.41 (1H, dd, J=51.7, 3.9 Hz), 5.29-5.16 (2H, m), 4.58-4.52 (2H, m), 4.36-4.17 (5H, m), 4.05-3.90 (2H, m), 3.82-3.71 (2H, m), 3.52-3.43 (2H, m), 2.76-2.63 (2H, m), 2.02-1.85 (2H, m).

³¹P-NMR (CD₃OD) δ: 58.0 (s), −0.97 (s).

Example 64: Synthesis of CDN54

(5R,7R,8R,12aR,14R,15R,15aR,16R)-15-Fluoro-2,10,16-trihydroxy-7-[1-(2-hydroxyethyl)-6-oxo-1,6-dihydro-9H-purin-9-yl]-14-(6,7,8,9-tetrahydro-2H-2,3,5,6-tetraazabenzo[cd]azulen-2-yl)octahydro-2H,10H,12H-5,8-methano-2$\lambda^5$,10$\lambda^5$-furo[3,2-1][1,3,6,9,11,2,10]pentaoxadiphosphacyclotetradecine-2,10-dione

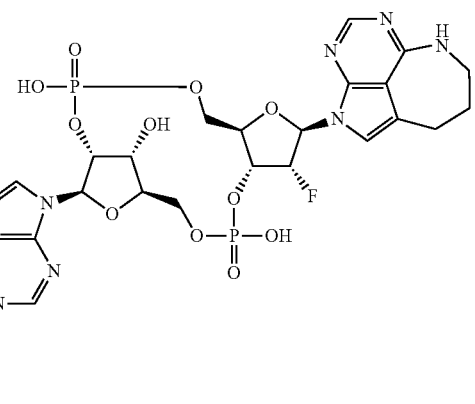

54

[Synthesis Scheme]
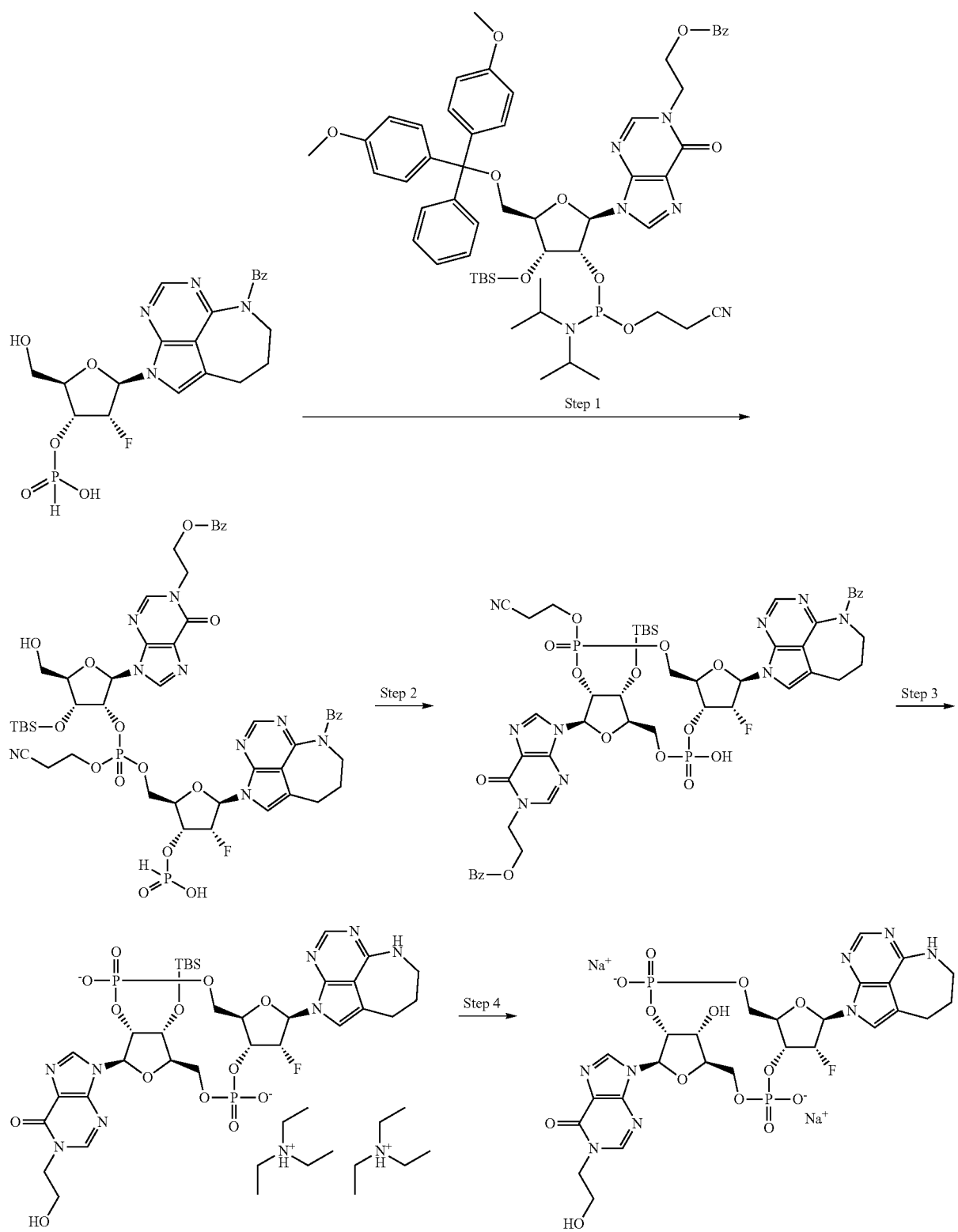
(Step 1)
With use of the compound obtained in step 8 of Example 44 (1.00 g) and the compound obtained in step 3 of Example 22 (1.13 g), the reaction was performed in the same manner as in step 1 of Example 63, and the resulting crude product was directly used for the subsequent reaction.

(Step 2)

2-{9-[(5R,7R,8R,12aR,14R,15R,15aR,16R)-14-(6-Benzoyl-6,7,8,9-tetrahydro-2H-2,3,5,6-tetraazabenzo[cd]azulen-2-yl)-16-{[tert-butyl(dimethyl)silyl]oxy}-10-(2-cyanoethoxy)-15-fluoro-2-hydroxy-2,10-dioxooctahydro-2H,10H,12H-5,8-methano-2λ$^5$,10λ$^5$-furo[3,2-1][1,3,6,9,11,2,10]pentaoxadiphosphacyclotetradecin-7-yl]-6-oxo-6,9-dihydro-1H-purin-1-yl}ethyl benzoate With use of the crude product obtained in step 1 above, the reaction was performed in the same manner as in step 2 of Example 62 to afford the title compound (602 mg: with impurities) as a mixture of diastereomers at the phosphorus atom.
MS(ESI)m/z: 1120 (M+H)$^+$.

(Step 3)

Bis(N,N-diethylethaneaminium) (5R,7R,8R,12aR,14R,15R,15aR,16R)-16-{[tert-butyl(dimethyl)silyl]oxy}-15-fluoro-7-[1-(2-hydroxyethyl)-6-oxo-1,6-dihydro-9H-purin-9-yl]-2,10-dioxo-14-(6,7,8,9-tetrahydro-2H-2,3,5,6-tetraazabenzo[cd]azulen-2-yl)octahydro-2H,10H,12H-5,8-methano-2λ$^5$,10λ$^5$-furo[3,2-1][1,3,6,9,11,2,10]pentaoxadiphosphacyclotetradecine-2,10-bis(olate)

With use of the compound obtained in step 2 above (602 mg), the reaction was performed in the same manner as in step 10 of Example 1 to afford the title compound (90.8 mg: with impurities).
MS(ESI)m/z: 859 (M+H)$^+$.

(Step 4)

Disodium (5R,7R,8R,12aR,14R,15R,15aR,16R)-15-fluoro-16-hydroxy-7-[1-(2-hydroxyethyl)-6-oxo-1,6-dihydro-9H-purin-9-yl]-2,10-dioxo-14-(6,7,8,9-tetrahydro-2H-2,3,5,6-tetraazabenzo[cd]azulen-2-yl)octahydro-2H,10H,12H-5,8-methano-2λ$^5$,10λ$^5$-furo[3,2-1][1,3,6,9,11,2,10]pentaoxadiphosphacyclotetradecine-2,10-bis(olate)

With use of the compound obtained in step 3 above (90.8 mg: with impurities), the reaction was performed in the same manner as in step 11 of Example 1, and the purification was then performed under the following [Purification Conditions] to afford the title compound as a triethylamine salt.
[Purification Conditions] C18 silica gel column chromatography [10 mM aqueous solution of triethylammonium acetate/acetonitrile] and preparative HPLC [10 mM aqueous solution of triethylammonium acetate/acetonitrile, acetonitrile: 1%-20% (0 min-40 min)].
The obtained triethylamine salt was subjected to salt exchange in the same manner as in [Conversion to Sodium Salt] described in step 11 of Example 1 to afford the title compound (40.4 mg).
MS(ESI)m/z: 745 (M+H)$^+$.
$^1$H-NMR (CD$_3$OD) δ: 8.56 (1H, s), 8.19 (1H, s), 8.03 (1H, s), 7.10 (1H, s), 6.46 (1H, d, J=18.7 Hz), 6.31 (1H, d, J=8.5 Hz), 5.51-5.32 (1H, m), 5.24-5.01 (2H, m), 4.61-4.56 (1H, m), 4.41-4.21 (5H, m), 4.21-3.97 (3H, m), 3.87-3.75 (2H, m), 3.54-3.41 (2H, m), 2.83-2.67 (2H, m), 2.02-1.85 (2H, m).
$^{31}$P-NMR (CD$_3$OD) δ: −0.59 (s), −0.81 (s).

Example 65: Synthesis of Drug-Linker 5

[Synthesis Scheme]

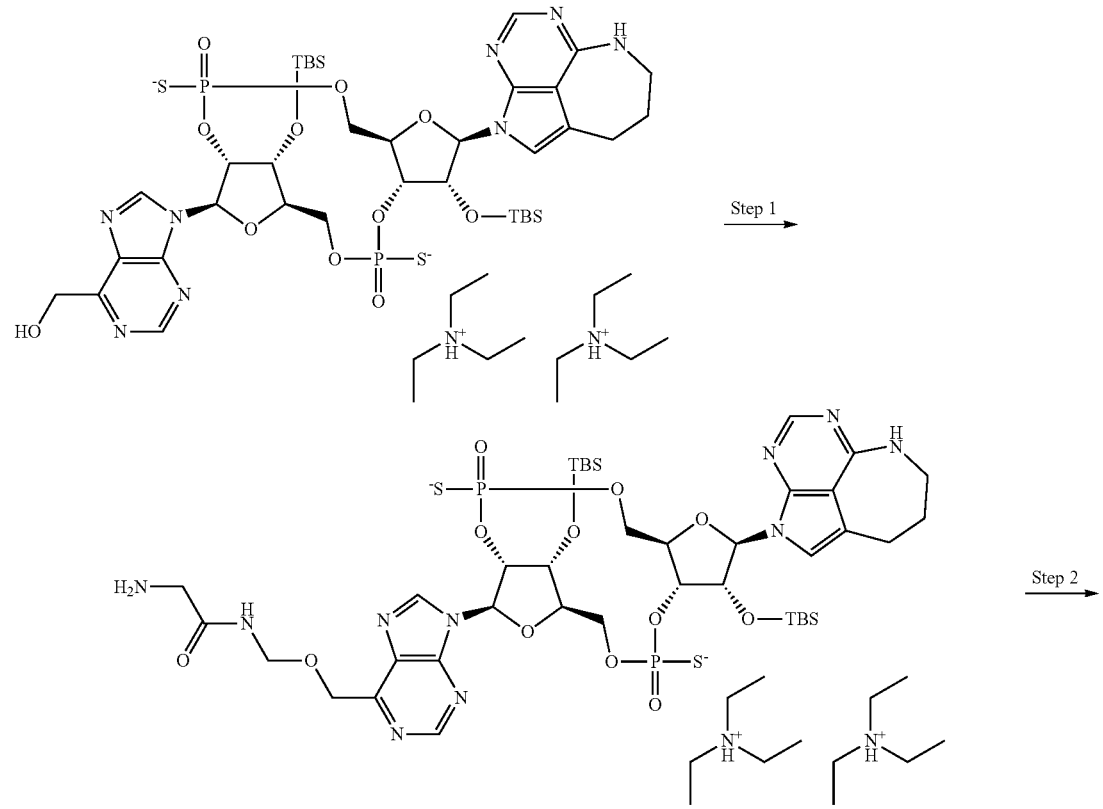

-continued

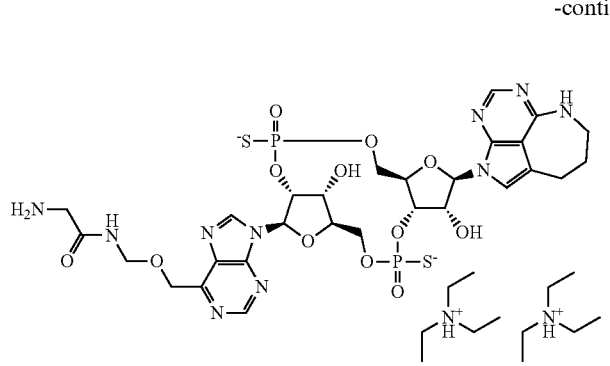 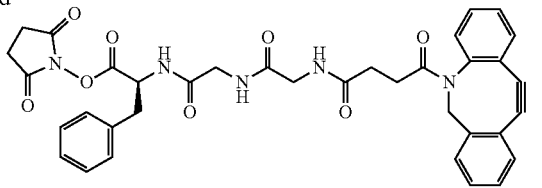

Step 3

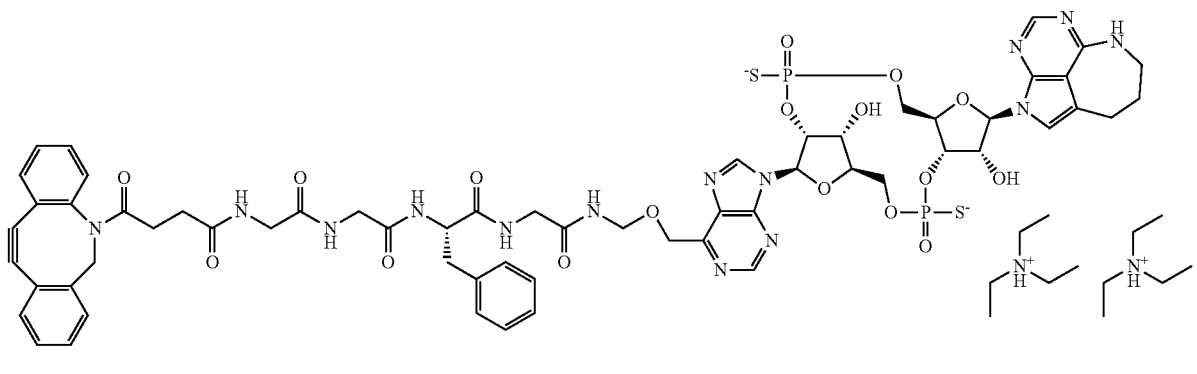

Drug-linker 5

(Step 1)

Bis(N,N-diethylethaneaminium) (5R,7R,8R,12aR,14R,15R,15aR,16R)-15,16-bis{[tert-butyl(dimethyl)silyl]oxy}-7-(6-{[(glycylamino)methoxy]methyl}-9H-purin-9-yl)-2,10-dioxo-14-(6,7,8,9-tetrahydro-2H-2,3,5,6-tetraazabenzo[cd]azulen-2-yl)octahydro-2H,10H,12H-5,8-methano-2$\lambda^5$,10$\lambda^5$-furo[3,2-1][1,3,6,9,11,2,10]pentaoxadiphosphacyclotetradecine-2,10-bis(thiolate)

With use of the compound obtained in step 7 of Example 17 (diastereomer 2) (80.6 mg), the reaction was performed in the same manner as in step 7-1 of Example 22 to afford the title compound (66.1 mg: with impurities).
MS(ESI)m/z: 1059 (M+H)$^+$.
(Step 2)

Bis(N,N-diethylethaneaminium) (5R,7R,8R,12aR,14R,15R,15aS,16R)-7-(6-{[(glycylamino)methoxy]methyl}-9H-purin-9-yl)-15,16-dihydroxy-2,10-dioxo-14-(6,7,8,9-tetrahydro-2H-2,3,5,6-tetraazabenzo[cd]azulen-2-yl)octahydro-2H,10H,12H-5,8-methano-2$\lambda^5$,10$\lambda^5$-furo[3,2-1][1,3,6,9,11,2,10]pentaoxadiphosphacyclotetradecine-2,10-bis(thiolate)

With use of the compound obtained in step 1 above (66.1 mg), the reaction was performed in the same manner as in step 8-1 of Example 22 to afford the title compound (40.4 mg: with impurities).
MS(ESI)m/z: 831 (M+H)$^+$.

(Step 3)

Bis(N,N-diethylethaneaminium) N-[4-(11,12-didehydrodibenzo[b,f]azocin-5 (6H)-yl)-4-oxobutanoyl]glycylglycyl-L-phenylalanyl-N-[({9-[(5R,7R,8R,12aR,14R,15R,15aS,16R)-15,16-dihydroxy-2,10-dioxo-2,10-disulfide-14-(6,7,8,9-tetrahydro-2H-2,3,5,6-tetraazabenzo[cd]azulen-2-yl)octahydro-2H,10H,12H-5,8-methano-2$\lambda^5$,10$\lambda^5$-furo[3,2-1][1,3,6,9,11,2,10]pentaoxadiphosphacyclotetradecin-7-yl]-9H-purin-6-yl}methoxy)methyl]glycinamide (Drug-Linker 5)

With use of the compound obtained in step 2 above (40.4 mg), the reaction was performed in the same manner as in step 9-1 of Example 22, and the resultant was then purified by C18 silica gel column chromatography [10 mM aqueous solution of triethylammonium acetate/acetonitrile] and preparative HPLC [10 mM aqueous solution of triethylammonium acetate/acetonitrile, acetonitrile: 10%-45% (0 min-30 min)] to afford the title compound (5.0 mg).

MS(ESI)m/z: 1379 (M+H)$^+$.

$^1$H-NMR (CD$_3$OD) δ: 9.17 (1H, s), 8.83 (1H, d, J=4.8 Hz), 8.01 (1H, d, J=3.6 Hz), 7.63-7.45 (2H, m), 7.40-7.34 (3H, m), 7.29-7.12 (8H, m), 7.09 (1H, s), 6.47 (1H, d, J=8.5 Hz), 6.31 (1H, d, J=6.7 Hz), 5.56-5.47 (2H, m), 5.05-4.91 (4H, m), 4.88-4.73 (3H, m), 4.57-4.30 (5H, m), 4.09-4.01 (1H, m), 4.00-3.55 (9H, m), 3.53-3.45 (2H, m), 3.18 (12H, q, J=7.3 Hz), 3.02-2.94 (1H, m), 2.90-2.71 (3H, m), 2.35-2.20 (2H, m), 2.04-1.92 (3H, m), 1.27 (18H, t, J=7.3 Hz).

Example 66: Synthesis of Drug-Linker 6
[Synthesis Scheme]
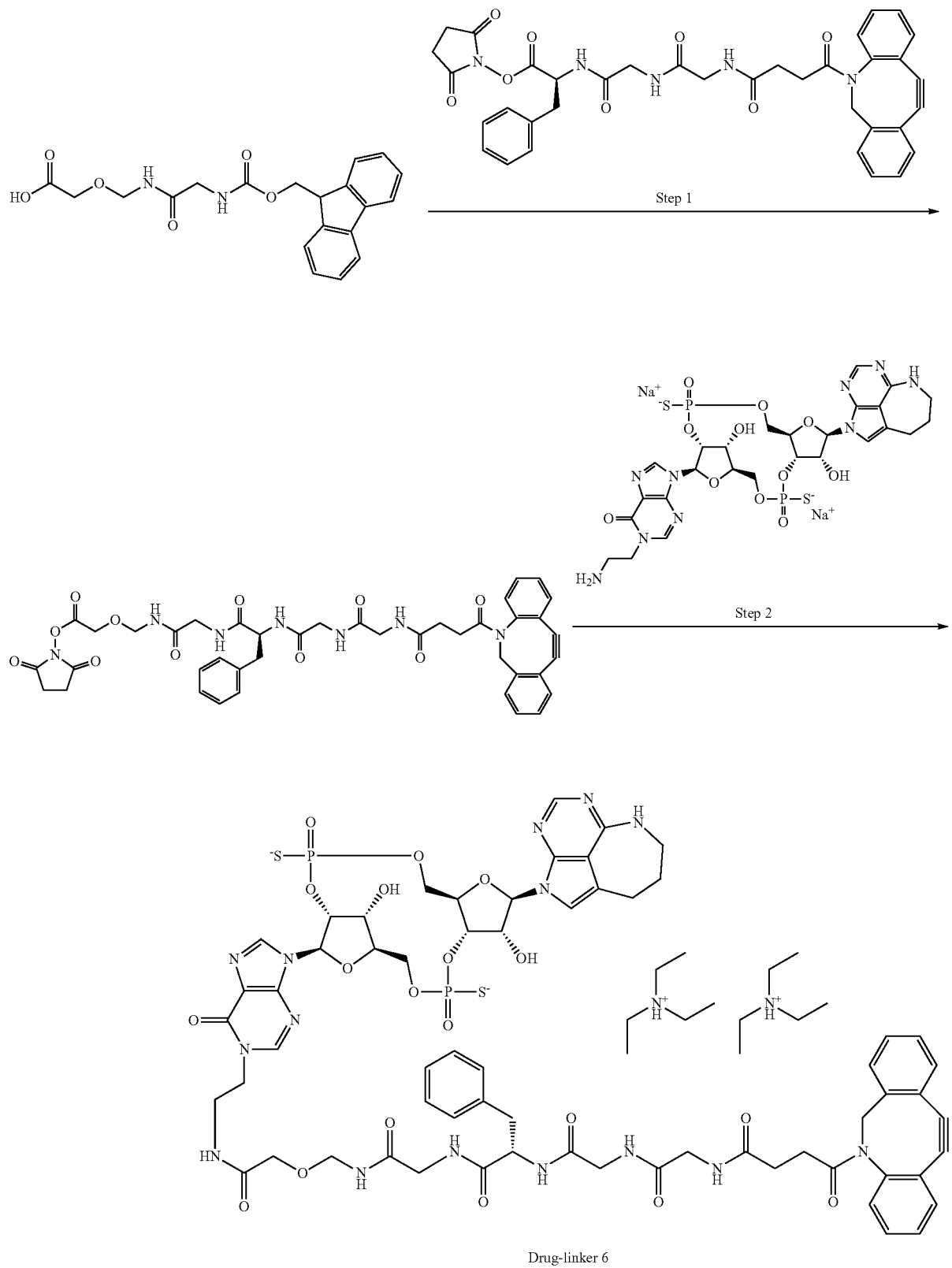
Drug-linker 6

(Step 1)

N-[4-(11,12-Didehydrodibenzo[b,f]azocin-5 (6H)-yl)-4-oxobutanoyl]glycylglycyl-L-phenylalanyl-N-({2-[(2,5-dioxopyrrolidin-1-yl)oxy]-2-oxoethoxy}methyl)glycinamide To a solution of {[(N-{[(9H-fluoren-9-yl)methoxy]carbonyl}glycyl)amino]methoxy}acetic acid (955 mg) as a compound known in the literature (WO 2014/057687) in N,N-dimethylformamide (8.0 mL), 1,8-diazabicyclo [5.4.0]-7-undecene (0.74 mL) was added, and the reaction mixture was stirred at room temperature for 1 hour (reaction mixture A). To a solution of the compound obtained in step 10 of Example 22 (938 mg) in N,N-dimethylformamide (8.0 mL), N-hydroxysuccinimide (229 mg) and 1-ethyl-3-(3-dimethylaminopropyl)-carbodiimide hydrochloride (380 mg) were added, and the reaction mixture was stirred at room temperature for 50 minutes (reaction mixture B). Reaction mixture A was added to reaction mixture B, and the resultant was stirred at room temperature for 1 hour. Dichloromethane (50 mL) and 10% aqueous solution of citric acid (10 mL) were added to the reaction mixture, which was subjected to extraction with dichloromethane. The organic layer was washed with brine, and then dried over anhydrous sodium sulfate. The drying agent was removed through filtration, and the filtrate was concentrated under reduced pressure. The residue was purified by silica gel column chromatography [chloroform/(lower layer of chloroform/methanol/water=7:3:1)]. To a solution of the compound obtained in N,N-dimethylformamide (8.0 mL), N-hydroxysuccinimide (229 mg) and 1-ethyl-3-(3-dimethylaminopropyl)-carbodiimide hydrochloride (380 mg) were added, and the reaction mixture was stirred at room temperature for 30 minutes. Dichloromethane (100 mL) and water (25 mL) were added to the reaction mixture, which was subjected to extraction with dichloromethane. The organic layer was washed with brine, and then dried over anhydrous sodium sulfate. The drying agent was removed through filtration, and the filtrate was concentrated under reduced pressure. The residue was purified by silica gel column chromatography [chloroform/methanol]. Fractions containing the targeted product was concentrated under reduced pressure, and diethyl ether was added to the residue to make a slurry. The obtained solid was collected through filtration to give the title compound (412 mg).

$^1$H-NMR (DMSO-$d_6$): 8.72 (1H, m), 8.32 (1H, m), 8.17-7.96 (3H, m), 7.71-7.15 (13H, m), 5.01 (1H, d, J=13.9 Hz), 4.70-4.48 (5H, m), 3.81-3.51 (7H, m), 3.05 (1H, dd, J=14.2, 3.9 Hz), 2.83 (4H, s), 2.80 (1H, m), 2.64 (1H, m), 2.28 (1H, m), 2.07 (1H, m), 1.79 (1H, m).

(Step 2)

Bis(N,N-diethylethaneaminium) N-[4-(11,12-didehydrodibenzo[b,f]azocin-5 (6H)-yl)-4-oxobutanoyl]glycylglycyl-L-phenylalanyl-N-({2-[(2-{9-[(5R,7R,8R,12aR,14R,15R,15aS,16R)-15,16-dihydroxy-2,10-dioxo-2,10-disulfide-14-(6,7,8,9-tetrahydro-2H-2,3,5,6-tetraazabenzo[cd]azulen-2-yl)octahydro-2H,10H,12H-5,8-methano-2$\lambda^5$,10$\lambda^5$-furo[3,2-1][1,3,6,9,11,2,10]pentaoxadiphosphacyclotetradecin-7-yl]-6-oxo-6,9-dihydro-1H-purin-1-yl}ethyl)amino]-2-oxoethoxy}methyl)glycinamide (Drug-Linker 6)

With use of the compound obtained in step 8-2 of Example 5 (20.0 mg) and the compound obtained in step 1 above (23.7 mg), the reaction was performed in the same manner as in step 4 of Example 21, and the resultant was then purified by C18 silica gel column chromatography [10 mM aqueous solution of triethylammonium acetate/acetonitrile], preparative HPLC [10 mM aqueous solution of triethylammonium acetate/acetonitrile, acetonitrile: 20%-45% (0 min-40 min)], and preparative HPLC [10 mM aqueous solution of triethylammonium acetate/methanol, methanol: 30%-80% (0 min-40 min)] to afford the title compound (14.1 mg).

MS(ESI)m/z: 1466 (M+H)$^+$.

$^1$H-NMR (CD$_3$OD) δ: 8.74-8.69 (1H, m), 8.17-8.12 (1H, m), 8.04-7.96 (1H, m), 7.65-7.13 (13H, m), 7.13-7.04 (1H, m), 6.33-6.23 (2H, m), 5.50-5.31 (2H, m), 5.07-4.94 (2H, m), 4.85-4.76 (1H, m), 4.71-4.26 (10H, m), 4.18-3.53 (13H, m), 3.53-3.33 (3H, m), 3.19 (12H, q, J=7.3 Hz), 3.05-2.92 (1H, m), 2.91-2.70 (3H, m), 2.40-2.20 (2H, m), 2.07-1.87 (2H, m), 1.29 (18H, t, J=7.3 Hz).

Example 67: Synthesis of Drug-Linker 7

[Synthesis Scheme]

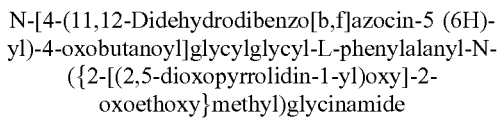

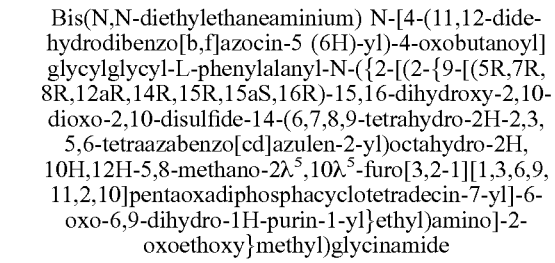

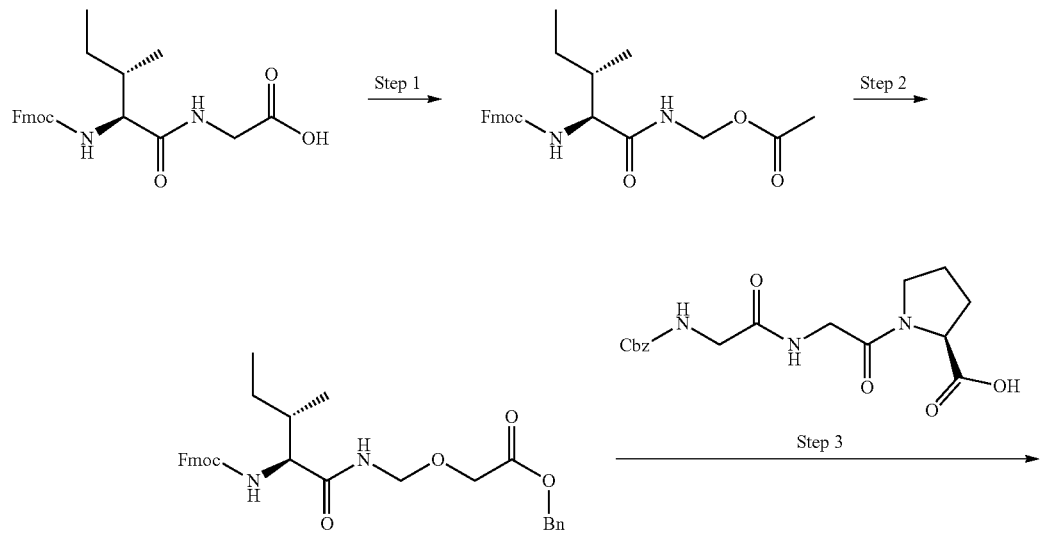

583
-continued
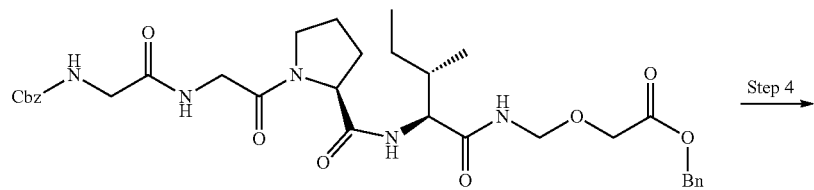
Step 4
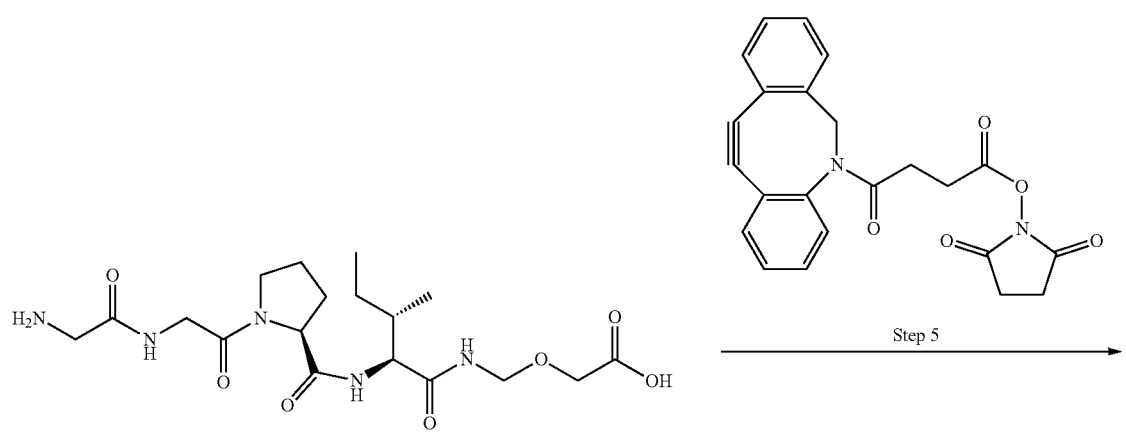
Step 5
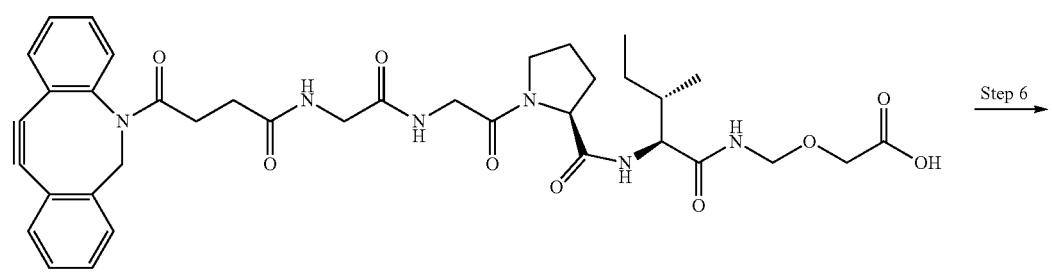
Step 6
584
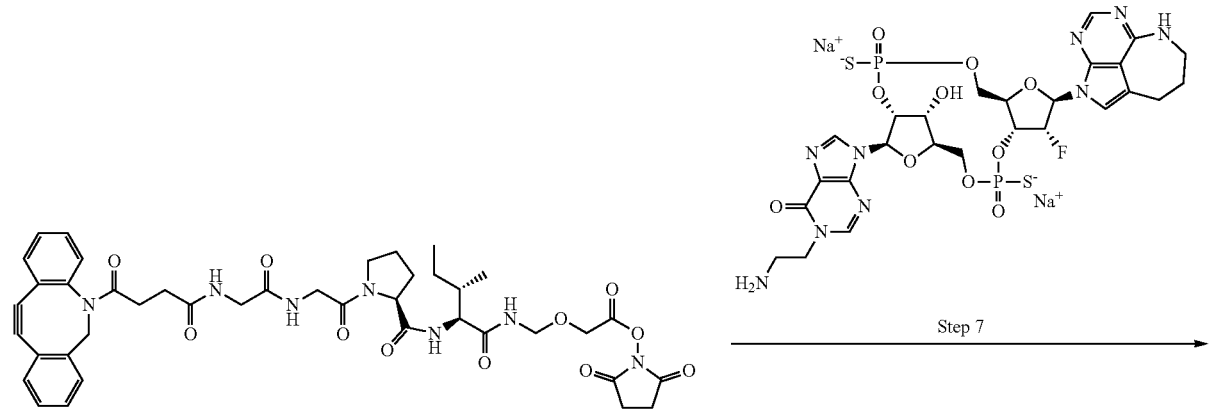
Step 7

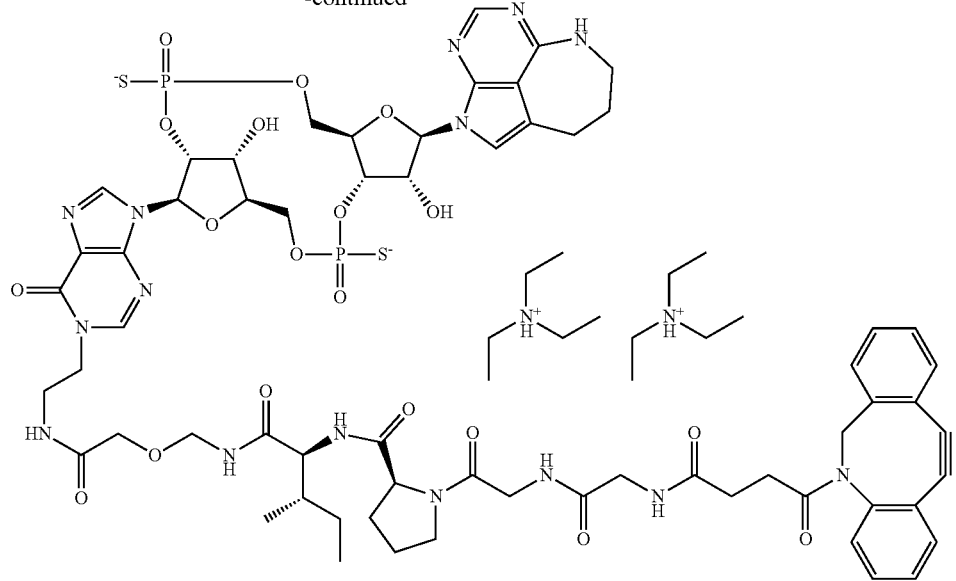

Drug-linker 7

(Step 1)

[(N-{[(9H-Fluoren-9-yl)methoxy]carbonyl}-L-isoleucyl)amino]methyl acetate

To a mixture of commercially available (Iris Biotech GmbH) N-{[(9H-fluoren-9-yl)methoxy]carbonyl}-L-isoleucylglycine (2.50 g) in tetrahydrofuran (45 mL)-toluene (15 mL), pyridine (0.588 mL) and lead tetraacetate (3.24 g) were added at room temperature, and the reaction mixture was stirred at 65° C. for 3 hours. The reaction mixture was diluted with ethyl acetate, and washed with water and brine in this order. After the organic layer was dried over anhydrous sodium sulfate, the drying agent was removed through filtration, and the filtrate was concentrated under reduced pressure. The residue was purified by silica gel column chromatography [hexane/ethyl acetate] to afford the title compound (2.06 g).

MS(ESI)m/z: 447 (M+Na)$^+$.

$^1$H-NMR (CDCl$_3$) δ: 7.77 (2H, d, J=7.9 Hz), 7.58 (2H, d, J=7.3 Hz), 7.40 (2H, t, J=7.3 Hz), 7.32 (2H, td, J=7.6, 1.2 Hz), 6.97-6.92 (1H, br m), 5.32-5.20 (3H, m), 4.47-4.37 (2H, m), 4.21 (1H, t, J=6.7 Hz), 4.05-4.01 (1H, m), 2.04 (3H, s), 1.92-1.84 (1H, br m), 1.51-1.41 (1H, br m), 1.17-1.07 (1H, br m), 0.93-0.89 (6H, m).

(Step 2)

Benzyl {[(N-{[(9H-fluoren-9-yl)methoxy]carbonyl}-L-isoleucyl)amino]methoxy}acetate To a suspension of the compound obtained in step 1 above (2.06 g) in tetrahydrofuran (48 mL), benzyl glycolate (1.38 mL) and p-toluenesulfonic acid monohydrate (92.3 mg) were added at 0° C., and the reaction mixture was stirred at room temperature for 4 hours. The reaction mixture was diluted with ethyl acetate and washed with saturated sodium hydrogen carbonate water, and the aqueous layer was then subjected to extraction with ethyl acetate. The organic layer was together washed with brine, and dried over anhydrous sodium sulfate. The drying agent was removed through filtration, and the filtrate was concentrated under reduced pressure. The residue was purified by silica gel column chromatography [hexane/ethyl acetate] to afford the title compound (1.72 g).

MS(ESI)m/z: 553 (M+Na)$^+$.

$^1$H-NMR (CDCl$_3$) δ: 7.76 (2H, d, J=7.9 Hz), 7.58 (2H, d, J=7.3 Hz), 7.42-7.29 (9H, m), 6.74-6.69 (1H, br m), 5.24-5.21 (1H, br m), 5.17 (2H, s), 4.86 (2H, d, J=6.7 Hz), 4.48-4.39 (2H, m), 4.23-4.19 (3H, m), 4.04-4.00 (1H, m), 1.95-1.87 (1H, br m), 1.50-1.41 (1H, br m), 1.15-1.07 (1H, br m), 0.93-0.89 (6H, m).

(Step 3)

N-[(Benzyloxy)carbonyl]glycylglycyl-L-prolyl-N-{[2-(benzyloxy)-2-oxoethoxy]methyl}-L-isoleucinamide To a suspension of the compound obtained in step 2 above (1.72 g) in acetonitrile (40 mL), 1,8-diazabicyclo [5.4.0]-7-undecene (0.290 mL) was added at room temperature, and the reaction mixture was stirred for 1 hour (reaction mixture A). To a suspension of commercially available N-[(benzyloxy)carbonyl]glycylglycyl-L-proline (1.41 g) in acetonitrile (20 mL), 3H-[1,2,3]triazolo[4,5-b]pyridin-3-ol (529 mg), 1-ethyl-3-(3-dimethylaminopropyl)-carbodiimide hydrochloride (746 mg), and N,N-diisopropylethylamine (0.678 mL) were added at room temperature, and the reaction mixture was stirred for 1 hour. This reaction mixture was added to reaction mixture A above at room temperature, and the resultant was stirred for 6 hours, and then concentrated under reduced pressure. The residue was purified by silica gel column chromatography [chloroform/methanol] to afford the title compound (1.56 g).

MS(ESI)m/z: 676 (M+Na)$^+$.

$^1$H-NMR (CD$_3$OD) δ: 7.37-7.27 (10H, m), 5.17 (2H, s), 5.09 (2H, s), 4.82-4.70 (2H, m), 4.56-4.44 (1H, m), 4.17-4.14 (3H, m), 4.07-3.96 (2H, m), 3.83-3.82 (2H, m), 3.64-3.48 (2H, m), 2.34-1.78 (5H, m), 1.61-1.51 (1H, m), 1.25-1.13 (1H, m), 0.95-0.87 (6H, m).

(Step 4)

Glycylglycyl-L-prolyl-N-[(carboxymethoxy)methyl]-L-isoleucinamide

To a mixture of the compound obtained in step 3 above (1.56 g) in methanol (8 mL)-tetrahydrofuran (24 mL)-dichloromethane (8 mL), 10% palladium-carbon (M) wet (1.4 g) was added, and the reaction mixture was stirred under the hydrogen atmosphere at room temperature for 23 hours. A mixture of methanol/tetrahydrofuran (1:1) (50 mL) was added to the reaction mixture, which was filtered with a Celite. The Celite was washed with a mixture of methanol/tetrahydrofuran (1:1). After the filtrate was concentrated under reduced pressure, methanol (20 mL), tetrahydrofuran (20 mL), and 10% palladium-carbon (M) wet (1.0 g) were added to the residue, and the reaction mixture was stirred under the hydrogen atmosphere at room temperature for 3 hours. The reaction mixture was filtered with a Celite, and the Celite was then washed with methanol/tetrahydrofuran (1:1). The filtrate was concentrated under reduced pressure to afford a crude form of the title compound (1.02 g).

MS(ESI)m/z: 430 (M+H)$^+$.

(Step 5)

N-[4-(11,12-Didehydrodibenzo[b,f]azocin-5 (6H)-yl)-4-oxobutanoyl]glycylglycyl-L-prolyl-N-[(carboxymethoxy)methyl]-L-isoleucinamide To a solution of the compound obtained in step 4 above (1.02 g) in N,N-dimethylformamide (24 mL), 1-{[4-(11,12-didehydrodibenzo[b,f]azocin-5 (6H)-yl)-4-oxobutanoyl]oxy}pyrrolidine-2,5-dione (956 mg) and N,N-diisopropylethylamine (0.496 mL) were added, and the reaction mixture was stirred at room temperature for 1 hour. The reaction mixture was concentrated under reduced pressure, and the residue was purified by silica gel column chromatography [chloroform/methanol]. Fractions containing the targeted product were concentrated under reduced pressure, and ethyl acetate was added to the residue to solidify. The obtained solid was collected through filtration to give the title compound (1.06 g).

MS(ESI)m/z: 739 (M+Na)$^+$, 715 (M−H)$^−$.

$^1$H-NMR (CD$_3$OD) δ: 7.64-7.59 (2H, m), 7.48-7.44 (3H, m), 7.38-7.23 (3H, m), 5.15-5.12 (1H, m), 4.74-4.70 (2H, m), 4.64-4.48 (1H, m), 4.25-4.18 (1H, m), 4.11-3.96 (3H, m), 3.91-3.85 (1H, m), 3.78-3.57 (5H, m), 2.84-2.75 (1H, m), 2.39-2.16 (3H, br m), 2.08-1.84 (5H, br m), 1.61-1.52 (1H, br m), 1.23-1.15 (1H, br m), 0.96-0.87 (6H, m).

(Step 6)

N-[4-(11,12-Didehydrodibenzo[b,f]azocin-5 (6H)-yl)-4-oxobutanoyl]glycylglycyl-L-prolyl-N-({2-[(2,5-dioxopyrrolidin-1-yl)oxy]-2-oxoethoxy}methyl)-L-isoleucinamide To a suspension of the compound obtained in step 5 above (1.06 g) in N,N-dimethylformamide (16 mL), N-hydroxysuccinimide (187 mg) and 1-ethyl-3-(3-dimethylaminopropyl)-carbodiimide hydrochloride (312 mg) were added, and the reaction mixture was stirred at room temperature for 16 hours. The reaction mixture was diluted with chloroform, and washed three times with water. After the organic layer was dried over anhydrous sodium sulfate, the drying agent was removed through filtration, and the filtrate was concentrated under reduced pressure. Ethyl acetate was added to the residue, and the obtained solid was collected through filtration. To the solid collected through filtration, diethyl ether was added to make a slurry, and the solid was then collected through filtration to give the title compound (767 mg).

MS(ESI)m/z: 836 (M+Na)$^+$.

$^1$H-NMR (CD$_3$OD) δ: 7.68-7.56 (2H, m), 7.48-7.44 (3H, m), 7.38-7.23 (3H, m), 5.15-5.12 (1H, m), 4.83-4.70 (2H, m), 4.64-4.50 (3H, m), 4.24-3.55 (8H, m), 2.83-2.76 (5H, m), 2.38-2.18 (3H, m), 2.11-1.84 (5H, br m), 1.60-1.52 (1H, m), 1.25-1.13 (1H, m), 0.98-0.87 (6H, m).

(Step 7)

Bis(N,N-diethylethaneaminium) N-[4-(11,12-didehydrodibenzo[b,f]azocin-5 (6H)-yl)-4-oxobutanoyl]glycylglycyl-L-prolyl-N-({2-[(2-{9-[(5R,7R,8R,12aR,14R,15R,15aS,16R)-15,16-dihydroxy-2,10-dioxo-2,10-disulfide-14-(6,7,8,9-tetrahydro-2H-2,3,5,6-tetraazabenzo[cd]azulen-2-yl)octahydro-2H,10H,12H-5,8-methano-215,105-furo[3,2-1][1,3,6,9,11,2,10]pentaoxadiphosphacyclotetradecin-7-yl]-6-oxo-6,9-dihydro-1H-purin-1-yl}ethyl)amino]-2-oxoethoxy}methyl)-L-isoleucinamide (Drug-Linker 7)

With use of the compound obtained in step 8-2 of Example 5 (20.0 mg) and the compound obtained in step 6 above (20.9 mg), the reaction was performed in the same manner as in step 4 of Example 21, and the resultant was then purified by C18 silica gel column chromatography [10 mM aqueous solution of triethylammonium acetate/acetonitrile], preparative HPLC [10 mM aqueous solution of triethylammonium acetate/acetonitrile, acetonitrile: 20%-45% (0 min-40 min)], and preparative HPLC [10 mM aqueous solution of triethylammonium acetate/methanol, methanol: 30%-80% (0 min-40 min)] to afford the title compound (11.9 mg).

MS(ESI)m/z: 1472 (M+H)$^+$ $^1$H-NMR (CD$_3$OD) δ: 8.71 (1H, brs), 8.19-8.13 (1H, m), 8.02 (1H, s), 7.64-7.56 (2H, m), 7.48-7.41 (3H, m), 7.37-7.08 (4H, m), 6.34-6.23 (2H, m), 5.48-5.36 (2H, m), 5.16-5.08 (1H, m), 4.98-4.55 (6H, m), 4.52-4.15 (7H, m), 4.07-3.81 (6H, m), 3.80-3.45 (8H, m), 3.19 (12H, q, J=7.3 Hz), 2.93-2.85 (2H, m), 2.85-2.71 (1H, m), 2.45-2.30 (1H, m), 2.30-2.11 (2H, m), 2.08-1.83 (6H, m), 1.66-1.45 (1H, m), 1.29 (18H, t, J=7.3 Hz), 1.28-1.10 (1H, m), 1.01-0.85 (7H, m).

Example 68: Synthesis of Drug-Linker 8
[Synthesis Scheme]
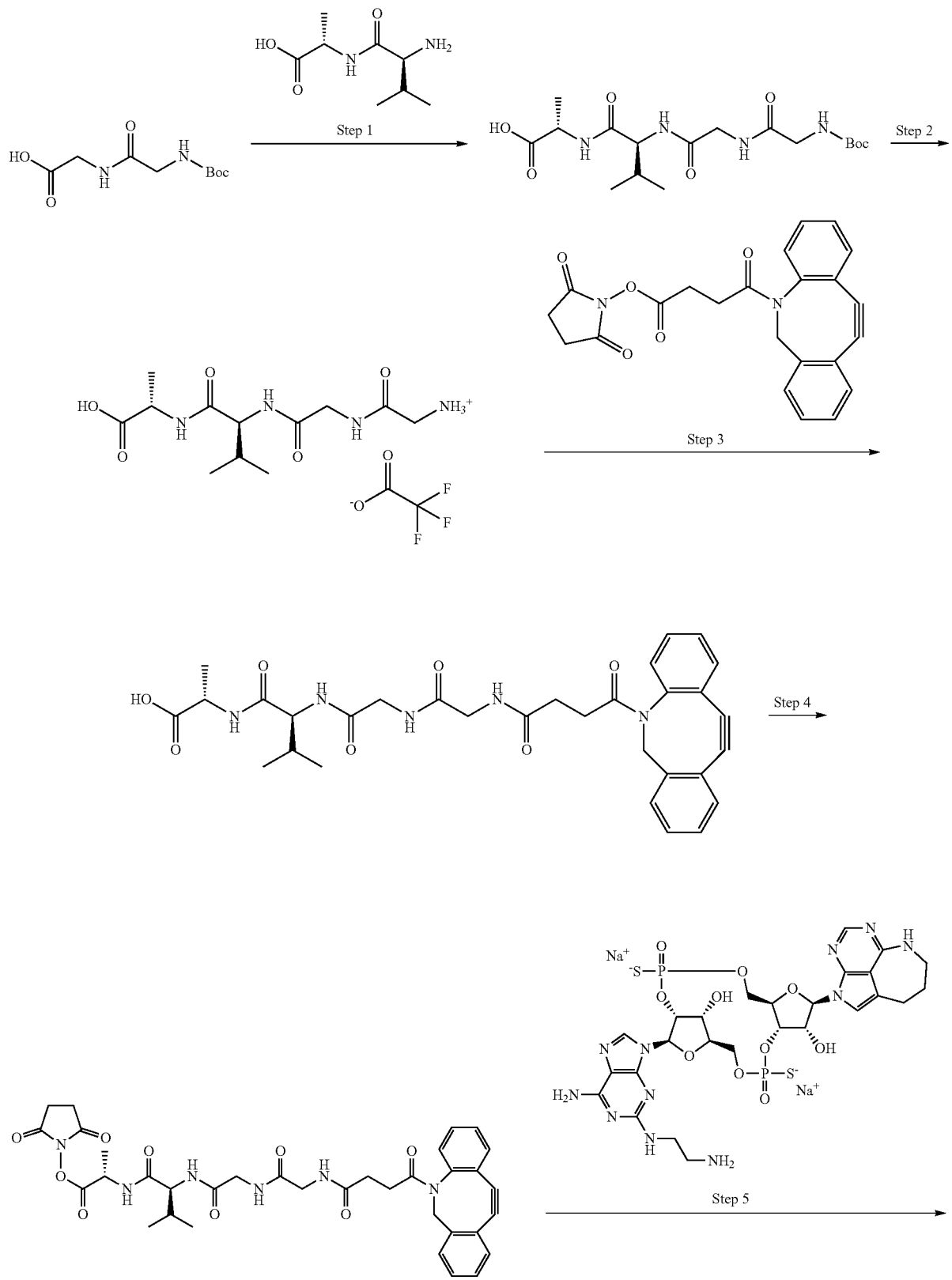

-continued

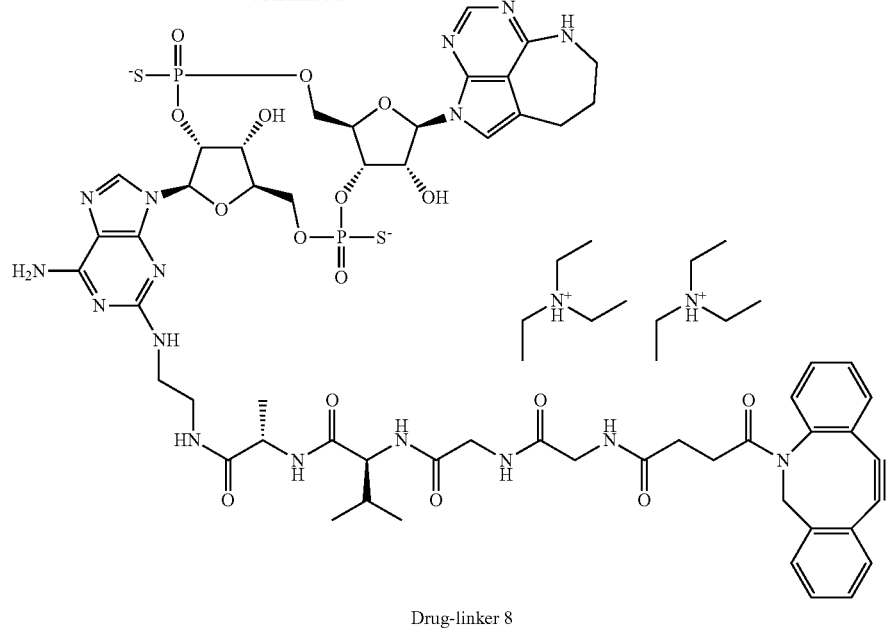

Drug-linker 8

(Step 1)

N-(tert-Butoxycarbonyl)glycylglycyl-L-valyl-L-alanine

To a solution of commercially available (Chemfun Medical Technology (Shanghai) Co., Ltd.) N-(tert-butoxycarbonyl)glycylglycine (5.00 g) and N-hydroxysuccinimide (2.97 g) in N,N-dimethylformamide (50 mL), 1-ethyl-3-(3-dimethylaminopropyl)-carbodiimide hydrochloride (4.95 g) was added under the nitrogen atmosphere at 0° C., and the temperature was increased to room temperature and the reaction mixture was stirred for 1 hour. Triethylamine (3.6 mL) and commercially available (KOKUSAN CHEMICAL Co., Ltd.) L-valyl-L-alanine (4.05 g) were added to the reaction mixture, which was stirred at the same temperature for 6 hours. The reaction mixture was concentrated under reduced pressure, and the residue was purified by silica gel column chromatography [dichloromethane/methanol]. Fractions containing the targeted product was concentrated under reduced pressure, and diethyl ether was added thereto to make a slurry. The obtained solid was collected through filtration to give the title compound (4.99 g).

MS(ESI)m/z: 401 (M−H)⁻.

¹H-NMR (DMSO-d₆) δ: 12.43 (1H, br), 8.27 (1H, d, J=6.8 Hz), 7.92 (1H, t, J=5.4 Hz), 7.79 (1H, d, J=9.3 Hz), 6.99 (1H, t, J=5.9 Hz), 4.19 (1H, t, J=8.1 Hz), 4.13 (1H, m), 3.73 (2H, d, J=5.4 Hz), 3.52 (2H, d, J=5.9 Hz), 1.92 (1H, dd, m), 1.35 (9H, s), 1.24 (3H, d, J=7.3 Hz), 0.85 (3H, d, J=6.3 Hz), 0.79 (3H, d, J=6.8 Hz).

(Step 2)

N-(Azaniumylacetyl)glycyl-L-valyl-L-alanine trifluoroacetate

With use of the compound obtained in step 1 above (1.00 g), the reaction was performed in the same manner as in step 1 of Example 21 to afford a crude form of the title compound (1.10 g).

MS(ESI)m/z: 301 (M−H)⁻.

¹H-NMR (DMSO-d₆) δ: 12.49 (1H, br), 8.54 (1H, t, J=5.6 Hz), 8.34 (1H, d, J=6.8 Hz), 8.03 (1H, d, J=9.3 Hz), 8.00 (3H, brs), 4.24 (1H, dd, J=8.8, 6.8 Hz), 4.17 (1H, m), 3.93-3.84 (2H, m), 3.62-3.58 (2H, m), 1.96 (1H, m), 1.27 (3H, d, J=7.3 Hz), 0.89 (3H, d, J=6.8 Hz), 0.84 (3H, d, J=6.8 Hz).

(Step 3)

N-[4-(11,12-Didehydrodibenzo[b,f]azocin-5 (6H)-yl)-4-oxobutanoyl]glycylglycyl-L-valyl-L-alanine With use of the compound obtained in step 2 above (861 mg), the reaction was performed in the same manner as in step 2 of Example 21 to afford the title compound (737 mg).

MS(ESI)m/z: 590 (M+H)⁺.

¹H-NMR (DMSO-d₆) δ: 12.46 (1H, s), 8.28 (1H, t, J=8.1 Hz), 8.18 (1H, t, J=5.9 Hz), 8.13 (0.5H, t, J=5.6 Hz), 8.04 (0.5H, t, J=5.9 Hz), 7.99 (0.5H, t, J=5.9 Hz), 7.73 (0.5H, d, J=1.5 Hz), 7.67 (1H, m), 7.61 (1H, m), 7.53-7.44 (3H, m), 7.40-7.28 (3H, m), 5.03 (0.5H, d, J=6.3 Hz), 5.00 (0.5H, d, J=6.3 Hz), 4.21 (1H, dd, J=9.0, 7.1 Hz), 4.18-4.08 (1H, m), 3.78-3.67 (2H, m), 3.65-3.55 (3H, m), 2.72-2.59 (1H, m), 2.28 (1H, d, J=7.8 Hz), 2.09-2.03 (1H, m), 1.99-1.91 (1H, m), 1.79 (1H, m), 1.25 (1.5H, d, J=5.4 Hz), 1.24 (1.5H, d, J=5.4 Hz), 0.87 (3H, d, J=6.8 Hz), 0.82-0.79 (3H, m).

(Step 4)

2,5-Dioxopyrrolidin-1-yl N-[4-(11,12-didehydrodibenzo[b,f]azocin-5 (6H)-yl)-4-oxobutanoyl]glycylglycyl-L-valyl-L-alaninate With use of the compound obtained in step 3 above (260 mg), the reaction was performed in the same manner as in step 3 of Example 21 to afford the title compound (84 mg).

MS(ESI)m/z: 687 (M+H)⁺.

¹H-NMR (DMSO-d₆) δ: 8.73 (1H, t, J=7.0 Hz), 8.18 (0.5H, t, J=5.7 Hz), 8.12 (0.5H, t, J=5.7 Hz), 8.04 (0.5H, t, J=5.7 Hz), 7.98 (0.5H, t, J=5.7 Hz), 7.84-7.60 (3H, m), 7.52-7.44 (3H, m), 7.40-7.28 (3H, m), 5.03 (0.5H, d, J=6.0 Hz), 5.00 (0.5H, d, J=6.0 Hz), 4.69-4.58 (1H, m), 4.22 (1H, t, J=7.6 Hz), 3.80-3.54 (5H, m), 2.80 (4H, s), 2.73-2.59 (1H, m), 2.34-2.24 (1H, m), 2.11-2.02 (1H, m), 1.99-1.91 (1H, m), 1.79 (1H, m), 1.45 (1.5H, d, J=3.6 Hz), 1.43 (1.5H, d,

J=3.6 Hz), 0.85 (3H, d, J=6.7 Hz), 0.83-0.79 (3H, m).
(Step 5)

Bis(N,N-diethylethaneaminium) N-[4-(11,12-didehydrodibenzo[b,f]azocin-5 (6H)-yl)-4-oxobutanoyl]glycylglycyl-L-valyl-N-[2-({6-amino-9-[(5R,7R,8R,12aR,14R,15R,15aS,16R)-15,16-dihydroxy-2,10-dioxo-2,10-disulfide-14-(6,7,8,9-tetrahydro-2H-2,3,5,6-tetraazabenzo[cd]azulen-2-yl)octahydro-2H,10H,12H-5,8-methano-2λ$^5$,10λ$^5$-furo[3,2-1][1,3,6,9,11,2,10]pentaoxadiphosphacyclotetradecin-7-yl]-9H-purin-2-yl}amino)ethyl]-L-alaninamide (Drug-Linker 8)

With use of the compound obtained in step 8-2 of Example 8 (5.3 mg) and the compound obtained in step 4 above (4.5 mg), the reaction was performed in the same manner as in step 1 of Example 23, and the resultant was then purified by preparative HPLC [10 mM aqueous solution of triethylammonium acetate/acetonitrile, acetonitrile: 25%-35% (0 min-30 min)] to afford the title compound (5.1 mg).

MS(ESI)m/z: 1359 (M+H)$^+$.

$^1$H-NMR (CD$_3$OD) δ: 8.37 (1H, brs), 8.02 (1H, s), 7.66-7.13 (9H, m), 6.33 (1H, d, J=6.7 Hz), 6.13 (1H, d, J=9.1 Hz), 5.49-5.42 (2H, m), 5.13-5.04 (1H, m), 4.83-4.80 (1H, m), 4.51-3.63 (14H, m), 3.51-3.37 (4H, m), 3.14 (12H, q, J=7.3 Hz), 2.90-2.72 (5H, m), 2.36-1.96 (6H, m), 1.34-1.25 (21H, m), 0.98-0.86 (6H, m).

Example 69: Synthesis of Drug-Linker 9

[Synthesis Scheme]

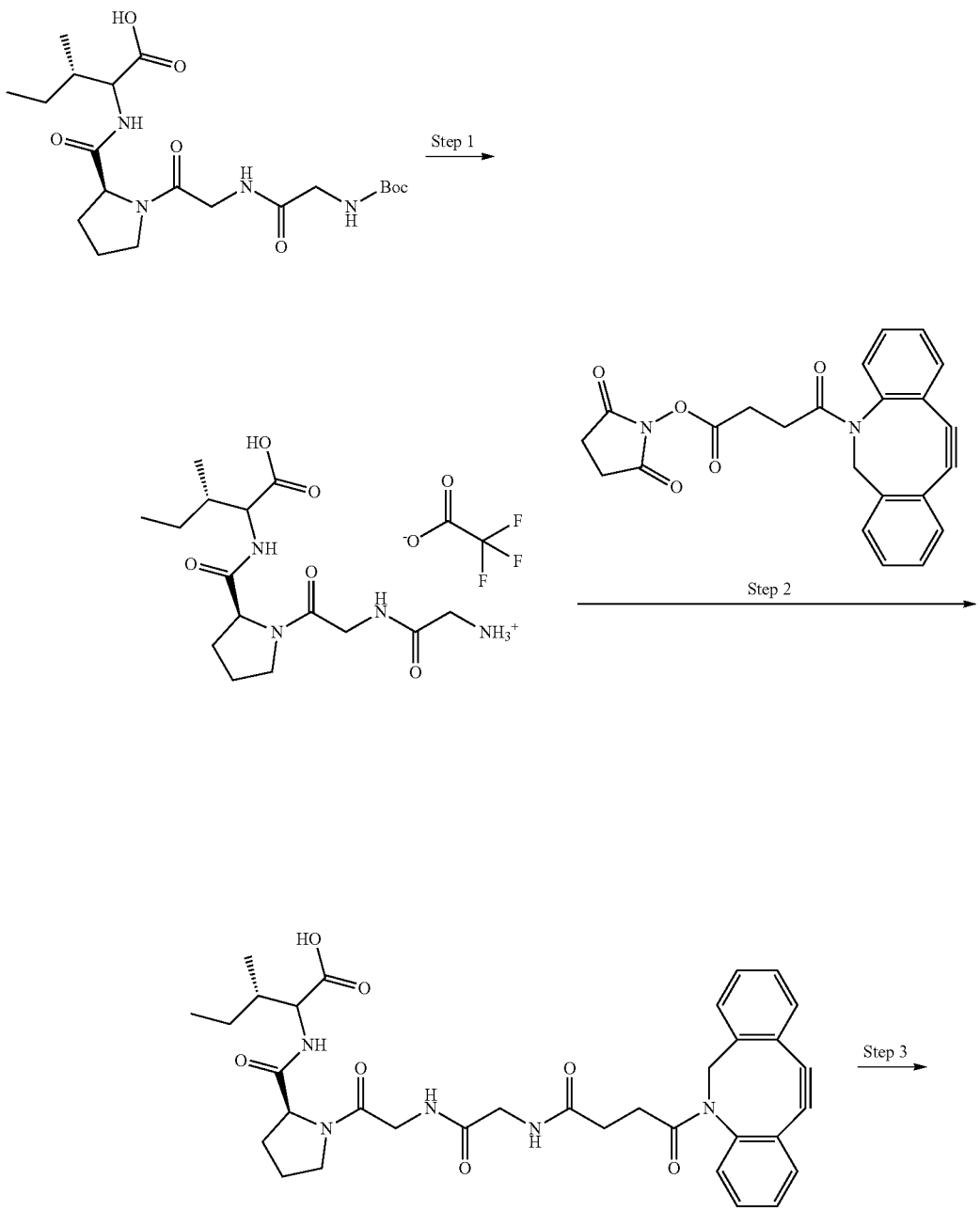

-continued

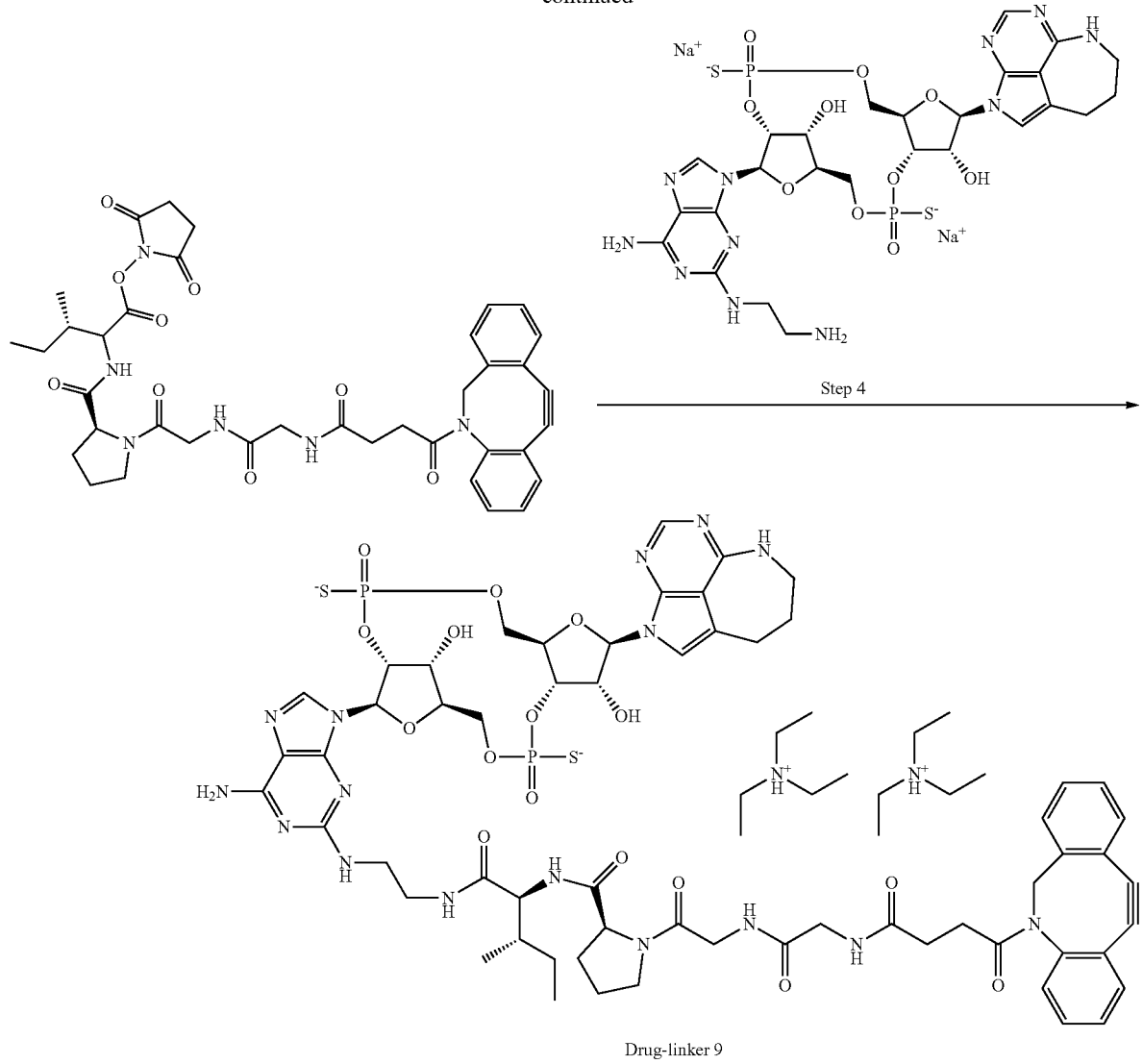

Drug-linker 9

(Step 1)

N-(Azaniumylacetyl)glycyl-L-prolyl-L-isoleucine trifluoroacetate

With use of commercially available (Hangzhou Peptide Biochem Co., Ltd.) N-(tert-butoxycarbonyl)glycylglycyl-L-prolyl-L-isoleucine (1.00 g), the reaction was performed in the same manner as in step 1 of Example 21 to afford a crude form of the title compound (1.02 g).

MS(ESI)m/z: 343 (M+H)$^+$.

$^1$H-NMR (DMSO-d$_6$) δ: 12.61 (1H, s), 8.51 (0.7H, t, J=5.1 Hz), 8.48 (0.3H, t, J=4.9 Hz), 8.35 (0.3H, d, J=8.8 Hz), 8.05 (0.7H, d, J=8.3 Hz), 7.99 (3H, brs), 4.55 (0.3H, dd, J=8.3, 2.4 Hz), 4.46 (0.7H, dd, J=8.8, 2.9 Hz), 4.23 (0.3H, dd, J=8.5, 5.6 Hz), 4.15 (0.7H, dd, J=8.3, 5.9 Hz), 4.06 (0.7H, dd, J=17.6, 5.4 Hz), 3.99-3.95 (1H, m), 3.63-3.36 (4.3H, m), 2.28-2.20 (0.3H, m), 2.07-2.00 (0.7H, m), 1.96-1.74 (4H, m), 1.46-1.36 (1H, m), 1.26-1.13 (1H, m), 0.89-0.83 (6H, m).

(Step 2)

N-[4-(11,12-Didehydrodibenzo[b,f]azocin-5 (6H)-yl)-4-oxobutanoyl]glycylglycyl-L-prolyl-L-isoleucine With use of the compound obtained in step 1 above (1.02 g), the reaction was performed in the same manner as in step 2 of Example 21 to afford the title compound (993 mg).

MS(ESI)m/z: 630 (M+H)$^+$.

$^1$H-NMR (DMSO-d$_6$) δ: 12.57 (1H, s), 8.30 (0.3H, dd, J=8.5, 3.6 Hz), 8.14-8.06 (1H, m), 8.00 (0.7H, d, J=7.9 Hz), 7.88-7.80 (1H, m), 7.70-7.66 (1H, m), 7.63-7.60 (1H, m), 7.53-7.27 (6H, m), 5.04 (0.7H, d, J=14.5 Hz), 5.02 (0.3H, d, J=14.5 Hz), 4.56 (0.3H, dd, J=8.5, 2.4 Hz), 4.47-4.43 (0.7H, m), 4.20 (0.3H, dd, J=8.2, 5.7 Hz), 4.12 (0.7H, m), 3.99-3.36 (7H, m), 2.68-2.58 (1H, m), 2.34-2.18 (1.3H, m), 2.09-1.74 (6.7H, m), 1.44-1.34 (1H, m), 1.25-1.12 (1H, m), 0.87-0.80 (6H, m).

(Step 3)

2,5-Dioxopyrrolidin-1-yl N-[4-(11,12-didehydrodibenzo[b,f]azocin-5 (6H)-yl)-4-oxobutanoyl]glycylglycyl-L-prolyl-L-isoleucinate With use of the compound obtained in step 2 above (300 mg), the reaction was performed in the same manner as in step 3 of Example 21 to afford the title compound (287 mg).

MS(ESI)m/z: 727 (M+H)⁺.

¹H-NMR (DMSO-d₆) δ: 8.77-8.67 (0.3H, m), 8.50 (0.5H, d, J=8.3 Hz), 8.31 (0.2H, m), 8.10-8.04 (1H, m), 7.88-7.79 (1H, m), 7.68-7.57 (2H, m), 7.49-7.26 (6H, m), 5.01 (1H, d, J=14.2 Hz), 4.80-4.42 (2H, m), 3.97-3.84 (1H, m), 3.79-3.34 (6H, m), 2.78 (4H, s), 2.64-2.57 (1H, m), 2.30-1.74 (8H, m), 1.56-1.17 (2H, m), 1.00-0.80 (6H, m).

(Step 4)

Bis(N,N-diethylethaneaminium) N-[4-(11,12-didehydrodibenzo[b,f]azocin-5 (6H)-yl)-4-oxobutanoyl]glycylglycyl-L-prolyl-N-[2-({6-amino-9-[(5R,7R,8R,12aR,14R,15R,15aS,16R)-15,16-dihydroxy-2,10-dioxo-2,10-disulfide-14-(6,7,8,9-tetrahydro-2H-2,3,5,6-tetraazabenzo[cd]azulen-2-yl)octahydro-2H,10H,12H-5,8-methano-2λ⁵,10λ⁵-furo[3,2-1][1,3,6,9,11,2,10]pentaoxadiphosphacyclotetradecin-7-yl]-9H-purin-2-yl}amino)ethyl]-L-isoleucinamide (Drug-Linker 9)

With use of the compound obtained in step 8-2 of Example 8 (51.8 mg) and the compound obtained in step 3 above (36.9 mg), the reaction was performed in the same manner as in step 1 of Example 23, and the resultant was then purified by preparative HPLC [10 mM aqueous solution of triethylammonium acetate/acetonitrile, acetonitrile: 20%-35% (0 min-30 min)] to afford the title compound (62.5 mg).

MS(ESI)m/z: 1397 (M−H)⁻.

Example 70: Synthesis of Drug-Linker 10

[Synthesis Scheme]

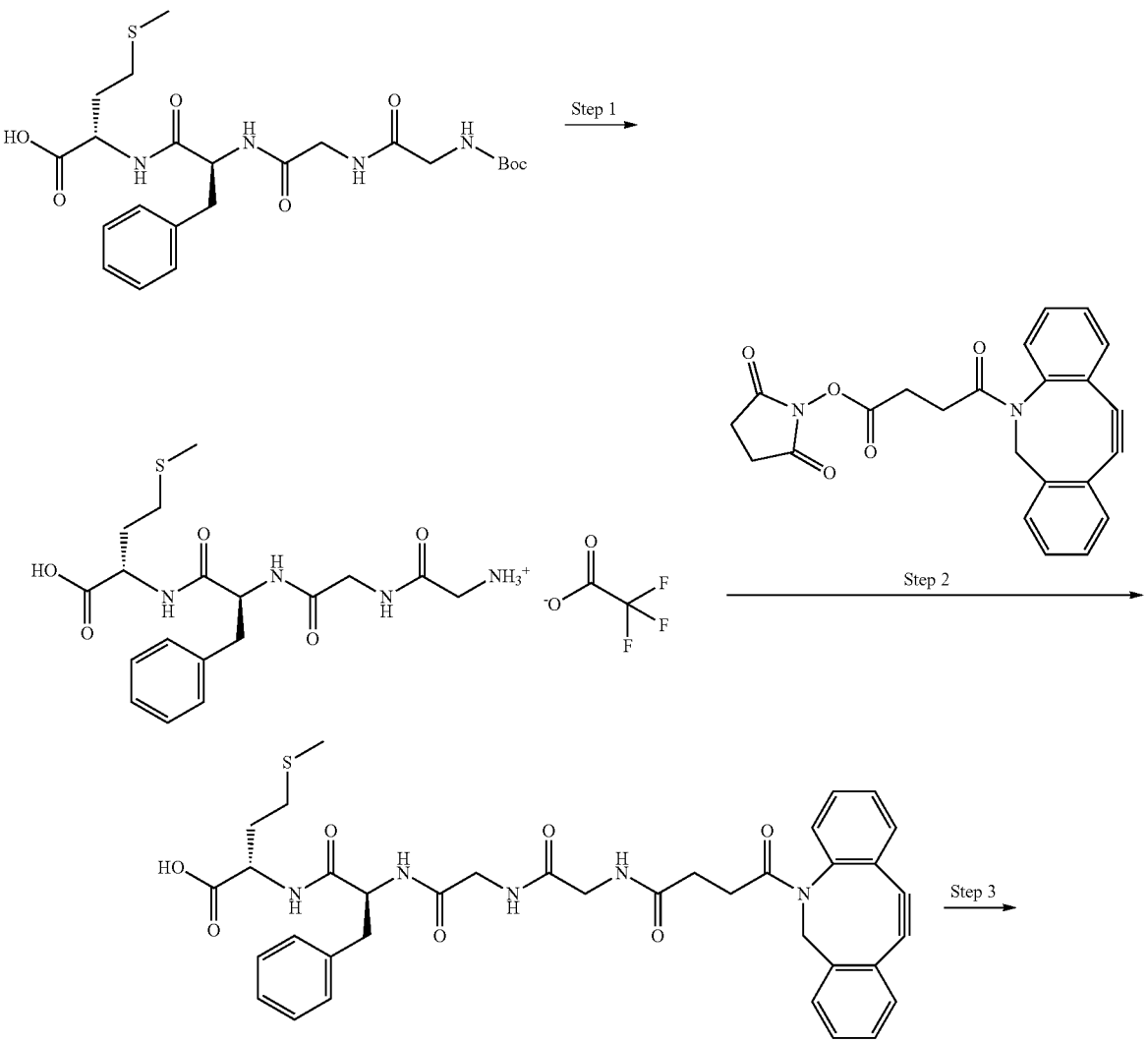

-continued

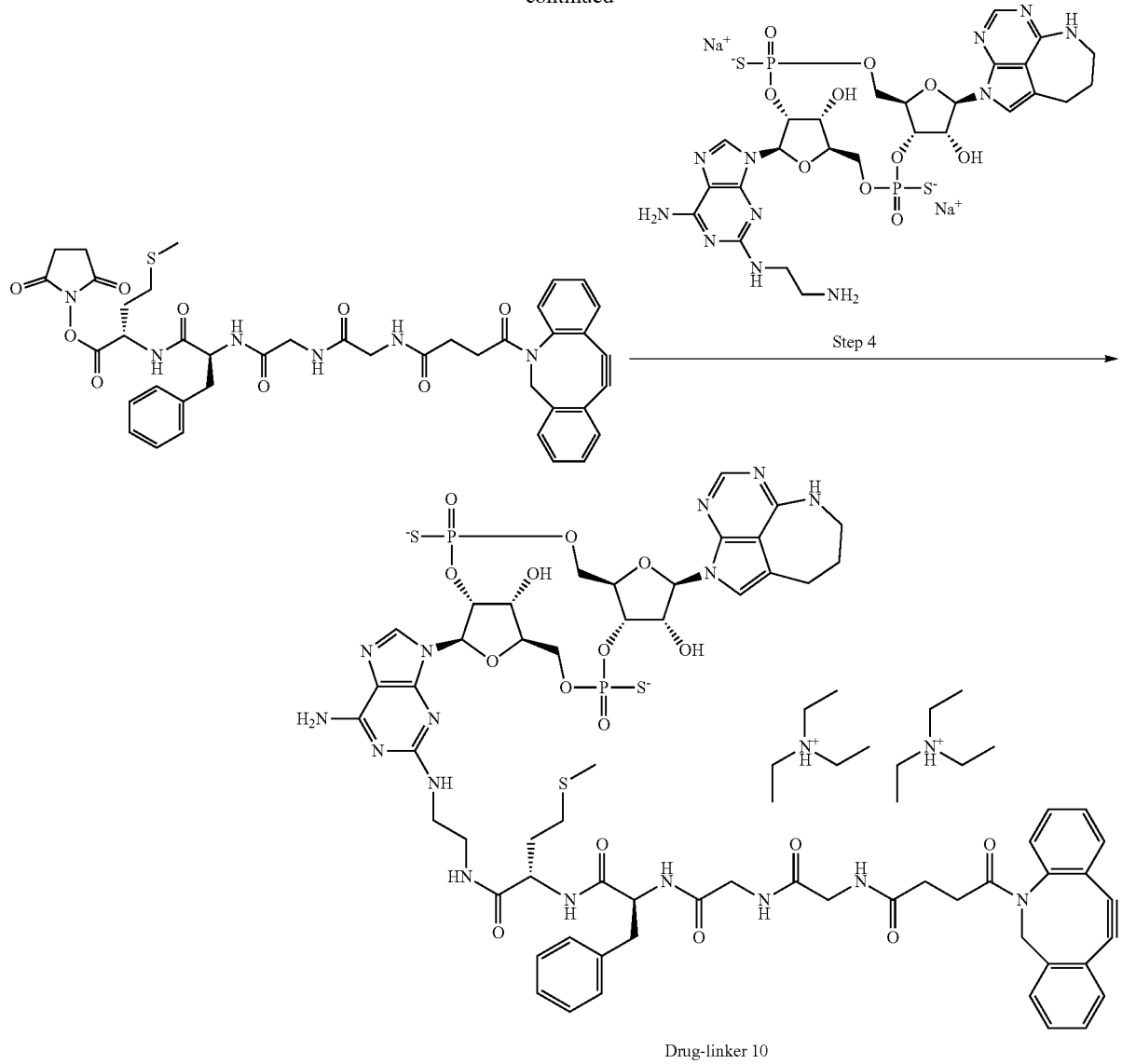

Drug-linker 10

(Step 1)

N-(Azaniumylacetyl)glycyl-L-phenylalanyl-L-methionine trifluoroacetate

With use of commercially available (Hangzhou Peptide Biochem Co., Ltd.) N-(tert-butoxycarbonyl)glycylglycyl-L-phenylalanyl-L-methionine (1.00 g), the reaction was performed in the same manner as in step 1 of Example 21 to afford a crude form of the title compound (1.19 g).

MS(ESI)m/z: 411 (M+H)$^+$.

$^1$H-NMR (DMSO-d$_6$) δ: 8.48 (1H, t, J=5.4 Hz), 8.41 (1H, d, J=7.8 Hz), 8.27 (1H, d, J=8.3 Hz), 7.97 (3H, m), 7.28-7.18 (5H, m), 4.58 (1H, m), 4.32 (1H, m), 3.85 (1H, dd, J=17.1, 5.9 Hz), 3.68 (1H, dd, J=16.6, 5.4 Hz), 3.56 (2H, m), 3.04 (1H, dd, J=13.9, 3.7 Hz), 2.74 (1H, dd, J=13.7, 10.3 Hz), 2.47 (1H, m), 2.05 (3H, s), 2.00 (1H, m), 1.88 (1H, m), 1.48 (1H, d, J=10.3 Hz). (only observable peaks are shown)

(Step 2)

N-[4-(11,12-Didehydrodibenzo[b,f]azocin-5 (6H)-yl)-4-oxobutanoyl]glycylglycyl-L-phenylalanyl-L-methionine With use of the compound obtained in step 1 above (1.03 g), the reaction was performed in the same manner as in step 2 of Example 21 to afford the title compound (652 mg).

MS(ESI)m/z: 698 (M+H)$^+$.

$^1$H-NMR (DMSO-d$_6$) δ: 12.67 (1H, brs), 8.28 (0.7H, d, J=7.9 Hz), 8.25 (0.3H, d, J=7.9 Hz), 8.17 (0.7H, t, J=5.7 Hz), 8.10 (0.3H, t, J=5.7 Hz), 8.04-7.93 (2H, m), 7.73-7.15 (13H, m), 5.00 (1H, d, J=13.9 Hz), 4.56-4.49 (1H, m), 4.35-4.28

(1H, m), 3.74-3.49 (5H, m), 3.03 (1H, dd, J=13.9, 3.6 Hz), 2.79-2.22 (5H, m), 2.11-1.76 (4H, m), 2.02 (2.1H, s), 2.02 (0.9H, s).

(Step 3)

2,5-Dioxopyrrolidin-1-yl N-[4-(11,12-didehydrodibenzo[b,f]azocin-5 (6H)-yl)-4-oxobutanoyl] glycylglycyl-L-phenylalanyl-L-methioninate With use of the compound obtained in step 2 above (201 mg), the reaction was performed in the same manner as in step 3 of Example 21 to afford the title compound (95 mg).

MS(ESI)m/z: 795 (M+H)+.

$^1$H-NMR (DMSO-d$_6$) δ: 8.84-8.59 (1H, m), 8.17-7.96 (3H, m), 7.72-7.15 (13H, m), 5.01 (0.55H, d, J=14.5 Hz), 5.00 (0.45H, d, J=13.9 Hz), 4.86-4.74 (1H, m), 4.56-4.48 (1H, m), 3.75-3.50 (5H, m), 3.05-2.52 (6H, m), 2.82 (4H, brs), 2.33-1.73 (4H, m), 2.05 (3H, s).

(Step 4)

Bis(N,N-diethylethaneaminium) N-[4-(11,12-didehydrodibenzo[b,f]azocin-5 (6H)-yl)-4-oxobutanoyl] glycylglycyl-L-phenylalanyl-N-[2-({6-amino-9-[(5R,7R,8R,12aR,14R,15R,15aS,16R)-15,16-dihydroxy-2,10-dioxo-2,10-disulfide-14-(6,7,8,9-tetrahydro-2H-2,3,5,6-tetraazabenzo[cd]azulen-2-yl) octahydro-2H,10H,12H-5,8-methano-2λ$^5$,10λ$^5$-furo [3,2-1][1,3,6,9,11,2,10] pentaoxadiphosphacyclotetradecin-7-yl]-9H-purin-2-yl}amino)ethyl]-L-methioninamide (Drug-Linker 10)

With use of the compound obtained in step 8-2 of Example 8 (6.0 mg) and the compound obtained in step 3 above (5.5 mg), the reaction was performed in the same manner as in step 1 of Example 23, and the resultant was then purified by preparative HPLC [10 mM aqueous solution of triethylammonium acetate/acetonitrile, acetonitrile: 20%-40% (0 min-30 min)] to afford the title compound (2.0 mg).

MS(ESI)m/z: 1467 (M+H)+.

$^1$H-NMR (CD$_3$OD) δ: 8.23 (1H, brs), 7.93 (1H, s), 7.54-7.07 (14H, m), 6.23 (1H, d, J=6.7 Hz), 6.05-5.98 (1H, m), 5.41-5.31 (2H, m), 5.00-4.93 (1H, m), 4.73-4.69 (1H, m), 4.41-3.52 (14H, m), 3.44-2.62 (12H, m), 3.08 (12H, q, J=7.3 Hz), 2.38-2.13 (3H, m), 2.02-1.80 (8H, m), 1.19 (18H, t, J=7.3 Hz).

Example 71: Synthesis of Drug-Linker 11

[Synthesis Scheme]

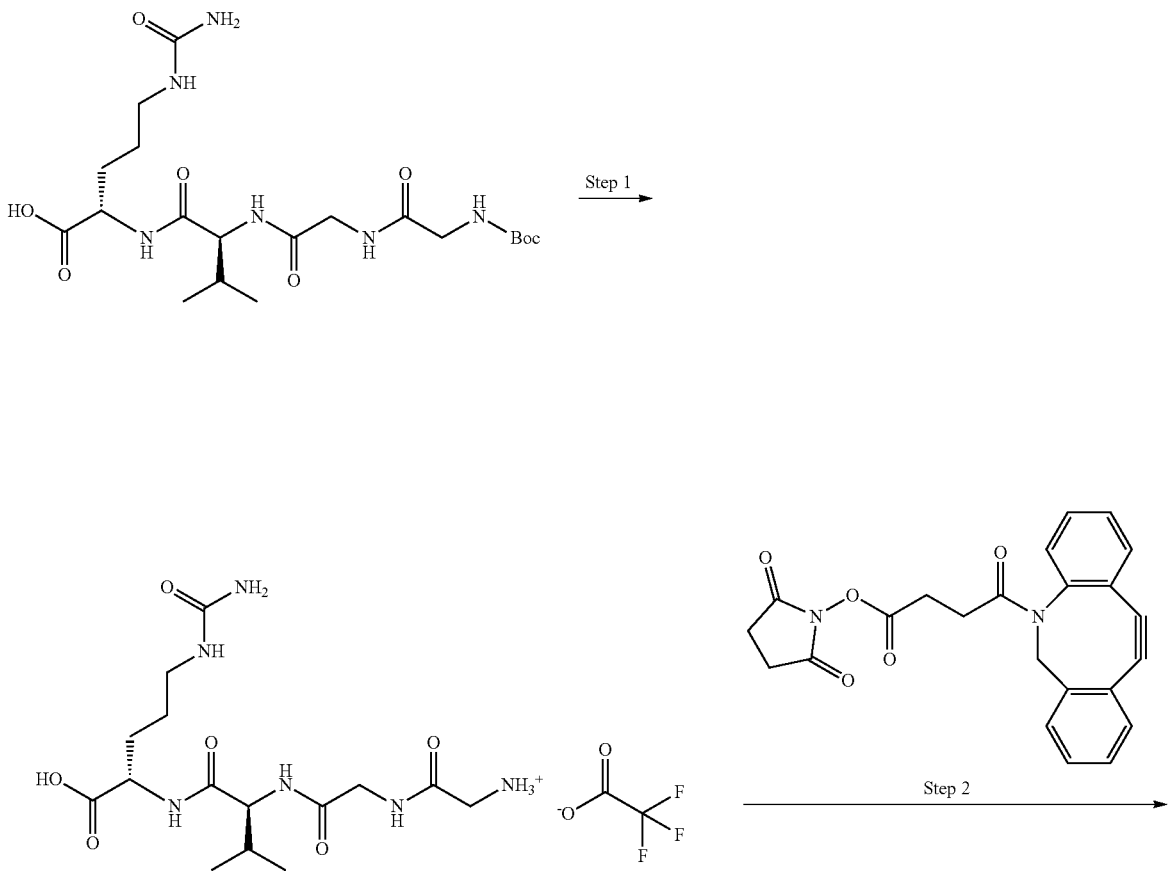

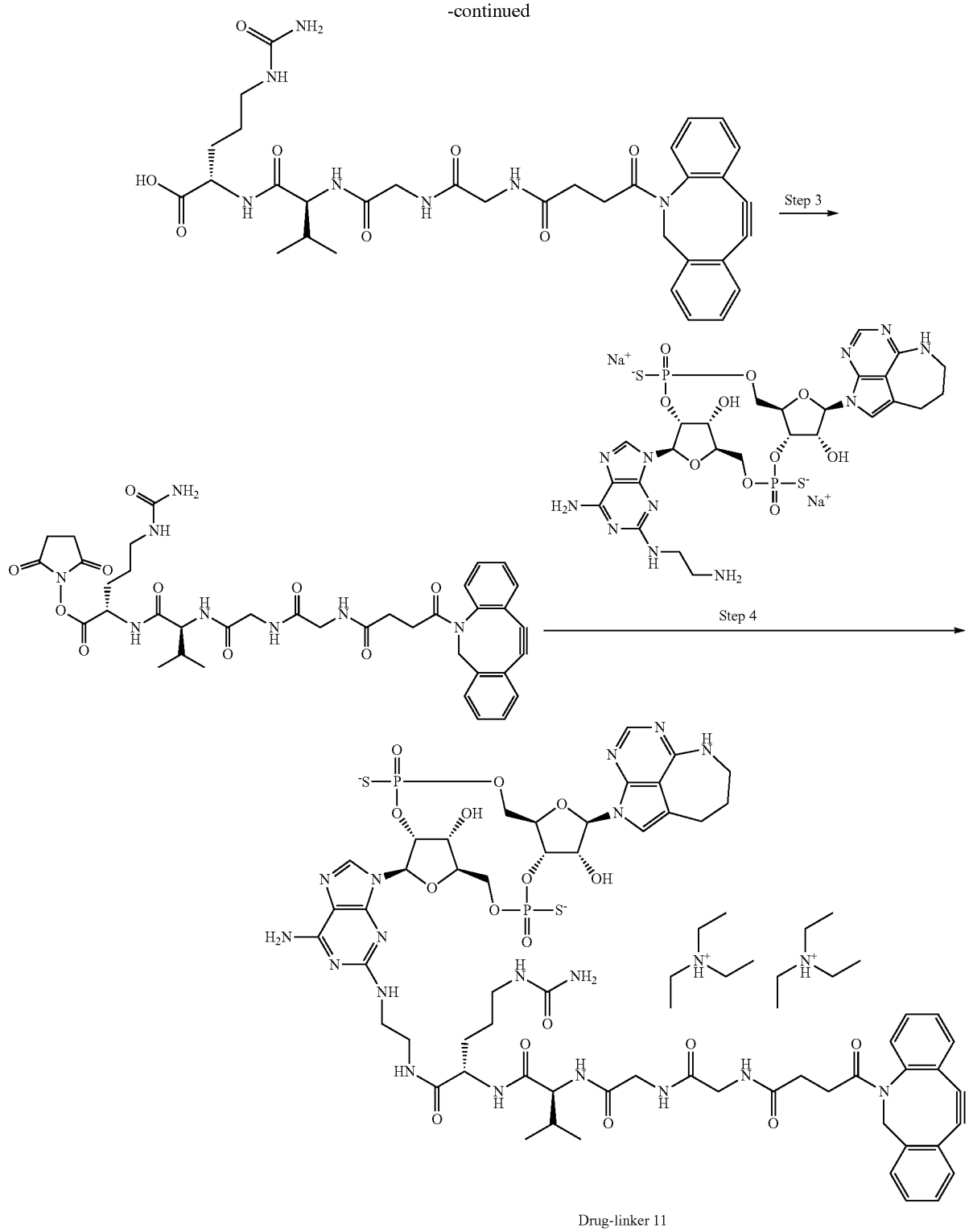

Drug-linker 11

(Step 1)

N-(Azaniumylacetyl)glycyl-L-valyl-N⁵-carbamoyl-L-ornithine trifluoroacetate

With use of commercially available (Hangzhou Peptide Biochem Co., Ltd.) N-(tert-butoxycarbonyl)glycylglycyl-L-valyl-$N^5$-carbamoyl-L-ornithine (1.00 g), the reaction was performed in the same manner as in step 1 of Example 21 to afford a crude form of the title compound (1.02 g).

MS(ESI)m/z: 389 (M+H)⁺.

¹H-NMR (DMSO-$d_6$) δ: 12.52 (1H, brs), 8.55 (1H, t, J=5.4 Hz), 8.29 (1H, d, J=7.3 Hz), 8.03-7.96 (4H, m), 5.97 (1H, brs), 5.40 (1H, brs), 4.26 (1H, t, J=7.8 Hz), 4.11 (1H, m), 3.93-3.85 (2H, m), 3.60 (2H, d, J=5.9 Hz), 2.95 (2H, brs), 1.97 (1H, m), 1.69 (1H, m), 1.56 (1H, m), 1.39 (2H, m), 0.88 (3H, d, J=6.8 Hz), 0.84 (3H, d, J=6.8 Hz). (only observable peaks are shown)
(Step 2)

N-[4-(11,12-Didehydrodibenzo[b,f]azocin-5 (6H)-yl)-4-oxobutanoyl]glycylglycyl-L-valyl-$N^5$-carbamoyl-L-ornithine With use of the compound obtained in step 1 above (1.02 g), the reaction was performed in the same manner as in step 2 of Example 21 to afford the title compound (795 mg).
MS(ESI)m/z: 676 (M+H)$^+$.
$^1$H-NMR (DMSO-d$_6$) δ: 12.49 (1H, s), 8.28-8.22 (1H, m), 8.18 (0.5H, t, J=6.0 Hz), 8.13 (0.5H, t, J=5.7 Hz), 8.06 (0.5H, t, J=5.7 Hz), 8.01 (0.5H, t, J=6.0 Hz), 7.75-7.71 (1H, m), 7.69-7.65 (1H, m), 7.62-7.59 (1H, m), 7.52-7.43 (3H, m), 7.40-7.28 (3H, m), 5.93 (1H, t, J=5.7 Hz), 5.38 (2H, brs), 5.02 (0.5H, d, J=13.9 Hz), 5.01 (0.5H, d, J=13.9 Hz), 4.24 (1H, dd, J=8.8, 7.0 Hz), 4.10 (1H, m), 3.79-3.54 (5H, m), 2.93 (2H, q, J=6.4 Hz), 2.73-2.60 (1H, m), 2.29 (1H, m), 2.09-1.91 (2H, m), 1.79 (1H, m), 1.72-1.63 (1H, m), 1.60-1.50 (1H, m), 1.43-1.33 (2H, m), 0.86 (3H, d, J=6.7 Hz), 0.81 (1.5H, d, J=6.7 Hz), 0.80 (1.5H, d, J=6.7 Hz).
(Step 3)

2,5-Dioxopyrrolidin-1-yl N-[4-(11,12-didehydrodibenzo[b,f]azocin-5 (6H)-yl)-4-oxobutanoyl]glycylglycyl-L-valyl-$N^5$-carbamoyl-L-ornithinate With use of the compound obtained in step 2 above (300 mg), the reaction was performed in the same manner as in step 3 of Example 21 to afford the title compound (177 mg).
MS(ESI)m/z: 773 (M+H)$^+$.
$^1$H-NMR (DMSO-d$_6$) δ: 8.75 (1H, t, J=6.1 Hz), 8.20 (0.5H, t, J=6.1 Hz), 8.15 (0.5H, t, J=5.6 Hz), 8.06 (0.5H, t, J=5.9 Hz), 8.02 (0.5H, t, J=5.9 Hz), 7.83 (0.5H, d, J=8.8 Hz), 7.77 (0.5H, d, J=8.8 Hz), 7.72 (0.5H, d, J=7.8 Hz), 7.67 (0.5H, d, J=6.3 Hz), 7.62-7.59 (1H, m), 7.52-7.44 (3H, m), 7.39-7.29 (3H, m), 6.03 (1H, brs), 5.43 (2H, brs), 5.03 (0.5H, d, J=13.7 Hz), 5.01 (0.5H, d, J=14.2 Hz), 4.59-4.54 (1H, m), 4.25 (1H, m), 3.79-3.68 (5H, m), 2.97 (2H, q, J=6.5 Hz), 2.80 (4H, s), 2.71-2.60 (1H, m), 2.28 (1H, m), 2.10-2.03 (1H, m), 2.00-1.93 (1H, m), 1.88-1.72 (3H, m), 1.54-1.49 (2H, m), 0.85 (3H, d, J=5.4 Hz), 0.81 (1.5H, d, J=4.9 Hz), 0.80 (1.5H, d, J=6.8 Hz).
(Step 4)

Bis(N,N-diethylethaneaminium) N-[4-(11,12-didehydrodibenzo[b,f]azocin-5 (6H)-yl)-4-oxobutanoyl]glycylglycyl-L-valyl-N-[2-({6-amino-9-[(5R,7R,8R,12aR,14R,15R,15aS,16R)-15,16-dihydroxy-2,10-dioxo-2,10-disulfide-14-(6,7,8,9-tetrahydro-2H-2,3,5,6-tetraazabenzo[cd]azulen-2-yl)octahydro-2H,10H,12H-5,8-methano-2$\lambda^5$,10$\lambda^5$-furo[3,2-1][1,3,6,9,11,2,10]pentaoxadiphosphacyclotetradecin-7-yl]-9H-purin-2-yl}amino)ethyl]-$N^5$-carbamoyl-L-ornithinamide (Drug-Linker 11)

With use of the compound obtained in step 8-2 of Example 8 (5.0 mg) and the compound obtained in step 3 above (3.8 mg), the reaction was performed in the same manner as in step 1 of Example 23, and the resultant was then purified by preparative HPLC [10 mM aqueous solution of triethylammonium acetate/acetonitrile, acetonitrile: 20%-35% (0 min-30 min)] to afford the title compound (3.0 mg).
MS(ESI)m/z: 1443 (M–H)$^-$.

Example 72: Synthesis of Drug-Linker 12

[Synthesis Scheme]

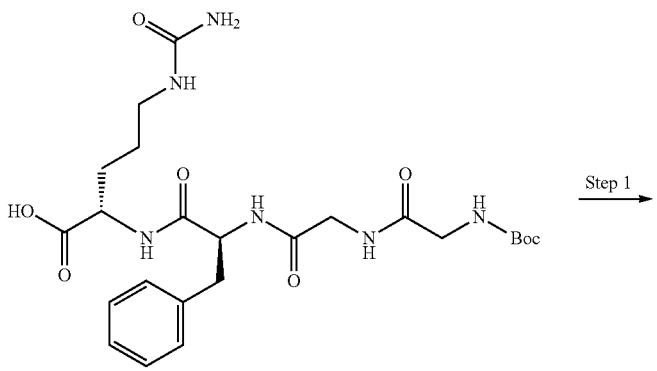

607
608
-continued
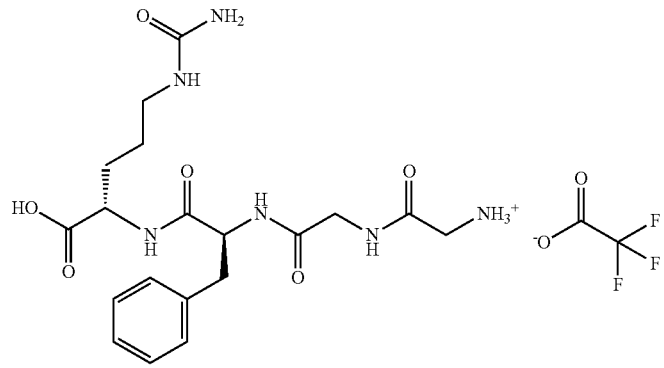
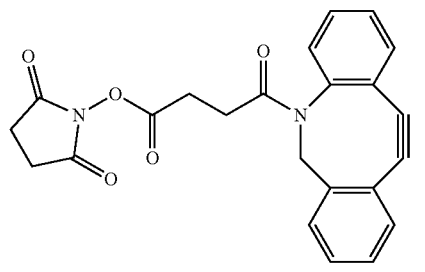
Step 2
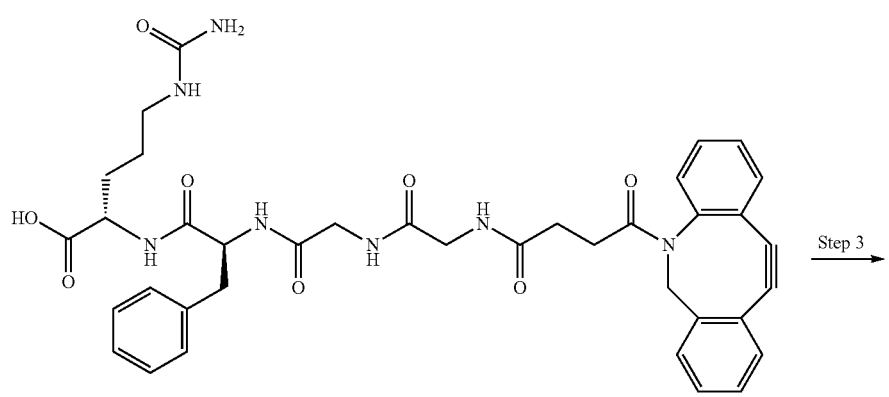
Step 3
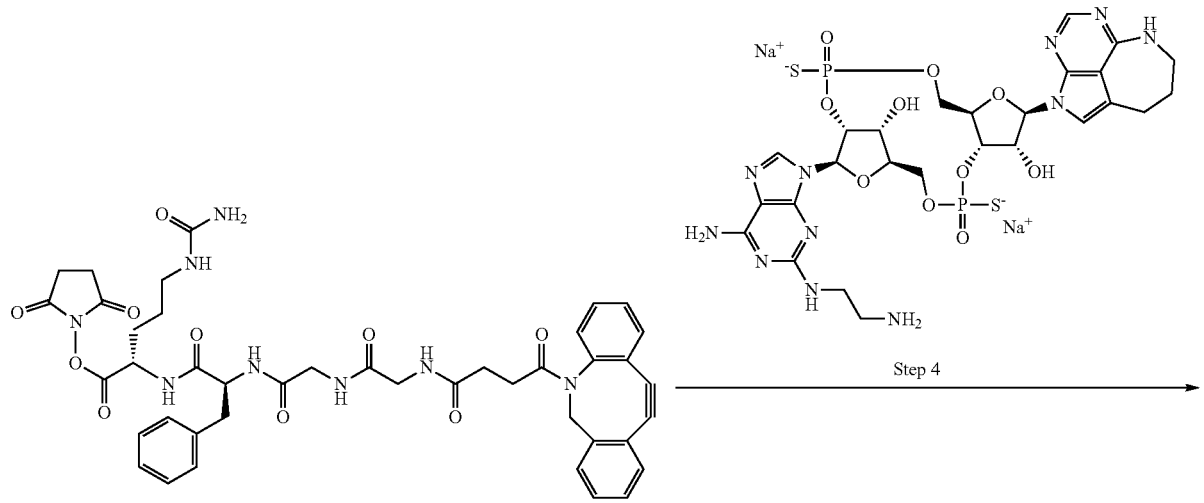
Step 4

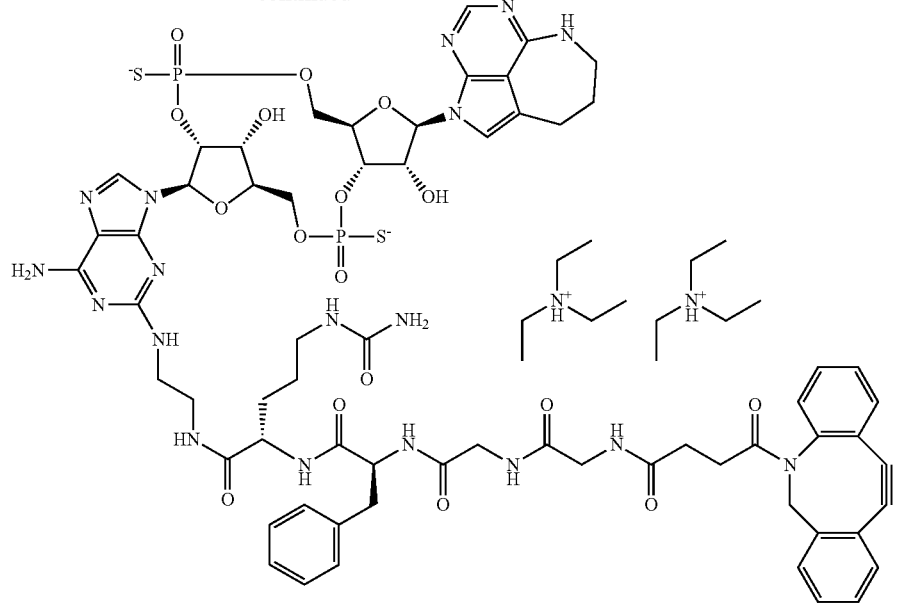

Drug-linker 12

(Step 1)

N-(Azaniumylacetyl)glycyl-L-phenylalanyl-$N^5$-carbamoyl-L-ornithine trifluoroacetate With use of commercially available (Hangzhou Peptide Biochem Co., Ltd.) N-(tert-butoxycarbonyl)glycylglycyl-L-phenylalanyl-$N^5$-carbamoyl-L-ornithine (1.00 g), the reaction was performed in the same manner as in step 1 of Example 21 to afford a crude form of the title compound (1.05 g).

MS(ESI)m/z: 437 (M+H)$^+$.

$^1$H-NMR (DMSO-$d_6$) δ: 12.63 (1H, brs), 8.49 (1H, t, J=5.4 Hz), 8.40 (1H, d, J=7.8 Hz), 8.26 (1H, d, J=8.3 Hz), 7.97 (3H, brs), 7.28-7.17 (5H, m), 6.00 (1H, brs), 5.41 (2H, brs), 4.60 (1H, m), 4.17 (1H, m), 3.85 (1H, dd, J=16.6, 5.4 Hz), 3.67 (1H, dd, J=16.6, 5.4 Hz), 3.56 (2H, d, J=5.9 Hz), 3.03 (1H, dd, J=13.9, 3.7 Hz), 2.96 (2H, brs), 2.73 (1H, dd, J=13.9, 10.5 Hz), 1.73 (1H, m), 1.58 (1H, m), 1.40 (2H, m).

(Step 2)

N-[4-(11,12-Didehydrodibenzo[b,f]azocin-5 (6H)-yl)-4-oxobutanoyl]glycylglycyl-L-phenylalanyl-$N^5$-carbamoyl-L-ornithine With use of the compound obtained in step 1 above (1.05 g), the reaction was performed in the same manner as in step 2 of Example 21 to afford the title compound (550 mg).

MS(ESI)m/z: 724 (M+H)$^+$.

$^1$H-NMR (DMSO-$d_6$) δ: 12.60 (1H, s), 8.29 (1H, t, J=9.1 Hz), 8.17 (0.5H, t, J=5.7 Hz), 8.10 (0.5H, t, J=5.7 Hz), 8.04-7.94 (2H, m), 7.72-7.14 (13H, m), 5.94 (1H, br), 5.39 (2H, s), 5.01 (0.5H, d, J=13.9 Hz), 5.00 (0.5H, d, J=14.5 Hz), 4.56 (1H, m), 4.15 (1H, m), 3.74-3.49 (5H, m), 3.04-2.93 (3H, m), 2.77-2.58 (2H, m), 2.28 (1H, m), 2.05 (1H, m), 1.83-1.70 (2H, m), 1.62-1.52 (1H, m), 1.46-1.32 (2H, m).

(Step 3)

2,5-Dioxopyrrolidin-1-yl N-[4-(11,12-didehydrodibenzo[b,f]azocin-5 (6H)-yl)-4-oxobutanoyl] glycylglycyl-L-phenylalanyl-$N^5$-carbamoyl-L-ornithinate With use of the compound obtained in step 2 above (225 mg), the reaction was performed in the same manner as in step 3 of Example 21 to afford the title compound (226 mg).

MS(ESI)m/z: 821 (M+H)$^+$.

$^1$H-NMR (DMSO-$d_6$) δ: 8.80 (1H, t, J=7.6 Hz), 8.19-7.96 (3H, m), 7.72-7.15 (13H, m), 6.03-5.89 (1H, br), 5.43 (2H, brs), 5.01 (0.5H, d, J=14.0 Hz), 4.99 (0.5H, d, J=14.0 Hz), 4.65-4.53 (2H, m), 3.74-3.50 (5H, m), 3.03-2.95 (3H, m), 2.81 (4H, s), 2.78-2.58 (2H, m), 2.28 (1H, m), 2.07 (1H, m), 1.91-1.73 (3H, m), 1.56-1.49 (2H, m).

(Step 4)

Bis(N,N-diethylethaneaminium) N-[4-(11,12-didehydrodibenzo[b,f]azocin-5 (6H)-yl)-4-oxobutanoyl] glycylglycyl-L-phenylalanyl-N-[2-({6-amino-9-[(5R,7R,8R,12aR,14R,15R,15aS,16R)-15,16-dihydroxy-2,10-dioxo-2,10-disulfide-14-(6,7,8,9-tetrahydro-2H-2,3,5,6-tetraazabenzo[cd]azulen-2-yl) octahydro-2H,10H,12H-5,8-methano-$2\lambda^5,10\lambda^5$-furo [3,2-1][1,3,6,9,11,2,10] pentaoxadiphosphacyclotetradecin-7-yl]-9H-purin-2-yl}amino)ethyl]-$N^5$-carbamoyl-L-ornithinamide (Drug-Linker 12)

With use of the compound obtained in step 8-2 of Example 8 (5.1 mg) and the compound obtained in step 3 above (4.0 mg), the reaction was performed in the same manner as in step 1 of Example 23, and the resultant was then purified by preparative HPLC [10 mM aqueous solution of triethylammonium acetate/acetonitrile, acetonitrile: 20%-35% (0 min-30 min)] to afford the title compound (4.6 mg).

MS(ESI)m/z: 1493 (M+H)$^+$.

$^1$H-NMR (CD$_3$OD) δ: 8.31 (1H, brs), 8.02 (1H, s), 7.62-7.14 (14H, m), 6.32 (1H, d, J=6.0 Hz), 6.11 (1H, brd, J=5.4 Hz), 5.55-5.41 (2H, m), 5.06 (1H, dd, J=13.9, 11.5 Hz), 4.86-2.73 (28H, m), 3.19 (12H, q, J=7.5 Hz), 2.39-2.16 (2H, m), 2.04-1.94 (3H, m), 1.84-1.74 (1H, m), 1.73-1.62 (1H, m), 1.51-1.37 (2H, m), 1.29 (18H, t, J=7.3 Hz).
Example 73: Synthesis of Drug-Linker 13
[Synthesis Scheme]
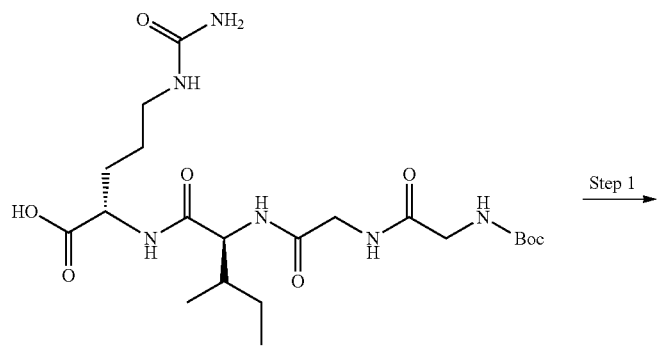
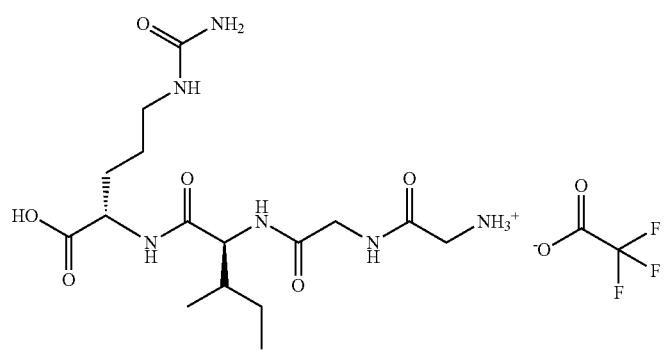
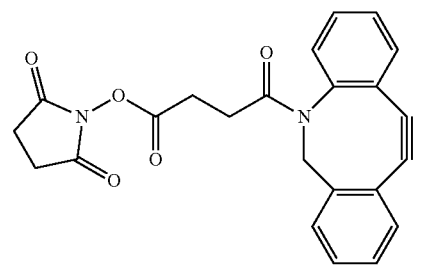
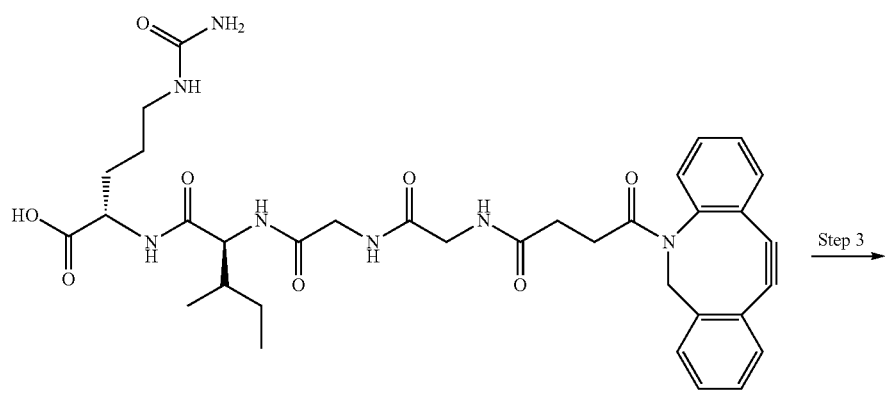

-continued

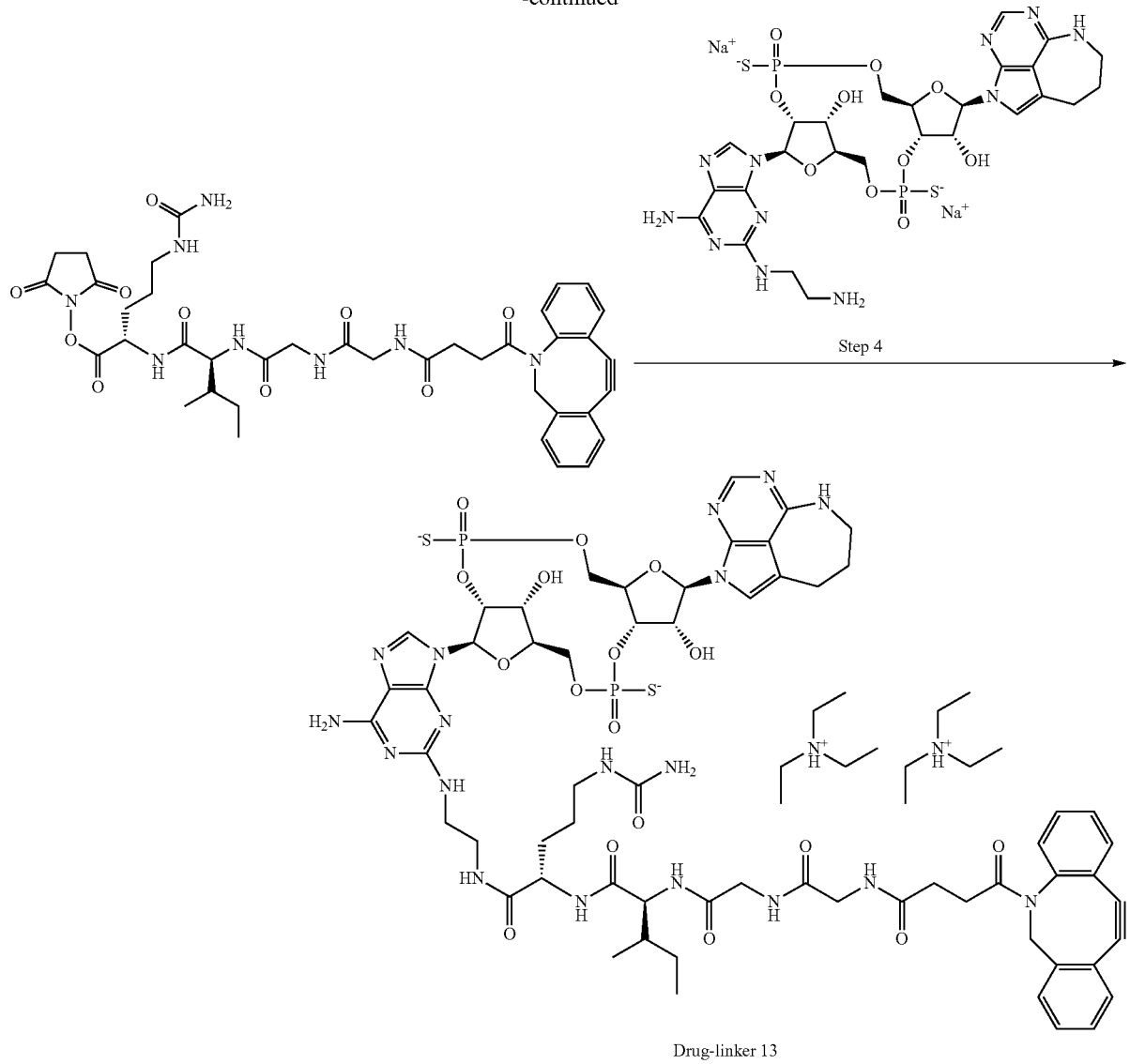

Drug-linker 13

(Step 1)

N-(Azaniumylacetyl)glycyl-L-isoleucyl-$N^5$-carbamoyl-L-ornithine trifluoroacetate With use of commercially available (Hangzhou Peptide Biochem Co., Ltd.) N-(tert-butoxycarbonyl)glycylglycyl-L-isoleucyl-$N^5$-carbamoyl-L-ornithine (1.00 g), the reaction was performed in the same manner as in step 1 of Example 21 to afford a crude form of the title compound (1.09 g).

MS(ESI)m/z: 403 (M+H)$^+$.

$^1$H-NMR (DMSO-d$_6$) δ: 8.54 (1H, t, J=5.4 Hz), 8.30 (1H, d, J=7.3 Hz), 8.03 (1H, d, J=9.3 Hz), 7.99 (3H, brs), 5.99 (1H, brs), 4.27 (1H, t, J=8.1 Hz), 4.11 (1H, m), 3.92-3.83 (2H, m), 3.60 (2H, m), 2.95 (2H, m), 1.71 (2H, m), 1.56 (1H, m), 1.48-1.33 (3H, m), 1.08 (1H, m), 0.86 (3H, d, J=6.8 Hz), 0.81 (3H, t, J=7.3 Hz). (only observable peaks are shown)

(Step 2)

N-[4-(11,12-Didehydrodibenzo[b,f]azocin-5 (6H)-yl)-4-oxobutanoyl]glycylglycyl-L-isoleucyl-$N^5$-carbamoyl-L-ornithine With use of the compound obtained in step 1 above (1.08 g), the reaction was performed in the same manner as in step 2 of Example 21 to afford the title compound (524 mg).

MS(ESI)m/z: 690 (M+H)$^+$.

$^1$H-NMR (DMSO-d$_6$) δ: 12.47 (1H, brs), 8.25 (1H, t, J=6.0 Hz), 8.17 (0.5H, t, J=5.7 Hz), 8.12 (0.5H, t, J=6.0 Hz), 8.04 (0.5H, t, J=6.0 Hz), 7.99 (0.5H, t, J=6.0 Hz), 7.76-7.66 (2H, m), 7.62-7.59 (1H, m), 7.52-7.29 (6H, m), 5.92 (1H, t, J=5.4 Hz), 5.38 (2H, s), 5.02 (0.5H, d, J=14.5 Hz), 5.01 (0.5H, d, J=13.9 Hz), 4.25 (1H, t, J=8.2 Hz), 4.09 (1H, m), 3.78-3.54 (5H, m), 2.93 (2H, q, J=6.4 Hz), 2.73-2.59 (1H, m), 2.33-2.24 (1H, m), 2.10-2.02 (1H, m), 1.79 (1H, ddd, J=16.6, 7.3, 5.7 Hz), 1.74-1.63 (2H, m), 1.60-1.50 (1H, m), 1.45-1.33 (3H, m), 1.09-1.00 (1H, m), 0.84 (3H, d, J=6.7 Hz), 0.79 (1.5H, t, J=6.7 Hz), 0.77 (1.5H, t, J=7.0 Hz).

(Step 3)

2,5-Dioxopyrrolidin-1-yl N-[4-(11,12-didehydrodibenzo[b,f]azocin-5 (6H)-yl)-4-oxobutanoyl]glycylglycyl-L-isoleucyl-$N^5$-carbamoyl-L-ornithinate With use of the compound obtained in step 2 above (250 mg), the reaction was performed in the same manner as in step 3 of Example 21 to afford the title compound (224 mg).

MS(ESI)m/z: 787 (M+H)$^+$.

$^1$H-NMR (DMSO-d$_6$) δ: 8.75 (1H, t, J=6.4 Hz), 8.19 (0.5H, t, J=5.8 Hz), 8.14 (0.5H, t, J=5.8 Hz), 8.06 (0.5H, t, J=5.8 Hz), 8.01 (0.5H, t, J=5.8 Hz), 7.89-7.65 (2H, m), 7.63-7.58 (1H, m), 7.53-7.27 (6H, m), 5.96 (1H, m), 5.42 (2H, brs), 5.02 (0.5H, d, J=14.0 Hz), 5.01 (0.5H, d, J=14.0 Hz), 4.64-4.51 (1H, m), 4.26 (1H, t, J=8.2 Hz), 3.79-3.55 (5H, m), 3.01-2.93 (2H, m), 2.80 (4H, brs), 2.73-2.58 (1H, m), 2.28 (1H, m), 2.12-2.02 (1H, m), 1.87-1.68 (4H, m), 1.54-1.38 (3H, m), 1.11-1.02 (1H, m), 0.83 (3H, d, J=6.7 Hz), 0.78 (1.5H, t, J=6.7 Hz), 0.76 (1.5H, t, J=6.7 Hz).

(Step 4)

Bis(N,N-diethylethaneaminium) N-[4-(11,12-didehydrodibenzo[b,f]azocin-5 (6H)-yl)-4-oxobutanoyl]glycylglycyl-L-isoleucyl-N-[2-({6-amino-9-[(5R,7R,8R,12aR,14R,15R,15aS,16R)-15,16-dihydroxy-2,10-dioxo-2,10-disulfide-14-(6,7,8,9-tetrahydro-2H-2,3,5,6-tetraazabenzo[cd]azulen-2-yl)octahydro-2H,10H,12H-5,8-methano-2λ$^5$,10λ$^5$-furo[3,2-l][1,3,6,9,11,2,10]pentaoxadiphosphacyclotetradecin-7-yl]-9H-purin-2-yl}amino)ethyl]-$N^5$-carbamoyl-L-ornithinamide (Drug-Linker 13)

With use of the compound obtained in step 8-2 of Example 8 (5.4 mg) and the compound obtained in step 3 above (4.0 mg), the reaction was performed in the same manner as in step 1 of Example 23, and the resultant was then purified by preparative HPLC [10 mM aqueous solution of triethylammonium acetate/acetonitrile, acetonitrile: 20%-35% (0 min-30 min)] to afford the title compound (4.7 mg).

MS(ESI)m/z: 1457 (M−H)$^−$.

Example 74: Synthesis of Drug-Linker 14

[Synthesis Scheme]

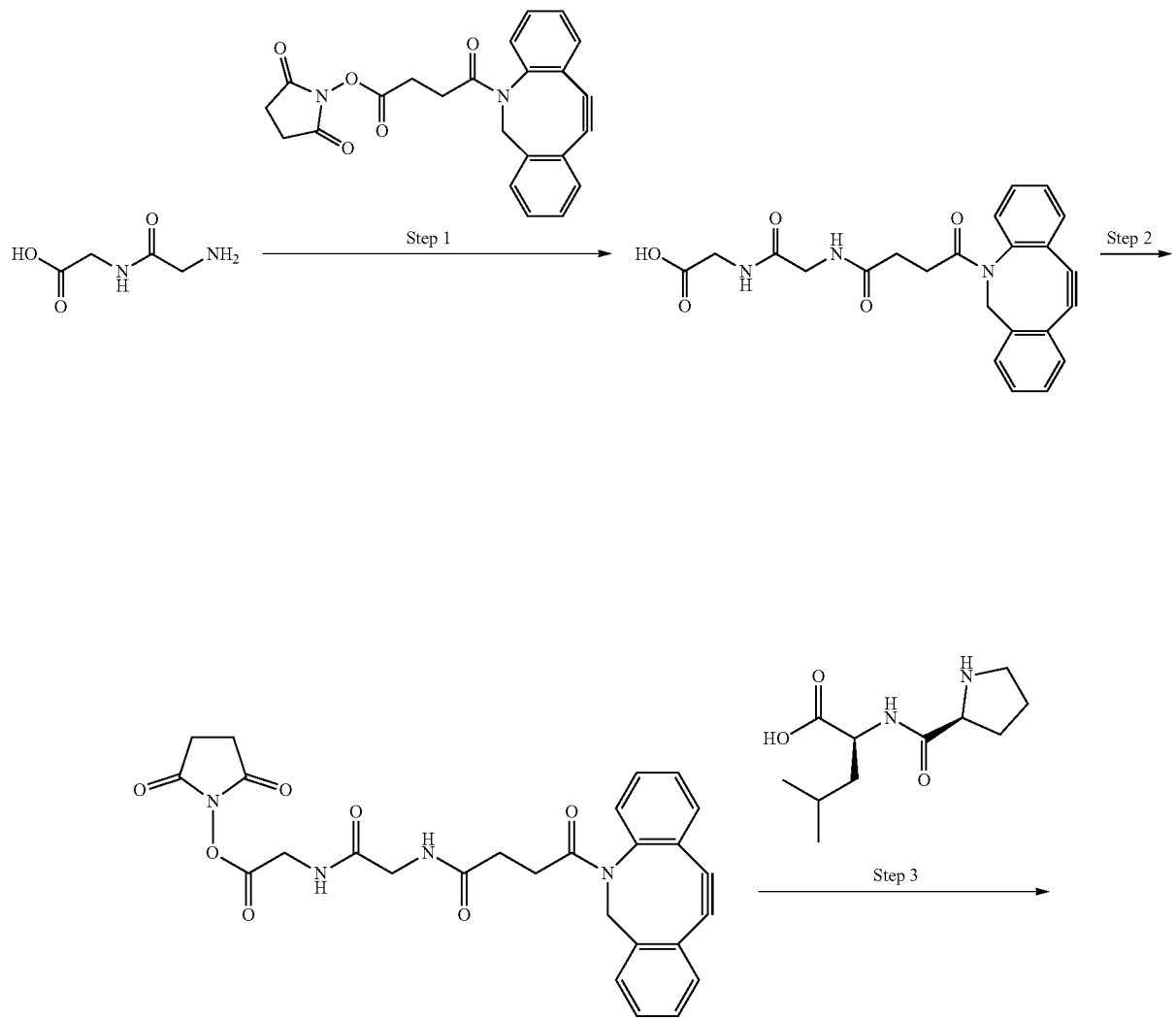

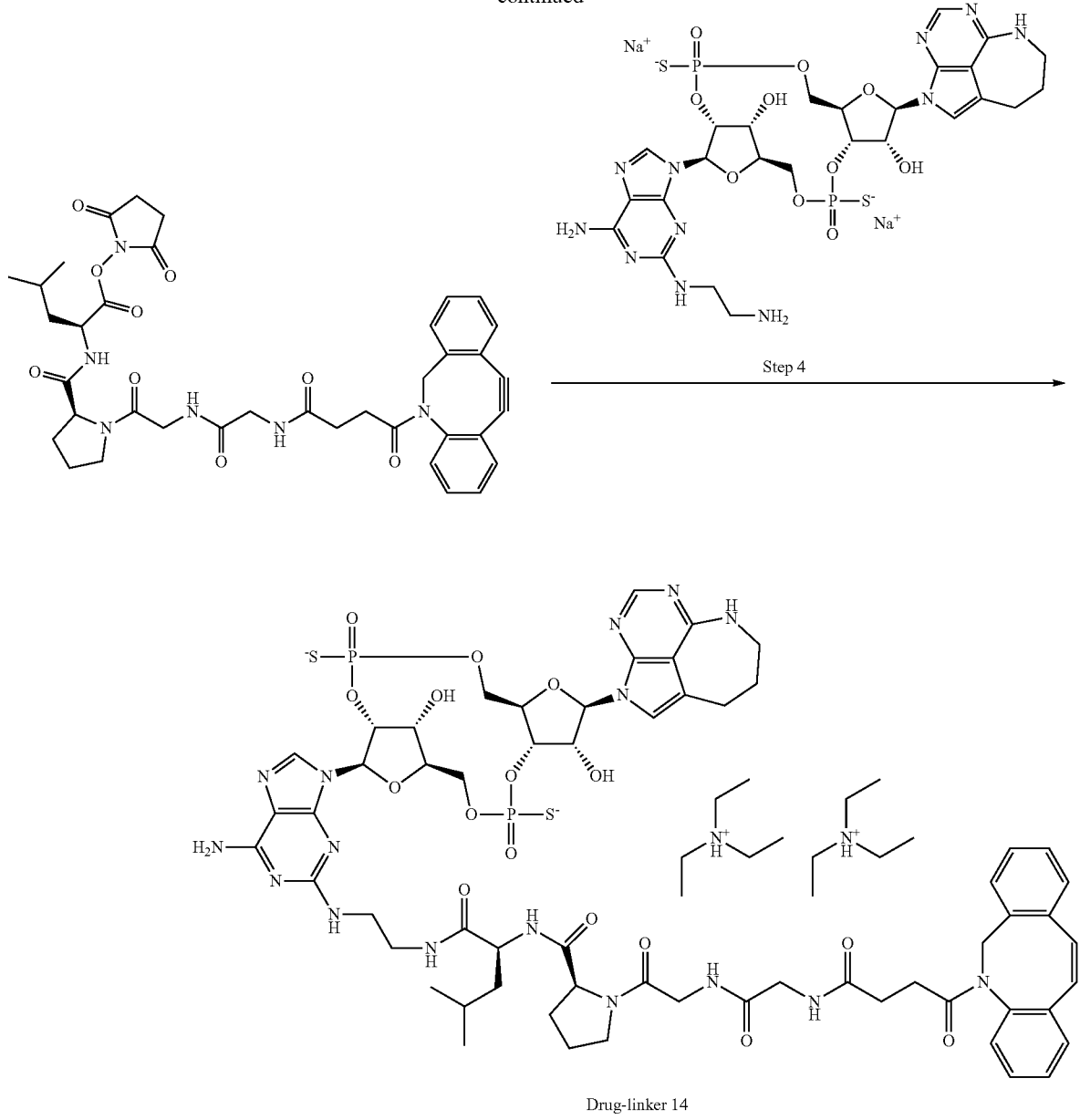

Drug-linker 14

(Step 1)

N-[4-(11,12-Didehydrodibenzo[b,f]azocin-5 (6H)-yl)-4-oxobutanoyl]glycylglycine

With use of commercially available (Tokyo Chemical Industry Co., Ltd.) glycylglycine (0.61 g), the reaction was performed in the same manner as in step 2 of Example 21 to afford the title compound (1.08 g).

MS(ESI)m/z: 420 (M+H)$^+$.

$^1$H-NMR (DMSO-d$_6$) δ: 12.57 (1H, s), 8.12 (1H, t, J=6.0 Hz), 8.07 (1H, t, J=5.7 Hz), 7.69-7.67 (1H, m), 7.62-7.60 (1H, m), 7.52-7.29 (6H, m), 5.03 (1H, d, J=13.9 Hz), 3.73 (2H, d, J=6.0 Hz), 3.70-3.55 (3H, m), 2.64 (1H, m), 2.28 (1H, m), 2.06 (1H, ddd, J=15.3, 7.7, 5.6 Hz), 1.79 (1H, ddd, J=16.5, 7.4, 5.6 Hz).

(Step 2)

2,5-Dioxopyrrolidin-1-yl N-[4-(11,12-didehydrodibenzo[b,f]azocin-5 (6H)-yl)-4-oxobutanoyl] glycylglycinate With use of the compound obtained in step 1 above (1.07 g), the reaction was performed in the same manner as in step 3 of Example 21 to afford the title compound (942 mg).

MS(ESI)m/z: 517 (M+H)$^+$.

$^1$H-NMR (DMSO-d$_6$) δ: 8.40 (1H, t, J=6.0 Hz), 8.19 (1H, t, J=6.0 Hz), 7.69-7.67 (1H, m), 7.64-7.62 (1H, m), 7.53-7.29 (6H, m), 5.05 (1H, d, J=14.5 Hz), 4.26 (1H, dd, J=18.1, 6.0 Hz), 4.19 (1H, dd, J=18.1, 6.0 Hz), 3.72-3.59 (3H, m), 2.81 (4H, brs), 2.68-2.59 (1H, m), 2.33-2.24 (1H, m), 2.07 (1H, ddd, J=15.4, 7.6, 5.7 Hz), 1.80 (1H, ddd, J=16.3, 7.3, 5.4 Hz).

(Step 3)

2,5-Dioxopyrrolidin-1-yl N-[4-(11,12-didehydrodibenzo[b,f]azocin-5 (6H)-yl)-4-oxobutanoyl]glycylglycyl-L-prolyl-L-leucinate To a suspension of the compound obtained in step 2 above (250 mg) and commercially available (KOKUSAN CHEMICAL Co., Ltd.) and L-prolyl-L-leucine (166 mg) in N,N-dimethylformamide (5.0 mL), N,N-diisopropylethylamine (0.25 mL) was added, and the reaction mixture was stirred at room temperature for 2.5 hours. Thereto, L-prolyl-L-leucine (833 mg) was further added, and the reaction mixture was stirred overnight. After the reaction mixture was concentrated under reduced pressure, chloroform (50 mL) and 10% aqueous solution of citric acid (10 mL) were added to the residue, and the resultant was subjected to extraction with chloroform. The organic layer was concentrated under reduced pressure, and the residue was partially purified by silica gel column chromatography [chloroform/lower layer of (chloroform:methanol:water=7:3:1)]. To a solution of the crude product in N,N-dimethylformamide (5.0 mL), N-hydroxysuccinimide (67 mg) and 1-ethyl-3-(3-dimethylaminopropyl)-carbodiimide hydrochloride (111 mg) were added, and the reaction mixture was stirred at room temperature for 1.5 hours. The reaction mixture was concentrated under reduced pressure, chloroform (40 mL) and water (15 mL) were added to the residue, and the resultant was subjected to extraction with chloroform. After the organic layer was dried over anhydrous sodium sulfate, the drying agent was removed through filtration, and the filtrate was concentrated under reduced pressure. The residue was purified by silica gel column chromatography [chloroform/methanol], [ethyl acetate/methanol] in this order to afford the title compound (127 mg).

MS(ESI)m/z: 727 (M+H)$^+$.

$^1$H-NMR (DMSO-d$_6$) δ: 8.85 (0.3H, m), 8.56 (0.5H, d, J=7.3 Hz), 8.33 (0.2H, m), 8.09 (1H, m), 7.91-7.79 (1H, m), 7.70-7.28 (8H, m), 5.04 (0.7H, d, J=14.5), 5.03 (0.3H, d, J=13.9), 4.71-4.29 (2H, m), 4.01-3.30 (7H, m), 2.79 (4H, brs), 2.63 (1H, m), 2.33-1.64 (10H, m), 0.93-0.83 (6H, m).

(Step 4)

Bis(N,N-diethylethaneaminium) N-[4-(11,12-didehydrodibenzo[b,f]azocin-5 (6H)-yl)-4-oxobutanoyl]glycylglycyl-L-prolyl-N-[2-({6-amino-9-[(5R,7R,8R,12aR,14R,15R,15aS,16R)-15,16-dihydroxy-2,10-dioxo-2,10-disulfide-14-(6,7,8,9-tetrahydro-2H-2,3,5,6-tetraazabenzo[cd]azulen-2-yl)octahydro-2H,10H,12H-5,8-methano-2λ$^5$,10λ$^5$-furo[3,2-l][1,3,6,9,11,2,10]pentaoxadiphosphacyclotetradecin-7-yl]-9H-purin-2-yl}amino)ethyl]-L-isoleucinamide (Drug-Linker 14)

With use of the compound obtained in step 8-2 of Example 8 (6.9 mg) and the compound obtained in step 3 above (4.7 mg), the reaction was performed in the same manner as in step 1 of Example 23, and the resultant was then purified by preparative HPLC [10 mM aqueous solution of triethylammonium acetate/acetonitrile, acetonitrile: 20%-40% (0 min-30 min)] to afford the title compound (7.2 mg).

MS(ESI)m/z: 1397 (M−H)$^−$.

Example 75: Synthesis of Drug-Linker 15

[Synthesis Scheme]

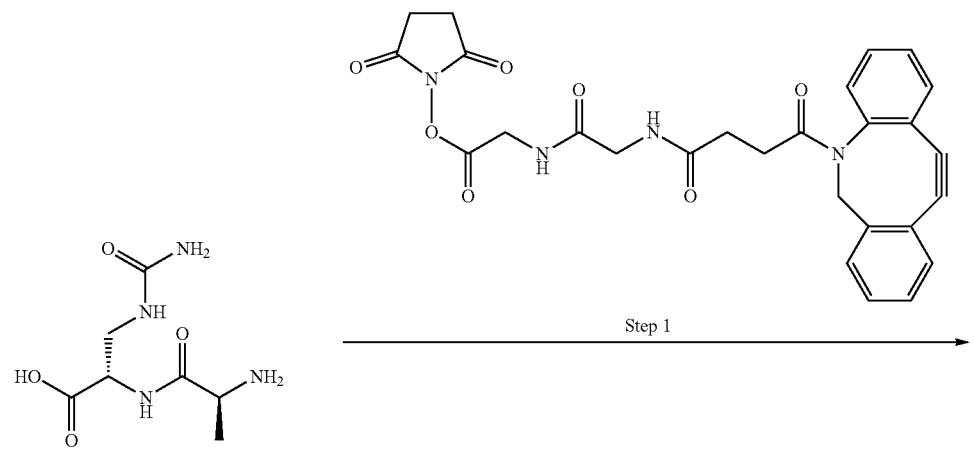

-continued

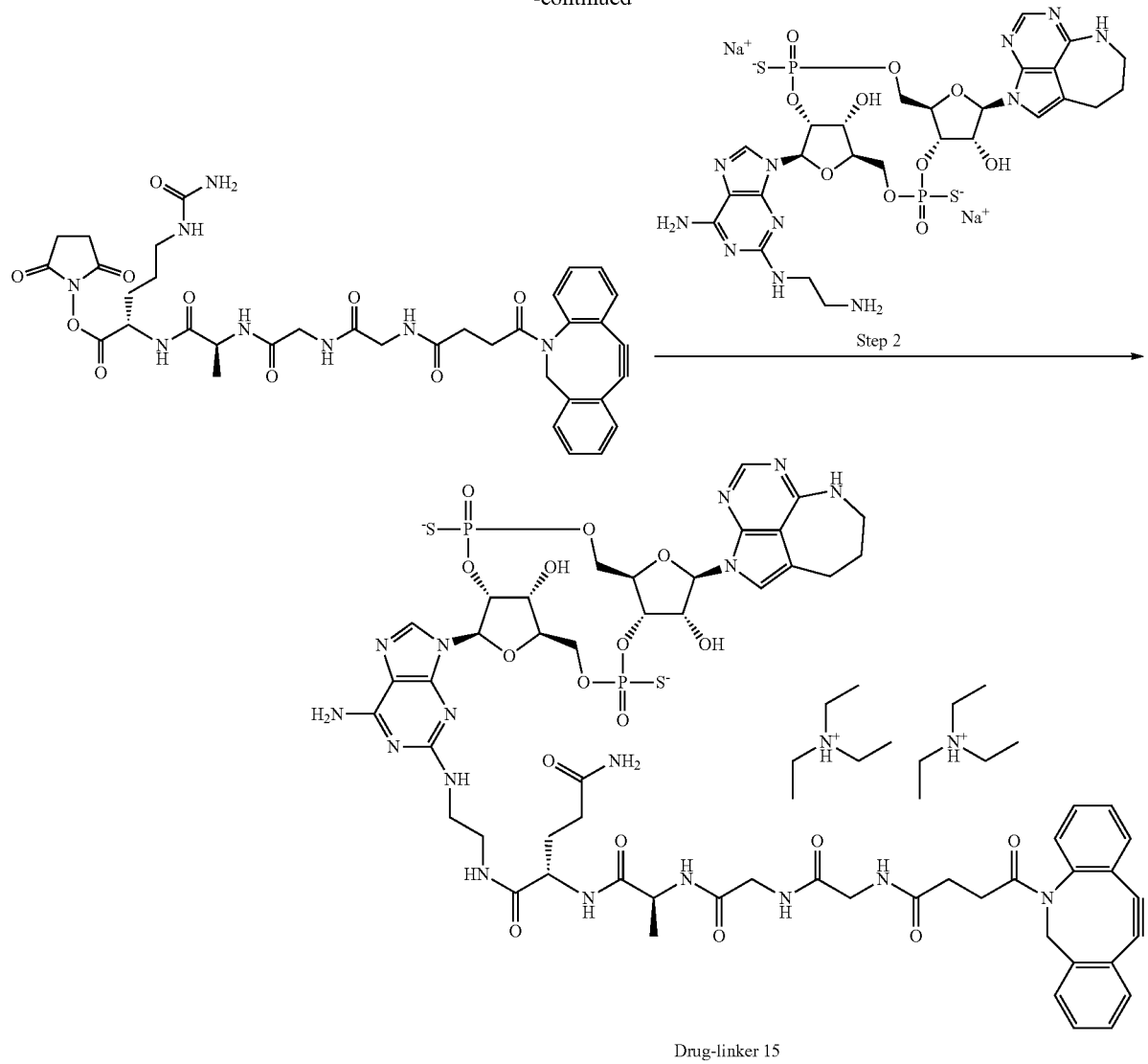

Drug-linker 15

(Step 1)

2,5-Dioxopyrrolidin-1-yl N-[4-(11,12-didehydrod-ibenzo[b,f]azocin-5 (6H)-yl)-4-oxobutanoyl] glycylglycyl-L-alanyl-L-glutaminate With use of commercially available (Wako Pure Chemical Industries, Ltd.) L-alanyl-L-glutamine (263 mg) and the compound obtained in step 2 of Example 74 (250 mg), the reaction was performed in the same manner as in step 3 of Example 74 to afford the title compound (90 mg).

MS(ESI)m/z: 716 (M+H)$^+$.

$^1$H-NMR (DMSO-d$_6$) δ: 8.59 (0.8H, d, J=7.3 Hz), 8.48 (0.2H, m), 8.20-7.92 (3H, m), 7.70-7.25 (9H, m), 6.85 (1H, brs), 5.02 (1H, d, J=13.9 Hz), 4.62 (1H, m), 4.33 (1H, m), 3.75-3.56 (5H, m), 2.80 (4H, brs), 2.64 (1H, m), 2.33-2.21 (3H, m), 2.15-2.03 (2H, m), 1.99-1.87 (1H, m), 1.83-1.76 (1H, m), 1.24-1.17 (3H, m).

(Step 2)

Bis(N,N-diethylethaneaminium) N-[4-(11,12-dide-hydrodibenzo[b,f]azocin-5 (6H)-yl)-4-oxobutanoyl] glycylglycyl-L-alanyl-N$^1$-[2-({6-amino-9-[(5R,7R,8R,12aR,14R,15R,15aS,16R)-15,16-dihydroxy-2,10-dioxo-2,10-disulfide-14-(6,7,8,9-tetrahydro-2H-2,3,5,6-tetraazabenzo[cd]azulen-2-yl)octahydro-2H,10H,12H-5,8-methano-2λ$^5$,10λ$^5$-furo[3,2-l][1,3,6,9,11,2,10]pentaoxadiphosphacyclotetradecin-7-yl]-9H-purin-2-yl}amino)ethyl]-L-glutamamide (Drug-Linker 15)

With use of the compound obtained in step 8-2 of Example 8 (6.9 mg) and the compound obtained in step 1 above (4.7 mg), the reaction was performed in the same manner as in step 1 of Example 23, and the resultant was then purified by preparative HPLC [10 mM aqueous solution of triethylammonium acetate/acetonitrile, acetonitrile: 20%-40% (0 min-30 min)] to afford the title compound (3.9 mg).

MS(ESI)m/z: 1388 (M+H)$^+$.

$^1$H-NMR (CD$_3$OD) δ: 8.38-8.35 (1H, m), 8.02 (1H, s), 7.66-7.13 (9H, m), 6.33 (1H, d, J=6.7 Hz), 6.14-6.10 (1H, m), 5.51-5.42 (2H, m), 5.14-5.06 (1H, m), 4.84-4.79 (1H, m), 4.53-3.64 (14H, m), 3.56-3.11 (6H, m), 3.15 (12H, q, J=7.5 Hz), 2.92-2.69 (4H, m), 2.42-1.93 (8H, m), 1.45-1.24 (3H, m), 1.27 (18H, t, J=7.3 Hz).
Example 76: Synthesis of Drug-Linker 16
[Synthesis Scheme]
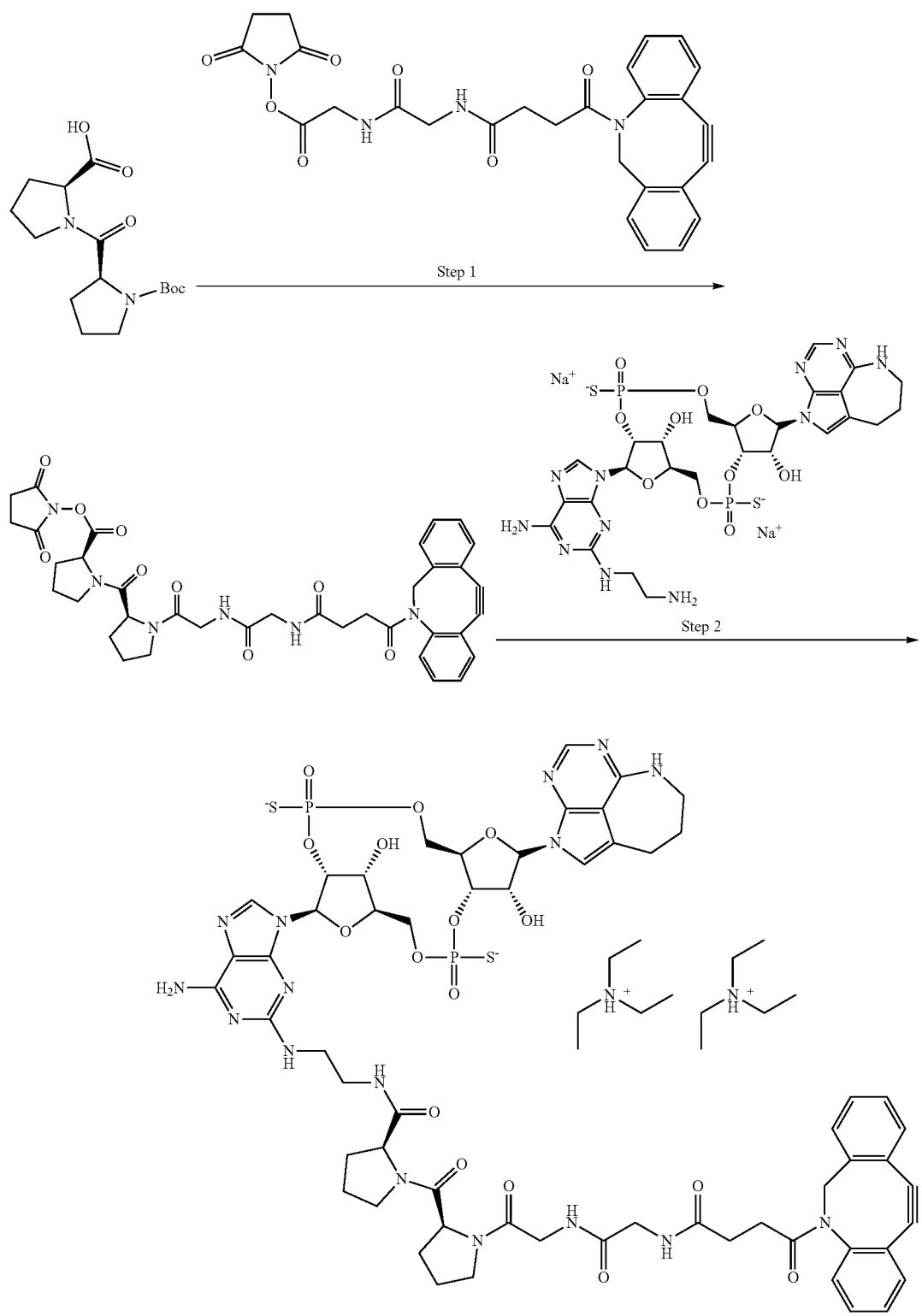
Drug-linker 16

(Step 1)

2,5-Dioxopyrrolidin-1-yl N-[4-(11,12-didehydrodibenzo[b,f]azocin-5 (6H)-yl)-4-oxobutanoyl]glycylglycyl-L-prolyl-L-prolinate With use of commercially available (Cool Pharm Ltd.)$_1$-(tert-butoxycarbonyl)-L-prolyl-L-proline (777 mg), the reaction was performed in the same manner as in step 1 of Example 21 to afford a crude form of 1-[(2S)-pyrrolidin-1-ium-2-carbonyl]-L-proline trifluoroacetate. With use of this crude product and the compound obtained in step 2 of Example 74 (428 mg), the reaction was performed in the same manner as in step 3 of Example 74 to afford the title compound (238 mg).

MS(ESI)m/z: 711 (M+H)$^+$.

$^1$H-NMR (DMSO-d$_6$) δ: 8.12-8.08 (1H, m), 7.90 (0.2H, s), 7.82 (0.8H, d, J=4.8 Hz), 7.70-7.61 (2H, m), 7.52-7.29 (6H, m), 5.07-5.01 (1H, m), 4.88-4.86 (0.2H, m), 4.77-4.74 (0.2H, m), 4.69-4.62 (0.8H, m), 4.60-4.56 (0.8H, m), 4.02-3.38 (9H, m), 2.79 (4H, brs), 2.68-2.58 (1H, m), 2.37-2.24 (2H, m), 2.16-1.73 (9H, m).

(Step 2)

Bis(N,N-diethylethaneaminium) N-[4-(11,12-didehydrodibenzo[b,f]azocin-5 (6H)-yl)-4-oxobutanoyl]glycylglycyl-L-prolyl-N-[2-({6-amino-9-[(5R,7R,8R,12aR,14R,15R,15aS,16R)-15,16-dihydroxy-2,10-dioxo-2,10-disulfide-14-(6,7,8,9-tetrahydro-2H-2,3,5,6-tetraazabenzo[cd]azulen-2-yl)octahydro-2H,10H,12H-5,8-methano-2λ$^5$,10λ$^5$-furo[3,2-l][1,3,6,9,11,2,10]pentaoxadiphosphacyclotetradecin-7-yl]-9H-purin-2-yl}amino)ethyl]-L-prolinamide (Drug-Linker 16)

With use of the compound obtained in step 8-2 of Example 8 (6.9 mg) and the compound obtained in step 1 above (4.6 mg), the reaction was performed in the same manner as in step 1 of Example 23, and the resultant was then purified by preparative HPLC [10 mM aqueous solution of triethylammonium acetate/acetonitrile, acetonitrile: 20%-40% (0 min-30 min)] to afford the title compound (5.8 mg).

MS(ESI)m/z: 1383 (M+H)$^+$.

Example 77: Synthesis of Drug-Linker 17

[Synthesis Scheme]

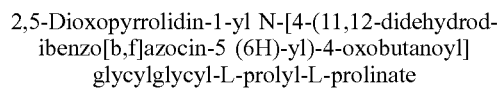

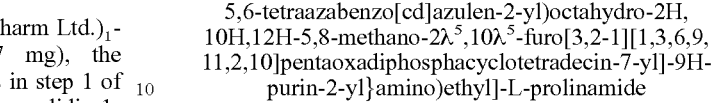

-continued
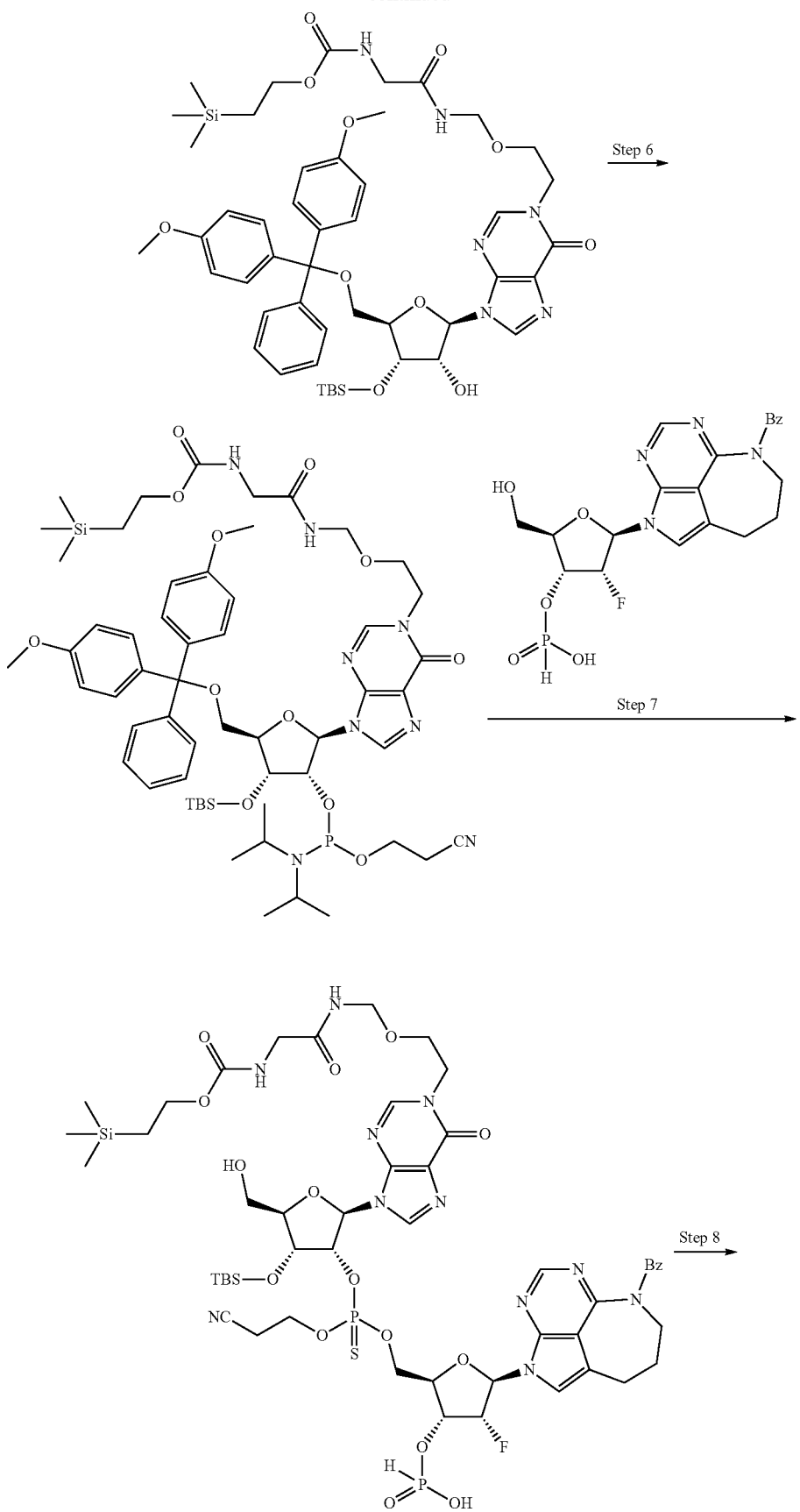

-continued
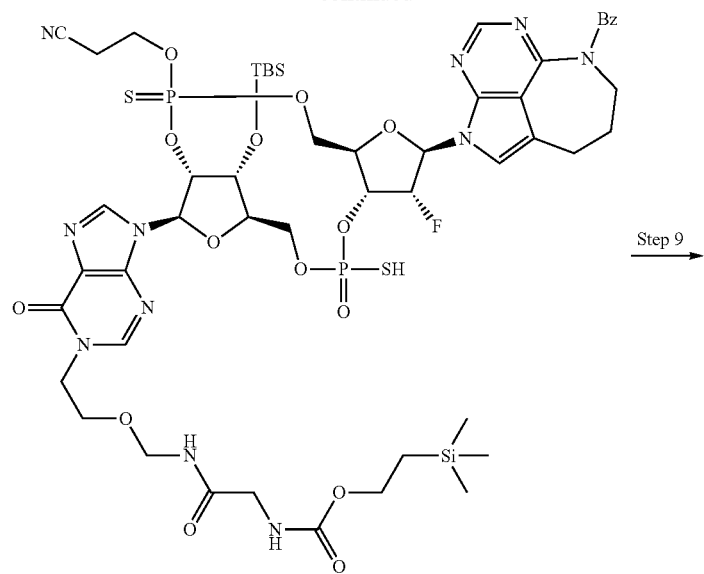
Step 9
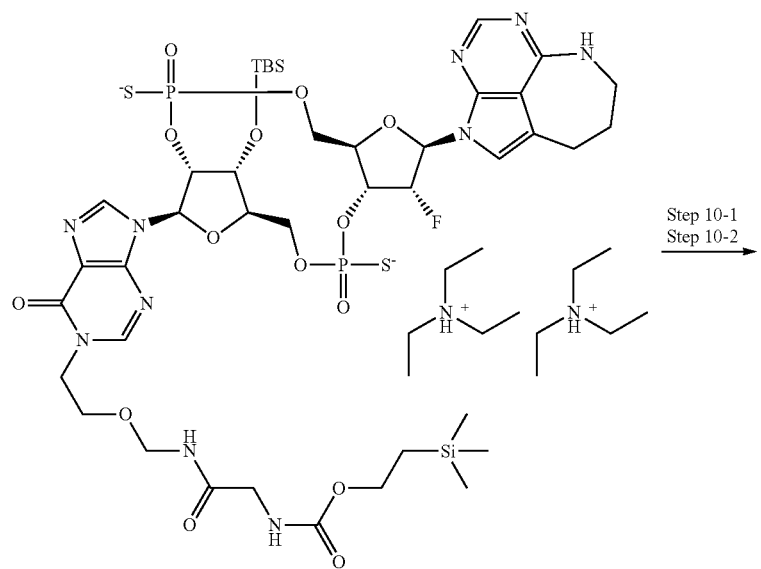
Step 10-1
Step 10-2
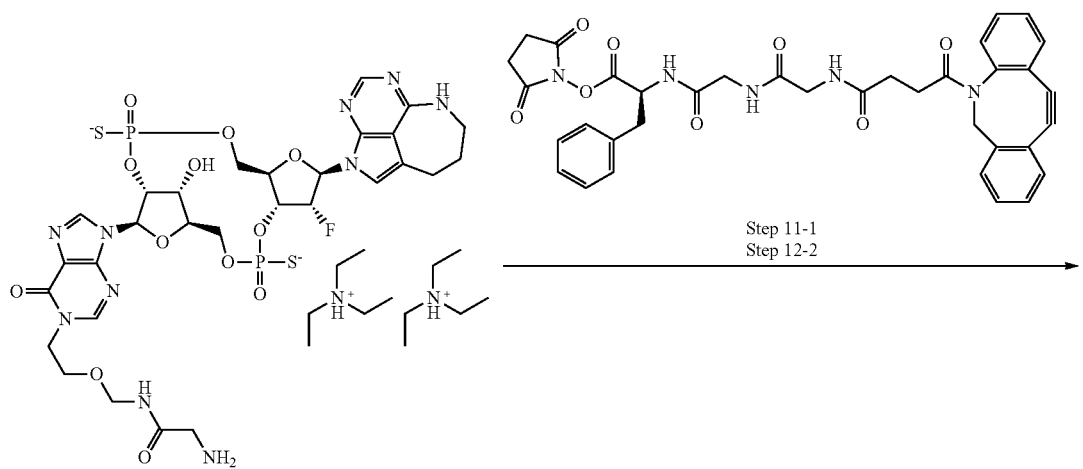
Step 11-1
Step 12-2

-continued

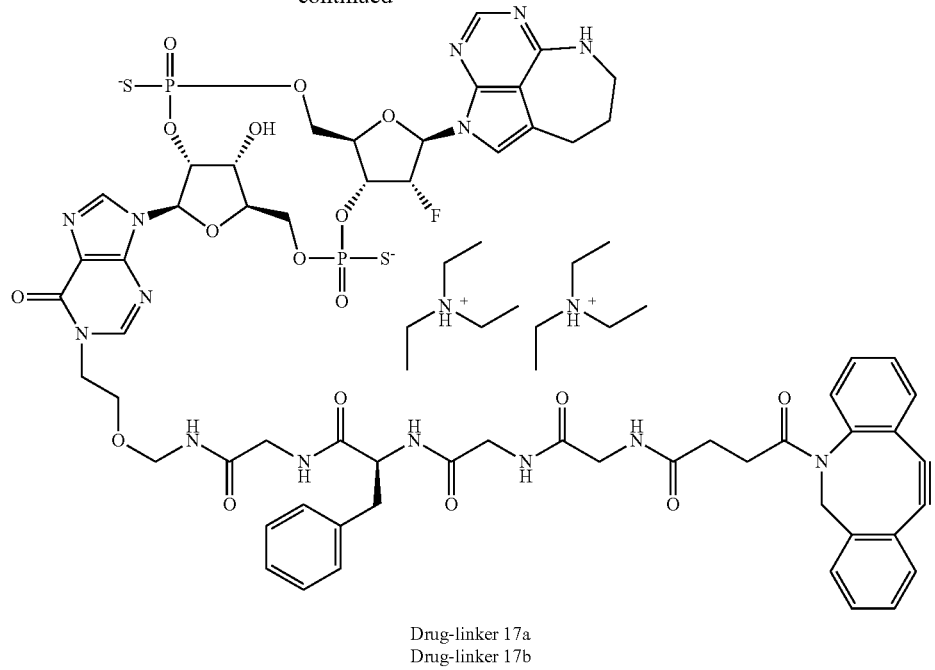

Drug-linker 17a
Drug-linker 17b (Step 1)

[(N-{[2-(Trimethylsilyl)ethoxy]carbonyl}glycyl)amino]methyl acetate

With use of commercially available (Sundia) N-{[2-(trimethylsilyl)ethoxy]carbonyl}glycylglycine (9.32 g), the reaction was performed in the same manner as in step 1 of Example 67 to afford the title compound (8.24 g).

$^1$H-NMR (CDCl$_3$) δ: 7.14 (1H, brs), 5.27 (2H, d, J=7.3 Hz), 5.20 (1H, brs), 4.22-4.16 (2H, m), 3.88 (2H, d, J=6.0 Hz), 2.08 (3H, s), 1.04-0.97 (2H, m), 0.05 (9H, s).

(Step 2)

2',3',5'-Tris-O-[tert-butyl(dimethyl)silyl]-1-(2-hydroxyethyl)inosine

To a mixed solution of 2',3',5'-tris-O-[tert-butyl(dimethyl)silyl]inosine (31.3 g) as a compound known in the literature (Chem. Pharm. Bull. 1987, 35 (1), 72-79) in tetrahydrofuran (75 mL)-N,N-dimethylacetamide (75 mL), 2-bromoethanol (4.82 mL) and 1,8-diazabicyclo [5.4.0]-7-undecene (7.65 mL) were added, and the reaction mixture was stirred at room temperature for 23 hours. Water and ethyl acetate were added to the reaction mixture, which was subjected to extraction with ethyl acetate. The organic layer was washed with brine and dried over anhydrous sodium sulfate, and the drying agent was then removed through filtration, and the filtrate was concentrated under reduced pressure. The residue was purified by silica gel column chromatography [hexane/ethyl acetate] to afford the title compound (29.4 g).

MS(ESI)m/z: 655 (M+H)$^+$.

$^1$H-NMR (CDCl$_3$) δ: 8.16 (1H, s), 7.99 (1H, d, J=2.4 Hz), 5.97 (1H, d, J=4.2 Hz), 4.40-4.25 (3H, m), 4.18-4.06 (3H, m), 4.03-3.92 (2H, m), 3.79 (1H, dd, J=11.5, 2.4 Hz), 3.08-2.83 (1H, brm), 0.96 (9H, s), 0.92 (9H, s), 0.82 (9H, s), 0.15 (3H, s), 0.14 (3H, s), 0.09 (3H, s), 0.08 (3H, s), -0.02 (3H, s), -0.15 (3H, s).

(Step 3)

2',3',5'-Tris-O-[tert-butyl(dimethyl)silyl]-1-(2-{[(N-{[2-(trimethylsilyl)ethoxy]carbonyl}glycyl)amino]methoxy}ethyl)inosine To a solution of the compound obtained in step 2 above (15.6 g) in toluene (46.8 mL), the compound obtained in step 1 above (10.4 g) and pyridine (9.63 mL) were added, and the reaction mixture was stirred at 110° C. for 12 hours. The compound obtained in step 1 above (3.46 g) was further added to the reaction mixture, which was stirred at 110° C. for 1 day. A saturated aqueous solution of sodium hydrogen carbonate and dichloromethane were added to the reaction mixture, which was subjected to extraction with dichloromethane. After the organic layer was dried over anhydrous sodium sulfate, the drying agent was removed through filtration, and the filtrate was concentrated under reduced pressure. The residue was purified by silica gel column chromatography [hexane/ethyl acetate] to afford the title compound (20.6 g: with impurities).

MS(ESI)m/z: 885 (M+H)$^+$.

(Step 4)

5'-O-[Bis(4-methoxyphenyl)(phenyl)methyl]-1-(2-{[(N-{[2-(trimethylsilyl)ethoxy]carbonyl}glycyl)amino]methoxy}ethyl)inosine To a solution of the compound obtained in step 3 above (20.6 g) in tetrahydrofuran (50 mL), triethylamine trihydrofluoride (10 mL) was added, and the reaction mixture was stirred at room temperature for 17 hours. To the reaction mixture, a mixture of 1 M solution of triethylammonium hydrogen carbonate (50 mL) and triethylamine (10 mL) was slowly added under ice-cooling, and the reaction mixture was then concentrated under reduced pressure. The residue was partially purified by C18 silica gel column chromatography [water/acetonitrile], and then freeze-dried. The obtained crude form was azeotroped with pyridine, and 4,4'-dimethoxytrityl chloride (4.73 g) was added to a solution of the residue in pyridine (50 mL) at 0° C., and the reaction mixture was stirred at 4° C. for 17 hours. Methanol (2 mL) was added to the reaction mixture, which was stirred at room temperature for 15 minutes, and then concentrated under reduced pressure. The residue was purified by silica gel column chromatography [hexane/ethyl acetate/methanol/0.1% triethylamine] to afford the title compound (9.18 g: with impurities).

MS(ESI)m/z: 845 (M+H)$^+$.

$^1$H-NMR (CDCl$_3$) δ: 7.94 (1H, s), 7.88 (1H, s), 7.65 (1H, brs), 7.41-7.36 (2H, m), 7.32-7.15 (7H, m), 6.83-6.76 (4H, m), 5.96 (1H, d, J=6.1 Hz), 5.73-5.65 (2H, m), 4.87-4.80 (1H, m), 4.76-4.61 (2H, m), 4.44-4.39 (1H, m), 4.35-4.30 (1H, m), 4.22-4.05 (4H, m), 3.83-3.73 (2H, m), 3.77 (6H, s), 3.72-3.67 (2H, m), 3.48-3.32 (3H, m), 0.99-0.91 (2H, m), 0.02 (9H, s).

(Step 5)

5'-O-[Bis(4-methoxyphenyl)(phenyl)methyl]-3'-O-[tert-butyl(dimethyl)silyl]-1-(2-{[(N-{[2-(trimethylsilyl)ethoxy]carbonyl}glycyl)amino]methoxy}ethyl)inosine With use of the compound obtained in step 4 above (5.96 g), the reaction was performed in the same manner as in step 3 of Example 5 to afford the title compound (2.33 g) and 5'-O-[bis(4-methoxyphenyl)(phenyl)methyl]-2'-O-[tert-butyl(dimethyl)silyl]-1-(2-{[(N-{[2-(trimethylsilyl)ethoxy]carbonyl}glycyl)amino]methoxy}ethyl)inosine (2.45 g) as a regioisomer of the title compound.

MS(ESI)m/z: 959 (M+H)$^+$.

$^1$H-NMR (CDCl$_3$) δ: 7.99 (1H, s), 7.93 (1H, s), 7.45-7.39 (2H, m), 7.35-7.18 (7H, m), 7.05 (1H, brs), 6.84-6.77 (4H, m), 5.92 (1H, d, J=5.4 Hz), 5.46 (1H, brs), 4.71-4.61 (3H, m), 4.54-4.51 (1H, m), 4.22-4.10 (5H, m), 3.81-3.76 (2H, m), 3.78 (3H, s), 3.78 (3H, s), 3.74 (2H, d, J=6.0 Hz), 3.48 (1H, dd, J=10.9, 4.2 Hz), 3.26 (1H, dd, J=10.9, 4.2 Hz), 3.16 (1H, d, J=6.7 Hz), 1.00-0.93 (2H, m), 0.89 (9H, s), 0.09 (3H, s), 0.02 (9H, s), 0.02 (3H, s).

Regioisomer (2'-O-TBS Form)

MS(ESI)m/z: 959 (M+H)$^+$.

$^1$H-NMR (CDCl$_3$) δ: 7.99 (1H, s), 7.91 (1H, s), 7.48-7.42 (2H, m), 7.37-7.18 (8H, m), 6.85-6.78 (4H, m), 5.96 (1H, d, J=5.4 Hz), 5.63 (1H, brs), 4.88 (1H, t, J=5.1 Hz), 4.66 (2H, d, J=6.7 Hz), 4.36-4.32 (1H, m), 4.27-4.19 (2H, m), 4.18-4.10 (3H, m), 3.81-3.74 (4H, m), 3.78 (3H, s), 3.78 (3H, s), 3.50 (1H, dd, J=10.9, 3.6 Hz), 3.38 (1H, dd, J=10.9, 3.6 Hz), 2.73 (1H, d, J=4.2 Hz), 0.97-0.90 (2H, m), 0.86 (9H, s), 0.02 (3H, s), 0.01 (9H, s), −0.09 (3H, s).

(Step 6)

5'-O-[Bis(4-methoxyphenyl)(phenyl)methyl]-3'-O-[tert-butyl(dimethyl)silyl]-2'-O-{(2-cyanoethoxy)[di(propan-2-yl)amino]phosphanyl}-1-(2-{[(N-{[2-(trimethylsilyl)ethoxy]carbonyl}glycyl)amino]methoxy}ethyl)inosine With use of the compound obtained in step 5 above (2.33 g), the reaction was performed in the same manner as in step 4 of Example 5 to afford the title compound (2.72 g) as a mixture of diastereomers at the phosphorus atom (diastereomer ratio=6:4).

MS(ESI)m/z: 1159 (M+H)$^+$.

$^1$H-NMR (CDCl$_3$) δ: 8.03 (0.4H, s), 8.02 (0.6H, s), 7.95 (0.6H, s), 7.92 (0.4H, s), 7.46-7.40 (2H, m), 7.35-7.17 (7H, m), 6.88 (1H, brs), 6.84-6.78 (4H, m), 6.15 (0.6H, d, J=4.2 Hz), 6.10 (0.4H, d, J=4.8 Hz), 5.34 (1H, brs), 4.86-4.61 (3H, m), 4.48-4.42 (1H, m), 4.29-4.09 (5H, m), 3.83-3.44 (9H, m), 3.79 (3H, s), 3.78 (3H, s), 3.32-3.23 (1H, m), 2.58-2.49 (1H, m), 2.44-2.38 (1H, m), 1.15 (3.6H, d, J=6.7 Hz), 1.11 (6H, d, J=6.7 Hz), 1.04-0.92 (2H, m), 0.97 (2.4H, d, J=6.7 Hz), 0.85 (3.6H, s), 0.84 (5.4H, s), 0.09 (1.2H, s), 0.06 (1.8H, s), 0.03 (9H, s), 0.00 (3H, s).

(Step 7)

With use of the compound obtained in step 8 of Example 44 (2.15 g), the reaction was performed in the same manner as in step 7 of Example 1 to afford an acetonitrile solution of 6-benzoyl-2-{2-deoxy-2-fluoro-3-O-[hydroxy (oxo)-λ$^5$-phosphanyl]-β-D-ribofuranosyl}-6,7,8,9-tetrahydro-2H-2,3,5,6-tetraazabenzo[cd]azulene. With use of the obtained acetonitrile solution and the compound obtained in step 6 above (2.72 g), the reaction was performed in the same manner as in step 8 of Example 1, and the resulting crude product was directly used for the subsequent reaction.

(Step 8)

2-(Trimethylsilyl)ethyl (2-{[(2-{9-[(5R,7R,8R,12aR,14R,15R,15aR,16R)-14-(6-benzoyl-6,7,8,9-tetrahydro-2H-2,3,5,6-tetraazabenzo[cd]azulen-2-yl)-16-{[tert-butyl(dimethyl)silyl]oxy}-10-(2-cyanoethoxy)-15-fluoro-2-oxo-2-sulfanyl-10-sulfanylideneoctahydro-2H,10H,12H-5,8-methano-2λ$^5$,10λ$^5$-furo[3,2-1][1,3,6,9,11,2,10]pentaoxadiphosphacyclotetradecin-7-yl]-6-oxo-6,9-dihydro-1H-purin-1-yl]ethoxy)methyl]amino}-2-oxoethyl)carbamate With use of the crude product obtained in step 7 above, the reaction was performed in the same manner as in step 9 of Example 1 to afford the title compound (1.47 g: with impurities) as a mixture of diastereomers at the phosphorus atom.

MS(ESI)m/z: 1278 (M+H)$^+$.

(Step 9)

Bis(N,N-diethylethaneaminium) (5R,7R,8R,12aR,14R,15R,15aR,16R)-16-{[tert-butyl(dimethyl)silyl]oxy}-15-fluoro-2,10-dioxo-7-[6-oxo-1-(2-{[(N-{[2-(trimethylsilyl)ethoxy]carbonyl}glycyl)amino]methoxy}ethyl)-1,6-dihydro-9H-purin-9-yl]-14-(6,7,8,9-tetrahydro-2H-2,3,5,6-tetraazabenzo[cd]azulen-2-yl)octahydro-2H,10H,12H-5,8-methano-2λ$^5$,10λ$^5$-furo[3,2-1][1,3,6,9,11,2,10]pentaoxadiphosphacyclotetradecine-2,10-bis (thiolate)

To a mixed solution of the compound obtained in step 8 above (1.47 g) in methanol (10 mL)-tetrahydrofuran (10 mL), 28% ammonia water (10 mL) was added, and the reaction mixture was stirred at 50° C. for 6 hours. After the reaction mixture was concentrated under reduced pressure, the residue was purified by C18 silica gel column chroma tography [10 mM aqueous solution of triethylammonium acetate/acetonitrile] to afford diastereomer 1 (204 mg: with impurities) and diastereomer 2 (205 mg: with impurities) of the title compound.

Diastereomer 1 (Less Polar)

MS(ESI)m/z: 1121 (M+H)$^+$.

Diastereomer 2 (More Polar)

MS(ESI)m/z: 1121 (M+H)$^+$.

(Step 10-1)

Bis(N,N-diethylethaneaminium) (5R,7R,8R,12aR, 14R,15R,15aR,16R)-15-fluoro-7-(1-{2-[(glycylamino)methoxy]ethyl}-6-oxo-1,6-dihydro-9H-purin-9-yl)-16-hydroxy-2,10-dioxo-14-(6,7,8,9-tetrahydro-2H-2,3,5,6-tetraazabenzo[cd]azulen-2-yl)octahydro-2H,10H,12H-5,8-methano-2λ$^5$,10λ$^5$-furo[3,2-l][1,3,6,9,11,2,10]pentaoxadiphosphacyclotetradecine-2,10-bis(thiolate)

With use of the compound obtained in step 9 above (diastereomer 1) (204 mg), the reaction was performed in the same manner as in step 9-1 of Example 11, and the resultant was then purified by C18 silica gel column chromatography [10 mM aqueous solution of triethylammonium acetate/acetonitrile] and preparative HPLC [10 mM aqueous solution of triethylammonium acetate/acetonitrile-methanol solution (1:1), acetonitrile-methanol solution (1:1): 10%-50% (0 min-40 min)] to afford the title compound (40.7 mg: with impurities).

MS(ESI)m/z: 863 (M+H)$^+$.

(Step 10-2)

Bis(N,N-diethylethaneaminium) (5R,7R,8R,12aR, 14R,15R,15aR,16R)-15-fluoro-7-(1-{2-[(glycylamino)methoxy]ethyl}-6-oxo-1,6-dihydro-9H-purin-9-yl)-16-hydroxy-2,10-dioxo-14-(6,7,8,9-tetrahydro-2H-2,3,5,6-tetraazabenzo[cd]azulen-2-yl)octahydro-2H,10H,12H-5,8-methano-2λ$^5$,10λ$^5$-furo[3,2-l][1,3,6,9,11,2,10]pentaoxadiphosphacyclotetradecine-2,10-bis(thiolate)

With use of the compound obtained in step 9 above (diastereomer 2) (205 mg), the reaction was performed in the same manner as in step 9-1 of Example 11, and the resultant was then purified by C18 silica gel column chromatography [10 mM aqueous solution of triethylammonium acetate/acetonitrile] and preparative HPLC [10 mM aqueous solution of triethylammonium acetate/acetonitrile-methanol solution (1:1), acetonitrile-methanol solution (1:1): 10%-50% (0 min-40 min)] to afford the title compound (50.8 mg: with impurities).

MS(ESI)m/z: 863 (M+H)$^+$.

(Step 11-1)

Bis(N,N-diethylethaneaminium) N-[4-(11,12-didehydrodibenzo[b,f]azocin-5 (6H)-yl)-4-oxobutanoyl]glycylglycyl-L-phenylalanyl-N-[(2-{9-[(5R,7R,8R, 12aR,14R,15R,15aR,16R)-15-fluoro-16-hydroxy-2,10-dioxo-2,10-disulfide-14-(6,7,8,9-tetrahydro-2H-2,3,5,6-tetraazabenzo[cd]azulen-2-yl)octahydro-2H,10H,12H-5,8-methano-2λ$^5$,10λ$^5$-furo[3,2-l][1,3,6,9,11,2,10]pentaoxadiphosphacyclotetradecin-7-yl]-6-oxo-6,9-dihydro-1H-purin-1-yl}ethoxy)methyl]glycinamide (Drug-Linker 17a: Diastereomer 1)

With use of the compound obtained in step 10-1 above (40.7 mg), the reaction was performed in the same manner as in step 9-1 of Example 22, and the resultant was then purified by C18 silica gel column chromatography [10 mM aqueous solution of triethylammonium acetate/acetonitrile], preparative HPLC [10 mM aqueous solution of triethylammonium acetate/acetonitrile, acetonitrile: 20%-45% (0 min-40 min)], and preparative HPLC [10 mM aqueous solution of triethylammonium acetate/methanol, methanol: 40%-90% (0 min-40 min)] to afford the title compound (25.1 mg).

MS(ESI)m/z: 1411 (M+H)$^+$.

$^1$H-NMR (CD$_3$OD) δ: 8.58 (1H, s), 8.09 (1H, s), 8.04 (1H, s), 7.57-7.49 (2H, m), 7.43-7.34 (3H, m), 7.32-7.08 (9H, m), 6.47 (1H, d, J=16.9 Hz), 6.23 (1H, d, J=7.9 Hz), 5.56-5.37 (2H, m), 5.31-5.17 (1H, m), 5.03 (1H, d, J=13.9 Hz), 4.79 (1H, d, J=4.2 Hz), 4.64-4.38 (6H, m), 4.36-4.21 (4H, m), 4.05-3.60 (10H, m), 3.53-3.42 (3H, m), 3.18 (12H, q, J=7.3 Hz), 3.01-2.92 (1H, m), 2.86-2.73 (1H, m), 2.70-2.54 (2H, m), 2.37-2.16 (2H, m), 2.06-1.77 (3H, m), 1.28 (18H, t, J=7.3 Hz).

(Step 11-2)

Bis(N,N-diethylethaneaminium) N-[4-(11,12-didehydrodibenzo[b,f]azocin-5 (6H)-yl)-4-oxobutanoyl]glycylglycyl-L-phenylalanyl-N-[(2-{9-[(5R,7R,8R, 12aR,14R,15R,15aR,16R)-15-fluoro-16-hydroxy-2,10-dioxo-2,10-disulfide-14-(6,7,8,9-tetrahydro-2H-2,3,5,6-tetraazabenzo[cd]azulen-2-yl)octahydro-2H,10H,12H-5,8-methano-2λ$^5$,10λ$^5$-furo[3,2-l][1,3,6,9,11,2,10]pentaoxadiphosphacyclotetradecin-7-yl]-6-oxo-6,9-dihydro-1H-purin-1-yl}ethoxy)methyl]glycinamide (Drug-Linker 17b: Diastereomer 2)

With use of the compound obtained in step 10-2 above (50.8 mg), the reaction was performed in the same manner as in step 9-1 of Example 22, and the resultant was then purified by C18 silica gel column chromatography [10 mM aqueous solution of triethylammonium acetate/acetonitrile], preparative HPLC [10 mM aqueous solution of triethylammonium acetate/acetonitrile, acetonitrile: 25%-45% (0 min-40 min)], and preparative HPLC [10 mM aqueous solution of triethylammonium acetate/methanol, methanol: 45%-90% (0 min-40 min)] to afford the title compound (23.4 mg).

MS(ESI)m/z: 1411 (M+H)$^+$.

$^1$H-NMR (CD$_3$OD) δ: 8.67 (1H, s), 8.14 (1H, s), 8.02 (1H, s), 7.67-7.50 (2H, m), 7.43-7.36 (3H, m), 7.34-7.12 (9H, m), 6.48 (1H, d, J=15.1 Hz), 6.26 (1H, t, J=8.8 Hz), 5.60-5.31 (3H, m), 5.09-5.00 (1H, m), 4.61-4.22 (9H, m), 4.11-3.59 (13H, m), 3.50-3.44 (2H, m), 3.18 (12H, q, J=7.3 Hz), 3.04-2.93 (1H, m), 2.87-2.74 (3H, m), 2.39-2.22 (2H, m), 2.06-1.85 (3H, m), 1.28 (18H, t, J=7.3 Hz).

Example 78: Synthesis of Drug-Linker 18

[Synthesis Scheme]

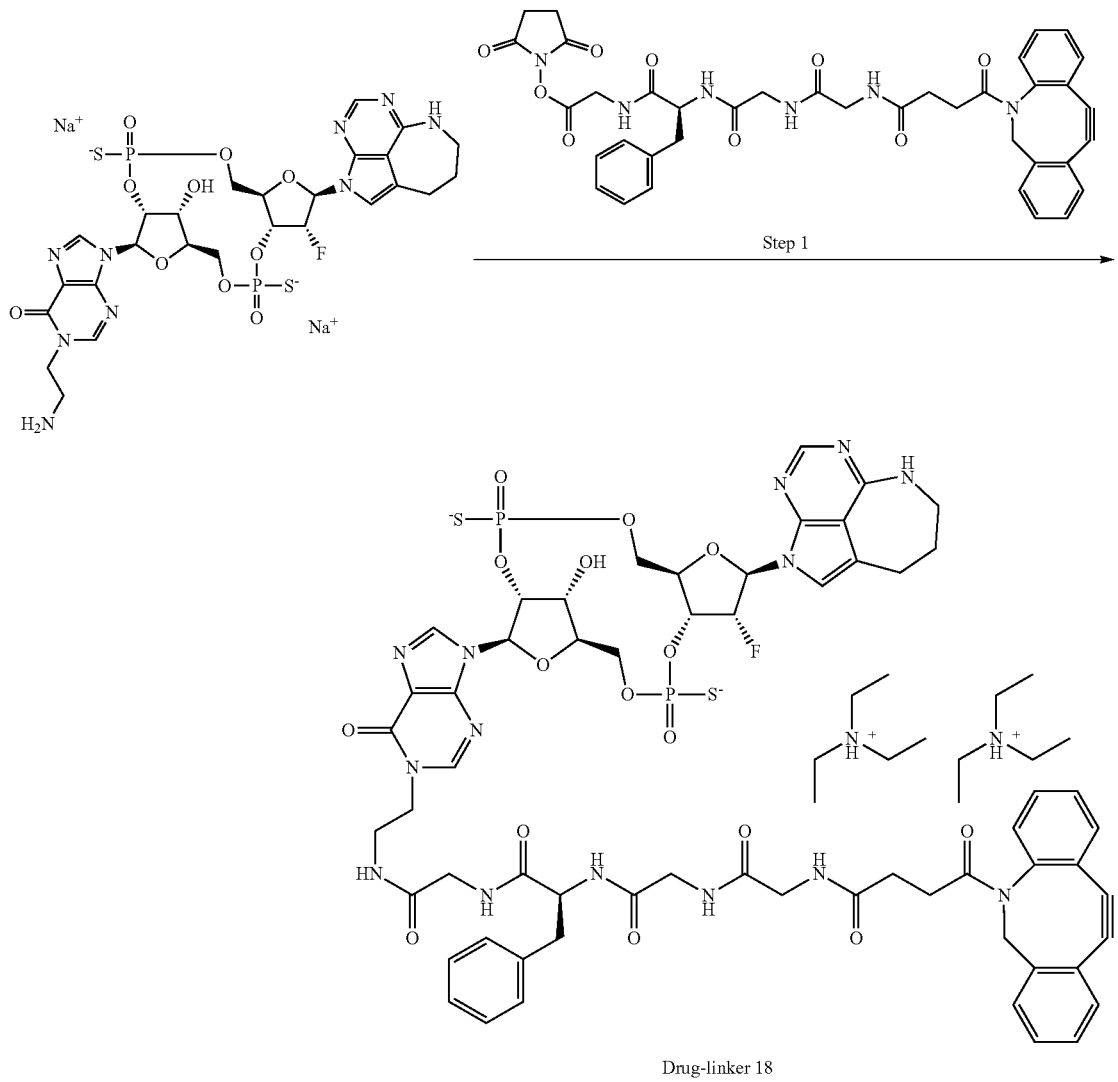

Drug-linker 18

(Step 1)

Bis(N,N-diethylethaneaminium) N-[4-(11,12-didehydrodibenzo[b,f]azocin-5 (6H)-yl)-4-oxobutanoyl]glycylglycyl-L-phenylalanyl-N-(2-{9-[(5R,7R,8R,12aR,14R,15R,15aR,16R)-15-fluoro-16-hydroxy-2,10-dioxo-2,10-disulfide-14-(6,7,8,9-tetrahydro-2H-2,3,5,6-tetraazabenzo[cd]azulen-2-yl)octahydro-2H,10H,12H-5,8-methano-2$\lambda^5$,10$\lambda^5$-furo[3,2-1][1,3,6,9,11,2,10]pentaoxadiphosphacyclotetradecin-7-yl]-6-oxo-6,9-dihydro-1H-purin-1-yl}ethyl)glycinamide (Drug-Linker 18)

With use of the compound obtained in step 7-2 of Example 45 (10.0 mg) and the compound obtained in step 3 of Example 21 (8.8 mg), the reaction was performed in the same manner as in step 4 of Example 21, and the resultant was then purified by C18 silica gel column chromatography [10 mM aqueous solution of triethylammonium acetate/acetonitrile], preparative HPLC [10 mM aqueous solution of triethylammonium acetate/acetonitrile, acetonitrile: 25%-50% (0 min-40 min)], and preparative HPLC [10 mM aqueous solution of triethylammonium acetate/methanol, methanol: 45%-90% (0 min-40 min)] to afford the title compound (10.9 mg).

MS(ESI)m/z: 1381 (M+H)$^+$.

$^1$H-NMR (CD$_3$OD) δ: 8.61 (1H, s), 8.03 (1H, s), 8.02 (1H, s), 7.64-7.49 (2H, m), 7.44-7.37 (3H, m), 7.35-7.11 (9H, m), 6.48 (1H, dd, J=15.1, 1.8 Hz), 6.24 (1H, d, J=8.5 Hz), 5.62-5.39 (3H, m), 5.03 (1H, dd, J=18.4, 14.2 Hz), 4.55-4.37 (5H, m), 4.29-4.18 (2H, m), 4.04-3.91 (3H, m), 3.87-3.52 (8H, m), 3.50-3.41 (3H, m), 3.19 (12H, q, J=7.3 Hz), 3.18-3.10 (1H, m), 3.02-2.92 (1H, m), 2.86-2.66 (3H, m), 2.40-2.21 (2H, m), 2.06-1.84 (3H, m), 1.29 (18H, t, J=7.3 Hz).

Example 79: Synthesis of Drug-Linker 19

[Synthesis Scheme]

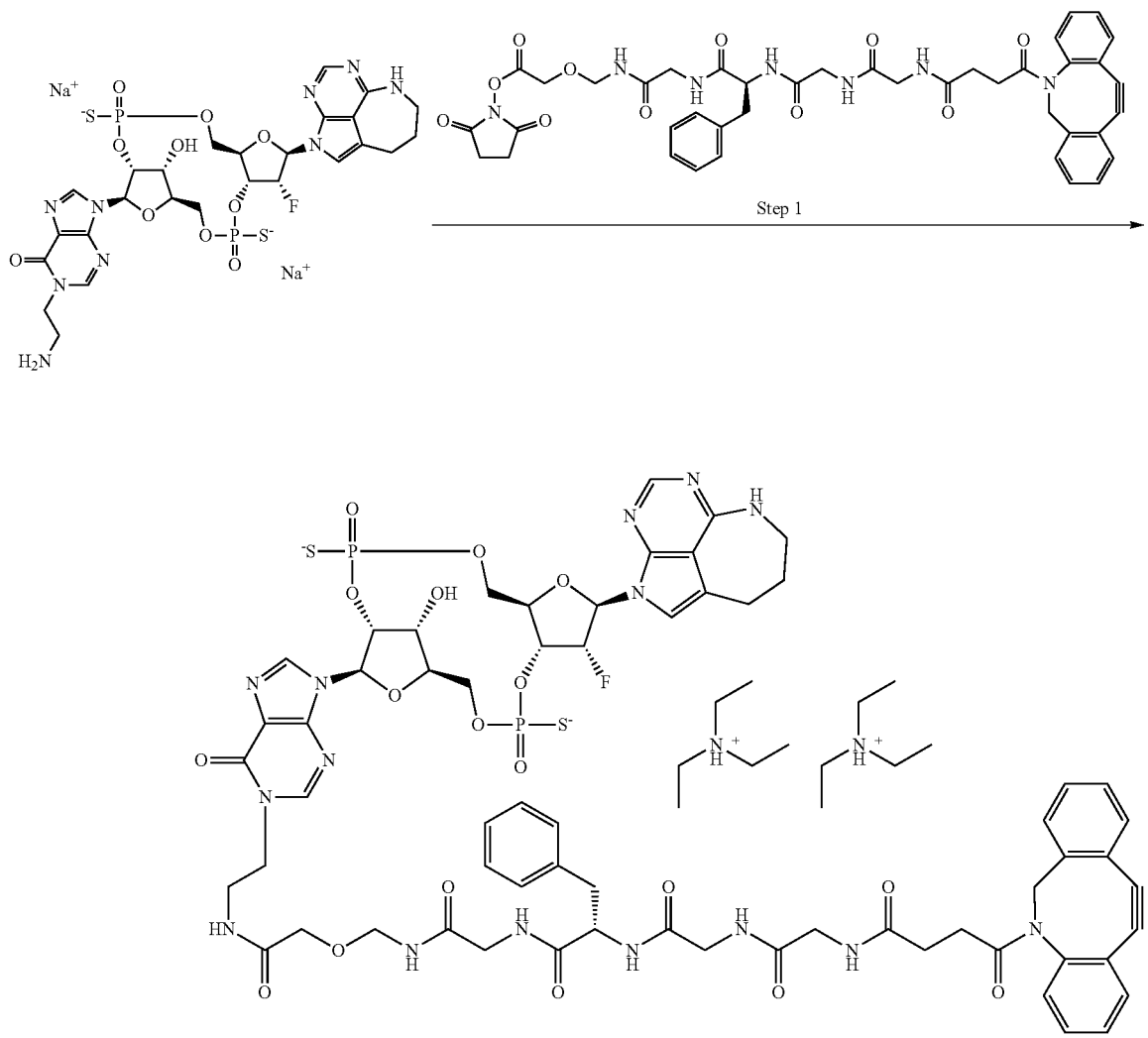

Drug-linker 19

(Step 1)

Bis(N,N-diethylethaneaminium) N-[4-(11,12-didehydrodibenzo[b,f]azocin-5 (6H)-yl)-4-oxobutanoyl]glycylglycyl-L-phenylalanyl-N-({2-[(2-{9-[(5R,7R,8R,12aR,14R,15R,15aR,16R)-15-fluoro-16-hydroxy-2,10-dioxo-2,10-disulfide-14-(6,7,8,9-tetrahydro-2H-2,3,5,6-tetraazabenzo[cd]azulen-2-yl)octahydro-2H,10H,12H-5,8-methano-2$\lambda^5$,10$\lambda^5$-furo[3,2-l][1,3,6,9,11,2,10]pentaoxadiphosphacyclotetradecin-7-yl]-6-oxo-6,9-dihydro-1H-purin-1-yl}ethyl)amino]-2-oxoethoxy}methyl)glycinamide (Drug-Linker 19)

With use of the compound obtained in step 7-2 of Example 45 (20.0 mg) and the compound obtained in step 1 of Example 66 (19.8 mg), the reaction was performed in the same manner as in step 4 of Example 21, and the resultant was then purified by C18 silica gel column chromatography [10 mM aqueous solution of triethylammonium acetate/acetonitrile], preparative HPLC [10 mM aqueous solution of triethylammonium acetate/acetonitrile, acetonitrile: 20%-45% (0 min-40 min)], and preparative HPLC [10 mM aqueous solution of triethylammonium acetate/methanol, methanol: 30%-80% (0 min-40 min)] to afford the title compound (22.1 mg).

MS(ESI)m/z: 1468 (M+H)$^+$.

$^1$H-NMR (CD$_3$OD) δ: 8.66 (1H, brs), 8.10 (1H, brs), 8.04-7.96 (1H, m), 7.66-7.35 (5H, m), 7.33-7.12 (9H, m), 6.52-6.41 (1H, m), 6.28-6.22 (1H, m), 5.64-5.31 (3H, m), 5.07-4.99 (1H, m), 4.70-4.20 (9H, m), 4.11-3.51 (14H, m), 3.50-3.30 (3H, m), 3.27-3.10 (1H, m), 3.19 (12H, q, J=7.3 Hz), 3.07-2.93 (1H, m), 2.89-2.65 (3H, m), 2.41-2.18 (2H, m), 2.05-1.82 (2H, m), 1.29 (18H, t, J=7.3 Hz).

Example 80: Synthesis of Drug-Linker 20

[Synthesis Scheme]

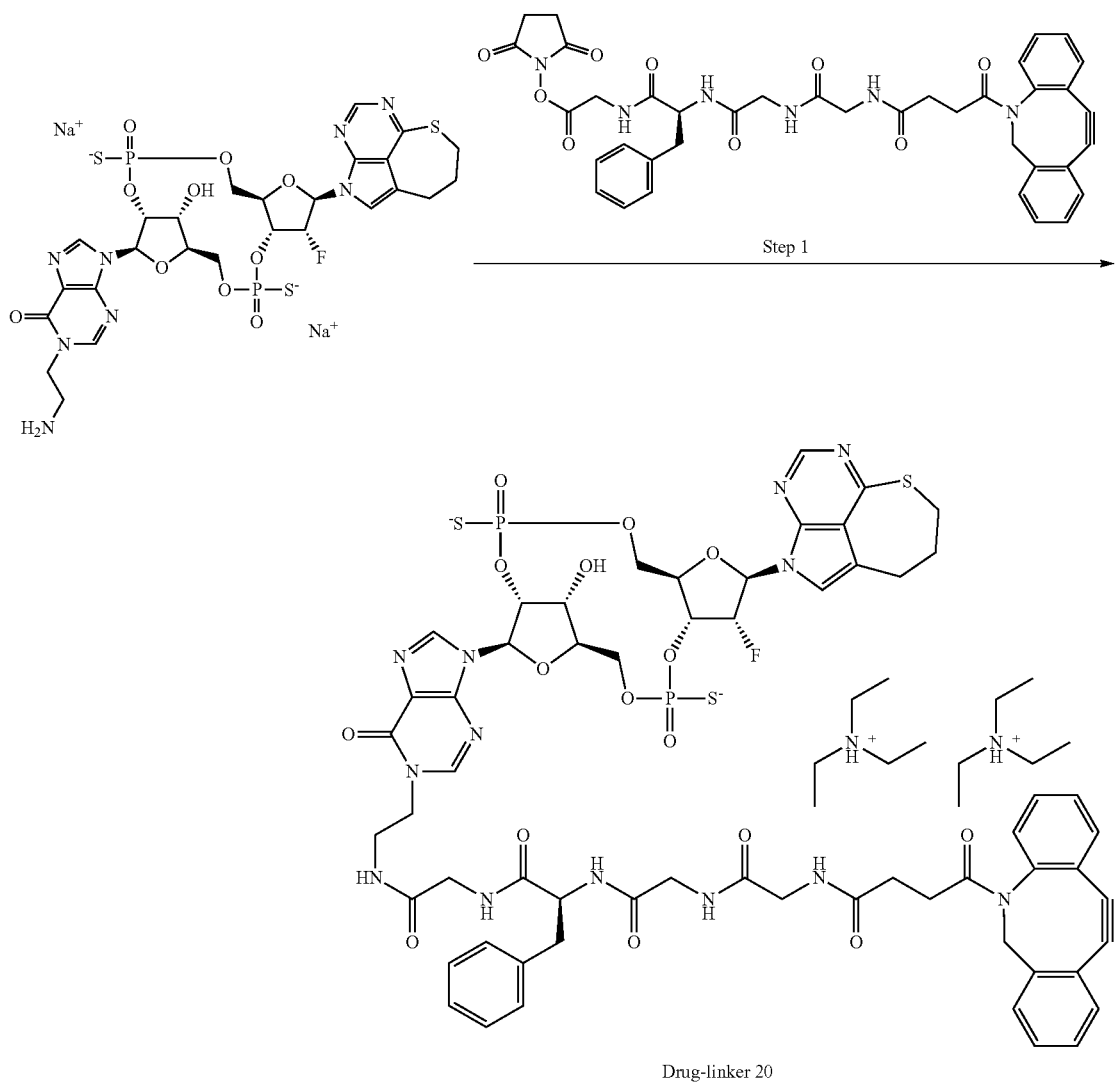

Drug-linker 20

(Step 1)

Bis(N,N-diethylethaneaminium) N-[4-(11,12-dide-hydrodibenzo[b,f]azocin-5 (6H)-yl)-4-oxobutanoyl] glycylglycyl-L-phenylalanyl-N-(2-{9-[(5R,7R,8R,12aR,14R,15R,15aR,16R)-14-(8,9-dihydro-6-thia-2,3,5-triazabenzo[cd]azulen-2 (7H)-yl)-15-fluoro-16-hydroxy-2,10-dioxo-2,10-disulfideoctahydro-2H,10H,12H-5,8-methano-2$\lambda^5$,10$\lambda^5$-furo[3,2-1][1,3,6,9,11,2,10]pentaoxadiphosphacyclotetradecin-7-yl]-6-oxo-6,9-dihydro-1H-purin-1-yl}ethyl)glycinamide (Drug-Linker 20)

With use of the compound obtained in step 4-2 of Example 59 (25.0 mg) and the compound obtained in step 3 of Example 21 (25.8 mg), the reaction was performed in the same manner as in step 4 of Example 21, and the resultant was then purified by C18 silica gel column chromatography [10 mM aqueous solution of triethylammonium acetate/acetonitrile], preparative HPLC [10 mM aqueous solution of triethylammonium acetate/acetonitrile, acetonitrile: 30%-50% (0 min-40 min)], and preparative HPLC [10 mM aqueous solution of triethylammonium acetate/methanol, methanol: 50%-90% (0 min-40 min)] to afford the title compound (33.1 mg).

MS(ESI)m/z: 1398 (M+H)$^+$.

$^1$H-NMR (CD$_3$OD) δ: 8.58 (1H, brs), 8.39 (1H, d, J=8.5 Hz), 8.00 (1H, brs), 7.71 (1H, brs), 7.64-7.49 (2H, m), 7.44-7.37 (3H, m), 7.32-7.10 (8H, m), 6.59 (1H, d, J=15.1 Hz), 6.23 (1H, d, J=8.5 Hz), 5.65-5.36 (3H, m), 5.03 (1H, dd, J=16.6, 14.2 Hz), 4.57-4.38 (5H, m), 4.30-4.17 (2H, m), 4.07-3.95 (2H, m), 3.94-3.50 (9H, m), 3.50-3.35 (1H, m), 3.19 (12H, q, J=7.3 Hz), 3.18-3.07 (3H, m), 3.04-2.73 (4H, m), 2.40-2.11 (4H, m), 2.05-1.92 (1H, m), 1.29 (18H, t, J=7.3 Hz).

Example 81: Synthesis of Drug-Linker 21

[Synthesis Scheme]

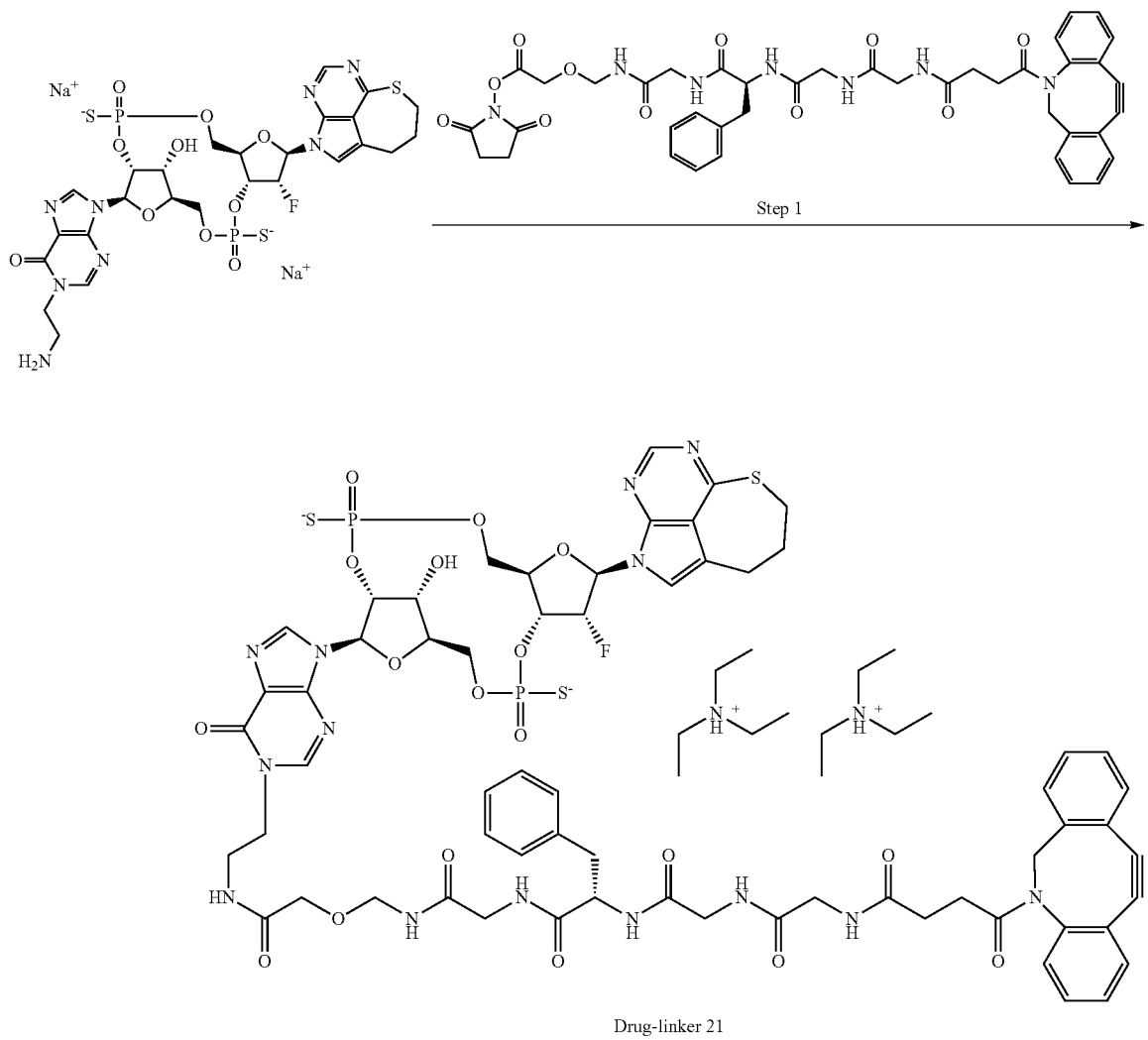

Drug-linker 21

(Step 1)

Bis(N,N-diethylethaneaminium) N-[4-(11,12-didehydrodibenzo[b,f]azocin-5 (6H)-yl)-4-oxobutanoyl]glycylglycyl-L-phenylalanyl-N-({2-[(2-{9-[(5R,7R,8R,12aR,14R,15R,15aR,16R)-14-(8,9-dihydro-6-thia-2,3,5-triazabenzo[cd]azulen-2 (7H)-yl)-15-fluoro-16-hydroxy-2,10-dioxo-2,10-disulfideoctahydro-2H,10H,12H-5,8-methano-2λ$^5$,10λ$^5$-furo[3,2-l][1,3,6,9,11,2,10]pentaoxadiphosphacyclotetradecin-7-yl]-6-oxo-6,9-dihydro-1H-purin-1-yl}ethyl)amino]-2-oxoethoxy}methyl)glycinamide (Drug-Linker 21)

With use of the compound obtained in step 4-2 of Example 59 (15.0 mg) and the compound obtained in step 1 of Example 66 (17.4 mg), the reaction was performed in the same manner as in step 4 of Example 21, and the resultant was then purified by C18 silica gel column chromatography [10 mM aqueous solution of triethylammonium acetate/acetonitrile], preparative HPLC [10 mM aqueous solution of triethylammonium acetate/acetonitrile, acetonitrile: 25%-50% (0 min-40 min)], and preparative HPLC [10 mM aqueous solution of triethylammonium acetate/methanol, methanol: 40%-90% (0 min-40 min)] to afford the title compound (21.8 mg).

MS(ESI)m/z: 1485 (M+H)$^+$.

$^1$H-NMR (CD$_3$OD) δ: 8.61 (1H, brs), 8.41-8.34 (1H, m), 8.10-8.05 (1H, m), 7.72-7.37 (6H, m), 7.32-7.12 (8H, m), 6.63-6.50 (1H, m), 6.27-6.22 (1H, m), 5.65-5.31 (3H, m), 5.07-4.94 (1H, m), 4.68-4.20 (10H, m), 4.11-3.53 (14H, m), 3.26-3.08 (2H, m), 3.19 (12H, q, J=7.3 Hz), 3.06-2.67 (4H, m), 2.40-2.11 (4H, m), 2.05-1.88 (1H, m), 1.29 (18H, t, J=7.3 Hz).

Example 82: Synthesis of Drug-Linker 22

[Synthesis Scheme]

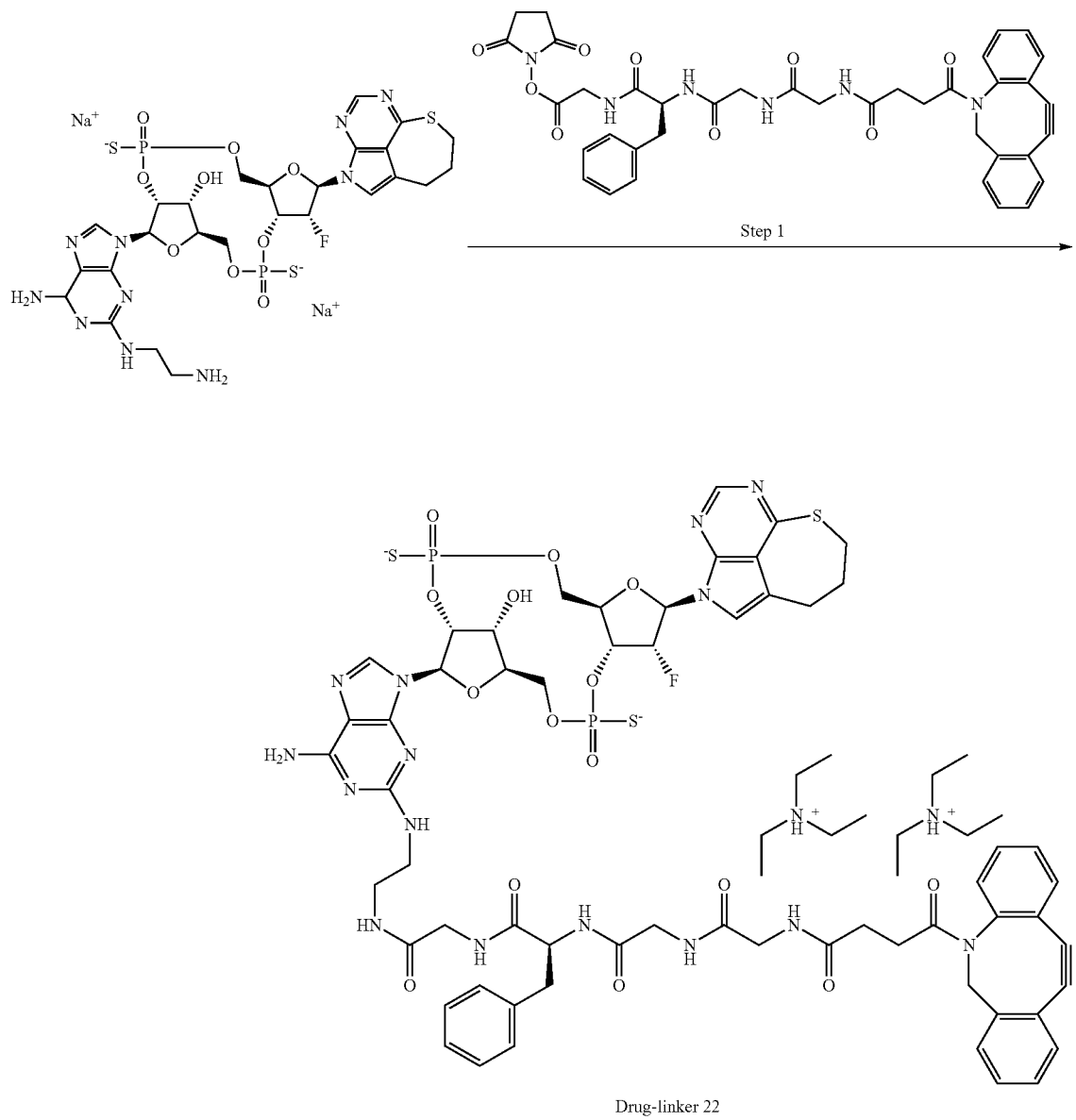

(Step 1)

Bis(N,N-diethylethaneaminium) N-[4-(11,12-didehydrodibenzo[b,f]azocin-5 (6H)-yl)-4-oxobutanoyl] glycylglycyl-L-phenylalanyl-N-[2-({6-amino-9-[(5R,7R,8R,12aR,14R,15R,15aR,16R)-14-(8,9-dihydro-6-thia-2,3,5-triazabenzo[cd]azulen-2 (7H)-yl)-15-fluoro-16-hydroxy-2,10-dioxo-2,10-disulfideoctahydro-2H,10H,12H-5,8-methano-2$\lambda^5$,10$\lambda^5$-furo[3,2-l][1,3,6,9,11,2,10]pentaoxadiphosphacyclotetradecin-7-yl]-9H-purin-2-yl}amino)ethyl]glycinamide (Drug-Linker 22)

With use of the compound obtained in step 4-2 of Example 61 (4.4 mg) and the compound obtained in step 3 of Example 21 (3.5 mg), the reaction was performed in the same manner as in step 4 of Example 21, and the resultant was then purified by preparative HPLC [10 mM aqueous solution of triethylammonium acetate/acetonitrile, acetonitrile: 25%-45% (0 min-30 min)] to afford the title compound (6.4 mg).

MS(ESI)m/z: 1412 (M+H)$^+$.

$^1$H-NMR (CD$_3$OD) δ: 8.37 (1H, d, J=1.2 Hz), 8.10-7.98 (1H, m), 7.75 (1H, s), 7.62-7.13 (13H, m), 6.59 (1H, d, J=16.3 Hz), 6.01 (1H, brs), 5.82-5.62 (1H, m), 5.54-5.33 (2H, m), 5.04 (1H, d, J=14.5 Hz), 4.57-3.48 (14H, m), 3.35-2.65 (12H, m), 3.17 (12H, q, J=7.3 Hz), 2.35-2.11 (4H, m), 2.00-1.92 (1H, m), 1.28 (18H, t, J=7.3 Hz).

Example 83: Synthesis of Drug-Linker 23
[Synthesis Scheme]
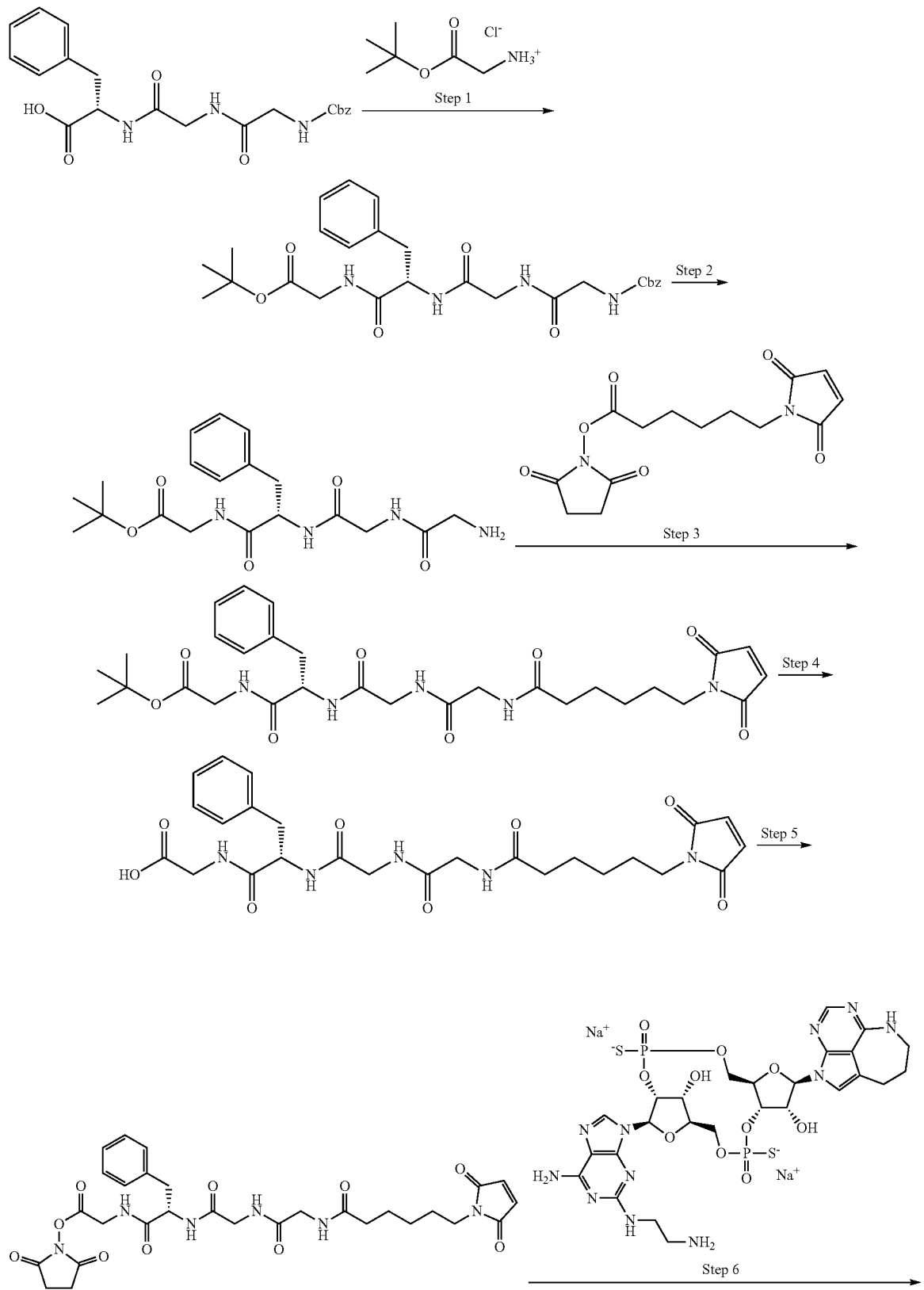

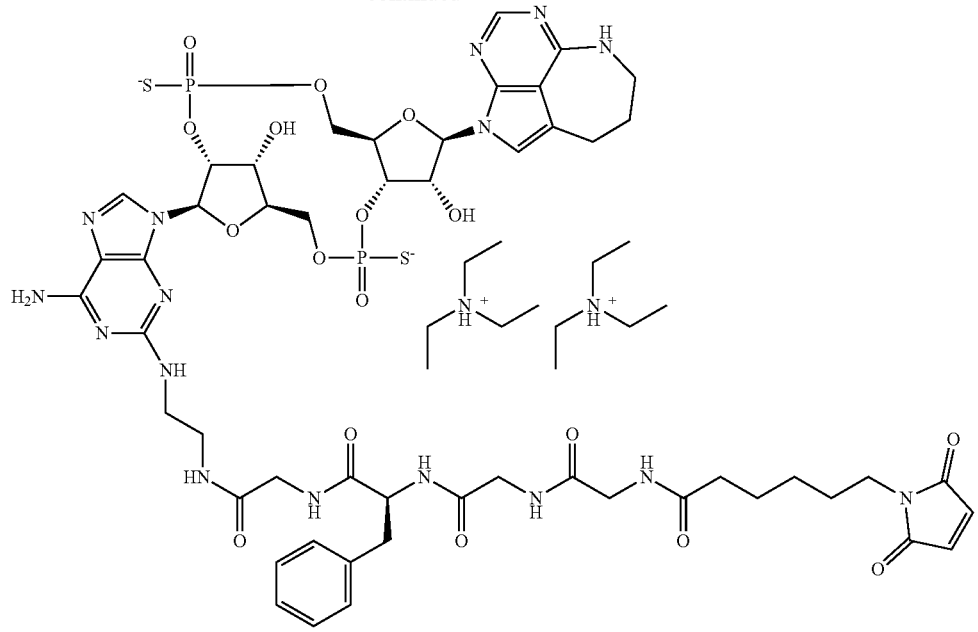

Drug-linker 23

(Step 1)

tert-Butyl N-[(benzyloxy)carbonyl]glycylglycyl-L-phenylalanylglycinate

To a solution of commercially available (Bachem Holding AG) N-[(benzyloxy)carbonyl]glycylglycyl-L-phenylalanine (5.00 g) and glycine tert-butyl ester hydrochloride (2.03 g) in N,N-dimethylformamide (50 mL), N,N-diisopropylethylamine (4.11 mL) and 1-ethyl-3-(3-dimethylaminopropyl)-carbodiimide hydrochloride (3.01 g) were added under ice-cooling, and the reaction mixture was stirred with increasing the temperature to room temperature overnight. The reaction mixture was poured into a two-layer mixture of chloroform and a saturated aqueous solution of sodium hydrogen carbonate, and subjected to extraction with chloroform. The organic layer was washed with water and brine, and then dried over anhydrous sodium sulfate. The drying agent was removed through filtration, and the filtrate was concentrated under reduced pressure, and azeotroped twice with toluene. The residue was purified by silica gel column chromatography [dichloromethane/methanol] to afford the title compound (4.51 g).

MS(ESI)m/z: 527 (M+H)$^+$.

$^1$H-NMR (DMSO-$d_6$) δ: 8.40 (1H, t, J=5.7 Hz), 8.15 (1H, d, J=9.1 Hz), 8.00 (1H, t, J=5.7 Hz), 7.51 (1H, t, J=6.0 Hz), 7.38-7.16 (10H, m), 5.03 (2H, s), 4.52 (1H, m), 3.80-3.54 (6H, m), 3.05 (1H, dd, J=13.9, 3.6 Hz), 2.76 (1H, dd, J=14.2, 10.6 Hz), 1.41 (9H, s).

(Step 2)

tert-Butyl glycylglycyl-L-phenylalanylglycinate

To a mixture of the compound obtained in step 1 above (4.51 g) in methanol (20 mL)-dichloromethane (80 mL), 10% palladium-carbon (M) wet (750 mg) was added, and the reaction mixture was stirred under the hydrogen atmosphere at room temperature overnight. Thereto, 10% palladium-carbon (M) wet (1.5 g) was further added, and the reaction mixture was stirred under the hydrogen atmosphere at room temperature overnight. The reaction mixture was filtered with a Celite, and the filtrate was concentrated under reduced pressure. The residue was purified by amino silica gel column chromatography [dichloromethane/methanol] to afford the title compound (3.18 g).

MS(ESI)m/z: 393 (M+H)$^+$.

$^1$H-NMR (DMSO-$d_6$): 8.42 (1H, t, J=6.1 Hz), 8.20 (1H, d, J=8.8 Hz), 8.00 (1H, brs), 7.28-7.16 (5H, m), 4.53 (1H, m), 3.78-3.73 (3H, m), 3.61 (1H, brd, J=16.1 Hz), 3.06 (3H, dd, J=15.4, 5.6 Hz), 2.76 (1H, dd, J=14.2, 10.3 Hz), 1.88 (2H, br), 1.41 (9H, s).

(Step 3)

tert-Butyl N-[6-(2,5-dioxo-2,5-dihydro-1H-pyrrol-1-yl)hexanoyl]glycylglycyl-L-phenylalanylglycinate The compound obtained in step 2 above (2.65 g) and commercially available (Tokyo Chemical Industry Co., Ltd.) N-succinimidyl 6-maleimidehexanoate (2.20 g) were dissolved in N,N-dimethylformamide (20 mL), and the reaction mixture was stirred at room temperature for 7 hours. After the reaction mixture was concentrated under reduced pressure, the residue was poured into a two-layer mixture of dichloromethane and water, and subjected to extraction with dichloromethane. The organic layer was washed three times with water, and once with brine and then dried over anhydrous sodium sulfate. The drying agent was removed through filtration, and the filtrate was concentrated under reduced pressure. The residue was purified by silica gel column chromatography [dichloromethane/methanol] to afford the title compound (3.52 g).

MS(ESI)m/z: 586 (M+H)$^+$.

$^1$H-NMR (CDCl$_3$) δ: 7.28-7.17 (5H, m), 7.09 (1H, t, J=5.1 Hz), 6.96 (1H, t, J=5.1 Hz), 6.91 (1H, d, J=8.3 Hz), 6.68 (2H, s), 6.52 (1H, t, J=4.9 Hz), 4.86 (1H, q, J=7.3 Hz), 4.02-3.88 (5H, m), 3.82 (1H, dd, J=18.1, 4.9 Hz), 3.51 (2H, t, J=7.1

Hz), 3.15 (1H, dd, J=14.2, 6.3 Hz), 3.04 (1H, dd, J=13.7, 7.3 Hz), 2.25 (2H, t, J=7.6 Hz), 1.70-1.57 (4H, m), 1.45 (9H, s), 1.32 (2H, s).
(Step 4)

N-[6-(2,5-Dioxo-2,5-dihydro-1H-pyrrol-1-yl)hexanoyl]glycylglycyl-L-phenylalanylglycine To a solution of the compound obtained in step 3 above (1.00 g) in dichloromethane (9.0 mL), trifluoroacetic acid (4.5 mL) was added at 0° C., and the reaction mixture was stirred at room temperature for 2.5 hours. The reaction mixture was concentrated under reduced pressure, and azeotroped twice with toluene. The residue was purified by silica gel column chromatography [dichloromethane/methanol] to afford the title compound (534 mg).
MS(ESI)m/z: 530 (M+H)$^+$.
$^1$H-NMR (DMSO-d$_6$) δ: 12.59 (1H, br), 8.34 (1H, t, J=5.9 Hz), 8.10 (1H, d, J=8.8 Hz), 8.07 (1H, t, J=5.9 Hz), 7.99 (1H, t, J=5.6 Hz), 7.27-7.16 (5H, m), 7.00 (2H, s), 4.52 (1H, m), 3.76 (2H, d, J=5.9 Hz), 3.74 (1H, m), 3.66 (2H, d, J=5.4 Hz), 3.57 (1H, dd, J=16.8, 5.6 Hz), 3.36 (2H, t, J=7.1 Hz), 3.04 (1H, dd, J=13.9, 4.1 Hz), 2.77 (1H, dd, J=13.9, 10.0 Hz), 2.10 (2H, t, J=7.3 Hz), 1.51-1.43 (4H, m), 1.19 (2H, m).
(Step 5)

2,5-Dioxopyrrolidin-1-yl N-[6-(2,5-dioxo-2,5-dihydro-1H-pyrrol-1-yl)hexanoyl]glycylglycyl-L-phenylalanylglycinate With use of the compound obtained in step 4 above (462 mg), the reaction was performed in the same manner as in step 3 of Example 21 to afford the title compound (258 mg).
MS(ESI)m/z: 627 (M+H)$^+$.
$^1$H-NMR (DMSO-d$_6$) δ: 8.70 (0.85H, t, J=6.1 Hz), 8.44 (0.15H, t, J=5.9 Hz), 8.17 (0.85H, d, J=8.8 Hz), 8.11 (0.15H, d, J=8.8 Hz), 8.06 (1H, t, J=5.6 Hz), 7.99-7.95 (1H, m), 7.27-7.16 (5H, m), 6.99 (2H, s), 4.53 (1H, m), 4.28 (1.7H, d, J=5.9 Hz), 3.85 (0.3H, d, J=5.9 Hz), 3.74 (1H, dd, J=17.1, 5.9 Hz), 3.66 (2H, d, J=5.9 Hz), 3.58 (1H, dd, J=16.8, 5.6 Hz), 3.36 (2H, t, J=7.1 Hz), 3.04 (1H, dd, J=13.9, 4.1 Hz), 2.81 (4H, brs), 2.77 (1H, dd, J=10.0, 3.7 Hz), 2.10 (2H, t, J=7.3 Hz), 1.51-1.44 (4H, m), 1.20 (2H, d, J=7.3 Hz).
(Step 6)

Bis(N,N-diethylethaneaminium) N-[6-(2,5-dioxo-2,5-dihydro-1H-pyrrol-1-yl)hexanoyl]glycylglycyl-L-phenylalanyl-N-[2-({6-amino-9-[(5R,7R,8R,12aR,14R,15R,15aS,16R)-15,16-dihydroxy-2,10-dioxo-2,10-disulfide-14-(6,7,8,9-tetrahydro-2H-2,3,5,6-tetraazabenzo[cd]azulen-2-yl)octahydro-2H,10H,12H-5,8-methano-2λ$^5$,10λ$^5$-furo[3,2-1][1,3,6,9,11,2,10]pentaoxadiphosphacyclotetradecin-7-yl]-9H-purin-2-yl}amino)ethyl]glycinamide (Drug-Linker 23)
With use of the compound obtained in step 8-2 of Example 8 (9.5 mg) and the compound obtained in step 5 above (7.5 mg), the reaction was performed in the same manner as in step 1 of Example 23, and the resultant was then purified by preparative HPLC [10 mM aqueous solution of triethylammonium acetate/acetonitrile, acetonitrile: 10%-30% (0 min-30 min)] to afford the title compound (7.8 mg).
MS(ESI)m/z: 1299 (M+H)$^+$.
$^1$H-NMR (CD$_3$OD) δ: 8.35 (1H, s), 8.02 (1H, s), 7.29-7.15 (6H, m), 6.76 (2H, s), 6.32 (1H, d, J=6.7 Hz), 6.11 (1H, d, 8.5 Hz), 5.48-5.36 (2H, m), 4.82-4.79 (1H, m), 4.50-4.25 (6H, m), 4.06-3.81 (7H, m), 3.61-3.37 (9H, m), 3.17-2.89 (4H, m), 3.14 (12H, q, J=7.3 Hz), 2.21-1.96 (4H, m), 1.58-1.48 (4H, m), 1.30-1.21 (2H, m), 1.27 (18H, t, J=7.3 Hz).

Example 84: Synthesis of Glycan-Remodeled Antibody 3

Figure 28:
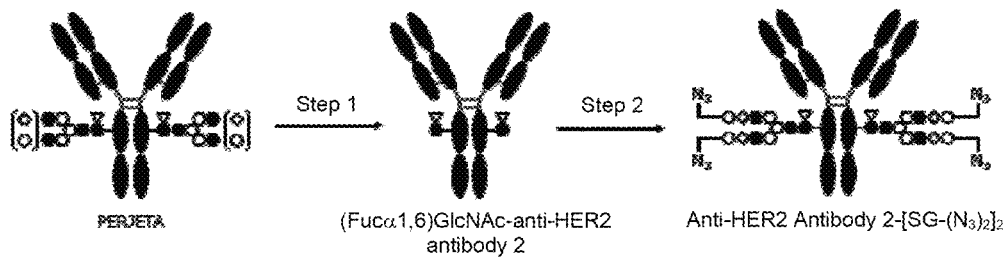
FIG. 28 shows the Synthesis Scheme representing Example 84: Synthesis of Glycan-Remodeled Antibody 3, Preparation of Anti-HER2 Antibody 2-[SG-(N$_3$)$_2$]$_2$.

Preparation of Anti-HER2 Antibody 2-[SG-(N$_3$)$_2$]$_2$
See FIG. 28. [Synthesis Scheme]
(Step 1)
Preparation of (Fucα1,6)GlcNAc-Anti-HER2 Antibody 2
Commercially available PERJETA® intravenous infusion drip 420 mg/14 mL (Chugai Pharmaceutical Co., Ltd.) (3.5 mL) was subjected to buffer exchange in accordance with Common Operation C to provide a phosphate-buffered saline solution (6.0 mL, 15.39 mg/mL, pH 6.0). The same operations as in step 1 of Example 25 were performed to afford a 20 mM phosphate buffer solution of the title antibody (12.96 mg/mL, 7.5 mL, pH 6.0).
(Step 2)
Preparation of Anti-HER2 Antibody 2-[SG-(N$_3$)$_2$]$_2$
With use of the 20 mM phosphate buffer solution of the antibody obtained in step 1 above (12.96 mg/mL, 7.5 mL, pH 6.0) and [N$_3$-PEG (3)]$_2$-SG(10)Ox (22.5 mg), the same operations as in step 2 of Example 25 were performed to afford a phosphate-buffered saline solution of the title antibody (10.21 mg/mL, 9.0 mL, pH 6.0).

Example 85: Synthesis of Glycan-Remodeled Antibody 4

Figure 29:
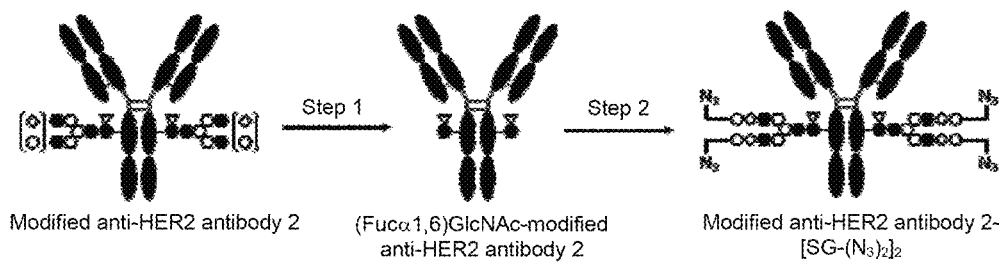
FIG. 29 shows the Synthesis Scheme representing Example 85: Synthesis of Glycan-Remodeled Antibody 4, Preparation of Modified Anti-HER2 Antibody 2-[SG-(N$_3$)$_2$]$_2$.

Preparation of Modified Anti-HER2 Antibody 2-[SG-(N$_3$)$_2$]$_2$
See FIG. 29. [Synthesis Scheme]
(Step 1)
Preparation of (Fucα1,6)GlcNAc-Modified Anti-HER2 Antibody 2
With use of phosphate-buffered saline solution of a modified anti-HER2 antibody 2 prepared in accordance with Reference Example 5 (24 mL, 12.25 mg/mL, pH 6.0), the same operations as in step 1 of Example 25 were performed to afford a 20 mM phosphate buffer solution of the title antibody (20.86 mg/mL, 12.5 mL, pH 6.0).
(Step 2)
Preparation of Modified Anti-HER2 Antibody 2-[SG-(N$_3$)$_2$]$_2$
With use of the 20 mM phosphate buffer solution of the antibody obtained in step 1 above (20.86 mg/mL, 12.5 mL, pH 6.0) and [N$_3$-PEG (3)]$_2$-SG(10)Ox (52 mg), the same operations as in step 2 of Example 25 were performed to afford a phosphate-buffered saline solution of the title antibody (10.87 mg/mL, 22 mL, pH 6.0).

Example 86: Synthesis of Glycan-Remodeled Antibody 5

Figure 30:
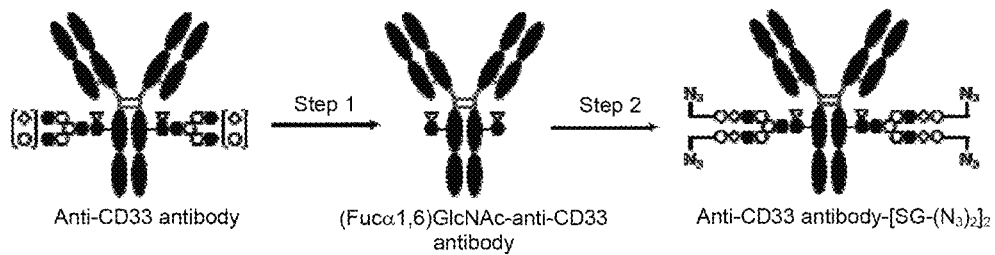
FIG. 30 shows the Synthesis Scheme representing Example 86: Synthesis of Glycan-Remodeled Antibody 5, Preparation of Anti-CD33 Antibody-[SG-(N$_3$)$_2$]$_2$.

Preparation of Anti-CD33 Antibody-[SG-(N$_3$)$_2$]$_2$
See FIG. 30. [Synthesis Scheme]
(Step 1)
Preparation of (Fucα1,6)GlcNAc-Anti-CD33 Antibody
With use of phosphate-buffered saline solution of an anti-CD33 antibody prepared in accordance with Reference Example 6 (9.0 mL, 11.56 mg/mL, pH 6.0), the same operations as in step 1 of Example 25 was performed to afford a 20 mM phosphate buffer solution of the title antibody (11.62 mg/mL, 8 mL, pH 6.0).

(Step 2)
Preparation of Anti-CD33 Antibody-[SG-(N$_3$)$_2$]$_2$

With use of the 20 mM phosphate buffer solution of the antibody obtained in step 1 above (11.62 mg/mL, 8 mL, pH 6.0) and [N$_3$-PEG (3)]$_2$-SG(10)Ox (21.5 mg), the same operations as step 2 of Example 25 were performed to afford a phosphate-buffered saline solution of the title antibody (10.01 mg/mL, 8 mL, pH 6.0).

Example 87: Synthesis of Glycan-Remodeled Antibody 6

Figure 31:
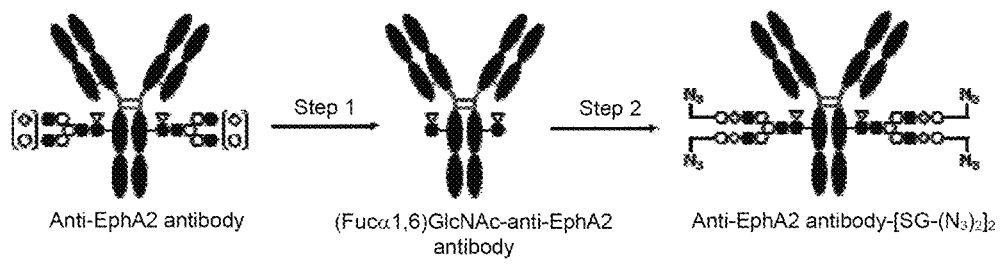
FIG. 31 shows the Synthesis Scheme representing Example 87: Synthesis of Glycan-Remodeled Antibody 6, Preparation of Anti-EphA2 Antibody-[SG-(N$_3$)$_2$]$_2$.

Preparation of Anti-EphA2 Antibody-[SG-(N$_3$)$_2$]$_2$
See FIG. 31. [Synthesis Scheme]
(Step 1)
Preparation of (Fucα1,6)GlcNAc-Anti-EphA2 Antibody With use of phosphate-buffered saline solution of an anti-EphA2 antibody prepared in accordance with Reference Example 7 (8.0 mL, 12.83 mg/mL, pH 6.0), the same operations as in step 1 of Example 25 were performed to afford a 20 mM phosphate buffer solution of the title antibody (13.51 mg/mL, 7 mL, pH 6.0).
(Step 2)
Preparation of Anti-EphA2 Antibody-[SG-(N$_3$)$_2$]$_2$ With use of the 20 mM phosphate buffer solution of the antibody obtained in step 1 above (13.51 mg/mL, 7 mL, pH 6.0) and [N$_3$-PEG (3)]$_2$-SG(10)Ox (21.7 mg), the same operations as in step 2 of Example 25 were performed to afford a phosphate-buffered saline solution of the title antibody (8.91 mg/mL, 7.5 mL, pH 6.0).

Example 88: Synthesis of Glycan-Remodeled Antibody 7

Figure 32:
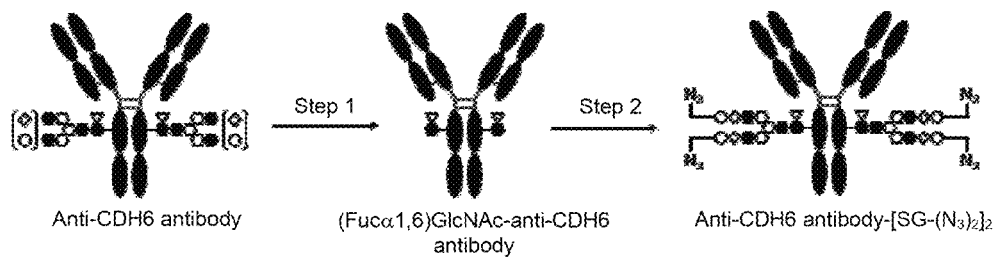
FIG. 32 shows the Synthesis Scheme representing Example 88: Synthesis of Glycan-Remodeled Antibody 7, Preparation of Anti-CDH6 Antibody-[SG-(N$_3$)$_2$]$_2$.

Preparation of Anti-CDH6 Antibody-[SG-(N$_3$)$_2$]$_2$
See FIG. 32. [Synthesis Scheme]
(Step 1)
Preparation of (Fucα1,6)GlcNAc-Anti-CDH6 Antibody HBS or buffer (25 mM histidine/5% sorbitol, pH=6.0) (5.0 mL, 20.0 mg/mL) of an anti-CDH6 antibody prepared in accordance with Reference Example 8 was subjected to buffer exchange to phosphate-buffered saline solution (pH=6.0) in accordance with Common Operation C, and the same operations as in step 1 of Example 25 were then performed to afford a 20 mM phosphate buffer solution of the title antibody (9.58 mg/mL, 9.0 mL, pH 6.0).
(Step 2)
Preparation of Anti-CDH6 Antibody-[SG-(N$_3$)$_2$]$_2$ With use of the 20 mM phosphate buffer solution of the antibody obtained in step 1 above (9.58 mg/mL, 9.0 mL, pH 6.0) and [N$_3$-PEG (3)]$_2$-SG(10)Ox (24.5 mg), the same operations as in step 2 of Example 25 were performed to afford a phosphate-buffered saline solution of the title antibody (10.69 mg/mL, 7.5 mL, pH 6.0).

Example 89: Synthesis of Glycan-Remodeled Antibody 8

Figure 33:
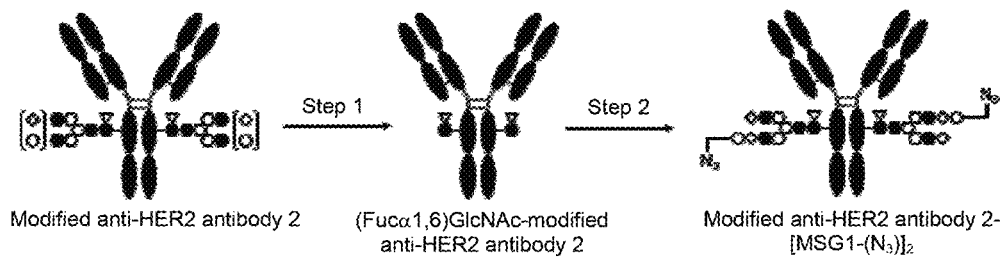
FIG. 33 shows the Synthesis Scheme representing Example 89: Synthesis of Glycan-Remodeled Antibody 8, Preparation of Modified Anti-HER2 Antibody 2-[MSG1-(N$_3$)]$_2$.

Preparation of Modified Anti-HER2 Antibody 2-[MSG1-(N$_3$)]$_2$
See FIG. 33. [Synthesis Scheme]
(Step 1)
Preparation of (Fucα1,6)GlcNAc-Modified Anti-HER2 Antibody 2

The same reaction as in step 1 of Example 85 was performed for a buffer solution of the raw material antibody (10 mL, 12.25 mg/mL, pH 6.0) to afford a 20 mM phosphate buffer solution of the title antibody (14.84 mg/mL, 7.5 mL, pH 6.0).
(Step 2)
Preparation of Modified Anti-HER2 Antibody 2-[MSG1-(N$_3$)]$_2$ With use of the 20 mM phosphate buffer solution of the antibody obtained in step 1 above (14.84 mg/mL, 7.5 mL, pH 6.0) and [N$_3$-PEG (3)]-MSG1 (9)-Ox (compound 1-11 in WO 2018/003983) (19 mg), the same operations as in step 2 of Example 25 were performed to afford a phosphate-buffered saline solution of the title antibody (10.48 mg/mL, 9.25 mL, pH 6.0).

Example 90: Synthesis of Antibody-Drug Conjugate 5 (Synthesis of Anti-HER2 Antibody-CDN Conjugate 4)

A phosphate-buffered saline solution of glycan-remodeled antibody 1 (pH 6.0) (10.97 mg/mL, 0.500 mL) was diluted with propylene glycol (0.250 mL). To this solution, a mixture of a dimethyl sulfoxide solution of drug-linker 1 (10 mM, 0.091 mL, 24 equivalents per antibody molecule) and propylene glycol (0.159 mL) was added, and the resultant was reacted with a tube rotator (MTR-103, AS ONE Corporation) at room temperature for 3 days. The reaction mixture was purified in accordance with the method described in Common Operation D to afford a solution of the targeted antibody-drug conjugate in ABS (3.5 mL).

Analysis was performed in accordance with the methods described in Common Operations E and G to acquire the following results.
Antibody concentration: 0.49 mg/mL
Antibody yield: 1.71 mg (31%)
Average number of conjugated drug molecules: 3.6

Example 91: Synthesis of Antibody-Drug Conjugate 6 (Synthesis of Anti-HER2 Antibody-CDN Conjugate 5)

A phosphate-buffered saline solution of glycan-remodeled antibody 1 (pH 6.0) (10.97 mg/mL, 0.500 mL) was diluted with propylene glycol (0.250 mL). To this solution, a mixture of a dimethyl sulfoxide solution of drug-linker 2a (10 mM, 0.091 mL, 24 equivalents per antibody molecule) and propylene glycol (0.159 mL) was added, and the resultant was reacted with a tube rotator (MTR-103, AS ONE Corporation) at room temperature for 2 days. The reaction mixture was purified in accordance with the method described in Common Operation D to afford a solution of the targeted antibody-drug conjugate in ABS (3.5 mL).

Analysis was performed in accordance with the methods described in Common Operations E and G to acquire the following results.
Antibody concentration: 0.91 mg/ml
Antibody yield: 3.17 mg (58%)
Average number of conjugated drug molecules: 3.6

Example 92: Synthesis of Antibody-Drug Conjugate 7 (Synthesis of Anti-HER2 Antibody-CDN Conjugate 6)

A phosphate-buffered saline solution of glycan-remodeled antibody 1 (pH 6.0) (10.70 mg/mL, 4.00 mL) was diluted with propylene glycol (2.00 mL). To this solution, a mixture of a dimethyl sulfoxide solution of drug-linker 2b (10 mM, 0.707 mL, 24 equivalents per antibody molecule) and propylene glycol (1.293 mL) was added, and the resultant was reacted with a tube rotator (MTR-103, AS ONE Corporation) at room temperature for 3 days. The reaction mixture was purified in accordance with the method described in Common Operation D to afford a solution of the targeted antibody-drug conjugate in ABS (24.5 mL).

Analysis was performed in accordance with the methods described in Common Operations E and G to acquire the following results.
Antibody concentration: 0.96 mg/mL
Antibody yield: 23.57 mg (59%)
Average number of conjugated drug molecules: 3.7

Example 93: Synthesis of Antibody-Drug Conjugate 8 (Synthesis of Anti-HER2 Antibody-CDN Conjugate 7)

A phosphate-buffered saline solution of glycan-remodeled antibody 1 (pH 6.0) (10.70 mg/mL, 4.00 mL) was diluted with propylene glycol (2.00 mL). To this solution, a mixture of a dimethyl sulfoxide solution of drug-linker 5 (10 mM, 0.707 mL, 24 equivalents per antibody molecule) and propylene glycol (1.293 mL) was added, and the resultant was reacted with a tube rotator (MTR-103, AS ONE Corporation) at room temperature for 2 days. The reaction mixture was purified in accordance with the method described in Common Operation D to afford a solution of the targeted antibody-drug conjugate in ABS (24.5 mL).

Analysis was performed in accordance with the methods described in Common Operations E and G to acquire the following results.
Antibody concentration: 1.10 mg/mL
Antibody yield: 26.86 mg (67%)
Average number of conjugated drug molecules: 3.7

Example 94: Synthesis of Antibody-Drug Conjugate 9 (Synthesis of Anti-HER2 Antibody-CDN Conjugate 8)

A phosphate-buffered saline solution of glycan-remodeled antibody 1 (pH 6.0) (10.70 mg/mL, 4.00 mL) was diluted with propylene glycol (2.00 mL). To this solution, a mixture of a dimethyl sulfoxide solution of drug-linker 6 (10 mM, 0.707 mL, 24 equivalents per antibody molecule) and propylene glycol (1.293 mL) was added, and the resultant was reacted with a tube rotator (MTR-103, AS ONE Corporation) at room temperature for 2 days. The reaction mixture was purified in accordance with the method described in Common Operation D to afford a solution of the targeted antibody-drug conjugate in ABS (24.5 mL).

Analysis was performed in accordance with the methods described in Common Operations E and G to acquire the following results.
Antibody concentration: 1.34 mg/mL
Antibody yield: 32.92 mg (82%)
Average number of conjugated drug molecules: 3.7

Example 95: Synthesis of Antibody-Drug Conjugate 10 (Synthesis of Anti-LPS Antibody-CDN Conjugate 2)

A phosphate-buffered saline solution of glycan-remodeled antibody 2 (pH 6.0) (10.55 mg/mL, 0.500 mL) was diluted with propylene glycol (0.250 mL). To this solution, a mixture of a dimethyl sulfoxide solution of drug-linker 2a (10 mM, 0.087 mL, 24 equivalents per antibody molecule) and propylene glycol (0.163 mL) was added, and the resultant was reacted with a tube rotator (MTR-103, AS ONE Corporation) at room temperature for 2 days. The reaction mixture was purified in accordance with the method described in Common Operation D to afford a solution of the targeted antibody-drug conjugate in ABS (3.5 mL).

Analysis was performed in accordance with the methods described in Common Operations E and G to acquire the following results.
Antibody concentration: 0.88 mg/mL
Antibody yield: 3.08 mg (62%)
Average number of conjugated drug molecules: 3.6

Example 96: Synthesis of Antibody-Drug Conjugate 11 (Synthesis of Anti-EphA2 Antibody-CDN Conjugate 1)

A phosphate-buffered saline solution of glycan-remodeled antibody 6 (pH 6.0) (8.91 mg/mL, 0.500 mL) was diluted with propylene glycol (0.250 mL). To this solution, a mixture of a dimethyl sulfoxide solution of drug-linker 2b (10 mM, 0.073 mL, 24 equivalents per antibody molecule) and propylene glycol (0.177 mL) was added, and the resultant was reacted with a tube rotator (MTR-103, AS ONE Corporation) at room temperature for 2 days. The reaction mixture was purified in accordance with the method described in Common Operation D to afford a solution of the targeted antibody-drug conjugate in ABS (3.5 mL).

Analysis was performed in accordance with the methods described in Common Operations E and F to acquire the following results.
Antibody concentration: 0.60 mg/mL
Antibody yield: 2.10 mg (47%)
Average number of conjugated drug molecules: 3.8

Example 97: Synthesis of Antibody-Drug Conjugate 12 (Synthesis of Anti-CD33 Antibody-CDN Conjugate 1)

A phosphate-buffered saline solution of glycan-remodeled antibody 5 (pH 6.0) (10.01 mg/mL, 0.500 mL) was diluted with propylene glycol (0.250 mL). To this solution, a mixture of a dimethyl sulfoxide solution of drug-linker 2b (10 mM, 0.083 mL, 24 equivalents per antibody molecule) and propylene glycol (0.167 mL) was added, and the resultant was reacted with a tube rotator (MTR-103, AS ONE Corporation) at room temperature for 2 days. The reaction mixture was purified in accordance with the method described in Common Operation D to afford a solution of the targeted antibody-drug conjugate in ABS (3.5 mL).

Analysis was performed in accordance with the methods described in Common Operations E and G to acquire the following results.
Antibody concentration: 0.73 mg/mL
Antibody yield: 2.57 mg (51%)
Average number of conjugated drug molecules: 3.9

Example 98: Synthesis of Antibody-Drug Conjugate 13 (Synthesis of Anti-CDH6 Antibody-CDN Conjugate 1)

A phosphate-buffered saline solution of glycan-remodeled antibody 7 (pH 6.0) (10.69 mg/mL, 0.500 mL) was diluted with propylene glycol (0.250 mL). To this solution, a mixture of a dimethyl sulfoxide solution of drug-linker 2b (10 mM, 0.088 mL, 24 equivalents per antibody molecule) and propylene glycol (0.162 mL) was added, and the resultant was reacted with a tube rotator (MTR-103, AS ONE Corporation) at room temperature for 3 days. The reaction mixture was purified in accordance with the method described in Common Operation D to afford a solution of the targeted antibody-drug conjugate in ABS (3.5 mL).

Analysis was performed in accordance with the methods described in Common Operations E and G to acquire the following results.

Antibody concentration: 0.96 mg/mL
Antibody yield: 3.37 mg (63%)
Average number of conjugated drug molecules: 3.8

Example 99: Synthesis of Antibody-Drug Conjugate 14 (Synthesis of Anti-HER2 Antibody 2-CDN Conjugate 1)

A phosphate-buffered saline solution of glycan-remodeled antibody 3 (pH 6.0) (10.21 mg/mL, 1.50 mL) was diluted with propylene glycol (0.750 mL). To this solution, a mixture of a dimethyl sulfoxide solution of drug-linker 3 (10 mM, 0.253 mL, 24 equivalents per antibody molecule) and propylene glycol (0.497 mL) was added, and the resultant was reacted with a tube rotator (MTR-103, AS ONE Corporation) at room temperature for 2 days. The reaction mixture was purified in accordance with the method described in Common Operation D to afford a solution of the targeted antibody-drug conjugate in ABS (9.5 mL).

Analysis was performed in accordance with the methods described in Common Operations E and G to acquire the following results.

Antibody concentration: 1.02 mg/mL
Antibody yield: 9.73 mg (64%)
Average number of conjugated drug molecules: 3.7

Example 100: Synthesis of Antibody-Drug Conjugate 15 (Synthesis of Anti-HER2 Antibody-CDN Conjugate 9)

A phosphate-buffered saline solution of glycan-remodeled antibody 1 (pH 6.0) (10.70 mg/mL, 0.500 mL) was diluted with propylene glycol (0.250 mL). To this solution, a mixture of a dimethyl sulfoxide solution of drug-linker 8 (10 mM, 0.088 mL, 24 equivalents per antibody molecule) and propylene glycol (0.162 mL) was added, and the resultant was reacted with a tube rotator (MTR-103, AS ONE Corporation) at room temperature for 2 days. The reaction mixture was purified in accordance with the method described in Common Operation D to afford a solution of the targeted antibody-drug conjugate in ABS (3.5 mL).

Analysis was performed in accordance with the methods described in Common Operations E and G to acquire the following results.

Antibody concentration: 0.93 mg/mL
Antibody yield: 3.24 mg (61%)
Average number of conjugated drug molecules: 3.6

Example 101: Synthesis of Antibody-Drug Conjugate 16 (Synthesis of Anti-HER2 Antibody-CDN Conjugate 10)

A phosphate-buffered saline solution of glycan-remodeled antibody 1 (pH 6.0) (10.35 mg/mL, 13.50 mL) was diluted with propylene glycol (6.750 mL). To this solution, a mixture of a dimethyl sulfoxide solution of drug-linker 9 (10 mM, 2.310 mL, 24 equivalents per antibody molecule) and propylene glycol (4.440 mL) was added, and the resultant was reacted with a tube rotator (MTR-103, AS ONE Corporation) at room temperature for 2 days. The reaction mixture was purified in accordance with the method described in Common Operation D to afford a solution of the targeted antibody-drug conjugate in ABS (74.3 mL).

Analysis was performed in accordance with the methods described in Common Operations E and G to acquire the following results.

Antibody concentration: 1.36 mg/mL
Antibody yield: 100.8 mg (72%)
Average number of conjugated drug molecules: 3.7

Example 102: Synthesis of Antibody-Drug Conjugate 17 (Synthesis of Anti-HER2 Antibody-CDN Conjugate 11)

A phosphate-buffered saline solution of glycan-remodeled antibody 1 (pH 6.0) (10.70 mg/mL, 0.500 mL) was diluted with propylene glycol (0.250 mL). To this solution, a mixture of a dimethyl sulfoxide solution of drug-linker 10 (10 mM, 0.088 mL, 24 equivalents per antibody molecule) and propylene glycol (0.162 mL) was added, and the resultant was reacted with a tube rotator (MTR-103, AS ONE Corporation) at room temperature for 3 days. The reaction mixture was purified in accordance with the method described in Common Operation D to afford a solution of the targeted antibody-drug conjugate in ABS (3.5 mL).

Analysis was performed in accordance with the methods described in Common Operations E and G to acquire the following results.

Antibody concentration: 0.63 mg/mL
Antibody yield: 2.22 mg (42%)
Average number of conjugated drug molecules: 3.5

Example 103: Synthesis of Antibody-Drug Conjugate 18 (Synthesis of Anti-HER2 Antibody-CDN Conjugate 12)

A phosphate-buffered saline solution of glycan-remodeled antibody 1 (pH 6.0) (10.70 mg/mL, 0.500 mL) was diluted with propylene glycol (0.250 mL). To this solution, a mixture of a dimethyl sulfoxide solution of drug-linker 11 (10 mM, 0.088 mL, 24 equivalents per antibody molecule) and propylene glycol (0.162 mL) was added, and the resultant was reacted with a tube rotator (MTR-103, AS ONE Corporation) at room temperature for 3 days. The reaction mixture was purified in accordance with the method described in Common Operation D to afford a solution of the targeted antibody-drug conjugate in ABS (3.5 mL).

Analysis was performed in accordance with the methods described in Common Operations E and G to acquire the following results.

Antibody concentration: 0.94 mg/mL
Antibody yield: 3.29 mg (62%)
Average number of conjugated drug molecules: 3.6

Example 104: Synthesis of Antibody-Drug Conjugate 19 (Synthesis of Anti-HER2 Antibody-CDN Conjugate 13)

A phosphate-buffered saline solution of glycan-remodeled antibody 1 (pH 6.0) (10.70 mg/mL, 0.500 mL) was diluted with propylene glycol (0.250 mL). To this solution, a mixture of a dimethyl sulfoxide solution of drug-linker 12 (10 mM, 0.088 mL, 24 equivalents per antibody molecule) and propylene glycol (0.162 mL) was added, and the resultant was reacted with a tube rotator (MTR-103, AS ONE Corporation) at room temperature for 3 days. The reaction mixture was purified in accordance with the method described in Common Operation D to afford a solution of the targeted antibody-drug conjugate in ABS (3.5 mL).

Analysis was performed in accordance with the methods described in Common Operations E and G to acquire the following results.
Antibody concentration: 0.92 mg/mL
Antibody yield: 3.20 mg (60%)
Average number of conjugated drug molecules: 3.5

Example 105: Synthesis of Antibody-Drug Conjugate 20 (Synthesis of Anti-HER2 Antibody-CDN Conjugate 14)

A phosphate-buffered saline solution of glycan-remodeled antibody 1 (pH 6.0) (10.70 mg/mL, 0.500 mL) was diluted with propylene glycol (0.250 mL). To this solution, a mixture of a dimethyl sulfoxide solution of drug-linker 13 (10 mM, 0.088 mL, 24 equivalents per antibody molecule) and propylene glycol (0.162 mL) was added, and the resultant was reacted with a tube rotator (MTR-103, AS ONE Corporation) at room temperature for 3 days. The reaction mixture was purified in accordance with the method described in Common Operation D to afford a solution of the targeted antibody-drug conjugate in ABS (3.5 mL).

Analysis was performed in accordance with the methods described in Common Operations E and G to acquire the following results.
Antibody concentration: 1.01 mg/mL
Antibody yield: 3.52 mg (66%)
Average number of conjugated drug molecules: 3.5

Example 106: Synthesis of Antibody-Drug Conjugate 21 (Synthesis of Anti-HER2 Antibody-CDN Conjugate 15)

A phosphate-buffered saline solution of glycan-remodeled antibody 1 (pH 6.0) (10.70 mg/mL, 0.500 mL) was diluted with propylene glycol (0.250 mL). To this solution, a mixture of a dimethyl sulfoxide solution of drug-linker 14 (10 mM, 0.088 mL, 24 equivalents per antibody molecule) and propylene glycol (0.162 mL) was added, and the resultant was reacted with a tube rotator (MTR-103, AS ONE Corporation) at room temperature for 2 days. The reaction mixture was purified in accordance with the method described in Common Operation D to afford a solution of the targeted antibody-drug conjugate in ABS (3.5 mL).

Analysis was performed in accordance with the methods described in Common Operations E and G to acquire the following results.
Antibody concentration: 0.78 mg/mL
Antibody yield: 2.74 mg (51%)
Average number of conjugated drug molecules: 3.6

Example 107: Synthesis of Antibody-Drug Conjugate 22 (Synthesis of Anti-HER2 Antibody-CDN Conjugate 16)

A phosphate-buffered saline solution of glycan-remodeled antibody 1 (pH 6.0) (10.70 mg/mL, 0.500 mL) was diluted with propylene glycol (0.250 mL). To this solution, a mixture of a dimethyl sulfoxide solution of drug-linker 15 (10 mM, 0.088 mL, 24 equivalents per antibody molecule) and propylene glycol (0.162 mL) was added, and the resultant was reacted with a tube rotator (MTR-103, AS ONE Corporation) at room temperature for 2 days. The reaction mixture was purified in accordance with the method described in Common Operation D to afford a solution of the targeted antibody-drug conjugate in ABS (3.5 mL).

Analysis was performed in accordance with the methods described in Common Operations E and G to acquire the following results.
Antibody concentration: 1.32 mg/mL
Antibody yield: 4.61 mg (86%)
Average number of conjugated drug molecules: 3.6

Example 108: Synthesis of Antibody-Drug Conjugate 23 (Synthesis of Anti-HER2 Antibody-CDN Conjugate 17)

A phosphate-buffered saline solution of glycan-remodeled antibody 1 (pH 6.0) (10.70 mg/mL, 0.500 mL) was diluted with propylene glycol (0.250 mL). To this solution, a mixture of a dimethyl sulfoxide solution of drug-linker 16 (10 mM, 0.088 mL, 24 equivalents per antibody molecule) and propylene glycol (0.162 mL) was added, and the resultant was reacted with a tube rotator (MTR-103, AS ONE Corporation) at room temperature for 2 days. The reaction mixture was purified in accordance with the method described in Common Operation D to afford a solution of the targeted antibody-drug conjugate in ABS (3.5 mL).

Analysis was performed in accordance with the methods described in Common Operations E and G to acquire the following results.
Antibody concentration: 0.93 mg/mL
Antibody yield: 3.25 mg (61%)
Average number of conjugated drug molecules: 3.6

Example 109: Synthesis of Antibody-Drug Conjugate 24 (Synthesis of Anti-HER2 Antibody-CDN Conjugate 18)

A phosphate-buffered saline solution of glycan-remodeled antibody 1 (pH 6.0) (10.70 mg/mL, 4.00 mL) was diluted with propylene glycol (2.00 mL). To this solution, a mixture of a dimethyl sulfoxide solution of drug-linker 7 (10 mM, 0.707 mL, 24 equivalents per antibody molecule) and propylene glycol (1.293 mL) was added, and the resultant was reacted with a tube rotator (MTR-103, AS ONE Corporation) at room temperature for 3 days. The reaction mixture was purified in accordance with the method described in Common Operation D to afford a solution of the targeted antibody-drug conjugate in ABS (24.5 mL).

Analysis was performed in accordance with the methods described in Common Operations E and G to acquire the following results.
Antibody concentration: 1.33 mg/mL
Antibody yield: 32.64 mg (82%)
Average number of conjugated drug molecules: 3.7

Example 110: Synthesis of Antibody-Drug Conjugate 25 (Synthesis of Anti-HER2 Antibody 2-CDN Conjugate 2)

A phosphate-buffered saline solution of glycan-remodeled antibody 4 (pH 6.0) (10.87 mg/mL, 8.00 mL) was diluted with propylene glycol (4.00 mL). To this solution, a mixture of a dimethyl sulfoxide solution of drug-linker 17a (10 mM, 1.079 mL, 18 equivalents per antibody molecule) and propylene glycol (2.921 mL) was added, and the resultant was reacted with a tube rotator (MTR-103, AS ONE Corporation) at room temperature for 3 days. The reaction mixture was purified in accordance with the method described in Common Operation D to afford a solution of the targeted antibody-drug conjugate in ABS (44.5 mL).

Analysis was performed in accordance with the methods described in Common Operations E and G to acquire the following results.
- Antibody concentration: 1.16 mg/mL
- Antibody yield: 51.5 mg (59%)
- Average number of conjugated drug molecules: 3.8

Example 111: Synthesis of Antibody-Drug Conjugate 26 (Synthesis of Anti-HER2 Antibody 2-CDN Conjugate 3)

A phosphate-buffered saline solution of glycan-remodeled antibody 4 (pH 6.0) (10.87 mg/mL, 8.00 mL) was diluted with propylene glycol (4.00 mL). To this solution, a mixture of a dimethyl sulfoxide solution of drug-linker 17b (10 mM, 1.079 mL, 18 equivalents per antibody molecule) and propylene glycol (2.921 mL) was added, and the resultant was reacted with a tube rotator (MTR-103, AS ONE Corporation) at room temperature for 3 days. The reaction mixture was purified in accordance with the method described in Common Operation D to afford a solution of the targeted antibody-drug conjugate in ABS (44.5 mL).

Analysis was performed in accordance with the methods described in Common Operations E and G to acquire the following results.
- Antibody concentration: 1.24 mg/mL
- Antibody yield: 54.99 mg (63%)
- Average number of conjugated drug molecules: 3.9

Example 112: Synthesis of Antibody-Drug Conjugate 27 (Synthesis of Anti-HER2 Antibody 2-CDN Conjugate 4)

A phosphate-buffered saline solution of glycan-remodeled antibody 4 (pH 6.0) (10.89 mg/mL, 1.00 mL) was diluted with propylene glycol (0.500 mL). To this solution, a mixture of a dimethyl sulfoxide solution of drug-linker 19 (10 mM, 0.180 mL, 24 equivalents per antibody molecule) and propylene glycol (0.320 mL) was added, and the resultant was reacted with a tube rotator (MTR-103, AS ONE Corporation) at room temperature for 3 days. The reaction mixture was purified in accordance with the method described in Common Operation D to afford a solution of the targeted antibody-drug conjugate in ABS (7.0 mL).

Analysis was performed in accordance with the methods described in Common Operations E and G to acquire the following results.
- Antibody concentration: 0.79 mg/mL
- Antibody yield: 5.53 mg (51%)
- Average number of conjugated drug molecules: 3.9

Example 113: Synthesis of Antibody-Drug Conjugate 28 (Synthesis of Anti-HER2 Antibody 2-CDN Conjugate 5)

A phosphate-buffered saline solution of glycan-remodeled antibody 4 (pH 6.0) (10.89 mg/mL, 1.00 mL) was diluted with propylene glycol (0.500 mL). To this solution, a mixture of a dimethyl sulfoxide solution of drug-linker 21 (10 mM, 0.180 mL, 24 equivalents per antibody molecule) and propylene glycol (0.320 mL) was added, and the resultant was reacted with a tube rotator (MTR-103, AS ONE Corporation) at room temperature for 3 days. The reaction mixture was purified in accordance with the method described in Common Operation D to afford a solution of the targeted antibody-drug conjugate in ABS (7.0 mL).

Analysis was performed in accordance with the methods described in Common Operations E and G to acquire the following results.
- Antibody concentration: 0.84 mg/mL
- Antibody yield: 5.91 mg (54%)
- Average number of conjugated drug molecules: 3.9

Example 114: Synthesis of Antibody-Drug Conjugate 29 (Synthesis of Anti-HER2 Antibody 2-CDN Conjugate 6)

A phosphate-buffered saline solution of glycan-remodeled antibody 4 (pH 6.0) (10.89 mg/mL, 1.00 mL) was diluted with propylene glycol (0.500 mL). To this solution, a mixture of a dimethyl sulfoxide solution of drug-linker 22 (10 mM, 0.180 mL, 24 equivalents per antibody molecule) and propylene glycol (0.320 mL) was added, and the resultant was reacted with a tube rotator (MTR-103, AS ONE Corporation) at room temperature for 2 days. The reaction mixture was purified in accordance with the method described in Common Operation D to afford a solution of the targeted antibody-drug conjugate in ABS (5.0 mL).

Analysis was performed in accordance with the methods described in Common Operations E and G to acquire the following results.
- Antibody concentration: 0.92 mg/mL
- Antibody yield: 4.60 mg (42%)
- Average number of conjugated drug molecules: 3.5

Example 115: Synthesis of Antibody-Drug Conjugate 30 (Synthesis of Anti-HER2 Antibody 2-CDN Conjugate 7)

A phosphate-buffered saline solution of glycan-remodeled antibody 4 (pH 6.0) (10.89 mg/mL, 1.00 mL) was diluted with propylene glycol (0.500 mL). To this solution, a mixture of a dimethyl sulfoxide solution of drug-linker 18 (10 mM, 0.180 mL, 24 equivalents per antibody molecule) and propylene glycol (0.320 mL) was added, and the resultant was reacted with a tube rotator (MTR-103, AS ONE Corporation) at room temperature for 2 days. The reaction mixture was purified in accordance with the method described in Common Operation D to afford a solution of the targeted antibody-drug conjugate in ABS (7.0 mL).

Analysis was performed in accordance with the methods described in Common Operations E and G to acquire the following results.
- Antibody concentration: 1.08 mg/mL
- Antibody yield: 7.53 mg (69%)
- Average number of conjugated drug molecules: 3.9

Example 116: Synthesis of Antibody-Drug Conjugate 31 (Synthesis of Anti-HER2 Antibody 2-CDN Conjugate 8)

A phosphate-buffered saline solution of glycan-remodeled antibody 4 (pH 6.0) (10.89 mg/mL, 1.00 mL) was diluted with propylene glycol (0.500 mL). To this solution, a mixture of a dimethyl sulfoxide solution of drug-linker 20 (10 mM, 0.180 mL, 24 equivalents per antibody molecule) and propylene glycol (0.320 mL) was added, and the resultant was reacted with a tube rotator (MTR-103, AS ONE Corporation) at room temperature for 2 days. The reaction mixture was purified in accordance with the method described in Common Operation D to afford a solution of the targeted antibody-drug conjugate in ABS (7.0 mL).

Analysis was performed in accordance with the methods described in Common Operations E and G to acquire the following results.
- Antibody concentration: 1.09 mg/mL
- Antibody yield: 7.62 mg (70%)
- Average number of conjugated drug molecules: 3.8

Example 117: Synthesis of Antibody-Drug Conjugate 32 (Synthesis of Anti-HER2 Antibody 2-CDN Conjugate 9)

A phosphate-buffered saline solution of glycan-remodeled antibody 8 (pH 6.0) (10.48 mg/mL, 1.00 mL) was diluted with propylene glycol (0.500 mL). To this solution, a mixture of a dimethyl sulfoxide solution of drug-linker 17a (10 mM, 0.087 mL, 12 equivalents per antibody molecule) and propylene glycol (0.413 mL) was added, and the resultant was reacted with a tube rotator (MTR-103, AS ONE Corporation) at room temperature for 2 days. The reaction mixture was purified in accordance with the method described in Common Operation D to afford a solution of the targeted antibody-drug conjugate in ABS (7.0 mL).

Analysis was performed in accordance with the methods described in Common Operations E and G to acquire the following results.

Antibody concentration: 0.77 mg/mL
Antibody yield: 5.36 mg (51%)
Average number of conjugated drug molecules: 1.8

Example 118: Synthesis of Antibody-Drug Conjugate 33 (Synthesis of Anti-HER2 Antibody 2-CDN Conjugate 10)

A phosphate-buffered saline solution of glycan-remodeled antibody 8 (pH 6.0) (10.48 mg/mL, 1.00 mL) was diluted with propylene glycol (0.500 mL). To this solution, a mixture of a dimethyl sulfoxide solution of drug-linker 17b (10 mM, 0.087 mL, 12 equivalents per antibody molecule) and propylene glycol (0.413 mL) was added, and the resultant was reacted with a tube rotator (MTR-103, AS ONE Corporation) at room temperature for 2 days. The reaction mixture was purified in accordance with the method described in Common Operation D to afford a solution of the targeted antibody-drug conjugate in ABS (7.0 mL).

Analysis was performed in accordance with the methods described in Common Operations E and G to acquire the following results.

Antibody concentration: 0.91 mg/mL
Antibody yield: 6.34 mg (61%)
Average number of conjugated drug molecules: 1.8

Example 119: Synthesis of Antibody-Drug Conjugate 34 (Synthesis of Anti-HER2 Antibody-CDN Conjugate 19)

A phosphate buffer solution of an anti-HER2 antibody prepared in accordance with Reference Example 1 was subjected to buffer exchange in accordance with Common Operation C to prepare an antibody solution in phosphate-buffered saline/5 mM EDTA (7.69 mg/mL). To this antibody solution (0.65 mL), an aqueous solution of tris(2-carboxyethyl) phosphine hydrochloride (10 mM, 20.7 μL) and an aqueous solution of dipotassium hydrogen phosphate (1 M, 9.8 μL) were added. After confirming that the pH of the reaction mixture was within 7.4+1.0, the reaction mixture was stirred at 37° C. for 2 hours. A DMSO solution of drug-linker 23 (10 mM, 0.0689 mL) was added thereto, and the resultant was reacted with tube rotator (MTR-103, AS ONE Corporation) at room temperature for 1 hour. An aqueous solution of N-acetyl-L-cysteine (100 mM, 6.9 μL) was added to the reaction mixture to quench the reaction. The reaction mixture was subjected to buffer exchange in accordance with the method described in Common Operation C to afford an ABS solution of the targeted antibody-drug conjugate (1.6 mL).

Analysis was performed in accordance with the methods described in Common Operations E and G to acquire the following results.

Antibody concentration: 1.46 mg/mL
Antibody yield: 2.34 mg (47%)
Average number of conjugated drug molecules: 6.5

Example 120: Synthesis of Drug-Linker 24

[Synthesis Scheme]

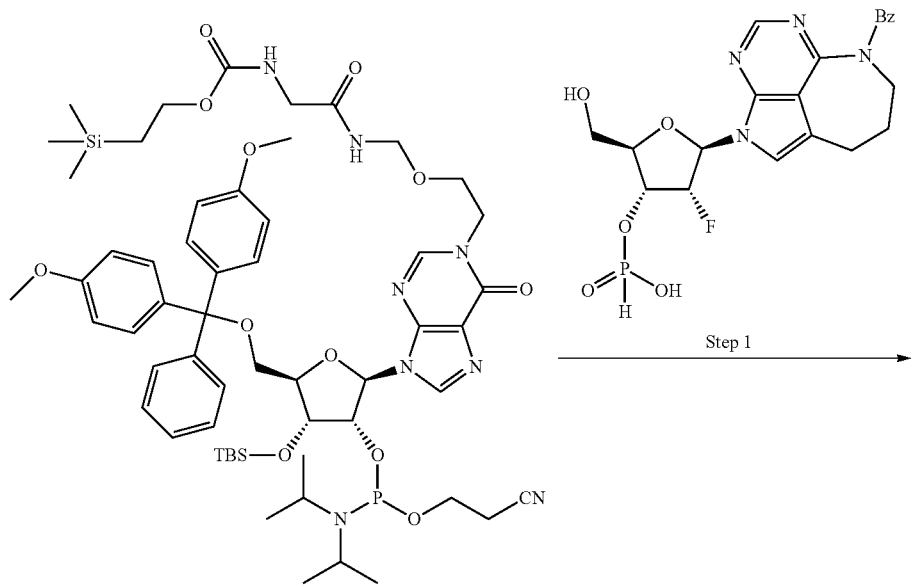

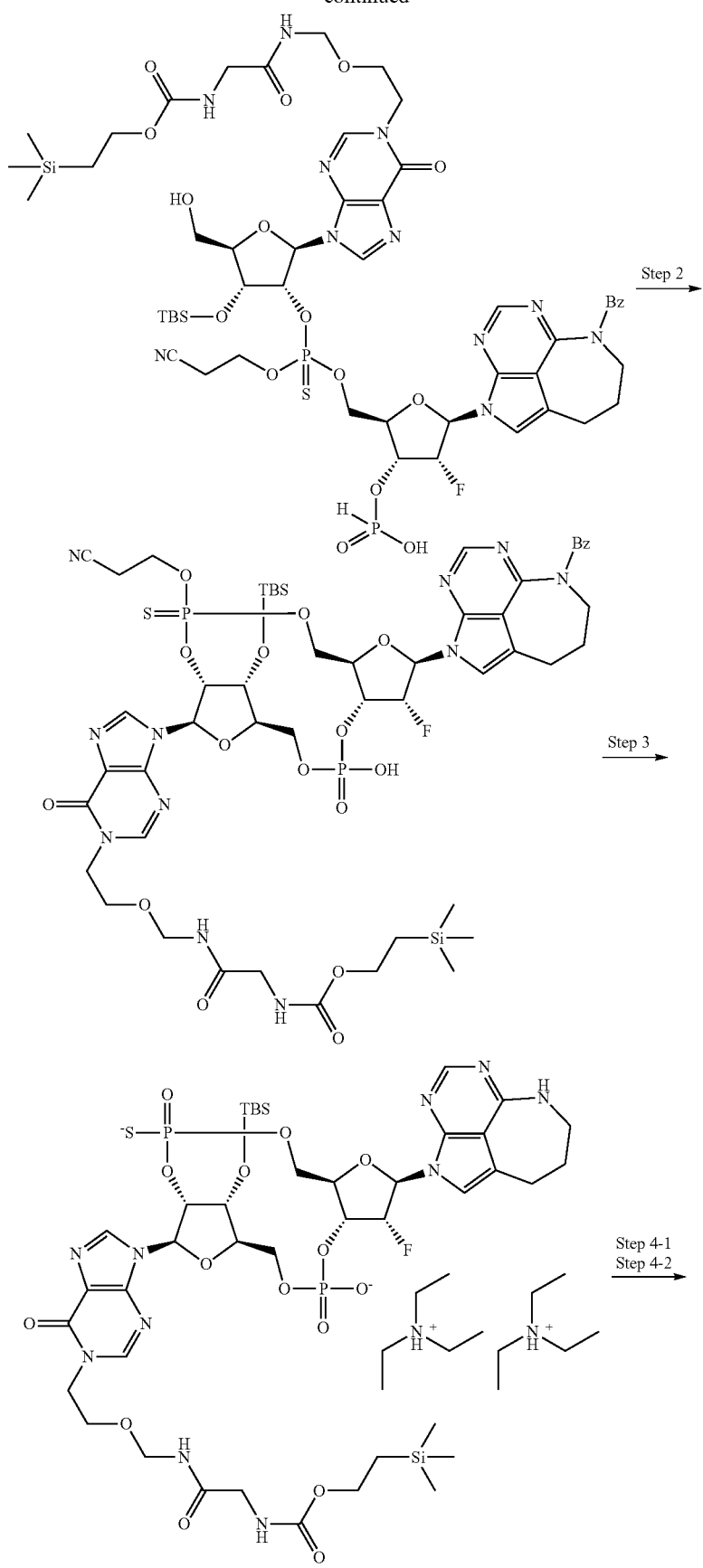

-continued
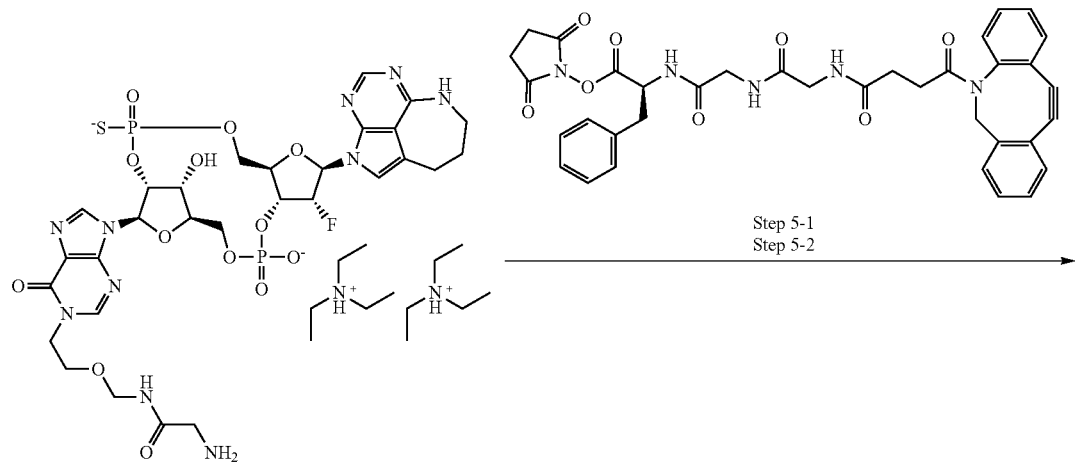
Step 5-1
Step 5-2
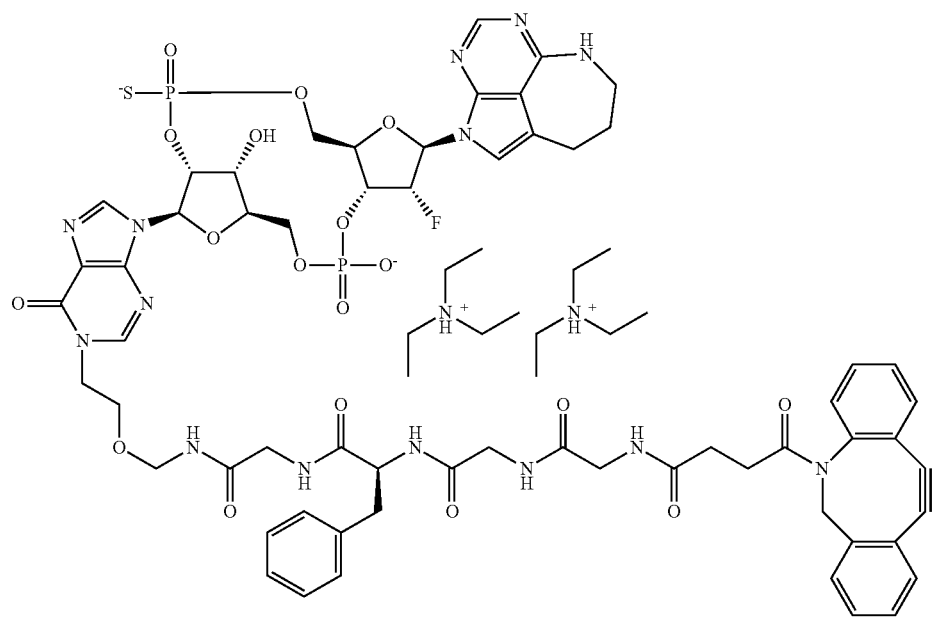
Drug-linker 24a
Drug-linker 24b (Step 1)

With use of the compound obtained in step 8 of Example 44 (1.55 g), the reaction was performed in the same manner as in step 7 of Example 1 to afford an acetonitrile solution of 6-benzoyl-2-{2-deoxy-2-fluoro-3-O-[hydroxy (oxo)-$\lambda^5$-phosphanyl]-β-D-ribofuranosyl}-6,7,8,9-tetrahydro-2H-2,3,5,6-tetraazabenzo[cd]azulene. With use of the obtained acetonitrile solution and the compound obtained in step 6 of Example 77 (1.96 g), the reaction was performed in the same manner as in step 8 of Example 1, and the resulting crude product was directly used for the subsequent reaction.

(Step 2)

2-(Trimethylsilyl)ethyl (2-{[(2-{9-[(5R,7R,8R,12aR,14R,15R,15aR,16R)-14-(6-benzoyl-6,7,8,9-tetrahydro-2H-2,3,5,6-tetraazabenzo[cd]azulen-2-yl)-16-{[tert-butyl(dimethyl)silyl]oxy}-10-(2-cyanoethoxy)-15-fluoro-2-hydroxy-2-oxo-10-sulfanylideneoctahydro-2H,10H,12H-5,8-methano-2$\lambda^5$,10$\lambda^5$-furo[3,2-1][1,3,6,9,11,2,10]pentaoxadiphosphacyclotetradecin-7-yl]-6-oxo-6,9-dihydro-1H-purin-1-yl}ethoxy)methyl]amino}-2-oxoethyl)carbamate With use of the crude product obtained in step 1 above, the reaction was performed in the same manner as in step 2 of Example 62 to afford the title compound (1.07 g: with impurities) as a mixture of diastereomers at the phosphorus atom.

MS(ESI)m/z: 1262 (M+H)$^+$.

(Step 3)

Bis(N,N-diethylethaneaminium) (5R,7R,8R,12aR,14R,15R,16R)-16-{[tert-butyl(dimethyl)silyl]oxy}-15-fluoro-2,10-dioxo-7-[6-oxo-1-(2-{[(N-{[2-(trimethylsilyl)ethoxy]carbonyl}glycyl)amino]methoxy}ethyl)-1,6-dihydro-9H-purin-9-yl]-10-sulfide-14-(6,7,8,9-tetrahydro-2H-2,3,5,6-tetraazabenzo[cd]azulen-2-yl)octahydro-2H,10H,12H-5,8-methano-2$\lambda^5$,10$\lambda^5$-furo[3,2-1][1,3,6,9,11,2,10]pentaoxadiphosphacyclotetradecin-2-olate With use of the compound (1.07 g) obtained in step 2 above, the reaction was performed in the same manner as in step 10 of Example 1, and the resultant was then purified by C18 silica gel column chromatography [10 mM aqueous solution of triethylammonium acetate/acetonitrile] and preparative HPLC [10 mM aqueous solution of triethylammonium acetate/acetonitrile-methanol (1:1), acetonitrile-methanol (1:1): 25%-90% (0 min-40 min)] to afford diastereomer 1 (67.8 mg: with impurities) and diastereomer 2 (56.6 mg: with impurities) of the title compound.

Diastereomer 1 (Less Polar)
MS(ESI)m/z: 1105 (M+H)$^+$.
Diastereomer 2 (More Polar)
MS(ESI)m/z: 1105 (M+H)$^+$.

(Step 4-1)

Bis(N,N-diethylethaneaminium) (5R,7R,8R,12aR,14R,15R,16R)-15-fluoro-7-(1-{2-[(glycylamino)methoxy]ethyl}-6-oxo-1,6-dihydro-9H-purin-9-yl)-16-hydroxy-2,10-dioxo-10-sulfide-14-(6,7,8,9-tetrahydro-2H-2,3,5,6-tetraazabenzo[cd]azulen-2-yl)octahydro-2H,10H,12H-5,8-methano-2$\lambda^5$,10$\lambda^5$-furo[3,2-1][1,3,6,9,11,2,10]pentaoxadiphosphacyclotetradecin-2-olate With use of the compound obtained in step 3 above (diastereomer 1) (67.8 mg), the reaction was performed in the same manner as in step 9-1 of Example 11, and the resultant was then purified by C18 silica gel column chromatography [10 mM aqueous solution of triethylammonium acetate/acetonitrile] and preparative HPLC [10 mM aqueous solution of triethylammonium acetate/acetonitrile-methanol (1:1), acetonitrile-methanol (1:1): 10%-60% (0 min-30 min)] to afford the title compound (33.7 mg: with impurities).

MS(ESI)m/z: 847 (M+H)$^+$.

(Step 4-2)

Bis(N,N-diethylethaneaminium) (5R,7R,8R,12aR,14R,15R,16R)-15-fluoro-7-(1-{2-[(glycylamino)methoxy]ethyl}-6-oxo-1,6-dihydro-9H-purin-9-yl)-16-hydroxy-2,10-dioxo-10-sulfide-14-(6,7,8,9-tetrahydro-2H-2,3,5,6-tetraazabenzo[cd]azulen-2-yl)octahydro-2H,10H,12H-5,8-methano-2$\lambda^5$,10$\lambda^5$-furo[3,2-1][1,3,6,9,11,2,10]pentaoxadiphosphacyclotetradecin-2-olate With use of the compound obtained in step 3 above (diastereomer 2) (56.6 mg), the reaction was performed in the same manner as in step 9-1 of Example 11, and the resultant was then purified by C18 silica gel column chromatography [10 mM aqueous solution of triethylammonium acetate/acetonitrile] and preparative HPLC [10 mM aqueous solution of triethylammonium acetate/acetonitrile-methanol (1:1), acetonitrile-methanol (1:1): 10%-60% (0 min-30 min)] to afford the title compound (32.6 mg: with impurities).

MS(ESI)m/z: 847 (M+H)$^+$.

(Step 5-1)

Bis(N,N-diethylethaneaminium) N-[4-(11,12-didehydrodibenzo[b,f]azocin-5 (6H)-yl)-4-oxobutanoyl]glycylglycyl-L-phenylalanyl-N-[(2-{9-[(5R,7R,8R,12aR,14R,15R,15aR,16R)-15-fluoro-16-hydroxy-2-oxide-2,10-dioxo-10-sulfide-14-(6,7,8,9-tetrahydro-2H-2,3,5,6-tetraazabenzo[cd]azulen-2-yl)octahydro-2H,10H,12H-5,8-methano-2$\lambda^5$,10$\lambda^5$-furo[3,2-1][1,3,6,9,11,2,10]pentaoxadiphosphacyclotetradecin-7-yl]-6-oxo-6,9-dihydro-1H-purin-1-yl}ethoxy)methyl]glycinamide (Diastereomer 1)

With use of the compound obtained in step 4-1 above (33.7 mg) and the compound obtained in step 11 of Example 22 (21.3 mg), the reaction was performed in the same manner as in step 9-1 of Example 22, and the purification was performed under the following [Purification Conditions] to afford the title compound (11.2 mg).

[Purification Conditions] C18 silica gel column chromatography [10 mM aqueous solution of triethylammonium acetate/acetonitrile] and preparative HPLC [10 mM aqueous solution of triethylammonium acetate/methanol, methanol: 40%-90% (0 min-40 min)].

MS(ESI)m/z: 1395 (M+H)$^+$.

$^1$H-NMR (CD$_3$OD) δ: 8.57-8.54 (1H, m), 8.16-8.10 (1H, m), 8.04 (1H, s), 7.64-7.49 (2H, m), 7.44-7.34 (3H, m), 7.33-7.11 (9H, m), 6.46 (1H, d, J=18.1 Hz), 6.26 (1H, d, J=8.5 Hz), 5.54-5.30 (2H, m), 5.18-5.00 (2H, m), 4.75-4.71 (1H, m), 4.65-4.20 (10H, m), 4.13-3.93 (2H, m), 3.88-3.60 (8H, m), 3.55-3.40 (2H, m), 3.26-3.15 (1H, m), 3.18 (12H, q, J=7.3 Hz), 3.02-2.91 (1H, m), 2.87-2.61 (3H, m), 2.38-2.18 (2H, m), 2.06-1.80 (3H, m), 1.28 (18H, t, J=7.3 Hz).

(Step 5-2)

Bis(N,N-diethylethaneaminium) N-[4-(11,12-didehydrodibenzo[b,f]azocin-5 (6H)-yl)-4-oxobutanoyl]glycylglycyl-L-phenylalanyl-N-[(2-{9-[(5R,7R,8R,12aR,14R,15R,15aR,16R)-15-fluoro-16-hydroxy-2-oxide-2,10-dioxo-10-sulfide-14-(6,7,8,9-tetrahydro-2H-2,3,5,6-tetraazabenzo[cd]azulen-2-yl)octahydro-2H,10H,12H-5,8-methano-2$\lambda^5$,10$\lambda^5$-furo[3,2-1][1,3,6,9,11,2,10]pentaoxadiphosphacyclotetradecin-7-yl]-6-oxo-6,9-dihydro-1H-purin-1-yl}ethoxy)methyl]glycinamide (Diastereomer 2)

With use of the compound obtained in step 4-2 above (32.6 mg) and the compound obtained in step 11 of Example 22 (20.6 mg), the reaction was performed in the same manner as in step 9-1 of Example 22, and the purification was performed under the following [Purification Conditions] to afford the title compound (16.7 mg).

[Purification Conditions] C18 silica gel column chromatography [10 mM aqueous solution of triethylammonium acetate/acetonitrile], preparative HPLC [10 mM aqueous solution of triethylammonium acetate/methanol, methanol: 40%-90% (0 min-40 min)], and preparative HPLC [100 mM hexafluoro-2-propanol, 8 mM aqueous solution of triethylamine/acetonitrile, acetonitrile: 10%-45% (0 min-40 min)].

MS(ESI)m/z: 1395 (M+H)$^+$.

$^1$H-NMR (CD$_3$OD) δ: 8.58 (1H, s), 8.17-8.13 (1H, m), 8.02 (1H, s), 7.64-7.50 (2H, m), 7.42-7.35 (4H, m), 7.32-7.12 (8H, m), 6.49 (1H, d, J=16.3 Hz), 6.27 (1H, dd, J=8.2, 6.3 Hz), 5.50-5.21 (3H, m), 5.08-5.00 (1H, m), 4.66-4.23 (9H, m), 4.14-3.98 (3H, m), 3.91-3.52 (9H, m), 3.48-3.41 (2H, m), 3.23-3.12 (1H, m), 3.18 (12H, q, J=7.3 Hz), 3.03-2.94 (1H, m), 2.85-2.75 (3H, m), 2.40-2.23 (2H, m), 2.06-1.87 (3H, m), 1.28 (18H, t, J=7.3 Hz).

Example 121: Synthesis of Drug-Linker 25

[Synthesis Scheme]

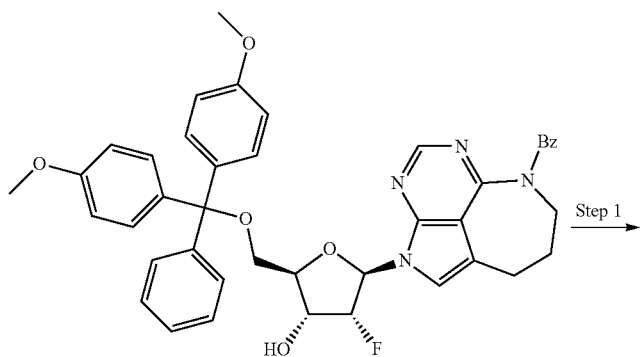

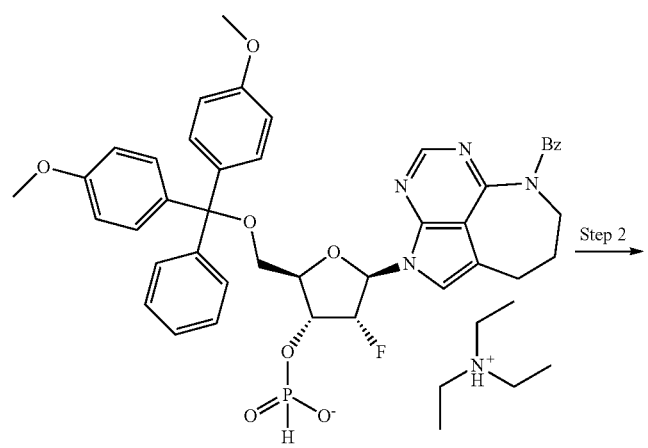

-continued
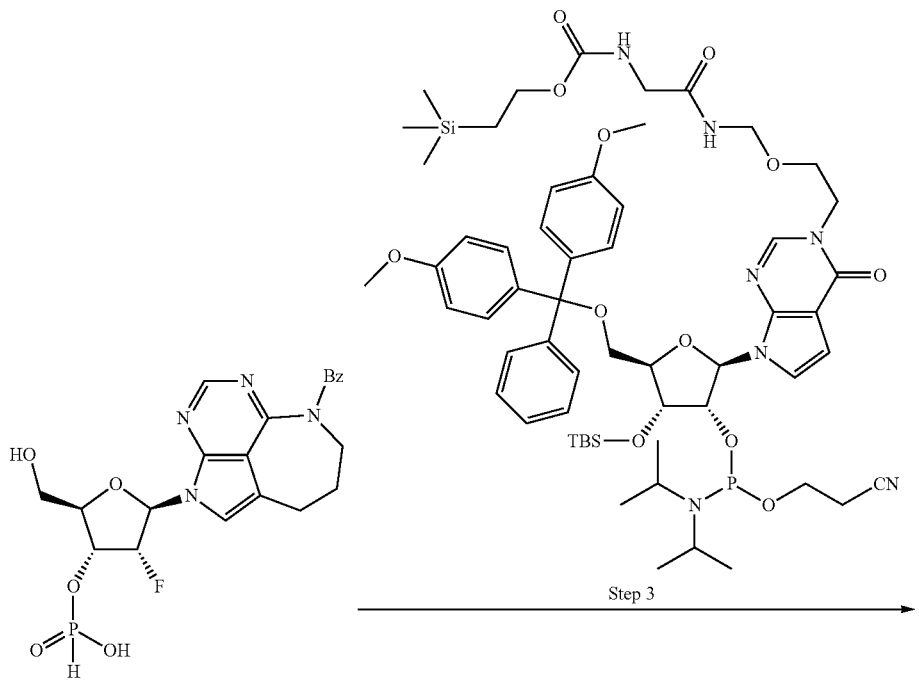
Step 3
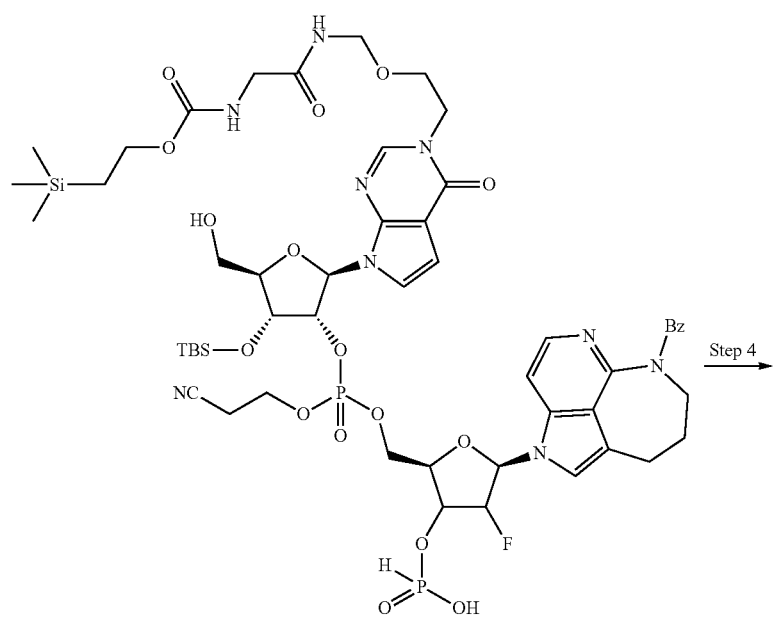
Step 4

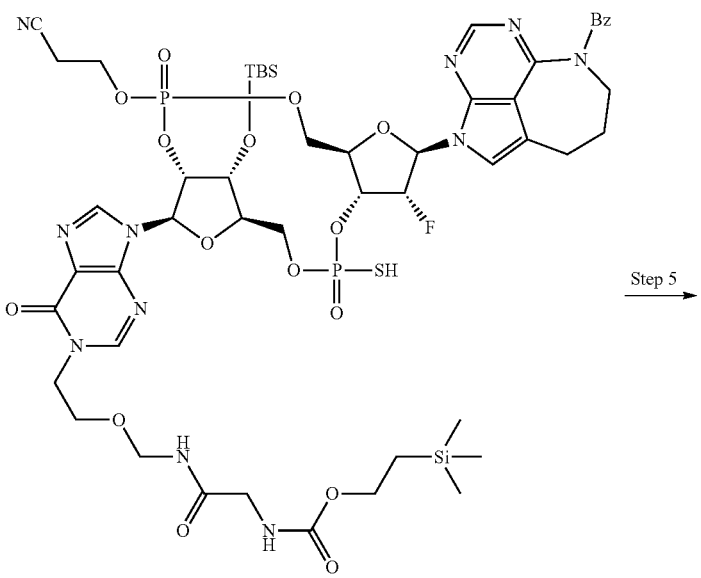
Step 5 →
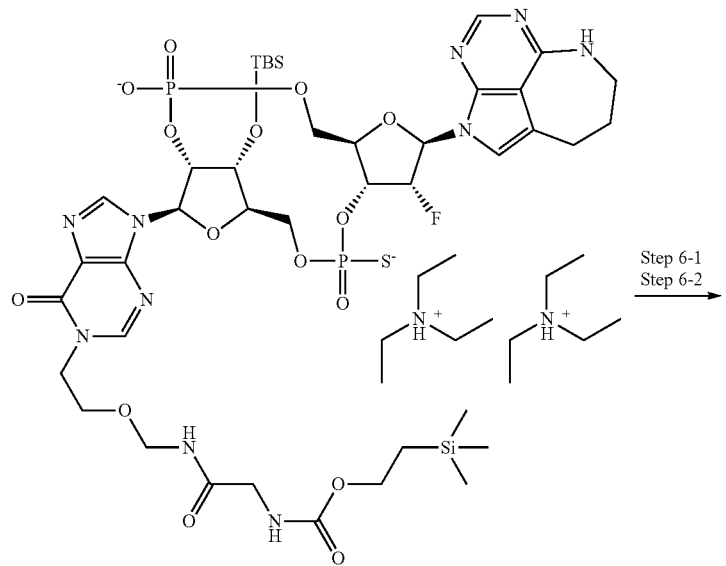
Step 6-1
Step 6-2
→
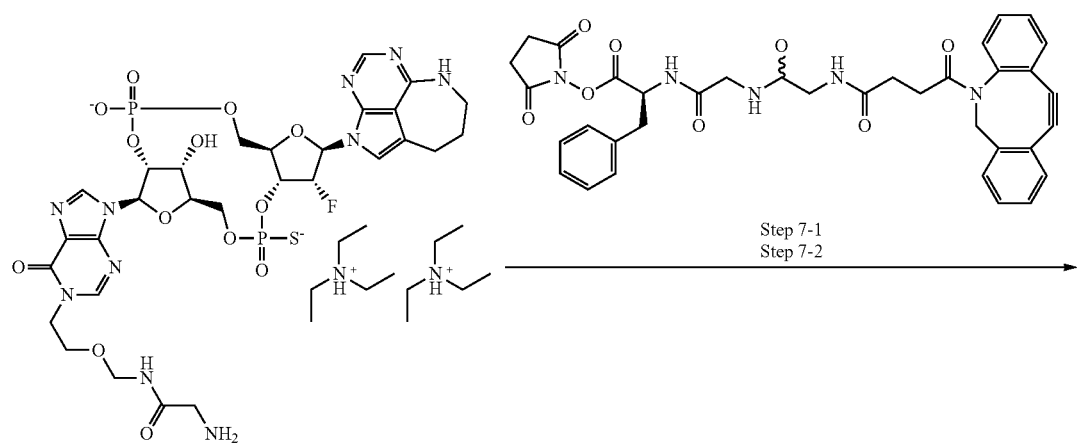
Step 7-1
Step 7-2
→

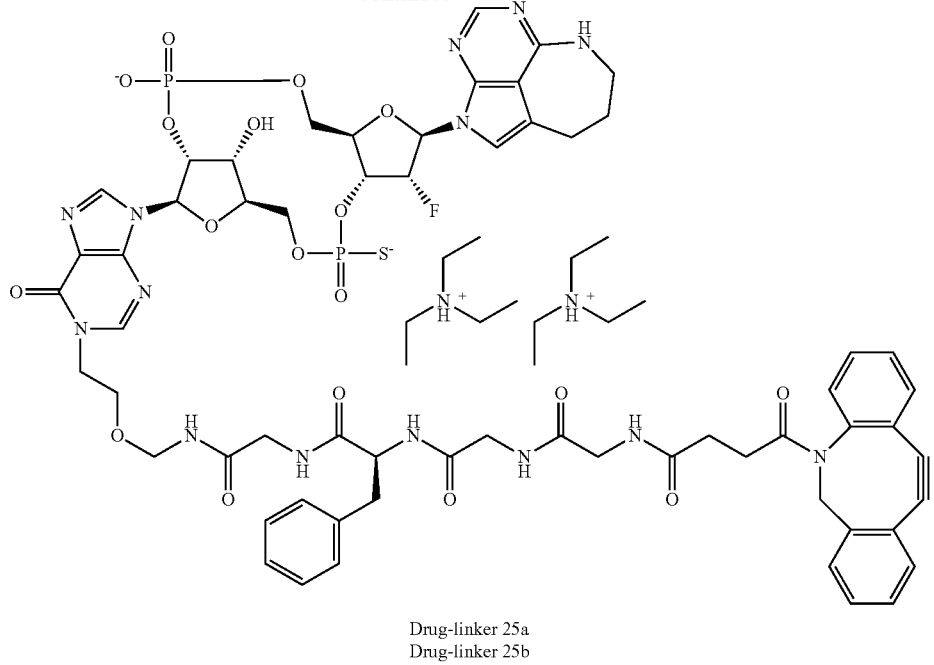

Drug-linker 25a
Drug-linker 25b (Step 1)

N,N-Diethylethaneaminium 6-benzoyl-2-{5-O-[bis(4-methoxyphenyl)(phenyl)methyl]-2-deoxy-2-fluoro-3-O-[oxide(oxo)-$\lambda^5$-phosphanyl]-β-D-ribofuranosyl}-6,7,8,9-tetrahydro-2H-2,3,5,6-tetraazabenzo[cd]azulene To a solution of the compound obtained in step 7 of Example 44 (1.49 g) in pyridine (10.4 mL), diphenyl phosphite (599 μL) was added under ice-cooling, and the temperature was increased to room temperature and the reaction mixture was stirred for 30 minutes. Diphenyl phosphite (200 μL) was further added thereto, and the reaction mixture was further stirred for 2 hours. Water (1.5 mL) was added to the reaction mixture under ice-cooling, and the reaction mixture was stirred at room temperature for 30 minutes, and then concentrated under reduced pressure. The residue was purified by silica gel column chromatography [ethyl acetate/methanol/0.1% triethylamine] to afford the title compound (1.41 g).

MS(ESI)m/z: 779 (M+H)$^+$.

$^1$H-NMR (CD$_3$OD) δ: 8.01 (1H, s), 7.54 (1H, s), 7.42-7.39 (2H, m), 7.32-7.19 (10H, m), 7.14-7.09 (2H, s), 6.84 (1H, dd, J=628.7, 1.8 Hz), 6.83-6.79 (4H, m), 6.53 (1H, dd, J=17.5, 1.8 Hz), 5.54 (1H, ddd, J=52.1, 4.0, 2.0 Hz), 5.37-5.27 (1H, m), 4.31-4.21 (3H, m), 3.55 (1H, dd, J=11.2, 2.1 Hz), 3.38 (1H, dd, J=10.9, 3.0 Hz), 3.34 (6H, s), 3.19 (6H, q, J=7.5 Hz), 2.84-2.69 (2H, m), 2.18-2.12 (2H, m), 1.29 (9H, t, J=7.3 Hz).

(Step 2)

6-Benzoyl-2-{2-deoxy-2-fluoro-3-O-[hydroxy(oxo)-$\lambda^5$-phosphanyl]-β-D-ribofuranosyl}-6,7,8,9-tetrahydro-2H-2,3,5,6-tetraazabenzo[cd]azulene To a solution of the compound obtained in step 1 above (1.41 g) in dichloromethane (20.0 mL), water (289 μL) and a solution of dichloroacetic acid (1.14 mL) in dichloromethane (20.0 mL) were added, and the reaction mixture was stirred at room temperature for 10 minutes. Pyridine (2.19 mL) was added to the reaction mixture to quench the reaction, and the reaction mixture was then concentrated under reduced pressure. A pyridine salt of trifluoroacetic acid (402 mg) was added to the residue, and the resultant was azeotroped three times with dehydrated acetonitrile (15 mL), with about 10 mL of acetonitrile allowed to remain after the last operation. The obtained acetonitrile solution was directly used for the subsequent reaction.

MS(ESI)m/z: 477 (M+H)$^+$.

(Step 3)

With use of the compound obtained in step 6 of Example 77 (2.15 g) and the acetonitrile solution of the compound obtained in step 2 above, the reaction was performed in the same manner as in step 1 of Example 63, and the resulting crude product was directly used for the subsequent reaction.

(Step 4)

2-(Trimethylsilyl)ethyl (2-{[(2-{9-[(5R,7R,8R,12aR,14R,15R,15aR,16R)-14-(6-benzoyl-6,7,8,9-tetrahydro-2H-2,3,5,6-tetraazabenzo[cd]azulen-2-yl)-16-{[tert-butyl(dimethyl)silyl]oxy}-10-(2-cyanoethoxy)-15-fluoro-2,10-dioxo-2-sulfanyloctahydro-2H,10H,12H-5,8-methano-2$\lambda^5$,10$\lambda^5$-furo[3,2-1][1,3,6,9,11,2,10]pentaoxadiphosphacyclotetradecin-7-yl]-6-oxo-6,9-dihydro-1H-purin-1-yl}ethoxy)methyl]amino}-2-oxoethyl)carbamate With use of the crude product obtained in step 3 above, the reaction was performed in the same manner as in step 9 of Example 1 to afford the title compound (1.00 g: with impurities).

MS(ESI)m/z: 1262 (M+H)$^+$.

(Step 5)

Bis(N,N-diethylethaneaminium) (5R,7R,8R,12aR, 14R,15R,15aR,16R)-16-{[tert-butyl(dimethyl)silyl] oxy}-15-fluoro-2,10-dioxo-7-[6-oxo-1-(2-{[(N-{[2-(trimethylsilyl)ethoxy]carbonyl}glycyl)amino] methoxy}ethyl)-1,6-dihydro-9H-purin-9-yl]-2-sulfide-14-(6,7,8,9-tetrahydro-2H-2,3,5,6-tetraazabenzo[cd]azulen-2-yl)octahydro-2H,10H, 12H-5,8-methano-2$\lambda^5$,10$\lambda^5$-furo[3,2-1][1,3,6,9,11,2, 10]pentaoxadiphosphacyclotetradecin-10-olate With use of the compound obtained in step 4 above (1.00 g), the reaction was performed in the same manner as in step 10 of Example 1 to afford diastereomer 1 (191 mg: with impurities) and diastereomer 2 (369 mg: with impurities) of the title compound.
Diastereomer 1 (Less Polar)
MS(ESI)m/z: 1105 (M+H)$^+$.
Diastereomer 2 (More Polar)
MS(ESI)m/z: 1105 (M+H)$^+$.
(Step 6-1)

Bis(N,N-diethylethaneaminium) (5R,7R,8R,12aR, 14R,15R,15aR,16R)-15-fluoro-7-(1-{2-[(glycylamino)methoxy]ethyl}-6-oxo-1,6-dihydro-9H-purin-9-yl)-16-hydroxy-2,10-dioxo-2-sulfide-14-(6,7,8,9-tetrahydro-2H-2,3,5,6-tetraazabenzo[cd]azulen-2-yl)octahydro-2H,10H,12H-5,8-methano-2$\lambda^5$,10$\lambda^5$-furo[3,2-1][1,3,6,9,11,2,10] pentaoxadiphosphacyclotetradecin-10-olate With use of the compound obtained in step 5 above (diastereomer 1) (191 mg), the reaction was performed in the same manner as in step 5 of Example 40 to afford the title compound (21.9 mg: with impurities).
MS(ESI)m/z: 847 (M+H)$^+$.
$^1$H-NMR (CD$_3$OD) δ: 8.39 (1H, s), 8.03 (1H, s), 7.71 (1H, s), 7.24 (1H, s), 6.45 (1H, d, J=17.5 Hz), 6.15 (1H, d, J=8.5 Hz), 5.79-5.65 (2H, m), 5.46-5.36 (1H, m), 4.63-4.23 (9H, m), 4.01-3.95 (1H, m), 3.65-3.57 (2H, m), 3.52-3.37 (5H, m), 3.15 (12H, q, J=7.3 Hz), 2.76-2.68 (1H, m), 2.39-2.30 (1H, m), 1.92-1.82 (2H, m), 1.28 (18H, t, J=7.6 Hz).
(Step 6-2)

Bis(N,N-diethylethaneaminium) (5R,7R,8R,12aR, 14R,15R,15aR,16R)-15-fluoro-7-(1-{2-[(glycylamino)methoxy]ethyl}-6-oxo-1,6-dihydro-9H-purin-9-yl)-16-hydroxy-2,10-dioxo-2-sulfide-14-(6,7,8, 9-tetrahydro-2H-2,3,5,6-tetraazabenzo[cd]azulen-2-yl)octahydro-2H,10H,12H-5,8-methano-2$\lambda^5$,10$\lambda^5$-furo[3,2-1][1,3,6,9,11,2,10] pentaoxadiphosphacyclotetradecin-10-olate With use of the compound obtained in step 5 above (diastereomer 2) (369 mg), the reaction was performed in the same manner as in step 5 of Example 40 to afford the title compound (137 mg: with impurities).
MS(ESI)m/z: 847 (M+H)$^+$.
$^1$H-NMR (CD$_3$OD) δ: 8.96 (1H, s), 8.14 (1H, s), 8.02 (1H, s), 7.04 (1H, s), 6.46 (1H, d, J=19.3 Hz), 6.28 (1H, d, J=8.5 Hz), 5.61 (1H, dd, J=52.0, 4.2 Hz), 5.38-5.23 (2H, m), 4.69-4.63 (2H, m), 4.56 (1H, d, J=10.3 Hz), 4.39-4.30 (4H, m), 4.26-4.17 (3H, m), 3.97-3.91 (1H, m), 3.84-3.72 (2H, m), 3.52-3.46 (2H, m), 3.32-3.25 (2H, m), 2.97 (12H, q, J=7.3 Hz), 2.74-2.63 (2H, m), 2.03-1.84 (2H, m), 1.21 (18H, t, J=7.3 Hz).

(Step 7-1)

Bis(N,N-diethylethaneaminium) N-[4-(11,12-didehydrodibenzo[b,f]azocin-5 (6H)-yl)-4-oxobutanoyl] glycylglycyl-L-phenylalanyl-N-[(2-{9-[(5R,7R,8R, 12aR,14R,15R,15aR,16R)-15-fluoro-16-hydroxy-10-oxide-2,10-dioxo-2-sulfide-14-(6,7,8,9-tetrahydro-2H-2,3,5,6-tetraazabenzo[cd]azulen-2-yl)octahydro-2H,10H,12H-5,8-methano-2$\lambda^5$,10$\lambda^5$-furo[3,2-1][1,3, 6,9,11,2,10]pentaoxadiphosphacyclotetradecin-7-yl]-6-oxo-6,9-dihydro-1H-purin-1-yl}ethoxy)methyl] glycinamide (Drug-Linker 25a: Diastereomer 1)
With use of the compound obtained in step 6-1 above (21.9 mg), the reaction was performed in the same manner as in step 9-1 of Example 22, and the purification was then performed under the following [Purification Conditions] to afford the title compound (26.3 mg).
[Purification Conditions] preparative HPLC [10 mM aqueous solution of triethylammonium acetate/acetonitrile, acetonitrile: 30%-50% (0 min-30 min)] and Sep-Pak® C18 [water/acetonitrile/0.1% triethylamine].
MS(ESI)m/z: 1395 (M+H)$^+$.
$^1$H-NMR (CD$_3$OD) δ: 8.58 (1H, d, J=4.2 Hz), 8.08-8.02 (2H, m), 7.64-7.13 (14H, m), 6.46 (1H, d, J=18.1 Hz), 6.26-6.21 (1H, m), 5.45 (1H, d, J=53.2 Hz), 5.35-5.18 (2H, m), 5.07-5.01 (1H, m), 4.62-4.13 (10H, m), 4.09-3.90 (2H, m), 3.87-3.43 (11H, m), 3.21-3.09 (1H, m), 3.18 (12H, q, J=7.3 Hz), 3.00-2.89 (1H, m), 2.83-2.52 (3H, m), 2.37-2.21 (2H, m), 2.03-1.79 (3H, m), 1.28 (18H, t, J=7.3 Hz).
(Step 7-2)

Bis(N,N-diethylethaneaminium) N-[4-(11,12-didehydrodibenzo[b,f]azocin-5 (6H)-yl)-4-oxobutanoyl] glycylglycyl-L-phenylalanyl-N-[(2-{9-[(5R,7R,8R, 12aR,14R,15R,15aR,16R)-15-fluoro-16-hydroxy-10-oxide-2,10-dioxo-2-sulfide-14-(6,7,8,9-tetrahydro-2H-2,3,5,6-tetraazabenzo[cd]azulen-2-yl)octahydro-2H,10H,12H-5,8-methano-2$\lambda^5$,10$\lambda^5$-furo[3,2-1][1,3, 6,9,11,2,10]pentaoxadiphosphacyclotetradecin-7-yl]-6-oxo-6,9-dihydro-1H-purin-1-yl}ethoxy)methyl] glycinamide (Drug-Linker 25b: Diastereomer 2)
With use of the compound obtained in step 6-2 above (47.5 mg), the reaction was performed in the same manner as in step 9-1 of Example 22, and the purification was then performed under the following [Purification Conditions] to afford the title compound (15.1 mg).
[Purification Conditions] preparative HPLC [10 mM aqueous solution of triethylammonium acetate/acetonitrile, acetonitrile: 30%-50% (0 min-30 min)] and Sep-Pak® C18 [water/acetonitrile/0.1% triethylamine].
MS(ESI)m/z: 1395 (M+H)$^+$.
$^1$H-NMR (CD$_3$OD) δ: 8.99 (1H, d, J=3.6 Hz), 8.14 (1H, d, J=1.8 Hz), 8.02-8.00 (1H, m), 7.64-7.13 (13H, m), 7.01-6.98 (1H, m), 6.47 (1H, dd, J=19.0, 2.7 Hz), 6.27 (1H, dd, J=8.5, 4.2 Hz), 5.67-5.52 (1H, m), 5.37-5.16 (2H, m), 5.08-5.01 (1H, m), 4.67-4.14 (11H, m), 4.10-3.61 (10H, m), 3.47-3.42 (2H, m), 3.17-3.10 (1H, m), 3.15 (12H, q, J=7.5 Hz), 3.00-2.92 (1H, m), 2.84-2.75 (1H, m), 2.63-2.54 (2H, m), 2.32-2.20 (2H, m), 2.03-1.79 (3H, m), 1.28 (18H, t, J=7.3 Hz).

Example 122: Synthesis of Drug-Linker 26
[Synthesis Scheme]
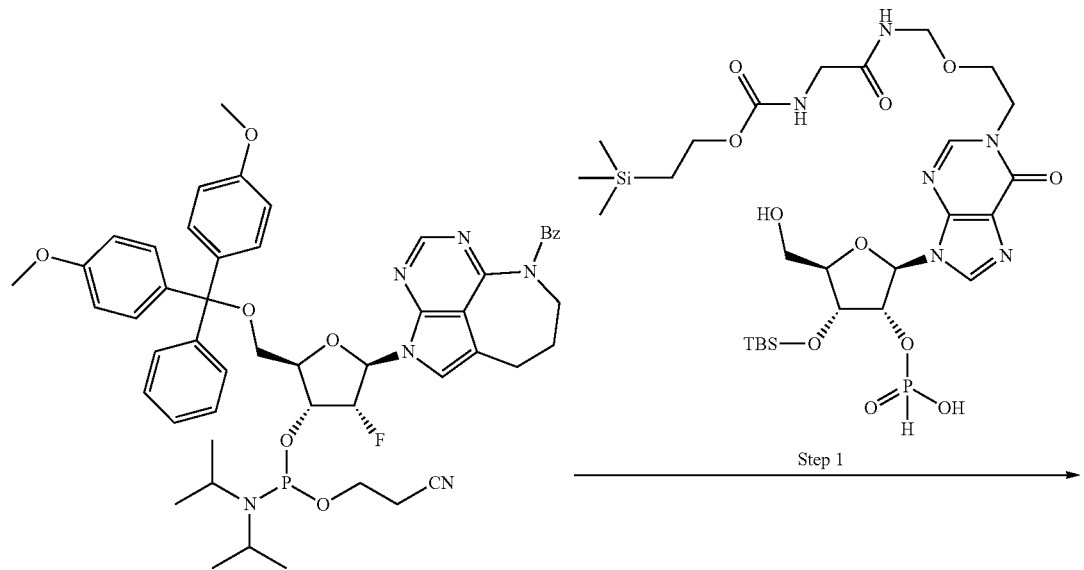
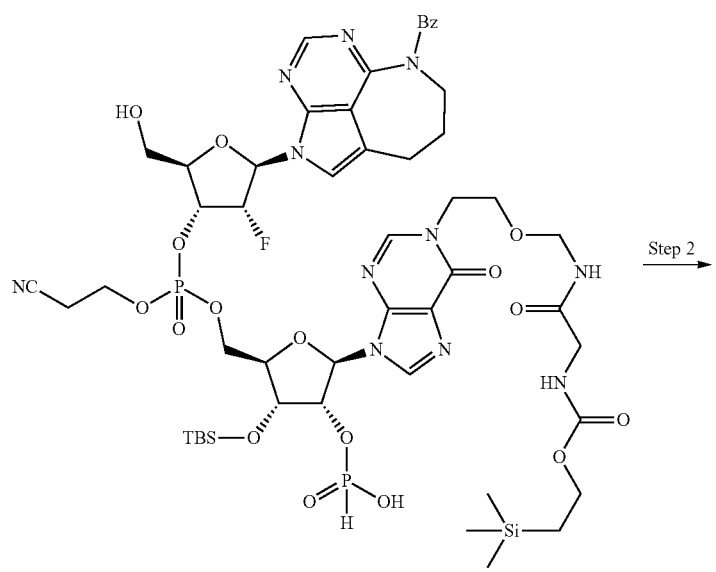

-continued
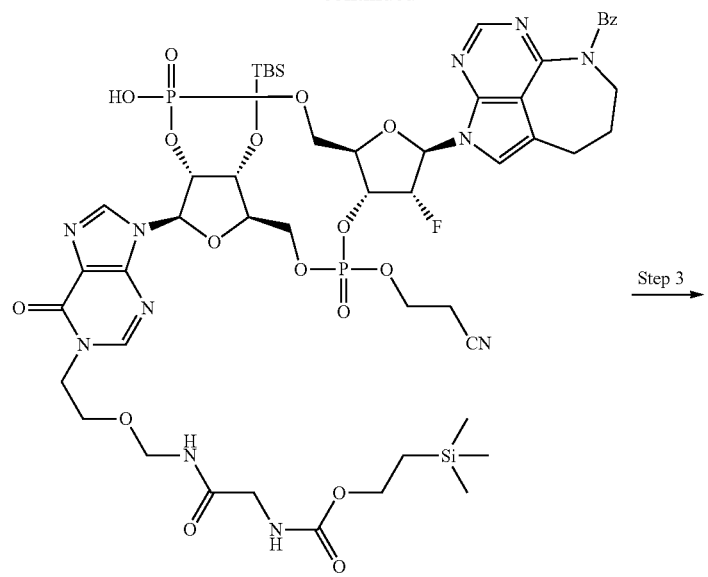
Step 3
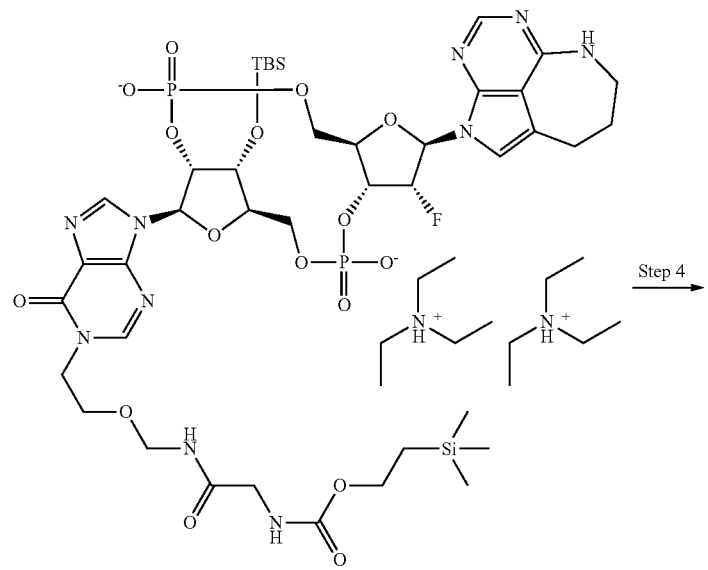
Step 4
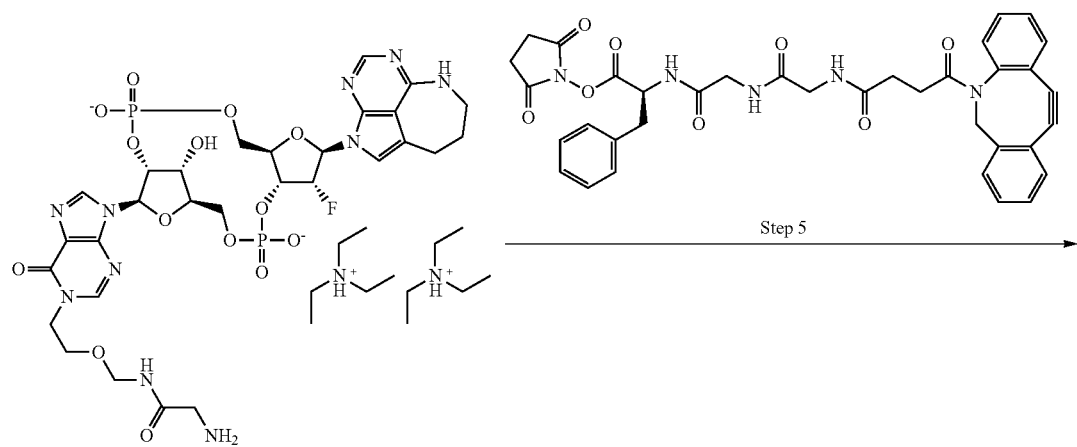
Step 5

-continued

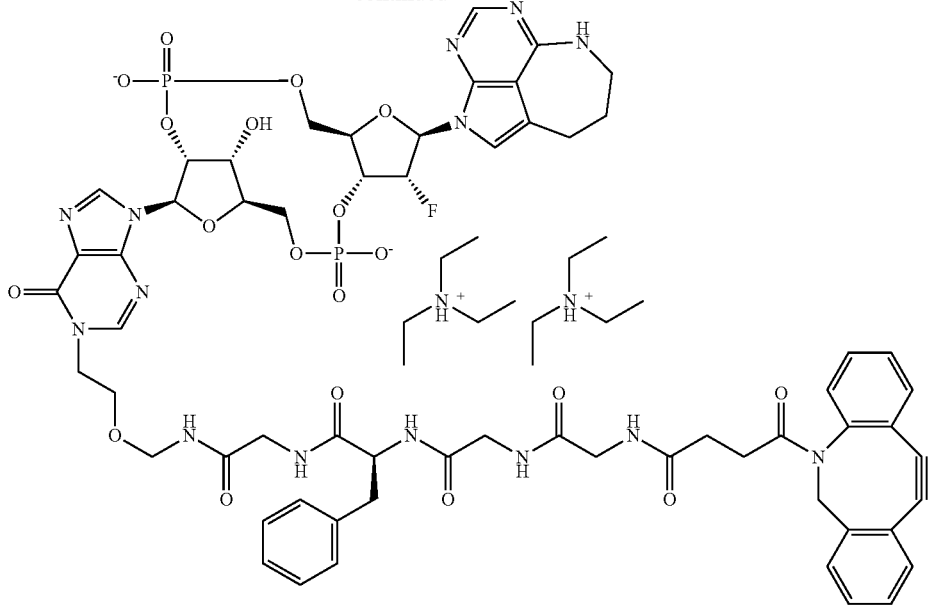

Drug-linker 26

(Step 1)

With use of the compound obtained in step 6 of Example 77 (1.26 g), the reaction was performed in the same manner as in step 7 of Example 1 to afford an acetonitrile solution of 3'-O-[tert-butyl(dimethyl)silyl]-2'-O-[hydroxy (oxo)-λ$^5$-phosphanyl]-1-(2-{[(N-{[2-(trimethylsilyl)ethoxy]carbonyl}glycyl)amino]methoxy}ethyl)inosine. With use of the obtained acetonitrile solution and the compound obtained in step 8 of Example 44 (1.00 g), the reaction was performed in the same manner as in step 1 of Example 63, and the resulting crude product was directly used for the subsequent reaction.

(Step 2)

2-(Trimethylsilyl)ethyl (2-{[(2-{9-[(5R,7R,8R,12aR,14R,15R,15aR,16R)-14-(6-benzoyl-6,7,8,9-tetrahydro-2H-2,3,5,6-tetraazabenzo[cd]azulen-2-yl)-16-{[tert-butyl(dimethyl)silyl]oxy}-10-(2-cyanoethoxy)-15-fluoro-2-hydroxy-2,10-dioxooctahydro-2H,10H,12H-5,8-methano-2λ$^5$,10λ$^5$-furo[3,2-l][1,3,6,9,11,2,10]pentaoxadiphosphacyclotetradecin-7-yl]-6-oxo-6,9-dihydro-1H-purin-1-yl}ethoxy)methyl]amino}-2-oxoethyl)carbamate With use of the crude product obtained in step 1 above, the reaction was performed in the same manner as in step 2 of Example 62 to afford the title compound (678 mg: with impurities).

MS(ESI)m/z: 1246 (M+H)$^+$.

(Step 3)

2-(Trimethylsilyl)ethyl (2-{[(2-{9-[(5R,7R,8R,12aR,14R,15R,15aR,16R)-14-(6-benzoyl-6,7,8,9-tetrahydro-2H-2,3,5,6-tetraazabenzo[cd]azulen-2-yl)-16-{[tert-butyl(dimethyl)silyl]oxy}-10-(2-cyanoethoxy)-15-fluoro-2-hydroxy-2,10-dioxooctahydro-2H,10H,12H-5,8-methano-2λ$^5$,10λ$^5$-furo[3,2-l][1,3,6,9,11,2,10]pentaoxadiphosphacyclotetradecin-7-yl]-6-oxo-6,9-dihydro-1H-purin-1-yl}ethoxy)methyl]amino}-2-oxoethyl)carbamate With use of the compound obtained in step 2 above (678 mg), the reaction was performed in the same manner as in step 10 of Example 1, and the resultant was then purified by C18 silica gel column chromatography [10 mM aqueous solution of triethylammonium acetate/acetonitrile] and preparative HPLC [10 mM aqueous solution of triethylammonium acetate/acetonitrile-methanol solution (1:1), acetonitrile-methanol solution (1:1): 25%-90% (0 min-30 min)] to afford the title compound (99.6 mg: with impurities).

MS(ESI)m/z: 1089 (M+H)$^+$.

(Step 4)

Bis(N,N-diethylethaneaminium) (5R,7R,8R,12aR,14R,15R,16R)-15-fluoro-7-(1-{2-[(glycylamino)methoxy]ethyl}-6-oxo-1,6-dihydro-9H-purin-9-yl)-16-hydroxy-2,10-dioxo-14-(6,7,8,9-tetrahydro-2H-2,3,5,6-tetraazabenzo[cd]azulen-2-yl)octahydro-2H,10H,12H-5,8-methano-2λ$^5$,10λ$^5$-furo[3,2-l][1,3,6,9,11,2,10]pentaoxadiphosphacyclotetradecine-2,10-bis(olate)

With use of the compound obtained in step 3 above (99.6 mg), the reaction was performed in the same manner as in step 9-1 of Example 11, and the resultant was then purified by C18 silica gel column chromatography [10 mM aqueous solution of triethylammonium acetate/acetonitrile] and preparative HPLC [10 mM aqueous solution of triethylammonium acetate/acetonitrile-methanol solution (1:1), acetonitrile-methanol solution (1:1): 10%-60% (0 min-30 min)] to afford the title compound (60.8 mg: with impurities).
MS(ESI)m/z: 831 (M+H)$^+$.
(Step 5)

Bis(N,N-diethylethaneaminium) N-[4-(11,12-didehydrodibenzo[b,f]azocin-5 (6H)-yl)-4-oxobutanoyl]glycylglycyl-L-phenylalanyl-N-[(2-{9-[(5R,7R,8R,12aR,14R,15R,15aR,16R)-15-fluoro-16-hydroxy-2,10-dioxide-2,10-dioxo-14-(6,7,8,9-tetrahydro-2H-2,3,5,6-tetraazabenzo[cd]azulen-2-yl)octahydro-2H,10H,12H-5,8-methano-2λ$^5$,10λ$^5$-furo[3,2-1][1,3,6,9,11,2,10]pentaoxadiphosphacyclotetradecin-7-yl]-6-oxo-6,9-dihydro-1H-purin-1-yl}ethoxy)methyl]glycinamide With use of the compound obtained in step 4 above (60.8 mg) and the compound obtained in step 11 of Example 22 (21.3 mg), the reaction was performed in the same manner as in step 9-1 of Example 22, and the purification was performed under the following [Purification Conditions] to afford the title compound (30.5 mg).
[Purification Conditions] C18 silica gel column chromatography [10 mM aqueous solution of triethylammonium acetate/acetonitrile] and preparative HPLC [100 mM hexafluoro-2-propanol, 8 mM aqueous solution of triethylamine/acetonitrile, acetonitrile: 10%-45% (0 min-40 min)].
MS(ESI)m/z: 1379 (M+H)$^+$.
$^1$H-NMR (CD$_3$OD) δ: 8.56 (1H, s), 8.16-8.10 (1H, m), 8.05 (1H, s), 7.63-7.49 (2H, m), 7.45-7.35 (3H, m), 7.33-7.12 (9H, m), 6.45 (1H, d, J=18.3 Hz), 6.27 (1H, d, J=9.8 Hz), 5.55-4.99 (4H, m), 4.65-4.42 (5H, m), 4.38-4.01 (8H, m), 3.89-3.60 (9H, m), 3.52-3.42 (2H, m), 3.18 (12H, q, J=7.3 Hz), 3.00-2.91 (1H, m), 2.87-2.60 (3H, m), 2.38-2.19 (2H, m), 2.04-1.81 (3H, m), 1.28 (18H, t, J=7.3 Hz).

Example 123: Synthesis of Antibody-Drug Conjugate 35 (Synthesis of Anti-HER2 Antibody 2-CDN Conjugate 11)

A phosphate-buffered saline solution of glycan-remodeled antibody 4 (pH 6.0) (10.87 mg/mL, 1.00 mL) was diluted with propylene glycol (0.500 mL). To this solution, a mixture of a dimethyl sulfoxide solution of drug-linker 24a (10 mM, 0.135 mL, 18 equivalents per antibody molecule) and propylene glycol (0.365 mL) was added, and the resultant was reacted with a tube rotator (MTR-103, AS ONE Corporation) at room temperature for 2 days. The reaction mixture was purified in accordance with the method described in Common Operation D to afford a solution of the targeted antibody-drug conjugate in ABS (7.0 mL).
Analysis was performed in accordance with the methods described in Common Operations E and F to acquire the following results.
Antibody concentration: 1.08 mg/mL
Antibody yield: 7.54 mg (69%)
Average number of conjugated drug molecules: 3.8

Example 124: Synthesis of Antibody-Drug Conjugate 36 (Synthesis of Anti-HER2 Antibody 2-CDN Conjugate 12)

A phosphate-buffered saline solution of glycan-remodeled antibody 4 (pH 6.0) (10.87 mg/mL, 1.00 mL) was diluted with propylene glycol (0.500 mL). To this solution, a mixture of a dimethyl sulfoxide solution of drug-linker 24b (10 mM, 0.135 mL, 18 equivalents per antibody molecule) and propylene glycol (0.365 mL) was added, and the resultant was reacted with a tube rotator (MTR-103, AS ONE Corporation) at room temperature for 2 days. The reaction mixture was purified in accordance with the method described in Common Operation D to afford a solution of the targeted antibody-drug conjugate in ABS (7.0 mL).
Analysis was performed in accordance with the methods described in Common Operations E and F to acquire the following results.
Antibody concentration: 1.12 mg/mL
Antibody yield: 7.85 mg (72%)
Average number of conjugated drug molecules: 3.8

Example 125: Synthesis of Antibody-Drug Conjugate 37 (Synthesis of Anti-HER2 Antibody 2-CDN Conjugate 13)

A phosphate-buffered saline solution of glycan-remodeled antibody 4 (pH 6.0) (10.87 mg/mL, 2.00 mL) was diluted with propylene glycol (1.00 mL). To this solution, a mixture of a dimethyl sulfoxide solution of drug-linker 26 (10 mM, 0.270 mL, 18 equivalents per antibody molecule) and propylene glycol (0.730 mL) was added, and the resultant was reacted with a tube rotator (MTR-103, AS ONE Corporation) at room temperature for 2 days. The reaction mixture was purified in accordance with the method described in Common Operation D to afford a solution of the targeted antibody-drug conjugate in ABS (14.0 mL).
Analysis was performed in accordance with the methods described in Common Operations E and F to acquire the following results.
Antibody concentration: 1.05 mg/mL
Antibody yield: 14.71 mg (68%)
Average number of conjugated drug molecules: 3.8

Example 126: Synthesis of Antibody-Drug Conjugate 38 (Synthesis of Anti-HER2 Antibody 2-CDN Conjugate 14)

A phosphate-buffered saline solution of glycan-remodeled antibody 4 (pH 6.0) (10.89 mg/mL, 3.00 mL) was diluted with propylene glycol (1.50 mL). To this solution, a mixture of a dimethyl sulfoxide solution of drug-linker 25a (10 mM, 0.540 mL, 24 equivalents per antibody molecule) and propylene glycol (0.960 mL) was added, and the resultant was reacted with a tube rotator (MTR-103, AS ONE Corporation) at room temperature for 3 days. The reaction mixture was purified in accordance with the method described in Common Operation D to afford a solution of the targeted antibody-drug conjugate in ABS (19 mL).
Analysis was performed in accordance with the methods described in Common Operations E and G to acquire the following results.
Antibody concentration: 1.38 mg/mL
Antibody yield: 26.28 mg (80%)
Average number of conjugated drug molecules: 3.7

Example 127: Synthesis of Antibody-Drug Conjugate 39 (Synthesis of Anti-HER2 Antibody 2-CDN Conjugate 15)

A phosphate-buffered saline solution of glycan-remodeled antibody 4 (pH 6.0) (10.89 mg/mL, 0.500 mL) was diluted with propylene glycol (0.250 mL). To this solution, a mixture of a dimethyl sulfoxide solution of drug-linker 25b (10 mM, 0.090 mL, 24 equivalents per antibody molecule) and propylene glycol (0.160 mL) was added, and the resultant was reacted with a tube rotator (MTR-103, AS ONE Corporation) at room temperature for 2 days. The reaction mixture was purified in accordance with the method described in Common Operation D to afford a solution of the targeted antibody-drug conjugate in ABS (3.5 mL).

Analysis was performed in accordance with the methods described in Common Operations E and G to acquire the following results.

Antibody concentration: 0.93 mg/mL
Antibody yield: 3.25 mg (60%)
Average number of conjugated drug molecules: 3.5

Reference Example 1: Production of Anti-HER2 Antibody

Herein, "trastuzumab", which is also referred to as HER-CEPTIN®, huMAb4D5-8, or rhuMAb4D5-8, is a humanized IgG1 antibody including a light chain consisting of an amino acid sequence represented by SEQ ID NO: 1 and a heavy chain consisting of an amino acid sequence represented by SEQ ID NO: 2. U.S. Pat. No. 5,821,337 was referred to for the amino acid sequence. FIG. 4 shows the amino acid sequences of the light chain (SEQ ID NO: 1) and heavy chain (SEQ ID NO: 2) of trastuzumab.

From the anti-HER2 antibody used herein, an IgG1 antibody of constant-region-modified trastuzumab (hereinafter, also referred to as the modified anti-HER2 antibody) was designed and produced by causing mutation of leucine (L) into alanine (A) at positions 234 and 235 specified by EU Index numbering in the amino acid sequence of the heavy chain of trastuzumab (herein, also referred to as LALA mutation). FIG. 5 shows the amino acid sequences of the light chain (SEQ ID NO: 1) and heavy chain (SEQ ID NO: 3) of the modified anti-HER2 antibody.

Reference Example 2: Production of Anti-LPS Antibody

An anti-LPS antibody was produced with reference to WO 2015/046505. The isotype of the anti-LPS antibody used in Examples is IgG1, and the anti-LPS antibody has LALA mutation (hereinafter, also referred to as the modified anti-LPS antibody). SEQ ID NO: 26 and SEQ ID NO: 27 respectively show the amino acid sequences of the light chain and heavy chain of the modified anti-LPS antibody used in Examples.

Reference Example 3: Synthesis of ML-RR-CDA-2Na$^+$

ML-RR-CDA·2Na$^+$ used herein as a reference compound was synthesized in accordance with a method described in Patent Literature 3 (WO 2014/189805).

Reference Example 4: Synthesis of 2',3'-cGAMP

With use of cGAS, 2',3'-cGAMP used herein as a reference compound was enzymatically synthesized from ATP and GTP. Preparation of cGAS and the enzymatic reaction were performed by using a method described in a literature (Immunity, 2013, 39, 1019-1031, Cell Rep. 2014, 6, 421-430) with appropriate modification. Purification was performed by column chromatography using a weakly-basic anion exchange resin (DIAION WA10) and a synthetic adsorbent (SEPABEADS SP207SS).

Reference Example 5: Production of Anti-HER2 Antibody 2

"Pertuzumab", which is also referred as PERJETA®, is a humanized IgG1 antibody including a light chain consisting of an amino acid sequence represented by SEQ ID NO: 28 and a heavy chain consisting of an amino acid sequence represented by SEQ ID NO: 29. WO 2004/008099 was referred to for the amino acid sequence. Herein, pertuzumab is also referred to as anti-HER2 antibody 2. FIG. 17 shows the amino acid sequences of the light chain (SEQ ID NO: 28) and heavy chain (SEQ ID NO: 29) of pertuzumab.

Herein designed and produced was anti-HER2 antibody 2 having not only LALA mutation but also a constant region of G1m3 allotype with mutation of lysine (K) into arginine (R) at position 214 specified by EU Index numbering in the amino acid sequence of the heavy chain (herein, also referred to as modified anti-HER2 antibody 2). FIG. 18 shows the amino acid sequences of the light chain (SEQ ID NO: 28) and heavy chain (SEQ ID NO: 30) of modified anti-HER2 antibody 2 used in Examples.

Reference Example 6: Production of Anti-CD33 Antibody

An anti-CD33 antibody was produced with reference to WO 2014/057687. The isotype of the anti-CD33 antibody used in Examples is IgG1, and the anti-CD33 antibody has LALA mutation. FIG. 19 shows the amino acid sequences of the light chain (SEQ ID NO: 31) and heavy chain (SEQ ID NO: 32) of the anti-CD33 antibody used in Examples.

Reference Example 7: Production of Anti-EphA2 Antibody

An anti-EphA2 antibody was produced with reference to WO 2009/028639. The isotype of the anti-EphA2 antibody used in Examples is IgG1. FIG. 20 shows the amino acid sequences of the light chain (SEQ ID NO: 33) and heavy chain (SEQ ID NO: 34) of the anti-EphA2 antibody used in Examples.

Reference Example 8: Production of Anti-CDH6 Antibody

An anti-CDH6 antibody was produced with reference to WO 2018/212136. The isotype of the anti-CDH6 antibody used in Examples is IgG1, and the anti-CDH6 antibody has not only LALA mutation but also mutation of proline (P) into glycine (G) at position 329 specified by EU Index numbering in the amino acid sequence of the heavy chain. FIG. 21 shows the amino acid sequences of the light chain (SEQ ID NO: 35) and heavy chain (SEQ ID NO: 36) of the anti-CDH6 antibody used in Examples.

(Test Example 1) Evaluation of STING Agonist Activity with Reporter Cells

<Reporter Gene Assay>

Human STING agonist activity was evaluated by using THP1-Dual™ cells (HAQ-mutated) (InvivoGen, CA, US), with which the activation of the pathway of interferon regulatory factor-3 (IRF3), which is present in the downstream of the STING pathway, can be confirmed. Mouse STING agonist activity was evaluated by using RAW-Dual™ cells (InvivoGen).

Assay was performed as follows. First, a test compound diluted with PBS was aliquoted into a transparent 96-well plate (Corning Incorporated, NY, US) at 20 μL/well. Subsequently, reporter cells suspended in assay buffer (an RPMI1640 medium or DMEM medium containing 10% bovine serum albumin) were added at 180 μL/well (1×10$^5$ cells/well) to initiate stimulation. After the cells were cultured in an environment at 37° C. and 5% $CO_2$ for 24 hours, the resultant was centrifuged to collect the supernatant. To a white 384-well plate, 6 μL of the supernatant collected was added, and 15 μL of QUANTI-Luc (InvivoGen) solution was added thereto. After the resultant was well mixed together, emission was measured by using a plate reader (PerkinElmer, Inc., MA, US). The maximum count value for cells treated with 1.37 to 100 μM ML-RR-CDA·2Na⁺ (Compound 21 in WO 2014/189805) was defined as 100% and the count for cells treated with PBS as 0%, and a concentration required for the test compound to give a count of 50% was calculated as the EC50 (μM) value by using GraphPad Prism (GraphPad Software, CA, US). Table 1 shows the results of the human STING agonist activity test.

TABLE 1

| Compound number | THP1-Dual cells IRF EC50 (μM) |
|---|---|
| 1a | 5.9 |
| 1b | 0.3 |
| 2a | 4.7 |
| 4a | 2.1 |
| 4b | 1.5 |
| 5a | 2.4 |
| 6a | 0.6 |
| 6b | 2.1 |
| 7a | 3.5 |
| 7b | 6.1 |
| 8a | 3.1 |
| 8b | 6.6 |
| 9a | 5.7 |
| 9b | 2.4 |
| 10a | 6.3 |
| 11a | 4.0 |
| 12b | 1.8 |
| 17a | 4.4 |
| 17b | 1.0 |
| 20b | 0.40 |
| 21b | 0.70 |
| 22b | 4.3 |
| 23a | 2.6 |
| 23b | 0.055 |
| 25a | 1.3 |
| 25b | 0.9 |
| 26a | 1.4 |
| 26b | 1.2 |
| 32a | 1.2 |
| 32b | 6.4 |
| 33a | 0.18 |
| 34a | 0.20 |
| 34b | 0.55 |
| 35a | 2.0 |
| 35b | 3.4 |
| 36a | 2.0 |
| 36b | 2.0 |
| 37a | 0.98 |
| 37b | 4.5 |
| 38a | 0.45 |
| 38b | 1.6 |
| 39a | 0.19 |
| 39b | 0.41 |
| 40a | 3.4 |
| 40b | 3.2 |
| 41a | 1.1 |
| 41b | 3.6 |
| 42a | 4.2 |
| 42b | 4.7 |

TABLE 1-continued

| Compound number | THP1-Dual cells IRF EC50 (μM) |
|---|---|
| 44a | 0.21 |
| 44b | 0.35 |
| 45a | 1.2 |
| 45b | 3.1 |
| 46a | 3.9 |
| 46b | 0.87 |
| 47a | 0.58 |
| 48a | 0.035 |
| 48b | 0.039 |
| 49a | 0.33 |
| 49b | 0.41 |
| 50a | 0.34 |
| 50b | 0.20 |
| 51a | 0.32 |
| 51b | 0.43 |
| 52a | 0.31 |
| 52b | 0.46 |
| 53a | 6.0 |
| 54 | 4.0 |
| ML-RR-CDA•2Na⁺ | 4.2 |
| 2'3'-cGAMP | 21.8 |

These results revealed that the present compounds have agonist activity against human STING. In addition, the present compounds were confirmed to have agonist activity comparable to or higher than those of existing CDNs against mouse STING.

(Test Example 2) Protein Thermal Shift Assay with Recombinant STING C-Terminal Binding Domain Protein (i) Construction of Expression Plasmids
<Construction of Expression Plasmid for Human TMEM173>

For a plasmid for expression of human STING (hereinafter, occasionally referred to as human TMEM173) in mammalian cells, a human TMEM173 cDNA Clone (Accession NM_198282.3, an expression plasmid for H232 (REF)-mutated STING) (GeneCopoeia, Inc., MD, US) with mutation of arginine (R) into histidine (H) at position 232 (hereinafter, referred to as H232 mutation or REF mutation) was purchased. SEQ ID NO: 4 and SEQ ID NO: 5 respectively show the amino acid sequence of human H232 (REF)-mutated STING and the nucleotide sequence therefor. In addition, an expression plasmid for wild-type STING and that for mutated STING were produced through site-specific mutagenesis based on an Inverse PCR method using the expression plasmid for H232-mutated STING as a template. Specifically, PCR was first performed by using two primers (5'-CGTGCTGGCATCAAGGATCGGGTT-TAC-3' (H232R (WT) fwd) (SEQ ID NO: 12) and 5'-GT-CACCGGTCTGCTGGGGCAGTTTATC-3' (H232R (WT) rev)) (SEQ ID NO: 13) and a KOD-Plus-Mutagenesis Kit (SMK-101) (TOYOBO CO., LTD.), and the targeted expression plasmid for wild-type (R232) STING was confirmed to be successfully constructed through DNA sequencing. SEQ ID NO: 6 and SEQ ID NO: 7 respectively show the amino acid sequence of human wild-type STING and the nucleotide sequence therefor.

Next, an HAQ (R71H, G230A, and R293Q)-mutated form was produced in the same manner as for the expression plasmid for wild-type STING. Specifically, PCR was performed by using two primers (5'-GCTGACCGTGCTGG-CATCAAGGATCGGGTTTAC-3' (H232R/G230A fwd) (SEQ ID NO: 14) and 5'-GGTCTGCTGGGGCAGTT- TATCCAGG-3' (H232R/G230A rev) (SEQ ID NO: 15)) and the Mutagenesis Kit with the expression plasmid for H232-mutated STING as a template. A plasmid for G230A-mutated STING was obtained by introducing mutation simultaneously at two positions. Further, PCR was performed by using two primers (5'-CACCACATC-CACTCCAGGTACCGG-3' (R71H fwd) (SEQ ID NO: 16) and 5'-CAGCTCCTCAGCCAGGCTGCAGAC-3' (R71H rev) (SEQ ID NO: 17)) and the Mutagenesis Kit with the expression plasmid for G230A-mutated STING plasmid as a template to afford an expression plasmid for R71H/G230A-mutated STING.

Subsequently, PCR was performed by using two primers (5'-CAGACACTTGAGGACATCCTGGCAG-3' (R293Q fwd) (SEQ ID NO: 18) and 5'-GCAGAAGAGTTTGGCCTGCTCAA-3' (R293Q rev) (SEQ ID NO: 19)) and the Mutagenesis Kit with the expression plasmid for R71H/G230A-mutated STING as a template to afford an expression plasmid for the HAQ (R71H/G230A/R293Q)-mutated form. SEQ ID NO: 8 and SEQ ID NO: 9 respectively show the amino acid sequence of human HAQ-mutated STING and the nucleotide sequence therefor.

FIG. 6 shows the amino acid sequences of human wild-type STING, REF-type STING, and HAQ-type STING.

<Construction of Expression Plasmid for Recombinant STING C-Terminal Binding Domain Protein, Etc.>

Human STING C-terminal binding domain (aa139-342) protein (UniProt entry Q86WV6) cDNA was produced from an expression plasmid for each full-length human TMEM173 cDNA clone (wild-type, H232-mutated, and HAQ-mutated) through PCR with two primers (5'-ACCTGTATTTTCAGGGCCTGGCCCCAGCT-GAGATCTCTG-3' (hST Fw_v2) (SEQ ID NO: 20) and 5'-CAGAATTCGCAAGCTTT-TAAGTAACCTCTTCCTTTTCCTCCTGC-3' (hST Rv_V3) (SEQ ID NO: 21)). Each PCR product was inserted into pET15b, a vector for expression with *Escherichia coli*, with use of an In-Fusion HD Cloning Kit (Takara Bio Inc.) so that a 6×His tag consisting of six nucleotides of histidine, an Avidin tag, and a TEV protease cleavage site were included at the N terminus to construct expression plasmids for the pET15b-HisAviTEV-hSTING (139-342) human wild-type, pET15b-HisAviTEV-hSTING (139-342) human REF-mutated, and pET15b-HisAviTEV-hSTING (139-342) human AQ-mutated forms.

For cDNA for expression of mouse STING C-terminal binding domain (aa138-341) protein (UniProt entry Q3TBT3), cDNA corresponding to the amino acids at positions 138 to 341 in the sequence of mouse TMEM173 cDNA was artificially synthesized by Eurofins Genomics K. K. and used. SEQ ID NO: 10 and SEQ ID NO: 11 respectively show the amino acid sequence of mouse STING and the nucleotide sequence therefor. The cDNA synthesized was inserted into pET15b, a vector for expression with *Escherichia coli*, with use of an In-Fusion HD Cloning Kit so that a 6×His tag consisting of six nucleotides of histidine, an Avidin tag, and a TEV protease cleavage site were included at the N terminus to construct an expression plasmid for the pET15b-HisAviTEV-mSTING (138-341) mouse wild-type form.

Artificially synthesized *E. coli* BirA (UniProt entry P06709) cDNA was inserted into a pCDF_Duet-1 vector to construct an expression plasmid for pCDF_Duet-1 BirA (1-321).

(ii) Method for Preparing STING C-Terminal Binding Domain Protein

The thus-produced expression plasmids for pET15b-HisAviTEV-hSTING (139-342) (human wild-type, human REF-mutated, and human AQ-mutated STING C-terminal binding domain proteins) and expression plasmid for pET15b-HisAviTEV-mSTING (138-341) (mouse wild-type STING C-terminal binding domain protein) were each transformed with Competent *E. coli* Rosetta 2 (DE3) (Merck Millipore, MA, US) concomitantly with the expression plasmid for pCDF_Duet-1 BirA (1-321) to produce HisAviTEV-STING-expressing strains. Each of these expression strains was added to a TB medium containing 100 µg/mL ampicillin, 50 µg/mL streptomycin, and 30 µg/mL kanamycin, cultured at 37° C., then exposed to 100 µM IPTG for inducible expression, and further cultured at 16° C.

The culture solution was centrifuged, and the resulting bacterial cells were suspended in 50 mM HEPES pH 8.0, 500 mM NaCl, 20 mM imidazole, 1 mM DTT, 5% (w/v) glycerol, Complete EDTA free, and then subjected to freeze-thawing. After addition of Lysozyme and DNase I, proteins were extracted by ultrasonic disintegration, and centrifugation was performed and the resulting supernatant was collected. The supernatant obtained was purified by using an AKTA express chromatography system (GE Healthcare, IL, US) with a HisTrap FF column (GE Healthcare), and eluted with buffer (20 mM HEPES pH 7.5, 120 mM NaCl, 20% Glycerol, 0.8 mM DTT) through a Superdex 200 16/60 column (GE Healthcare). Fractions containing proteins of targeted molecular weights were collected with SEC as His-Avi-TEV-hSTING (139-342) human wild-type protein, HisAviTEV-hSTING (139-342) human REF-mutated protein, HisAviTEV-hSTING (139-342) human AQ-mutated protein, and His-Avi-TEV-mSTING (138-341) mouse wild-type protein. The protein concentrations were measured by using a NanoDrop2000 (Thermo Fisher Scientific, MA, US), and the proteins were cryopreserved at −80° C. until use.

SEQ ID NO: 22, SEQ ID NO: 23, SEQ ID NO: 24, and SEQ ID NO: 25 respectively show the amino acid sequences of HisAviTEV-hSTING (139-342) human wild-type protein, HisAviTEV-hSTING (139-342) human REF-mutated protein, HisAviTEV-hSTING (139-342) human AQ-modified protein, and His-Avi-TEV-mSTING (138-341) mouse wild-type protein.

(iii) STING Binding Test

The binding ability of each compound to the STING C-terminal binding domain proteins was evaluated by protein thermal shift assay, which uses the elevation of thermal denaturation temperature of protein as an index.

Specifically, 3 µL of a test compound (final concentration: 0.5 mM), 3 µL of SYPRO Orange Protein Gel Stain (Thermo Fisher Scientific) (final concentration: 20-fold), and 6 µL of a STING protein were mixed with use of assay buffer (20 mM Tris-HCl pH 7.5, 120 mM NaCl) in a 384-well real-time PCR plate, and mixed together with a plate shaker. With a real-time PCR system (Thermo Fisher Scientific), the temperature was increased from 25° C. to 95° C. at a rate of 0.03° C./sec, and the thermal denaturation temperature of the protein was measured by using fluorescence emitted from SYPRO Orange as an index. From the measurement acquired, Tm (the midpoint of the unfolding transition) (° C.) was determined as a temperature at which the increase rate of fluorescence intensity was maximized by using the analysis software Protein Thermal Shift software (Thermo Fisher Scientific). The Tm value for a well with no compound was subtracted from the Tm value for each test compound to calculate the Tm shift caused by the compound as ΔTm (° C.). Table 2 shows the results of the test on binding to the STING proteins.

TABLE 2

| Compound number | ΔTm (° C) | | | |
| --- | --- | --- | --- | --- |
| | Hu-WT | Hu-REF | Hu-AQ | Ms-WT |
| 1a | 8.4 | 3.4 | 12.0 | 14.3 |
| 4a | 11.5 | 5.2 | 17.0 | 17.5 |
| 4b | 9.8 | 3.5 | 13.1 | 14.9 |
| 6a | 10.6 | 5.7 | 14.8 | 15.7 |
| 6b | 8.4 | 3.4 | 11.3 | 12.9 |
| 7a | 8.0 | 3.9 | 9.7 | 11.5 |
| 7b | 7.2 | 2.8 | 9.5 | 13.2 |
| 8a | 7.6 | 2.8 | 10.8 | 11.5 |
| 12a | 8.0 | 3.0 | 9.6 | 11.9 |
| 17a | 7.3 | 2.7 | 10.7 | 12.6 |
| 17b | 7.4 | 2.2 | 10.4 | 12.6 |
| 20a | 7.5 | 3.7 | 9.7 | 12.4 |
| 23a | 9.7 | 4.2 | 12.2 | 15.6 |
| 25a | 11.4 | 6.2 | 15.0 | 16.0 |
| 25b | 10.6 | 4.6 | 13.1 | 15.8 |
| 26b | 9.1 | 3.9 | 11.5 | 14.1 |
| 34a | 14.7 | 8.8 | 18.9 | 20.3 |
| 34b | 12.0 | 6.5 | 14.0 | 16.7 |
| 35a | 11.0 | 6.6 | 13.1 | 13.5 |
| 35b | 10.3 | 5.8 | 12.6 | 14.2 |
| 36a | 10.8 | 5.8 | 13.3 | 15.4 |
| 36b | 10.1 | 5.5 | 11.8 | 19.3 |
| 37a | 11.2 | 5.2 | 13.6 | 15.3 |
| 37b | 8.1 | 3.4 | 9.4 | 12.3 |
| 39a | 10.4 | 5.7 | 12.9 | 15.0 |
| 39b | 8.9 | 3.7 | 10.5 | 13.1 |
| 42a | 6.5 | 2.8 | 9.0 | 11.2 |
| 42b | 5.3 | 1.4 | 7.4 | 10.6 |
| 44a | 13.4 | 8.7 | 18.2 | 19.3 |
| 44b | 11.4 | 6.2 | 14.3 | 17.0 |
| 45a | 8.9 | 4.4 | 10.8 | 12.3 |
| 45b | 7.5 | 3.1 | 9.1 | 12.1 |
| 48a | 15.9 | 9.3 | 22.2 | 16.0 |
| 48b | 14.0 | 7.3 | 17.8 | 15.8 |
| 49b | 12.6 | 6.6 | 16.1 | 19.3 |
| 50a | 12.3 | 6.5 | 15.6 | 13.0 |
| 50b | 12.3 | 6.3 | 15.3 | 7.4 |
| 51b | 9.9 | 4.3 | 11.6 | 17.0 |
| 52a | 10.9 | 5.6 | 13.5 | 14.3 |
| 52b | 9.2 | 4.4 | 10.8 | 12.3 |
| 53a | 9.6 | 5.4 | 11.6 | 14.3 |
| 54 | 8.3 | 3.4 | 9.8 | 12.1 |
| ML-RR-CDA•2Na+ | 7.0 | 2.7 | 12.7 | 15.2 |
| 2'3'-cGAMP | 13.7 | 4.1 | 24.3 | 25.8 |

These results revealed that the present compounds have binding activity to human wild-type STING and mutated STING, and mouse wild-type STING.

(Test Example 3) Anti-Tumor Test (1)

Mice: Before use for experiment, 5-week-old female BALB/c mice (BALB/cAnNCrlCrlj) (Charles River Laboratories Japan, Inc.) were habituated under SPF conditions for 4 days or longer.

Measurement, calculation formula: In all the studies, the major axis and minor axis of a tumor were measured twice or three times per week by using an electronic digital caliper (CD15-CX, Mitutoyo Corporation) to calculate tumor volume ($mm^3$). The calculation formula is as follows.

Tumor volume ($mm^3$)=0.5×Major axis (mm)×[Minor axis (mm)]$^2$

Each test compound was diluted with physiological saline (Otsuka Pharmaceutical Factory, Inc.) for use. In administration of it, 50 µL was intratumorally administered.

Cells of the mouse colorectal cancer cell line CT26.WT (CRL2638) purchased from the American Type Culture Collection were used. CT26.WT cells were suspended in physiological saline, $1.0 \times 10^6$ cells were subcutaneously transplanted into the right axilla of each BALB/c mouse (Day 0), and 7 days thereafter the mice were randomly grouped. Each test compound in a dose of 10 µg was intratumorally administered on Day 7, 9, and 11, three times in total. A group with administration of physiological saline was set as a group with a vehicle. The number of mice in each group was five or six.

The results are shown in FIGS. 7a and 7b. In each graph, the line with solid squares corresponds to the group with a vehicle, the line with open squares to the group with administration of compound No. 6a, the line with open inverted triangles to the group with administration of compound No. 8b, and the line with open circles to the group with administration of compound No. 9b. The vertical axis represents tumor volume ($mm^3$), and the horizontal axis represents days after tumor transplantation. The tumor growth progressed in the group with a vehicle. In contrast to this, the tumor growth was significantly suppressed in the groups with administration of a compound.

These results confirmed anti-tumor effect of intratumor administration of the cyclic dinucleotide derivatives.

(Test Example 4) Anti-Tumor Test (2)

A human HER2 gene was introduced into the mouse colorectal cancer cell line CT26.WT (CRL2638) purchased from the American Type Culture Collection to produce CT26.WT-hHER2 cells. Specifically, cDNA was amplified by using a plasmid including cDNA for human HER2 (Clone ID IOH82145; Thermo Fisher Scientific), and inserted into a pQCXIN retroviral vector (Takara Bio Inc.) by using an In-Fusion HD Cloning Kit (Clontech Laboratories, Inc.). The human HER2-inserted pQCXIN retroviral vector was transfected into an EcoPack2-293 cell line (Takara Bio Inc.) with Lipofectamine 3000 (Thermo Fisher Scientific), the supernatant which contained virus was collected, and CT26.WT cells were infected with the virus. The cells were maintained in a medium with 250 µg/mL Geneticin (Thermo Fisher Scientific).

Each antibody-CDN conjugate was diluted with acetate buffer (10 mM Acetate Buffer, 5% Sorbitol, pH 5.5) (NACALAI TESQUE, INC.) for use. In administration of it, 200 µL was administered into the tail vein.

CT26.WT-hHER2 cells were suspended in physiological saline, $5.0 \times 10^6$ cells were subcutaneously transplanted into the right axilla of each BALB/c mouse (Day 0), and 7 days thereafter the mice were randomly grouped. Each antibody-CDN conjugate in a dose of 30 µg was administered into the tail vein on Day 7, once in total. A group with administration of acetate buffer was set as a group with a vehicle. The number of mice in each group was eight.

The results are shown in FIG. 8. In each graph, the line with solid squares corresponds to the group with a vehicle, the line with open triangles to the group with administration of anti-HER2 antibody-CDN conjugate (1), which was formed by conjugating the compound of Example 8b to the modified anti-HER2 antibody produced in Reference Example 1, and the line with solid triangles to the group with administration of anti-LPS antibody-CDN conjugate (1), which was similarly formed by conjugating the compound of Example 8b to the modified anti-LPS antibody produced in Reference Example 2. The vertical axis represents tumor volume ($mm^3$), and the horizontal axis represents days after tumor transplantation. The tumor growth progressed in the group with a vehicle and the group with administration of anti-LPS antibody-CDN conjugate (1), which does not bind to HER2. In contrast to this, the tumor growth was significantly suppressed in the group with administration of anti-HER2 antibody-CDN conjugate (1).

These results confirmed antibody-target-dependent anti-tumor effect of intravenous administration of anti-HER2 antibody-CDN conjugate (1).

(Test Example 5) Anti-Tumor Test (3)

CT26.WT-hHER2 cells were suspended in physiological saline, $5.0 \times 10^6$ cells were subcutaneously transplanted into the right axilla of each BALB/c mouse (Day 0), and 6 days thereafter the mice were randomly grouped. Each antibody-CDN conjugate in a dose of 30 μg was administered into the tail vein on Day 6, once in total. A group with administration of acetate buffer was set as a group with a vehicle. The number of mice in each group was six or eight.

The results are shown in FIG. 9. In the graph, the line with solid squares corresponds to the group with a vehicle, the line with open squares to the group with administration of anti-HER2 antibody-CDN conjugate (2), and the line with open triangles to the group with administration of anti-HER2 antibody-CDN conjugate (3). The vertical axis represents tumor volume (mm³), and the horizontal axis represents days after tumor transplantation. The tumor growth progressed in the group with a vehicle. In contrast to this, the tumor growth was significantly suppressed in the groups with administration of anti-HER2 antibody-CDN conjugates (2) and (3).

These results confirmed potent anti-tumor effect of the anti-HER2 antibody-CDN conjugates.

(Test Example 6) Anti-Tumor Test (4)

CT26.WT-hHER2 cells were suspended in physiological saline, $5.0 \times 10^6$ cells were subcutaneously transplanted into the right axilla of each BALB/c mouse (Day 0), and 7 days thereafter the mice were randomly grouped. Antibody-CDN conjugate (19) in a dose of 30 μg was administered into the tail vein on Day 7, once in total. A group with administration of acetate buffer was set as a group with a vehicle. The number of mice in each group was six.

The results are shown in FIG. 10. In the graph, the line with solid squares corresponds to the group with a vehicle, and the line with open triangles to the group with administration of anti-HER2 antibody-CDN conjugate (19). In anti-HER2 antibody-CDN conjugate (19), a drug-linker is conjugated to the antibody through cysteine conjugation. The vertical axis represents tumor volume (mm³), and the horizontal axis represents days after tumor transplantation. The tumor growth progressed in the group with a vehicle. In contrast to this, the tumor growth was significantly suppressed in the group with administration of anti-HER2 antibody-CDN conjugate (19).

These results confirmed the potent anti-tumor effect of the anti-HER2 antibody-CDN conjugate with cysteine conjugation of the antibody and the drug-linker.

(Test Example 7) Anti-Tumor Test (5)

CT26.WT-hHER2 cells were suspended in physiological saline, $5.0 \times 10^6$ cells were subcutaneously transplanted into the right axilla of each BALB/c mouse (Day 0), and 6 days thereafter the mice were randomly grouped. Each antibody-CDN conjugate in a dose of 30 μg was administered into the tail vein on Day 6, once in total. A group with administration of acetate buffer was set as a group with a vehicle. The number of mice in each group was five.

The results are shown in FIG. 11. In the graph, the line with solid squares corresponds to the group with a vehicle, the line with open triangles to the group with administration of anti-HER2 antibody-CDN conjugate (9), the line with open inverted triangles to the group with administration of anti-HER2 antibody-CDN conjugate (10), the line with open rhombuses to the group with administration of anti-HER2 antibody-CDN conjugate (11), the line with open circles to the group with administration of anti-HER2 antibody-CDN conjugate (12), and the line with open squares to the group with administration of anti-HER2 antibody-CDN conjugate (1). In each of anti-HER2 antibody-CDN conjugates (9), (10), (11), (12), and (1), the compound of Example 8b is conjugated via a linker, where the linkers are different from each other. The vertical axis represents tumor volume (mm³), and the horizontal axis represents days after tumor transplantation. The tumor growth progressed in the group with a vehicle. In contrast to this, the tumor growth was significantly suppressed in the groups with administration of anti-HER2 antibody-CDN conjugates (9), (10), (11), and (12), as with the case of the group with administration of anti-HER2 antibody-CDN conjugate (1).

These results confirmed that anti-HER2 antibody-CDN conjugates exhibit anti-tumor effect even for different linkers.

(Test Example 8) Anti-Tumor Test (6)

CT26.WT-hHER2 cells were suspended in physiological saline, $5.0 \times 10^6$ cells were subcutaneously transplanted into the right axilla of each BALB/c mouse (Day 0), and 7 days thereafter the mice were randomly grouped. Each specimen for administration was administered into the tail vein on Day 7, once in total. A group with administration of acetate buffer was set as a group with a vehicle. The number of mice in each group was five.

The results are shown in Table 12. In the graph, the line with solid squares corresponds to the group with a vehicle, the line with open triangles to the group with administration of 60 μg of anti-HER2 antibody 2-CDN conjugate (1), the line with solid inverted triangles to the group with administration of 59 μg of anti-HER2 antibody 2, and the line with solid circles to the group with administration of 1.2 μg of compound No. 8b. Each of the doses of anti-HER2 antibody 2 and compound No. 8b is the equivalent of the corresponding component constituting anti-HER2 antibody 2-CDN conjugate (1). The vertical axis represents tumor volume (mm³), and the horizontal axis represents days after tumor transplantation. The tumor growth progressed in the group with a vehicle. In contrast to this, the tumor growth was significantly suppressed in the group with administration of anti-HER2 antibody 2-CDN conjugate (1). However, the tumor growth was not suppressed in each group with administration of the equivalent of anti-HER2 antibody 2 or compound No. 8b.

These results confirmed that anti-HER2 antibody 2-CDN conjugate (1) exhibits anti-tumor effect, and that the equivalent of anti-HER2 antibody 2 and the equivalent of compound No. 8b do not exhibit anti-tumor effect when being administered into the tail vein.

(Test Example 9) Anti-Tumor Test (7)

CT26.WT-hHER2 cells were suspended in physiological saline, $5.0 \times 10^6$ cells were subcutaneously transplanted into the right axilla of each BALB/c mouse (Day 0), and 7 days thereafter the mice were randomly grouped. Each antibody-CDN conjugate in a dose of 30 μg was administered into the tail vein on Day 7, once in total. A group with administration of acetate buffer was set as a group with a vehicle. The number of mice in each group was five or six.

The results are shown in FIGS. 13(a) to 13(c). In each graph, the line with solid squares corresponds to the group with a vehicle, and each line with open symbols to a group with administration of an evaluated subject of anti-HER2 antibody 2-CDN conjugates (2), (3), (4), (5), (6), (7), and (8). The vertical axis represents tumor volume ($mm^3$), and the horizontal axis represents days after tumor transplantation. The tumor growth progressed in the group with a vehicle. In contrast to this, the tumor growth was significantly suppressed in the groups with administration of anti-HER2 antibody 2-CDN conjugates (2), (3), (4), (5), (6), (7), and (8).

These results confirmed potent anti-tumor effect of the anti-HER2 antibody 2-CDN conjugates.

(Test Example 10) Anti-Tumor Test (8)

CT26.WT-hHER2 cells were suspended in physiological saline, $5.0 \times 10^6$ cells were subcutaneously transplanted into the right axilla of each BALB/c mouse (Day 0), and 7 days thereafter the mice were randomly grouped. Each antibody-CDN conjugate in a dose of 60 μg was administered into the tail vein on Day 7, once in total. A group with administration of acetate buffer was set as a group with a vehicle. The number of mice in each group was five.

The results are shown in FIG. 14. In the graph, the line with solid squares corresponds to the group with a vehicle, the line with open triangles to the group with administration of anti-HER2 antibody 2-CDN conjugate (9), and the line with open circles to the group with administration of anti-HER2 antibody 2-CDN conjugate (10). Anti-HER2 antibody 2-CDN conjugates (9) and (10) are antibody-CDN conjugates using an MSG-type glycan-remodeled antibody with the average number of conjugated drug molecules being approximately 2. The vertical axis represents tumor volume ($mm^3$), and the horizontal axis represents days after tumor transplantation. The tumor growth progressed in the group with a vehicle. In contrast to this, the tumor growth was significantly suppressed in the groups with administration of anti-HER2 antibody 2-CDN conjugates (9) and (10).

These results confirmed potent anti-tumor effect of the anti-HER2 antibody 2-CDN conjugates with the average number of conjugated drug molecules being approximately 2.

(Test Example 11) Anti-Tumor Test (9)

A human EphA2 gene was introduced into the mouse colorectal cancer cell line CT26.WT (CRL2638) purchased from the American Type Culture Collection to produce CT26.WT-hEphA2 cells. Specifically, cDNA was amplified by using pDONR221 including cDNA for human EphA2 (Thermo Fisher Scientific), and inserted into a pLNCX retroviral vector (Takara Bio Inc.) by using a Gateway vector conversion system (Thermo Fisher Scientific). The human EphA2-inserted pLNCX retroviral vector was transfected into an EcoPack2-293 cell line (Takara Bio Inc.) with Lipofectamine 2000 (Thermo Fisher Scientific), the supernatant which contained virus was collected, and CT26.WT cells were infected with the virus. The cells were maintained in a medium with 500 μg/mL Geneticin (Thermo Fisher Scientific).

CT26.WT-hEphA2 cells were suspended in phosphate buffer, $1.9 \times 10^6$ cells were subcutaneously transplanted into the right axilla of each BALB/c mouse (Day 0), and 7 days thereafter the mice were randomly grouped. Each of the anti-EphA2 antibody and anti-EphA2 antibody-CDN conjugate (1) in a dose of 60 μg was administered into the tail vein on Day 7, once in total. A group with administration of acetate buffer was set as a group with a vehicle. The number of mice in each group was eight.

The results are shown in FIG. 15. In the graph, the line with solid squares corresponds to the group with a vehicle, the line with open circles to the group with administration of the anti-EphA2 antibody, and the line with open triangles to the group with administration of anti-EphA2 antibody-CDN conjugate (1). The vertical axis represents tumor volume ($mm^3$), and the horizontal axis represents days after tumor transplantation. The tumor growth progressed in the group with a vehicle. The tumor growth was not suppressed in the group with administration of the anti-EphA2 antibody. In contrast to these, the tumor growth was significantly suppressed in the group with administration of anti-EphA2 antibody-CDN conjugate (1).

These results, with use of a model in which the anti-EphA2 antibody does not exhibit anti-tumor effect, confirmed potent anti-tumor effect of the anti-EphA2 antibody-CDN conjugate.

(Test Example 12) Anti-Tumor Test (10)

A human CD33 gene was introduced into the mouse lymphoid cell line P388D1 (CCL-46) purchased from the American Type Culture Collection to produce P388D1-hCD33 cells. Specifically, a pLVSIN lentiviral vector (Takara Bio Inc.) with cDNA for human CD33 inserted therein was produced, and transfected into a Lenti-X293T cell line (Takara Bio Inc.) by using a Lentiviral High Titer Packaging Mix (Takara Bio Inc.), the supernatant which contained virus was collected, and P388D1 cells were infected with the virus. The cells were maintained in a medium with 2 μg/mL Puromycin (Thermo Fisher Scientific).

Four-week-old female DBA/2 mice (DBA/2NCrl) (Charles River Laboratories Japan, Inc.) were purchased, and habituated under SPF conditions for 5 days before use for experiment.

P388D1-hCD33 cells were suspended in phosphate buffer, $1.0 \times 10^6$ cells were subcutaneously transplanted into the right axilla of each DBA/2 mouse (Day 0), and 4 days thereafter the mice were randomly grouped. Each of the anti-CD33 antibody and anti-CD33 antibody-CDN conjugate (1) in a dose of 60 μg was administered into the tail vein on Day 4, once in total. A group with administration of acetate buffer was set as a group with a vehicle. The number of mice in each group was 10.

The results are shown in FIG. 16. In the graph, the line with solid squares corresponds to the group with a vehicle, the line with open circles to the group with administration of the anti-CD33 antibody, and the line with open triangles to the group with administration of anti-CD33 antibody-CDN conjugate (1). The vertical axis represents tumor volume ($mm^3$), and the horizontal axis represents days after tumor transplantation. The tumor growth progressed in the group with a vehicle. The tumor growth was not suppressed in the group with administration of the anti-CD33 antibody. In contrast to these, the tumor growth was significantly suppressed in the group with administration of anti-CD33 antibody-CDN conjugate (1).

These results, with use of a model in which the anti-CD33 antibody does not exhibit anti-tumor effect, confirmed potent anti-tumor effect of the anti-CD33 antibody-CDN conjugate.

(Test Example 13) Anti-Tumor Test (11)

CT26.WT-hHER2 cells were suspended in physiological saline, $5.0 \times 10^6$ cells were subcutaneously transplanted into the right axilla of each BALB/c mouse (Day 0), and 7 days thereafter the mice were randomly grouped. Each antibody-CDN conjugate in a dose of 60 μg was administered into the tail vein on Day 7, once in total. A group with administration of acetate buffer was set as a group with a vehicle. The number of mice in each group was six.

The results are shown in FIG. 22. In the graph, the line with solid squares corresponds to the group with a vehicle, the line with open triangles to the group with administration of anti-HER2 antibody 2-CDN conjugate (11), and the line with open circles to the group with administration of anti-HER2 antibody 2-CDN conjugate (12). Compound No. 52a and compound No. 52b conjugated to anti-HER2 antibody 2-CDN conjugates (11) and (12), respectively, are each a CDN having a phosphate group. The vertical axis represents tumor volume (mm$^3$), and the horizontal axis represents days after tumor transplantation. The tumor growth progressed in the group with a vehicle. In contrast to this, the tumor growth was significantly suppressed in the groups with administration of anti-HER2 antibody 2-CDN conjugates (11) and (12).

These results confirmed potent anti-tumor effect of anti-HER2 antibody 2-CDN conjugates (11) and (12) with a CDN having a phosphate group conjugated.

INDUSTRIAL APPLICABILITY

The present invention provides novel CDN derivatives that have potent STING agonist activity and exhibit potent anti-tumor effect. In addition, the present invention provides antibody-drug conjugates including the novel CDN derivatives. These are useful as therapeutic agents for diseases associated with STING agonist activity (e.g., cancer).

Free Text of Sequence Listing

SEQ ID NO: 1: Amino acid sequence of light chain of trastuzumab

SEQ ID NO: 2: Amino acid sequence of heavy chain of trastuzumab

SEQ ID NO: 3: Amino acid sequence of heavy chain of modified anti-HER2 antibody

SEQ ID NO: 4: Amino acid sequence of human H232 (REF)-mutated STING

SEQ ID NO: 5: Nucleic acid sequence for human H232 (REF)-mutated STING

SEQ ID NO: 6: Amino acid sequence of human wild-type STING

SEQ ID NO: 7: Nucleic acid sequence for human wild-type STING

SEQ ID NO: 8: Amino acid sequence of human HAQ-mutated STING

SEQ ID NO: 9: Nucleic acid sequence for human HAQ-mutated STING

SEQ ID NO: 10: Amino acid sequence of mouse STING

SEQ ID NO: 11: Nucleic acid sequence for mouse STING

SEQ ID NOs: 12 to 21: Primer sequences

SEQ ID NO: 22: Amino acid sequence of HisAviTEV-hSTING (139-342) human wild-type protein SEQ ID NO: 23: Amino acid sequence of HisAviTEV-hSTING (139-342) human REF-mutated protein SEQ ID NO: 24: Amino acid sequence of HisAviTEV-hSTING (139-342) human AQ-mutated protein SEQ ID NO: 25: Amino acid sequence of His-Avi-TEV-mSTING (138-341) mouse wild-type protein SEQ ID NO: 26: Amino acid sequence of light chain of modified anti-LPS antibody SEQ ID NO: 27: Amino acid sequence of heavy chain of modified anti-LPS antibody SEQ ID NO: 28: Amino acid sequence of pertuzumab light chain SEQ ID NO: 29: Amino acid sequence of pertuzumab heavy chain SEQ ID NO: 30: Amino acid sequence of heavy chain of modified anti-HER2 antibody 2

SEQ ID NO: 31: Amino acid sequence of anti-CD33 antibody light chain

SEQ ID NO: 32: Amino acid sequence of anti-CD33 antibody heavy chain

SEQ ID NO: 33: Amino acid sequence of anti-EphA2 antibody light chain

SEQ ID NO: 34: Amino acid sequence of anti-EphA2 antibody heavy chain

SEQ ID NO: 35: Amino acid sequence of anti-CDH6 antibody light chain

SEQ ID NO: 36: Amino acid sequence of anti-CDH6 antibody heavy chain

---

The invention claimed is:

1. An antibody-drug conjugate represented by formula (II):

Ab─[L─D]$_{m1}$     (II)

wherein $m^1$ is in the range of 1 to 10;

Ab represents an antibody or an antigen-binding fragment of the antibody, where a glycan of the antibody is optionally remodeled, and wherein the antibody or the antigen-binding fragment of the antibody is not an anti-EGFR antibody or antigen-binding fragment, an anti-TROP2 antibody or antigen-binding fragment, or an anti-CD70 antibody or antigen-binding fragment;

L represents a linker linking Ab and D and is represented by -Lb-La-Lp-Lc-*, wherein the asterisk indicates bonding to D;

Lp is a peptide that consists of two to four amino acids;

La is selected from the following group:

—C(=O)—(CH$_2$CH$_2$)n$^2$-C(=O)—,
—C(=O)—(CH$_2$CH$_2$)n$^2$-CH$_2$—C(=O)—,
—C(=O)—(CH$_2$CH$_2$)n$^2$-C(=O)—NH—(CH$_2$CH$_2$)n$^3$-C(=O)—,
—C(=O)—(CH$_2$CH$_2$)n$^2$-C(=O)—NH—(CH$_2$CH$_2$)n$^3$-CH$_2$—C(=O)—,
—C(=O)—(CH$_2$CH$_2$)n$^2$-C(=O)—NH—(CH$_2$CH$_2$O)n$^3$-CH$_2$—C(=O)—,
(CH$_2$)n$^4$-O—C(=O)—, and
(CH$_2$)n$^9$-C(=O)—, wherein $n^2$ represents an integer of 1 to 3, $n^3$ represents an integer of 1 to 5, $n^4$ represents an integer of 0 to 2, and $n^9$ represents an integer of 2 to 7;

Lb represents a spacer bonding La and a glycan or remodeled glycan of Ab or a spacer bonding La and a cysteine residue of Ab; and Lc represents —NH—CH$_2$—, —NH-phenyl group —CH$_2$—O(C=O)—, or —NH-heteroaryl group —CH$_2$—O(C=O)—, or is absent;

Ab bonds directly from an amino acid residue of Ab to L, or optionally bonds via a glycan or remodeled glycan of Ab to L; and D represents a compound represented by formula (I):

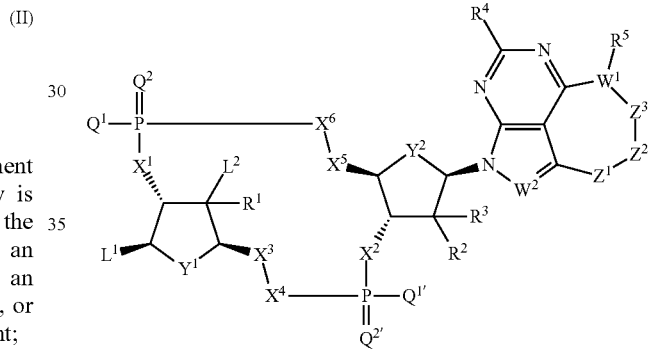

wherein

L bonds to any —NH$_2$ or hydroxy group included in $L^1$;

$L^1$ represents a group selected from the group consisting of the following formulas:

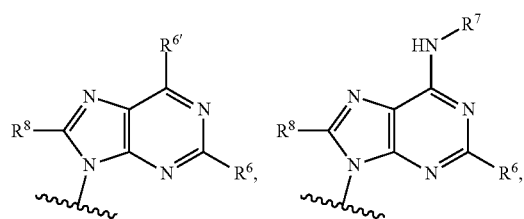

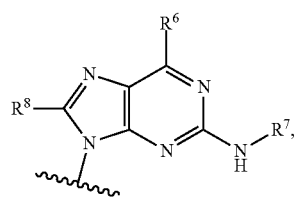

-continued

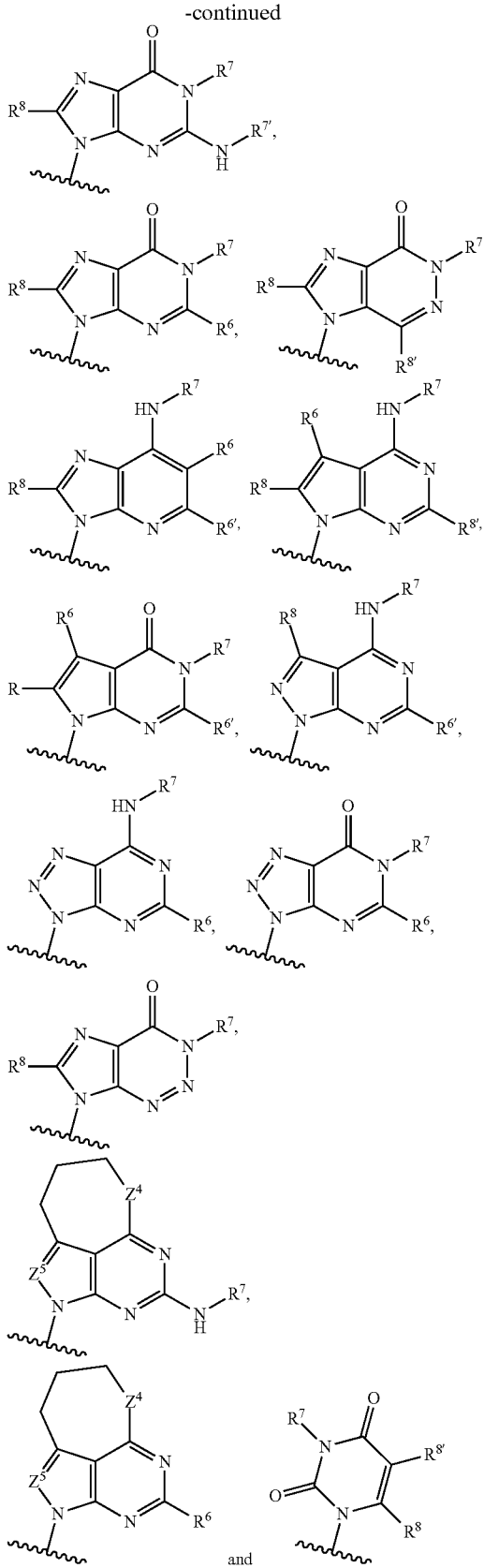

and optionally substituted at any position with one to three groups selected from the group consisting of a hydroxy group, —NH$_2$, a 2-hydroxyacetylaminomethyl group, and a 2-[(2-hydroxyacetyl)amino]ethyl group,
wherein
R$^6$ and R$^{6'}$ each independently represent a hydrogen atom, —NH$_2$, or a C1-C6 alkyl group;
R$^7$ and R$^{7'}$ each independently represent a hydrogen atom or a C1-C6 alkyl group, wherein the C1-C6 alkyl group is optionally substituted with one or two oxo groups;
R$^8$ and R$^{8'}$ each independently represent a hydrogen atom;
Z$^4$ represents —CH$_2$—, —NH—, or an oxygen atom; and
Z$^5$ represents a nitrogen atom or —CH═,
L$^2$ represents a hydrogen atom;
Q$^1$ and Q$^{1'}$ each independently represent a hydroxy group, a thiol group, or a borano group (BH$_3^-$);
Q$^2$ and Q$^{2'}$ each independently represent an oxygen atom or a sulfur atom;
X$^1$ and X$^2$ each independently represent an oxygen atom;
Y$^1$ and Y$^2$ each represent an oxygen atom or —CH$_2$—;
X$^3$ and X$^4$ represent a group selected from (iii) and (iv):
(iii) when Y$^1$ is an oxygen atom, X$^3$-X$^4$ represents —CH$_2$—O— or —CH$_2$—S—; and
(iv) when Y$^1$ is —CH$_2$—, X$^3$-X$^4$ represents —O—CH$_2$—;
X$^5$ and X$^6$ represent a group selected from (v) and (vi):
(v) when Y$^2$ is an oxygen atom, X$^5$-X$^6$ represents —CH$_2$—O— or —CH$_2$—S—; and
(vi) when Y$^2$ is —CH$_2$—, X$^5$-X$^6$ represents —O—CH$_2$—;
R$^1$, R$^2$ and R$^3$ each independently represent a hydrogen atom, a halogen atom, —OR', —OC(═O)R', —N$_3$, or —NHR', wherein R' represents a hydrogen atom, a C1-C6 alkyl group, a C2-C6 alkenyl group, a C2-C6 alkynyl group, or a C3-C6 cycloalkyl group, and the C1-C6 alkyl group, C2-C6 alkenyl group, or C2-C6 alkynyl group is optionally substituted with one to six halogen atoms;
W$^1$ represents a nitrogen atom, an oxygen atom, a sulfur atom, or —CH—;
W$^2$ represents a nitrogen atom or —CH═;
R$^4$ represents a hydrogen atom;
R$^5$ represents a group selected from (vii) to (x):
(vii) when W$^1$ is a nitrogen atom, R$^5$ represents a hydrogen atom, a C1-C6 alkyl group, or a hydroxy C1-C6 alkyl group;
(viii) when W$^1$ is an oxygen atom, R$^5$ is absent;
(ix) when W$^1$ is a sulfur atom, R$^5$ is absent; and
(x) when W$^1$ is —CH—, R$^5$ represents a hydrogen atom;
Z$^1$—Z$^2$—Z$^3$ together represents —CH$_2$—CH$_2$—CH$_2$—, —CH$_2$—CH$_2$—R'''—, —CH═CH—CH$_2$—, —CH$_2$—CH(CH$_3$)—CH$_2$—, or —CH$_2$—CH$_2$—CH(CH$_3$)—, wherein R''' represents —O— or —CH$_2$—CH$_2$—.

2. The antibody-drug conjugate according to claim 1, wherein W$^1$ is a nitrogen atom.

3. The antibody-drug conjugate according to claim 2, wherein W$^1$ is a nitrogen atom, and R$^5$ is a hydrogen atom.

4. The antibody-drug conjugate according to claim 1, wherein W$^1$ is an oxygen atom.

5. The antibody-drug conjugate according to claim 1, wherein W$^1$ is a sulfur atom.

6. The antibody-drug conjugate according to claim 1, wherein W$^1$ is —CH—.

7. The antibody-drug conjugate according to claim 6, wherein W$^1$ is —CH—, and R$^5$ is a hydrogen atom.

8. The antibody-drug conjugate according to claim 1, wherein $Z^1$, $Z^2$ and $Z^3$ together form —CH$_2$—CH$_2$—CH$_2$— or —CH=CH—CH$_2$—.

9. The antibody-drug conjugate according to claim 1, wherein $Z^1$, $Z^2$ and $Z^3$ together form —CH$_2$—CH(CH$_3$)—CH$_2$— or —CH$_2$—CH$_2$—CH(CH$_3$)—.

10. The antibody-drug conjugate according to claim 1, wherein $Z^1$, $Z^2$ and $Z^3$ together form —CH$_2$—CH$_2$—R'''—, wherein R''' represents —O— or —CH$_2$—CH$_2$—.

11. The antibody-drug conjugate according to claim 1, wherein $W^2$ is —CH=.

12. The antibody-drug conjugate according to claim 1, wherein $W^2$ is a nitrogen atom.

13. The antibody-drug conjugate according to claim 1, wherein $L^1$ is a group selected from the group consisting of the following formulas:

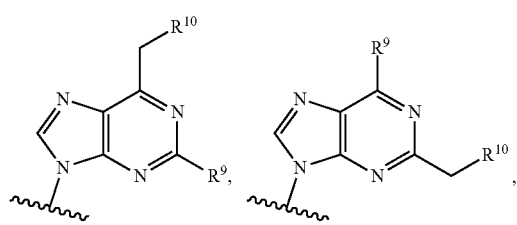

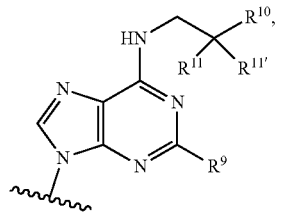

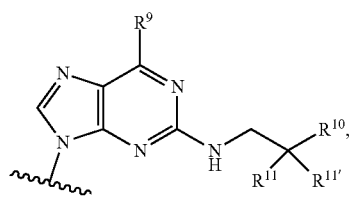

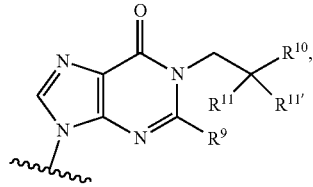

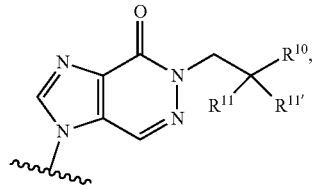

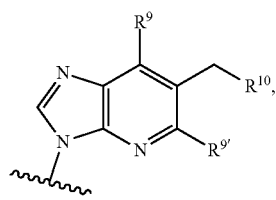

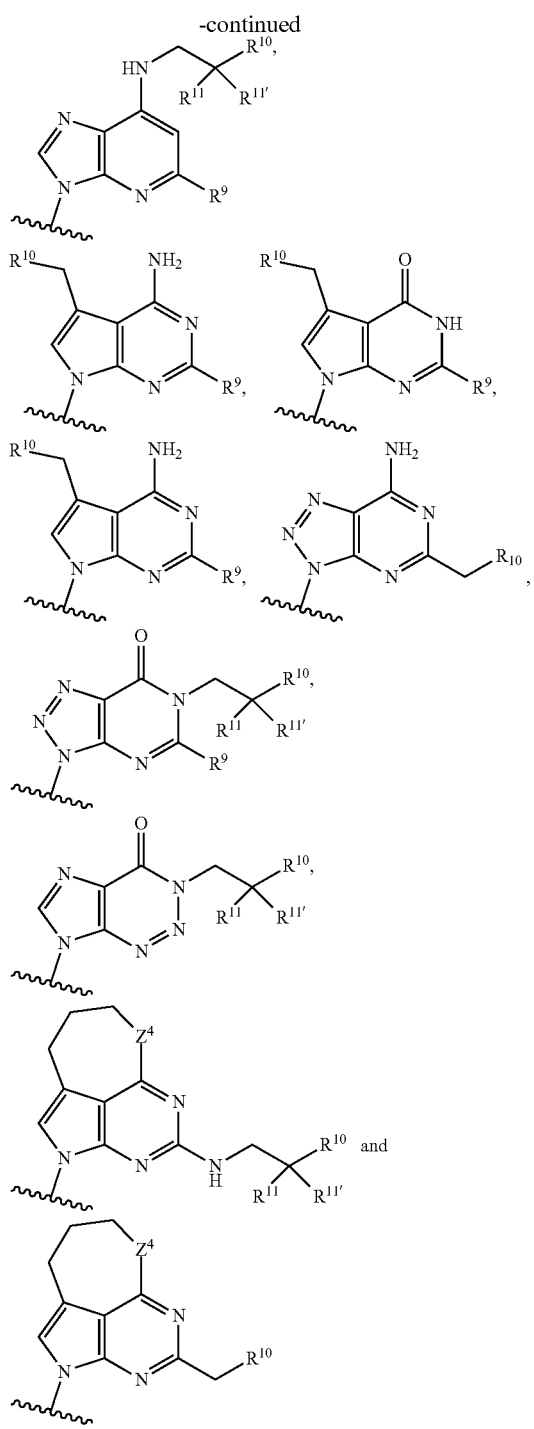

wherein
$R^9$ and $R^{9'}$ each represent a hydrogen atom, a hydroxy group, or —NH$_2$;
$R^{10}$ represents a hydroxy group, —NH$_2$, —NHC(=O)CH$_2$OH, —CH$_2$NHC(=O)CH$_2$OH, —CH$_2$CH$_2$NHC(=O)CH$_2$OH, a hydroxy C1-C3 alkyl group, or an amino C1-C3 alkyl group;
$R^{11}$ and $R^{11'}$ each independently represent a hydrogen atom, a fluorine atom, or a methyl group, or $R^{11}$ and $R^{11'}$ bond together to form cyclopropane; and
$Z^4$ represents —CH$_2$—, —NH—, or an oxygen atom.

14. The antibody-drug conjugate according to claim 1, wherein $L^1$ is a group selected from the group consisting of the following formulas:

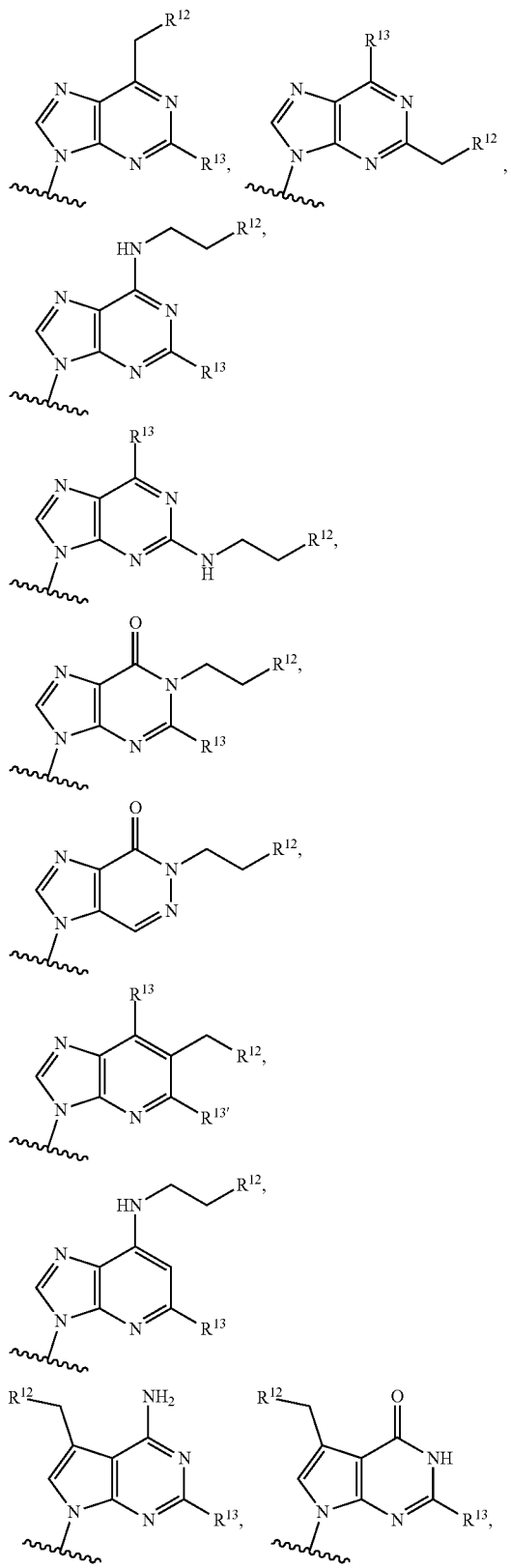

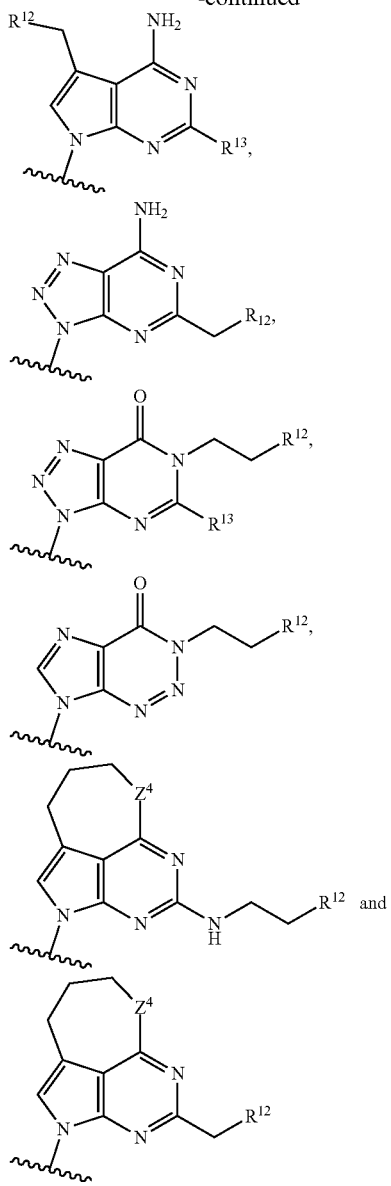

wherein
$R^{13}$ and $R^{13'}$ each independently represent a hydrogen atom, a hydroxy group, or —$NH_2$; and
$R^{12}$ represents a hydroxy group, —$NH_2$, —$CH_2OH$, —$NHC(=O)CH_2OH$, —$CH_2NHC(=O)CH_2OH$, or —$CH_2CH_2NHC(=O)CH_2OH$.

15. The antibody-drug conjugate according to claim 1, wherein $L^1$ is a group selected from the group consisting of the following formulas:

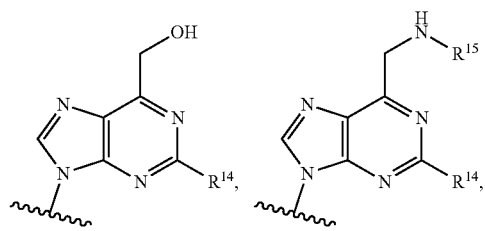

-continued

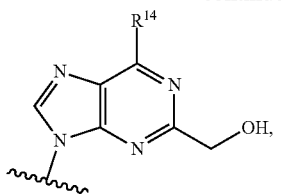
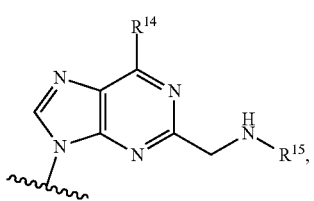
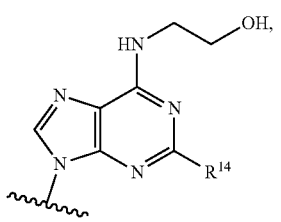
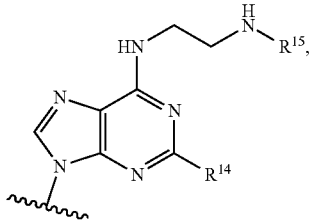
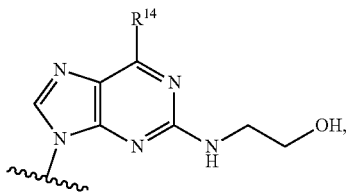
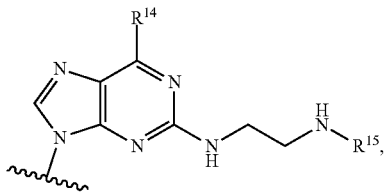
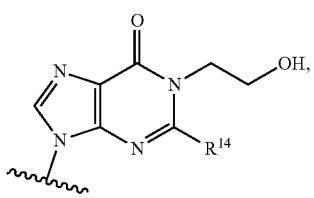
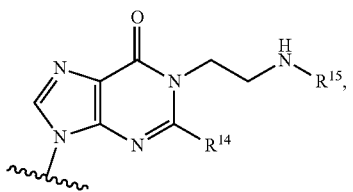

-continued

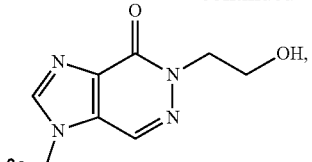
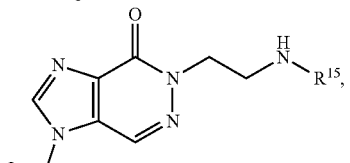
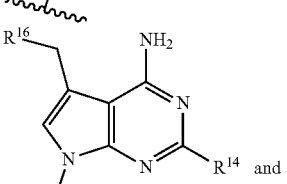
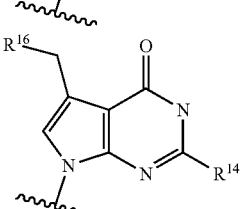

wherein
$R^{14}$ represents a hydrogen atom or —$NH_2$;
$R^{15}$ represents a hydrogen atom or —C(=O)$CH_2$OH; and
$R^{16}$ represents a hydroxy group, —$NH_2$, —$CH_2$OH, —$CH_2CH_2$OH, —$CH_2NH_2$, or —$CH_2CH_2NH_2$.

16. The antibody-drug conjugate according to claim 1, wherein $Q^1$ and $Q^{1'}$ each independently represent a hydroxy group or a thiol group.

17. The antibody-drug conjugate according to claim 1, wherein $Y^1$ and $Y^2$ each represent an oxygen atom.

18. The antibody-drug conjugate according to claim 1, wherein $X^3$ and $X^4$ represent —$CH_2$—O—.

19. The antibody-drug conjugate according to claim 1, wherein $X^5$ and $X^6$ represent —$CH_2$—O—.

20. The antibody-drug conjugate according to claim 1, wherein $R^1$, $R^2$, and $R^3$ are each independently a hydrogen atom, a hydroxy group, or a fluorine atom.

21. The antibody-drug conjugate according to claim 1, wherein D is represented by either one of the following two formulas:

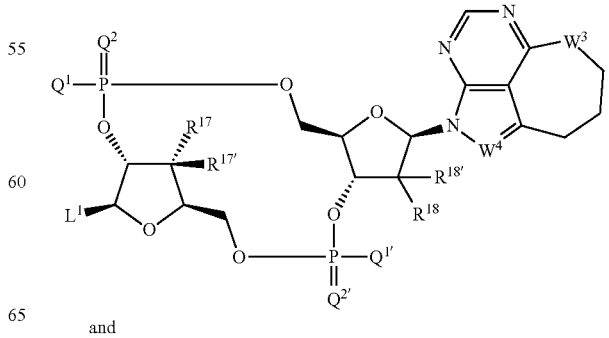

and

761

-continued

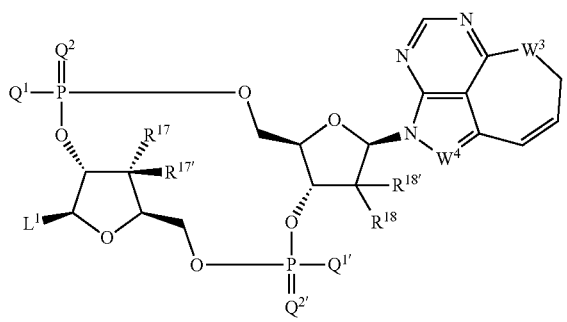

wherein

R[17], R[17'], R[18], and R[18'] each independently represent a hydrogen atom, a halogen atom, a hydroxy group, or —NH$_2$, provided that either R[17] or R[17'] is a hydrogen atom;

W[3] represents —NH—, an oxygen atom, a sulfur atom, or —CH$_2$—; and

W[4] represents —CH= or a nitrogen atom.

22. The antibody-drug conjugate according to claim 21, wherein D is represented by either one of the following two formulas:

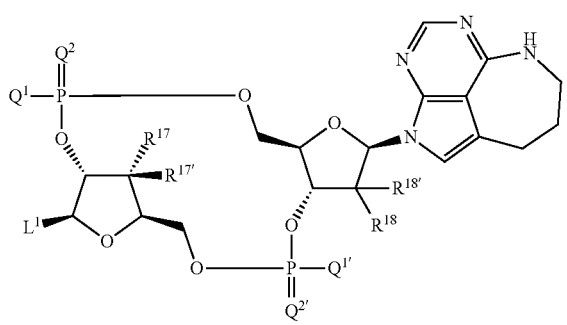

and

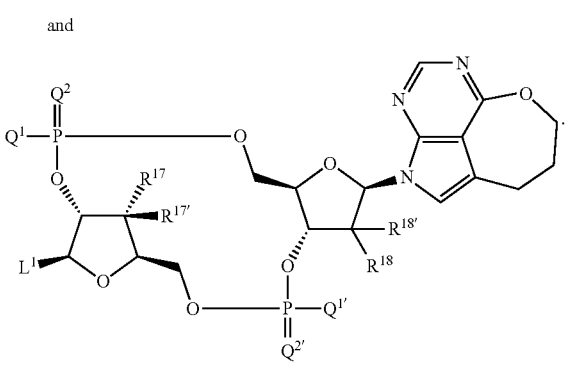

23. The antibody-drug conjugate according to claim 21, wherein D is represented by any one of the following eight formulas:

762

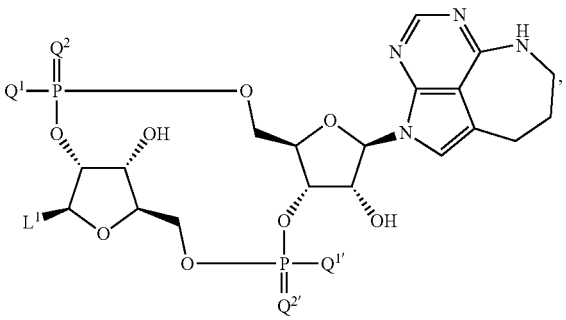

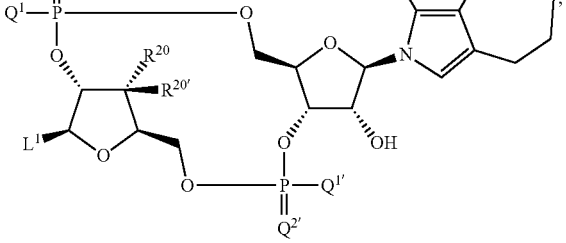

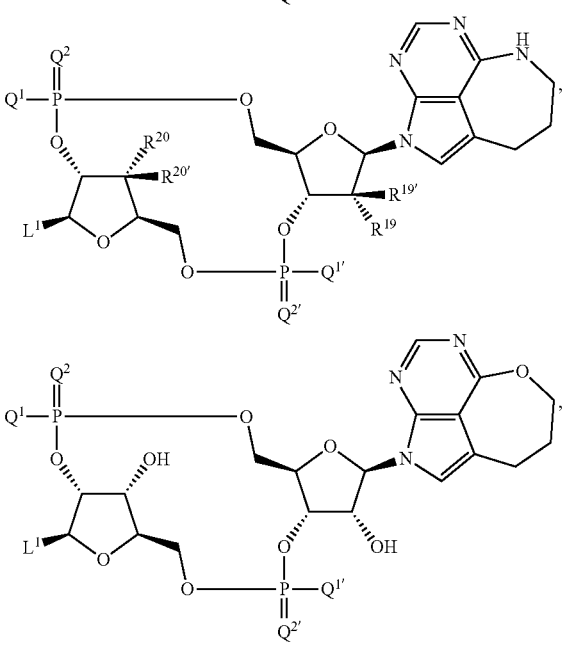

763

-continued

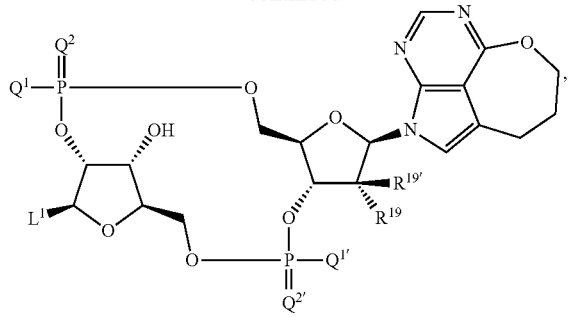

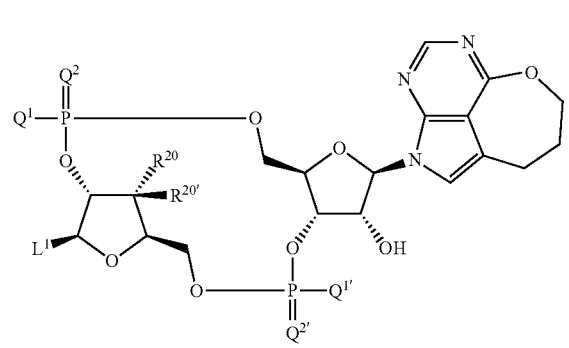

and

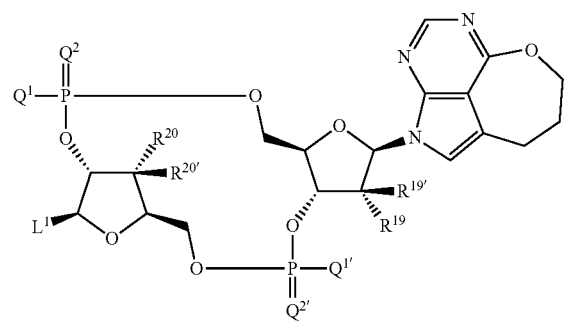

wherein
R$^{19}$, R$^{19'}$, R$^{20}$, and R$^{20'}$ each independently represent a hydrogen atom or a fluorine atom, provided that either R$^{20}$ or R$^{20'}$ is a hydrogen atom.

24. The antibody-drug conjugate according to claim 21, wherein D is represented by any one of the following four formulas:

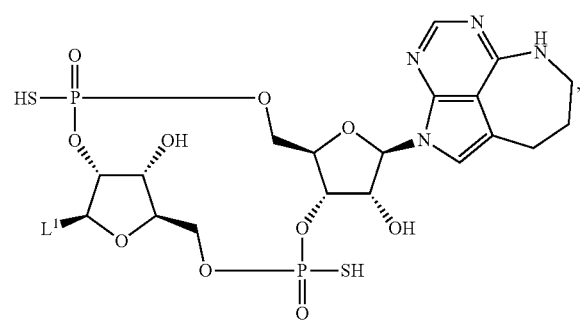

764

-continued

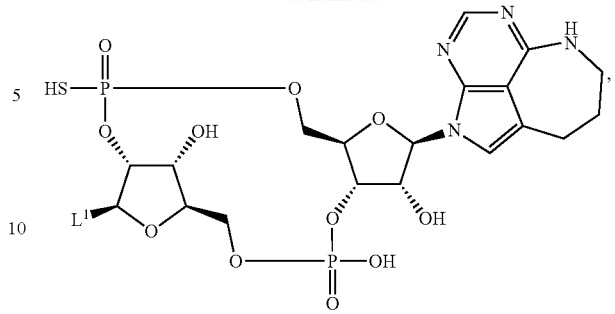

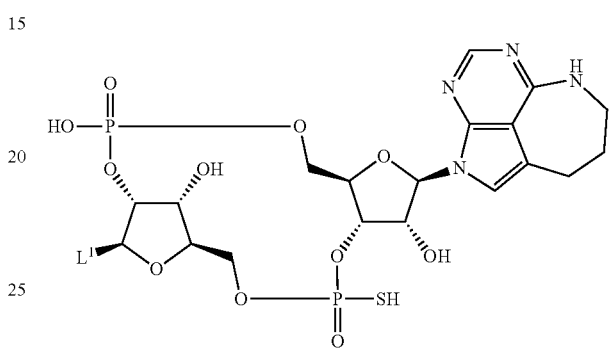

and

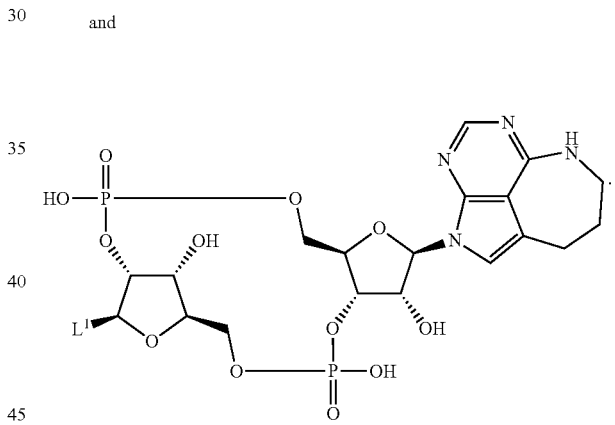

25. The antibody-drug conjugate according to claim 21, wherein D is represented by any one of the following four formulas:

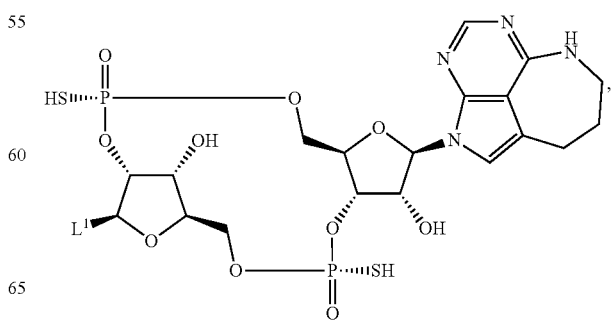

765
-continued

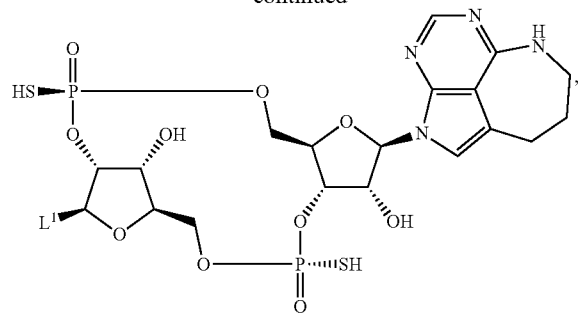

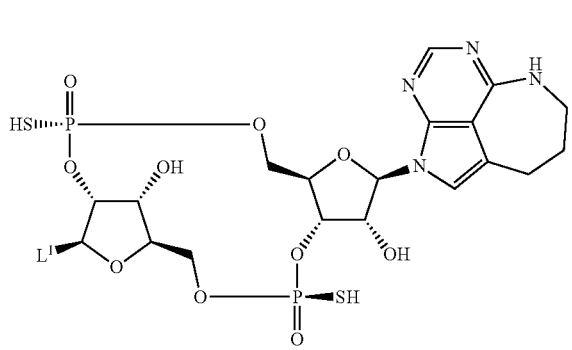

and

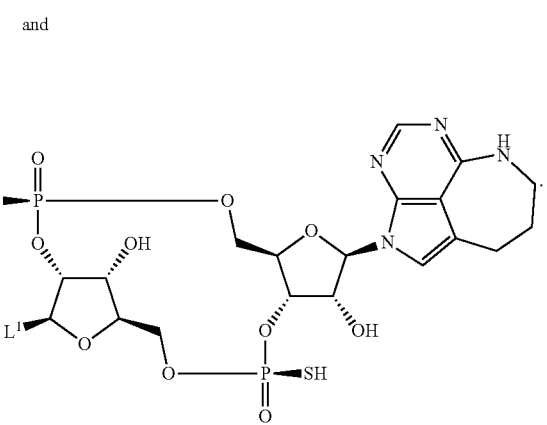

26. The antibody-drug conjugate according to claim 21, wherein D is represented by any one of the following four formulas:

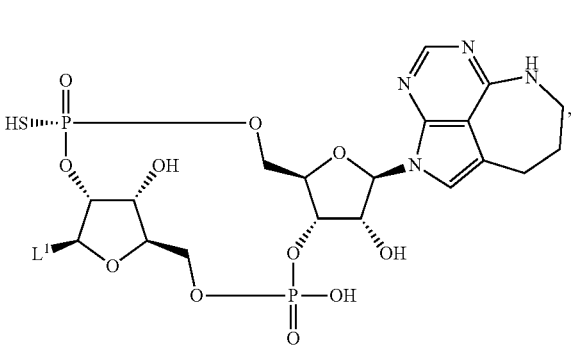

766
-continued

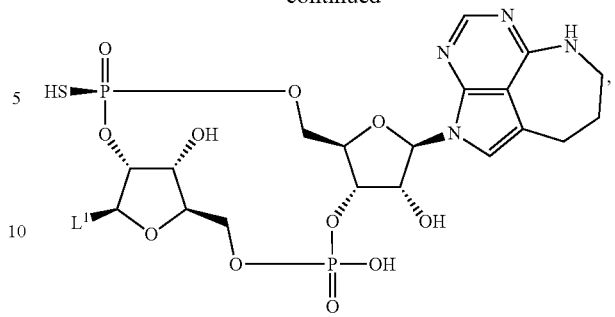

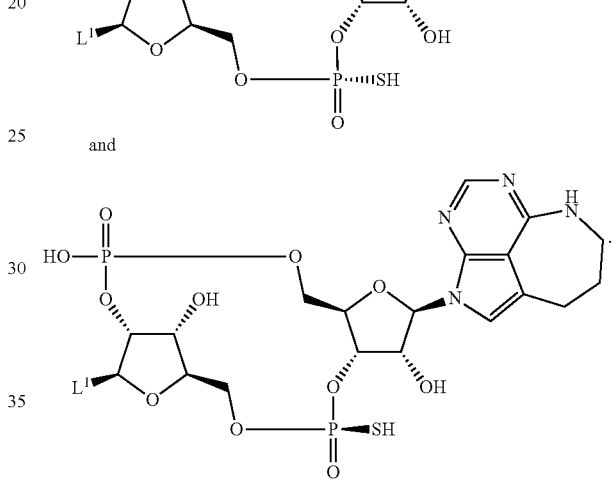

and

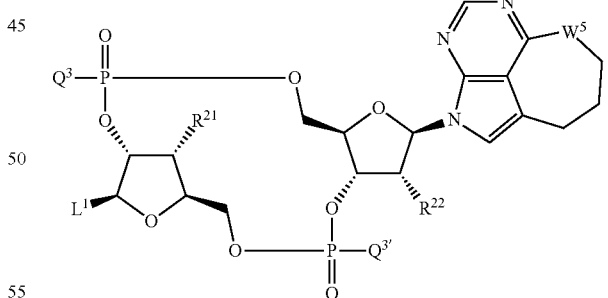

27. The antibody-drug conjugate according to claim 1, wherein D is represented by the following formula:

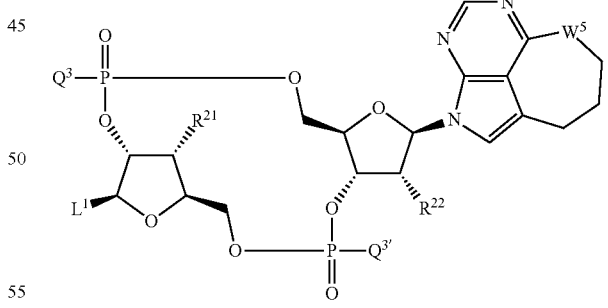

wherein

Q$^3$ and Q$^{3'}$ each independently represent a hydroxy group or a thiol group;

R$^{21}$ and R$^{22}$ each independently represent a hydroxy group or a fluorine atom; and W$^5$ represents —NH— or a sulfur atom.

28. The antibody-drug conjugate according to claim 27, wherein D is represented by either one of the following two formulas:

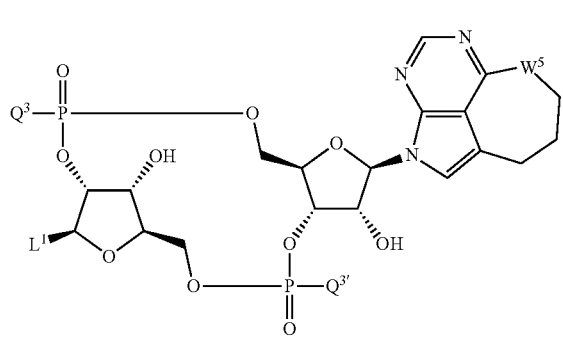

and

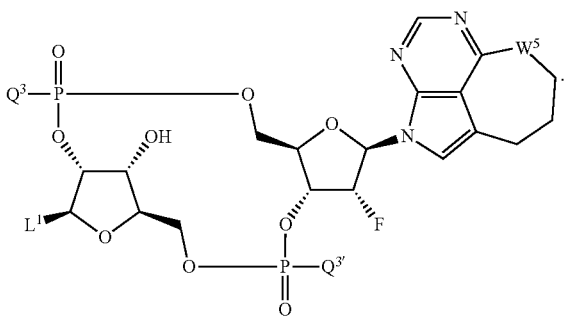

29. The antibody-drug conjugate according to claim 1, wherein $L^1$ is represented by any one of the following four formulas:

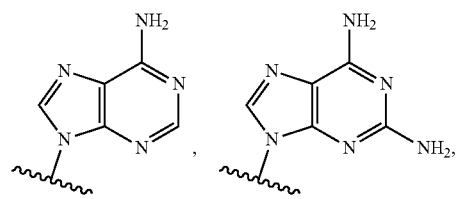

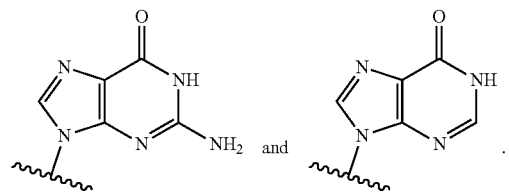

30. The antibody-drug conjugate according to claim 1, wherein $L^1$ is represented by any one of the following four formulas:

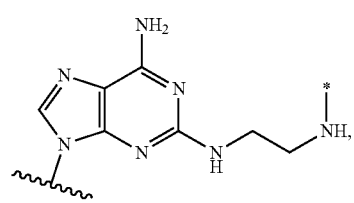

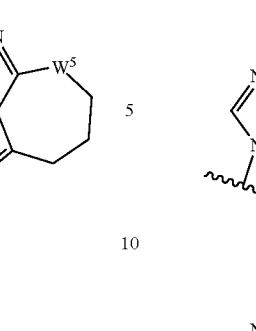

-continued

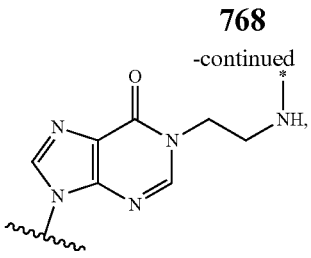

and

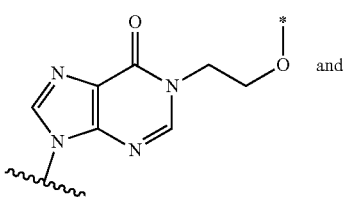

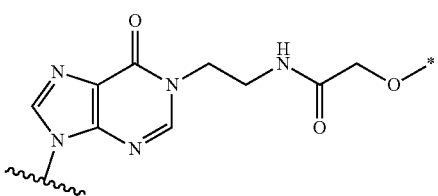

wherein
each asterisk indicates bonding to L.

31. The antibody-drug conjugate according to claim 27, wherein D is represented by any one of the following four formulas:

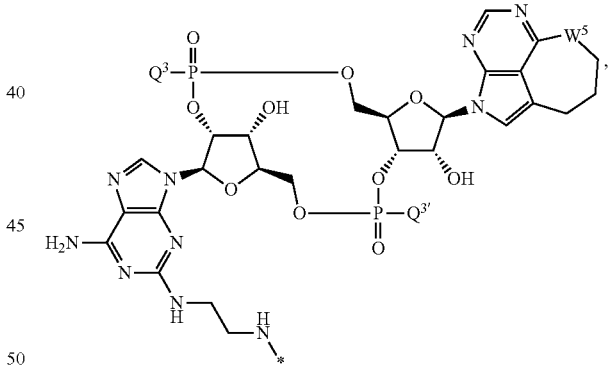

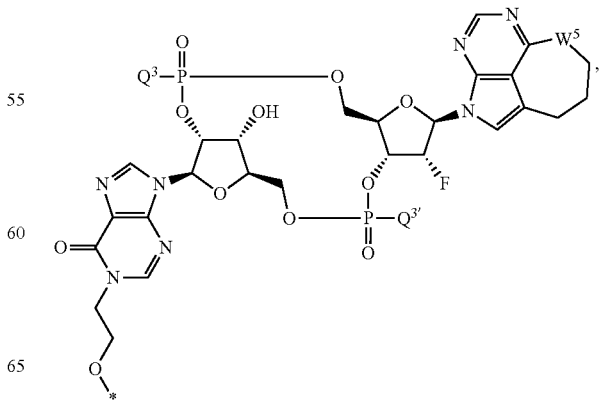

769
-continued
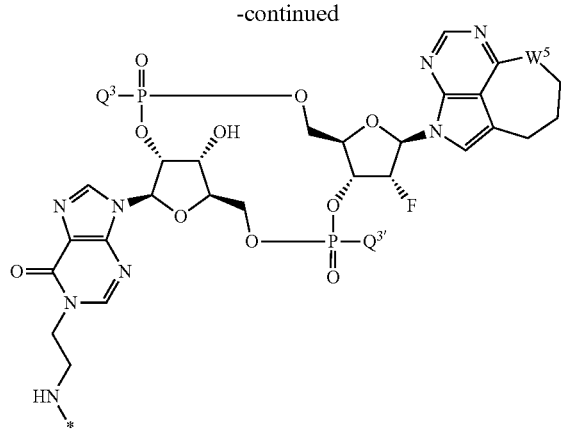
and
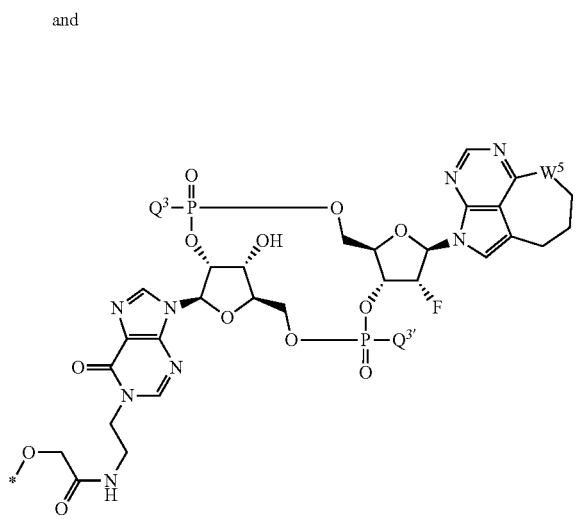
wherein
each asterisk indicates bonding to L.
32. The antibody-drug conjugate according to claim 27, wherein D is represented by any one of the following four formulas:
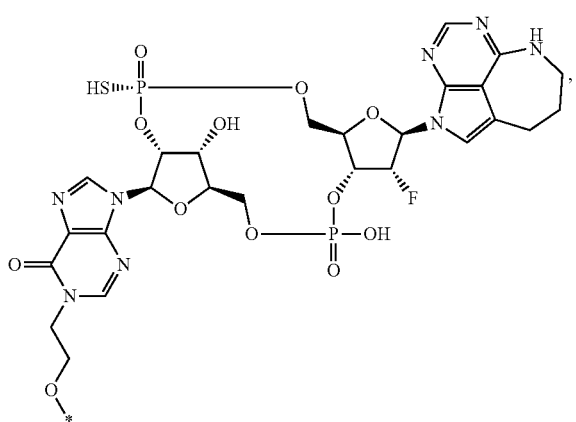
770
-continued
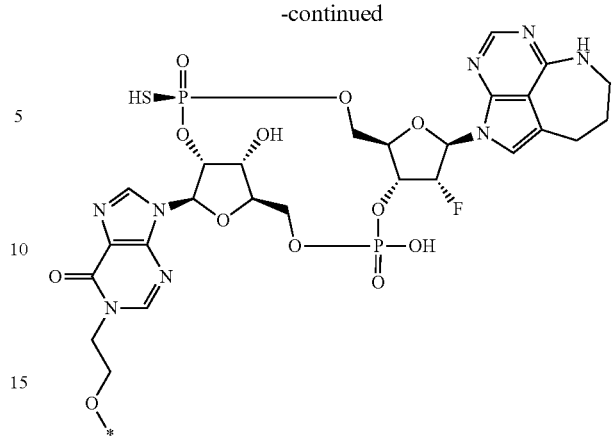
and
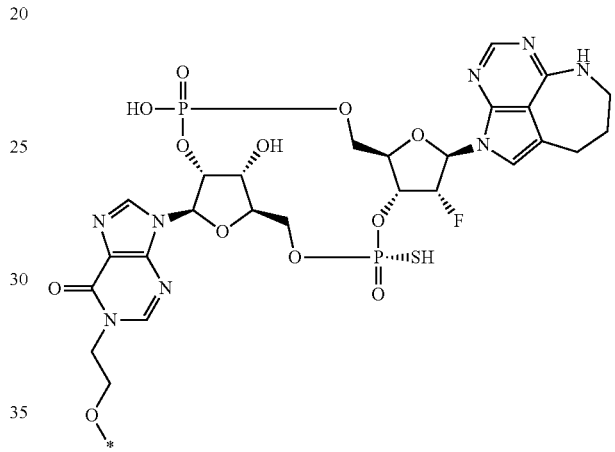
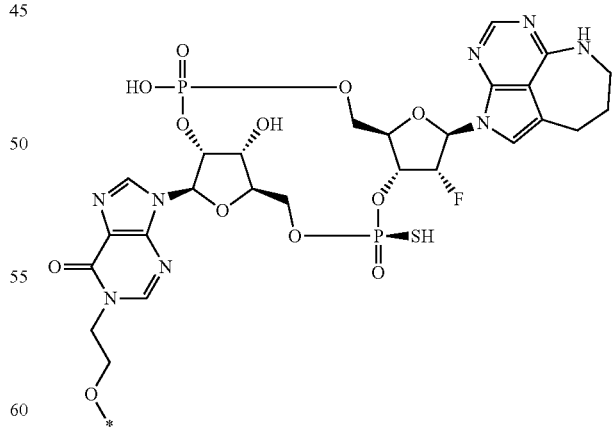
wherein
each asterisk indicates bonding to L.
33. The antibody-drug conjugate according to claim 27, wherein D is represented by any one of the following three formulas:

771
772
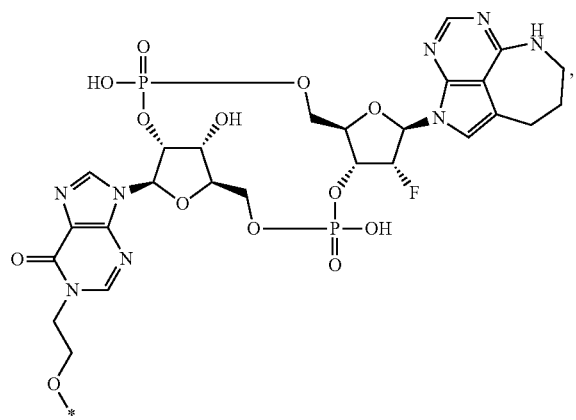
and
wherein
each asterisk indicates bonding to L.
34. The antibody-drug conjugate according to claim 27, wherein D is represented by any one of the following four formulas:

wherein
each asterisk indicates bonding to L.

35. The antibody-drug conjugate according to claim 1, wherein
Lp is a peptide that consists of two to four amino acids cleavable in a target cell.

36. The antibody-drug conjugate according to claim 1, wherein Lc is absent.

37. The antibody-drug conjugate according to claim 1, wherein Lc is —NH—CH$_2$—.

38. The antibody-drug conjugate according to claim 1, wherein Lp represents any one selected from the group consisting of:
-GGVA-, -VA-, -GGFG-, -FG-, -GGPI-, -PI-, -GGVCit-, -VCit-, -GGVK-, -VK-, -GGFCit-, -FCit-, -GGFM-, -FM-, -GGLM-, -LM-, -GGICit-, and -ICit-.

39. The antibody-drug conjugate according to claim 38, wherein Lp is any one of -GGVA-, -VA-, -GGFG-, -FG-, -GGVCit-, -VCit-, -GGFCit-, and -FCit-.

40. The antibody-drug conjugate according to claim 1, wherein Lp is any one of -GGFG-, -GGPI-, -GGVA-, -GGFM-, -GGVCit-, -GGFCit-, -GGICit-, -GGPL-, -GGAQ-, and -GGPP-.

41. The antibody-drug conjugate according to claim 40, wherein Lp is -GGFG- or -GGPI-.

42. The antibody-drug conjugate according to claim 1, wherein La represents any one selected from the group consisting of:
—C(=O)—CH$_2$CH$_2$—C(=O)—,
—C(=O)—CH$_2$CH$_2$—C(=O)—NH—(CH$_2$CH$_2$O)$_3$—CH$_2$—C(=O)—,
—C(=O)—CH$_2$CH$_2$—C(=O)—NH—(CH$_2$CH$_2$O)$_4$—CH$_2$—C(=O)—, and
(CH$_2$)$_5$—C(=O)—.

43. The antibody-drug conjugate according to claim 1, wherein Lb is represented by any one of the following formulas:

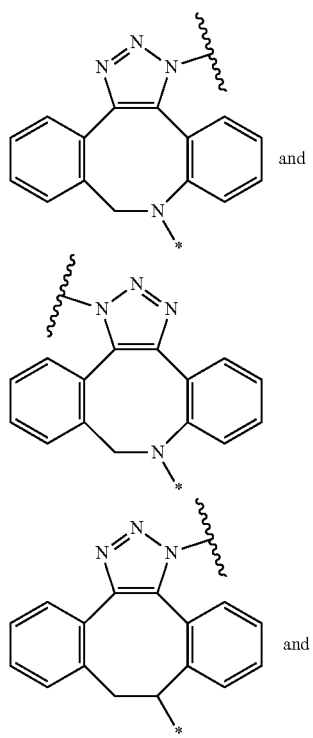

and

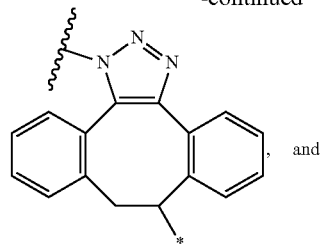

, and

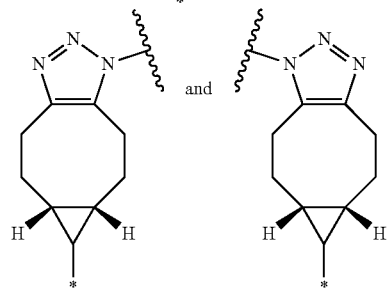

wherein, in the structural formulas for Lb shown above, each asterisk indicates bonding to La, and each wavy line indicates bonding to a glycan or remodeled glycan of Ab.

44. The antibody-drug conjugate according to claim 1, wherein Lb is -(succinimid-3-yl-N)—, wherein -(succinimid-3-yl-N)— represents the following structural formula:

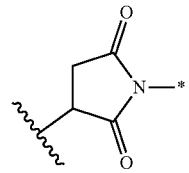 [SMILES: *C1CC(=O)N(*)C1=O]

wherein the asterisk indicates bonding to La, and the wavy line indicates bonding to a side chain of a cysteine residue of the antibody through forming thioether.

45. The antibody-drug conjugate according to claim 1, wherein linker L is represented by -Lb-La-Lp-Lc-*, wherein the asterisk indicates bonding to D;
Lp is -GGFG- or -GGPI-;
La represents —C(=O)—CH$_2$CH$_2$—C(=O)—;
Lb represents the following formula:

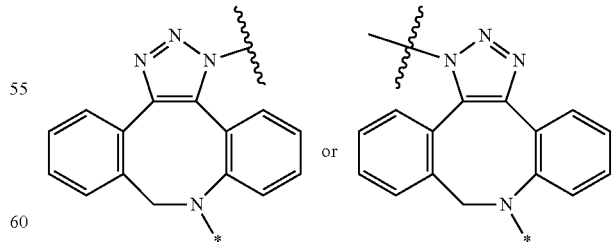

wherein, in the structural formulas for Lb shown above, each asterisk indicates bonding to La, and each wavy line indicates bonding to a glycan or remodeled glycan of Ab; and
Lc represents —NH—CH$_2$—.

46. The antibody-drug conjugate according to claim 1, wherein the average number of conjugated drug molecules per antibody molecule in the antibody-drug conjugate is in the range of 1 to 10.

47. The antibody-drug conjugate according to claim 46, wherein the average number of conjugated drug molecules per antibody molecule in the antibody-drug conjugate is in the range of 1 to 5.

48. The antibody-drug conjugate according to claim 1, wherein the antibody bonds via a glycan bonding to Asn297 of the antibody (N297 glycan) to L.

49. The antibody-drug conjugate according to claim 48, wherein the N297 glycan is a remodeled glycan.

50. The antibody-drug conjugate according to claim 48, wherein the N297 glycan is N297-(Fuc) MSG1 or N297-(Fuc) SG.

51. The antibody-drug conjugate according to claim 1, wherein the antibody or an antigen-binding fragment of the antibody is an anti-HER2 antibody, an anti-HER3 antibody, an anti-DLL3 antibody, an anti-FAP antibody, an anti-CDH11 antibody, an anti-CDH6 antibody, an anti-A33 antibody, an anti-CanAg antibody, an anti-CD19 antibody, an anti-CD20 antibody, an anti-CD22 antibody, an anti-CD30 antibody, an anti-CD33 antibody, an anti-CD56 antibody, an anti-CD98 antibody, an anti-CEA antibody, an anti-Cripto antibody, an anti-EphA2 antibody, an anti-G250 antibody, an anti-MUC1 antibody, an anti-GPNMB antibody, an anti-Integrin antibody, an anti-PSMA antibody, an anti-Tenascin-C antibody, an anti-SLC44A4 antibody, an anti-Mesothelin antibody, an anti-ENPP3 antibody, an anti-CD47 antibody, an anti-GPR20 antibody, or an anti-DR5 antibody or an antigen-binding fragment of the antibody.

52. The antibody-drug conjugate according to claim 51, wherein the antibody or an antigen-binding fragment of the antibody is an anti-HER2 antibody or an antigen-binding fragment of the antibody.

53. The antibody-drug conjugate according to claim 52, wherein the antibody or an antigen-binding fragment of the antibody is any one of the following (i) to (iii):
(i) is an antibody comprising a light chain consisting of an amino acid sequence represented by SEQ ID NO: 1 and a heavy chain consisting of an amino acid sequence represented by SEQ ID NO: 2 or an antigen-binding fragment of the antibody, or an antibody comprising a light chain consisting of an amino acid sequence represented by SEQ ID NO: 1 and a heavy chain consisting of an amino acid sequence represented by SEQ ID NO: 3 or an antigen-binding fragment of the antibody;
(ii) the antibody or an antigen-binding fragment of the antibody as defined in (i) wherein a part of the amino acid residues in the constant region is substituted; and
(iii) a protein produced in host cells by using a gene (a) which is modified by genetical engineering from a gene (b) of the antibody or an antigen-binding fragment of the antibody as defined in (i).

54. The antibody-drug conjugate according to claim 52, wherein the antibody or an antigen-binding fragment of the antibody is any one of the following (i) to (iii):
(i) an antibody comprising a light chain consisting of an amino acid sequence represented by SEQ ID NO: 28 and a heavy chain consisting of an amino acid sequence represented by SEQ ID NO: 29 or an antigen-binding fragment of the antibody, or an antibody comprising a light chain consisting of an amino acid sequence represented by SEQ ID NO: 28 and a heavy chain consisting of an amino acid sequence represented by SEQ ID NO: 30 or an antigen-binding fragment of the antibody;
(ii) the antibody or an antigen-binding fragment of the antibody as defined in (i) wherein a part of the amino acid residues in the constant region is substituted; and
(iii) a protein produced in host cells by using a gene (a) which is modified by genetical engineering from a gene (b) of the antibody or an antigen-binding fragment of the antibody as defined in (i).

55. The antibody-drug conjugate according to claim 51, wherein the antibody or an antigen-binding fragment of the antibody is any one of the following (i) to (iii):
(i) an antibody comprising a light chain consisting of an amino acid sequence represented by SEQ ID NO: 31 and a heavy chain consisting of an amino acid sequence represented by SEQ ID NO: 32 or an antigen-binding fragment of the antibody, an antibody comprising a light chain consisting of an amino acid sequence represented by SEQ ID NO: 33 and a heavy chain consisting of an amino acid sequence represented by SEQ ID NO: 34 or an antigen-binding fragment of the antibody, or an antibody comprising a light chain consisting of an amino acid sequence represented by SEQ ID NO: 35 and a heavy chain consisting of an amino acid sequence represented by SEQ ID NO: 36 or an antigen-binding fragment of the antibody;
(ii) the antibody or an antigen-binding fragment of the antibody as defined in (i) wherein a part of the amino acid residues in the constant region is substituted; and
(iii) a protein produced in host cells by using a gene (a) which is modified by genetical engineering from a gene (b) of the antibody or an antigen-binding fragment of the antibody as defined in (i).

56. A STING agonist comprising the antibody-drug conjugate according to claim 1.

57. A pharmaceutical composition comprising the antibody-drug conjugate according to claim 1.

58. An anti-tumor agent comprising the antibody-drug conjugate according to claim 1.

59. The anti-tumor agent according to claim 58, wherein the tumor is lung cancer, kidney cancer, urothelial cancer, colorectal cancer, prostate cancer, glioblastoma multiforme, ovarian cancer, pancreatic cancer, breast cancer, melanoma, liver cancer, bladder cancer, gastric cancer, esophageal cancer, endometrial cancer, testicular cancer, uterine cervix cancer, placental choriocarcinoma, glioblastoma multiforme, brain tumor, head-and-neck cancer, thyroid cancer, mesothelioma, gastrointestinal stromal tumor (GIST), gallbladder cancer, bile duct cancer, adrenal cancer, squamous cell carcinoma, leukemia, malignant lymphoma, plasmacytoma, myeloma, or sarcoma.

60. The antibody-drug conjugate according to claim 1, wherein the antibody or an antigen-binding fragment of the antibody is any one selected from the group consisting of IgG being IgG1, IgG2, IgG3, or IgG4, IgE, IgM, IgD, IgA being IgA1 or IgA2, and IgY.

61. The antibody-drug conjugate according to claim 60, wherein the antibody or an antigen-binding fragment of the antibody is IgG1.

62. The antibody-drug conjugate according to claim 61, wherein a part of the amino acid residues in the constant region is substituted.

63. The antibody-drug conjugate according to claim 62, wherein the substitution comprises substitution of leucine with alanine at positions 234 and 235 specified by EU Index numbering.

64. The antibody-drug conjugate according to claim 1, wherein the antibody or an antigen-binding fragment of the antibody is a protein produced in host cells by using a gene (a) which is modified by genetical engineering from a gene (b) of the antibody or an antigen-binding fragment of the antibody.

65. The antibody-drug conjugate according to claim 53, wherein the substitution comprises substitution of leucine with alanine at positions 234 and 235 specified by EU Index numbering.

66. The antibody-drug conjugate according to claim 54, wherein the substitution comprises substitution of leucine with alanine at positions 234 and 235 specified by EU Index numbering.

67. The antibody-drug conjugate according to claim 52, wherein one or two amino acids are deleted at the carboxyl terminus of the heavy chain of the antibody or an antigen-binding fragment of the antibody.

68. The antibody-drug conjugate according to claim 45, wherein -La-Lp-Lc-* is —C(=O)—CH₂CH₂—C(=O)-GGFG-NH—CH₂—.

69. The antibody-drug conjugate according to claim 51, wherein $m^1$ is in the range of 3 to 5;

Ab represents an anti-CDH6 antibody, where a glycan of the antibody is remodeled;

Lp is -GGFG-;

La represents —C(=O)—CH₂CH₂—C(=O)—;

Lb represents the following formula:

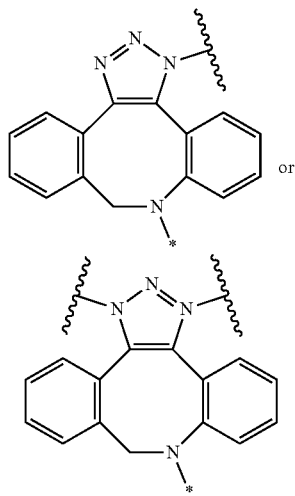

or wherein, in the structural formulas for Lb shown above, each asterisk indicates bonding to La, and each wavy line indicates bonding to a remodeled glycan of Ab; and Lc represents —NH—CH₂—;

Ab bonds via a glycan bonding to Asn297 of the antibody (N297-(Fuc) SG) to L; and D represents a compound represented by the following formula:

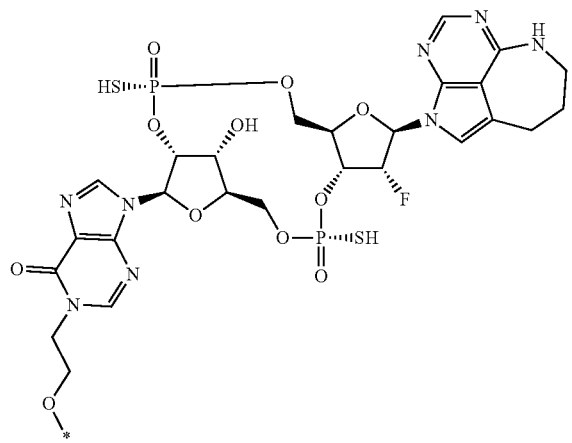 [SMILES: *OCCn1cnc2c(ncn2[C@@H]2O[C@@H]3CO[P@@](=O)(S)O[C@H]4[C@@H](F)[C@H](n5cc6c7c(ncnc75)NCCC6)O[C@@H]4CO[P@@](=O)(S)O[C@@H]2[C@@H]3O)c1=O]

wherein the asterisk indicates bonding to L.

70. The antibody-drug conjugate according to claim 69, wherein a part of the amino acid residues in the constant region of the antibody is substituted.

71. The antibody-drug conjugate according to claim 69, wherein the antibody comprises a light chain consisting of an amino acid sequence represented by SEQ ID NO: 35 and a heavy chain consisting of an amino acid sequence represented by SEQ ID NO: 36, wherein a part of the amino acid residues in the constant region of the antibody is substituted.

72. The antibody-drug conjugate according to claim 71, wherein the antibody is IgG1.

73. The antibody-drug conjugate according to claim 69, wherein one or two amino acids are deleted at the carboxyl terminus of the heavy chain of the antibody.

* * * * *

SEQUENCE LISTING

```
<160> NUMBER OF SEQ ID NOS: 36

<210> SEQ ID NO 1
<211> LENGTH: 214
<212> TYPE: PRT
<213> ORGANISM: Artificial Sequence
<220> FEATURE:
<223> OTHER INFORMATION: Trastuzumab Light Chain

<400> SEQUENCE: 1

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30
```

-continued

```
Val Ala Trp Tyr Gln Gln Lys Pro Gly Lys Ala Pro Lys Leu Leu Ile
         35                  40                  45

Tyr Ser Ala Ser Phe Leu Tyr Ser Gly Val Pro Ser Arg Phe Ser Gly
 50                  55                  60

Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln His Tyr Thr Thr Pro Pro
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
            210

<210> SEQ ID NO 2
<211> LENGTH: 450
<212> TYPE: PRT
<213> ORGANISM: Artificial Sequence
<220> FEATURE:
<223> OTHER INFORMATION: Trastuzumab Heavy Chain

<400> SEQUENCE: 2

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Asn Ile Lys Asp Thr
             20                  25                  30

Tyr Ile His Trp Val Arg Gln Ala Pro Gly Lys Gly Leu Glu Trp Val
         35                  40                  45

Ala Arg Ile Tyr Pro Thr Asn Gly Tyr Thr Arg Tyr Ala Asp Ser Val
 50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175
```

```
Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 3
<211> LENGTH: 450
<212> TYPE: PRT
<213> ORGANISM: Artificial Sequence
<220> FEATURE:
<223> OTHER INFORMATION: Modified HER2 antibody Heavy Chain

<400> SEQUENCE: 3

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80
```

Leu Gln Met Asn Ser Leu Arg Ala Glu Asp Thr Ala Val Tyr Tyr Cys
                 85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
                195                 200                 205

Pro Ser Asn Thr Lys Val Asp Lys Lys Val Glu Pro Lys Ser Cys Asp
            210                 215                 220

Lys Thr His Thr Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
            290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
            370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
                435                 440                 445

Gly Lys
    450

<210> SEQ ID NO 4
<211> LENGTH: 379
<212> TYPE: PRT
<213> ORGANISM: Homo sapiens

<400> SEQUENCE: 4

Met Pro His Ser Ser Leu His Pro Ser Ile Pro Cys Pro Arg Gly His
1               5                   10                  15

Gly Ala Gln Lys Ala Ala Leu Val Leu Leu Ser Ala Cys Leu Val Thr
            20                  25                  30

Leu Trp Gly Leu Gly Glu Pro Pro Glu His Thr Leu Arg Tyr Leu Val
        35                  40                  45

Leu His Leu Ala Ser Leu Gln Leu Gly Leu Leu Asn Gly Val Cys
50                  55                  60

Ser Leu Ala Glu Glu Leu Arg His Ile His Ser Arg Tyr Arg Gly Ser
65                  70                  75                  80

Tyr Trp Arg Thr Val Arg Ala Cys Leu Gly Cys Pro Leu Arg Arg Gly
                85                  90                  95

Ala Leu Leu Leu Leu Ser Ile Tyr Phe Tyr Ser Leu Pro Asn Ala
            100                 105                 110

Val Gly Pro Pro Phe Thr Trp Met Leu Ala Leu Leu Gly Leu Ser Gln
        115                 120                 125

Ala Leu Asn Ile Leu Leu Gly Leu Lys Gly Leu Ala Pro Ala Glu Ile
    130                 135                 140

Ser Ala Val Cys Glu Lys Gly Asn Phe Asn Val Ala His Gly Leu Ala
145                 150                 155                 160

Trp Ser Tyr Tyr Ile Gly Tyr Leu Arg Leu Ile Leu Pro Glu Leu Gln
                165                 170                 175

Ala Arg Ile Arg Thr Tyr Asn Gln His Tyr Asn Asn Leu Leu Arg Gly
            180                 185                 190

Ala Val Ser Gln Arg Leu Tyr Ile Leu Leu Pro Leu Asp Cys Gly Val
        195                 200                 205

Pro Asp Asn Leu Ser Met Ala Asp Pro Asn Ile Arg Phe Leu Asp Lys
    210                 215                 220

Leu Pro Gln Gln Thr Gly Asp Arg Ala Gly Ile Lys Asp Arg Val Tyr
225                 230                 235                 240

Ser Asn Ser Ile Tyr Glu Leu Leu Glu Asn Gly Gln Arg Ala Gly Thr
                245                 250                 255

Cys Val Leu Glu Tyr Ala Thr Pro Leu Gln Thr Leu Phe Ala Met Ser
            260                 265                 270

Gln Tyr Ser Gln Ala Gly Phe Ser Arg Glu Asp Arg Leu Glu Gln Ala
        275                 280                 285

Lys Leu Phe Cys Arg Thr Leu Glu Asp Ile Leu Ala Asp Ala Pro Glu
    290                 295                 300

Ser Gln Asn Asn Cys Arg Leu Ile Ala Tyr Gln Glu Pro Ala Asp Asp
305                 310                 315                 320

Ser Ser Phe Ser Leu Ser Gln Glu Val Leu Arg His Leu Arg Gln Glu
                325                 330                 335

Glu Lys Glu Glu Val Thr Val Gly Ser Leu Lys Thr Ser Ala Val Pro
            340                 345                 350

Ser Thr Ser Thr Met Ser Gln Glu Pro Glu Leu Leu Ile Ser Gly Met
        355                 360                 365

Glu Lys Pro Leu Pro Leu Arg Thr Asp Phe Ser
    370                 375

<210> SEQ ID NO 5
<211> LENGTH: 1140
<212> TYPE: DNA
<213> ORGANISM: Homo sapiens -continued

```
<400> SEQUENCE: 5 atgcccact ccagcctgca tccatccatc ccgtgtccca ggggtcacgg ggcccagaag     60
gcagccttgg ttctgctgag tgcctgcctg gtgacccttt gggggctagg agagccacca    120
gagcacactc tccggtacct ggtgctccac ctagcctccc tgcagctggg actgctgtta    180
aacgggtct gcagcctggc tgaggagctg cgccacatcc actccaggta ccggggcagc    240
tactggagga ctgtgcgggc ctgcctgggc tgcccctcc gccgtggggc cctgttgctg    300
ctgtccatct atttctacta ctccctccca aatgcggtcg gcccgccctt cacttggatg    360
cttgccctcc tgggcctctc gcaggcactg aacatcctcc tgggcctcaa gggcctggcc    420
ccagctgaga tctctgcagt gtgtgaaaaa gggaatttca acgtggccca tgggctggca    480
tggtcatatt acatcggata tctgcggctg atcctgccag agctccaggc ccggattcga    540
acttacaatc agcattacaa caacctgcta cggggtgcag tgagccagcg gctgtatatt    600
ctcctcccat ggactgtgg ggtgcctgat aacctgagta tggctgaccc caacattcgc    660
ttcctggata aactgcccca gcagaccggt gaccatgctg gcatcaagga tcgggtttac    720
agcaacagca tctatgagct tctggagaac gggcagcggg cgggcacctg tgtcctggag    780
tacgccaccc cctttgcagac tttgtttgcc atgtcacaat acagtcaagc tggctttagc    840
cgggaggata ggcttgagca ggccaaactc ttctgccgga cacttgagga catcctggca    900
gatgccctg agtctcagaa caactgccgc tcattgcct accaggaacc tgcagatgac    960
agcagcttct cgctgtccca ggaggttctc cggcacctgc ggcaggagga aaaggaagag   1020
gttactgtgg gcagcttgaa gacctcagcg gtgcccagta cctccacgat gtcccaagag   1080
cctgagctcc tcatcagtgg aatggaaaag ccctccctc tccgcacgga tttctcttag   1140

<210> SEQ ID NO 6
<211> LENGTH: 379
<212> TYPE: PRT
<213> ORGANISM: Homo sapiens

<400> SEQUENCE: 6

Met Pro His Ser Ser Leu His Pro Ser Ile Pro Cys Pro Arg Gly His
1               5                   10                  15

Gly Ala Gln Lys Ala Ala Leu Val Leu Leu Ser Ala Cys Leu Val Thr
            20                  25                  30

Leu Trp Gly Leu Gly Glu Pro Pro Glu His Thr Leu Arg Tyr Leu Val
        35                  40                  45

Leu His Leu Ala Ser Leu Gln Leu Gly Leu Leu Asn Gly Val Cys
    50                  55                  60

Ser Leu Ala Glu Glu Leu Arg His Ile His Ser Arg Tyr Arg Gly Ser
65                  70                  75                  80

Tyr Trp Arg Thr Val Arg Ala Cys Leu Gly Cys Pro Leu Arg Arg Gly
                85                  90                  95

Ala Leu Leu Leu Leu Ser Ile Tyr Phe Tyr Tyr Ser Leu Pro Asn Ala
            100                 105                 110

Val Gly Pro Pro Phe Thr Trp Met Leu Ala Leu Leu Gly Leu Ser Gln
        115                 120                 125

Ala Leu Asn Ile Leu Leu Gly Leu Lys Gly Leu Ala Pro Ala Glu Ile
    130                 135                 140

Ser Ala Val Cys Glu Lys Gly Asn Phe Asn Val Ala His Gly Leu Ala
145                 150                 155                 160

Trp Ser Tyr Tyr Ile Gly Tyr Leu Arg Leu Ile Leu Pro Glu Leu Gln
```

|  |  | 165 |  |  | 170 |  |  | 175 |  |  |  |
|---|---|---|---|---|---|---|---|---|---|---|---|

Ala Arg Ile Arg Thr Tyr Asn Gln His Tyr Asn Asn Leu Leu Arg Gly
                    180                     185                     190

Ala Val Ser Gln Arg Leu Tyr Ile Leu Pro Leu Asp Cys Gly Val
            195                     200                     205

Pro Asp Asn Leu Ser Met Ala Asp Pro Asn Ile Arg Phe Leu Asp Lys
    210                     215                     220

Leu Pro Gln Gln Thr Gly Asp His Ala Gly Ile Lys Asp Arg Val Tyr
225                     230                     235                     240

Ser Asn Ser Ile Tyr Glu Leu Leu Glu Asn Gly Gln Arg Ala Gly Thr
                245                     250                     255

Cys Val Leu Glu Tyr Ala Thr Pro Leu Gln Thr Leu Phe Ala Met Ser
            260                     265                     270

Gln Tyr Ser Gln Ala Gly Phe Ser Arg Glu Asp Arg Leu Glu Gln Ala
        275                     280                     285

Lys Leu Phe Cys Arg Thr Leu Glu Asp Ile Leu Ala Asp Ala Pro Glu
    290                     295                     300

Ser Gln Asn Asn Cys Arg Leu Ile Ala Tyr Gln Glu Pro Ala Asp Asp
305                     310                     315                     320

Ser Ser Phe Ser Leu Ser Gln Glu Val Leu Arg His Leu Arg Gln Glu
                325                     330                     335

Glu Lys Glu Glu Val Thr Val Gly Ser Leu Lys Thr Ser Ala Val Pro
            340                     345                     350

Ser Thr Ser Thr Met Ser Gln Glu Pro Glu Leu Leu Ile Ser Gly Met
        355                     360                     365

Glu Lys Pro Leu Pro Leu Arg Thr Asp Phe Ser
    370                     375

<210> SEQ ID NO 7
<211> LENGTH: 1140
<212> TYPE: DNA
<213> ORGANISM: Homo sapiens

<400> SEQUENCE: 7

| atgcccact ccagcctgca tccatccatc ccgtgtccca ggggtcacgg ggcccagaag | 60 |
|---|---|
| gcagccttgg ttctgctgag tgcctgcctg gtgacccttt ggggctagg agagccacca | 120 |
| gagcacactc tccggtacct ggtgctccac ctagcctccc tgcagctggg actgctgtta | 180 |
| aacggggtct gcagcctggc tgaggagctg cgccacatcc actccaggta ccggggcagc | 240 |
| tactggagga ctgtgcgggc ctgcctgggc tgccccctcc gccgtggggc cctgttgctg | 300 |
| ctgtccatct atttctacta ctccctccca aatgcggtcg gccgcccctt cacttggatg | 360 |
| cttgccctcc tgggcctctc gcaggcactg aacatcctcc tgggcctcaa gggcctggcc | 420 |
| ccagctgaga tctctgcagt gtgtgaaaaa ggaatttca acgtggccca tgggctggca | 480 |
| tggtcatatt acatcggata tctgcggctg atcctgccag agctccaggc ccggattcga | 540 |
| acttacaatc agcattacaa caacctgcta cggggtgcag tgagccagcg gctgtatatt | 600 |
| ctcctcccat tggactgtgg ggtgcctgat aacctgagta tggctgaccc caacattcgc | 660 |
| ttcctggata aactgcccca gcagaccggt gaccgtgctg gcatcaagga tcgggtttac | 720 |
| agcaacagca tctatgagct tctggagaac gggcagcggg cgggcacctg tgtcctggag | 780 |
| tacgccaccc ccttgcagac tttgtttgcc atgtcacaat acagtcaagc tggctttagc | 840 |
| cgggaggata ggcttgagca ggccaaactc ttctgccgga cacttgagga catcctggca | 900 |

-continued

```
gatgcccctg agtctcagaa caactgccgc ctcattgcct accaggaacc tgcagatgac      960
agcagcttct cgctgtccca ggaggttctc cggcacctgc ggcaggagga aaaggaagag     1020
gttactgtgg gcagcttgaa gacctcagcg gtgcccagta cctccacgat gtcccaagag     1080
cctgagctcc tcatcagtgg aatggaaaag cccctccctc tccgcacgga tttctcttag     1140
```

<210> SEQ ID NO 8
<211> LENGTH: 379
<212> TYPE: PRT
<213> ORGANISM: Homo sapiens

<400> SEQUENCE: 8

```
Met Pro His Ser Ser Leu His Pro Ser Ile Pro Cys Pro Arg Gly His
1               5                   10                  15

Gly Ala Gln Lys Ala Ala Leu Val Leu Leu Ser Ala Cys Leu Val Thr
            20                  25                  30

Leu Trp Gly Leu Gly Glu Pro Pro Glu His Thr Leu Arg Tyr Leu Val
        35                  40                  45

Leu His Leu Ala Ser Leu Gln Leu Gly Leu Leu Leu Asn Gly Val Cys
    50                  55                  60

Ser Leu Ala Glu Glu Leu His His Ile His Ser Arg Tyr Arg Gly Ser
65                  70                  75                  80

Tyr Trp Arg Thr Val Arg Ala Cys Leu Gly Cys Pro Leu Arg Arg Gly
                85                  90                  95

Ala Leu Leu Leu Ser Ile Tyr Phe Tyr Ser Leu Pro Asn Ala
            100                 105                 110

Val Gly Pro Pro Phe Thr Trp Met Leu Ala Leu Leu Gly Leu Ser Gln
        115                 120                 125

Ala Leu Asn Ile Leu Leu Gly Leu Lys Gly Leu Ala Pro Ala Glu Ile
    130                 135                 140

Ser Ala Val Cys Glu Lys Gly Asn Phe Asn Val Ala His Gly Leu Ala
145                 150                 155                 160

Trp Ser Tyr Tyr Ile Gly Tyr Leu Arg Leu Ile Leu Pro Glu Leu Gln
                165                 170                 175

Ala Arg Ile Arg Thr Tyr Asn Gln His Tyr Asn Asn Leu Leu Arg Gly
            180                 185                 190

Ala Val Ser Gln Arg Leu Tyr Ile Leu Leu Pro Leu Asp Cys Gly Val
        195                 200                 205

Pro Asp Asn Leu Ser Met Ala Asp Pro Asn Ile Arg Phe Leu Asp Lys
    210                 215                 220

Leu Pro Gln Gln Thr Ala Asp Arg Ala Gly Ile Lys Asp Arg Val Tyr
225                 230                 235                 240

Ser Asn Ser Ile Tyr Glu Leu Leu Glu Asn Gly Gln Arg Ala Gly Thr
                245                 250                 255

Cys Val Leu Glu Tyr Ala Thr Pro Leu Gln Thr Leu Phe Ala Met Ser
            260                 265                 270

Gln Tyr Ser Gln Ala Gly Phe Ser Arg Glu Asp Arg Leu Glu Gln Ala
        275                 280                 285

Lys Leu Phe Cys Gln Thr Leu Glu Asp Ile Leu Ala Asp Ala Pro Glu
    290                 295                 300

Ser Gln Asn Asn Cys Arg Leu Ile Ala Tyr Gln Glu Pro Ala Asp Asp
305                 310                 315                 320

Ser Ser Phe Ser Leu Ser Gln Glu Val Leu Arg His Leu Arg Gln Glu
                325                 330                 335
```

```
Glu Lys Glu Glu Val Thr Val Gly Ser Leu Lys Thr Ser Ala Val Pro
            340                 345                 350

Ser Thr Ser Thr Met Ser Gln Glu Pro Glu Leu Leu Ile Ser Gly Met
        355                 360                 365

Glu Lys Pro Leu Pro Leu Arg Thr Asp Phe Ser
    370                 375

<210> SEQ ID NO 9
<211> LENGTH: 1140
<212> TYPE: DNA
<213> ORGANISM: Homo sapiens

<400> SEQUENCE: 9 atgcccact ccagcctgca tccatccatc ccgtgtccca ggggtcacgg ggcccagaag     60
gcagccttgg ttctgctgag tgcctgcctg gtgacccttt gggggctagg agagccacca    120
gagcacactc tccggtacct ggtgctccac ctagcctccc tgcagctggg actgctgtta    180
aacgggtct gcagcctggc tgaggagctg caccacatcc actccaggta ccggggcagc    240
tactggagga ctgtgcgggc ctgcctgggc tgccccctcc gccgtggggc cctgttgctg    300
ctgtccatct atttctacta ctccctccca aatgcggtcg gcccgccctt cacttggatg    360
cttgccctcc tgggcctctc gcaggcactg aacatcctcc tgggcctcaa gggcctggcc    420
ccagctgaga tctctgcagt gtgtgaaaaa gggaatttca acgtggccca tgggctggca    480
tggtcatatt acatcggata tctgcggctg atcctgccag agctccaggc ccggattcga    540
acttacaatc agcattacaa caacctgcta cggggtgcag tgagccagcg gctgtatatt    600
ctcctcccat tggactgtgg ggtgcctgat aacctgagta tggctgaccc caacattcgc    660
ttcctggata aactgcccca gcagaccgct gaccgtgctg gcatcaagga tcgggtttac    720
agcaacagca tctatgagct tctggagaac gggcagcggg cgggcacctg tgtcctggag    780
tacgccaccc ccttgcagac tttgtttgcc atgtcacaat acagtcaagc tggctttagc    840
cgggaggata ggcttgagca ggccaaactc ttctgccaga cacttgagga catcctggca    900
gatgcccctg agtctcagaa caactgccgc ctcattgcct accaggaacc tgcagatgac    960
agcagcttct cgctgtccca ggaggttctc cggcacctgc ggcaggagga aaaggaagag   1020
gttactgtgg gcagcttgaa gacctcagcg gtgcccagta cctccacgat gtcccaagag   1080
cctgagctcc tcatcagtgg aatggaaaag cccctccctc tccgcacgga tttctcttag   1140

<210> SEQ ID NO 10
<211> LENGTH: 378
<212> TYPE: PRT
<213> ORGANISM: Mus musculus

<400> SEQUENCE: 10

Met Pro Tyr Ser Asn Leu His Pro Ala Ile Pro Arg Pro Arg Gly His
1               5                   10                  15

Arg Ser Lys Tyr Val Ala Leu Ile Phe Leu Val Ala Ser Leu Met Ile
            20                  25                  30

Leu Trp Val Ala Lys Asp Pro Pro Asn His Thr Leu Lys Tyr Leu Ala
        35                  40                  45

Leu His Leu Ala Ser His Glu Leu Gly Leu Leu Lys Asn Leu Cys
    50                  55                  60

Cys Leu Ala Glu Glu Leu Cys His Val Gln Ser Arg Tyr Gln Gly Ser
65                  70                  75                  80

Tyr Trp Lys Ala Val Arg Ala Cys Leu Gly Cys Pro Ile His Cys Met
```

```
                      85                  90                  95
Ala Met Ile Leu Leu Ser Ser Tyr Phe Tyr Phe Leu Gln Asn Thr Ala
                100                 105                 110

Asp Ile Tyr Leu Ser Trp Met Phe Gly Leu Leu Val Leu Tyr Lys Ser
            115                 120                 125

Leu Ser Met Leu Leu Gly Leu Gln Ser Leu Thr Pro Ala Glu Val Ser
        130                 135                 140

Ala Val Cys Glu Glu Lys Lys Leu Asn Val Ala His Gly Leu Ala Trp
145                 150                 155                 160

Ser Tyr Tyr Ile Gly Tyr Leu Arg Leu Ile Leu Pro Gly Leu Gln Ala
                165                 170                 175

Arg Ile Arg Met Phe Asn Gln Leu His Asn Asn Met Leu Ser Gly Ala
            180                 185                 190

Gly Ser Arg Arg Leu Tyr Ile Leu Phe Pro Leu Asp Cys Gly Val Pro
        195                 200                 205

Asp Asn Leu Ser Val Val Asp Pro Asn Ile Arg Phe Arg Asp Met Leu
    210                 215                 220

Pro Gln Gln Asn Ile Asp Arg Ala Gly Ile Lys Asn Arg Val Tyr Ser
225                 230                 235                 240

Asn Ser Val Tyr Glu Ile Leu Glu Asn Gly Gln Pro Ala Gly Val Cys
                245                 250                 255

Ile Leu Glu Tyr Ala Thr Pro Leu Gln Thr Leu Phe Ala Met Ser Gln
            260                 265                 270

Asp Ala Lys Ala Gly Phe Ser Arg Glu Asp Arg Leu Glu Gln Ala Lys
        275                 280                 285

Leu Phe Cys Arg Thr Leu Glu Glu Ile Leu Glu Asp Val Pro Glu Ser
    290                 295                 300

Arg Asn Asn Cys Arg Leu Ile Val Tyr Gln Glu Pro Thr Asp Gly Asn
305                 310                 315                 320

Ser Phe Ser Leu Ser Gln Glu Val Leu Arg His Ile Arg Gln Glu Glu
                325                 330                 335

Lys Glu Glu Val Thr Met Asn Ala Pro Met Thr Ser Val Ala Pro Pro
            340                 345                 350

Pro Ser Val Leu Ser Gln Glu Pro Arg Leu Leu Ile Ser Gly Met Asp
        355                 360                 365

Gln Pro Leu Pro Leu Arg Thr Asp Leu Ile
    370                 375

<210> SEQ ID NO 11
<211> LENGTH: 1137
<212> TYPE: DNA
<213> ORGANISM: Mus musculus

<400> SEQUENCE: 11
atgccatact ccaacctgca tccagccatc ccacggccca gaggtcaccg ctccaaatat     60
gtagccctca tctttctggt ggccagcctg atgatccttt gggtggcaaa ggatccacca    120
aatcacactc tgaagtacct agcacttcac ctagcctcgc acgaacttgg actactgttg    180
aaaaacctct gctgtctggc tgaagagctg tgccatgtcc agtccaggta ccagggcagc    240
tactggaagg ctgtgcgcgc tgcctgggga tgccccatcc actgtatggc tatgattcta    300
ctatcgtctt atttctattt cctccaaaac actgctgaca tatacctcag ttggatgttt    360
ggccttctgg tcctctataa gtccctaagc atgctcctgg ccttcagag cttgactcca    420 gcggaagtct ctgcagtctg tgaagaaaag aagttaaatg ttgcccacgg gctggcctgg    480
```

-continued

```
tcatactaca ttgggtactt gcggttgatc ttaccagggc tccaggcccg gatccgaatg    540
ttcaatcagc tacataacaa catgctcagt ggtgcaggga gccgaagact gtacatcctc    600
tttccattgg actgtggggt gcctgacaac ctgagtgtag ttgacccaa cattcgattc     660 cgagatatgc tgccccagca aaacatcgac cgtgctggca tcaagaatcg ggtttattcc    720
aacagcgtct acgagattct ggagaacgga cagccagcag gcgtctgtat cctggagtac    780
gccaccccct tgcagaccct gtttgccatg tcacaggatg ccaaagctgg cttcagtcgg    840
gaggatcggc ttgagcaggc taaactcttc tgccggacac ttgaggaaat cctggaagat    900
gtccccgagt ctcgaaataa ctgccgcctc attgtctacc aagaaccac agacggaaac     960 agtttctcac tgtctcagga ggtgctccgg cacattcgtc aggaagaaaa ggaggaggtt    1020
accatgaatg ccccccatgac ctcagtggca cctcctcct ccgtactgtc ccaagagcca    1080
agactcctca tcagtggtat ggatcagcct ctcccactcc gcactgacct catctga       1137
```

```
<210> SEQ ID NO 12
<211> LENGTH: 27
<212> TYPE: DNA
<213> ORGANISM: Artificial Sequence
<220> FEATURE:
<223> OTHER INFORMATION: primer

<400> SEQUENCE: 12
cgtgctggca tcaaggatcg ggtttac                                         27

<210> SEQ ID NO 13
<211> LENGTH: 27
<212> TYPE: DNA
<213> ORGANISM: Artificial Sequence
<220> FEATURE:
<223> OTHER INFORMATION: primer

<400> SEQUENCE: 13
gtcaccggtc tgctggggca gtttatc                                         27

<210> SEQ ID NO 14
<211> LENGTH: 33
<212> TYPE: DNA
<213> ORGANISM: Artificial Sequence
<220> FEATURE:
<223> OTHER INFORMATION: primer

<400> SEQUENCE: 14
gctgaccgtg ctggcatcaa ggatcgggtt tac                                  33

<210> SEQ ID NO 15
<211> LENGTH: 25
<212> TYPE: DNA
<213> ORGANISM: Artificial Sequence
<220> FEATURE:
<223> OTHER INFORMATION: primer

<400> SEQUENCE: 15
ggtctgctgg ggcagtttat ccagg                                           25

<210> SEQ ID NO 16
<211> LENGTH: 24
<212> TYPE: DNA
<213> ORGANISM: Artificial Sequence
<220> FEATURE:
<223> OTHER INFORMATION: primer
```

<400> SEQUENCE: 16
caccacatcc actccaggta ccgg                                          24

<210> SEQ ID NO 17
<211> LENGTH: 24
<212> TYPE: DNA
<213> ORGANISM: Artificial Sequence
<220> FEATURE:
<223> OTHER INFORMATION: primer

<400> SEQUENCE: 17
cagctcctca gccaggctgc agac                                          24

<210> SEQ ID NO 18
<211> LENGTH: 25
<212> TYPE: DNA
<213> ORGANISM: Artificial Sequence
<220> FEATURE:
<223> OTHER INFORMATION: primer

<400> SEQUENCE: 18
cagacacttg aggacatcct ggcag                                         25

<210> SEQ ID NO 19
<211> LENGTH: 23
<212> TYPE: DNA
<213> ORGANISM: Artificial Sequence
<220> FEATURE:
<223> OTHER INFORMATION: primer

<400> SEQUENCE: 19
gcagaagagt ttggcctgct caa                                           23

<210> SEQ ID NO 20
<211> LENGTH: 39
<212> TYPE: DNA
<213> ORGANISM: Artificial Sequence
<220> FEATURE:
<223> OTHER INFORMATION: primer

<400> SEQUENCE: 20
acctgtattt tcagggcctg gccccagctg agatctctg                          39

<210> SEQ ID NO 21
<211> LENGTH: 44
<212> TYPE: DNA
<213> ORGANISM: Artificial Sequence
<220> FEATURE:
<223> OTHER INFORMATION: primer

<400> SEQUENCE: 21
cagaattcgc aagcttttaa gtaacctctt cctttcctc ctgc                     44

<210> SEQ ID NO 22
<211> LENGTH: 243
<212> TYPE: PRT
<213> ORGANISM: Artificial Sequence
<220> FEATURE:
<223> OTHER INFORMATION: HisAviTEV-hSTING (139-342) human WT

<400> SEQUENCE: 22

Met Gly Ser Ser His His His His His His Ser Ser Gly Ser Gly Leu
1               5                   10                  15

Asn Asp Ile Phe Glu Ala Gln Lys Ile Glu Trp His Glu Gly Gly Ser
            20                  25                  30

-continued

```
Glu Asn Leu Tyr Phe Gln Gly Leu Ala Pro Ala Glu Ile Ser Ala Val
             35                  40                  45

Cys Glu Lys Gly Asn Phe Asn Val Ala His Gly Leu Ala Trp Ser Tyr
 50                  55                  60

Tyr Ile Gly Tyr Leu Arg Leu Ile Leu Pro Glu Leu Gln Ala Arg Ile
 65                  70                  75                  80

Arg Thr Tyr Asn Gln His Tyr Asn Asn Leu Leu Arg Gly Ala Val Ser
                 85                  90                  95

Gln Arg Leu Tyr Ile Leu Leu Pro Leu Asp Cys Gly Val Pro Asp Asn
                100                 105                 110

Leu Ser Met Ala Asp Pro Asn Ile Arg Phe Leu Asp Lys Leu Pro Gln
            115                 120                 125

Gln Thr Gly Asp Arg Ala Gly Ile Lys Asp Arg Val Tyr Ser Asn Ser
        130                 135                 140

Ile Tyr Glu Leu Leu Glu Asn Gly Gln Arg Ala Gly Thr Cys Val Leu
145                 150                 155                 160

Glu Tyr Ala Thr Pro Leu Gln Thr Leu Phe Ala Met Ser Gln Tyr Ser
                165                 170                 175

Gln Ala Gly Phe Ser Arg Glu Asp Arg Leu Glu Gln Ala Lys Leu Phe
            180                 185                 190

Cys Arg Thr Leu Glu Asp Ile Leu Ala Asp Ala Pro Glu Ser Gln Asn
        195                 200                 205

Asn Cys Arg Leu Ile Ala Tyr Gln Glu Pro Ala Asp Asp Ser Ser Phe
    210                 215                 220

Ser Leu Ser Gln Glu Val Leu Arg His Leu Arg Gln Glu Glu Lys Glu
225                 230                 235                 240

Glu Val Thr

<210> SEQ ID NO 23
<211> LENGTH: 243
<212> TYPE: PRT
<213> ORGANISM: Artificial Sequence
<220> FEATURE:
<223> OTHER INFORMATION: HisAviTEV-hSTING (139-342) human REF mutant

<400> SEQUENCE: 23

Met Gly Ser Ser His His His His His His Ser Ser Gly Ser Gly Leu
 1               5                  10                  15

Asn Asp Ile Phe Glu Ala Gln Lys Ile Glu Trp His Glu Gly Gly Ser
             20                  25                  30

Glu Asn Leu Tyr Phe Gln Gly Leu Ala Pro Ala Glu Ile Ser Ala Val
             35                  40                  45

Cys Glu Lys Gly Asn Phe Asn Val Ala His Gly Leu Ala Trp Ser Tyr
 50                  55                  60

Tyr Ile Gly Tyr Leu Arg Leu Ile Leu Pro Glu Leu Gln Ala Arg Ile
 65                  70                  75                  80

Arg Thr Tyr Asn Gln His Tyr Asn Asn Leu Leu Arg Gly Ala Val Ser
                 85                  90                  95

Gln Arg Leu Tyr Ile Leu Leu Pro Leu Asp Cys Gly Val Pro Asp Asn
                100                 105                 110

Leu Ser Met Ala Asp Pro Asn Ile Arg Phe Leu Asp Lys Leu Pro Gln
            115                 120                 125

Gln Thr Gly Asp His Ala Gly Ile Lys Asp Arg Val Tyr Ser Asn Ser
        130                 135                 140
```

```
Ile Tyr Glu Leu Leu Glu Asn Gly Gln Arg Ala Gly Thr Cys Val Leu
145                 150                 155                 160

Glu Tyr Ala Thr Pro Leu Gln Thr Leu Phe Ala Met Ser Gln Tyr Ser
                165                 170                 175

Gln Ala Gly Phe Ser Arg Glu Asp Arg Leu Glu Gln Ala Lys Leu Phe
            180                 185                 190

Cys Arg Thr Leu Glu Asp Ile Leu Ala Asp Ala Pro Glu Ser Gln Asn
        195                 200                 205

Asn Cys Arg Leu Ile Ala Tyr Gln Glu Pro Ala Asp Asp Ser Ser Phe
        210                 215                 220

Ser Leu Ser Gln Glu Val Leu Arg His Leu Arg Gln Glu Glu Lys Glu
225                 230                 235                 240

Glu Val Thr

<210> SEQ ID NO 24
<211> LENGTH: 243
<212> TYPE: PRT
<213> ORGANISM: Artificial Sequence
<220> FEATURE:
<223> OTHER INFORMATION: HisAviTEV-hSTING (139-342) human AQ mutant

<400> SEQUENCE: 24

Met Gly Ser Ser His His His His His His Ser Ser Gly Ser Gly Leu
1               5                   10                  15

Asn Asp Ile Phe Glu Ala Gln Lys Ile Glu Trp His Glu Gly Gly Ser
                20                  25                  30

Glu Asn Leu Tyr Phe Gln Gly Leu Ala Pro Ala Glu Ile Ser Ala Val
            35                  40                  45

Cys Glu Lys Gly Asn Phe Asn Val Ala His Gly Leu Ala Trp Ser Tyr
        50                  55                  60

Tyr Ile Gly Tyr Leu Arg Leu Ile Leu Pro Glu Leu Gln Ala Arg Ile
65                  70                  75                  80

Arg Thr Tyr Asn Gln His Tyr Asn Asn Leu Leu Arg Gly Ala Val Ser
                85                  90                  95

Gln Arg Leu Tyr Ile Leu Leu Pro Leu Asp Cys Gly Val Pro Asp Asn
            100                 105                 110

Leu Ser Met Ala Asp Pro Asn Ile Arg Phe Leu Asp Lys Leu Pro Gln
        115                 120                 125

Gln Thr Ala Asp Arg Ala Gly Ile Lys Asp Arg Val Tyr Ser Asn Ser
    130                 135                 140

Ile Tyr Glu Leu Leu Glu Asn Gly Gln Arg Ala Gly Thr Cys Val Leu
145                 150                 155                 160

Glu Tyr Ala Thr Pro Leu Gln Thr Leu Phe Ala Met Ser Gln Tyr Ser
                165                 170                 175

Gln Ala Gly Phe Ser Arg Glu Asp Arg Leu Glu Gln Ala Lys Leu Phe
            180                 185                 190

Cys Gln Thr Leu Glu Asp Ile Leu Ala Asp Ala Pro Glu Ser Gln Asn
        195                 200                 205

Asn Cys Arg Leu Ile Ala Tyr Gln Glu Pro Ala Asp Asp Ser Ser Phe
        210                 215                 220

Ser Leu Ser Gln Glu Val Leu Arg His Leu Arg Gln Glu Glu Lys Glu
225                 230                 235                 240

Glu Val Thr

<210> SEQ ID NO 25
```

```
<211> LENGTH: 243
<212> TYPE: PRT
<213> ORGANISM: Artificial Sequence
<220> FEATURE:
<223> OTHER INFORMATION: HisAviTEV-hSTING (139-342) mouse WT

<400> SEQUENCE: 25

Met Gly Ser Ser His His His His Ser Ser Gly Ser Gly Leu
1               5                   10                  15

Asn Asp Ile Phe Glu Ala Gln Lys Ile Glu Trp His Glu Gly Gly Ser
            20                  25                  30

Glu Asn Leu Tyr Phe Gln Gly Leu Thr Pro Ala Glu Val Ser Ala Val
        35                  40                  45

Cys Glu Glu Lys Lys Leu Asn Val Ala His Gly Leu Ala Trp Ser Tyr
50                  55                  60

Tyr Ile Gly Tyr Leu Arg Leu Ile Leu Pro Gly Leu Gln Ala Arg Ile
65                  70                  75                  80

Arg Met Phe Asn Gln Leu His Asn Asn Met Leu Ser Gly Ala Gly Ser
                85                  90                  95

Arg Arg Leu Tyr Ile Leu Phe Pro Leu Asp Cys Gly Val Pro Asp Asn
            100                 105                 110

Leu Ser Val Val Asp Pro Asn Ile Arg Phe Arg Asp Met Leu Pro Gln
        115                 120                 125

Gln Asn Ile Asp Arg Ala Gly Ile Lys Asn Arg Val Tyr Ser Asn Ser
    130                 135                 140

Val Tyr Glu Ile Leu Glu Asn Gly Gln Pro Ala Gly Val Cys Ile Leu
145                 150                 155                 160

Glu Tyr Ala Thr Pro Leu Gln Thr Leu Phe Ala Met Ser Gln Asp Ala
                165                 170                 175

Lys Ala Gly Phe Ser Arg Glu Asp Arg Leu Glu Gln Ala Lys Leu Phe
            180                 185                 190

Cys Arg Thr Leu Glu Glu Ile Leu Glu Asp Val Pro Glu Ser Arg Asn
        195                 200                 205

Asn Cys Arg Leu Ile Val Tyr Gln Glu Pro Thr Asp Gly Asn Ser Phe
    210                 215                 220

Ser Leu Ser Gln Glu Val Leu Arg His Ile Arg Gln Glu Glu Lys Glu
225                 230                 235                 240

Glu Val Thr

<210> SEQ ID NO 26
<211> LENGTH: 214
<212> TYPE: PRT
<213> ORGANISM: Artificial Sequence
<220> FEATURE:
<223> OTHER INFORMATION: Modified LPS Antibody Light Chain

<400> SEQUENCE: 26

Asn Ile Val Met Thr Gln Ser Pro Asp Ser Leu Ala Val Ser Leu Gly
1               5                   10                  15

Glu Arg Ala Thr Ile Ser Cys Lys Ala Ser Glu Asn Val Gly Asn Ser
            20                  25                  30

Val Ser Trp Tyr Gln Gln Lys Pro Gly Gln Ser Pro Lys Pro Leu Ile
        35                  40                  45

Tyr Gly Ala Ser Asn Arg Tyr Thr Gly Val Pro Asp Arg Phe Ser Gly
    50                  55                  60

Ser Gly Ser Ala Thr Asp Phe Thr Leu Thr Ile Ser Ser Leu Gln Ala
65                  70                  75                  80
```

```
Glu Asp Val Ala Val Tyr His Cys Gly Gln Ser Tyr Ser Tyr Pro Tyr
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 27
<211> LENGTH: 451
<212> TYPE: PRT
<213> ORGANISM: Artificial Sequence
<220> FEATURE:
<223> OTHER INFORMATION: Modified LPS Antibody Heavy Chain

<400> SEQUENCE: 27

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr
            20                  25                  30

Trp Ile Asn Trp Val Arg Gln Ala Pro Gly Gln Gly Leu Glu Trp Met
        35                  40                  45

Gly Asn Ile Tyr Pro Gly Thr Arg Ser Ser Asn Tyr Asn Glu Lys Phe
    50                  55                  60

Lys Asn Arg Val Thr Leu Thr Val Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Val Tyr Tyr Asp His Val Gly Tyr Tyr Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220
```

```
Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
        290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
        370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
            435                 440                 445

Pro Gly Lys
    450

<210> SEQ ID NO 28
<211> LENGTH: 214
<212> TYPE: PRT
<213> ORGANISM: Artificial Sequence
<220> FEATURE:
<223> OTHER INFORMATION: Pertuzumab Light Chain

<400> SEQUENCE: 28

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125
```

```
Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 29
<211> LENGTH: 449
<212> TYPE: PRT
<213> ORGANISM: Artificial Sequence
<220> FEATURE:
<223> OTHER INFORMATION: Pertuzumab Heavy Chain

<400> SEQUENCE: 29

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270
```

```
Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys
```

<210> SEQ ID NO 30
<211> LENGTH: 449
<212> TYPE: PRT
<213> ORGANISM: Artificial Sequence
<220> FEATURE:
<223> OTHER INFORMATION: Modified HER2 Antibody2 Heavy Chain

<400> SEQUENCE: 30

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
            35                  40                  45

Ala Asp Val Asn Pro Asn Ser Gly Gly Ser Ile Tyr Asn Gln Arg Phe
50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Asn Leu Gly Pro Ser Phe Tyr Phe Asp Tyr Trp Gly Gln Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
            130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175
```

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 31
<211> LENGTH: 218
<212> TYPE: PRT
<213> ORGANISM: Artificial Sequence
<220> FEATURE:
<223> OTHER INFORMATION: Anti-CD33 Antibody Light Chain

<400> SEQUENCE: 31

Asp Ile Gln Leu Thr Gln Ser Pro Ser Thr Leu Ser Ala Ser Val Gly
1               5                   10                  15

Asp Arg Val Thr Ile Thr Cys Arg Ala Ser Glu Ser Leu Asp Asn Tyr
            20                  25                  30

Gly Ile Arg Phe Leu Thr Trp Phe Gln Gln Lys Pro Gly Lys Ala Pro
        35                  40                  45

Lys Leu Leu Met Tyr Ala Ala Ser Asn Gln Gly Ser Gly Val Pro Ser
    50                  55                  60

Arg Phe Ser Gly Ser Gly Ser Gly Thr Glu Phe Thr Leu Thr Ile Ser
65                  70                  75                  80

Ser Leu Gln Pro Asp Asp Phe Ala Thr Tyr Tyr Cys Gln Gln Thr Lys

```
                    85                  90                  95
Glu Val Pro Trp Ser Phe Gly Gln Gly Thr Lys Val Glu Val Lys Arg
                100                 105                 110

Thr Val Ala Ala Pro Ser Val Phe Ile Phe Pro Pro Ser Asp Glu Gln
                115                 120                 125

Leu Lys Ser Gly Thr Ala Ser Val Val Cys Leu Leu Asn Asn Phe Tyr
            130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
                180                 185                 190

His Lys Val Tyr Ala Cys Glu Val Thr His Gln Gly Leu Ser Ser Pro
            195                 200                 205

Val Thr Lys Ser Phe Asn Arg Gly Glu Cys
            210                 215

<210> SEQ ID NO 32
<211> LENGTH: 446
<212> TYPE: PRT
<213> ORGANISM: Artificial Sequence
<220> FEATURE:
<223> OTHER INFORMATION: Anti-CD33 Antibody Heavy Chain

<400> SEQUENCE: 32

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Ile Thr Asp Ser
            20                  25                  30

Asn Ile His Trp Val Arg Gln Ala Pro Gly Gln Ser Leu Glu Trp Ile
        35                  40                  45

Gly Tyr Ile Tyr Pro Tyr Asn Gly Gly Thr Asp Tyr Asn Gln Lys Phe
    50                  55                  60

Lys Asn Arg Ala Thr Leu Thr Val Asp Asn Pro Thr Asn Thr Ala Tyr
65                  70                  75                  80

Met Glu Leu Ser Ser Leu Arg Ser Glu Asp Thr Ala Phe Tyr Tyr Cys
                85                  90                  95

Val Asn Gly Asn Pro Trp Leu Ala Tyr Trp Gly Gln Gly Thr Leu Val
                100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
            130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
            195                 200                 205

Lys Val Asp Lys Arg Val Glu Pro Lys Ser Cys Asp Lys Thr His Thr
        210                 215                 220

Cys Pro Pro Cys Pro Ala Pro Glu Ala Ala Gly Gly Pro Ser Val Phe
```

```
            225                 230                 235                 240
Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
                260                 265                 270

Lys Phe Asn Trp Tyr Val Asp Gly Val Glu Val His Asn Ala Lys Thr
                275                 280                 285

Lys Pro Arg Glu Glu Gln Tyr Asn Ser Thr Tyr Arg Val Val Ser Val
                290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
                340                 345                 350

Ser Arg Glu Glu Met Thr Lys Asn Gln Val Ser Leu Thr Cys Leu Val
                355                 360                 365

Lys Gly Phe Tyr Pro Ser Asp Ile Ala Val Glu Trp Glu Ser Asn Gly
                370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
                420                 425                 430

Asn His Tyr Thr Gln Lys Ser Leu Ser Leu Ser Pro Gly Lys
                435                 440                 445

<210> SEQ ID NO 33
<211> LENGTH: 219
<212> TYPE: PRT
<213> ORGANISM: Artificial Sequence
<220> FEATURE:
<223> OTHER INFORMATION: Anti-EphA2 Antibody Light Chain

<400> SEQUENCE: 33

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Ile Val His Ser
                20                  25                  30

Ser Gly Ile Thr Tyr Leu Glu Trp Tyr Leu Gln Lys Pro Gly Gln Ser
            35                  40                  45

Pro Gln Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Tyr Thr Phe Gly Gln Gly Thr Lys Val Glu Ile Lys
                100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
```

```
145                 150                 155                 160
Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
                195                 200                 205

Pro Val Thr Lys Ser Phe Asn Arg Gly Glu Cys
            210                 215

<210> SEQ ID NO 34
<211> LENGTH: 449
<212> TYPE: PRT
<213> ORGANISM: Artificial Sequence
<220> FEATURE:
<223> OTHER INFORMATION: Anti-EphA2 Antibody Heavy Chain

<400> SEQUENCE: 34

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ile Asp Tyr
            20                  25                  30

Ser Met His Trp Val Arg Gln Ala Pro Gly Gln Gly Leu Glu Trp Met
        35                  40                  45

Gly Trp Ile Asn Thr Tyr Thr Gly Glu Pro Thr Tyr Ser Asp Asp Phe
    50                  55                  60

Lys Gly Arg Val Thr Ile Thr Ala Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Thr Tyr Tyr Arg Tyr Glu Arg Asp Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
```

```
                290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Glu Glu Met Thr Lys Asn Gln Val Ser Leu Thr
                355                 360                 365

Cys Leu Val Lys Gly Phe Tyr Pro Ser Asp Ile Ala Val Glu Trp Glu
                370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
                435                 440                 445

Lys

<210> SEQ ID NO 35
<211> LENGTH: 213
<212> TYPE: PRT
<213> ORGANISM: Artificial Sequence
<220> FEATURE:
<223> OTHER INFORMATION: Anti-CDH6 Antibody Light Chain

<400> SEQUENCE: 35

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Ile Tyr Lys Asn
                20                  25                  30

Leu Ala Trp Tyr Gln Gln Lys Pro Gly Lys Ala Pro Lys Leu Leu Ile
                35                  40                  45

Tyr Asp Ala Asn Thr Leu Gln Thr Gly Val Pro Ser Arg Phe Ser Gly
                50                  55                  60

Ser Gly Ser Gly Ser Asp Phe Thr Leu Thr Ile Ser Ser Leu Gln Pro
65                  70                  75                  80

Glu Asp Phe Ala Thr Tyr Phe Cys Gln Gln Tyr Tyr Ser Gly Trp Ala
                85                  90                  95

Phe Gly Gln Gly Thr Lys Val Glu Ile Lys Arg Thr Val Ala Ala Pro
                100                 105                 110

Ser Val Phe Ile Phe Pro Pro Ser Asp Glu Gln Leu Lys Ser Gly Thr
                115                 120                 125

Ala Ser Val Val Cys Leu Leu Asn Asn Phe Tyr Pro Arg Glu Ala Lys
                130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
                180                 185                 190

Cys Glu Val Thr His Gln Gly Leu Ser Ser Pro Val Thr Lys Ser Phe
                195                 200                 205
```

```
Asn Arg Gly Glu Cys
        210

<210> SEQ ID NO 36
<211> LENGTH: 452
<212> TYPE: PRT
<213> ORGANISM: Artificial Sequence
<220> FEATURE:
<223> OTHER INFORMATION: Anti-CDH6 Antibody Heavy Chain

<400> SEQUENCE: 36

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Arg Asn
            20                  25                  30

Phe Met His Trp Val Arg Gln Ala Pro Gly Gln Gly Leu Glu Trp Met
        35                  40                  45

Gly Trp Ile Tyr Pro Gly Asp Gly Glu Thr Glu Tyr Ala Gln Lys Phe
    50                  55                  60

Gln Gly Arg Val Thr Ile Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Val Tyr Gly Gly Phe Ala Gly Gly Tyr Phe Asp Phe Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Ala Ala
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Gly Ala Pro
                325                 330                 335

Ile Glu Lys Thr Ile Ser Lys Ala Lys Gly Gln Pro Arg Glu Pro Gln
            340                 345                 350
```

```
Val Tyr Thr Leu Pro Pro Ser Arg Glu Glu Met Thr Lys Asn Gln Val
        355             360             365
Ser Leu Thr Cys Leu Val Lys Gly Phe Tyr Pro Ser Asp Ile Ala Val
    370             375             380
Glu Trp Glu Ser Asn Gly Gln Pro Glu Asn Asn Tyr Lys Thr Thr Pro
385             390             395             400
Pro Val Leu Asp Ser Asp Gly Ser Phe Phe Leu Tyr Ser Lys Leu Thr
            405             410             415
Val Asp Lys Ser Arg Trp Gln Gln Gly Asn Val Phe Ser Cys Ser Val
            420             425             430
Met His Glu Ala Leu His Asn His Tyr Thr Gln Lys Ser Leu Ser Leu
        435             440             445
Ser Pro Gly Lys
    450
```